United States Patent
Kai et al.

(10) Patent No.: US 8,575,197 B2
(45) Date of Patent: *Nov. 5, 2013

(54) PYROLINONE DERIVATIVE AND PHARMACEUTICAL COMPOSITION COMPRISING THE SAME

(75) Inventors: Hiroyuki Kai, Osaka (JP); Yoshiyuki Taoda, Osaka (JP); Takeshi Endoh, Osaka (JP); Kentaro Asahi, Osaka (JP); Hiroyuki Tobinaga, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 6 days.

This patent is subject to a terminal disclaimer.

(21) Appl. No.: 13/121,072

(22) PCT Filed: Sep. 24, 2009

(86) PCT No.: PCT/JP2009/066473
§ 371 (c)(1),
(2), (4) Date: Mar. 25, 2011

(87) PCT Pub. No.: WO2010/035727
PCT Pub. Date: Apr. 1, 2010

(65) Prior Publication Data
US 2011/0183939 A1   Jul. 28, 2011

(30) Foreign Application Priority Data
Sep. 25, 2008   (JP) .................................. 2008-245668

(51) Int. Cl.
| | |
|---|---|
| *A61K 31/4418* | (2006.01) |
| *A61K 31/443* | (2006.01) |
| *A61K 31/4439* | (2006.01) |
| *A61K 31/422* | (2006.01) |
| *A61K 31/4245* | (2006.01) |
| *A61K 31/402* | (2006.01) |
| *A61K 31/4025* | (2006.01) |
| *C07D 207/38* | (2006.01) |
| *C07D 271/06* | (2006.01) |
| *C07D 261/08* | (2006.01) |
| *C07D 409/10* | (2006.01) |
| *C07D 403/14* | (2006.01) |
| *C07D 413/14* | (2006.01) |
| *C07D 401/04* | (2006.01) |

(52) U.S. Cl.
USPC ........... 514/333; 514/340; 514/343; 514/364; 514/378; 514/422; 514/423; 546/256; 546/269.1; 546/272.1; 546/278.7; 548/131; 548/247; 548/518; 548/525; 548/527; 548/540

(58) Field of Classification Search
None
See application file for complete search history.

(56) References Cited

U.S. PATENT DOCUMENTS

| | | |
|---|---|---|
| 3,244,725 A | 4/1966 | Taub et al. |
| 2005/0209260 A1 | 9/2005 | Broka et al. |
| 2006/0035245 A1 | 2/2006 | Ason et al. |
| 2007/0037974 A1 | 2/2007 | Brotherton-Pleiss et al. |
| 2007/0049534 A1 | 3/2007 | Dillon et al. |
| 2007/0049609 A1 | 3/2007 | Broka et al. |
| 2007/0049610 A1 | 3/2007 | Dillon et al. |
| 2007/0049758 A1 | 3/2007 | Dillon et al. |
| 2007/0148185 A1 | 6/2007 | Rathore et al. |
| 2007/0203236 A1 | 8/2007 | Smith et al. |
| 2010/0210632 A1 | 8/2010 | Kai et al. |

FOREIGN PATENT DOCUMENTS

| | | |
|---|---|---|
| JP | 49-88863 | 8/1974 |
| JP | 49-88864 | 8/1974 |
| WO | 02/94767 | 11/2002 |

(Continued)

OTHER PUBLICATIONS

Byrn et al., Solid-State Chemistry of Drugs (2nd Ed. 1999) (pp. 233-247, 234).*

(Continued)

*Primary Examiner* — Joseph K. McKane
*Assistant Examiner* — Alicia L Otton
(74) *Attorney, Agent, or Firm* — Wenderoth, Lind & Ponack, L.L.P.

(57) ABSTRACT

The present invention provides a novel $P2X_3$ and/or $P2X_{2/3}$ receptor antagonist.
A compound represented by the formula (I):

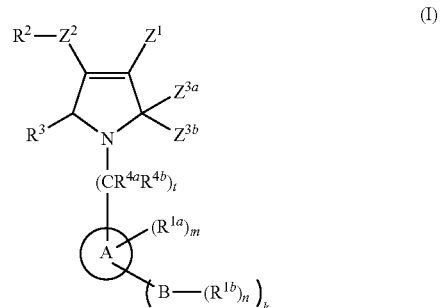

wherein $Z^1$ is optionally protected hydroxy, etc.; $Z^2$ is —C(=O)—, etc.; $Z^{3a}$ and $Z^{3b}$ are taken together =O or =S; t is an integer of 0 to 4; $R^{4a}$ and $R^{4b}$ are each independently, hydrogen or substituted or unsubstituted lower alkyl, etc.; m and n are each independently an integer of 0 to 2; k is an integer of 0 or 1; Ring A is an aromatic carbocyclic ring or a heterocyclic ring, etc.; B is aromatic carbocyclic ring-diyl or heterocyclic ring-diyl, etc.; $R^{1a}$ and $R^{1b}$ are each independently halogen, hydroxy, substituted or unsubstituted lower alkyl, etc.; $R^2$ is substituted or unsubstituted alkyl, etc.; $R^3$ is substituted or unsubstituted alkyl, substituted or unsubstituted aryl or a substituted or unsubstituted heterocyclic group, etc.; or its pharmaceutically acceptable salt, or a solvate thereof is provided.

3 Claims, No Drawings

(56) References Cited

FOREIGN PATENT DOCUMENTS

| WO | 02/094767 | 11/2002 |
|---|---|---|
| WO | 03/030897 | 4/2003 |
| WO | 2004/001058 | 12/2003 |
| WO | 2005/027882 | 3/2005 |
| WO | 2005/095359 | 10/2005 |
| WO | 2006/007864 | 1/2006 |
| WO | 2006/097337 | 9/2006 |
| WO | 2008/055945 | 5/2008 |
| WO | 2008/120725 | 10/2008 |
| WO | 2008/127275 | 10/2008 |
| WO | 2009/051801 | 4/2009 |
| WO | 2009/113795 | 9/2009 |
| WO | 2009/133294 | 11/2009 |

OTHER PUBLICATIONS

International Search Report issued Dec. 22, 2009 in International (PCT) Application No. PCT/JP2009/066473.

English Abstract for Russian Patent Publication No. 2 320 661, published Mar. 2008.

Kennedy, "P2X Receptors: Targets for Novel Analgesics?", The Neuroscientist, vol. 11, No. 4, 2005, pp. 345-356.

Cockayne et al., "$P2X_2$ Knockout Mice and $P2X_2$ /$P2X_3$ Double Knockout Mice Reveal a Role for the $P2X_2$ Receptor Subunit in Mediating Multiple Sensory Effects of ATP" J. Physiol., vol. 567.2, 2005, pp. 621-639.

Gein et al., "Synthesis and Antiinflammatory and Analgesic Activity of 1-(2-Aminoethyl)-5-Aryl-4-Acyl-3-Hydroxy-3-Pyrrolin-2-Ones", Pharmaceutical Chemistry Journal, vol. 39, No. 9, 2005, pp. 484-487.

Gein et al., "Synthesis and Pharmacological Activity of 5-Aryl-4-Acetyl-1-Carboxyalkyl-Tetrahydropyrrole-2,3-Diones", Pharmaceutical Chemistry Journal, vol. 31, No. 5, 1997, pp. 251-254.

Shieh et al., "P2X Receptor Ligands and Pain", Expert Opin. Ther. Patents, vol. 16, No. 8, 2006, pp. 1113-1127.

North, "$P2X_3$ Receptors and Peripheral Pain Mechanisms", J. Physiol., vol. 554, No. 2, 2003, pp. 301-308.

Kennedy et al., "Crossing the Pain Barrier: P2 Receptors as Targets for Novel Analgesics" J. Physiol., vol. 553, No. 3, 2003, pp. 683-694.

Gever et al., "Pharmacology of P2X Channels", Pflugers Arch—Eur. J. Physiol., vol. 452, 2006, pp. 513-537.

Jarvis et al., "A-317491, A Novel Potent and Selective Non-Nucleotide Antagonist of $P2X_3$ and $P2X_{2/3}$ Receptors, Reduces Chronic Inflammatory and Neuropathic Pain in the Rat", PNAS, vol. 99, No. 26, 2002, pp. 17179-17184.

Koz'minykh et al., "Synthesis and Pharmacological Activity of 3-Hydroxy-1,5-Diaryl-4-Pivaloyl-2,5-Dihydro-2-Pyrrolones", Pharmaceutical Chemistry Journal, vol. 36, No. 4, 2002, pp. 188-191.

Yavari et al., "Triphenylphosphine-Mediated Reaction Between Dimethyl Acetylenedicarboxylate and NH-Acids Derived from Diaminobenzenes", Phosphorus, Sulfur, and Silicon, vol. 181, 2006, pp. 771-777.

Cockayne et al., "Urinary Bladder Hyporeflexia and Reduced Pain-Related Behaviour in $P2X_3$-Deficent Mice", Nature, vol. 407, 2000, pp. 1011-1015.

Souslova at al. "Warm-Coding Deficits and Aberrant Inflammatory Pain in Mice Lacking $P2X_3$ Receptors" Nature, vol. 407, 2000, pp. 1015-1017.

Gein et al., "Anti-Inflammatory and Analgesic Activity of 5-Aryl-4-Acyl-1-Heteryl-3-Hydroxy-3-Pyrrolin-2-Ones", Pharmaceutical Chemistry Journal, vol. 42, No. 5, 2008, pp. 255-257.

Gein et al., "Synthesis and Biological Activity of 5-Aryl-4-Acyl-3-Hydroxy-1-Morpholinoalkyl-3-Pyrrolin-2-Ones". Pharmaceutical Chemistry Journal, vol. 41, No. 5, 2007, pp. 256-263.

Khimiko-Farmatsevticheskii Zhurnal, vol. 31, No. 11, 1997, pp. 35-36.

First page and English Abstract for Russian Patent Publication No. 2 259 369, published Aug. 2005.

International Preliminary Report on Patentability together with English translation of the Written Opinion issued May 19, 2011 in corresponding International (PCT) Application No. PCT/JP2009/066473.

\* cited by examiner

PYROLINONE DERIVATIVE AND PHARMACEUTICAL COMPOSITION COMPRISING THE SAME

TECHNICAL FIELD

The invention relates to P2X receptor, specifically to a compound useful for the treatment of diseases or conditions associated with a P2X$_3$ receptor, specifically to a P2X$_3$ and/or P2X$_2$/$_3$ receptor, and a pharmaceutical composition comprising such compound.

BACKGROUND ART

ATP (adenosine triphosphate) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 6, Non-Patent Document 7).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 8).

ATP is known to cause pain, and studies with P2X$_3$ knockout and knockdown methodologies have shown that P2X$_3$ receptor mediates transmission of chronic pain. P2X$_3$ receptors are expressed in a specific manner on peripheral sensory nerve to form a homo-complex or hetero-complex with P2X$_2$ (P2X$_2$/$_3$) (Non-Patent Document 1).

Later, the compound A-317491 was reported as a specific antagonist to P2X$_3$ and P2X$_2$/$_3$ receptors. A-317491 is tri-substituted-N-[(1S)-1,2,3,4-tetrahydro-1-naphthalenyl]benzamide derivative represented by the formula:

[Chemical Formula 1]

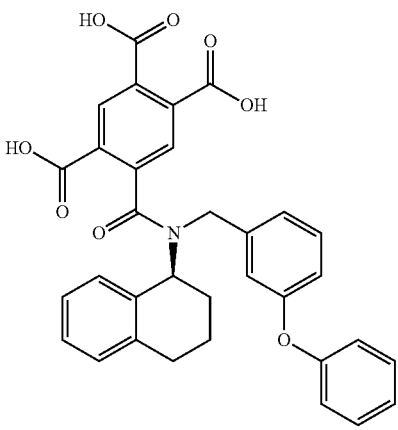

(Patent Document 1). It was reported to exhibit an antagonist activity to P2X$_3$ and P2X$_2$/$_3$ receptors and analgesic action in neuropathic pain model and inflammatory pain model (Non-Patent Document 9). This indicates that pain sensation is transmitted via P2X$_3$ or P2X$_2$/$_3$ receptor and that a P2X$_3$ or P2X$_2$/$_3$ receptor antagonist is useful as an analgesic. Also, compounds that exhibit P2X$_3$ or P2X$_2$/$_3$ receptor antagonizing effect are described in Patent Documents 2-7.

Additionally, it was recently reported that vesical reflex was strongly reduced in P2X$_3$ knockout mouse (Non-Patent Document 2), suggesting that a P2X$_3$ antagonist is useful in the treatment of diseases caused by overactive bladder.

Patent document 12 discloses that the compounds having similar chemical structures to the compound of the invention, however, does not disclose that the compounds having an analgesic effect and a P2X$_3$ or P2X$_2$/$_3$ receptor antagonizing effect. Non-Patent documents 3, 4, 10, and 11 disclose that the compounds having similar chemical structures to the compound of the invention and an analgesic effect, however, does not disclose that the compound having a P2X$_3$ or P2X$_2$/$_3$ receptor antagonizing effect.

[Patent Document 1] WO02/094767
[Patent Document 2] WO2005/095359
[Patent Document 3] US20070037974
[Patent Document 4] US20070049758
[Patent Document 5] US20070049610
[Patent Document 6] US20070049609
[Patent Document 7] US20070049534
[Non-Patent Document 1] Neuroscientist 11 (2005) pp. 345-356
[Non-Patent Document 2] J. Physiol. 567.2 (2005) pp. 621-639
[Non-Patent Document 3] Pharmaceutical Chemistry Journal Vol. 39, No. 9, (2005), pp 484-487
[Non-Patent Document 4] Pharmaceutical Chemistry Journal Vol. 31, No. 5, (1997), pp 251-254
[Non-Patent Document 5] Expert Opin. Ther. Patens (2006) 16(8) 113-1127.
[Non-Patent Document 6] J. Physiology (2003), 554(2), 301-308
[Non-Patent Document 7] J. Physiology (2003), 553(3), 683-694
[Non-Patent Document 8] Pflungers Arch Eur J physiol (2006), 452, 513-537
[Non-Patent Document 9] PNAS (2002), 99(26), 17179-17184
[Non-Patent Document 10] Khimiko-Farmatsevticheskii Zhurnal, Vol 31, No. 11, (1997) 35-36
[Non-Patent Document 11] Pharmaceutical Chemistry Journal Vol 36, No. 4, (2002), 188-191
[Non-Patent Document 12] Phosphorus, Sulfur and Silicon and the Related Elements (2006), 181(4), 771-777

DISCLOSURE OF INVENTION

Problems to be Resolved by the Invention

The present invention provides a novel P2X$_3$ and/or P2X$_2$/$_3$ receptor antagonist.

Means of Solving the Problems

During studies to solve the problems described above, the inventors have discovered novel compounds that bind specifically to P2X$_3$ and/or P2X$_2$/$_3$ receptor and exhibit an antagonizing effect, and thus, achieved the inventions described bellow.

(1) A compound represented by the formula (I):

[Chemical Formula 2]

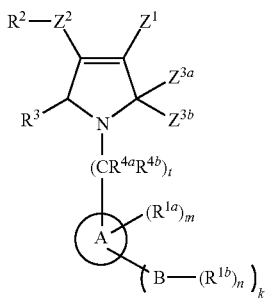

wherein
$Z^1$ is optionally protected hydroxy or optionally protected mercapto;
$Z^2$ is —C(=O)—, —C(=S)— or —S(O)v-, or

[Chemical Formula 3]

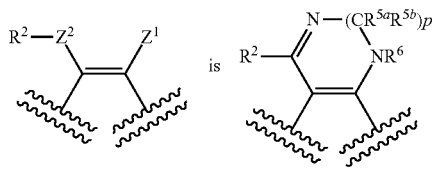

wherein $R^{5a}$ and $R^{5b}$ are each independently hydrogen or lower alkyl;
$R^6$ is hydrogen, substituted or unsubstituted lower alkyl, substituted or unsubstituted acyl or substituted or unsubstituted lower alkoxycarbonyl;
p is an integer of 0 to 2;
v is an integer of 0 to 2;
$Z^{3a}$ and $Z^{3b}$ are each independently hydrogen or unsubstituted lower alkyl, or taken together =O or =S;
t is an integer of 0 to 4;
$R^{4a}$ and $R^{4b}$ are each independently, hydrogen or substituted or unsubstituted lower alkyl;
m and n are each independently an integer of 0 to 2;
k is an integer of 0 or 1;
Ring A is cycloalkane, cycloalkene, an aromatic carbocyclic ring or a heterocyclic ring;
B is cycloalkene-diyl, cycloalkene-diyl, aromatic carbocyclic ring-diyl or heterocyclic ring-diyl;
$R^{1a}$ and $R^{1b}$ are each independently halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted thiocarbamoyl, substituted or unsubstituted amino, substituted sulfinyl, substituted sulfonyl, substituted or unsubstituted sulfamoyl, cyano, nitro or —C($R^{7a}$)=N—O—$R^{7b}$;
$R^{7a}$ and $R^{7b}$ are each independently hydrogen or substituted or unsubstituted lower alkyl;
$R^2$ is substituted or unsubstituted alkyl, substituted or unsubstituted alkenyl, substituted or unsubstituted alkynyl, substituted or unsubstituted alkoxy, substituted or unsubstituted aryloxy, hydroxy, substituted or unsubstituted amino, substituted or unsubstituted cycloalkyl or substituted or unsubstituted cycloalkenyl, substituted or unsubstituted aryl or a substituted or unsubstituted heterocyclic group;

$R^3$ is substituted or unsubstituted alkyl, substituted or unsubstituted alkoxycarbonyl, substituted or unsubstituted aryloxycarbonyl, carboxy, substituted or unsubstituted carbamoyl, substituted or unsubstituted cycloalkyl, substituted or unsubstituted cycloalkenyl, substituted or unsubstituted aryl or a substituted or unsubstituted heterocyclic group;

provided that a compound of the following (i) to (viii) is excluded;

(i) a compound wherein Ring A is thiadiazole, k is 0 and $R^{1a}$ is methylthio;

(ii) a compound wherein Ring A is benzothiophene, k is 0, $R^{1a}$ is methylsulfonyl and $R^2$ is substituted or unsubstituted furyl or substituted or unsubstituted phenyl;

(iii) a compound wherein Ring A is thiazole or 7H-purine, and $R^2$ is substituted or unsubstituted furyl;

(iv) a compound wherein $R^3$ is a group represented by the formula:

[Chemical Formula 4]

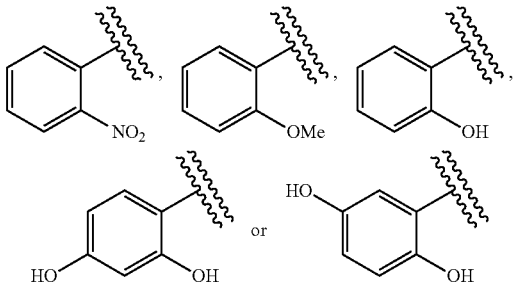

t is an integer of 1 to 2 and Ring A is furan or benzene;

(v) a compound wherein $R^2$ is t-butyl or 4-methyloxyphenyl;

(vi) a compound wherein $R^2$ is substituted or unsubstituted alkyl provided that substituted or unsubstituted i-propyl and substituted or unsubstituted i-butyl are excluded, $R^3$ is a substituted or unsubstituted carbocyclic ring or a substituted or unsubstituted heterocyclic ring, and k is 0;

(vii) a compound wherein $R^2$ is substituted or unsubstituted cycloalkyl, substituted or unsubstituted cycloalkenyl, substituted or unsubstituted aryl or a substituted or unsubstituted heterocyclic group, and $R^3$ is pentane-3-yl; and (viii) a compound represented by the formula:

[Chemical Formula 5]

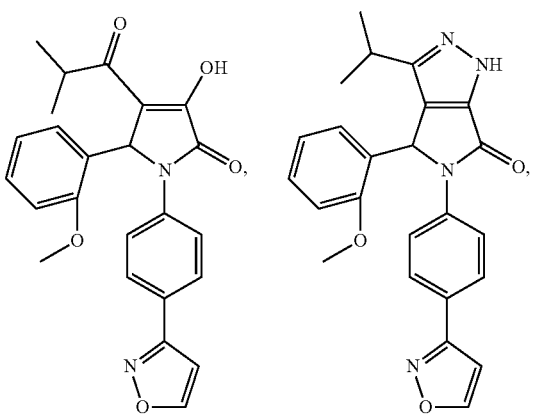

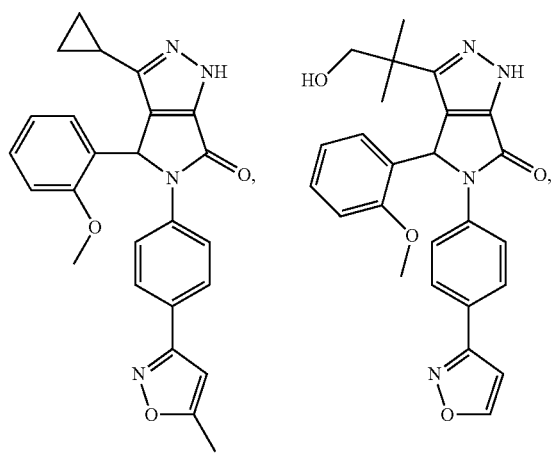
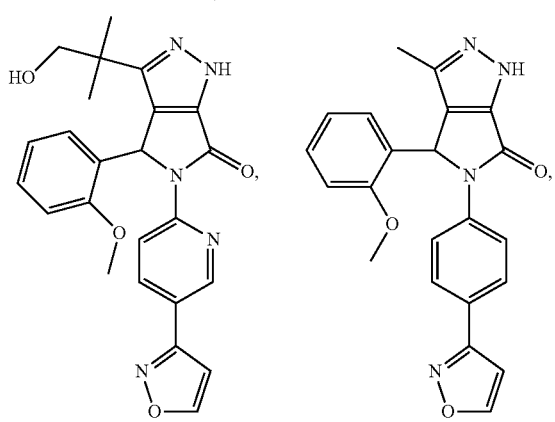
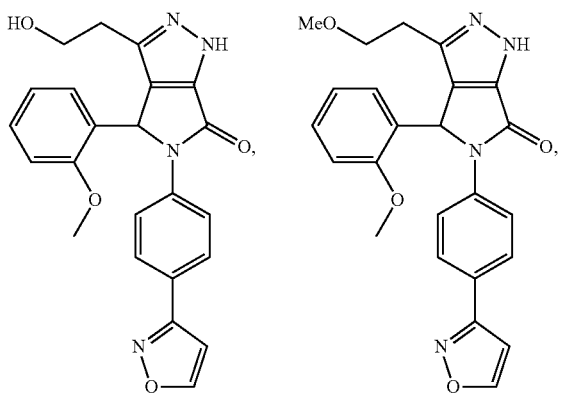
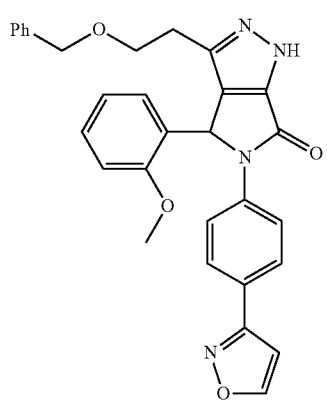

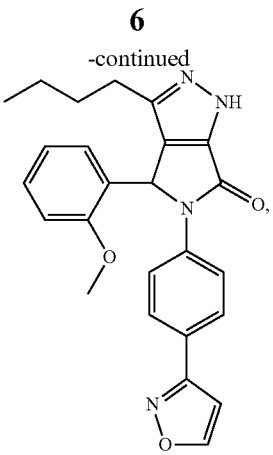

or its pharmaceutically acceptable salt, or a solvate thereof.

(2) The compound according to the above (1), wherein $R^2$ is a group represented by the formula:

[Chemical Formula 6]

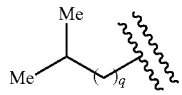

wherein Me is methyl, q is an integer of 0 to 4; and $R^3$ is a group represented by the formula:

[Chemical Formula 7]

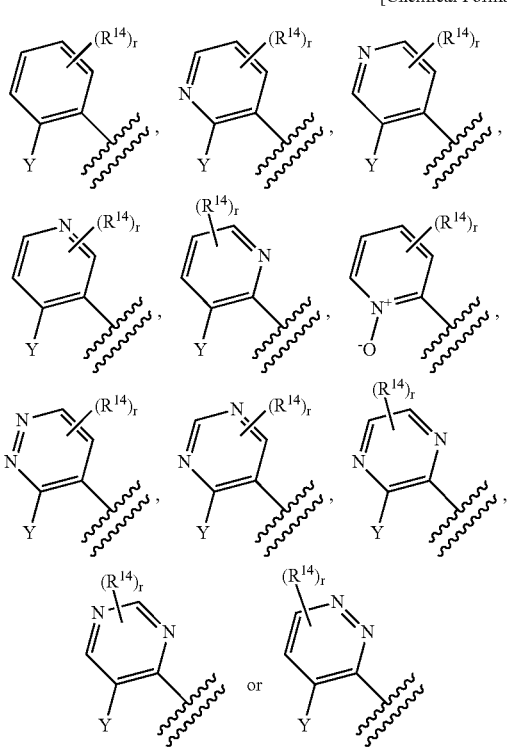

wherein Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl or a substituted or unsubstituted heterocyclic group, or Y and $R^{14}$ may form a substituted or unsubstituted heterocyclic group with adjacent carbon atom;

$R^{14}$ is halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano or nitro; and r is an integer of 0 to 2, or its pharmaceutically acceptable salt, or a solvate thereof.

(2') A compound represented by the formula (I);

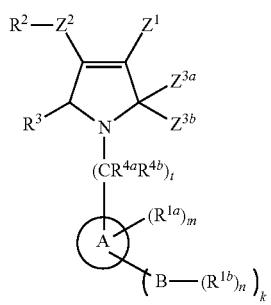
(I)

wherein
$Z^1$ is optionally protected hydroxy or optionally protected mercapto;
$Z^2$ is —C(=O)—, —C(=S)— or —S(O)v-, or

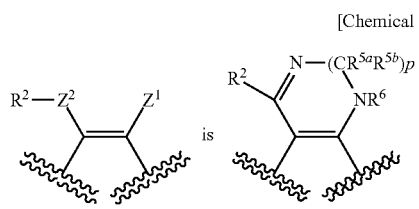
[Chemical Formula 9]

wherein $R^{5a}$ and $R^{5b}$ are each independently hydrogen or lower alkyl;
$R^6$ is hydrogen, substituted or unsubstituted lower alkyl, substituted or unsubstituted acyl or substituted or unsubstituted lower alkoxycarbonyl;
p is an integer of 0 to 2;
v is an integer of 0 to 2;
$Z^{3a}$ and $Z^{3b}$ are each independently hydrogen, substituted or unsubstituted lower alkyl, or taken together =O or =S;
$Z^{3a}$ and $Z^{3b}$ are each independently hydrogen, substituted or unsubstituted lower alkyl, or taken together =O or =S;
t is an integer of 0 to 4;
$R^{4a}$ and $R^{4b}$ are each independently, hydrogen or substituted or unsubstituted lower alkyl;
m and n are each independently an integer of 0 to 2;
k is an integer of 0 or 1;
Ring A is cycloalkane, cycloalkene, an aromatic carbocyclic ring or a heterocyclic ring;

B is cycloalkane-diyl, cycloalkene-diyl, aromatic carbocyclic ring-diyl or heterocyclic ring-diyl;

$R^{1a}$ and $R^{1b}$ are each independently halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted thiocarbamoyl, substituted or unsubstituted amino, substituted sulfinyl, substituted sulfonyl, substituted or unsubstituted sulfamoyl, cyano, nitro or —C($R^{7a}$)=N—O—$R^{7b}$;

$R^{7a}$ and $R^{7b}$ are each independently hydrogen or substituted or unsubstituted lower alkyl;

$R^2$ is a group represented by the formula:

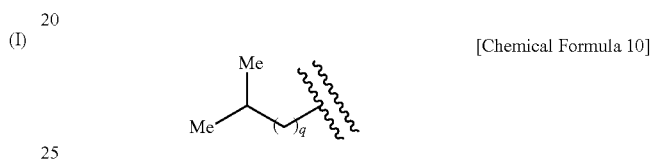
[Chemical Formula 10]

wherein Me is methyl, q is an integer of 0 to 4;
$R^3$ is a group represented by the formula:

[Chemical Formula 11]

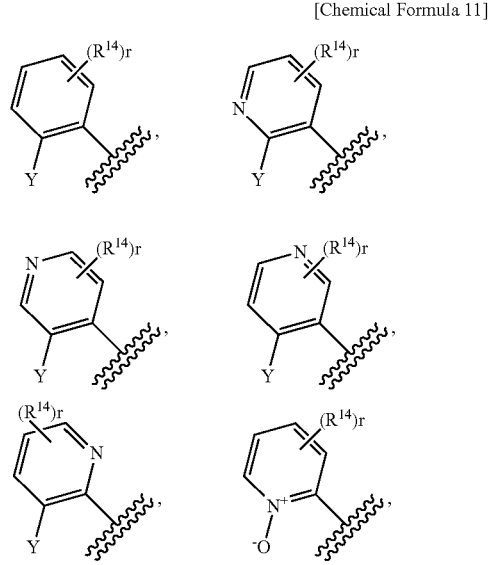

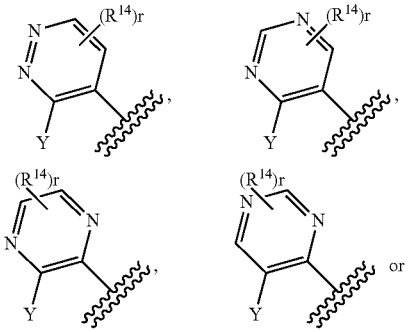
or

-continued

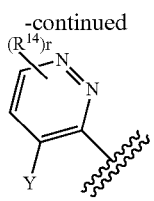

wherein Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl or a substituted or unsubstituted heterocyclic group, or Y and $R^{14}$ may form a substituted or unsubstituted heterocyclic group with adjacent carbon atom;

$R^{14}$ is halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano or nitro; and r is an integer of 0 to 2;

provided that the following compounds are excluded:

[Chemical Formula 12]

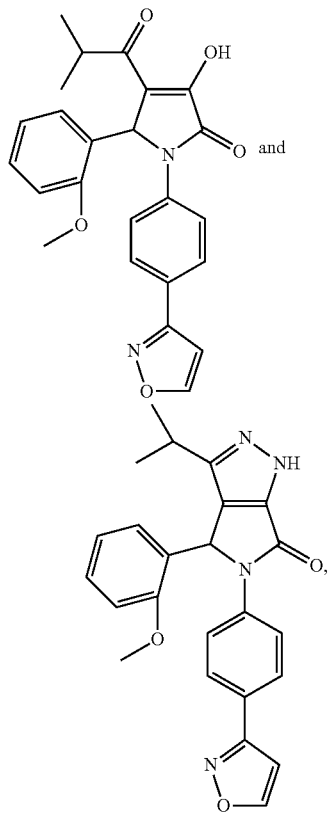

or its pharmaceutically acceptable salt, or a solvate thereof.

(3) The compound according to the above (2) or (2'), wherein $Z^{3a}$ and $Z^{3b}$ are taken together =O, or its pharmaceutically acceptable salt, or a solvate thereof.

(4) The compound according to any one of the above (2), (2') or (3), wherein t is 0, or its pharmaceutically acceptable salt, or a solvate thereof.

(5) The compound according to any one of the above (2) to (4) or (2'), wherein $Z^2$ is —C(=O)—, —C(=S)— or —S(O)$_2$—, or its pharmaceutically acceptable salt, or a solvate thereof.

(6) The compound according to any one of the above (2) to (5) or (2'), wherein $Z^2$ is —C(=O)—, or its pharmaceutically acceptable salt, or a solvate thereof.

(7) The compound according to any one of the above (2) to (6) or (2'), wherein the group represented by the formula:

[Chemical Formula 13]

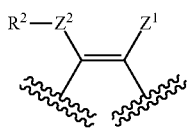

wherein $Z^1$, $Z^2$ and $R^2$ are as defined in the above (1), is a group represented by the formula:

[Chemical Formula 14]

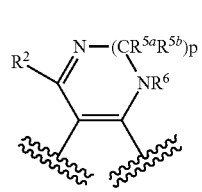

wherein. $R^2$, $R^{5a}$, $R^{5b}$, $R^6$, and p are as defined in the above (1), or its pharmaceutically acceptable salt, or a solvate thereof.

(8) The compound according to any one of the above (2) to (6) or (2'), wherein the group represented by the formula:

[Chemical Formula 15]

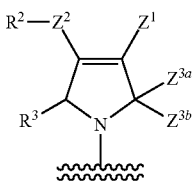

wherein $Z^1$, $Z^2$, $Z^{3a}$, $Z^{3b}$, $R^2$, and $R^3$ are as defined in the above (1), is a group represented by the formula:

[Chemical Formula 16]

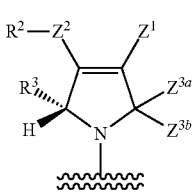

wherein $Z^1$, $Z^2$, $Z^{3a}$, $Z^{3b}$, $R^2$ and $R^3$ are as defined in the above (1), or its pharmaceutically acceptable salt, or a solvate thereof.

(9) A compound represented by the formula (I):

[Chemical Formula 17]

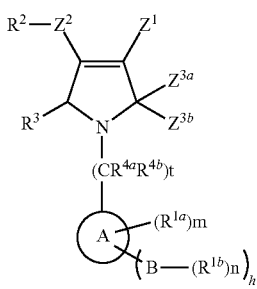

wherein $Z^1$, $Z^2$, $Z^{3a}$, $Z^{3b}$, $R^{1a}$, $R^{1b}$, $R^2$, $R^3$, $R^{4a}$, $R^{4b}$, Ring A, B, h, m, n, and $t$ are as defined in the above (1), or its pharmaceutically acceptable salt, or a solvate thereof; is a compound represented by the formula (I');

[Chemical Formula 18]

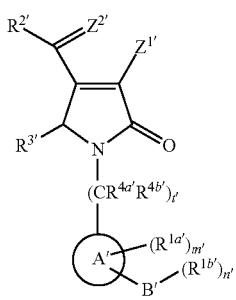

(I')

wherein
$Z^{1\prime}$ is optionally protected hydroxy or optionally protected mercapto;
$Z^{2\prime}$ is O or S, or

[Chemical Formula 19]

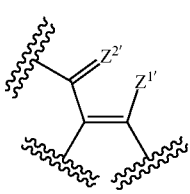 is 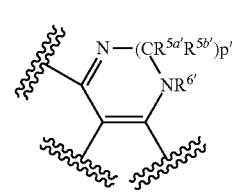

wherein $R^{5a\prime}$ and $R^{5b\prime}$ are each independently hydrogen or lower alkyl;
$R^6$ is hydrogen, substituted or unsubstituted lower alkyl, substituted or unsubstituted acyl or substituted or unsubstituted lower alkoxycarbonyl;
p' is an integer of 0 to 2;
t' is an integer of 0 to 4;
$R^{4a\prime}$ and $R^{4b\prime}$ are each independently hydrogen or lower alkyl;
m' and n' are each independently an integer of 0 to 2;
Ring A' is cycloalkane, cycloalkene, an aromatic carbocyclic ring or a heterocyclic ring;

B' is cycloalkane-diyl, cycloalkene-diyl, aromatic carbocyclic ring-diyl or heterocyclic ring-diyl;
when n' is 0, B' may be methylthio, trifluoromethylthio, or —C($R^{7a\prime}$)=N—O—$R^{7b\prime}$;
$R^{1a\prime}$ and $R^{1b\prime}$ are each independently halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano, or nitro;
$R^{2\prime}$ and $R^{3\prime}$ are each independently substituted or unsubstituted alkyl, substituted or unsubstituted cycloalkyl, substituted or unsubstituted cycloalkenyl, substituted or unsubstituted aryl or a substituted or unsubstituted heterocyclic group;
$R^{7a\prime}$ and $R^{7b\prime}$ are each independently hydrogen or substituted or unsubstituted lower alkyl;
provided that a compound wherein Ring A' is thiadiazole and B' is methylthio is excluded,
or its pharmaceutically acceptable salt, or a solvate thereof.

(10) The compound according to the above (9), wherein $R^{3\prime}$ is a group represented by the formula:

[Chemical Formula 20]

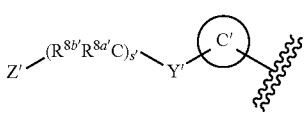

wherein Ring C' is a substituted or unsubstituted aromatic carbocyclic ring or a substituted or unsubstituted aromatic heterocyclic ring;
Y' is —O—, —S—, or —$NR^{9\prime}$—;
$R^{9\prime}$ is hydrogen or lower alkyl;
Z' is hydroxy, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted lower alkylsulfinyl, substituted or unsubstituted alkylsulfamoyl or cyano;
$R^{8a\prime}$ and $R^{8b\prime}$ are each independently hydrogen or substituted or unsubstituted lower alkyl;
s' is an integer of 1 to 4,
or its pharmaceutically acceptable salt, or a solvate thereof.

(11) The compound according to the above (9) or (10), wherein Y' is —O—, or its pharmaceutically acceptable salt, or a solvate thereof.

(12) The compound according to any one of the above (9) to (11), wherein t' is 0, or its pharmaceutically acceptable salt, or a solvate thereof.

(13) The compound according to any one of the above (9) to (12), wherein a group represented by the formula:

[Chemical Formula 21]

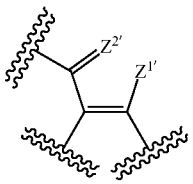 is 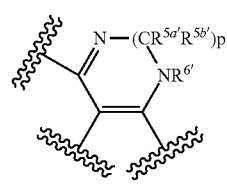

t' and p' are 0;
R² is a group represented by the formula:

[Chemical Formula 22]

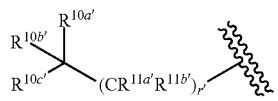

wherein $R^{10a'}$ and $R^{10b'}$ are each independently hydroxy, halogen, substituted or unsubstituted alkyl, substituted or unsubstituted lower alkoxy, substituted or unsubstituted lower alkoxycarbonyl, carboxy, substituted or unsubstituted carbamoyl, substituted or unsubstituted cycloalkyl, substituted or unsubstituted cycloalkenyl, substituted or unsubstituted aryl, a substituted or unsubstituted heterocyclic group, or $R^{10a'}$ and $R^{10b'}$ are taken together may form a substituted or unsubstituted non-aromatic carbocyclic ring or a substituted or unsubstituted non-aromatic heterocyclic ring with an adjacent carbon atom;

$R^{10c'}$ is hydrogen, hydroxy, halogen, substituted or unsubstituted alkyl, substituted or unsubstituted lower alkoxy, substituted or unsubstituted lower alkoxycarbonyl, carboxy, substituted or unsubstituted lower alkylcarbamoyl, substituted or unsubstituted cycloalkyl, substituted or unsubstituted cycloalkenyl, substituted or unsubstituted aryl or a substituted or unsubstituted heterocyclic group;

$R^{11a'}$ and $R^{11b'}$ are each independently hydrogen or lower alkyl, or taken together =O;

r' is an integer of 0 to 4;

provided that a compound wherein all of $R^{10a'}$, $R^{10b'}$ and $R^{10c'}$ are methyl; and the following compounds;

[Chemical Formula 23]

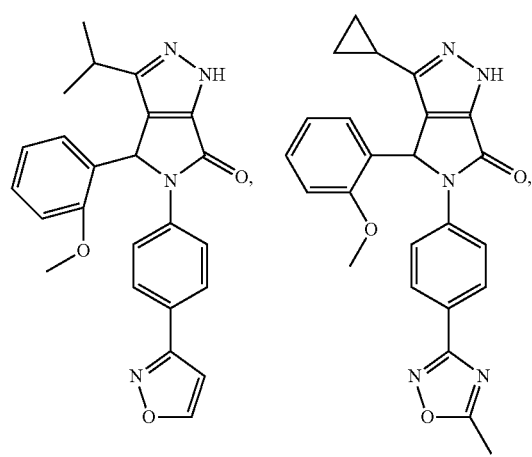

are excluded, or its pharmaceutically acceptable salt, or a solvate thereof.

(14) The compound according to the above (13), wherein $R^{10a'}$ and $R^{10b'}$ are lower alkyl, and $R^{10c'}$ is carboxy, hydroxyalkyl, substituted or unsubstituted aryl, substituted or unsubstituted heteroaryl, or substituted or unsubstituted lower alkylcarbamoyl, or its pharmaceutically acceptable salt, or a solvate thereof.

(15) The compound according to any one of the above (10) to (12), wherein
$Z^{1'}$ is optionally protected hydroxy;
$Z^{2'}$ is O;
$R^{2'}$ is a group represented by the formula:

[Chemical Formula 24]

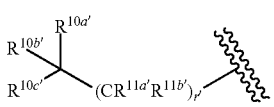

wherein $R^{10a'}$ and $R^{10b'}$ are each independently hydroxy, halogen, substituted or unsubstituted alkyl, substituted or unsubstituted lower alkoxy, substituted or unsubstituted lower alkoxycarbonyl, carboxy, substituted or unsubstituted lower alkylcarbamoyl, substituted or unsubstituted cycloalkyl, substituted or unsubstituted cycloalkenyl, substituted or unsubstituted aryl, a substituted or unsubstituted heterocyclic group, or $R^{10a'}$ and $R^{10b'}$ are taken together may form a substituted or unsubstituted non-aromatic carbocyclic ring or a substituted or unsubstituted non-aromatic heterocyclic ring with an adjacent carbon atom;

$R^{10c'}$ is hydrogen, hydroxy, halogen, substituted or unsubstituted alkyl, substituted or unsubstituted lower alkoxy, substituted or unsubstituted lower alkoxycarbonyl, carboxy, substituted or unsubstituted lower alkylcarbamoyl, substituted or unsubstituted cycloalkyl, substituted or unsubstituted cycloalkenyl, substituted or unsubstituted aryl or a substituted or unsubstituted heterocyclic group;

$R^{11a'}$ and $R^{11b'}$ are each independently hydrogen or lower alkyl;

r' is an integer of 0 to 4, or its pharmaceutically acceptable salt, or a solvate thereof.

(16) The compound according to any one of the above (10) to (12), wherein
$Z^{1'}$ is optionally protected hydroxy; $^{2'}$ is a group represented by the formula:

$Z^{2'}$ is O;
R

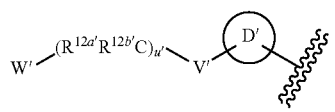

[Chemical Formula 25]

wherein Ring D' is a substituted or unsubstituted aromatic carbocyclic ring or a substituted or unsubstituted aromatic heterocyclic ring;

V' is —C(=O)—, —O—C(=O)—, —NR$^{13'}$—C(=O)—NR$^{13'}$—, —NR$^{13'}$—C(=O)—, —C(=O)—NR$^{13'}$—, —O—, —S— or —NR$^{13'}$—;

R$^{13'}$ is hydrogen or lower alkyl;

W' is hydroxy, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted lower alkylsulfinyl, substituted or unsubstituted sulfamoyl, or cyano;

R$^{12a'}$ and R$^{12b'}$ are each independently hydrogen or substituted or unsubstituted lower alkyl;

u' is an integer of 1 to 4;

provided that the following compounds:

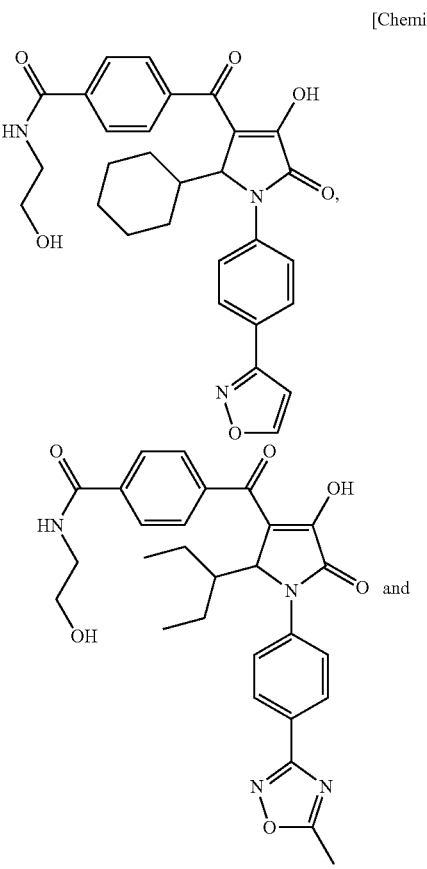

[Chemical Formula 26]

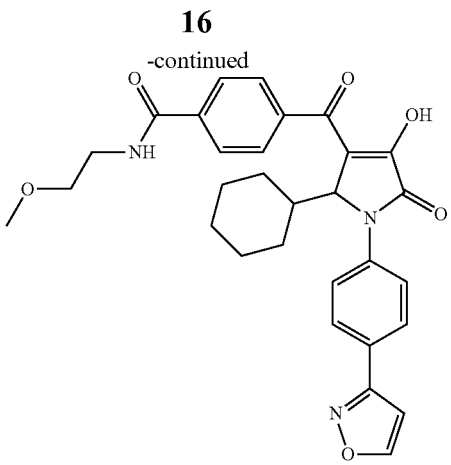

are excluded, or its pharmaceutically acceptable salt, or a solvate thereof.

(17) The compound according to the above (15) or (16), wherein t' is 0, or its pharmaceutically acceptable salt, or a solvate thereof.

(18) A pharmaceutical composition comprising the compound according to any one of the above (1) to (17) or (2'), or its pharmaceutically acceptable salt, or a solvate thereof.

(19) A pharmaceutical composition having an antagonistic activity for P2X$_3$ and/or P2X$_{2/3}$ receptor, comprising the compound according to any one of the above (1) to (17) or (2'), or its pharmaceutically acceptable salt, or a solvate thereof.

(20) A method for preventing or treating a disease related to P2X$_3$ and/or P2X$_{2/3}$ receptor characterized by administration of the compound according to any one of the above (1) to (17) or (2'), or its pharmaceutically acceptable salt, or a solvate thereof.

(21) Use of the compound according to any one of the above (1) to (17) or (2'), or its pharmaceutically acceptable salt, or a solvate thereof for treating and/or preventing a disease related to P2X$_3$ and/or P2X$_{2/3}$ receptor.

(22) Use of the compound according to any one of the above (1) to (17) or (2'), or its pharmaceutically acceptable salt, or a solvate thereof in the manufacturing of an agent for treating and/or preventing a disease related to P2X$_3$ and/or P2X$_{2/3}$ receptor.

BEST MODE FOR CARRYING OUT THE INVENTION

As used throughout the specification, the following terms have the following meaning unless specifically indicated.

The term "alkyl" includes a straight or branched chain monovalent hydrocarbon group containing from 1 to 10, preferably from 1 to 8, more preferably from 1 to 6 carbons, such as methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl and n-decyl, and the like.

Preferable "alkyl" for R$^2$ is isopropyl, isobutyl, and the like.

The term "lower alkyl" includes a straight or branched chain monovalent hydrocarbon group containing from 1 to 6, preferably from 1 to 3 carbons, such as, methyl, ethyl, n-propyl, isopropyl, n-butyl, isobutyl, sec-butyl, tert-butyl, n-pentyl, isopentyl, neo-pentyl, n-hexyl, isohexyl, and the like.

Preferable "lower alkyl" for R$^{1a}$ is C1-C4 alkyl such as methyl, ethyl, n-propyl, isopropyl, terl-butyl, and the like.

Preferable "lower alkyl" for $R^{1b}$ is C1-C3 alkyl such as methyl, ethyl, and the like.

Preferable "lower alkyl" for Y is C1-C3 alkyl such as methyl, ethyl, n-propyl, isopropyl, and the like.

The term "acyl" includes a group of the formula R—CO—, wherein R is, for example, "lower alkyl" as defined above or "lower alkenyl", "aryl", "a heterocyclic group", "cycloalkyl" or "cycloalkenyl" as defined bellow.

Preferable "acyl" for $R^{1a}$ is C1-C3 alkylcarbonyl such as acetyl and the like.

The term "cycloalkane" includes a monocyclic or polycyclic saturated cyclic carbocyclic ring containing from 3 to 10 carbons. Monocyclic cycloalkane includes, for example, cyclopropane, cyclobutane, cyclopentane, cyclohexane, cycloheptane, cyclooctane, cyclononane, cyclodecane, etc. Polycyclic cycloalkane includes norbornanane, tetrahydronaphthalene, etc.

Preferable "cycloalkane" for Ring A is C3-C6 monocyclic cycloalkane such as cyclohexane and the like.

The term "cycloalkyl" includes a monovalent group derived from "cycloalkane" as defined above.

Monocyclic cycloalkyl includes, for example, cyclopropyl, cyclobutyl, cyclopentyl, cyclohexyl, cycloheptyl, cyclooctyl, cyclononyl, cyclodecyl, etc. Polycyclic cycloalkyl includes norbornanyl, tetrahydronaphthalene-5-yl, tetrahydronaphthalene-6-yl, etc.

Preferable "cycloalkyl" for Ring $R^2$ is C3-C6 monocyclic cycloalkyl such as cyclopentyl, cyclohexyl, and the like.

The term "cycloalkane-diyl" includes a divalent group derived from "cycloalkane" as defined above. Monocyclic cycloalkane-diyl includes, for example, cyclopropane-diyl, cyclobutane-diyl, cyclopentane-diyl, cyclohexane-diyl, cycloheptane-diyl, cyclooctane-diyl, cyclonone-diyl, cyclodecane-diyl, etc. Polycyclic cycloalkane-diyl includes norbornane-diyl, etc.

Preferable "cycloalkane-diyl" for B is C3-C6 monocyclic cycloalkane-diyl such as cyclopentane-diyl, cyclohexane-diyl, and the like.

The term "cycloalkene" includes a non-aromatic monocyclic or polycyclic ring of 3 to 10 carbons containing at least one carbon-carbon double bond. Monocyclic cycloalkene includes, for example, cyclopentene, cyclohexene, etc. Polycyclic cycloalkene includes norborne, indene, etc.

The term "cycloalkenyl" includes a monovalent group derived from "cycloalkene" as defined above. Monocyclic cycloalkenyl includes cyclopentenyl, cyclohexenyl, etc. Polycyclic cycloalkenyl includes norbornyl, indene-1-yl, indene-2-yl, indene-3-yl, etc.

The term "cycloalkene-diyl" includes a divalent group derived from "cycloalkene" as defined above. Monocyclic cycloalkene-diyl includes cyclopentene-diyl, cyclohexene-diyl, etc. Polycyclic cycloalkene-diyl includes norbornene-diyl, etc.

Preferable "cycloalkene-diyl" for B is C3-C6 monocyclic cycloalkene-diyl such as cyclopentene-diyl, cyclohexene-diyl, and the like.

The term "aromatic carbocyclic ring" includes an aromatic hydrocarbocyclic ring which is monocyclic or fused-cyclic, such as benzene ring, naphthalene ring, anthracene ring, phenanthrene ring, etc.

Benzene ring is preferable as "aromatic carbocyclic ring" for ring A.

The term "aryl" includes a monovalent group derived from "aromatic carbocyclic ring" as defined above. For example, phenyl, 1-naphthyl, 2-naphthyl, anthryl, phenanthryl, etc. are exemplified.

Preferable "aryl" for $R^3$ is phenyl.

The term "aromatic carbocyclic ring-diyl" includes a divalent group derived from "aromatic carbocyclic ring" as defined above. For example, 1,2-phenylene, 1,3-phenylene, 1,4-phenylene, 1,2-naphthalene etc.

Preferable "aromatic carbocyclic ring-diyl" for B is 1,2-phenylene, 1,3-phenylene, 1,4-phenylene, and the like. More preferably, 1,4-phenylene and the like are exemplified.

The term "heterocyclic ring" includes an aromatic or a non-aromatic monocyclic or fused-cyclic ring, which includes a five- to seven-membered ring having at least one nitrogen atom, oxygen atom, and/or sulphur atom in the ring; a fused ring consisting of two or more said five- to seven-membered rings; or a fused ring consisting of said five- to seven-membered ring having at least one nitrogen atom, oxygen atom, and/or sulphur atom in the ring fused to one or more "aromatic carbocyclic ring", "cycloalkane" or "cycloalkene" as defined above.

For example, a non-aromatic heterocyclic ring such as pyrroline, pyrrolidine, imidazole, pyrazole, piperidine, piperazine, morpholine, thiomorpholine, tetrahydropyrane, dihydropyridine, dihydropyridazine, dioxane, oxathiolane, thiane, tetrahydrofuran, tetrahydropyran, tetrahydrothiazole, tetrahydroisothiazole, etc.;

a monocyclic aromatic heterocyclic ring such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, oxadiazole, etc; and a fused heterocyclic ring such as indole, isoindole, indazole, indolizine, indoline, isoindoline, quinoline, isoquinoline, cinnoline, phthalazine, quinazoline, naphthyridine, quinoxaline, purine, pteridine, benzopyrane, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazole, benzodioxane, tetrahydroquinoline, tetrahydrobenzothiophene, etc. are exemplified.

Preferable "heterocyclic ring" for Ring A is piperidine, thiophene, furan, pyridine, benzothiophene, benzothiazole, benzoxazole, and the like.

The term "heterocyclic group" includes a monovalent group derived from "heterocyclic ring" as defined above. For example, non-aromatic heterocyclic groups such as pyrrolinyl, pyrrolidino, pyrrolidinyl, imidazolynyl, imidazolidinyl, pyrazolinyl, pyrazolidinyl, piperidino, piperidyl, piperidino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;

monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl and oxadiazolyl, etc; and fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolynyl, benzodioxanyl, tetrahydroquinoline, tetrahydrobenzothienyl, etc. are exemplified.

Preferable "heterocyclic group" for Y is pyperidino, morpholino, and the like.

The term "heterocyclic ring-diyl" includes a divalent group derived from "heterocyclic ring" as defined above. For example, non-aromatic heterocyclic ring-diyl such as pyrrolin-diyl, pyrrolidin-diyl, imidazole-diyl, imidazolidin-diyl, pyrazolin-diyl, pyrazolidin-diyl, piperidin-diyl, piperazine-diyl, morpholin-diyl, thiomorpholin-diyl, tetrahydropyran-diyl, dihydropyridine-diyl, dihydropyridazin-diyl, dihydropyrazin-diyl, dioxan-diyl, oxathiolan-diyl, thian-diyl, tetrahydrofuran-diyl, tetrahydropyran-diyl, tetrahydrothiazol-diyl, tetrahydroisothiazol-diyl, etc.;

a monocyclic aromatic heterocyclic ring-diyl such as pyrrole-diyl, pyrazine-diyl, pyrazole-diyl, tetrazole-diyl, furan-diyl, thiophene-diyl, pyridine-diyl, imidazole-diyl, triazole-diyl, tetrazole-diyl, triazine-diyl, pyridazine-diyl, pyrimidine-diyl, pyrazine-diyl, isoxazole-diyl, thiazole-diyl, isothiazole-diyl, thiadiazole-diyl, oxazole-diyl, oxadiazole-diyl, etc; and a fused heterocyclic ring-diyl such as indole-diyl, isoindole-diyl, indazole-diyl, indolizine-diyl, indoline-diyl, isoindoline-diyl, quinoline-diyl, isoquinoline-diyl, cinnoline-diyl, phthalazine-diyl, quinazoline-diyl, naphthyridine-diyl, quinoxaline-diyl, purine-diyl, pteridine-diyl, benzopyrane-diyl, benzimidazole-diyl, benzisoxazole-diyl, benzoxazole-diyl, benzoxadiazole-diyl, benzisothiazole-diyl, benzothiazole-diyl, benzothiadiazole-diyl, benzofuran-diyl, isobenzofuran-diyl, benzothiophene-diyl, benzotriazole-diyl, imidazopyridine-diyl, triazolopyridine-diyl, imidazothiazole-diyl, pyrazinopyridazine-diyl, benzimidazole-diyl, benzodioxane-diyl, tetrahydroquinoline-diyl, tetrahydrobenzothiophene-diyl, etc. are exemplified.

Preferable "heterocyclic ring-diyl" for B is pyrole-diyl, pyrazine-diyl, pyrazole-diyl, tetrazole-diyl, furan-diyl, thiophene-diyl, pyridine-diyl, imidazole-diyl, triazole-diyl, tetrazole-diyl, triazine-diyl, pyridazine-diyl, pyrimidine-diyl, pyrazine-diyl, isoxazole-diyl, thiazole-diyl, isothiazole-diyl, thiadiazole-diyl, oxazole-diyl, oxadiazole-diyl, and the like.

More preferably, dihydrothiazole-diyl, pyroridine-diyl, thiazole-diyl, thiophene-diyl, pyrrol-diyl, furan-diyl, isoxazole-diyl, thiadiazole-diyl, and the like are exemplified.

The term "non-aromatic carbocyclic ring" includes "cycloalkane" as defined above, "cycloalkene" as defined above, a fused ring consisting of "aromatic carbocyclic ring" as defined above fused to "cycloalkane" as defined above, and a fused ring consisting of "aromatic carbocyclic ring" as defined above fused to "cycloalkene" as defined above. As a fused ring, indene and the like are exemplified.

The term "aromatic heterocyclic ring" includes aromatic rings of "heterocyclic ring" as defined above. "Aromatic heterocyclic ring" includes a five- to seven-membered aromatic ring having at least one nitrogen atom, oxygen atom, and/or sulphur atom in the ring; a fused aromatic ring consisting of two or more said rings; and a fused ring consisting of a five- to seven-membered aromatic ring having at least one nitrogen atom, oxygen atom, and/or sulphur atom in the ring fused to one or more "aromatic carbocyclic ring" as defined above.

For example, a monocyclic aromatic heterocyclic ring such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole, etc; and a fused aromatic heterocyclic ring such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazoline, etc. are exemplified.

The term "heteroaryl" includes a monovalent group derived from "aromatic heterocyclic ring" as defined above. "Heteroaryl" includes a five- to seven-membered aromatic group having at least one nitrogen atom, oxygen atom, and/or sulphur atom in the ring; a fused aromatic group consisting of two or more said rings; and a fused ring consisting of a five- to seven-membered aromatic group having at least one nitrogen atom, oxygen atom, and/or sulphur atom in the ring fused to one or more "aromatic carbocyclic ring" as defined above.

For example, monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and fused heterocyclic aromatic groups such as indolyl, isoindolyl, indazolyl, indolizinyl, isoindolinyl, quinolyl, isoquinolyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolynyl, etc. are exemplified.

The term "non-Aromatic heterocyclic ring" includes non-aromatic rings of "heterocyclic ring" as defined above. "Non-aromatic heterocyclic ring" includes, a five- to seven-membered non-aromatic ring having at least one nitrogen atom, oxygen atom, and/or sulphur atom in the ring; a fused non-aromatic ring consisting of two or more said rings; a fused ring consisting of a five- to seven-membered aromatic ring having at least one nitrogen atom, oxygen atom, and/or sulphur atom in the ring fused to one or more "cycloalkane" as defined above or "cycloalkene" as defined above; or a fused ring consisting of a five- to seven-membered non-aromatic heterocyclic ring having at least one nitrogen atom, oxygen atom, and/or sulphur atom in the ring fused to one or more "aromatic carbocyclic ring" as defined above or "non-aromatic carbocyclic ring" as defined above For example, non-aromatic heterocyclic ring such as pyrroline, pyrrolidine, imidazoline, imidazolidine, pyrazoline, pyrazolidine, piperidine, piperazine, morpholine, thiomorpholine, thiomorpholine, tetrahydropyrane, dihydropyridine, dihydropyridazine, dihydropyrazine, dioxane, oxathiolane, thiane, tetrahydrofuran, tetrahydropyran, tetrahydrothiazolin, tetrahydroisothiazole, etc.;

a fused non-aromatic heterocyclic ring such as indoline, isoindoline, benzopyrane, benzodioxane, tetrahydroquinoline, tetrahydrobenzothiophene, etc. are exemplified.

The term "halogen" means fluorine, chlorine, bromine and iodine.

The term "lower alkoxy" includes a group of the formula RO— wherein R is as defined above for lower alkyl, such as methoxy, ethoxy, propoxy, isopropoxy, butoxy, isobutoxy, sec-butoxy, tert-butoxy, pentoxy, isopentoxy, neopentoxy, hexoxy, etc.

Preferable "lower alkoxy" for Y is C1-C4 alkoxy such as methoxy, ethoxy, propoxy, isopropoxy, butoxy, and the like.

The term "lower alkylthio" includes a group of the formula RS— wherein R is as defined above for lower alkyl, such as methylthio, ethylthio, propylthio, isopropylthio, butylthio, isobutylthio, sec-butylthio, tert-butylthio, pentylthio, isopentylthio, neopentylthio, hexylthio, etc.

Preferable "lower alkylthio" for $R^{1a}$ is C1-C4 alkylthio such as methylthio and the like.

The term "lower alkoxycarbonyl" includes a group of the formula R—O—C(=O)— wherein R is as defined above for lower alkyl, such as methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, etc.

Preferable "lower alkoxycarbonyl" for $R^{1a}$, $R^3$ and Y is C1-C4 alkoxycarbonyl such as methyloxycarbonyl, ethyloxycarbonyl, and the like.

The term "lower alkylcarbamoyl" includes mono- or di-lower alkylcarbamoyl wherein alkyl moiety contains from 1 to 6 carbons, such as methylcarbamoyl, ethylcarbamoyl, n-propylcarbamoyl, isopropylcarbamoyl, n-butylcarbamoyl, dimethylcarbamoyl, diethylcarbamoyl, dipropylcarbamoyl, etc.

Preferable "lower alkylcarbamoyl" for $R^{1a}$ is C1-C4 alkoxycarbamoyl such as methylcarbamoyl, dimethylcarbamoyl, and the like.

The term "thiocarbamoyl" includes a group of the formula —C(=S)—$NR^XR^Y$ wherein $R^X$ and $R^Y$ are each independently hydrogen, "alkyl" or "alkenyl" as defined above, or "aryl", "heteroaryl", "non-aromatic carbocyclic group", non-aromatic heterocyclic group", "arylalkyl" or "heteroaryl alkyl" as defined below, and these are optionally and independently substituted with hydroxy, carboxy, "alkyl", "alkenyl", "alkynyl", "halogen", "alkyloxy", "alkenyloxy", "alkynyloxy", "alkylthio", "carbamoyl", "alkyloxycarbonyl", "aryloxycarbonyl" as defined above or below, and the like.

The term "sulfinyl" includes a group of the formula —S(=O)—R wherein R is "alkyl" or "alkenyl" as defined above, or "aryl", "heteroaryl", "non-aromatic carbocyclic group", non-aromatic heterocyclic group", "arylalkyl" or "heteroaryl alkyl" as defined below, and these are optionally and independently substituted with hydroxy, carboxy, "alkyl", "alkenyl", "alkynyl", "halogen", "alkyloxy", "alkenyloxy", "alkynyloxy", "alkylthio", "carbamoyl", "alkyloxycarbonyl", "aryloxycarbonyl" as defined above or below, and the like.

Preferable "sulfinyl" for $R^{1a}$ and Y is C1-C4 alkylsulfinyl such as methylsulfinyl, and the like.

The term "sulfonyl" includes a group of the formula —S(=O)$_2$—R wherein R is "alkyl" or "alkenyl" as defined above, or "aryl", "heteroaryl", "non-aromatic carbocyclic group", non-aromatic heterocyclic group", "arylalkyl" or "heteroaryl alkyl" as defined below, and these are optionally and independently substituted with hydroxy, carboxy, "alkyl", "alkenyl", "alkynyl", "halogen", "alkyloxy", "alkenyloxy", "alkynyloxy", "alkylthio", "carbamoyl", "alkyloxycarbonyl", "aryloxycarbonyl" as defined above or below, and the like.

Preferable "sulfonyl" for $R^{1a}$ and Y is C1-C4 alkylsulfonyl such as methylsulfonyl, and the like.

The term "sulfamoyl" includes a group of the formula —S(=O)$_2$—$NR^XR^Y$ wherein $R^X$ and $R^Y$ are each independently hydrogen, "alkyl" or "alkenyl" as defined above, or "aryl", "heteroaryl", "non-aromatic carbocyclic group", non-aromatic heterocyclic group", "arylalkyl" or "heteroaryl alkyl" as defined below, and these are optionally and independently substituted with hydroxy, carboxy, "alkyl", "alkenyl", "alkynyl", "halogen", "alkyloxy", "alkenyloxy", "alkynyloxy", "alkylthio", "carbamoyl", "alkyloxycarbonyl", "aryloxycarbonyl" as defined above or below, and the like.

Substituents for "substituted lower alkyl", "substituted tert-butyl", "substituted i-propyl", "substituted lower alkenyl", "substituted lower alkynyl", "substituted lower alkoxy", "substituted lower alkylthio", "substituted lower alkoxycarbonyl", and "substituted lower alkylcarbamoyl" include but are not limited to one or more same or different substituents selected from the group consisting of:

hydroxy, carboxy, halogen (F, Cl, Br, I), lower haloalkoxy (e.g., $CF_3O$), cycloalkyl (e.g., cyclopropyl), cycloalkenyl (e.g., cyclopropenyl), lower alkoxy (e.g., methoxy, ethoxy, propoxy, butoxy, etc.), lower alkenyloxy (e.g., vinyloxy, allyloxy, etc.), lower alkoxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), azido, aryl (e.g., phenyl, etc.), aralkyl (e.g., benzyl, etc.), aralkyloxy (e.g., benzyloxy), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), carbamoyl, lower alkylcarbamoyl (e.g., methylcarbamoyl, ethylcarbamoyl, dimethylcarbamoyl, etc.), sulfamoyl, lower alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, tri-lower alkylsilyl (e.g., trimethylsilyl, etc.), and oxo.

Preferable substituents for "substituted lower alkyl" of $R^{1a}$ and $R^{1b}$ are hydroxy, halogen, nitro, cyano, lower haloalkoxy, lower alkenyloxy and the like. More preferable substituents are hydroxy, lower alkoxy and the like.

Preferable substituents for "substituted lower alkoxy" and "substituted lower alkylthio" of $R^{1a}$ and $R^{1b}$ are halogen, hydroxy and the like.

Preferable substituents for "substituted lower alkyl" Y are hydroxy, halogen, cyano, carboxy, carbamoyl, lower alkoxy, lower haloalkoxy, lower alkylcarbamoyl, amino, lower alkylamino, amino substituted with lower alkylsulfonyl, lower alkyloxycarbonylmethyloxy and the like.

More preferable substituents are hydroxy, halogen, cyano carboxy, carbamoyl, lower alkoxy, lower alkylcarbamoyl, amino, lower alkylamino, amino substituted with lower alkylsulfonyl, lower alkyloxycarbonylmethyloxy and the like.

Preferable substituents for "substituted lower alkoxy" and "substituted lower alkylthio" of Y are halogen, carboxy, cyano, hydroxy, lower alkyl, lower alkyl substituted with hydroxy, lower alkoxy, lower haloalkoxy, lower alkenyloxy, lower alkoxycarbonyl, amino, lower alkylamino, amino substituted with lower alkylsulfonyl, lower alkylsulfinyl, lower alkylsulfonyl, carbamoyl, lower alkylcarbamoyl, carbamoyl substituted with amino, carbamoyl substituted with hydroxy, lower alkylsulfinyl, lower alkylsulfonyl, cycloalkyl, a heterocyclic group and the like.

More preferable substituents are halogen, carboxy, cyano, carbamoyl, lower alkylcarbamoyl, imino substituted with hydroxy, lower alkoxy, amino, lower alkylamino, lower alkoxycarbonyl, lower alkylsulfinyl, tetrazolyl and the like.

Substituents for "substituted acyl" are as defined above for "substituted lower alkyl". If R in acyl (R—C(=O)—) is "aryl", "a heterocyclic group", "cycloalkyl" or "cycloalkenyl", then each ring may be substituted with lower alkyl (e.g., methyl, ethyl, isopropyl, tert-butyl, etc.), lower haloalkyl (e.g., $CF_3$, $CH_2CF_3$, $CH_2CCl_3$, etc.), lower alkenyl, lower alkynyl (e.g., ethynyl), etc.

Substituents for "substituted carbamoyl", "substituted thiocarbamoyl" and "substituted sulfamoyl" are one or more same or different groups selected from, but are not limited to, the group consisting of:

hydroxy, carboxy, halogen (F, Cl, Br, I), lower alkyl (e.g., methyl), lower alkenyl (e.g., vinyl), lower alkynyl (e.g., ethynyl), cycloalkyl (e.g., cyclopropyl), cycloalkenyl (e.g., cyclopropenyl), lower alkoxycarbonyl (e.g., methoxycarbonyl, ethoxycarbonyl, tert-butoxycarbonyl, etc.), amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, aryl (e.g., phenyl, etc.), cyano, isocyano, isocyanato, thiocyanato, isothiocyanato and acyl (e.g., formyl, acetyl, etc.).

Preferable substituents for "substituted carbamoyl", "substituted thiocarbamoyl" and "substituted sulfamoyl" of $R^{1a}$ and $R^{1b}$ are lower alkyl, lower alkenyl, lower alkynyl, amino, lower alkylamino, acyl amino, hydroxy amino and the like.

More preferable substituents are lower alkyl, lower alkylamino and the like.

Preferable substituents for "substituted carbamoyl" of Y are lower alkyl, lower alkyl substituted with hydroxy, lower alkyl substituted with lower alkoxy, lower alkyl substituted with cyano, lower alkenyl, lower alkynyl, lower alkylamino, acyl amino and the like.

More preferable substituents are lower alkyl, lower alkyl substituted with hydroxy, lower alkyl substituted with lower alkoxy, lower alkyl substituted with cyano, lower alkylamino and the like.

Substituents for "substituted amino" are one or more same or different groups selected from, but are not limited to, the group consisting of:

hydroxy, halogen (F, Cl, Br, I), lower haloalkyl (e.g., $CF_3$, $CH_2CF_3$, $CH_2CCl_3$, etc.), hydroxy(lower)alkyl (e.g., hydroxyethyl, $—C(CH_3)_2CH_2OH$, etc.), lower haloalkoxy (e.g., $CF_3O$), lower alkyl (e.g., methyl, ethyl, isopropyl, tert-butyl, etc.), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy, etc.), lower alkyloxycarbonyl (tert-butyloxycarbonyl, etc.), lower alkenyloxy (e.g., vinyloxy, allyloxy, etc.), amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), aryl (e.g., phenyl, etc.), aralkyl (e.g., benzyl, etc.), cyano and acyl (e.g., formyl, acetyl, etc.).

Preferable substituents for "substituted amino" of $R^{1a}$ and $R^{1b}$ are lower alkyl, lower alkenyl, lower alkynyl, lower haloalkyl, lower hydroxyalkyl, lower alkoxy, lower haloalkoxy, lower alkenyloxy, acyl and the like.

More preferable substituents are lower alkyl, acyl and the like.

Preferable substituents for "substituted amino" of Y are lower alkyl, acetyl, lower alkyloxycarbonyl, carbamoyl, lower alkylsulfonyl and the like.

Substituents for "substituted cycloalkyl", "substituted cycloalkenyl", "substituted aryl", "a substituted heterocyclic group", "substituted heteroaryl", "substituted phenyl", and "substituted pyridyl" are one or more same or different groups selected from, but are not limited to, the group consisting of:

hydroxy, carboxy, halogen (F, Cl, Br, I), lower haloalkyl (e.g., $CF_3$, $CH_2CF_3$, $CH_2CCl_3$, etc.), lower haloalkoxy (e.g., $CF_3O$), lower alkyl (e.g., methyl, ethyl, isopropyl, tert-butyl, etc.), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy, etc.), lower alkenyloxy (e.g., vinyloxy, allyloxy, etc.), lower alkoxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), azido, aryl (e.g., phenyl, etc.), aralkyl (e.g., benzyl, etc.), aralkyloxy (e.g., benzyloxy, etc.), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), substituted or unsubstituted carbamoyl (e.g., carbamoyl, N-methyl-N-methoxycarbamoyl, etc.), substituted or unsubstituted lower alkylcarbamoyl (e.g., methylcarbamoyl, ethylcarbamoyl, dimethylcarbamoyl, hydroxy ethylcarbamoyl, trifluoromethylcarbamoyl, trifluoro ethylcarbamoyl, etc.), sulfamoyl, lower alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido and oxo.

Preferable substituents for "substituted cycloalkyl", "substituted cycloalkenyl", "substituted aryl", "a substituted heterocyclic group", "substituted heteroaryl", "substituted phenyl", and "substituted pyridyl" are halogen, lower alkyl, lower haloalkyl, lower alkoxy, lower haloalkoxy and the like.

The halogen moiety in said "lower haloalkyl" and "lower haloalkoxy" is as defined above for "halogen".

The alkyl or lower alkyl moiety in said "lower haloalkyl", "lower alkylamino", "lower alkylimino", "lower alkylsulfonyl", "lower alkylsulfamoyl", "lower alkylcarbamoyl", "aralkyl" and "aralkylamino" is as defined above for "lower alkyl".

The lower alkoxy moiety of said "lower haloalkoxy" and "lower alkoxyimino" is as defined above for "lower alkoxy".

The term "lower alkenyl" includes a straight or branched chain alkenyl containing from 2 to 6 carbons, preferably containing from 2 to 3 carbons, having one or more double bonds at any position. For example, vinyl, propenyl, isopropenyl, butenyl, isobutenyl, prenyl, butadienyl, pentenyl, isopentenyl, pentadienyl, hexenyl, isohexenyl, hexadienyl, etc. are exemplified.

The lower alkenyl moiety of "lower alkenyloxy" is as defined above for "lower alkenyl".

The term "lower alkynyl" includes a straight or branched chain alkynyl containing from 2 to 6 carbons, preferably containing from 2 to 3 carbons. For example, ethynyl, propynyl, butynyl, pentynyl, hexynyl, etc. are exemplified. They have one or more triple bonds at any position, and optionally, have a double bond.

The term "aralkyl" includes a group "lower alkyl" as defined above substituted with above "aryl" as defined above. For example, benzyl, phenethyl and the like are exemplified.

The aryl moiety of "aralkylamino" and "aralkyl" is as defined above for "aryl".

The acyl moiety of "acyl", "acylamino" and "acylimino" is as defined above for "acyl".

The protecting groups for "hydroxy optionally protected" and "mercapto optionally protected" are well known in the art and include for example, a group that forms ether and substituted ether, such as methyl, methoxymethyl, t-butoxymethyl, 1-ethoxyethyl and benzyl, etc.; a group that forms silyl ether, such as trimethylsilyl, triethylsilyl, tert-butyldimethylsilyl and methyldiisopropylsilyl; a group that forms ester, such as formate, acetate and trichloroacetate, etc.; a group that forms carbonate, such as methyl carbonate, 2,2,2-trichloroethyl carbonate, and p-nitrophenyl carbonate, etc.; a group that forms sulfonyl, such as methanesulfonyl, p-toluenesulfonyl, etc.

Preferable protective groups for "optionally protected hydroxy" and "optionally protected mercapto" are ether, a group that forms substituted ether and the like. More preferable are a group formed by substituted ether and the like.

In addition, one or more hydrogen, carbon or other atoms of a compound of Formula (I) can be replaced by an isotope of the hydrogen, carbon or other atoms. Compounds of Formula (I) include all radiolabeled forms of compounds of Formula (I) "radiolabeled," "radiolabeled form", and the like of a compound of Formula I, each of which is encompassed by the invention, is useful as a research and/or diagnostic tool in metabolism pharmacokinetic studies and in binding assays. Examples of isotopes that can be incorporated into a compound of Formula (I) of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of Formula (I) can be prepared by introducing tritium into the particular compound of Formula (I), for example, by catalytic dehalogenation with tritium. This method may include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}C$-labeled compounds can be prepared by employing starting materials having a $^{14}C$ carbon.

Preferred embodiments of the compound (I') of the invention are as follows. Each variant is as defined above.

$Z^{1\prime}$ is hydroxy.

$Z^{2\prime}$ is O.

[Chemical Formula 27]

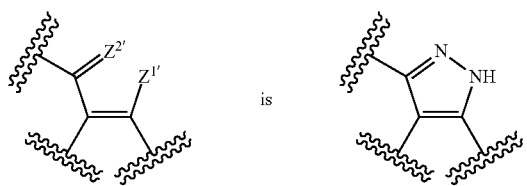

is

Ring A' is an aromatic carbocyclic ring or a heterocyclic ring.

For example, an aromatic carbocyclic ring and an aromatic heterocyclic ring are exemplified as A'.

For example, benzene ring and pyridine ring are exemplified as Ring A'.

$R^{2\prime}$ is substituted or unsubstituted aryl, or a substituted or unsubstituted aromatic heterocyclic group (e.g., thienyl, pyridyl, imidazolyl, pyrimidinyl, isoxazolyl, thiazolyl, isothiazolyl, thiadiazolyl, oxazolyl, pyrazolyl, oxadiazolyl, etc.).

For example, substituted or unsubstituted phenyl is exemplified as $R^{2\prime}$.

For example, substituted or unsubstituted pyridyl is exemplified as $R^{2\prime}$.

For example, substituted or unsubstituted tert-butyl is exemplified as $R^{2\prime}$.

$R^{3\prime}$ is substituted or unsubstituted alkyl, substituted or unsubstituted cycloalkyl, or substituted or unsubstituted phenyl.

For example, substituted or unsubstituted alkyl, substituted or unsubstituted cycloalkyl, substituted or unsubstituted aryl and substituted or an unsubstituted heterocyclic group are exemplified as $R^{3\prime}$.

For example, a group represented by the following formula:

[Chemical Formula 28]

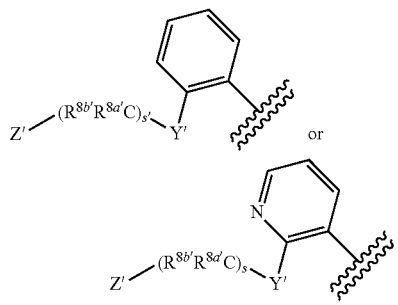

are exemplified as $R^{3\prime}$.

Ring D' is benzene ring or pyridine ring.

V' is "—O—C(=O)—", "—C(=O)—O—", "—NR$^{13\prime}$—C(=O)—" or "—C(=O)—NR$^{13\prime}$—".

$R^{4a\prime}$ and $R^{4b\prime}$ are each independently hydrogen or lower alkyl.

For example, hydrogen is exemplified as $R^{4a\prime}$ and $R^{4b\prime}$.

t' is 0.

m' is an integer of 0 to 2.

For example, m' is 1 or 2.

For example, m' is 0.

$R^{1a\prime}$ is halogen, substituted or unsubstituted lower alkyl, carboxy, substituted or unsubstituted lower alkoxycarbonyl, substituted or unsubstituted aryl or a substituted or unsubstituted heterocyclic group.

For example, substituted or unsubstituted lower alkoxycarbonyl, substituted or unsubstituted phenyl, and a substituted or unsubstituted aromatic heterocyclic group (e.g., thienyl, pyridyl, imidazolyl, pyrimidinyl, isoxazolyl, thiazolyl, isothiazolyl, thiadiazolyl, oxazolyl, pyrazolyl, oxadiazolyl, etc.) are exemplified as $R^{1a\prime}$.

For example, substituted or unsubstituted lower alkoxycarbonyl, substituted or unsubstituted aryl and a substituted or unsubstituted heterocyclic group are exemplified as $R^{1a\prime}$.

For example, substituted or unsubstituted lower alkoxycarbonyl, substituted or unsubstituted aryl and a substituted or unsubstituted heterocyclic group are exemplified as $R^{1a\prime}$.

For example, substituted or unsubstituted lower alkoxycarbonyl, substituted or unsubstituted phenyl, a substituted or unsubstituted aromatic heterocyclic group (e.g., thienyl, pyridyl, imidazolyl, pyrimidinyl, isoxazolyl, thiazolyl, isothiazolyl, thiadiazolyl, oxazolyl, pyrazolyl, oxadiazolyl, etc.) are exemplified as $R^{1a\prime}$.

$R^{1b'}$ is halogen, substituted or unsubstituted lower alkyl, carboxy, substituted or unsubstituted lower alkoxycarbonyl, substituted or unsubstituted aryl or a substituted or unsubstituted heterocyclic group.

For example, halogen, substituted or unsubstituted lower alkyl, carboxy, and substituted or unsubstituted lower alkoxycarbonyl are exemplified as $R^{1b'}$.

Further, a compound represented by all combination of alternatives in each substituent as defined above is preferable.

Preferable embodiments of the compound (I') of the present invention are as follows.

A compound wherein
$Z^{2'}$ is O;
t' is 0;
$R^{2'}$ is substituted or unsubstituted tert-butyl, or substituted or unsubstituted i-propyl; and
—$R^{3'}$ is a group represented by the formula:

[Chemical Formula 29]

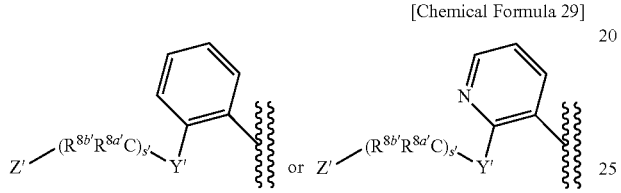

A compound wherein
$Z^{2'}$ is O;
t' is 0; and
—$R^{2'}$ is a group represented by the formula:

[Chemical Formula 30]

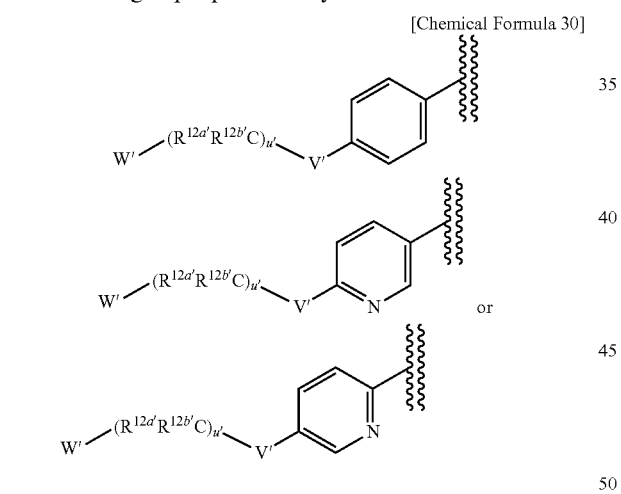

$R^{3'}$ is substituted or unsubstituted aryl or a substituted or unsubstituted heterocyclic group.

A compound wherein

[Chemical Formula 31]

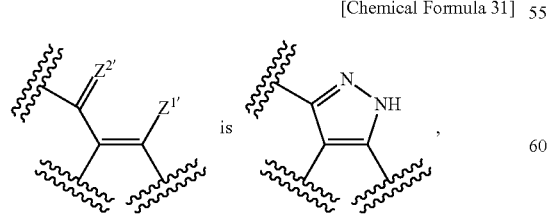

t' is 0;
$R^{2'}$ is substituted or unsubstituted tert-butyl, or substituted or unsubstituted i-propyl; and $R^{3'}$ is a group represented by the formula:

[Chemical Formula 32]

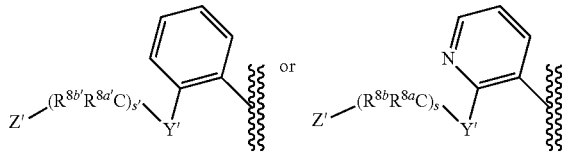

Further, a compound represented by all combination of alternatives in each substituent as defined above is preferable.

Preferable embodiments of the compound (I) of the present invention are as follows. Each variant is as defined above.

$R^2$ is a group represented by the formula:

[Chemical Formula 33]

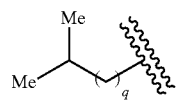

wherein Me is methyl and q is an integer of 0 to 4.

For example, a group represented by the formula:

[Chemical Formula 34]

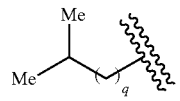

wherein Me is methyl and q is an integer of 0 to 1 as $R^2$.

$R^3$ is a group represented by the formula:

[Chemical Formula 35]

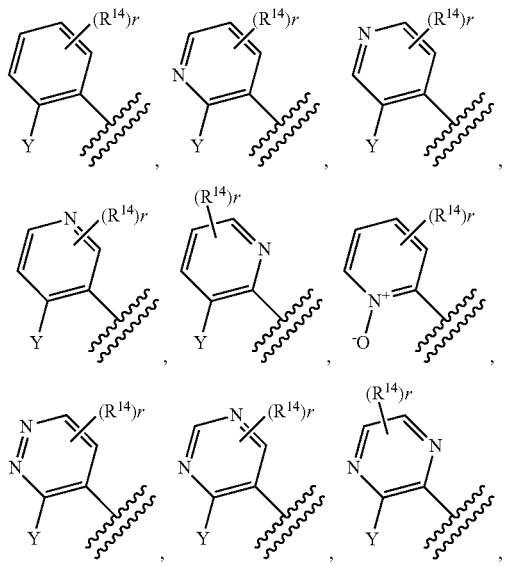

-continued

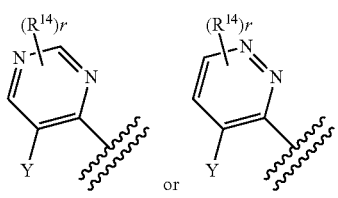

or

For example, a group represented by the formula:

[Chemical Formula 36]

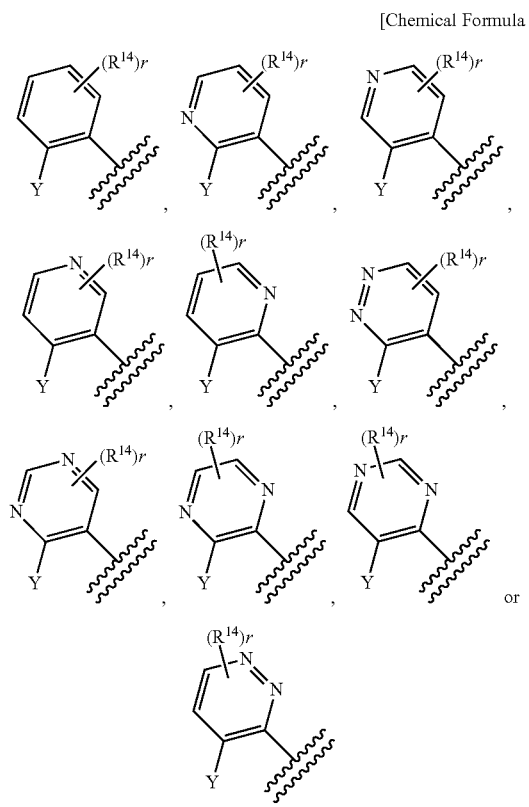

are exemplified as $R^3$.

For example, a group represented by the formula:

[Chemical Formula 37]

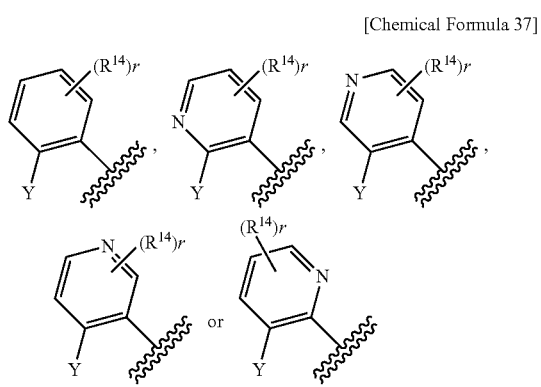

are exemplified as $R^3$.

For example, a group represented by the formula:

[Chemical Formula 38]

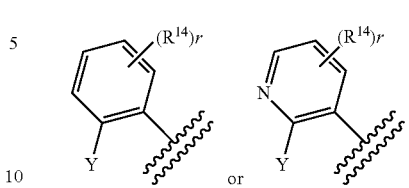

are exemplified as $R^3$.

Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl, or a substituted or unsubstituted heterocyclic group.

For example, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl and substituted sulfonyl are exemplified as Y.

For example, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl and substituted sulfonyl are exemplified as Y.

$R^{14}$ is halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano or nitro.

For example, halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano and nitro are exemplified as $R^{14}$.

r is an integer of 0 to 2.

Further, a compound represented by all combination of alternatives in each substituent as defined above is preferable.

Further, more preferable embodiments of the compound (I) of the present invention are as follows.

(a) A compound wherein
$R^2$ is a group represented by the formula:

[Chemical Formula 39]

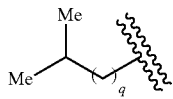

wherein Me is methyl and q is an integer of 0 to 1; and
$R^3$ is a group represented by the formula:

[Chemical Formula 40]

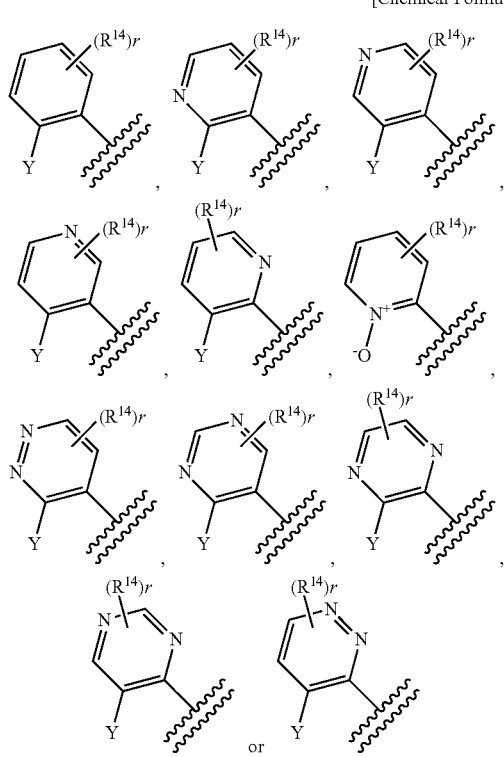

wherein Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl or a substituted or unsubstituted heterocyclic group; or Y and $R^{14}$ may form a substituted or unsubstituted heterocyclic group with adjacent carbon atom;
$R^{14}$ is halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano or nitro; and
r is an integer of 0 to 2;
provided that the compounds represented by the following formula:

[Chemical Formula 41]

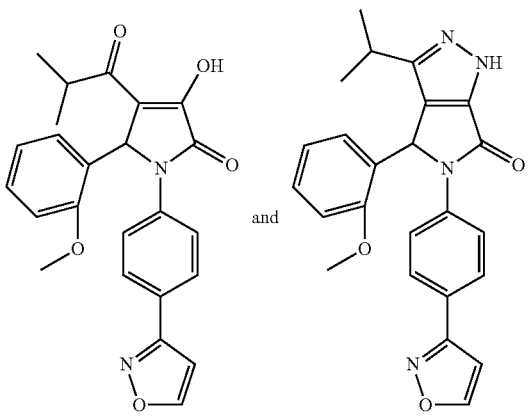

are excluded,
or its pharmaceutically acceptable salt, or a solvate thereof.
Further, more preferable embodiments of the compound (I) of the present invention are as follows.
(b) A compound wherein $R^2$ is a group represented by the formula:

[Chemical Formula 42]

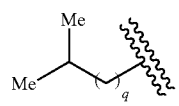

wherein Me is methyl and q is an integer of 0 to 1; and $R^3$ is a group represented by the formula:

[Chemical Formula 43]

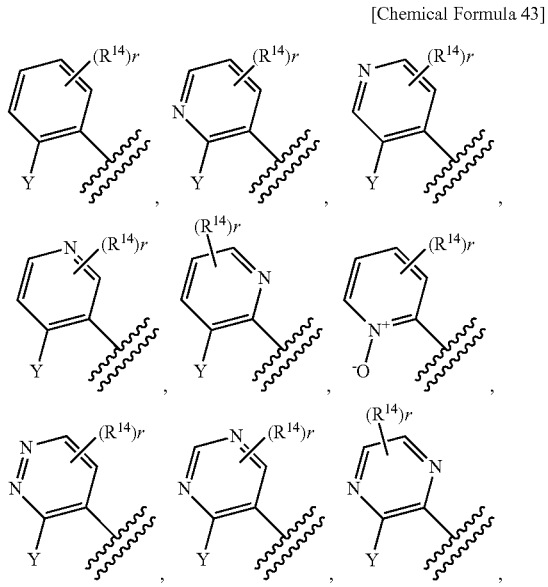

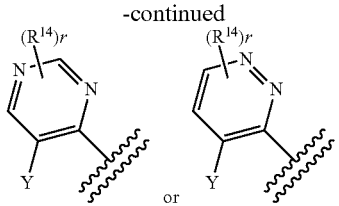

wherein Y is substituted or unsubstituted alkoxy, substituted or unsubstituted alkylthio, substituted or unsubstituted lower alkoxycarbonyl, substituted or unsubstituted carbamoyl, substituted or unsubstituted lower alkylsulfamoyl, substituted or unsubstituted amino, cyano, carboxy, substituted sulfinyl, substituted sulfonyl, a substituted or unsubstituted heterocyclic group;

$R^{14}$ is halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano or nitro; and r is an integer of 0 to 2;

provided that the compounds represented by the following formula:

[Chemical Formula 44]

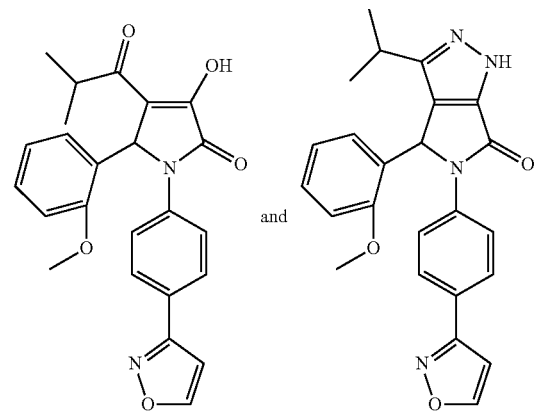

are excluded, or its pharmaceutically acceptable salt, or a solvate thereof.

Further, more preferable embodiments of the compound (I) of the present invention are as follows.

(c) A compound wherein $R^2$ is a group represented by the formula:

[Chemical Formula 45]

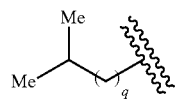

wherein Me is methyl and q is an integer of 0 to 1; and $R^3$ is a group represented by the formula:

[Chemical Formula 46]

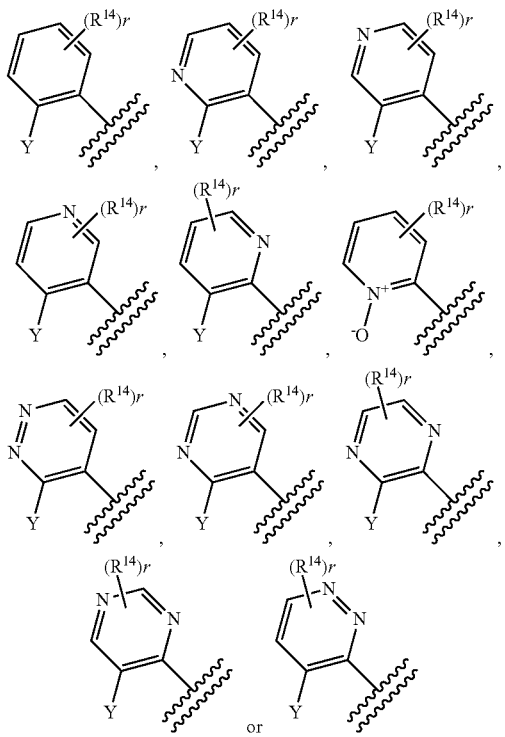

wherein Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl or a substituted or unsubstituted heterocyclic group; and r is 0 provided that the compounds represented by the following formula:

[Chemical Formula 47]

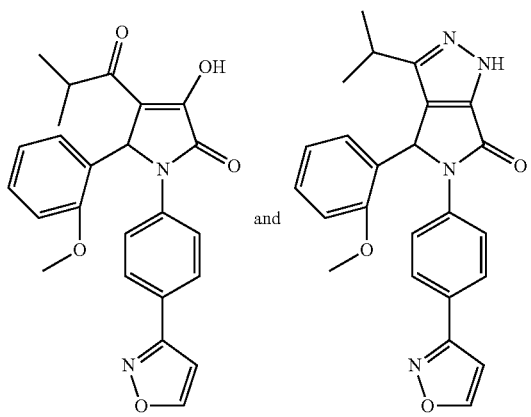

are excluded, or its pharmaceutically acceptable salt, or a solvate thereof.

Further, more preferable embodiments of the compound (I) of the present invention are as follows.

(d) A compound wherein
$Z^1$ is hydroxy;
$Z^2$ is —C(=O)—;
$Z^{3a}$ and $Z^{3b}$ are taken together =O;
$R^2$ is a group represented by the formula:

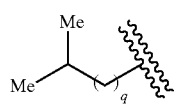
[Chemical Formula 48]

wherein Me is methyl and q is an integer of 0 to 1;
$R^3$ is a group represented by the formula:

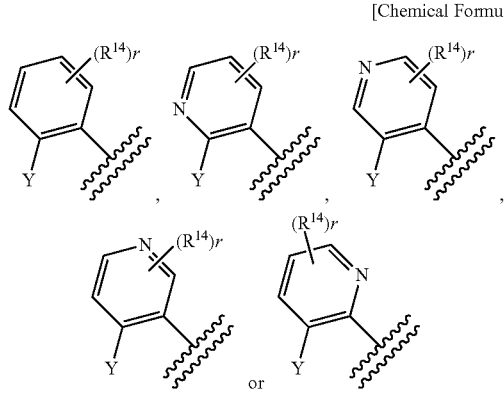
[Chemical Formula 49]

wherein Y is hydroxy, halogen, cyano, carboxy, substituted or unsubstituted lower alkyl, substituted or unsubstituted lower alkoxy, substituted or unsubstituted lower alkoxycarbonyl, substituted or unsubstituted acyl, substituted or unsubstituted carbamoyl, substituted or unsubstituted thiocarbamoyl, substituted or unsubstituted lower alkylthio, substituted or unsubstituted lower alkylsulfamoyl, substituted or unsubstituted amino, substituted sulfinyl, substituted sulfonyl or a substituted or unsubstituted heterocyclic group; and
r is 0;
t is 0;
k is an integer of 0 or 1;
m is an integer of 0 or 1;
n is an integer of 0 or 1;
$R^{1a}$ and $R^{1b}$ are each independently halogen, hydroxy, substituted or unsubstituted lower alkyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted thiocarbamoyl, substituted or unsubstituted amino, substituted sulfinyl, substituted sulfonyl, substituted or unsubstituted sulfamoyl, cyano, nitro or —C($R^{7a}$)=N—O—$R^{7b}$; and
$R^{7a}$ and $R^{7b}$ are each independently hydrogen or substituted or unsubstituted lower alkyl;
provided that the compounds represented by the following formula:

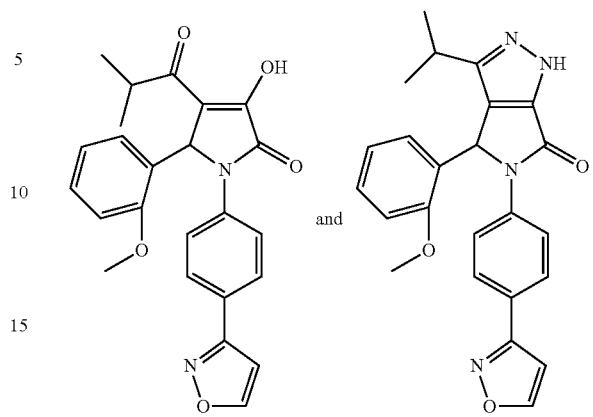
[Chemical Formula 48]

are excluded,
or its pharmaceutically acceptable salt, or a solvate thereof.
Further, more preferable embodiments of the compound (I) of the present invention are as follows.

(e) A compound wherein
$Z^1$ is hydroxy;
$Z^2$ is —C(=O)—;
$Z^{3a}$ and $Z^{3b}$ are taken together =O;
Ring A is benzene or pyridine;
B is aromatic carbocyclic ring-diyl or aromatic heterocyclic ring-diyl;
$R^2$ is a group represented by the formula:

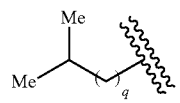
[Chemical Formula 49]

wherein Me is methyl and q is an integer of 0 or 1;
$R^3$ is a group represented by the formula:

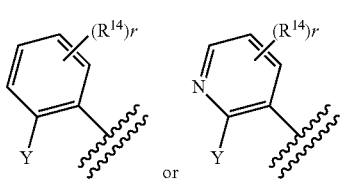
[Chemical Formula 50]

wherein Y is substituted or unsubstituted lower alkyl, substituted or unsubstituted lower alkoxy, substituted or unsubstituted lower alkylthio, or substituted or unsubstituted amino; and
r is 0;
t is 0;
k is 1;
m is an integer of 0 or L
n is an integer of 0 or 1; and
$R^{1a}$ and $R^{1b}$ are each independently halogen, substituted or unsubstituted lower alkyl, substituted or unsubstituted lower alkoxy, or substituted or unsubstituted lower alkylthio
provided that the compounds represented by the following formula:

[Chemical Formula 51]

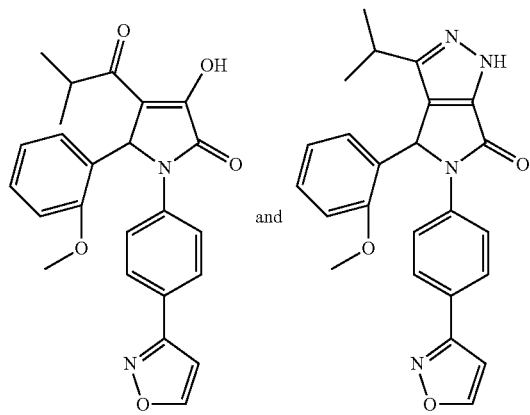

are excluded,
or its pharmaceutically acceptable salt, or a solvate thereof.

Further, more preferable embodiments of the compound (I) of the present invention are as follows.

(f) A compound wherein
$Z^1$ is hydroxy;
$Z^2$ is —C(=O)—;
$Z^{3a}$ and $Z^{3b}$ are taken together =O;
Ring A is benzene or pyridine;
B is aromatic carbocyclic ring-diyl or aromatic heterocyclic ring-diyl;
$R^2$ is a group represented by the formula:

[Chemical Formula 52]

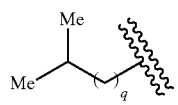

wherein Me is methyl and q is an integer of 0 to 1;
$R^3$ is a group represented by the formula:

[Chemical Formula 53]

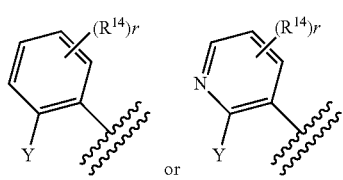

wherein Y is substituted lower alkoxy, substituted lower alkylthio, or substituted amino; and
r is 0;
t is 0;
k is 1;
m is 0 or 1;
n is 0 or 1; and
$R^{1a}$ and $R^{1b}$ are each independently halogen, substituted or unsubstituted lower alkyl, substituted or unsubstituted lower alkoxy, or substituted or unsubstituted lower alkylthio;
provided that the compounds represented by the following formula:

[Chemical Formula 54]

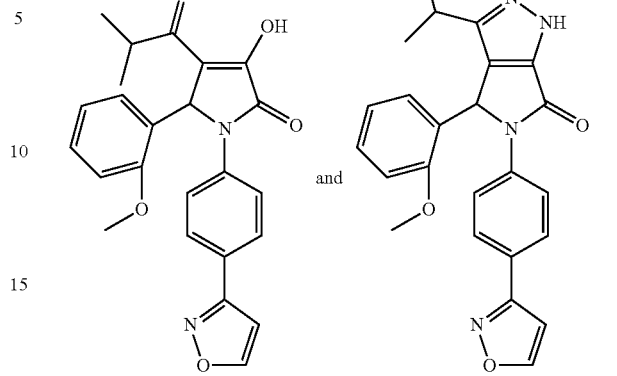

are excluded,
or its pharmaceutically acceptable salt, or a solvate thereof.

(g) A compound as defined in the above (a) to (f), wherein Y is lower alkoxy substituted with one or more substituents selected from Substituent group A (Substituent group A: hydroxy, carbamoyl, lower alkylcarbamoyl, imino substituted with hydroxy, lower alkoxy, amino, lower alkylamino, lower alkoxycarbonyl, lower alkylsulfinyl and lower alkylsulfonyl), or its pharmaceutically acceptable salt, or a solvate thereof.

(h) A compound as defined in the above (a) to (g), wherein the formula represented by the formula:

[Chemical Formula 93]

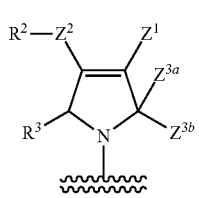

is a formula represented by the formula:

[Chemical Formula 94]

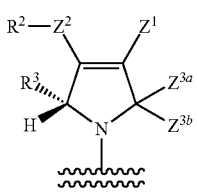

wherein each substituent is as defined in the above (a) to (e), or its pharmaceutically acceptable salt, or a solvate thereof.

General procedures for the synthesis of the compound of the invention are described bellow. Starting materials and reaction reagents used in such synthesis are commercially available or can be prepared according to methods well known in the art using compounds commercially available.

The compound (I) of the invention, i.e., the compound of the general formula (I) (compounds represented by other formulae also can be referred to as such manner), may be prepared via the routes as described bellow.

39

[Route 1]

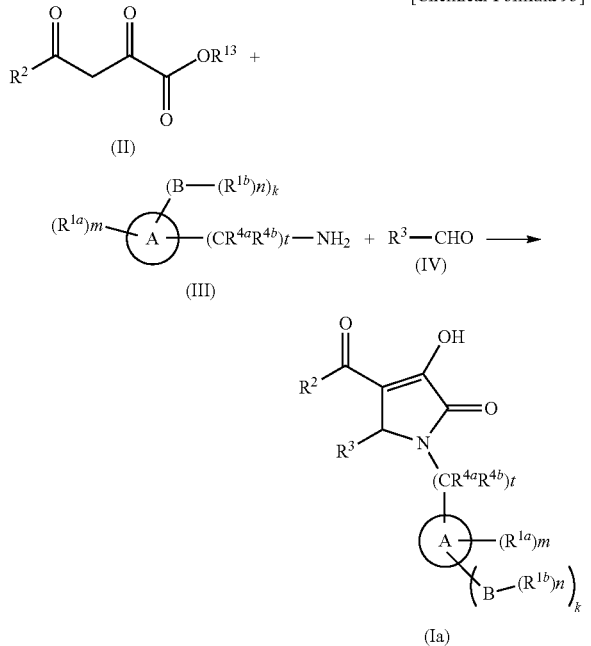

wherein, $R^{13}$ is substituted or unsubstituted lower alkyl; all other variables are as defined above.

As shown, the compound of the invention of the general formula (Ia) may be prepared by the reaction of compound (II), compound (III) and compound (IV) without solvent or in an appropriate solvent, in the presence or absence of acid.

In this reaction, compound (III) and compound (IV) may be used in an amount of one equivalent or more, preferably 1 to 3 equivalents, in respect of compound (II).

Acid that may be used includes acetic acid, para-toluenesulfonic acid, hydrochloric acid, etc.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof.

The temperature for such reaction may be −10° C. to 160° C., preferably 20° C. to 120° C. Reaction time depends on the compound, such reaction may be conducted for 10 minutes to 80 hours.

Optionally, desired compound (Ia) thus obtained may be purified according to conventional methods (e.g., column chromatography, recrystallization, etc.).

[Route 2]

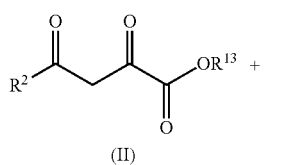

40

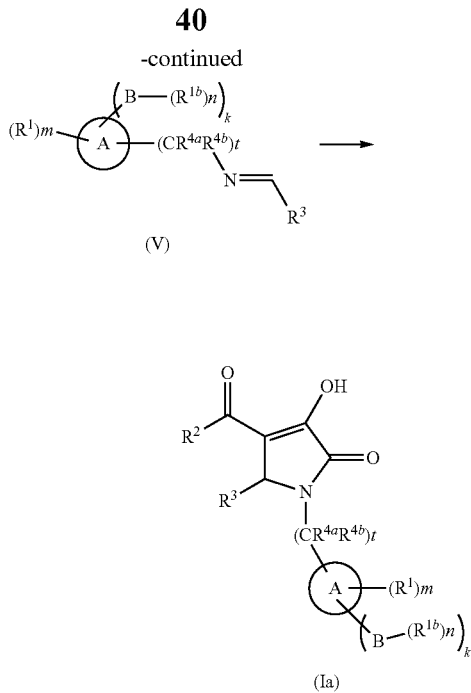

wherein all variables are as defined above.

As shown, the compound of the invention represented by the general formula (Ia) may be prepared by the reaction of compound (II) and compound (V) without solvent or in an appropriate solvent, in the presence or absence of acid.

In this reaction, compound (V) can be used in an amount of one equivalent or more, preferably 1 to 3 equivalents, in respect of compound (II).

Acid that may be used includes acetic acid, para-toluenesulfonic acid, hydrochloric acid, etc.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof.

The temperature for such reaction may be −10° C. to 160° C., preferably 20° C. to 120° C. Although reaction time depends on the compound, such reaction may be conducted for 10 minutes to 80 hours.

Optionally, desired compound (Ia) thus obtained may be purified according to conventional methods (e.g., column chromatography, recrystallization, etc.).

[Route 3]

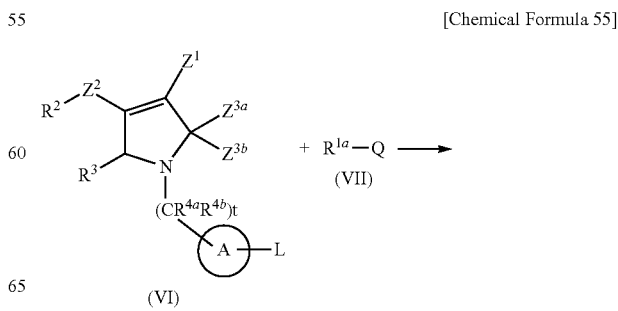

-continued

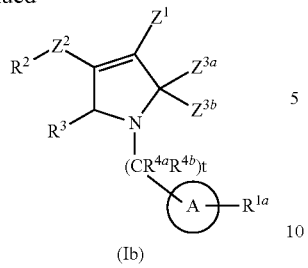

(Ib)

wherein, one of L and Q is dihydroxyborane, di(lower)alkylborane or di(lower)alkoxyborane and the other is halogen or —OSO$_2$(C$_i$F$_{2i+1}$) wherein i is an integer 1 to 4, and all other variants are as defined above.

As shown, the compound of the invention represented by the general formula (Ib) may be prepared by Suzuki coupling of compound (VI) with compound (VII) in an appropriate solvent, in the presence of a palladium catalyst and a base.

In this reaction, compound (VII) can be used in an amount of one equivalent or more, preferably 1 to 3 equivalents, in respect of compound (VI).

Base that may be used includes metal hydroxide (e.g., sodium hydroxide, potassium hydroxide, potassium phosphate, etc.), metal hydride (e.g., sodium hydride, lithium hydride, etc.), metal carbonate (e.g., sodium carbonate, potassium carbonate, cesium carbonate, etc.), etc. Such base can be used in an amount of one equivalent or more, preferably 1 to 5 equivalents, in respect of compound (VI).

Palladium catalyst that can be used includes tris(dibenzylideneacetone)dipalladium(0), palladium acetate (II), dichlorobis(triphenylphosphine)palladium (II) or tetrakis(triphenylphosphine)palladium(II), etc., and may be used in an amount of 0.001 equivalent or more, preferably 0.01 to 1 equivalent, in respect of compound (VI).

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, dimethoxyethane, etc.), N,N-dimethylformamide, water and mixture thereof, etc.

The temperature for such reaction may be −10° C. to 180° C., preferably 20° C. to 120° C., optionally under microwave radiation. Although reaction time depends on the compound, such reaction may be conducted for 10 minute to 80 hours.

Optionally, desired compound (Ib) thus obtained may be purified according to conventional methods (e.g., column chromatography, recrystallization, etc.).

[Route 4]

[Chemical Formula 56]

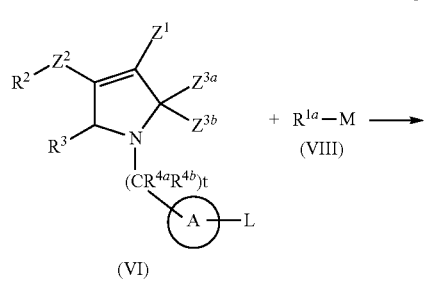

(VI)

+ R$^{1a}$—M ⟶

(VIII)

-continued

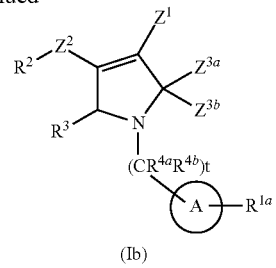

(Ib)

wherein, one of L and M is trialkyltin (e.g., —SnBu$_3$, etc.) and the other is halogen or —OSO$_2$(C$_i$F$_{2i+1}$) wherein i is an integer 1 to 4 and all other variants are as defined above.

As shown, the compound of the invention represented by the general formula (Ib) may be prepared by Stille coupling of compound (VI) with compound (VIII) in an appropriate solvent in the presence of a catalyst.

In this reaction, compound (VIII) can be used in an amount of one equivalent or more, preferably 1 to 3 equivalents, in respect of compound (VI).

Catalyst can be used include tris(dibenzylideneacetone)dipalladium(0), palladium acetate (II), dichlorobis(triphenylphosphine)palladium(II) or tetrakis(triphenylphosphine)palladium(II), etc., and may be used in an amount of 0.001 equivalent or more, preferably 0.01 to 1 equivalent, in respect of compound (VI). Optionally, phosphine ligand such as tri-tert-butylphosphine, 2-(di-tert-butylphosphino)biphenyl, 2-(dicyclohexylphosphino)biphenyl, triphenylphosphine, tris(2-furyl)phosphine, etc. may be added in twice molar amounts in respect of the catalyst.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, dimethoxyethane, etc.), N,N-dimethylformamide and mixture thereof, etc.

The temperature for such reaction may be −10° C. to 180° C., preferably 20° C. to 120° C., optionally under microwave radiation. Although reaction time depends on the compound, such reaction may be conducted for 10 minutes to 80 hours.

Optionally, desired compound (Ib) thus obtained may be purified according to conventional methods (e.g., column chromatography, recrystallization, etc.).

[Route 5]

[Chemical Formula 57]

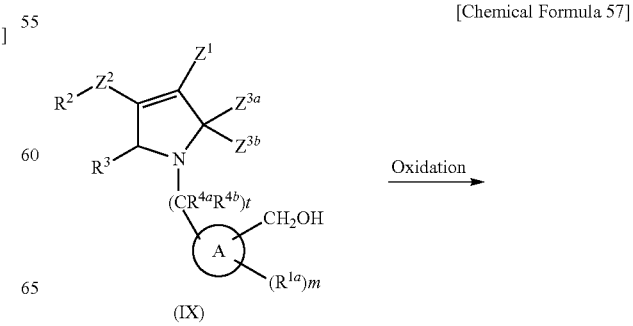

(IX)

Oxidation ⟶

-continued

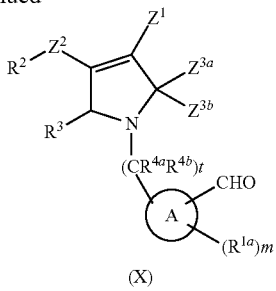

(X)

wherein all other variants are as defined above.

As shown, the compound of the invention represented by the general formula (X) may be prepared by the reaction of the compound (IX) in an appropriate solvent, in the presence of an oxidizing agent.

Oxidizing agent that may be used includes manganese dioxide, 2-iodoxybenzoic acid, etc., and may be used in an amount of one equivalent or more, preferably 1 to 1.5 equivalents, in respect of compound (IX).

Solvent that may be used includes aromatic hydrocarbons (e.g., toluene, benzene, xylene, etc.), saturated hydrocarbons (e.g., cyclohexane, hexanes, etc.), halogenated hydrocarbons (e.g., dichloromethane, 1,2-dichloroethane, etc.), ethers (e.g., tetrahydrofuran, dioxane, etc.), ketones (e.g., acetone, methylethyl ketone, etc.), nitriles (e.g., acetonitrile, etc.) and mixture thereof, etc.

The temperature for such reaction may be $-10°$ C. to $150°$ C., preferably $20°$ C. to $100°$ C. Although reaction time depends on the compound, such reaction may be conducted for 10 minutes to 80 hours.

The compound (IX) obtained may be used in the next step as a crude product or after purification according to conventional methods (e.g., column chromatography, recrystallization, etc.).

[Route 5 (Continued)]

[Chemical Formula 58]

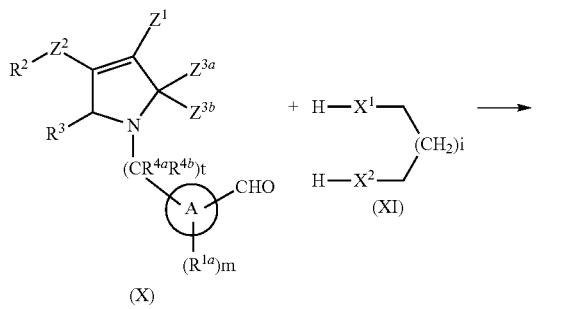

wherein, i is an integer 0 to 3; $X^1$ and $X^2$ are independently $NR^{14}$, O or S; $R^{14}$ is hydrogen or lower alkyl; all other variables are as defined above.

As shown, the compound of the invention represented by the general formula (Ic) may be prepared by the reaction of compound (X) and compound (XI) without solvent or in an appropriate solvent, in the presence or absence of an acid.

In this reaction, compound (XI) can be used in an amount of one equivalent or more, preferably 1 to 3 equivalents, in respect of compound (X).

Acid that may be used includes p-toluenesulfonic acid, sulfuric acid, p-toluenesulfonic acid pyridinium salt, etc.

Solvent that may be used includes aromatic hydrocarbons (e.g., toluene, benzene, xylene, etc.), saturated hydrocarbons (e.g., cyclohexane, hexanes, etc.), and mixture thereof.

The temperature for such reaction may be $-10°$ C. to $170°$ C., preferably $20°$ C. to $150°$ C. Reaction time depends on the compound, such reaction may be conducted for 10 minutes to 80 hours.

Optionally, desired compound (Ic) thus obtained may be purified according to conventional methods (e.g., column chromatography, recrystallization, etc.).

[Route 6]

[Chemical Formula 59]

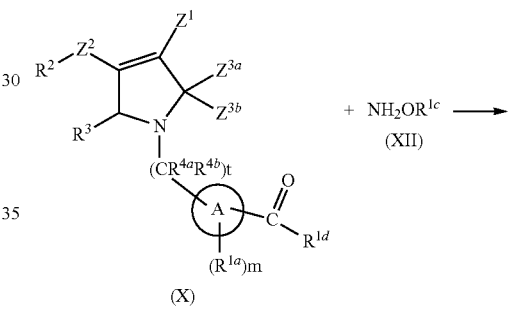

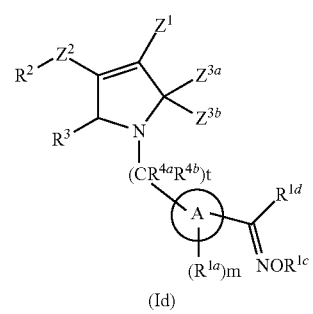

wherein all variables are as defined above.

As shown, the compound of the invention represented by the general formula (Id) may be prepared by the reaction of compound (X) and compound (XII) or a salt thereof in an appropriate solvent. The compound (XII) or a salt thereof can be used in an amount of 1 to 4 equivalents, preferably 1 to 2.5 equivalents, in respect of compound (X).

Salts of compound (XII) include mineral acid salts such as hydrochloride, sulfate, etc. Such salt is neutralized with a base when it is used in the reaction.

Base that may be used includes sodium acetate, amines (pyridinium, etc.), etc., and can be used in an amount of 1 to 3 equivalents, preferably 1 to 2 equivalents, in respect of the salt of compound (XI).

Solvent that may be used includes aromatic hydrocarbons (e.g., toluene, benzene, xylene, etc.), halogenated hydrocarbons (e.g., chloroform, 1,2-dichloroethane, etc.), ethers (e.g., tetrahydrofuran, dioxane, etc.), alcohols (e.g., methanol, enthanol, n-propanol, iso-propanol, etc.), water and mixture thereof, etc.

Reaction temperature is 0° C. to 150° C., preferably 20° C. to 120° C.

Reaction time is generally from about 10 minutes to 24 hours.

Optionally, desired compound (Id) thus obtained may be purified according to conventional methods (e.g., column chromatography, recrystallization, etc.).

[Route 7]

[Chemical Formula 60]

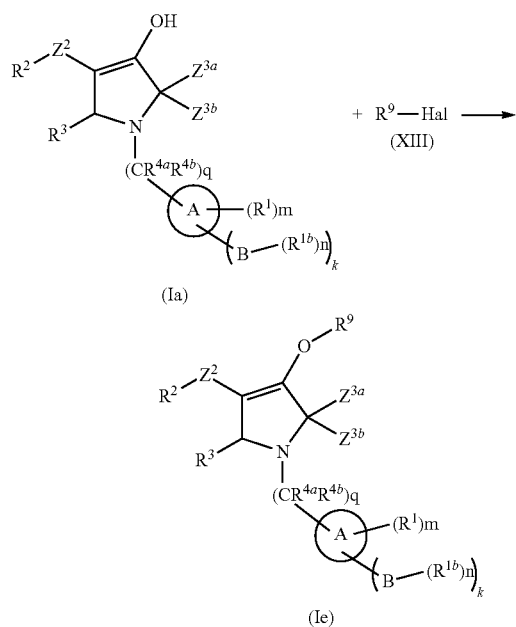

wherein, Hal is halogen; $R^9$ is a hydroxy protecting group; all other variables are as defined above.

As shown, the compound of the invention represented by the general formula (Ie) may be prepared by the reaction of the compound (Ia) and the compound (XIII) in an appropriate solvent in the presence of a base. The compound (XII) can be used in an amount of 1 to 4 equivalents, preferably 1 to 2.5 equivalents, in respect of compound (Ia).

Base that may be used includes sodium hydride, sodium methoxide, amines, etc. (triethylamine, pyridinium, etc.) and can be used in an amount of 1 to 3 equivalents, preferably 1 to 2 equivalents, in respect of the salt of compound (Ia).

Solvent that may be used includes aromatic hydrocarbons (e.g., toluene, benzene, xylene, etc.), halogenated hydrocarbons (e.g., chloroform, 1,2-dichloroethane, etc.), ethers (e.g., tetrahydrofuran, dioxane, etc.), N,N-dimethylformamide, dimethylsulfoxide and mixture thereof, etc.

Reaction temperature is −20° C. to 150° C., preferably 0° C. to 120° C.

Reaction time is generally from about 10 minutes to 24 hours.

Optionally, desired compound (Ie) thus obtained may be purified according to conventional methods (e.g., column chromatography, recrystallization, etc.).

[Route 8]

[Chemical Formula 61]

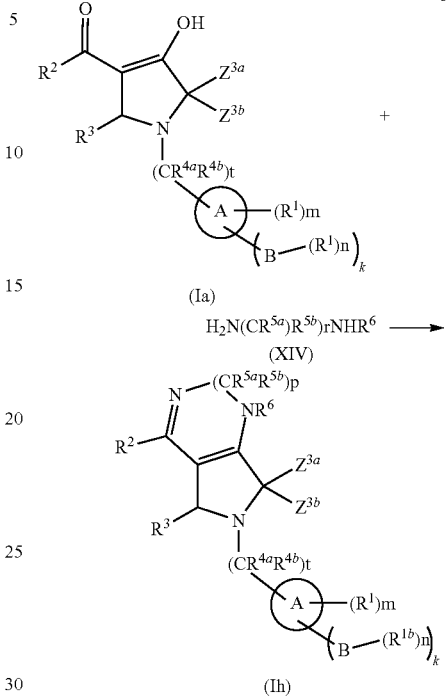

wherein the variables are as defined above.

As shown, the compound of the invention represented by the general formula (Ih) may be prepared by the reaction of compound (Ia) and compound (XIV) in an appropriate solvent. The compound (XIV) can be used in an amount of 1 to 4 equivalents, preferably 1 to 2.5 equivalents, in respect of compound (Ia).

Solvent that may be used includes acetic acid, hydrocarbons (e.g., benzene, toluene, xylene, etc.), ethers (e.g., tetrahydrofuran, dioxane, etc.), alcohols (e.g., methanol, enthanol, n-propanol, isopropanol, etc.) and mixture thereof, etc.

Reaction temperature is 0° C. to 150° C., preferably 50° C. to 130° C.

Reaction time is generally from about 10 minutes to 24 hours.

Optionally, desired compound (Ih) thus obtained may be purified according to conventional methods (e.g., column chromatography, recrystallization, etc.).

[Route 9]

[Chemical Formula 62]

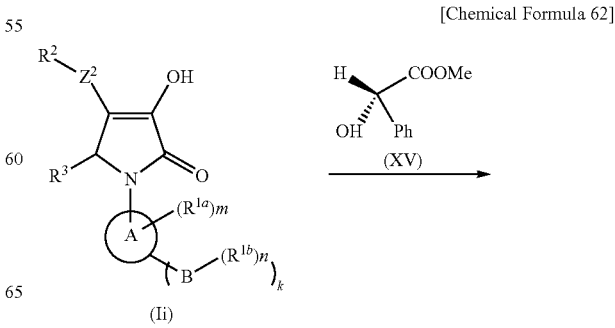

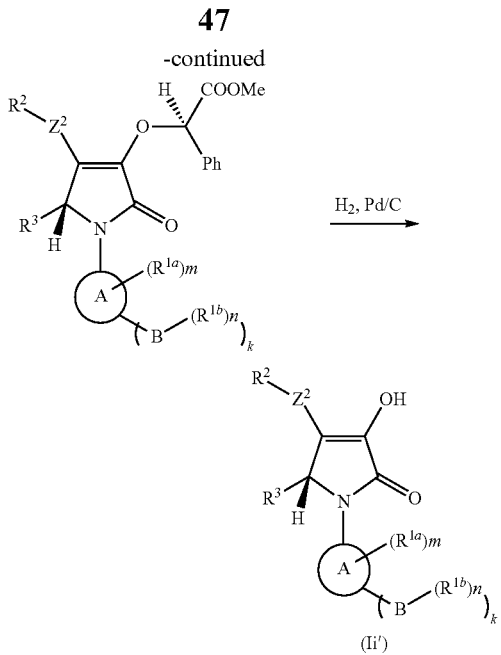

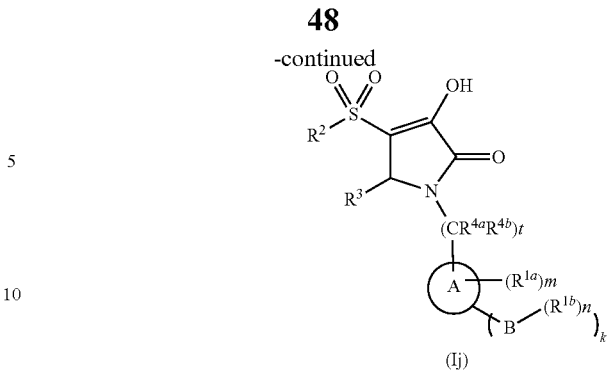

wherein $R^{14}$ and $R^{15}$ are each independently substituted or unsubstituted lower alkyl and the other variants are as defined above.

As shown, the compound of the invention represented by the general formula (Ij) may be prepared by reacting the compound (III), compound (IV), and compound (XIX) without solvent or in an appropriate solvent, in the presence or absence of an acid.

The compound (XIX) may be prepared by reacting the compound (XVII) and the compound (XVIII) without solvent or in an appropriate solvent, in the presence or absence of a base.

In this reaction, the compound (XVII) can be used in an amount of 1 or more equivalents, preferably 1 to 3 equivalents, in respect of compound (XVIII).

Base that may be used includes sodium hydride, sodium methoxide, potassium t-butoxide and the like.

Solvent that may be used includes alcohols (e.g., methanol, enthanol, etc.), aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof, etc.

The temperature for such reaction may be −10° C. to 150° C., preferably 20° C. to 100° C. Reaction time depends on the compound, such reaction may be conducted for 10 minutes to 80 hours.

Optionally, desired compound (Ia) thus obtained may be purified according to conventional methods (e.g., column chromatography, recrystallization, etc.).

In this reaction, compound (III) and compound (IV) may be used in an amount of one equivalent or more, preferably 1 to 3 equivalents, in respect of compound (XIX).

Acid that may be used includes acetic acid, p-toluenesulfonic acid, hydrochloric acid and the like.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof.

The temperature for such reaction may be −10° C. to 150° C., preferably 20° C. to 100° C. Reaction time depends on the compound, such reaction may be conducted for 10 minutes to 80 hours.

Optionally, desired compound (Ia) thus obtained may be purified according to conventional methods (e.g., column chromatography, recrystallization, etc.).

wherein the variables are as defined above.

In this reaction, compound (II) and a reagent for optical resolution (XV) (e.g., (R) or (S)-methyl-2-hydroxy-2-phenylacetate) are reacted with a condensing agent (e.g., Diisopropyl Azodicarboxylate) in an appropriate solvent to give a mixture. The mixture is purified according to conventional methods (e.g., column chromatography, recrystallization, etc.) to isolate a diastereomer having a desired configuration. The obtained diastereomer is subjected to a deprotection reaction (e.g., hydrogenation, lithium chloride, etc.) to obtain a desired enantiomer. The reagent for optical resolution can be used in an amount of 1 to 4 equivalents, preferably 1 to 2.5 equivalents, in respect of compound (Ii).

Solvent that may be used includes aromatic hydrocarbons (e.g., toluene, benzene, xylene, etc.), saturated hydrocarbons (e.g., cyclohexane, hexane, 1,3-dimethyl-2-imidazolidinone, etc.), ethers (e.g., tetrahydrofuran, diethyl ether, dioxane, etc.), amides (e.g., dimethylformamide, dimethylacetoamide, N-methylpyrolidone, etc.), and mixture thereof, etc.

The temperature for such reaction may be −10° C. to 150° C., preferably 0° C. to 80° C. Although reaction time depends on the compound, such reaction may be conducted for 10 minutes to 48 hours.

[Route 10]

[Chemical Formula 63]

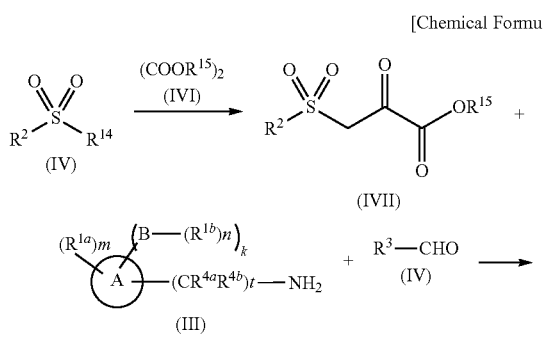

The compounds of the invention can form salts with pharmaceutically acceptable acids or bases, such as salts with an inorganic acid such as hydrochloric acid, sulfuric acid, nitric acid, phosphoric acid, hydrofluoric acid, hydrobromic acid, etc.; salts with an organic acid such as formic acid, acetic acid, oxalic acid, succinic acid, maleic acid, tartaric acid, lactic acid, citric acid, fumaric acid, etc.; salts with an organic base such as ammonium, trimethyl ammonium, triethyl ammonium, etc.; salts with an alkali metal such as sodium, potassium, etc.; salts with an alkali earth metal such as calcium, magnesium, etc.

Also, the compounds of the invention and pharmaceutically acceptable salts thereof as described above can be prepared in a form of solvate (preferably hydrate) thereof. Such solvate includes solvates with an organic solvent and/or water. Any number of solvent molecules can be coordinated to form such solvate.

The compound (I) of the invention is not limited to certain isomer, and thus, all possible isomers and racemates are encompassed by the invention. Also, the invention is intended to encompass tautomers as shown bellow.

[Chemical Formula 64]

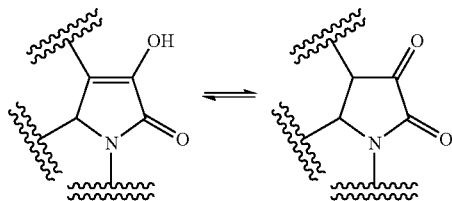

The compound of the invention may be isolated enantiomer having certain configuration or a mixture thereof. For example, the compound of the invention can be isolated enantiomer having a certain configuration at position 5 of the pyrrolidinone ring or a mixture of such enantiomers. One skilled in the art can readily isolate an enantiomer having such certain configuration using conventional techniques such as recrystallization, enzyme reaction, chromatography, etc.

The compound of the invention represented above by the general formula (I) has an antagonizing action on $P2X_3$ and/or $P2X_{2/3}$ receptor, and therefore, is useful as a therapeutic agent for diseases associated with a $P2X_3$ and/or $P2X_{2/3}$ receptor. Since $P2X_3$ and/or $P2X_{2/3}$ receptor is believed to associate with pain and diseases in urinary system (Nature 407, 26, 1011-1015 (2000), Nature, Vol. 407, No. 26, 1015-1017 (2000), Non-Patent Document 1, Non-Patent Document 2, etc.), the compound of the invention is useful in the treatment of, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, pain associated with ABC syndrome, pain associated with multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, and overactive bladder, incontinence, pollakiuria, urinary urgency, cystatrophia, prostatic hypertrophy, prostatitis, prostate pain, detrusor hyperreflesxia, dysuria, nervous pollakiuria, chronic prostatitis, chronic cystitis, etc.

The compound of the invention can be a drug with reduced side-effect such as effect on motor function because it has a high affinity for ATP receptor, especially $P2X_3$ receptor, and also has high subtype selectivity and high selectivity for other receptors. Also, the compound of the invention is advantageous because of its high stability and high oral absorptivity, good bioavailability, low clearance, long half-life, prolonged duration of action, and/or low activity of hepatic enzyme inhibition, etc.

In another embodiment, the invention provides a pharmaceutical composition comprising an effective amount of the compound of the invention, in combination with a pharmaceutically acceptable carrier.

For use of the compound of the invention as a medicament, a pharmaceutical composition can be prepared according to conventional methods, using pharmaceutically acceptable carriers well known in the art, such as excipients, binders, disintegrants, lubricants, colourants, flavors, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of the compound in a formulation can be varied depending on its dosage form, route for administration, dosing regimen, etc.

Means for administration of the pharmaceutical composition may be selected depending on dosage form, age, sex, body weight, severity of the disease, and other factors, etc., and route for administration can be selected from various routes such as oral, subcutaneous, transdermal, rectal, intranasal, buccal, etc.

Dose of the compound of the invention in a pharmaceutical composition of the invention can be determined depending on the choice of route for administration, age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.01 to 1 mg/kg/day. Such pharmaceutical composition of the invention may be administered once a day or in several times at a divided dosage in a day.

Preferred embodiments of the compound of the invention are represented by the formula (a) to (f):

[Chemical Formula 65]

(a)
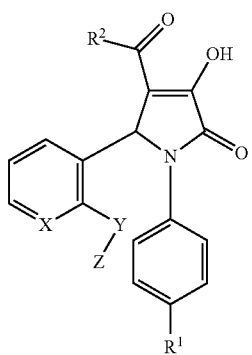

(b)
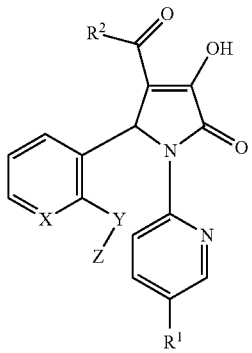

(c)
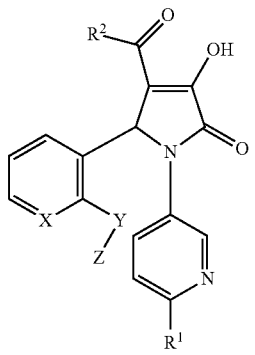

(d)
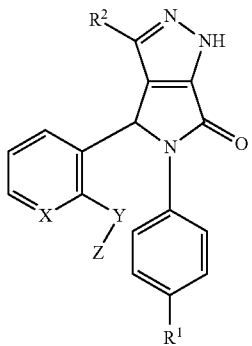

(e)
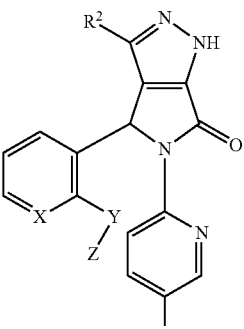

(f)
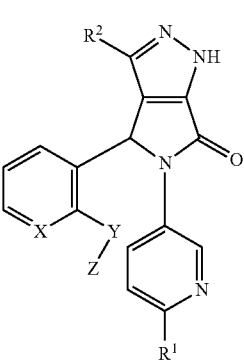

TABLE 1

| | $R^1$ |
|---|---|
| R1A | COOEt |
| R1B | $CF_3$ |
| R1C | $SCF_3$ |
| R1D | isoxazol-3-yl |
| R1E | 3-Me-isoxazol-5-yl |
| R1F | 5-Me-isoxazol-3-yl |
| R1G | 1,2,4-oxadiazol-3-yl |
| R1H | 1,3,4-oxadiazol-2-yl |
| R1I | 5-Me-1,2,4-oxadiazol-3-yl |
| R1J | 3-Me-1,2,4-oxadiazol-5-yl |
| R1K | C(Me)=NOMe |
| R1L | CH=NOMe |
| R1M | 2-oxazolinyl |
| R1N | 2-thiazolinyl |
| R1O | 2-thiazolyl |
| R1P | 2- or 3-thienyl |
| R1Q | 2- or 3-furyl |

TABLE 2

| | $R^2$ |
|---|---|
| R2A | iPr |
| R2B | cPr |
| R2C | tBu |
| R2D | Ph |
| R2E | 4-Cl or F—Ph |
| R2F | 4-$CF_3$—Ph |
| R2G | 4-$Me_2$N—Ph |
| R2H | 2- or 3-thienyl |
| R2I | 3-pyridyl |
| R2J | 6-MeO-3-pyridyl |
| R2K | 2- or 3- or 4-MeO—Ph |
| R2L | $HOCH_2C(Me)_2$ |
| R2M | $HOCOC(Me)_2$ |
| R2N | $MeC(CH_2OH)_2$ |
| R2O | $Me_2NCOC(Me)_2$ |

TABLE 2-continued

| | R² |
|---|---|
| R2P | MeNHCOC(Me)₂ |
| R2Q | H₂NCOC(Me)₂ |

TABLE 3

| | Z |
|---|---|
| ZA | Me |
| ZB | Et |
| ZC | iPr |
| ZD | CHF₂ |
| ZE | CF₃ |
| ZF | HOCH₂CH₂ |
| ZG | MeOCH₂CH₂ |
| ZH | NCCH₂ |
| ZI | MeSCH₂CH₂ |
| ZJ | MeSOCH₂CH₂ |
| ZK | Me₂NCH₂CH₂ |
| ZL | AcNHCH2CH2 |
| ZM | MsNHCH₂CH₂ |
| ZN | EtOCOCH₂ |
| ZO | HOCOCH₂ |
| ZP | HOCOCH₂CH₂ |
| ZQ | HOCOCH(Me) |
| ZR | HOCOC(Me)₂ |
| ZS | Me₂NCOCH₂ |
| ZT | MeHNCOCH₂ |
| ZU | H₂NCOCH₂ |

TABLE 4

| | X |
|---|---|
| XA | CH |
| XB | N |

TABLE 5

| | Y |
|---|---|
| YA | O |
| YB | S | wherein
Ac is acetyl, Ms is mesyl, Me is methyl, Et is ethyl, Pr is propyl, iPr is isopropyl, nBu is n-butyl, tBu is t-butyl, cPr is cyclopropyl, cBu is cyclobutyl, cPent is cyclopentyl, cHex is cyclohexyl, Ph is phenyl; and the combination of $R^1$, $R^2$, Z, X and Y, i.e., (R1,R2,Z,X,Y), is any one of the following combinations:
(R1,R2,Z,X,Y)=(R1A,R2A,ZA,XA,YA), (R1B,R2A,ZA,XA,YA), (R1C,R2A,ZA,XA,YA), (R1D,R2A,ZA,XA,YA), (R1E,R2A,ZA,XA,YA), (R1F,R2A,ZA,XA,YA), (R1G,R2A,ZA,XA,YA), (R1H,R2A,ZA,XA,YA), (R1I,R2A,ZA,XA,YA), (R1J,R2A,ZA,XA,YA), (R1K,R2A,ZA,XA,YA), (R1L,R2A,ZA,XA,YA), (R1M,R2A,ZA,XA,YA), (R1N,R2A,ZA,XA,YA), (R1O,R2A,ZA,XA,YA), (R1P,R2A,ZA,XA,YA), (R1Q,R2A,ZA,XA,YA), (R1A,R2B,ZA,XA,YA), (R1B,R2B,ZA,XA,YA), (R1C,R2B,ZA,XA,YA), (R1D,R2B,ZA,XA,YA), (R1E,R2B,ZA,XA,YA), (R1F,R2B,ZA,XA,YA), (R1G,R2B,ZA,XA,YA), (R1H,R2B,ZA,XA,YA), (R1I,R2B,ZA,XA,YA), (R1J,R2B,ZA,XA,YA), (R1K,R2B,ZA,XA,YA), (R1L,R2B,ZA,XA,YA), (R1M,R2B,ZA,XA,YA), (R1N,R2B,ZA,XA,YA), (R1O,R2B,ZA,XA,YA), (R1P,R2B,ZA,XA,YA), (R1Q,R2B,ZA,XA,YA), (R1A,R2C,ZA,XA,YA), (R1B,R2C,ZA,XA,YA), (R1C,R2C,ZA,XA,YA), (R1D,R2C,ZA,XA,YA), (R1E,R2C,ZA,XA,YA), (R1F,R2C,ZA,XA,YA), (R1G,R2C,ZA,XA,YA), (R1H,R2C,ZA,XA,YA), (R1I,R2C,ZA,XA,YA), (R1J,R2C,ZA,XA,YA), (R1K,R2C,ZA,XA,YA), (R1L,R2C,ZA,XA,YA), (R1M,R2C,ZA,XA,YA), (R1N,R2C,ZA,XA,YA), (R1O,R2C,ZA,XA,YA), (R1P,R2C,ZA,XA,YA), (R1Q,R22C,ZA,XA,YA), (R1A,R2D,ZA,XA,YA), (R1B,R2D,ZA,XA,YA), (R1C,R2D,ZA,XA,YA), (R1D,R2D,ZA,XA,YA), (R1E,R2D,ZA,XA,YA), (R1F,R2D,ZA,XA,YA), (R1G,R2D,ZA,XA,YA), (R1H,R2D,ZA,XA,YA), (R1I,R2D,ZA,XA,YA), (R1J,R2D,ZA,XA,YA), (R1K,R2D,ZA,XA,YA), (R1L,R2D,ZA,XA,YA), (R1M,R2D,ZA,XA,YA), (R1N,R2D,ZA,XA,YA), (R1O,R2D,ZA,XA,YA), (R1P,R2D,ZA,XA,YA), (R1Q,R2D,ZA,XA,YA), (R1A,R2E,ZA,XA,YA), (R1B,R2E,ZA,XA,YA), (R1C,R2E,ZA,XA,YA), (R1D,R2E,ZA,XA,YA), (R1E,R2E,ZA,XA,YA), (R1F,R2E,ZA,XA,YA), (R1G,R2E,ZA,XA,YA), (R1H,R2E,ZA,XA,YA), (R1I,R2E,ZA,XA,YA), (R1J,R2E,ZA,XA,YA), (R1K,R2E,ZA,XA,YA), (R1L,R2E,ZA,XA,YA), (R1M,R2E,ZA,XA,YA), (R1N,R2E,ZA,XA,YA), (R1O,R2E,ZA,XA,YA), (R1P,R2E,ZA,XA,YA), (R1Q,R2E,ZA,XA,YA), (R1A,R2F,ZA,XA,YA), (R1B,R2F,ZA,XA,YA), (R1C,R2F,ZA,XA,YA), (R1D,R2F,ZA,XA,YA), (R1E,R2F,ZA,XA,YA), (R1,R2F,ZA,XA,YA), (R1G,R2F,ZA,XA,YA), (R1H,R2F,ZA,XA,YA), (R1I,R2F,ZA,XA,YA), (R1J,R2F,ZA,XA,YA), (R1K,R2F,ZA,XA,YA), (R1L,R2F,ZA,XA,YA), (R1M,R2F,ZA,XA,YA), (R1N,R2F,ZA,XA,YA), (R1O,R2F,ZA,XA,YA), (R1P,R2F,ZA,XA,YA), (R1Q,R2F,ZA,XA,YA), (R1A,R2G,ZA,XA,YA), (R1B,R2G,ZA,XA,YA), (R1C,R2G,ZA,XA,YA), (R1D,R2G,ZA,XA,YA), (R1E,R2G,ZA,XA,YA), (R1F,R2G,ZA,XA,YA), (R1G,R2G,ZA,XA,YA), (R1H,R2G,ZA,XA,YA), (R1I,R2G,ZA,XA,YA), (R1J,R2G,ZA,XA,YA), (R1K,R2G,ZA,XA,YA), (R1L,R2G,ZA,XA,YA), (R1M,R2G,ZA,XA,YA), (R1N,R2G,ZA,XA,YA), (R1O,R2G,ZA,XA,YA), (R1P,R2G,ZA,XA,YA), (R1Q,R2G,ZA,XA,YA), (R1A,R2H,ZA,XA,YA), (R1B,R2H,ZA,XA,YA), (R1C,R2H,ZA,XA,YA), (R1D,R2H,ZA,XA,YA), (R1E,R2H,ZA,XA,YA), (R1F,R2H,ZA,XA,YA), (R1G,R2H,ZA,XA,YA), (R1H,R2H,ZA,XA,YA), (R1I,R2H,ZA,XA,YA), (R1J,R2H,ZA,XA,YA), (R1K,R2H,ZA,XA,YA), (R1L,R2H,ZA,XA,YA), (R1M,R2H,ZA,XA,YA), (R1N,R2H,ZA,XA,YA), (R1O,R2H,ZA,XA,YA), (R1P,R2H,ZA,XA,YA), (R1Q,R2H,ZA,XA,YA), (R1A,R2I,ZA,XA,YA), (R1B,R2I,ZA,XA,YA), (R1C,R2I,ZA,XA,YA), (R1D,R2I,ZA,XA,YA), (R1E,R2I,ZA,XA,YA), (R1F,R2I,ZA,XA,YA), (R1G,R2I,ZA,XA,YA), (R1H,R2I,ZA,XA,YA), (R1I,R2I,ZA,XA,YA), (R1J,R2I,ZA,XA,YA), (R1K,R2I,ZA,XA,YA), (R1L,R2I,ZA,XA,YA), (R1M,R2I,ZA,XA,YA), (R1N,R2I,ZA,XA,YA), (R1O,R2I,ZA,XA,YA), (R1P,R2I,ZA,XA,YA), (R1Q,R2I,ZA,XA,YA), (R1A,R2J,ZA,XA,YA), (R1B,R2J,ZA,XA,YA), (R1C,R2J,ZA,XA,YA), (R1D,R2J,ZA,XA,YA), (R1E,R2J,ZA,XA,YA), (R1F,R2J,ZA,XA,YA), (R1G,R2J,ZA,XA,YA), (R1H,R2J,ZA,XA,YA), (R1I,R2J,ZA,XA,YA), (R1J,R2J,ZA,XA,YA), (R1K,R2J,ZA,XA,YA), (R1L,R2J,ZA,XA,YA), (R1M,R2J,ZA,XA,YA), (R1N,R2J,ZA,XA,YA), (R1O,R2J,ZA,XA,YA), (R1P,R2J,ZA,XA,YA), (R1Q,R2J,ZA,XA,YA), (R1A,R2K,ZA,XA,YA), (R1B,R2K,ZA,XA,YA), (R1C,R2K,ZA,XA,YA), (R1D,R2K,ZA,XA,YA), (R1E,R2K,ZA,XA,YA), (R1F,R2K,ZA,XA,YA), (R1G,R2K,ZA,XA,YA), (R1H,R2K,ZA,XA,YA), (R1I,R2K,ZA,XA,YA), (R1J,R2K,ZA,XA,YA), (R1K,R2K,ZA,XA,YA), (R1L,R2K,ZA,XA,YA), (R1M,R2K,ZA,XA,YA), (R1N,R2K,ZA,XA,YA), (R1O,R2K,ZA,XA,YA), (R1P,R2K,ZA,XA,YA), (R1Q,R2K,ZA,XA,YA), (R1A,R2L,ZA,XA,YA), (R1B,R2L,ZA,XA,YA), (R1C,R2L,ZA,XA,YA), (R1D,R2L,ZA,XA,YA), (R1E,R2L,ZA,XA,YA), (R1F,R2L,ZA,XA,YA), (R1G,R2L,ZA,XA,YA), (R1H,R2L,ZA, XA,YA), (R1I,R2L,ZA,XA,YA), (R1J,R2L,ZA,XA,YA), (R1K,R2L,ZA,XA,YA), (R1L,R2L,ZA,XA,YA), (R1M,R2L,ZA,XA,YA), (R1N,R2L,ZA,XA,YA), (R1O,R2L,ZA,XA,YA), (R1P,R2L,ZA,XA,YA), (R1Q,R2L,ZA,XA,YA), (R1A,R2M,ZA,XA,YA), (R1B,R2M,ZA,XA,YA), (R1C,R2M,ZA,XA,YA), (R1D,R2M,ZA,XA,YA), (R1E,R2M,ZA,XA,YA), (R1F,R2M,ZA,XA,YA), (R1G,R2M,ZA,XA,YA), (R1H,R2M,ZA,XA,YA), (R1I,R2M,ZA,XA,YA), (R1J,R2M,ZA,XA,YA), (R1K,R2M,ZA,XA,YA), (R1L,R2M,ZA,XA,YA), (R1M,R2M,ZA,XA,YA), (R1N,R2M,ZA,XA,YA), (R1O,R2M,ZA,XA,YA), (R1P,R2M,ZA,XA,YA), (R1Q,R2M,ZA,XA,YA), (R1A,R2N,ZA,XA,YA), (R1B,R2N,ZA,XA,YA), (R1C,R2N,ZA,XA,YA), (R1D,R2N,ZA,XA,YA), (R1E,R2N,ZA,XA,YA), (R1F,R2N,ZA,XA,YA), (R1G,R2N,ZA,XA,YA), (R1H,R2N,ZA,XA,YA), (R1I,R2N,ZA,XA,YA), (R1J,R2N,ZA,XA,YA), (R1K,R2N,ZA,XA,YA), (R1L,R2N,ZA,XA,YA), (R1M,R2N,ZA,XA,YA), (R1N,R2N,ZA,XA,YA), (R1O,R2N,ZA,XA,YA), (R1P,R2N,ZA,XA,YA), (R1Q,R2N,ZA,XA,YA), (R1A,R2O,ZA,XA,YA), (R1B,R2O,ZA,XA,YA), (R1C,R2O,ZA,XA,YA), (R1D,R2O,ZA,XA,YA), (R1E,R2O,ZA,XA,YA), (R1F,R2O,ZA,XA,YA), (R1G,R2O,ZA,XA,YA), (R1H,R2O,ZA,XA,YA), (R1I,R2O,ZA,XA,YA), (R1J,R2O,ZA,XA,YA), (R1K,R2O,ZA,XA,YA), (R1L,R2O,ZA,XA,YA), (R1M,R2O,ZA,XA,YA), (R1N,R2O,ZA,XA,YA), (R1O,R2O,ZA,XA,YA), (R1P,R2O,ZA,XA,YA), (R1Q,R2O,ZA,XA,YA), (R1A,R2P,ZA,XA,YA), (R1B,R2P,ZA,XA,YA), (R1C,R2P,ZA,XA,YA), (R1D,R2P,ZA,XA,YA), (R1E,R2P,ZA,XA,YA), (R1F,R2P,ZA,XA,YA), (R1G,R2P,ZA,XA,YA), (R1H,R2P,ZA,XA,YA), (R1I,R2P,ZA,XA,YA), (R1J,R2P,ZA,XA,YA), (R1K,R2P,ZA,XA,YA), (R1L,R2P,ZA,XA,YA), (R1M,R2P,ZA,XA,YA), (R1N,R2P,ZA,XA,YA), (R1O,R2P,ZA,XA,YA), (R1P,R2P,ZA,XA,YA), (R1Q,R2P,ZA,XA,YA), (R1A,R2Q,ZA,XA,YA), (R1B,R2Q,ZA,XA,YA), (R1C,R2Q,ZA,XA,YA), (R1D,R2Q,ZA,XA,YA), (R1E,R2Q,ZA,XA,YA), (R1F,R2Q,ZA,XA,YA), (R1G,R2Q,ZA,XA,YA), (R1H,R2Q,ZA,XA,YA), (R1I,R2Q,ZA,XA,YA), (R1J,R2Q,ZA,XA,YA), (R1K,R2Q,ZA,XA,YA), (R1L,R2Q,ZA,XA,YA), (R1M,R2Q,ZA,XA,YA), (R1N,R2Q,ZA,XA,YA), (R1O,R2Q,ZA,XA,YA), (R1P,R2Q,ZA,XA,YA), (R1Q,R2Q,ZA,XA,YA), (R1A,R2A,ZB,XA,YA), (R1B,R2A,ZB,XA,YA), (R1C,R2A,ZB,XA,YA), (R1D,R2A,ZB,XA,YA), (R1E,R2A,ZB,XA,YA), (R1F,R2A,ZB,XA,YA), (R1G,R2A,ZB,XA,YA), (R1H,R2A,ZB,XA,YA), (R1I,R2A,ZB,XA,YA), (R1J,R2A,ZB,XA,YA), (R1K,R2A,ZB,XA,YA), (R1L,R2A,ZB,XA,YA), (R1M,R2A,ZB,XA,YA), (R1N,R2A,ZB,XA,YA), (R1O,R2A,ZB,XA,YA), (R1P,R2A,ZB,XA,YA), (R1Q,R2A,ZB,XA,YA), (R1A,R2B,ZB,XA,YA), (R1B,R2B,ZB,XA,YA), (R1C,R2B,ZB,XA,YA), (R1D,R2B,ZB,XA,YA), (R1E,R2B,ZB,XA,YA), (R1F,R2B,ZB,XA,YA), (R1G,R2B,ZB,XA,YA), (R1H,R2B,ZB,XA,YA), (R1I,R2B,ZB,XA,YA), (R1J,R2B,ZB,XA,YA), (R1K,R2B,ZB,XA,YA), (R1L,R2B,ZB,XA,YA), (R1M,R2B,ZB,XA,YA), (R1N,R2B,ZB,XA,YA), (R1O,R2B,ZB,XA,YA), (R1P,R2B,ZB,XA,YA), (R1Q,R2B,ZB,XA,YA), (R1A,R2C,ZB,XA,YA), (R1B,R2C,ZB,XA,YA), (R1C,R2C,ZB,XA,YA), (R1D,R2C,ZB,XA,YA), (R1E,R2C,ZB,XA,YA), (R1F,R2C,ZB,XA,YA), (R1G,R2C,ZB,XA,YA), (R1H,R2C,ZB,XA,YA), (R1I,R2C,ZB,XA,YA), (R1J,R2C,ZB,XA,YA), (R1K,R2C,ZB,XA,YA), (R1L,R2C,ZB,XA,YA), (R1M,R2C,ZB,XA,YA), (R1N,R2C,ZB,XA,YA), (R1O,R2C,ZB,XA,YA), (R1P,R2C,ZB,XA,YA), (R1Q,R2C,ZB,XA,YA), (R1A,R2D,ZB,XA,YA), (R1B,R2D,ZB,XA,YA), (R1C,R2D,ZB,XA,YA), (R1D,R2D,ZB,XA,YA), (R1E,R2D,ZB,XA,YA), (R1F,R2D,ZB,XA,YA), (R1G,R2D,ZB,XA,YA), (R1H,R2D,ZB,XA,YA), (R1I,R2D,ZB,XA,YA), (R1J,R2D,ZB,XA,YA), (R1K,R2D,ZB,XA,YA), (R1L,R2D,ZB,XA,YA), (R1M,R2D,ZB,XA,YA), (R1N,R2D,ZB,XA,YA), (R1O,R2D,ZB,XA,YA), (R1P,R2D,ZB,XA,YA), (R1Q,R2D,ZB,XA,YA), (R1A,R2E,ZB,XA,YA), (R1B,R2E,ZB,XA,YA), (R1C,R2E,ZB,XA,YA), (R1D,R2E,ZB,XA,YA), (R1E,R2E,ZB,XA,YA), (R1F,R2E,ZB,XA,YA), (R1G,R2E,ZB,XA,YA), (R1H,R2E,ZB,XA,YA), (R1I,R2E,ZB,XA,YA), (R1J,R2E,ZB,XA,YA), (R1K,R2E,ZB,XA,YA), (R1L,R2E,ZB,XA,YA), (R1M,R2E,ZB,XA,YA), (R1N,R2E,ZB,XA,YA), (R1O,R2E,ZB,XA,YA), (R1P,R2E,ZB,XA,YA), (R1Q,R2E,ZB,XA,YA), (R1A,R2F,ZB,XA,YA), (R1B,R2F,ZB,XA,YA), (R1C,R2F,ZB,XA,YA), (R1D,R2F,ZB,XA,YA), (R1E,R2F,ZB,XA,YA), (R1F,R2F,ZB,XA,YA), (R1G,R2F,ZB,XA,YA), (R1H,R2F,ZB,XA,YA), (R1I,R2F,ZB,XA,YA), (R1J,R2F,ZB,XA,YA), (R1K,R2F,ZB,XA,YA), (R1L,R2F,ZB,XA,YA), (R1M,R2F,ZB,XA,YA), (R1N,R2F,ZB,XA,YA), (R1O,R2F,ZB,XA,YA), (R1P,R2F,ZB,XA,YA), (R1Q,R2F,ZB,XA,YA), (R1A,R2G,ZB,XA,YA), (R1B,R2G,ZB,XA,YA), (R1C,R2G,ZB,XA,YA), (R1D,R2G,ZB,XA,YA), (R1E,R2G,ZB,XA,YA), (R1F,R2G,ZB,XA,YA), (R1G,R2G,ZB,XA,YA), (R1H,R2G,ZB,XA,YA), (R1I,R2G,ZB,XA,YA), (R1J,R2G,ZB,XA,YA), (R1K,R2G,ZB,XA,YA), (R1L,R2G,ZB,XA,YA), (R1M,R2G,ZB,XA,YA), (R1N,R2G,ZB,XA,YA), (R1O,R2G,ZB,XA,YA), (R1P,R2G,ZB,XA,YA), (R1Q,R2G,ZB,XA,YA), (R1A,R2H,ZB,XA,YA), (R1B,R2H,ZB,XA,YA), (R1C,R2H,ZB,XA,YA), (R1D,R2H,ZB,XA,YA), (R1E,R2H,ZB,XA,YA), (R1F,R2H,ZB,XA,YA), (R1G,R2H,ZB,XA,YA), (R1H,R2H,ZB,XA,YA), (R1I,R2H,ZB,XA,YA), (R1J,R2H,ZB,XA,YA), (R1K,R2H,ZB,XA,YA), (R1L,R2H,ZB,XA,YA), (R1M,R2H,ZB,XA,YA), (R1N,R2H,ZB,XA,YA), (R1O,R2H,ZB,XA,YA), (R1P,R2H,ZB,XA,YA), (R1Q,R2H,ZB,XA,YA), (R1A,R2I,ZB,XA,YA), (R1B,R2I,ZB,XA,YA), (R1C,R2I,ZB,XA,YA), (R1D,R2I,ZB,XA,YA), (R1E,R2I,ZB,XA,YA), (R1F,R2I,ZB,XA,YA), (R1G,R2I,ZB,XA,YA), (R1H,R2I,ZB,XA,YA), (R1I,R2I,ZB,XA,YA), (R1J,R2I,ZB,XA,YA), (R1K,R2I,ZB,XA,YA), (R1L,R2I,ZB,XA,YA), (R1M,R2I,ZB,XA,YA), (R1N,R2I,ZB,XA,YA), (R1O,R2I,ZB,XA,YA), (R1P,R2I,ZB,XA,YA), (R1Q,R2I,ZB,XA,YA), (R1A,R2J,ZB,XA,YA), (R1B,R2J,ZB,XA,YA), (R1C,R2J,ZB,XA,YA), (R1D,R2J,ZB,XA,YA), (R1E,R2J,ZB,XA,YA), (R1F,R2J,ZB,XA,YA), (R1G,R2J,ZB,XA,YA), (R1H,R2J,ZB,XA,YA), (R1I,R2J,ZB,XA,YA), (R1J,R2J,ZB,XA,YA), (R1K,R2J,ZB,XA,YA), (R1L,R2J,ZB,XA,YA), (R1M,R2J,ZB,XA,YA), (R1N,R2J,ZB,XA,YA), (R1O,R2J,ZB,XA,YA), (R1P,R2J,ZB,XA,YA), (R1Q,R2J,ZB,XA,YA), (R1A,R2K,ZB,XA,YA), (R1B,R2K,ZB,XA,YA), (R1C,R2K,ZB,XA,YA), (R1D,R2K,ZB,XA,YA), (R1E,R2K,ZB,XA,YA), (R1F,R2K,ZB,XA,YA), (R1G,R2K,ZB,XA,YA), (R1H,R2K,ZB,XA,YA), (R1I,R2K,ZB,XA,YA), (R1J,R2K,ZB,XA,YA), (R1K,R2K,ZB,XA,YA), (R1L,R2K,ZB,XA,YA), (R1M,R2K,ZB,XA,YA), (R1N,R2K,ZB,XA,YA), (R1O,R2K,ZB,XA,YA), (R1P,R2K,ZB,XA,YA), (R1Q,R2K,ZB,XA,YA), (R1A,R2L,ZB,XA,YA), (R1B,R2L,ZB,XA,YA), (R1C,R2L,ZB,XA,YA), (R1D,R2L,ZB,XA,YA), (R1E,R2L,ZB,XA,YA), (R1F,R2L,ZB,XA,YA), (R1G,R2L,ZB,XA,YA), (R1H,R2L,ZB,XA,YA), (R1I,R2L,ZB,XA,YA), (R1J,R2L,ZB,XA,YA), (R1K,R2L,ZB,XA,YA), (R1L,R2L,ZB,XA,YA), (R1M,R2L,ZB,XA,YA), (R1N,R2L,ZB,XA,YA), (R1O,R2L,ZB,XA,YA), (R1P,R2L,ZB,XA,YA), (R1Q,R2L,ZB,XA,YA), (R1A,R2M,ZB,XA,YA), (R1B,R2M,ZB,XA,YA), (R1C,R2M,ZB,XA,YA), (R1D,R2M,ZB,XA,YA), (R1E,R2M,ZB,XA,YA), (R1F,R2M,ZB,XA,YA), (R1G,R2M,ZB,XA,YA), (R1H,R2M,ZB,XA,YA), (R1I,R2M,ZB,XA,YA), (R1J,R2M,ZB,XA,YA), (R1K,R2M,ZB,XA,YA), (R1L,R2M,ZB,XA,YA), (R1M,R2M,ZB,XA,YA), (R1N,R2M,ZB,XA,YA), (R1O,R2M,ZB,XA,YA), (R1P,R2M,ZB,XA,YA), (R1Q,R2M,ZB,XA,YA), (R1A,R2N,ZB,XA,YA), (R1B,R2N,ZB,XA,YA), (R1C,R2N,ZB,XA,YA), (R1D,R2N,ZB,XA,YA), (R1E,R2N,ZB,XA,YA), (R1F,R2N,ZB,XA,YA), (R1G,R2N,ZB,XA,YA), (R1H,R2N,ZB,XA,YA), (R1I,R2N,ZB,XA,YA), (R1J,R2N,ZB,XA,YA), (R1K,R2N,ZB,XA,YA), (R1L,R2N,ZB,XA,YA), (R1M,R2N,ZB,XA,YA), (R1N,R2N,ZB,XA,YA), (R1O,R2N,ZB,XA,YA), (R1P,R2N,ZB,XA,YA), (R1Q,R2N,ZB,XA,YA), (R1A,R2O,ZB,XA,YA), (R1B,R2O,ZB,XA,YA), (R1C,R2O,ZB,XA,YA), (R1D,R2O,ZB,XA,YA), (R1E,R2O,ZB,XA,YA), (R1F,R2O,ZB,XA,YA), (R1G,R2O,ZB,XA,YA), (R1H,R2O,ZB,XA,YA), (R1I,R2O,ZB,XA,YA), (R1J,R2O,ZB,XA,YA), (R1K,R2O,ZB,XA,YA), (R1L,R2O,ZB,XA,YA), (R1M,R2O,ZB,XA,YA), (R1N,R2O,ZB,XA,YA), (R1O,R2O,ZB,XA,YA), (R1P,R2O,ZB,XA,YA), (R1Q,R2O,ZB,XA,YA), (R1A,R2P,ZB,XA,YA), (R1B,R2P,ZB,XA,YA), (R1C,R2P,ZB,XA,YA), (R1D,R2P,ZB,XA,YA), (R1E,R2P,ZB,XA,YA), (R1F,R2P,ZB,XA,YA), (R1G,R2P,ZB,XA,YA), (R1H,R2P,ZB,XA,YA), (R1I,R2P,ZB,XA,YA), (R1J,R2P,ZB,XA,YA), (R1K,R2P,ZB,XA,YA), (R1L,R2P,ZB,XA,YA), (R1M,R2P,ZB,XA,YA), (R1N,R2P,ZB,XA,YA), (R1O,R2P,ZB,XA,YA), (R1P,R2P,ZB,XA,YA), (R1Q,R2P,ZB,XA,YA), (R1A,R2Q,ZB,XA,YA), (R1B,R2Q,ZB,XA,YA), (R1C,R2Q,ZB,XA,YA), (R1D,R2Q,ZB,XA,YA), (R1E,R2Q,ZB,XA,YA), (R1F,R2Q,ZB,XA,YA), (R1G,R2Q,ZB,XA,YA), (R1H,R2Q,ZB,XA,YA), (R1I,R2Q,ZB,XA,YA), (R1J,R2Q,ZB,XA,YA), (R1K,R2Q,ZB,XA,YA), (R1L,R2Q,ZB,XA,YA), (R1M,R2Q,ZB,XA,YA), (R1N,R2Q,ZB,XA,YA), (R1O,R2Q,ZB,XA,YA), (R1P,R2Q,ZB,XA,YA), (R1Q,R2Q,ZB,XA,YA), (R1A,R2A,ZC,XA,YA), (R1B,R2A,ZC,XA,YA), (R1C,R2A,ZC,XA,YA), (R1D,R2A,ZC,XA,YA), (R1E,R2A,ZC,XA,YA), (R1F,R2A,ZC,XA,YA), (R1G,R2A,ZC,XA,YA), (R1H,R2A,ZC,XA,YA), (R1I,R2A,ZC,XA,YA), (R1J,R2A,ZC,XA,YA), (R1K,R2A,ZC,XA,YA), (R1L,R2A,ZC,XA,YA), (R1M,R2A,ZC,XA,YA), (R1N,R2A,ZC,XA,YA), (R1O,R2A,ZC,XA,YA), (R1P,R2A,ZC,XA,YA), (R1Q,R2A,ZC,XA,YA), (R1A,R2B,ZC,XA,YA), (R1B,R2B,ZC,XA,YA), (R1C,R2B,ZC,XA,YA), (R1D,R2B,ZC,XA,YA), (R1E,R2B,ZC,XA,YA), (R1F,R2B,ZC,XA,YA), (R1G,R2B,ZC,XA,YA), (R1H,R2B,ZC,XA,YA), (R1I,R2B,ZC,XA,YA), (R1J,R2B,ZC,XA,YA), (R1K,R2B,ZC,XA,YA), (R1L,R2B,ZC,XA,YA), (R1M,R2B,ZC,XA,YA), (R1N,R2B,ZC,XA,YA), (R1O,R2B,ZC,XA,YA), (R1P,R2B,ZC,XA,YA), (R1Q,R2B,ZC,XA,YA), (R1A,R2C,ZC,XA,YA), (R1B,R22C,ZC,XA,YA), (R1C,R2C,ZC,XA,YA), (R1D,R2C,ZC,XA,YA), (R1E,R2C,ZC,XA,YA), (R1F,R2C,ZC,XA,YA), (R1G,R2C,ZC,XA,YA), (R1H,R2C,ZC,XA,YA), (R1I,R2C,ZC,XA,YA), (R1J,R2C,ZC,XA,YA), (R1K,R2C,ZC,XA,YA), (R1L,R2C,ZC,XA,YA), (R1M,R2C,ZC,XA,YA), (R1N,R2C,ZC,XA,YA), (R1O,R2C,ZC,XA,YA), (R1P,R2C,ZC,XA,YA), (R1Q,R2C,ZC,XA,YA), (R1A,R2D,ZC,XA,YA), (R1B,R2D,ZC,XA,YA), (R1C,R2D,ZC,XA,YA), (R1D,R2D,ZC,XA,YA), (R1E,R2D,ZC,XA,YA), (R1F,R2D,ZC,XA,YA), (R1G,R2D,ZC,XA,YA), (R1H,R2D,ZC,XA,YA), (R1I,R2D,ZC,XA,YA), (R1J,R2D,ZC,XA,YA), (R1K,R2D,ZC,XA,YA), (R1L,R2D,ZC,XA,YA), (R1M,R2D,ZC,XA,YA), (R1N,R2D,ZC,XA,YA), (R1O,R2D,ZC,XA,YA), (R1P,R2D,ZC,XA,YA), (R1Q,R2D,ZC,XA,YA), (R1A,R2E,ZC,XA,YA), (R1B,R2E,ZC,XA,YA), (R1C,R2E,ZC,XA,YA), (R1D,R2E,ZC,XA,YA), (R1E,R2E,ZC,XA,YA), (R1F,R2E,ZC,XA,YA), (R1G,R2E,ZC,XA,YA), (R1H,R2E,ZC,XA,YA), (R1I,R2E,ZC,XA,YA), (R1J,R2E,ZC,XA,YA), (R1K,R2E,ZC,XA,YA), (R1L,R2E,ZC,XA,YA), (R1M,R2E,ZC,XA,YA), (R1N,R2E,ZC,XA,YA), (R1O,R2E,ZC,XA,YA), (R1P,R2E,ZC,XA,YA), (R1Q,R2E,ZC,XA,YA), (R1A,R2F,ZC,XA,YA), (R1B,R2F,ZC,XA,YA), (R1C,R2F,ZC,XA,YA), (R1D,R2F,ZC,XA,YA), (R1E,R2F,ZC,XA,YA), (R1F,R2F,ZC,XA,YA), (R1G,R2F,ZC,XA,YA), (R1H,R2F,ZC,XA,YA), (R1I,R2F,ZC,XA,YA), (R1J,R2F,ZC,XA,YA), (R1K,R2F,ZC,XA,YA), (R1L,R2F,ZC,XA,YA), (R1M,R2F,ZC,XA,YA), (R1N,R2F,ZC,XA,YA), (R1O,R2F,ZC,XA,YA), (R1P,R2F,ZC,XA,YA), (R1Q,R2F,ZC,XA,YA), (R1A,R2G,ZC,XA,YA), (R1B,R2G,ZC,XA,YA), (R1C,R2G,ZC,XA,YA), (R1D,R2G,ZC,XA,YA), (R1E,R2G,ZC,XA,YA), (R1F,R2G,ZC,XA,YA), (R1G,R2G,ZC,XA,YA), (R1H,R2G,ZC,XA,YA), (R1I,R2G,ZC,XA,YA), (R1J,R2G,ZC,XA,YA), (R1K,R2G,ZC,XA,YA), (R1L,R2G,ZC,XA,YA), (R1M,R2G,ZC,XA,YA), (R1N,R2G,ZC,XA,YA), (R1O,R2G,ZC,XA,YA), (R1P,R2G,ZC,XA,YA), (R1Q,R2G,ZC,XA,YA), (R1A,R2H,ZC,XA,YA), (R1B,R2H,ZC,XA,YA), (R1C,R2H,ZC,XA,YA), (R1D,R2H,ZC,XA,YA), (R1E,R2H,ZC,XA,YA), (R1F,R2H,ZC,XA,YA), (R1G,R2H,ZC,XA,YA), (R1H,R2H,ZC,XA,YA), (R1I,R2H,ZC,XA,YA), (R1J,R2H,ZC,XA,YA), (R1K,R2H,ZC,XA,YA), (R1L,R2H,ZC,XA,YA), (R1M,R2H,ZC,XA,YA), (R1N,R2H,ZC,XA,YA), (R1O,R2H,ZC,XA,YA), (R1P,R2H,ZC,XA,YA), (R1Q,R2H,ZC,XA,YA), (R1A,R2I,ZC,XA,YA), (R1B,R2I,ZC,XA,YA), (R1C,R2I,ZC,XA,YA), (R1D,R2I,ZC,XA,YA), (R1E,R2I,ZC,XA,YA), (R1F,R2I,ZC,XA,YA), (R1G,R2I,ZC,XA,YA), (R1H,R2I,ZC,XA,YA), (R1I,R2I,ZC,XA,YA), (R1J,R2I,ZC,XA,YA), (R1K,R2I,ZC,XA,YA), (R1L,R2I,ZC,XA,YA), (R1M,R2I,ZC,XA,YA), (R1N,R2I,ZC,XA,YA), (R1O,R2I,ZC,XA,YA), (R1P,R2I,ZC,XA,YA), (R1Q,R2I,ZC,XA,YA), (R1A,R2J,ZC,XA,YA), (R1B,R2J,ZC,XA,YA), (R1C,R2J,ZC,XA,YA), (R1D,R2J,ZC,XA,YA), (R1E,R2J,ZC,XA,YA), (R1F,R2J,ZC,XA,YA), (R1G,R2J,ZC,XA,YA), (R1H,R2J,ZC,XA,YA), (R1I,R2J,ZC,XA,YA), (R1J,R2J,ZC,XA,YA), (R1K,R2J,ZC,XA,YA), (R1L,R2J,ZC,XA,YA), (R1M,R2J,ZC,XA,YA), (R1N,R2J,ZC,XA,YA), (R1O,R2J,ZC,XA,YA), (R1P,R2J,ZC,XA,YA), (R1Q,R2J,ZC,XA,YA), (R1A,R2K,ZC,XA,YA), (R1B,R2K,ZC,XA,YA), (R1C,R2K,ZC,XA,YA), (R1D,R2K,ZC,XA,YA), (R1E,R2K,ZC,XA,YA), (R1F,R2K,ZC,XA,YA), (R1G,R2K,ZC,XA,YA), (R1H,R2K,ZC,XA,YA), (R1I,R2K,ZC,XA,YA), (R1J,R2K,ZC,XA,YA), (R1K,R2K,ZC,XA,YA), (R1L,R2K,ZC,XA,YA), (R1M,R2K,ZC,XA,YA), (R1N,R2K,ZC,XA,YA), (R1O,R2K,ZC,XA,YA), (R1P,R2K,ZC,XA,YA), (R1Q,R2K,ZC,XA,YA), (R1A,R2L,ZC,XA,YA), (R1B,R2L,ZC,XA,YA), (R1C,R2L,ZC,XA,YA), (R1D,R2L,ZC,XA,YA), (R1E,R2L,ZC,XA,YA), (R1F,R2L,ZC,XA,YA), (R1G,R2L,ZC,XA,YA), (R1H,R2L,ZC,XA,YA), (R1I,R2L,ZC,XA,YA), (R1J,R2L,ZC,XA,YA), (R1K,R2L,ZC,XA,YA), (R1L,R2L,ZC,XA,YA), (R1M,R2L,ZC,XA,YA), (R1N,R2L,ZC,XA,YA), (R1O,R2L,ZC,XA,YA), (R1P,R2L,ZC,XA,YA), (R1Q,R2L,ZC,XA,YA), (R1A,R2M,ZC,XA,YA), (R1B,R2M,ZC,XA,YA), (R1C,R2M,ZC,XA,YA), (R1D,R2M,ZC,XA,YA), (R1E,R2M,ZC,XA,YA), (R1F,R2M,ZC,XA,YA), (R1G,R2M,ZC,XA,YA), (R1H,R2M,ZC,XA,YA), (R1I,R2M,ZC,XA,YA), (R1J,R2M,ZC,XA,YA), (R1K,R2M,ZC,XA,YA), (R1L,R2M,ZC,XA,YA), (R1M,R2M,ZC,XA,YA), (R1N,R2M,ZC,XA,YA), (R1O,R2M,ZC,XA,YA), (R1P,R2M,ZC,XA,YA), (R1Q,R2M,ZC,XA,YA), (R1A,R2N,ZC,XA,YA), (R1B,R2N,ZC,XA,YA), (R1C,R2N,ZC,XA,YA), (R1D,R2N,ZC,XA,YA), (R1E,R2N,ZC,XA,YA), (R1F,R2N,ZC,XA,YA), (R1G,R2N,ZC,XA,YA), (R1H,R2N,ZC,XA,YA), (R1I,R2N,ZC,XA,YA), (R1J,R2N,ZC,XA,YA), (R1K,R2N,ZC,XA,YA), (R1L,R2N,ZC,XA,YA), (R1M,R2N,ZC,XA,YA), (R1N,R2N,ZC,XA,YA), (R1O,R2N,ZC,XA,YA), (R1P,R2N,ZC,XA,YA), (R1Q,R2N,ZC,XA,YA), (R1A,R2O,ZC,XA,YA), (R1B,R2O,ZC,XA,YA), (R1C,R2O,ZC,XA,YA), (R1D,R2O,ZC,XA,YA), (R1E,R2O,ZC,XA,YA), (R1F,R2O,ZC,XA,YA), (R1G,R2O,ZC,XA,YA), (R1H,R2O,ZC,XA,YA), (R1I,R2O,ZC,XA,YA), (R1J,R2O,ZC,XA,YA), (R1K,R2O,ZC,XA,YA), (R1L,R2O,ZC,XA,YA), (R1M,R2O,ZC,XA,YA), (R1N,R2O,ZC,XA,YA), (R1O,R2O,ZC,XA,YA), (R1P,R2O,ZC,XA,YA), (R1Q,R2O,ZC,XA,YA), (R1A,R2P,ZC,XA,YA), (R1B,R2P,ZC,XA,YA), (R1C,R2P,ZC,XA,YA), (R1D,R2P,ZC,XA,YA), (R1E,R2P,ZC,XA,YA), (R1F,R2P,ZC,XA,YA), (R1G,R2P,ZC,XA,YA), (R1H,R2P,ZC,XA,YA), (R1I,R2P,ZC,XA,YA), (R1J,R2P,ZC,XA,YA), (R1K,R2P,ZC,XA,YA), (R1L,R2P,ZC,XA,YA), (R1M,R2P,ZC,XA,YA), (R1N,R2P,ZC,XA,YA), (R1O,R2P,ZC,XA,YA), (R1P,R2P,ZC,XA,YA), (R1Q,R2P,ZC,XA,YA), (R1A,R2Q,ZC,XA,YA), (R1B,R2Q,ZC,XA,YA), (R1C,R2Q,ZC,XA,YA), (R1D,R2Q,ZC,XA,YA), (R1E,R2Q,ZC,XA,YA), (R1F,R2Q,ZC,XA,YA), (R1G,R2Q,ZC,XA,YA), (R1H,R2Q,ZC,XA,YA), (R1I,R2Q,ZC,XA,YA), (R1J,R2Q,ZC,XA,YA), (R1K,R2Q,ZC,XA,YA), (R1L,R2Q,ZC,XA,YA), (R1M,R2Q,ZC,XA,YA), (R1N,R2Q,ZC,XA,YA), (R1O,R2Q,ZC,XA,YA), (R1P,R2Q,ZC,XA,YA), (R1Q,R2Q,ZC,XA,YA), (R1A,R2A,ZD,XA,YA), (R1B,R2A,ZD,XA,YA), (R1C,R2A,ZD,XA,YA), (R1D,R2A,ZD,XA,YA), (R1E,R2A,ZD,XA,YA), (R1F,R2A,ZD,XA,YA), (R1G,R2A,ZD,XA,YA), (R1H,R2A,ZD,XA,YA), (R1I,R2A,ZD,XA,YA), (R1J,R2A,ZD,XA,YA), (R1K,R2A,ZD,XA,YA), (R1L,R2A,ZD,XA,YA), (R1M,R2A,ZD,XA,YA), (R1N,R2A,ZD,XA,YA), (R1O,R2A,ZD,XA,YA), (R1P,R2A,ZD,XA,YA), (R1Q,R2A,ZD,XA,YA), (R1A,R2B,ZD,XA,YA), (R1B,R2B,ZD,XA,YA), (R1C,R2B,ZD,XA,YA), (R1D,R2B,ZD,XA,YA), (R1E,R2B,ZD,XA,YA), (R1F,R2B,ZD,XA,YA), (R1G,R2B,ZD,XA,YA), (R1H,R2B,ZD,XA,YA), (R1I,R2B,ZD,XA,YA), (R1J,R2B,ZD,XA,YA), (R1K,R2B,ZD,XA,YA), (R1L,R2B,ZD,XA,YA), (R1M,R2B,ZD,XA,YA), (R1N,R2B,ZD,XA,YA), (R1O,R2B,ZD,XA,YA), (R1P,R2B,ZD,XA,YA), (R1Q,R2B,ZD,XA,YA), (R1A,R2C,ZD,XA,YA), (R1B,R2C,ZD,XA,YA), (R1C,R2C,ZD,XA,YA), (R1D,R2C,ZD,XA,YA), (R1E,R2C,ZD,XA,YA), (R1F,R22C,ZD,XA,YA), (R1G,R2C,ZD,XA,YA), (R1H,R2C,ZD,XA,YA), (R1I,R2C,ZD,XA,YA), (R1J,R22C,ZD,XA,YA), (R1K,R2C,ZD,XA,YA), (R1L,R2C,ZD,XA,YA), (R1M,R2C,ZD,XA,YA), (R1N,R2C,ZD,XA,YA), (R1O,R2C,ZD,XA,YA), (R1P,R2C,ZD,XA,YA), (R1Q,R2C,ZD,XA,YA), (R1A,R2D,ZD,XA,YA), (R1B,R2D,ZD,XA,YA), (R1C,R2D,ZD,XA,YA), (R1D,R2D,ZD,XA,YA), (R1E,R2D,ZD,XA,YA), (R1F,R2D,ZD,XA,YA), (R1G,R2D,ZD,XA,YA), (R1H,R2D,ZD,XA,YA), (R1I,R2D,ZD,XA,YA), (R1J,R2D,ZD,XA,YA), (R1K,R2D,ZD,XA,YA), (R1L,R2D,ZD,XA,YA), (R1M,R2D,ZD,XA,YA), (R1N,R2D,ZD,XA,YA), (R1O,R2D,ZD,XA,YA), (R1P,R2D,ZD,XA,YA), (R1Q,R2D,ZD,XA,YA), (R1A,R2E,ZD,XA,YA), (R1B,R2E,ZD,XA,YA), (R1C,R2E,ZD,XA,YA), (R1D,R2E,ZD,XA,YA), (R1E,R2E,ZD,XA,YA), (R1F,R2E,ZD,XA,YA), (R1G,R2E,ZD,XA,YA), (R1H,R2E,ZD,XA,YA), (R1I,R2E,ZD,XA,YA), (R1J,R2E,ZD,XA,YA), (R1K,R2E,ZD,XA,YA), (R1L,R2E,ZD,XA,YA), (R1M,R2E,ZD,XA,YA), (R1N,R2E,ZD,XA,YA), (R1O,R2E,ZD,XA,YA), (R1P,R2E,ZD,XA,YA), (R1Q,R2E,ZD,XA,YA), (R1A,R2F,ZD,XA,YA), (R1B,R2F,ZD,XA,YA), (R1C,R2F,ZD,XA,YA), (R1D,R2F,ZD,XA,YA), (R1E,R2F,ZD,XA,YA), (R1F,R2F,ZD,XA,YA), (R1G,R2F,ZD,XA,YA), (R1H,R2F,ZD,XA,YA), (R1I,R2F,ZD,XA,YA), (R1J,R2F,ZD,XA,YA), (R1K,R2F,ZD,XA,YA), (R1L,R2F,ZD,XA,YA), (R1M,R2F,ZD,XA,YA), (R1N,R2F,ZD,XA,YA), (R1O,R2F,ZD,XA,YA), (R1P,R2F,ZD,XA,YA), (R1Q,R2F,ZD,XA,YA), (R1A,R2G,ZD,XA,YA), (R1B,R2G,ZD,XA,YA), (R1C,R2G,ZD,XA,YA), (R1D,R2G,ZD,XA,YA), (R1E,R2G,ZD,XA,YA), (R1F,R2G,ZD,XA,YA), (R1G,R2G,ZD,XA,YA), (R1H,R2G,ZD,XA,YA), (R1I,R2G,ZD,XA,YA), (R1J,R2G,ZD,XA,YA), (R1K,R2G,ZD,XA,YA), (R1L,R2G,ZD,XA,YA), (R1M,R2G,ZD,XA,YA), (R1N,R2G,ZD,XA,YA), (R1O,R2G,ZD,XA,YA), (R1P,R2G,ZD,XA,YA), (R1Q,R2G,ZD,XA,YA), (R1A,R2H,ZD,XA,YA), (R1B,R2H,ZD,XA,YA), (R1C,R2H,ZD,XA,YA), (R1D,R2H,ZD,XA,YA), (R1E,R2H,ZD,XA,YA), (R1F,R2H,ZD,XA,YA), (R1G,R2H,ZD,XA,YA), (R1H,R2H,ZD,XA,YA), (R1I,R2H,ZD,XA,YA), (R1J,R2H,ZD,XA,YA), (R1K,R2H,ZD,XA,YA), (R1L,R2H,ZD,XA,YA), (R1M,R2H,ZD,XA,YA), (R1N,R2H,ZD,XA,YA), (R1O,R2H,ZD,XA,YA), (R1P,R2H,ZD,XA,YA), (R1Q,R2H,ZD,XA,YA), (R1A,R2I,ZD,XA,YA), (R1B,R2I,ZD,XA,YA), (R1C,R2I,ZD,XA,YA), (R1D,R2I,ZD,XA,YA), (R1E,R2I,ZD,XA,YA), (R1F,R2I,ZD,XA,YA), (R1G,R2I,ZD,XA,YA), (R1H,R2I,ZD,XA,YA), (R1I,R2I,ZD,XA,YA), (R1J,R2I,ZD,XA,YA), (R1K,R2I,ZD,XA,YA), (R1L,R2I,ZD,XA,YA), (R1M,R2I,ZD,XA,YA), (R1N,R2I,ZD,XA,YA), (R1O,R2I,ZD,XA,YA), (R1P,R2I,ZD,XA,YA), (R1Q,R2I,ZD,XA,YA), (R1A,R2J,ZD,XA,YA), (R1B,R2J,ZD,XA,YA), (R1C,R2J,ZD,XA,YA), (R1D,R2J,ZD,XA,YA), (R1E,R2J,ZD,XA,YA), (R1F,R2J,ZD,XA,YA), (R1G,R2J,ZD,XA,YA), (R1H,R2J,ZD,XA,YA), (R1I,R2J,ZD,XA,YA), (R1J,R2J,ZD,XA,YA), (R1K,R2J,ZD,XA,YA), (R1L,R2J,ZD,XA,YA), (R1M,R2J,ZD,XA,YA), (R1N,R2J,ZD,XA,YA), (R1O,R2J,ZD,XA,YA), (R1P,R2J,ZD,XA,YA), (R1Q,R2J,ZD,XA,YA), (R1A,R2K,ZD,XA,YA), (R1B,R2K,ZD,XA,YA), (R1C,R2K,ZD,XA,YA), (R1D,R2K,ZD,XA,YA), (R1E,R2K,ZD,XA,YA), (R1F,R2K,ZD,XA,YA), (R1G,R2K,ZD,XA,YA), (R1H,R2K,ZD,XA,YA), (R1I,R2K,ZD,XA,YA), (R1J,R2K,ZD,XA,YA), (R1K,R2K,ZD,XA,YA), (R1L,R2K,ZD,XA,YA), (R1M,R2K,ZD,XA,YA), (R1N,R2K,ZD,XA,YA), (R1O,R2K,ZD,XA,YA), (R1P,R2K,ZD,XA,YA), (R1Q,R2K,ZD,XA,YA), (R1A,R2L,ZD,XA,YA), (R1B,R2L,ZD,XA,YA), (R1C,R2L,ZD,XA,YA), (R1D,R2L,ZD,XA,YA), (R1E,R2L,ZD,XA,YA), (R1F,R2L,ZD,XA,YA), (R1G,R2L,ZD,XA,YA), (R1H,R2L,ZD,XA,YA), (R1I,R2L,ZD,XA,YA), (R1J,R2L,ZD,XA,YA), (R1K,R2L,ZD,XA,YA), (R1L,R2L,ZD,XA,YA), (R1M,R2L,ZD,XA,YA), (R1N,R2L,ZD,XA,YA), (R1O,R2L,ZD,XA,YA), (R1P,R2L,ZD,XA,YA), (R1Q,R2L,ZD,XA,YA), (R1A,R2M,ZD,XA,YA), (R1B,R2M,ZD,XA,YA), (R1C,R2M,ZD,XA,YA), (R1D,R2M,ZD,XA,YA), (R1E,R2M,ZD,XA,YA), (R1F,R2M,ZD,XA,YA), (R1G,R2M,ZD,XA,YA), (R1H,R2M,ZD,XA,YA), (R1I,R2M,ZD,XA,YA), (R1J,R2M,ZD,XA,YA), (R1K,R2M,ZD,XA,YA), (R1L,R2M,ZD,XA,YA), (R1M,R2M,ZD,XA,YA), (R1N,R2M,ZD,XA,YA), (R1O,R2M,ZD,XA,YA), (R1P,R2M,ZD,XA,YA), (R1Q,R2M,ZD,XA,YA), (R1A,R2N,ZD,XA,YA), (R1B,R2N,ZD,XA,YA), (R1C,R2N,ZD,XA,YA), (R1D,R2N,ZD,XA,YA), (R1E,R2N,ZD,XA,YA), (R1F,R2N,ZD,XA,YA), (R1G,R2N,ZD,XA,YA), (R1H,R2N,ZD,XA,YA), (R1I,R2N,ZD,XA,YA), (R1J,R2N,ZD,XA,YA), (R1K,R2N,ZD,XA,YA), (R1L,R2N,ZD,XA,YA), (R1M,R2N,ZD,XA,YA), (R1N,R2N,ZD,XA,YA), (R1O,R2N,ZD,XA,YA), (R1P,R2N,ZD,XA,YA), (R1Q,R2N,ZD,XA,YA), (R1A,R2O,ZD,XA,YA), (R1B,R2O,ZD,XA,YA), (R1C,R2O,ZD,XA,YA), (R1D,R2O,ZD,XA,YA), (R1E,R2O,ZD,XA,YA), (R1F,R2O,ZD,XA,YA), (R1G,R2O,ZD,XA,YA), (R1H,R2O,ZD,XA,YA), (R1I,R2O,ZD,XA,YA), (R1J,R2O,ZD,XA,YA), (R1K,R2O,ZD,XA,YA), (R1L,R2O,ZD,XA,YA), (R1M,R2O,ZD,XA,YA), (R1N,R2O,ZD,XA,YA), (R1O,R2O,ZD,XA,YA), (R1P,R2O,ZD,XA,YA), (R1Q,R2O,ZD,XA,YA), (R1A,R2P,ZD,XA,YA), (R1B,R2P,ZD,XA,YA), (R1C,R2P,ZD,XA,YA), (R1D,R2P,ZD,XA,YA), (R1E,R2P,ZD,XA,YA), (R1F,R2P,ZD,XA,YA), (R1G,R2P,ZD,XA,YA), (R1H,R2P,ZD,XA,YA), (R1I,R2P,ZD,XA,YA), (R1J,R2P,ZD,XA,YA), (R1K,R2P,ZD,XA,YA), (R1L,R2P,ZD,XA,YA), (R1M,R2P,ZD,XA,YA), (R1N,R2P,ZD,XA,YA), (R1O,R2P,ZD,XA,YA), (R1P,R2P,ZD,XA,YA), (R1Q,R2P,ZD,XA,YA), (R1A,R2Q,ZD,XA,YA), (R1B,R2Q,ZD,XA,YA), (R1C,R2Q,ZD,XA,YA), (R1D,R2Q,ZD,XA,YA), (R1E,R2Q,ZD,XA,YA), (R1F,R2Q,ZD,XA,YA), (R1G,R2Q,ZD,XA,YA), (R1H,R2Q,ZD,XA,YA), (R1I,R2Q,ZD,XA,YA), (R1J,R2Q,ZD,XA,YA), (R1K,R2Q,ZD,XA,YA), (R1L,R2Q,ZD,XA,YA), (R1M,R2Q,ZD,XA,YA), (R1N,R2Q,ZD,XA,YA), (R1O,R2Q,ZD,XA,YA), (R1P,R2Q,ZD,XA,YA), (R1Q,R2Q,ZD,XA,YA), (R1A,R2A,ZE,XA,YA), (R1B,R2A,ZE,XA,YA), (R1C,R2A,ZE,XA,YA), (R1D,R2A,ZE,XA,YA), (R1E,R2A,ZE,XA,YA), (R1F,R2A,ZE,XA,YA), (R1G,R2A,ZE,XA,YA), (R1H,R2A,ZE,XA,YA), (R1I,R2A,ZE,XA,YA), (R1J,R2A,ZE,XA,YA), (R1K,R2A,ZE,XA,YA), (R1L,R2A,ZE,XA,YA), (R1M,R2A,ZE,XA,YA), (R1N,R2A,ZE,XA,YA), (R1O,R2A,ZE,XA,YA), (R1P,R2A,ZE,XA,YA), (R1Q,R2A,ZE,XA,YA), (R1A,R2B,ZE,XA,YA), (R1B,R2B,ZE,XA,YA), (R1C,R2B,ZE,XA,YA), (R1D,R2B,ZE,XA,YA), (R1E,R2B,ZE,XA,YA), (R1F,R2B,ZE,XA,YA), (R1G,R2B,ZE,XA,YA), (R1H,R2B,ZE,XA,YA), (R1I,R2B,ZE,XA,YA), (R1J,R2B,ZE,XA,YA), (R1K,R2B,ZE,XA,YA), (R1L,R2B,ZE,XA,YA), (R1M,R2B,ZE,XA,YA), (R1N,R2B,ZE,XA,YA), (R1O,R2B,ZE,XA,YA), (R1P,R2B,ZE,XA,YA), (R1Q,R2B,ZE,XA,YA), (R1A,R2C,ZE,XA,YA), (R1B,R2C,ZE,XA,YA), (R1C,R2C,ZE,XA,YA), (R1D,R2C,ZE,XA,YA), (R1E,R2C,ZE,XA,YA), (R1F,R2C,ZE,XA,YA), (R1G,R2C,ZE,XA,YA), (R1H,R2C,ZE,XA,YA), (R1I,R2C,ZE,XA,YA), (R1J,R2C,ZE,XA,YA), (R1K,R2C,ZE,XA,YA), (R1L,R2C,ZE,XA,YA), (R1M,R2C,ZE,XA,YA), (R1N,R2C,ZE,XA,YA), (R1O,R2C,ZE,XA,YA), (R1P,R2C,ZE,XA,YA), (R1Q,R22C,ZE,XA,YA), (R1A,R2D,ZE,XA,YA), (R1B,R2D,ZE,XA,YA), (R1C,R2D,ZE,XA,YA), (R1D,R2D,ZE,XA,YA), (R1E,R2D,ZE,XA,YA), (R1F,R2D,ZE,XA,YA), (R1G,R2D,ZE,XA,YA), (R1H,R2D,ZE,XA,YA), (R1I,R2D,ZE,XA,YA), (R1J,R2D,ZE,XA,YA), (R1K,R2D,ZE,XA,YA), (R1L,R2D,ZE,XA,YA), (R1M,R2D,ZE,XA,YA), (R1N,R2D,ZE,XA,YA), (R1O,R2D,ZE,XA,YA), (R1P,R2D,ZE,XA,YA), (R1Q,R2D,ZE,XA,YA), (R1A,R2E,ZE,XA,YA), (R1B,R2E,ZE,XA,YA), (R1C,R2E,ZE,XA,YA), (R1D,R2E,ZE,XA,YA), (R1E,R2E,ZE,XA,YA), (R1F,R2E,ZE,XA,YA), (R1G,R2E,ZE,XA,YA), (R1H,R2E,ZE,XA,YA), (R1I,R2E,ZE,XA,YA), (R1J,R2E,ZE,XA,YA), (R1K,R2E,ZE,XA,YA), (R1L,R2E,ZE,XA,YA), (R1M,R2E,ZE,XA,YA), (R1N,R2E,ZE,XA,YA), (R1O,R2E,ZE,XA,YA), (R1P,R2E,ZE,XA,YA), (R1Q,R2E,ZE,XA,YA), (R1A,R2F,ZE,XA,YA), (R1B,R2F,ZE,XA,YA), (R1C,R2F,ZE,XA,YA), (R1D,R2F,ZE,XA,YA), (R1E,R2F,ZE,XA,YA), (R1F,R2F,ZE,XA,YA), (R1G,R2F,ZE,XA,YA), (R1H,R2F,ZE,XA,YA), (R1I,R2F,ZE,XA,YA), (R1J,R2F,ZE,XA,YA), (R1K,R2F,ZE,XA,YA), (R1L,R2F,ZE,XA,YA), (R1M,R2F,ZE,XA,YA), (R1N,R2F,ZE,XA,YA), (R1O,R2F,ZE,XA,YA), (R1P,R2F,ZE,XA,YA), (R1Q,R2F,ZE,XA,YA), (R1A,R2G,ZE,XA,YA), (R1B,R2G,ZE,XA,YA), (R1C,R2G,ZE,XA,YA), (R1D,R2G,ZE,XA,YA), (R1E,R2G,ZE,XA,YA), (R1F,R2G,ZE,XA,YA), (R1G,R2G,ZE,XA,YA), (R1H,R2G,ZE,XA,YA), (R1I,R2G,ZE,XA,YA), (R1J,R2G,ZE,XA,YA), (R1K,R2G,ZE,XA,YA), (R1L,R2G,ZE,XA,YA), (R1M,R2G,ZE,XA,YA), (R1N,R2G,ZE,XA,YA), (R1O,R2G,ZE,XA,YA), (R1P,R2G,ZE,XA,YA), (R1Q,R2G,ZE,XA,YA), (R1A,R2H,ZE,XA,YA), (R1B,R2H,ZE,XA,YA), (R1C,R2H,ZE,XA,YA), (R1D,R2H,ZE,XA,YA), (R1E,R2H,ZE,XA,YA), (R1F,R2H,ZE,XA,YA), (R1G,R2H,ZE,XA,YA), (R1H,R2H,ZE,XA,YA), (R1I,R2H,ZE,XA,YA), (R1J,R2H,ZE,XA,YA), (R1K,R2H,ZE,XA,YA), (R1L,R2H,ZE,XA,YA), (R1M,R2H,ZE,XA,YA), (R1N,R2H,ZE,XA,YA), (R1O,R2H,ZE,XA,YA), (R1P,R2H,ZE,XA,YA), (R1Q,R2H,ZE,XA,YA), (R1A,R2I,ZE,XA,YA), (R1B,R2I,ZE,XA,YA), (R1C,R2I,ZE,XA,YA), (R1D,R2I,ZE,XA,YA), (R1E,R2I,ZE,XA,YA), (R1F,R2I,ZE,XA,YA), (R1G,R2I,ZE,XA,YA), (R1H,R2I,ZE,XA,YA), (R1I,R2I,ZE,XA,YA), (R1J,R2I,ZE,XA,YA), (R1K,R2I,ZE,XA,YA), (R1L,R2I,ZE,XA,YA), (R1M,R2I,ZE,XA,YA), (R1N,R2I,ZE,XA,YA), (R1O,R2I,ZE,XA,YA), (R1P,R2I,ZE,XA,YA), (R1Q,R2I,ZE,XA,YA), (R1A,R2J,ZE,XA,YA), (R1B,R2J,ZE,XA,YA), (R1C,R2J,ZE,XA,YA), (R1D,R2J,ZE,XA,YA), (R1E,R2J,ZE,XA,YA), (R1F,R2J,ZE,XA,YA), (R1G,R2J,ZE,XA,YA), (R1H,R2J,ZE,XA,YA), (R1I,R2J,ZE,XA,YA), (R1J,R2J,ZE,XA,YA), (R1K,R2J,ZE,XA,YA), (R1L,R2J,ZE,XA,YA), (R1M,R2J,ZE,XA,YA), (R1N,R2J,ZE,XA,YA), (R1O,R2J,ZE,XA,YA), (R1P,R2J,ZE,XA,YA), (R1Q,R2J,ZE,XA,YA), (R1A,R2K,ZE,XA,YA), (R1B,R2K,ZE,XA,YA), (R1C,R2K,ZE,XA,YA), (R1D,R2K,ZE,XA,YA), (R1E,R2K,ZE,XA,YA), (R1F,R2K,ZE,XA,YA), (R1G,R2K,ZE,XA,YA), (R1H,R2K,ZE,XA,YA), (R1I,R2K,ZE,XA,YA), (R1J,R2K,ZE,XA,YA), (R1K,R2K,ZE,XA,YA), (R1L,R2K,ZE,XA,YA), (R1M,R2K,ZE,XA,YA), (R1N,R2K,ZE,XA,YA), (R1O,R2K,ZE,XA,YA), (R1P,R2K,ZE,XA,YA), (R1Q,R2K,ZE,XA,YA), (R1A,R2L,ZE,XA,YA), (R1B,R2L,ZE,XA,YA), (R1C,R2L,ZE,XA,YA), (R1D,R2L,ZE,XA,YA), (R1E,R2L,ZE,XA,YA), (R1F,R2L,ZE,XA,YA), (R1G,R2L,ZE,XA,YA), (R1H,R2L,ZE,XA,YA), (R1I,R2L,ZE,XA,YA), (R1J,R2L,ZE,XA,YA), (R1K,R2L,ZE,XA,YA), (R1L,R2L,ZE,XA,YA), (R1M,R2L,ZE,XA,YA), (R1N,R2L,ZE,XA,YA), (R1O,R2L,ZE,XA,YA), (R1P,R2L,ZE,XA,YA), (R1Q,R2L,ZE,XA,YA), (R1A,R2M,ZE,XA,YA), (R1B,R2M,ZE,XA,YA), (R1C,R2M,ZE,XA,YA), (R1D,R2M,ZE,XA,YA), (R1E,R2M,ZE,XA,YA), (R1F,R2M,ZE,XA,YA), (R1G,R2M,ZE,XA,YA), (R1H,R2M,ZE,XA,YA), (R1I,R2M,ZE,XA,YA), (R1J,R2M,ZE,XA,YA), (R1K,R2M,ZE,XA,YA), (R1L,R2M,ZE,XA,YA), (R1M,R2M,ZE,XA,YA), (R1N,R2M,ZE,XA,YA), (R1O,R2M,ZE,XA,YA), (R1P,R2M,ZE,XA,YA), (R1Q,R2M,ZE,XA,YA), (R1A,R2N,ZE,XA,YA), (R1B,R2N,ZE,XA,YA), (R1C,R2N,ZE,XA,YA), (R1D,R2N,ZE,XA,YA), (R1E,R2N,ZE,XA,YA), (R1F,R2N,ZE,XA,YA), (R1G,R2N,ZE,XA,YA), (R1H,R2N,ZE,XA,YA), (R1I,R2N,ZE,XA,YA), (R1J,R2N,ZE,XA,YA), (R1K,R2N,ZE,XA,YA), (R1L,R2N,ZE,XA,YA), (R1M,R2N,ZE,XA,YA), (R1N,R2N,ZE,XA,YA), (R1O,R2N,ZE,XA,YA), (R1P,R2N,ZE,XA,YA), (R1Q,R2N,ZE,XA,YA), (R1A,R2O,ZE,XA,YA), (R1B,R2O,ZE,XA,YA), (R1C,R2O,ZE,XA,YA), (R1D,R2O,ZE,XA,YA), (R1E,R2O,ZE,XA,YA), (R1F,R2O,ZE,XA,YA), (R1G,R2O,ZE,XA,YA), (R1H,R2O,ZE,XA,YA), (R1I,R2O,ZE,XA,YA), (R1J,R2O,ZE,XA,YA), (R1K,R2O,ZE,XA,YA), (R1L,R2O,ZE,XA,YA), (R1M,R2O,ZE,XA,YA), (R1N,R2O,ZE,XA,YA), (R1O,R2O,ZE,XA,YA), (R1P,R2O,ZE,XA,YA), (R1Q,R2O,ZE,XA,YA), (R1A,R2P,ZE,XA,YA), (R1B,R2P,ZE,XA,YA), (R1C,R2P,ZE,XA,YA), (R1D,R2P,ZE,XA,YA), (R1E,R2P,ZE,XA,YA), (R1F,R2P,ZE,XA,YA), (R1G,R2P,ZE,XA,YA), (R1H,R2P,ZE,XA,YA), (R1I,R2P,ZE,XA,YA), (R1J,R2P,ZE,XA,YA), (R1K,R2P,ZE,XA,YA), (R1L,R2P,ZE,XA,YA), (R1M,R2P,ZE,XA,YA), (R1N,R2P,ZE,XA,YA), (R1O,R2P,ZE,XA,YA), (R1P,R2P,ZE,XA,YA), (R1Q,R2P,ZE,XA,YA), (R1A,R2Q,ZE,XA,YA), (R1B,R2Q,ZE,XA,YA), (R1C,R2Q,ZE,XA,YA), (R1D,R2Q,ZE,XA,YA), (R1E,R2Q,ZE,XA,YA), (R1F,R2Q,ZE,XA,YA), (R1G,R2Q,ZE,XA,YA), (R1H,R2Q,ZE,XA,YA), (R1I,R2Q,ZE,XA,YA), (R1J,R2Q,ZE,XA,YA), (R1K,R2Q,ZE,XA,YA), (R1L,R2Q,ZE,XA,YA), (R1M,R2Q,ZE,XA,YA), (R1N,R2Q,ZE,XA,YA), (R1O,R2Q,ZE,XA,YA), (R1P,R2Q,ZE,XA,YA), (R1Q,R2Q,ZE,XA,YA), (R1A,R2A,ZF,XA,YA), (R1B,R2A,ZF,XA,YA), (R1C,R2A,ZF,XA,YA), (R1D,R2A,ZF,XA,YA), (R1E,R2A,ZF,XA,YA), (R1F,R2A,ZF,XA,YA), (R1G,R2A,ZF,XA,YA), (R1H,R2A,ZF,XA,YA), (R1I,R2A,ZF,XA,YA), (R1J,R2A,ZF,XA,YA), (R1K,R2A,ZF,XA,YA), (R1L,R2A,ZF,XA,YA), (R1M,R2A,ZF,XA,YA), (R1N,R2A,ZF,XA,YA), (R1O,R2A,ZF,XA,YA), (R1P,R2A,ZF,XA,YA), (R1Q,R2A,ZF,XA,YA), (R1A,R2B,ZF,XA,YA), (R1B,R2B,ZF,XA,YA), (R1C,R2B,ZF,XA,YA), (R1D,R2B,ZF,XA,YA), (R1E,R2B,ZF,XA,YA), (R1F,R2B,ZF,XA,YA), (R1G,R2B,ZF,XA,YA), (R1H,R2B,ZF,XA,YA), (R1I,R2B,ZF,XA,YA), (R1J,R2B,ZF,XA,YA), (R1K,R2B,ZF,XA,YA), (R1L,R2B,ZF,XA,YA), (R1M,R2B,ZF,XA,YA), (R1N,R2B,ZF,XA,YA), (R1O,R2B,ZF,XA,YA), (R1P,R2B,ZF,XA,YA), (R1Q,R2B,ZF,XA,YA), (R1A,R2C,ZF,XA,YA), (R1B,R2C,ZF,XA,YA), (R1C,R2C,ZF,XA,YA), (R1D,R2C,ZF,XA,YA), (R1E,R2C,ZF,XA,YA), (R1F,R2C,ZF,XA,YA), (R1G,R2C,ZF,XA,YA), (R1H,R2C,ZF,XA,YA), (R1I,R2C,ZF,XA,YA), (R1J,R2C,ZF,XA,YA), (R1K,R2C,ZF,XA,YA), (R1L,R2C,ZF,XA,YA), (R1M,R2C,ZF,XA,YA), (R1N,R2C,ZF,XA,YA), (R1O,R2C,ZF,XA,YA), (R1P,R2C,ZF,XA,YA), (R1Q,R2C,ZF,XA,YA), (R1A,R2D,ZF,XA,YA), (R1B,R2D,ZF,XA,YA), (R1C,R2D,ZF,XA,YA), (R1D,R2D,ZF,XA,YA), (R1E,R2D,ZF,XA,YA), (R1F,R2D,ZF,XA,YA), (R1G,R2D,ZF,XA,YA), (R1H,R2D,ZF,XA,YA), (R1I,R2D,ZF,XA,YA), (R1J,R2D,ZF,XA,YA), (R1K,R2D,ZF,XA,YA), (R1L,R2D,ZF,XA,YA), (R1M,R2D,ZF,XA,YA), (R1N,R2D,ZF,XA,YA), (R1O,R2D,ZF,XA,YA), (R1P,R2D,ZF,XA,YA), (R1Q,R2D,ZF,XA,YA), (R1A,R2E,ZF,XA,YA), (R1B,R2E,ZF,XA,YA), (R1C,R2E,ZF,XA,YA), (R1D,R2E,ZF,XA,YA), (R1E,R2E,ZF,XA,YA), (R1F,R2E,ZF,XA,YA), (R1G,R2E,ZF,XA,YA), (R1H,R2E,ZF,XA,YA), (R1I,R2E,ZF,XA,YA), (R1J,R2E,ZF,XA,YA), (R1K,R2E,ZF,XA,YA), (R1L,R2E,ZF,XA,YA), (R1M,R2E,ZF,XA,YA), (R1N,R2E,ZF,XA,YA), (R1O,R2E,ZF,XA,YA), (R1P,R2E,ZF,XA,YA), (R1Q,R2E,ZF,XA,YA), (R1A,R2F,ZF,XA,YA), (R1B,R2F,ZF,XA,YA), (R1C,R2F,ZF,XA,YA), (R1D,R2F,ZF,XA,YA), (R1E,R2F,ZF,XA,YA), (R1F,R2F,ZF,XA,YA), (R1G,R2F,ZF,XA,YA), (R1H,R2F,ZF,XA,YA), (R1I,R2F,ZF,XA,YA), (R1J,R2F,ZF,XA,YA), (R1K,R2F,ZF,XA,YA), (R1L,R2F,ZF,XA,YA), (R1M,R2F,ZF,XA,YA), (R1N,R2F,ZF,XA,YA), (R1O,R2F,ZF,XA,YA), (R1P,R2F,ZF,XA,YA), (R1Q,R2F,ZF,XA,YA), (R1A,R2G,ZF,XA,YA), (R1B,R2G,ZF,XA,YA), (R1C,R2G,ZF,XA,YA), (R1D,R2G,ZF,XA,YA), (R1E,R2G,ZF,XA,YA), (R1F,R2G,ZF,XA,YA), (R1G,R2G,ZF,XA,YA), (R1H,R2G,ZF,XA,YA), (R1I,R2G,ZF,XA,YA), (R1J,R2G,ZF,XA,YA), (R1K,R2G,ZF,XA,YA), (R1L,R2G,ZF,XA,YA), (R1M,R2G,ZF,XA,YA), (R1N,R2G,ZF,XA,YA), (R1O,R2G,ZF,XA,YA), (R1P,R2G,ZF,XA,YA), (R1Q,R2G,ZF,XA,YA), (R1A,R2H,ZF,XA,YA), (R1B,R2H,ZF,XA,YA), (R1C,R2H,ZF,XA,YA), (R1D,R2H,ZF,XA,YA), (R1E,R2H,ZF,XA,YA), (R1F,R2H,ZF,XA,YA), (R1G,R2H,ZF,XA,YA), (R1H,R2H,ZF,XA,YA), (R1I,R2H,ZF,XA,YA), (R1J,R2H,ZF,XA,YA), (R1K,R2H,ZF,XA,YA), (R1L,R2H,ZF,XA,YA), (R1M,R2H,ZF,XA,YA), (R1N,R2H,ZF,XA,YA), (R1O,R2H,ZF,XA,YA), (R1P,R2H,ZF,XA,YA), (R1Q,R2H,ZF,XA,YA), (R1A,R2I,ZF,XA,YA), (R1B,R2I,ZF,XA,YA), (R1C,R2I,ZF,XA,YA), (R1D,R2I,ZF,XA,YA), (R1E,R2I,ZF,XA,YA), (R1F,R2I,ZF,XA,YA), (R1G,R2I,ZF,XA,YA), (R1H,R2I,ZF,XA,YA), (R1I,R2I,ZF,XA,YA), (R1J,R2I,ZF,XA,YA), (R1K,R2I,ZF,XA,YA), (R1L,R2I,ZF,XA,YA), (R1M,R2I,ZF,XA,YA), (R1N,R2I,ZF,XA,YA), (R1O,R2I,ZF,XA,YA), (R1P,R2I,ZF,XA,YA), (R1Q,R2I,ZF,XA,YA), (R1A,R2J,ZF,XA,YA), (R1B,R2J,ZF,XA,YA), (R1C,R2J,ZF,XA,YA), (R1D,R2J,ZF,XA,YA), (R1E,R2J,ZF,XA,YA), (R1F,R2J,ZF,XA,YA), (R1G,R2J,ZF,XA,YA), (R1H,R2J,ZF,XA,YA), (R1I,R2J,ZF,XA,YA), (R1J,R2J,ZF,XA,YA), (R1K,R2J,ZF,XA,YA), (R1L,R2J,ZF,XA,YA), (R1M,R2J,ZF,XA,YA), (R1N,R2J,ZF,XA,YA), (R1O,R2J,ZF,XA,YA), (R1P,R2J,ZF,XA,YA), (R1Q,R2J,ZF,XA,YA), (R1A,R2K,ZF,XA,YA), (R1B,R2K,ZF,XA,YA), (R1C,R2K,ZF,XA,YA), (R1D,R2K,ZF,XA,YA), (R1E,R2K,ZF,XA,YA), (R1F,R2K,ZF,XA,YA), (R1G,R2K,ZF,XA,YA), (R1H,R2K,ZF,XA,YA), (R1I,R2K,ZF,XA,YA), (R1J,R2K,ZF,XA,YA), (R1K,R2K,ZF,XA,YA), (R1L,R2K,ZF,XA,YA), (R1M,R2K,ZF,XA,YA), (R1N,R2K,ZF,XA,YA), (R1O,R2K,ZF,XA,YA), (R1P,R2K,ZF,XA,YA), (R1Q,R2K,ZF,XA,YA), (R1A,R2L,ZF,XA,YA), (R1B,R2L,ZF,XA,YA), (R1C,R2L,ZF,XA,YA), (R1D,R2L,ZF,XA,YA), (R1E,R2L,ZF,XA,YA), (R1F,R2L,ZF,XA,YA), (R1G,R2L,ZF,XA,YA), (R1H,R2L,ZF,XA,YA), (R1I,R2L,ZF,XA,YA), (R1J,R2L,ZF,XA,YA), (R1K,R2L,ZF,XA,YA), (R1L,R2L,ZF,XA,YA), (R1M,R2L,ZF,XA,YA), (R1N,R2L,ZF,XA,YA), (R1O,R2L,ZF,XA,YA), (R1P,R2L,ZF,XA,YA), (R1Q,R2L,ZF,XA,YA), (R1A,R2M,ZF,XA,YA), (R1B,R2M,ZF,XA,YA), (R1C,R2M,ZF,XA,YA), (R1D,R2M,ZF,XA,YA), (R1E,R2M,ZF,XA,YA), (R1F,R2M,ZF,XA,YA), (R1G,R2M,ZF,XA,YA), (R1H,R2M,ZF,XA,YA), (R1I,R2M,ZF,XA,YA), (R1J,R2M,ZF,XA,YA), (R1K,R2M,ZF,XA,YA), (R1L,R2M,ZF,XA,YA), (R1M,R2M,ZF,XA,YA), (R1N,R2M,ZF,XA,YA), (R1O,R2M,ZF,XA,YA), (R1P,R2M,ZF,XA,YA), (R1Q,R2M,ZF,XA,YA), (R1A,R2N,ZF,XA,YA), (R1B,R2N,ZF,XA,YA), (R1C,R2N,ZF,XA,YA), (R1D,R2N,ZF,XA,YA), (R1E,R2N,ZF,XA,YA), (R1F,R2N,ZF,XA,YA), (R1G,R2N,ZF,XA,YA), (R1H,R2N,ZF,XA,YA), (R1I,R2N,ZF,XA,YA), (R1J,R2N,ZF,XA,YA), (R1K,R2N,ZF,XA,YA), (R1L,R2N,ZF,XA,YA), (R1M,R2N,ZF,XA,YA), (R1N,R2N,ZF,XA,YA), (R1O,R2N,ZF,XA,YA), (R1P,R2N,ZF,XA,YA), (R1Q,R2N,ZF,XA,YA), (R1A,R2O,ZF,XA,YA), (R1B,R2O,ZF,XA,YA), (R1C,R2O,ZF,XA,YA), (R1D,R2O,ZF,XA,YA), (R1E,R2O,ZF,XA,YA), (R1F,R2O,ZF,XA,YA), (R1G,R2O,ZF,XA,YA), (R1H,R2O,ZF,XA,YA), (R1I,R2O,ZF,XA,YA), (R1J,R2O,ZF,XA,YA), (R1K,R2O,ZF,XA,YA), (R1L,R2O,ZF,XA,YA), (R1M,R2O,ZF,XA,YA), (R1N,R2O,ZF,XA,YA), (R1O,R2O,ZF,XA,YA), (R1P,R2O,ZF,XA,YA), (R1Q,R2O,ZF,XA,YA), (R1A,R2P,ZF,XA,YA), (R1B,R2P,ZF,XA,YA), (R1C,R2P,ZF,XA,YA), (R1D,R2P,ZF,XA,YA), (R1E,R2P,ZF,XA,YA), (R1F,R2P,ZF,XA,YA), (R1G,R2P,ZF,XA,YA), (R1H,R2P,ZF,XA,YA), (R1I,R2P,ZF,XA,YA), (R1J,R2P,ZF,XA,YA), (R1K,R2P,ZF,XA,YA), (R1L,R2P,ZF,XA,YA), (R1M,R2P,ZF,XA,YA), (R1N,R2P,ZF,XA,YA), (R1O,R2P,ZF,XA,YA), (R1P,R2P,ZF,XA,YA), (R1Q,R2P,ZF,XA,YA), (R1A,R2Q,ZF,XA,YA), (R1B,R2Q,ZF,XA,YA), (R1C,R2Q,ZF,XA,YA), (R1D,R2Q,ZF,XA,YA), (R1E,R2Q,ZF,XA,YA), (R1F,R2Q,ZF,XA,YA), (R1G,R2Q,ZF,XA,YA), (R1H,R2Q,ZF,XA,YA), (R1I,R2Q,ZF,XA,YA), (R1J,R2Q,ZF,XA,YA), (R1K,R2Q,ZF,XA,YA), (R1L,R2Q,ZF,XA,YA), (R1M,R2Q,ZF,XA,YA), (R1N,R2Q,ZF,XA,YA), (R1O,R2Q,ZF,XA,YA), (R1P,R2Q,ZF,XA,YA), (R1Q,R2Q,ZF,XA,YA), (R1A,R2A,ZG,XA,YA), (R1B,R2A,ZG,XA,YA), (R1C,R2A,ZG,XA,YA), (R1D,R2A,ZG,XA,YA), (R1E,R2A,ZG,XA,YA), (R1F,R2A,ZG,XA,YA), (R1G,R2A,ZG,XA,YA), (R1H,R2A,ZG,XA,YA), (R1I,R2A,ZG,XA,YA), (R1J,R2A,ZG,XA,YA), (R1K,R2A,ZG,XA,YA), (R1L,R2A,ZG,XA,YA), (R1M,R2A,ZG,XA,YA), (R1N,R2A,ZG,XA,YA), (R1O,R2A,ZG,XA,YA), (R1P,R2A,ZG,XA,YA), (R1Q,R2A,ZG,XA,YA), (R1A,R2B,ZG,XA,YA), (R1B,R2B,ZG,XA,YA), (R1C,R2B,ZG,XA,YA), (R1D,R2B,ZG,XA,YA), (R1E,R2B,ZG,XA,YA), (R1F,R2B,ZG,XA,YA), (R1G,R2B,ZG,XA,YA), (R1H,R2B,ZG,XA,YA), (R1I,R2B,ZG,XA,YA), (R1J,R2B,ZG,XA,YA), (R1K,R2B,ZG,XA,YA), (R1L,R2B,ZG,XA,YA), (R1M,R2B,ZG,XA,YA), (R1N,R2B,ZG,XA,YA), (R1O,R2B,ZG,XA,YA), (R1P,R2B,ZG,XA,YA), (R1Q,R2B,ZG,XA,YA), (R1A,R2C,ZG,XA,YA), (R1B,R2C,ZG,XA,YA), (R1C,R2C,ZG,XA,YA), (R1D,R2C,ZG,XA,YA), (R1E,R2C,ZG,XA,YA), (R1F,R2C,ZG,XA,YA), (R1G,R2C,ZG,XA,YA), (R1H,R2C,ZG,XA,YA), (R1I,R2C,ZG,XA,YA), (R1J,R2C,ZG,XA,YA), (R1K,R2C,ZG,XA,YA), (R1L,R2C,ZG,XA,YA), (R1M,R2C,ZG,XA,YA), (R1N,R2C,ZG,XA,YA), (R1O,R2C,ZG,XA,YA), (R1P,R2C,ZG,XA,YA), (R1Q,R2C,ZG,XA,YA), (R1A,R2D,ZG,XA,YA), (R1B,R2D,ZG,XA,YA), (R1C,R2D,ZG,XA,YA), (R1D,R2D,ZG,XA,YA), (R1E,R2D,ZG,XA,YA), (R1F,R2D,ZG,XA,YA), (R1G,R2D,ZG,XA,YA), (R1H,R2D,ZG,XA,YA), (R1I,R2D,ZG,XA,YA), (R1J,R2D,ZG,XA,YA), (R1K,R2D,ZG,XA,YA), (R1L,R2D,ZG,XA,YA), (R1M,R2D,ZG,XA,YA), (R1N,R2D,ZG,XA,YA), (R1O,R2D,ZG,XA,YA), (R1P,R2D,ZG,XA,YA), (R1Q,R2D,ZG,XA,YA), (R1A,R2E,ZG,XA,YA), (R1B,R2E,ZG,XA,YA), (R1C,R2E,ZG,XA,YA), (R1D,R2E,ZG,XA,YA), (R1E,R2E,ZG,XA,YA), (R1F,R2E,ZG,XA,YA), (R1G,R2E,ZG,XA,YA), (R1H,R2E,ZG,XA,YA), (R1I,R2E,ZG,XA,YA), (R1J,R2E,ZG,XA,YA), (R1K,R2E,ZG,XA,YA), (R1L,R2E,ZG,XA,YA), (R1M,R2E,ZG,XA,YA), (R1N,R2E,ZG,XA,YA), (R1O,R2E,ZG,XA,YA), (R1P,R2E,ZG,XA,YA), (R1Q,R2E,ZG,XA,YA), (R1A,R2F,ZG,XA,YA), (R1B,R2F,ZG,XA,YA), (R1C,R2F,ZG,XA,YA), (R1D,R2F,ZG,XA,YA), (R1E,R2F,ZG,XA,YA), (R1F,R2F,ZG,XA,YA), (R1G,R2F,ZG,XA,YA), (R1H,R2F,ZG,XA,YA), (R1I,R2F,ZG,XA,YA), (R1J,R2F,ZG,XA,YA), (R1K,R2F,ZG,XA,YA), (R1L,R2F,ZG,XA,YA), (R1M,R2F,ZG,XA,YA), (R1N,R2F,ZG,XA,YA), (R1O,R2F,ZG,XA,YA), (R1P,R2F,ZG,XA,YA), (R1Q,R2F,ZG,XA,YA), (R1A,R2G,ZG,XA,YA), (R1B,R2G,ZG,XA,YA), (R1C,R2G,ZG,XA,YA), (R1D,R2G,ZG,XA,YA), (R1E,R2G,ZG,XA,YA), (R1F,R2G,ZG,XA,YA), (R1G,R2G,ZG,XA,YA), (R1H,R2G,ZG,XA,YA), (R1I,R2G,ZG,XA,YA), (R1J,R2G,ZG,XA,YA), (R1K,R2G,ZG,XA,YA), (R1L,R2G,ZG,XA,YA), (R1M,R2G,ZG,XA,YA), (R1N,R2G,ZG,XA,YA), (R1O,R2G,ZG,XA,YA), (R1P,R2G,ZG,XA,YA), (R1Q,R2G,ZG,XA,YA), (R1A,R2H,ZG,XA,YA), (R1B,R2H,ZG,XA,YA), (R1C,R2H,ZG,XA,YA), (R1D,R2H,ZG,XA,YA), (R1E,R2H,ZG,XA,YA), (R1F,R2H,ZG,XA,YA), (R1G,R2H,ZG,XA,YA), (R1H,R2H,ZG,XA,YA), (R1I,R2H,ZG,XA,YA), (R1J,R2H,ZG,XA,YA), (R1K,R2H,ZG,XA,YA), (R1L,R2H,ZG,XA,YA), (R1M,R2H,ZG,XA,YA), (R1N,R2H,ZG,XA,YA), (R1O,R2H,ZG,XA,YA), (R1P,R2H,ZG,XA,YA), (R1Q,R2H,ZG,XA,YA), (R1A,R2I,ZG,XA,YA), (R1B,R2I,ZG,XA,YA), (R1C,R2I,ZG,XA,YA), (R1D,R2I,ZG,XA,YA), (R1E,R2I,ZG,XA,YA), (R1F,R2I,ZG,XA,YA), (R1G,R2I,ZG,XA,YA), (R1H,R2I,ZG,XA,YA), (R1I,R2I,ZG,XA,YA), (R1J,R2I,ZG,XA,YA), (R1K,R2I,ZG,XA,YA), (R1L,R2I,ZG,XA,YA), (R1M,R2I,ZG,XA,YA), (R1N,R2I,ZG,XA,YA), (R1O,R2I,ZG,XA,YA), (R1P,R2I,ZG,XA,YA), (R1Q,R2I,ZG,XA,YA), (R1A,R2J,ZG,XA,YA), (R1B,R2J,ZG,XA,YA), (R1C,R2J,ZG,XA,YA), (R1D,R2J,ZG,XA,YA), (R1E,R2J,ZG,XA,YA), (R1F,R2J,ZG,XA,YA), (R1G,R2J,ZG,XA,YA), (R1H,R2J,ZG,XA,YA), (R1I,R2J,ZG,XA,YA), (R1J,R2J,ZG,XA,YA), (R1K,R2J,ZG,XA,YA), (R1L,R2J,ZG,XA,YA), (R1M,R2J,ZG,XA,YA), (R1N,R2J,ZG,XA,YA), (R1O,R2J,ZG,XA,YA), (R1P,R2J,ZG,XA,YA), (R1Q,R2J,ZG,XA,YA), (R1A,R2K,ZG,XA,YA), (R1B,R2K,ZG,XA,YA), (R1C,R2K,ZG,XA,YA), (R1D,R2K,ZG,XA,YA), (R1E,R2K,ZG,XA,YA), (R1F,R2K,ZG,XA,YA), (R1G,R2K,ZG,XA,YA), (R1H,R2K,ZG,XA,YA), (R1I,R2K,ZG,XA,YA), (R1J,R2K,ZG,XA,YA), (R1K,R2K,ZG,XA,YA), (R1L,R2K,ZG,XA,YA), (R1M,R2K,ZG,XA,YA), (R1N,R2K,ZG,XA,YA), (R1O,R2K,ZG,XA,YA), (R1P,R2K,ZG,XA,YA), (R1Q,R2K,ZG,XA,YA), (R1A,R2L,ZG,XA,YA), (R1B,R2L,ZG,XA,YA), (R1C,R2L,ZG,XA,YA), (R1D,R2L,ZG,XA,YA), (R1E,R2L,ZG,XA,YA), (R1F,R2L,ZG,XA,YA), (R1G,R2L,ZG,XA,YA), (R1H,R2L,ZG,XA,YA), (R1I,R2L,ZG,XA,YA), (R1J,R2L,ZG,XA,YA), (R1K,R2L,ZG,XA,YA), (R1L,R2L,ZG,XA,YA), (R1M,R2L,ZG,XA,YA), (R1N,R2L,ZG,XA,YA), (R1O,R2L,ZG,XA,YA), (R1P,R2L,ZG,XA,YA), (R1Q,R2L,ZG,XA,YA), (R1A,R2M,ZG,XA,YA), (R1B,R2M,ZG,XA,YA), (R1C,R2M,XA,YA), (R1D,R2M,ZG,XA,YA), (R1E,R2M,ZG,XA,YA), (R1F,R2M,ZG,XA,YA), (R1G,R2M,ZG,XA,YA), (R1H,R2M,ZG,XA,YA), (R1I,R2M,ZG,XA,YA), (R1J,R2M,ZG,XA,YA), (R1K,R2M,ZG,XA,YA), (R1L,R2M,ZG,XA,YA), (R1M,R2M,ZG,XA,YA), (R1N,R2M,ZG,XA,YA), (R1O,R2M,ZG,XA,YA), (R1P,R2M,ZG,XA,YA), (R1Q,R2M,ZG,XA,YA), (R1A,R2N,ZG,XA,YA), (R1B,R2N,ZG,XA,YA), (R1C,R2N,ZG,XA,YA), (R1D,R2N,ZG,XA,YA), (R1E,R2N,ZG,XA,YA), (R1F,R2N,ZG,XA,YA), (R1G,R2N,ZG,XA,YA), (R1H,R2N,ZG,XA,YA), (R1I,R2N,ZG,XA,YA), (R1J,R2N,ZG,XA,YA), (R1K,R2N,ZG,XA,YA), (R1L,R2N,ZG,XA,YA), (R1M,R2N,ZG,XA,YA), (R1N,R2N,ZG,XA,YA), (R1O,R2N,ZG,XA,YA), (R1P,R2N,ZG,XA,YA), (R1Q,R2N,ZG,XA,YA), (R1A,R2O,ZG,XA,YA), (R1B,R2O,ZG,XA,YA), (R1C,R2O,ZG,XA,YA), (R1D,R2O,ZG,XA,YA), (R1E,R2O,ZG,XA,YA), (R1F,R2O,ZG,XA,YA), (R1G,R2O,ZG,XA,YA), (R1H,R2O,ZG,XA,YA), (R1I,R2O,ZG,XA,YA), (R1J,R2O,ZG,XA,YA), (R1K,R2O,ZG,XA,YA), (R1L,R2O,ZG,XA,YA), (R1M,R2O,ZG,XA,YA), (R1N,R2O,ZG,XA,YA), (R1O,R2O,ZG,XA,YA), (R1P,R2O,ZG,XA,YA), (R1Q,R2O,ZG,XA,YA), (R1A,R2P,ZG,XA,YA), (R1B,R2P,ZG,XA,YA), (R1C,R2P,ZG,XA,YA), (R1D,R2P,ZG,XA,YA), (R1E,R2P,ZG,XA,YA), (R1F,R2P,ZG,XA,YA), (R1G,R2P,ZG,XA,YA), (R1H,R2P,ZG,XA,YA), (R1I,R2P,ZG,XA,YA), (R1J,R2P,ZG,XA,YA), (R1K,R2P,ZG,XA,YA), (R1L,R2P,ZG,XA,YA), (R1M,R2P,ZG,XA,YA), (R1N,R2P,ZG,XA,YA), (R1O,R2P,ZG,XA,YA), (R1P,R2P,ZG,XA,YA), (R1Q,R2P,ZG,XA,YA), (R1A,R2Q,ZG,XA,YA), (R1B,R2Q,ZG,XA,YA), (R1C,R2Q,ZG,XA,YA), (R1D,R2Q,ZG,XA,YA), (R1E,R2Q,ZG,XA,YA), (R1F,R2Q,ZG,XA,YA), (R1G,R2Q,ZG,XA,YA), (R1H,R2Q,ZG,XA,YA), (R1I,R2Q,ZG,XA,YA), (R1J,R2Q,ZG,XA,YA), (R1K,R2Q,ZG,XA,YA), (R1L,R2Q,ZG,XA,YA), (R1M,R2Q,ZG,XA,YA), (R1N,R2Q,ZG,XA,YA), (R1O,R2Q,ZG,XA,YA), (R1P,R2Q,ZG,XA,YA), (R1Q,R2Q,ZG,XA,YA), (R1A,R2A,ZH,XA,YA), (R1B,R2A,ZH,XA,YA), (R1C,R2A,ZH,XA,YA), (R1D,R2A,ZH,XA,YA), (R1E,R2A,ZH,XA,YA), (R1F,R2A,ZH,XA,YA), (R1G,R2A,ZH,XA,YA), (R1H,R2A,ZH,XA,YA), (R1I,R2A,ZH,XA,YA), (R1J,R2A,ZH,XA,YA), (R1K,R2A,ZH,XA,YA), (R1L,R2A,ZH,XA,YA), (R1M,R2A,ZH,XA,YA), (R1N,R2A,ZH,XA,YA), (R1O,R2A,ZH,XA,YA), (R1P,R2A,ZH,XA,YA), (R1Q,R2A,ZH,XA,YA), (R1A,R2B,ZH,XA,YA), (R1B,R2B,ZH,XA,YA), (R1C,R2B,ZH,XA,YA), (R1D,R2B,ZH,XA,YA), (R1E,R2B,ZH,XA,YA), (R1F,R2B,ZH,XA,YA), (R1G,R2B,ZH,XA,YA), (R1H,R2B,ZH,XA,YA), (R1I,R2B,ZH,XA,YA), (R1J,R2B,ZH,XA,YA), (R1K,R2B,ZH,XA,YA), (R1L,R2B,ZH,XA,YA), (R1M,R2B,ZH,XA,YA), (R1N,R2B,ZH,XA,YA), (R1O,R2B,ZH,XA,YA), (R1P,R2B,ZH,XA,YA), (R1Q,R2B,ZH,XA,YA), (R1A,R2C,ZH,XA,YA), (R1B,R2C,ZH,XA,YA), (R1C,R2C,ZH,XA,YA), (R1D,R2C,ZH,XA,YA), (R1E,R2C,ZH,XA,YA), (R1F,R22C,ZH,XA,YA), (R1G,R2C,ZH,XA,YA), (R1H,R2C,ZH,XA,YA), (R1I,R2C,ZH,XA,YA), (R1J,R2C,ZH,XA,YA), (R1K,R2C,ZH,XA,YA), (R1L,R2C,ZH,XA,YA), (R1M,R2C,ZH,XA,YA), (R1N,R2C,ZH,XA,YA), (R1O,R2C,ZH,XA,YA), (R1P,R2C,ZH,XA,YA), (R1Q,R2C,ZH,XA,YA), (R1A,R2D,ZH,XA,YA), (R1B,R2D,ZH,XA,YA), (R1C,R2D,ZH,XA,YA), (R1D,R2D,ZH,XA,YA), (R1E,R2D,ZH,XA,YA), (R1F,R2D,ZH,XA,YA), (R1G,R2D,ZH,XA,YA), (R1H,R2D,ZH,XA,YA), (R1I,R2D,ZH,XA,YA), (R1J,R2D,ZH,XA,YA), (R1K,R2D,ZH,XA,YA), (R1L,R2D,ZH,XA,YA), (R1M,R2D,ZH,XA,YA), (R1N,R2D,ZH,XA,YA), (R1O,R2D,ZH,XA,YA), (R1P,R2D,ZH,XA,YA), (R1Q,R2D,ZH,XA,YA), (R1A,R2E,ZH,XA,YA), (R1B,R2E,ZH,XA,YA), (R1C,R2E,ZH,XA,YA), (R1D,R2E,ZH,XA,YA), (R1E,R2E,ZH,XA,YA), (R1F,R2E,ZH,XA,YA), (R1G,R2E,ZH,XA,YA), (R1H,R2E,ZH,XA,YA), (R1I,R2E,ZH,XA,YA), (R1J,R2E,ZH,XA,YA), (R1K,R2E,ZH,XA,YA), (R1L, R2E,ZH,XA,YA), (R1M,R2E,ZH,XA,YA), (R1N,R2E,ZH,XA,YA), (R1O,R2E,ZH,XA,YA), (R1P,R2E,ZH,XA,YA), (R1Q,R2E,ZH,XA,YA), (R1A,R2F,ZH,XA,YA), (R1B,R2F,ZH,XA,YA), (R1C,R2F,ZH,XA,YA), (R1D,R2F,ZH,XA,YA), (R1E,R2F,ZH,XA,YA), (R1F,R2F,ZH,XA,YA), (R1G,R2F,ZH,XA,YA), (R1H,R2F,ZH,XA,YA), (R1I,R2F,ZH,XA,YA), (R1J,R2F,ZH,XA,YA), (R1K,R2F,ZH,XA,YA), (R1L,R2F,ZH,XA,YA), (R1M,R2F,ZH,XA,YA), (R1N,R2F,ZH,XA,YA), (R1O,R2F,ZH,XA,YA), (R1P,R2F,ZH,XA,YA), (R1Q,R2F,ZH,XA,YA), (R1A,R2G,ZH,XA,YA), (R1B,R2G,ZH,XA,YA), (R1C,R2G,ZH,XA,YA), (R1D,R2G,ZH,XA,YA), (R1E,R2G,ZH,XA,YA), (R1F,R2G,ZH,XA,YA), (R1G,R2G,ZH,XA,YA), (R1H,R2G,ZH,XA,YA), (R1I,R2G,ZH,XA,YA), (R1J,R2G,ZH,XA,YA), (R1K,R2G,ZH,XA,YA), (R1L,R2G,ZH,XA,YA), (R1M,R2G,ZH,XA,YA), (R1N,R2G,ZH,XA,YA), (R1O,R2G,ZH,XA,YA), (R1P,R2G,ZH,XA,YA), (R1Q,R2G,ZH,XA,YA), (R1A,R2H,ZH,XA,YA), (R1B,R2H,ZH,XA,YA), (R1C,R2H,ZH,XA,YA), (R1D,R2H,ZH,XA,YA), (R1E,R2H,ZH,XA,YA), (R1F,R2H,ZH,XA,YA), (R1G,R2H,ZH,XA,YA), (R1H,R2H,ZH,XA,YA), (R1I,R2H,ZH,XA,YA), (R1J,R2H,ZH,XA,YA), (R1K,R2H,ZH,XA,YA), (R1L,R2H,ZH,XA,YA), (R1M,R2H,ZH,XA,YA), (R1N,R2H,ZH,XA,YA), (R1O,R2H,ZH,XA,YA), (R1P,R2H,ZH,XA,YA), (R1Q,R2H,ZH,XA,YA), (R1A,R2I,ZH,XA,YA), (R1B,R2I,ZH,XA,YA), (R1C,R2I,ZH,XA,YA), (R1D,R2I,ZH,XA,YA), (R1E,R2I,ZH,XA,YA), (R1F,R2I,ZH,XA,YA), (R1G,R2I,ZH,XA,YA), (R1H,R2I,ZH,XA,YA), (R1I,R2I,ZH,XA,YA), (R1J,R2I,ZH,XA,YA), (R1K,R2I,ZH,XA,YA), (R1L,R2I,ZH,XA,YA), (R1M,R2I,ZH,XA,YA), (R1N,R2I,ZH,XA,YA), (R1O,R2I,ZH,XA,YA), (R1P,R2I,ZH,XA,YA), (R1Q,R2I,ZH,XA,YA), (R1A,R2J,ZH,XA,YA), (R1B,R2J,ZH,XA,YA), (R1C,R2J,ZH,XA,YA), (R1D,R2J,ZH,XA,YA), (R1E,R2J,ZH,XA,YA), (R1F,R2J,ZH,XA,YA), (R1G,R2J,ZH,XA,YA), (R1H,R2J,ZH,XA,YA), (R1I,R2J,ZH,XA,YA), (R1J,R2J,ZH,XA,YA), (R1K,R2J,ZH,XA,YA), (R1L,R2J,ZH,XA,YA), (R1M,R2J,ZH,XA,YA), (R1N,R2J,ZH,XA,YA), (R1O,R2J,ZH,XA,YA), (R1P,R2J,ZH,XA,YA), (R1Q,R2J,ZH,XA,YA), (R1A,R2K,ZH,XA,YA), (R1B,R2K,ZH,XA,YA), (R1C,R2K,ZH,XA,YA), (R1D,R2K,ZH,XA,YA), (R1E,R2K,ZH,XA,YA), (R1F,R2K,ZH,XA,YA), (R1G,R2K,ZH,XA,YA), (R1H,R2K,ZH,XA,YA), (R1I,R2K,ZH,XA,YA), (R1J,R2K,ZH,XA,YA), (R1K,R2K,ZH,XA,YA), (R1L,R2K,ZH,XA,YA), (R1M,R2K,ZH,XA,YA), (R1N,R2K,ZH,XA,YA), (R1O,R2K,ZH,XA,YA), (R1P,R2K,ZH,XA,YA), (R1Q,R2K,ZH,XA,YA), (R1A,R2L,ZH,XA,YA), (R1B,R2L,ZH,XA,YA), (R1C,R2L,ZH,XA,YA), (R1D,R2L,ZH,XA,YA), (R1E,R2L,ZH,XA,YA), (R1F,R2L,ZH,XA,YA), (R1G,R2L,ZH,XA,YA), (R1H,R2L,ZH,XA,YA), (R1I,R2L,ZH,XA,YA), (R1J,R2L,ZH,XA,YA), (R1K,R2L,ZH,XA,YA), (R1L,R2L,ZH,XA,YA), (R1M,R2L,ZH,XA,YA), (R1N,R2L,ZH,XA,YA), (R1O,R2L,ZH,XA,YA), (R1P,R2L,ZH,XA,YA), (R1Q,R2L,ZH,XA,YA), (R1A,R2M,ZH,XA,YA), (R1B,R2M,ZH,XA,YA), (R1C,R2M,ZH,XA,YA), (R1D,R2M,ZH,XA,YA), (R1E,R2M,ZH,XA,YA), (R1F,R2M,ZH,XA,YA), (R1G,R2M,ZH,XA,YA), (R1H,R2M,ZH,XA,YA), (R1I,R2M,ZH,XA,YA), (R1J,R2M,ZH,XA,YA), (R1K,R2M,ZH,XA,YA), (R1L,R2M,ZH,XA,YA), (R1M,R2M,ZH,XA,YA), (R1N,R2M,ZH,XA,YA), (R1O,R2M,ZH,XA,YA), (R1P,R2M,ZH,XA,YA), (R1Q,R2M,ZH,XA,YA), (R1A,R2N,ZH,XA,YA), (R1B,R2N,ZH,XA,YA), (R1C,R2N,ZH,XA,YA), (R1D,R2N,ZH,XA,YA), (R1E,R2N,ZH,XA,YA), (R1F,R2N,ZH,XA,YA), (R1G,R2N,ZH,XA,YA), (R1H,R2N,ZH,XA,YA), (R1I,R2N,ZH,XA,YA), (R1J,R2N,ZH,XA,YA), (R1K,R2N,ZH,XA,YA), (R1L,R2N,ZH,XA,YA), (R1M,R2N,ZH,XA,YA), (R1N,R2N,ZH,XA,YA), (R1O,R2N,ZH,XA,YA), (R1P,R2N,ZH,XA,YA), (R1Q,R2N,ZH,XA,YA), (R1A,R2O,ZH,XA,YA), (R1B,R2O,ZH,XA,YA), (R1C,R2O,ZH,XA,YA), (R1D,R2O,ZH,XA,YA), (R1E,R2O,ZH,XA,YA), (R1F,R2O,ZH,XA,YA), (R1G,R2O,ZH,XA,YA), (R1H,R2O,ZH,XA,YA), (R1I,R2O,ZH,XA,YA), (R1J,R2O,ZH,XA,YA), (R1K,R2O,ZH,XA,YA), (R1L,R2O,ZH,XA,YA), (R1M,R2O,ZH,XA,YA), (R1N,R2O,ZH,XA,YA), (R1O,R2O,ZH,XA,YA), (R1P,R2O,ZH,XA,YA), (R1Q,R2O,ZH,XA,YA), (R1A,R2P,ZH,XA,YA), (R1B,R2P,ZH,XA,YA), (R1C,R2P,ZH,XA,YA), (R1D,R2P,ZH,XA,YA), (R1E,R2P,ZH,XA,YA), (R1F,R2P,ZH,XA,YA), (R1G,R2P,ZH,XA,YA), (R1H,R2P,ZH,XA,YA), (R1I,R2P,ZH,XA,YA), (R1J,R2P,ZH,XA,YA), (R1K,R2P,ZH,XA,YA), (R1L,R2P,ZH,XA,YA), (R1M,R2P,ZH,XA,YA), (R1N,R2P,ZH,XA,YA), (R1O,R2P,ZH,XA,YA), (R1P,R2P,ZH,XA,YA), (R1Q,R2P,ZH,XA,YA), (R1A,R2Q,ZH,XA,YA), (R1B,R2Q,ZH,XA,YA), (R1C,R2Q,ZH,XA,YA), (R1D,R2Q,ZH,XA,YA), (R1E,R2Q,ZH,XA,YA), (R1F,R2Q,ZH,XA,YA), (R1G,R2Q,ZH,XA,YA), (R1H,R2Q,ZH,XA,YA), (R1I,R2Q,ZH,XA,YA), (R1J,R2Q,ZH,XA,YA), (R1K,R2Q,ZH,XA,YA), (R1L,R2Q,ZH,XA,YA), (R1M,R2Q,ZH,XA,YA), (R1N,R2Q,ZH,XA,YA), (R1O,R2Q,ZH,XA,YA), (R1P,R2Q,ZH,XA,YA), (R1Q,R2Q,ZH,XA,YA), (R1A,R2A,ZI,XA,YA), (R1B,R2A,ZI,XA,YA), (R1C,R2A,ZI,XA,YA), (R1D,R2A,ZI,XA,YA), (R1E,R2A,ZI,XA,YA), (R1F,R2A,ZI,XA,YA), (R1G,R2A,ZI,XA,YA), (R1H,R2A,ZI,XA,YA), (R1I,R2A,ZI,XA,YA), (R1J,R2A,ZI,XA,YA), (R1K,R2A,ZI,XA,YA), (R1L,R2A,ZI,XA,YA), (R1M,R2A,ZI,XA,YA), (R1N,R2A,ZI,XA,YA), (R1O,R2A,ZI,XA,YA), (R1P,R2A,ZI,XA,YA), (R1Q,R2A,ZI,XA,YA), (R1A,R2B,ZI,XA,YA), (R1B,R2B,ZI,XA,YA), (R1C,R2B,ZI,XA,YA), (R1D,R2B,ZI,XA,YA), (R1E,R2B,ZI,XA,YA), (R1F,R2B,ZI,XA,YA), (R1G,R2B,ZI,XA,YA), (R1H,R2B,ZI,XA,YA), (R1I,R2B,ZI,XA,YA), (R1J,R2B,ZI,XA,YA), (R1K,R2B,ZI,XA,YA), (R1L,R2B,ZI,XA,YA), (R1M,R2B,ZI,XA,YA), (R1N,R2B,ZI,XA,YA), (R1O,R2B,ZI,XA,YA), (R1P,R2B,ZI,XA,YA), (R1Q,R2B,ZI,XA,YA), (R1A,R2C,ZI,XA,YA), (R1B,R2C,ZI,XA,YA), (R1C,R2C,ZI,XA,YA), (R1D,R2C,ZI,XA,YA), (R1E,R2C,ZI,XA,YA), (R1F,R2C,ZI,XA,YA), (R1G,R2C,ZI,XA,YA), (R1H,R2C,ZI,XA,YA), (R1I,R22C,ZI,XA,YA), (R1J,R2C,ZI,XA,YA), (R1K,R2C,ZI,XA,YA), (R1L,R2C,ZI,XA,YA), (R1M,R22C,ZI,XA,YA), (R1N,R2C,ZI,XA,YA), (R1O,R2C,ZI,XA,YA), (R1P,R2C,ZI,XA,YA), (R1Q,R22C,ZI,XA,YA), (R1A,R2D,ZI,XA,YA), (R1B,R2D,ZI,XA,YA), (R1C,R2D,ZI,XA,YA), (R1D,R2D,ZI,XA,YA), (R1E,R2D,ZI,XA,YA), (R1F,R2D,ZI,XA,YA), (R1G,R2D,ZI,XA,YA), (R1H,R2D,ZI,XA,YA), (R1I,R2D,ZI,XA,YA), (R1J,R2D,ZI,XA,YA), (R1K,R2D,ZI,XA,YA), (R1L,R2D,ZI,XA,YA), (R1M,R2D,ZI,XA,YA), (R1N,R2D,ZI,XA,YA), (R1O,R2D,ZI,XA,YA), (R1P,R2D,ZI,XA,YA), (R1Q,R2D,ZI,XA,YA), (R1A,R2E,ZI,XA,YA), (R1B,R2E,ZI,XA,YA), (R1C,R2E,ZI,XA,YA), (R1D,R2E,ZI,XA,YA), (R1E,R2E,ZI,XA,YA), (R1F,R2E,ZI,XA,YA), (R1G,R2E,ZI,XA,YA), (R1H,R2E,ZI,XA,YA), (R1I,R2E,ZI,XA,YA), (R1J,R2E,ZI,XA,YA), (R1K,R2E,ZI,XA,YA), (R1L,R2E,ZI,XA,YA), (R1M,R2E,ZI,XA,YA), (R1N,R2E,ZI,XA,YA), (R1O,R2E,ZI,XA,YA), (R1P,R2E,ZI,XA,YA), (R1Q,R2E,ZI,XA,YA), (R1A,R2F,ZI,XA,YA), (R1B,R2F,ZI,XA,YA), (R1C,R2F,ZI,XA,YA), (R1D,R2F,ZI,XA,YA), (R1E,R2F,ZI,XA,YA), (R1F,R2F,ZI,XA,YA), (R1G,R2F,ZI,XA,YA), (R1H,R2F,ZI,XA,YA), (R1I,R2F,ZI,XA,YA), (R1J,R2F,ZI,XA,YA), (R1K,R2F,ZI,XA,YA), (R1L,R2F,ZI,XA,YA), (R1M,R2F,ZI,XA,YA), (R1N,R2F,ZI,XA,YA), (R1O,R2F,ZI,XA,YA), (R1P,R2F,ZI,XA,YA), (R1Q,R2F,ZI,XA,YA), (R1A,R2G,ZI,XA,YA), (R1B,R2G,ZI,XA,YA), (R1C,R2G,ZI,XA,YA), (R1D,R2G,ZI,XA,YA), (R1E,R2G,ZI,XA,YA), (R1F,R2G,ZI,XA,YA), (R1G,R2G,ZI,XA,YA), (R1H,R2G,ZI,XA,YA), (R1I,R2G,ZI,XA,YA), (R1J,R2G, ZI,XA,YA), (R1K,R2G,ZI,XA,YA), (R1L,R2G,ZI,XA,YA), (R1M,R2G,ZI,XA,YA), (R1N,R2G,ZI,XA,YA), (R1O,R2G,ZI,XA,YA), (R1P,R2G,ZI,XA,YA), (R1Q,R2G,ZI,XA,YA), (R1A,R2H,ZI,XA,YA), (R1B,R2H,ZI,XA,YA), (R1C,R2H,ZI,XA,YA), (R1D,R2H,ZI,XA,YA), (R1E,R2H,ZI,XA,YA), (R1F,R2H,ZI,XA,YA), (R1G,R2H,ZI,XA,YA), (R1H,R2H,ZI,XA,YA), (R1I,R2H,ZI,XA,YA), (R1J,R2H,ZI,XA,YA), (R1K,R2H,ZI,XA,YA), (R1L,R2H,ZI,XA,YA), (R1M,R2H,ZI,XA,YA), (R1N,R2H,ZI,XA,YA), (R1O,R2H,ZI,XA,YA), (R1P,R2H,ZI,XA,YA), (R1Q,R2H,ZI,XA,YA), (R1A,R2I,ZI,XA,YA), (R1B,R2I,ZI,XA,YA), (R1C,R2I,ZI,XA,YA), (R1D,R2I,ZI,XA,YA), (R1E,R2I,ZI,XA,YA), (R1F,R2I,ZI,XA,YA), (R1G,R2I,ZI,XA,YA), (R1H,R2I,ZI,XA,YA), (R1I,R2I,ZI,XA,YA), (R1J,R2I,ZI,XA,YA), (R1K,R2I,ZI,XA,YA), (R1L,R2I,ZI,XA,YA), (R1M,R2I,ZI,XA,YA), (R1N,R2I,ZI,XA,YA), (R1O,R2I,ZI,XA,YA), (R1P,R2I,ZI,XA,YA), (R1Q,R2I,ZI,XA,YA), (R1A,R2J,ZI,XA,YA), (R1B,R2J,ZI,XA,YA), (R1C,R2J,ZI,XA,YA), (R1D,R2J,ZI,XA,YA), (R1E,R2J,ZI,XA,YA), (R1F,R2J,ZI,XA,YA), (R1G,R2J,ZI,XA,YA), (R1H,R2J,ZI,XA,YA), (R1I,R2J,ZI,XA,YA), (R1J,R2J,ZI,XA,YA), (R1K,R2J,ZI,XA,YA), (R1L,R2J,ZI,XA,YA), (R1M,R2J,ZI,XA,YA), (R1N,R2J,ZI,XA,YA), (R1O,R2J,ZI,XA,YA), (R1P,R2J,ZI,XA,YA), (R1Q,R2J,ZI,XA,YA), (R1A,R2K,ZI,XA,YA), (R1B,R2K,ZI,XA,YA), (R1C,R2K,ZI,XA,YA), (R1D,R2K,ZI,XA,YA), (R1E,R2K,ZI,XA,YA), (R1F,R2K,ZI,XA,YA), (R1G,R2K,ZI,XA,YA), (R1H,R2K,ZI,XA,YA), (R1I,R2K,ZI,XA,YA), (R1J,R2K,ZI,XA,YA), (R1K,R2K,ZI,XA,YA), (R1L,R2K,ZI,XA,YA), (R1M,R2K,ZI,XA,YA), (R1N,R2K,ZI,XA,YA), (R1O,R2K,ZI,XA,YA), (R1P,R2K,ZI,XA,YA), (R1Q,R2K,ZI,XA,YA), (R1A,R2L,ZI,XA,YA), (R1B,R2L,ZI,XA,YA), (R1C,R2L,ZI,XA,YA), (R1D,R2L,ZI,XA,YA), (R1E,R2L,ZI,XA,YA), (R1F,R2L,ZI,XA,YA), (R1G,R2L,ZI,XA,YA), (R1H,R2L,ZI,XA,YA), (R1I,R2L,ZI,XA,YA), (R1J,R2L,ZI,XA,YA), (R1K,R2L,ZI,XA,YA), (R1L,R2L,ZI,XA,YA), (R1M,R2L,ZI,XA,YA), (R1N,R2L,ZI,XA,YA), (R1O,R2L,ZI,XA,YA), (R1P,R2L,ZI,XA,YA), (R1Q,R2L,ZI,XA,YA), (R1A,R2M,ZI,XA,YA), (R1B,R2M,ZI,XA,YA), (R1C,R2M,ZI,XA,YA), (R1D,R2M,ZI,XA,YA), (R1E,R2M,ZI,XA,YA), (R1F,R2M,ZI,XA,YA), (R1G,R2M,ZI,XA,YA), (R1H,R2M,ZI,XA,YA), (R1I,R2M,ZI,XA,YA), (R1J,R2M,ZI,XA,YA), (R1K,R2M,ZI,XA,YA), (R1L,R2M,ZI,XA,YA), (R1M,R2M,ZI,XA,YA), (R1N,R2M,ZI,XA,YA), (R1O,R2M,ZI,XA,YA), (R1P,R2M,ZI,XA,YA), (R1Q,R2M,ZI,XA,YA), (R1A,R2N,ZI,XA,YA), (R1B,R2N,ZI,XA,YA), (R1C,R2N,ZI,XA,YA), (R1D,R2N,ZI,XA,YA), (R1E,R2N,ZI,XA,YA), (R1F,R2N,ZI,XA,YA), (R1G,R2N,ZI,XA,YA), (R1H,R2N,ZI,XA,YA), (R1I,R2N,ZI,XA,YA), (R1J,R2N,ZI,XA,YA), (R1K,R2N,ZI,XA,YA), (R1L,R2N,ZI,XA,YA), (R1M,R2N,ZI,XA,YA), (R1N,R2N,ZI,XA,YA), (R1O,R2N,ZI,XA,YA), (R1P,R2N,ZI,XA,YA), (R1Q,R2N,ZI,XA,YA), (R1A,R2O,ZI,XA,YA), (R1B,R2O,ZI,XA,YA), (R1C,R2O,ZI,XA,YA), (R1D,R2O,ZI,XA,YA), (R1E,R2O,ZI,XA,YA), (R1F,R2O,ZI,XA,YA), (R1G,R2O,ZI,XA,YA), (R1H,R2O,ZI,XA,YA), (R1I,R2O,ZI,XA,YA), (R1J,R2O,ZI,XA,YA), (R1K,R2O,ZI,XA,YA), (R1L,R2O,ZI,XA,YA), (R1M,R2O,ZI,XA,YA), (R1N,R2O,ZI,XA,YA), (R1O,R2O,ZI,XA,YA), (R1P,R2O,ZI,XA,YA), (R1Q,R2O,ZI,XA,YA), (R1A,R2P,ZI,XA,YA), (R1B,R2P,ZI,XA,YA), (R1C,R2P,ZI,XA,YA), (R1D,R2P,ZI,XA,YA), (R1E,R2P,ZI,XA,YA), (R1F,R2P,ZI,XA,YA), (R1G,R2P,ZI,XA,YA), (R1H,R2P,ZI,XA,YA), (R1I,R2P,ZI,XA,YA), (R1J,R2P,ZI,XA,YA), (R1K,R2P,ZI,XA,YA), (R1L,R2P,ZI,XA,YA), (R1M,R2P,ZI,XA,YA), (R1N,R2P,ZI,XA,YA), (R1O,R2P,ZI,XA,YA), (R1P,R2P,ZI,XA,YA), (R1Q,R2P,ZI,XA,YA), (R1A,R2Q,ZI,XA,YA), (R1B,R2Q,ZI,XA,YA), (R1C,R2Q,ZI,XA,YA), (R1D,R2Q,ZI,XA,YA), (R1E,R2Q,ZI,XA,YA), (R1F,R2Q,ZI,XA,YA), (R1G,R2Q,ZI,XA,YA), (R1H,R2Q,ZI,XA,YA), (R1I,R2Q,ZI,XA,YA), (R1J,R2Q,ZI,XA,YA), (R1K,R2Q,ZI,XA,YA), (R1L,R2Q,ZI,XA,YA), (R1M,R2Q,ZI,XA,YA), (R1N,R2Q,ZI,XA,YA), (R1O,R2Q,ZI,XA,YA), (R1P,R2Q,ZI,XA,YA), (R1Q,R2Q,ZI,XA,YA), (R1A,R2A,ZJ,XA,YA), (R1B,R2A,ZJ,XA,YA), (R1C,R2A,ZJ,XA,YA), (R1D,R2A,ZJ,XA,YA), (R1E,R2A,ZJ,XA,YA), (R1F,R2A,ZJ,XA,YA), (R1G,R2A,ZJ,XA,YA), (R1H,R2A,ZJ,XA,YA), (R1I,R2A,ZJ,XA,YA), (R1J,R2A,ZJ,XA,YA), (R1K,R2A,ZJ,XA,YA), (R1L,R2A,ZJ,XA,YA), (R1M,R2A,ZJ,XA,YA), (R1N,R2A,ZJ,XA,YA), (R1O,R2A,ZJ,XA,YA), (R1P,R2A,ZJ,XA,YA), (R1Q,R2A,ZJ,XA,YA), (R1A,R2B,ZJ,XA,YA), (R1B,R2B,ZJ,XA,YA), (R1C,R2B,ZJ,XA,YA), (R1D,R2B,ZJ,XA,YA), (R1E,R2B,ZJ,XA,YA), (R1F,R2B,ZJ,XA,YA), (R1G,R2B,ZJ,XA,YA), (R1H,R2B,ZJ,XA,YA), (R1I,R2B,ZJ,XA,YA), (R1J,R2B,ZJ,XA,YA), (R1K,R2B,ZJ,XA,YA), (R1L,R2B,ZJ,XA,YA), (R1M,R2B,ZJ,XA,YA), (R1N,R2B,ZJ,XA,YA), (R1O,R2B,ZJ,XA,YA), (R1P,R2B,ZJ,XA,YA), (R1Q,R2B,ZJ,XA,YA), (R1A,R2C,ZJ,XA,YA), (R1B,R2C,ZJ,XA,YA), (R1C,R2C,ZJ,XA,YA), (R1D,R2C,ZJ,XA,YA), (R1E,R2C,ZJ,XA,YA), (R1F,R2C,ZJ,XA,YA), (R1G,R2C,ZJ,XA,YA), (R1H,R2C,ZJ,XA,YA), (R1I,R2C,ZJ,XA,YA), (R1J,R2C,ZJ,XA,YA), (R1K,R2C,ZJ,XA,YA), (R1L,R2C,ZJ,XA,YA), (R1M,R2C,ZJ,XA,YA), (R1N,R2C,ZJ,XA,YA), (R1O,R2C,ZJ,XA,YA), (R1P,R2C,ZJ,XA,YA), (R1Q,R2C,ZJ,XA,YA), (R1A,R2D,ZJ,XA,YA), (R1B,R2D,ZJ,XA,YA), (R1C,R2D,ZJ,XA,YA), (R1D,R2D,ZJ,XA,YA), (R1E,R2D,ZJ,XA,YA), (R1F,R2D,ZJ,XA,YA), (R1G,R2D,ZJ,XA,YA), (R1H,R2D,ZJ,XA,YA), (R1I,R2D,ZJ,XA,YA), (R1J,R2D,ZJ,XA,YA), (R1K,R2D,ZJ,XA,YA), (R1L,R2D,ZJ,XA,YA), (R1M,R2D,ZJ,XA,YA), (R1N,R2D,ZJ,XA,YA), (R1O,R2D,ZJ,XA,YA), (R1P,R2D,ZJ,XA,YA), (R1Q,R2D,ZJ,XA,YA), (R1A,R2E,ZJ,XA,YA), (R1B,R2E,ZJ,XA,YA), (R1C,R2E,ZJ,XA,YA), (R1D,R2E,ZJ,XA,YA), (R1E,R2E,ZJ,XA,YA), (R1F,R2E,ZJ,XA,YA), (R1G,R2E,ZJ,XA,YA), (R1H,R2E,ZJ,XA,YA), (R1I,R2E,ZJ,XA,YA), (R1J,R2E,ZJ,XA,YA), (R1K,R2E,ZJ,XA,YA), (R1L,R2E,ZJ,XA,YA), (R1M,R2E,ZJ,XA,YA), (R1N,R2E,ZJ,XA,YA), (R1O,R2E,ZJ,XA,YA), (R1P,R2E,ZJ,XA,YA), (R1Q,R2E,ZJ,XA,YA), (R1A,R2F,ZJ,XA,YA), (R1B,R2F,ZJ,XA,YA), (R1C,R2F,ZJ,XA,YA), (R1D,R2F,ZJ,XA,YA), (R1E,R2F,ZJ,XA,YA), (R1F,R2F,ZJ,XA,YA), (R1G,R2F,ZJ,XA,YA), (R1H,R2F,ZJ,XA,YA), (R1I,R2F,ZJ,XA,YA), (R1J,R2F,ZJ,XA,YA), (R1K,R2F,ZJ,XA,YA), (R1L,R2F,ZJ,XA,YA), (R1M,R2F,ZJ,XA,YA), (R1N,R2F,ZJ,XA,YA), (R1O,R2F,ZJ,XA,YA), (R1P,R2F,ZJ,XA,YA), (R1Q,R2F,ZJ,XA,YA), (R1A,R2G,ZJ,XA,YA), (R1B,R2G,ZJ,XA,YA), (R1C,R2G,ZJ,XA,YA), (R1D,R2G,ZJ,XA,YA), (R1E,R2G,ZJ,XA,YA), (R1F,R2G,ZJ,XA,YA), (R1G,R2G,ZJ,XA,YA), (R1H,R2G,ZJ,XA,YA), (R1I,R2G,ZJ,XA,YA), (R1J,R2G,ZJ,XA,YA), (R1K,R2G,ZJ,XA,YA), (R1L,R2G,ZJ,XA,YA), (R1M,R2G,ZJ,XA,YA), (R1N,R2G,ZJ,XA,YA), (R1O,R2G,ZJ,XA,YA), (R1P,R2G,ZJ,XA,YA), (R1Q,R2G,ZJ,XA,YA), (R1A,R2H,ZJ,XA,YA), (R1B,R2H,ZJ,XA,YA), (R1C,R2H,ZJ,XA,YA), (R1D,R2H,ZJ,XA,YA), (R1E,R2H,ZJ,XA,YA), (R1F,R2H,ZJ,XA,YA), (R1G,R2H,ZJ,XA,YA), (R1H,R2H,ZJ,XA,YA), (R1I,R2H,ZJ,XA,YA), (R1J,R2H,ZJ,XA,YA), (R1K,R2H,ZJ,XA,YA), (R1L,R2H,ZJ,XA,YA), (R1M,R2H,ZJ,XA,YA), (R1N,R2H,ZJ,XA,YA), (R1O,R2H,ZJ,XA,YA), (R1P,R2H,ZJ,XA,YA), (R1Q,R2H,ZJ,XA,YA), (R1A,R2I,ZJ,XA,YA), (R1B,R2I,ZJ,XA,YA), (R1C,R2I,ZJ,XA,YA), (R1D,R2I,ZJ,XA,YA), (R1E,R2I,ZJ,XA,YA), (R1F,R2I,ZJ,XA,YA), (R1G,R2I,ZJ,XA,YA), (R1H,R2I,ZJ,XA,YA), (R1I,R2I,ZJ,XA,YA), (R1J,R2I,ZJ,XA,YA), (R1K,R2I,ZJ,XA,YA), (R1L,R2I,ZJ,XA,YA), (R1M,R2I,ZJ,XA,YA), (R1N,R2I,ZJ,XA,YA), (R1O,R2I,ZJ,XA,YA), (R1P,R2I,ZJ,XA,YA), (R1Q,R2I,ZJ,XA,YA), (R1A,R2J,ZJ,XA,YA), (R1B,R2J,ZJ,XA,YA), (R1C,R2J,ZJ,XA,YA), (R1D,R2J,ZJ,XA,YA), (R1E,R2J,ZJ,XA,YA), (R1F,R2J,ZJ,XA,YA), (R1G,R2J,ZJ,XA,YA), (R1H,R2J,ZJ,XA,YA), (R1I,R2J,ZJ,XA,YA), (R1J,R2J,ZJ,XA,YA), (R1K,R2J,ZJ,XA,YA), (R1L,R2J,ZJ,XA,YA), (R1M,R2J,ZJ,XA,YA), (R1N,R2J,ZJ,XA,YA), (R1O,R2J,ZJ,XA,YA), (R1P,R2J,ZJ,XA,YA), (R1Q,R2J,ZJ,XA,YA), (R1A,R2K,ZJ,XA,YA), (R1B,R2K,ZJ,XA,YA), (R1C,R2K,ZJ,XA,YA), (R1D,R2K,ZJ,XA,YA), (R1E,R2K,ZJ,XA,YA), (R1F,R2K,ZJ,XA,YA), (R1G,R2K,ZJ,XA,YA), (R1H,R2K,ZJ,XA,YA), (R1I,R2K,ZJ,XA,YA), (R1J,R2K,ZJ,XA,YA), (R1K,R2K,ZJ,XA,YA), (R1L,R2K,ZJ,XA,YA), (R1M,R2K,ZJ,XA,YA), (R1N,R2K,ZJ,XA,YA), (R1O,R2K,ZJ,XA,YA), (R1P,R2K,ZJ,XA,YA), (R1Q,R2K,ZJ,XA,YA), (R1A,R2L,ZJ,XA,YA), (R1B,R2L,ZJ,XA,YA), (R1C,R2L,ZJ,XA,YA), (R1D,R2L,ZJ,XA,YA), (R1E,R2L,ZJ,XA,YA), (R1F,R2L,ZJ,XA,YA), (R1G,R2L,ZJ,XA,YA), (R1H,R2L,ZJ,XA,YA), (R1I,R2L,ZJ,XA,YA), (R1J,R2L,ZJ,XA,YA), (R1K,R2L,ZJ,XA,YA), (R1L,R2L,ZJ,XA,YA), (R1M,R2L,ZJ,XA,YA), (R1N,R2L,ZJ,XA,YA), (R1O,R2L,ZJ,XA,YA), (R1P,R2L,ZJ,XA,YA), (R1Q,R2L,ZJ,XA,YA), (R1A,R2M,ZJ,XA,YA), (R1B,R2M,ZJ,XA,YA), (R1C,R2M,ZJ,XA,YA), (R1D,R2M,ZJ,XA,YA), (R1E,R2M,ZJ,XA,YA), (R1F,R2M,ZJ,XA,YA), (R1G,R2M,ZJ,XA,YA), (R1H,R2M,ZJ,XA,YA), (R1I,R2M,ZJ,XA,YA), (R1J,R2M,ZJ,XA,YA), (R1K,R2M,ZJ,XA,YA), (R1L,R2M,ZJ,XA,YA), (R1M,R2M,ZJ,XA,YA), (R1N,R2M,ZJ,XA,YA), (R1O,R2M,ZJ,XA,YA), (R1P,R2M,ZJ,XA,YA), (R1Q,R2M,ZJ,XA,YA), (R1A,R2N,ZJ,XA,YA), (R1B,R2N,ZJ,XA,YA), (R1C,R2N,ZJ,XA,YA), (R1D,R2N,ZJ,XA,YA), (R1E,R2N,ZJ,XA,YA), (R1F,R2N,ZJ,XA,YA), (R1G,R2N,ZJ,XA,YA), (R1H,R2N,ZJ,XA,YA), (R1I,R2N,ZJ,XA,YA), (R1J,R2N,ZJ,XA,YA), (R1K,R2N,ZJ,XA,YA), (R1L,R2N,ZJ,XA,YA), (R1M,R2N,ZJ,XA,YA), (R1N,R2N,ZJ,XA,YA), (R1O,R2N,ZJ,XA,YA), (R1P,R2N,ZJ,XA,YA), (R1Q,R2N,ZJ,XA,YA), (R1A,R2O,ZJ,XA,YA), (R1B,R2O,ZJ,XA,YA), (R1C,R2O,ZJ,XA,YA), (R1D,R2O,ZJ,XA,YA), (R1E,R2O,ZJ,XA,YA), (R1F,R2O,ZJ,XA,YA), (R1G,R2O,ZJ,XA,YA), (R1H,R2O,ZJ,XA,YA), (R1I,R2O,ZJ,XA,YA), (R1J,R2O,ZJ,XA,YA), (R1K,R2O,ZJ,XA,YA), (R1L,R2O,ZJ,XA,YA), (R1M,R2O,ZJ,XA,YA), (R1N,R2O,ZJ,XA,YA), (R1O,R2O,ZJ,XA,YA), (R1P,R2O,ZJ,XA,YA), (R1Q,R2O,ZJ,XA,YA), (R1A,R2P,ZJ,XA,YA), (R1B,R2P,ZJ,XA,YA), (R1C,R2P,ZJ,XA,YA), (R1D,R2P,ZJ,XA,YA), (R1E,R2P,ZJ,XA,YA), (R1F,R2P,ZJ,XA,YA), (R1G,R2P,ZJ,XA,YA), (R1H,R2P,ZJ,XA,YA), (R1I,R2P,ZJ,XA,YA), (R1J,R2P,ZJ,XA,YA), (R1K,R2P,ZJ,XA,YA), (R1L,R2P,ZJ,XA,YA), (R1M,R2P,ZJ,XA,YA), (R1N,R2P,ZJ,XA,YA), (R1O,R2P,ZJ,XA,YA), (R1P,R2P,ZJ,XA,YA), (R1Q,R2P,ZJ,XA,YA), (R1A,R2Q,ZJ,XA,YA), (R1B,R2Q,ZJ,XA,YA), (R1C,R2Q,ZJ,XA,YA), (R1D,R2Q,ZJ,XA,YA), (R1E,R2Q,ZJ,XA,YA), (R1F,R2Q,ZJ,XA,YA), (R1G,R2Q,ZJ,XA,YA), (R1H,R2Q,ZJ,XA,YA), (R1I,R2Q,ZJ,XA,YA), (R1J,R2Q,ZJ,XA,YA), (R1K,R2Q,ZJ,XA,YA), (R1L,R2Q,ZJ,XA,YA), (R1M,R2Q,ZJ,XA,YA), (R1N,R2Q,ZJ,XA,YA), (R1O,R2Q,ZJ,XA,YA), (R1P,R2Q,ZJ,XA,YA), (R1Q,R2Q,ZJ,XA,YA), (R1A,R2A,ZK,XA,YA), (R1B,R2A,ZK,XA,YA), (R1C,R2A,ZK,XA,YA), (R1D,R2A,ZK,XA,YA), (R1E,R2A,ZK,XA,YA), (R1F,R2A,ZK,XA,YA), (R1G,R2A,ZK,XA,YA), (R1H,R2A,ZK,XA,YA), (R1I,R2A,ZK,XA,YA), (R1J,R2A,ZK,XA,YA), (R1K,R2A,ZK,XA,YA), (R1L,R2A,ZK,XA,YA), (R1M,R2A,ZK,XA,YA), (R1N,R2A,ZK,XA,YA), (R1O,R2A,ZK,XA,YA), (R1P,R2A,ZK,XA,YA), (R1Q,R2A,ZK,XA,YA), (R1A,R2B,ZK,XA,YA), (R1B,R2B,ZK,XA,YA), (R1C,R2B,ZK,XA,YA), (R1D,R2B,ZK,XA,YA), (R1E,R2B,ZK,XA,YA), (R1F,R2B,ZK,XA,YA), (R1G,R2B,ZK,XA,YA), (R1H,R2B,ZK,XA,YA), (R1I,R2B,ZK,XA,YA), (R1J,R2B,ZK,XA,YA), (R1K,R2B,ZK,XA,YA), (R1L,R2B,ZK,XA,YA), (R1M,R2B,ZK,XA,YA), (R1N,R2B,ZK,XA,YA), (R1O,R2B,ZK,XA,YA), (R1P,R2B,ZK,XA,YA), (R1Q,R2B,ZK,XA,YA), (R1A,R2C,ZK,XA,YA), (R1B,R2C,ZK,XA,YA), (R1C,R2C,ZK,XA,YA), (R1D,R2C,ZK,XA,YA), (R1E,R2C,ZK,XA,YA), (R1F,R2C,ZK,XA,YA), (R1G,R2C,ZK,XA,YA), (R1H,R2C,ZK,XA,YA), (R1I,R2C,ZK,XA,YA), (R1J,R2C,ZK,XA,YA), (R1K,R2C,ZK,XA,YA), (R1L,R2C,ZK,XA,YA), (R1M,R2C,ZK,XA,YA), (R1N,R2C,ZK,XA,YA), (R1O,R2C,ZK,XA,YA), (R1P,R2C,ZK,XA,YA), (R1Q,R2C,ZK,XA,YA), (R1A,R2D,ZK,XA,YA), (R1B,R2D,ZK,XA,YA), (R1C,R2D,ZK,XA,YA), (R1D,R2D,ZK,XA,YA), (R1E,R2D,ZK,XA,YA), (R1F,R2D,ZK,XA,YA), (R1G,R2D,ZK,XA,YA), (R1H,R2D,ZK,XA,YA), (R1I,R2D,ZK,XA,YA), (R1J,R2D,ZK,XA,YA), (R1K,R2D,ZK,XA,YA), (R1L,R2D,ZK,XA,YA), (R1M,R2D,ZK,XA,YA), (R1N,R2D,ZK,XA,YA), (R1O,R2D,ZK,XA,YA), (R1P,R2D,ZK,XA,YA), (R1Q,R2D,ZK,XA,YA), (R1A,R2E,ZK,XA,YA), (R1B,R2E,ZK,XA,YA), (R1C,R2E,ZK,XA,YA), (R1D,R2E,ZK,XA,YA), (R1E,R2E,ZK,XA,YA), (R1F,R2E,ZK,XA,YA), (R1G,R2E,ZK,XA,YA), (R1H,R2E,ZK,XA,YA), (R1I,R2E,ZK,XA,YA), (R1J,R2E,ZK,XA,YA), (R1K,R2E,ZK,XA,YA), (R1L,R2E,ZK,XA,YA), (R1M,R2E,ZK,XA,YA), (R1N,R2E,ZK,XA,YA), (R1O,R2E,ZK,XA,YA), (R1P,R2E,ZK,XA,YA), (R1Q,R2E,ZK,XA,YA), (R1A,R2F,ZK,XA,YA), (R1B,R2F,ZK,XA,YA), (R1C,R2F,ZK,XA,YA), (R1D,R2F,ZK,XA,YA), (R1E,R2F,ZK,XA,YA), (R1F,R2F,ZK,XA,YA), (R1G,R2F,ZK,XA,YA), (R1H,R2F,ZK,XA,YA), (R1I,R2F,ZK,XA,YA), (R1J,R2F,ZK,XA,YA), (R1K,R2F,ZK,XA,YA), (R1L,R2F,ZK,XA,YA), (R1M,R2F,ZK,XA,YA), (R1N,R2F,ZK,XA,YA), (R1O,R2F,ZK,XA,YA), (R1P,R2F,ZK,XA,YA), (R1Q,R2F,ZK,XA,YA), (R1A,R2G,ZK,XA,YA), (R1B,R2G,ZK,XA,YA), (R1C,R2G,ZK,XA,YA), (R1D,R2G,ZK,XA,YA), (R1E,R2G,ZK,XA,YA), (R1F,R2G,ZK,XA,YA), (R1G,R2G,ZK,XA,YA), (R1H,R2G,ZK,XA,YA), (R1I,R2G,ZK,XA,YA), (R1J,R2G,ZK,XA,YA), (R1K,R2G,ZK,XA,YA), (R1L,R2G,ZK,XA,YA), (R1M,R2G,ZK,XA,YA), (R1N,R2G,ZK,XA,YA), (R1O,R2G,ZK,XA,YA), (R1P,R2G,ZK,XA,YA), (R1Q,R2G,ZK,XA,YA), (R1A,R2H,ZK,XA,YA), (R1B,R2H,ZK,XA,YA), (R1C,R2H,ZK,XA,YA), (R1D,R2H,ZK,XA,YA), (R1E,R2H,ZK,XA,YA), (R1F,R2H,ZK,XA,YA), (R1G,R2H,ZK,XA,YA), (R1H,R2H,ZK,XA,YA), (R1I,R2H,ZK,XA,YA), (R1J,R2H,ZK,XA,YA), (R1K,R2H,ZK,XA,YA), (R1L,R2H,ZK,XA,YA), (R1M,R2H,ZK,XA,YA), (R1N,R2H,ZK,XA,YA), (R1O,R2H,ZK,XA,YA), (R1P,R2H,ZK,XA,YA), (R1Q,R2H,ZK,XA,YA), (R1A,R2I,ZK,XA,YA), (R1B,R2I,ZK,XA,YA), (R1C,R2I,ZK,XA,YA), (R1D,R2I,ZK,XA,YA), (R1E,R2I,ZK,XA,YA), (R1F,R2I,ZK,XA,YA), (R1G,R2I,ZK,XA,YA), (R1H,R2I,ZK,XA,YA), (R1I,R2I,ZK,XA,YA), (R1J,R2I,ZK,XA,YA), (R1K,R2I,ZK,XA,YA), (R1L,R2I,ZK,XA,YA), (R1M,R2I,ZK,XA,YA), (R1N,R2I,ZK,XA,YA), (R1O,R2I,ZK,XA,YA), (R1P,R2I,ZK,XA,YA), (R1Q,R2I,ZK,XA,YA), (R1A,R2J,ZK,XA,YA), (R1B,R2J,ZK,XA,YA), (R1C,R2J,ZK,XA,YA), (R1D,R2J,ZK,XA,YA), (R1E,R2J,ZK,XA,YA), (R1F,R2J,ZK,XA,YA), (R1G,R2J,ZK,XA,YA), (R1H,R2J,ZK,XA,YA), (R1I,R2J,ZK,XA,YA), (R1J,R2J,ZK,XA,YA), (R1K,R2J,ZK,XA,YA), (R1L,R2J,ZK,XA,YA), (R1M,R2J,ZK,XA,YA), (R1N,R2J,ZK,XA,YA), (R1O,R2J,ZK,XA,YA), (R1P,R2J,ZK,XA,YA), (R1Q,R2J,ZK,XA,YA), (R1A,R2K,ZK,XA,YA), (R1B,R2K,ZK,XA,YA), (R1C,R2K,ZK,XA,YA), (R1D,R2K,ZK,XA,YA), (R1E,R2K,ZK,XA,YA), (R1F,R2K,ZK,XA,YA), (R1G,R2K,ZK,XA,YA), (R1H,R2K,ZK,XA,YA), (R1I,R2K,ZK,XA,YA), (R1J,R2K,ZK,XA,YA), (R1K,R2K,ZK,XA,YA), (R1L,R2K,ZK,XA,YA), (R1M,R2K,ZK,XA,YA), (R1N,R2K,ZK,XA,YA), (R1O,R2K,ZK,XA,YA), (R1P,R2K,ZK,XA,YA), (R1Q,R2K,ZK, XA,YA), (R1A,R2L,ZK,XA,YA), (R1B,R2L,ZK,XA,YA), (R1C,R2L,ZK,XA,YA), (R1D,R2L,ZK,XA,YA), (R1E,R2L,ZK,XA,YA), (R1F,R2L,ZK,XA,YA), (R1G,R2L,ZK,XA,YA), (R1H,R2L,ZK,XA,YA), (R1I,R2L,ZK,XA,YA), (R1J,R2L,ZK,XA,YA), (R1K,R2L,ZK,XA,YA), (R1L,R2L,ZK,XA,YA), (R1M,R2L,ZK,XA,YA), (R1N,R2L,ZK,XA,YA), (R1O,R2L,ZK,XA,YA), (R1P,R2L,ZK,XA,YA), (R1Q,R2L,ZK,XA,YA), (R1A,R2M,ZK,XA,YA), (R1B,R2M,ZK,XA,YA), (R1C,R2M,ZK,XA,YA), (R1D,R2M,ZK,XA,YA), (R1E,R2M,ZK,XA,YA), (R1F,R2M,ZK,XA,YA), (R1G,R2M,ZK,XA,YA), (R1H,R2M,ZK,XA,YA), (R1I,R2M,ZK,XA,YA), (R1J,R2M,ZK,XA,YA), (R1K,R2M,ZK,XA,YA), (R1L,R2M,ZK,XA,YA), (R1M,R2M,ZK,XA,YA), (R1N,R2M,ZK,XA,YA), (R1O,R2M,ZK,XA,YA), (R1P,R2M,ZK,XA,YA), (R1Q,R2M,ZK,XA,YA), (R1A,R2N,ZK,XA,YA), (R1B,R2N,ZK,XA,YA), (R1C,R2N,ZK,XA,YA), (R1D,R2N,ZK,XA,YA), (R1E,R2N,ZK,XA,YA), (R1F,R2N,ZK,XA,YA), (R1G,R2N,ZK,XA,YA), (R1H,R2N,ZK,XA,YA), (R1I,R2N,ZK,XA,YA), (R1J,R2N,ZK,XA,YA), (R1K,R2N,ZK,XA,YA), (R1L,R2N,ZK,XA,YA), (R1M,R2N,ZK,XA,YA), (R1N,R2N,ZK,XA,YA), (R1O,R2N,ZK,XA,YA), (R1P,R2N,ZK,XA,YA), (R1Q,R2N,ZK,XA,YA), (R1A,R2O,ZK,XA,YA), (R1B,R2O,ZK,XA,YA), (R1C,R2O,ZK,XA,YA), (R1D,R2O,ZK,XA,YA), (R1E,R2O,ZK,XA,YA), (R1F,R2O,ZK,XA,YA), (R1G,R2O,ZK,XA,YA), (R1H,R2O,ZK,XA,YA), (R1I,R2O,ZK,XA,YA), (R1J,R2O,ZK,XA,YA), (R1K,R2O,ZK,XA,YA), (R1L,R2O,ZK,XA,YA), (R1M,R2O,ZK,XA,YA), (R1N,R2O,ZK,XA,YA), (R1O,R2O,ZK,XA,YA), (R1P,R2O,ZK,XA,YA), (R1Q,R2O,ZK,XA,YA), (R1A,R2P,ZK,XA,YA), (R1B,R2P,ZK,XA,YA), (R1C,R2P,ZK,XA,YA), (R1D,R2P,ZK,XA,YA), (R1E,R2P,ZK,XA,YA), (R1F,R2P,ZK,XA,YA), (R1G,R2P,ZK,XA,YA), (R1H,R2P,ZK,XA,YA), (R1I,R2P,ZK,XA,YA), (R1J,R2P,ZK,XA,YA), (R1K,R2P,ZK,XA,YA), (R1L,R2P,ZK,XA,YA), (R1M,R2P,ZK,XA,YA), (R1N,R2P,ZK,XA,YA), (R1O,R2P,ZK,XA,YA), (R1P,R2P,ZK,XA,YA), (R1Q,R2P,ZK,XA,YA), (R1A,R2Q,ZK,XA,YA), (R1B,R2Q,ZK,XA,YA), (R1C,R2Q,ZK,XA,YA), (R1D,R2Q,ZK,XA,YA), (R1E,R2Q,ZK,XA,YA), (R1F,R2Q,ZK,XA,YA), (R1G,R2Q,ZK,XA,YA), (R1H,R2Q,ZK,XA,YA), (R1I,R2Q,ZK,XA,YA), (R1J,R2Q,ZK,XA,YA), (R1K,R2Q,ZK,XA,YA), (R1L,R2Q,ZK,XA,YA), (R1M,R2Q,ZK,XA,YA), (R1N,R2Q,ZK,XA,YA), (R1O,R2Q,ZK,XA,YA), (R1P,R2Q,ZK,XA,YA), (R1Q,R2Q,ZK,XA,YA), (R1A,R2A,ZL,XA,YA), (R1B,R2A,ZL,XA,YA), (R1C,R2A,ZL,XA,YA), (R1D,R2A,ZL,XA,YA), (R1E,R2A,ZL,XA,YA), (R1F,R2A,ZL,XA,YA), (R1G,R2A,ZL,XA,YA), (R1H,R2A,ZL,XA,YA), (R1I,R2A,ZL,XA,YA), (R1J,R2A,ZL,XA,YA), (R1K,R2A,ZL,XA,YA), (R1L,R2A,ZL,XA,YA), (R1M,R2A,ZL,XA,YA), (R1N,R2A,ZL,XA,YA), (R1O,R2A,ZL,XA,YA), (R1P,R2A,ZL,XA,YA), (R1Q,R2A,ZL,XA,YA), (R1A,R2B,ZL,XA,YA), (R1B,R2B,ZL,XA,YA), (R1C,R2B,ZL,XA,YA), (R1D,R2B,ZL,XA,YA), (R1E,R2B,ZL,XA,YA), (R1F,R2B,ZL,XA,YA), (R1G,R2B,ZL,XA,YA), (R1H,R2B,ZL,XA,YA), (R1I,R2B,ZL,XA,YA), (R1J,R2B,ZL,XA,YA), (R1K,R2B,ZL,XA,YA), (R1L,R2B,ZL,XA,YA), (R1M,R2B,ZL,XA,YA), (R1N,R2B,ZL,XA,YA), (R1O,R2B,ZL,XA,YA), (R1P,R2B,ZL,XA,YA), (R1Q,R2B,ZL,XA,YA), (R1A,R2C,ZL,XA,YA), (R1B,R2C,ZL,XA,YA), (R1C,R2C,ZL,XA,YA), (R1D,R2C,ZL,XA,YA), (R1E,R2C,ZL,XA,YA), (R1F,R2C,ZL,XA,YA), (R1G,R2C,ZL,XA,YA), (R1H,R2C,ZL,XA,YA), (R1I,R2C,ZL,XA,YA), (R1J,R2C,ZL,XA,YA), (R1K,R2C,ZL,XA,YA), (R1L,R2C,ZL,XA,YA), (R1M,R2C,ZL,XA,YA), (R1N,R2C,ZL,XA,YA), (R1O,R2C,ZL,XA,YA), (R1P,R2C,ZL,XA,YA), (R1Q,R2C,ZL,XA,YA), (R1A,R2D,ZL,XA,YA), (R1B,R2D,ZL,XA,YA), (R1C,R2D,ZL,XA,YA), (R1D,R2D,ZL,XA,YA), (R1E,R2D,ZL,XA,YA), (R1F,R2D,ZL,XA,YA), (R1G,R2D,ZL,XA,YA), (R1H,R2D,ZL,XA,YA), (R1I,R2D,ZL,XA,YA), (R1J,R2D,ZL,XA,YA), (R1K,R2D,ZL,XA,YA), (R1L,R2D,ZL,XA,YA), (R1M,R2D,ZL,XA,YA), (R1N,R2D,ZL,XA,YA), (R1O,R2D,ZL,XA,YA), (R1P,R2D,ZL,XA,YA), (R1Q,R2D,ZL,XA,YA), (R1A,R2E,ZL,XA,YA), (R1B,R2E,ZL,XA,YA), (R1C,R2E,ZL,XA,YA), (R1D,R2E,ZL,XA,YA), (R1E,R2E,ZL,XA,YA), (R1F,R2E,ZL,XA,YA), (R1G,R2E,ZL,XA,YA), (R1H,R2E,ZL,XA,YA), (R1I,R2E,ZL,XA,YA), (R1J,R2E,ZL,XA,YA), (R1K,R2E,ZL,XA,YA), (R1L,R2E,ZL,XA,YA), (R1M,R2E,ZL,XA,YA), (R1N,R2E,ZL,XA,YA), (R1O,R2E,ZL,XA,YA), (R1P,R2E,ZL,XA,YA), (R1Q,R2E,ZL,XA,YA), (R1A,R2F,ZL,XA,YA), (R1B,R2F,ZL,XA,YA), (R1C,R2F,ZL,XA,YA), (R1D,R2F,ZL,XA,YA), (R1E,R2F,ZL,XA,YA), (R1F,R2F,ZL,XA,YA), (R1G,R2F,ZL,XA,YA), (R1H,R2F,ZL,XA,YA), (R1I,R2F,ZL,XA,YA), (R1J,R2F,ZL,XA,YA), (R1K,R2F,ZL,XA,YA), (R1L,R2F,ZL,XA,YA), (R1M,R2F,ZL,XA,YA), (R1N,R2F,ZL,XA,YA), (R1O,R2F,ZL,XA,YA), (R1P,R2F,ZL,XA,YA), (R1Q,R2F,ZL,XA,YA), (R1A,R2G,ZL,XA,YA), (R1B,R2G,ZL,XA,YA), (R1C,R2G,ZL,XA,YA), (R1D,R2G,ZL,XA,YA), (R1E,R2G,ZL,XA,YA), (R1F,R2G,ZL,XA,YA), (R1G,R2G,ZL,XA,YA), (R1H,R2G,ZL,XA,YA), (R1I,R2G,ZL,XA,YA), (R1J,R2G,ZL,XA,YA), (R1K,R2G,ZL,XA,YA), (R1L,R2G,ZL,XA,YA), (R1M,R2G,ZL,XA,YA), (R1N,R2G,ZL,XA,YA), (R1O,R2G,ZL,XA,YA), (R1P,R2G,ZL,XA,YA), (R1Q,R2G,ZL,XA,YA), (R1A,R2H,ZL,XA,YA), (R1B,R2H,ZL,XA,YA), (R1C,R2H,ZL,XA,YA), (R1D,R2H,ZL,XA,YA), (R1E,R2H,ZL,XA,YA), (R1F,R2H,ZL,XA,YA), (R1G,R2H,ZL,XA,YA), (R1H,R2H,ZL,XA,YA), (R1I,R2H,ZL,XA,YA), (R1J,R2H,ZL,XA,YA), (R1K,R2H,ZL,XA,YA), (R1L,R2H,ZL,XA,YA), (R1M,R2H,ZL,XA,YA), (R1N,R2H,ZL,XA,YA), (R1O,R2H,ZL,XA,YA), (R1P,R2H,ZL,XA,YA), (R1Q,R2H,ZL,XA,YA), (R1A,R2I,ZL,XA,YA), (R1B,R2I,ZL,XA,YA), (R1C,R2I,ZL,XA,YA), (R1D,R2I,ZL,XA,YA), (R1E,R2I,ZL,XA,YA), (R1F,R2I,ZL,XA,YA), (R1G,R2I,ZL,XA,YA), (R1H,R2I,ZL,XA,YA), (R1I,R2I,ZL,XA,YA), (R1J,R2I,ZL,XA,YA), (R1K,R2I,ZL,XA,YA), (R1L,R2I,ZL,XA,YA), (R1M,R2I,ZL,XA,YA), (R1N,R2I,ZL,XA,YA), (R1O,R2I,ZL,XA,YA), (R1P,R2I,ZL,XA,YA), (R1Q,R2I,ZL,XA,YA), (R1A,R2J,ZL,XA,YA), (R1B,R2J,ZL,XA,YA), (R1C,R2J,ZL,XA,YA), (R1D,R2J,ZL,XA,YA), (R1E,R2J,ZL,XA,YA), (R1F,R2J,ZL,XA,YA), (R1G,R2J,ZL,XA,YA), (R1H,R2J,ZL,XA,YA), (R1I,R2J,ZL,XA,YA), (R1J,R2J,ZL,XA,YA), (R1K,R2J,ZL,XA,YA), (R1L,R2J,ZL,XA,YA), (R1M,R2J,ZL,XA,YA), (R1N,R2J,ZL,XA,YA), (R1O,R2J,ZL,XA,YA), (R1P,R2J,ZL,XA,YA), (R1Q,R2J,ZL,XA,YA), (R1A,R2K,ZL,XA,YA), (R1B,R2K,ZL,XA,YA), (R1C,R2K,ZL,XA,YA), (R1D,R2K,ZL,XA,YA), (R1E,R2K,ZL,XA,YA), (R1F,R2K,ZL,XA,YA), (R1G,R2K,ZL,XA,YA), (R1H,R2K,ZL,XA,YA), (R1I,R2K,ZL,XA,YA), (R1J,R2K,ZL,XA,YA), (R1K,R2K,ZL,XA,YA), (R1L,R2K,ZL,XA,YA), (R1M,R2K,ZL,XA,YA), (R1N,R2K,ZL,XA,YA), (R1O,R2K,ZL,XA,YA), (R1P,R2K,ZL,XA,YA), (R1Q,R2K,ZL,XA,YA), (R1A,R2L,ZL,XA,YA), (R1B,R2L,ZL,XA,YA), (R1C,R2L,ZL,XA,YA), (R1D,R2L,ZL,XA,YA), (R1E,R2L,ZL,XA,YA), (R1F,R2L,ZL,XA,YA), (R1G,R2L,ZL,XA,YA), (R1H,R2L,ZL,XA,YA), (R1I,R2L,ZL,XA,YA), (R1J,R2L,ZL,XA,YA), (R1K,R2L,ZL,XA,YA), (R1L,R2L,ZL,XA,YA), (R1M,R2L,ZL,XA,YA), (R1N,R2L,ZL,XA,YA), (R1O,R2L,ZL,XA,YA), (R1P,R2L,ZL,XA,YA), (R1Q,R2L,ZL,XA,YA), (R1A,R2M,ZL,XA,YA), (R1B,R2M,ZL,XA,YA), (R1C,R2M,ZL,XA,YA), (R1D,R2M,ZL,XA,YA), (R1E,R2M,ZL,XA,YA), (R1F,R2M,ZL,XA,YA), (R1G,R2M,ZL,XA,YA), (R1H,R2M,ZL,XA,YA), (R1I,R2M,ZL,XA,YA), (R1J,R2M,ZL,XA,YA), (R1K,R2M,ZL,XA,YA), (R1L,R2M,ZL,XA,YA), (R1M, R2M,ZL,XA,YA), (R1N,R2M,ZL,XA,YA), (R1O,R2M,ZL,XA,YA), (R1P,R2M,ZL,XA,YA), (R1Q,R2M,ZL,XA,YA), (R1A,R2N,ZL,XA,YA), (R1B,R2N,ZL,XA,YA), (R1C,R2N,ZL,XA,YA), (R1D,R2N,ZL,XA,YA), (R1E,R2N,ZL,XA,YA), (R1F,R2N,ZL,XA,YA), (R1G,R2N,ZL,XA,YA), (R1H,R2N,ZL,XA,YA), (R1I,R2N,ZL,XA,YA), (R1J,R2N,ZL,XA,YA), (R1K,R2N,ZL,XA,YA), (R1L,R2N,ZL,XA,YA), (R1M,R2N,ZL,XA,YA), (R1N,R2N,ZL,XA,YA), (R1O,R2N,ZL,XA,YA), (R1P,R2N,ZL,XA,YA), (R1Q,R2N,ZL,XA,YA), (R1A,R2O,ZL,XA,YA), (R1B,R2O,ZL,XA,YA), (R1C,R2O,ZL,XA,YA), (R1D,R2O,ZL,XA,YA), (R1E,R2O,ZL,XA,YA), (R1F,R2O,ZL,XA,YA), (R1G,R2O,ZL,XA,YA), (R1H,R2O,ZL,XA,YA), (R1I,R2O,ZL,XA,YA), (R1J,R2O,ZL,XA,YA), (R1K,R2O,ZL,XA,YA), (R1L,R2O,ZL,XA,YA), (R1M,R2O,ZL,XA,YA), (R1N,R2O,ZL,XA,YA), (R1O,R2O,ZL,XA,YA), (R1P,R2O,ZL,XA,YA), (R1Q,R2O,ZL,XA,YA), (R1A,R2P,ZL,XA,YA), (R1B,R2P,ZL,XA,YA), (R1C,R2P,ZL,XA,YA), (R1D,R2P,ZL,XA,YA), (R1E,R2P,ZL,XA,YA), (R1F,R2P,ZL,XA,YA), (R1G,R2P,ZL,XA,YA), (R1H,R2P,ZL,XA,YA), (R1I,R2P,ZL,XA,YA), (R1J,R2P,ZL,XA,YA), (R1K,R2P,ZL,XA,YA), (R1L,R2P,ZL,XA,YA), (R1M,R2P,ZL,XA,YA), (R1N,R2P,ZL,XA,YA), (R1O,R2P,ZL,XA,YA), (R1P,R2P,ZL,XA,YA), (R1Q,R2P,ZL,XA,YA), (R1A,R2Q,ZL,XA,YA), (R1B,R2Q,ZL,XA,YA), (R1C,R2Q,ZL,XA,YA), (R1D,R2Q,ZL,XA,YA), (R1E,R2Q,ZL,XA,YA), (R1F,R2Q,ZL,XA,YA), (R1G,R2Q,ZL,XA,YA), (R1H,R2Q,ZL,XA,YA), (R1I,R2Q,ZL,XA,YA), (R1J,R2Q,ZL,XA,YA), (R1K,R2Q,ZL,XA,YA), (R1L,R2Q,ZL,XA,YA), (R1M,R2Q,ZL,XA,YA), (R1N,R2Q,ZL,XA,YA), (R1O,R2Q,ZL,XA,YA), (R1P,R2Q,ZL,XA,YA), (R1Q,R2Q,ZL,XA,YA), (R1A,R2A,ZM,XA,YA), (R1B,R2A,ZM,XA,YA), (R1C,R2A,ZM,XA,YA), (R1D,R2A,ZM,XA,YA), (R1E,R2A,ZM,XA,YA), (R1F,R2A,ZM,XA,YA), (R1G,R2A,ZM,XA,YA), (R1H,R2A,ZM,XA,YA), (R1I,R2A,ZM,XA,YA), (R1J,R2A,ZM,XA,YA), (R1K,R2A,ZM,XA,YA), (R1L,R2A,ZM,XA,YA), (R1M,R2A,ZM,XA,YA), (R1N,R2A,ZM,XA,YA), (R1O,R2A,ZM,XA,YA), (R1P,R2A,ZM,XA,YA), (R1Q,R2A,ZM,XA,YA), (R1A,R2B,ZM,XA,YA), (R1B,R2B,ZM,XA,YA), (R1C,R2B,ZM,XA,YA), (R1D,R2B,ZM,XA,YA), (R1E,R2B,ZM,XA,YA), (R1F,R2B,ZM,XA,YA), (R1G,R2B,ZM,XA,YA), (R1H,R2B,ZM,XA,YA), (R1I,R2B,ZM,XA,YA), (R1J,R2B,ZM,XA,YA), (R1K,R2B,ZM,XA,YA), (R1L,R2B,ZM,XA,YA), (R1M,R2B,ZM,XA,YA), (R1N,R2B,ZM,XA,YA), (R1O,R2B,ZM,XA,YA), (R1P,R2B,ZM,XA,YA), (R1Q,R2B,ZM,XA,YA), (R1A,R2C,ZM,XA,YA), (R1B,R2C,ZM,XA,YA), (R1C,R2C,ZM,XA,YA), (R1D,R2C,ZM,XA,YA), (R1E,R2C,ZM,XA,YA), (R1F,R22C,ZM,XA,YA), (R1G,R2C,ZM,XA,YA), (R1H,R2C,ZM,XA,YA), (R1I,R2C,ZM,XA,YA), (R1J,R2C,ZM,XA,YA), (R1K,R2C,ZM,XA,YA), (R1L,R2C,ZM,XA,YA), (R1M,R2C,ZM,XA,YA), (R1N,R2C,ZM,XA,YA), (R1O,R2C,ZM,XA,YA), (R1P,R2C,ZM,XA,YA), (R1Q,R2C,ZM,XA,YA), (R1A,R2D,ZM,XA,YA), (R1B,R2D,ZM,XA,YA), (R1C,R2D,ZM,XA,YA), (R1D,R2D,ZM,XA,YA), (R1E,R2D,ZM,XA,YA), (R1F,R2D,ZM,XA,YA), (R1G,R2D,ZM,XA,YA), (R1H,R2D,ZM,XA,YA), (R1I,R2D,ZM,XA,YA), (R1J,R2D,ZM,XA,YA), (R1K,R2D,ZM,XA,YA), (R1L,R2D,ZM,XA,YA), (R1M,R2D,ZM,XA,YA), (R1N,R2D,ZM,XA,YA), (R1O,R2D,ZM,XA,YA), (R1P,R2D,ZM,XA,YA), (R1Q,R2D,ZM,XA,YA), (R1A,R2E,ZM,XA,YA), (R1B,R2E,ZM,XA,YA), (R1C,R2E,ZM,XA,YA), (R1D,R2E,ZM,XA,YA), (R1E,R2E,ZM,XA,YA), (R1F,R2E,ZM,XA,YA), (R1G,R2E,ZM,XA,YA), (R1H,R2E,ZM,XA,YA), (R1I,R2E,ZM,XA,YA), (R1J,R2E,ZM,XA,YA), (R1K,R2E,ZM,XA,YA), (R1L,R2E,ZM,XA,YA), (R1M,R2E,ZM,XA,YA), (R1N,R2E,ZM,XA,YA), (R1O,R2E,ZM,XA,YA), (R1P,R2E,ZM,XA,YA), (R1Q,R2E,ZM,XA,YA), (R1A,R2F,ZM,XA,YA), (R1B,R2F,ZM,XA,YA), (R1C,R2F,ZM,XA,YA), (R1D,R2F,ZM,XA,YA), (R1E,R2F,ZM,XA,YA), (R1F,R2F,ZM,XA,YA), (R1G,R2F,ZM,XA,YA), (R1H,R2F,ZM,XA,YA), (R1I,R2F,ZM,XA,YA), (R1J,R2F,ZM,XA,YA), (R1K,R2F,ZM,XA,YA), (R1L,R2F,ZM,XA,YA), (R1M,R2F,ZM,XA,YA), (R1N,R2F,ZM,XA,YA), (R1O,R2F,ZM,XA,YA), (R1P,R2F,ZM,XA,YA), (R1Q,R2F,ZM,XA,YA), (R1A,R2G,ZM,XA,YA), (R1B,R2G,ZM,XA,YA), (R1C,R2G,ZM,XA,YA), (R1D,R2G,ZM,XA,YA), (R1E,R2G,ZM,XA,YA), (R1F,R2G,ZM,XA,YA), (R1G,R2G,ZM,XA,YA), (R1H,R2G,ZM,XA,YA), (R1I,R2G,ZM,XA,YA), (R1J,R2G,ZM,XA,YA), (R1K,R2G,ZM,XA,YA), (R1L,R2G,ZM,XA,YA), (R1M,R2G,ZM,XA,YA), (R1N,R2G,ZM,XA,YA), (R1O,R2G,ZM,XA,YA), (R1P,R2G,ZM,XA,YA), (R1Q,R2G,ZM,XA,YA), (R1A,R2H,ZM,XA,YA), (R1B,R2H,ZM,XA,YA), (R1C,R2H,ZM,XA,YA), (R1D,R2H,ZM,XA,YA), (R1E,R2H,ZM,XA,YA), (R1F,R2H,ZM,XA,YA), (R1G,R2H,ZM,XA,YA), (R1H,R2H,ZM,XA,YA), (R1I,R2H,ZM,XA,YA), (R1J,R2H,ZM,XA,YA), (R1K,R2H,ZM,XA,YA), (R1L,R2H,ZM,XA,YA), (R1M,R2H,ZM,XA,YA), (R1N,R2H,ZM,XA,YA), (R1O,R2H,ZM,XA,YA), (R1P,R2H,ZM,XA,YA), (R1Q,R2H,ZM,XA,YA), (R1A,R2I,ZM,XA,YA), (R1B,R2I,ZM,XA,YA), (R1C,R2I,ZM,XA,YA), (R1D,R2I,ZM,XA,YA), (R1E,R2I,ZM,XA,YA), (R1F,R2I,ZM,XA,YA), (R1G,R2I,ZM,XA,YA), (R1H,R2I,ZM,XA,YA), (R1I,R2I,ZM,XA,YA), (R1J,R2I,ZM,XA,YA), (R1K,R2I,ZM,XA,YA), (R1L,R2I,ZM,XA,YA), (R1M,R2I,ZM,XA,YA), (R1N,R2I,ZM,XA,YA), (R1O,R2I,ZM,XA,YA), (R1P,R2I,ZM,XA,YA), (R1Q,R2I,ZM,XA,YA), (R1A,R2J,ZM,XA,YA), (R1B,R2J,ZM,XA,YA), (R1C,R2J,ZM,XA,YA), (R1D,R2J,ZM,XA,YA), (R1E,R2J,ZM,XA,YA), (R1F,R2J,ZM,XA,YA), (R1G,R2J,ZM,XA,YA), (R1H,R2J,ZM,XA,YA), (R1I,R2J,ZM,XA,YA), (R1J,R2J,ZM,XA,YA), (R1K,R2J,ZM,XA,YA), (R1L,R2J,ZM,XA,YA), (R1M,R2J,ZM,XA,YA), (R1N,R2J,ZM,XA,YA), (R1O,R2J,ZM,XA,YA), (R1P,R2J,ZM,XA,YA), (R1Q,R2J,ZM,XA,YA), (R1A,R2K,ZM,XA,YA), (R1B,R2K,ZM,XA,YA), (R1C,R2K,ZM,XA,YA), (R1D,R2K,ZM,XA,YA), (R1E,R2K,ZM,XA,YA), (R1F,R2K,ZM,XA,YA), (R1G,R2K,ZM,XA,YA), (R1H,R2K,ZM,XA,YA), (R1L R2K,ZM,XA,YA), (R1J,R2K,ZM,XA,YA), (R1K,R2K,ZM,XA,YA), (R1L,R2K,ZM,XA,YA), (R1M,R2K,ZM,XA,YA), (R1N,R2K,ZM,XA,YA), (R1O,R2K,ZM,XA,YA), (R1P,R2K,ZM,XA,YA), (R1Q,R2K,ZM,XA,YA), (R1A,R2L,ZM,XA,YA), (R1B,R2L,ZM,XA,YA), (R1C,R2L,ZM,XA,YA), (R1D,R2L,ZM,XA,YA), (R1E,R2L,ZM,XA,YA), (R1F,R2L,ZM,XA,YA), (R1G,R2L,ZM,XA,YA), (R1H,R2L,ZM,XA,YA), (R1I,R2L,ZM,XA,YA), (R1J,R2L,ZM,XA,YA), (R1K,R2L,ZM,XA,YA), (R1L,R2L,ZM,XA,YA), (R1M,R2L,ZM,XA,YA), (R1N,R2L,ZM,XA,YA), (R1O,R2L,ZM,XA,YA), (R1P,R2L,ZM,XA,YA), (R1Q,R2L,ZM,XA,YA), (R1A,R2M,ZM,XA,YA), (R1B,R2M,ZM,XA,YA), (R1C,R2M,ZM,XA,YA), (R1D,R2M,ZM,XA,YA), (R1E,R2M,ZM,XA,YA), (R1F,R2M,ZM,XA,YA), (R1G,R2M,ZM,XA,YA), (R1H,R2M,ZM,XA,YA), (R1I,R2M,ZM,XA,YA), (R1J,R2M,ZM,XA,YA), (R1K,R2M,ZM,XA,YA), (R1L,R2M,ZM,XA,YA), (R1M,R2M,ZM,XA,YA), (R1N,R2M,ZM,XA,YA), (R1O,R2M,ZM,XA,YA), (R1P,R2M,ZM,XA,YA), (R1Q,R2M,ZM,XA,YA), (R1A,R2N,ZM,XA,YA), (R1B,R2N,ZM,XA,YA), (R1C,R2N,ZM,XA,YA), (R1D,R2N,ZM,XA,YA), (R1E,R2N,ZM,XA,YA), (R1F,R2N,ZM,XA,YA), (R1G,R2N,ZM,XA,YA), (R1H,R2N,ZM,XA,YA), (R1I,R2N,ZM,XA,YA), (R1J,R2N,ZM,XA,YA), (R1K,R2N,ZM,XA,YA), (R1L,R2N,ZM,XA,YA), (R1M,R2N,ZM,XA,YA), (R1N,R2N,ZM,XA,YA), (R1O,R2N,ZM,XA,YA), (R1P,R2N,ZM,XA,YA), (R1Q,R2N,ZM,XA,YA), (R1A,R2O,ZM,XA,YA), (R1B,R2O, ZM,XA,YA), (R1C,R2O,ZM,XA,YA), (R1D,R2O,ZM,XA, YA), (R1E,R2O,ZM,XA,YA), (R1F,R2O,ZM,XA,YA), (R1G,R2O,ZM,XA,YA), (R1H,R2O,ZM,XA,YA), (R1I, R2O,ZM,XA,YA), (R1J,R2O,ZM,XA,YA), (R1K,R2O,ZM, XA,YA), (R1L,R2O,ZM,XA,YA), (R1M,R2O,ZM,XA,YA), (R1N,R2O,ZM,XA,YA), (R1O,R2O,ZM,XA,YA), (R1P, R2O,ZM,XA,YA), (R1Q,R2O,ZM,XA,YA), (R1A,R2P,ZM, XA,YA), (R1B,R2P,ZM,XA,YA), (R1C,R2P,ZM,XA,YA), (R1D,R2P,ZM,XA,YA), (R1E,R2P,ZM,XA,YA), (R1F,R2P, ZM,XA,YA), (R1G,R2P,ZM,XA,YA), (R1H,R2P,ZM,XA, YA), (R1I,R2P,ZM,XA,YA), (R1J,R2P,ZM,XA,YA), (R1K, R2P,ZM,XA,YA), (R1L,R2P,ZM,XA,YA), (R1M,R2P,ZM, XA,YA), (R1N,R2P,ZM,XA,YA), (R1O,R2P,ZM,XA,YA), (R1P,R2P,ZM,XA,YA), (R1Q,R2P,ZM,XA,YA), (R1A, R2Q,ZM,XA,YA), (R1B,R2Q,ZM,XA,YA), (R1C,R2Q,ZM, XA,YA), (R1D,R2Q,ZM,XA,YA), (R1E,R2Q,ZM,XA,YA), (R1F,R2Q,ZM,XA,YA), (R1G,R2Q,ZM,XA,YA), (R1H, R2Q,ZM,XA,YA), (R1I,R2Q,ZM,XA,YA), (R1J,R2Q,ZM, XA,YA), (R1K,R2Q,ZM,XA,YA), (R1L,R2Q,ZM,XA,YA), (R1M,R2Q,ZM,XA,YA), (R1N,R2Q,ZM,XA,YA), (R1O, R2Q,ZM,XA,YA), (R1P,R2Q,ZM,XA,YA), (R1Q,R2Q,ZM, XA,YA), (R1A,R2A,ZN,XA,YA), (R1B,R2A,ZN,XA,YA), (R1C,R2A,ZN,XA,YA), (R1D,R2A,ZN,XA,YA), (R1E, R2A,ZN,XA,YA), (R1F,R2A,ZN,XA,YA), (R1G,R2A,ZN, XA,YA), (R1H,R2A,ZN,XA,YA), (R1I,R2A,ZN,XA,YA), (R1J,R2A,ZN,XA,YA), (R1K,R2A,ZN,XA,YA), (R1L, R2A,ZN,XA,YA), (R1M,R2A,ZN,XA,YA), (R1N,R2A,ZN, XA,YA), (R1O,R2A,ZN,XA,YA), (R1P,R2A,ZN,XA,YA), (R1Q,R2A,ZN,XA,YA), (R1A,R2B,ZN,XA,YA), (R1B, R2B,ZN,XA,YA), (R1C,R2B,ZN,XA,YA), (R1D,R2B,ZN, XA,YA), (R1E,R2B,ZN,XA,YA), (R1F,R2B,ZN,XA,YA), (R1G,R2B,ZN,XA,YA), (R1H,R2B,ZN,XA,YA), (R1I,R2B, ZN,XA,YA), (R1J,R2B,ZN,XA,YA), (R1K,R2B,ZN,XA, YA), (R1L,R2B,ZN,XA,YA), (R1M,R2B,ZN,XA,YA), (R1N,R2B,ZN,XA,YA), (R1O,R2B,ZN,XA,YA), (R1P, R2B,ZN,XA,YA), (R1Q,R2B,ZN,XA,YA), (R1A,R22C,ZN, XA,YA), (R1B,R2C,ZN,XA,YA), (R1C,R2C,ZN,XA,YA), (R1D,R2C,ZN,XA,YA), (R1E,R2C,ZN,XA,YA), (R1F,R2C, ZN,XA,YA), (R1G,R2C,ZN,XA,YA), (R1H,R2C,ZN,XA, YA), (R1I,R2C,ZN,XA,YA), (R1J,R2C,ZN,XA,YA), (R1K, R2C,ZN,XA,YA), (R1L,R2C,ZN,XA,YA), (R1M,R2C,ZN, XA,YA), (R1N,R2C,ZN,XA,YA), (R1O,R2C,ZN,XA,YA), (R1P,R2C,ZN,XA,YA), (R1Q,R2C,ZN,XA,YA), (R1A, R2D,ZN,XA,YA), (R1B,R2D,ZN,XA,YA), (R1C,R2D,ZN, XA,YA), (R1D,R2D,ZN,XA,YA), (R1E,R2D,ZN,XA,YA), (R1F,R2D,ZN,XA,YA), (R1G,R2D,ZN,XA,YA), (R1H, R2D,ZN,XA,YA), (R1I,R2D,ZN,XA,YA), (R1J,R2D,ZN, XA,YA), (R1K,R2D,ZN,XA,YA), (R1L,R2D,ZN,XA,YA), (R1M,R2D,ZN,XA,YA), (R1N,R2D,ZN,XA,YA), (R1O, R2D,ZN,XA,YA), (R1P,R2D,ZN,XA,YA), (R1Q,R2D,ZN, XA,YA), (R1A,R2E,ZN,XA,YA), (R1B,R2E,ZN,XA,YA), (R1C,R2E,ZN,XA,YA), (R1D,R2E,ZN,XA,YA), (R1E,R2E, ZN,XA,YA), (R1F,R2E,ZN,XA,YA), (R1G,R2E,ZN,XA, YA), (R1H,R2E,ZN,XA,YA), (R1I,R2E,ZN,XA,YA), (R1J, R2E,ZN,XA,YA), (R1K,R2E,ZN,XA,YA), (R1L,R2E,ZN, XA,YA), (R1M,R2E,ZN,XA,YA), (R1N,R2E,ZN,XA,YA), (R1O,R2E,ZN,XA,YA), (R1P,R2E,ZN,XA,YA), (R1Q,R2E, ZN,XA,YA), (R1A,R2F,ZN,XA,YA), (R1B,R2F,ZN,XA, YA), (R1C,R2F,ZN,XA,YA), (R1D,R2F,ZN,XA,YA), (R1E, R2F,ZN,XA,YA), (R1F,R2F,ZN,XA,YA), (R1G,R2F,ZN, XA,YA), (R1H,R2F,ZN,XA,YA), (R1I,R2F,ZN,XA,YA), (R1J,R2F,ZN,XA,YA), (R1K,R2F,ZN,XA,YA), (R1L,R2F, ZN,XA,YA), (R1M,R2F,ZN,XA,YA), (R1N,R2F,ZN,XA, YA), (R1O,R2F,ZN,XA,YA), (R1P,R2F,ZN,XA,YA), (R1Q, R2F,ZN,XA,YA), (R1A,R2G,ZN,XA,YA), (R1B,R2G,ZN, XA,YA), (R1C,R2G,ZN,XA,YA), (R1D,R2G,ZN,XA,YA), (R1E,R2G,ZN,XA,YA), (R1F,R2G,ZN,XA,YA), (R1G, R2G,ZN,XA,YA), (R1H,R2G,ZN,XA,YA), (R1I,R2G,ZN, XA,YA), (R1J,R2G,ZN,XA,YA), (R1K,R2G,ZN,XA,YA), (R1L,R2G,ZN,XA,YA), (R1M,R2G,ZN,XA,YA), (R1N, R2G,ZN,XA,YA), (R1O,R2G,ZN,XA,YA), (R1P,R2G,ZN, XA,YA), (R1Q,R2G,ZN,XA,YA), (R1A,R2H,ZN,XA,YA), (R1B,R2H,ZN,XA,YA), (R1C,R2H,ZN,XA,YA), (R1D, R2H,ZN,XA,YA), (R1E,R2H,ZN,XA,YA), (R1F,R2H,ZN, XA,YA), (R1G,R2H,ZN,XA,YA), (R1H,R2H,ZN,XA,YA), (R1I,R2H,ZN,XA,YA), (R1J,R2H,ZN,XA,YA), (R1K,R2H, ZN,XA,YA), (R1L,R2H,ZN,XA,YA), (R1M,R2H,ZN,XA, YA), (R1N,R2H,ZN,XA,YA), (R1O,R2H,ZN,XA,YA), (R1P,R2H,ZN,XA,YA), (R1Q,R2H,ZN,XA,YA), (R1A,R2I, ZN,XA,YA), (R1B,R2I,ZN,XA,YA), (R1C,R2I,ZN,XA, YA), (R1D,R2I,ZN,XA,YA), (R1E,R2I,ZN,XA,YA), (R1F, R2I,ZN,XA,YA), (R1G,R2I,ZN,XA,YA), (R1H,R2I,ZN, XA,YA), (R1I,R2I,ZN,XA,YA), (R1J,R2I,ZN,XA,YA), (R1K,R2I,ZN,XA,YA), (R1L,R2I,ZN,XA,YA), (R1M,R2I, ZN,XA,YA), (R1N,R2I,ZN,XA,YA), (R1O,R2I,ZN,XA, YA), (R1P,R2I,ZN,XA,YA), (R1Q,R2I,ZN,XA,YA), (R1A, R2J,ZN,XA,YA), (R1B,R2J,ZN,XA,YA), (R1C,R2J,ZN, XA,YA), (R1D,R2J,ZN,XA,YA), (R1E,R2J,ZN,XA,YA), (R1F,R2J,ZN,XA,YA), (R1G,R2J,ZN,XA,YA), (R1H,R2J, ZN,XA,YA), (R1I,R2J,ZN,XA,YA), (R1J,R2J,ZN,XA,YA), (R1K,R2J,ZN,XA,YA), (R1L,R2J,ZN,XA,YA), (R1M,R2J, ZN,XA,YA), (R1N,R2J,ZN,XA,YA), (R1O,R2J,ZN,XA, YA), (R1P,R2J,ZN,XA,YA), (R1Q,R2J,ZN,XA,YA), (R1A, R2K,ZN,XA,YA), (R1B,R2K,ZN,XA,YA), (R1C,R2K,ZN, XA,YA), (R1D,R2K,ZN,XA,YA), (R1E,R2K,ZN,XA,YA), (R1F,R2K,ZN,XA,YA), (R1G,R2K,ZN,XA,YA), (R1H, R2K,ZN,XA,YA), (R1I,R2K,ZN,XA,YA), (R1J,R2K,ZN, XA,YA), (R1K,R2K,ZN,XA,YA), (R1L,R2K,ZN,XA,YA), (R1M,R2K,ZN,XA,YA), (R1N,R2K,ZN,XA,YA), (R1O, R2K,ZN,XA,YA), (R1P,R2K,ZN,XA,YA), (R1Q,R2K,ZN, XA,YA), (R1A,R2L,ZN,XA,YA), (R1B,R2L,ZN,XA,YA), (R1C,R2L,ZN,XA,YA), (R1D,R2L,ZN,XA,YA), (R1E,R2L, ZN,XA,YA), (R1F,R2L,ZN,XA,YA), (R1G,R2L,ZN,XA, YA), (R1H,R2L,ZN,XA,YA), (R1I,R2L,ZN,XA,YA), (R1J, R2L,ZN,XA,YA), (R1K,R2L,ZN,XA,YA), (R1L,R2L,ZN, XA,YA), (R1M,R2L,ZN,XA,YA), (R1N,R2L,ZN,XA,YA), (R1O,R2L,ZN,XA,YA), (R1P,R2L,ZN,XA,YA), (R1Q,R2L, ZN,XA,YA), (R1A,R2M,ZN,XA,YA), (R1B,R2M,ZN,XA, YA), (R1C,R2M,ZN,XA,YA), (R1D,R2M,ZN,XA,YA), (R1E,R2M,ZN,XA,YA), (R1F,R2M,ZN,XA,YA), (R1G, R2M,ZN,XA,YA), (R1H,R2M,ZN,XA,YA), (R1I,R2M,ZN, XA,YA), (R1J,R2M,ZN,XA,YA), (R1K,R2M,ZN,XA,YA), (R1L,R2M,ZN,XA,YA), (R1M,R2M,ZN,XA,YA), (R1N, R2M,ZN,XA,YA), (R1O,R2M,ZN,XA,YA), (R1P,R2M,ZN, XA,YA), (R1Q,R2M,ZN,XA,YA), (R1A,R2N,ZN,XA,YA), (R1B,R2N,ZN,XA,YA), (R1C,R2N,ZN,XA,YA), (R1D, R2N,ZN,XA,YA), (R1E,R2N,ZN,XA,YA), (R1F,R2N,ZN, XA,YA), (R1G,R2N,ZN,XA,YA), (R1H,R2N,ZN,XA,YA), (R1I,R2N,ZN,XA,YA), (R1J,R2N,ZN,XA,YA), (R1K,R2N, ZN,XA,YA), (R1L,R2N,ZN,XA,YA), (R1M,R2N,ZN,XA, YA), (R1N,R2N,ZN,XA,YA), (R1O,R2N,ZN,XA,YA), (R1P,R2N,ZN,XA,YA), (R1Q,R2N,ZN,XA,YA), (R1A, R2O,ZN,XA,YA), (R1B,R2O,ZN,XA,YA), (R1C,R2O,ZN, XA,YA), (R1D,R2O,ZN,XA,YA), (R1E,R2O,ZN,XA,YA), (R1F,R2O,ZN,XA,YA), (R1G,R2O,ZN,XA,YA), (R1H, R2O,ZN,XA,YA), (R1I,R2O,ZN,XA,YA), (R1J,R2O,ZN, XA,YA), (R1K,R2O,ZN,XA,YA), (R1L,R2O,ZN,XA,YA), (R1M,R2O,ZN,XA,YA), (R1N,R2O,ZN,XA,YA), (R1O, R2O,ZN,XA,YA), (R1P,R2O,ZN,XA,YA), (R1Q,R2O,ZN, XA,YA), (R1A,R2P,ZN,XA,YA), (R1B,R2P,ZN,XA,YA), (R1C,R2P,ZN,XA,YA), (R1D,R2P,ZN,XA,YA), (R1E,R2P, ZN,XA,YA), (R1F,R2P,ZN,XA,YA), (R1G,R2P,ZN,XA, YA), (R1H,R2P,ZN,XA,YA), (R1I,R2P,ZN,XA,YA), (R1J, R2P,ZN,XA,YA), (R1K,R2P,ZN,XA,YA), (R1L,R2P,ZN, XA,YA), (R1M,R2P,ZN,XA,YA), (R1N,R2P,ZN,XA,YA), (R1O,R2P,ZN,XA,YA), (R1P,R2P,ZN,XA,YA), (R1Q,R2P,ZN,XA,YA), (R1A,R2Q,ZN,XA,YA), (R1B,R2Q,ZN,XA,YA), (R1C,R2Q,ZN,XA,YA), (R1D,R2Q,ZN,XA,YA), (R1E,R2Q,ZN,XA,YA), (R1F,R2Q,ZN,XA,YA), (R1G,R2Q,ZN,XA,YA), (R1H,R2Q,ZN,XA,YA), (R1I,R2Q,ZN,XA,YA), (R1J,R2Q,ZN,XA,YA), (R1K,R2Q,ZN,XA,YA), (R1L,R2Q,ZN,XA,YA), (R1M,R2Q,ZN,XA,YA), (R1N,R2Q,ZN,XA,YA), (R1O,R2Q,ZN,XA,YA), (R1P,R2Q,ZN,XA,YA), (R1Q,R2Q,ZN,XA,YA), (R1A,R2A,ZO,XA,YA), (R1B,R2A,ZO,XA,YA), (R1C,R2A,ZO,XA,YA), (R1D,R2A,ZO,XA,YA), (R1E,R2A,ZO,XA,YA), (R1F,R2A,ZO,XA,YA), (R1G,R2A,ZO,XA,YA), (R1H,R2A,ZO,XA,YA), (R1I,R2A,ZO,XA,YA), (R1J,R2A,ZO,XA,YA), (R1K,R2A,ZO,XA,YA), (R1L,R2A,ZO,XA,YA), (R1M,R2A,ZO,XA,YA), (R1N,R2A,ZO,XA,YA), (R1O,R2A,ZO,XA,YA), (R1P,R2A,ZO,XA,YA), (R1Q,R2A,ZO,XA,YA), (R1A,R2B,ZO,XA,YA), (R1B,R2B,ZO,XA,YA), (R1C,R2B,ZO,XA,YA), (R1D,R2B,ZO,XA,YA), (R1E,R2B,ZO,XA,YA), (R1F,R2B,ZO,XA,YA), (R1G,R2B,ZO,XA,YA), (R1H,R2B,ZO,XA,YA), (R1I,R2B,ZO,XA,YA), (R1J,R2B,ZO,XA,YA), (R1K,R2B,ZO,XA,YA), (R1L,R2B,ZO,XA,YA), (R1M,R2B,ZO,XA,YA), (R1N,R2B,ZO,XA,YA), (R1O,R2B,ZO,XA,YA), (R1P,R2B,ZO,XA,YA), (R1Q,R2B,ZO,XA,YA), (R1A,R2C,ZO,XA,YA), (R1B,R2C,ZO,XA,YA), (R1C,R2C,ZO,XA,YA), (R1D,R2C,ZO,XA,YA), (R1E,R2C,ZO,XA,YA), (R1F,R2C,ZO,XA,YA), (R1G,R22C,ZO,XA,YA), (R1H,R2C,ZO,XA,YA), (R1I,R2C,ZO,XA,YA), (R1J,R2C,ZO,XA,YA), (R1K,R2C,ZO,XA,YA), (R1L,R2C,ZO,XA,YA), (R1M,R2C,ZO,XA,YA), (R1N,R2C,ZO,XA,YA), (R1O,R2C,ZO,XA,YA), (R1P,R2C,ZO,XA,YA), (R1Q,R2C,ZO,XA,YA), (R1A,R2D,ZO,XA,YA), (R1B,R2D,ZO,XA,YA), (R1C,R2D,ZO,XA,YA), (R1D,R2D,ZO,XA,YA), (R1E,R2D,ZO,XA,YA), (R1F,R2D,ZO,XA,YA), (R1G,R2D,ZO,XA,YA), (R1H,R2D,ZO,XA,YA), (R1I,R2D,ZO,XA,YA), (R1J,R2D,ZO,XA,YA), (R1K,R2D,ZO,XA,YA), (R1L,R2D,ZO,XA,YA), (R1M,R2D,ZO,XA,YA), (R1N,R2D,ZO,XA,YA), (R1O,R2D,ZO,XA,YA), (R1P,R2D,ZO,XA,YA), (R1Q,R2D,ZO,XA,YA), (R1A,R2E,ZO,XA,YA), (R1B,R2E,ZO,XA,YA), (R1C,R2E,ZO,XA,YA), (R1D,R2E,ZO,XA,YA), (R1E,R2E,ZO,XA,YA), (R1F,R2E,ZO,XA,YA), (R1G,R2E,ZO,XA,YA), (R1H,R2E,ZO,XA,YA), (R1I,R2E,ZO,XA,YA), (R1J,R2E,ZO,XA,YA), (R1K,R2E,ZO,XA,YA), (R1L,R2E,ZO,XA,YA), (R1M,R2E,ZO,XA,YA), (R1N,R2E,ZO,XA,YA), (R1O,R2E,ZO,XA,YA), (R1P,R2E,ZO,XA,YA), (R1Q,R2E,ZO,XA,YA), (R1A,R2F,ZO,XA,YA), (R1B,R2F,ZO,XA,YA), (R1C,R2F,ZO,XA,YA), (R1D,R2F,ZO,XA,YA), (R1E,R2F,ZO,XA,YA), (R1F,R2F,ZO,XA,YA), (R1G,R2F,ZO,XA,YA), (R1H,R2F,ZO,XA,YA), (R1I,R2F,ZO,XA,YA), (R1J,R2F,ZO,XA,YA), (R1K,R2F,ZO,XA,YA), (R1L,R2F,ZO,XA,YA), (R1M,R2F,ZO,XA,YA), (R1N,R2F,ZO,XA,YA), (R1O,R2F,ZO,XA,YA), (R1P,R2F,ZO,XA,YA), (R1Q,R2F,ZO,XA,YA), (R1A,R2G,ZO,XA,YA), (R1B,R2G,ZO,XA,YA), (R1C,R2G,ZO,XA,YA), (R1D,R2G,ZO,XA,YA), (R1E,R2G,ZO,XA,YA), (R1F,R2G,ZO,XA,YA), (R1G,R2G,ZO,XA,YA), (R1H,R2G,ZO,XA,YA), (R1I,R2G,ZO,XA,YA), (R1J,R2G,ZO,XA,YA), (R1K,R2G,ZO,XA,YA), (R1L,R2G,ZO,XA,YA), (R1M,R2G,ZO,XA,YA), (R1N,R2G,ZO,XA,YA), (R1O,R2G,ZO,XA,YA), (R1P,R2G,ZO,XA,YA), (R1Q,R2G,ZO,XA,YA), (R1A,R2H,ZO,XA,YA), (R1B,R2H,ZO,XA,YA), (R1C,R2H,ZO,XA,YA), (R1D,R2H,ZO,XA,YA), (R1E,R2H,ZO,XA,YA), (R1F,R2H,ZO,XA,YA), (R1G,R2H,ZO,XA,YA), (R1H,R2H,ZO,XA,YA), (R1I,R2H,ZO,XA,YA), (R1J,R2H,ZO,XA,YA), (R1K,R2H,ZO,XA,YA), (R1L,R2H,ZO,XA,YA), (R1M,R2H,ZO,XA,YA), (R1N,R2H,ZO,XA,YA), (R1O,R2H,ZO,XA,YA), (R1P,R2H,ZO,XA,YA), (R1Q,R2H,ZO,XA,YA), (R1A,R2I,ZO,XA,YA), (R1B,R2I,ZO,XA,YA), (R1C,R2I,ZO,XA,YA), (R1D,R2I,ZO,XA,YA), (R1E,R2I,ZO,XA,YA), (R1F,R2I,ZO,XA,YA), (R1G,R2I,ZO,XA,YA), (R1H,R2I,ZO,XA,YA), (R1I,R2I,ZO,XA,YA), (R1J,R2I,ZO,XA,YA), (R1K,R2I,ZO,XA,YA), (R1L,R2I,ZO,XA,YA), (R1M,R2I,ZO,XA,YA), (R1N,R2I,ZO,XA,YA), (R1O,R2I,ZO,XA,YA), (R1P,R2I,ZO,XA,YA), (R1Q,R2I,ZO,XA,YA), (R1A,R2J,ZO,XA,YA), (R1B,R2J,ZO,XA,YA), (R1C,R2J,ZO,XA,YA), (R1D,R2J,ZO,XA,YA), (R1E,R2J,ZO,XA,YA), (R1F,R2J,ZO,XA,YA), (R1G,R2J,ZO,XA,YA), (R1H,R2J,ZO,XA,YA), (R1I,R2J,ZO,XA,YA), (R1J,R2J,ZO,XA,YA), (R1K,R2J,ZO,XA,YA), (R1L,R2J,ZO,XA,YA), (R1M,R2J,ZO,XA,YA), (R1N,R2J,ZO,XA,YA), (R1O,R2J,ZO,XA,YA), (R1P,R2J,ZO,XA,YA), (R1Q,R2J,ZO,XA,YA), (R1A,R2K,ZO,XA,YA), (R1B,R2K,ZO,XA,YA), (R1C,R2K,ZO,XA,YA), (R1D,R2K,ZO,XA,YA), (R1E,R2K,ZO,XA,YA), (R1F,R2K,ZO,XA,YA), (R1G,R2K,ZO,XA,YA), (R1H,R2K,ZO,XA,YA), (R1I,R2K,ZO,XA,YA), (R1J,R2K,ZO,XA,YA), (R1K,R2K,ZO,XA,YA), (R1L,R2K,ZO,XA,YA), (R1M,R2K,ZO,XA,YA), (R1N,R2K,ZO,XA,YA), (R1O,R2K,ZO,XA,YA), (R1P,R2K,ZO,XA,YA), (R1Q,R2K,ZO,XA,YA), (R1A,R2L,ZO,XA,YA), (R1B,R2L,ZO,XA,YA), (R1C,R2L,ZO,XA,YA), (R1D,R2L,ZO,XA,YA), (R1E,R2L,ZO,XA,YA), (R1F,R2L,ZO,XA,YA), (R1G,R2L,ZO,XA,YA), (R1H,R2L,ZO,XA,YA), (R1I,R2L,ZO,XA,YA), (R1J,R2L,ZO,XA,YA), (R1K,R2L,ZO,XA,YA), (R1L,R2L,ZO,XA,YA), (R1M,R2L,ZO,XA,YA), (R1N,R2L,ZO,XA,YA), (R1O,R2L,ZO,XA,YA), (R1P,R2L,ZO,XA,YA), (R1Q,R2L,ZO,XA,YA), (R1A,R2M,ZO,XA,YA), (R1B,R2M,ZO,XA,YA), (R1C,R2M,ZO,XA,YA), (R1D,R2M,ZO,XA,YA), (R1E,R2M,ZO,XA,YA), (R1F,R2M,ZO,XA,YA), (R1G,R2M,ZO,XA,YA), (R1H,R2M,ZO,XA,YA), (R1I,R2M,ZO,XA,YA), (R1J,R2M,ZO,XA,YA), (R1K,R2M,ZO,XA,YA), (R1L,R2M,ZO,XA,YA), (R1M,R2M,ZO,XA,YA), (R1N,R2M,ZO,XA,YA), (R1O,R2M,ZO,XA,YA), (R1P,R2M,ZO,XA,YA), (R1Q,R2M,ZO,XA,YA), (R1A,R2N,ZO,XA,YA), (R1B,R2N,ZO,XA,YA), (R1C,R2N,ZO,XA,YA), (R1D,R2N,ZO,XA,YA), (R1E,R2N,ZO,XA,YA), (R1F,R2N,ZO,XA,YA), (R1G,R2N,ZO,XA,YA), (R1H,R2N,ZO,XA,YA), (R1I,R2N,ZO,XA,YA), (R1J,R2N,ZO,XA,YA), (R1K,R2N,ZO,XA,YA), (R1L,R2N,ZO,XA,YA), (R1M,R2N,ZO,XA,YA), (R1N,R2N,ZO,XA,YA), (R1O,R2N,ZO,XA,YA), (R1P,R2N,ZO,XA,YA), (R1Q,R2N,ZO,XA,YA), (R1A,R2O,ZO,XA,YA), (R1B,R2O,ZO,XA,YA), (R1C,R2O,ZO,XA,YA), (R1D,R2O,ZO,XA,YA), (R1E,R2O,ZO,XA,YA), (R1F,R2O,ZO,XA,YA), (R1G,R2O,ZO,XA,YA), (R1H,R2O,ZO,XA,YA), (R1I,R2O,ZO,XA,YA), (R1J,R2O,ZO,XA,YA), (R1K,R2O,ZO,XA,YA), (R1L,R2O,ZO,XA,YA), (R1M,R2O,ZO,XA,YA), (R1N,R2O,ZO,XA,YA), (R1O,R2O,ZO,XA,YA), (R1P,R2O,ZO,XA,YA), (R1Q,R2O,ZO,XA,YA), (R1A,R2P,ZO,XA,YA), (R1B,R2P,ZO,XA,YA), (R1C,R2P,ZO,XA,YA), (R1D,R2P,ZO,XA,YA), (R1E,R2P,ZO,XA,YA), (R1F,R2P,ZO,XA,YA), (R1G,R2P,ZO,XA,YA), (R1H,R2P,ZO,XA,YA), (R1I,R2P,ZO,XA,YA), (R1J,R2P,ZO,XA,YA), (R1K,R2P,ZO,XA,YA), (R1L,R2P,ZO,XA,YA), (R1M,R2P,ZO,XA,YA), (R1N,R2P,ZO,XA,YA), (R1O,R2P,ZO,XA,YA), (R1P,R2P,ZO,XA,YA), (R1Q,R2P,ZO,XA,YA), (R1A,R2Q,ZO,XA,YA), (R1B,R2Q,ZO,XA,YA), (R1C,R2Q,ZO,XA,YA), (R1D,R2Q,ZO,XA,YA), (R1E,R2Q,ZO,XA,YA), (R1F,R2Q,ZO,XA,YA), (R1G,R2Q,ZO,XA,YA), (R1H,R2Q,ZO,XA,YA), (R1I,R2Q,ZO,XA,YA), (R1J,R2Q,ZO,XA,YA), (R1K,R2Q,ZO,XA,YA), (R1L,R2Q,ZO,XA,YA), (R1M,R2Q,ZO,XA,YA), (R1N,R2Q,ZO,XA,YA), (R1O,R2Q,ZO,XA,YA), (R1P,R2Q,ZO,XA,YA), (R1Q,R2Q,ZO,XA,YA), (R1A,R2A,ZP,XA,YA), (R1B,R2A,ZP,XA,YA), (R1C,R2A,ZP,XA,YA), (R1D,R2A,ZP,XA,YA), (R1E,R2A, ZP,XA,YA), (R1F,R2A,ZP,XA,YA), (R1G,R2A,ZP,XA,YA), (R1H,R2A,ZP,XA,YA), (R1I,R2A,ZP,XA,YA), (R1J,R2A, ZP,XA,YA), (R1K,R2A,ZP,XA,YA), (R1L,R2A,ZP,XA, YA), (R1M,R2A,ZP,XA,YA), (R1N,R2A,ZP,XA,YA), (R1O,R2A,ZP,XA,YA), (R1P,R2A,ZP,XA,YA), (R1Q,R2A, ZP,XA,YA), (R1A,R2B,ZP,XA,YA), (R1B,R2B,ZP,XA, YA), (R1C,R2B,ZP,XA,YA), (R1D,R2B,ZP,XA,YA), (R1E, R2B,ZP,XA,YA), (R1F,R2B,ZP,XA,YA), (R1G,R2B,ZP, XA,YA), (R1H,R2B,ZP,XA,YA), (R1I,R2B,ZP,XA,YA), (R1J,R2B,ZP,XA,YA), (R1K,R2B,ZP,XA,YA), (R1L,R2B, ZP,XA,YA), (R1M,R2B,ZP,XA,YA), (R1N,R2B,ZP,XA, YA), (R1O,R2B,ZP,XA,YA), (R1P,R2B,ZP,XA,YA), (R1Q, R2B,ZP,XA,YA), (R1A,R2C,ZP,XA,YA), (R1B,R2C,ZP, XA,YA), (R1C,R2C,ZP,XA,YA), (R1D,R2C,ZP,XA,YA), (R1E,R2C,ZP,XA,YA), (R1F,R2C,ZP,XA,YA), (R1G,R2C, ZP,XA,YA), (R1H,R2C,ZP,XA,YA), (R1I,R2C,ZP,XA,YA), (R1J,R2C,ZP,XA,YA), (R1K,R2C,ZP,XA,YA), (R1L,R2C, ZP,XA,YA), (R1M,R2C,ZP,XA,YA), (R1N,R2C,ZP,XA, YA), (R1O,R2C,ZP,XA,YA), (R1P,R2C,ZP,XA,YA), (R1Q, R2C,ZP,XA,YA), (R1A,R2D,ZP,XA,YA), (R1B,R2D,ZP, XA,YA), (R1C,R2D,ZP,XA,YA), (R1D,R2D,ZP,XA,YA), (R1E,R2D,ZP,XA,YA), (R1F,R2D,ZP,XA,YA), (R1G,R2D, ZP,XA,YA), (R1H,R2D,ZP,XA,YA), (R1I,R2D,ZP,XA,YA), (R1J,R2D,ZP,XA,YA), (R1K,R2D,ZP,XA,YA), (R1L,R2D, ZP,XA,YA), (R1M,R2D,ZP,XA,YA), (R1N,R2D,ZP,XA, YA), (R1O,R2D,ZP,XA,YA), (R1P,R2D,ZP,XA,YA), (R1Q, R2D,ZP,XA,YA), (R1A,R2E,ZP,XA,YA), (R1B,R2E,ZP, XA,YA), (R1C,R2E,ZP,XA,YA), (R1D,R2E,ZP,XA,YA), (R1E,R2E,ZP,XA,YA), (R1F,R2E,ZP,XA,YA), (R1G,R2E, ZP,XA,YA), (R1H,R2E,ZP,XA,YA), (R1I,R2E,ZP,XA,YA), (R1J,R2E,ZP,XA,YA), (R1K,R2E,ZP,XA,YA), (R1L,R2E, ZP,XA,YA), (R1M,R2E,ZP,XA,YA), (R1N,R2E,ZP,XA, YA), (R1O,R2E,ZP,XA,YA), (R1P,R2E,ZP,XA,YA), (R1Q, R2E,ZP,XA,YA), (R1A,R2F,ZP,XA,YA), (R1B,R2F,ZP,XA, YA), (R1C,R2F,ZP,XA,YA), (R1D,R2F,ZP,XA,YA), (R1E, R2F,ZP,XA,YA), (R1F,R2F,ZP,XA,YA), (R1G,R2F,ZP,XA, YA), (R1H,R2F,ZP,XA,YA), (R1I,R2F,ZP,XA,YA), (R1J, R2F,ZP,XA,YA), (R1K,R2F,ZP,XA,YA), (R1L,R2F,ZP,XA, YA), (R1M,R2F,ZP,XA,YA), (R1N,R2F,ZP,XA,YA), (R1O, R2F,ZP,XA,YA), (R1P,R2F,ZP,XA,YA), (R1Q,R2F,ZP,XA, YA), (R1A,R2G,ZP,XA,YA), (R1B,R2G,ZP,XA,YA), (R1C, R2G,ZP,XA,YA), (R1D,R2G,ZP,XA,YA), (R1E,R2G,ZP, XA,YA), (R1F,R2G,ZP,XA,YA), (R1G,R2G,ZP,XA,YA), (R1H,R2G,ZP,XA,YA), (R1I,R2G,ZP,XA,YA), (R1J,R2G, ZP,XA,YA), (R1K,R2G,ZP,XA,YA), (R1L,R2G,ZP,XA, YA), (R1M,R2G,ZP,XA,YA), (R1N,R2G,ZP,XA,YA), (R1O,R2G,ZP,XA,YA), (R1P,R2G,ZP,XA,YA), (R1Q,R2G, ZP,XA,YA), (R1A,R2H,ZP,XA,YA), (R1B,R2H,ZP,XA, YA), (R1C,R2H,ZP,XA,YA), (R1D,R2H,ZP,XA,YA), (R1E, R2H,ZP,XA,YA), (R1F,R2H,ZP,XA,YA), (R1G,R2H,ZP, XA,YA), (R1H,R2H,ZP,XA,YA), (R1I,R2H,ZP,XA,YA), (R1J,R2H,ZP,XA,YA), (R1K,R2H,ZP,XA,YA), (R1L,R2H, ZP,XA,YA), (R1M,R2H,ZP,XA,YA), (R1N,R2H,ZP,XA, YA), (R1O,R2H,ZP,XA,YA), (R1P,R2H,ZP,XA,YA), (R1Q, R2H,ZP,XA,YA), (R1A,R2I,ZP,XA,YA), (R1B,R2I,ZP,XA, YA), (R1C,R2I,ZP,XA,YA), (R1D,R2I,ZP,XA,YA), (R1E, R2I,ZP,XA,YA), (R1F,R2I,ZP,XA,YA), (R1G,R2I,ZP,XA, YA), (R1H,R2I,ZP,XA,YA), (R1I,R2I,ZP,XA,YA), (R1J, R2I,ZP,XA,YA), (R1K,R2I,ZP,XA,YA), (R1L,R2I,ZP,XA, YA), (R1M,R2I,ZP,XA,YA), (R1N,R2I,ZP,XA,YA), (R1O, R2I,ZP,XA,YA), (R1P,R2I,ZP,XA,YA), (R1Q,R2I,ZP,XA, YA), (R1A,R2J,ZP,XA,YA), (R1B,R2J,ZP,XA,YA), (R1C, R2J,ZP,XA,YA), (R1D,R2J,ZP,XA,YA), (R1E,R2J,ZP,XA, YA), (R1F,R2J,ZP,XA,YA), (R1G,R2J,ZP,XA,YA), (R1H, R2J,ZP,XA,YA), (R1I,R2J,ZP,XA,YA), (R1J,R2J,ZP,XA, YA), (R1K,R2J,ZP,XA,YA), (R1L,R2J,ZP,XA,YA), (R1M, R2J,ZP,XA,YA), (R1N,R2J,ZP,XA,YA), (R1O,R2J,ZP,XA, YA), (R1P,R2J,ZP,XA,YA), (R1Q,R2J,ZP,XA,YA), (R1A, R2K,ZP,XA,YA), (R1B,R2K,ZP,XA,YA), (R1C,R2K,ZP, XA,YA), (R1D,R2K,ZP,XA,YA), (R1E,R2K,ZP,XA,YA), (R1F,R2K,ZP,XA,YA), (R1G,R2K,ZP,XA,YA), (R1H,R2K, ZP,XA,YA), (R1I,R2K,ZP,XA,YA), (R1J,R2K,ZP,XA,YA), (R1K,R2K,ZP,XA,YA), (R1L,R2K,ZP,XA,YA), (R1M,R2K, ZP,XA,YA), (R1N,R2K,ZP,XA,YA), (R1O,R2K,ZP,XA, YA), (R1P,R2K,ZP,XA,YA), (R1Q,R2K,ZP,XA,YA), (R1A, R2L,ZP,XA,YA), (R1B,R2L,ZP,XA,YA), (R1C,R2L,ZP, XA,YA), (R1D,R2L,ZP,XA,YA), (R1E,R2L,ZP,XA,YA), (R1F,R2L,ZP,XA,YA), (R1G,R2L,ZP,XA,YA), (R1H,R2L, ZP,XA,YA), (R1I,R2L,ZP,XA,YA), (R1J,R2L,ZP,XA,YA), (R1K,R2L,ZP,XA,YA), (R1L,R2L,ZP,XA,YA), (R1M,R2L, ZP,XA,YA), (R1N,R2L,ZP,XA,YA), (R1O,R2L,ZP,XA, YA), (R1P,R2L,ZP,XA,YA), (R1Q,R2L,ZP,XA,YA), (R1A, R2M,ZP,XA,YA), (R1B,R2M,ZP,XA,YA), (R1C,R2M,ZP, XA,YA), (R1D,R2M,ZP,XA,YA), (R1E,R2M,ZP,XA,YA), (R1F,R2M,ZP,XA,YA), (R1G,R2M,ZP,XA,YA), (R1H, R2M,ZP,XA,YA), (R1I,R2M,ZP,XA,YA), (R1J,R2M,ZP, XA,YA), (R1K,R2M,ZP,XA,YA), (R1L,R2M,ZP,XA,YA), (R1M,R2M,ZP,XA,YA), (R1N,R2M,ZP,XA,YA), (R1O, R2M,ZP,XA,YA), (R1P,R2M,ZP,XA,YA), (R1Q,R2M,ZP, XA,YA), (R1A,R2N,ZP,XA,YA), (R1B,R2N,ZP,XA,YA), (R1C,R2N,ZP,XA,YA), (R1D,R2N,ZP,XA,YA), (R1E,R2N, ZP,XA,YA), (R1F,R2N,ZP,XA,YA), (R1G,R2N,ZP,XA,YA), (R1H,R2N,ZP,XA,YA), (R1I,R2N,ZP,XA,YA), (R1J,R2N, ZP,XA,YA), (R1K,R2N,ZP,XA,YA), (R1L,R2N,ZP,XA, YA), (R1M,R2N,ZP,XA,YA), (R1N,R2N,ZP,XA,YA), (R1O,R2N,ZP,XA,YA), (R1P,R2N,ZP,XA,YA), (R1Q,R2N, ZP,XA,YA), (R1A,R2O,ZP,XA,YA), (R1B,R2O,ZP,XA, YA), (R1C,R2O,ZP,XA,YA), (R1D,R2O,ZP,XA,YA), (R1E, R2O,ZP,XA,YA), (R1F,R2O,ZP,XA,YA), (R1G,R2O,ZP, XA,YA), (R1H,R2O,ZP,XA,YA), (R1I,R2O,ZP,XA,YA), (R1J,R2O,ZP,XA,YA), (R1K,R2O,ZP,XA,YA), (R1L,R2O, ZP,XA,YA), (R1M,R2O,ZP,XA,YA), (R1N,R2O,ZP,XA, YA), (R1O,R2O,ZP,XA,YA), (R1P,R2O,ZP,XA,YA), (R1Q, R2O,ZP,XA,YA), (R1A,R2P,ZP,XA,YA), (R1B,R2P,ZP,XA, YA), (R1C,R2P,ZP,XA,YA), (R1D,R2P,ZP,XA,YA), (R1E, R2P,ZP,XA,YA), (R1F,R2P,ZP,XA,YA), (R1G,R2P,ZP,XA, YA), (R1H,R2P,ZP,XA,YA), (R1I,R2P,ZP,XA,YA), (R1J, R2P,ZP,XA,YA), (R1K,R2P,ZP,XA,YA), (R1L,R2P,ZP,XA, YA), (R1M,R2P,ZP,XA,YA), (R1N,R2P,ZP,XA,YA), (R1O, R2P,ZP,XA,YA), (R1P,R2P,ZP,XA,YA), (R1Q,R2P,ZP,XA, YA), (R1A,R2Q,ZP,XA,YA), (R1B,R2Q,ZP,XA,YA), (R1C, R2Q,ZP,XA,YA), (R1D,R2Q,ZP,XA,YA), (R1E,R2Q,ZP, XA,YA), (R1F,R2Q,ZP,XA,YA), (R1G,R2Q,ZP,XA,YA), (R1H,R2Q,ZP,XA,YA), (R1I,R2Q,ZP,XA,YA), (R1J,R2Q, ZP,XA,YA), (R1K,R2Q,ZP,XA,YA), (R1L,R2Q,ZP,XA, YA), (R1M,R2Q,ZP,XA,YA), (R1N,R2Q,ZP,XA,YA), (R1O,R2Q,ZP,XA,YA), (R1P,R2Q,ZP,XA,YA), (R1Q,R2Q, ZP,XA,YA), (R1A,R2A,ZQ,XA,YA), (R1B,R2A,ZQ,XA, YA), (R1C,R2A,ZQ,XA,YA), (R1D,R2A,ZQ,XA,YA), (R1E,R2A,ZQ,XA,YA), (R1F,R2A,ZQ,XA,YA), (R1G, R2A,ZQ,XA,YA), (R1H,R2A,ZQ,XA,YA), (R1I,R2A,ZQ, XA,YA), (R1J,R2A,ZQ,XA,YA), (R1K,R2A,ZQ,XA,YA), (R1L,R2A,ZQ,XA,YA), (R1M,R2A,ZQ,XA,YA), (R1N, R2A,ZQ,XA,YA), (R1O,R2A,ZQ,XA,YA), (R1P,R2A,ZQ, XA,YA), (R1Q,R2A,ZQ,XA,YA), (R1A,R2B,ZQ,XA,YA), (R1B,R2B,ZQ,XA,YA), (R1C,R2B,ZQ,XA,YA), (R1D, R2B,ZQ,XA,YA), (R1E,R2B,ZQ,XA,YA), (R1F,R2B,ZQ, XA,YA), (R1G,R2B,ZQ,XA,YA), (R1H,R2B,ZQ,XA,YA), (R1I,R2B,ZQ,XA,YA), (R1J,R2B,ZQ,XA,YA), (R1K,R2B, ZQ,XA,YA), (R1L,R2B,ZQ,XA,YA), (R1M,R2B,ZQ,XA, YA), (R1N,R2B,ZQ,XA,YA), (R1O,R2B,ZQ,XA,YA), (R1P,R2B,ZQ,XA,YA), (R1Q,R2B,ZQ,XA,YA), (R1A, R2C,ZQ,XA,YA), (R1B,R2C,ZQ,XA,YA), (R1C,R2C,ZQ, XA,YA), (R1D,R22C,ZQ,XA,YA), (R1E,R2C,ZQ,XA,YA), (R1F,R2C,ZQ,XA,YA), (R1G,R2C,ZQ,XA,YA), (R1H, R2C,ZQ,XA,YA), (R1I,R2C,ZQ,XA,YA), (R1J,R2C,ZQ, XA,YA), (R1K,R2C,ZQ,XA,YA), (R1L,R2C,ZQ,XA,YA), (R1M,R2C,ZQ,XA,YA), (R1N,R2C,ZQ,XA,YA), (R1O, R2C,ZQ,XA,YA), (R1P,R2C,ZQ,XA,YA), (R1Q,R2C,ZQ, XA,YA), (R1A,R2D,ZQ,XA,YA), (R1B,R2D,ZQ,XA,YA), (R1C,R2D,ZQ,XA,YA), (R1D,R2D,ZQ,XA,YA), (R1E, R2D,ZQ,XA,YA), (R1F,R2D,ZQ,XA,YA), (R1G,R2D,ZQ, XA,YA), (R1H,R2D,ZQ,XA,YA), (R1I,R2D,ZQ,XA,YA), (R1J,R2D,ZQ,XA,YA), (R1K,R2D,ZQ,XA,YA), (R1L, R2D,ZQ,XA,YA), (R1M,R2D,ZQ,XA,YA), (R1N,R2D,ZQ, XA,YA), (R1O,R2D,ZQ,XA,YA), (R1P,R2D,ZQ,XA,YA), (R1Q,R2D,ZQ,XA,YA), (R1A,R2E,ZQ,XA,YA), (R1B, R2E,ZQ,XA,YA), (R1C,R2E,ZQ,XA,YA), (R1D,R2E,ZQ, XA,YA), (R1E,R2E,ZQ,XA,YA), (R1F,R2E,ZQ,XA,YA), (R1G,R2E,ZQ,XA,YA), (R1H,R2E,ZQ,XA,YA), (R1I,R2E, ZQ,XA,YA), (R1J,R2E,ZQ,XA,YA), (R1K,R2E,ZQ,XA, YA), (R1L,R2E,ZQ,XA,YA), (R1M,R2E,ZQ,XA,YA), (R1N,R2E,ZQ,XA,YA), (R1O,R2E,ZQ,XA,YA), (R1P,R2E, ZQ,XA,YA), (R1Q,R2E,ZQ,XA,YA), (R1A,R2F,ZQ,XA, YA), (R1B,R2F,ZQ,XA,YA), (R1C,R2F,ZQ,XA,YA), (R1D, R2F,ZQ,XA,YA), (R1E,R2F,ZQ,XA,YA), (R1F,R2F,ZQ, XA,YA), (R1G,R2F,ZQ,XA,YA), (R1H,R2F,ZQ,XA,YA), (R1I,R2F,ZQ,XA,YA), (R1J,R2F,ZQ,XA,YA), (R1K,R2F, ZQ,XA,YA), (R1L,R2F,ZQ,XA,YA), (R1M,R2F,ZQ,XA, YA), (R1N,R2F,ZQ,XA,YA), (R1O,R2F,ZQ,XA,YA), (R1P, R2F,ZQ,XA,YA), (R1Q,R2F,ZQ,XA,YA), (R1A,R2G,ZQ, XA,YA), (R1B,R2G,ZQ,XA,YA), (R1C,R2G,ZQ,XA,YA), (R1D,R2G,ZQ,XA,YA), (R1E,R2G,ZQ,XA,YA), (R1F, R2G,ZQ,XA,YA), (R1G,R2G,ZQ,XA,YA), (R1H,R2G,ZQ, XA,YA), (R1I,R2G,ZQ,XA,YA), (R1J,R2G,ZQ,XA,YA), (R1K,R2G,ZQ,XA,YA), (R1L,R2G,ZQ,XA,YA), (R1M, R2G,ZQ,XA,YA), (R1N,R2G,ZQ,XA,YA), (R1O,R2G,ZQ, XA,YA), (R1P,R2G,ZQ,XA,YA), (R1Q,R2G,ZQ,XA,YA), (R1A,R2H,ZQ,XA,YA), (R1B,R2H,ZQ,XA,YA), (R1C, R2H,ZQ,XA,YA), (R1D,R2H,ZQ,XA,YA), (R1E,R2H,ZQ, XA,YA), (R1F,R2H,ZQ,XA,YA), (R1G,R2H,ZQ,XA,YA), (R1H,R2H,ZQ,XA,YA), (R1I,R2H,ZQ,XA,YA), (R1J,R2H, ZQ,XA,YA), (R1K,R2H,ZQ,XA,YA), (R1L,R2H,ZQ,XA, YA), (R1M,R2H,ZQ,XA,YA), (R1N,R2H,ZQ,XA,YA), (R1O,R2H,ZQ,XA,YA), (R1P,R2H,ZQ,XA,YA), (R1Q, R2H,ZQ,XA,YA), (R1A,R2I,ZQ,XA,YA), (R1B,R2I,ZQ, XA,YA), (R1C,R2I,ZQ,XA,YA), (R1D,R2I,ZQ,XA,YA), (R1E,R2I,ZQ,XA,YA), (R1F,R2I,ZQ,XA,YA), (R1G,R2I, ZQ,XA,YA), (R1H,R2I,ZQ,XA,YA), (R1I,R2I,ZQ,XA,YA), (R1J,R2I,ZQ,XA,YA), (R1K,R2I,ZQ,XA,YA), (R1L,R2I, ZQ,XA,YA), (R1M,R2I,ZQ,XA,YA), (R1N,R2I,ZQ,XA, YA), (R1 O,R2I,ZQ,XA,YA), (R1P,R2I,ZQ,XA,YA), (R1Q, R2I,ZQ,XA,YA), (R1A,R2J,ZQ,XA,YA), (R1B,R2J,ZQ, XA,YA), (R1C,R2J,ZQ,XA,YA), (R1D,R2J,ZQ,XA,YA), (R1E,R2J,ZQ,XA,YA), (R1F,R2J,ZQ,XA,YA), (R1G,R2J, ZQ,XA,YA), (R1H,R2J,ZQ,XA,YA), (R1I,R2J,ZQ,XA, YA), (R1J,R2J,ZQ,XA,YA), (R1K,R2J,ZQ,XA,YA), (R1L, R2J,ZQ,XA,YA), (R1M,R2J,ZQ,XA,YA), (R1N,R2J,ZQ, XA,YA), (R1O,R2J,ZQ,XA,YA), (R1P,R2J,ZQ,XA,YA), (R1Q,R2J,ZQ,XA,YA), (R1A,R2K,ZQ,XA,YA), (R1B, R2K,ZQ,XA,YA), (R1C,R2K,ZQ,XA,YA), (R1D,R2K,ZQ, XA,YA), (R1E,R2K,ZQ,XA,YA), (R1F,R2K,ZQ,XA,YA), (R1G,R2K,ZQ,XA,YA), (R1H,R2K,ZQ,XA,YA), (R1I, R2K,ZQ,XA,YA), (R1J,R2K,ZQ,XA,YA), (R1K,R2K,ZQ, XA,YA), (R1L,R2K,ZQ,XA,YA), (R1M,R2K,ZQ,XA,YA), (R1N,R2K,ZQ,XA,YA), (R1O,R2K,ZQ,XA,YA), (R1P, R2K,ZQ,XA,YA), (R1Q,R2K,ZQ,XA,YA), (R1A,R2L,ZQ, XA,YA), (R1B,R2L,ZQ,XA,YA), (R1C,R2L,ZQ,XA,YA), (R1D,R2L,ZQ,XA,YA), (R1E,R2L,ZQ,XA,YA), (R1F,R2L, ZQ,XA,YA), (R1G,R2L,ZQ,XA,YA), (R1H,R2L,ZQ,XA, YA), (R1I,R2L,ZQ,XA,YA), (R1J,R2L,ZQ,XA,YA), (R1K, R2L,ZQ,XA,YA), (R1L,R2L,ZQ,XA,YA), (R1M,R2L,ZQ, XA,YA), (R1N,R2L,ZQ,XA,YA), (R1O,R2L,ZQ,XA,YA), (R1P,R2L,ZQ,XA,YA), (R1Q,R2L,ZQ,XA,YA), (R1A, R2M,ZQ,XA,YA), (R1B,R2M,ZQ,XA,YA), (R1C,R2M,ZQ, XA,YA), (R1D,R2M,ZQ,XA,YA), (R1E,R2M,ZQ,XA,YA), (R1F,R2M,ZQ,XA,YA), (R1G,R2M,ZQ,XA,YA), (R1H, R2M,ZQ,XA,YA), (R1I,R2M,ZQ,XA,YA), (R1J,R2M,ZQ, XA,YA), (R1K,R2M,ZQ,XA,YA), (R1L,R2M,ZQ,XA,YA), (R1M,R2M,ZQ,XA,YA), (R1N,R2M,ZQ,XA,YA), (R1O, R2M,ZQ,XA,YA), (R1P,R2M,ZQ,XA,YA), (R1Q,R2M,ZQ, XA,YA), (R1A,R2N,ZQ,XA,YA), (R1B,R2N,ZQ,XA,YA), (R1C,R2N,ZQ,XA,YA), (R1D,R2N,ZQ,XA,YA), (R1E, R2N,ZQ,XA,YA), (R1F,R2N,ZQ,XA,YA), (R1G,R2N,ZQ, XA,YA), (R1H,R2N,ZQ,XA,YA), (R1I,R2N,ZQ,XA,YA), (R1J,R2N,ZQ,XA,YA), (R1K,R2N,ZQ,XA,YA), (R1L, R2N,ZQ,XA,YA), (R1M,R2N,ZQ,XA,YA), (R1N,R2N,ZQ, XA,YA), (R1O,R2N,ZQ,XA,YA), (R1P,R2N,ZQ,XA,YA), (R1Q,R2N,ZQ,XA,YA), (R1A,R2O,ZQ,XA,YA), (R1B, R2O,ZQ,XA,YA), (R1C,R2O,ZQ,XA,YA), (R1D,R2O,ZQ, XA,YA), (R1E,R2O,ZQ,XA,YA), (R1F,R2O,ZQ,XA,YA), (R1G,R2O,ZQ,XA,YA), (R1H,R2O,ZQ,XA,YA), (R1I, R2O,ZQ,XA,YA), (R1J,R2O,ZQ,XA,YA), (R1K,R2O,ZQ, XA,YA), (R1L,R2O,ZQ,XA,YA), (R1M,R2O,ZQ,XA,YA), (R1N,R2O,ZQ,XA,YA), (R1O,R2O,ZQ,XA,YA), (R1P, R2O,ZQ,XA,YA), (R1Q,R2O,ZQ,XA,YA), (R1A,R2P, XA,YA), (R1B,R2P,ZQ,XA,YA), (R1C,R2P,ZQ,XA,YA), (R1D,R2P,ZQ,XA,YA), (R1E,R2P,ZQ,XA,YA), (R1F,R2P, ZQ,XA,YA), (R1G,R2P,ZQ,XA,YA), (R1H,R2P,ZQ,XA, YA), (R1I,R2P,ZQ,XA,YA), (R1J,R2P,ZQ,XA,YA), (R1K, R2P,ZQ,XA,YA), (R1L,R2P,ZQ,XA,YA), (R1M,R2P,ZQ, XA,YA), (R1N,R2P,ZQ,XA,YA), (R1O,R2P,ZQ,XA,YA), (R1P,R2P,ZQ,XA,YA), (R1Q,R2P,ZQ,XA,YA), (R1A,R2Q, ZQ,XA,YA), (R1B,R2Q,ZQ,XA,YA), (R1C,R2Q,ZQ,XA, YA), (R1D,R2Q,ZQ,XA,YA), (R1E,R2Q,ZQ,XA,YA), (R1F,R2Q,ZQ,XA,YA), (R1G,R2Q,ZQ,XA,YA), (R1H, R2Q,ZQ,XA,YA), (R1I,R2Q,ZQ,XA,YA), (R1J,R2Q,ZQ, XA,YA), (R1K,R2Q,ZQ,XA,YA), (R1L,R2Q,ZQ,XA,YA), (R1M,R2Q,ZQ,XA,YA), (R1N,R2Q,ZQ,XA,YA), (R1O, R2Q,ZQ,XA,YA), (R1P,R2Q,ZQ,XA,YA), (R1Q,R2Q,ZQ, XA,YA), (R1A,R2A,ZR,XA,YA), (R1B,R2A,ZR,XA,YA), (R1C,R2A,ZR,XA,YA), (R1D,R2A,ZR,XA,YA), (R1E, R2A,ZR,XA,YA), (R1F,R2A,ZR,XA,YA), (R1G,R2A,ZR, XA,YA), (R1H,R2A,ZR,XA,YA), (R1I,R2A,ZR,XA,YA), (R1J,R2A,ZR,XA,YA), (R1K,R2A,ZR,XA,YA), (R1L,R2A, ZR,XA,YA), (R1M,R2A,ZR,XA,YA), (R1N,R2A,ZR,XA, YA), (R1O,R2A,ZR,XA,YA), (R1P,R2A,ZR,XA,YA), (R1Q,R2A,ZR,XA,YA), (R1A,R2B,ZR,XA,YA), (R1B, R2B,ZR,XA,YA), (R1C,R2B,ZR,XA,YA), (R1D,R2B,ZR, XA,YA), (R1E,R2B,ZR,XA,YA), (R1F,R2B,ZR,XA,YA), (R1G,R2B,ZR,XA,YA), (R1H,R2B,ZR,XA,YA), (R1I,R2B, ZR,XA,YA), (R1J,R2B,ZR,XA,YA), (R1K,R2B,ZR,XA, YA), (R1L,R2B,ZR,XA,YA), (R1M,R2B,ZR,XA,YA), (R1N,R2B,ZR,XA,YA), (R1O,R2B,ZR,XA,YA), (R1P,R2B, ZR,XA,YA), (R1Q,R2B,ZR,XA,YA), (R1A,R2C,ZR,XA, YA), (R1B,R2C,ZR,XA,YA), (R1C,R22C,ZR,XA,YA), (R1D,R2C,ZR,XA,YA), (R1E,R2C,ZR,XA,YA), (R1F,R2C, ZR,XA,YA), (R1G,R2C,ZR,XA,YA), (R1H,R2C,ZR,XA, YA), (R1I,R2C,ZR,XA,YA), (R1J,R2C,ZR,XA,YA), (R1K, R2C,ZR,XA,YA), (R1L,R2C,ZR,XA,YA), (R1M,R2C,ZR, XA,YA), (R1N,R2C,ZR,XA,YA), (R1O,R2C,ZR,XA,YA), (R1P,R2C,ZR,XA,YA), (R1Q,R2C,ZR,XA,YA), (R1A, R2D,ZR,XA,YA), (R1B,R2D,ZR,XA,YA), (R1C,R2D,ZR, XA,YA), (R1D,R2D,ZR,XA,YA), (R1E,R2D,ZR,XA,YA), (R1F,R2D,ZR,XA,YA), (R1G,R2D,ZR,XA,YA), (R1H, R2D,ZR,XA,YA), (R1I,R2D,ZR,XA,YA), (R1J,R2D,ZR, XA,YA), (R1K,R2D,ZR,XA,YA), (R1L,R2D,ZR,XA,YA), (R1M,R2D,ZR,XA,YA), (R1N,R2D,ZR,XA,YA), (R1O, R2D,ZR,XA,YA), (R1P,R2D,ZR,XA,YA), (R1Q,R2D,ZR, XA,YA), (R1A,R2E,ZR,XA,YA), (R1B,R2E,ZR,XA,YA), (R1C,R2E,ZR,XA,YA), (R1D,R2E,ZR,XA,YA), (R1E,R2E, ZR,XA,YA), (R1F,R2E,ZR,XA,YA), (R1G,R2E,ZR,XA, YA), (R1H,R2E,ZR,XA,YA), (R1I,R2E,ZR,XA,YA), (R1J, R2E,ZR,XA,YA), (R1K,R2E,ZR,XA,YA), (R1L,R2E,ZR, XA,YA), (R1M,R2E,ZR,XA,YA), (R1N,R2E,ZR,XA,YA), (R1O,R2E,ZR,XA,YA), (R1P,R2E,ZR,XA,YA), (R1Q,R2E, ZR,XA,YA), (R1A,R2F,ZR,XA,YA), (R1B,R2F,ZR,XA, YA), (R1C,R2F,ZR,XA,YA), (R1D,R2F,ZR,XA,YA), (R1E, R2F,ZR,XA,YA), (R1F,R2F,ZR,XA,YA), (R1G,R2F,ZR, XA,YA), (R1H,R2F,ZR,XA,YA), (R1I,R2F,ZR,XA,YA), (R1J,R2F,ZR,XA,YA), (R1K,R2F,ZR,XA,YA), (R1L,R2F, ZR,XA,YA), (R1M,R2F,ZR,XA,YA), (R1N,R2F,ZR,XA, YA), (R1O,R2F,ZR,XA,YA), (R1P,R2F,ZR,XA,YA), (R1Q, R2F,ZR,XA,YA), (R1A,R2G,ZR,XA,YA), (R1B,R2G,ZR, XA,YA), (R1C,R2G,ZR,XA,YA), (R1D,R2G,ZR,XA,YA), (R1E,R2G,ZR,XA,YA), (R1F,R2G,ZR,XA,YA), (R1G, R2G,ZR,XA,YA), (R1H,R2G,ZR,XA,YA), (R1I,R2G,ZR, XA,YA), (R1J,R2G,ZR,XA,YA), (R1K,R2G,ZR,XA,YA), (R1L,R2G,ZR,XA,YA), (R1M,R2G,ZR,XA,YA), (R1N, R2G,ZR,XA,YA), (R1O,R2G,ZR,XA,YA), (R1P,R2G,ZR, XA,YA), (R1Q,R2G,ZR,XA,YA), (R1A,R2H,ZR,XA,YA), (R1B,R2H,ZR,XA,YA), (R1C,R2H,ZR,XA,YA), (R1D, R2H,ZR,XA,YA), (R1E,R2H,ZR,XA,YA), (R1F,R2H,ZR, XA,YA), (R1G,R2H,ZR,XA,YA), (R1H,R2H,ZR,XA,YA), (R1I,R2H,ZR,XA,YA), (R1J,R2H,ZR,XA,YA), (R1K,R2H, ZR,XA,YA), (R1L,R2H,ZR,XA,YA), (R1M,R2H,ZR,XA, YA), (R1N,R2H,ZR,XA,YA), (R1O,R2H,ZR,XA,YA), (R1P,R2H,ZR,XA,YA), (R1Q,R2H,ZR,XA,YA), (R1A,R2I, ZR,XA,YA), (R1B,R2I,ZR,XA,YA), (R1C,R2I,ZR,XA, YA), (R1D,R2I,ZR,XA,YA), (R1E,R2I,ZR,XA,YA), (R1F, R2I,ZR,XA,YA), (R1G,R2I,ZR,XA,YA), (R1H,R2I,ZR,XA, YA), (R1I,R2I,ZR,XA,YA), (R1J,R2I,ZR,XA,YA), (R1K, R2I,ZR,XA,YA), (R1L,R2I,ZR,XA,YA), (R1M,R2I,ZR, XA,YA), (R1N,R2I,ZR,XA,YA), (R1O,R2I,ZR,XA,YA), (R1P,R2I,ZR,XA,YA), (R1Q,R2I,ZR,XA,YA), (R1A,R2J, ZR,XA,YA), (R1B,R2J,ZR,XA,YA), (R1C,R2J,ZR,XA, YA), (R1D,R2J,ZR,XA,YA), (R1E,R2J,ZR,XA,YA), (R1F, R2J,ZR,XA,YA), (R1G,R2J,ZR,XA,YA), (R1H,R2J,ZR, XA,YA), (R1I,R2J,ZR,XA,YA), (R1J,R2J,ZR,XA,YA), (R1K,R2J,ZR,XA,YA), (R1L,R2J,ZR,XA,YA), (R1M,R2J, ZR,XA,YA), (R1N,R2J,ZR,XA,YA), (R1O,R2J,ZR,XA, YA), (R1P,R2J,ZR,XA,YA), (R1Q,R2J,ZR,XA,YA), (R1A, R2K,ZR,XA,YA), (R1B,R2K,ZR,XA,YA), (R1C,R2K,ZR, XA,YA), (R1D,R2K,ZR,XA,YA), (R1E,R2K,ZR,XA,YA), (R1F,R2K,ZR,XA,YA), (R1G,R2K,ZR,XA,YA), (R1H, R2K,ZR,XA,YA), (R1I,R2K,ZR,XA,YA), (R1J,R2K,ZR, XA,YA), (R1K,R2K,ZR,XA,YA), (R1L,R2K,ZR,XA,YA), (R1M,R2K,ZR,XA,YA), (R1N,R2K,ZR,XA,YA), (R1O, R2K,ZR,XA,YA), (R1P,R2K,ZR,XA,YA), (R1Q,R2K,ZR, XA,YA), (R1A,R2L,ZR,XA,YA), (R1B,R2L,ZR,XA,YA), (R1C,R2L,ZR,XA,YA), (R1D,R2L,ZR,XA,YA), (R1E,R2L, ZR,XA,YA), (R1F,R2L,ZR,XA,YA), (R1G,R2L,ZR,XA, YA), (R1H,R2L,ZR,XA,YA), (R1I,R2L,ZR,XA,YA), (R1J, R2L,ZR,XA,YA), (R1K,R2L,ZR,XA,YA), (R1L,R2L,ZR, XA,YA), (R1M,R2L,ZR,XA,YA), (R1N,R2L,ZR,XA,YA), (R1O,R2L,ZR,XA,YA), (R1P,R2L,ZR,XA,YA), (R1Q,R2L, ZR,XA,YA), (R1A,R2M,ZR,XA,YA), (R1B,R2M,ZR,XA, YA), (R1C,R2M,ZR,XA,YA), (R1D,R2M,ZR,XA,YA), (R1E,R2M,ZR,XA,YA), (R1F,R2M,ZR,XA,YA), (R1G, R2M,ZR,XA,YA), (R1H,R2M,ZR,XA,YA), (R1I,R2M,ZR, XA,YA), (R1J,R2M,ZR,XA,YA), (R1K,R2M,ZR,XA,YA), (R1L,R2M,ZR,XA,YA), (R1M,R2M,ZR,XA,YA), (R1N, R2M,ZR,XA,YA), (R1O,R2M,ZR,XA,YA), (R1P,R2M, XA,YA), (R1Q,R2M,ZR,XA,YA), (R1A,R2N,ZR,XA,YA), (R1B,R2N,ZR,XA,YA), (R1C,R2N,ZR,XA,YA), (R1D, R2N,ZR,XA,YA), (R1E,R2N,ZR,XA,YA), (R1F,R2N,ZR, XA,YA), (R1G,R2N,ZR,XA,YA), (R1H,R2N,ZR,XA,YA), (R1I,R2N,ZR,XA,YA), (R1J,R2N,ZR,XA,YA), (R1K,R2N, ZR,XA,YA), (R1L,R2N,ZR,XA,YA), (R1M,R2N,ZR,XA, YA), (R1N,R2N,ZR,XA,YA), (R1O,R2N,ZR,XA,YA), (R1P,R2N,ZR,XA,YA), (R1Q,R2N,ZR,XA,YA), (R1A, R2O,ZR,XA,YA), (R1B,R2O,ZR,XA,YA), (R1C,R2O,ZR, XA,YA), (R1D,R2O,ZR,XA,YA), (R1E,R2O,ZR,XA,YA), (R1F,R2O,ZR,XA,YA), (R1G,R2O,ZR,XA,YA), (R1H, R2O,ZR,XA,YA), (R1I,R2O,ZR,XA,YA), (R1J,R2O,ZR, XA,YA), (R1K,R2O,ZR,XA,YA), (R1L,R2O,ZR,XA,YA), (R1M,R2O,ZR,XA,YA), (R1N,R2O,ZR,XA,YA), (R1O, R2O,ZR,XA,YA), (R1P,R2O,ZR,XA,YA), (R1Q,R2O,ZR, XA,YA), (R1A,R1P,ZR,XA,YA), (R1B,R2P,ZR,XA,YA), (R1C,R2P,ZR,XA,YA), (R1D,R2P,ZR,XA,YA), (R1E,R2P, ZR,XA,YA), (R1F,R2P,ZR,XA,YA), (R1G,R2P,ZR,XA, YA), (R1H,R2P,ZR,XA,YA), (R1I,R2P,ZR,XA,YA), (R1J, R2P,ZR,XA,YA), (R1K,R2P,ZR,XA,YA), (R1L,R2P,ZR, XA,YA), (R1M,R2P,ZR,XA,YA), (R1N,R2P,ZR,XA,YA), (R1O,R2P,ZR,XA,YA), (R1P,R2P,ZR,XA,YA), (R1Q,R2P, ZR,XA,YA), (R1A,R2Q,ZR,XA,YA), (R1B,R2Q,ZR,XA, YA), (R1C,R2Q,ZR,XA,YA), (R1D,R2Q,ZR,XA,YA), (R1E,R2Q,ZR,XA,YA), (R1F,R2Q,ZR,XA,YA), (R1G, R2Q,ZR,XA,YA), (R1H,R2Q,ZR,XA,YA), (R1I,R2Q,ZR, XA,YA), (R1J,R2Q,ZR,XA,YA), (R1K,R2Q,ZR,XA,YA), (R1L,R2Q,ZR,XA,YA), (R1M,R2Q,ZR,XA,YA), (R1N, R2Q,ZR,XA,YA), (R1O,R2Q,ZR,XA,YA), (R1P,R2Q,ZR, XA,YA), (R1Q,R2Q,ZR,XA,YA), (R1A,R2A,ZS,XA,YA), (R1B,R2A,ZS,XA,YA), (R1C,R2A,ZS,XA,YA), (R1D, R2A,ZS,XA,YA), (R1E,R2A,ZS,XA,YA), (R1F,R2A,ZS, XA,YA), (R1G,R2A,ZS,XA,YA), (R1H,R2A,ZS,XA,YA), (R1I,R2A,ZS,XA,YA), (R1J,R2A,ZS,XA,YA), (R1K,R2A, ZS,XA,YA), (R1L,R2A,ZS,XA,YA), (R1M,R2A,ZS,XA, YA), (R1N,R2A,ZS,XA,YA), (R1O,R2A,ZS,XA,YA), (R1P, R2A,ZS,XA,YA), (R1Q,R2A,ZS,XA,YA), (R1A,R2B,ZS, XA,YA), (R1B,R2B,ZS,XA,YA), (R1C,R2B,ZS,XA,YA), (R1D,R2B,ZS,XA,YA), (R1E,R2B,ZS,XA,YA), (R1F,R2B, ZS,XA,YA), (R1G,R2B,ZS,XA,YA), (R1H,R2B,ZS,XA, YA), (R1I,R2B,ZS,XA,YA), (R1J,R2B,ZS,XA,YA), (R1K, R2B,ZS,XA,YA), (R1L,R2B,ZS,XA,YA), (R1M,R2B,ZS, XA,YA), (R1N,R2B,ZS,XA,YA), (R1O,R2B,ZS,XA,YA), (R1P,R2B,ZS,XA,YA), (R1Q,R2B,ZS,XA,YA), (R1A,R2C, ZS,XA,YA), (R1B,R2C,ZS,XA,YA), (R1C,R2C,ZS,XA, YA), (R1D,R2C,ZS,XA,YA), (R1E,R2C,ZS,XA,YA), (R1F, R2C,ZS,XA,YA), (R1G,R2C,ZS,XA,YA), (R1H,R2C,ZS, XA,YA), (R1I,R2C,ZS,XA,YA), (R1J,R2C,ZS,XA,YA), (R1K,R2C,ZS,XA,YA), (R1L,R2C,ZS,XA,YA), (R1M, R2C,ZS,XA,YA), (R1N,R2C,ZS,XA,YA), (R1O,R2C,ZS, XA,YA), (R1P,R2C,ZS,XA,YA), (R1Q,R2C,ZS,XA,YA), (R1A,R2D,ZS,XA,YA), (R1B,R2D,ZS,XA,YA), (R1C, R2D,ZS,XA,YA), (R1D,R2D,ZS,XA,YA), (R1E,R2D,ZS, XA,YA), (R1F,R2D,ZS,XA,YA), (R1G,R2D,ZS,XA,YA), (R1H,R2D,ZS,XA,YA), (R1I,R2D,ZS,XA,YA), (R1J,R2D, ZS,XA,YA), (R1K,R2D,ZS,XA,YA), (R1L,R2D,ZS,XA, YA), (R1M,R2D,ZS,XA,YA), (R1N,R2D,ZS,XA,YA), (R1O,R2D,ZS,XA,YA), (R1P,R2D,ZS,XA,YA), (R1Q,R2D, ZS,XA,YA), (R1A,R2E,ZS,XA,YA), (R1B,R2E,ZS,XA, YA), (R1C,R2E,ZS,XA,YA), (R1D,R2E,ZS,XA,YA), (R1E, R2E,ZS,XA,YA), (R1F,R2E,ZS,XA,YA), (R1G,R2E,ZS, XA,YA), (R1H,R2E,ZS,XA,YA), (R1I,R2E,ZS,XA,YA), (R1J,R2E,ZS,XA,YA), (R1K,R2E,ZS,XA,YA), (R1L,R2E, ZS,XA,YA), (R1M,R2E,ZS,XA,YA), (R1N,R2E,ZS,XA, YA), (R1O,R2E,ZS,XA,YA), (R1P,R2E,ZS,XA,YA), (R1Q, R2E,ZS,XA,YA), (R1A,R2F,ZS,XA,YA), (R1B,R2F,ZS, XA,YA), (R1C,R2F,ZS,XA,YA), (R1D,R2F,ZS,XA,YA), (R1E,R2F,ZS,XA,YA), (R1F,R2F,ZS,XA,YA), (R1G,R2F, ZS,XA,YA), (R1H,R2F,ZS,XA,YA), (R1I,R2F,ZS,XA,YA), (R1J,R2F,ZS,XA,YA), (R1K,R2F,ZS,XA,YA), (R1L,R2F,ZS,XA,YA), (R1M,R2F,ZS,XA,YA), (R1N,R2F,ZS,XA,YA), (R1O,R2F,ZS,XA,YA), (R1P,R2F,ZS,XA,YA), (R1Q,R2F,ZS,XA,YA), (R1A,R2G,ZS,XA,YA), (R1B,R2G,ZS,XA,YA), (R1C,R2G,ZS,XA,YA), (R1D,R2G,ZS,XA,YA), (R1E,R2G,ZS,XA,YA), (R1F,R2G,ZS,XA,YA), (R1G,R2G,ZS,XA,YA), (R1H,R2G,ZS,XA,YA), (R1I,R2G,ZS,XA,YA), (R1J,R2G,ZS,XA,YA), (R1K,R2G,ZS,XA,YA), (R1L,R2G,ZS,XA,YA), (R1M,R2G,ZS,XA,YA), (R1N,R2G,ZS,XA,YA), (R1O,R2G,ZS,XA,YA), (R1P,R2G,ZS,XA,YA), (R1Q,R2G,ZS,XA,YA), (R1A,R2H,ZS,XA,YA), (R1B,R2H,ZS,XA,YA), (R1C,R2H,ZS,XA,YA), (R1D,R2H,ZS,XA,YA), (R1E,R2H,ZS,XA,YA), (R1F,R2H,ZS,XA,YA), (R1G,R2H,ZS,XA,YA), (R1H,R2H,ZS,XA,YA), (R1I,R2H,ZS,XA,YA), (R1J,R2H,ZS,XA,YA), (R1K,R2H,ZS,XA,YA), (R1L,R2H,ZS,XA,YA), (R1M,R2H,ZS,XA,YA), (R1N,R2H,ZS,XA,YA), (R1O,R2H,ZS,XA,YA), (R1P,R2H,ZS,XA,YA), (R1Q,R2H,ZS,XA,YA), (R1A,R2I,ZS,XA,YA), (R1B,R2I,ZS,XA,YA), (R1C,R2I,ZS,XA,YA), (R1D,R2I,ZS,XA,YA), (R1E,R2I,ZS,XA,YA), (R1F,R2I,ZS,XA,YA), (R1G,R2I,ZS,XA,YA), (R1H,R2I,ZS,XA,YA), (R1I,R2I,ZS,XA,YA), (R1J,R2I,ZS,XA,YA), (R1K,R2I,ZS,XA,YA), (R1L,R2I,ZS,XA,YA), (R1M,R2I,ZS,XA,YA), (R1N,R2I,ZS,XA,YA), (R1O,R2I,ZS,XA,YA), (R1P,R2I,ZS,XA,YA), (R1Q,R2I,ZS,XA,YA), (R1A,R2J,ZS,XA,YA), (R1B,R2J,ZS,XA,YA), (R1C,R2J,ZS,XA,YA), (R1D,R2J,ZS,XA,YA), (R1E,R2J,ZS,XA,YA), (R1F,R2J,ZS,XA,YA), (R1G,R2J,ZS,XA,YA), (R1H,R2J,ZS,XA,YA), (R1I,R2J,ZS,XA,YA), (R1J,R2J,ZS,XA,YA), (R1K,R2J,ZS,XA,YA), (R1L,R2J,ZS,XA,YA), (R1M,R2J,ZS,XA,YA), (R1N,R2J,ZS,XA,YA), (R1O,R2J,ZS,XA,YA), (R1P,R2J,ZS,XA,YA), (R1Q,R2J,ZS,XA,YA), (R1A,R2K,ZS,XA,YA), (R1B,R2K,ZS,XA,YA), (R1C,R2K,ZS,XA,YA), (R1D,R2K,ZS,XA,YA), (R1E,R2K,ZS,XA,YA), (R1F,R2K,ZS,XA,YA), (R1G,R2K,ZS,XA,YA), (R1H,R2K,ZS,XA,YA), (R1I,R2K,ZS,XA,YA), (R1J,R2K,ZS,XA,YA), (R1K,R2K,ZS,XA,YA), (R1L,R2K,ZS,XA,YA), (R1M,R2K,ZS,XA,YA), (R1N,R2K,ZS,XA,YA), (R1O,R2K,ZS,XA,YA), (R1P,R2K,ZS,XA,YA), (R1Q,R2K,ZS,XA,YA), (R1A,R2L,ZS,XA,YA), (R1B,R2L,ZS,XA,YA), (R1C,R2L,ZS,XA,YA), (R1D,R2L,ZS,XA,YA), (R1E,R2L,ZS,XA,YA), (R1F,R2L,ZS,XA,YA), (R1G,R2L,ZS,XA,YA), (R1H,R2L,ZS,XA,YA), (R1I,R2L,ZS,XA,YA), (R1J,R2L,ZS,XA,YA), (R1K,R2L,ZS,XA,YA), (R1L,R2L,ZS,XA,YA), (R1M,R2L,ZS,XA,YA), (R1N,R2L,ZS,XA,YA), (R1O,R2L,ZS,XA,YA), (R1P,R2L,ZS,XA,YA), (R1Q,R2L,ZS,XA,YA), (R1A,R2M,ZS,XA,YA), (R1B,R2M,ZS,XA,YA), (R1C,R2M,ZS,XA,YA), (R1D,R2M,ZS,XA,YA), (R1E,R2M,ZS,XA,YA), (R1F,R2M,ZS,XA,YA), (R1G,R2M,ZS,XA,YA), (R1H,R2M,ZS,XA,YA), (R1I,R2M,ZS,XA,YA), (R1J,R2M,ZS,XA,YA), (R1K,R2M,ZS,XA,YA), (R1L,R2M,ZS,XA,YA), (R1M,R2M,ZS,XA,YA), (R1N,R2M,ZS,XA,YA), (R1O,R2M,ZS,XA,YA), (R1P,R2M,ZS,XA,YA), (R1Q,R2M,ZS,XA,YA), (R1A,R2N,ZS,XA,YA), (R1B,R2N,ZS,XA,YA), (R1C,R2N,ZS,XA,YA), (R1D,R2N,ZS,XA,YA), (R1E,R2N,ZS,XA,YA), (R1F,R2N,ZS,XA,YA), (R1G,R2N,ZS,XA,YA), (R1H,R2N,ZS,XA,YA), (R1I,R2N,ZS,XA,YA), (R1J,R2N,ZS,XA,YA), (R1K,R2N,ZS,XA,YA), (R1L,R2N,ZS,XA,YA), (R1M,R2N,ZS,XA,YA), (R1N,R2N,ZS,XA,YA), (R1O,R2N,ZS,XA,YA), (R1P,R2N,ZS,XA,YA), (R1Q,R2N,ZS,XA,YA), (R1A,R2O,ZS,XA,YA), (R1B,R2O,ZS,XA,YA), (R1C,R2O,ZS,XA,YA), (R1D,R2O,ZS,XA,YA), (R1E,R2O,ZS,XA,YA), (R1F,R2O,ZS,XA,YA), (R1G,R2O,ZS,XA,YA), (R1H,R2O,ZS,XA,YA), (R1I,R2O,ZS,XA,YA), (R1J,R2O,ZS,XA,YA), (R1K,R2O,ZS,XA,YA), (R1L,R2O,ZS,XA,YA), (R1M,R2O,ZS,XA,YA), (R1N,R2O,ZS,XA,YA), (R1O,R2O,ZS,XA,YA), (R1P,R2O,ZS,XA,YA), (R1Q,R2O,ZS,XA,YA), (R1A,R2P,ZS,XA,YA), (R1B,R2P,ZS,XA,YA), (R1C,R2P,ZS,XA,YA), (R1D,R2P,ZS,XA,YA), (R1E,R2P,ZS,XA,YA), (R1F,R2P,ZS,XA,YA), (R1G,R2P,ZS,XA,YA), (R1H,R2P,ZS,XA,YA), (R1I,R2P,ZS,XA,YA), (R1J,R2P,ZS,XA,YA), (R1K,R2P,ZS,XA,YA), (R1L,R2P,ZS,XA,YA), (R1M,R2P,ZS,XA,YA), (R1N,R2P,ZS,XA,YA), (R1O,R2P,ZS,XA,YA), (R1P,R2P,ZS,XA,YA), (R1Q,R2P,ZS,XA,YA), (R1A,R2Q,ZS,XA,YA), (R1B,R2Q,ZS,XA,YA), (R1C,R2Q,ZS,XA,YA), (R1D,R2Q,ZS,XA,YA), (R1E,R2Q,ZS,XA,YA), (R1F,R2Q,ZS,XA,YA), (R1G,R2Q,ZS,XA,YA), (R1H,R2Q,ZS,XA,YA), (R1I,R2Q,ZS,XA,YA), (R1J,R2Q,ZS,XA,YA), (R1K,R2Q,ZS,XA,YA), (R1L,R2Q,ZS,XA,YA), (R1M,R2Q,ZS,XA,YA), (R1N,R2Q,ZS,XA,YA), (R1O,R2Q,ZS,XA,YA), (R1P,R2Q,ZS,XA,YA), (R1Q,R2Q,ZS,XA,YA), (R1A,R2A,ZT,XA,YA), (R1B,R2A,ZT,XA,YA), (R1C,R2A,ZT,XA,YA), (R1D,R2A,ZT,XA,YA), (R1E,R2A,ZT,XA,YA), (R1F,R2A,ZT,XA,YA), (R1G,R2A,ZT,XA,YA), (R1H,R2A,ZT,XA,YA), (R1I,R2A,ZT,XA,YA), (R1J,R2A,ZT,XA,YA), (R1K,R2A,ZT,XA,YA), (R1L,R2A,ZT,XA,YA), (R1M,R2A,ZT,XA,YA), (R1N,R2A,ZT,XA,YA), (R1O,R2A,ZT,XA,YA), (R1P,R2A,ZT,XA,YA), (R1Q,R2A,ZT,XA,YA), (R1A,R2B,ZT,XA,YA), (R1B,R2B,ZT,XA,YA), (R1C,R2B,ZT,XA,YA), (R1D,R2B,ZT,XA,YA), (R1E,R2B,ZT,XA,YA), (R1F,R2B,ZT,XA,YA), (R1G,R2B,ZT,XA,YA), (R1H,R2B,ZT,XA,YA), (R1I,R2B,ZT,XA,YA), (R1J,R2B,ZT,XA,YA), (R1K,R2B,ZT,XA,YA), (R1L,R2B,ZT,XA,YA), (R1M,R2B,ZT,XA,YA), (R1N,R2B,ZT,XA,YA), (R1O,R2B,ZT,XA,YA), (R1P,R2B,ZT,XA,YA), (R1Q,R2B,ZT,XA,YA), (R1A,R2C,ZT,XA,YA), (R1B,R2C,ZT,XA,YA), (R1C,R2C,ZT,XA,YA), (R1D,R2C,ZT,XA,YA), (R1E,R2C,ZT,XA,YA), (R1F,R2C,ZT,XA,YA), (R1G,R2C,ZT,XA,YA), (R1H,R2C,ZT,XA,YA), (R1I,R2C,ZT,XA,YA), (R1J,R2C,ZT,XA,YA), (R1K,R2C,ZT,XA,YA), (R1L,R2C,ZT,XA,YA), (R1M,R2C,ZT,XA,YA), (R1N,R2C,ZT,XA,YA), (R1O,R2C,ZT,XA,YA), (R1P,R2C,ZT,XA,YA), (R1Q,R2C,ZT,XA,YA), (R1A,R2D,ZT,XA,YA), (R1B,R2D,ZT,XA,YA), (R1C,R2D,ZT,XA,YA), (R1D,R2D,ZT,XA,YA), (R1E,R2D,ZT,XA,YA), (R1F,R2D,ZT,XA,YA), (R1G,R2D,ZT,XA,YA), (R1H,R2D,ZT,XA,YA), (R1I,R2D,ZT,XA,YA), (R1J,R2D,ZT,XA,YA), (R1K,R2D,ZT,XA,YA), (R1L,R2D,ZT,XA,YA), (R1M,R2D,ZT,XA,YA), (R1N,R2D,ZT,XA,YA), (R1O,R2D,ZT,XA,YA), (R1P,R2D,ZT,XA,YA), (R1Q,R2D,ZT,XA,YA), (R1A,R2E,ZT,XA,YA), (R1B,R2E,ZT,XA,YA), (R1C,R2E,ZT,XA,YA), (R1D,R2E,ZT,XA,YA), (R1E,R2E,ZT,XA,YA), (R1F,R2E,ZT,XA,YA), (R1G,R2E,ZT,XA,YA), (R1H,R2E,ZT,XA,YA), (R1I,R2E,ZT,XA,YA), (R1J,R2E,ZT,XA,YA), (R1K,R2E,ZT,XA,YA), (R1L,R2E,ZT,XA,YA), (R1M,R2E,ZT,XA,YA), (R1N,R2E,ZT,XA,YA), (R1O,R2E,ZT,XA,YA), (R1P,R2E,ZT,XA,YA), (R1Q,R2E,ZT,XA,YA), (R1A,R2F,ZT,XA,YA), (R1B,R2F,ZT,XA,YA), (R1C,R2F,ZT,XA,YA), (R1D,R2F,ZT,XA,YA), (R1E,R2F,ZT,XA,YA), (R1F,R2F,ZT,XA,YA), (R1G,R2F,ZT,XA,YA), (R1H,R2F,ZT,XA,YA), (R1I,R2F,ZT,XA,YA), (R1J,R2F,ZT,XA,YA), (R1K,R2F,ZT,XA,YA), (R1L,R2F,ZT,XA,YA), (R1M,R2F,ZT,XA,YA), (R1N,R2F,ZT,XA,YA), (R1O,R2F,ZT,XA,YA), (R1P,R2F,ZT,XA,YA), (R1Q,R2F,ZT,XA,YA), (R1A,R2G,ZT,XA,YA), (R1B,R2G,ZT,XA,YA), (R1C,R2G,ZT,XA,YA), (R1D,R2G,ZT,XA,YA), (R1E,R2G,ZT,XA,YA), (R1F,R2G,ZT,XA,YA), (R1G,R2G,ZT,XA,YA), (R1H,R2G,ZT,XA,YA), (R1I,R2G,ZT,XA,YA), (R1J,R2G,ZT,XA,YA), (R1K,R2G,ZT,XA,YA), (R1L,R2G,ZT,XA,YA), (R1M,R2G,ZT,XA,YA), (R1N,R2G,ZT,XA,YA), (R1O,R2G,ZT,XA,YA), (R1P,R2G,ZT,XA,YA), (R1Q,R2G,ZT,XA,YA), (R1A,R2H,ZT,XA,YA), (R1B,R2H,ZT,XA,YA), (R1C,R2H,ZT,XA,YA), (R1D,R2H,ZT,XA,YA), (R1E,R2H,ZT,XA,YA), (R1F,R2H,ZT,XA,YA), (R1G,R2H,ZT,XA,YA), (R1H,R2H,ZT,XA,YA), (R1I,R2H,ZT,XA,YA), (R1J,R2H,ZT,XA,YA), (R1K,R2H,ZT,XA,YA), (R1L,R2H,ZT,XA,YA), (R1M,R2H,ZT,XA,YA), (R1N,R2H,ZT,XA,YA), (R1O,R2H,ZT,XA,YA), (R1P,R2H,ZT,XA,YA), (R1Q,R2H,ZT,XA,YA), (R1A,R2I,ZT,XA,YA), (R1B,R2I,ZT,XA,YA), (R1C,R2I,ZT,XA,YA), (R1D,R2I,ZT,XA,YA), (R1E,R2I,ZT,XA,YA), (R1F,R2I,ZT,XA,YA), (R1G,R2I,ZT,XA,YA), (R1H,R2I,ZT,XA,YA), (R1I,R2I,ZT,XA,YA), (R1J,R2I,ZT,XA,YA), (R1K,R2I,ZT,XA,YA), (R1L,R2I,ZT,XA,YA), (R1M,R2I,ZT,XA,YA), (R1N,R2I,ZT,XA,YA), (R1O,R2I,ZT,XA,YA), (R1P,R2I,ZT,XA,YA), (R1Q,R2I,ZT,XA,YA), (R1A,R2J,ZT,XA,YA), (R1B,R2J,ZT,XA,YA), (R1C,R2J,ZT,XA,YA), (R1D,R2J,ZT,XA,YA), (R1E,R2J,ZT,XA,YA), (R1F,R2J,ZT,XA,YA), (R1G,R2J,ZT,XA,YA), (R1H,R2J,ZT,XA,YA), (R1I,R2J,ZT,XA,YA), (R1J,R2J,ZT,XA,YA), (R1K,R2J,ZT,XA,YA), (R1L,R2J,ZT,XA,YA), (R1M,R2J,ZT,XA,YA), (R1N,R2J,ZT,XA,YA), (R1O,R2J,ZT,XA,YA), (R1P,R2J,ZT,XA,YA), (R1Q,R2J,ZT,XA,YA), (R1A,R2K,ZT,XA,YA), (R1B,R2K,ZT,XA,YA), (R1C,R2K,ZT,XA,YA), (R1D,R2K,ZT,XA,YA), (R1E,R2K,ZT,XA,YA), (R1F,R2K,ZT,XA,YA), (R1G,R2K,ZT,XA,YA), (R1H,R2K,ZT,XA,YA), (R1I,R2K,ZT,XA,YA), (R1J,R2K,ZT,XA,YA), (R1K,R2K,ZT,XA,YA), (R1L,R2K,ZT,XA,YA), (R1M,R2K,ZT,XA,YA), (R1N,R2K,ZT,XA,YA), (R1O,R2K,ZT,XA,YA), (R1P,R2K,ZT,XA,YA), (R1Q,R2K,ZT,XA,YA), (R1A,R2L,ZT,XA,YA), (R1B,R2L,ZT,XA,YA), (R1C,R2L,ZT,XA,YA), (R1D,R2L,ZT,XA,YA), (R1E,R2L,ZT,XA,YA), (R1F,R2L,ZT,XA,YA), (R1G,R2L,ZT,XA,YA), (R1H,R2L,ZT,XA,YA), (R1I,R2L,ZT,XA,YA), (R1J,R2L,ZT,XA,YA), (R1K,R2L,ZT,XA,YA), (R1L,R2L,ZT,XA,YA), (R1M,R2L,ZT,XA,YA), (R1N,R2L,ZT,XA,YA), (R1O,R2L,ZT,XA,YA), (R1P,R2L,ZT,XA,YA), (R1Q,R2L,ZT,XA,YA), (R1A,R2M,ZT,XA,YA), (R1B,R2M,ZT,XA,YA), (R1C,R2M,ZT,XA,YA), (R1D,R2M,ZT,XA,YA), (R1E,R2M,ZT,XA,YA), (R1F,R2M,ZT,XA,YA), (R1G,R2M,ZT,XA,YA), (R1H,R2M,ZT,XA,YA), (R1I,R2M,ZT,XA,YA), (R1J,R2M,ZT,XA,YA), (R1K,R2M,ZT,XA,YA), (R1L,R2M,ZT,XA,YA), (R1M,R2M,ZT,XA,YA), (R1N,R2M,ZT,XA,YA), (R1O,R2M,ZT,XA,YA), (R1P,R2M,ZT,XA,YA), (R1Q,R2M,ZT,XA,YA), (R1A,R2N,ZT,XA,YA), (R1B,R2N,ZT,XA,YA), (R1C,R2N,ZT,XA,YA), (R1D,R2N,ZT,XA,YA), (R1E,R2N,ZT,XA,YA), (R1F,R2N,ZT,XA,YA), (R1G,R2N,ZT,XA,YA), (R1H,R2N,ZT,XA,YA), (R1I,R2N,ZT,XA,YA), (R1J,R2N,ZT,XA,YA), (R1K,R2N,ZT,XA,YA), (R1L,R2N,ZT,XA,YA), (R1M,R2N,ZT,XA,YA), (R1N,R2N,ZT,XA,YA), (R1O,R2N,ZT,XA,YA), (R1P,R2N,ZT,XA,YA), (R1Q,R2N,ZT,XA,YA), (R1A,R2O,ZT,XA,YA), (R1B,R2O,ZT,XA,YA), (R1C,R2O,ZT,XA,YA), (R1D,R2O,ZT,XA,YA), (R1E,R2O,ZT,XA,YA), (R1F,R2O,ZT,XA,YA), (R1G,R2O,ZT,XA,YA), (R1H,R2O,ZT,XA,YA), (R1I,R2O,ZT,XA,YA), (R1J,R2O,ZT,XA,YA), (R1K,R2O,ZT,XA,YA), (R1L,R2O,ZT,XA,YA), (R1M,R2O,ZT,XA,YA), (R1N,R2O,ZT,XA,YA), (R1O,R2O,ZT,XA,YA), (R1P,R2O,ZT,XA,YA), (R1Q,R2O,ZT,XA,YA), (R1A,R2P,ZT,XA,YA), (R1B,R2P,ZT,XA,YA), (R1C,R2P,ZT,XA,YA), (R1D,R2P,ZT,XA,YA), (R1E,R2P,ZT,XA,YA), (R1F,R2P,ZT,XA,YA), (R1G,R2P,ZT,XA,YA), (R1H,R2P,ZT,XA,YA), (R1I,R2P,ZT,XA,YA), (R1J,R2P,ZT,XA,YA), (R1K,R2P,ZT,XA,YA), (R1L,R2P,ZT,XA,YA), (R1M,R2P,ZT,XA,YA), (R1N,R2P,ZT,XA,YA), (R1O,R2P,ZT,XA,YA), (R1P,R2P,ZT,XA,YA), (R1Q,R2P,ZT,XA,YA), (R1A,R2Q,ZT,XA,YA), (R1B,R2Q,ZT,XA,YA), (R1C,R2Q,ZT,XA,YA), (R1D,R2Q,ZT,XA,YA), (R1E,R2Q,ZT,XA,YA), (R1F,R2Q,ZT,XA,YA), (R1G,R2Q,ZT,XA,YA), (R1H,R2Q,ZT,XA,YA), (R1I,R2Q,ZT,XA,YA), (R1J,R2Q,ZT,XA,YA), (R1K,R2Q,ZT,XA,YA), (R1L,R2Q,ZT,XA,YA), (R1M,R2Q,ZT,XA,YA), (R1N,R2Q,ZT,XA,YA), (R1O,R2Q,ZT,XA,YA), (R1P,R2Q,ZT,XA,YA), (R1Q,R2Q,ZT,XA,YA), (R1A,R2A,ZU,XA,YA), (R1B,R2A,ZU,XA,YA), (R1C,R2A,ZU,XA,YA), (R1D,R2A,ZU,XA,YA), (R1E,R2A,ZU,XA,YA), (R1F,R2A,ZU,XA,YA), (R1G,R2A,ZU,XA,YA), (R1H,R2A,ZU,XA,YA), (R1I,R2A,ZU,XA,YA), (R1J,R2A,ZU,XA,YA), (R1K,R2A,ZU,XA,YA), (R1L,R2A,ZU,XA,YA), (R1M,R2A,ZU,XA,YA), (R1N,R2A,ZU,XA,YA), (R1O,R2A,ZU,XA,YA), (R1P,R2A,ZU,XA,YA), (R1Q,R2A,ZU,XA,YA), (R1A,R2B,ZU,XA,YA), (R1B,R2B,ZU,XA,YA), (R1C,R2B,ZU,XA,YA), (R1D,R2B,ZU,XA,YA), (R1E,R2B,ZU,XA,YA), (R1F,R2B,ZU,XA,YA), (R1G,R2B,ZU,XA,YA), (R1H,R2B,ZU,XA,YA), (R1I,R2B,ZU,XA,YA), (R1J,R2B,ZU,XA,YA), (R1K,R2B,ZU,XA,YA), (R1L,R2B,ZU,XA,YA), (R1M,R2B,ZU,XA,YA), (R1N,R2B,ZU,XA,YA), (R1O,R2B,ZU,XA,YA), (R1P,R2B,ZU,XA,YA), (R1Q,R2B,ZU,XA,YA), (R1A,R2C,ZU,XA,YA), (R1B,R2C,ZU,XA,YA), (R1C,R2C,ZU,XA,YA), (R1D,R2C,ZU,XA,YA), (R1E,R2C,ZU,XA,YA), (R1F,R2C,ZU,XA,YA), (R1G,R2C,ZU,XA,YA), (R1H,R2C,ZU,XA,YA), (R1I,R2C,ZU,XA,YA), (R1J,R2C,ZU,XA,YA), (R1K,R2C,ZU,XA,YA), (R1L,R2C,ZU,XA,YA), (R1M,R2C,ZU,XA,YA), (R1N,R2C,ZU,XA,YA), (R1O,R2C,ZU,XA,YA), (R1P,R2C,ZU,XA,YA), (R1Q,R2C,ZU,XA,YA), (R1A,R2D,ZU,XA,YA), (R1B,R2D,ZU,XA,YA), (R1C,R2D,ZU,XA,YA), (R1D,R2D,ZU,XA,YA), (R1E,R2D,ZU,XA,YA), (R1F,R2D,ZU,XA,YA), (R1G,R2D,ZU,XA,YA), (R1H,R2D,ZU,XA,YA), (R1I,R2D,ZU,XA,YA), (R1J,R2D,ZU,XA,YA), (R1K,R2D,ZU,XA,YA), (R1L,R2D,ZU,XA,YA), (R1M,R2D,ZU,XA,YA), (R1N,R2D,ZU,XA,YA), (R1O,R2D,ZU,XA,YA), (R1P,R2D,ZU,XA,YA), (R1Q,R2D,ZU,XA,YA), (R1A,R2E,ZU,XA,YA), (R1B,R2E,ZU,XA,YA), (R1C,R2E,ZU,XA,YA), (R1D,R2E,ZU,XA,YA), (R1E,R2E,ZU,XA,YA), (R1F,R2E,ZU,XA,YA), (R1G,R2E,ZU,XA,YA), (R1H,R2E,ZU,XA,YA), (R1I,R2E,ZU,XA,YA), (R1J,R2E,ZU,XA,YA), (R1K,R2E,ZU,XA,YA), (R1L,R2E,ZU,XA,YA), (R1M,R2E,ZU,XA,YA), (R1N,R2E,ZU,XA,YA), (R1O,R2E,ZU,XA,YA), (R1P,R2E,ZU,XA,YA), (R1Q,R2E,ZU,XA,YA), (R1A,R2F,ZU,XA,YA), (R1B,R2F,ZU,XA,YA), (R1C,R2F,ZU,XA,YA), (R1D,R2F,ZU,XA,YA), (R1E,R2F,ZU,XA,YA), (R1F,R2F,ZU,XA,YA), (R1G,R2F,ZU,XA,YA), (R1H,R2F,ZU,XA,YA), (R1I,R2F,ZU,XA,YA), (R1J,R2F,ZU,XA,YA), (R1K,R2F,ZU,XA,YA), (R1L,R2F,ZU,XA,YA), (R1M,R2F,ZU,XA,YA), (R1N,R2F,ZU,XA,YA), (R1O,R2F,ZU,XA,YA), (R1P,R2F,ZU,XA,YA), (R1Q,R2F,ZU,XA,YA), (R1A,R2G,ZU,XA,YA), (R1B,R2G,ZU,XA,YA), (R1C,R2G,ZU,XA,YA), (R1D,R2G,ZU,XA,YA), (R1E,R2G,ZU,XA,YA), (R1F,R2G,ZU,XA,YA), (R1G,R2G,ZU,XA,YA), (R1H,R2G,ZU,XA,YA), (R1I,R2G,ZU,XA,YA), (R1J,R2G,ZU,XA,YA), (R1K,R2G,ZU,XA,YA), (R1L,R2G,ZU,XA,YA), (R1M,R2G,ZU,XA,YA), (R1N,R2G,ZU,XA,YA), (R1O,R2G,ZU,XA,YA), (R1P,R2G,ZU,XA,YA), (R1Q,R2G,ZU,XA,YA), (R1A,R2H,ZU,XA,YA), (R1B,R2H,ZU,XA,YA), (R1C,R2H,ZU,XA,YA), (R1D,R2H,ZU,XA,YA), (R1E,R2H,ZU,XA,YA), (R1F,R2H,ZU,XA,YA), (R1G,R2H,ZU,XA,YA), (R1H,R2H,ZU,XA,YA), (R1I,R2H,ZU,XA,YA), (R1J,R2H,ZU,XA,YA), (R1K,R2H,ZU,XA,YA), (R1L,R2H,ZU,XA,YA), (R1M,R2H,ZU,XA,YA), (R1N,R2H,ZU,XA,YA), (R1O,R2H,ZU,XA,YA), (R1P,R2H,ZU,XA,YA), (R1Q,R2H,ZU,XA,YA), (R1A,R2I,ZU,XA,YA), (R1B,R2I,ZU,XA,YA), (R1C,R2I,ZU,XA,YA), (R1D,R2I,ZU,XA,YA), (R1E,R2I,ZU,XA,YA), (R1F,R2I,ZU,XA,YA), (R1G,R2I,ZU,XA,YA), (R1H,R2I,ZU,XA,YA), (R1I,R2I,ZU,XA,YA), (R1J,R2I,ZU,XA,YA), (R1K,R2I,ZU,XA,YA), (R1L,R2I,ZU,XA,YA), (R1M,R2I,ZU,XA,YA), (R1N,R2I,ZU,XA,YA), (R1O,R2I,ZU,XA,YA), (R1P,R2I,ZU,XA,YA), (R1Q,R2I,ZU,XA,YA), (R1A,R2J,ZU,XA,YA), (R1B,R2J,ZU,XA,YA), (R1C,R2J,ZU,XA,YA), (R1D,R2J,ZU,XA, YA), (R1E,R2J,ZU,XA,YA), (R1F,R2J,ZU,XA,YA), (R1G, R2J,ZU,XA,YA), (R1H,R2J,ZU,XA,YA), (R1I,R2J,ZU,XA, YA), (R1J,R2J,ZU,XA,YA), (R1K,R2J,ZU,XA,YA), (R1L, R2J,ZU,XA,YA), (R1M,R2J,ZU,XA,YA), (R1N,R2J,ZU, XA,YA), (R1O,R2J,ZU,XA,YA), (R1P,R2J,ZU,XA,YA), (R1Q,R2J,ZU,XA,YA), (R1A,R2K,ZU,XA,YA), (R1B, R2K,ZU,XA,YA), (R1C,R2K,ZU,XA,YA), (R1D,R2K,ZU, XA,YA), (R1E,R2K,ZU,XA,YA), (R1F,R2K,ZU,XA,YA), (R1G,R2K,ZU,XA,YA), (R1H,R2K,ZU,XA,YA), (R1I, R2K,ZU,XA,YA), (R1J,R2K,ZU,XA,YA), (R1K,R2K,ZU, XA,YA), (R1L,R2K,ZU,XA,YA), (R1M,R2K,ZU,XA,YA), (R1N,R2K,ZU,XA,YA), (R1O,R2K,ZU,XA,YA), (R1P, R2K,ZU,XA,YA), (R1Q,R2K,ZU,XA,YA), (R1A,R2L,ZU, XA,YA), (R1B,R2L,ZU,XA,YA), (R1C,R2L,ZU,XA,YA), (R1D,R2L,ZU,XA,YA), (R1E,R2L,ZU,XA,YA), (R1F,R2L, ZU,XA,YA), (R1G,R2L,ZU,XA,YA), (R1H,R2L,ZU,XA, YA), (R1I,R2L,ZU,XA,YA), (R1J,R2L,ZU,XA,YA), (R1K, R2L,ZU,XA,YA), (R1L,R2L,ZU,XA,YA), (R1M,R2L,ZU, XA,YA), (R1N,R2L,ZU,XA,YA), (R1O,R2L,ZU,XA,YA), (R1P,R2L,ZU,XA,YA), (R1Q,R2L,ZU,XA,YA), (R1A, R2M,ZU,XA,YA), (R1B,R2M,ZU,XA,YA), (R1C,R2M,ZU, XA,YA), (R1D,R2M,ZU,XA,YA), (R1E,R2M,ZU,XA,YA), (R1F,R2M,ZU,XA,YA), (R1G,R2M,ZU,XA,YA), (R1H, R2M,ZU,XA,YA), (R1I,R2M,ZU,XA,YA), (R1J,R2M,ZU, XA,YA), (R1K,R2M,ZU,XA,YA), (R1L,R2M,ZU,XA,YA), (R1M,R2M,ZU,XA,YA), (R1N,R2M,ZU,XA,YA), (R1O, R2M,ZU,XA,YA), (R1P,R2M,ZU,XA,YA), (R1Q,R2M,ZU, XA,YA), (R1A,R2N,ZU,XA,YA), (R1B,R2N,ZU,XA,YA), (R1C,R2N,ZU,XA,YA), (R1D,R2N,ZU,XA,YA), (R1E, R2N,ZU,XA,YA), (R1F,R2N,ZU,XA,YA), (R1G,R2N,ZU, XA,YA), (R1H,R2N,ZU,XA,YA), (R1I,R2N,ZU,XA,YA), (R1J,R2N,ZU,XA,YA), (R1K,R2N,ZU,XA,YA), (R1L, R2N,ZU,XA,YA), (R1M,R2N,ZU,XA,YA), (R1N,R2N,ZU, XA,YA), (R1 O,R2N,ZU,XA,YA), (R1P,R2N,ZU,XA,YA), (R1Q,R2N,ZU,XA,YA), (R1A,R2O,ZU,XA,YA), (R1B, R2O,ZU,XA,YA), (R1C,R2O,ZU,XA,YA), (R1D,R2O,ZU, XA,YA), (R1E,R2O,ZU,XA,YA), (R1F,R2O,ZU,XA,YA), (R1G,R2O,ZU,XA,YA), (R1H,R2O,ZU,XA,YA), (R1I, R2O,ZU,XA,YA), (R1J,R2O,ZU,XA,YA), (R1K,R2O,ZU, XA,YA), (R1L,R2O,ZU,XA,YA), (R1M,R2O,ZU,XA,YA), (R1N,R2O,ZU,XA,YA), (R1O,R2O,ZU,XA,YA), (R1P, R2O,ZU,XA,YA), (R1Q,R2O,ZU,XA,YA), (R1A,R2P,ZU, XA,YA), (R1B,R2P,ZU,XA,YA), (R1C,R2P,ZU,XA,YA), (R1D,R2P,ZU,XA,YA), (R1E,R2P,ZU,XA,YA), (R1F,R2P, ZU,XA,YA), (R1G,R2P,ZU,XA,YA), (R1H,R2P,ZU,XA, YA), (R1I,R2P,ZU,XA,YA), (R1J,R2P,ZU,XA,YA), (R1K, R2P,ZU,XA,YA), (R1L,R2P,ZU,XA,YA), (R1M,R2P,ZU, XA,YA), (R1N,R2P,ZU,XA,YA), (R1O,R2P,ZU,XA,YA), (R1P,R2P,ZU,XA,YA), (R1Q,R2P,ZU,XA,YA), (R1A,R2Q, ZU,XA,YA), (R1B,R2Q,ZU,XA,YA), (R1C,R2Q,ZU,XA, YA), (R1D,R2Q,ZU,XA,YA), (R1E,R2Q,ZU,XA,YA), (R1F,R2Q,ZU,XA,YA), (R1G,R2Q,ZU,XA,YA), (R1H, R2Q,ZU,XA,YA), (R1I,R2Q,ZU,XA,YA), (R1J,R2Q,ZU, XA,YA), (R1K,R2Q,ZU,XA,YA), (R1L,R2Q,ZU,XA,YA), (R1M,R2Q,ZU,XA,YA), (R1N,R2Q,ZU,XA,YA), (R1O, R2Q,ZU,XA,YA), (R1P,R2Q,ZU,XA,YA), (R1Q,R2Q,ZU, XA,YA), (R1A,R2A,ZA,XB,YA), (R1B,R2A,ZA,XB,YA), (R1C,R2A,ZA,XB,YA), (R1D,R2A,ZA,XB,YA), (R1E, R2A,ZA,XB,YA), (R1F,R2A,ZA,XB,YA), (R1G,R2A,ZA, XB,YA), (R1H,R2A,ZA,XB,YA), (R1I,R2A,ZA,XB,YA), (R1J,R2A,ZA,XB,YA), (R1K,R2A,ZA,XB,YA), (R1L,R2A, ZA,XB,YA), (R1M,R2A,ZA,XB,YA), (R1N,R2A,ZA,XB, YA), (R1O,R2A,ZA,XB,YA), (R1P,R2A,ZA,XB,YA), (R1Q,R2A,ZA,XB,YA), (R1A,R2B,ZA,XB,YA), (R1B, R2B,ZA,XB,YA), (R1C,R2B,ZA,XB,YA), (R1D,R2B,ZA, XB,YA), (R1E,R2B,ZA,XB,YA), (R1F,R2B,ZA,XB,YA), (R1G,R2B,ZA,XB,YA), (R1H,R2B,ZA,XB,YA), (R1I,R2B, ZA,XB,YA), (R1J,R2B,ZA,XB,YA), (R1K,R2B,ZA,XB, YA), (R1L,R2B,ZA,XB,YA), (R1M,R2B,ZA,XB,YA), (R1N,R2B,ZA,XB,YA), (R1O,R2B,ZA,XB,YA), (R1P,R2B, ZA,XB,YA), (R1Q,R2B,ZA,XB,YA), (R1A,R2C,ZA,XB, YA), (R1B,R2C,ZA,XB,YA), (R1C,R2C,ZA,XB,YA), (R1D,R2C,ZA,XB,YA), (R1E,R2C,ZA,XB,YA), (R1F,R2C, ZA,XB,YA), (R1G,R2C,ZA,XB,YA), (R1H,R2C,ZA,XB, YA), (R1I,R2C,ZA,XB,YA), (R1J,R2C,ZA,XB,YA), (R1K, R2C,ZA,XB,YA), (R1L,R2C,ZA,XB,YA), (R1M,R2C,ZA, XB,YA), (R1N,R2C,ZA,XB,YA), (R1O,R2C,ZA,XB,YA), (R1P,R2C,ZA,XB,YA), (R1Q,R2C,ZA,XB,YA), (R1A, R2D,ZA,XB,YA), (R1B,R2D,ZA,XB,YA), (R1C,R2D,ZA, XB,YA), (R1D,R2D,ZA,XB,YA), (R1E,R2D,ZA,XB,YA), (R1F,R2D,ZA,XB,YA), (R1G,R2D,ZA,XB,YA), (R1H, R2D,ZA,XB,YA), (R1I,R2D,ZA,XB,YA), (R1J,R2D,ZA, XB,YA), (R1K,R2D,ZA,XB,YA), (R1L,R2D,ZA,XB,YA), (R1M,R2D,ZA,XB,YA), (R1N,R2D,ZA,XB,YA), (R1O, R2D,ZA,XB,YA), (R1P,R2D,ZA,XB,YA), (R1Q,R2D,ZA, XB,YA), (R1A,R2E,ZA,XB,YA), (R1B,R2E,ZA,XB,YA), (R1C,R2E,ZA,XB,YA), (R1D,R2E,ZA,XB,YA), (R1E,R2E, ZA,XB,YA), (R1F,R2E,ZA,XB,YA), (R1G,R2E,ZA,XB, YA), (R1H,R2E,ZA,XB,YA), (R1I,R2E,ZA,XB,YA), (R1J, R2E,ZA,XB,YA), (R1K,R2E,ZA,XB,YA), (R1L,R2E,ZA, XB,YA), (R1M,R2E,ZA,XB,YA), (R1N,R2E,ZA,XB,YA), (R1O,R2E,ZA,XB,YA), (R1P,R2E,ZA,XB,YA), (R1Q,R2E, ZA,XB,YA), (R1A,R2F,ZA,XB,YA), (R1B,R2F,ZA,XB, YA), (R1C,R2F,ZA,XB,YA), (R1D,R2F,ZA,XB,YA), (R1E, R2F,ZA,XB,YA), (R1F,R2F,ZA,XB,YA), (R1G,R2F,ZA, XB,YA), (R1H,R2F,ZA,XB,YA), (R1I,R2F,ZA,XB,YA), (R1J,R2F,ZA,XB,YA), (R1K,R2F,ZA,XB,YA), (R1L,R2F, ZA,XB,YA), (R1M,R2F,ZA,XB,YA), (R1N,R2F,ZA,XB, YA), (R1O,R2F,ZA,XB,YA), (R1P,R2F,ZA,XB,YA), (R1Q, R2F,ZA,XB,YA), (R1A,R2G,ZA,XB,YA), (R1B,R2G,ZA, XB,YA), (R1C,R2G,ZA,XB,YA), (R1D,R2G,ZA,XB,YA), (R1E,R2G,ZA,XB,YA), (R1F,R2G,ZA,XB,YA), (R1G, R2G,ZA,XB,YA), (R1H,R2G,ZA,XB,YA), (R1I,R2G,ZA, XB,YA), (R1J,R2G,ZA,XB,YA), (R1K,R2G,ZA,XB,YA), (R1L,R2G,ZA,XB,YA), (R1M,R2G,ZA,XB,YA), (R1N, R2G,ZA,XB,YA), (R1O,R2G,ZA,XB,YA), (R1P,R2G,ZA, XB,YA), (R1Q,R2G,ZA,XB,YA), (R1A,R2H,ZA,XB,YA), (R1B,R2H,ZA,XB,YA), (R1C,R2H,ZA,XB,YA), (R1D, R2H,ZA,XB,YA), (R1E,R2H,ZA,XB,YA), (R1F,R2H,ZA, XB,YA), (R1G,R2H,ZA,XB,YA), (R1H,R2H,ZA,XB,YA), (R1I,R2H,ZA,XB,YA), (R1J,R2H,ZA,XB,YA), (R1K,R2H, ZA,XB,YA), (R1L,R2H,ZA,XB,YA), (R1M,R2H,ZA,XB, YA), (R1N,R2H,ZA,XB,YA), (R1O,R2H,ZA,XB,YA), (R1P,R2H,ZA,XB,YA), (R1Q,R2H,ZA,XB,YA), (R1A,R2I, ZA,XB,YA), (R1B,R2I,ZA,XB,YA), (R1C,R2I,ZA,XB, YA), (R1D,R2I,ZA,XB,YA), (R1E,R2I,ZA,XB,YA), (R1F, R2I,ZA,XB,YA), (R1G,R2I,ZA,XB,YA), (R1H,R2I,ZA,XB, YA), (R1I,R2I,ZA,XB,YA), (R1J,R2I,ZA,XB,YA), (R1K, R2I,ZA,XB,YA), (R1L,R2I,ZA,XB,YA), (R1M,R2I,ZA, XB,YA), (R1N,R2I,ZA,XB,YA), (R1O,R2I,ZA,XB,YA), (R1P,R2I,ZA,XB,YA), (R1Q,R2I,ZA,XB,YA), (R1A,R2J, ZA,XB,YA), (R1B,R2J,ZA,XB,YA), (R1C,R2J,ZA,XB, YA), (R1D,R2J,ZA,XB,YA), (R1E,R2J,ZA,XB,YA), (R1F, R2J,ZA,XB,YA), (R1G,R2J,ZA,XB,YA), (R1H,R2J,ZA, XB,YA), (R1I,R2J,ZA,XB,YA), (R1J,R2J,ZA,XB,YA), (R1K,R2J,ZA,XB,YA), (R1L,R2J,ZA,XB,YA), (R1M,R2J, ZA,XB,YA), (R1N,R2J,ZA,XB,YA), (R1O,R2J,ZA,XB, YA), (R1P,R2J,ZA,XB,YA), (R1Q,R2J,ZA,XB,YA), (R1A, R2K,ZA,XB,YA), (R1B,R2K,ZA,XB,YA), (R1C,R2K,ZA, XB,YA), (R1D,R2K,ZA,XB,YA), (R1E,R2K,ZA,XB,YA), (R1F,R2K,ZA,XB,YA), (R1G,R2K,ZA,XB,YA), (R1H, R2K,ZA,XB,YA), (R1I,R2K,ZA,XB,YA), (R1J,R2K,ZA, XB,YA), (R1K,R2K,ZA,XB,YA), (R1L,R2K,ZA,XB,YA), (R1M,R2K,ZA,XB,YA), (R1N,R2K,ZA,XB,YA), (R1O, R2K,ZA,XB,YA), (R1P,R2K,ZA,XB,YA), (R1Q,R2K,ZA, XB,YA), (R1A,R2L,ZA,XB,YA), (R1B,R2L,ZA,XB,YA), (R1C,R2L,ZA,XB,YA), (R1D,R2L,ZA,XB,YA), (R1E,R2L, ZA,XB,YA), (R1F,R2L,ZA,XB,YA), (R1G,R2L,ZA,XB, YA), (R1H,R2L,ZA,XB,YA), (R1I,R2L,ZA,XB,YA), (R1J, R2L,ZA,XB,YA), (R1K,R2L,ZA,XB,YA), (R1L,R2L,ZA, XB,YA), (R1M,R2L,ZA,XB,YA), (R1N,R2L,ZA,XB,YA), (R1O,R2L,ZA,XB,YA), (R1P,R2L,ZA,XB,YA), (R1Q,R2L, ZA,XB,YA), (R1A,R2M,ZA,XB,YA), (R1B,R2M,ZA,XB, YA), (R1C,R2M,ZA,XB,YA), (R1D,R2M,ZA,XB,YA), (R1E,R2M,ZA,XB,YA), (R1F,R2M,ZA,XB,YA), (R1G, R2M,ZA,XB,YA), (R1H,R2M,ZA,XB,YA), (R1I,R2M,ZA, XB,YA), (R1J,R2M,ZA,XB,YA), (R1K,R2M,ZA,XB,YA), (R1L,R2M,ZA,XB,YA), (R1M,R2M,ZA,XB,YA), (R1N, R2M,ZA,XB,YA), (R1O,R2M,ZA,XB,YA), (R1P,R2M,ZA, XB,YA), (R1Q,R2M,ZA,XB,YA), (R1A,R2N,ZA,XB,YA), (R1B,R2N,ZA,XB,YA), (R1C,R2N,ZA,XB,YA), (R1D, R2N,ZA,XB,YA), (R1E,R2N,ZA,XB,YA), (R1F,R2N,ZA, XB,YA), (R1G,R2N,ZA,XB,YA), (R1H,R2N,ZA,XB,YA), (R1I,R2N,ZA,XB,YA), (R1J,R2N,ZA,XB,YA), (R1K,R2N, ZA,XB,YA), (R1L,R2N,ZA,XB,YA), (R1M,R2N,ZA,XB, YA), (R1N,R2N,ZA,XB,YA), (R1O,R2N,ZA,XB,YA), (R1P,R2N,ZA,XB,YA), (R1Q,R2N,ZA,XB,YA), (R1A, R2O,ZA,XB,YA), (R1B,R2O,ZA,XB,YA), (R1C,R2O,ZA, XB,YA), (R1D,R2O,ZA,XB,YA), (R1E,R2O,ZA,XB,YA), (R1F,R2O,ZA,XB,YA), (R1G,R2O,ZA,XB,YA), (R1H, R2O,ZA,XB,YA), (R1I,R2O,ZA,XB,YA), (R1J,R2O,ZA, XB,YA), (R1K,R2O,ZA,XB,YA), (R1L,R2O,ZA,XB,YA), (R1M,R2O,ZA,XB,YA), (R1N,R2O,ZA,XB,YA), (R1O, R2O,ZA,XB,YA), (R1P,R2O,ZA,XB,YA), (R1Q,R2O,ZA, XB,YA), (R1A,R2P,ZA,XB,YA), (R1B,R2P,ZA,XB,YA), (R1C,R2P,ZA,XB,YA), (R1D,R2P,ZA,XB,YA), (R1E,R2P, ZA,XB,YA), (R1F,R2P,ZA,XB,YA), (R1G,R2P,ZA,XB, YA), (R1H,R2P,ZA,XB,YA), (R1I,R2P,ZA,XB,YA), (R1J, R2P,ZA,XB,YA), (R1K,R2P,ZA,XB,YA), (R1L,R2P,ZA, XB,YA), (R1M,R2P,ZA,XB,YA), (R1N,R2P,ZA,XB,YA), (R1O,R2P,ZA,XB,YA), (R1P,R2P,ZA,XB,YA), (R1Q,R2P, ZA,XB,YA), (R1A,R2Q,ZA,XB,YA), (R1B,R2Q,ZA,XB, YA), (R1C,R2Q,ZA,XB,YA), (R1D,R2Q,ZA,XB,YA), (R1E,R2Q,ZA,XB,YA), (R1F,R2Q,ZA,XB,YA), (R1G, R2Q,ZA,XB,YA), (R1H,R2Q,ZA,XB,YA), (R1I,R2Q,ZA, XB,YA), (R1J,R2Q,ZA,XB,YA), (R1K,R2Q,ZA,XB,YA), (R1L,R2Q,ZA,XB,YA), (R1M,R2Q,ZA,XB,YA), (R1N, R2Q,ZA,XB,YA), (R1O,R2Q,ZA,XB,YA), (R1P,R2Q,ZA, XB,YA), (R1Q,R2Q,ZA,XB,YA), (R1A,R2A,ZB,XB,YA), (R1B,R2A,ZB,XB,YA), (R1C,R2A,ZB,XB,YA), (R1D, R2A,ZB,XB,YA), (R1E,R2A,ZB,XB,YA), (R1F,R2A,ZB, XB,YA), (R1G,R2A,ZB,XB,YA), (R1H,R2A,ZB,XB,YA), (R1I,R2A,ZB,XB,YA), (R1J,R2A,ZB,XB,YA), (R1K,R2A, ZB,XB,YA), (R1L,R2A,ZB,XB,YA), (R1M,R2A,ZB,XB, YA), (R1N,R2A,ZB,XB,YA), (R1O,R2A,ZB,XB,YA), (R1P, R2A,ZB,XB,YA), (R1Q,R2A,ZB,XB,YA), (R1A,R2B,ZB, XB,YA), (R1B,R2B,ZB,XB,YA), (R1C,R2B,ZB,XB,YA), (R1D,R2B,ZB,XB,YA), (R1E,R2B,ZB,XB,YA), (R1F,R2B, ZB,XB,YA), (R1G,R2B,ZB,XB,YA), (R1H,R2B,ZB,XB, YA), (R1I,R2B,ZB,XB,YA), (R1J,R2B,ZB,XB,YA), (R1K, R2B,ZB,XB,YA), (R1L,R2B,ZB,XB,YA), (R1M,R2B,ZB, XB,YA), (R1N,R2B,ZB,XB,YA), (R1O,R2B,ZB,XB,YA), (R1P,R2B,ZB,XB,YA), (R1Q,R2B,ZB,XB,YA), (R1A,R2C, ZB,XB,YA), (R1B,R2C,ZB,XB,YA), (R1C,R2C,ZB,XB, YA), (R1D,R2C,ZB,XB,YA), (R1E,R2C,ZB,XB,YA), (R1F, R2C,ZB,XB,YA), (R1G,R2C,ZB,XB,YA), (R1H,R2C,ZB, XB,YA), (R1I,R2C,ZB,XB,YA), (R1J,R2C,ZB,XB,YA), (R1K,R2C,ZB,XB,YA), (R1L,R2C,ZB,XB,YA), (R1M, R2C,ZB,XB,YA), (R1N,R2C,ZB,XB,YA), (R1O,R2C,ZB, XB,YA), (R1P,R2C,ZB,XB,YA), (R1Q,R2C,ZB,XB,YA), (R1A,R2D,ZB,XB,YA), (R1B,R2D,ZB,XB,YA), (R1C, R2D,ZB,XB,YA), (R1D,R2D,ZB,XB,YA), (R1E,R2D,ZB, XB,YA), (R1F,R2D,ZB,XB,YA), (R1G,R2D,ZB,XB,YA), (R1H,R2D,ZB,XB,YA), (R1I,R2D,ZB,XB,YA), (R1J,R2D, ZB,XB,YA), (R1K,R2D,ZB,XB,YA), (R1L,R2D,ZB,XB, YA), (R1M,R2D,ZB,XB,YA), (R1N,R2D,ZB,XB,YA), (R1O,R2D,ZB,XB,YA), (R1P,R2D,ZB,XB,YA), (R1Q, R2D,ZB,XB,YA), (R1A,R2E,ZB,XB,YA), (R1B,R2E,ZB, XB,YA), (R1C,R2E,ZB,XB,YA), (R1D,R2E,ZB,XB,YA), (R1E,R2E,ZB,XB,YA), (R1F,R2E,ZB,XB,YA), (R1G,R2E, ZB,XB,YA), (R1H,R2E,ZB,XB,YA), (R1I,R2E,ZB,XB, YA), (R1J,R2E,ZB,XB,YA), (R1K,R2E,ZB,XB,YA), (R1L, R2E,ZB,XB,YA), (R1M,R2E,ZB,XB,YA), (R1N,R2E,ZB, XB,YA), (R1O,R2E,ZB,XB,YA), (R1P,R2E,ZB,XB,YA), (R1Q,R2E,ZB,XB,YA), (R1A,R2F,ZB,XB,YA), (R1B,R2F, ZB,XB,YA), (R1C,R2F,ZB,XB,YA), (R1D,R2F,ZB,XB, YA), (R1E,R2F,ZB,XB,YA), (R1F,R2F,ZB,XB,YA), (R1G, R2F,ZB,XB,YA), (R1H,R2F,ZB,XB,YA), (R1I,R2F,ZB,XB, YA), (R1J,R2F,ZB,XB,YA), (R1K,R2F,ZB,XB,YA), (R1L, R2F,ZB,XB,YA), (R1M,R2F,ZB,XB,YA), (R1N,R2F,ZB, XB,YA), (R1O,R2F,ZB,XB,YA), (R1P,R2F,ZB,XB,YA), (R1Q,R2F,ZB,XB,YA), (R1A,R2G,ZB,XB,YA), (R1B,R2G, ZB,XB,YA), (R1C,R2G,ZB,XB,YA), (R1D,R2G,ZB,XB, YA), (R1E,R2G,ZB,XB,YA), (R1F,R2G,ZB,XB,YA), (R1G, R2G,ZB,XB,YA), (R1H,R2G,ZB,XB,YA), (R1I,R2G,ZB, XB,YA), (R1J,R2G,ZB,XB,YA), (R1K,R2G,ZB,XB,YA), (R1L,R2G,ZB,XB,YA), (R1M,R2G,ZB,XB,YA), (R1N, R2G,ZB,XB,YA), (R1O,R2G,ZB,XB,YA), (R1P,R2G,ZB, XB,YA), (R1Q,R2G,ZB,XB,YA), (R1A,R2H,ZB,XB,YA), (R1B,R2H,ZB,XB,YA), (R1C,R2H,ZB,XB,YA), (R1D, R2H,ZB,XB,YA), (R1E,R2H,ZB,XB,YA), (R1F,R2H,ZB, XB,YA), (R1G,R2H,ZB,XB,YA), (R1H,R2H,ZB,XB,YA), (R1I,R2H,ZB,XB,YA), (R1J,R2H,ZB,XB,YA), (R1K,R2H, ZB,XB,YA), (R1L,R2H,ZB,XB,YA), (R1M,R2H,ZB,XB, YA), (R1N,R2H,ZB,XB,YA), (R1O,R2H,ZB,XB,YA), (R1P, R2H,ZB,XB,YA), (R1Q,R2H,ZB,XB,YA), (R1A,R2I,ZB, XB,YA), (R1B,R2I,ZB,XB,YA), (R1C,R2I,ZB,XB,YA), (R1D,R2I,ZB,XB,YA), (R1E,R2I,ZB,XB,YA), (R1F,R2I, ZB,XB,YA), (R1G,R2I,ZB,XB,YA), (R1H,R2I,ZB,XB,YA), (R1I,R2I,ZB,XB,YA), (R1J,R2I,ZB,XB,YA), (R1K,R2I,ZB, XB,YA), (R1L,R2I,ZB,XB,YA), (R1M,R2I,ZB,XB,YA), (R1N,R2I,ZB,XB,YA), (R1O,R2I,ZB,XB,YA), (R1P,R2I, ZB,XB,YA), (R1Q,R2I,ZB,XB,YA), (R1A,R2J,ZB,XB, YA), (R1B,R2J,ZB,XB,YA), (R1C,R2J,ZB,XB,YA), (R1D, R2J,ZB,XB,YA), (R1E,R2J,ZB,XB,YA), (R1F,R2J,ZB,XB, YA), (R1G,R2J,ZB,XB,YA), (R1H,R2J,ZB,XB,YA), (R1I, R2J,ZB,XB,YA), (R1J,R2J,ZB,XB,YA), (R1K,R2J,ZB,XB, YA), (R1L,R2J,ZB,XB,YA), (R1M,R2J,ZB,XB,YA), (R1N, R2J,ZB,XB,YA), (R1O,R2J,ZB,XB,YA), (R1P,R2J,ZB,XB, YA), (R1Q,R2J,ZB,XB,YA), (R1A,R2K,ZB,XB,YA), (R1B, R2K,ZB,XB,YA), (R1C,R2K,ZB,XB,YA), (R1D,R2K,ZB, XB,YA), (R1E,R2K,ZB,XB,YA), (R1F,R2K,ZB,XB,YA), (R1G,R2K,ZB,XB,YA), (R1H,R2K,ZB,XB,YA), (R1I,R2K, ZB,XB,YA), (R1J,R2K,ZB,XB,YA), (R1K,R2K,ZB,XB, YA), (R1L,R2K,ZB,XB,YA), (R1M,R2K,ZB,XB,YA), (R1N,R2K,ZB,XB,YA), (R1O,R2K,ZB,XB,YA), (R1P, R2K,ZB,XB,YA), (R1Q,R2K,ZB,XB,YA), (R1A,R2L,ZB, XB,YA), (R1B,R2L,ZB,XB,YA), (R1C,R2L,ZB,XB,YA), (R1D,R2L,ZB,XB,YA), (R1E,R2L,ZB,XB,YA), (R1F,R2L, ZB,XB,YA), (R1G,R2L,ZB,XB,YA), (R1H,R2L,ZB,XB, YA), (R1I,R2L,ZB,XB,YA), (R1J,R2L,ZB,XB,YA), (R1K, R2L,ZB,XB,YA), (R1L,R2L,ZB,XB,YA), (R1M,R2L,ZB, XB,YA), (R1N,R2L,ZB,XB,YA), (R1O,R2L,ZB,XB,YA), (R1P,R2L,ZB,XB,YA), (R1Q,R2L,ZB,XB,YA), (R1A,R2M, ZB,XB,YA), (R1B,R2M,ZB,XB,YA), (R1C,R2M,ZB,XB, YA), (R1D,R2M,ZB,XB,YA), (R1E,R2M,ZB,XB,YA), (R1F,R2M,ZB,XB,YA), (R1G,R2M,ZB,XB,YA), (R1H, R2M,ZB,XB,YA), (R1I,R2M,ZB,XB,YA), (R1J,R2M,ZB, XB,YA), (R1K,R2M,ZB,XB,YA), (R1L,R2M,ZB,XB,YA), (R1M,R2M,ZB,XB,YA), (R1N,R2M,ZB,XB,YA), (R1O,R2M,ZB,XB,YA), (R1P,R2M,ZB,XB,YA), (R1Q,R2M,ZB,XB,YA), (R1A,R2N,ZB,XB,YA), (R1B,R2N,ZB,XB,YA), (R1C,R2N,ZB,XB,YA), (R1D,R2N,ZB,XB,YA), (R1E,R2N,ZB,XB,YA), (R1F,R2N,ZB,XB,YA), (R1G,R2N,ZB,XB,YA), (R1H,R2N,ZB,XB,YA), (R1I,R2N,ZB,XB,YA), (R1J,R2N,ZB,XB,YA), (R1K,R2N,ZB,XB,YA), (R1L,R2N,ZB,XB,YA), (R1M,R2N,ZB,XB,YA), (R1N,R2N,ZB,XB,YA), (R1O,R2N,ZB,XB,YA), (R1P,R2N,ZB,XB,YA), (R1Q,R2N,ZB,XB,YA), (R1A,R2O,ZB,XB,YA), (R1B,R2O,ZB,XB,YA), (R1C,R2O,ZB,XB,YA), (R1D,R2O,ZB,XB,YA), (R1E,R2O,ZB,XB,YA), (R1F,R2O,ZB,XB,YA), (R1G,R2O,ZB,XB,YA), (R1H,R2O,ZB,XB,YA), (R1I,R2O,ZB,XB,YA), (R1J,R2O,ZB,XB,YA), (R1K,R2O,ZB,XB,YA), (R1L,R2O,ZB,XB,YA), (R1M,R2O,ZB,XB,YA), (R1N,R2O,ZB,XB,YA), (R1O,R2O,ZB,XB,YA), (R1P,R2O,ZB,XB,YA), (R1Q,R2O,ZB,XB,YA), (R1A,R2P,ZB,XB,YA), (R1B,R2P,ZB,XB,YA), (R1C,R2P,ZB,XB,YA), (R1D,R2P,ZB,XB,YA), (R1E,R2P,ZB,XB,YA), (R1F,R2P,ZB,XB,YA), (R1G,R2P,ZB,XB,YA), (R1H,R2P,ZB,XB,YA), (R1I,R2P,ZB,XB,YA), (R1J,R2P,ZB,XB,YA), (R1K,R2P,ZB,XB,YA), (R1L,R2P,ZB,XB,YA), (R1M,R2P,ZB,XB,YA), (R1N,R2P,ZB,XB,YA), (R1O,R2P,ZB,XB,YA), (R1P,R2P,ZB,XB,YA), (R1Q,R2P,ZB,XB,YA), (R1A,R2Q,ZB,XB,YA), (R1B,R2Q,ZB,XB,YA), (R1C,R2Q,ZB,XB,YA), (R1D,R2Q,ZB,XB,YA), (R1E,R2Q,ZB,XB,YA), (R1F,R2Q,ZB,XB,YA), (R1G,R2Q,ZB,XB,YA), (R1H,R2Q,ZB,XB,YA), (R1I,R2Q,ZB,XB,YA), (R1J,R2Q,ZB,XB,YA), (R1K,R2Q,ZB,XB,YA), (R1L,R2Q,ZB,XB,YA), (R1M,R2Q,ZB,XB,YA), (R1N,R2Q,ZB,XB,YA), (R1O,R2Q,ZB,XB,YA), (R1P,R2Q,ZB,XB,YA), (R1Q,R2Q,ZB,XB,YA), (R1A,R2A,ZC,XB,YA), (R1B,R2A,ZC,XB,YA), (R1C,R2A,ZC,XB,YA), (R1D,R2A,ZC,XB,YA), (R1E,R2A,ZC,XB,YA), (R1F,R2A,ZC,XB,YA), (R1G,R2A,ZC,XB,YA), (R1H,R2A,ZC,XB,YA), (R1I,R2A,ZC,XB,YA), (R1J,R2A,ZC,XB,YA), (R1K,R2A,ZC,XB,YA), (R1L,R2A,ZC,XB,YA), (R1M,R2A,ZC,XB,YA), (R1N,R2A,ZC,XB,YA), (R1O,R2A,ZC,XB,YA), (R1P,R2A,ZC,XB,YA), (R1Q,R2A,ZC,XB,YA), (R1A,R2B,ZC,XB,YA), (R1B,R2B,ZC,XB,YA), (R1C,R2B,ZC,XB,YA), (R1D,R2B,ZC,XB,YA), (R1E,R2B,ZC,XB,YA), (R1F,R2B,ZC,XB,YA), (R1G,R2B,ZC,XB,YA), (R1H,R2B,ZC,XB,YA), (R1I,R2B,ZC,XB,YA), (R1J,R2B,ZC,XB,YA), (R1K,R2B,ZC,XB,YA), (R1L,R2B,ZC,XB,YA), (R1M,R2B,ZC,XB,YA), (R1N,R2B,ZC,XB,YA), (R1O,R2B,ZC,XB,YA), (R1P,R2B,ZC,XB,YA), (R1Q,R2B,ZC,XB,YA), (R1A,R2C,ZC,XB,YA), (R1B,R2C,ZC,XB,YA), (R1C,R2C,ZC,XB,YA), (R1D,R2C,ZC,XB,YA), (R1E,R2C,ZC,XB,YA), (R1F,R2C,ZC,XB,YA), (R1G,R2C,ZC,XB,YA), (R1H,R2C,ZC,XB,YA), (R1I,R2C,ZC,XB,YA), (R1J,R2C,ZC,XB,YA), (R1K,R2C,ZC,XB,YA), (R1L,R2C,ZC,XB,YA), (R1M,R2C,ZC,XB,YA), (R1N,R2C,ZC,XB,YA), (R1O,R22C,ZC,XB,YA), (R1P,R2C,ZC,XB,YA), (R1Q,R2C,ZC,XB,YA), (R1A,R2D,ZC,XB,YA), (R1B,R2D,ZC,XB,YA), (R1C,R2D,ZC,XB,YA), (R1D,R2D,ZC,XB,YA), (R1E,R2D,ZC,XB,YA), (R1F,R2D,ZC,XB,YA), (R1G,R2D,ZC,XB,YA), (R1H,R2D,ZC,XB,YA), (R1I,R2D,ZC,XB,YA), (R1J,R2D,ZC,XB,YA), (R1K,R2D,ZC,XB,YA), (R1L,R2D,ZC,XB,YA), (R1M,R2D,ZC,XB,YA), (R1N,R2D,ZC,XB,YA), (R1O,R2D,ZC,XB,YA), (R1P,R2D,ZC,XB,YA), (R1Q,R2D,ZC,XB,YA), (R1A,R2E,ZC,XB,YA), (R1B,R2E,ZC,XB,YA), (R1C,R2E,ZC,XB,YA), (R1D,R2E,ZC,XB,YA), (R1E,R2E,ZC,XB,YA), (R1F,R2E,ZC,XB,YA), (R1G,R2E,ZC,XB,YA), (R1H,R2E,ZC,XB,YA), (R1I,R2E,ZC,XB,YA), (R1J,R2E,ZC,XB,YA), (R1K,R2E,ZC,XB,YA), (R1L,R2E,ZC,XB,YA), (R1M,R2E,ZC,XB,YA), (R1N,R2E,ZC,XB,YA), (R1O,R2E,ZC,XB,YA), (R1P,R2E,ZC,XB,YA), (R1Q,R2E,ZC,XB,YA), (R1A,R2F,ZC,XB,YA), (R1B,R2F,ZC,XB,YA), (R1C,R2F,ZC,XB,YA), (R1D,R2F,ZC,XB,YA), (R1E,R2F,ZC,XB,YA), (R1F,R2F,ZC,XB,YA), (R1G,R2F,ZC,XB,YA), (R1H,R2F,ZC,XB,YA), (R1I,R2F,ZC,XB,YA), (R1J,R2F,ZC,XB,YA), (R1K,R2F,ZC,XB,YA), (R1L,R2F,ZC,XB,YA), (R1M,R2F,ZC,XB,YA), (R1N,R2F,ZC,XB,YA), (R1 O,R2F,ZC,XB,YA), (R1P,R2F,ZC,XB,YA), (R1Q,R2F,ZC,XB,YA), (R1A,R2G,ZC,XB,YA), (R1B,R2G,ZC,XB,YA), (R1C,R2G,ZC,XB,YA), (R1D,R2G,ZC,XB,YA), (R1E,R2G,ZC,XB,YA), (R1F,R2G,ZC,XB,YA), (R1G,R2G,ZC,XB,YA), (R1H,R2G,ZC,XB,YA), (R1I,R2G,ZC,XB,YA), (R1J,R2G,ZC,XB,YA), (R1K,R2G,ZC,XB,YA), (R1L,R2G,ZC,XB,YA), (R1M,R2G,ZC,XB,YA), (R1N,R2G,ZC,XB,YA), (R1O,R2G,ZC,XB,YA), (R1P,R2G,ZC,XB,YA), (R1Q,R2G,ZC,XB,YA), (R1A,R2H,ZC,XB,YA), (R1B,R2H,ZC,XB,YA), (R1C,R2H,ZC,XB,YA), (R1D,R2H,ZC,XB,YA), (R1E,R2H,ZC,XB,YA), (R1F,R2H,ZC,XB,YA), (R1G,R2H,ZC,XB,YA), (R1H,R2H,ZC,XB,YA), (R1I,R2H,ZC,XB,YA), (R1J,R2H,ZC,XB,YA), (R1K,R2H,ZC,XB,YA), (R1L,R2H,ZC,XB,YA), (R1M,R2H,ZC,XB,YA), (R1N,R2H,ZC,XB,YA), (R1O,R2H,ZC,XB,YA), (R1P,R2H,ZC,XB,YA), (R1Q,R2H,ZC,XB,YA), (R1A,R2I,ZC,XB,YA), (R1B,R2I,ZC,XB,YA), (R1C,R2I,ZC,XB,YA), (R1D,R2I,ZC,XB,YA), (R1E,R2I,ZC,XB,YA), (R1F,R2I,ZC,XB,YA), (R1G,R2I,ZC,XB,YA), (R1H,R2I,ZC,XB,YA), (R1I,R2I,ZC,XB,YA), (R1J,R2I,ZC,XB,YA), (R1K,R2I,ZC,XB,YA), (R1L,R2I,ZC,XB,YA), (R1M,R2I,ZC,XB,YA), (R1N,R2I,ZC,XB,YA), (R1O,R2I,ZC,XB,YA), (R1P,R2I,ZC,XB,YA), (R1Q,R2I,ZC,XB,YA), (R1A,R2J,ZC,XB,YA), (R1B,R2J,ZC,XB,YA), (R1C,R2J,ZC,XB,YA), (R1D,R2J,ZC,XB,YA), (R1E,R2J,ZC,XB,YA), (R1F,R2J,ZC,XB,YA), (R1G,R2J,ZC,XB,YA), (R1H,R2J,ZC,XB,YA), (R1I,R2J,ZC,XB,YA), (R1J,R2J,ZC,XB,YA), (R1K,R2J,ZC,XB,YA), (R1L,R2J,ZC,XB,YA), (R1M,R2J,ZC,XB,YA), (R1N,R2J,ZC,XB,YA), (R1O,R2J,ZC,XB,YA), (R1P,R2J,ZC,XB,YA), (R1Q,R2J,ZC,XB,YA), (R1A,R2K,ZC,XB,YA), (R1B,R2K,ZC,XB,YA), (R1C,R2K,ZC,XB,YA), (R1D,R2K,ZC,XB,YA), (R1E,R2K,ZC,XB,YA), (R1F,R2K,ZC,XB,YA), (R1G,R2K,ZC,XB,YA), (R1H,R2K,ZC,XB,YA), (R1I,R2K,ZC,XB,YA), (R1J,R2K,ZC,XB,YA), (R1K,R2K,ZC,XB,YA), (R1L,R2K,ZC,XB,YA), (R1M,R2K,ZC,XB,YA), (R1N,R2K,ZC,XB,YA), (R1O,R2K,ZC,XB,YA), (R1P,R2K,ZC,XB,YA), (R1Q,R2K,ZC,XB,YA), (R1A,R2L,ZC,XB,YA), (R1B,R2L,ZC,XB,YA), (R1C,R2L,ZC,XB,YA), (R1D,R2L,ZC,XB,YA), (R1E,R2L,ZC,XB,YA), (R1F,R2L,ZC,XB,YA), (R1G,R2L,ZC,XB,YA), (R1H,R2L,ZC,XB,YA), (R1I,R2L,ZC,XB,YA), (R1J,R2L,ZC,XB,YA), (R1K,R2L,ZC,XB,YA), (R1L,R2L,ZC,XB,YA), (R1M,R2L,ZC,XB,YA), (R1N,R2L,ZC,XB,YA), (R1O,R2L,ZC,XB,YA), (R1P,R2L,ZC,XB,YA), (R1Q,R2L,ZC,XB,YA), (R1A,R2M,ZC,XB,YA), (R1B,R2M,ZC,XB,YA), (R1C,R2M,ZC,XB,YA), (R1D,R2M,ZC,XB,YA), (R1E,R2M,ZC,XB,YA), (R1F,R2M,ZC,XB,YA), (R1G,R2M,ZC,XB,YA), (R1H,R2M,ZC,XB,YA), (R1I,R2M,ZC,XB,YA), (R1J,R2M,ZC,XB,YA), (R1K,R2M,ZC,XB,YA), (R1L,R2M,ZC,XB,YA), (R1M,R2M,ZC,XB,YA), (R1N,R2M,ZC,XB,YA), (R1O,R2M,ZC,XB,YA), (R1P,R2M,ZC,XB,YA), (R1Q,R2M,ZC,XB,YA), (R1A,R2N,ZC,XB,YA), (R1B,R2N,ZC,XB,YA), (R1C,R2N,ZC,XB,YA), (R1D,R2N,ZC,XB,YA), (R1E,R2N,ZC,XB,YA), (R1F,R2N,ZC,XB,YA), (R1G,R2N,ZC,XB,YA), (R1H,R2N,ZC,XB,YA), (R1I,R2N,ZC,XB,YA), (R1J,R2N,ZC,XB,YA), (R1K,R2N,ZC,XB,YA), (R1L,R2N,ZC,XB,YA), (R1M,R2N,ZC,XB,YA), (R1N,R2N,ZC,XB,YA), (R1O,R2N,ZC,XB,YA), (R1P,R2N,ZC,XB,YA), (R1Q,R2N,ZC,XB,YA), (R1A,R2O,ZC,XB,YA), (R1B,R2O,ZC,XB,YA), (R1C,R2O,ZC,XB,YA), (R1D,R2O,ZC,XB,YA), (R1E,R2O,ZC,XB,YA), (R1F,R2O,ZC,XB,YA), (R1G,R2O, ZC,XB,YA), (R1H,R2O,ZC,XB,YA), (R1I,R2O,ZC,XB, YA), (R1J,R2O,ZC,XB,YA), (R1K,R2O,ZC,XB,YA), (R1L, R2O,ZC,XB,YA), (R1M,R2O,ZC,XB,YA), (R1N,R2O,ZC, XB,YA), (R1O,R2O,ZC,XB,YA), (R1P,R2O,ZC,XB,YA), (R1Q,R2O,ZC,XB,YA), (R1A,R2P,ZC,XB,YA), (R1B,R2P, ZC,XB,YA), (R1C,R2P,ZC,XB,YA), (R1D,R2P,ZC,XB, YA), (R1E,R2P,ZC,XB,YA), (R1F,R2P,ZC,XB,YA), (R1G, R2P,ZC,XB,YA), (R1H,R2P,ZC,XB,YA), (R1I,R2P,ZC,XB, YA), (R1J,R2P,ZC,XB,YA), (R1K,R2P,ZC,XB,YA), (R1L, R2P,ZC,XB,YA), (R1M,R2P,ZC,XB,YA), (R1N,R2P,ZC, XB,YA), (R1O,R2P,ZC,XB,YA), (R1P,R2P,ZC,XB,YA), (R1Q,R2P,ZC,XB,YA), (R1A,R2Q,ZC,XB,YA), (R1B,R2Q, ZC,XB,YA), (R1C,R2Q,ZC,XB,YA), (R1D,R2Q,ZC,XB, YA), (R1E,R2Q,ZC,XB,YA), (R1F,R2Q,ZC,XB,YA), (R1G, R2Q,ZC,XB,YA), (R1H,R2Q,ZC,XB,YA), (R1I,R2Q,ZC, XB,YA), (R1J,R2Q,ZC,XB,YA), (R1K,R2Q,ZC,XB,YA), (R1L,R2Q,ZC,XB,YA), (R1M,R2Q,ZC,XB,YA), (R1N, R2Q,ZC,XB,YA), (R1O,R2Q,ZC,XB,YA), (R1P,R2Q,ZC, XB,YA), (R1Q,R2Q,ZC,XB,YA), (R1A,R2A,ZD,XB,YA), (R1B,R2A,ZD,XB,YA), (R1C,R2A,ZD,XB,YA), (R1D, R2A,ZD,XB,YA), (R1E,R2A,ZD,XB,YA), (R1F,R2A,ZD, XB,YA), (R1G,R2A,ZD,XB,YA), (R1H,R2A,ZD,XB,YA), (R1I,R2A,ZD,XB,YA), (R1J,R2A,ZD,XB,YA), (R1K,R2A, ZD,XB,YA), (R1L,R2A,ZD,XB,YA), (R1M,R2A,ZD,XB, YA), (R1N,R2A,ZD,XB,YA), (R1O,R2A,ZD,XB,YA), (R1P,R2A,ZD,XB,YA), (R1Q,R2A,ZD,XB,YA), (R1A, R2B,ZD,XB,YA), (R1B,R2B,ZD,XB,YA), (R1C,R2B,ZD, XB,YA), (R1D,R2B,ZD,XB,YA), (R1E,R2B,ZD,XB,YA), (R1F,R2B,ZD,XB,YA), (R1G,R2B,ZD,XB,YA), (R1H,R2B, ZD,XB,YA), (R1I,R2B,ZD,XB,YA), (R1J,R2B,ZD,XB, YA), (R1K,R2B,ZD,XB,YA), (R1L,R2B,ZD,XB,YA), (R1M,R2B,ZD,XB,YA), (R1N,R2B,ZD,XB,YA), (R1O, R2B,ZD,XB,YA), (R1P,R2B,ZD,XB,YA), (R1Q,R2B,ZD, XB,YA), (R1A,R2C,ZD,XB,YA), (R1B,R2C,ZD,XB,YA), (R1C,R2C,ZD,XB,YA), (R1D,R2C,ZD,XB,YA), (R1E, R2C,ZD,XB,YA), (R1F,R2C,ZD,XB,YA), (R1G,R2C,ZD, XB,YA), (R1H,R2C,ZD,XB,YA), (R1I,R2C,ZD,XB,YA), (R1J,R2C,ZD,XB,YA), (R1K,R2C,ZD,XB,YA), (R1L,R2C, ZD,XB,YA), (R1M,R2C,ZD,XB,YA), (R1N,R2C,ZD,XB, YA), (R1O,R22C,ZD,XB,YA), (R1P,R2C,ZD,XB,YA), (R1Q,R2C,ZD,XB,YA), (R1A,R2D,ZD,XB,YA), (R1B, R2D,ZD,XB,YA), (R1C,R2D,ZD,XB,YA), (R1D,R2D,ZD, XB,YA), (R1E,R2D,ZD,XB,YA), (R1F,R2D,ZD,XB,YA), (R1G,R2D,ZD,XB,YA), (R1H,R2D,ZD,XB,YA), (R1I,R2D, ZD,XB,YA), (R1J,R2D,ZD,XB,YA), (R1K,R2D,ZD,XB, YA), (R1L,R2D,ZD,XB,YA), (R1M,R2D,ZD,XB,YA), (R1N,R2D,ZD,XB,YA), (R1O,R2D,ZD,XB,YA), (R1P, R2D,ZD,XB,YA), (R1Q,R2D,ZD,XB,YA), (R1A,R2E,ZD, XB,YA), (R1B,R2E,ZD,XB,YA), (R1C,R2E,ZD,XB,YA), (R1D,R2E,ZD,XB,YA), (R1E,R2E,ZD,XB,YA), (R1F,R2E, ZD,XB,YA), (R1G,R2E,ZD,XB,YA), (R1H,R2E,ZD,XB, YA), (R1I,R2E,ZD,XB,YA), (R1J,R2E,ZD,XB,YA), (R1K, R2E,ZD,XB,YA), (R1L,R2E,ZD,XB,YA), (R1M,R2E,ZD, XB,YA), (R1N,R2E,ZD,XB,YA), (R1O,R2E,ZD,XB,YA), (R1P,R2E,ZD,XB,YA), (R1Q,R2E,ZD,XB,YA), (R1A,R2F, ZD,XB,YA), (R1B,R2F,ZD,XB,YA), (R1C,R2F,ZD,XB, YA), (R1D,R2F,ZD,XB,YA), (R1E,R2F,ZD,XB,YA), (R1F, R2F,ZD,XB,YA), (R1G,R2F,ZD,XB,YA), (R1H,R2F,ZD, XB,YA), (R1I,R2F,ZD,XB,YA), (R1J,R2F,ZD,XB,YA), (R1K,R2F,ZD,XB,YA), (R1L,R2F,ZD,XB,YA), (R1M,R2F, ZD,XB,YA), (R1N,R2F,ZD,XB,YA), (R1O,R2F,ZD,XB, YA), (R1P,R2F,ZD,XB,YA), (R1Q,R2F,ZD,XB,YA), (R1A, R2G,ZD,XB,YA), (R1B,R2G,ZD,XB,YA), (R1C,R2G,ZD, XB,YA), (R1D,R2G,ZD,XB,YA), (R1E,R2G,ZD,XB,YA), (R1F,R2G,ZD,XB,YA), (R1G,R2G,ZD,XB,YA), (R1H, R2G,ZD,XB,YA), (R1I,R2G,ZD,XB,YA), (R1J,R2G,ZD, XB,YA), (R1K,R2G,ZD,XB,YA), (R1L,R2G,ZD,XB,YA), (R1M,R2G,ZD,XB,YA), (R1N,R2G,ZD,XB,YA), (R1O, R2G,ZD,XB,YA), (R1P,R2G,ZD,XB,YA), (R1Q,R2G,ZD, XB,YA), (R1A,R2H,ZD,XB,YA), (R1B,R2H,ZD,XB,YA), (R1C,R2H,ZD,XB,YA), (R1D,R2H,ZD,XB,YA), (R1E, R2H,ZD,XB,YA), (R1F,R2H,ZD,XB,YA), (R1G,R2H,ZD, XB,YA), (R1H,R2H,ZD,XB,YA), (R1I,R2H,ZD,XB,YA), (R1J,R2H,ZD,XB,YA), (R1K,R2H,ZD,XB,YA), (R1L,R2H, ZD,XB,YA), (R1M,R2H,ZD,XB,YA), (R1N,R2H,ZD,XB, YA), (R1O,R2H,ZD,XB,YA), (R1P,R2H,ZD,XB,YA), (R1Q,R2H,ZD,XB,YA), (R1A,R2I,ZD,XB,YA), (R1B,R2I, ZD,XB,YA), (R1C,R2I,ZD,XB,YA), (R1D,R2I,ZD,XB, YA), (R1E,R2I,ZD,XB,YA), (R1F,R2I,ZD,XB,YA), (R1G, R2I,ZD,XB,YA), (R1H,R2I,ZD,XB,YA), (R1I,R2I,ZD,XB, YA), (R1J,R2I,ZD,XB,YA), (R1K,R2I,ZD,XB,YA), (R1L, R2I,ZD,XB,YA), (R1M,R2I,ZD,XB,YA), (R1N,R2I,ZD, XB,YA), (R1O,R2I,ZD,XB,YA), (R1P,R2I,ZD,XB,YA), (R1Q,R2I,ZD,XB,YA), (R1A,R2J,ZD,XB,YA), (R1B,R2J, ZD,XB,YA), (R1C,R2J,ZD,XB,YA), (R1D,R2J,ZD,XB, YA), (R1E,R2J,ZD,XB,YA), (R1F,R2J,ZD,XB,YA), (R1G, R2J,ZD,XB,YA), (R1H,R2J,ZD,XB,YA), (R1I,R2J,ZD,XB, YA), (R1J,R2J,ZD,XB,YA), (R1K,R2J,ZD,XB,YA), (R1L, R2J,ZD,XB,YA), (R1M,R2J,ZD,XB,YA), (R1N,R2J,ZD, XB,YA), (R1O,R2J,ZD,XB,YA), (R1P,R2J,ZD,XB,YA), (R1Q,R2J,ZD,XB,YA), (R1A,R2K,ZD,XB,YA), (R1B,R2K, ZD,XB,YA), (R1C,R2K,ZD,XB,YA), (R1D,R2K,ZD,XB, YA), (R1E,R2K,ZD,XB,YA), (R1F,R2K,ZD,XB,YA), (R1G, R2K,ZD,XB,YA), (R1H,R2K,ZD,XB,YA), (R1I,R2K,ZD, XB,YA), (R1J,R2K,ZD,XB,YA), (R1K,R2K,ZD,XB,YA), (R1L,R2K,ZD,XB,YA), (R1M,R2K,ZD,XB,YA), (R1N, R2K,ZD,XB,YA), (R1O,R2K,ZD,XB,YA), (R1P,R2K,ZD, XB,YA), (R1Q,R2K,ZD,XB,YA), (R1A,R2L,ZD,XB,YA), (R1B,R2L,ZD,XB,YA), (R1C,R2L,ZD,XB,YA), (R1D,R2L, ZD,XB,YA), (R1E,R2L,ZD,XB,YA), (R1F,R2L,ZD,XB, YA), (R1G,R2L,ZD,XB,YA), (R1H,R2L,ZD,XB,YA), (R1I, R2L,ZD,XB,YA), (R1J,R2L,ZD,XB,YA), (R1K,R2L,ZD, XB,YA), (R1L,R2L,ZD,XB,YA), (R1M,R2L,ZD,XB,YA), (R1N,R2L,ZD,XB,YA), (R1O,R2L,ZD,XB,YA), (R1P,R2L, ZD,XB,YA), (R1Q,R2L,ZD,XB,YA), (R1A,R2M,ZD,XB, YA), (R1B,R2M,ZD,XB,YA), (R1C,R2M,ZD,XB,YA), (R1D,R2M,ZD,XB,YA), (R1E,R2M,ZD,XB,YA), (R1F, R2M,ZD,XB,YA), (R1G,R2M,ZD,XB,YA), (R1H,R2M,ZD, XB,YA), (R1I,R2M,ZD,XB,YA), (R1J,R2M,ZD,XB,YA), (R1K,R2M,ZD,XB,YA), (R1L,R2M,ZD,XB,YA), (R1M, R2M,ZD,XB,YA), (R1N,R2M,ZD,XB,YA), (R1O,R2M,ZD, XB,YA), (R1P,R2M,ZD,XB,YA), (R1Q,R2M,ZD,XB,YA), (R1A,R2N,ZD,XB,YA), (R1B,R2N,ZD,XB,YA), (R1C, R2N,ZD,XB,YA), (R1D,R2N,ZD,XB,YA), (R1E,R2N,ZD, XB,YA), (R1F,R2N,ZD,XB,YA), (R1G,R2N,ZD,XB,YA), (R1H,R2N,ZD,XB,YA), (R1I,R2N,ZD,XB,YA), (R1J,R2N, ZD,XB,YA), (R1K,R2N,ZD,XB,YA), (R1L,R2N,ZD,XB, YA), (R1M,R2N,ZD,XB,YA), (R1N,R2N,ZD,XB,YA), (R1O,R2N,ZD,XB,YA), (R1P,R2N,ZD,XB,YA), (R1Q, R2N,ZD,XB,YA), (R1A,R2O,ZD,XB,YA), (R1B,R2O,ZD, XB,YA), (R1C,R2O,ZD,XB,YA), (R1D,R2O,ZD,XB,YA), (R1E,R2O,ZD,XB,YA), (R1F,R2O,ZD,XB,YA), (R1G, R2O,ZD,XB,YA), (R1H,R2O,ZD,XB,YA), (R1I,R2O,ZD, XB,YA), (R1J,R2O,ZD,XB,YA), (R1K,R2O,ZD,XB,YA), (R1L,R2O,ZD,XB,YA), (R1M,R2O,ZD,XB,YA), (R1N, R2O,ZD,XB,YA), (R1O,R2O,ZD,XB,YA), (R1P,R2O,ZD, XB,YA), (R1Q,R2O,ZD,XB,YA), (R1A,R2P,ZD,XB,YA), (R1B,R2P,ZD,XB,YA), (R1C,R2P,ZD,XB,YA), (R1D,R2P, ZD,XB,YA), (R1E,R2P,ZD,XB,YA), (R1F,R2P,ZD,XB,YA), (R1G,R2P,ZD,XB,YA), (R1H,R2P,ZD,XB,YA), (R1I,R2P, ZD,XB,YA), (R1J,R2P,ZD,XB,YA), (R1K,R2P,ZD,XB, YA), (R1L,R2P,ZD,XB,YA), (R1M,R2P,ZD,XB,YA), (R1N, R2P,ZD,XB,YA), (R1O,R2P,ZD,XB,YA), (R1P,R2P,ZD, XB,YA), (R1Q,R2P,ZD,XB,YA), (R1A,R2Q,ZD,XB,YA), (R1B,R2Q,ZD,XB,YA), (R1C,R2Q,ZD,XB,YA), (R1D,R2Q,ZD,XB,YA), (R1E,R2Q,ZD,XB,YA), (R1F,R2Q,ZD,XB,YA), (R1G,R2Q,ZD,XB,YA), (R1H,R2Q,ZD,XB,YA), (R1I,R2Q,ZD,XB,YA), (R1J,R2Q,ZD,XB,YA), (R1K,R2Q,ZD,XB,YA), (R1L,R2Q,ZD,XB,YA), (R1M,R2Q,ZD,XB,YA), (R1N,R2Q,ZD,XB,YA), (R1O,R2Q,ZD,XB,YA), (R1P,R2Q,ZD,XB,YA), (R1Q,R2Q,ZD,XB,YA), (R1A,R2A,ZE,XB,YA), (R1B,R2A,ZE,XB,YA), (R1C,R2A,ZE,XB,YA), (R1D,R2A,ZE,XB,YA), (R1E,R2A,ZE,XB,YA), (R1F,R2A,ZE,XB,YA), (R1G,R2A,ZE,XB,YA), (R1H,R2A,ZE,XB,YA), (R1I,R2A,ZE,XB,YA), (R1J,R2A,ZE,XB,YA), (R1K,R2A,ZE,XB,YA), (R1L,R2A,ZE,XB,YA), (R1M,R2A,ZE,XB,YA), (R1N,R2A,ZE,XB,YA), (R1O,R2A,ZE,XB,YA), (R1P,R2A,ZE,XB,YA), (R1Q,R2A,ZE,XB,YA), (R1A,R2B,ZE,XB,YA), (R1B,R2B,ZE,XB,YA), (R1C,R2B,ZE,XB,YA), (R1D,R2B,ZE,XB,YA), (R1E,R2B,ZE,XB,YA), (R1F,R2B,ZE,XB,YA), (R1G,R2B,ZE,XB,YA), (R1H,R2B,ZE,XB,YA), (R1I,R2B,ZE,XB,YA), (R1J,R2B,ZE,XB,YA), (R1K,R2B,ZE,XB,YA), (R1L,R2B,ZE,XB,YA), (R1M,R2B,ZE,XB,YA), (R1N,R2B,ZE,XB,YA), (R1O,R2B,ZE,XB,YA), (R1P,R2B,ZE,XB,YA), (R1Q,R2B,ZE,XB,YA), (R1A,R2C,ZE,XB,YA), (R1B,R2C,ZE,XB,YA), (R1C,R2C,ZE,XB,YA), (R1D,R2C,ZE,XB,YA), (R1E,R2C,ZE,XB,YA), (R1F,R2C,ZE,XB,YA), (R1G,R2C,ZE,XB,YA), (R1H,R2C,ZE,XB,YA), (R1I,R2C,ZE,XB,YA), (R1J,R2C,ZE,XB,YA), (R1K,R2C,ZE,XB,YA), (R1L,R2C,ZE,XB,YA), (R1M,R2C,ZE,XB,YA), (R1N,R2C,ZE,XB,YA), (R1O,R2C,ZE,XB,YA), (R1P,R2C,ZE,XB,YA), (R1Q,R2C,ZE,XB,YA), (R1A,R2D,ZE,XB,YA), (R1B,R2D,ZE,XB,YA), (R1C,R2D,ZE,XB,YA), (R1D,R2D,ZE,XB,YA), (R1E,R2D,ZE,XB,YA), (R1F,R2D,ZE,XB,YA), (R1G,R2D,ZE,XB,YA), (R1H,R2D,ZE,XB,YA), (R1I,R2D,ZE,XB,YA), (R1J,R2D,ZE,XB,YA), (R1K,R2D,ZE,XB,YA), (R1L,R2D,ZE,XB,YA), (R1M,R2D,ZE,XB,YA), (R1N,R2D,ZE,XB,YA), (R1O,R2D,ZE,XB,YA), (R1P,R2D,ZE,XB,YA), (R1Q,R2D,ZE,XB,YA), (R1A,R2E,ZE,XB,YA), (R1B,R2E,ZE,XB,YA), (R1C,R2E,ZE,XB,YA), (R1D,R2E,ZE,XB,YA), (R1E,R2E,ZE,XB,YA), (R1F,R2E,ZE,XB,YA), (R1G,R2E,ZE,XB,YA), (R1H,R2E,ZE,XB,YA), (R1I,R2E,ZE,XB,YA), (R1J,R2E,ZE,XB,YA), (R1K,R2E,ZE,XB,YA), (R1L,R2E,ZE,XB,YA), (R1M,R2E,ZE,XB,YA), (R1N,R2E,ZE,XB,YA), (R1O,R2E,ZE,XB,YA), (R1P,R2E,ZE,XB,YA), (R1Q,R2E,ZE,XB,YA), (R1A,R2F,ZE,XB,YA), (R1B,R2F,ZE,XB,YA), (R1C,R2F,ZE,XB,YA), (R1D,R2F,ZE,XB,YA), (R1E,R2F,ZE,XB,YA), (R1F,R2F,ZE,XB,YA), (R1G,R2F,ZE,XB,YA), (R1H,R2F,ZE,XB,YA), (R1I,R2F,ZE,XB,YA), (R1J,R2F,ZE,XB,YA), (R1K,R2F,ZE,XB,YA), (R1L,R2F,ZE,XB,YA), (R1M,R2F,ZE,XB,YA), (R1N,R2F,ZE,XB,YA), (R1O,R2F,ZE,XB,YA), (R1P,R2F,ZE,XB,YA), (R1Q,R2F,ZE,XB,YA), (R1A,R2G,ZE,XB,YA), (R1B,R2G,ZE,XB,YA), (R1C,R2G,ZE,XB,YA), (R1D,R2G,ZE,XB,YA), (R1E,R2G,ZE,XB,YA), (R1F,R2G,ZE,XB,YA), (R1G,R2G,ZE,XB,YA), (R1H,R2G,ZE,XB,YA), (R1I,R2G,ZE,XB,YA), (R1J,R2G,ZE,XB,YA), (R1K,R2G,ZE,XB,YA), (R1L,R2G,ZE,XB,YA), (R1M,R2G,ZE,XB,YA), (R1N,R2G,ZE,XB,YA), (R1O,R2G,ZE,XB,YA), (R1P,R2G,ZE,XB,YA), (R1Q,R2G,ZE,XB,YA), (R1A,R2H,ZE,XB,YA), (R1B,R2H,ZE,XB,YA), (R1C,R2H,ZE,XB,YA), (R1D,R2H,ZE,XB,YA), (R1E,R2H,ZE,XB,YA), (R1F,R2H,ZE,XB,YA), (R1G,R2H,ZE,XB,YA), (R1H,R2H,ZE,XB,YA), (R1I,R2H,ZE,XB,YA), (R1J,R2H,ZE,XB,YA), (R1K,R2H,ZE,XB,YA), (R1L,R2H,ZE,XB,YA), (R1M,R2H,ZE,XB,YA), (R1N,R2H,ZE,XB,YA), (R1O,R2H,ZE,XB,YA), (R1P,R2H,ZE,XB,YA), (R1Q,R2H,ZE,XB,YA), (R1A,R2I,ZE,XB,YA), (R1B,R2I,ZE,XB,YA), (R1C,R2I,ZE,XB,YA), (R1D,R2I,ZE,XB,YA), (R1E,R2I,ZE,XB,YA), (R1F,R2I,ZE,XB,YA), (R1G,R2I,ZE,XB,YA), (R1H,R2I,ZE,XB,YA), (R1I,R2I,ZE,XB,YA), (R1J,R2I,ZE,XB,YA), (R1K,R2I,ZE,XB,YA), (R1L,R2I,ZE,XB,YA), (R1M,R2I,ZE,XB,YA), (R1N,R2I,ZE,XB,YA), (R1O,R2I,ZE,XB,YA), (R1P,R2I,ZE,XB,YA), (R1Q,R2I,ZE,XB,YA), (R1A,R2J,ZE,XB,YA), (R1B,R2J,ZE,XB,YA), (R1C,R2J,ZE,XB,YA), (R1D,R2J,ZE,XB,YA), (R1E,R2J,ZE,XB,YA), (R1F,R2J,ZE,XB,YA), (R1G,R2J,ZE,XB,YA), (R1H,R2J,ZE,XB,YA), (R1I,R2J,ZE,XB,YA), (R1J,R2J,ZE,XB,YA), (R1K,R2J,ZE,XB,YA), (R1L,R2J,ZE,XB,YA), (R1M,R2J,ZE,XB,YA), (R1N,R2J,ZE,XB,YA), (R1O,R2J,ZE,XB,YA), (R1P,R2J,ZE,XB,YA), (R1Q,R2J,ZE,XB,YA), (R1A,R2K,ZE,XB,YA), (R1B,R2K,ZE,XB,YA), (R1C,R2K,ZE,XB,YA), (R1D,R2K,ZE,XB,YA), (R1E,R2K,ZE,XB,YA), (R1F,R2K,ZE,XB,YA), (R1G,R2K,ZE,XB,YA), (R1H,R2K,ZE,XB,YA), (R1I,R2K,ZE,XB,YA), (R1J,R2K,ZE,XB,YA), (R1K,R2K,ZE,XB,YA), (R1L,R2K,ZE,XB,YA), (R1M,R2K,ZE,XB,YA), (R1N,R2K,ZE,XB,YA), (R1O,R2K,ZE,XB,YA), (R1P,R2K,ZE,XB,YA), (R1Q,R2K,ZE,XB,YA), (R1A,R2L,ZE,XB,YA), (R1B,R2L,ZE,XB,YA), (R1C,R2L,ZE,XB,YA), (R1D,R2L,ZE,XB,YA), (R1E,R2L,ZE,XB,YA), (R1F,R2L,ZE,XB,YA), (R1G,R2L,ZE,XB,YA), (R1H,R2L,ZE,XB,YA), (R1I,R2L,ZE,XB,YA), (R1J,R2L,ZE,XB,YA), (R1K,R2L,ZE,XB,YA), (R1L,R2L,ZE,XB,YA), (R1M,R2L,ZE,XB,YA), (R1N,R2L,ZE,XB,YA), (R1O,R2L,ZE,XB,YA), (R1P,R2L,ZE,XB,YA), (R1Q,R2L,ZE,XB,YA), (R1A,R2M,ZE,XB,YA), (R1B,R2M,ZE,XB,YA), (R1C,R2M,ZE,XB,YA), (R1D,R2M,ZE,XB,YA), (R1E,R2M,ZE,XB,YA), (R1F,R2M,ZE,XB,YA), (R1G,R2M,ZE,XB,YA), (R1H,R2M,ZE,XB,YA), (R1I,R2M,ZE,XB,YA), (R1J,R2M,ZE,XB,YA), (R1K,R2M,ZE,XB,YA), (R1L,R2M,ZE,XB,YA), (R1M,R2M,ZE,XB,YA), (R1N,R2M,ZE,XB,YA), (R1O,R2M,ZE,XB,YA), (R1P,R2M,ZE,XB,YA), (R1Q,R2M,ZE,XB,YA), (R1A,R2N,ZE,XB,YA), (R1B,R2N,ZE,XB,YA), (R1C,R2N,ZE,XB,YA), (R1D,R2N,ZE,XB,YA), (R1E,R2N,ZE,XB,YA), (R1F,R2N,ZE,XB,YA), (R1G,R2N,ZE,XB,YA), (R1H,R2N,ZE,XB,YA), (R1I,R2N,ZE,XB,YA), (R1J,R2N,ZE,XB,YA), (R1K,R2N,ZE,XB,YA), (R1L,R2N,ZE,XB,YA), (R1M,R2N,ZE,XB,YA), (R1N,R2N,ZE,XB,YA), (R1O,R2N,ZE,XB,YA), (R1P,R2N,ZE,XB,YA), (R1Q,R2N,ZE,XB,YA), (R1A,R2O,ZE,XB,YA), (R1B,R2O,ZE,XB,YA), (R1C,R2O,ZE,XB,YA), (R1D,R2O,ZE,XB,YA), (R1E,R2O,ZE,XB,YA), (R1F,R2O,ZE,XB,YA), (R1G,R2O,ZE,XB,YA), (R1H,R2O,ZE,XB,YA), (R1I,R2O,ZE,XB,YA), (R1J,R2O,ZE,XB,YA), (R1K,R2O,ZE,XB,YA), (R1L,R2O,ZE,XB,YA), (R1M,R2O,ZE,XB,YA), (R1N,R2O,ZE,XB,YA), (R1O,R2O,ZE,XB,YA), (R1P,R2O,ZE,XB,YA), (R1Q,R2O,ZE,XB,YA), (R1A,R2P,ZE,XB,YA), (R1B,R2P,ZE,XB,YA), (R1C,R2P,ZE,XB,YA), (R1D,R2P,ZE,XB,YA), (R1E,R2P,ZE,XB,YA), (R1F,R2P,ZE,XB,YA), (R1G,R2P,ZE,XB,YA), (R1H,R2P,ZE,XB,YA), (R1I,R2P,ZE,XB,YA), (R1J,R2P,ZE,XB,YA), (R1K,R2P,ZE,XB,YA), (R1L,R2P,ZE,XB,YA), (R1M,R2P,ZE,XB,YA), (R1N,R2P,ZE,XB,YA), (R1O,R2P,ZE,XB,YA), (R1P,R2P,ZE,XB,YA), (R1Q,R2P,ZE,XB,YA), (R1A,R2Q,ZE,XB,YA), (R1B,R2Q,ZE,XB,YA), (R1C,R2Q,ZE,XB,YA), (R1D,R2Q,ZE,XB,YA), (R1E,R2Q,ZE,XB,YA), (R1F,R2Q,ZE,XB,YA), (R1G,R2Q,ZE,XB,YA), (R1H,R2Q,ZE,XB,YA), (R1I,R2Q,ZE,XB,YA), (R1J,R2Q,ZE,XB,YA), (R1K,R2Q,ZE,XB,YA), (R1L,R2Q,ZE,XB,YA), (R1M,R2Q,ZE,XB,YA), (R1N,R2Q,ZE,XB,YA), (R1O,R2Q,ZE,XB,YA), (R1P,R2Q,ZE,XB,YA), (R1Q,R2Q,ZE,XB,YA), (R1A,R2A,ZF,XB,YA), (R1B,R2A,ZF,XB,YA), (R1C,R2A,ZF,XB,YA), (R1D,R2A,ZF,XB,YA), (R1E,R2A,ZF,XB,YA), (R1F,R2A,ZF,XB,YA), (R1G,R2A,ZF,XB,YA), (R1H,R2A,ZF,XB,YA), (R1I,R2A,ZF,XB,YA), (R1J,R2A,ZF,XB,YA), (R1K,R2A,ZF,XB,YA), (R1L,R2A,ZF,XB,YA), (R1M,R2A,ZF,XB,YA), (R1N,R2A,ZF,XB,YA), (R1O,R2A,ZF,XB,YA), (R1P,R2A,ZF,XB,YA), (R1Q, R2A,ZF,XB,YA), (R1A,R2B,ZF,XB,YA), (R1B,R2B,ZF, XB,YA), (R1C,R2B,ZF,XB,YA), (R1D,R2B,ZF,XB,YA), (R1E,R2B,ZF,XB,YA), (R1F,R2B,ZF,XB,YA), (R1G,R2B, ZF,XB,YA), (R1H,R2B,ZF,XB,YA), (R1I,R2B,ZF,XB,YA), (R1J,R2B,ZF,XB,YA), (R1K,R2B,ZF,XB,YA), (R1L,R2B, ZF,XB,YA), (R1M,R2B,ZF,XB,YA), (R1N,R2B,ZF,XB, YA), (R1O,R2B,ZF,XB,YA), (R1P,R2B,ZF,XB,YA), (R1Q, R2B,ZF,XB,YA), (R1A,R2C,ZF,XB,YA), (R1B,R2C,ZF, XB,YA), (R1C,R22C,ZF,XB,YA), (R1D,R2C,ZF,XB,YA), (R1E,R2C,ZF,XB,YA), (R1F,R2C,ZF,XB,YA), (R1G,R22C, ZF,XB,YA), (R1H,R2C,ZF,XB,YA), (R1I,R2C,ZF,XB,YA), (R1J,R2C,ZF,XB,YA), (R1K,R22C,ZF,XB,YA), (R1L,R2C, ZF,XB,YA), (R1M,R2C,ZF,XB,YA), (R1N,R2C,ZF,XB, YA), (R1 O,R2C,ZF,XB,YA), (R1P,R2C,ZF,XB,YA), (R1Q, R2C,ZF,XB,YA), (R1A,R2D,ZF,XB,YA), (R1B,R2D,ZF, XB,YA), (R1C,R2D,ZF,XB,YA), (R1D,R2D,ZF,XB,YA), (R1E,R2D,ZF,XB,YA), (R1F,R2D,ZF,XB,YA), (R1G,R2D, ZF,XB,YA), (R1H,R2D,ZF,XB,YA), (R1I,R2D,ZF,XB,YA), (R1J,R2D,ZF,XB,YA), (R1K,R2D,ZF,XB,YA), (R1L,R2D, ZF,XB,YA), (R1M,R2D,ZF,XB,YA), (R1N,R2D,ZF,XB, YA), (R1O,R2D,ZF,XB,YA), (R1P,R2D,ZF,XB,YA), (R1Q, R2D,ZF,XB,YA), (R1A,R2E,ZF,XB,YA), (R1B,R2E,ZF, XB,YA), (R1C,R2E,ZF,XB,YA), (R1D,R2E,ZF,XB,YA), (R1E,R2E,ZF,XB,YA), (R1F,R2E,ZF,XB,YA), (R1G,R2E, ZF,XB,YA), (R1H,R2E,ZF,XB,YA), (R1I,R2E,ZF,XB,YA), (R1J,R2E,ZF,XB,YA), (R1K,R2E,ZF,XB,YA), (R1L,R2E, ZF,XB,YA), (R1M,R2E,ZF,XB,YA), (R1N,R2E,ZF,XB, YA), (R1O,R2E,ZF,XB,YA), (R1P,R2E,ZF,XB,YA), (R1Q, R2E,ZF,XB,YA), (R1A,R2F,ZF,XB,YA), (R1B,R2F,ZF, YA), (R1C,R2F,ZF,XB,YA), (R1D,R2F,ZF,XB,YA), (R1E, R2F,ZF,XB,YA), (R1F,R2F,ZF,XB,YA), (R1G,R2F,ZF, YA), (R1H,R2F,ZF,XB,YA), (R1I,R2F,ZF,XB,YA), (R1J, R2F,ZF,XB,YA), (R1K,R2F,ZF,XB,YA), (R1L,R2F,ZF, YA), (R1M,R2F,ZF,XB,YA), (R1N,R2F,ZF,XB,YA), (R1O, R2F,ZF,XB,YA), (R1P,R2F,ZF,XB,YA), (R1Q,R2F,ZF,XB, YA), (R1A,R2G,ZF,XB,YA), (R1B,R2G,ZF,XB,YA), (R1C, R2G,ZF,XB,YA), (R1D,R2G,ZF,XB,YA), (R1E,R2G,ZF, XB,YA), (R1F,R2G,ZF,XB,YA), (R1G,R2G,ZF,XB,YA), (R1H,R2G,ZF,XB,YA), (R1I,R2G,ZF,XB,YA), (R1J,R2G, ZF,XB,YA), (R1K,R2G,ZF,XB,YA), (R1L,R2G,ZF,XB, YA), (R1M,R2G,ZF,XB,YA), (R1N,R2G,ZF,XB,YA), (R1O, R2G,ZF,XB,YA), (R1P,R2G,ZF,XB,YA), (R1Q,R2G,ZF, XB,YA), (R1A,R2H,ZF,XB,YA), (R1B,R2H,ZF,XB,YA), (R1C,R2H,ZF,XB,YA), (R1D,R2H,ZF,XB,YA), (R1E,R2H, ZF,XB,YA), (R1F,R2H,ZF,XB,YA), (R1G,R2H,ZF,XB,YA), (R1H,R2H,ZF,XB,YA), (R1I,R2H,ZF,XB,YA), (R1J,R2H, ZF,XB,YA), (R1K,R2H,ZF,XB,YA), (R1L,R2H,ZF,XB, YA), (R1M,R2H,ZF,XB,YA), (R1N,R2H,ZF,XB,YA), (R1O, R2H,ZF,XB,YA), (R1P,R2H,ZF,XB,YA), (R1Q,R2H,ZF, XB,YA), (R1A,R2I,ZF,XB,YA), (R1B,R2I,ZF,XB,YA), (R1C,R2I,ZF,XB,YA), (R1D,R2I,ZF,XB,YA), (R1E,R2I,ZF, XB,YA), (R1F,R2I,ZF,XB,YA), (R1G,R2I,ZF,XB,YA), (R1H,R2I,ZF,XB,YA), (R1I,R2I,ZF,XB,YA), (R1J,R2I,ZF, XB,YA), (R1K,R2I,ZF,XB,YA), (R1L,R2I,ZF,XB,YA), (R1M,R2I,ZF,XB,YA), (R1N,R2I,ZF,XB,YA), (R1O,R2I, ZF,XB,YA), (R1P,R2I,ZF,XB,YA), (R1Q,R2I,ZF,XB,YA), (R1A,R2J,ZF,XB,YA), (R1B,R2J,ZF,XB,YA), (R1C,R2J, ZF,XB,YA), (R1D,R2J,ZF,XB,YA), (R1E,R2J,ZF,XB,YA), (R1F,R2J,ZF,XB,YA), (R1G,R2J,ZF,XB,YA), (R1H,R2J,ZF, XB,YA), (R1I,R2J,ZF,XB,YA), (R1J,R2J,ZF,XB,YA), (R1K,R2J,ZF,XB,YA), (R1L,R2J,ZF,XB,YA), (R1M,R2J, ZF,XB,YA), (R1N,R2J,ZF,XB,YA), (R1O,R2J,ZF,XB,YA), (R1P,R2J,ZF,XB,YA), (R1Q,R2J,ZF,XB,YA), (R1A,R2K, ZF,XB,YA), (R1B,R2K,ZF,XB,YA), (R1C,R2K,ZF,XB, YA), (R1D,R2K,ZF,XB,YA), (R1E,R2K,ZF,XB,YA), (R1F, R2K,ZF,XB,YA), (R1G,R2K,ZF,XB,YA), (R1H,R2K,ZF, XB,YA), (R1I,R2K,ZF,XB,YA), (R1J,R2K,ZF,XB,YA), (R1K,R2K,ZF,XB,YA), (R1L,R2K,ZF,XB,YA), (R1M,R2K, ZF,XB,YA), (R1N,R2K,ZF,XB,YA), (R1O,R2K,ZF,XB, YA), (R1P,R2K,ZF,XB,YA), (R1Q,R2K,ZF,XB,YA), (R1A, R2L,ZF,XB,YA), (R1B,R2L,ZF,XB,YA), (R1C,R2L,ZF,XB, YA), (R1D,R2L,ZF,XB,YA), (R1E,R2L,ZF,XB,YA), (R1F, R2L,ZF,XB,YA), (R1G,R2L,ZF,XB,YA), (R1H,R2L,ZF, XB,YA), (R1I,R2L,ZF,XB,YA), (R1J,R2L,ZF,XB,YA), (R1K,R2L,ZF,XB,YA), (R1L,R2L,ZF,XB,YA), (R1M,R2L, ZF,XB,YA), (R1N,R2L,ZF,XB,YA), (R1O,R2L,ZF,XB,YA), (R1P,R2L,ZF,XB,YA), (R1Q,R2L,ZF,XB,YA), (R1A,R2M, ZF,XB,YA), (R1B,R2M,ZF,XB,YA), (R1C,R2M,ZF,XB, YA), (R1D,R2M,ZF,XB,YA), (R1E,R2M,ZF,XB,YA), (R1F, R2M,ZF,XB,YA), (R1G,R2M,ZF,XB,YA), (R1H,R2M,ZF, XB,YA), (R1I,R2M,ZF,XB,YA), (R1J,R2M,ZF,XB,YA), (R1K,R2M,ZF,XB,YA), (R1L,R2M,ZF,XB,YA), (R1M, R2M,ZF,XB,YA), (R1N,R2M,ZF,XB,YA), (R1O,R2M,ZF, XB,YA), (R1P,R2M,ZF,XB,YA), (R1Q,R2M,ZF,XB,YA), (R1A,R2N,ZF,XB,YA), (R1B,R2N,ZF,XB,YA), (R1C,R2N, ZF,XB,YA), (R1D,R2N,ZF,XB,YA), (R1E,R2N,ZF,XB, YA), (R1F,R2N,ZF,XB,YA), (R1G,R2N,ZF,XB,YA), (R1H, R2N,ZF,XB,YA), (R1I,R2N,ZF,XB,YA), (R1J,R2N,ZF,XB, YA), (R1K,R2N,ZF,XB,YA), (R1L,R2N,ZF,XB,YA), (R1M, R2N,ZF,XB,YA), (R1N,R2N,ZF,XB,YA), (R1O,R2N,ZF, XB,YA), (R1P,R2N,ZF,XB,YA), (R1Q,R2N,ZF,XB,YA), (R1A,R2O,ZF,XB,YA), (R1B,R2O,ZF,XB,YA), (R1C,R2O, ZF,XB,YA), (R1D,R2O,ZF,XB,YA), (R1E,R2O,ZF,XB, YA), (R1F,R2O,ZF,XB,YA), (R1G,R2O,ZF,XB,YA), (R1H, R2O,ZF,XB,YA), (R1I,R2O,ZF,XB,YA), (R1J,R2O,ZF,XB, YA), (R1K,R2O,ZF,XB,YA), (R1L,R2O,ZF,XB,YA), (R1M, R2O,ZF,XB,YA), (R1N,R2O,ZF,XB,YA), (R1O,R2O,ZF, XB,YA), (R1P,R2O,ZF,XB,YA), (R1Q,R2O,ZF,XB,YA), (R1A,R2P,ZF,XB,YA), (R1B,R2P,ZF,XB,YA), (R1C,R2P, ZF,XB,YA), (R1D,R2P,ZF,XB,YA), (R1E,R2P,ZF,XB,YA), (R1F,R2P,ZF,XB,YA), (R1G,R2P,ZF,XB,YA), (R1B,R2P, ZF,XB,YA), (R1I,R2P,ZF,XB,YA), (R1J,R2P,ZF,XB,YA), (R1K,R2P,ZF,XB,YA), (R1L,R2P,ZF,XB,YA), (R1M,R2P, ZF,XB,YA), (R1N,R2P,ZF,XB,YA), (R1O,R2P,ZF,XB,YA), (R1P,R2P,ZF,XB,YA), (R1Q,R2P,ZF,XB,YA), (R1A,R2Q, ZF,XB,YA), (R1B,R2Q,ZF,XB,YA), (R1C,R2Q,ZF,XB, YA), (R1D,R2Q,ZF,XB,YA), (R1E,R2Q,ZF,XB,YA), (R1F, R2Q,ZF,XB,YA), (R1G,R2Q,ZF,XB,YA), (R1H,R2Q,ZF, XB,YA), (R1I,R2Q,ZF,XB,YA), (R1J,R2Q,ZF,XB,YA), (R1K,R2Q,ZF,XB,YA), (R1L,R2Q,ZF,XB,YA), (R1M,R2Q, ZF,XB,YA), (R1N,R2Q,ZF,XB,YA), (R1O,R2Q,ZF,XB, YA), (R1P,R2Q,ZF,XB,YA), (R1Q,R2Q,ZF,XB,YA), (R1A, R2A,ZG,XB,YA), (R1B,R2A,ZG,XB,YA), (R1C,R2A,ZG, XB,YA), (R1D,R2A,ZG,XB,YA), (R1E,R2A,ZG,XB,YA), (R1F,R2A,ZG,XB,YA), (R1G,R2A,ZG,XB,YA), (R1H, R2A,ZG,XB,YA), (R1I,R2A,ZG,XB,YA), (R1J,R2A,ZG, XB,YA), (R1K,R2A,ZG,XB,YA), (R1L,R2A,ZG,XB,YA), (R1M,R2A,ZG,XB,YA), (R1N,R2A,ZG,XB,YA), (R1O, R2A,ZG,XB,YA), (R1P,R2A,ZG,XB,YA), (R1Q,R2A,ZG, XB,YA), (R1A,R2B,ZG,XB,YA), (R1B,R2B,ZG,XB,YA), (R1C,R2B,ZG,XB,YA), (R1D,R2B,ZG,XB,YA), (R1E, R2B,ZG,XB,YA), (R1F,R2B,ZG,XB,YA), (R1G,R2B,ZG, XB,YA), (R1H,R2B,ZG,XB,YA), (R1I,R2B,ZG,XB,YA), (R1J,R2B,ZG,XB,YA), (R1K,R2B,ZG,XB,YA), (R1L,R2B, ZG,XB,YA), (R1M,R2B,ZG,XB,YA), (R1N,R2B,ZG,XB, YA), (R1O,R2B,ZG,XB,YA), (R1P,R2B,ZG,XB,YA), (R1Q, R2B,ZG,XB,YA), (R1A,R2C,ZG,XB,YA), (R1B,R2C,ZG, XB,YA), (R1C,R2C,ZG,XB,YA), (R1D,R2C,ZG,XB,YA), (R1E,R2C,ZG,XB,YA), (R1F,R2C,ZG,XB,YA), (R1G,R2C, ZG,XB,YA), (R1H,R2C,ZG,XB,YA), (R1I,R2C,ZG,XB, YA), (R1J,R2C,ZG,XB,YA), (R1K,R2C,ZG,XB,YA), (R1L, R2C,ZG,XB,YA), (R1M,R2C,ZG,XB,YA), (R1N,R2C,ZG, XB,YA), (R1O,R2C,ZG,XB,YA), (R1P,R2C,ZG,XB,YA), (R1Q,R2C,ZG,XB,YA), (R1A,R2D,ZG,XB,YA), (R1B, R2D,ZG,XB,YA), (R1C,R2D,ZG,XB,YA), (R1D,R2D,ZG, XB,YA), (R1E,R2D,ZG,XB,YA), (R1F,R2D,ZG,XB,YA), (R1G,R2D,ZG,XB,YA), (R1H,R2D,ZG,XB,YA), (R1I,R2D, ZG,XB,YA), (R1J,R2D,ZG,XB,YA), (R1K,R2D,ZG,XB, YA), (R1L,R2D,ZG,XB,YA), (R1M,R2D,ZG,XB,YA), (R1N,R2D,ZG,XB,YA), (R1O,R2D,ZG,XB,YA), (R1P, R2D,ZG,XB,YA), (R1Q,R2D,ZG,XB,YA), (R1A,R2E,ZG, XB,YA), (R1B,R2E,ZG,XB,YA), (R1C,R2E,ZG,XB,YA), (R1D,R2E,ZG,XB,YA), (R1E,R2E,ZG,XB,YA), (R1F,R2E, ZG,XB,YA), (R1G,R2E,ZG,XB,YA), (R1H,R2E,ZG,XB, YA), (R1I,R2E,ZG,XB,YA), (R1J,R2E,ZG,XB,YA), (R1K, R2E,ZG,XB,YA), (R1L,R2E,ZG,XB,YA), (R1M,R2E,ZG, XB,YA), (R1N,R2E,ZG,XB,YA), (R1O,R2E,ZG,XB,YA), (R1P,R2E,ZG,XB,YA), (R1Q,R2E,ZG,XB,YA), (R1A,R2F, ZG,XB,YA), (R1B,R2F,ZG,XB,YA), (R1C,R2F,ZG,XB, YA), (R1D,R2F,ZG,XB,YA), (R1E,R2F,ZG,XB,YA), (R1F, R2F,ZG,XB,YA), (R1G,R2F,ZG,XB,YA), (R1H,R2F,ZG, XB,YA), (R1I,R2F,ZG,XB,YA), (R1J,R2F,ZG,XB,YA), (R1K,R2F,ZG,XB,YA), (R1L,R2F,ZG,XB,YA), (R1M,R2F, ZG,XB,YA), (R1N,R2F,ZG,XB,YA), (R1O,R2F,ZG,XB, YA), (R1P,R2F,ZG,XB,YA), (R1Q,R2F,ZG,XB,YA), (R1A, R2G,ZG,XB,YA), (R1B,R2G,ZG,XB,YA), (R1C,R2G,ZG, XB,YA), (R1D,R2G,ZG,XB,YA), (R1E,R2G,ZG,XB,YA), (R1F,R2G,ZG,XB,YA), (R1G,R2G,ZG,XB,YA), (R1H, R2G,ZG,XB,YA), (R1I,R2G,ZG,XB,YA), (R1J,R2G,ZG, XB,YA), (R1K,R2G,ZG,XB,YA), (R1L,R2G,ZG,XB,YA), (R1M,R2G,ZG,XB,YA), (R1N,R2G,ZG,XB,YA), (R1O, R2G,ZG,XB,YA), (R1P,R2G,ZG,XB,YA), (R1Q,R2G,ZG, XB,YA), (R1A,R2H,ZG,XB,YA), (R1B,R2H,ZG,XB,YA), (R1C,R2H,ZG,XB,YA), (R1D,R2H,ZG,XB,YA), (R1E, R2H,ZG,XB,YA), (R1F,R2H,ZG,XB,YA), (R1G,R2H,ZG, XB,YA), (R1H,R2H,ZG,XB,YA), (R1I,R2H,ZG,XB,YA), (R1J,R2H,ZG,XB,YA), (R1K,R2H,ZG,XB,YA), (R1L,R2H, ZG,XB,YA), (R1M,R2H,ZG,XB,YA), (R1N,R2H,ZG,XB, YA), (R1O,R2H,ZG,XB,YA), (R1P,R2H,ZG,XB,YA), (R1Q,R2H,ZG,XB,YA), (R1A,R2I,ZG,XB,YA), (R1B,R2I, ZG,XB,YA), (R1C,R2I,ZG,XB,YA), (R1D,R2I,ZG,XB, YA), (R1E,R2I,ZG,XB,YA), (R1F,R2I,ZG,XB,YA), (R1G, R2I,ZG,XB,YA), (R1H,R2I,ZG,XB,YA), (R1I,R2I,ZG,XB, YA), (R1J,R2I,ZG,XB,YA), (R1K,R2I,ZG,XB,YA), (R1L, R2I,ZG,XB,YA), (R1M,R2I,ZG,XB,YA), (R1N,R2I,ZG, XB,YA), (R1O,R2I,ZG,XB,YA), (R1P,R2I,ZG,XB,YA), (R1Q,R2I,ZG,XB,YA), (R1A,R2J,ZG,XB,YA), (R1B,R2J, ZG,XB,YA), (R1C,R2J,ZG,XB,YA), (R1D,R2J,ZG,XB, YA), (R1E,R2J,ZG,XB,YA), (R1F,R2J,ZG,XB,YA), (R1G, R2J,ZG,XB,YA), (R1H,R2J,ZG,XB,YA), (R1I,R2J,ZG,XB, YA), (R1J,R2J,ZG,XB,YA), (R1K,R2J,ZG,XB,YA), (R1L, R2J,ZG,XB,YA), (R1M,R2J,ZG,XB,YA), (R1N,R2J,ZG, XB,YA), (R1O,R2J,ZG,XB,YA), (R1P,R2J,ZG,XB,YA), (R1Q,R2J,ZG,XB,YA), (R1A,R2K,ZG,XB,YA), (R1B,R2K, ZG,XB,YA), (R1C,R2K,ZG,XB,YA), (R1D,R2K,ZG,XB, YA), (R1E,R2K,ZG,XB,YA), (R1F,R2K,ZG,XB,YA), (R1G, R2K,ZG,XB,YA), (R1H,R2K,ZG,XB,YA), (R1I,R2K,ZG, XB,YA), (R1J,R2K,ZG,XB,YA), (R1K,R2K,ZG,XB,YA), (R1L,R2K,ZG,XB,YA), (R1M,R2K,ZG,XB,YA), (R1N, R2K,ZG,XB,YA), (R1O,R2K,ZG,XB,YA), (R1P,R2K,ZG, XB,YA), (R1Q,R2K,ZG,XB,YA), (R1A,R2L,ZG,XB,YA), (R1B,R2L,ZG,XB,YA), (R1C,R2L,ZG,XB,YA), (R1D,R2L, ZG,XB,YA), (R1E,R2L,ZG,XB,YA), (R1F,R2L,ZG,XB, YA), (R1G,R2L,ZG,XB,YA), (R1H,R2L,ZG,XB,YA), (R1I, R2L,ZG,XB,YA), (R1J,R2L,ZG,XB,YA), (R1K,R2L,ZG, XB,YA), (R1L,R2L,ZG,XB,YA), (R1M,R2L,ZG,XB,YA), (R1N,R2L,ZG,XB,YA), (R1O,R2L,ZG,XB,YA), (R1P,R2L, ZG,XB,YA), (R1Q,R2L,ZG,XB,YA), (R1A,R2M,ZG,XB, YA), (R1B,R2M,ZG,XB,YA), (R1C,R2M,ZG,XB,YA), (R1D,R2M,ZG,XB,YA), (R1E,R2M,ZG,XB,YA), (R1F, R2M,ZG,XB,YA), (R1G,R2M,ZG,XB,YA), (R1H,R2M,ZG, XB,YA), (R1I,R2M,ZG,XB,YA), (R1J,R2M,ZG,XB,YA), (R1K,R2M,ZG,XB,YA), (R1L,R2M,ZG,XB,YA), (R1M, R2M,ZG,XB,YA), (R1N,R2M,ZG,XB,YA), (R1O,R2M,ZG, XB,YA), (R1P,R2M,ZG,XB,YA), (R1Q,R2M,ZG,XB,YA), (R1A,R2N,ZG,XB,YA), (R1B,R2N,ZG,XB,YA), (R1C, R2N,ZG,XB,YA), (R1D,R2N,ZG,XB,YA), (R1E,R2N,ZG, XB,YA), (R1F,R2N,ZG,XB,YA), (R1G,R2N,ZG,XB,YA), (R1H,R2N,ZG,XB,YA), (R1I,R2N,ZG,XB,YA), (R1J,R2N, ZG,XB,YA), (R1K,R2N,ZG,XB,YA), (R1L,R2N,ZG,XB, YA), (R1M,R2N,ZG,XB,YA), (R1N,R2N,ZG,XB,YA), (R1O,R2N,ZG,XB,YA), (R1P,R2N,ZG,XB,YA), (R1Q, R2N,ZG,XB,YA), (R1A,R2O,ZG,XB,YA), (R1B,R2O,ZG, XB,YA), (R1C,R2O,ZG,XB,YA), (R1D,R2O,ZG,XB,YA), (R1E,R2O,ZG,XB,YA), (R1F,R2O,ZG,XB,YA), (R1G, R2O,ZG,XB,YA), (R1H,R2O,ZG,XB,YA), (R1I,R2O,ZG, XB,YA), (R1J,R2O,ZG,XB,YA), (R1K,R2O,ZG,XB,YA), (R1L,R2O,ZG,XB,YA), (R1M,R2O,ZG,XB,YA), (R1N, R2O,ZG,XB,YA), (R1O,R2O,ZG,XB,YA), (R1P,R2O,ZG, XB,YA), (R1Q,R2O,ZG,XB,YA), (R1A,R2P,ZG,XB,YA), (R1B,R2P,ZG,XB,YA), (R1C,R2P,ZG,XB,YA), (R1D,R2P, ZG,XB,YA), (R1E,R2P,ZG,XB,YA), (R1F,R2P,ZG,XB,YA), (R1G,R2P,ZG,XB,YA), (R1H,R2P,ZG,XB,YA), (R1I,R2P, ZG,XB,YA), (R1J,R2P,ZG,XB,YA), (R1K,R2P,ZG,XB, YA), (R1L,R2P,ZG,XB,YA), (R1M,R2P,ZG,XB,YA), (R1N, R2P,ZG,XB,YA), (R1O,R2P,ZG,XB,YA), (R1P,R2P,ZG, XB,YA), (R1Q,R2P,ZG,XB,YA), (R1A,R2Q,ZG,XB,YA), (R1B,R2Q,ZG,XB,YA), (R1C,R2Q,ZG,XB,YA), (R1D, R2Q,ZG,XB,YA), (R1E,R2Q,ZG,XB,YA), (R1F,R2Q,ZG, XB,YA), (R1G,R2Q,ZG,XB,YA), (R1H,R2Q,ZG,XB,YA), (R1I,R2Q,ZG,XB,YA), (R1J,R2Q,ZG,XB,YA), (R1K,R2Q, ZG,XB,YA), (R1L,R2Q,ZG,XB,YA), (R1M,R2Q,ZG,XB, YA), (R1N,R2Q,ZG,XB,YA), (R1O,R2Q,ZG,XB,YA), (R1P,R2Q,ZG,XB,YA), (R1Q,R2Q,ZG,XB,YA), (R1A, R2A,ZH,XB,YA), (R1B,R2A,ZH,XB,YA), (R1C,R2A,ZH, XB,YA), (R1D,R2A,ZH,XB,YA), (R1E,R2A,ZH,XB,YA), (R1F,R2A,ZH,XB,YA), (R1G,R2A,ZH,XB,YA), (R1H, R2A,ZH,XB,YA), (R1I,R2A,ZH,XB,YA), (R1J,R2A,ZH, XB,YA), (R1K,R2A,ZH,XB,YA), (R1L,R2A,ZH,XB,YA), (R1M,R2A,ZH,XB,YA), (R1N,R2A,ZH,XB,YA), (R1O, R2A,ZH,XB,YA), (R1P,R2A,ZH,XB,YA), (R1Q,R2A,ZH, XB,YA), (R1A,R2B,ZH,XB,YA), (R1B,R2B,ZH,XB,YA), (R1C,R2B,ZH,XB,YA), (R1D,R2B,ZH,XB,YA), (R1E, R2B,ZH,XB,YA), (R1F,R2B,ZH,XB,YA), (R1G,R2B,ZH, XB,YA), (R1H,R2B,ZH,XB,YA), (R1I,R2B,ZH,XB,YA), (R1J,R2B,ZH,XB,YA), (R1K,R2B,ZH,XB,YA), (R1L,R2B, ZH,XB,YA), (R1M,R2B,ZH,XB,YA), (R1N,R2B,ZH,XB, YA), (R1O,R2B,ZH,XB,YA), (R1P,R2B,ZH,XB,YA), (R1Q, R2B,ZH,XB,YA), (R1A,R2C,ZH,XB,YA), (R1B,R2C,ZH, XB,YA), (R1C,R2C,ZH,XB,YA), (R1D,R2C,ZH,XB,YA), (R1E,R2C,ZH,XB,YA), (R1F,R2C,ZH,XB,YA), (R1G,R2C, ZH,XB,YA), (R1H,R2C,ZH,XB,YA), (R1I,R2C,ZH,XB, YA), (R1J,R2C,ZH,XB,YA), (R1K,R22C,ZH,XB,YA), (R1L,R2C,ZH,XB,YA), (R1M,R2C,ZH,XB,YA), (R1N, R2C,ZH,XB,YA), (R1O,R2C,ZH,XB,YA), (R1P,R2C,ZH, XB,YA), (R1Q,R2C,ZH,XB,YA), (R1A,R2D,ZH,XB,YA), (R1B,R2D,ZH,XB,YA), (R1C,R2D,ZH,XB,YA), (R1D, R2D,ZH,XB,YA), (R1E,R2D,ZH,XB,YA), (R1F,R2D,ZH, XB,YA), (R1G,R2D,ZH,XB,YA), (R1H,R2D,ZH,XB,YA), (R1I,R2D,ZH,XB,YA), (R1J,R2D,ZH,XB,YA), (R1K,R2D, ZH,XB,YA), (R1L,R2D,ZH,XB,YA), (R1M,R2D,ZH,XB, YA), (R1N,R2D,ZH,XB,YA), (R1O,R2D,ZH,XB,YA), (R1P,R2D,ZH,XB,YA), (R1Q,R2D,ZH,XB,YA), (R1A,R2E, ZH,XB,YA), (R1B,R2E,ZH,XB,YA), (R1C,R2E,ZH,XB, YA), (R1D,R2E,ZH,XB,YA), (R1E,R2E,ZH,XB,YA), (R1F, R2E,ZH,XB,YA), (R1G,R2E,ZH,XB,YA), (R1H,R2E,ZH, XB,YA), (R1I,R2E,ZH,XB,YA), (R1J,R2E,ZH,XB,YA), (R1K,R2E,ZH,XB,YA), (R1L,R2E,ZH,XB,YA), (R1M, R2E,ZH,XB,YA), (R1N,R2E,ZH,XB,YA), (R1O,R2E,ZH,XB,YA), (R1P,R2E,ZH,XB,YA), (R1Q,R2E,ZH,XB,YA), (R1A,R2F,ZH,XB,YA), (R1B,R2F,ZH,XB,YA), (R1C,R2F,ZH,XB,YA), (R1D,R2F,ZH,XB,YA), (R1E,R2F,ZH,XB,YA), (R1F,R2F,ZH,XB,YA), (R1G,R2F,ZH,XB,YA), (R1H,R2F,ZH,XB,YA), (R1I,R2F,ZH,XB,YA), (R1J,R2F,ZH,XB,YA), (R1K,R2F,ZH,XB,YA), (R1L,R2F,ZH,XB,YA), (R1M,R2F,ZH,XB,YA), (R1N,R2F,ZH,XB,YA), (R1O,R2F,ZH,XB,YA), (R1P,R2F,ZH,XB,YA), (R1Q,R2F,ZH,XB,YA), (R1A,R2G,ZH,XB,YA), (R1B,R2G,ZH,XB,YA), (R1C,R2G,ZH,XB,YA), (R1D,R2G,ZH,XB,YA), (R1E,R2G,ZH,XB,YA), (R1F,R2G,ZH,XB,YA), (R1G,R2G,ZH,XB,YA), (R1H,R2G,ZH,XB,YA), (R1I,R2G,ZH,XB,YA), (R1J,R2G,ZH,XB,YA), (R1K,R2G,ZH,XB,YA), (R1L,R2G,ZH,XB,YA), (R1M,R2G,ZH,XB,YA), (R1N,R2G,ZH,XB,YA), (R1O,R2G,ZH,XB,YA), (R1P,R2G,ZH,XB,YA), (R1Q,R2G,ZH,XB,YA), (R1A,R2H,ZH,XB,YA), (R1B,R2H,ZH,XB,YA), (R1C,R2H,ZH,XB,YA), (R1D,R2H,ZH,XB,YA), (R1E,R2H,ZH,XB,YA), (R1F,R2H,ZH,XB,YA), (R1G,R2H,ZH,XB,YA), (R1H,R2H,ZH,XB,YA), (R1I,R2H,ZH,XB,YA), (R1J,R2H,ZH,XB,YA), (R1K,R2H,ZH,XB,YA), (R1L,R2H,ZH,XB,YA), (R1M,R2H,ZH,XB,YA), (R1N,R2H,ZH,XB,YA), (R1O,R2H,ZH,XB,YA), (R1P,R2H,ZH,XB,YA), (R1Q,R2H,ZH,XB,YA), (R1A,R2I,ZH,XB,YA), (R1B,R2I,ZH,XB,YA), (R1C,R2I,ZH,XB,YA), (R1D,R2I,ZH,XB,YA), (R1E,R2I,ZH,XB,YA), (R1F,R2I,ZH,XB,YA), (R1G,R2I,ZH,XB,YA), (R1H,R2I,ZH,XB,YA), (R1I,R2I,ZH,XB,YA), (R1J,R2I,ZH,XB,YA), (R1K,R2I,ZH,XB,YA), (R1L,R2I,ZH,XB,YA), (R1M,R2I,ZH,XB,YA), (R1N,R2I,ZH,XB,YA), (R1O,R2I,ZH,XB,YA), (R1P,R2I,ZH,XB,YA), (R1Q,R2I,ZH,XB,YA), (R1A,R2J,ZH,XB,YA), (R1B,R2J,ZH,XB,YA), (R1C,R2J,ZH,XB,YA), (R1D,R2J,ZH,XB,YA), (R1E,R2J,ZH,XB,YA), (R1F,R2J,ZH,XB,YA), (R1G,R2J,ZH,XB,YA), (R1H,R2J,ZH,XB,YA), (R1I,R2J,ZH,XB,YA), (R1J,R2J,ZH,XB,YA), (R1K,R2J,ZH,XB,YA), (R1L,R2J,ZH,XB,YA), (R1M,R2J,ZH,XB,YA), (R1N,R2J,ZH,XB,YA), (R1O,R2J,ZH,XB,YA), (R1P,R2J,ZH,XB,YA), (R1Q,R2J,ZH,XB,YA), (R1A,R2K,ZH,XB,YA), (R1B,R2K,ZH,XB,YA), (R1C,R2K,ZH,XB,YA), (R1D,R2K,ZH,XB,YA), (R1E,R2K,ZH,XB,YA), (R1F,R2K,ZH,XB,YA), (R1G,R2K,ZH,XB,YA), (R1H,R2K,ZH,XB,YA), (R1I,R2K,ZH,XB,YA), (R1J,R2K,ZH,XB,YA), (R1K,R2K,ZH,XB,YA), (R1L,R2K,ZH,XB,YA), (R1M,R2K,ZH,XB,YA), (R1N,R2K,ZH,XB,YA), (R1O,R2K,ZH,XB,YA), (R1P,R2K,ZH,XB,YA), (R1Q,R2K,ZH,XB,YA), (R1A,R2L,ZH,XB,YA), (R1B,R2L,ZH,XB,YA), (R1C,R2L,ZH,XB,YA), (R1D,R2L,ZH,XB,YA), (R1E,R2L,ZH,XB,YA), (R1F,R2L,ZH,XB,YA), (R1G,R2L,ZH,XB,YA), (R1H,R2L,ZH,XB,YA), (R1I,R2L,ZH,XB,YA), (R1J,R2L,ZH,XB,YA), (R1K,R2L,ZH,XB,YA), (R1L,R2L,ZH,XB,YA), (R1M,R2L,ZH,XB,YA), (R1N,R2L,ZH,XB,YA), (R1O,R2L,ZH,XB,YA), (R1P,R2L,ZH,XB,YA), (R1Q,R2L,ZH,XB,YA), (R1A,R2M,ZH,XB,YA), (R1B,R2M,ZH,XB,YA), (R1C,R2M,ZH,XB,YA), (R1D,R2M,ZH,XB,YA), (R1E,R2M,ZH,XB,YA), (R1F,R2M,ZH,XB,YA), (R1G,R2M,ZH,XB,YA), (R1H,R2M,ZH,XB,YA), (R1I,R2M,ZH,XB,YA), (R1J,R2M,ZH,XB,YA), (R1K,R2M,ZH,XB,YA), (R1L,R2M,ZH,XB,YA), (R1M,R2M,ZH,XB,YA), (R1N,R2M,ZH,XB,YA), (R1O,R2M,ZE,XB,YA), (R1P,R2M,ZH,XB,YA), (R1Q,R2M,ZH,XB,YA), (R1A,R2N,ZH,XB,YA), (R1B,R2N,ZH,XB,YA), (R1C,R2N,ZH,XB,YA), (R1D,R2N,ZH,XB,YA), (R1E,R2N,ZH,XB,YA), (R1F,R2N,ZH,XB,YA), (R1G,R2N,ZH,XB,YA), (R1H,R2N,ZH,XB,YA), (R1I,R2N,ZH,XB,YA), (R1J,R2N,ZH,XB,YA), (R1K,R2N,ZH,XB,YA), (R1L,R2N,ZH,XB,YA), (R1M,R2N,ZH,XB,YA), (R1N,R2N,ZH,XB,YA), (R1O,R2N,ZH,XB,YA), (R1P,R2N,ZH,XB,YA), (R1Q,R2N,ZH,XB,YA), (R1A,R2O,ZH,XB,YA), (R1B,R2O,ZH,XB,YA), (R1C,R2O,ZH,XB,YA), (R1D,R2O,ZH,XB,YA), (R1E,R2O,ZH,XB,YA), (R1F,R2O,ZH,XB,YA), (R1G,R2O,ZH,XB,YA), (R1H,R2O,ZH,XB,YA), (R1I,R2O,ZH,XB,YA), (R1J,R2O,ZH,XB,YA), (R1K,R2O,ZH,XB,YA), (R1L,R2O,ZH,XB,YA), (R1M,R2O,ZH,XB,YA), (R1N,R2O,ZH,XB,YA), (R1O,R2O,ZH,XB,YA), (R1P,R2O,ZH,XB,YA), (R1Q,R2O,ZH,XB,YA), (R1A,R2P,ZH,XB,YA), (R1B,R2P,ZH,XB,YA), (R1C,R2P,ZH,XB,YA), (R1D,R2P,ZH,XB,YA), (R1E,R2P,ZH,XB,YA), (R1F,R2P,ZH,XB,YA), (R1G,R2P,ZH,XB,YA), (R1H,R2P,ZH,XB,YA), (R1I,R2P,ZH,XB,YA), (R1J,R2P,ZH,XB,YA), (R1K,R2P,ZH,XB,YA), (R1L,R2P,ZH,XB,YA), (R1M,R2P,ZH,XB,YA), (R1N,R2P,ZH,XB,YA), (R1O,R2P,ZH,XB,YA), (R1P,R2P,ZH,XB,YA), (R1Q,R2P,ZH,XB,YA), (R1A,R2Q,ZH,XB,YA), (R1B,R2Q,ZH,XB,YA), (R1C,R2Q,ZH,XB,YA), (R1D,R2Q,ZH,XB,YA), (R1E,R2Q,ZH,XB,YA), (R1F,R2Q,ZH,XB,YA), (R1G,R2Q,ZH,XB,YA), (R1H,R2Q,ZH,XB,YA), (R1I,R2Q,ZH,XB,YA), (R1J,R2Q,ZH,XB,YA), (R1K,R2Q,ZH,XB,YA), (R1L,R2Q,ZH,XB,YA), (R1M,R2Q,ZH,XB,YA), (R1N,R2Q,ZH,XB,YA), (R1O,R2Q,ZH,XB,YA), (R1P,R2Q,ZH,XB,YA), (R1Q,R2Q,ZH,XB,YA), (R1A,R2A,ZI,XB,YA), (R1B,R2A,ZI,XB,YA), (R1C,R2A,ZI,XB,YA), (R1D,R2A,ZI,XB,YA), (R1E,R2A,ZI,XB,YA), (R1F,R2A,ZI,XB,YA), (R1G,R2A,ZI,XB,YA), (R1H,R2A,ZI,XB,YA), (R1I,R2A,ZI,XB,YA), (R1J,R2A,ZI,XB,YA), (R1K,R2A,ZI,XB,YA), (R1L,R2A,ZI,XB,YA), (R1M,R2A,ZI,XB,YA), (R1N,R2A,ZI,XB,YA), (R1O,R2A,ZI,XB,YA), (R1P,R2A,ZI,XB,YA), (R1Q,R2A,ZI,XB,YA), (R1A,R2B,ZI,XB,YA), (R1B,R2B,ZI,XB,YA), (R1C,R2B,ZI,XB,YA), (R1D,R2B,ZI,XB,YA), (R1E,R2B,ZI,XB,YA), (R1F,R2B,ZI,XB,YA), (R1G,R2B,ZI,XB,YA), (R1H,R2B,ZI,XB,YA), (R1I,R2B,ZI,XB,YA), (R1J,R2B,ZI,XB,YA), (R1K,R2B,ZI,XB,YA), (R1L,R2B,ZI,XB,YA), (R1M,R2B,ZI,XB,YA), (R1N,R2B,ZI,XB,YA), (R1O,R2B,ZI,XB,YA), (R1P,R2B,ZI,XB,YA), (R1Q,R2B,ZI,XB,YA), (R1A,R2C,ZI,XB,YA), (R1B,R2C,ZI,XB,YA), (R1C,R2C,ZI,XB,YA), (R1D,R2C,ZI,XB,YA), (R1E,R2C,ZI,XB,YA), (R1F,R2C,ZI,XB,YA), (R1G,R2C,ZI,XB,YA), (R1H,R2C,ZI,XB,YA), (R1I,R2C,ZI,XB,YA), (R1J,R2C,ZI,XB,YA), (R1K,R2C,ZI,XB,YA), (R1L,R2C,ZI,XB,YA), (R1M,R2C,ZI,XB,YA), (R1N,R2C,ZI,XB,YA), (R1O,R2C,ZI,XB,YA), (R1P,R2C,ZI,XB,YA), (R1Q,R2C,ZI,XB,YA), (R1A,R2D,ZI,XB,YA), (R1B,R2D,ZI,XB,YA), (R1C,R2D,ZI,XB,YA), (R1D,R2D,ZI,XB,YA), (R1E,R2D,ZI,XB,YA), (R1F,R2D,ZI,XB,YA), (R1G,R2D,ZI,XB,YA), (R1H,R2D,ZI,XB,YA), (R1I,R2D,ZI,XB,YA), (R1J,R2D,ZI,XB,YA), (R1K,R2D,ZI,XB,YA), (R1L,R2D,ZI,XB,YA), (R1M,R2D,ZI,XB,YA), (R1N,R2D,ZI,XB,YA), (R1O,R2D,ZI,XB,YA), (R1P,R2D,ZI,XB,YA), (R1Q,R2D,ZI,XB,YA), (R1A,R2E,ZI,XB,YA), (R1B,R2E,ZI,XB,YA), (R1C,R2E,ZI,XB,YA), (R1D,R2E,ZI,XB,YA), (R1E,R2E,ZI,XB,YA), (R1F,R2E,ZI,XB,YA), (R1G,R2E,ZI,XB,YA), (R1H,R2E,ZI,XB,YA), (R1I,R2E,ZI,XB,YA), (R1J,R2E,ZI,XB,YA), (R1K,R2E,ZI,XB,YA), (R1L,R2E,ZI,XB,YA), (R1M,R2E,ZI,XB,YA), (R1N,R2E,ZI,XB,YA), (R1O,R2E,ZI,XB,YA), (R1P,R2E,ZI,XB,YA), (R1Q,R2E,ZI,XB,YA), (R1A,R2F,ZI,XB,YA), (R1B,R2F,ZI,XB,YA), (R1C,R2F,ZI,XB,YA), (R1D,R2F,ZI,XB,YA), (R1E,R2F,ZI,XB,YA), (R1F,R2F,ZI,XB,YA), (R1G,R2F,ZI,XB,YA), (R1H,R2F,ZI,XB,YA), (R1I,R2F,ZI,XB,YA), (R1J,R2F,ZI,XB,YA), (R1K,R2F,ZI,XB,YA), (R1L,R2F,ZI,XB,YA), (R1M,R2F,ZI,XB,YA), (R1N,R2F,ZI,XB,YA), (R1O,R2F,ZI,XB,YA), (R1P,R2F,ZI,XB,YA), (R1Q,R2F,ZI,XB,YA), (R1A,R2G,ZI,XB,YA), (R1B,R2G,ZI,XB,YA), (R1C,R2G,ZI,XB,YA), (R1D,R2G,ZI,XB,YA), (R1E,R2G,ZI,XB,YA), (R1F,R2G,ZI,XB,YA), (R1G,R2G,ZI,XB,YA), (R1H,R2G,ZI,XB,YA), (R1I,R2G,ZI,XB,YA), (R1J,R2G,ZI,XB,YA), (R1K,R2G,ZI,XB,YA), (R1L,R2G,ZI,XB,YA), (R1M,R2G,ZI,XB,YA), (R1N, R2G,ZI,XB,YA), (R1O,R2G,ZI,XB,YA), (R1P,R2G,ZI,XB,YA), (R1Q,R2G,ZI,XB,YA), (R1A,R2H,ZI,XB,YA), (R1B,R2H,ZI,XB,YA), (R1C,R2H,ZI,XB,YA), (R1D,R2H,ZI,XB,YA), (R1E,R2H,ZI,XB,YA), (R1F,R2H,ZI,XB,YA), (R1G,R2H,ZI,XB,YA), (R1H,R2H,ZI,XB,YA), (R1I,R2H,ZI,XB,YA), (R1J,R2H,ZI,XB,YA), (R1K,R2H,ZI,XB,YA), (R1L,R2H,ZI,XB,YA), (R1M,R2H,ZI,XB,YA), (R1N,R2H,ZI,XB,YA), (R1O,R2H,ZI,XB,YA), (R1P,R2H,ZI,XB,YA), (R1Q,R2H,ZI,XB,YA), (R1A,R2I,ZI,XB,YA), (R1B,R2I,ZI,XB,YA), (R1C,R2I,ZI,XB,YA), (R1D,R2I,ZI,XB,YA), (R1E,R2I,ZI,XB,YA), (R1F,R2I,ZI,XB,YA), (R1G,R2I,ZI,XB,YA), (R1H,R2I,ZI,XB,YA), (R1I,R2I,ZI,XB,YA), (R1J,R2I,ZI,XB,YA), (R1K,R2I,ZI,XB,YA), (R1L,R2I,ZI,XB,YA), (R1M,R2I,ZI,XB,YA), (R1N,R2I,ZI,XB,YA), (R1O,R2I,ZI,XB,YA), (R1P,R2I,ZI,XB,YA), (R1Q,R2I,ZI,XB,YA), (R1A,R2J,ZI,XB,YA), (R1B,R2J,ZI,XB,YA), (R1C,R2J,ZI,XB,YA), (R1D,R2J,ZI,XB,YA), (R1E,R2J,ZI,XB,YA), (R1F,R2J,ZI,XB,YA), (R1G,R2J,ZI,XB,YA), (R1H,R2J,ZI,XB,YA), (R1I,R2J,ZI,XB,YA), (R1J,R2J,ZI,XB,YA), (R1K,R2J,ZI,XB,YA), (R1L,R2J,ZI,XB,YA), (R1M,R2J,ZI,XB,YA), (R1N,R2J,ZI,XB,YA), (R1O,R2J,ZI,XB,YA), (R1P,R2J,ZI,XB,YA), (R1Q,R2J,ZI,XB,YA), (R1A,R2K,ZI,XB,YA), (R1B,R2K,ZI,XB,YA), (R1C,R2K,ZI,XB,YA), (R1D,R2K,ZI,XB,YA), (R1E,R2K,ZI,XB,YA), (R1F,R2K,ZI,XB,YA), (R1G,R2K,ZI,XB,YA), (R1H,R2K,ZI,XB,YA), (R1I,R2K,ZI,XB,YA), (R1J,R2K,ZI,XB,YA), (R1K,R2K,ZI,XB,YA), (R1L,R2K,ZI,XB,YA), (R1M,R2K,ZI,XB,YA), (R1N,R2K,ZI,XB,YA), (R1O,R2K,ZI,XB,YA), (R1P,R2K,ZI,XB,YA), (R1Q,R2K,ZI,XB,YA), (R1A,R2L,ZI,XB,YA), (R1B,R2L,ZI,XB,YA), (R1C,R2L,ZI,XB,YA), (R1D,R2L,ZI,XB,YA), (R1E,R2L,ZI,XB,YA), (R1F,R2L,ZI,XB,YA), (R1G,R2L,ZI,XB,YA), (R1H,R2L,ZI,XB,YA), (R1I,R2L,ZI,XB,YA), (R1J,R2L,ZI,XB,YA), (R1K,R2L,ZI,XB,YA), (R1L,R2L,ZI,XB,YA), (R1M,R2L,ZI,XB,YA), (R1N,R2L,ZI,XB,YA), (R1O,R2L,ZI,XB,YA), (R1P,R2L,ZI,XB,YA), (R1Q,R2L,ZI,XB,YA), (R1A,R2M,ZI,XB,YA), (R1B,R2M,ZI,XB,YA), (R1C,R2M,ZI,XB,YA), (R1D,R2M,ZI,XB,YA), (R1E,R2M,ZI,XB,YA), (R1F,R2M,ZI,XB,YA), (R1G,R2M,ZI,XB,YA), (R1H,R2M,ZI,XB,YA), (R1I,R2M,ZI,XB,YA), (R1J,R2M,ZI,XB,YA), (R1K,R2M,ZI,XB,YA), (R1L,R2M,ZI,XB,YA), (R1M,R2M,ZI,XB,YA), (R1N,R2M,ZI,XB,YA), (R1O,R2M,ZI,XB,YA), (R1P,R2M,ZI,XB,YA), (R1Q,R2M,ZI,XB,YA), (R1A,R2N,ZI,XB,YA), (R1B,R2N,ZI,XB,YA), (R1C,R2N,ZI,XB,YA), (R1D,R2N,ZI,XB,YA), (R1E,R2N,ZI,XB,YA), (R1F,R2N,ZI,XB,YA), (R1G,R2N,ZI,XB,YA), (R1H,R2N,ZI,XB,YA), (R1I,R2N,ZI,XB,YA), (R1J,R2N,ZI,XB,YA), (R1K,R2N,ZI,XB,YA), (R1L,R2N,ZI,XB,YA), (R1M,R2N,ZI,XB,YA), (R1N,R2N,ZI,XB,YA), (R1O,R2N,ZI,XB,YA), (R1P,R2N,ZI,XB,YA), (R1Q,R2N,ZI,XB,YA), (R1A,R2O,ZI,XB,YA), (R1B,R2O,ZI,XB,YA), (R1C,R2O,ZI,XB,YA), (R1D,R2O,ZI,XB,YA), (R1E,R2O,ZI,XB,YA), (R1F,R2O,ZI,XB,YA), (R1G,R2O,ZI,XB,YA), (R1H,R2O,ZI,XB,YA), (R1I,R2O,ZI,XB,YA), (R1J,R2O,ZI,XB,YA), (R1K,R2O,ZI,XB,YA), (R1L,R2O,ZI,XB,YA), (R1M,R2O,ZI,XB,YA), (R1N,R2O,ZI,XB,YA), (R1O,R2O,ZI,XB,YA), (R1P,R2O,ZI,XB,YA), (R1Q,R2O,ZI,XB,YA), (R1A,R2P,ZI,XB,YA), (R1B,R2P,ZI,XB,YA), (R1C,R2P,ZI,XB,YA), (R1D,R2P,ZI,XB,YA), (R1E,R2P,ZI,XB,YA), (R1F,R2P,ZI,XB,YA), (R1G,R2P,ZI,XB,YA), (R1H,R2P,ZI,XB,YA), (R1I,R2P,ZI,XB,YA), (R1J,R2P,ZI,XB,YA), (R1K,R2P,ZI,XB,YA), (R1L,R2P,ZI,XB,YA), (R1M,R2P,ZI,XB,YA), (R1N,R2P,ZI,XB,YA), (R1O,R2P,ZI,XB,YA), (R1P,R2P,ZI,XB,YA), (R1Q,R2P,ZI,XB,YA), (R1A,R2Q,ZI,XB,YA), (R1B,R2Q,ZI,XB,YA), (R1C,R2Q,ZI,XB,YA), (R1D,R2Q,ZI,XB,YA), (R1E,R2Q,ZI,XB,YA), (R1F,R2Q,ZI,XB,YA), (R1G,R2Q,ZI,XB,YA), (R1H,R2Q,ZI,XB,YA), (R1I,R2Q,ZI,XB,YA), (R1J,R2Q,ZI,XB,YA), (R1K,R2Q,ZI,XB,YA), (R1L,R2Q,ZI,XB,YA), (R1M,R2Q,ZI,XB,YA), (R1N,R2Q,ZI,XB,YA), (R1O,R2Q,ZI,XB,YA), (R1P,R2Q,ZI,XB,YA), (R1Q,R2Q,ZI,XB,YA), (R1A,R2A,ZJ,XB,YA), (R1B,R2A,ZJ,XB,YA), (R1C,R2A,ZJ,XB,YA), (R1D,R2A,ZJ,XB,YA), (R1E,R2A,ZJ,XB,YA), (R1F,R2A,ZJ,XB,YA), (R1G,R2A,ZJ,XB,YA), (R1H,R2A,ZJ,XB,YA), (R1I,R2A,ZJ,XB,YA), (R1J,R2A,ZJ,XB,YA), (R1K,R2A,ZJ,XB,YA), (R1L,R2A,ZJ,XB,YA), (R1M,R2A,ZJ,XB,YA), (R1N,R2A,ZJ,XB,YA), (R1O,R2A,ZJ,XB,YA), (R1P,R2A,ZJ,XB,YA), (R1Q,R2A,ZJ,XB,YA), (R1A,R2B,ZJ,XB,YA), (R1B,R2B,ZJ,XB,YA), (R1C,R2B,ZJ,XB,YA), (R1D,R2B,ZJ,XB,YA), (R1E,R2B,ZJ,XB,YA), (R1F,R2B,ZJ,XB,YA), (R1G,R2B,ZJ,XB,YA), (R1H,R2B,ZJ,XB,YA), (R1I,R2B,ZJ,XB,YA), (R1J,R2B,ZJ,XB,YA), (R1K,R2B,ZJ,XB,YA), (R1L,R2B,ZJ,XB,YA), (R1M,R2B,ZJ,XB,YA), (R1N,R2B,ZJ,XB,YA), (R1O,R2B,ZJ,XB,YA), (R1P,R2B,ZJ,XB,YA), (R1Q,R2B,ZJ,XB,YA), (R1A,R2C,ZJ,XB,YA), (R1B,R2C,ZJ,XB,YA), (R1C,R2C,ZJ,XB,YA), (R1D,R2C,ZJ,XB,YA), (R1E,R2C,ZJ,XB,YA), (R1F,R2C,ZJ,XB,YA), (R1G,R2C,ZJ,XB,YA), (R1H,R2C,ZJ,XB,YA), (R1I,R2C,ZJ,XB,YA), (R1J,R2C,ZJ,XB,YA), (R1K,R2C,ZJ,XB,YA), (R1L,R2C,ZJ,XB,YA), (R1M,R2C,ZJ,XB,YA), (R1N,R2C,ZJ,XB,YA), (R1O,R2C,ZJ,XB,YA), (R1P,R2C,ZJ,XB,YA), (R1Q,R2C,ZJ,XB,YA), (R1A,R2D,ZJ,XB,YA), (R1B,R2D,ZJ,XB,YA), (R1C,R2D,ZJ,XB,YA), (R1D,R2D,ZJ,XB,YA), (R1E,R2D,ZJ,XB,YA), (R1F,R2D,ZJ,XB,YA), (R1G,R2D,ZJ,XB,YA), (R1H,R2D,ZJ,XB,YA), (R1I,R2D,ZJ,XB,YA), (R1J,R2D,ZJ,XB,YA), (R1K,R2D,ZJ,XB,YA), (R1L,R2D,ZJ,XB,YA), (R1M,R2D,ZJ,XB,YA), (R1N,R2D,ZJ,XB,YA), (R1O,R2D,ZJ,XB,YA), (R1P,R2D,ZJ,XB,YA), (R1Q,R2D,ZJ,XB,YA), (R1A,R2E,ZJ,XB,YA), (R1B,R2E,ZJ,XB,YA), (R1C,R2E,ZJ,XB,YA), (R1D,R2E,ZJ,XB,YA), (R1E,R2E,ZJ,XB,YA), (R1F,R2E,ZJ,XB,YA), (R1G,R2E,ZJ,XB,YA), (R1H,R2E,ZJ,XB,YA), (R1I,R2E,ZJ,XB,YA), (R1J,R2E,ZJ,XB,YA), (R1K,R2E,ZJ,XB,YA), (R1L,R2E,ZJ,XB,YA), (R1M,R2E,ZJ,XB,YA), (R1N,R2E,ZJ,XB,YA), (R1O,R2E,ZJ,XB,YA), (R1P,R2E,ZJ,XB,YA), (R1Q,R2E,ZJ,XB,YA), (R1A,R2F,ZJ,XB,YA), (R1B,R2F,ZJ,XB,YA), (R1C,R2F,ZJ,XB,YA), (R1D,R2F,ZJ,XB,YA), (R1E,R2F,ZJ,XB,YA), (R1F,R2F,ZJ,XB,YA), (R1G,R2F,ZJ,XB,YA), (R1H,R2F,ZJ,XB,YA), (R1I,R2F,ZJ,XB,YA), (R1J,R2F,ZJ,XB,YA), (R1K,R2F,ZJ,XB,YA), (R1L,R2F,ZJ,XB,YA), (R1M,R2F,ZJ,XB,YA), (R1N,R2F,ZJ,XB,YA), (R1O,R2F,ZJ,XB,YA), (R1P,R2F,ZJ,XB,YA), (R1Q,R2F,ZJ,XB,YA), (R1A,R2G,ZJ,XB,YA), (R1B,R2G,ZJ,XB,YA), (R1C,R2G,ZJ,XB,YA), (R1D,R2G,ZJ,XB,YA), (R1E,R2G,ZJ,XB,YA), (R1F,R2G,ZJ,XB,YA), (R1G,R2G,ZJ,XB,YA), (R1H,R2G,ZJ,XB,YA), (R1I,R2G,ZJ,XB,YA), (R1J,R2G,ZJ,XB,YA), (R1K,R2G,ZJ,XB,YA), (R1L,R2G,ZJ,XB,YA), (R1M,R2G,ZJ,XB,YA), (R1N,R2G,ZJ,XB,YA), (R1O,R2G,ZJ,XB,YA), (R1P,R2G,ZJ,XB,YA), (R1Q,R2G,ZJ,XB,YA), (R1A,R2H,ZJ,XB,YA), (R1B,R2H,ZJ,XB,YA), (R1C,R2H,ZJ,XB,YA), (R1D,R2H,ZJ,XB,YA), (R1E,R2H,ZJ,XB,YA), (R1F,R2H,ZJ,XB,YA), (R1G,R2H,ZJ,XB,YA), (R1H,R2H,ZJ,XB,YA), (R1I,R2H,ZJ,XB,YA), (R1J,R2H,ZJ,XB,YA), (R1K,R2H,ZJ,XB,YA), (R1L,R2H,ZJ,XB,YA), (R1M,R2H,ZJ,XB,YA), (R1N,R2H,ZJ,XB,YA), (R1O,R2H,ZJ,XB,YA), (R1P,R2H,ZJ,XB,YA), (R1Q,R2H,ZJ,XB,YA), (R1A,R2I,ZJ,XB,YA), (R1B,R2I,ZJ,XB,YA), (R1C,R2I,ZJ,XB,YA), (R1D,R2I,ZJ,XB,YA), (R1E,R2I,ZJ,XB,YA), (R1F,R2I,ZJ,XB,YA), (R1G,R2I,ZJ,XB,YA), (R1H,R2I,ZJ,XB,YA), (R1I,R2I,ZJ,XB,YA), (R1J,R2I,ZJ,XB,YA), (R1K,R2I,ZJ,XB,YA), (R1L,R1I,ZJ,XB,YA), (R1M,R2I,ZJ,XB,YA), (R1N,R2I,ZJ,XB,YA), (R1O,R2I,ZJ,XB,YA), (R1P,R2I,ZJ,XB,YA), (R1Q,R2I,ZJ,XB,YA), (R1A,R2J,ZJ,XB,YA), (R1B,R2J,ZJ,XB,YA), (R1C,R2J,ZJ,XB,YA), (R1D,R2J,ZJ,XB,YA), (R1E,R2J,ZJ,XB,YA), (R1F,R2J,ZJ,XB,YA), (R1G,R2J,ZJ, XB,YA), (R1H,R2J,ZJ,XB,YA), (R1I,R2J,ZJ,XB,YA), (R1J, R2J,ZJ,XB,YA), (R1K,R2J,ZJ,XB,YA), (R1L,R2J,ZJ,XB, YA), (R1M,R2J,ZJ,XB,YA), (R1N,R2J,ZJ,XB,YA), (R1O, R2J,ZJ,XB,YA), (R1P,R2J,ZJ,XB,YA), (R1Q,R2J,ZJ,XB, YA), (R1A,R2K,ZJ,XB,YA), (R1B,R2K,ZJ,XB,YA), (R1C, R2K,ZJ,XB,YA), (R1D,R2K,ZJ,XB,YA), (R1E,R2K,ZJ, XB,YA), (R1F,R2K,ZJ,XB,YA), (R1G,R2K,ZJ,XB,YA), (R1H,R2K,ZJ,XB,YA), (R1I,R2K,ZJ,XB,YA), (R1J,R2K, ZJ,XB,YA), (R1K,R2K,ZJ,XB,YA), (R1L,R2K,ZJ,XB,YA), (R1M,R2K,ZJ,XB,YA), (R1N,R2K,ZJ,XB,YA), (R1O,R2K, ZJ,XB,YA), (R1P,R2K,ZJ,XB,YA), (R1Q,R2K,ZJ,XB,YA), (R1A,R2L,ZJ,XB,YA), (R1B,R2L,ZJ,XB,YA), (R1C,R2L, ZJ,XB,YA), (R1D,R2L,ZJ,XB,YA), (R1E,R2L,ZJ,XB,YA), (R1F,R2L,ZJ,XB,YA), (It 1G,R2L,ZJ,XB,YA), (R1H,R2L, ZJ,XB,YA), (R1I,R2L,ZJ,XB,YA), (R1J,R2L,ZJ,XB,YA), (R1K,R2L,ZJ,XB,YA), (R1L,R2L,ZJ,XB,YA), (R1M,R2L, ZJ,XB,YA), (R1N,R2L,ZJ,XB,YA), (R1O,R2L,ZJ,XB,YA), (R1P,R2L,ZJ,XB,YA), (R1Q,R2L,ZJ,XB,YA), (R1A,R2M, ZJ,XB,YA), (R1B,R2M,ZJ,XB,YA), (R1C,R2M,ZJ,XB, YA), (R1D,R2M,ZJ,XB,YA), (R1E,R2M,ZJ,XB,YA), (R1F, R2M,ZJ,XB,YA), (R1G,R2M,ZJ,XB,YA), (R1H,R2M,ZJ, XB,YA), (R1I,R2M,ZJ,XB,YA), (R1J,R2M,ZJ,XB,YA), (R1K,R2M,ZJ,XB,YA), (R1L,R2M,ZJ,XB,YA), (R1M, R2M,ZJ,XB,YA), (R1N,R2M,ZJ,XB,YA), (R1O,R2M,ZJ, XB,YA), (R1P,R2M,ZJ,XB,YA), (R1Q,R2M,ZJ,XB,YA), (R1A,R2N,ZJ,XB,YA), (R1B,R2N,ZJ,XB,YA), (R1C,R2N, ZJ,XB,YA), (R1D,R2N,ZJ,XB,YA), (R1E,R2N,ZJ,XB,YA), (R1F,R2N,ZJ,XB,YA), (R1G,R2N,ZJ,XB,YA), (R1H,R2N, ZJ,XB,YA), (R1I,R2N,ZJ,XB,YA), (R1J,R2N,ZJ,XB,YA), (R1K,R2N,ZJ,XB,YA), (R1L,R2N,ZJ,XB,YA), (R1M,R2N, ZJ,XB,YA), (R1N,R2N,ZJ,XB,YA), (R1O,R2N,ZJ,XB,YA), (R1P,R2N,ZJ,XB,YA), (R1Q,R2N,ZJ,XB,YA), (R1A,R2O, ZJ,XB,YA), (R1B,R2O,ZJ,XB,YA), (R1C,R2O,ZJ,XB,YA), (R1D,R2O,ZJ,XB,YA), (R1E,R2O,ZJ,XB,YA), (R1F,R2O, ZJ,XB,YA), (R1G,R2O,ZJ,XB,YA), (R1H,R2O,ZJ,XB,YA), (R1I,R2O,ZJ,XB,YA), (R1J,R2O,ZJ,XB,YA), (R1K,R2O, ZJ,XB,YA), (R1L,R2O,ZJ,XB,YA), (R1M,R2O,ZJ,XB,YA), (R1N,R2O,ZJ,XB,YA), (R1O,R2O,ZJ,XB,YA), (R1P,R2O, ZJ,XB,YA), (R1Q,R2O,ZJ,XB,YA), (R1A,R2P,ZJ,XB,YA), (R1B,R2P,ZJ,XB,YA), (R1C,R2P,ZJ,XB,YA), (R1D,R2P, ZJ,XB,YA), (R1E,R2P,ZJ,XB,YA), (R1F,R2P,ZJ,XB,YA), (R1G,R2P,ZJ,XB,YA), (R1H,R2P,ZJ,XB,YA), (R1I,R2P,ZJ, XB,YA), (R1J,R2P,ZJ,XB,YA), (R1K,R2P,ZJ,XB,YA), (R1L,R2P,ZJ,XB,YA), (R1M,R2P,ZJ,XB,YA), (R1N,R2P, ZJ,XB,YA), (R1O,R2P,ZJ,XB,YA), (R1P,R2P,ZJ,XB,YA), (R1Q,R2P,ZJ,XB,YA), (R1A,R2Q,ZJ,XB,YA), (R1B,R2Q, ZJ,XB,YA), (R1C,R2Q,ZJ,XB,YA), (R1D,R2Q,ZJ,XB,YA), (R1E,R2Q,ZJ,XB,YA), (R1F,R2Q,ZJ,XB,YA), (R1G,R2Q, ZJ,XB,YA), (R1H,R2Q,ZJ,XB,YA), (R1I,R2Q,ZJ,XB,YA), (R1J,R2Q,ZJ,XB,YA), (R1K,R2Q,ZJ,XB,YA), (R1L,R2Q, ZJ,XB,YA), (R1M,R2Q,ZJ,XB,YA), (R1N,R2Q,ZJ,XB, YA), (R1O,R2Q,ZJ,XB,YA), (R1P,R2Q,ZJ,XB,YA), (R1Q, R2Q,ZJ,XB,YA), (R1A,R2A,ZK,XB,YA), (R1B,R2A,ZK, XB,YA), (R1C,R2A,ZK,XB,YA), (R1D,R2A,ZK,XB,YA), (R1E,R2A,ZK,XB,YA), (R1F,R2A,ZK,XB,YA), (R1G, R2A,ZK,XB,YA), (R1H,R2A,ZK,XB,YA), (R1I,R2A,ZK, XB,YA), (R1J,R2A,ZK,XB,YA), (R1K,R2A,ZK,XB,YA), (R1L,R2A,ZK,XB,YA), (R1M,R2A,ZK,XB,YA), (R1N, R2A,ZK,XB,YA), (R1O,R2A,ZK,XB,YA), (R1P,R2A,ZK, XB,YA), (R1Q,R2A,ZK,XB,YA), (R1A,R2B,ZK,XB,YA), (R1B,R2B,ZK,XB,YA), (R1C,R2B,ZK,XB,YA), (R1D, R2B,ZK,XB,YA), (R1E,R2B,ZK,XB,YA), (R1F,R2B,ZK, XB,YA), (R1G,R2B,ZK,XB,YA), (R1H,R2B,ZK,XB,YA), (R1I,R2B,ZK,XB,YA), (R1J,R2B,ZK,XB,YA), (R1K,R2B, ZK,XB,YA), (R1L,R2B,ZK,XB,YA), (R1M,R2B,ZK,XB, YA), (R1N,R2B,ZK,XB,YA), (R1O,R2B,ZK,XB,YA), (R1P, R2B,ZK,XB,YA), (R1Q,R2B,ZK,XB,YA), (R1A,R2C,ZK, XB,YA), (R1B,R2C,ZK,XB,YA), (R1C,R22C,ZK,XB,YA), (R1D,R2C,ZK,XB,YA), (R1E,R2C,ZK,XB,YA), (R1F,R2C, ZK,XB,YA), (R1G,R2C,ZK,XB,YA), (R1H,R2C,ZK,XB, YA), (R1I,R2C,ZK,XB,YA), (R1J,R2C,ZK,XB,YA), (R1K, R2C,ZK,XB,YA), (R1L,R2C,ZK,XB,YA), (R1M,R2C,ZK, XB,YA), (R1N,R2C,ZK,XB,YA), (R1O,R2C,ZK,XB,YA), (R1P,R2C,ZK,XB,YA), (R1Q,R2C,ZK,XB,YA), (R1A, R2D,ZK,XB,YA), (R1B,R2D,ZK,XB,YA), (R1C,R2D,ZK, XB,YA), (R1D,R2D,ZK,XB,YA), (R1E,R2D,ZK,XB,YA), (R1F,R2D,ZK,XB,YA), (R1G,R2D,ZK,XB,YA), (R1H, R2D,ZK,XB,YA), (R1I,R2D,ZK,XB,YA), (R1J,R2D,ZK, XB,YA), (R1K,R2D,ZK,XB,YA), (R1L,R2D,ZK,XB,YA), (R1M,R2D,ZK,XB,YA), (R1N,R2D,ZK,XB,YA), (R1O, R2D,ZK,XB,YA), (R1P,R2D,ZK,XB,YA), (R1Q,R2D,ZK, XB,YA), (R1A,R2E,ZK,XB,YA), (R1B,R2E,ZK,XB,YA), (R1C,R2E,ZK,XB,YA), (R1D,R2E,ZK,XB,YA), (R1E,R2E, ZK,XB,YA), (R1F,R2E,ZK,XB,YA), (R1G,R2E,ZK,XB, YA), (R1H,R2E,ZK,XB,YA), (R1I,R2E,ZK,XB,YA), (R1J, R2E,ZK,XB,YA), (R1K,R2E,ZK,XB,YA), (R1L,R2E,ZK, XB,YA), (R1M,R2E,ZK,XB,YA), (R1N,R2E,ZK,XB,YA), (R1O,R2E,ZK,XB,YA), (R1P,R2E,ZK,XB,YA), (R1Q,R2E, ZK,XB,YA), (R1A,R2F,ZK,XB,YA), (R1B,R2F,ZK,XB, YA), (R1C,R2F,ZK,XB,YA), (R1D,R2F,ZK,XB,YA), (R1E, R2F,ZK,XB,YA), (R1F,R2F,ZK,XB,YA), (R1G,R2F,ZK, XB,YA), (R1H,R2F,ZK,XB,YA), (R1I,R2F,ZK,XB,YA), (R1J,R2F,ZK,XB,YA), (R1K,R2F,ZK,XB,YA), (R1L,R2F, ZK,XB,YA), (R1M,R2F,ZK,XB,YA), (R1N,R2F,ZK,XB, YA), (R1O,R2F,ZK,XB,YA), (R1P,R2F,ZK,XB,YA), (R1Q, R2F,ZK,XB,YA), (R1A,R2G,ZK,XB,YA), (R1B,R2G,ZK, XB,YA), (R1C,R2G,ZK,XB,YA), (R1D,R2G,ZK,XB,YA), (R1E,R2G,ZK,XB,YA), (R1F,R2G,ZK,XB,YA), (R1G, R2G,ZK,XB,YA), (R1H,R2G,ZK,XB,YA), (R1I,R2G,ZK, XB,YA), (R1J,R2G,ZK,XB,YA), (R1K,R2G,ZK,XB,YA), (R1L,R2G,ZK,XB,YA), (R1M,R2G,ZK,XB,YA), (R1N, R2G,ZK,XB,YA), (R1O,R2G,ZK,XB,YA), (R1P,R2G,ZK, XB,YA), (R1Q,R2G,ZK,XB,YA), (R1A,R2H,ZK,XB,YA), (R1B,R2H,ZK,XB,YA), (R1C,R2H,ZK,XB,YA), (R1D, R2H,ZK,XB,YA), (R1E,R2H,ZK,XB,YA), (R1F,R2H,ZK, XB,YA), (R1G,R2H,ZK,XB,YA), (R1H,R2H,ZK,XB,YA), (R1I,R2H,ZK,XB,YA), (R1J,R2H,ZK,XB,YA), (R1K,R2H, ZK,XB,YA), (R1L,R2H,ZK,XB,YA), (R1M,R2H,ZK,XB, YA), (R1N,R2H,ZK,XB,YA), (R1O,R2H,ZK,XB,YA), (R1P,R2H,ZK,XB,YA), (R1Q,R2H,ZK,XB,YA), (R1A,R2I, ZK,XB,YA), (R1B,R2I,ZK,XB,YA), (R1C,R2I,ZK,XB, YA), (R1D,R2I,ZK,XB,YA), (R1E,R2I,ZK,XB,YA), (R1F, R2I,ZK,XB,YA), (R1G,R2I,ZK,XB,YA), (R1H,R2I,ZK,XB, YA), (R1I,R2I,ZK,XB,YA), (R1J,R21,ZK,XB,YA), (R1K, R2I,ZK,XB,YA), (R1L,R2I,ZK,XB,YA), (R1M,R2I,ZK, XB,YA), (R1N,R2I,ZK,XB,YA), (R1O,R2I,ZK,XB,YA), (R1P,R2I,ZK,XB,YA), (R1Q,R2I,ZK,XB,YA), (R1A,R2J, ZK,XB,YA), (R1B,R2J,ZK,XB,YA), (R1C,R2J,ZK,XB, YA), (R1D,R2J,ZK,XB,YA), (R1E,R2J,ZK,XB,YA), (R1F, R2J,ZK,XB,YA), (R1G,R2J,ZK,XB,YA), (R1H,R2J,ZK, XB,YA), (R1I,R2J,ZK,XB,YA), (R1J,R2J,ZK,XB,YA), (R1K,R2J,ZK,XB,YA), (R1L,R2J,ZK,XB,YA), (R1M,R2J, ZK,XB,YA), (R1N,R2J,ZK,XB,YA), (R1O,R2J,ZK,XB, YA), (R1P,R2J,ZK,XB,YA), (R1Q,R2J,ZK,XB,YA), (R1A, R2K,ZK,XB,YA), (R1B,R2K,ZK,XB,YA), (R1C,R2K,ZK, XB,YA), (R1D,R2K,ZK,XB,YA), (R1E,R2K,ZK,XB,YA), (R1F,R2K,ZK,XB,YA), (R1G,R2K,ZK,XB,YA), (R1H, R2K,ZK,XB,YA), (R1I,R2K,ZK,XB,YA), (R1J,R2K,ZK, XB,YA), (R1K,R2K,ZK,XB,YA), (R1L,R2K,ZK,XB,YA), (R1M,R2K,ZK,XB,YA), (R1N,R2K,ZK,XB,YA), (R1O, R2K,ZK,XB,YA), (R1P,R2K,ZK,XB,YA), (R1Q,R2K,ZK, XB,YA), (R1A,R2L,ZK,XB,YA), (R1B,R2L,ZK,XB,YA), (R1C,R2L,ZK,XB,YA), (R1D,R2L,ZK,XB,YA), (R1E,R2L, ZK,XB,YA), (R1F,R2L,ZK,XB,YA), (R1G,R2L,ZK,XB, YA), (R1H,R2L,ZK,XB,YA), (R1I,R2L,ZK,XB,YA), (R1J, R2L,ZK,XB,YA), (R1K,R2L,ZK,XB,YA), (R1L,R2L,ZK, XB,YA), (R1M,R2L,ZK,XB,YA), (R1N,R2L,ZK,XB,YA), (R1O,R2L,ZK,XB,YA), (R1P,R2L,ZK,XB,YA), (R1Q,R2L, ZK,XB,YA), (R1A,R2M,ZK,XB,YA), (R1B,R2M,ZK,XB, YA), (R1C,R2M,ZK,XB,YA), (R1D,R2M,ZK,XB,YA), (R1E,R2M,ZK,XB,YA), (R1F,R2M,ZK,XB,YA), (R1G, R2M,ZK,XB,YA), (R1H,R2M,ZK,XB,YA), (R1I,R2M,ZK, XB,YA), (R1J,R2M,ZK,XB,YA), (R1K,R2M,ZK,XB,YA), (R1L,R2M,ZK,XB,YA), (R1M,R2M,ZK,XB,YA), (R1N, R2M,ZK,XB,YA), (R1O,R2M,ZK,XB,YA), (R1P,R2M,ZK, XB,YA), (R1Q,R2M,ZK,XB,YA), (R1A,R2N,ZK,XB,YA), (R1B,R2N,ZK,XB,YA), (R1C,R2N,ZK,XB,YA), (R1D, R2N,ZK,XB,YA), (R1E,R2N,ZK,XB,YA), (R1F,R2N,ZK, XB,YA), (R1G,R2N,ZK,XB,YA), (R1H,R2N,ZK,XB,YA), (R1I,R2N,ZK,XB,YA), (R1J,R2N,ZK,XB,YA), (R1K,R2N, ZK,XB,YA), (R1L,R2N,ZK,XB,YA), (R1M,R2N,ZK,XB, YA), (R1N,R2N,ZK,XB,YA), (R1O,R2N,ZK,XB,YA), (R1P,R2N,ZK,XB,YA), (R1Q,R2N,ZK,XB,YA), (R1A, R2O,ZK,XB,YA), (R1B,R2O,ZK,XB,YA), (R1C,R2O,ZK, XB,YA), (R1D,R2O,ZK,XB,YA), (R1E,R2O,ZK,XB,YA), (R1F,R2O,ZK,XB,YA), (R1G,R2O,ZK,XB,YA), (R1H, R2O,ZK,XB,YA), (R1I,R2O,ZK,XB,YA), (R1J,R2O,ZK, XB,YA), (R1K,R2O,ZK,XB,YA), (R1L,R2O,ZK,XB,YA), (R1M,R2O,ZK,XB,YA), (R1N,R2O,ZK,XB,YA), (R1O, R2O,ZK,XB,YA), (R1P,R2O,ZK,XB,YA), (R1Q,R2O,ZK, XB,YA), (R1A,R2P,ZK,XB,YA), (R1B,R2P,ZK,XB,YA), (R1C,R2P,ZK,XB,YA), (R1D,R2P,ZK,XB,YA), (R1E,R2P, ZK,XB,YA), (R1F,R2P,ZK,XB,YA), (R1G,R2P,ZK,XB, YA), (R1H,R2P,ZK,XB,YA), (R1I,R2P,ZK,XB,YA), (R1J, R2P,ZK,XB,YA), (R1K,R2P,ZK,XB,YA), (R1L,R2P,ZK, XB,YA), (R1M,R2P,ZK,XB,YA), (R1N,R2P,ZK,XB,YA), (R1O,R2P,ZK,XB,YA), (R1P,R2P,ZK,XB,YA), (R1Q,R2P, ZK,XB,YA), (R1A,R2Q,ZK,XB,YA), (R1B,R2Q,ZK,XB, YA), (R1C,R2Q,ZK,XB,YA), (R1D,R2Q,ZK,XB,YA), (R1E,R2Q,ZK,XB,YA), (R1F,R2Q,ZK,XB,YA), (R1G, R2Q,ZK,XB,YA), (R1H,R2Q,ZK,XB,YA), (R1I,R2Q,ZK, XB,YA), (R1J,R2Q,ZK,XB,YA), (R1K,R2Q,ZK,XB,YA), (R1L,R2Q,ZK,XB,YA), (R1M,R2Q,ZK,XB,YA), (R1N, R2Q,ZK,XB,YA), (R1O,R2Q,ZK,XB,YA), (R1P,R2Q,ZK, XB,YA), (R1Q,R2Q,ZK,XB,YA), (R1A,R2A,ZL,XB,YA), (R1B,R2A,ZL,XB,YA), (R1C,R2A,ZL,XB,YA), (R1D, R2A,ZL,XB,YA), (R1E,R2A,ZL,XB,YA), (R1F,R2A,ZL, XB,YA), (R1G,R2A,ZL,XB,YA), (R1H,R2A,ZL,XB,YA), (R1I,R2A,ZL,XB,YA), (R1J,R2A,ZL,XB,YA), (R1K,R2A, ZL,XB,YA), (R1L,R2A,ZL,XB,YA), (R1M,R2A,ZL,XB, YA), (R1N,R2A,ZL,XB,YA), (R1O,R2A,ZL,XB,YA), (R1P, R2A,ZL,XB,YA), (R1Q,R2A,ZL,XB,YA), (R1A,R2B,ZL, XB,YA), (R1B,R2B,ZL,XB,YA), (R1C,R2B,ZL,XB,YA), (R1D,R2B,ZL,XB,YA), (R1E,R2B,ZL,XB,YA), (R1F,R2B, ZL,XB,YA), (R1G,R2B,ZL,XB,YA), (R1H,R2B,ZL,XB, YA), (R1I,R2B,ZL,XB,YA), (R1J,R2B,ZL,XB,YA), (R1K, R2B,ZL,XB,YA), (R1L,R2B,ZL,XB,YA), (R1M,R2B,ZL, XB,YA), (R1N,R2B,ZL,XB,YA), (R1O,R2B,ZL,XB,YA), (R1P,R2B,ZL,XB,YA), (R1Q,R2B,ZL,XB,YA), (R1A,R2C, ZL,XB,YA), (R1B,R2C,ZL,XB,YA), (R1C,R2C,ZL,XB, YA), (R1D,R2C,ZL,XB,YA), (R1E,R2C,ZL,XB,YA), (R1F, R2C,ZL,XB,YA), (R1G,R2C,ZL,XB,YA), (R1H,R2C,ZL, XB,YA), (R1I,R2C,ZL,XB,YA), (R1J,R2C,ZL,XB,YA), (R1K,R2C,ZL,XB,YA), (R1L,R2C,ZL,XB,YA), (R1M, R2C,ZL,XB,YA), (R1N,R2C,ZL,XB,YA), (R1O,R2C,ZL, XB,YA), (R1P,R2C,ZL,XB,YA), (R1Q,R2C,ZL,XB,YA), (R1A,R2D,ZL,XB,YA), (R1B,R2D,ZL,XB,YA), (R1C, R2D,ZL,XB,YA), (R1D,R2D,ZL,XB,YA), (R1E,R2D,ZL, XB,YA), (R1F,R2D,ZL,XB,YA), (R1G,R2D,ZL,XB,YA), (R1H,R2D,ZL,XB,YA), (R1I,R2D,ZL,XB,YA), (R1J,R2D, ZL,XB,YA), (R1K,R2D,ZL,XB,YA), (R1L,R2D,ZL,XB, YA), (R1M,R2D,ZL,XB,YA), (R1N,R2D,ZL,XB,YA), (R1O,R2D,ZL,XB,YA), (R1P,R2D,ZL,XB,YA), (R1Q,R2D, ZL,XB,YA), (R1A,R2E,ZL,XB,YA), (R1B,R2E,ZL,XB, YA), (R1C,R2E,ZL,XB,YA), (R1D,R2E,ZL,XB,YA), (R1E, R2E,ZL,XB,YA), (R1F,R2E,ZL,XB,YA), (R1G,R2E,ZL, XB,YA), (R1H,R2E,ZL,XB,YA), (R1I,R2E,ZL,XB,YA), (R1J,R2E,ZL,XB,YA), (R1K,R2E,ZL,XB,YA), (R1L,R2E, ZL,XB,YA), (R1M,R2E,ZL,XB,YA), (R1N,R2E,ZL,XB, YA), (R1O,R2E,ZL,XB,YA), (R1P,R2E,ZL,XB,YA), (R1Q, R2E,ZL,XB,YA), (R1A,R2F,ZL,XB,YA), (R1B,R2F,ZL, XB,YA), (R1C,R2F,ZL,XB,YA), (R1D,R2F,ZL,XB,YA), (R1E,R2F,ZL,XB,YA), (R1F,R2F,ZL,XB,YA), (R1G,R2F, ZL,XB,YA), (R1H,R2F,ZL,XB,YA), (R1I,R2F,ZL,XB,YA), (R1J,R2F,ZL,XB,YA), (R1K,R2F,ZL,XB,YA), (R1L,R2F, ZL,XB,YA), (R1M,R2F,ZL,XB,YA), (R1N,R2F,ZL,XB, YA), (R1O,R2F,ZL,XB,YA), (R1P,R2F,ZL,XB,YA), (R1Q, R2F,ZL,XB,YA), (R1A,R2G,ZL,XB,YA), (R1B,R2G,ZL, XB,YA), (R1C,R2G,ZL,XB,YA), (R1D,R2G,ZL,XB,YA), (R1E,R2G,ZL,XB,YA), (R1F,R2G,ZL,XB,YA), (R1G,R2G, ZL,XB,YA), (R1H,R2G,ZL,XB,YA), (R1I,R2G,ZL,XB, YA), (R1J,R2G,ZL,XB,YA), (R1K,R2G,ZL,XB,YA), (R1L, R2G,ZL,XB,YA), (R1M,R2G,ZL,XB,YA), (R1N,R2G,ZL, XB,YA), (R1O,R2G,ZL,XB,YA), (R1P,R2G,ZL,XB,YA), (R1Q,R2G,ZL,XB,YA), (R1A,R2H,ZL,XB,YA), (R1B, R2H,ZL,XB,YA), (R1C,R2H,ZL,XB,YA), (R1D,R2H,ZL, XB,YA), (R1E,R2H,ZL,XB,YA), (R1F,R2H,ZL,XB,YA), (R1G,R2H,ZL,XB,YA), (R1H,R2H,ZL,XB,YA), (R1I,R2H, ZL,XB,YA), (R1J,R2H,ZL,XB,YA), (R1K,R2H,ZL,XB, YA), (R1L,R2H,ZL,XB,YA), (R1M,R2H,ZL,XB,YA), (R1N,R2H,ZL,XB,YA), (R1O,R2H,ZL,XB,YA), (R1P,R2H, ZL,XB,YA), (R1Q,R2H,ZL,XB,YA), (R1A,R2I,ZL,XB, YA), (R1B,R2I,ZL,XB,YA), (R1C,R2I,ZL,XB,YA), (R1D, R2I,ZL,XB,YA), (R1E,R2I,ZL,XB,YA), (R1F,R2I,ZL,XB, YA), (R1G,R2I,ZL,XB,YA), (R1H,R2I,ZL,XB,YA), (R1I, R2I,ZL,XB,YA), (R1J,R2I,ZL,XB,YA), (R1K,R2I,ZL,XB, YA), (R1L,R2I,ZL,XB,YA), (R1M,R2I,ZL,XB,YA), (R1N, R2I,ZL,XB,YA), (R1O,R2I,ZL,XB,YA), (R1P,R2I,ZL,XB, YA), (R1Q,R2I,ZL,XB,YA), (R1A,R2J,ZL,XB,YA), (R1B, R2J,ZL,XB,YA), (R1C,R2J,ZL,XB,YA), (R1D,R2J,ZL,XB, YA), (R1E,R2J,ZL,XB,YA), (R1F,R2J,ZL,XB,YA), (R1G, R2J,ZL,XB,YA), (R1H,R2J,ZL,XB,YA), (R1I,R2J,ZL,XB, YA), (R1J,R2J,ZL,XB,YA), (R1K,R2J,ZL,XB,YA), (R1L, R2J,ZL,XB,YA), (R1M,R2J,ZL,XB,YA), (R1N,R2J,ZL,XB, YA), (R1O,R2J,ZL,XB,YA), (R1P,R2J,ZL,XB,YA), (R1Q, R2J,ZL,XB,YA), (R1A,R2K,ZL,XB,YA), (R1B,R2K,ZL, XB,YA), (R1C,R2K,ZL,XB,YA), (R1D,R2K,ZL,XB,YA), (R1E,R2K,ZL,XB,YA), (R1F,R2K,ZL,XB,YA), (R1G,R2K, ZL,XB,YA), (R1H,R2K,ZL,XB,YA), (R1I,R2K,ZL,XB, YA), (R1J,R2K,ZL,XB,YA), (R1K,R2K,ZL,XB,YA), (R1L, R2K,ZL,XB,YA), (R1M,R2K,ZL,XB,YA), (R1N,R2K,ZL, XB,YA), (R1O,R2K,ZL,XB,YA), (R1P,R2K,ZL,XB,YA), (R1Q,R2K,ZL,XB,YA), (R1A,R2L,ZL,XB,YA), (R1B,R2L, ZL,XB,YA), (R1C,R2L,ZL,XB,YA), (R1D,R2L,ZL,XB, YA), (R1E,R2L,ZL,XB,YA), (R1F,R2L,ZL,XB,YA), (R1G, R2L,ZL,XB,YA), (R1H,R2L,ZL,XB,YA), (R1I,R2L,ZL, XB,YA), (R1J,R2L,ZL,XB,YA), (R1K,R2L,ZL,XB,YA), (R1L,R2L,ZL,XB,YA), (R1M,R2L,ZL,XB,YA), (R1N,R2L, ZL,XB,YA), (R1O,R2L,ZL,XB,YA), (R1P,R2L,ZL,XB, YA), (R1Q,R2L,ZL,XB,YA), (R1A,R2M,ZL,XB,YA), (R1B,R2M,ZL,XB,YA), (R1C,R2M,ZL,XB,YA), (R1D, R2M,ZL,XB,YA), (R1E,R2M,ZL,XB,YA), (R1F,R2M,ZL, XB,YA), (R1G,R2M,ZL,XB,YA), (R1H,R2M,ZL,XB,YA), (R1I,R2M,ZL,XB,YA), (R1J,R2M,ZL,XB,YA), (R1K,R2M, ZL,XB,YA), (R1L,R2M,ZL,XB,YA), (R1M,R2M,ZL,XB, YA), (R1N,R2M,ZL,XB,YA), (R1O,R2M,ZL,XB,YA), (R1P,R2M,ZL,XB,YA), (R1Q,R2M,ZL,XB,YA), (R1A, R2N,ZL,XB,YA), (R1B,R2N,ZL,XB,YA), (R1C,R2N,ZL, XB,YA), (R1D,R2N,ZL,XB,YA), (R1E,R2N,ZL,XB,YA), (R1F,R2N,ZL,XB,YA), (R1G,R2N,ZL,XB,YA), (R1H,R2N, ZL,XB,YA), (R1I,R2N,ZL,XB,YA), (R1J,R2N,ZL,XB,YA), (R1K,R2N,ZL,XB,YA), (R1L,R2N,ZL,XB,YA), (R1M, R2N,ZL,XB,YA), (R1N,R2N,ZL,XB,YA), (R1O,R2N,ZL, XB,YA), (R1P,R2N,ZL,XB,YA), (R1Q,R2N,ZL,XB,YA), (R1A,R2O,ZL,XB,YA), (R1B,R2O,ZL,XB,YA), (R1C, R2O,ZL,XB,YA), (R1D,R2O,ZL,XB,YA), (R1E,R2O,ZL, XB,YA), (R1F,R2O,ZL,XB,YA), (R1G,R2O,ZL,XB,YA), (R1H,R2O,ZL,XB,YA), (R1I,R2O,ZL,XB,YA), (R1J,R2O, ZL,XB,YA), (R1K,R2O,ZL,XB,YA), (R1L,R2O,ZL,XB, YA), (R1M,R2O,ZL,XB,YA), (R1N,R2O,ZL,XB,YA), (R1O,R2O,ZL,XB,YA), (R1P,R2O,ZL,XB,YA), (R1Q,R2O, ZL,XB,YA), (R1A,R2P,ZL,XB,YA), (R1B,R2P,ZL,XB,YA), (R1C,R2P,ZL,XB,YA), (R1D,R2P,ZL,XB,YA), (R1E,R2P, ZL,XB,YA), (R1F,R2P,ZL,XB,YA), (R1G,R2P,ZL,XB,YA), (R1H,R2P,ZL,XB,YA), (R1I,R2P,ZL,XB,YA), (R1J,R2P, ZL,XB,YA), (R1K,R2P,ZL,XB,YA), (R1L,R2P,ZL,XB,YA), (R1M,R2P,ZL,XB,YA), (R1N,R2P,ZL,XB,YA), (R1O,R2P, ZL,XB,YA), (R1P,R2P,ZL,XB,YA), (R1Q,R2P,ZL,XB,YA), (R1A,R2Q,ZL,XB,YA), (R1B,R2Q,ZL,XB,YA), (R1C, R2Q,ZL,XB,YA), (R1D,R2Q,ZL,XB,YA), (R1E,R2Q,ZL, XB,YA), (R1F,R2Q,ZL,XB,YA), (R1G,R2Q,ZL,XB,YA), (R1H,R2Q,ZL,XB,YA), (R1I,R2Q,ZL,XB,YA), (R1J,R2Q, ZL,XB,YA), (R1K,R2Q,ZL,XB,YA), (R1L,R2Q,ZL,XB, YA), (R1M,R2Q,ZL,XB,YA), (R1N,R2Q,ZL,XB,YA), (R1O,R2Q,ZL,XB,YA), (R1P,R2Q,ZL,XB,YA), (R1Q,R2Q, ZL,XB,YA), (R1A,R2A,ZM,XB,YA), (R1B,R2A,ZM,XB, YA), (R1C,R2A,ZM,XB,YA), (R1D,R2A,ZM,XB,YA), (R1E,R2A,ZM,XB,YA), (R1F,R2A,ZM,XB,YA), (R1G, R2A,ZM,XB,YA), (R1H,R2A,ZM,XB,YA), (R1I,R2A,ZM, XB,YA), (R1J,R2A,ZM,XB,YA), (R1K,R2A,ZM,XB,YA), (R1L,R2A,ZM,XB,YA), (R1M,R2A,ZM,XB,YA), (R1N, R2A,ZM,XB,YA), (R1O,R2A,ZM,XB,YA), (R1P,R2A,ZM, XB,YA), (R1Q,R2A,ZM,XB,YA), (R1A,R2B,ZM,XB,YA), (R1B,R2B,ZM,XB,YA), (R1C,R2B,ZM,XB,YA), (R1D, R2B,ZM,XB,YA), (R1E,R2B,ZM,XB,YA), (R1F,R2B,ZM, XB,YA), (R1G,R2B,ZM,XB,YA), (R1H,R2B,ZM,XB,YA), (R1I,R2B,ZM,XB,YA), (R1J,R2B,ZM,XB,YA), (R1K,R2B, ZM,XB,YA), (R1L,R2B,ZM,XB,YA), (R1M,R2B,ZM,XB, YA), (R1N,R2B,ZM,XB,YA), (R1O,R2B,ZM,XB,YA), (R1P,R2B,ZM,XB,YA), (R1Q,R2B,ZM,XB,YA), (R1A, R2C,ZM,XB,YA), (R1B,R2C,ZM,XB,YA), (R1C,R2C,ZM, XB,YA), (R1D,R2C,ZM,XB,YA), (R1E,R2C,ZM,XB,YA), (R1F,R2C,ZM,XB,YA), (R1G,R2C,ZM,XB,YA), (R1H, R2C,ZM,XB,YA), (R1I,R2C,ZM,XB,YA), (R1J,R2C,ZM, XB,YA), (R1K,R2C,ZM,XB,YA), (R1L,R2C,ZM,XB,YA), (R1M,R2C,ZM,XB,YA), (R1N,R2C,ZM,XB,YA), (R1O, R2C,ZM,XB,YA), (R1P,R2C,ZM,XB,YA), (R1Q,R2C,ZM, XB,YA), (R1A,R2D,ZM,XB,YA), (R1B,R2D,ZM,XB,YA), (R1C,R2D,ZM,XB,YA), (R1D,R2D,ZM,XB,YA), (R1E, R2D,ZM,XB,YA), (R1F,R2D,ZM,XB,YA), (R1G,R2D,ZM, XB,YA), (R1H,R2D,ZM,XB,YA), (R1I,R2D,ZM,XB,YA), (R1J,R2D,ZM,XB,YA), (R1K,R2D,ZM,XB,YA), (R1L, R2D,ZM,XB,YA), (R1M,R2D,ZM,XB,YA), (R1N,R2D, ZM,XB,YA), (R1O,R2D,ZM,XB,YA), (R1P,R2D,ZM,XB, YA), (R1Q,R2D,ZM,XB,YA), (R1A,R2E,ZM,XB,YA), (R1B,R2E,ZM,XB,YA), (R1C,R2E,ZM,XB,YA), (R1D, R2E,ZM,XB,YA), (R1E,R2E,ZM,XB,YA), (R1F,R2E,ZM, XB,YA), (R1G,R2E,ZM,XB,YA), (R1H,R2E,ZM,XB,YA), (R1I,R2E,ZM,XB,YA), (R1J,R2E,ZM,XB,YA), (R1K,R2E, ZM,XB,YA), (R1L,R2E,ZM,XB,YA), (R1M,R2E,ZM,XB, YA), (R1N,R2E,ZM,XB,YA), (R1O,R2E,ZM,XB,YA), (R1P,R2E,ZM,XB,YA), (R1Q,R2E,ZM,XB,YA), (R1A,R2F, ZM,XB,YA), (R1B,R2F,ZM,XB,YA), (R1C,R2F,ZM,XB, YA), (R1D,R2F,ZM,XB,YA), (R1E,R2F,ZM,XB,YA), (R1F, R2F,ZM,XB,YA), (R1G,R2F,ZM,XB,YA), (R1H,R2F,ZM, XB,YA), (R1I,R2F,ZM,XB,YA), (R1J,R2F,ZM,XB,YA), (R1K,R2F,ZM,XB,YA), (R1L,R2F,ZM,XB,YA), (R1M, R2F,ZM,XB,YA), (R1N,R2F,ZM,XB,YA), (R1O,R2F,ZM, XB,YA), (R1P,R2F,ZM,XB,YA), (R1Q,R2F,ZM,XB,YA), (R1A,R2G,ZM,XB,YA), (R1B,R2G,ZM,XB,YA), (R1C, R2G,ZM,XB,YA), (R1D,R2G,ZM,XB,YA), (R1E,R2G, ZM,XB,YA), (R1F,R2G,ZM,XB,YA), (R1G,R2G,ZM,XB,YA), (R1H,R2G,ZM,XB,YA), (R1I,R2G,ZM,XB,YA), (R1J,R2G, ZM,XB,YA), (R1K,R2G,ZM,XB,YA), (R1L,R2G,ZM,XB, YA), (R1M,R2G,ZM,XB,YA), (R1N,R2G,ZM,XB,YA), (R1O,R2G,ZM,XB,YA), (R1P,R2G,ZM,XB,YA), (R1Q, R2G,ZM,XB,YA), (R1A,R2H,ZM,XB,YA), (R1B,R2H,ZM, XB,YA), (R1C,R2H,ZM,XB,YA), (R1D,R2H,ZM,XB,YA), (R1E,R2H,ZM,XB,YA), (R1F,R2H,ZM,XB,YA), (R1G, R2H,ZM,XB,YA), (R1H,R2H,ZM,XB,YA), (R1I,R2H,ZM, XB,YA), (R1J,R2H,ZM,XB,YA), (R1K,R2H,ZM,XB,YA), (R1L,R2H,ZM,XB,YA), (R1M,R2H,ZM,XB,YA), (R1N, R2H,ZM,XB,YA), (R1O,R2H,ZM,XB,YA), (R1P,R2H,ZM, XB,YA), (R1Q,R2H,ZM,XB,YA), (R1A,R2I,ZM,XB,YA), (R1B,R2I,ZM,XB,YA), (R1C,R2I,ZM,XB,YA), (R1D,R2I, ZM,XB,YA), (R1E,R2I,ZM,XB,YA), (R1F,R2I,ZM,XB, YA), (R1G,R2I,ZM,XB,YA), (R1H,R2I,ZM,XB,YA), (R1I, R2I,ZM,XB,YA), (R1J,R2I,ZM,XB,YA), (R1K,R2I,ZM, XB,YA), (R1L,R2I,ZM,XB,YA), (R1M,R2I,ZM,XB,YA), (R1N,R2I,ZM,XB,YA), (R1O,R2I,ZM,XB,YA), (R1P,R2I, ZM,XB,YA), (R1Q,R2I,ZM,XB,YA), (R1A,R2J,ZM,XB, YA), (R1B,R2J,ZM,XB,YA), (R1C,R2J,ZM,XB,YA), (R1D, R2J,ZM,XB,YA), (R1E,R2J,ZM,XB,YA), (R1F,R2J,ZM, XB,YA), (R1G,R2J,ZM,XB,YA), (R1H,R2J,ZM,XB,YA), (R1I,R2J,ZM,XB,YA), (R1J,R2J,ZM,XB,YA), (R1K,R2J, ZM,XB,YA), (R1L,R2J,ZM,XB,YA), (R1M,R2J,ZM,XB, YA), (R1N,R2J,ZM,XB,YA), (R1O,R2J,ZM,XB,YA), (R1P, R2J,ZM,XB,YA), (R1Q,R2J,ZM,XB,YA), (R1A,R2K,ZM, XB,YA), (R1B,R2K,ZM,XB,YA), (R1C,R2K,ZM,XB,YA), (R1D,R2K,ZM,XB,YA), (R1E,R2K,ZM,XB,YA), (R1F, R2K,ZM,XB,YA), (R1G,R2K,ZM,XB,YA), (R1H,R2K,ZM, XB,YA), (R1I,R2K,ZM,XB,YA), (R1J,R2K,ZM,XB,YA), (R1K,R2K,ZM,XB,YA), (R1L,R2K,ZM,XB,YA), (R1M, R2K,ZM,XB,YA), (R1N,R2K,ZM,XB,YA), (R1O,R2K,ZM, XB,YA), (R1P,R2K,ZM,XB,YA), (R1Q,R2K,ZM,XB,YA), (R1A,R2L,ZM,XB,YA), (R1B,R2L,ZM,XB,YA), (R1C, R2L,ZM,XB,YA), (R1D,R2L,ZM,XB,YA), (R1E,R2L,ZM, XB,YA), (R1F,R2L,ZM,XB,YA), (R1G,R2L,ZM,XB,YA), (R1H,R2L,ZM,XB,YA), (R1I,R2L,ZM,XB,YA), (R1J,R2L, ZM,XB,YA), (R1K,R2L,ZM,XB,YA), (R1L,R2L,ZM,XB, YA), (R1M,R2L,ZM,XB,YA), (R1N,R2L,ZM,XB,YA), (R1O,R2L,ZM,XB,YA), (R1P,R2L,ZM,XB,YA), (R1Q, R2L,ZM,XB,YA), (R1A,R2M,ZM,XB,YA), (R1B,R2M, ZM,XB,YA), (R1C,R2M,ZM,XB,YA), (R1D,R2M,ZM,XB, YA), (R1E,R2M,ZM,XB,YA), (R1F,R2M,ZM,XB,YA), (R1G,R2M,ZM,XB,YA), (R1H,R2M,ZM,XB,YA), (R1I, R2M,ZM,XB,YA), (R1J,R2M,ZM,XB,YA), (R1K,R2M, ZM,XB,YA), (R1L,R2M,ZM,XB,YA), (R1M,R2M,ZM,XB, YA), (R1N,R2M,ZM,XB,YA), (R1O,R2M,ZM,XB,YA), (R1P,R2M,ZM,XB,YA), (R1Q,R2M,ZM,XB,YA), (R1A, R2N,ZM,XB,YA), (R1B,R2N,ZM,XB,YA), (R1C,R2N,ZM, XB,YA), (R1D,R2N,ZM,XB,YA), (R1E,R2N,ZM,XB,YA), (R1F,R2N,ZM,XB,YA), (R1G,R2N,ZM,XB,YA), (R1H, R2N,ZM,XB,YA), (R1I,R2N,ZM,XB,YA), (R1J,R2N,ZM, XB,YA), (R1K,R2N,ZM,XB,YA), (R1L,R2N,ZM,XB,YA), (R1M,R2N,ZM,XB,YA), (R1N,R2N,ZM,XB,YA), (R1O, R2N,ZM,XB,YA), (R1P,R2N,ZM,XB,YA), (R1Q,R2N,ZM, XB,YA), (R1A,R2O,ZM,XB,YA), (R1B,R2O,ZM,XB,YA), (R1C,R2O,ZM,XB,YA), (R1D,R2O,ZM,XB,YA), (R1E, R2O,ZM,XB,YA), (R1F,R2O,ZM,XB,YA), (R1G,R2O, XB,YA), (R1H,R2O,ZM,XB,YA), (R1I,R2O,ZM,XB,YA), (R1J,R2O,ZM,XB,YA), (R1K,R2O,ZM,XB,YA), (R1L, R2O,ZM,XB,YA), (R1M,R2O,ZM,XB,YA), (R1N,R2O, ZM,XB,YA), (R1O,R2O,ZM,XB,YA), (R1P,R2O,ZM,XB, YA), (R1Q,R2O,ZM,XB,YA), (R1A,R2P,ZM,XB,YA), (R1B,R2P,ZM,XB,YA), (R1C,R2P,ZM,XB,YA), (R1D,R2P, ZM,XB,YA), (R1E,R2P,ZM,XB,YA), (R1F,R2P,ZM,XB, YA), (R1G,R2P,ZM,XB,YA), (R1H,R2P,ZM,XB,YA), (R1I, R2P,ZM,XB,YA), (R1J,R2P,ZM,XB,YA), (R1K,R2P,ZM, XB,YA), (R1L,R2P,ZM,XB,YA), (R1M,R2P,ZM,XB,YA), (R1N,R2P,ZM,XB,YA), (R1O,R2P,ZM,XB,YA), (R1P,R2P, ZM,XB,YA), (R1Q,R2P,ZM,XB,YA), (R1A,R2Q,ZM,XB, YA), (R1B,R2Q,ZM,XB,YA), (R1C,R2Q,ZM,XB,YA), (R1D,R2Q,ZM,XB,YA), (R1E,R2Q,ZM,XB,YA), (R1F, R2Q,ZM,XB,YA),(R1G,R2Q,ZM,XB,YA),(R1H,R2Q,ZM, XB,YA), (R1I,R2Q,ZM,XB,YA), (R1J,R2Q,ZM,XB,YA), (R1K,R2Q,ZM,XB,YA), (R1L,R2Q,ZM,XB,YA), (R1M, R2Q,ZM,XB,YA),(R1N,R2Q,ZM,XB,YA),(R1O,R2Q,ZM, XB,YA), (R1P,R2Q,ZM,XB,YA), (R1Q,R2Q,ZM,XB,YA), (R1A,R2A,ZN,XB,YA), (R1B,R2A,ZN,XB,YA), (R1C, R2A,ZN,XB,YA), (R1D,R2A,ZN,XB,YA), (R1E,R2A,ZN, XB,YA), (R1F,R2A,ZN,XB,YA), (R1G,R2A,ZN,XB,YA), (R1H,R2A,ZN,XB,YA), (R1I,R2A,ZN,XB,YA), (R1J,R2A, ZN,XB,YA), (R1K,R2A,ZN,XB,YA), (R1L,R2A,ZN,XB, YA), (R1M,R2A,ZN,XB,YA), (R1N,R2A,ZN,XB,YA), (R1O,R2A,ZN,XB,YA), (R1P,R2A,ZN,XB,YA), (R1Q, R2A,ZN,XB,YA), (R1A,R2B,ZN,XB,YA), (R1B,R2B,ZN, XB,YA), (R1C,R2B,ZN,XB,YA), (R1D,R2B,ZN,XB,YA), (R1E,R2B,ZN,XB,YA), (R1F,R2B,ZN,XB,YA), (R1G,R2B, ZN,XB,YA), (R1H,R2B,ZN,XB,YA), (R1I,R2B,ZN,XB, YA), (R1J,R2B,ZN,XB,YA), (R1K,R2B,ZN,XB,YA), (R1L, R2B,ZN,XB,YA), (R1M,R2B,ZN,XB,YA), (R1N,R2B,ZN, XB,YA), (R1O,R2B,ZN,XB,YA), (R1P,R2B,ZN,XB,YA), (R1Q,R2B,ZN,XB,YA), (R1A,R2C,ZN,XB,YA), (R1B, R2C,ZN,XB,YA), (R1C,R2C,ZN,XB,YA), (R1D,R2C,ZN, XB,YA), (R1E,R2C,ZN,XB,YA), (R1F,R2C,ZN,XB,YA), (R1G,R2C,ZN,XB,YA), (R1H,R2C,ZN,XB,YA), (R1I,R2C, ZN,XB,YA), (R1J,R2C,ZN,XB,YA), (R1K,R2C,ZN,XB, YA), (R1L,R2C,ZN,XB,YA), (R1M,R2C,ZN,XB,YA), (R1N,R22C,ZN,XB,YA), (R1O,R2C,ZN,XB,YA), (R1P, R2C,ZN,XB,YA), (R1Q,R2C,ZN,XB,YA), (R1A,R2D,ZN, XB,YA), (R1B,R2D,ZN,XB,YA), (R1C,R2D,ZN,XB,YA), (R1D,R2D,ZN,XB,YA), (R1E,R2D,ZN,XB,YA), (R1F, R2D,ZN,XB,YA), (R1G,R2D,ZN,XB,YA), (R1H,R2D,ZN, XB,YA), (R1I,R2D,ZN,XB,YA), (R1J,R2D,ZN,XB,YA), (R1K,R2D,ZN,XB,YA), (R1L,R2D,ZN,XB,YA), (R1M, R2D,ZN,XB,YA), (R1N,R2D,ZN,XB,YA), (R1O,R2D,ZN, XB,YA), (R1P,R2D,ZN,XB,YA), (R1Q,R2D,ZN,XB,YA), (R1A,R2E,ZN,XB,YA), (R1B,R2E,ZN,XB,YA), (R1C,R2E, ZN,XB,YA), (R1D,R2E,ZN,XB,YA), (R1E,R2E,ZN,XB, YA), (R1F,R2E,ZN,XB,YA), (R1G,R2E,ZN,XB,YA), (R1H, R2E,ZN,XB,YA), (R1I,R2E,ZN,XB,YA), (R1J,R2E,ZN, XB,YA), (R1K,R2E,ZN,XB,YA), (R1L,R2E,ZN,XB,YA), (R1M,R2E,ZN,XB,YA), (R1N,R2E,ZN,XB,YA), (R1O, R2E,ZN,XB,YA), (R1P,R2E,ZN,XB,YA), (R1Q,R2E,ZN, XB,YA), (R1A,R2F,ZN,XB,YA), (R1B,R2F,ZN,XB,YA), (R1C,R2F,ZN,XB,YA), (R1D,R2F,ZN,XB,YA), (R1E,R2F, ZN,XB,YA), (R1F,R2F,ZN,XB,YA), (R1G,R2F,ZN,XB, YA), (R1H,R2F,ZN,XB,YA), (R1I,R2F,ZN,XB,YA), (R1J, R2F,ZN,XB,YA), (R1K,R2F,ZN,XB,YA), (R1L,R2F,ZN, XB,YA), (R1M,R2F,ZN,XB,YA), (R1N,R2F,ZN,XB,YA), (R1O,R2F,ZN,XB,YA), (R1P,R2F,ZN,XB,YA), (R1Q,R2F, ZN,XB,YA), (R1A,R2G,ZN,XB,YA), (R1B,R2G,ZN,XB, YA), (R1C,R2G,ZN,XB,YA), (R1D,R2G,ZN,XB,YA), (R1E,R2G,ZN,XB,YA), (R1F,R2G,ZN,XB,YA), (R1G, R2G,ZN,XB,YA), (R1H,R2G,ZN,XB,YA), (R1I,R2G,ZN, XB,YA), (R1J,R2G,ZN,XB,YA), (R1K,R2G,ZN,XB,YA), (R1L,R2G,ZN,XB,YA), (R1M,R2G,ZN,XB,YA), (R1N, R2G,ZN,XB,YA), (R1O,R2G,ZN,XB,YA), (R1P,R2G,ZN, XB,YA), (R1Q,R2G,ZN,XB,YA), (R1A,R2H,ZN,XB,YA), (R1B,R2H,ZN,XB,YA), (R1C,R2H,ZN,XB,YA), (R1D, R2H,ZN,XB,YA), (R1E,R2H,ZN,XB,YA), (R1F,R2H,ZN, XB,YA), (R1G,R2H,ZN,XB,YA), (R1H,R2H,ZN,XB,YA), (R1I,R2H,ZN,XB,YA), (R1J,R2H,ZN,XB,YA), (R1K,R2H, ZN,XB,YA), (R1L,R2H,ZN,XB,YA), (R1M,R2H,ZN,XB, YA), (R1N,R2H,ZN,XB,YA), (R1O,R2H,ZN,XB,YA), (R1P,R2H,ZN,XB,YA), (R1Q,R2H,ZN,XB,YA), (R1A,R2I, ZN,XB,YA), (R1B,R2I,ZN,XB,YA), (R1C,R2I,ZN,XB, YA), (R1D,R2I,ZN,XB,YA), (R1E,R2I,ZN,XB,YA), (R1F, R2I,ZN,XB,YA),(R1G,R2I,ZN,XB,YA),(R1H,R2I,ZN,XB, YA), (R1I,R2I,ZN,XB,YA), (R1J,R2I,ZN,XB,YA), (R1K, R2I,ZN,XB,YA), (R1L,R2I,ZN,XB,YA), (R1M,R2I,ZN, XB,YA), (R1N,R2I,ZN,XB,YA), (R1O,R2I,ZN,XB,YA), (R1P,R2I,ZN,XB,YA), (R1Q,R2I,ZN,XB,YA), (R1A,R2J, ZN,XB,YA), (R1B,R2J,ZN,XB,YA), (R1C,R2J,ZN,XB, YA), (R1D,R2J,ZN,XB,YA), (R1E,R2J,ZN,XB,YA), (R1F, R2J,ZN,XB,YA), (R1G,R2J,ZN,XB,YA), (R1H,R2J,ZN, XB,YA), (R1I,R2J,ZN,XB,YA), (R1J,R2J,ZN,XB,YA), (R1K,R2J,ZN,XB,YA), (R1L,R2J,ZN,XB,YA), (R1M,R2J, ZN,XB,YA), (R1N,R2J,ZN,XB,YA), (R1O,R2J,ZN,XB, YA), (R1P,R2J,ZN,XB,YA), (R1Q,R2J,ZN,XB,YA), (R1A, R2K,ZN,XB,YA), (R1B,R2K,ZN,XB,YA), (R1C,R2K,ZN, XB,YA), (R1D,R2K,ZN,XB,YA), (R1E,R2K,ZN,XB,YA), (R1F,R2K,ZN,XB,YA), (R1G,R2K,ZN,XB,YA), (R1H, R2K,ZN,XB,YA), (R1I,R2K,ZN,XB,YA), (R1J,R2K,ZN, XB,YA), (R1K,R2K,ZN,XB,YA), (R1L,R2K,ZN,XB,YA), (R1M,R2K,ZN,XB,YA), (R1N,R2K,ZN,XB,YA), (R1O, R2K,ZN,XB,YA), (R1P,R2K,ZN,XB,YA), (R1Q,R2K,ZN, XB,YA), (R1A,R2L,ZN,XB,YA), (R1B,R2L,ZN,XB,YA), (R1C,R2L,ZN,XB,YA), (R1D,R2L,ZN,XB,YA), (R1E,R2L, ZN,XB,YA), (R1F,R2L,ZN,XB,YA), (R1G,R2L,ZN,XB, YA), (R1H,R2L,ZN,XB,YA), (R1I,R2L,ZN,XB,YA), (R1J, R2L,ZN,XB,YA), (R1K,R2L,ZN,XB,YA), (R1L,R2L,ZN, XB,YA), (R1M,R2L,ZN,XB,YA), (R1N,R2L,ZN,XB,YA), (R1O,R2L,ZN,XB,YA), (R1P,R2L,ZN,XB,YA), (R1Q,R2L, ZN,XB,YA), (R1A,R2M,ZN,XB,YA), (R1B,R2M,ZN,XB, YA), (R1C,R2M,ZN,XB,YA), (R1D,R2M,ZN,XB,YA), (R1E,R2M,ZN,XB,YA), (R1F,R2M,ZN,XB,YA), (R1G, R2M,ZN,XB,YA), (R1H,R2M,ZN,XB,YA), (R1I,R2M,ZN, XB,YA), (R1J,R2M,ZN,XB,YA), (R1K,R2M,ZN,XB,YA), (R1L,R2M,ZN,XB,YA), (R1M,R2M,ZN,XB,YA), (R1N, R2M,ZN,XB,YA), (R1O,R2M,ZN,XB,YA), (R1P,R2M, ZN,XB,YA), (R1Q,R2M,ZN,XB,YA), (R1A,R2N,ZN,XB,YA), (R1B,R2N,ZN,XB,YA), (R1C,R2N,ZN,XB,YA), (R1D, R2N,ZN,XB,YA), (R1E,R2N,ZN,XB,YA), (R1F,R2N, XB,YA), (R1G,R2N,ZN,XB,YA), (R1H,R2N,ZN,XB,YA), (R1I,R2N,ZN,XB,YA), (R1J,R2N,ZN,XB,YA), (R1K,R2N, ZN,XB,YA), (R1L,R2N,ZN,XB,YA), (R1M,R2N,ZN,XB, YA), (R1N,R2N,ZN,XB,YA), (R1O,R2N,ZN,XB,YA), (R1P,R2N,ZN,XB,YA), (R1Q,R2N,ZN,XB,YA), (R1A, R2O,ZN,XB,YA), (R1B,R2O,ZN,XB,YA), (R1C,R2O,ZN, XB,YA), (R1D,R2O,ZN,XB,YA), (R1E,R2O,ZN,XB,YA), (R1F,R2O,ZN,XB,YA), (R1G,R2O,ZN,XB,YA), (R1H, R2O,ZN,XB,YA), (R1I,R2O,ZN,XB,YA), (R1J,R2O,ZN, XB,YA), (R1K,R2O,ZN,XB,YA), (R1L,R2O,ZN,XB,YA), (R1M,R2O,ZN,XB,YA), (R1N,R2O,ZN,XB,YA), (R1O, R2O,ZN,XB,YA), (R1P,R2O,ZN,XB,YA), (R1Q,R2O,ZN, XB,YA), (R1A,R2P,ZN,XB,YA), (R1B,R2P,ZN,XB,YA), (R1C,R2P,ZN,XB,YA), (R1D,R2P,ZN,XB,YA), (R1E,R2P, ZN,XB,YA), (R1F,R2P,ZN,XB,YA), (R1G,R2P,ZN,XB, YA), (R1H,R2P,ZN,XB,YA), (R1I,R2P,ZN,XB,YA), (R1J, R2P,ZN,XB,YA), (R1K,R2P,ZN,XB,YA), (R1L,R2P,ZN, XB,YA), (R1M,R2P,ZN,XB,YA), (R1N,R2P,ZN,XB,YA), (R1O,R2P,ZN,XB,YA), (R1P,R2P,ZN,XB,YA), (R1Q,R2P, ZN,XB,YA), (R1A,R2Q,ZN,XB,YA), (R1B,R2Q,ZN,XB, YA), (R1C,R2Q,ZN,XB,YA), (R1D,R2Q,ZN,XB,YA), (R1E,R2Q,ZN,XB,YA), (R1F,R2Q,ZN,XB,YA), (R1G,R2Q,ZN,XB,YA), (R1H,R2Q,ZN,XB,YA), (R1I,R2Q,ZN,XB,YA), (R1J,R2Q,ZN,XB,YA), (R1K,R2Q,ZN,XB,YA), (R1L,R2Q,ZN,XB,YA), (R1M,R2Q,ZN,XB,YA), (R1N,R2Q,ZN,XB,YA), (R1O,R2Q,ZN,XB,YA), (R1P,R2Q,ZN,XB,YA), (R1Q,R2Q,ZN,XB,YA), (R1A,R2A,ZO,XB,YA), (R1B,R2A,ZO,XB,YA), (R1C,R2A,ZO,XB,YA), (R1D,R2A,ZO,XB,YA), (R1E,R2A,ZO,XB,YA), (R1F,R2A,ZO,XB,YA), (R1G,R2A,ZO,XB,YA), (R1H,R2A,ZO,XB,YA), (R1I,R2A,ZO,XB,YA), (R1J,R2A,ZO,XB,YA), (R1K,R2A,ZO,XB,YA), (R1L,R2A,ZO,XB,YA), (R1M,R2A,ZO,XB,YA), (R1N,R2A,ZO,XB,YA), (R1O,R2A,ZO,XB,YA), (R1P,R2A,ZO,XB,YA), (R1Q,R2A,ZO,XB,YA), (R1A,R2B,ZO,XB,YA), (R1B,R2B,ZO,XB,YA), (R1C,R2B,ZO,XB,YA), (R1D,R2B,ZO,XB,YA), (R1E,R2B,ZO,XB,YA), (R1F,R2B,ZO,XB,YA), (R1G,R2B,ZO,XB,YA), (R1H,R2B,ZO,XB,YA), (R1I,R2B,ZO,XB,YA), (R1J,R2B,ZO,XB,YA), (R1K,R2B,ZO,XB,YA), (R1L,R2B,ZO,XB,YA), (R1M,R2B,ZO,XB,YA), (R1N,R2B,ZO,XB,YA), (R1O,R2B,ZO,XB,YA), (R1P,R2B,ZO,XB,YA), (R1Q,R2B,ZO,XB,YA), (R1A,R2C,ZO,XB,YA), (R1B,R2C,ZO,XB,YA), (R1C,R2C,ZO,XB,YA), (R1D,R2C,ZO,XB,YA), (R1E,R2C,ZO,XB,YA), (R1F,R2C,ZO,XB,YA), (R1G,R2C,ZO,XB,YA), (R1H,R2C,ZO,XB,YA), (R1I,R2C,ZO,XB,YA), (R1J,R2C,ZO,XB,YA), (R1K,R2C,ZO,XB,YA), (R1L,R2C,ZO,XB,YA), (R1M,R2C,ZO,XB,YA), (R1N,R2C,ZO,XB,YA), (R1O,R2C,ZO,XB,YA), (R1P,R22C,ZO,XB,YA), (R1Q,R2C,ZO,XB,YA), (R1A,R2D,ZO,XB,YA), (R1B,R2D,ZO,XB,YA), (R1C,R2D,ZO,XB,YA), (R1D,R2D,ZO,XB,YA), (R1E,R2D,ZO,XB,YA), (R1F,R2D,ZO,XB,YA), (R1G,R2D,ZO,XB,YA), (R1H,R2D,ZO,XB,YA), (R1I,R2D,ZO,XB,YA), (R1J,R2D,ZO,XB,YA), (R1K,R2D,ZO,XB,YA), (R1L,R2D,ZO,XB,YA), (R1M,R2D,ZO,XB,YA), (R1N,R2D,ZO,XB,YA), (R1O,R2D,ZO,XB,YA), (R1P,R2D,ZO,XB,YA), (R1Q,R2D,ZO,XB,YA), (R1A,R2E,ZO,XB,YA), (R1B,R2E,ZO,XB,YA), (R1C,R2E,ZO,XB,YA), (R1D,R2E,ZO,XB,YA), (R1E,R2E,ZO,XB,YA), (R1F,R2E,ZO,XB,YA), (R1G,R2E,ZO,XB,YA), (R1H,R2E,ZO,XB,YA), (R1I,R2E,ZO,XB,YA), (R1J,R2E,ZO,XB,YA), (R1K,R2E,ZO,XB,YA), (R1L,R2E,ZO,XB,YA), (R1M,R2E,ZO,XB,YA), (R1N,R2E,ZO,XB,YA), (R1O,R2E,ZO,XB,YA), (R1P,R2E,ZO,XB,YA), (R1Q,R2E,ZO,XB,YA), (R1A,R2F,ZO,XB,YA), (R1B,R2F,ZO,XB,YA), (R1C,R2F,ZO,XB,YA), (R1D,R2F,ZO,XB,YA), (R1E,R2F,ZO,XB,YA), (R1F,R2F,ZO,XB,YA), (R1G,R2F,ZO,XB,YA), (R1H,R2F,ZO,XB,YA), (R1I,R2F,ZO,XB,YA), (R1J,R2F,ZO,XB,YA), (R1K,R2F,ZO,XB,YA), (R1L,R2F,ZO,XB,YA), (R1M,R2F,ZO,XB,YA), (R1N,R2F,ZO,XB,YA), (R1O,R2F,ZO,XB,YA), (R1P,R2F,ZO,XB,YA), (R1Q,R2F,ZO,XB,YA), (R1A,R2G,ZO,XB,YA), (R1B,R2G,ZO,XB,YA), (R1C,R2G,ZO,XB,YA), (R1D,R2G,ZO,XB,YA), (R1E,R2G,ZO,XB,YA), (R1F,R2G,ZO,XB,YA), (R1G,R2G,ZO,XB,YA), (R1H,R2G,ZO,XB,YA), (R1I,R2G,ZO,XB,YA), (R1J,R2G,ZO,XB,YA), (R1K,R2G,ZO,XB,YA), (R1L,R2G,ZO,XB,YA), (R1M,R2G,ZO,XB,YA), (R1N,R2G,ZO,XB,YA), (R1O,R2G,ZO,XB,YA), (R1P,R2G,ZO,XB,YA), (R1Q,R2G,ZO,XB,YA), (R1A,R2H,ZO,XB,YA), (R1B,R2H,ZO,XB,YA), (R1C,R2H,ZO,XB,YA), (R1D,R2H,ZO,XB,YA), (R1E,R2H,ZO,XB,YA), (R1F,R2H,ZO,XB,YA), (R1G,R2H,ZO,XB,YA), (R1H,R2H,ZO,XB,YA), (R1I,R2H,ZO,XB,YA), (R1J,R2H,ZO,XB,YA), (R1K,R2H,ZO,XB,YA), (R1L,R2H,ZO,XB,YA), (R1M,R2H,ZO,XB,YA), (R1N,R2H,ZO,XB,YA), (R1O,R2H,ZO,XB,YA), (R1P,R2H,ZO,XB,YA), (R1Q,R2H,ZO,XB,YA), (R1A,R2I,ZO,XB,YA), (R1B,R2I,ZO,XB,YA), (R1C,R2I,ZO,XB,YA), (R1D,R2I,ZO,XB,YA), (R1E,R2I,ZO,XB,YA), (R1F,R2I,ZO,XB,YA), (R1G,R2I,ZO,XB,YA), (R1H,R2I,ZO,XB,YA), (R1I,R2I,ZO,XB,YA), (R1J,R2I,ZO,XB,YA), (R1K,R2I,ZO,XB,YA), (R1L,R2I,ZO,XB,YA), (R1M,R2I,ZO,XB,YA), (R1N,R2I,ZO,XB,YA), (R1O,R2I,ZO,XB,YA), (R1P,R2I,ZO,XB,YA), (R1Q,R2I,ZO,XB,YA), (R1A,R2J,ZO,XB,YA), (R1B,R2J,ZO,XB,YA), (R1C,R2J,ZO,XB,YA), (R1D,R2J,ZO,XB,YA), (R1E,R2J,ZO,XB,YA), (R1F,R2J,ZO,XB,YA), (R1G,R2J,ZO,XB,YA), (R1H,R2J,ZO,XB,YA), (R1I,R2J,ZO,XB,YA), (R1J,R2J,ZO,XB,YA), (R1K,R2J,ZO,XB,YA), (R1L,R2J,ZO,XB,YA), (R1M,R2J,ZO,XB,YA), (R1N,R2J,ZO,XB,YA), (R1O,R2J,ZO,XB,YA), (R1P,R2J,ZO,XB,YA), (R1Q,R2J,ZO,XB,YA), (R1A,R2K,ZO,XB,YA), (R1B,R2K,ZO,XB,YA), (R1C,R2K,ZO,XB,YA), (R1D,R2K,ZO,XB,YA), (R1E,R2K,ZO,XB,YA), (R1F,R2K,ZO,XB,YA), (R1G,R2K,ZO,XB,YA), (R1H,R2K,ZO,XB,YA), (R1I,R2K,ZO,XB,YA), (R1J,R2K,ZO,XB,YA), (R1K,R2K,ZO,XB,YA), (R1L,R2K,ZO,XB,YA), (R1M,R2K,ZO,XB,YA), (R1N,R2K,ZO,XB,YA), (R1O,R2K,ZO,XB,YA), (R1P,R2K,ZO,XB,YA), (R1Q,R2K,ZO,XB,YA), (R1A,R2L,ZO,XB,YA), (R1B,R2L,ZO,XB,YA), (R1C,R2L,ZO,XB,YA), (R1D,R2L,ZO,XB,YA), (R1E,R2L,ZO,XB,YA), (R1F,R2L,ZO,XB,YA), (R1G,R2L,ZO,XB,YA), (R1H,R2L,ZO,XB,YA), (R1I,R2L,ZO,XB,YA), (R1J,R2L,ZO,XB,YA), (R1K,R2L,ZO,XB,YA), (R1L,R2L,ZO,XB,YA), (R1M,R2L,ZO,XB,YA), (R1N,R2L,ZO,XB,YA), (R1O,R2L,ZO,XB,YA), (R1P,R2L,ZO,XB,YA), (R1Q,R2L,ZO,XB,YA), (R1A,R2M,ZO,XB,YA), (R1B,R2M,ZO,XB,YA), (R1C,R2M,ZO,XB,YA), (R1D,R2M,ZO,XB,YA), (R1E,R2M,ZO,XB,YA), (R1F,R2M,ZO,XB,YA), (R1G,R2M,ZO,XB,YA), (R1H,R2M,ZO,XB,YA), (R1I,R2M,ZO,XB,YA), (R1J,R2M,ZO,XB,YA), (R1K,R2M,ZO,XB,YA), (R1L,R2M,ZO,XB,YA), (R1M,R2M,ZO,XB,YA), (R1N,R2M,ZO,XB,YA), (R1O,R2M,ZO,XB,YA), (R1P,R2M,ZO,XB,YA), (R1Q,R2M,ZO,XB,YA), (R1A,R2N,ZO,XB,YA), (R1B,R2N,ZO,XB,YA), (R1C,R2N,ZO,XB,YA), (R1D,R2N,ZO,XB,YA), (R1E,R2N,ZO,XB,YA), (R1F,R2N,ZO,XB,YA), (R1G,R2N,ZO,XB,YA), (R1H,R2N,ZO,XB,YA), (R1I,R2N,ZO,XB,YA), (R1J,R2N,ZO,XB,YA), (R1K,R2N,ZO,XB,YA), (R1L,R2N,ZO,XB,YA), (R1M,R2N,ZO,XB,YA), (R1N,R2N,ZO,XB,YA), (R1O,R2N,ZO,XB,YA), (R1P,R2N,ZO,XB,YA), (R1Q,R2N,ZO,XB,YA), (R1A,R2O,ZO,XB,YA), (R1B,R2O,ZO,XB,YA), (R1C,R2O,ZO,XB,YA), (R1D,R2O,ZO,XB,YA), (R1E,R2O,ZO,XB,YA), (R1F,R2O,ZO,XB,YA), (R1G,R2O,ZO,XB,YA), (R1H,R2O,ZO,XB,YA), (R1I,R2O,ZO,XB,YA), (R1J,R2O,ZO,XB,YA), (R1K,R2O,ZO,XB,YA), (R1L,R2O,ZO,XB,YA), (R1M,R2O,ZO,XB,YA), (R1N,R2O,ZO,XB,YA), (R1O,R2O,ZO,XB,YA), (R1P,R2O,ZO,XB,YA), (R1Q,R2O,ZO,XB,YA), (R1A,R2P,ZO,XB,YA), (R1B,R2P,ZO,XB,YA), (R1C,R2P,ZO,XB,YA), (R1D,R2P,ZO,XB,YA), (R1E,R2P,ZO,XB,YA), (R1F,R2P,ZO,XB,YA), (R1G,R2P,ZO,XB,YA), (R1H,R2P,ZO,XB,YA), (R1I,R2P,ZO,XB,YA), (R1J,R2P,ZO,XB,YA), (R1K,R2P,ZO,XB,YA), (R1L,R2P,ZO,XB,YA), (R1M,R2P,ZO,XB,YA), (R1N,R2P,ZO,XB,YA), (R1O,R2P,ZO,XB,YA), (R1P,R2P,ZO,XB,YA), (R1Q,R2P,ZO,XB,YA), (R1A,R2Q,ZO,XB,YA), (R1B,R2Q,ZO,XB,YA), (R1C,R2Q,ZO,XB,YA), (R1D,R2Q,ZO,XB,YA), (R1E,R2Q,ZO,XB,YA), (R1F,R2Q,ZO,XB,YA), (R1G,R2Q,ZO,XB,YA), (R1H,R2Q,ZO,XB,YA), (R1I,R2Q,ZO,XB,YA), (R1J,R2Q,ZO,XB,YA), (R1K,R2Q,ZO,XB,YA), (R1L,R2Q,ZO,XB,YA), (R1M,R2Q,ZO,XB,YA), (R1N,R2Q,ZO,XB,YA), (R1O,R2Q,ZO,XB,YA), (R1P,R2Q,ZO,XB,YA), (R1Q,R2Q,ZO,XB,YA), (R1A,R2A,ZP,XB,YA), (R1B,R2A,ZP,XB,YA), (R1C,R2A,ZP,XB,YA), (R1D,R2A,ZP,XB,YA), (R1E,R2A,ZP,XB,YA), (R1F,R2A,ZP,XB,YA), (R1G,R2A,ZP,XB,YA), (R1H,R2A,ZP,XB,YA), (R1I,R2A,ZP,XB,YA), (R1J,R2A,ZP,XB,YA), (R1K,R2A,ZP,XB,YA), (R1L,R2A,ZP,XB,YA), (R1M,R2A,ZP,XB,YA), (R1N,R2A,ZP,XB,YA), (R1O,R2A,ZP,XB, YA), (R1P,R2A,ZP,XB,YA), (R1Q,R2A,ZP,XB,YA), (R1A, R2B,ZP,XB,YA), (R1B,R2B,ZP,XB,YA), (R1C,R2B,ZP, XB,YA), (R1D,R2B,ZP,XB,YA), (R1E,R2B,ZP,XB,YA), (R1F,R2B,ZP,XB,YA), (R1G,R2B,ZP,XB,YA), (R1H,R2B, ZP,XB,YA), (R1I,R2B,ZP,XB,YA), (R1J,R2B,ZP,XB,YA), (R1K,R2B,ZP,XB,YA), (R1L,R2B,ZP,XB,YA), (R1M,R2B, ZP,XB,YA), (R1N,R2B,ZP,XB,YA), (R1O,R2B,ZP,XB,YA), (R1P,R2B,ZP,XB,YA), (R1Q,R2B,ZP,XB,YA), (R1A,R2C, ZP,XB,YA), (R1B,R2C,ZP,XB,YA), (R1C,R2C,ZP,XB,YA), (R1D,R2C,ZP,XB,YA), (R1E,R2C,ZP,XB,YA), (R1F,R2C, ZP,XB,YA), (R1G,R2C,ZP,XB,YA), (R1H,R2C,ZP,XB,YA), (R1I,R2C,ZP,XB,YA), (R1J,R2C,ZP,XB,YA), (R1K,R2C, ZP,XB,YA), (R1L,R2C,ZP,XB,YA), (R1M,R2C,ZP,XB, YA), (R1N,R2C,ZP,XB,YA), (R1O,R2C,ZP,XB,YA), (R1P, R2C,ZP,XB,YA), (R1Q,R2C,ZP,XB,YA), (R1A,R2D,ZP, XB,YA), (R1B,R2D,ZP,XB,YA), (R1C,R2D,ZP,XB,YA), (R1D,R2D,ZP,XB,YA), (R1E,R2D,ZP,XB,YA), (R1F,R2D, ZP,XB,YA), (R1G,R2D,ZP,XB,YA), (R1H,R2D,ZP,XB, YA), (R1I,R2D,ZP,XB,YA), (R1J,R2D,ZP,XB,YA), (R1K, R2D,ZP,XB,YA), (R1L,R2D,ZP,XB,YA), (R1M,R2D,ZP, XB,YA), (R1N,R2D,ZP,XB,YA), (R1O,R2D,ZP,XB,YA), (R1P,R2D,ZP,XB,YA), (R1Q,R2D,ZP,XB,YA), (R1A,R2E, ZP,XB,YA), (R1B,R2E,ZP,XB,YA), (R1C,R2E,ZP,XB,YA), (R1D,R2E,ZP,XB,YA), (R1E,R2E,ZP,XB,YA), (R1F,R2E, ZP,XB,YA), (R1G,R2E,ZP,XB,YA), (R1H,R2E,ZP,XB,YA), (R1I,R2E,ZP,XB,YA), (R1J,R2E,ZP,XB,YA), (R1K,R2E, ZP,XB,YA), (R1L,R2E,ZP,XB,YA), (R1M,R2E,ZP,XB,YA), (R1N,R2E,ZP,XB,YA), (R1O,R2E,ZP,XB,YA), (R1P,R2E, ZP,XB,YA), (R1Q,R2E,ZP,XB,YA), (R1A,R2F,ZP,XB,YA), (R1B,R2F,ZP,XB,YA), (R1C,R2F,ZP,XB,YA), (R1D,R2F, ZP,XB,YA), (R1E,R2F,ZP,XB,YA), (R1F,R2F,ZP,XB,YA), (R1G,R2F,ZP,XB,YA), (R1H,R2F,ZP,XB,YA), (R1I,R2F, ZP,XB,YA), (R1J,R2F,ZP,XB,YA), (R1K,R2F,ZP,XB,YA), (R1L,R2F,ZP,XB,YA), (R1M,R2F,ZP,XB,YA), (R1N,R2F, ZP,XB,YA), (R1O,R2F,ZP,XB,YA), (R1P,R2F,ZP,XB,YA), (R1Q,R2F,ZP,XB,YA), (R1A,R2G,ZP,XB,YA), (R1B,R2G, ZP,XB,YA), (R1C,R2G,ZP,XB,YA), (R1D,R2G,ZP,XB, YA), (R1E,R2G,ZP,XB,YA), (R1F,R2G,ZP,XB,YA), (R1G, R2G,ZP,XB,YA), (R1H,R2G,ZP,XB,YA), (R1I,R2G,ZP,XB, YA), (R1J,R2G,ZP,XB,YA), (R1K,R2G,ZP,XB,YA), (R1L, R2G,ZP,XB,YA), (R1M,R2G,ZP,XB,YA), (R1N,R2G,ZP, XB,YA), (R1O,R2G,ZP,XB,YA), (R1P,R2G,ZP,XB,YA), (R1Q,R2G,ZP,XB,YA), (R1A,R2H,ZP,XB,YA), (R1B,R2H, ZP,XB,YA), (R1C,R2H,ZP,XB,YA), (R1D,R2H,ZP,XB, YA), (R1E,R2H,ZP,XB,YA), (R1F,R2H,ZP,XB,YA), (R1G, R2H,ZP,XB,YA), (R1H,R2H,ZP,XB,YA), (R1I,R2H,ZP,XB, YA), (R1J,R2H,ZP,XB,YA), (R1K,R2H,ZP,XB,YA), (R1L, R2H,ZP,XB,YA), (R1M,R2H,ZP,XB,YA), (R1N,R2H,ZP, XB,YA), (R1O,R2H,ZP,XB,YA), (R1P,R2H,ZP,XB,YA), (R1Q,R2H,ZP,XB,YA), (R1A,R2I,ZP,XB,YA), (R1B,R2I, ZP,XB,YA), (R1C,R2I,ZP,XB,YA), (R1D,R2I,ZP,XB,YA), (R1E,R2I,ZP,XB,YA), (R1F,R2I,ZP,XB,YA), (R1G,R2I,ZP, XB,YA), (R1H,R2I,ZP,XB,YA), (R1I,R2I,ZP,XB,YA), (R1J, R2I,ZP,XB,YA), (R1K,R2I,ZP,XB,YA), (R1L,R2I,ZP,XB, YA), (R1M,R2I,ZP,XB,YA), (R1N,R2I,ZP,XB,YA), (R1O, R2I,ZP,XB,YA), (R1P,R2I,ZP,XB,YA), (R1Q,R2I,ZP,XB, YA), (R1A,R2J,ZP,XB,YA), (R1B,R2J,ZP,XB,YA), (R1C, R2J,ZP,XB,YA), (R1D,R2J,ZP,XB,YA), (R1E,R2J,ZP,XB, YA), (R1F,R2J,ZP,XB,YA), (R1G,R2J,ZP,XB,YA), (R1H, R2J,ZP,XB,YA), (R1I,R2J,ZP,XB,YA), (R1J,R2J,ZP,XB, YA), (R1K,R2J,ZP,XB,YA), (R1L,R2J,ZP,XB,YA), (R1M, R2J,ZP,XB,YA), (R1N,R2J,ZP,XB,YA), (R1O,R2J,ZP,XB, YA), (R1P,R2J,ZP,XB,YA), (R1Q,R2J,ZP,XB,YA), (R1A, R2K,ZP,XB,YA), (R1B,R2K,ZP,XB,YA), (R1C,R2K,ZP, XB,YA), (R1D,R2K,ZP,XB,YA), (R1E,R2K,ZP,XB,YA), (R1F,R2K,ZP,XB,YA), (R1G,R2K,ZP,XB,YA), (R1H,R2K, ZP,XB,YA), (R1I,R2K,ZP,XB,YA), (R1J,R2K,ZP,XB,YA), (R1K,R2K,ZP,XB,YA), (R1L,R2K,ZP,XB,YA), (R1M,R2K, ZP,XB,YA), (R1N,R2K,ZP,XB,YA), (R1O,R2K,ZP,XB, YA), (R1P,R2K,ZP,XB,YA), (R1Q,R2K,ZP,XB,YA), (R1A, R2L,ZP,XB,YA), (R1B,R2L,ZP,XB,YA), (R1C,R2L,ZP,XB, YA), (R1D,R2L,ZP,XB,YA), (R1E,R2L,ZP,XB,YA), (R1F, R2L,ZP,XB,YA), (R1G,R2L,ZP,XB,YA), (R1H,R2L,ZP,XB, YA), (R1I,R2L,ZP,XB,YA), (R1J,R2L,ZP,XB,YA), (R1K, R2L,ZP,XB,YA), (R1L,R2L,ZP,XB,YA), (R1M,R2L,ZP, XB,YA), (R1N,R2L,ZP,XB,YA), (R1O,R2L,ZP,XB,YA), (R1P,R2L,ZP,XB,YA), (R1Q,R2L,ZP,XB,YA), (R1A,R2M, ZP,XB,YA), (R1B,R2M,ZP,XB,YA), (R1C,R2M,ZP,XB, YA), (R1D,R2M,ZP,XB,YA), (R1E,R2M,ZP,XB,YA), (R1F, R2M,ZP,XB,YA), (R1G,R2M,ZP,XB,YA), (R1H,R2M,ZP, XB,YA), (R1I,R2M,ZP,XB,YA), (R1J,R2M,ZP,XB,YA), (R1K,R2M,ZP,XB,YA), (R1L,R2M,ZP,XB,YA), (R1M, R2M,ZP,XB,YA), (R1N,R2M,ZP,XB,YA), (R1O,R2M,ZP, XB,YA), (R1P,R2M,ZP,XB,YA), (R1Q,R2M,ZP,XB,YA), (R1A,R2N,ZP,XB,YA), (R1B,R2N,ZP,XB,YA), (R1C,R2N, ZP,XB,YA), (R1D,R2N,ZP,XB,YA), (R1E,R2N,ZP,XB,YA), (R1F,R2N,ZP,XB,YA), (R1G,R2N,ZP,XB,YA), (R1H,R2N, ZP,XB,YA), (R1I,R2N,ZP,XB,YA), (R1J,R2N,ZP,XB,YA), (R1K,R2N,ZP,XB,YA), (R1L,R2N,ZP,XB,YA), (R1M,R2N, ZP,XB,YA), (R1N,R2N,ZP,XB,YA), (R1O,R2N,ZP,XB, YA), (R1P,R2N,ZP,XB,YA), (R1Q,R2N,ZP,XB,YA), (R1A, R2O,ZP,XB,YA), (R1B,R2O,ZP,XB,YA), (R1C,R2O,ZP, XB,YA), (R1D,R2O,ZP,XB,YA), (R1E,R2O,ZP,XB,YA), (R1F,R2O,ZP,XB,YA), (R1G,R2O,ZP,XB,YA), (R1H,R2O, ZP,XB,YA), (R1I,R2O,ZP,XB,YA), (R1J,R2O,ZP,XB,YA), (R1K,R2O,ZP,XB,YA), (R1L,R2O,ZP,XB,YA), (R1M,R2O, ZP,XB,YA), (R1N,R2O,ZP,XB,YA), (R1O,R2O,ZP,XB, YA), (R1P,R2O,ZP,XB,YA), (R1Q,R2O,ZP,XB,YA), (R1A, R2P,ZP,XB,YA), (R1B,R2P,ZP,XB,YA), (R1C,R2P,ZP,XB, YA), (R1D,R2P,ZP,XB,YA), (R1E,R2P,ZP,XB,YA), (R1F, R2P,ZP,XB,YA), (R1G,R2P,ZP,XB,YA), (R1H,R2P,ZP,XB, YA), (R1I,R2P,ZP,XB,YA), (R1J,R2P,ZP,XB,YA), (R1K, R2P,ZP,XB,YA), (R1L,R2P,ZP,XB,YA), (R1M,R2P,ZP,XB, YA), (R1N,R2P,ZP,XB,YA), (R1O,R2P,ZP,XB,YA), (R1P, R2P,ZP,XB,YA), (R1Q,R2P,ZP,XB,YA), (R1A,R2Q,ZP,XB, YA), (R1B,R2Q,ZP,XB,YA), (R1C,R2Q,ZP,XB,YA), (R1D, R2Q,ZP,XB,YA), (R1E,R2Q,ZP,XB,YA), (R1F,R2Q,ZP,XB, YA), (R1G,R2Q,ZP,XB,YA), (R1H,R2Q,ZP,XB,YA), (R1I, R2Q,ZP,XB,YA), (R1J,R2Q,ZP,XB,YA), (R1K,R2Q,ZP,XB, YA), (R1L,R2Q,ZP,XB,YA), (R1M,R2Q,ZP,XB,YA), (R1N, R2Q,ZP,XB,YA), (R1O,R2Q,ZP,XB,YA), (R1P,R2Q,ZP, XB,YA), (R1Q,R2Q,ZP,XB,YA), (R1A,R2A,ZQ,XB,YA), (R1B,R2A,ZQ,XB,YA), (R1C,R2A,ZQ,XB,YA), (R1D, R2A,ZQ,XB,YA), (R1E,R2A,ZQ,XB,YA), (R1F,R2A,ZQ, XB,YA), (R1G,R2A,ZQ,XB,YA), (R1H,R2A,ZQ,XB,YA), (R1I,R2A,ZQ,XB,YA), (R1J,R2A,ZQ,XB,YA), (R1K,R2A, ZQ,XB,YA), (R1L,R2A,ZQ,XB,YA), (R1M,R2A,ZQ,XB, YA), (R1N,R2A,ZQ,XB,YA), (R1O,R2A,ZQ,XB,YA), (R1P,R2A,ZQ,XB,YA), (R1Q,R2A,ZQ,XB,YA), (R1A, R2B,ZQ,XB,YA), (R1B,R2B,ZQ,XB,YA), (R1C,R2B,ZQ, XB,YA), (R1D,R2B,ZQ,XB,YA), (R1E,R2B,ZQ,XB,YA), (R1F,R2B,ZQ,XB,YA), (R1G,R2B,ZQ,XB,YA), (R1H,R2B, ZQ,XB,YA), (R1I,R2B,ZQ,XB,YA), (R1J,R2B,ZQ,XB, YA), (R1K,R2B,ZQ,XB,YA), (R1L,R2B,ZQ,XB,YA), (R1M,R2B,ZQ,XB,YA), (R1N,R2B,ZQ,XB,YA), (R1O, R2B,ZQ,XB,YA), (R1P,R2B,ZQ,XB,YA), (R1Q,R2B,ZQ, XB,YA), (R1A,R2C,ZQ,XB,YA), (R1B,R2C,ZQ,XB,YA), (R1C,R2C,ZQ,XB,YA), (R1D,R2C,ZQ,XB,YA), (R1E, R2C,ZQ,XB,YA), (R1F,R2C,ZQ,XB,YA), (R1G,R2C,ZQ, XB,YA), (R1H,R2C,ZQ,XB,YA), (R1I,R2C,ZQ,XB,YA), (R1J,R2C,ZQ,XB,YA), (R1K,R2C,ZQ,XB,YA), (R1L,R2C, ZQ,XB,YA), (R1M,R22C,ZQ,XB,YA), (R1N,R2C,ZQ,XB, YA), (R1O,R2C,ZQ,XB,YA), (R1P,R2C,ZQ,XB,YA), (R1Q, R2C,ZQ,XB,YA), (R1A,R2D,ZQ,XB,YA), (R1B,R2D,ZQ, XB,YA), (R1C,R2D,ZQ,XB,YA), (R1D,R2D,ZQ,XB,YA), (R1E,R2D,ZQ,XB,YA), (R1F,R2D,ZQ,XB,YA), (R1G,R2D,ZQ,XB,YA), (R1H,R2D,ZQ,XB,YA), (R1I,R2D,ZQ,XB,YA), (R1J,R2D,ZQ,XB,YA), (R1K,R2D,ZQ,XB,YA), (R1L,R2D,ZQ,XB,YA), (R1M,R2D,ZQ,XB,YA), (R1N,R2D,ZQ,XB,YA), (R1O,R2D,ZQ,XB,YA), (R1P,R2D,ZQ,XB,YA), (R1Q,R2D,ZQ,XB,YA), (R1A,R2E,ZQ,XB,YA), (R1B,R2E,ZQ,XB,YA), (R1C,R2E,ZQ,XB,YA), (R1D,R2E,ZQ,XB,YA), (R1E,R2E,ZQ,XB,YA), (R1F,R2E,ZQ,XB,YA), (R1G,R2E,ZQ,XB,YA), (R1H,R2E,ZQ,XB,YA), (R1I,R2E,ZQ,XB,YA), (R1J,R2E,ZQ,XB,YA), (R1K,R2E,ZQ,XB,YA), (R1L,R2E,ZQ,XB,YA), (R1M,R2E,ZQ,XB,YA), (R1N,R2E,ZQ,XB,YA), (R1O,R2E,ZQ,XB,YA), (R1P,R2E,ZQ,XB,YA), (R1Q,R2E,ZQ,XB,YA), (R1A,R2F,ZQ,XB,YA), (R1B,R2F,ZQ,XB,YA), (R1C,R2F,ZQ,XB,YA), (R1D,R2F,ZQ,XB,YA), (R1E,R2F,ZQ,XB,YA), (R1F,R2F,ZQ,XB,YA), (R1G,R2F,ZQ,XB,YA), (R1H,R2F,ZQ,XB,YA), (R1I,R2F,ZQ,XB,YA), (R1J,R2F,ZQ,XB,YA), (R1K,R2F,ZQ,XB,YA), (R1L,R2F,ZQ,XB,YA), (R1M,R2F,ZQ,XB,YA), (R1N,R2F,ZQ,XB,YA), (R1O,R2F,ZQ,XB,YA), (R1P,R2F,ZQ,XB,YA), (R1Q,R2F,ZQ,XB,YA), (R1A,R2G,ZQ,XB,YA), (R1B,R2G,ZQ,XB,YA), (R1C,R2G,ZQ,XB,YA), (R1D,R2G,ZQ,XB,YA), (R1E,R2G,ZQ,XB,YA), (R1F,R2G,ZQ,XB,YA), (R1G,R2G,ZQ,XB,YA), (R1H,R2G,ZQ,XB,YA), (R1I,R2G,ZQ,XB,YA), (R1J,R2G,ZQ,XB,YA), (R1K,R2G,ZQ,XB,YA), (R1L,R2G,ZQ,XB,YA), (R1M,R2G,ZQ,XB,YA), (R1N,R2G,ZQ,XB,YA), (R1O,R2G,ZQ,XB,YA), (R1P,R2G,ZQ,XB,YA), (R1Q,R2G,ZQ,XB,YA), (R1A,R2H,ZQ,XB,YA), (R1B,R2H,ZQ,XB,YA), (R1C,R2H,ZQ,XB,YA), (R1D,R2H,ZQ,XB,YA), (R1E,R2H,ZQ,XB,YA), (R1F,R2H,ZQ,XB,YA), (R1G,R2H,ZQ,XB,YA), (R1H,R2H,ZQ,XB,YA), (R1I,R2H,ZQ,XB,YA), (R1J,R2H,ZQ,XB,YA), (R1K,R2H,ZQ,XB,YA), (R1L,R2H,ZQ,XB,YA), (R1M,R2H,ZQ,XB,YA), (R1N,R2H,ZQ,XB,YA), (R1O,R2H,ZQ,XB,YA), (R1P,R2H,ZQ,XB,YA), (R1Q,R2H,ZQ,XB,YA), (R1A,R2I,ZQ,XB,YA), (R1B,R2I,ZQ,XB,YA), (R1C,R2I,ZQ,XB,YA), (R1D,R2I,ZQ,XB,YA), (R1E,R2I,ZQ,XB,YA), (R1F,R2I,ZQ,XB,YA), (R1G,R2I,ZQ,XB,YA), (R1H,R2I,ZQ,XB,YA), (R1I,R2I,ZQ,XB,YA), (R1J,R2I,ZQ,XB,YA), (R1K,R2I,ZQ,XB,YA), (R1L,R2I,ZQ,XB,YA), (R1M,R2I,ZQ,XB,YA), (R1N,R2I,ZQ,XB,YA), (R1O,R2I,ZQ,XB,YA), (R1P,R2I,ZQ,XB,YA), (R1Q,R2I,ZQ,XB,YA), (R1A,R2J,ZQ,XB,YA), (R1B,R2J,ZQ,XB,YA), (R1C,R2J,ZQ,XB,YA), (R1D,R2J,ZQ,XB,YA), (R1E,R2J,ZQ,XB,YA), (R1F,R2J,ZQ,XB,YA), (R1G,R2J,ZQ,XB,YA), (R1H,R2J,ZQ,XB,YA), (R1I,R2J,ZQ,XB,YA), (R1J,R2J,ZQ,XB,YA), (R1K,R2J,ZQ,XB,YA), (R1L,R2J,ZQ,XB,YA), (R1M,R2J,ZQ,XB,YA), (R1N,R2J,ZQ,XB,YA), (R1O,R2J,ZQ,XB,YA), (R1P,R2J,ZQ,XB,YA), (R1Q,R2J,ZQ,XB,YA), (R1A,R2K,ZQ,XB,YA), (R1B,R2K,ZQ,XB,YA), (R1C,R2K,ZQ,XB,YA), (R1D,R2K,ZQ,XB,YA), (R1E,R2K,ZQ,XB,YA), (R1F,R2K,ZQ,XB,YA), (R1G,R2K,ZQ,XB,YA), (R1H,R2K,ZQ,XB,YA), (R1I,R2K,ZQ,XB,YA), (R1J,R2K,ZQ,XB,YA), (R1K,R2K,ZQ,XB,YA), (R1L,R2K,ZQ,XB,YA), (R1M,R2K,ZQ,XB,YA), (R1N,R2K,ZQ,XB,YA), (R1O,R2K,ZQ,XB,YA), (R1P,R2K,ZQ,XB,YA), (R1Q,R2K,ZQ,XB,YA), (R1A,R2L,ZQ,XB,YA), (R1B,R2L,ZQ,XB,YA), (R1C,R2L,ZQ,XB,YA), (R1D,R2L,ZQ,XB,YA), (R1E,R2L,ZQ,XB,YA), (R1F,R2L,ZQ,XB,YA), (R1G,R2L,ZQ,XB,YA), (R1H,R2L,ZQ,XB,YA), (R1I,R2L,ZQ,XB,YA), (R1J,R2L,ZQ,XB,YA), (R1K,R2L,ZQ,XB,YA), (R1L,R2L,ZQ,XB,YA), (R1M,R2L,ZQ,XB,YA), (R1N,R2L,ZQ,XB,YA), (R1O,R2L,ZQ,XB,YA), (R1P,R2L,ZQ,XB,YA), (R1Q,R2L,ZQ,XB,YA), (R1A,R2M,ZQ,XB,YA), (R1B,R2M,ZQ,XB,YA), (R1C,R2M,ZQ,XB,YA), (R1D,R2M,ZQ,XB,YA), (R1E,R2M,ZQ,XB,YA), (R1F,R2M,ZQ,XB,YA), (R1G,R2M,ZQ,XB,YA), (R1H,R2M,ZQ,XB,YA), (R1I,R2M,ZQ,XB,YA), (R1J,R2M,ZQ,XB,YA), (R1K,R2M,ZQ,XB,YA), (R1L,R2M,ZQ,XB,YA), (R1M,R2M,ZQ,XB,YA), (R1N,R2M,ZQ,XB,YA), (R1O,R2M,ZQ,XB,YA), (R1P,R2M,ZQ,XB,YA), (R1Q,R2M,ZQ,XB,YA), (R1A,R2N,ZQ,XB,YA), (R1B,R2N,ZQ,XB,YA), (R1C,R2N,ZQ,XB,YA), (R1D,R2N,ZQ,XB,YA), (R1E,R2N,ZQ,XB,YA), (R1F,R2N,ZQ,XB,YA), (R1G,R2N,ZQ,XB,YA), (R1H,R2N,ZQ,XB,YA), (R1I,R2N,ZQ,XB,YA), (R1J,R2N,ZQ,XB,YA), (R1K,R2N,ZQ,XB,YA), (R1L,R2N,ZQ,XB,YA), (R1M,R2N,ZQ,XB,YA), (R1N,R2N,ZQ,XB,YA), (R1O,R2N,ZQ,XB,YA), (R1P,R2N,ZQ,XB,YA), (R1Q,R2N,ZQ,XB,YA), (R1A,R2O,ZQ,XB,YA), (R1B,R2O,ZQ,XB,YA), (R1C,R2O,ZQ,XB,YA), (R1D,R2O,ZQ,XB,YA), (R1E,R2O,ZQ,XB,YA), (R1F,R2O,ZQ,XB,YA), (R1G,R2O,ZQ,XB,YA), (R1H,R2O,ZQ,XB,YA), (R1I,R2O,ZQ,XB,YA), (R1J,R2O,ZQ,XB,YA), (R1K,R2O,ZQ,XB,YA), (R1L,R2O,ZQ,XB,YA), (R1M,R2O,ZQ,XB,YA), (R1N,R2O,ZQ,XB,YA), (R1O,R2O,ZQ,XB,YA), (R1P,R2O,ZQ,XB,YA), (R1Q,R2O,ZQ,XB,YA), (R1A,R2P,ZQ,XB,YA), (R1B,R2P,ZQ,XB,YA), (R1C,R2P,ZQ,XB,YA), (R1D,R2P,ZQ,XB,YA), (R1E,R2P,ZQ,XB,YA), (R1F,R2P,ZQ,XB,YA), (R1G,R2P,ZQ,XB,YA), (R1H,R2P,ZQ,XB,YA), (R1I,R2P,ZQ,XB,YA), (R1J,R2P,ZQ,XB,YA), (R1K,R2P,ZQ,XB,YA), (R1L,R2P,ZQ,XB,YA), (R1M,R2P,ZQ,XB,YA), (R1N,R2P,ZQ,XB,YA), (R1O,R2P,ZQ,XB,YA), (R1P,R2P,ZQ,XB,YA), (R1Q,R2P,ZQ,XB,YA), (R1A,R2Q,ZQ,XB,YA), (R1B,R2Q,ZQ,XB,YA), (R1C,R2Q,ZQ,XB,YA), (R1D,R2Q,ZQ,XB,YA), (R1E,R2Q,ZQ,XB,YA), (R1F,R2Q,ZQ,XB,YA), (R1G,R2Q,ZQ,XB,YA), (R1H,R2Q,ZQ,XB,YA), (R1I,R2Q,ZQ,XB,YA), (R1J,R2Q,ZQ,XB,YA), (R1K,R2Q,ZQ,XB,YA), (R1L,R2Q,ZQ,XB,YA), (R1M,R2Q,ZQ,XB,YA), (R1N,R2Q,ZQ,XB,YA), (R1O,R2Q,ZQ,XB,YA), (R1P,R2Q,ZQ,XB,YA), (R1Q,R2Q,ZQ,XB,YA), (R1A,R2A,ZR,XB,YA), (R1B,R2A,ZR,XB,YA), (R1C,R2A,ZR,XB,YA), (R1D,R2A,ZR,XB,YA), (R1E,R2A,ZR,XB,YA), (R1F,R2A,ZR,XB,YA), (R1G,R2A,ZR,XB,YA), (R1H,R2A,ZR,XB,YA), (R1I,R2A,ZR,XB,YA), (R1J,R2A,ZR,XB,YA), (R1K,R2A,ZR,XB,YA), (R1L,R2A,ZR,XB,YA), (R1M,R2A,ZR,XB,YA), (R1N,R2A,ZR,XB,YA), (R1O,R2A,ZR,XB,YA), (R1P,R2A,ZR,XB,YA), (R1Q,R2A,ZR,XB,YA), (R1A,R2B,ZR,XB,YA), (R1B,R2B,ZR,XB,YA), (R1C,R2B,ZR,XB,YA), (R1D,R2B,ZR,XB,YA), (R1E,R2B,ZR,XB,YA), (R1F,R2B,ZR,XB,YA), (R1G,R2B,ZR,XB,YA), (R1H,R2B,ZR,XB,YA), (R1I,R2B,ZR,XB,YA), (R1J,R2B,ZR,XB,YA), (R1K,R2B,ZR,XB,YA), (R1L,R2B,ZR,XB,YA), (R1M,R2B,ZR,XB,YA), (R1N,R2B,ZR,XB,YA), (R1O,R2B,ZR,XB,YA), (R1P,R2B,ZR,XB,YA), (R1Q,R2B,ZR,XB,YA), (R1A,R2C,ZR,XB,YA), (R1B,R2C,ZR,XB,YA), (R1C,R2C,ZR,XB,YA), (R1D,R2C,ZR,XB,YA), (R1E,R2C,ZR,XB,YA), (R1F,R2C,ZR,XB,YA), (R1G,R2C,ZR,XB,YA), (R1H,R2C,ZR,XB,YA), (R1I,R2C,ZR,XB,YA), (R1J,R2C,ZR,XB,YA), (R1K,R2C,ZR,XB,YA), (R1L,R2C,ZR,XB,YA), (R1M,R2C,ZR,XB,YA), (R1N,R2C,ZR,XB,YA), (R1O,R2C,ZR,XB,YA), (R1P,R2C,ZR,XB,YA), (R1Q,R2C,ZR,XB,YA), (R1A,R2D,ZR,XB,YA), (R1B,R2D,ZR,XB,YA), (R1C,R2D,ZR,XB,YA), (R1D,R2D,ZR,XB,YA), (R1E,R2D,ZR,XB,YA), (R1F,R2D,ZR,XB,YA), (R1G,R2D,ZR,XB,YA), (R1H,R2D,ZR,XB,YA), (R1I,R2D,ZR,XB,YA), (R1J,R2D,ZR,XB,YA), (R1K,R2D,ZR,XB,YA), (R1L,R2D,ZR,XB,YA), (R1M,R2D,ZR,XB,YA), (R1N,R2D,ZR,XB,YA), (R1O,R2D,ZR,XB,YA), (R1P,R2D,ZR,XB,YA), (R1Q,R2D,ZR,XB,YA), (R1A,R2E,ZR,XB,YA), (R1B,R2E,ZR,XB,YA), (R1C,R2E,ZR,XB,YA), (R1D,R2E,ZR,XB,YA), (R1E,R2E,ZR,XB,YA), (R1F,R2E,ZR,XB,YA), (R1G,R2E,ZR,XB,YA), (R1H,R2E,ZR,XB,YA), (R1I,R2E,ZR,XB,YA), (R1J,R2E,ZR,XB,YA), (R1K,R2E,ZR,XB,YA), (R1L,R2E,ZR,XB,YA), (R1M,R2E,ZR,XB,YA), (R1N,R2E,ZR,XB,YA), (R1O,R2E,ZR,XB,YA), (R1P,R2E,ZR,XB,YA), (R1Q,R2E,ZR,XB,YA), (R1A,R2F,ZR,XB,YA), (R1B,R2F,ZR,XB,YA), (R1C,R2F,ZR,XB,YA), (R1D,R2F,ZR,XB,YA), (R1E,R2F,ZR,XB,YA), (R1F,R2F,ZR,XB,YA), (R1G,R2F,ZR,XB,YA), (R1H,R2F,ZR,XB,YA), (R1I,R2F,ZR,XB,YA), (R1J,R2F,ZR,XB,YA), (R1K,R2F,ZR,XB,YA), (R1L,R2F,ZR,XB,YA), (R1M,R2F,ZR,XB,YA), (R1N,R2F,ZR,XB,YA), (R1O,R2F,ZR,XB,YA), (R1P,R2F,ZR,XB,YA), (R1Q,R2F,ZR,XB,YA), (R1A,R2G,ZR,XB,YA), (R1B,R2G,ZR,XB,YA), (R1C,R2G,ZR,XB,YA), (R1D,R2G,ZR,XB,YA), (R1E,R2G,ZR,XB,YA), (R1F,R2G,ZR,XB,YA), (R1G,R2G,ZR,XB,YA), (R1H,R2G,ZR,XB,YA), (R1I,R2G,ZR,XB,YA), (R1J,R2G,ZR,XB,YA), (R1K,R2G,ZR,XB,YA), (R1L,R2G,ZR,XB,YA), (R1M,R2G,ZR,XB,YA), (R1N,R2G,ZR,XB,YA), (R1O,R2G,ZR,XB,YA), (R1P,R2G,ZR,XB,YA), (R1Q,R2G,ZR,XB,YA), (R1A,R2H,ZR,XB,YA), (R1B,R2H,ZR,XB,YA), (R1C,R2H,ZR,XB,YA), (R1D,R2H,ZR,XB,YA), (R1E,R2H,ZR,XB,YA), (R1F,R2H,ZR,XB,YA), (R1G,R2H,ZR,XB,YA), (R1H,R2H,ZR,XB,YA), (R1I,R2H,ZR,XB,YA), (R1J,R2H,ZR,XB,YA), (R1K,R2H,ZR,XB,YA), (R1L,R2H,ZR,XB,YA), (R1M,R2H,ZR,XB,YA), (R1N,R2H,ZR,XB,YA), (R1O,R2H,ZR,XB,YA), (R1P,R2H,ZR,XB,YA), (R1Q,R2H,ZR,XB,YA), (R1A,R2I,ZR,XB,YA), (R1B,R2I,ZR,XB,YA), (R1C,R2I,ZR,XB,YA), (R1D,R2I,ZR,XB,YA), (R1E,R2I,ZR,XB,YA), (R1F,R2I,ZR,XB,YA), (R1G,R2I,ZR,XB,YA), (R1H,R2I,ZR,XB,YA), (R1I,R2I,ZR,XB,YA), (R1J,R2I,ZR,XB,YA), (R1K,R2I,ZR,XB,YA), (R1L,R2I,ZR,XB,YA), (R1M,R2I,ZR,XB,YA), (R1N,R2I,ZR,XB,YA), (R1O,R2I,ZR,XB,YA), (R1P,R2I,ZR,XB,YA), (R1Q,R2I,ZR,XB,YA), (R1A,R2J,ZR,XB,YA), (R1B,R2J,ZR,XB,YA), (R1C,R2J,ZR,XB,YA), (R1D,R2J,ZR,XB,YA), (R1E,R2J,ZR,XB,YA), (R1F,R2J,ZR,XB,YA), (R1G,R2J,ZR,XB,YA), (R1H,R2J,ZR,XB,YA), (R1I,R2J,ZR,XB,YA), (R1J,R2J,ZR,XB,YA), (R1K,R2J,ZR,XB,YA), (R1L,R2J,ZR,XB,YA), (R1M,R2J,ZR,XB,YA), (R1N,R2J,ZR,XB,YA), (R1O,R2J,ZR,XB,YA), (R1P,R2J,ZR,XB,YA), (R1Q,R2J,ZR,XB,YA), (R1A,R2K,ZR,XB,YA), (R1B,R2K,ZR,XB,YA), (R1C,R2K,ZR,XB,YA), (R1D,R2K,ZR,XB,YA), (R1E,R2K,ZR,XB,YA), (R1F,R2K,ZR,XB,YA), (R1G,R2K,ZR,XB,YA), (R1H,R2K,ZR,XB,YA), (R1I,R2K,ZR,XB,YA), (R1J,R2K,ZR,XB,YA), (R1K,R2K,ZR,XB,YA), (R1L,R2K,ZR,XB,YA), (R1M,R2K,ZR,XB,YA), (R1N,R2K,ZR,XB,YA), (R1O,R2K,ZR,XB,YA), (R1P,R2K,ZR,XB,YA), (R1Q,R2K,ZR,XB,YA), (R1A,R2L,ZR,XB,YA), (R1B,R2L,ZR,XB,YA), (R1C,R2L,ZR,XB,YA), (R1D,R2L,ZR,XB,YA), (R1E,R2L,ZR,XB,YA), (R1F,R2L,ZR,XB,YA), (R1G,R2L,ZR,XB,YA), (R1H,R2L,ZR,XB,YA), (R1I,R2L,ZR,XB,YA), (R1J,R2L,ZR,XB,YA), (R1K,R2L,ZR,XB,YA), (R1L,R2L,ZR,XB,YA), (R1M,R2L,ZR,XB,YA), (R1N,R2L,ZR,XB,YA), (R1O,R2L,ZR,XB,YA), (R1P,R2L,ZR,XB,YA), (R1Q,R2L,ZR,XB,YA), (R1A,R2M,ZR,XB,YA), (R1B,R2M,ZR,XB,YA), (R1C,R2M,ZR,XB,YA), (R1D,R2M,ZR,XB,YA), (R1E,R2M,ZR,XB,YA), (R1F,R2M,ZR,XB,YA), (R1G,R2M,ZR,XB,YA), (R1H,R2M,ZR,XB,YA), (R1I,R2M,ZR,XB,YA), (R1J,R2M,ZR,XB,YA), (R1K,R2M,ZR,XB,YA), (R1L,R2M,ZR,XB,YA), (R1M,R2M,ZR,XB,YA), (R1N,R2M,ZR,XB,YA), (R1O,R2M,ZR,XB,YA), (R1P,R2M,ZR,XB,YA), (R1Q,R2M,ZR,XB,YA), (R1A,R2N,ZR,XB,YA), (R1B,R2N,ZR,XB,YA), (R1C,R2N,ZR,XB,YA), (R1D,R2N,ZR,XB,YA), (R1E,R2N,ZR,XB,YA), (R1F,R2N,ZR,XB,YA), (R1G,R2N,ZR,XB,YA), (R1H,R2N,ZR,XB,YA), (R1I,R2N,ZR,XB,YA), (R1J,R2N,ZR,XB,YA), (R1K,R2N,ZR,XB,YA), (R1L,R2N,ZR,XB,YA), (R1M,R2N,ZR,XB,YA), (R1N,R2N,ZR,XB,YA), (R1O,R2N,ZR,XB,YA), (R1P,R2N,ZR,XB,YA), (R1Q,R2N,ZR,XB,YA), (R1A,R2O,ZR,XB,YA), (R1B,R2O,ZR,XB,YA), (R1C,R2O,ZR,XB,YA), (R1D,R2O,ZR,XB,YA), (R1E,R2O,ZR,XB,YA), (R1F,R2O,ZR,XB,YA), (R1G,R2O,ZR,XB,YA), (R1H,R2O,ZR,XB,YA), (R1I,R2O,ZR,XB,YA), (R1J,R2O,ZR,XB,YA), (R1K,R2O,ZR,XB,YA), (R1L,R2O,ZR,XB,YA), (R1M,R2O,ZR,XB,YA), (R1N,R2O,ZR,XB,YA), (R1O,R2O,ZR,XB,YA), (R1P,R2O,ZR,XB,YA), (R1Q,R2O,ZR,XB,YA), (R1A,R2P,ZR,XB,YA), (R1B,R2P,ZR,XB,YA), (R1C,R2P,ZR,XB,YA), (R1D,R2P,ZR,XB,YA), (R1E,R2P,ZR,XB,YA), (R1F,R2P,ZR,XB,YA), (R1G,R2P,ZR,XB,YA), (R1H,R2P,ZR,XB,YA), (R1I,R2P,ZR,XB,YA), (R1J,R2P,ZR,XB,YA), (R1K,R2P,ZR,XB,YA), (R1L,R2P,ZR,XB,YA), (R1M,R2P,ZR,XB,YA), (R1N,R2P,ZR,XB,YA), (R1O,R2P,ZR,XB,YA), (R1P,R2P,ZR,XB,YA), (R1Q,R2P,ZR,XB,YA), (R1A,R2Q,ZR,XB,YA), (R1B,R2Q,ZR,XB,YA), (R1C,R2Q,ZR,XB,YA), (R1D,R2Q,ZR,XB,YA), (R1E,R2Q,ZR,XB,YA), (R1F,R2Q,ZR,XB,YA), (R1G,R2Q,ZR,XB,YA), (R1H,R2Q,ZR,XB,YA), (R1I,R2Q,ZR,XB,YA), (R1J,R2Q,ZR,XB,YA), (R1K,R2Q,ZR,XB,YA), (R1L,R2Q,ZR,XB,YA), (R1M,R2Q,ZR,XB,YA), (R1N,R2Q,ZR,XB,YA), (R1O,R2Q,ZR,XB,YA), (R1P,R2Q,ZR,XB,YA), (R1Q,R2Q,ZR,XB,YA), (R1A,R2A,ZS,XB,YA), (R1B,R2A,ZS,XB,YA), (R1C,R2A,ZS,XB,YA), (R1D,R2A,ZS,XB,YA), (R1E,R2A,ZS,XB,YA), (R1F,R2A,ZS,XB,YA), (R1G,R2A,ZS,XB,YA), (R1H,R2A,ZS,XB,YA), (R1I,R2A,ZS,XB,YA), (R1J,R2A,ZS,XB,YA), (R1K,R2A,ZS,XB,YA), (R1L,R2A,ZS,XB,YA), (R1M,R2A,ZS,XB,YA), (R1N,R2A,ZS,XB,YA), (R1O,R2A,ZS,XB,YA), (R1P,R2A,ZS,XB,YA), (R1Q,R2A,ZS,XB,YA), (R1A,R2B,ZS,XB,YA), (R1B,R2B,ZS,XB,YA), (R1C,R2B,ZS,XB,YA), (R1D,R2B,ZS,XB,YA), (R1E,R2B,ZS,XB,YA), (R1F,R2B,ZS,XB,YA), (R1G,R2B,ZS,XB,YA), (R1H,R2B,ZS,XB,YA), (R1I,R2B,ZS,XB,YA), (R1J,R2B,ZS,XB,YA), (R1K,R2B,ZS,XB,YA), (R1L,R2B,ZS,XB,YA), (R1M,R2B,ZS,XB,YA), (R1N,R2B,ZS,XB,YA), (R1O,R2B,ZS,XB,YA), (R1P,R2B,ZS,XB,YA), (R1Q,R2B,ZS,XB,YA), (R1A,R2C,ZS,XB,YA), (R1B,R2C,ZS,XB,YA), (R1C,R2C,ZS,XB,YA), (R1D,R2C,ZS,XB,YA), (R1E,R2C,ZS,XB,YA), (R1F,R2C,ZS,XB,YA), (R1G,R2C,ZS,XB,YA), (R1H,R2C,ZS,XB,YA), (R1I,R2C,ZS,XB,YA), (R1J,R2C,ZS,XB,YA), (R1K,R2C,ZS,XB,YA), (R1L,R2C,ZS,XB,YA), (R1M,R2C,ZS,XB,YA), (R1N,R2C,ZS,XB,YA), (R1O,R2C,ZS,XB,YA), (R1P,R2C,ZS,XB,YA), (R1Q,R2C,ZS,XB,YA), (R1A,R2D,ZS,XB,YA), (R1B,R2D,ZS,XB,YA), (R1C,R2D,ZS,XB,YA), (R1D,R2D,ZS,XB,YA), (R1E,R2D,ZS,XB,YA), (R1F,R2D,ZS,XB,YA), (R1G,R2D,ZS,XB,YA), (R1H,R2D,ZS,XB,YA), (R1I,R2D,ZS,XB,YA), (R1J,R2D,ZS,XB,YA), (R1K,R2D,ZS,XB,YA), (R1L,R2D,ZS,XB,YA), (R1M,R2D,ZS,XB,YA), (R1N,R2D,ZS,XB,YA), (R1O,R2D,ZS,XB,YA), (R1P,R2D,ZS,XB,YA), (R1Q,R2D,ZS,XB,YA), (R1A,R2E,ZS,XB,YA), (R1B,R2E,ZS,XB,YA), (R1C,R2E,ZS,XB,YA), (R1D,R2E,ZS,XB,YA), (R1E,R2E,ZS,XB,YA), (R1F,R2E,ZS,XB,YA), (R1G,R2E,ZS,XB,YA), (R1H,R2E,ZS,XB,YA), (R1I,R2E,ZS,XB,YA), (R1J,R2E,ZS,XB,YA), (R1K,R2E,ZS,XB,YA), (R1L,R2E,ZS,XB,YA), (R1M,R2E,ZS,XB,YA), (R1N,R2E,ZS,XB,YA), (R1O,R2E,ZS,XB,YA), (R1P,R2E,ZS,XB,YA), (R1Q,R2E,ZS,XB,YA), (R1A,R2F,ZS,XB,YA), (R1B,R2F,ZS,XB,YA), (R1C,R2F,ZS,XB,YA), (R1D,R2F,ZS,XB,YA), (R1E,R2F,ZS,XB,YA), (R1F,R2F,ZS,XB,YA), (R1G,R2F,ZS,XB,YA), (R1H,R2F,ZS,XB,YA), (R1I,R2F,ZS,XB,YA), (R1J,R2F,ZS,XB,YA), (R1K,R2F,ZS,XB,YA), (R1L,R2F,ZS,XB,YA), (R1M,R2F,ZS,XB,YA), (R1N,R2F,ZS,XB,YA), (R1O,R2F,ZS,XB,YA), (R1P,R2F,ZS,XB,YA), (R1Q,R2F,ZS,XB,YA), (R1A,R2G,ZS,XB,YA), (R1B,R2G,ZS,XB,YA), (R1C,R2G,ZS,XB,YA), (R1D,R2G,ZS,XB,YA), (R1E,R2G,ZS,XB,YA), (R1F,R2G,ZS,XB,YA), (R1G,R2G,ZS,XB,YA), (R1H,R2G,ZS,XB,YA), (R1I,R2G,ZS,XB,YA), (R1J,R2G,ZS,XB,YA), (R1K,R2G,ZS,XB,YA), (R1L,R2G,ZS,XB,YA), (R1M, R2G,ZS,XB,YA), (R1N,R2G,ZS,XB,YA), (R1O,R2G,ZS,XB,YA), (R1P,R2G,ZS,XB,YA), (R1Q,R2G,ZS,XB,YA), (R1A,R2H,ZS,XB,YA), (R1B,R2H,ZS,XB,YA), (R1C,R2H,ZS,XB,YA), (R1D,R2H,ZS,XB,YA), (R1E,R2H,ZS,XB,YA), (R1F,R2H,ZS,XB,YA), (R1G,R2H,ZS,XB,YA), (R1H,R2H,ZS,XB,YA), (R1I,R2H,ZS,XB,YA), (R1J,R2H,ZS,XB,YA), (R1K,R2H,ZS,XB,YA), (R1L,R2H,ZS,XB,YA), (R1M,R2H,ZS,XB,YA), (R1N,R2H,ZS,XB,YA), (R1O,R2H,ZS,XB,YA), (R1P,R2H,ZS,XB,YA), (R1Q,R2H,ZS,XB,YA), (R1A,R2I,ZS,XB,YA), (R1B,R2I,ZS,XB,YA), (R1C,R2I,ZS,XB,YA), (R1D,R2I,ZS,XB,YA), (R1E,R2I,ZS,XB,YA), (R1F,R2I,ZS,XB,YA), (R1G,R2I,ZS,XB,YA), (R1H,R2I,ZS,XB,YA), (R1I,R2I,ZS,XB,YA), (R1J,R2I,ZS,XB,YA), (R1K,R2I,ZS,XB,YA), (R1L,R2I,ZS,XB,YA), (R1M,R2I,ZS,XB,YA), (R1N,R2I,ZS,XB,YA), (R1O,R2I,ZS,XB,YA), (R1P,R2I,ZS,XB,YA), (R1Q,R2I,ZS,XB,YA), (R1A,R2J,ZS,XB,YA), (R1B,R2J,ZS,XB,YA), (R1C,R2J,ZS,XB,YA), (R1D,R2J,ZS,XB,YA), (R1E,R2J,ZS,XB,YA), (R1F,R2J,ZS,XB,YA), (R1G,R2J,ZS,XB,YA), (R1H,R2J,ZS,XB,YA), (R1I,R2J,ZS,XB,YA), (R1J,R2J,ZS,XB,YA), (R1K,R2J,ZS,XB,YA), (R1L,R2J,ZS,XB,YA), (R1M,R2J,ZS,XB,YA), (R1N,R2J,ZS,XB,YA), (R1O,R2J,ZS,XB,YA), (R1P,R2J,ZS,XB,YA), (R1Q,R2J,ZS,XB,YA), (R1A,R2K,ZS,XB,YA), (R1B,R2K,ZS,XB,YA), (R1C,R2K,ZS,XB,YA), (R1D,R2K,ZS,XB,YA), (R1E,R2K,ZS,XB,YA), (R1F,R2K,ZS,XB,YA), (R1G,R2K,ZS,XB,YA), (R1H,R2K,ZS,XB,YA), (R1I,R2K,ZS,XB,YA), (R1J,R2K,ZS,XB,YA), (R1K,R2K,ZS,XB,YA), (R1L,R2K,ZS,XB,YA), (R1M,R2K,ZS,XB,YA), (R1N,R2K,ZS,XB,YA), (R1O,R2K,ZS,XB,YA), (R1P,R2K,ZS,XB,YA), (R1Q,R2K,ZS,XB,YA), (R1A,R2L,ZS,XB,YA), (R1B,R2L,ZS,XB,YA), (R1C,R2L,ZS,XB,YA), (R1D,R2L,ZS,XB,YA), (R1E,R2L,ZS,XB,YA), (R1F,R2L,ZS,XB,YA), (R1G,R2L,ZS,XB,YA), (R1H,R2L,ZS,XB,YA), (R1I,R2L,ZS,XB,YA)(R1J,R2L,ZS,XB,YA), (R1K,R2L,ZS,XB,YA), (R1L,R2L,ZS,XB,YA), (R1M,R2L,ZS,XB,YA), (R1N,R2L,ZS,XB,YA), (R1O,R2L,ZS,XB,YA), (R1P,R2L,ZS,XB,YA), (R1Q,R2L,ZS,XB,YA), (R1A,R2M,ZS,XB,YA), (R1B,R2M,ZS,XB,YA), (R1C,R2M,ZS,XB,YA), (R1D,R2M,ZS,XB,YA), (R1E,R2M,ZS,XB,YA), (R1F,R2M,ZS,XB,YA), (R1G,R2M,ZS,XB,YA), (R1H,R2M,ZS,XB,YA), (R1I,R2M,ZS,XB,YA), (R1J,R2M,ZS,XB,YA), (R1K,R2M,ZS,XB,YA), (R1L,R2M,ZS,XB,YA), (R1M,R2M,ZS,XB,YA), (R1N,R2M,ZS,XB,YA), (R1O,R2M,ZS,XB,YA), (R1P,R2M,ZS,XB,YA), (R1Q,R2M,ZS,XB,YA), (R1A,R2N,ZS,XB,YA), (R1B,R2N,ZS,XB,YA), (R1C,R2N,ZS,XB,YA), (R1D,R2N,ZS,XB,YA), (R1E,R2N,ZS,XB,YA), (R1F,R2N,ZS,XB,YA), (R1G,R2N,ZS,XB,YA), (R1H,R2N,ZS,XB,YA), (R1I,R2N,ZS,XB,YA), (R1J,R2N,ZS,XB,YA), (R1K,R2N,ZS,XB,YA), (R1L,R2N,ZS,XB,YA), (R1M,R2N,ZS,XB,YA), (R1N,R2N,ZS,XB,YA), (R1O,R2N,ZS,XB,YA), (R1P,R2N,ZS,XB,YA), (R1Q,R2N,ZS,XB,YA), (R1A,R2O,ZS,XB,YA), (R1B,R2O,ZS,XB,YA), (R1C,R2O,ZS,XB,YA), (R1D,R2O,ZS,XB,YA), (R1E,R2O,ZS,XB,YA), (R1F,R2O,ZS,XB,YA), (R1G,R2O,ZS,XB,YA), (R1H,R2O,ZS,XB,YA), (R1I,R2O,ZS,XB,YA), (R1J,R2O,ZS,XB,YA), (R1K,R2O,ZS,XB,YA), (R1L,R2O,ZS,XB,YA), (R1M,R2O,ZS,XB,YA), (R1N,R2O,ZS,XB,YA), (R1O,R2O,ZS,XB,YA), (R1P,R2O,ZS,XB,YA), (R1Q,R2O,ZS,XB,YA), (R1A,R2P,ZS,XB,YA), (R1B,R2P,ZS,XB,YA), (R1C,R2P,ZS,XB,YA), (R1D,R2P,ZS,XB,YA), (R1E,R2P,ZS,XB,YA), (R1F,R2P,ZS,XB,YA), (R1G,R2P,ZS,XB,YA), (R1H,R2P,ZS,XB,YA), (R1I,R2P,ZS,XB,YA), (R1J,R2P,ZS,XB,YA), (R1K,R2P,ZS,XB,YA), (R1L,R2P,ZS,XB,YA), (R1M,R2P,ZS,XB,YA), (R1N,R2P,ZS,XB,YA), (R1O,R2P,ZS,XB,YA), (R1P,R2P,ZS,XB,YA), (R1Q,R2P,ZS,XB,YA), (R1A,R2Q,ZS,XB,YA), (R1B,R2Q,ZS,XB,YA), (R1C,R2Q,ZS,XB,YA), (R1D,R2Q,ZS,XB,YA), (R1E,R2Q,ZS,XB,YA), (R1F,R2Q,ZS,XB,YA), (R1G,R2Q,ZS,XB,YA), (R1H,R2Q,ZS,XB,YA), (R1I,R2Q,ZS,XB,YA), (R1J,R2Q,ZS,XB,YA), (R1K,R2Q,ZS,XB,YA), (R1L,R2Q,ZS,XB,YA), (R1M,R2Q,ZS,XB,YA), (R1N,R2Q,ZS,XB,YA), (R1O,R2Q,ZS,XB,YA), (R1P,R2Q,ZS,XB,YA), (R1Q,R2Q,ZS,XB,YA), (R1A,R2A,ZT,XB,YA), (R1B,R2A,ZT,XB,YA), (R1C,R2A,ZT,XB,YA), (R1D,R2A,ZT,XB,YA), (R1E,R2A,ZT,XB,YA), (R1F,R2A,ZT,XB,YA), (R1G,R2A,ZT,XB,YA), (R1H,R2A,ZT,XB,YA), (R1I,R2A,ZT,XB,YA), (R1J,R2A,ZT,XB,YA), (R1K,R2A,ZT,XB,YA), (R1L,R2A,ZT,XB,YA), (R1M,R2A,ZT,XB,YA), (R1N,R2A,ZT,XB,YA), (R1O,R2A,ZT,XB,YA), (R1P,R2A,ZT,XB,YA), (R1Q,R2A,ZT,XB,YA), (R1A,R2B,ZT,XB,YA), (R1B,R2B,ZT,XB,YA), (R1C,R2B,ZT,XB,YA), (R1D,R2B,ZT,XB,YA), (R1E,R2B,ZT,XB,YA), (R1F,R2B,ZT,XB,YA), (R1G,R2B,ZT,XB,YA), (R1H,R2B,ZT,XB,YA), (R1I,R2B,ZT,XB,YA), (R1J,R2B,ZT,XB,YA), (R1K,R2B,ZT,XB,YA), (R1L,R2B,ZT,XB,YA), (R1M,R2B,ZT,XB,YA), (R1N,R2B,ZT,XB,YA), (R1O,R2B,ZT,XB,YA), (R1P,R2B,ZT,XB,YA), (R1Q,R2B,ZT,XB,YA), (R1A,R2C,ZT,XB,YA), (R1B,R2C,ZT,XB,YA), (R1C,R2C,ZT,XB,YA), (R1D,R22C,ZT,XB,YA), (R1E,R2C,ZT,XB,YA), (R1F,R2C,ZT,XB,YA), (R1G,R2C,ZT,XB,YA), (R1H,R2C,ZT,XB,YA), (R1I,R2C,ZT,XB,YA), (R1J,R2C,ZT,XB,YA), (R1K,R2C,ZT,XB,YA), (R1L,R2C,ZT,XB,YA), (R1M,R2C,ZT,XB,YA), (R1N,R2C,ZT,XB,YA), (R1O,R2C,ZT,XB,YA), (R1P,R2C,ZT,XB,YA), (R1Q,R2C,ZT,XB,YA), (R1A,R2D,ZT,XB,YA), (R1B,R2D,ZT,XB,YA), (R1C,R2D,ZT,XB,YA), (R1D,R2D,ZT,XB,YA), (R1E,R2D,ZT,XB,YA), (R1F,R2D,ZT,XB,YA), (R1G,R2D,ZT,XB,YA), (R1H,R2D,ZT,XB,YA), (R1I,R2D,ZT,XB,YA), (R1J,R2D,ZT,XB,YA), (R1K,R2D,ZT,XB,YA), (R1L,R2D,ZT,XB,YA), (R1M,R2D,ZT,XB,YA), (R1N,R2D,ZT,XB,YA), (R1O,R2D,ZT,XB,YA), (R1P,R2D,ZT,XB,YA), (R1Q,R2D,ZT,XB,YA), (R1A,R2E,ZT,XB,YA), (R1B,R2E,ZT,XB,YA), (R1C,R2E,ZT,XB,YA), (R1D,R2E,ZT,XB,YA), (R1E,R2E,ZT,XB,YA), (R1F,R2E,ZT,XB,YA), (R1G,R2E,ZT,XB,YA), (R1H,R2E,ZT,XB,YA), (R1I,R2E,ZT,XB,YA), (R1J,R2E,ZT,XB,YA), (R1K,R2E,ZT,XB,YA), (R1L,R2E,ZT,XB,YA), (R1M,R2E,ZT,XB,YA), (R1N,R2E,ZT,XB,YA), (R1O,R2E,ZT,XB,YA), (R1P,R2E,ZT,XB,YA), (R1Q,R2E,ZT,XB,YA), (R1A,R2F,ZT,XB,YA), (R1B,R2F,ZT,XB,YA), (R1C,R2F,ZT,XB,YA), (R1D,R2F,ZT,XB,YA), (R1E,R2F,ZT,XB,YA), (R1F,R2F,ZT,XB,YA), (R1G,R2F,ZT,XB,YA), (R1H,R2F,ZT,XB,YA), (R1I,R2F,ZT,XB,YA), (R1J,R2F,ZT,XB,YA), (R1K,R2F,ZT,XB,YA), (R1L,R2F,ZT,XB,YA), (R1M,R2F,ZT,XB,YA), (R1N,R2F,ZT,XB,YA), (R1O,R2F,ZT,XB,YA), (R1P,R2F,ZT,XB,YA), (R1Q,R2F,ZT,XB,YA), (R1A,R2G,ZT,XB,YA), (R1B,R2G,ZT,XB,YA), (R1C,R2G,ZT,XB,YA), (R1D,R2G,ZT,XB,YA), (R1E,R2G,ZT,XB,YA), (R1F,R2G,ZT,XB,YA), (R1G,R2G,ZT,XB,YA), (R1H,R2G,ZT,XB,YA), (R1I,R2G,ZT,XB,YA), (R1J,R2G,ZT,XB,YA), (R1K,R2G,ZT,XB,YA), (R1L,R2G,ZT,XB,YA), (R1M,R2G,ZT,XB,YA), (R1N,R2G,ZT,XB,YA), (R1O,R2G,ZT,XB,YA), (R1P,R2G,ZT,XB,YA), (R1Q,R2G,ZT,XB,YA), (R1A,R2H,ZT,XB,YA), (R1B,R2H,ZT,XB,YA), (R1C,R2H,ZT,XB,YA), (R1D,R2H,ZT,XB,YA), (R1E,R2H,ZT,XB,YA), (R1F,R2H,ZT,XB,YA), (R1G,R2H,ZT,XB,YA), (R1H,R2H,ZT,XB,YA), (R1I,R2H,ZT,XB,YA), (R1J,R2H,ZT,XB,YA), (R1K,R2H,ZT,XB,YA), (R1L,R2H,ZT,XB,YA), (R1M,R2H,ZT,XB,YA), (R1N,R2H,ZT,XB,YA), (R1O,R2H,ZT,XB,YA), (R1P,R2H,ZT,XB,YA), (R1Q,R2H,ZT,XB,YA), (R1A,R2I,ZT,XB,YA), (R1B,R2I,ZT,XB,YA), (R1C,R2I,ZT,XB,YA), (R1D,R2I,ZT,XB,YA), (R1E,R2I,ZT,XB,YA), (R1F,R2I,ZT,XB,YA), (R1G,R2I,ZT,XB,YA), (R1H,R2I,ZT,XB,YA), (R1I,R2I,ZT,XB,YA), (R1J,R2I,ZT,XB,YA), (R1K,R2I,ZT,XB,YA), (R1L,R2I,ZT,XB,YA), (R1M,R2I, ZT,XB,YA), (R1N,R2I,ZT,XB,YA), (R1O,R2I,ZT,XB,YA), (R1P,R2I,ZT,XB,YA), (R1Q,R2I,ZT,XB,YA), (R1A,R2J,ZT,XB,YA), (R1B,R2J,ZT,XB,YA), (R1C,R2J,ZT,XB,YA), (R1D,R2J,ZT,XB,YA), (R1E,R2J,ZT,XB,YA), (R1F,R2J,ZT,XB,YA), (R1G,R2J,ZT,XB,YA), (R1H,R2J,ZT,XB,YA), (R1I,R2J,ZT,XB,YA), (R1J,R2J,ZT,XB,YA), (R1K,R2J,ZT,XB,YA), (R1L,R2J,ZT,XB,YA), (R1M,R2J,ZT,XB,YA), (R1N,R2J,ZT,XB,YA), (R1O,R2J,ZT,XB,YA), (R1P,R2J,ZT,XB,YA), (R1Q,R2J,ZT,XB,YA), (R1A,R2K,ZT,XB,YA), (R1B,R2K,ZT,XB,YA), (R1C,R2K,ZT,XB,YA), (R1D,R2K,ZT,XB,YA), (R1E,R2K,ZT,XB,YA), (R1F,R2K,ZT,XB,YA), (R1G,R2K,ZT,XB,YA), (R1H,R2K,ZT,XB,YA), (R1I,R2K,ZT,XB,YA), (R1J,R2K,ZT,XB,YA), (R1K,R2K,ZT,XB,YA), (R1L,R2K,ZT,XB,YA), (R1M,R2K,ZT,XB,YA), (R1N,R2K,ZT,XB,YA), (R1O,R2K,ZT,XB,YA), (R1P,R2K,ZT,XB,YA), (R1Q,R2K,ZT,XB,YA), (R1A,R2L,ZT,XB,YA), (R1B,R2L,ZT,XB,YA), (R1C,R2L,ZT,XB,YA), (R1D,R2L,ZT,XB,YA), (R1E,R2L,ZT,XB,YA), (R1F,R2L,ZT,XB,YA), (R1G,R2L,ZT,XB,YA), (R1H,R2L,ZT,XB,YA), (R1I,R2L,ZT,XB,YA), (R1J,R2L,ZT,XB,YA), (R1K,R2L,ZT,XB,YA), (R1L,R2L,ZT,XB,YA), (R1M,R2L,ZT,XB,YA), (R1N,R2L,ZT,XB,YA), (R1O,R2L,ZT,XB,YA), (R1P,R2L,ZT,XB,YA), (R1Q,R2L,ZT,XB,YA), (R1A,R2M,ZT,XB,YA), (R1B,R2M,ZT,XB,YA), (R1C,R2M,ZT,XB,YA), (R1D,R2M,ZT,XB,YA), (R1E,R2M,ZT,XB,YA), (R1F,R2M,ZT,XB,YA), (R1G,R2M,ZT,XB,YA), (R1H,R2M,ZT,XB,YA), (R1I,R2M,ZT,XB,YA), (R1J,R2M,ZT,XB,YA), (R1K,R2M,ZT,XB,YA), (R1L,R2M,ZT,XB,YA), (R1M,R2M,ZT,XB,YA), (R1N,R2M,ZT,XB,YA), (R1O,R2M,ZT,XB,YA), (R1P,R2M,ZT,XB,YA), (R1Q,R2M,ZT,XB,YA), (R1A,R2N,ZT,XB,YA), (R1B,R2N,ZT,XB,YA), (R1C,R2N,ZT,XB,YA), (R1D,R2N,ZT,XB,YA), (R1E,R2N,ZT,XB,YA), (R1F,R2N,ZT,XB,YA), (R1G,R2N,ZT,XB,YA), (R1H,R2N,ZT,XB,YA), (R1I,R2N,ZT,XB,YA), (R1J,R2N,ZT,XB,YA), (R1K,R2N,ZT,XB,YA), (R1L,R2N,ZT,XB,YA), (R1M,R2N,ZT,XB,YA), (R1N,R2N,ZT,XB,YA), (R1O,R2N,ZT,XB,YA), (R1P,R2N,ZT,XB,YA), (R1Q,R2N,ZT,XB,YA), (R1A,R2O,ZT,XB,YA), (R1B,R2O,ZT,XB,YA), (R1C,R2O,ZT,XB,YA), (R1D,R2O,ZT,XB,YA), (R1E,R2O,ZT,XB,YA), (R1F,R2O,ZT,XB,YA), (R1G,R2O,ZT,XB,YA), (R1H,R2O,ZT,XB,YA), (R1I,R2O,ZT,XB,YA), (R1J,R2O,ZT,XB,YA), (R1K,R2O,ZT,XB,YA), (R1L,R2O,ZT,XB,YA), (R1M,R2O,ZT,XB,YA), (R1N,R2O,ZT,XB,YA), (R1O,R2O,ZT,XB,YA), (R1P,R2O,ZT,XB,YA), (R1Q,R2O,ZT,XB,YA), (R1A,R2P,ZT,XB,YA), (R1B,R2P,ZT,XB,YA), (R1C,R2P,ZT,XB,YA), (R1D,R2P,ZT,XB,YA), (R1E,R2P,ZT,XB,YA), (R1F,R2P,ZT,XB,YA), (R1G,R2P,ZT,XB,YA), (R1H,R2P,ZT,XB,YA), (R1I,R2P,ZT,XB,YA), (R1J,R2P,ZT,XB,YA), (R1K,R2P,ZT,XB,YA), (R1L,R2P,ZT,XB,YA), (R1M,R2P,ZT,XB,YA), (R1N,R2P,ZT,XB,YA), (R1O,R2P,ZT,XB,YA), (R1P,R2P,ZT,XB,YA), (R1Q,R2P,ZT,XB,YA), (R1A,R2Q,ZT,XB,YA), (R1B,R2Q,ZT,XB,YA), (R1C,R2Q,ZT,XB,YA), (R1D,R2Q,ZT,XB,YA), (R1E,R2Q,ZT,XB,YA), (R1F,R2Q,ZT,XB,YA), (R1G,R2Q,ZT,XB,YA), (R1H,R2Q,ZT,XB,YA), (R1I,R2Q,ZT,XB,YA), (R1J,R2Q,ZT,XB,YA), (R1K,R2Q,ZT,XB,YA), (R1L,R2Q,ZT,XB,YA), (R1M,R2Q,ZT,XB,YA), (R1N,R2Q,ZT,XB,YA), (R1O,R2Q,ZT,XB,YA), (R1P,R2Q,ZT,XB,YA), (R1Q,R2Q,ZT,XB,YA), (R1A,R2A,ZU,XB,YA), (R1B,R2A,ZU,XB,YA), (R1C,R2A,ZU,XB,YA), (R1D,R2A,ZU,XB,YA), (R1E,R2A,ZU,XB,YA), (R1F,R2A,ZU,XB,YA), (R1G,R2A,ZU,XB,YA), (R1H,R2A,ZU,XB,YA), (R1I,R2A,ZU,XB,YA), (R1J,R2A,ZU,XB,YA), (R1K,R2A,ZU,XB,YA), (R1L,R2A,ZU,XB,YA), (R1M,R2A,ZU,XB,YA), (R1N,R2A,ZU,XB,YA), (R1O,R2A,ZU,XB,YA), (R1P,R2A,ZU,XB,YA), (R1Q,R2A,ZU,XB,YA), (R1A,R2B,ZU,XB,YA), (R1B,R2B,ZU,XB,YA), (R1C,R2B,ZU,XB,YA), (R1D,R2B,ZU,XB,YA), (R1E,R2B,ZU,XB,YA), (R1F,R2B,ZU,XB,YA), (R1G,R2B,ZU,XB,YA), (R1H,R2B,ZU,XB,YA), (R1I,R2B,ZU,XB,YA), (R1J,R2B,ZU,XB,YA), (R1K,R2B,ZU,XB,YA), (R1L,R2B,ZU,XB,YA), (R1M,R2B,ZU,XB,YA), (R1N,R2B,ZU,XB,YA), (R1O,R2B,ZU,XB,YA), (R1P,R2B,ZU,XB,YA), (R1Q,R2B,ZU,XB,YA), (R1A,R2C,ZU,XB,YA), (R1B,R2C,ZU,XB,YA), (R1C,R2C,ZU,XB,YA), (R1D,R2C,ZU,XB,YA), (R1E,R2C,ZU,XB,YA), (R1F,R2C,ZU,XB,YA), (R1G,R2C,ZU,XB,YA), (R1H,R2C,ZU,XB,YA), (R1R2C,ZU,XB,YA), (R1J,R2C,ZU,XB,YA), (R1K,R2C,ZU,XB,YA), (R1L,R2C,ZU,XB,YA), (R1M,R2C,ZU,XB,YA), (R1N,R2C,ZU,XB,YA), (R1O,R2C,ZU,XB,YA), (R1P,R2C,ZU,XB,YA), (R1Q,R22C,ZU,XB,YA), (R1A,R2D,ZU,XB,YA), (R1B,R2D,ZU,XB,YA), (R1C,R2D,ZU,XB,YA), (R1D,R2D,ZU,XB,YA), (R1E,R2D,ZU,XB,YA), (R1F,R2D,ZU,XB,YA), (R1G,R2D,ZU,XB,YA), (R1H,R2D,ZU,XB,YA), (R1I,R2D,ZU,XB,YA), (R1J,R2D,ZU,XB,YA), (R1K,R2D,ZU,XB,YA), (R1L,R2D,ZU,XB,YA), (R1M,R2D,ZU,XB,YA), (R1N,R2D,ZU,XB,YA), (R1O,R2D,ZU,XB,YA), (R1P,R2D,ZU,XB,YA), (R1Q,R2D,ZU,XB,YA), (R1A,R2E,ZU,XB,YA), (R1B,R2E,ZU,XB,YA), (R1C,R2E,ZU,XB,YA), (R1D,R2E,ZU,XB,YA), (R1E,R2E,ZU,XB,YA), (R1F,R2E,ZU,XB,YA), (R1G,R2E,ZU,XB,YA), (R1H,R2E,ZU,XB,YA), (R1I,R2E,ZU,XB,YA), (R1J,R2E,ZU,XB,YA), (R1K,R2E,ZU,XB,YA), (R1L,R2E,ZU,XB,YA), (R1M,R2E,ZU,XB,YA), (R1N,R2E,ZU,XB,YA), (R1O,R2E,ZU,XB,YA), (R1P,R2E,ZU,XB,YA), (R1Q,R2E,ZU,XB,YA), (R1A,R2F,ZU,XB,YA), (R1B,R2F,ZU,XB,YA), (R1C,R2F,ZU,XB,YA), (R1D,R2F,ZU,XB,YA), (R1E,R2F,ZU,XB,YA), (R1F,R2F,ZU,XB,YA), (R1G,R2F,ZU,XB,YA), (R1H,R2F,ZU,XB,YA), (R1I,R2F,ZU,XB,YA), (R1J,R2F,ZU,XB,YA), (R1K,R2F,ZU,XB,YA), (R1L,R2F,ZU,XB,YA), (R1M,R2F,ZU,XB,YA), (R1N,R2F,ZU,XB,YA), (R1O,R2F,ZU,XB,YA), (R1P,R2F,ZU,XB,YA), (R1Q,R2F,ZU,XB,YA), (R1A,R2G,ZU,XB,YA), (R1B,R2G,ZU,XB,YA), (R1C,R2G,ZU,XB,YA), (R1D,R2G,ZU,XB,YA), (R1E,R2G,ZU,XB,YA), (R1F,R2G,ZU,XB,YA), (R1G,R2G,ZU,XB,YA), (R1H,R2G,ZU,XB,YA), (R1I,R2G,ZU,XB,YA), (R1J,R2G,ZU,XB,YA), (R1K,R2G,ZU,XB,YA), (R1L,R2G,ZU,XB,YA), (R1M,R2G,ZU,XB,YA), (R1N,R2G,ZU,XB,YA), (R1O,R2G,ZU,XB,YA), (R1P,R2G,ZU,XB,YA), (R1Q,R2G,ZU,XB,YA), (R1A,R2H,ZU,XB,YA), (R1B,R2H,ZU,XB,YA), (R1C,R2H,ZU,XB,YA), (R1D,R2H,ZU,XB,YA), (R1E,R2H,ZU,XB,YA), (R1F,R2H,ZU,XB,YA), (R1G,R2H,ZU,XB,YA), (R1H,R2H,ZU,XB,YA), (R1R2H,ZU,XB,YA), (R1J,R2H,ZU,XB,YA), (R1K,R2H,ZU,XB,YA), (R1L,R2H,ZU,XB,YA), (R1M,R2H,ZU,XB,YA), (R1N,R2H,ZU,XB,YA), (R1O,R2H,ZU,XB,YA), (R1P,R2H,ZU,XB,YA), (R1Q,R2H,ZU,XB,YA), (R1A,R2I,ZU,XB,YA), (R1B,R2I,ZU,XB,YA), (R1C,R2I,ZU,XB,YA), (R1D,R2I,ZU,XB,YA), (R1E,R2I,ZU,XB,YA), (R1F,R2I,ZU,XB,YA), (R1G,R2I,ZU,XB,YA), (R1H,R2I,ZU,XB,YA), (R1I,R2I,ZU,XB,YA), (R1J,R2I,ZU,XB,YA), (R1K,R2I,ZU,XB,YA), (R1L,R2I,ZU,XB,YA), (R1M,R2I,ZU,XB,YA), (R1N,R2I,ZU,XB,YA), (R1O,R2I,ZU,XB,YA), (R1P,R2I,ZU,XB,YA), (R1Q,R2I,ZU,XB,YA), (R1A,R2J,ZU,XB,YA), (R1B,R2J,ZU,XB,YA), (R1C,R2J,ZU,XB,YA), (R1D,R2J,ZU,XB,YA), (R1E,R2J,ZU,XB,YA), (R1F,R2J,ZU,XB,YA), (R1G,R2J,ZU,XB,YA), (R1H,R2J,ZU,XB,YA), (R1I,R2J,ZU,XB,YA), (R1J,R2J,ZU,XB,YA), (R1K,R2J,ZU,XB,YA), (R1L,R2J,ZU,XB,YA), (R1M,R2J,ZU,XB,YA), (R1N,R2J,ZU,XB,YA), (R1O,R2J,ZU,XB,YA), (R1P,R2J,ZU,XB,YA), (R1Q,R2J,ZU,XB,YA), (R1A,R2K,ZU,XB,YA), (R1B,R2K,ZU,XB,YA), (R1C,R2K,ZU,XB,YA), (R1D,R2K,ZU,XB,YA), (R1E,R2K,ZU,XB,YA), (R1F,R2K,ZU,XB,YA), (R1G,R2K,ZU,XB,YA), (R1H,R2K,ZU,XB,YA), (R1I,R2K,ZU,XB,YA), (R1J,R2K,ZU, XB,YA), (R1K,R2K,ZU,XB,YA), (R1L,R2K,ZU,XB,YA), (R1M,R2K,ZU,XB,YA), (R1N,R2K,ZU,XB,YA), (R1O,R2K,ZU,XB,YA), (R1P,R2K,ZU,XB,YA), (R1Q,R2K,ZU,XB,YA), (R1A,R2L,ZU,XB,YA), (R1B,R2L,ZU,XB,YA), (R1C,R2L,ZU,XB,YA), (R1D,R2L,ZU,XB,YA), (R1E,R2L,ZU,XB,YA), (R1F,R2L,ZU,XB,YA), (R1G,R2L,ZU,XB,YA), (R1H,R2L,ZU,XB,YA), (R1I,R2L,ZU,XB,YA), (R1J,R2L,ZU,XB,YA), (R1K,R2L,ZU,XB,YA), (R1L,R2L,ZU,XB,YA), (R1M,R2L,ZU,XB,YA), (R1N,R2L,ZU,XB,YA), (R1O,R2L,ZU,XB,YA), (R1P,R2L,ZU,XB,YA), (R1Q,R2L,ZU,XB,YA), (R1A,R2M,ZU,XB,YA), (R1B,R2M,ZU,XB,YA), (R1C,R2M,ZU,XB,YA), (R1D,R2M,ZU,XB,YA), (R1E,R2M,ZU,XB,YA), (R1F,R2M,ZU,XB,YA), (R1G,R2M,ZU,XB,YA), (R1H,R2M,ZU,XB,YA), (R1I,R2M,ZU,XB,YA), (R1J,R2M,ZU,XB,YA), (R1K,R2M,ZU,XB,YA), (R1L,R2M,ZU,XB,YA), (R1M,R2M,ZU,XB,YA), (R1N,R2M,ZU,XB,YA), (R1O,R2M,ZU,XB,YA), (R1P,R2M,ZU,XB,YA), (R1Q,R2M,ZU,XB,YA), (R1A,R2N,ZU,XB,YA), (R1B,R2N,ZU,XB,YA), (R1C,R2N,ZU,XB,YA), (R1D,R2N,ZU,XB,YA), (R1E,R2N,ZU,XB,YA), (R1F,R2N,ZU,XB,YA), (R1G,R2N,ZU,XB,YA), (R1H,R2N,ZU,XB,YA), (R1I,R2N,ZU,XB,YA), (R1J,R2N,ZU,XB,YA), (R1K,R2N,ZU,XB,YA), (R1L,R2N,ZU,XB,YA), (R1M,R2N,ZU,XB,YA), (R1N,R2N,ZU,XB,YA), (R1O,R2N,ZU,XB,YA), (R1P,R2N,ZU,XB,YA), (R1Q,R2N,ZU,XB,YA), (R1A,R2O,ZU,XB,YA), (R1B,R2O,ZU,XB,YA), (R1C,R2O,ZU,XB,YA), (R1D,R2O,ZU,XB,YA), (R1E,R2O,ZU,XB,YA), (R1F,R2O,ZU,XB,YA), (R1G,R2O,ZU,XB,YA), (R1H,R2O,ZU,XB,YA), (R1I,R2O,ZU,XB,YA), (R1J,R2O,ZU,XB,YA), (R1K,R2O,ZU,XB,YA), (R1L,R2O,ZU,XB,YA), (R1M,R2O,ZU,XB,YA), (R1N,R2O,ZU,XB,YA), (R1O,R2O,ZU,XB,YA), (R1P,R2O,ZU,XB,YA), (R1Q,R2O,ZU,XB,YA), (R1A,R2P,ZU,XB,YA), (R1B,R2P,ZU,XB,YA), (R1C,R2P,ZU,XB,YA), (R1D,R2P,ZU,XB,YA), (R1E,R2P,ZU,XB,YA), (R1F,R2P,ZU,XB,YA), (R1G,R2P,ZU,XB,YA), (R1H,R2P,ZU,XB,YA), (R1I,R2P,ZU,XB,YA), (R1J,R2P,ZU,XB,YA), (R1K,R2P,ZU,XB,YA), (R1L,R2P,ZU,XB,YA), (R1M,R2P,ZU,XB,YA), (R1N,R2P,ZU,XB,YA), (R1O,R2P,ZU,XB,YA), (R1P,R2P,ZU,XB,YA), (R1Q,R2P,ZU,XB,YA), (R1A,R2Q,ZU,XB,YA), (R1B,R2Q,ZU,XB,YA), (R1C,R2Q,ZU,XB,YA), (R1D,R2Q,ZU,XB,YA), (R1E,R2Q,ZU,XB,YA), (R1F,R2Q,ZU,XB,YA), (R1G,R2Q,ZU,XB,YA), (R1H,R2Q,ZU,XB,YA), (R1I,R2Q,ZU,XB,YA), (R1J,R2Q,ZU,XB,YA), (R1K,R2Q,ZU,XB,YA), (R1L,R2Q,ZU,XB,YA), (R1M,R2Q,ZU,XB,YA), (R1N,R2Q,ZU,XB,YA), (R1O,R2Q,ZU,XB,YA), (R1P,R2Q,ZU,XB,YA), (R1Q,R2Q,ZU,XB,YA), (R1A,R2A,ZA,XA,YB), (R1B,R2A,ZA,XA,YB), (R1C,R2A,ZA,XA,YB), (R1D,R2A,ZA,XA,YB), (R1E,R2A,ZA,XA,YB), (R1F,R2A,ZA,XA,YB), (R1G,R2A,ZA,XA,YB), (R1H,R2A,ZA,XA,YB), (R1I,R2A,ZA,XA,YB), (R1J,R2A,ZA,XA,YB), (R1K,R2A,ZA,XA,YB), (R1L,R2A,ZA,XA,YB), (R1M,R2A,ZA,XA,YB), (R1N,R2A,ZA,XA,YB), (R1O,R2A,ZA,XA,YB), (R1P,R2A,ZA,XA,YB), (R1Q,R2A,ZA,XA,YB), (R1A,R2B,ZA,XA,YB), (R1B,R2B,ZA,XA,YB), (R1C,R2B,ZA,XA,YB), (R1D,R2B,ZA,XA,YB), (R1E,R2B,ZA,XA,YB), (R1F,R2B,ZA,XA,YB), (R1G,R2B,ZA,XA,YB), (R1H,R2B,ZA,XA,YB), (R1I,R2B,ZA,XA,YB), (R1J,R2B,ZA,XA,YB), (R1K,R2B,ZA,XA,YB), (R1L,R2B,ZA,XA,YB), (R1M,R2B,ZA,XA,YB), (R1N,R2B,ZA,XA,YB), (R1O,R2B,ZA,XA,YB), (R1P,R2B,ZA,XA,YB), (R1Q,R2B,ZA,XA,YB), (R1A,R2C,ZA,XA,YB), (R1B,R2C,ZA,XA,YB), (R1C,R2C,ZA,XA,YB), (R1D,R2C,ZA,XA,YB), (R1E,R2C,ZA,XA,YB), (R1F,R2C,ZA,XA,YB), (R1G,R2C,ZA,XA,YB), (R1H,R2C,ZA,XA,YB), (R1I,R2C,ZA,XA,YB), (R1J,R2C,ZA,XA,YB), (R1K,R2C,ZA,XA,YB), (R1L,R2C,ZA,XA,YB), (R1M,R2C,ZA,XA,YB), (R1N,R2C,ZA,XA,YB), (R1O,R2C,ZA,XA,YB), (R1P,R2C,ZA,XA,YB), (R1Q,R2C,ZA,XA,YB), (R1A,R2D,ZA,XA,YB), (R1B,R2D,ZA,XA,YB), (R1C,R2D,ZA,XA,YB), (R1D,R2D,ZA,XA,YB), (R1E,R2D,ZA,XA,YB), (R1F,R2D,ZA,XA,YB), (R1G,R2D,ZA,XA,YB), (R1H,R2D,ZA,XA,YB), (R1I,R2D,ZA,XA,YB), (R1J,R2D,ZA,XA,YB), (R1K,R2D,ZA,XA,YB), (R1L,R2D,ZA,XA,YB), (R1M,R2D,ZA,XA,YB), (R1N,R2D,ZA,XA,YB), (R1O,R2D,ZA,XA,YB), (R1P,R2D,ZA,XA,YB), (R1Q,R2D,ZA,XA,YB), (R1A,R2E,ZA,XA,YB), (R1B,R2E,ZA,XA,YB), (R1C,R2E,ZA,XA,YB), (R1D,R2E,ZA,XA,YB), (R1E,R2E,ZA,XA,YB), 1F,R2E,ZA,XA,YB), (R1G,R2E,ZA,XA,YB), (R1H,R2E,ZA,XA,YB), (R1I,R2E,ZA,XA,YB), (R1J,R2E,ZA,XA,YB), (R1K,R2E,ZA,XA,YB), (R1L,R2E,ZA,XA,YB), (R1M,R2E,ZA,XA,YB), (R1N,R2E,ZA,XA,YB), (R1O,R2E,ZA,XA,YB), (R1P,R2E,ZA,XA,YB), (R1Q,R2E,ZA,XA,YB), (R1A,R2F,ZA,XA,YB), (R1B,R2F,ZA,XA,YB), (R1C,R2F,ZA,XA,YB), (R1D,R2F,ZA,XA,YB), (R1E,R2F,ZA,XA,YB), (R1F,R2F,ZA,XA,YB), (R1G,R2F,ZA,XA,YB), (R1H,R2F,ZA,XA,YB), (R1I2F,ZA,XA,YB), (R1J,R2F,ZA,XA,YB), (R1K,R2F,ZA,XA,YB), (R1L,R2F,ZA,XA,YB), (R1M,R2F,ZA,XA,YB), (R1N,R2F,ZA,XA,YB), (R1O,R2F,ZA,XA,YB), (R1P,R2F,ZA,XA,YB), (R1Q,R2F,ZA,XA,YB), (R1A,R2G,ZA,XA,YB), (R1B,R2G,ZA,XA,YB), (R1C,R2G,ZA,XA,YB), (R1D,R2G,ZA,XA,YB), (R1E,R2G,ZA,XA,YB), (R1F,R2G,ZA,XA,YB), (R1G,R2G,ZA,XA,YB), (R1H,R2G,ZA,XA,YB), (R1I,R2G,ZA,XA,YB), (R1J,R2G,ZA,XA,YB), (R1K,R2G,ZA,XA,YB), (R1L,R2G,ZA,XA,YB), (R1M,R2G,ZA,XA,YB), (R1N,R2G,ZA,XA,YB), (R1O,R2G,ZA,XA,YB), (R1P,R2G,ZA,XA,YB), (R1Q,R2G,ZA,XA,YB), (R1A,R2H,ZA,XA,YB), (R1B,R2H,ZA,XA,YB), (R1C,R2H,ZA,XA,YB), (R1D,R2H,ZA,XA,YB), (R1E,R2H,ZA,XA,YB), (R1F,R2H,ZA,XA,YB), (R1G,R2H,ZA,XA,YB), (R1H,R2H,ZA,XA,YB), (R1I,R2H,ZA,XA,YB), (R1J,R2H,ZA,XA,YB), (R1K,R2H,ZA,XA,YB), (R1L,R2H,ZA,XA,YB), (R1M,R2H,ZA,XA,YB), (R1N,R2H,ZA,XA,YB), (R1O,R2H,ZA,XA,YB), (R1P,R2H,ZA,XA,YB), (R1Q,R2H,ZA,XA,YB), (R1A,R2I,ZA,XA,YB), (R1B,R2I,ZA,XA,YB), (R1C,R2I,ZA,XA,YB), (R1D,R2I,ZA,XA,YB), (R1E,R2I,ZA,XA,YB), (R1F,R2I,ZA,XA,YB), (R1G,R2I,ZA,XA,YB), (R1H,R2I,ZA,XA,YB), (R1I,R2I,ZA,XA,YB), (R1J,R2I,ZA,XA,YB), (R1K,R2I,ZA,XA,YB), (R1L,R2I,ZA,XA,YB), (R1M,R2I,ZA,XA,YB), (R1N,R2I,ZA,XA,YB), (R1O,R2I,ZA,XA,YB), (R1P,R2I,ZA,XA,YB), (R1Q,R2I,ZA,XA,YB), (R1A,R2J,ZA,XA,YB), (R1B,R2J,ZA,XA,YB), (R1C,R2J,ZA,XA,YB), (R1D,R2J,ZA,XA,YB), (R1E,R2J,ZA,XA,YB), (R1F,R2J,ZA,XA,YB), (R1G,R2J,ZA,XA,YB), (R1H,R2J,ZA,XA,YB), (R1I,R2J,ZA,XA,YB), (R1J,R2J,ZA,XA,YB), (R1K,R2J,ZA,XA,YB), (R1L,R2J,ZA,XA,YB), (R1M,R2J,ZA,XA,YB), (R1N,R2J,ZA,XA,YB), (R1O,R2J,ZA,XA,YB), (R1P,R2J,ZA,XA,YB), (R1Q,R2J,ZA,XA,YB), (R1A,R2K,ZA,XA,YB), (R1B,R2K,ZA,XA,YB), (R1C,R2K,ZA,XA,YB), (R1D,R2K,ZA,XA,YB), (R1E,R2K,ZA,XA,YB), (R1F,R2K,ZA,XA,YB), (R1G,R2K,ZA,XA,YB), (R1H,R2K,ZA,XA,YB), (R1I,R2K,ZA,XA,YB), (R1J,R2K,ZA,XA,YB), (R1K,R2K,ZA,XA,YB), (R1L,R2K,ZA,XA,YB), (R1M,R2K,ZA,XA,YB), (R1N,R2K,ZA,XA,YB), (R1O,R2K,ZA,XA,YB), (R1P,R2K,ZA,XA,YB), (R1Q,R2K,ZA,XA,YB), (R1A,R2L,ZA,XA,YB), (R1B,R2L,ZA,XA,YB), (R1C,R2L,ZA,XA,YB), (R1D,R2L,ZA,XA,YB), (R1E,R2L,ZA,XA,YB), (R1F,R2L,ZA,XA,YB), (R1G,R2L,ZA,XA,YB), (R1H,R2L,ZA,XA,YB), (R1I,R2L,ZA,XA,YB), (R1J,R2L,ZA,XA,YB), (R1K,R2L,ZA,XA,YB), (R1L,R2L,ZA,XA,YB), (R1M,R2L,ZA,XA,YB), (R1N,R2L,ZA,XA,YB), (R1O,R2L,ZA,XA,YB), (R1P,R2L,ZA,XA,YB), (R1Q,R2L,ZA,XA,YB), (R1A,R2M,ZA,XA,YB), (R1B,R2M,ZA,XA,YB), (R1C,R2M,ZA,XA,YB), (R1D,R2M,ZA,XA,YB), (R1E, R2M,ZA,XA,YB), (R1F,R2M,ZA,XA,YB), (R1G,R2M,ZA, XA,YB), (R1H,R2M,ZA,XA,YB), (R1I,R2M,ZA,XA,YB), (R1J,R2M,ZA,XA,YB), (R1K,R2M,ZA,XA,YB), (R1L, R2M,ZA,XA,YB), (R1M,R2M,ZA,XA,YB), (R1N,R2M, ZA,XA,YB), (R1O,R2M,ZA,XA,YB), (R1P,R2M,ZA,XA, YB), (R1Q,R2M,ZA,XA,YB), (R1A,R2N,ZA,XA,YB), (R1B,R2N,ZA,XA,YB), (R1C,R2N,ZA,XA,YB), (R1D, R2N,ZA,XA,YB), (R1E,R2N,ZA,XA,YB), (R1F,R2N,ZA, XA,YB), (R1G,R2N,ZA,XA,YB), (R1H,R2N,ZA,XA,YB), (R1I,R2N,ZA,XA,YB), (R1J,R2N,ZA,XA,YB), (R1K,R2N, ZA,XA,YB), (R1L,R2N,ZA,XA,YB), (R1M,R2N,ZA,XA, YB), (R1N,R2N,ZA,XA,YB), (R1O,R2N,ZA,XA,YB), (R1P,R2N,ZA,XA,YB), (R1Q,R2N,ZA,XA,YB), (R1A, R2O,ZA,XA,YB), (R1B,R2O,ZA,XA,YB), (R1C,R2O,ZA, XA,YB), (R1D,R2O,ZA,XA,YB), (R1E,R2O,ZA,XA,YB), (R1F,R2O,ZA,XA,YB), (R1G,R2O,ZA,XA,YB), (R1H, R2O,ZA,XA,YB), (R1I,R2O,ZA,XA,YB), (R1J,R2O,ZA, XA,YB), (R1K,R2O,ZA,XA,YB), (R1L,R2O,ZA,XA,YB), (R1M,R2O,ZA,XA,YB), (R1N,R2O,ZA,XA,YB), (R1O, R2O,ZA,XA,YB), (R1P,R2O,ZA,XA,YB), (R1Q,R2O,ZA, XA,YB), (R1A,R2P,ZA,XA,YB), (R1B,R2P,ZA,XA,YB), (R1C,R2P,ZA,XA,YB), (R1D,R2P,ZA,XA,YB), (R1E,R2P, ZA,XA,YB), (R1F,R2P,ZA,XA,YB), (R1G,R2P,ZA,XA, YB), (R1H,R2P,ZA,XA,YB), (R1I,R2P,ZA,XA,YB), (R1J, R2P,ZA,XA,YB), (R1K,R2P,ZA,XA,YB), (R1L,R2P,ZA, XA,YB), (R1M,R2P,ZA,XA,YB), (R1N,R2P,ZA,XA,YB), (R1O,R2P,ZA,XA,YB), (R1P,R2P,ZA,XA,YB), (R1Q,R2P, ZA,XA,YB), (R1A,R2Q,ZA,XA,YB), (R1B,R2Q,ZA,XA, YB), (R1C,R2Q,ZA,XA,YB), (R1D,R2Q,ZA,XA,YB), (R1E,R2Q,ZA,XA,YB), (R1F,R2Q,ZA,XA,YB), (R1G, R2Q,ZA,XA,YB), (R1H,R2Q,ZA,XA,YB), (R1I,R2Q,ZA, XA,YB), (R1J,R2Q,ZA,XA,YB), (R1K,R2Q,ZA,XA,YB), (R1L,R2Q,ZA,XA,YB), (R1M,R2Q,ZA,XA,YB), (R1N, R2Q,ZA,XA,YB), (R1O,R2Q,ZA,XA,YB), (R1P,R2Q,ZA, XA,YB), (R1Q,R2Q,ZA,XA,YB), (R1A,R2A,ZB,XA,YB), (R1B,R2A,ZB,XA,YB), (R1C,R2A,ZB,XA,YB), (R1D, R2A,ZB,XA,YB), (R1E,R2A,ZB,XA,YB), (R1F,R2A,ZB, XA,YB), (R1G,R2A,ZB,XA,YB), (R1H,R2A,ZB,XA,YB), (R1I,R2A,ZB,XA,YB), (R1J,R2A,ZB,XA,YB), (R1K,R2A, ZB,XA,YB), (R1L,R2A,ZB,XA,YB), (R1M,R2A,ZB,XA, YB), (R1N,R2A,ZB,XA,YB), (R1O,R2A,ZB,XA,YB), (R1P,R2A,ZB,XA,YB), (R1Q,R2A,ZB,XA,YB), (R1A, R2B,ZB,XA,YB), (R1B,R2B,ZB,XA,YB), (R1C,R2B,ZB, XA,YB), (R1D,R2B,ZB,XA,YB), (R1E,R2B,ZB,XA,YB), (R1F,R2B,ZB,XA,YB), (R1G,R2B,ZB,XA,YB), (R1H, R2B,ZB,XA,YB), (R1I,R2B,ZB,XA,YB), (R1J,R2B,ZB, XA,YB), (R1K,R2B,ZB,XA,YB), (R1L,R2B,ZB,XA,YB), (R1M,R2B,ZB,XA,YB), (R1N,R2B,ZB,XA,YB), (R1O, R2B,ZB,XA,YB), (R1P,R2B,ZB,XA,YB), (R1Q,R2B,ZB, XA,YB), (R1A,R2C,ZB,XA,YB), (R1B,R2C,ZB,XA,YB), (R1C,R2C,ZB,XA,YB), (R1D,R2C,ZB,XA,YB), (R1E, R2C,ZB,XA,YB), (R1F,R2C,ZB,XA,YB), (R1G,R2C,ZB, XA,YB), (R1H,R2C,ZB,XA,YB), (R1I,R2C,ZB,XA,YB), (R1J,R2C,ZB,XA,YB), (R1K,R2C,ZB,XA,YB), (R1L,R2C, ZB,XA,YB), (R1M,R2C,ZB,XA,YB), (R1N,R2C,ZB,XA, YB), (R1O,R2C,ZB,XA,YB), (R1P,R2C,ZB,XA,YB), (R1Q,R2C,ZB,XA,YB), (R1A,R2D,ZB,XA,YB), (R1B, R2D,ZB,XA,YB), (R1C,R2D,ZB,XA,YB), (R1D,R2D,ZB, XA,YB), (R1E,R2D,ZB,XA,YB), (R1F,R2D,ZB,XA,YB), (R1G,R2D,ZB,XA,YB), (R1H,R2D,ZB,XA,YB), (R1I, R2D,ZB,XA,YB), (R1J,R2D,ZB,XA,YB), (R1K,R2D,ZB, XA,YB), (R1L,R2D,ZB,XA,YB), (R1M,R2D,ZB,XA,YB), (R1N,R2D,ZB,XA,YB), (R1O,R2D,ZB,XA,YB), (R1P, R2D,ZB,XA,YB), (R1Q,R2D,ZB,XA,YB), (R1A,R2E,ZB, XA,YB), (R1B,R2E,ZB,XA,YB), (R1C,R2E,ZB,XA,YB), (R1D,R2E,ZB,XA,YB), (R1E,R2E,ZB,XA,YB), (R1F,R2E, ZB,XA,YB), (R1G,R2E,ZB,XA,YB), (R1H,R2E,ZB,XA, YB), (R1I,R2E,ZB,XA,YB), (R1J,R2E,ZB,XA,YB), (R1K, R2E,ZB,XA,YB), (R1L,R2E,ZB,XA,YB), (R1M,R2E,ZB, XA,YB), (R1N,R2E,ZB,XA,YB), (R1O,R2E,ZB,XA,YB), (R1P,R2E,ZB,XA,YB), (R1Q,R2E,ZB,XA,YB), (R1A,R2F, ZB,XA,YB), (R1B,R2F,ZB,XA,YB), (R1C,R2F,ZB,XA, YB), (R1D,R2F,ZB,XA,YB), (R1E,R2F,ZB,XA,YB), (R1F, R2F,ZB,XA,YB), (R1G,R2F,ZB,XA,YB), (R1H,R2F,ZB, XA,YB), (R1I,R2F,ZB,XA,YB), (R1J,R2F,ZB,XA,YB), (R1K,R2F,ZB,XA,YB), (R1L,R2F,ZB,XA,YB), (R1M,R2F, ZB,XA,YB), (R1N,R2F,ZB,XA,YB), (R1O,R2F,ZB,XA, YB), (R1P,R2F,ZB,XA,YB), (R1Q,R2F,ZB,XA,YB), (R1A, R2G,ZB,XA,YB), (R1B,R2G,ZB,XA,YB), (R1C,R2G,ZB, XA,YB), (R1D,R2G,ZB,XA,YB), (R1E,R2G,ZB,XA,YB), (R1F,R2G,ZB,XA,YB), (R1G,R2G,ZB,XA,YB), (R1H, R2G,ZB,XA,YB), (R1I,R2G,ZB,XA,YB), (R1J,R2G,ZB, XA,YB), (R1K,R2G,ZB,XA,YB), (R1L,R2G,ZB,XA,YB), (R1M,R2G,ZB,XA,YB), (R1N,R2G,ZB,XA,YB), (R1O, R2G,ZB,XA,YB), (R1P,R2G,ZB,XA,YB), (R1Q,R2G,ZB, XA,YB), (R1A,R2H,ZB,XA,YB), (R1B,R2H,ZB,XA,YB), (R1C,R2H,ZB,XA,YB), (R1D,R2H,ZB,XA,YB), (R1E, R2H,ZB,XA,YB), (R1F,R2H,ZB,XA,YB), (R1G,R2H,ZB, XA,YB), (R1H,R2H,ZB,XA,YB), (R1I,R2H,ZB,XA,YB), (R1J,R2H,ZB,XA,YB), (R1K,R2H,ZB,XA,YB), (R1L, R2H,ZB,XA,YB), (R1M,R2H,ZB,XA,YB), (R1N,R2H,ZB, XA,YB), (R1O,R2H,ZB,XA,YB), (R1P,R2H,ZB,XA,YB), (R1Q,R2H,ZB,XA,YB), (R1A,R2I,ZB,XA,YB), (R1B,R2I, ZB,XA,YB), (R1C,R2I,ZB,XA,YB), (R1D,R2I,ZB,XA, YB), (R1E,R2I,ZB,XA,YB), (R1F,R2I,ZB,XA,YB), (R1G, R2I,ZB,XA,YB), (R1H,R2I,ZB,XA,YB), (R1I,R2I,ZB,XA, YB), (R1J,R2I,ZB,XA,YB), (R1K,R2I,ZB,XA,YB), (R1L, R2I,ZB,XA,YB), (R1M,R2I,ZB,XA,YB), (R1N,R2I,ZB, XA,YB), (R1O,R2I,ZB,XA,YB), (R1P,R2I,ZB,XA,YB), (R1Q,R2I,ZB,XA,YB), (R1A,R2J,ZB,XA,YB), (R1B,R2J, ZB,XA,YB), (R1C,R2J,ZB,XA,YB), (R1D,R2J,ZB,XA, YB), (R1E,R2J,ZB,XA,YB), (R1F,R2J,ZB,XA,YB), (R1G, R2J,ZB,XA,YB), (R1H,R2J,ZB,XA,YB), (R1I,R2J,ZB,XA, YB), (R1J,R2J,ZB,XA,YB), (R1K,R2J,ZB,XA,YB), (R1L, R2J,ZB,XA,YB), (R1M,R2J,ZB,XA,YB), (R1N,R2J,ZB, XA,YB), (R1O,R2J,ZB,XA,YB), (R1P,R2J,ZB,XA,YB), (R1Q,R2J,ZB,XA,YB), (R1A,R2K,ZB,XA,YB), (R1B, R2K,ZB,XA,YB), (R1C,R2K,ZB,XA,YB), (R1D,R2K,ZB, XA,YB), (R1E,R2K,ZB,XA,YB), (R1F,R2K,ZB,XA,YB), (R1G,R2K,ZB,XA,YB), (R1H,R2K,ZB,XA,YB), (R1I, R2K,ZB,XA,YB), (R1J,R2K,ZB,XA,YB), (R1K,R2K,ZB, XA,YB), (R1L,R2K,ZB,XA,YB), (R1M,R2K,ZB,XA,YB), (R1N,R2K,ZB,XA,YB), (R1O,R2K,ZB,XA,YB), (R1P, R2K,ZB,XA,YB), (R1Q,R2K,ZB,XA,YB), (R1A,R2L,ZB, XA,YB), (R1B,R2L,ZB,XA,YB), (R1C,R2L,ZB,XA,YB), (R1D,R2L,ZB,XA,YB), (R1E,R2L,ZB,XA,YB), (R1F,R2L, ZB,XA,YB), (R1G,R2L,ZB,XA,YB), (R1H,R2L,ZB,XA, YB), (R1I,R2L,ZB,XA,YB), (R1J,R2L,ZB,XA,YB), (R1K, R2L,ZB,XA,YB), (R1L,R2L,ZB,XA,YB), (R1M,R2L,ZB, XA,YB), (R1N,R2L,ZB,XA,YB), (R1O,R2L,ZB,XA,YB), (R1P,R2L,ZB,XA,YB), (R1Q,R2L,ZB,XA,YB), (R1A, R2M,ZB,XA,YB), (R1B,R2M,ZB,XA,YB), (R1C,R2M,ZB, XA,YB), (R1D,R2M,ZB,XA,YB), (R1E,R2M,ZB,XA,YB), (R1F,R2M,ZB,XA,YB), (R1G,R2M,ZB,XA,YB), (R1H, R2M,ZB,XA,YB), (R1I,R2M,ZB,XA,YB), (R1J,R2M,ZB, XA,YB), (R1K,R2M,ZB,XA,YB), (R1L,R2M,ZB,XA,YB), (R1M,R2M,ZB,XA,YB), (R1N,R2M,ZB,XA,YB), (R1O, R2M,ZB,XA,YB), (R1P,R2M,ZB,XA,YB), (R1Q,R2M,ZB, XA,YB), (R1A,R2N,ZB,XA,YB), (R1B,R2N,ZB,XA,YB), (R1C,R2N,ZB,XA,YB), (R1D,R2N,ZB,XA,YB), (R1E, R2N,ZB,XA,YB), (R1F,R2N,ZB,XA,YB), (R1G,R2N,ZB, XA,YB), (R1H,R2N,ZB,XA,YB), (R1I,R2N,ZB,XA,YB), (R1J,R2N,ZB,XA,YB), (R1K,R2N,ZB,XA,YB), (R1L, R2N,ZB,XA,YB), (R1M,R2N,ZB,XA,YB), (R1N,R2N,ZB,XA,YB), (R1O,R2N,ZB,XA,YB), (R1P,R2N,ZB,XA,YB), (R1Q,R2N,ZB,XA,YB), (R1A,R2O,ZB,XA,YB), (R1B,R2O,ZB,XA,YB), (R1C,R2O,ZB,XA,YB), (R1D,R2O,ZB,XA,YB), (R1E,R2O,ZB,XA,YB), (R1F,R2O,ZB,XA,YB), (R1G,R2O,ZB,XA,YB), (R1H,R2O,ZB,XA,YB), (R1I,R2O,ZB,XA,YB), (R1J,R2O,ZB,XA,YB), (R1K,R2O,ZB,XA,YB), (R1L,R2O,ZB,XA,YB), (R1M,R2O,ZB,XA,YB), (R1N,R2O,ZB,XA,YB), (R1O,R2O,ZB,XA,YB), (R1P,R2O,ZB,XA,YB), (R1Q,R2O,ZB,XA,YB), (R1A,R2P,ZB,XA,YB), (R1B,R2P,ZB,XA,YB), (R1C,R2P,ZB,XA,YB), (R1D,R2P,ZB,XA,YB), (R1E,R2P,ZB,XA,YB), (R1F,R2P,ZB,XA,YB), (R1G,R2P,ZB,XA,YB), (R1H,R2P,ZB,XA,YB), (R1I,R2P,ZB,XA,YB), (R1J,R2P,ZB,XA,YB), (R1K,R2P,ZB,XA,YB), (R1L,R2P,ZB,XA,YB), (R1M,R2P,ZB,XA,YB), (R1N,R2P,ZB,XA,YB), (R1O,R2P,ZB,XA,YB), (R1P,R2P,ZB,XA,YB), (R1Q,R2P,ZB,XA,YB), (R1A,R2Q,ZB,XA,YB), (R1B,R2Q,ZB,XA,YB), (R1C,R2Q,ZB,XA,YB), (R1D,R2Q,ZB,XA,YB), (R1E,R2Q,ZB,XA,YB), (R1F,R2Q,ZB,XA,YB), (R1G,R2Q,ZB,XA,YB), (R1H,R2Q,ZB,XA,YB), (R1I,R2Q,ZB,XA,YB), (R1J,R2Q,ZB,XA,YB), (R1K,R2Q,ZB,XA,YB), (R1L,R2Q,ZB,XA,YB), (R1M,R2Q,ZB,XA,YB), (R1N,R2Q,ZB,XA,YB), (R1O,R2Q,ZB,XA,YB), (R1P,R2Q,ZB,XA,YB), (R1Q,R2Q,ZB,XA,YB), (R1A,R2A,ZC,XA,YB), (R1B,R2A,ZC,XA,YB), (R1C,R2A,ZC,XA,YB), (R1D,R2A,ZC,XA,YB), (R1E,R2A,ZC,XA,YB), (R1F,R2A,ZC,XA,YB), (R1G,R2A,ZC,XA,YB), (R1H,R2A,ZC,XA,YB), (R1I,R2A,ZC,XA,YB), (R1J,R2A,ZC,XA,YB), (R1K,R2A,ZC,XA,YB), (R1L,R2A,ZC,XA,YB), (R1M,R2A,ZC,XA,YB), (R1N,R2A,ZC,XA,YB), (R1O,R2A,ZC,XA,YB), (R1P,R2A,ZC,XA,YB), (R1Q,R2A,ZC,XA,YB), (R1A,R2B,ZC,XA,YB), (R1B,R2B,ZC,XA,YB), (R1C,R2B,ZC,XA,YB), (R1D,R2B,ZC,XA,YB), (R1E,R2B,ZC,XA,YB), (R1F,R2B,ZC,XA,YB), (R1G,R2B,ZC,XA,YB), (R1H,R2B,ZC,XA,YB), (R1I,R2B,ZC,XA,YB), (R1J,R2B,ZC,XA,YB), (R1K,R2B,ZC,XA,YB), (R1L,R2B,ZC,XA,YB), (R1M,R2B,ZC,XA,YB), (R1N,R2B,ZC,XA,YB), (R1O,R2B,ZC,XA,YB), (R1P,R2B,ZC,XA,YB), (R1Q,R2B,ZC,XA,YB), (R1A,R2C,ZC,XA,YB), (R1B,R2C,ZC,XA,YB), (R1C,R2C,ZC,XA,YB), (R1D,R2C,ZC,XA,YB), (R1E,R2C,ZC,XA,YB), (R1F,R2C,ZC,XA,YB), (R1G,R2C,ZC,XA,YB), (R1H,R22C,ZC,XA,YB), (R1I,R2C,ZC,XA,YB), (R1J,R2C,ZC,XA,YB), (R1K,R2C,ZC,XA,YB), (R1L,R22C,ZC,XA,YB), (R1M,R2C,ZC,XA,YB), (R1N,R2C,ZC,XA,YB), (R1O,R2C,ZC,XA,YB), (R1P,R2C,ZC,XA,YB), (R1Q,R2C,ZC,XA,YB), (R1A,R2D,ZC,XA,YB), (R1B,R2D,ZC,XA,YB), (R1C,R2D,ZC,XA,YB), (R1D,R2D,ZC,XA,YB), (R1E,R2D,ZC,XA,YB), (R1F,R2D,ZC,XA,YB), (R1G,R2D,ZC,XA,YB), (R1H,R2D,ZC,XA,YB), (R1I,R2D,ZC,XA,YB), (R1J,R2D,ZC,XA,YB), (R1K,R2D,ZC,XA,YB), (R1L,R2D,ZC,XA,YB), (R1M,R2D,ZC,XA,YB), (R1N,R2D,ZC,XA,YB), (R1O,R2D,ZC,XA,YB), (R1P,R2D,ZC,XA,YB), (R1Q,R2D,ZC,XA,YB), (R1A,R2E,ZC,XA,YB), (R1B,R2E,ZC,XA,YB), (R1C,R2E,ZC,XA,YB), (R1D,R2E,ZC,XA,YB), (R1E,R2E,ZC,XA,YB), (R1F,R2E,ZC,XA,YB), (R1G,R2E,ZC,XA,YB), (R1H,R2E,ZC,XA,YB), (R1I,R2E,ZC,XA,YB), (R1J,R2E,ZC,XA,YB), (R1K,R2E,ZC,XA,YB), (R1L,R2E,ZC,XA,YB), (R1M,R2E,ZC,XA,YB), (R1N,R2E,ZC,XA,YB), (R1O,R2E,ZC,XA,YB), (R1P,R2E,ZC,XA,YB), (R1Q,R2E,ZC,XA,YB), (R1A,R2F,ZC,XA,YB), (R1B,R2F,ZC,XA,YB), (R1C,R2F,ZC,XA,YB), (R1D,R2F,ZC,XA,YB), (R1E,R2F,ZC,XA,YB), (R1F,R2F,ZC,XA,YB), (R1G,R2F,ZC,XA,YB), (R1H,R2F,ZC,XA,YB), (R1I,R2F,ZC,XA,YB), (R1J,R2F,ZC,XA,YB), (R1K,R2F,ZC,XA,YB), (R1L,R2F,ZC,XA,YB), (R1M,R2F,ZC,XA,YB), (R1N,R2F,ZC,XA,YB), (R1O,R2F,ZC,XA,YB), (R1P,R2F,ZC,XA,YB), (R1Q,R2F,ZC,XA,YB), (R1A,R2G,ZC,XA,YB), (R1B,R2G,ZC,XA,YB), (R1C,R2G,ZC,XA,YB), (R1D,R2G,ZC,XA,YB), (R1E,R2G,ZC,XA,YB), (R1F,R2G,ZC,XA,YB), (R1G,R2G,ZC,XA,YB), (R1H,R2G,ZC,XA,YB), (R1I,R2G,ZC,XA,YB), (R1J,R2G,ZC,XA,YB), (R1K,R2G,ZC,XA,YB), (R1L,R2G,ZC,XA,YB), (R1M,R2G,ZC,XA,YB), (R1N,R2G,ZC,XA,YB), (R1O,R2G,ZC,XA,YB), (R1P,R2G,ZC,XA,YB), (R1Q,R2G,ZC,XA,YB), (R1A,R2H,ZC,XA,YB), (R1B,R2H,ZC,XA,YB), (R1C,R2H,ZC,XA,YB), (R1D,R2H,ZC,XA,YB), (R1E,R2H,ZC,XA,YB), (R1F,R2H,ZC,XA,YB), (R1G,R2H,ZC,XA,YB), (R1H,R2H,ZC,XA,YB), (R1I,R2H,ZC,XA,YB), (R1J,R2H,ZC,XA,YB), (R1K,R2H,ZC,XA,YB), (R1L,R2H,ZC,XA,YB), (R1M,R2H,ZC,XA,YB), (R1N,R2H,ZC,XA,YB), (R1O,R2H,ZC,XA,YB), (R1P,R2H,ZC,XA,YB), (R1Q,R2H,ZC,XA,YB), (R1A,R2I,ZC,XA,YB), (R1B,R2I,ZC,XA,YB), (R1C,R2I,ZC,XA,YB), (R1D,R2I,ZC,XA,YB), (R1E,R2I,ZC,XA,YB), (R1F,R2I,ZC,XA,YB), (R1G,R2I,ZC,XA,YB), (R1H,R2I,ZC,XA,YB), (R1I,R2I,ZC,XA,YB), (R1J,R2I,ZC,XA,YB), (R1K,R2I,ZC,XA,YB), (R1L,R2I,ZC,XA,YB), (R1M,R2I,ZC,XA,YB), (R1N,R2I,ZC,XA,YB), (R1O,R2I,ZC,XA,YB), (R1P,R2I,ZC,XA,YB), (R1Q,R2I,ZC,XA,YB), (R1A,R2J,ZC,XA,YB), (R1B,R2J,ZC,XA,YB), (R1C,R2J,ZC,XA,YB), (R1D,R2J,ZC,XA,YB), (R1E,R2J,ZC,XA,YB), (R1F,R2J,ZC,XA,YB), (R1G,R2J,ZC,XA,YB), (R1H,R2J,ZC,XA,YB), (R1I,R2J,ZC,XA,YB), (R1J,R2J,ZC,XA,YB), (R1K,R2J,ZC,XA,YB), (R1L,R2J,ZC,XA,YB), (R1M,R2J,ZC,XA,YB), (R1N,R2J,ZC,XA,YB), (R1O,R2J,ZC,XA,YB), (R1P,R2J,ZC,XA,YB), (R1Q,R2J,ZC,XA,YB), (R1A,R2K,ZC,XA,YB), (R1B,R2K,ZC,XA,YB), (R1C,R2K,ZC,XA,YB), (R1D,R2K,ZC,XA,YB), (R1E,R2K,ZC,XA,YB), (R1F,R2K,ZC,XA,YB), (R1G,R2K,ZC,XA,YB), (R1H,R2K,ZC,XA,YB), (R1I,R2K,ZC,XA,YB), (R1J,R2K,ZC,XA,YB), (R1K,R2K,ZC,XA,YB), (R1L,R2K,ZC,XA,YB), (R1M,R2K,ZC,XA,YB), (R1N,R2K,ZC,XA,YB), (R1O,R2K,ZC,XA,YB), (R1P,R2K,ZC,XA,YB), (R1Q,R2K,ZC,XA,YB), (R1A,R2L,ZC,XA,YB), (R1B,R2L,ZC,XA,YB), (R1C,R2L,ZC,XA,YB), (R1D,R2L,ZC,XA,YB), (R1E,R2L,ZC,XA,YB), (R1F,R2L,ZC,XA,YB), (R1G,R2L,ZC,XA,YB), (R1H,R2L,ZC,XA,YB), (R1I,R2L,ZC,XA,YB), (R1J,R2L,ZC,XA,YB), (R1K,R2L,ZC,XA,YB), (R1L,R2L,ZC,XA,YB), (R1M,R2L,ZC,XA,YB), (R1N,R2L,ZC,XA,YB), (R1O,R2L,ZC,XA,YB), (R1P,R2L,ZC,XA,YB), (R1Q,R2L,ZC,XA,YB), (R1A,R2M,ZC,XA,YB), (R1B,R2M,ZC,XA,YB), (R1C,R2M,ZC,XA,YB), (R1D,R2M,ZC,XA,YB), (R1E,R2M,ZC,XA,YB), (R1F,R2M,ZC,XA,YB), (R1G,R2M,ZC,XA,YB), (R1H,R2M,ZC,XA,YB), (R1I,R2M,ZC,XA,YB), (R1J,R2M,ZC,XA,YB), (R1K,R2M,ZC,XA,YB), (R1L,R2M,ZC,XA,YB), (R1M,R2M,ZC,XA,YB), (R1N,R2M,ZC,XA,YB), (R1O,R2M,ZC,XA,YB), (R1P,R2M,ZC,XA,YB), (R1Q,R2M,ZC,XA,YB), (R1A,R2N,ZC,XA,YB), (R1B,R2N,ZC,XA,YB), (R1C,R2N,ZC,XA,YB), (R1D,R2N,ZC,XA,YB), (R1E,R2N,ZC,XA,YB), (R1F,R2N,ZC,XA,YB), (R1G,R2N,ZC,XA,YB), (R1H,R2N,ZC,XA,YB), (R1I,R2N,ZC,XA,YB), (R1J,R2N,ZC,XA,YB), (R1K,R2N,ZC,XA,YB), (R1L,R2N,ZC,XA,YB), (R1M,R2N,ZC,XA,YB), (R1N,R2N,ZC,XA,YB), (R1O,R2N,ZC,XA,YB), (R1P,R2N,ZC,XA,YB), (R1Q,R2N,ZC,XA,YB), (R1A,R2O,ZC,XA,YB), (R1B,R2O,ZC,XA,YB), (R1C,R2O,ZC,XA,YB), (R1D,R2O,ZC,XA,YB), (R1E,R2O,ZC,XA,YB), (R1F,R2O,ZC,XA,YB), (R1G,R2O,ZC,XA,YB), (R1H,R2O,ZC,XA,YB), (R1I,R2O,ZC,XA,YB), (R1J,R2O,ZC,XA,YB), (R1K,R2O,ZC,XA,YB), (R1L,R2O,ZC,XA,YB), (R1M,R2O,ZC,XA,YB), (R1N,R2O,ZC,XA,YB), (R1O,R2O,ZC,XA,YB), (R1P,R2O,ZC,XA,YB), (R1Q,R2O,ZC,XA,YB), (R1A,R2P,ZC,XA,YB), (R1B,R2P,ZC,XA,YB), (R1C,R2P,ZC,XA,YB), (R1D,R2P,ZC,XA,YB), (R1E,R2P,ZC,XA,YB), (R1F,R2P,ZC,XA,YB), (R1G,R2P,ZC,XA,YB), (R1H,R2P,ZC,XA,YB), (R1I,R2P,ZC,XA,YB), (R1J,R2P,ZC,XA,YB), (R1K,R2P,ZC,XA,YB), (R1L,R2P,ZC,XA,YB), (R1M,R2P,ZC,XA,YB), (R1N,R2P,ZC,XA,YB), (R1O,R2P,ZC,XA,YB), (R1P,R2P,ZC,XA,YB), (R1Q,R2P,ZC,XA,YB), (R1A,R2Q,ZC,XA,YB), (R1B,R2Q,ZC,XA,YB), (R1C,R2Q,ZC,XA,YB), (R1D,R2Q,ZC,XA,YB), (R1E,R2Q,ZC,XA,YB), (R1F,R2Q,ZC,XA,YB), (R1G,R2Q,ZC,XA,YB), (R1H,R2Q,ZC,XA,YB), (R1I,R2Q,ZC,XA,YB), (R1J,R2Q,ZC,XA,YB), (R1K,R2Q,ZC,XA,YB), (R1L,R2Q,ZC,XA,YB), (R1M,R2Q,ZC,XA,YB), (R1N,R2Q,ZC,XA,YB), (R1O,R2Q,ZC,XA,YB), (R1P,R2Q,ZC,XA,YB), (R1Q,R2Q,ZC,XA,YB), (R1A,R2A,ZD,XA,YB), (R1B,R2A,ZD,XA,YB), (R1C,R2A,ZD,XA,YB), (R1D,R2A,ZD,XA,YB), (R1E,R2A,ZD,XA,YB), (R1F,R2A,ZD,XA,YB), (R1G,R2A,ZD,XA,YB), (R1H,R2A,ZD,XA,YB), (R1I,R2A,ZD,XA,YB), (R1J,R2A,ZD,XA,YB), (R1K,R2A,ZD,XA,YB), (R1L,R2A,ZD,XA,YB), (R1M,R2A,ZD,XA,YB), (R1N,R2A,ZD,XA,YB), (R1O,R2A,ZD,XA,YB), (R1P,R2A,ZD,XA,YB), (R1Q,R2A,ZD,XA,YB), (R1A,R2B,ZD,XA,YB), (R1B,R2B,ZD,XA,YB), (R1C,R2B,ZD,XA,YB), (R1D,R2B,ZD,XA,YB), (R1E,R2B,ZD,XA,YB), (R1F,R2B,ZD,XA,YB), (R1G,R2B,ZD,XA,YB), (R1H,R2B,ZD,XA,YB), (R1I,R2B,ZD,XA,YB), (R1J,R2B,ZD,XA,YB), (R1K,R2B,ZD,XA,YB), (R1L,R2B,ZD,XA,YB), (R1M,R2B,ZD,XA,YB), (R1N,R2B,ZD,XA,YB), (R1O,R2B,ZD,XA,YB), (R1P,R2B,ZD,XA,YB), (R1Q,R2B,ZD,XA,YB), (R1A,R2C,ZD,XA,YB), (R1B,R2C,ZD,XA,YB), (R1C,R2C,ZD,XA,YB), (R1D,R2C,ZD,XA,YB), (R1E,R2C,ZD,XA,YB), (R1F,R2C,ZD,XA,YB), (R1G,R2C,ZD,XA,YB), (R1H,R2C,ZD,XA,YB), (R1I,R2C,ZD,XA,YB), (R1J,R2C,ZD,XA,YB), (R1K,R2C,ZD,XA,YB), (R1L,R2C,ZD,XA,YB), (R1M,R2C,ZD,XA,YB), (R1N,R2C,ZD,XA,YB), (R1O,R2C,ZD,XA,YB), (R1P,R2C,ZD,XA,YB), (R1Q,R2C,ZD,XA,YB), (R1A,R2D,ZD,XA,YB), (R1B,R2D,ZD,XA,YB), (R1C,R2D,ZD,XA,YB), (R1D,R2D,ZD,XA,YB), (R1E,R2D,ZD,XA,YB), (R1F,R2D,ZD,XA,YB), (R1G,R2D,ZD,XA,YB), (R1H,R2D,ZD,XA,YB), (R1I,R2D,ZD,XA,YB), (R1J,R2D,ZD,XA,YB), (R1K,R2D,ZD,XA,YB), (R1L,R2D,ZD,XA,YB), (R1M,R2D,ZD,XA,YB), (R1N,R2D,ZD,XA,YB), (R1O,R2D,ZD,XA,YB), (R1P,R2D,ZD,XA,YB), (R1Q,R2D,ZD,XA,YB), (R1A,R2E,ZD,XA,YB), (R1B,R2E,ZD,XA,YB), (R1C,R2E,ZD,XA,YB), (R1D,R2E,ZD,XA,YB), (R1E,R2E,ZD,XA,YB), (R1F,R2E,ZD,XA,YB), (R1G,R2E,ZD,XA,YB), (R1H,R2E,ZD,XA,YB), (R1I,R2E,ZD,XA,YB), (R1J,R2E,ZD,XA,YB), (R1K,R2E,ZD,XA,YB), (R1L,R2E,ZD,XA,YB), (R1M,R2E,ZD,XA,YB), (R1N,R2E,ZD,XA,YB), (R1O,R2E,ZD,XA,YB), (R1P,R2E,ZD,XA,YB), (R1Q,R2E,ZD,XA,YB), (R1A,R2F,ZD,XA,YB), (R1B,R2F,ZD,XA,YB), (R1C,R2F,ZD,XA,YB), (R1D,R2F,ZD,XA,YB), (R1E,R2F,ZD,XA,YB), (R1F,R2F,ZD,XA,YB), (R1G,R2F,ZD,XA,YB), (R1H,R2F,ZD,XA,YB), (R1I,R2F,ZD,XA,YB), (R1J,R2F,ZD,XA,YB), (R1K,R2F,ZD,XA,YB), (R1L,R2F,ZD,XA,YB), (R1M,R2F,ZD,XA,YB), (R1N,R2F,ZD,XA,YB), (R1O,R2F,ZD,XA,YB), (R1P,R2F,ZD,XA,YB), (R1Q,R2F,ZD,XA,YB), (R1A,R2G,ZD,XA,YB), (R1B,R2G,ZD,XA,YB), (R1C,R2G,ZD,XA,YB), (R1D,R2G,ZD,XA,YB), (R1E,R2G,ZD,XA,YB), (R1F,R2G,ZD,XA,YB), (R1G,R2G,ZD,XA,YB), (R1H,R2G,ZD,XA,YB), (R1I,R2G,ZD,XA,YB), (R1J,R2G,ZD,XA,YB), (R1K,R2G,ZD,XA,YB), (R1L,R2G,ZD,XA,YB), (R1M,R2G,ZD,XA,YB), (R1N,R2G,ZD,XA,YB), (R1O,R2G,ZD,XA,YB), (R1P,R2G,ZD,XA,YB), (R1Q,R2G,ZD,XA,YB), (R1A,R2H,ZD,XA,YB), (R1B,R2H,ZD,XA,YB), (R1C,R2H,ZD,XA,YB), (R1D,R2H,ZD,XA,YB), (R1E,R2H,ZD,XA,YB), (R1F,R2H,ZD,XA,YB), (R1G,R2H,ZD,XA,YB), (R1H,R2H,ZD,XA,YB), (R1I,R2H,ZD,XA,YB), (R1J,R2H,ZD,XA,YB), (R1K,R2H,ZD,XA,YB), (R1L,R2H,ZD,XA,YB), (R1M,R2H,ZD,XA,YB), (R1N,R2H,ZD,XA,YB), (R1O,R2H,ZD,XA,YB), (R1P,R2H,ZD,XA,YB), (R1Q,R2H,ZD,XA,YB), (R1A,R2I,ZD,XA,YB), (R1B,R2I,ZD,XA,YB), (R1C,R2I,ZD,XA,YB), (R1D,R2I,ZD,XA,YB), (R1E,R2I,ZD,XA,YB), (R1F,R2I,ZD,XA,YB), (R1G,R2I,ZD,XA,YB), (R1H,R2I,ZD,XA,YB), (R1I,R2I,ZD,XA,YB), (R1J,R2I,ZD,XA,YB), (R1K,R2I,ZD,XA,YB), (R1L,R2I,ZD,XA,YB), (R1M,R2I,ZD,XA,YB), (R1N,R2I,ZD,XA,YB), (R1O,R2I,ZD,XA,YB), (R1P,R2I,ZD,XA,YB), (R1Q,R2I,ZD,XA,YB), (R1A,R2J,ZD,XA,YB), (R1B,R2J,ZD,XA,YB), (R1C,R2J,ZD,XA,YB), (R1D,R2J,ZD,XA,YB), (R1E,R2J,ZD,XA,YB), (R1F,R2J,ZD,XA,YB), (R1G,R2J,ZD,XA,YB), (R1H,R2J,ZD,XA,YB), (R1I,R2J,ZD,XA,YB), (R1J,R2J,ZD,XA,YB), (R1K,R2J,ZD,XA,YB), (R1L,R2J,ZD,XA,YB), (R1M,R2J,ZD,XA,YB), (R1N,R2J,ZD,XA,YB), (R1O,R2J,ZD,XA,YB), (R1P,R2J,ZD,XA,YB), (R1Q,R2J,ZD,XA,YB), (R1A,R2K,ZD,XA,YB), (R1B,R2K,ZD,XA,YB), (R1C,R2K,ZD,XA,YB), (R1D,R2K,ZD,XA,YB), (R1E,R2K,ZD,XA,YB), (R1F,R2K,ZD,XA,YB), (R1G,R2K,ZD,XA,YB), (R1H,R2K,ZD,XA,YB), (R1I,R2K,ZD,XA,YB), (R1J,R2K,ZD,XA,YB), (R1K,R2K,ZD,XA,YB), (R1L,R2K,ZD,XA,YB), (R1M,R2K,ZD,XA,YB), (R1N,R2K,ZD,XA,YB), (R1O,R2K,ZD,XA,YB), (R1P,R2K,ZD,XA,YB), (R1Q,R2K,ZD,XA,YB), (R1A,R2L,ZD,XA,YB), (R1B,R2L,ZD,XA,YB), (R1C,R2L,ZD,XA,YB), (R1D,R2L,ZD,XA,YB), (R1E,R2L,ZD,XA,YB), (R1F,R2L,ZD,XA,YB), (R1G,R2L,ZD,XA,YB), (R1H,R2L,ZD,XA,YB), (R1I,R2L,ZD,XA,YB), (R1J,R2L,ZD,XA,YB), (R1K,R2L,ZD,XA,YB), (R1L,R2L,ZD,XA,YB), (R1M,R2L,ZD,XA,YB), (R1N,R2L,ZD,XA,YB), (R1O,R2L,ZD,XA,YB), (R1P,R2L,ZD,XA,YB), (R1Q,R2L,ZD,XA,YB), (R1A,R2M,ZD,XA,YB), (R1B,R2M,ZD,XA,YB), (R1C,R2M,ZD,XA,YB), (R1D,R2M,ZD,XA,YB), (R1E,R2M,ZD,XA,YB), (R1F,R2M,ZD,XA,YB), (R1G,R2M,ZD,XA,YB), (R1H,R2M,ZD,XA,YB), (R1I,R2M,ZD,XA,YB), (R1J,R2M,ZD,XA,YB), (R1K,R2M,ZD,XA,YB), (R1L,R2M,ZD,XA,YB), (R1M,R2M,ZD,XA,YB), (R1N,R2M,ZD,XA,YB), (R1O,R2M,ZD,XA,YB), (R1P,R2M,ZD,XA,YB), (R1Q,R2M,ZD,XA,YB), (R1A,R2N,ZD,XA,YB), (R1B,R2N,ZD,XA,YB), (R1C,R2N,ZD,XA,YB), (R1D,R2N,ZD,XA,YB), (R1E,R2N,ZD,XA,YB), (R1F,R2N,ZD,XA,YB), (R1G,R2N,ZD,XA,YB), (R1H,R2N,ZD,XA,YB), (R1I,R2N,ZD,XA,YB), (R1J,R2N,ZD,XA,YB), (R1K,R2N,ZD,XA,YB), (R1L,R2N,ZD,XA,YB), (R1M,R2N,ZD,XA,YB), (R1N,R2N,ZD,XA,YB), (R1O,R2N,ZD,XA,YB), (R1P,R2N,ZD,XA,YB), (R1Q,R2N,ZD,XA,YB), (R1A,R2O,ZD,XA,YB), (R1B,R2O,ZD,XA,YB), (R1C,R2O,ZD,XA,YB), (R1D,R2O,ZD,XA,YB), (R1E,R2O,ZD,XA,YB), (R1F,R2O,ZD,XA,YB), (R1G,R2O,ZD,XA,YB), (R1H,R2O,ZD,XA,YB), (R1I,R2O,ZD,XA,YB), (R1J,R2O,ZD,XA,YB), (R1K,R2O,ZD,XA,YB), (R1L,R2O,ZD,XA,YB), (R1M,R2O,ZD,XA,YB), (R1N,R2O,ZD,XA,YB), (R1O,R2O,ZD,XA,YB), (R1P,R2O,ZD,XA,YB), (R1Q,R2O,ZD,XA,YB), (R1A,R2P,ZD,XA,YB), (R1B,R2P,ZD,XA,YB), (R1C,R2P,ZD,XA,YB), (R1D,R2P,ZD,XA,YB), (R1E,R2P,ZD,XA,YB), (R1F,R2P,ZD,XA,YB), (R1G,R2P,ZD,XA,YB), (R1H,R2P,ZD,XA,YB), (R1I,R2P,ZD,XA,YB), (R1J,R2P,ZD,XA,YB), (R1K,R2P,ZD,XA,YB), (R1L,R2P,ZD,XA,YB), (R1M,R2P,ZD,XA,YB), (R1N,R2P,ZD,XA,YB), (R1O,R2P,ZD,XA,YB), (R1P,R2P,ZD,XA,YB), (R1Q,R2P,ZD,XA,YB), (R1A,R2Q,ZD,XA,YB), (R1B,R2Q,ZD,XA,YB), (R1C,R2Q,ZD,XA,YB), (R1D,R2Q,ZD,XA,YB), (R1E,R2Q,ZD,XA,YB), (R1F,R2Q,ZD,XA,YB), (R1G,R2Q,ZD,XA,YB), (R1H,R2Q,ZD,XA,YB), (R1I,R2Q,ZD,XA,YB), (R1J,R2Q,ZD,XA,YB), (R1K,R2Q,ZD,XA,YB), (R1L, R2Q,ZD,XA,YB), (R1M,R2Q,ZD,XA,YB), (R1N,R2Q,ZD, XA,YB), (R1O,R2Q,ZD,XA,YB), (R1P,R2Q,ZD,XA,YB), (R1Q,R2Q,ZD,XA,YB), (R1A,R2A,ZE,XA,YB), (R1B, R2A,ZE,XA,YB), (R1C,R2A,ZE,XA,YB), (R1D,R2A,ZE, XA,YB), (R1E,R2A,ZE,XA,YB), (R1F,R2A,ZE,XA,YB), (R1G,R2A,ZE,XA,YB), (R1H,R2A,ZE,XA,YB), (R1I, R2A,ZE,XA,YB), (R1J,R2A,ZE,XA,YB), (R1K,R2A,ZE, XA,YB), (R1L,R2A,ZE,XA,YB), (R1M,R2A,ZE,XA,YB), (R1N,R2A,ZE,XA,YB), (R1O,R2A,ZE,XA,YB), (R1P, R2A,ZE,XA,YB), (R1Q,R2A,ZE,XA,YB), (R1A,R2B,ZE, XA,YB), (R1B,R2B,ZE,XA,YB), (R1C,R2B,ZE,XA,YB), (R1D,R2B,ZE,XA,YB), (R1E,R2B,ZE,XA,YB), (R1F,R2B, ZE,XA,YB), (R1G,R2B,ZE,XA,YB), (R1H,R2B,ZE,XA, YB), (R1I,R2B,ZE,XA,YB), (R1J,R2B,ZE,XA,YB), (R1K, R2B,ZE,XA,YB), (R1L,R2B,ZE,XA,YB), (R1M,R2B,ZE, XA,YB), (R1N,R2B,ZE,XA,YB), (R1O,R2B,ZE,XA,YB), (R1P,R2B,ZE,XA,YB), (R1Q,R2B,ZE,XA,YB), (R1A,R2C, ZE,XA,YB), (R1B,R2C,ZE,XA,YB), (R1C,R2C,ZE,XA, YB), (R1D,R2C,ZE,XA,YB), (R1E,R2C,ZE,XA,YB), (R1F, R2C,ZE,XA,YB), (R1G,R2C,ZE,XA,YB), (R1H,R2C,ZE, XA,YB), (R1I,R2C,ZE,XA,YB), (R1J,R2C,ZE,XA,YB), (R1K,R2C,ZE,XA,YB), (R1L,R2C,ZE,XA,YB), (R1M, R2C,ZE,XA,YB), (R1N,R2C,ZE,XA,YB), (R1O,R2C,ZE, XA,YB), (R1P,R2C,ZE,XA,YB), (R1Q,R2C,ZE,XA,YB), (R1A,R2D,ZE,XA,YB), (R1B,R2D,ZE,XA,YB), (R1C, R2D,ZE,XA,YB), (R1D,R2D,ZE,XA,YB), (R1E,R2D,ZE, XA,YB), (R1F,R2D,ZE,XA,YB), (R1G,R2D,ZE,XA,YB), (R1H,R2D,ZE,XA,YB), (R1I,R2D,ZE,XA,YB), (R1J,R2D, ZE,XA,YB), (R1K,R2D,ZE,XA,YB), (R1L,R2D,ZE,XA, YB), (R1M,R2D,ZE,XA,YB), (R1N,R2D,ZE,XA,YB), (R1O,R2D,ZE,XA,YB), (R1P,R2D,ZE,XA,YB), (R1Q, R2D,ZE,XA,YB), (R1A,R2E,ZE,XA,YB), (R1B,R2E,ZE, XA,YB), (R1C,R2E,ZE,XA,YB), (R1D,R2E,ZE,XA,YB), (R1E,R2E,ZE,XA,YB), (R1F,R2E,ZE,XA,YB), (R1G,R2E, ZE,XA,YB), (R1H,R2E,ZE,XA,YB), (R1I,R2E,ZE,XA, YB), (R1J,R2E,ZE,XA,YB), (R1K,R2E,ZE,XA,YB), (R1L, R2E,ZE,XA,YB), (R1M,R2E,ZE,XA,YB), (R1N,R2E,ZE, XA,YB), (R1O,R2E,ZE,XA,YB), (R1P,R2E,ZE,XA,YB), (R1Q,R2E,ZE,XA,YB), (R1A,R2F,ZE,XA,YB), (R1B,R2F, ZE,XA,YB), (R1C,R2F,ZE,XA,YB), (R1D,R2F,ZE,XA, YB), (R1E,R2F,ZE,XA,YB), (R1F,R2F,ZE,XA,YB), (R1G, R2F,ZE,XA,YB), (R1H,R2F,ZE,XA,YB), (R1I,R2F,ZE,XA, YB), (R1J,R2F,ZE,XA,YB), (R1K,R2F,ZE,XA,YB), (R1L, R2F,ZE,XA,YB), (R1M,R2F,ZE,XA,YB), (R1N,R2F,ZE, XA,YB), (R1O,R2F,ZE,XA,YB), (R1P,R2F,ZE,XA,YB), (R1Q,R2F,ZE,XA,YB), (R1A,R2G,ZE,XA,YB), (R1B, R2G,ZE,XA,YB), (R1C,R2G,ZE,XA,YB), (R1D,R2G,ZE, XA,YB), (R1E,R2G,ZE,XA,YB), (R1F,R2G,ZE,XA,YB), (R1G,R2G,ZE,XA,YB), (R1H,R2G,ZE,XA,YB), (R1I, R2G,ZE,XA,YB), (R1J,R2G,ZE,XA,YB), (R1K,R2G,ZE, XA,YB), (R1L,R2G,ZE,XA,YB), (R1M,R2G,ZE,XA,YB), (R1N,R2G,ZE,XA,YB), (R1O,R2G,ZE,XA,YB), (R1P, R2G,ZE,XA,YB), (R1Q,R2G,ZE,XA,YB), (R1A,R2H,ZE, XA,YB), (R1B,R2H,ZE,XA,YB), (R1C,R2H,ZE,XA,YB), (R1D,R2H,ZE,XA,YB), (R1E,R2H,ZE,XA,YB), (R1F, R2H,ZE,XA,YB), (R1G,R2H,ZE,XA,YB), (R1H,R2H,ZE, XA,YB), (R1I,R2H,ZE,XA,YB), (R1J,R2H,ZE,XA,YB), (R1K,R2H,ZE,XA,YB), (R1L,R2H,ZE,XA,YB), (R1M, R2H,ZE,XA,YB), (R1N,R2H,ZE,XA,YB), (R1O,R2H,ZE, XA,YB), (R1P,R2H,ZE,XA,YB), (R1Q,R2H,ZE,XA,YB), (R1A,R2I,ZE,XA,YB), (R1B,R2I,ZE,XA,YB), (R1C,R2I, ZE,XA,YB), (R1D,R2I,ZE,XA,YB), (R1E,R2I,ZE,XA, YB), (R1F,R2I,ZE,XA,YB), (R1G,R2I,ZE,XA,YB), (R1H, R2I,ZE,XA,YB), (R1I,R2I,ZE,XA,YB), (R1J,R2I,ZE,XA, YB), (R1K,R2I,ZE,XA,YB), (R1L,R2I,ZE,XA,YB), (R1M,R2I, ZE,XA,YB), (R1N,R2I,ZE,XA,YB), (R1O,R2I,ZE,XA, YB), (R1P,R2I,ZE,XA,YB), (R1Q,R2I,ZE,XA,YB), (R1A, R2J,ZE,XA,YB), (R1B,R2J,ZE,XA,YB), (R1C,R2J,ZE,XA, YB), (R1D,R2J,ZE,XA,YB), (R1E,R2J,ZE,XA,YB), (R1F, R2J,ZE,XA,YB), (R1G,R2J,ZE,XA,YB), (R1H,R2J,ZE, XA,YB), (R1I,R2J,ZE,XA,YB), (R1J,R2J,ZE,XA,YB), (R1K,R2J,ZE,XA,YB), (R1L,R2J,ZE,XA,YB), (R1M,R2J, ZE,XA,YB), (R1N,R2J,ZE,XA,YB), (R1O,R2J,ZE,XA, YB), (R1P,R2J,ZE,XA,YB), (R1Q,R2J,ZE,XA,YB), (R1A, R2K,ZE,XA,YB), (R1B,R2K,ZE,XA,YB), (R1C,R2K,ZE, XA,YB), (R1D,R2K,ZE,XA,YB), (R1E,R2K,ZE,XA,YB), (R1F,R2K,ZE,XA,YB), (R1G,R2K,ZE,XA,YB), (R1H, R2K,ZE,XA,YB), (R1I,R2K,ZE,XA,YB), (R1J,R2K,ZE, XA,YB), (R1K,R2K,ZE,XA,YB), (R1L,R2K,ZE,XA,YB), (R1M,R2K,ZE,XA,YB), (R1N,R2K,ZE,XA,YB), (R1O, R2K,ZE,XA,YB), (R1P,R2K,ZE,XA,YB), (R1Q,R2K,ZE, XA,YB), (R1A,R2L,ZE,XA,YB), (R1B,R2L,ZE,XA,YB), (R1C,R2L,ZE,XA,YB), (R1D,R2L,ZE,XA,YB), (R1E,R2L, ZE,XA,YB), (R1F,R2L,ZE,XA,YB), (R1G,R2L,ZE,XA, YB), (R1H,R2L,ZE,XA,YB), (R1I,R2L,ZE,XA,YB), (R1J, R2L,ZE,XA,YB), (R1K,R2L,ZE,XA,YB), (R1L,R2L,ZE, XA,YB), (R1M,R2L,ZE,XA,YB), (R1N,R2L,ZE,XA,YB), (R1O,R2L,ZE,XA,YB), (R1P,R2L,ZE,XA,YB), (R1Q,R2L, ZE,XA,YB), (R1A,R2M,ZE,XA,YB), (R1B,R2M,ZE,XA, YB), (R1C,R2M,ZE,XA,YB), (R1D,R2M,ZE,XA,YB), (R1E,R2M,ZE,XA,YB), (R1F,R2M,ZE,XA,YB), (R1G, R2M,ZE,XA,YB), (R1H,R2M,ZE,XA,YB), (R1I,R2M,ZE, XA,YB), (R1J,R2M,ZE,XA,YB), (R1K,R2M,ZE,XA,YB), (R1L,R2M,ZE,XA,YB), (R1M,R2M,ZE,XA,YB), (R1N, R2M,ZE,XA,YB), (R1O,R2M,ZE,XA,YB), (R1P,R2M,ZE, XA,YB), (R1Q,R2M,ZE,XA,YB), (R1A,R2N,ZE,XA,YB), (R1B,R2N,ZE,XA,YB), (R1C,R2N,ZE,XA,YB), (R1D, R2N,ZE,XA,YB), (R1E,R2N,ZE,XA,YB), (R1F,R2N,ZE, XA,YB), (R1G,R2N,ZE,XA,YB), (R1H,R2N,ZE,XA,YB), (R1I,R2N,ZE,XA,YB), (R1J,R2N,ZE,XA,YB), (R1K,R2N, ZE,XA,YB), (R1L,R2N,ZE,XA,YB), (R1M,R2N,ZE,XA, YB), (R1N,R2N,ZE,XA,YB), (R1O,R2N,ZE,XA,YB), (R1P,R2N,ZE,XA,YB), (R1Q,R2N,ZE,XA,YB), (R1A, R2O,ZE,XA,YB), (R1B,R2O,ZE,XA,YB), (R1C,R2O,ZE, XA,YB), (R1D,R2O,ZE,XA,YB), (R1E,R2O,ZE,XA,YB), (R1F,R2O,ZE,XA,YB), (R1G,R2O,ZE,XA,YB), (R1H, R2O,ZE,XA,YB), (R1I,R2O,ZE,XA,YB), (R1J,R2O,ZE, XA,YB), (R1K,R2O,ZE,XA,YB), (R1L,R2O,ZE,XA,YB), (R1M,R2O,ZE,XA,YB), (R1N,R2O,ZE,XA,YB), (R1O, R2O,ZE,XA,YB), (R1P,R2O,ZE,XA,YB), (R1Q,R2O,ZE, XA,YB), (R1A,R2P,ZE,XA,YB), (R1B,R2P,ZE,XA,YB), (R1C,R2P,ZE,XA,YB), (R1D,R2P,ZE,XA,YB), (R1E,R2P, ZE,XA,YB), (R1F,R2P,ZE,XA,YB), (R1G,R2P,ZE,XA, YB), (R1H,R2P,ZE,XA,YB), (R1I,R2P,ZE,XA,YB), (R1J, R2P,ZE,XA,YB), (R1K,R2P,ZE,XA,YB), (R1L,R2P,ZE, XA,YB), (R1M,R2P,ZE,XA,YB), (R1N,R2P,ZE,XA,YB), (R1O,R2P,ZE,XA,YB), (R1P,R2P,ZE,XA,YB), (R1Q,R2P, ZE,XA,YB), (R1A,R2Q,ZE,XA,YB), (R1B,R2Q,ZE,XA, YB), (R1C,R2Q,ZE,XA,YB), (R1D,R2Q,ZE,XA,YB), (R1E,R2Q,ZE,XA,YB), (R1F,R2Q,ZE,XA,YB), (R1G, R2Q,ZE,XA,YB), (R1H,R2Q,ZE,XA,YB), (R1I,R2Q,ZE, XA,YB), (R1J,R2Q,ZE,XA,YB), (R1K,R2Q,ZE,XA,YB), (R1L,R2Q,ZE,XA,YB), (R1M,R2Q,ZE,XA,YB), (R1N, R2Q,ZE,XA,YB), (R1O,R2Q,ZE,XA,YB), (R1P,R2Q,ZE, XA,YB), (R1Q,R2Q,ZE,XA,YB), (R1A,R2A,ZF,XA,YB), (R1B,R2A,ZF,XA,YB), (R1C,R2A,ZF,XA,YB), (R1D, R2A,ZF,XA,YB), (R1E,R2A,ZF,XA,YB), (R1F,R2A,ZF, XA,YB), (R1G,R2A,ZF,XA,YB), (R1H,R2A,ZF,XA,YB), (R1I,R2A,ZF,XA,YB), (R1J,R2A,ZF,XA,YB), (R1K,R2A, ZF,XA,YB), (R1L,R2A,ZF,XA,YB), (R1M,R2A,ZF,XA, YB), (R1N,R2A,ZF,XA,YB), (R1O,R2A,ZF,XA,YB), (R1P, R2A,ZF,XA,YB), (R1Q,R2A,ZF,XA,YB), (R1A,R2B,ZF, XA,YB), (R1B,R2B,ZF,XA,YB), (R1C,R2B,ZF,XA,YB), (R1D,R2B,ZF,XA,YB), (R1E,R2B,ZF,XA,YB), (R1F,R2B, ZF,XA,YB), (R1G,R2B,ZF,XA,YB), (R1H,R2B,ZF,XA,YB), (R1I,R2B,ZF,XA,YB), (R1J,R2B,ZF,XA,YB), (R1K,R2B,ZF,XA,YB), (R1L,R2B,ZF,XA,YB), (R1M,R2B,ZF,XA,YB), (R1N,R2B,ZF,XA,YB), (R1O,R2B,ZF,XA,YB), (R1P,R2B,ZF,XA,YB), (R1Q,R2B,ZF,XA,YB), (R1A,R2C,ZF,XA,YB), (R1B,R2C,ZF,XA,YB), (R1C,R2C,ZF,XA,YB), (R1D,R2C,ZF,XA,YB), (R1E,R2C,ZF,XA,YB), (R1F,R2C,ZF,XA,YB), (R1G,R2C,ZF,XA,YB), (R1H,R2C,ZF,XA,YB), (R1I,R2C,ZF,XA,YB), (R1J,R2C,ZF,XA,YB), (R1K,R2C,ZF,XA,YB), (R1L,R2C,ZF,XA,YB), (R1M,R2C,ZF,XA,YB), (R1N,R2C,ZF,XA,YB), (R1O,R2C,ZF,XA,YB), (R1P,R2C,ZF,XA,YB), (R1Q,R2C,ZF,XA,YB), (R1A,R2D,ZF,XA,YB), (R1B,R2D,ZF,XA,YB), (R1C,R2D,ZF,XA,YB), (R1D,R2D,ZF,XA,YB), (R1E,R2D,ZF,XA,YB), (R1F,R2D,ZF,XA,YB), (R1G,R2D,ZF,XA,YB), (R1H,R2D,ZF,XA,YB), (R1I,R2D,ZF,XA,YB), (R1J,R2D,ZF,XA,YB), (R1K,R2D,ZF,XA,YB), (R1L,R2D,ZF,XA,YB), (R1M,R2D,ZF,XA,YB), (R1N,R2D,ZF,XA,YB), (R1O,R2D,ZF,XA,YB), (R1P,R2D,ZF,XA,YB), (R1Q,R2D,ZF,XA,YB), (R1A,R2E,ZF,XA,YB), (R1B,R2E,ZF,XA,YB), (R1C,R2E,ZF,XA,YB), (R1D,R2E,ZF,XA,YB), (R1E,R2E,ZF,XA,YB), (R1F,R2E,ZF,XA,YB), (R1G,R2E,ZF,XA,YB), (R1H,R2E,ZF,XA,YB), (R1I,R2E,ZF,XA,YB), (R1J,R2E,ZF,XA,YB), (R1K,R2E,ZF,XA,YB), (R1L,R2E,ZF,XA,YB), (R1M,R2E,ZF,XA,YB), (R1N,R2E,ZF,XA,YB), (R1O,R2E,ZF,XA,YB), (R1P,R2E,ZF,XA,YB), (R1Q,R2E,ZF,XA,YB), (R1A,R2F,ZF,XA,YB), (R1B,R2F,ZF,XA,YB), (R1C,R2F,ZF,XA,YB), (R1D,R2F,ZF,XA,YB), (R1E,R2F,ZF,XA,YB), (R1F,R2F,ZF,XA,YB), (R1G,R2F,ZF,XA,YB), (R1H,R2F,ZF,XA,YB), (R1I,R2F,ZF,XA,YB), (R1J,R2F,ZF,XA,YB), (R1K,R2F,ZF,XA,YB), (R1L,R2F,ZF,XA,YB), (R1M,R2F,ZF,XA,YB), (R1N,R2F,ZF,XA,YB), (R1O,R2F,ZF,XA,YB), (R1P,R2F,ZF,XA,YB), (R1Q,R2F,ZF,XA,YB), (R1A,R2G,ZF,XA,YB), (R1B,R2G,ZF,XA,YB), (R1C,R2G,ZF,XA,YB), (R1D,R2G,ZF,XA,YB), (R1E,R2G,ZF,XA,YB), (R1F,R2G,ZF,XA,YB), (R1G,R2G,ZF,XA,YB), (R1H,R2G,ZF,XA,YB), (R1I,R2G,ZF,XA,YB), (R1J,R2G,ZF,XA,YB), (R1K,R2G,ZF,XA,YB), (R1L,R2G,ZF,XA,YB), (R1M,R2G,ZF,XA,YB), (R1N,R2G,ZF,XA,YB), (R1O,R2G,ZF,XA,YB), (R1P,R2G,ZF,XA,YB), (R1Q,R2G,ZF,XA,YB), (R1A,R2H,ZF,XA,YB), (R1B,R2H,ZF,XA,YB), (R1C,R2H,ZF,XA,YB), (R1D,R2H,ZF,XA,YB), (R1E,R2H,ZF,XA,YB), (R1F,R2H,ZF,XA,YB), (R1G,R2H,ZF,XA,YB), (R1H,R2H,ZF,XA,YB), (R1I,R2H,ZF,XA,YB), (R1J,R2H,ZF,XA,YB), (R1K,R2H,ZF,XA,YB), (R1L,R2H,ZF,XA,YB), (R1M,R2H,ZF,XA,YB), (R1N,R2H,ZF,XA,YB), (R1O,R2H,ZF,XA,YB), (R1P,R2H,ZF,XA,YB), (R1Q,R2H,ZF,XA,YB), (R1A,R2I,ZF,XA,YB), (R1B,R2I,ZF,XA,YB), (R1C,R2I,ZF,XA,YB), (R1D,R2I,ZF,XA,YB), (R1E,R2I,ZF,XA,YB), (R1F,R2I,ZF,XA,YB), (R1G,R2I,ZF,XA,YB), (R1H,R2I,ZF,XA,YB), (R1I,R2I,ZF,XA,YB), (R1J,R2I,ZF,XA,YB), (R1K,R2I,ZF,XA,YB), (R1L,R2I,ZF,XA,YB), (R1M,R2I,ZF,XA,YB), (R1N,R2I,ZF,XA,YB), (R1O,R2I,ZF,XA,YB), (R1P,R2I,ZF,XA,YB), (R1Q,R2I,ZF,XA,YB), (R1A,R2J,ZF,XA,YB), (R1B,R2J,ZF,XA,YB), (R1C,R2J,ZF,XA,YB), (R1D,R2J,ZF,XA,YB), (R1E,R2J,ZF,XA,YB), (R1F,R2J,ZF,XA,YB), (R1G,R2J,ZF,XA,YB), (R1H,R2J,ZF,XA,YB), (R1I,R2J,ZF,XA,YB), (R1J,R2J,ZF,XA,YB), (R1K,R2J,ZF,XA,YB), (R1L,R2J,ZF,XA,YB), (R1M,R2J,ZF,XA,YB), (R1N,R2J,ZF,XA,YB), (R1O,R2J,ZF,XA,YB), (R1P,R2J,ZF,XA,YB), (R1Q,R2J,ZF,XA,YB), (R1A,R2K,ZF,XA,YB), (R1B,R2K,ZF,XA,YB), (R1C,R2K,ZF,XA,YB), (R1D,R2K,ZF,XA,YB), (R1E,R2K,ZF,XA,YB), (R1F,R2K,ZF,XA,YB), (R1G,R2K,ZF,XA,YB), (R1H,R2K,ZF,XA,YB), (R1I,R2K,ZF,XA,YB), (R1J,R2K,ZF,XA,YB), (R1K,R2K,ZF,XA,YB), (R1L,R2K,ZF,XA,YB), (R1M,R2K,ZF,XA,YB), (R1N,R2K,ZF,XA,YB), (R1O,R2K,ZF,XA,YB), (R1P,R2K,ZF,XA,YB), (R1Q,R2K,ZF,XA,YB), (R1A,R2L,ZF,XA,YB), (R1B,R2L,ZF,XA,YB), (R1C,R2L,ZF,XA,YB), (R1D,R2L,ZF,XA,YB), (R1E,R2L,ZF,XA,YB), (R1F,R2L,ZF,XA,YB), (R1G,R2L,ZF,XA,YB), (R1H,R2L,ZF,XA,YB), (R1I,R2L,ZF,XA,YB), (R1J,R2L,ZF,XA,YB), (R1K,R2L,ZF,XA,YB), (R1L,R2L,ZF,XA,YB), (R1M,R2L,ZF,XA,YB), (R1N,R2L,ZF,XA,YB), (R1O,R2L,ZF,XA,YB), (R1P,R2L,ZF,XA,YB), (R1Q,R2L,ZF,XA,YB), (R1A,R2M,ZF,XA,YB), (R1B,R2M,ZF,XA,YB), (R1C,R2M,ZF,XA,YB), (R1D,R2M,ZF,XA,YB), (R1E,R2M,ZF,XA,YB), (R1F,R2M,ZF,XA,YB), (R1G,R2M,ZF,XA,YB), (R1H,R2M,ZF,XA,YB), (R1I,R2M,ZF,XA,YB), (R1J,R2M,ZF,XA,YB), (R1K,R2M,ZF,XA,YB), (R1L,R2M,ZF,XA,YB), (R1M,R2M,ZF,XA,YB), (R1N,R2M,ZF,XA,YB), (R1O,R2M,ZF,XA,YB), (R1P,R2M,ZF,XA,YB), (R1Q,R2M,ZF,XA,YB), (R1A,R2N,ZF,XA,YB), (R1B,R2N,ZF,XA,YB), (R1C,R2N,ZF,XA,YB), (R1D,R2N,ZF,XA,YB), (R1E,R2N,ZF,XA,YB), (R1F,R2N,ZF,XA,YB), (R1G,R2N,ZF,XA,YB), (R1H,R2N,ZF,XA,YB), (R1I,R2N,ZF,XA,YB), (R1J,R2N,ZF,XA,YB), (R1K,R2N,ZF,XA,YB), (R1L,R2N,ZF,XA,YB), (R1M,R2N,ZF,XA,YB), (R1N,R2N,ZF,XA,YB), (R1O,R2N,ZF,XA,YB), (R1P,R2N,ZF,XA,YB), (R1Q,R2N,ZF,XA,YB), (R1A,R2O,ZF,XA,YB), (R1B,R2O,ZF,XA,YB), (R1C,R2O,ZF,XA,YB), (R1D,R2O,ZF,XA,YB), (R1E,R2O,ZF,XA,YB), (R1F,R2O,ZF,XA,YB), (R1G,R2O,ZF,XA,YB), (R1H,R2O,ZF,XA,YB), (R1I,R2O,ZF,XA,YB), (R1J,R2O,ZF,XA,YB), (R1K,R2O,ZF,XA,YB), (R1L,R2O,ZF,XA,YB), (R1M,R2O,ZF,XA,YB), (R1N,R2O,ZF,XA,YB), (R1O,R2O,ZF,XA,YB), (R1P,R2O,ZF,XA,YB), (R1Q,R2O,ZF,XA,YB), (R1A,R2P,ZF,XA,YB), (R1B,R2P,ZF,XA,YB), (R1C,R2P,ZF,XA,YB), (R1D,R2P,ZF,XA,YB), (R1E,R2P,ZF,XA,YB), (R1F,R2P,ZF,XA,YB), (R1G,R2P,ZF,XA,YB), (R1H,R2P,ZF,XA,YB), (R1I,R2P,ZF,XA,YB), (R1J,R2P,ZF,XA,YB), (R1K,R2P,ZF,XA,YB), (R1L,R2P,ZF,XA,YB), (R1M,R2P,ZF,XA,YB), (R1N,R2P,ZF,XA,YB), (R1O,R2P,ZF,XA,YB), (R1P,R2P,ZF,XA,YB), (R1Q,R2P,ZF,XA,YB), (R1A,R2Q,ZF,XA,YB), (R1B,R2Q,ZF,XA,YB), (R1C,R2Q,ZF,XA,YB), (R1D,R2Q,ZF,XA,YB), (R1E,R2Q,ZF,XA,YB), (R1F,R2Q,ZF,XA,YB), (R1G,R2Q,ZF,XA,YB), (R1H,R2Q,ZF,XA,YB), (R1I,R2Q,ZF,XA,YB), (R1J,R2Q,ZF,XA,YB), (R1K,R2Q,ZF,XA,YB), (R1L,R2Q,ZF,XA,YB), (R1M,R2Q,ZF,XA,YB), (R1N,R2Q,ZF,XA,YB), (R1O,R2Q,ZF,XA,YB), (R1P,R2Q,ZF,XA,YB), (R1Q,R2Q,ZF,XA,YB), (R1A,R2A,ZG,XA,YB), (R1B,R2A,ZG,XA,YB), (R1C,R2A,ZG,XA,YB), (R1D,R2A,ZG,XA,YB), (R1E,R2A,ZG,XA,YB), (R1F,R2A,ZG,XA,YB), (R1G,R2A,ZG,XA,YB), (R1H,R2A,ZG,XA,YB), (R1I,R2A,ZG,XA,YB), (R1J,R2A,ZG,XA,YB), (R1K,R2A,ZG,XA,YB), (R1L,R2A,ZG,XA,YB), (R1M,R2A,ZG,XA,YB), (R1N,R2A,ZG,XA,YB), (R1O,R2A,ZG,XA,YB), (R1P,R2A,ZG,XA,YB), (R1Q,R2A,ZG,XA,YB), (R1A,R2B,ZG,XA,YB), (R1B,R2B,ZG,XA,YB), (R1C,R2B,ZG,XA,YB), (R1D,R2B,ZG,XA,YB), (R1E,R2B,ZG,XA,YB), (R1F,R2B,ZG,XA,YB), (R1G,R2B,ZG,XA,YB), (R1H,R2B,ZG,XA,YB), (R1I,R2B,ZG,XA,YB), (R1J,R2B,ZG,XA,YB), (R1K,R2B,ZG,XA,YB), (R1L,R2B,ZG,XA,YB), (R1M,R2B,ZG,XA,YB), (R1N,R2B,ZG,XA,YB), (R1O,R2B,ZG,XA,YB), (R1P,R2B,ZG,XA,YB), (R1Q,R2B,ZG,XA,YB), (R1A,R2C,ZG,XA,YB), (R1B,R2C,ZG,XA,YB), (R1C,R2C,ZG,XA,YB), (R1D,R2C,ZG,XA,YB), (R1E,R2C,ZG,XA,YB), (R1F,R2C,ZG,XA,YB), (R1G,R2C,ZG,XA,YB), (R1H,R2C,ZG,XA,YB), (R1I,R2C,ZG,XA,YB), (R1J,R2C,ZG,XA,YB), (R1K,R2C,ZG,XA,YB), (R1L,R2C,ZG,XA,YB), (R1M,R2C,ZG,XA,YB), (R1N,R2C,ZG,XA,YB), (R1O,R2C,ZG,XA,YB), (R1P,R2C,ZG,XA,YB), (R1Q,R2C,ZG,XA,YB), (R1A,R2D,ZG,XA,YB), (R1B,R2D,ZG,XA,YB), (R1C,R2D,ZG, XA,YB), (R1D,R2D,ZG,XA,YB), (R1E,R2D,ZG,XA,YB), (R1F,R2D,ZG,XA,YB), (R1G,R2D,ZG,XA,YB), (R1H, R2D,ZG,XA,YB), (R1I,R2D,ZG,XA,YB), (R1J,R2D,ZG, XA,YB), (R1K,R2D,ZG,XA,YB), (R1L,R2D,ZG,XA,YB), (R1M,R2D,ZG,XA,YB), (R1N,R2D,ZG,XA,YB), (R1O, R2D,ZG,XA,YB), (R1P,R2D,ZG,XA,YB), (R1Q,R2D,ZG, XA,YB), (R1A,R2E,ZG,XA,YB), (R1B,R2E,ZG,XA,YB), (R1C,R2E,ZG,XA,YB), (R1D,R2E,ZG,XA,YB), (R1E, R2E,ZG,XA,YB), (R1F,R2E,ZG,XA,YB), (R1G,R2E,ZG, XA,YB), (R1H,R2E,ZG,XA,YB), (R1I,R2E,ZG,XA,YB), (R1J,R2E,ZG,XA,YB), (R1K,R2E,ZG,XA,YB), (R1L,R2E, ZG,XA,YB), (R1M,R2E,ZG,XA,YB), (R1N,R2E,ZG,XA, YB), (R1O,R2E,ZG,XA,YB), (R1P,R2E,ZG,XA,YB), (R1Q,R2E,ZG,XA,YB), (R1A,R2F,ZG,XA,YB), (R1B,R2F, ZG,XA,YB), (R1C,R2F,ZG,XA,YB), (R1D,R2F,ZG,XA, YB), (R1E,R2F,ZG,XA,YB), (R1F,R2F,ZG,XA,YB), (R1G, R2F,ZG,XA,YB), (R1H,R2F,ZG,XA,YB), (R1I,R2F,ZG, XA,YB), (R1J,R2F,ZG,XA,YB), (R1K,R2F,ZG,XA,YB), (R1L,R2F,ZG,XA,YB), (R1M,R2F,ZG,XA,YB), (R1N,R2F, ZG,XA,YB), (R1O,R2F,ZG,XA,YB), (R1P,R2F,ZG,XA, YB), (R1Q,R2F,ZG,XA,YB), (R1A,R2G,ZG,XA,YB), (R1B,R2G,ZG,XA,YB), (R1C,R2G,ZG,XA,YB), (R1D, R2G,ZG,XA,YB), (R1E,R2G,ZG,XA,YB), (R1F,R2G,ZG, XA,YB), (R1G,R2G,ZG,XA,YB), (R1H,R2G,ZG,XA,YB), (R1I,R2G,ZG,XA,YB), (R1J,R2G,ZG,XA,YB), (R1K,R2G, ZG,XA,YB), (R1L,R2G,ZG,XA,YB), (R1M,R2G,ZG,XA, YB), (R1N,R2G,ZG,XA,YB), (R1O,R2G,ZG,XA,YB), (R1P,R2G,ZG,XA,YB), (R1Q,R2G,ZG,XA,YB), (R1A, R2H,ZG,XA,YB), (R1B,R2H,ZG,XA,YB), (R1C,R2H,ZG, XA,YB), (R1D,R2H,ZG,XA,YB), (R1E,R2H,ZG,XA,YB), (R1F,R2H,ZG,XA,YB), (R1G,R2H,ZG,XA,YB), (R1H, R2H,ZG,XA,YB), (R1I,R2H,ZG,XA,YB), (R1J,R2H,ZG, XA,YB), (R1K,R2H,ZG,XA,YB), (R1L,R2H,ZG,XA,YB), (R1M,R2H,ZG,XA,YB), (R1N,R2H,ZG,XA,YB), (R1O, R2H,ZG,XA,YB), (R1P,R2H,ZG,XA,YB), (R1Q,R2H,ZG, XA,YB), (R1A,R2I,ZG,XA,YB), (R1B,R2I,ZG,XA,YB), (R1C,R2I,ZG,XA,YB), (R1D,R2I,ZG,XA,YB), (R1E,R2I, ZG,XA,YB), (R1F,R2I,ZG,XA,YB), (R1G,R2I,ZG,XA, YB), (R1H,R2I,ZG,XA,YB), (R1I,R2I,ZG,XA,YB), (R1J, R2I,ZG,XA,YB), (R1K,R2I,ZG,XA,YB), (R1L,R2I,ZG, XA,YB), (R1M,R2I,ZG,XA,YB), (R1N,R2I,ZG,XA,YB), (R1O,R2I,ZG,XA,YB), (R1P,R2I,ZG,XA,YB), (R1Q,R2I, ZG,XA,YB), (R1A,R2J,ZG,XA,YB), (R1B,R2J,ZG,XA, YB), (R1C,R2J,ZG,XA,YB), (R1D,R2J,ZG,XA,YB), (R1E, R2J,ZG,XA,YB), (R1F,R2J,ZG,XA,YB), (R1G,R2J,ZG, XA,YB), (R1H,R2J,ZG,XA,YB), (R1I,R2J,ZG,XA,YB), (R1J,R2J,ZG,XA,YB), (R1K,R2J,ZG,XA,YB), (R1L,R2J, ZG,XA,YB), (R1M,R2J,ZG,XA,YB), (R1N,R2J,ZG,XA, YB), (R1O,R2J,ZG,XA,YB), (R1P,R2J,ZG,XA,YB), (R1Q, R2J,ZG,XA,YB), (R1A,R2K,ZG,XA,YB), (R1B,R2K,ZG, XA,YB), (R1C,R2K,ZG,XA,YB), (R1D,R2K,ZG,XA,YB), (R1E,R2K,ZG,XA,YB), (R1F,R2K,ZG,XA,YB), (R1G, R2K,ZG,XA,YB), (R1H,R2K,ZG,XA,YB), (R1I,R2K,ZG, XA,YB), (R1J,R2K,ZG,XA,YB), (R1K,R2K,ZG,XA,YB), (R1L,R2K,ZG,XA,YB), (R1M,R2K,ZG,XA,YB), (R1N, R2K,ZG,XA,YB), (R1O,R2K,ZG,XA,YB), (R1P,R2K,ZG, XA,YB), (R1Q,R2K,ZG,XA,YB), (R1A,R2L,ZG,XA,YB), (R1B,R2L,ZG,XA,YB), (R1C,R2L,ZG,XA,YB), (R1D, R2L,ZG,XA,YB), (R1E,R2L,ZG,XA,YB), (R1F,R2L,ZG, XA,YB), (R1G,R2L,ZG,XA,YB), (R1H,R2L,ZG,XA,YB), (R1I,R2L,ZG,XA,YB), (R1J,R2L,ZG,XA,YB), (R1K,R2L, ZG,XA,YB), (R1L,R2L,ZG,XA,YB), (R1M,R2L,ZG,XA, YB), (R1N,R2L,ZG,XA,YB), (R1O,R2L,ZG,XA,YB), (R1P,R2L,ZG,XA,YB), (R1Q,R2L,ZG,XA,YB), (R1A, R2M,ZG,XA,YB), (R1B,R2M,ZG,XA,YB), (R1C,R2M, ZG,XA,YB), (R1D,R2M,ZG,XA,YB), (R1E,R2M,ZG,XA, YB), (R1F,R2M,ZG,XA,YB), (R1G,R2M,ZG,XA,YB), (R1H,R2M,ZG,XA,YB), (R1I,R2M,ZG,XA,YB), (R1J, R2M,ZG,XA,YB), (R1K,R2M,ZG,XA,YB), (R1L,R2M, ZG,XA,YB), (R1M,R2M,ZG,XA,YB), (R1N,R2M,ZG,XA, YB), (R1O,R2M,ZG,XA,YB), (R1P,R2M,ZG,XA,YB), (R1Q,R2M,ZG,XA,YB), (R1A,R2N,ZG,XA,YB), (R1B, R2N,ZG,XA,YB), (R1C,R2N,ZG,XA,YB), (R1D,R2N,ZG, XA,YB), (R1E,R2N,ZG,XA,YB), (R1F,R2N,ZG,XA,YB), (R1G,R2N,ZG,XA,YB), (R1H,R2N,ZG,XA,YB), (R1I, R2N,ZG,XA,YB), (R1J,R2N,ZG,XA,YB), (R1K,R2N,ZG, XA,YB), (R1L,R2N,ZG,XA,YB), (R1M,R2N,ZG,XA,YB), (R1N,R2N,ZG,XA,YB), (R1O,R2N,ZG,XA,YB), (R1P, R2N,ZG,XA,YB), (R1Q,R2N,ZG,XA,YB), (R1A,R2O,ZG, XA,YB), (R1B,R2O,ZG,XA,YB), (R1C,R2O,ZG,XA,YB), (R1D,R2O,ZG,XA,YB), (R1E,R2O,ZG,XA,YB), (R1F, R2O,ZG,XA,YB), (R1G,R2O,ZG,XA,YB), (R1H,R2O,ZG, XA,YB), (R1I,R2O,ZG,XA,YB), (R1J,R2O,ZG,XA,YB), (R1K,R2O,ZG,XA,YB), (R1L,R2O,ZG,XA,YB), (R1M, R2O,ZG,XA,YB), (R1N,R2O,ZG,XA,YB), (R1O,R2O,ZG, XA,YB), (R1P,R2O,ZG,XA,YB), (R1Q,R2O,ZG,XA,YB), (R1A,R2P,ZG,XA,YB), (R1B,R2P,ZG,XA,YB), (R1C,R2P, ZG,XA,YB), (R1D,R2P,ZG,XA,YB), (R1E,R2P,ZG,XA, YB), (R1F,R2P,ZG,XA,YB), (R1G,R2P,ZG,XA,YB), (R1H, R2P,ZG,XA,YB), (R1I,R2P,ZG,XA,YB), (R1J,R2P,ZG,XA, YB), (R1K,R2P,ZG,XA,YB), (R1L,R2P,ZG,XA,YB), (R1M,R2P,ZG,XA,YB), (R1N,R2P,ZG,XA,YB), (R1O,R2P, ZG,XA,YB), (R1P,R2P,ZG,XA,YB), (R1Q,R2P,ZG,XA, YB), (R1A,R2Q,ZG,XA,YB), (R1B,R2Q,ZG,XA,YB), (R1C,R2Q,ZG,XA,YB), (R1D,R2Q,ZG,XA,YB), (R1E, R2Q,ZG,XA,YB), (R1F,R2Q,ZG,XA,YB), (R1G,R2Q,ZG, XA,YB), (R1H,R2Q,ZG,XA,YB), (R1I,R2Q,ZG,XA,YB), (R1J,R2Q,ZG,XA,YB), (R1K,R2Q,ZG,XA,YB), (R1L, R2Q,ZG,XA,YB), (R1M,R2Q,ZG,XA,YB), (R1N,R2Q,ZG, XA,YB), (R1O,R2Q,ZG,XA,YB), (R1P,R2Q,ZG,XA,YB), (R1Q,R2Q,ZG,XA,YB), (R1A,R2A,ZH,XA,YB), (R1B, R2A,ZH,XA,YB), (R1C,R2A,ZH,XA,YB), (R1D,R2A,ZH, XA,YB), (R1E,R2A,ZH,XA,YB), (R1F,R2A,ZH,XA,YB), (R1G,R2A,ZH,XA,YB), (R1H,R2A,ZH,XA,YB), (R1I, R2A,ZH,XA,YB), (R1J,R2A,ZH,XA,YB), (R1K,R2A,ZH, XA,YB), (R1L,R2A,ZH,XA,YB), (R1M,R2A,ZH,XA,YB), (R1N,R2A,ZH,XA,YB), (R1O,R2A,ZH,XA,YB), (R1P, R2A,ZH,XA,YB), (R1Q,R2A,ZH,XA,YB), (R1A,R2B,ZH, XA,YB), (R1B,R2B,ZH,XA,YB), (R1C,R2B,ZH,XA,YB), (R1D,R2B,ZH,XA,YB), (R1E,R2B,ZH,XA,YB), (R1F, R2B,ZH,XA,YB), (R1G,R2B,ZH,XA,YB), (R1H,R2B,ZH, XA,YB), (R1I,R2B,ZH,XA,YB), (R1J,R2B,ZH,XA,YB), (R1K,R2B,ZH,XA,YB), (R1L,R2B,ZH,XA,YB), (R1M, R2B,ZH,XA,YB), (R1N,R2B,ZH,XA,YB), (R1O,R2B,ZH, XA,YB), (R1P,R2B,ZH,XA,YB), (R1Q,R2B,ZH,XA,YB), (R1A,R2C,ZH,XA,YB), (R1B,R2C,ZH,XA,YB), (R1C, R2C,ZH,XA,YB), (R1D,R2C,ZH,XA,YB), (R1E,R2C,ZH, XA,YB), (R1F,R2C,ZH,XA,YB), (R1G,R2C,ZH,XA,YB), (R1H,R2C,ZH,XA,YB), (R1I,R2C,ZH,XA,YB), (R1J,R2C, ZH,XA,YB), (R1K,R2C,ZH,XA,YB), (R1L,R2C,ZH,XA, YB), (R1M,R2C,ZH,XA,YB), (R1N,R2C,ZH,XA,YB), (R1O,R2C,ZH,XA,YB), (R1P,R22C,ZH,XA,YB), (R1R2C, ZH,XA,YB), (R1A,R2D,ZH,XA,YB), (R1B,R2D,ZH,XA, YB), (R1C,R2D,ZH,XA,YB), (R1D,R2D,ZH,XA,YB), (R1E,R2D,ZH,XA,YB), (R1F,R2D,ZH,XA,YB), (R1G, R2D,ZH,XA,YB), (R1H,R2D,ZH,XA,YB), (R1I,R2D,ZH, XA,YB), (R1J,R2D,ZH,XA,YB), (R1K,R2D,ZH,XA,YB), (R1L,R2D,ZH,XA,YB), (R1M,R2D,ZH,XA,YB), (R1N, R2D,ZH,XA,YB), (R1O,R2D,ZH,XA,YB), (R1P,R2D,ZH, XA,YB), (R1Q,R2D,ZH,XA,YB), (R1A,R2E,ZH,XA,YB), (R1B,R2E,ZH,XA,YB), (R1C,R2E,ZH,XA,YB), (R1D, R2E,ZH,XA,YB), (R1E,R2E,ZH,XA,YB), (R1F,R2E,ZH, XA,YB), (R1G,R2E,ZH,XA,YB), (R1H,R2E,ZH,XA,YB), (R1I,R2E,ZH,XA,YB), (R1J,R2E,ZH,XA,YB), (R1K,R2E, ZH,XA,YB), (R1L,R2E,ZH,XA,YB), (R1M,R2E,ZH,XA, YB), (R1N,R2E,ZH,XA,YB), (R1O,R2E,ZH,XA,YB), (R1P,R2E,ZH,XA,YB), (R1Q,R2E,ZH,XA,YB), (R1A,R2F, ZH,XA,YB), (R1B,R2F,ZH,XA,YB), (R1C,R2F,ZH,XA, YB), (R1D,R2F,ZH,XA,YB), (R1E,R2F,ZH,XA,YB), (R1F, R2F,ZH,XA,YB), (R1G,R2F,ZH,XA,YB), (R1H,R2F,ZH, XA,YB), (R1I,R2F,ZH,XA,YB), (R1J,R2F,ZH,XA,YB), (R1K,R2F,ZH,XA,YB), (R1L,R2F,ZH,XA,YB), (R1M,R2F, ZH,XA,YB), (R1N,R2F,ZH,XA,YB), (R1O,R2F,ZH,XA, YB), (R1P,R2F,ZH,XA,YB), (R1Q,R2F,ZH,XA,YB), (R1A, R2G,ZH,XA,YB), (R1B,R2G,ZH,XA,YB), (R1C,R2G,ZH, XA,YB), (R1D,R2G,ZH,XA,YB), (R1E,R2G,ZH,XA,YB), (R1F,R2G,ZH,XA,YB), (R1G,R2G,ZH,XA,YB), (R1H, R2G,ZH,XA,YB), (R1I,R2G,ZH,XA,YB), (R1J,R2G,ZH, XA,YB), (R1K,R2G,ZH,XA,YB), (R1L,R2G,ZH,XA,YB), (R1M,R2G,ZH,XA,YB), (R1N,R2G,ZH,XA,YB), (R1O, R2G,ZH,XA,YB), (R1P,R2G,ZH,XA,YB), (R1Q,R2G,ZH, XA,YB), (R1A,R2H,ZH,XA,YB), (R1B,R2H,ZH,XA,YB), (R1C,R2H,ZH,XA,YB), (R1D,R2H,ZH,XA,YB), (R1E, R2H,ZH,XA,YB), (R1F,R2H,ZH,XA,YB), (R1G,R2H,ZH, XA,YB), (R1H,R2H,ZH,XA,YB), (R1I,R2H,ZH,XA,YB), (R1J,R2H,ZH,XA,YB), (R1K,R2H,ZH,XA,YB), (R1L, R2H,ZH,XA,YB), (R1M,R2H,ZH,XA,YB), (R1N,R2H,ZH, XA,YB), (R1O,R2H,ZH,XA,YB), (R1P,R2H,ZH,XA,YB), (R1Q,R2H,ZH,XA,YB), (R1A,R2I,ZH,XA,YB), (R1B,R2I, ZH,XA,YB), (R1C,R2I,ZH,XA,YB), (R1D,R2I,ZH,XA, YB), (R1E,R2I,ZH,XA,YB), (R1F,R2I,ZH,XA,YB), (R1G, R2 I,ZH,XA,YB), (R1H,R2I,ZH,XA,YB), (R1I,R2I,ZH, XA,YB), (R1J,R2I,ZH,XA,YB), (R1K,R2I,ZH,XA,YB), (R1L,R2I,ZH,XA,YB), (R1M,R2I,ZH,XA,YB), (R1N,R2I, ZH,XA,YB), (R1O,R2I,ZH,XA,YB), (R1P,R2I,ZH,XA, YB), (R1Q,R2I,ZH,XA,YB), (R1A,R2J,ZH,XA,YB), (R1B, R2J,ZH,XA,YB), (R1C,R2J,ZH,XA,YB), (R1D,R2J,ZH, XA,YB), (R1E,R2J,ZH,XA,YB), (R1F,R2J,ZH,XA,YB), (R1G,R2J,ZH,XA,YB), (R1H,R2J,ZH,XA,YB), (R1I,R2J, ZH,XA,YB), (R1J,R2J,ZH,XA,YB), (R1K,R2J,ZH,XA, YB), (R1L,R2J,ZH,XA,YB), (R1M,R2J,ZH,XA,YB), (R1N, R2J,ZH,XA,YB), (R1O,R2J,ZH,XA,YB), (R1P,R2J,ZH, XA,YB), (R1R2J,ZH,XA,YB), (R1A,R2K,ZH,XA,YB), (R1B,R2K,ZH,XA,YB), (R1C,R2K,ZH,XA,YB), (R1D, R2K,ZH,XA,YB), (R1E,R2K,ZH,XA,YB), (R1F,R2K,ZH, XA,YB), (R1G,R2K,ZH,XA,YB), (R1H,R2K,ZH,XA,YB), (R1I,R2K,ZH,XA,YB), (R1J,R2K,ZH,XA,YB), (R1K,R2K, ZH,XA,YB), (R1L,R2K,ZH,XA,YB), (R1M,R2K,ZH,XA, YB), (R1N,R2K,ZH,XA,YB), (R1O,R2K,ZH,XA,YB), (R1P,R2K,ZH,XA,YB), (R1Q,R2K,ZH,XA,YB), (R1A, R2L,ZH,XA,YB), (R1B,R2L,ZH,XA,YB), (R1C,R2L,ZH, XA,YB), (R1D,R2L,ZH,XA,YB), (R1E,R2L,ZH,XA,YB), (R1F,R2L,ZH,XA,YB), (R1G,R2L,ZH,XA,YB), (R1H, R2L,ZH,XA,YB), (R1I,R2L,ZH,XA,YB), (R1J,R2L,ZH, XA,YB), (R1K,R2L,ZH,XA,YB), (R1L,R2L,ZH,XA,YB), (R1M,R2L,ZH,XA,YB), (R1N,R2L,ZH,XA,YB), (R1O, R2L,ZH,XA,YB), (R1P,R2L,ZH,XA,YB), (R1Q,R2L,ZH, XA,YB), (R1A,R2M,ZH,XA,YB), (R1B,R2M,ZH,XA,YB), (R1C,R2M,ZH,XA,YB), (R1D,R2M,ZH,XA,YB), (R1E, R2M,ZH,XA,YB), (R1F,R2M,ZH,XA,YB), (R1G,R2M,ZH, XA,YB), (R1H,R2M,ZH,XA,YB), (R1I,R2M,ZH,XA,YB), (R1J,R2M,ZH,XA,YB), (R1K,R2M,ZH,XA,YB), (R1L, R2M,ZH,XA,YB), (R1M,R2M,ZH,XA,YB), (R1N,R2M, ZH,XA,YB), (R1O,R2M,ZH,XA,YB), (R1P,R2M,ZH,XA, YB), (R1Q,R2M,ZH,XA,YB), (R1A,R2N,ZH,XA,YB), (R1B,R2N,ZH,XA,YB), (R1C,R2N,ZH,XA,YB), (R1D, R2N,ZH,XA,YB), (R1E,R2N,ZH,XA,YB), (R1F,R2N,ZH, XA,YB), (R1G,R2N,ZH,XA,YB), (R1H,R2N,ZH,XA,YB), (R1I,R2N,ZH,XA,YB), (R1J,R2N,ZH,XA,YB), (R1K,R2N, ZH,XA,YB), (R1L,R2N,ZH,XA,YB), (R1M,R2N,ZH,XA, YB), (R1N,R2N,ZH,XA,YB), (R1O,R2N,ZH,XA,YB), (R1P,R2N,ZH,XA,YB), (R1Q,R2N,ZH,XA,YB), (R1A, R2O,ZH,XA,YB), (R1B,R2O,ZH,XA,YB), (R1C,R2O,ZH, XA,YB), (R1D,R2O,ZH,XA,YB), (R1E,R2O,ZH,XA,YB), (R1F,R2O,ZH,XA,YB), (R1G,R2O,ZH,XA,YB), (R1H, R2O,ZH,XA,YB), (R1I,R2O,ZH,XA,YB), (R1J,R2O,ZH, XA,YB), (R1K,R2O,ZH,XA,YB), (R1L,R2O,ZH,XA,YB), (R1M,R2O,ZH,XA,YB), (R1N,R2O,ZH,XA,YB), (R1O, R2O,ZH,XA,YB), (R1P,R2O,ZH,XA,YB), (R1Q,R2O,ZH, XA,YB), (R1A,R2P,ZH,XA,YB), (R1B,R2P,ZH,XA,YB), (R1C,R2P,ZH,XA,YB), (R1D,R2P,ZH,XA,YB), (R1E,R2P, ZH,XA,YB), (R1F,R2P,ZH,XA,YB), (R1G,R2P,ZH,XA, YB), (R1H,R2P,ZH,XA,YB), (R1I,R2P,ZH,XA,YB), (R1J, R2P,ZH,XA,YB), (R1K,R2P,ZH,XA,YB), (R1L,R2P,ZH, XA,YB), (R1M,R2P,ZH,XA,YB), (R1N,R2P,ZH,XA,YB), (R1O,R2P,ZH,XA,YB), (R1P,R2P,ZH,XA,YB), (R1Q,R2P, ZH,XA,YB), (R1A,R2Q,ZH,XA,YB), (R1B,R2Q,ZH,XA, YB), (R1C,R2Q,ZH,XA,YB), (R1D,R2Q,ZH,XA,YB), (R1E,R2Q,ZH,XA,YB), (R1F,R2Q,ZH,XA,YB), (R1G, R2Q,ZH,XA,YB), (R1H,R2Q,ZH,XA,YB), (R1I,R2Q,ZH, XA,YB), (R1J,R2Q,ZH,XA,YB), (R1K,R2Q,ZH,XA,YB), (R1L,R2Q,ZH,XA,YB), (R1M,R2Q,ZH,XA,YB), (R1N, R2Q,ZH,XA,YB), (R1O,R2Q,ZH,XA,YB), (R1P,R2Q,ZH, XA,YB), (R1Q,R2Q,ZH,XA,YB), (R1A,R2A,ZI,XA,YB), (R1B,R2A,ZI,XA,YB), (R1C,R2A,ZI,XA,YB), (R1D,R2A, ZI,XA,YB), (R1E,R2A,ZI,XA,YB), (R1F,R2A,ZI,XA,YB), (R1G,R2A,ZI,XA,YB), (R1H,R2A,ZI,XA,YB), (R1I,R2A, ZI,XA,YB), (R1J,R2A,ZI,XA,YB), (R1K,R2A,ZI,XA,YB), (R1L,R2A,ZI,XA,YB), (R1M,R2A,ZI,XA,YB), (R1N,R2A, ZI,XA,YB), (R1O,R2A,ZI,XA,YB), (R1P,R2A,ZI,XA,YB), (R1Q,R2A,ZI,XA,YB), (R1A,R2B,ZI,XA,YB), (R1B,R2B, ZI,XA,YB), (R1C,R2B,ZI,XA,YB), (R1D,R2B,ZI,XA,YB), (R1E,R2B,ZI,XA,YB), (R1F,R2B,ZI,XA,YB), (R1G,R2B, ZI,XA,YB), (R1H,R2B,ZI,XA,YB), (R1I,R2B,ZI,XA,YB), (R1J,R2B,ZI,XA,YB), (R1K,R2B,ZI,XA,YB), (R1L,R2B, ZI,XA,YB), (R1M,R2B,ZI,XA,YB), (R1N,R2B,ZI,XA, YB), (R1O,R2B,ZI,XA,YB), (R1P,R2B,ZI,XA,YB), (R1Q, R2B,ZI,XA,YB), (R1A,R2C,ZI,XA,YB), (R1B,R2C,ZI, XA,YB), (R1C,R2C,ZI,XA,YB), (R1D,R2C,ZI,XA,YB), (R1E,R2C,ZI,XA,YB), (R1F,R2C,ZI,XA,YB), (R1G,R2C, ZI,XA,YB), (R1H,R2C,ZI,XA,YB), (R1I,R2C,ZI,XA,YB), (R1J,R2C,ZI,XA,YB), (R1K,R2C,ZI,XA,YB), (R1L,R2C, ZI,XA,YB), (R1M,R2C,ZI,XA,YB), (R1N,R2C,ZI,XA, YB), (R1O,R2C,ZI,XA,YB), (R1P,R2C,ZI,XA,YB), (R1Q, R2C,ZI,XA,YB), (R1A,R2D,ZI,XA,YB), (R1B,R2D,ZI, XA,YB), (R1C,R2D,ZI,XA,YB), (R1D,R2D,ZI,XA,YB), (R1E,R2D,ZI,XA,YB), (R1F,R2D,ZI,XA,YB), (R1G,R2D, ZI,XA,YB), (R1H,R2D,ZI,XA,YB), (R1I,R2D,ZI,XA,YB), (R1J,R2D,ZI,XA,YB), (R1K,R2D,ZI,XA,YB), (R1L,R2D, ZI,XA,YB), (R1M,R2D,ZI,XA,YB), (R1N,R2D,ZI,XA, YB), (R1O,R2D,ZI,XA,YB), (R1P,R2D,ZI,XA,YB), (R1Q, R2D,ZI,XA,YB), (R1A,R2E,ZI,XA,YB), (R1B,R2E,ZI,XA, YB), (R1C,R2E,ZI,XA,YB), (R1D,R2E,ZI,XA,YB), (R1E, R2E,ZI,XA,YB), (R1F,R2E,ZI,XA,YB), (R1G,R2E,ZI,XA, YB), (R1H,R2E,ZI,XA,YB), (R1I,R2E,ZI,XA,YB), (R1J, R2E,ZI,XA,YB), (R1K,R2E,ZI,XA,YB), (R1L,R2E,ZI,XA, YB), (R1M,R2E,ZI,XA,YB), (R1N,R2E,ZI,XA,YB), (R1O, R2E,ZI,XA,YB), (R1P,R2E,ZI,XA,YB), (R1Q,R2E,ZI,XA, YB), (R1A,R2F,ZI,XA,YB), (R1B,R2F,ZI,XA,YB), (R1C, R2F,ZI,XA,YB), (R1D,R2F,ZI,XA,YB), (R1E,R2F,ZI,XA, YB), (R1F,R2F,ZI,XA,YB), (R1G,R2F,ZI,XA,YB), (R1H, R2F,ZI,XA,YB), (R1I,R2F,ZI,XA,YB), (R1J,R2F,ZI,XA, YB), (R1K,R2F,ZI,XA,YB), (R1L,R2F,ZI,XA,YB), (R1M, R2F,ZI,XA,YB), (R1N,R2F,ZI,XA,YB), (R1O,R2F,ZI,XA, YB), (R1P,R2F,ZI,XA,YB), (R1Q,R2F,ZI,XA,YB), (R1A, R2G,ZI,XA,YB), (R1B,R2G,ZI,XA,YB), (R1C,R2G,ZI, XA,YB), (R1D,R2G,ZI,XA,YB), (R1E,R2G,ZI,XA,YB), (R1F,R2G,ZI,XA,YB), (R1G,R2G,ZI,XA,YB), (R1H,R2G, ZI,XA,YB), (R1I,R2G,ZI,XA,YB), (R1J,R2G,ZI,XA,YB), (R1K,R2G,ZI,XA,YB), (R1L,R2G,ZI,XA,YB), (R1M,R2G,ZI,XA,YB), (R1N,R2G,ZI,XA,YB), (R1O,R2G,ZI,XA,YB), (R1P,R2G,ZI,XA,YB), (R1Q,R2G,ZI,XA,YB), (R1A,R2H,ZI,XA,YB), (R1B,R2H,ZI,XA,YB), (R1C,R2H,ZI,XA,YB), (R1D,R2H,ZI,XA,YB), (R1E,R2H,ZI,XA,YB), (R1F,R2H,ZI,XA,YB), (R1G,R2H,ZI,XA,YB), (R1H,R2H,ZI,XA,YB), (R1I,R2H,ZI,XA,YB), (R1J,R2H,ZI,XA,YB), (R1K,R2H,ZI,XA,YB), (R1L,R2H,ZI,XA,YB), (R1M,R2H,ZI,XA,YB), (R1N,R2H,ZI,XA,YB), (R1O,R2H,ZI,XA,YB), (R1P,R2H,ZI,XA,YB), (R1Q,R2H,ZI,XA,YB), (R1A,R2I,ZI,XA,YB), (R1B,R2I,ZI,XA,YB), (R1C,R2I,ZI,XA,YB), (R1D,R2I,ZI,XA,YB), (R1E,R2I,ZI,XA,YB), (R1F,R2I,ZI,XA,YB), (R1G,R2I,ZI,XA,YB), (R1H,R2I,ZI,XA,YB), (R1I,R2I,ZI,XA,YB), (R1J,R2I,ZI,XA,YB), (R1K,R2I,ZI,XA,YB), (R1L,R2I,ZI,XA,YB), (R1M,R2I,ZI,XA,YB), (R1N,R2I,ZI,XA,YB), (R1O,R2I,ZI,XA,YB), (R1P,R2I,ZI,XA,YB), (R1Q,R2I,ZI,XA,YB), (R1A,R2J,ZI,XA,YB), (R1B,R2J,ZI,XA,YB), (R1C,R2J,ZI,XA,YB), (R1D,R2J,ZI,XA,YB), (R1E,R2J,ZI,XA,YB), (R1F,R2J,ZI,XA,YB), (R1G,R2J,ZI,XA,YB), (R1H,R2J,ZI,XA,YB), (R1I,R2J,ZI,XA,YB), (R1J,R2J,ZI,XA,YB), (R1K,R2J,ZI,XA,YB), (R1L,R2J,ZI,XA,YB), (R1M,R2J,ZI,XA,YB), (R1N,R2J,ZI,XA,YB), (R1O,R2J,ZI,XA,YB), (R1P,R2J,ZI,XA,YB), (R1Q,R2J,ZI,XA,YB), (R1A,R2K,ZI,XA,YB), (R1B,R2K,ZI,XA,YB), (R1C,R2K,ZI,XA,YB), (R1D,R2K,ZI,XA,YB), (R1E,R2K,ZI,XA,YB), (R1F,R2K,ZI,XA,YB), (R1G,R2K,ZI,XA,YB), (R1H,R2K,ZI,XA,YB), (R1I,R2K,ZI,XA,YB), (R1J,R2K,ZI,XA,YB), (R1K,R2K,ZI,XA,YB), (R1L,R2K,ZI,XA,YB), (R1M,R2K,ZI,XA,YB), (R1N,R2K,ZI,XA,YB), (R1O,R2K,ZI,XA,YB), (R1P,R2K,ZI,XA,YB), (R1Q,R2K,ZI,XA,YB), (R1A,R2L,ZI,XA,YB), (R1B,R2L,ZI,XA,YB), (R1C,R2L,ZI,XA,YB), (R1D,R2L,ZI,XA,YB), (R1E,R2L,ZI,XA,YB), (R1F,R2L,ZI,XA,YB), (R1G,R2L,ZI,XA,YB), (R1H,R2L,ZI,XA,YB), (R1I,R2L,ZI,XA,YB), (R1J,R2L,ZI,XA,YB), (R1K,R2L,ZI,XA,YB), (R1L,R2L,ZI,XA,YB), (R1M,R2L,ZI,XA,YB), (R1N,R2L,ZI,XA,YB), (R1O,R2L,ZI,XA,YB), (R1P,R2L,ZI,XA,YB), (R1Q,R2L,ZI,XA,YB), (R1A,R2M,ZI,XA,YB), (R1B,R2M,ZI,XA,YB), (R1C,R2M,ZI,XA,YB), (R1D,R2M,ZI,XA,YB), (R1E,R2M,ZI,XA,YB), (R1F,R2M,ZI,XA,YB), (R1G,R2M,ZI,XA,YB), (R1H,R2M,ZI,XA,YB), (R1I,R2M,ZI,XA,YB), (R1J,R2M,ZI,XA,YB), (R1K,R2M,ZI,XA,YB), (R1L,R2M,ZI,XA,YB), (R1M,R2M,ZI,XA,YB), (R1N,R2M,ZI,XA,YB), (R1O,R2M,ZI,XA,YB), (R1P,R2M,ZI,XA,YB), (R1Q,R2M,ZI,XA,YB), (R1A,R2N,ZI,XA,YB), (R1B,R2N,ZI,XA,YB), (R1C,R2N,ZI,XA,YB), (R1D,R2N,ZI,XA,YB), (R1E,R2N,ZI,XA,YB), (R1F,R2N,ZI,XA,YB), (R1G,R2N,ZI,XA,YB), (R1H,R2N,ZI,XA,YB), (R1I,R2N,ZI,XA,YB), (R1J,R2N,ZI,XA,YB), (R1K,R2N,ZI,XA,YB), (R1L,R2N,ZI,XA,YB), (R1M,R2N,ZI,XA,YB), (R1N,R2N,ZI,XA,YB), (R1O,R2N,ZI,XA,YB), (R1P,R2N,ZI,XA,YB), (R1Q,R2N,ZI,XA,YB), (R1A,R2O,ZI,XA,YB), (R1B,R2O,ZI,XA,YB), (R1C,R2O,ZI,XA,YB), (R1D,R2O,ZI,XA,YB), (R1E,R2O,ZI,XA,YB), (R1F,R2O,ZI,XA,YB), (R1G,R2O,ZI,XA,YB), (R1H,R2O,ZI,XA,YB), (R1I,R2O,ZI,XA,YB), (R1J,R2O,ZI,XA,YB), (R1K,R2O,ZI,XA,YB), (R1L,R2O,ZI,XA,YB), (R1M,R2O,ZI,XA,YB), (R1N,R2O,ZI,XA,YB), (R1O,R2O,ZI,XA,YB), (R1P,R2O,ZI,XA,YB), (R1Q,R2O,ZI,XA,YB), (R1A,R2P,ZI,XA,YB), (R1B,R2P,ZI,XA,YB), (R1C,R2P,ZI,XA,YB), (R1D,R2P,ZI,XA,YB), (R1E,R2P,ZI,XA,YB), (R1F,R2P,ZI,XA,YB), (R1G,R2P,ZI,XA,YB), (R1H,R2P,ZI,XA,YB), (R1I,R2P,ZI,XA,YB), (R1J,R2P,ZI,XA,YB), (R1K,R2P,ZI,XA,YB), (R1L,R2P,ZI,XA,YB), (R1M,R2P,ZI,XA,YB), (R1N,R2P,ZI,XA,YB), (R1O,R2P,ZI,XA,YB), (R1P,R2P,ZI,XA,YB), (R1Q,R2P,ZI,XA,YB), (R1A,R2Q,ZI,XA,YB), (R1B,R2Q,ZI,XA,YB), (R1C,R2Q,ZI,XA,YB), (R1D,R2Q,ZI,XA,YB), (R1E,R2Q,ZI,XA,YB), (R1F,R2Q,ZI,XA,YB), (R1G,R2Q,ZI,XA,YB), (R1H,R2Q,ZI,XA,YB), (R1I,R2Q,ZI,XA,YB), (R1J,R2Q,ZI,XA,YB), (R1K,R2Q,ZI,XA,YB), (R1L,R2Q,ZI,XA,YB), (R1M,R2Q,ZI,XA,YB), (R1N,R2Q,ZI,XA,YB), (R1O,R2Q,ZI,XA,YB), (R1P,R2Q,ZI,XA,YB), (R1Q,R2Q,ZI,XA,YB), (R1A,R2A,ZJ,XA,YB), (R1B,R2A,ZJ,XA,YB), (R1C,R2A,ZJ,XA,YB), (R1D,R2A,ZJ,XA,YB), (R1E,R2A,ZJ,XA,YB), (R1F,R2A,ZJ,XA,YB), (R1G,R2A,ZJ,XA,YB), (R1H,R2A,ZJ,XA,YB), (R1I,R2A,ZJ,XA,YB), (R1J,R2A,ZJ,XA,YB), (R1K,R2A,ZJ,XA,YB), (R1L,R2A,ZJ,XA,YB), (R1M,R2A,ZJ,XA,YB), (R1N,R2A,ZJ,XA,YB), (R1O,R2A,ZJ,XA,YB), (R1P,R2A,ZJ,XA,YB), (R1Q,R2A,ZJ,XA,YB), (R1A,R2B,ZJ,XA,YB), (R1B,R2B,ZJ,XA,YB), (R1C,R2B,ZJ,XA,YB), (R1D,R2B,ZJ,XA,YB), (R1E,R2B,ZJ,XA,YB), (R1F,R2B,ZJ,XA,YB), (R1G,R2B,ZJ,XA,YB), (R1H,R2B,ZJ,XA,YB), (R1I,R2B,ZJ,XA,YB), (R1J,R2B,ZJ,XA,YB), (R1K,R2B,ZJ,XA,YB), (R1L,R2B,ZJ,XA,YB), (R1M,R2B,ZJ,XA,YB), (R1N,R2B,ZJ,XA,YB), (R1O,R2B,ZJ,XA,YB), (R1P,R2B,ZJ,XA,YB), (R1Q,R2B,ZJ,XA,YB), (R1A,R2C,ZJ,XA,YB), (R1B,R2C,ZJ,XA,YB), (R1C,R2C,ZJ,XA,YB), (R1D,R2C,ZJ,XA,YB), (R1E,R2C,ZJ,XA,YB), (R1F,R2C,ZJ,XA,YB), (R1G,R2C,ZJ,XA,YB), (R1H,R2C,ZJ,XA,YB), (R1I,R2C,ZJ,XA,YB), (R1J,R2C,ZJ,XA,YB), (R1K,R2C,ZJ,XA,YB), (R1L,R2C,ZJ,XA,YB), (R1M,R2C,ZJ,XA,YB), (R1N,R2C,ZJ,XA,YB), (R1O,R2C,ZJ,XA,YB), (R1P,R2C,ZJ,XA,YB), (R1Q,R2C,ZJ,XA,YB), (R1A,R2D,ZJ,XA,YB), (R1B,R2D,ZJ,XA,YB), (R1C,R2D,ZJ,XA,YB), (R1D,R2D,ZJ,XA,YB), (R1E,R2D,ZJ,XA,YB), (R1F,R2D,ZJ,XA,YB), (R1G,R2D,ZJ,XA,YB), (R1H,R2D,ZJ,XA,YB), (R1I,R2D,ZJ,XA,YB), (R1J,R2D,ZJ,XA,YB), (R1K,R2D,ZJ,XA,YB), (R1L,R2D,ZJ,XA,YB), (R1M,R2D,ZJ,XA,YB), (R1N,R2D,ZJ,XA,YB), (R1O,R2D,ZJ,XA,YB), (R1P,R2D,ZJ,XA,YB), (R1Q,R2D,ZJ,XA,YB), (R1A,R2E,ZJ,XA,YB), (R1B,R2E,ZJ,XA,YB), (R1C,R2E,ZJ,XA,YB), (R1D,R2E,ZJ,XA,YB), (R1E,R2E,ZJ,XA,YB), (R1F,R2E,ZJ,XA,YB), (R1G,R2E,ZJ,XA,YB), (R1H,R2E,ZJ,XA,YB), (R1I,R2E,ZJ,XA,YB), (R1J,R2E,ZJ,XA,YB), (R1K,R2E,ZJ,XA,YB), (R1L,R2E,ZJ,XA,YB), (R1M,R2E,ZJ,XA,YB), (R1N,R2E,ZJ,XA,YB), (R1O,R2E,ZJ,XA,YB), (R1P,R2E,ZJ,XA,YB), (R1Q,R2E,ZJ,XA,YB), (R1A,R2F,ZJ,XA,YB), (R1B,R2F,ZJ,XA,YB), (R1C,R2F,ZJ,XA,YB), (R1D,R2F,ZJ,XA,YB), (R1E,R2F,ZJ,XA,YB), (R1F,R2F,ZJ,XA,YB), (R1G,R2F,ZJ,XA,YB), (R1H,R2F,ZJ,XA,YB), (R1I,R2F,ZJ,XA,YB), (R1J,R2F,ZJ,XA,YB), (R1K,R2F,ZJ,XA,YB), (R1L,R2F,ZJ,XA,YB), (R1M,R2F,ZJ,XA,YB), (R1N,R2F,ZJ,XA,YB), (R1O,R2F,ZJ,XA,YB), (R1P,R2F,ZJ,XA,YB), (R1Q,R2F,ZJ,XA,YB), (R1A,R2G,ZJ,XA,YB), (R1B,R2G,ZJ,XA,YB), (R1C,R2G,ZJ,XA,YB), (R1D,R2G,ZJ,XA,YB), (R1E,R2G,ZJ,XA,YB), (R1F,R2G,ZJ,XA,YB), (R1G,R2G,ZJ,XA,YB), (R1H,R2G,ZJ,XA,YB), (R1I,R2G,ZJ,XA,YB), (R1J,R2G,ZJ,XA,YB), (R1K,R2G,ZJ,XA,YB), (R1L,R2G,ZJ,XA,YB), (R1M,R2G,ZJ,XA,YB), (R1N,R2G,ZJ,XA,YB), (R1O,R2G,ZJ,XA,YB), (R1P,R2G,ZJ,XA,YB), (R1Q,R2G,ZJ,XA,YB), (R1A,R2H,ZJ,XA,YB), (R1B,R2H,ZJ,XA,YB), (R1C,R2H,ZJ,XA,YB), (R1D,R2H,ZJ,XA,YB), (R1E,R2H,ZJ,XA,YB), (R1F,R2H,ZJ,XA,YB), (R1G,R2H,ZJ,XA,YB), (R1H,R2H,ZJ,XA,YB), (R1I,R2H,ZJ,XA,YB), (R1J,R2H,ZJ,XA,YB), (R1K,R2H,ZJ,XA,YB), (R1L,R2H,ZJ,XA,YB), (R1M,R2H,ZJ,XA,YB), (R1N,R2H,ZJ,XA,YB), (R1O,R2H,ZJ,XA,YB), (R1P,R2H,ZJ,XA,YB), (R1Q,R2H,ZJ,XA,YB), (R1A,R2I,ZJ,XA,YB), (R1B,R2I,ZJ,XA,YB), (R1C,R2I,ZJ,XA,YB), (R1D,R2I,ZJ,XA,YB), (R1E,R2I,ZJ,XA,YB), (R1F,R2I,ZJ,XA,YB), (R1G,R2I,ZJ,XA,YB), (R1H,R2I,ZJ,XA,YB), (R1I,R2I,ZJ,XA,YB), (R1J,R2I,ZJ,XA,YB), (R1K,R2I,ZJ,XA,YB), (R1L,R2I,ZJ,XA, YB), (R1M,R2I,ZJ,XA,YB), (R1N,R2I,ZJ,XA,YB), (R1O, R2I,ZJ,XA,YB), (R1P,R2I,ZJ,XA,YB), (R1Q,R2I,ZJ,XA, YB), (R1A,R2J,ZJ,XA,YB), (R1B,R2J,ZJ,XA,YB), (R1C, R2J,ZJ,XA,YB), (R1D,R2J,ZJ,XA,YB), (R1E,R2J,ZJ,XA, YB), (R1F,R2J,ZJ,XA,YB), (R1G,R2J,ZJ,XA,YB), (R1H, R2J,ZJ,XA,YB), (R1I,R2J,ZJ,XA,YB), (R1J,R2J,ZJ,XA, YB), (R1K,R2J,ZJ,XA,YB), (R1L,R2J,ZJ,XA,YB), (R1M, R2J,ZJ,XA,YB), (R1N,R2J,ZJ,XA,YB), (R1O,R2J,ZJ,XA, YB), (R1P,R2J,ZJ,XA,YB), (R1Q,R2J,ZJ,XA,YB), (R1A, R2K,ZJ,XA,YB), (R1B,R2K,ZJ,XA,YB), (R1C,R2K,ZJ, XA,YB), (R1D,R2K,ZJ,XA,YB), (R1E,R2K,ZJ,XA,YB), (R1F,R2K,ZJ,XA,YB), (R1G,R2K,ZJ,XA,YB), (R1H,R2K, ZJ,XA,YB), (R1I,R2K,ZJ,XA,YB), (R1J,R2K,ZJ,XA,YB), (R1K,R2K,ZJ,XA,YB), (R1L,R2K,ZJ,XA,YB), (R1M, R2K,ZJ,XA,YB), (R1N,R2K,ZJ,XA,YB), (R1O,R2K,ZJ, XA,YB), (R1P,R2K,ZJ,XA,YB), (R1Q,R2K,ZJ,XA,YB), (R1A,R2L,ZJ,XA,YB), (R1B,R2L,ZJ,XA,YB), (R1C,R2L, ZJ,XA,YB), (R1D,R2L,ZJ,XA,YB), (R1E,R2L,ZJ,XA,YB), (R1F,R2L,ZJ,XA,YB), (R1G,R2L,ZJ,XA,YB), (R1H,R2L, ZJ,XA,YB), (R1I,R2L,ZJ,XA,YB), (R1J,R2L,ZJ,XA,YB), (R1K,R2L,ZJ,XA,YB), (R1L,R2L,ZJ,XA,YB), (R1M,R2L, ZJ,XA,YB), (R1N,R2L,ZJ,XA,YB), (R1O,R2L,ZJ,XA, YB), (R1P,R2L,ZJ,XA,YB), (R1Q,R2L,ZJ,XA,YB), (R1A, R2M,ZJ,XA,YB), (R1B,R2M,ZJ,XA,YB), (R1C,R2M,ZJ, XA,YB), (R1D,R2M,ZJ,XA,YB), (R1E,R2M,ZJ,XA,YB), (R1F,R2M,ZJ,XA,YB), (R1G,R2M,ZJ,XA,YB), (R1H, R2M,ZJ,XA,YB), (R1I,R2M,ZJ,XA,YB), (R1J,R2M,ZJ, XA,YB), (R1K,R2M,ZJ,XA,YB), (R1L,R2M,ZJ,XA,YB), (R1M,R2M,ZJ,XA,YB), (R1N,R2M,ZJ,XA,YB), (R1O, R2M,ZJ,XA,YB), (R1P,R2M,ZJ,XA,YB), (R1Q,R2M,ZJ, XA,YB), (R1A,R2N,ZJ,XA,YB), (R1B,R2N,ZJ,XA,YB), (R1C,R2N,ZJ,XA,YB), (R1D,R2N,ZJ,XA,YB), (R1E,R2N, ZJ,XA,YB), (R1F,R2N,ZJ,XA,YB), (R1G,R2N,ZJ,XA, YB), (R1H,R2N,ZJ,XA,YB), (R1L R2N,ZJ,XA,YB), (R1J, R2N,ZJ,XA,YB), (R1K,R2N,ZJ,XA,YB), (R1L,R2N,ZJ, XA,YB), (R1M,R2N,ZJ,XA,YB), (R1N,R2N,ZJ,XA,YB), (R1O,R2N,ZJ,XA,YB), (R1P,R2N,ZJ,XA,YB), (R1Q,R2N, ZJ,XA,YB), (R1A,R2O,ZJ,XA,YB), (R1B,R2O,ZJ,XA, YB), (R1C,R2O,ZJ,XA,YB), (R1D,R2O,ZJ,XA,YB), (R1E, R2O,ZJ,XA,YB), (R1F,R2O,ZJ,XA,YB), (R1G,R2O,ZJ, XA,YB), (R1H,R2O,ZJ,XA,YB), (R1I,R2O,ZJ,XA,YB), (R1J,R2O,ZJ,XA,YB), (R1K,R2O,ZJ,XA,YB), (R1L,R2O, ZJ,XA,YB), (R1M,R2O,ZJ,XA,YB), (R1N,R2O,ZJ,XA, YB), (R1O,R2O,ZJ,XA,YB), (R1P,R2O,ZJ,XA,YB), (R1Q, R2O,ZJ,XA,YB), (R1A,R2P,ZJ,XA,YB), (R1B,R2P,ZJ,XA, YB), (R1C,R2P,ZJ,XA,YB), (R1D,R2P,ZJ,XA,YB), (R1E, R2P,ZJ,XA,YB), (R1F,R2P,ZJ,XA,YB), (R1G,R2P,ZJ,XA, YB), (R1H,R2P,ZJ,XA,YB), (R1I,R2P,ZJ,XA,YB), (R1J, R2P,ZJ,XA,YB), (R1K,R2P,ZJ,XA,YB), (R1L,R2P,ZJ,XA, YB), (R1M,R2P,ZJ,XA,YB), (R1N,R2P,ZJ,XA,YB), (R1O, R2P,ZJ,XA,YB), (R1P,R2P,ZJ,XA,YB), (R1Q,R2P,ZJ,XA, YB), (R1A,R2Q,ZJ,XA,YB), (R1B,R2Q,ZJ,XA,YB), (R1C, R2Q,ZJ,XA,YB), (R1D,R2Q,ZJ,XA,YB), (R1E,R2Q,ZJ, XA,YB), (R1F,R2Q,ZJ,XA,YB), (R1G,R2Q,ZJ,XA,YB), (R1H,R2Q,ZJ,XA,YB), (R1I,R2Q,ZJ,XA,YB), (R1J,R2Q, ZJ,XA,YB), (R1K,R2Q,ZJ,XA,YB), (R1L,R2Q,ZJ,XA, YB), (R1M,R2Q,ZJ,XA,YB), (R1N,R2Q,ZJ,XA,YB), (R1O,R2Q,ZJ,XA,YB), (R1P,R2Q,ZJ,XA,YB), (R1Q,R2Q, ZJ,XA,YB), (R1A,R2A,ZK,XA,YB), (R1B,R2A,ZK,XA, YB), (R1C,R2A,ZK,XA,YB), (R1D,R2A,ZK,XA,YB), (R1E,R2A,ZK,XA,YB), (R1F,R2A,ZK,XA,YB), (R1G, R2A,ZK,XA,YB), (R1H,R2A,ZK,XA,YB), (R1I,R2A,ZK, XA,YB), (R1J,R2A,ZK,XA,YB), (R1K,R2A,ZK,XA,YB), (R1L,R2A,ZK,XA,YB), (R1M,R2A,ZK,XA,YB), (R1N, R2A,ZK,XA,YB), (R1O,R2A,ZK,XA,YB), (R1P,R2A,ZK, XA,YB), (R1Q,R2A,ZK,XA,YB), (R1A,R2B,ZK,XA,YB), (R1B,R2B,ZK,XA,YB), (R1C,R2B,ZK,XA,YB), (R1D, R2B,ZK,XA,YB), (R1E,R2B,ZK,XA,YB), (R1F,R2B,ZK, XA,YB), (R1G,R2B,ZK,XA,YB), (R1H,R2B,ZK,XA,YB), (R1I,R2B,ZK,XA,YB), (R1J,R2B,ZK,XA,YB), (R1K,R2B, ZK,XA,YB), (R1L,R2B,ZK,XA,YB), (R1M,R2B,ZK,XA, YB), (R1N,R2B,ZK,XA,YB), (R1O,R2B,ZK,XA,YB), (R1P,R2B,ZK,XA,YB), (R1Q,R2B,ZK,XA,YB), (R1A, R2C,ZK,XA,YB), (R1B,R2C,ZK,XA,YB), (R1C,R2C,ZK, XA,YB), (R1D,R2C,ZK,XA,YB), (R1E,R2C,ZK,XA,YB), (R1F,R2C,ZK,XA,YB), (R1G,R2C,ZK,XA,YB), (R1H, R2C,ZK,XA,YB), (R1I,R2C,ZK,XA,YB), (R1J,R2C,ZK, XA,YB), (R1K,R2C,ZK,XA,YB), (R1L,R2C,ZK,XA,YB), (R1M,R2C,ZK,XA,YB), (R1N,R2C,ZK,XA,YB), (R1O, R2C,ZK,XA,YB), (R1P,R2C,ZK,XA,YB), (R1Q,R2C,ZK, XA,YB), (R1A,R2D,ZK,XA,YB), (R1B,R2D,ZK,XA,YB), (R1C,R2D,ZK,XA,YB), (R1D,R2D,ZK,XA,YB), (R1E, R2D,ZK,XA,YB), (R1F,R2D,ZK,XA,YB), (R1G,R2D,ZK, XA,YB), (R1H,R2D,ZK,XA,YB), (R1I,R2D,ZK,XA,YB), (R1J,R2D,ZK,XA,YB), (R1K,R2D,ZK,XA,YB), (R1L, R2D,ZK,XA,YB), (R1M,R2D,ZK,XA,YB), (R1N,R2D,ZK, XA,YB), (R1O,R2D,ZK,XA,YB), (R1P,R2D,ZK,XA,YB), (R1Q,R2D,ZK,XA,YB), (R1A,R2E,ZK,XA,YB), (R1B, R2E,ZK,XA,YB), (R1C,R2E,ZK,XA,YB), (R1D,R2E,ZK, XA,YB), (R1E,R2E,ZK,XA,YB), (R1F,R2E,ZK,XA,YB), (R1G,R2E,ZK,XA,YB), (R1H,R2E,ZK,XA,YB), (R1I,R2E, ZK,XA,YB), (R1J,R2E,ZK,XA,YB), (R1K,R2E,ZK,XA, YB), (R1L,R2E,ZK,XA,YB), (R1M,R2E,ZK,XA,YB), (R1N,R2E,ZK,XA,YB), (R1O,R2E,ZK,XA,YB), (R1P, R2E,ZK,XA,YB), (R1Q,R2E,ZK,XA,YB), (R1A,R2F,ZK, XA,YB), (R1B,R2F,ZK,XA,YB), (R1C,R2F,ZK,XA,YB), (R1D,R2F,ZK,XA,YB), (R1E,R2F,ZK,XA,YB), (R1F,R2F, ZK,XA,YB), (R1G,R2F,ZK,XA,YB), (R1H,R2F,ZK,XA, YB), (R1I,R2F,ZK,XA,YB), (R1J,R2F,ZK,XA,YB), (R1K, R2F,ZK,XA,YB), (R1L,R2F,ZK,XA,YB), (R1M,R2F,ZK, XA,YB), (R1N,R2F,ZK,XA,YB), (R1O,R2F,ZK,XA,YB), (R1P,R2F,ZK,XA,YB), (R1Q,R2F,ZK,XA,YB), (R1A,R2G, ZK,XA,YB), (R1B,R2G,ZK,XA,YB), (R1C,R2G,ZK,XA, YB), (R1D,R2G,ZK,XA,YB), (R1E,R2G,ZK,XA,YB), (R1F,R2G,ZK,XA,YB), (R1G,R2G,ZK,XA,YB), (R1H, R2G,ZK,XA,YB), (R1I,R2G,ZK,XA,YB), (R1J,R2G,ZK, XA,YB), (R1K,R2G,ZK,XA,YB), (R1L,R2G,ZK,XA,YB), (R1M,R2G,ZK,XA,YB), (R1N,R2G,ZK,XA,YB), (R1O, R2G,ZK,XA,YB), (R1P,R2G,ZK,XA,YB), (R1Q,R2G,ZK, XA,YB), (R1A,R2H,ZK,XA,YB), (R1B,R2H,ZK,XA,YB), (R1C,R2H,ZK,XA,YB), (R1D,R2H,ZK,XA,YB), (R1E, R2H,ZK,XA,YB), (R1F,R2H,ZK,XA,YB), (R1G,R2H,ZK, XA,YB), (R1H,R2H,ZK,XA,YB), (R1I,R2H,ZK,XA,YB), (R1J,R2H,ZK,XA,YB), (R1K,R2H,ZK,XA,YB), (R1L, R2H,ZK,XA,YB), (R1M,R2H,ZK,XA,YB), (R1N,R2H,ZK, XA,YB), (R1O,R2H,ZK,XA,YB), (R1P,R2H,ZK,XA,YB), (R1Q,R2H,ZK,XA,YB), (R1A,R2I,ZK,XA,YB), (R1B,R2I, ZK,XA,YB), (R1C,R2I,ZK,XA,YB), (R1D,R2I,ZK,XA, YB), (R1E,R2I,ZK,XA,YB), (R1F,R2I,ZK,XA,YB), (R1G, R2I,ZK,XA,YB), (R1H,R2I,ZK,XA,YB), (R1I,R2I,ZK,XA, YB), (R1J,R2I,ZK,XA,YB), (R1K,R2I,ZK,XA,YB), (R1L, R2I,ZK,XA,YB), (R1M,R2I,ZK,XA,YB), (R1N,R2I,ZK, XA,YB), (R1O,R2I,ZK,XA,YB), (R1P,R2I,ZK,XA,YB), (R1Q,R2I,ZK,XA,YB), (R1A,R2J,ZK,XA,YB), (R1B,R2J, ZK,XA,YB), (R1C,R2J,ZK,XA,YB), (R1D,R2J,ZK,XA, YB), (R1E,R2J,ZK,XA,YB), (R1F,R2J,ZK,XA,YB), (R1G, R2J,ZK,XA,YB), (R1H,R2J,ZK,XA,YB), (R1I,R2J,ZK, XA,YB), (R1J,R2J,ZK,XA,YB), (R1K,R2J,ZK,XA,YB), (R1L,R2J,ZK,XA,YB), (R1M,R2J,ZK,XA,YB), (R1N,R2J, ZK,XA,YB), (R1O,R2J,ZK,XA,YB), (R1P,R2J,ZK,XA, YB), (R1Q,R2J,ZK,XA,YB), (R1A,R2K,ZK,XA,YB), (R1B,R2K,ZK,XA,YB), (R1C,R2K,ZK,XA,YB), (R1D, R2K,ZK,XA,YB), (R1E,R2K,ZK,XA,YB), (R1F,R2K,ZK, XA,YB), (R1G,R2K,ZK,XA,YB), (R1H,R2K,ZK,XA,YB), R2K,ZK,XA,YB), (R1J,R2K,ZK,XA,YB), (R1K,R2K,ZK,XA,YB), (R1L,R2K,ZK,XA,YB), (R1M,R2K,ZK,XA,YB), (R1N,R2K,ZK,XA,YB), (R1O,R2K,ZK,XA,YB), (R1P,R2K,ZK,XA,YB), (R1Q,R2K,ZK,XA,YB), (R1A,R2L,ZK,XA,YB), (R1B,R2L,ZK,XA,YB), (R1C,R2L,ZK,XA,YB), (R1D,R2L,ZK,XA,YB), (R1E,R2L,ZK,XA,YB), (R1F,R2L,ZK,XA,YB), (R1G,R2L,ZK,XA,YB), (R1H,R2L,ZK,XA,YB), (R1I,R2L,ZK,XA,YB), (R1J,R2L,ZK,XA,YB), (R1K,R2L,ZK,XA,YB), (R1L,R2L,ZK,XA,YB), (R1M,R2L,ZK,XA,YB), (R1N,R2L,ZK,XA,YB), (R1O,R2L,ZK,XA,YB), (R1P,R2L,ZK,XA,YB), (R1Q,R2L,ZK,XA,YB), (R1A,R2M,ZK,XA,YB), (R1B,R2M,ZK,XA,YB), (R1C,R2M,ZK,XA,YB), (R1D,R2M,ZK,XA,YB), (R1E,R2M,ZK,XA,YB), (R1F,R2M,ZK,XA,YB), (R1G,R2M,ZK,XA,YB), (R1H,R2M,ZK,XA,YB), (R1I,R2M,ZK,XA,YB), (R1J,R2M,ZK,XA,YB), (R1K,R2M,ZK,XA,YB), (R1L,R2M,ZK,XA,YB), (R1M,R2M,ZK,XA,YB), (R1N,R2M,ZK,XA,YB), (R1O,R2M,ZK,XA,YB), (R1P,R2M,ZK,XA,YB), (R1Q,R2M,ZK,XA,YB), (R1A,R2N,ZK,XA,YB), (R1B,R2N,ZK,XA,YB), (R1C,R2N,ZK,XA,YB), (R1D,R2N,ZK,XA,YB), (R1E,R2N,ZK,XA,YB), (R1F,R2N,ZK,XA,YB), (R1G,R2N,ZK,XA,YB), (R1H,R2N,ZK,XA,YB), (R1I,R2N,ZK,XA,YB), (R1J,R2N,ZK,XA,YB), (R1K,R2N,ZK,XA,YB), (R1L,R2N,ZK,XA,YB), (R1M,R2N,ZK,XA,YB), (R1N,R2N,ZK,XA,YB), (R1O,R2N,ZK,XA,YB), (R1P,R2N,ZK,XA,YB), (R1Q,R2N,ZK,XA,YB), (R1A,R2O,ZK,XA,YB), (R1B,R2O,ZK,XA,YB), (R1C,R2O,ZK,XA,YB), (R1D,R2O,ZK,XA,YB), (R1E,R2O,ZK,XA,YB), (R1F,R2O,ZK,XA,YB), (R1G,R2O,ZK,XA,YB), (R1H,R2O,ZK,XA,YB), (R1I,R2O,ZK,XA,YB), (R1J,R2O,ZK,XA,YB), (R1K,R2O,ZK,XA,YB), (R1L,R2O,ZK,XA,YB), (R1M,R2O,ZK,XA,YB), (R1N,R2O,ZK,XA,YB), (R1O,R2O,ZK,XA,YB), (R1P,R2O,ZK,XA,YB), (R1Q,R2O,ZK,XA,YB), (R1A,R2P,ZK,XA,YB), (R1B,R2P,ZK,XA,YB), (R1C,R2P,ZK,XA,YB), (R1D,R2P,ZK,XA,YB), (R1E,R2P,ZK,XA,YB), (R1F,R2P,ZK,XA,YB), (R1G,R2P,ZK,XA,YB), (R1H,R2P,ZK,XA,YB), (R1I,R2P,ZK,XA,YB), (R1J,R2P,ZK,XA,YB), (R1K,R2P,ZK,XA,YB), (R1L,R2P,ZK,XA,YB), (R1M,R2P,ZK,XA,YB), (R1N,R2P,ZK,XA,YB), (R1O,R2P,ZK,XA,YB), (R1P,R2P,ZK,XA,YB), (R1Q,R2P,ZK,XA,YB), (R1A,R2Q,ZK,XA,YB), (R1B,R2Q,ZK,XA,YB), (R1C,R2Q,ZK,XA,YB), (R1D,R2Q,ZK,XA,YB), (R1E,R2Q,ZK,XA,YB), (R1F,R2Q,ZK,XA,YB), (R1G,R2Q,ZK,XA,YB), (R1H,R2Q,ZK,XA,YB), (R1I,R2Q,ZK,XA,YB), (R1J,R2Q,ZK,XA,YB), (R1K,R2Q,ZK,XA,YB), (R1L,R2Q,ZK,XA,YB), (R1M,R2Q,ZK,XA,YB), (R1N,R2Q,ZK,XA,YB), (R1O,R2Q,ZK,XA,YB), (R1P,R2Q,ZK,XA,YB), (R1Q,R2Q,ZK,XA,YB), (R1A,R2A,ZL,XA,YB), (R1B,R2A,ZL,XA,YB), (R1C,R2A,ZL,XA,YB), (R1D,R2A,ZL,XA,YB), (R1E,R2A,ZL,XA,YB), (R1F,R2A,ZL,XA,YB), (R1G,R2A,ZL,XA,YB), (R1H,R2A,ZL,XA,YB), (R1I,R2A,ZL,XA,YB), (R1J,R2A,ZL,XA,YB), (R1K,R2A,ZL,XA,YB), (R1L,R2A,ZL,XA,YB), (R1M,R2A,ZL,XA,YB), (R1N,R2A,ZL,XA,YB), (R1O,R2A,ZL,XA,YB), (R1P,R2A,ZL,XA,YB), (R1Q,R2A,ZL,XA,YB), (R1A,R2B,ZL,XA,YB), (R1B,R2B,ZL,XA,YB), (R1C,R2B,ZL,XA,YB), (R1D,R2B,ZL,XA,YB), (R1E,R2B,ZL,XA,YB), (R1F,R2B,ZL,XA,YB), (R1G,R2B,ZL,XA,YB), (R1H,R2B,ZL,XA,YB), (R1I,R2B,ZL,XA,YB), (R1J,R2B,ZL,XA,YB), (R1K,R2B,ZL,XA,YB), (R1L,R2B,ZL,XA,YB), (R1M,R2B,ZL,XA,YB), (R1N,R2B,ZL,XA,YB), (R1O,R2B,ZL,XA,YB), (R1P,R2B,ZL,XA,YB), (R1Q,R2B,ZL,XA,YB), (R1A,R2C,ZL,XA,YB), (R1B,R2C,ZL,XA,YB), (R1C,R2C,ZL,XA,YB), (R1D,R2C,ZL,XA,YB), (R1E,R2C,ZL,XA,YB), (R1F,R2C,ZL,XA,YB), (R1G,R22C,ZL,XA,YB), (R1H,R2C,ZL,XA,YB), (R1I,R2C,ZL,XA,YB), (R1J,R2C,ZL,XA,YB), (R1K,R22C,ZL,XA,YB), (R1L,R2C,ZL,XA,YB), (R1M,R2C,ZL,XA,YB), (R1N,R2C,ZL,XA,YB), (R1 O,R2C,ZL,XA,YB), (R1P,R2C,ZL,XA,YB), (R1Q,R2C,ZL,XA,YB), (R1A,R2D,ZL,XA,YB), (R1B,R2D,ZL,XA,YB), (R1C,R2D,ZL,XA,YB), (R1D,R2D,ZL,XA,YB), (R1E,R2D,ZL,XA,YB), (R1F,R2D,ZL,XA,YB), (R1G,R2D,ZL,XA,YB), (R1H,R2D,ZL,XA,YB), (R1I,R2D,ZL,XA,YB), (R1J,R2D,ZL,XA,YB), (R1K,R2D,ZL,XA,YB), (R1L,R2D,ZL,XA,YB), (R1M,R2D,ZL,XA,YB), (R1N,R2D,ZL,XA,YB), (R1O,R2D,ZL,XA,YB), (R1P,R2D,ZL,XA,YB), (R1Q,R2D,ZL,XA,YB), (R1A,R2E,ZL,XA,YB), (R1B,R2E,ZL,XA,YB), (R1C,R2E,ZL,XA,YB), (R1D,R2E,ZL,XA,YB), (R1E,R2E,ZL,XA,YB), (R1F,R2E,ZL,XA,YB), (R1G,R2E,ZL,XA,YB), (R1H,R2E,ZL,XA,YB), (R1I,R2E,ZL,XA,YB), (R1J,R2E,ZL,XA,YB), (R1K,R2E,ZL,XA,YB), (R1L,R2E,ZL,XA,YB), (R1M,R2E,ZL,XA,YB), (R1N,R2E,ZL,XA,YB), (R1O,R2E,ZL,XA,YB), (R1P,R2E,ZL,XA,YB), (R1Q,R2E,ZL,XA,YB), (R1A,R2F,ZL,XA,YB), (R1B,R2F,ZL,XA,YB), (R1C,R2F,ZL,XA,YB), (R1D,R2F,ZL,XA,YB), (R1E,R2F,ZL,XA,YB), (R1F,R2F,ZL,XA,YB), (R1G,R2F,ZL,XA,YB), (R1H,R2F,ZL,XA,YB), (R1I,R2F,ZL,XA,YB), (R1J,R2F,ZL,XA,YB), (R1K,R2F,ZL,XA,YB), (R1L,R2F,ZL,XA,YB), (R1M,R2F,ZL,XA,YB), (R1N,R2F,ZL,XA,YB), (R1O,R2F,ZL,XA,YB), (R1P,R2F,ZL,XA,YB), (R1Q,R2F,ZL,XA,YB), (R1A,R2G,ZL,XA,YB), (R1B,R2G,ZL,XA,YB), (R1C,R2G,ZL,XA,YB), (R1D,R2G,ZL,XA,YB), (R1E,R2G,ZL,XA,YB), (R1F,R2G,ZL,XA,YB), (R1G,R2G,ZL,XA,YB), (R1H,R2G,ZL,XA,YB), (R1I,R2G,ZL,XA,YB), (R1J,R2G,ZL,XA,YB), (R1K,R2G,ZL,XA,YB), (R1L,R2G,ZL,XA,YB), (R1M,R2G,ZL,XA,YB), (R1N,R2G,ZL,XA,YB), (R1O,R2G,ZL,XA,YB), (R1P,R2G,ZL,XA,YB), (R1Q,R2G,ZL,XA,YB), (R1A,R2H,ZL,XA,YB), (R1B,R2H,ZL,XA,YB), (R1C,R2H,ZL,XA,YB), (R1D,R2H,ZL,XA,YB), (R1E,R2H,ZL,XA,YB), (R1F,R2H,ZL,XA,YB), (R1G,R2H,ZL,XA,YB), (R1H,R2H,ZL,XA,YB), (R1I,R2H,ZL,XA,YB), (R1J,R2H,ZL,XA,YB), (R1K,R2H,ZL,XA,YB), (R1L,R2H,ZL,XA,YB), (R1M,R2H,ZL,XA,YB), (R1N,R2H,ZL,XA,YB), (R1O,R2H,ZL,XA,YB), (R1P,R2H,ZL,XA,YB), (R1Q,R2H,ZL,XA,YB), (R1A,R2I,ZL,XA,YB), (R1B,R2I,ZL,XA,YB), (R1C,R2I,ZL,XA,YB), (R1D,R2I,ZL,XA,YB), (R1E,R2I,ZL,XA,YB), (R1F,R2I,ZL,XA,YB), (R1G,R2I,ZL,XA,YB), (R1H,R2I,ZL,XA,YB), (R1I,R2I,ZL,XA,YB), (R1J,R2I,ZL,XA,YB), (R1K,R2I,ZL,XA,YB), (R1L,R2I,ZL,XA,YB), (R1M,R2I,ZL,XA,YB), (R1N,R2I,ZL,XA,YB), (R1O,R2I,ZL,XA,YB), (R1P,R2I,ZL,XA,YB), (R1Q,R2I,ZL,XA,YB), (R1A,R2J,ZL,XA,YB), (R1B,R2J,ZL,XA,YB), (R1C,R2J,ZL,XA,YB), (R1D,R2J,ZL,XA,YB), (R1E,R2J,ZL,XA,YB), (R1F,R2J,ZL,XA,YB), (R1G,R2J,ZL,XA,YB), (R1H,R2J,ZL,XA,YB), (R1I,R2J,ZL,XA,YB), (R1J,R2J,ZL,XA,YB), (R1K,R2J,ZL,XA,YB), (R1L,R2J,ZL,XA,YB), (R1M,R2J,ZL,XA,YB), (R1N,R2J,ZL,XA,YB), (R1O,R2J,ZL,XA,YB), (R1P,R2J,ZL,XA,YB), (R1Q,R2J,ZL,XA,YB), (R1A,R2K,ZL,XA,YB), (R1B,R2K,ZL,XA,YB), (R1C,R2K,ZL,XA,YB), (R1D,R2K,ZL,XA,YB), (R1E,R2K,ZL,XA,YB), (R1F,R2K,ZL,XA,YB), (R1G,R2K,ZL,XA,YB), (R1H,R2K,ZL,XA,YB), (R1I,R2K,ZL,XA,YB), (R1J,R2K,ZL,XA,YB), (R1K,R2K,ZL,XA,YB), (R1L,R2K,ZL,XA,YB), (R1M,R2K,ZL,XA,YB), (R1N,R2K,ZL,XA,YB), (R1O,R2K,ZL,XA,YB), (R1P,R2K,ZL,XA,YB), (R1Q,R2K,ZL,XA,YB), (R1A,R2L,ZL,XA,YB), (R1B,R2L,ZL,XA,YB), (R1C,R2L,ZL,XA,YB), (R1D,R2L,ZL,XA,YB), (R1E,R2L,ZL,XA,YB), (R1F,R2L,ZL,XA,YB), (R1G,R2L,ZL,XA,YB), (R1H,R2L,ZL,XA,YB), (R1I,R2L,ZL,XA,YB), (R1J,R2L,ZL,XA,YB), (R1K,R2L,ZL,XA,YB), (R1L,R2L,ZL,XA,YB), (R1M,R2L,ZL,XA,YB), (R1N,R2L,ZL,XA,YB), (R1O,R2L,ZL,XA,YB), (R1P,R2L,ZL,XA,YB), (R1Q,R2L,ZL,XA,YB), (R1A,R2M,ZL,XA,YB), (R1B,R2M,ZL,XA, YB), (R1C,R2M,ZL,XA,YB), (R1D,R2M,ZL,XA,YB), (R1E,R2M,ZL,XA,YB), (R1F,R2M,ZL,XA,YB), (R1G,R2M,ZL,XA,YB), (R1H,R2M,ZL,XA,YB), (R1I,R2M,ZL,XA,YB), (R1J,R2M,ZL,XA,YB), (R1K,R2M,ZL,XA,YB), (R1L,R2M,ZL,XA,YB), (R1M,R2M,ZL,XA,YB), (R1N,R2M,ZL,XA,YB), (R1O,R2M,ZL,XA,YB), (R1P,R2M,ZL,XA,YB), (R1Q,R2M,ZL,XA,YB), (R1A,R2N,ZL,XA,YB), (R1B,R2N,ZL,XA,YB), (R1C,R2N,ZL,XA,YB), (R1D,R2N,ZL,XA,YB), (R1E,R2N,ZL,XA,YB), (R1F,R2N,ZL,XA,YB), (R1G,R2N,ZL,XA,YB), (R1H,R2N,ZL,XA,YB), (R1I,R2N,ZL,XA,YB), (R1J,R2N,ZL,XA,YB), (R1K,R2N,ZL,XA,YB), (R1L,R2N,ZL,XA,YB), (R1M,R2N,ZL,XA,YB), (R1N,R2N,ZL,XA,YB), (R1O,R2N,ZL,XA,YB), (R1P,R2N,ZL,XA,YB), (R1Q,R2N,ZL,XA,YB), (R1A,R2O,ZL,XA,YB), (R1B,R2O,ZL,XA,YB), (R1C,R2O,ZL,XA,YB), (R1D,R2O,ZL,XA,YB), (R1E,R2O,ZL,XA,YB), (R1F,R2O,ZL,XA,YB), (R1G,R2O,ZL,XA,YB), (R1H,R2O,ZL,XA,YB), (R1L R2O,ZL,XA,YB), (R1J,R2O,ZL,XA,YB), (R1K,R2O,ZL,XA,YB), (R1L,R2O,ZL,XA,YB), (R1M,R2O,ZL,XA,YB), (R1N,R2O,ZL,XA,YB), (R1O,R2O,ZL,XA,YB), (R1P,R2O,ZL,XA,YB), (R1Q,R2O,ZL,XA,YB), (R1A,R2P,ZL,XA,YB), (R1B,R2P,ZL,XA,YB), (R1C,R2P,ZL,XA,YB), (R1D,R2P,ZL,XA,YB), (R1E,R2P,ZL,XA,YB), (R1F,R2P,ZL,XA,YB), (R1G,R2P,ZL,XA,YB), (R1H,R2P,ZL,XA,YB), (R1I,R2P,ZL,XA,YB), (R1J,R2P,ZL,XA,YB), (R1K,R2P,ZL,XA,YB), (R1L,R2P,ZL,XA,YB), (R1M,R2P,ZL,XA,YB), (R1N,R2P,ZL,XA,YB), (R1O,R2P,ZL,XA,YB), (R1P,R2P,ZL,XA,YB), (R1Q,R2P,ZL,XA,YB), (R1A,R2Q,ZL,XA,YB), (R1B,R2Q,ZL,XA,YB), (R1C,R2Q,ZL,XA,YB), (R1D,R2Q,ZL,XA,YB), (R1E,R2Q,ZL,XA,YB), (R1F,R2Q,ZL,XA,YB), (R1G,R2Q,ZL,XA,YB), (R1H,R2Q,ZL,XA,YB), (R1I,R2Q,ZL,XA,YB), (R1J,R2Q,ZL,XA,YB), (R1K,R2Q,ZL,XA,YB), (R1L,R2Q,ZL,XA,YB), (R1M,R2Q,ZL,XA,YB), (R1N,R2Q,ZL,XA,YB), (R1O,R2Q,ZL,XA,YB), (R1P,R2Q,ZL,XA,YB), (R1Q,R2Q,ZL,XA,YB), (R1A,R2A,ZM,XA,YB), (R1B,R2A,ZM,XA,YB), (R1C,R2A,ZM,XA,YB), (R1D,R2A,ZM,XA,YB), (R1E,R2A,ZM,XA,YB), (R1F,R2A,ZM,XA,YB), (R1G,R2A,ZM,XA,YB), (R1H,R2A,ZM,XA,YB), (R1I,R2A,ZM,XA,YB), (R1J,R2A,ZM,XA,YB), (R1K,R2A,ZM,XA,YB), (R1L,R2A,ZM,XA,YB), (R1M,R2A,ZM,XA,YB), (R1N,R2A,ZM,XA,YB), (R1O,R2A,ZM,XA,YB), (R1P,R2A,ZM,XA,YB), (R1Q,R2A,ZM,XA,YB), (R1A,R2B,ZM,XA,YB), (R1B,R2B,ZM,XA,YB), (R1C,R2B,ZM,XA,YB), (R1D,R2B,ZM,XA,YB), (R1E,R2B,ZM,XA,YB), (R1F,R2B,ZM,XA,YB), (R1G,R2B,ZM,XA,YB), (R1H,R2B,ZM,XA,YB), (R1I,R2B,ZM,XA,YB), (R1J,R2B,ZM,XA,YB), (R1K,R2B,ZM,XA,YB), (R1L,R2B,ZM,XA,YB), (R1M,R2B,ZM,XA,YB), (R1N,R2B,ZM,XA,YB), (R1O,R2B,ZM,XA,YB), (R1P,R2B,ZM,XA,YB), (R1Q,R2B,ZM,XA,YB), (R1A,R2C,ZM,XA,YB), (R1B,R2C,ZM,XA,YB), (R1C,R2C,ZM,XA,YB), (R1D,R2C,ZM,XA,YB), (R1E,R2C,ZM,XA,YB), (R1F,R2C,ZM,XA,YB), (R1G,R2C,ZM,XA,YB), (R1H,R22C,ZM,XA,YB), (R1I,R2C,ZM,XA,YB), (R1J,R2C,ZM,XA,YB), (R1K,R2C,ZM,XA,YB), (R1L,R2C,ZM,XA,YB), (R1M,R2C,ZM,XA,YB), (R1N,R2C,ZM,XA,YB), (R1O,R2C,ZM,XA,YB), (R1P,R2C,ZM,XA,YB), (R1Q,R2C,ZM,XA,YB), (R1A,R2D,ZM,XA,YB), (R1B,R2D,ZM,XA,YB), (R1C,R2D,ZM,XA,YB), (R1D,R2D,ZM,XA,YB), (R1E,R2D,ZM,XA,YB), (R1F,R2D,ZM,XA,YB), (R1G,R2D,ZM,XA,YB), (R1H,R2D,ZM,XA,YB), (R1I,R2D,ZM,XA,YB), (R1J,R2D,ZM,XA,YB), (R1K,R2D,ZM,XA,YB), (R1L,R2D,ZM,XA,YB), (R1M,R2D,ZM,XA,YB), (R1N,R2D,ZM,XA,YB), (R1O,R2D,ZM,XA,YB), (R1P,R2D,ZM,XA,YB), (R1Q,R2D,ZM,XA,YB), (R1A,R2E,ZM,XA,YB), (R1B,R2E,ZM,XA,YB), (R1C,R2E,ZM,XA,YB), (R1D,R2E,ZM,XA,YB), (R1E,R2E,ZM,XA,YB), (R1F,R2E,ZM,XA,YB), (R1G,R2E,ZM,XA,YB), (R1H,R2E,ZM,XA,YB), (R1I,R2E,ZM,XA,YB), (R1J,R2E,ZM,XA,YB), (R1K,R2E,ZM,XA,YB), (R1L,R2E,ZM,XA,YB), (R1M,R2E,ZM,XA,YB), (R1N,R2E,ZM,XA,YB), (R1O,R2E,ZM,XA,YB), (R1P,R2E,ZM,XA,YB), (R1Q,R2E,ZM,XA,YB), (R1A,R2F,ZM,XA,YB), (R1B,R2F,ZM,XA,YB), (R1C,R2F,ZM,XA,YB), (R1D,R2F,ZM,XA,YB), (R1E,R2F,ZM,XA,YB), (R1F,R2F,ZM,XA,YB), (R1G,R2F,ZM,XA,YB), (R1H,R2F,ZM,XA,YB), (R1I,R2F,ZM,XA,YB), (R1J,R2F,ZM,XA,YB), (R1K,R2F,ZM,XA,YB), (R1L,R2F,ZM,XA,YB), (R1M,R2F,ZM,XA,YB), (R1N,R2F,ZM,XA,YB), (R1O,R2F,ZM,XA,YB), (R1P,R2F,ZM,XA,YB), (R1Q,R2F,ZM,XA,YB), (R1A,R2G,ZM,XA,YB), (R1B,R2G,ZM,XA,YB), (R1C,R2G,ZM,XA,YB), (R1D,R2G,ZM,XA,YB), (R1E,R2G,ZM,XA,YB), (R1F,R2G,ZM,XA,YB), (R1G,R2G,ZM,XA,YB), (R1H,R2G,ZM,XA,YB), (R1I,R2G,ZM,XA,YB), (R1J,R2G,ZM,XA,YB), (R1K,R2G,ZM,XA,YB), (R1L,R2G,ZM,XA,YB), (R1M,R2G,ZM,XA,YB), (R1N,R2G,ZM,XA,YB), (R1O,R2G,ZM,XA,YB), (R1P,R2G,ZM,XA,YB), (R1Q,R2G,ZM,XA,YB), (R1A,R2H,ZM,XA,YB), (R1B,R2H,ZM,XA,YB), (R1C,R2H,ZM,XA,YB), (R1D,R2H,ZM,XA,YB), (R1E,R2H,ZM,XA,YB), (R1F,R2H,ZM,XA,YB), (R1G,R2H,ZM,XA,YB), (R1H,R2H,ZM,XA,YB), (R1I,R2H,ZM,XA,YB), (R1J,R2H,ZM,XA,YB), (R1K,R2H,ZM,XA,YB), (R1L,R2H,ZM,XA,YB), (R1M,R2H,ZM,XA,YB), (R1N,R2H,ZM,XA,YB), (R1O,R2H,ZM,XA,YB), (R1P,R2H,ZM,XA,YB), (R1Q,R2H,ZM,XA,YB), (R1A,R2I,ZM,XA,YB), (R1B,R2I,ZM,XA,YB), (R1C,R2I,ZM,XA,YB), (R1D,R2I,ZM,XA,YB), (R1E,R2I,ZM,XA,YB), (R1F,R2I,ZM,XA,YB), (R1G,R2I,ZM,XA,YB), (R1H,R2I,ZM,XA,YB), (R1I,R2I,ZM,XA,YB), (R1J,R2I,ZM,XA,YB), (R1K,R2I,ZM,XA,YB), (R1L,R2I,ZM,XA,YB), (R1M,R2I,ZM,XA,YB), (R1N,R2I,ZM,XA,YB), (R1O,R2I,ZM,XA,YB), (R1P,R2I,ZM,XA,YB), (R1Q,R2I,ZM,XA,YB), (R1A,R2J,ZM,XA,YB), (R1B,R2J,ZM,XA,YB), (R1C,R2J,ZM,XA,YB), (R1D,R2J,ZM,XA,YB), (R1E,R2J,ZM,XA,YB), (R1F,R2J,ZM,XA,YB), (R1G,R2J,ZM,XA,YB), (R1H,R2J,ZM,XA,YB), (R1I,R2J,ZM,XA,YB), (R1J,R2J,ZM,XA,YB), (R1K,R2J,ZM,XA,YB), (R1L,R2J,ZM,XA,YB), (R1M,R2J,ZM,XA,YB), (R1N,R2J,ZM,XA,YB), (R1O,R2J,ZM,XA,YB), (R1P,R2J,ZM,XA,YB), (R1Q,R2J,ZM,XA,YB), (R1A,R2K,ZM,XA,YB), (R1B,R2K,ZM,XA,YB), (R1C,R2K,ZM,XA,YB), (R1D,R2K,ZM,XA,YB), (R1E,R2K,ZM,XA,YB), (R1F,R2K,ZM,XA,YB), (R1G,R2K,ZM,XA,YB), (R1H,R2K,ZM,XA,YB), (R1I,R2K,ZM,XA,YB), (R1J,R2K,ZM,XA,YB), (R1K,R2K,ZM,XA,YB), (R1L,R2K,ZM,XA,YB), (R1M,R2K,ZM,XA,YB), (R1N,R2K,ZM,XA,YB), (R1O,R2K,ZM,XA,YB), (R1P,R2K,ZM,XA,YB), (R1Q,R2K,ZM,XA,YB), (R1A,R2L,ZM,XA,YB), (R1B,R2L,ZM,XA,YB), (R1C,R2L,ZM,XA,YB), (R1D,R2L,ZM,XA,YB), (R1E,R2L,ZM,XA,YB), (R1F,R2L,ZM,XA,YB), (R1G,R2L,ZM,XA,YB), (R1H,R2L,ZM,XA,YB), (R1I,R2L,ZM,XA,YB), (R1J,R2L,ZM,XA,YB), (R1K,R2L,ZM,XA,YB), (R1L,R2L,ZM,XA,YB), (R1M,R2L,ZM,XA,YB), (R1N,R2L,ZM,XA,YB), (R1O,R2L,ZM,XA,YB), (R1P,R2L,ZM,XA,YB), (R1Q,R2L,ZM,XA,YB), (R1A,R2M,ZM,XA,YB), (R1B,R2M,ZM,XA,YB), (R1C,R2M,ZM,XA,YB), (R1D,R2M,ZM,XA,YB), (R1E,R2M,ZM,XA,YB), (R1F,R2M,ZM,XA,YB), (R1G,R2M,ZM,XA,YB), (R1H,R2M,ZM,XA,YB), (R1I,R2M,ZM,XA,YB), (R1J,R2M,ZM,XA,YB), (R1K,R2M,ZM,XA,YB), (R1L,R2M,ZM,XA,YB), (R1M,R2M,ZM,XA,YB), (R1N,R2M,ZM,XA,YB), (R1O,R2M,ZM,XA,YB), (R1P,R2M,ZM,XA,YB), (R1Q,R2M,ZM,XA,YB), (R1A,R2N,ZM,XA,YB), (R1B,R2N,ZM,XA,YB), (R1C,R2N,ZM,XA,YB), (R1D,R2N,ZM,XA,YB), (R1E,R2N, ZM,XA,YB), (R1F,R2N,ZM,XA,YB), (R1G,R2N,ZM,XA,YB), (R1H,R2N,ZM,XA,YB), (R1I,R2N,ZM,XA,YB), (R1J,R2N,ZM,XA,YB), (R1K,R2N,ZM,XA,YB), (R1L,R2N,ZM,XA,YB), (R1M,R2N,ZM,XA,YB), (R1N,R2N,ZM,XA,YB), (R1O,R2N,ZM,XA,YB), (R1P,R2N,ZM,XA,YB), (R1Q,R2N,ZM,XA,YB), (R1A,R2O,ZM,XA,YB), (R1B,R2O,ZM,XA,YB), (R1C,R2O,ZM,XA,YB), (R1D,R2O,ZM,XA,YB), (R1E,R2O,ZM,XA,YB), (R1F,R2O,ZM,XA,YB), (R1G,R2O,ZM,XA,YB), (R1H,R2O,ZM,XA,YB), (R1I,R2O,ZM,XA,YB), (R1J,R2O,ZM,XA,YB), (R1K,R2O,ZM,XA,YB), (R1L,R2O,ZM,XA,YB), (R1M,R2O,ZM,XA,YB), (R1N,R2O,ZM,XA,YB), (R1O,R2O,ZM,XA,YB), (R1P,R2O,ZM,XA,YB), (R1Q,R2O,ZM,XA,YB), (R1A,R2P,ZM,XA,YB), (R1B,R2P,ZM,XA,YB), (R1C,R2P,ZM,XA,YB), (R1D,R2P,ZM,XA,YB), (R1E,R2P,ZM,XA,YB), (R1F,R2P,ZM,XA,YB), (R1G,R2P,ZM,XA,YB), (R1H,R2P,ZM,XA,YB), (R1I,R2P,ZM,XA,YB), (R1J,R2P,ZM,XA,YB), (R1K,R2P,ZM,XA,YB), (R1L,R2P,ZM,XA,YB), (R1M,R2P,ZM,XA,YB), (R1N,R2P,ZM,XA,YB), (R1O,R2P,ZM,XA,YB), (R1P,R2P,ZM,XA,YB), (R1Q,R2P,ZM,XA,YB), (R1A,R2Q,ZM,XA,YB), (R1B,R2Q,ZM,XA,YB), (R1C,R2Q,ZM,XA,YB), (R1D,R2Q,ZM,XA,YB), (R1E,R2Q,ZM,XA,YB), (R1F,R2Q,ZM,XA,YB), (R1G,R2Q,ZM,XA,YB), (R1H,R2Q,ZM,XA,YB), (R1I,R2Q,ZM,XA,YB), (R1J,R2Q,ZM,XA,YB), (R1K,R2Q,ZM,XA,YB), (R1L,R2Q,ZM,XA,YB), (R1M,R2Q,ZM,XA,YB), (R1N,R2Q,ZM,XA,YB), (R1O,R2Q,ZM,XA,YB), (R1P,R2Q,ZM,XA,YB), (R1Q,R2Q,ZM,XA,YB), (R1A,R2A,ZN,XA,YB), (R1B,R2A,ZN,XA,YB), (R1C,R2A,ZN,XA,YB), (R1D,R2A,ZN,XA,YB), (R1E,R2A,ZN,XA,YB), (R1F,R2A,ZN,XA,YB), (R1G,R2A,ZN,XA,YB), (R1H,R2A,ZN,XA,YB), (R1I,R2A,ZN,XA,YB), (R1J,R2A,ZN,XA,YB), (R1K,R2A,ZN,XA,YB), (R1L,R2A,ZN,XA,YB), (R1M,R2A,ZN,XA,YB), (R1N,R2A,ZN,XA,YB), (R1O,R2A,ZN,XA,YB), (R1P,R2A,ZN,XA,YB), (R1Q,R2A,ZN,XA,YB), (R1A,R2B,ZN,XA,YB), (R1B,R2B,ZN,XA,YB), (R1C,R2B,ZN,XA,YB), (R1D,R2B,ZN,XA,YB), (R1E,R2B,ZN,XA,YB), (R1F,R2B,ZN,XA,YB), (R1G,R2B,ZN,XA,YB), (R1H,R2B,ZN,XA,YB), (R1I,R2B,ZN,XA,YB), (R1J,R2B,ZN,XA,YB), (R1K,R2B,ZN,XA,YB), (R1L,R2B,ZN,XA,YB), (R1M,R2B,ZN,XA,YB), (R1N,R2B,ZN,XA,YB), (R1O,R2B,ZN,XA,YB), (R1P,R2B,ZN,XA,YB), (R1Q,R2B,ZN,XA,YB), (R1A,R2C,ZN,XA,YB), (R1B,R2C,ZN,XA,YB), (R1C,R2C,ZN,XA,YB), (R1D,R2C,ZN,XA,YB), (R1E,R2C,ZN,XA,YB), (R1F,R2C,ZN,XA,YB), (R1G,R22C,ZN,XA,YB), (R1H,R2C,ZN,XA,YB), (R1I,R2C,ZN,XA,YB), (R1J,R2C,ZN,XA,YB), (R1K,R2C,ZN,XA,YB), (R1L,R2C,ZN,XA,YB), (R1M,R2C,ZN,XA,YB), (R1N,R2C,ZN,XA,YB), (R1O,R2C,ZN,XA,YB), (R1P,R2C,ZN,XA,YB), (R1Q,R2C,ZN,XA,YB), (R1A,R2D,ZN,XA,YB), (R1B,R2D,ZN,XA,YB), (R1C,R2D,ZN,XA,YB), (R1D,R2D,ZN,XA,YB), (R1E,R2D,ZN,XA,YB), (R1F,R2D,ZN,XA,YB), (R1G,R2D,ZN,XA,YB), (R1H,R2D,ZN,XA,YB), (R1I,R2D,ZN,XA,YB), (R1J,R2D,ZN,XA,YB), (R1K,R2D,ZN,XA,YB), (R1L,R2D,ZN,XA,YB), (R1M,R2D,ZN,XA,YB), (R1N,R2D,ZN,XA,YB), (R1O,R2D,ZN,XA,YB), (R1P,R2D,ZN,XA,YB), (R1Q,R2D,ZN,XA,YB), (R1A,R2E,ZN,XA,YB), (R1B,R2E,ZN,XA,YB), (R1C,R2E,ZN,XA,YB), (R1D,R2E,ZN,XA,YB), (R1E,R2E,ZN,XA,YB), (R1F,R2E,ZN,XA,YB), (R1G,R2E,ZN,XA,YB), (R1H,R2E,ZN,XA,YB), (R1I,R2E,ZN,XA,YB), (R1J,R2E,ZN,XA,YB), (R1K,R2E,ZN,XA,YB), (R1L,R2E,ZN,XA,YB), (R1M,R2E,ZN,XA,YB), (R1N,R2E,ZN,XA,YB), (R1O,R2E,ZN,XA,YB), (R1P,R2E,ZN,XA,YB), (R1Q,R2E,ZN,XA,YB), (R1A,R2F,ZN,XA,YB), (R1B,R2F,ZN,XA,YB), (R1C,R2F,ZN,XA,YB), (R1D,R2F,ZN,XA,YB), (R1E,R2F,ZN,XA,YB), (R1F,R2F,ZN,XA,YB), (R1G,R2F,ZN,XA,YB), (R1H,R2F,ZN,XA,YB), (R1I,R2F,ZN,XA,YB), (R1J,R2F,ZN,XA,YB), (R1K,R2F,ZN,XA,YB), (R1L,R2F,ZN,XA,YB), (R1M,R2F,ZN,XA,YB), (R1N,R2F,ZN,XA,YB), (R1O,R2F,ZN,XA,YB), (R1P,R2F,ZN,XA,YB), (R1Q,R2F,ZN,XA,YB), (R1A,R2G,ZN,XA,YB), (R1B,R2G,ZN,XA,YB), (R1C,R2G,ZN,XA,YB), (R1D,R2G,ZN,XA,YB), (R1E,R2G,ZN,XA,YB), (R1F,R2G,ZN,XA,YB), (R1G,R2G,ZN,XA,YB), (R1H,R2G,ZN,XA,YB), (R1I,R2G,ZN,XA,YB), (R1J,R2G,ZN,XA,YB), (R1K,R2G,ZN,XA,YB), (R1L,R2G,ZN,XA,YB), (R1M,R2G,ZN,XA,YB), (R1N,R2G,ZN,XA,YB), (R1O,R2G,ZN,XA,YB), (R1P,R2G,ZN,XA,YB), (R1Q,R2G,ZN,XA,YB), (R1A,R2H,ZN,XA,YB), (R1B,R2H,ZN,XA,YB), (R1C,R2H,ZN,XA,YB), (R1D,R2H,ZN,XA,YB), (R1E,R2H,ZN,XA,YB), (R1F,R2H,ZN,XA,YB), (R1G,R2H,ZN,XA,YB), (R1H,R2H,ZN,XA,YB), (R1I,R2H,ZN,XA,YB), (R1J,R2H,ZN,XA,YB), (R1K,R2H,ZN,XA,YB), (R1L,R2H,ZN,XA,YB), (R1M,R2H,ZN,XA,YB), (R1N,R2H,ZN,XA,YB), (R1O,R2H,ZN,XA,YB), (R1P,R2H,ZN,XA,YB), (R1Q,R2H,ZN,XA,YB), (R1A,R2I,ZN,XA,YB), (R1B,R2I,ZN,XA,YB), (R1C,R2I,ZN,XA,YB), (R1D,R2I,ZN,XA,YB), (R1E,R2I,ZN,XA,YB), (R1F,R2I,ZN,XA,YB), (R1G,R2I,ZN,XA,YB), (R1H,R2I,ZN,XA,YB), (R1I,R2I,ZN,XA,YB), (R1J,R2I,ZN,XA,YB), (R1K,R2I,ZN,XA,YB), (R1L,R2I,ZN,XA,YB), (R1M,R2I,ZN,XA,YB), (R1N,R2I,ZN,XA,YB), (R1O,R2I,ZN,XA,YB), (R1P,R2I,ZN,XA,YB), (R1Q,R2I,ZN,XA,YB), (R1A,R2J,ZN,XA,YB), (R1B,R2J,ZN,XA,YB), (R1C,R2J,ZN,XA,YB), (R1D,R2J,ZN,XA,YB), (R1E,R2J,ZN,XA,YB), (R1F,R2J,ZN,XA,YB), (R1G,R2J,ZN,XA,YB), (R1H,R2J,ZN,XA,YB), (R1I,R2J,ZN,XA,YB), (R1J,R2J,ZN,XA,YB), (R1K,R2J,ZN,XA,YB), (R1L,R2J,ZN,XA,YB), (R1M,R2J,ZN,XA,YB), (R1N,R2J,ZN,XA,YB), (R1O,R2J,ZN,XA,YB), (R1P,R2J,ZN,XA,YB), (R1Q,R2J,ZN,XA,YB), (R1A,R2K,ZN,XA,YB), (R1B,R2K,ZN,XA,YB), (R1C,R2K,ZN,XA,YB), (R1D,R2K,ZN,XA,YB), (R1E,R2K,ZN,XA,YB), (R1F,R2K,ZN,XA,YB), (R1G,R2K,ZN,XA,YB), (R1H,R2K,ZN,XA,YB), (R1I,R2K,ZN,XA,YB), (R1J,R2K,ZN,XA,YB), (R1K,R2K,ZN,XA,YB), (R1L,R2K,ZN,XA,YB), (R1M,R2K,ZN,XA,YB), (R1N,R2K,ZN,XA,YB), (R1O,R2K,ZN,XA,YB), (R1P,R2K,ZN,XA,YB), (R1Q,R2K,ZN,XA,YB), (R1A,R2L,ZN,XA,YB), (R1B,R2L,ZN,XA,YB), (R1C,R2L,ZN,XA,YB), (R1D,R2L,ZN,XA,YB), (R1E,R2L,ZN,XA,YB), (R1F,R2L,ZN,XA,YB), (R1G,R2L,ZN,XA,YB), (R1H,R2L,ZN,XA,YB), (R1I,R2L,ZN,XA,YB), (R1J,R2L,ZN,XA,YB), (R1K,R2L,ZN,XA,YB), (R1L,R2L,ZN,XA,YB), (R1M,R2L,ZN,XA,YB), (R1N,R2L,ZN,XA,YB), (R1O,R2L,ZN,XA,YB), (R1P,R2L,ZN,XA,YB), (R1Q,R2L,ZN,XA,YB), (R1A,R2M,ZN,XA,YB), (R1B,R2M,ZN,XA,YB), (R1C,R2M,ZN,XA,YB), (R1D,R2M,ZN,XA,YB), (R1E,R2M,ZN,XA,YB), (R1F,R2M,ZN,XA,YB), (R1G,R2M,ZN,XA,YB), (R1H,R2M,ZN,XA,YB), (R1I,R2M,ZN,XA,YB), (R1J,R2M,ZN,XA,YB), (R1K,R2M,ZN,XA,YB), (R1L,R2M,ZN,XA,YB), (R1M,R2M,ZN,XA,YB), (R1N,R2M,ZN,XA,YB), (R1O,R2M,ZN,XA,YB), (R1P,R2M,ZN,XA,YB), (R1Q,R2M,ZN,XA,YB), (R1A,R2N,ZN,XA,YB), (R1B,R2N,ZN,XA,YB), (R1C,R2N,ZN,XA,YB), (R1D,R2N,ZN,XA,YB), (R1E,R2N,ZN,XA,YB), (R1F,R2N,ZN,XA,YB), (R1G,R2N,ZN,XA,YB), (R1H,R2N,ZN,XA,YB), (R1I,R2N,ZN,XA,YB), (R1J,R2N,ZN,XA,YB), (R1K,R2N,ZN,XA,YB), (R1L,R2N,ZN,XA,YB), (R1M,R2N,ZN,XA,YB), (R1N,R2N,ZN,XA,YB), (R1O,R2N,ZN,XA,YB), (R1P,R2N,ZN,XA,YB), (R1Q,R2N,ZN,XA,YB), (R1A,R2O,ZN,XA,YB), (R1B,R2O,ZN,XA,YB), (R1C,R2O,ZN,XA,YB), (R1D,R2O,ZN,XA,YB), (R1E,R2O,ZN,XA,YB), (R1F,R2O,ZN,XA,YB), (R1G,R2O,ZN,XA,YB), (R1H,R2O,ZN,XA,YB), (R1I,R2O,ZN,XA,YB), (R1J,R2O,ZN,XA,YB), (R1K,R2O,ZN,XA,YB), (R1L,R2O,ZN,XA,YB), (R1M,R2O,ZN,XA,YB), (R1N,R2O,ZN,XA,YB), (R1O,R2O,ZN,XA,YB), (R1P,R2O,ZN,XA,YB), (R1Q,R2O,ZN,XA,YB), (R1A,R2P,ZN,XA,YB), (R1B,R2P,ZN,XA,YB), (R1C,R2P,ZN,XA,YB), (R1D,R2P,ZN,XA,YB), (R1E,R2P,ZN,XA,YB), (R1F,R2P,ZN,XA,YB), (R1G,R2P,ZN,XA,YB), (R1H,R2P,ZN,XA,YB), (R1I,R2P,ZN,XA,YB), (R1J,R2P,ZN,XA,YB), (R1K,R2P,ZN,XA,YB), (R1L,R2P,ZN,XA,YB), (R1M,R2P,ZN,XA,YB), (R1N,R2P,ZN,XA,YB), (R1O,R2P,ZN,XA,YB), (R1P,R2P,ZN,XA,YB), (R1Q,R2P,ZN,XA,YB), (R1A,R2Q,ZN,XA,YB), (R1B,R2Q,ZN,XA,YB), (R1C,R2Q,ZN,XA,YB), (R1D,R2Q,ZN,XA,YB), (R1E,R2Q,ZN,XA,YB), (R1F,R2Q,ZN,XA,YB), (R1G,R2Q,ZN,XA,YB), (R1H,R2Q,ZN,XA,YB), (R1I,R2Q,ZN,XA,YB), (R1J,R2Q,ZN,XA,YB), (R1K,R2Q,ZN,XA,YB), (R1L,R2Q,ZN,XA,YB), (R1M,R2Q,ZN,XA,YB), (R1N,R2Q,ZN,XA,YB), (R1O,R2Q,ZN,XA,YB), (R1P,R2Q,ZN,XA,YB), (R1Q,R2Q,ZN,XA,YB), (R1A,R2A,ZO,XA,YB), (R1B,R2A,ZO,XA,YB), (R1C,R2A,ZO,XA,YB), (R1D,R2A,ZO,XA,YB), (R1E,R2A,ZO,XA,YB), (R1F,R2A,ZO,XA,YB), (R1G,R2A,ZO,XA,YB), (R1H,R2A,ZO,XA,YB), (R1I,R2A,ZO,XA,YB), (R1J,R2A,ZO,XA,YB), (R1K,R2A,ZO,XA,YB), (R1L,R2A,ZO,XA,YB), (R1M,R2A,ZO,XA,YB), (R1N,R2A,ZO,XA,YB), (R1O,R2A,ZO,XA,YB), (R1P,R2A,ZO,XA,YB), (R1Q,R2A,ZO,XA,YB), (R1A,R2B,ZO,XA,YB), (R1B,R2B,ZO,XA,YB), (R1C,R2B,ZO,XA,YB), (R1D,R2B,ZO,XA,YB), (R1E,R2B,ZO,XA,YB), (R1F,R2B,ZO,XA,YB), (R1G,R2B,ZO,XA,YB), (R1H,R2B,ZO,XA,YB), (R1I,R2B,ZO,XA,YB), (R1J,R2B,ZO,XA,YB), (R1K,R2B,ZO,XA,YB), (R1L,R2B,ZO,XA,YB), (R1M,R2B,ZO,XA,YB), (R1N,R2B,ZO,XA,YB), (R1O,R2B,ZO,XA,YB), (R1P,R2B,ZO,XA,YB), (R1Q,R2B,ZO,XA,YB), (R1A,R2C,ZO,XA,YB), (R1B,R2C,ZO,XA,YB), (R1C,R2C,ZO,XA,YB), (R1D,R2C,ZO,XA,YB), (R1E,R22C,ZO,XA,YB), (R1F,R2C,ZO,XA,YB), (R1G,R2C,ZO,XA,YB), (R1H,R2C,ZO,XA,YB), (R1I,R22C,ZO,XA,YB), (R1J,R2C,ZO,XA,YB), (R1K,R2C,ZO,XA,YB), (R1L,R2C,ZO,XA,YB), (R1M,R2C,ZO,XA,YB), (R1N,R2C,ZO,XA,YB), (R1O,R2C,ZO,XA,YB), (R1P,R2C,ZO,XA,YB), (R1Q,R2C,ZO,XA,YB), (R1A,R2D,ZO,XA,YB), (R1B,R2D,ZO,XA,YB), (R1C,R2D,ZO,XA,YB), (R1D,R2D,ZO,XA,YB), (R1E,R2D,ZO,XA,YB), (R1F,R2D,ZO,XA,YB), (R1G,R2D,ZO,XA,YB), (R1H,R2D,ZO,XA,YB), (R1I,R2D,ZO,XA,YB), (R1J,R2D,ZO,XA,YB), (R1K,R2D,ZO,XA,YB), (R1L,R2D,ZO,XA,YB), (R1M,R2D,ZO,XA,YB), (R1N,R2D,ZO,XA,YB), (R1O,R2D,ZO,XA,YB), (R1P,R2D,ZO,XA,YB), (R1Q,R2D,ZO,XA,YB), (R1A,R2E,ZO,XA,YB), (R1B,R2E,ZO,XA,YB), (R1C,R2E,ZO,XA,YB), (R1D,R2E,ZO,XA,YB), (R1E,R2E,ZO,XA,YB), (R1F,R2E,ZO,XA,YB), (R1G,R2E,ZO,XA,YB), (R1H,R2E,ZO,XA,YB), (R1I,R2E,ZO,XA,YB), (R1J,R2E,ZO,XA,YB), (R1K,R2E,ZO,XA,YB), (R1L,R2E,ZO,XA,YB), (R1M,R2E,ZO,XA,YB), (R1N,R2E,ZO,XA,YB), (R1O,R2E,ZO,XA,YB), (R1P,R2E,ZO,XA,YB), (R1Q,R2E,ZO,XA,YB), (R1A,R2F,ZO,XA,YB), (R1B,R2F,ZO,XA,YB), (R1C,R2F,ZO,XA,YB), (R1D,R2F,ZO,XA,YB), (R1E,R2F,ZO,XA,YB), (R1F,R2F,ZO,XA,YB), (R1G,R2F,ZO,XA,YB), (R1H,R2F,ZO,XA,YB), (R1I,R2F,ZO,XA,YB), (R1J,R2F,ZO,XA,YB), (R1K,R2F,ZO,XA,YB), (R1L,R2F,ZO,XA,YB), (R1M,R2F,ZO,XA,YB), (R1N,R2F,ZO,XA,YB), (R1O,R2F,ZO,XA,YB), (R1P,R2F,ZO,XA,YB), (R1Q,R2F,ZO,XA,YB), (R1A,R2G,ZO,XA,YB), (R1B,R2G,ZO,XA,YB), (R1C,R2G,ZO,XA,YB), (R1D,R2G,ZO,XA,YB), (R1E,R2G,ZO,XA,YB), (R1F,R2G,ZO,XA,YB), (R1G,R2G,ZO,XA,YB), (R1H,R2G,ZO,XA,YB), (R1I,R2G,ZO,XA,YB), (R1J,R2G,ZO,XA,YB), (R1K,R2G,ZO,XA,YB), (R1L,R2G,ZO,XA,YB), (R1M,R2G,ZO,XA,YB), (R1N,R2G,ZO,XA,YB), (R1O,R2G,ZO,XA,YB), (R1P,R2G,ZO,XA,YB), (R1Q,R2G,ZO,XA,YB), (R1A,R2H,ZO,XA,YB), (R1B,R2H,ZO,XA,YB), (R1C,R2H,ZO,XA,YB), (R1D,R2H,ZO,XA,YB), (R1E,R2H,ZO,XA,YB), (R1F,R2H,ZO,XA,YB), (R1G,R2H,ZO,XA,YB), (R1H,R2H,ZO,XA,YB), (R1I,R2H,ZO,XA,YB), (R1J,R2H,ZO,XA,YB), (R1K,R2H,ZO,XA,YB), (R1L,R2H,ZO,XA,YB), (R1M,R2H,ZO,XA,YB), (R1N,R2H,ZO,XA,YB), (R1O,R2H,ZO,XA,YB), (R1P,R2H,ZO,XA,YB), (R1Q,R2H,ZO,XA,YB), (R1A,R2I,ZO,XA,YB), (R1B,R2I,ZO,XA,YB), (R1C,R2I,ZO,XA,YB), (R1D,R2I,ZO,XA,YB), (R1E,R2I,ZO,XA,YB), (R1F,R2I,ZO,XA,YB), (R1G,R2I,ZO,XA,YB), (R1H,R2I,ZO,XA,YB), (R1I,R2I,ZO,XA,YB), (R1J,R2I,ZO,XA,YB), (R1K,R2I,ZO,XA,YB), (R1L,R2I,ZO,XA,YB), (R1M,R2I,ZO,XA,YB), (R1N,R2I,ZO,XA,YB), (R1O,R2I,ZO,XA,YB), (R1P,R2I,ZO,XA,YB), (R1Q,R2I,ZO,XA,YB), (R1A,R2J,ZO,XA,YB), (R1B,R2J,ZO,XA,YB), (R1C,R2J,ZO,XA,YB), (R1D,R2J,ZO,XA,YB), (R1E,R2J,ZO,XA,YB), (R1F,R2J,ZO,XA,YB), (R1G,R2J,ZO,XA,YB), (R1H,R2J,ZO,XA,YB), (R1I,R2J,ZO,XA,YB), (R1J,R2J,ZO,XA,YB), (R1K,R2J,ZO,XA,YB), (R1L,R2J,ZO,XA,YB), (R1M,R2J,ZO,XA,YB), (R1N,R2J,ZO,XA,YB), (R1O,R2J,ZO,XA,YB), (R1P,R2J,ZO,XA,YB), (R1Q,R2J,ZO,XA,YB), (R1A,R2K,ZO,XA,YB), (R1B,R2K,ZO,XA,YB), (R1C,R2K,ZO,XA,YB), (R1D,R2K,ZO,XA,YB), (R1E,R2K,ZO,XA,YB), (R1F,R2K,ZO,XA,YB), (R1G,R2K,ZO,XA,YB), (R1H,R2K,ZO,XA,YB), (R1I,R2K,ZO,XA,YB), (R1J,R2K,ZO,XA,YB), (R1K,R2K,ZO,XA,YB), (R1L,R2K,ZO,XA,YB), (R1M,R2K,ZO,XA,YB), (R1N,R2K,ZO,XA,YB), (R1O,R2K,ZO,XA,YB), (R1P,R2K,ZO,XA,YB), (R1Q,R2K,ZO,XA,YB), (R1A,R2L,ZO,XA,YB), (R1B,R2L,ZO,XA,YB), (R1C,R2L,ZO,XA,YB), (R1D,R2L,ZO,XA,YB), (R1E,R2L,ZO,XA,YB), (R1F,R2L,ZO,XA,YB), (R1G,R2L,ZO,XA,YB), (R1H,R2L,ZO,XA,YB), (R1I,R2L,ZO,XA,YB), (R1J,R2L,ZO,XA,YB), (R1K,R2L,ZO,XA,YB), (R1L,R2L,ZO,XA,YB), (R1M,R2L,ZO,XA,YB), (R1N,R2L,ZO,XA,YB), (R1O,R2L,ZO,XA,YB), (R1P,R2L,ZO,XA,YB), (R1Q,R2L,ZO,XA,YB), (R1A,R2M,ZO,XA,YB), (R1B,R2M,ZO,XA,YB), (R1C,R2M,ZO,XA,YB), (R1D,R2M,ZO,XA,YB), (R1E,R2M,ZO,XA,YB), (R1F,R2M,ZO,XA,YB), (R1G,R2M,ZO,XA,YB), (R1H,R2M,ZO,XA,YB), (R1I,R2M,ZO,XA,YB), (R1J,R2M,ZO,XA,YB), (R1K,R2M,ZO,XA,YB), (R1L,R2M,ZO,XA,YB), (R1M,R2M,ZO,XA,YB), (R1N,R2M,ZO,XA,YB), (R1O,R2M,ZO,XA,YB), (R1P,R2M,ZO,XA,YB), (R1Q,R2M,ZO,XA,YB), (R1A,R2N,ZO,XA,YB), (R1B,R2N,ZO,XA,YB), (R1C,R2N,ZO,XA,YB), (R1D,R2N,ZO,XA,YB), (R1E,R2N,ZO,XA,YB), (R1F,R2N,ZO,XA,YB), (R1G,R2N,ZO,XA,YB), (R1H,R2N,ZO,XA,YB), (R1I,R2N,ZO,XA,YB), (R1J,R2N,ZO,XA,YB), (R1K,R2N,ZO,XA,YB), (R1L,R2N,ZO,XA,YB), (R1M,R2N,ZO,XA,YB), (R1N,R2N,ZO,XA,YB), (R1O,R2N,ZO,XA,YB), (R1P,R2N,ZO,XA,YB), (R1Q,R2N,ZO,XA,YB), (R1A,R2O,ZO,XA,YB), (R1B,R2O,ZO,XA,YB), (R1C,R2O,ZO,XA,YB), (R1D,R2O,ZO,XA,YB), (R1E,R2O,ZO,XA,YB), (R1F,R2O,ZO,XA,YB), (R1G,R2O,ZO,XA,YB), (R1H,R2O,ZO,XA,YB), (R1I,R2O,ZO,XA,YB), (R1J,R2O,ZO,XA,YB), (R1K,R2O,ZO,XA,YB), (R1L,R2O,ZO,XA,YB), (R1M,R2O,ZO,XA,YB), (R1N,R2O,ZO,XA,YB), (R1O,R2O,ZO,XA,YB), (R1P,R2O,ZO,XA,YB), (R1Q,R2O,ZO,XA,YB), (R1A,R2P,ZO,XA,YB), (R1B,R2P,ZO,XA,YB), (R1C,R2P,ZO,XA,YB), (R1D,R2P,ZO,XA,YB), (R1E,R2P,ZO,XA,YB), (R1F,R2P,ZO,XA,YB), (R1G,R2P,ZO,XA,YB), (R1H,R2P,ZO,XA,YB), (R1I,R2P,ZO,XA,YB), (R1J,R2P,ZO,XA,YB), (R1K,R2P,ZO,XA,YB), (R1L,R2P,ZO,XA,YB), (R1M,R2P,ZO,XA,YB), (R1N,R2P,ZO,XA,YB), (R1O,R2P,ZO,XA,YB), (R1P,R2P,ZO,XA,YB), (R1Q,R2P,ZO,XA,YB), (R1A,R2Q,ZO,XA,YB), (R1B,R2Q,ZO,XA,YB), (R1C,R2Q,ZO,XA,YB), (R1D,R2Q,ZO,XA,YB), (R1E,R2Q,ZO,XA,YB), (R1F,R2Q,ZO,XA,YB), (R1G, R2Q,ZO,XA,YB), (R1H,R2Q,ZO,XA,YB), (R1I,R2Q,ZO, XA,YB), (R1J,R2Q,ZO,XA,YB), (R1K,R2Q,ZO,XA,YB), (R1L,R2Q,ZO,XA,YB), (R1M,R2Q,ZO,XA,YB), (R1N, R2Q,ZO,XA,YB), (R1O,R2Q,ZO,XA,YB), (R1P,R2Q,ZO, XA,YB), (R1Q,R2Q,ZO,XA,YB), (R1A,R2A,ZP,XA,YB), (R1B,R2A,ZP,XA,YB), (R1C, R2A,ZP,XA,YB), (R1D, R2A,ZP,XA,YB), (R1E,R2A,ZP,XA,YB), (R1F,R2A,ZP, XA,YB), (R1G,R2A,ZP,XA,YB), (R1H,R2A,ZP,XA,YB), (R1I,R2A,ZP,XA,YB), (R1J,R2A,ZP,XA,YB), (R1K,R2A, ZP,XA,YB), (R1L,R2A,ZP,XA,YB), (R1M,R2A,ZP,XA, YB), (R1N,R2A,ZP,XA,YB), (R1O,R2A,ZP,XA,YB), (R1P, R2A,ZP,XA,YB), (R1Q,R2A,ZP,XA,YB), (R1A,R2B,ZP, XA,YB), (R1B,R2B,ZP,XA,YB), (R1C,R2B,ZP,XA,YB), (R1D,R2B,ZP,XA,YB), (R1E,R2B,ZP,XA,YB), (R1F,R2B, ZP,XA,YB), (R1G,R2B,ZP,XA,YB), (R1H,R2B,ZP,XA, YB), (R1I,R2B,ZP,XA,YB), (R1J,R2B,ZP,XA,YB), (R1K, R2B,ZP,XA,YB), (R1L,R2B,ZP,XA,YB), (R1M,R2B,ZP, XA,YB), (R1N,R2B,ZP,XA,YB), (R1O,R2B,ZP,XA,YB), (R1P,R2B,ZP,XA,YB), (R1Q,R2B,ZP,XA,YB), (R1A,R2C, ZP,XA,YB), (R1B,R2C,ZP,XA,YB), (R1C,R2C,ZP,XA, YB), (R1D,R2C,ZP,XA,YB), (R1E,R2C,ZP,XA,YB), (R1F, R2C,ZP,XA,YB), (R1G,R2C,ZP,XA,YB), (R1H,R2C,ZP, XA,YB), (R1I,R2C,ZP,XA,YB), (R1J,R2C,ZP,XA,YB), (R1K,R2C,ZP,XA,YB), (R1L,R2C,ZP,XA,YB), (R1M,R2C, ZP,XA,YB), (R1N,R2C,ZP,XA,YB), (R1O,R2C,ZP,XA, YB), (R1P,R2C,ZP,XA,YB), (R1Q,R2C,ZP,XA,YB), (R1A, R2D,ZP,XA,YB), (R1B,R2D,ZP,XA,YB), (R1C,R2D,ZP, XA,YB), (R1D,R2D,ZP,XA,YB), (R1E,R2D,ZP,XA,YB), (R1F,R2D,ZP,XA,YB), (R1G,R2D,ZP,XA,YB), (R1H,R2D, ZP,XA,YB), (R1I,R2D,ZP,XA,YB), (R1J,R2D,ZP,XA,YB), (R1K,R2D,ZP,XA,YB), (R1L,R2D,ZP,XA,YB), (R1M, R2D,ZP,XA,YB), (R1N,R2D,ZP,XA,YB), (R1O,R2D,ZP, XA,YB), (R1P,R2D,ZP,XA,YB), (R1Q,R2D,ZP,XA,YB), (R1A,R2E,ZP,XA,YB), (R1B,R2E,ZP,XA,YB), (R1C,R2E, ZP,XA,YB), (R1D,R2E,ZP,XA,YB), (R1E,R2E,ZP,XA, YB), (R1F,R2E,ZP,XA,YB), (R1G,R2E,ZP,XA,YB), (R1H, R2E,ZP,XA,YB), (R1I,R2E,ZP,XA,YB), (R1J,R2E,ZP,XA, YB), (R1K,R2E,ZP,XA,YB), (R1L,R2E,ZP,XA,YB), (R1M, R2E,ZP,XA,YB), (R1N,R2E,ZP,XA,YB), (R1O,R2E,ZP, XA,YB), (R1P,R2E,ZP,XA,YB), (R1Q,R2E,ZP,XA,YB), (R1A,R2F,ZP,XA,YB), (R1B,R2F,ZP,XA,YB), (R1C,R2F, ZP,XA,YB), (R1D,R2F,ZP,XA,YB), (R1E,R2F,ZP,XA,YB), (R1F,R2F,ZP,XA,YB), (R1G,R2F,ZP,XA,YB), (R1H,R2F, ZP,XA,YB), (R1I,R2F,ZP,XA,YB), (R1J,R2F,ZP,XA,YB), (R1K,R2F,ZP,XA,YB), (R1L,R2F,ZP,XA,YB), (R1M,R2F, ZP,XA,YB), (R1N,R2F,ZP,XA,YB), (R1O,R2F,ZP,XA,YB), (R1P,R2F,ZP,XA,YB), (R1Q,R2F,ZP,XA,YB), (R1A,R2G, ZP,XA,YB), (R1B,R2G,ZP,XA,YB), (R1C,R2 G,ZP,XA, YB), (R1D,R2G,ZP,XA,YB), (R1E,R2G,ZP,XA,YB), (R1F, R2G,ZP,XA,YB), (R1G,R2G,ZP,XA,YB), (R1H,R2G,ZP, XA,YB), (R1I,R2G,ZP,XA,YB), (R1J,R2G,ZP,XA,YB), (R1K,R2G,ZP,XA,YB), (R1L,R2G,ZP,XA,YB), (R1M, R2G,ZP,XA,YB), (R1N,R2G,ZP,XA,YB), (R1O,R2G,ZP, XA,YB), (R1P,R2G,ZP,XA,YB), (R1Q,R2G,ZP,XA,YB), (R1A,R2H,ZP,XA,YB), (R1B,R2H,ZP,XA,YB), (R1C,R2H, ZP,XA,YB), (R1D,R2H,ZP,XA,YB), (R1E,R2H,ZP,XA, YB), (R1F,R2H,ZP,XA,YB), (R1G,R2H,ZP,XA,YB), (R1H, R2H,ZP,XA,YB), (R1I,R2H,ZP,XA,YB), (R1J,R2H,ZP,XA, YB), (R1K,R2H,ZP,XA,YB), (R1L,R2H,ZP,XA,YB), (R1M,R2H,ZP,XA,YB), (R1N,R2H,ZP,XA,YB), (R1O, R2H,ZP,XA,YB), (R1P,R2H,ZP,XA,YB), (R1Q,R2H,ZP, XA,YB), (R1A,R2I,ZP,XA,YB), (R1B,R2I,ZP,XA,YB), (R1C,R2I,ZP,XA,YB), (R1D,R2I,ZP,XA,YB), (R1E,R2I, ZP,XA,YB), (R1F,R2I,ZP,XA,YB), (R1G,R2I,ZP,XA,YB), (R1H,R2I,ZP,XA,YB), (R1I,R2I,ZP,XA,YB), (R1J,R2I,ZP, XA,YB), (R1K,R2I,ZP,XA,YB), (R1L,R2I,ZP,XA,YB), (R1M,R2I,ZP,XA,YB), (R1N,R2I,ZP,XA,YB), (R1O,R2I, ZP,XA,YB), (R1P,R2I,ZP,XA,YB), (R1Q,R2I,ZP,XA,YB), (R1A,R2J,ZP,XA,YB), (R1B,R2J,ZP,XA,YB), (R1C,R2J, ZP,XA,YB), (R1D,R2J,ZP,XA,YB), (R1E,R2J,ZP,XA,YB), (R1F,R2J,ZP,XA,YB), (R1G,R2J,ZP,XA,YB), (R1H,R2J, ZP,XA,YB), (R1I,R2J,ZP,XA,YB), (R1J,R2J,ZP,XA,YB), (R1K,R2J,ZP,XA,YB), (R1L,R2J,ZP,XA,YB), (R1M,R2J, ZP,XA,YB), (R1N,R2J,ZP,XA,YB), (R1O,R2J,ZP,XA,YB), (R1P,R2J,ZP,XA,YB), (R1Q,R2J,ZP,XA,YB), (R1A,R2K, ZP,XA,YB), (R1B,R2K,ZP,XA,YB), (R1C,R2K,ZP,XA, YB), (R1D,R2K,ZP,XA,YB), (R1E,R2K,ZP,XA,YB), (R1F, R2K,ZP,XA,YB), (R1G,R2K,ZP,XA,YB), (R1H,R2K,ZP, XA,YB), (R1I,R2K,ZP,XA,YB), (R1J,R2K,ZP,XA,YB), (R1K,R2K,ZP,XA,YB), (R1L,R2K,ZP,XA,YB), (R1M, R2K,ZP,XA,YB), (R1N,R2K,ZP,XA,YB), (R1O,R2K,ZP, XA,YB), (R1P,R2K,ZP,XA,YB), (R1Q,R2K,ZP,XA,YB), (R1A,R2L,ZP,XA,YB), (R1B,R2L,ZP,XA,YB), (R1C,R2L, ZP,XA,YB), (R1D,R2L,ZP,XA,YB), (R1E,R2L,ZP,XA, YB), (R1F,R2L,ZP,XA,YB), (R1G,R2L,ZP,XA,YB), (R1H, R2L,ZP,XA,YB), (R1I,R2L,ZP,XA,YB), (R1J,R2L,ZP,XA, YB), (R1K,R2L,ZP,XA,YB), (R1L,R2L,ZP,XA,YB), (R1M, R2L,ZP,XA,YB), (R1N,R2L,ZP,XA,YB), (R1O,R2L,ZP, XA,YB), (R1P,R2L,ZP,XA,YB), (R1Q,R2L,ZP,XA,YB), (R1A,R2M,ZP,XA,YB), (R1B,R2M,ZP,XA,YB), (R1C, R2M,ZP,XA,YB), (R1D,R2M,ZP,XA,YB), (R1E,R2M,ZP, XA,YB), (R1F,R2M,ZP,XA,YB), (R1G,R2M,ZP,XA,YB), (R1H,R2M,ZP,XA,YB), (R1I,R2M,ZP,XA,YB), (R1J,R2M, ZP,XA,YB), (R1K,R2M,ZP,XA,YB), (R1L,R2M,ZP,XA, YB), (R1M,R2M,ZP,XA,YB), (R1N,R2M,ZP,XA,YB), (R1O,R2M,ZP,XA,YB), (R1P,R2M,ZP,XA,YB), (R1Q, R2M,ZP,XA,YB), (R1A,R2N,ZP,XA,YB), (R1B,R2N,ZP, XA,YB), (R1C,R2N,ZP,XA,YB), (R1D,R2N,ZP,XA,YB), (R1E,R2N,ZP,XA,YB), (R1F,R2N,ZP,XA,YB), (R1G,R2N, ZP,XA,YB), (R1H,R2N,ZP,XA,YB), (R1I,R2N,ZP,XA, YB), (R1J,R2N,ZP,XA,YB), (R1K,R2N,ZP,XA,YB), (R1L, R2N,ZP,XA,YB), (R1M,R2N,ZP,XA,YB), (R1N,R2N,ZP, XA,YB), (R1O,R2N,ZP,XA,YB), (R1P,R2N,ZP,XA,YB), (R1Q,R2N,ZP,XA,YB), (R1A,R2O,ZP,XA,YB), (R1B, R2O,ZP,XA,YB), (R1C,R2O,ZP,XA,YB), (R1D,R2O,ZP, XA,YB), (R1E,R2O,ZP,XA,YB), (R1F,R2O,ZP,XA,YB), (R1G,R2O,ZP,XA,YB), (R1H,R2O,ZP,XA,YB), (R1I,R2O, ZP,XA,YB), (R1J,R2O,ZP,XA,YB), (R1K,R2O,ZP,XA, YB), (R1L,R2O,ZP,XA,YB), (R1M,R2O,ZP,XA,YB), (R1N,R2O,ZP,XA,YB), (R1O,R2O,ZP,XA,YB), (R1P,R2O, ZP,XA,YB), (R1Q,R2O,ZP,XA,YB), (R1A,R2P,ZP,XA, YB), (R1B,R2P,ZP,XA,YB), (R1C,R2P,ZP,XA,YB), (R1D, R2P,ZP,XA,YB), (R1E,R2P,ZP,XA,YB), (R1F,R2P,ZP,XA, YB), (R1G,R2P,ZP,XA,YB), (R1H,R2P,ZP,XA,YB), (R1I, R2P,ZP,XA,YB), (R1J,R2P,ZP,XA,YB), (R1K,R2P,ZP,XA, YB), (R1L,R2P,ZP,XA,YB), (R1M,R2P,ZP,XA,YB), (R1N, R2P,ZP,XA,YB), (R1O,R2P,ZP,XA,YB), (R1P,R2P,ZP,XA, YB), (R1Q,R2P,ZP,XA,YB), (R1A,R2Q,ZP,XA,YB), (R1B, R2Q,ZP,XA,YB), (R1C,R2Q,ZP,XA,YB), (R1D,R2Q,ZP, XA,YB), (R1E,R2Q,ZP,XA,YB), (R1F,R2Q,ZP,XA,YB), (R1G,R2Q,ZP,XA,YB), (R1H,R2Q,ZP,XA,YB), (R1I,R2Q, ZP,XA,YB), (R1J,R2Q,ZP,XA,YB), (R1K,R2Q,ZP,XA, YB), (R1L,R2Q,ZP,XA,YB), (R1M,R2Q,ZP,XA,YB), (R1N,R2Q,ZP,XA,YB), (R1O,R2Q,ZP,XA,YB), (R1P,R2Q, ZP,XA,YB), (R1Q,R2Q,ZP,XA,YB), (R1A,R2A,ZQ,XA, YB), (R1B,R2A,ZQ,XA,YB), (R1C,R2A,ZQ,XA,YB), (R1D,R2A,ZQ,XA,YB), (R1E,R2A,ZQ,XA,YB), (R1F, R2A,ZQ,XA,YB), (R1G,R2A,ZQ,XA,YB), (R1H,R2A,ZQ, XA,YB), (R1I,R2A,ZQ,XA,YB), (R1J,R2A,ZQ,XA,YB), (R1K,R2A,ZQ,XA,YB), (R1L,R2A,ZQ,XA,YB), (R1M, R2A,ZQ,XA,YB), (R1N,R2A,ZQ,XA,YB), (R1O,R2A,ZQ, XA,YB), (R1P,R2A,ZQ,XA,YB), (R1Q,R2A,ZQ,XA,YB), (R1A,R2B,ZQ,XA,YB), (R1B,R2B,ZQ,XA,YB), (R1C, R2B,ZQ,XA,YB), (R1D,R2B,ZQ,XA,YB), (R1E,R2B,ZQ, XA,YB), (R1F,R2B,ZQ,XA,YB), (R1G,R2B,ZQ,XA,YB), (R1H,R2B,ZQ,XA,YB), (R1I,R2B,ZQ,XA,YB), (R1J,R2B, ZQ,XA,YB), (R1K,R2B,ZQ,XA,YB), (R1L,R2B,ZQ,XA, YB), (R1M,R2B,ZQ,XA,YB), (R1N,R2B,ZQ,XA,YB), (R1O,R2B,ZQ,XA,YB), (R1P,R2B,ZQ,XA,YB), (R1Q, R2B,ZQ,XA,YB), (R1A,R2C,ZQ,XA,YB), (R1B,R2C,ZQ, XA,YB), (R1C,R2C,ZQ,XA,YB), (R1D,R2C,ZQ,XA,YB), (R1E,R2C,ZQ,XA,YB), (R1F,R2C,ZQ,XA,YB), (R1G, R2C,ZQ,XA,YB), (R1H,R2C,ZQ,XA,YB), (R1I,R2C,ZQ, XA,YB), (R1J,R2C,ZQ,XA,YB), (R1K,R2C,ZQ,XA,YB), (R1L,R2C,ZQ,XA,YB), (R1M,R2C,ZQ,XA,YB), (R1N, R2C,ZQ,XA,YB), (R1O,R2C,ZQ,XA,YB), (R1P,R2C,ZQ, XA,YB), (R1Q,R2C,ZQ,XA,YB), (R1A,R2D,ZQ,XA,YB), (R1B,R2D,ZQ,XA,YB), (R1C,R2D,ZQ,XA,YB), (R1D, R2D,ZQ,XA,YB), (R1E,R2D,ZQ,XA,YB), (R1F,R2D,ZQ, XA,YB), (R1G,R2D,ZQ,XA,YB), (R1H,R2D,ZQ,XA,YB), (R1I,R2D,ZQ,XA,YB), (R1J,R2D,ZQ,XA,YB), (R1K,R2D, ZQ,XA,YB), (R1L,R2D,ZQ,XA,YB), (R1M,R2D,ZQ,XA, YB), (R1N,R2D,ZQ,XA,YB), (R1O,R2D,ZQ,XA,YB), (R1P,R2D,ZQ,XA,YB), (R1Q,R2D,ZQ,XA,YB), (R1A, R2E,ZQ,XA,YB), (R1B,R2E,ZQ,XA,YB), (R1C,R2E,ZQ, XA,YB), (R1D,R2E,ZQ,XA,YB), (R1E,R2E,ZQ,XA,YB), (R1F,R2E,ZQ,XA,YB), (R1G,R2E,ZQ,XA,YB), (R1H, R2E,ZQ,XA,YB), (R1I,R2E,ZQ,XA,YB), (R1J,R2E,ZQ, XA,YB), (R1K,R2E,ZQ,XA,YB), (R1L,R2E,ZQ,XA,YB), (R1M,R2E,ZQ,XA,YB), (R1N,R2E,ZQ,XA,YB), (R1O, R2E,ZQ,XA,YB), (R1P,R2E,ZQ,XA,YB), (R1Q,R2E,ZQ, XA,YB), (R1A,R2F,ZQ,XA,YB), (R1B,R2F,ZQ,XA,YB), (R1C,R2F,ZQ,XA,YB), (R1D,R2F,ZQ,XA,YB), (R1E,R2F, ZQ,XA,YB), (R1F,R2F,ZQ,XA,YB), (R1G,R2F,ZQ,XA, YB), (R1H,R2F,ZQ,XA,YB), (R1I,R2F,ZQ,XA,YB), (R1J, R2F,ZQ,XA,YB), (R1K,R2F,ZQ,XA,YB), (R1L,R2F,ZQ, XA,YB), (R1M,R2F,ZQ,XA,YB), (R1N,R2F,ZQ,XA,YB), (R1O,R2F,ZQ,XA,YB), (R1P,R2F,ZQ,XA,YB), (R1Q,R2F, ZQ,XA,YB), (R1A,R2G,ZQ,XA,YB), (R1B,R2G,ZQ,XA, YB), (R1C,R2G,ZQ,XA,YB), (R1D,R2G,ZQ,XA,YB), (R1E,R2G,ZQ,XA,YB), (R1F,R2G,ZQ,XA,YB), (R1G, R2G,ZQ,XA,YB), (R1H,R2G,ZQ,XA,YB), (R1I,R2G,ZQ, XA,YB), (R1J,R2G,ZQ,XA,YB), (R1K,R2G,ZQ,XA,YB), (R1L,R2G,ZQ,XA,YB), (R1M,R2G,ZQ,XA,YB), (R1N, R2G,ZQ,XA,YB), (R1O,R2G,ZQ,XA,YB), (R1P,R2G,ZQ, XA,YB), (R1Q,R2G,ZQ,XA,YB), (R1A,R2H,ZQ,XA,YB), (R1B,R2H,ZQ,XA,YB), (R1C,R2H,ZQ,XA,YB), (R1D, R2H,ZQ,XA,YB), (R1E,R2H,ZQ,XA,YB), (R1F,R2H,ZQ, XA,YB), (R1G,R2H,ZQ,XA,YB), (R1H,R2H,ZQ,XA,YB), (R1I,R2H,ZQ,XA,YB), (R1J,R2H,ZQ,XA,YB), (R1K,R2H, ZQ,XA,YB), (R1L,R2H,ZQ,XA,YB), (R1M,R2H,ZQ,XA, YB), (R1N,R2H,ZQ,XA,YB), (R1O,R2H,ZQ,XA,YB), (R1P,R2H,ZQ,XA,YB), (R1Q,R2H,ZQ,XA,YB), (R1A,R2I, ZQ,XA,YB), (R1B,R2I,ZQ,XA,YB), (R1C,R2I,ZQ,XA, YB), (R1D,R2I,ZQ,XA,YB), (R1E,R2I,ZQ,XA,YB), (R1F, R2I,ZQ,XA,YB), (R1G,R2I,ZQ,XA,YB), (R1H,R2I,ZQ, XA,YB), (R1I,R2I,ZQ,XA,YB), (R1J,R2I,ZQ,XA,YB), (R1K,R2I,ZQ,XA,YB), (R1L,R2I,ZQ,XA,YB), (R1M,R2I, ZQ,XA,YB), (R1N,R2I,ZQ,XA,YB), (R1O,R2I,ZQ,XA, YB), (R1P,R2I,ZQ,XA,YB), (R1Q,R2I,ZQ,XA,YB), (R1A, R2J,ZQ,XA,YB), (R1B,R2J,ZQ,XA,YB), (R1C,R2J,ZQ, XA,YB), (R1D,R2J,ZQ,XA,YB), (R1E,R2J,ZQ,XA,YB), (R1F,R2J,ZQ,XA,YB), (R1G,R2J,ZQ,XA,YB), (R1H,R2J, ZQ,XA,YB), (R1I,R2J,ZQ,XA,YB), (R1J,R2J,ZQ,XA,YB), (R1K,R2J,ZQ,XA,YB), (R1L,R2J,ZQ,XA,YB), (R1M,R2J, ZQ,XA,YB), (R1N,R2J,ZQ,XA,YB), (R1O,R2J,ZQ,XA, YB), (R1P,R2J,ZQ,XA,YB), (R1Q,R2J,ZQ,XA,YB), (R1A, R2K,ZQ,XA,YB), (R1B,R2K,ZQ,XA,YB), (R1C,R2K,ZQ, XA,YB), (R1D,R2K,ZQ,XA,YB), (R1E,R2K,ZQ,XA,YB), (R1F,R2K,ZQ,XA,YB), (R1G,R2K,ZQ,XA,YB), (R1H, R2K,ZQ,XA,YB), (R1I,R2K,ZQ,XA,YB), (R1J,R2K,ZQ, XA,YB), (R1K,R2K,ZQ,XA,YB), (R1L,R2K,ZQ,XA,YB), (R1M,R2K,ZQ,XA,YB), (R1N,R2K,ZQ,XA,YB), (R1O, R2K,ZQ,XA,YB), (R1P,R2K,ZQ,XA,YB), (R1Q,R2K,ZQ, XA,YB), (R1A,R2L,ZQ,XA,YB), (R1B,R2L,ZQ,XA,YB), (R1C,R2L,ZQ,XA,YB), (R1D,R2L,ZQ,XA,YB), (R1E, R2L,ZQ,XA,YB), (R1F,R2L,ZQ,XA,YB), (R1G,R2L,ZQ, XA,YB), (R1H,R2L,ZQ,XA,YB), (R1I,R2L,ZQ,XA,YB), (R1J,R2L,ZQ,XA,YB), (R1K,R2L,ZQ,XA,YB), (R1L,R2L, ZQ,XA,YB), (R1M,R2L,ZQ,XA,YB), (R1N,R2L,ZQ,XA, YB), (R1O,R2L,ZQ,XA,YB), (R1P,R2L,ZQ,XA,YB), (R1Q,R2L,ZQ,XA,YB), (R1A,R2M,ZQ,XA,YB), (R1B, R2M,ZQ,XA,YB), (R1C,R2M,ZQ,XA,YB), (R1D,R2M, ZQ,XA,YB), (R1E,R2M,ZQ,XA,YB), (R1F,R2M,ZQ,XA, YB), (R1G,R2M,ZQ,XA,YB), (R1H,R2M,ZQ,XA,YB), (R1I,R2M,ZQ,XA,YB), (R1J,R2M,ZQ,XA,YB), (R1K, R2M,ZQ,XA,YB), (R1L,R2M,ZQ,XA,YB), (R1M,R2M, ZQ,XA,YB), (R1N,R2M,ZQ,XA,YB), (R1O,R2M,ZQ,XA, YB), (R1P,R2M,ZQ,XA,YB), (R1Q,R2M,ZQ,XA,YB), (R1A,R2N,ZQ,XA,YB), (R1B,R2N,ZQ,XA,YB), (R1C, R2N,ZQ,XA,YB), (R1D,R2N,ZQ,XA,YB), (R1E,R2N,ZQ, XA,YB), (R1F,R2N,ZQ,XA,YB), (R1G,R2N,ZQ,XA,YB), (R1H,R2N,ZQ,XA,YB), (R1I,R2N,ZQ,XA,YB), (R1J,R2N, ZQ,XA,YB), (R1K,R2N,ZQ,XA,YB), (R1L,R2N,ZQ,XA, YB), (R1M,R2N,ZQ,XA,YB), (R1N,R2N,ZQ,XA,YB), (R1O,R2N,ZQ,XA,YB), (R1P,R2N,ZQ,XA,YB), (R1Q, R2N,ZQ,XA,YB), (R1A,R2O,ZQ,XA,YB), (R1B,R2O,ZQ, XA,YB), (R1C,R2O,ZQ,XA,YB), (R1D,R2O,ZQ,XA,YB), (R1E,R2O,ZQ,XA,YB), (R1F,R2O,ZQ,XA,YB), (R1G, R2O,ZQ,XA,YB), (R1H,R2O,ZQ,XA,YB), (R1I,R2O,ZQ, XA,YB), (R1J,R2O,ZQ,XA,YB), (R1K,R2O,ZQ,XA,YB), (R1L,R2O,ZQ,XA,YB), (R1M,R2O,ZQ,XA,YB), (R1N, R2O,ZQ,XA,YB), (R1O,R2O,ZQ,XA,YB), (R1P,R2O,ZQ, XA,YB), (R1Q,R2O,ZQ,XA,YB), (R1A,R2P,ZQ,XA,YB), (R1B,R2P,ZQ,XA,YB), (R1C,R2P,ZQ,XA,YB), (R1D,R2P, ZQ,XA,YB), (R1E,R2P,ZQ,XA,YB), (R1F,R2P,ZQ,XA, YB), (R1G,R2P,ZQ,XA,YB), (R1H,R2P,ZQ,XA,YB), (R1I, R2P,ZQ,XA,YB), (R1J,R2P,ZQ,XA,YB), (R1K,R2P,ZQ, XA,YB), (R1L,R2P,ZQ,XA,YB), (R1M,R2P,ZQ,XA,YB), (R1N,R2P,ZQ,XA,YB), (R1O,R2P,ZQ,XA,YB), (R1P,R2P, ZQ,XA,YB), (R1Q,R2P,ZQ,XA,YB), (R1A,R2Q,ZQ,XA, YB), (R1B,R2Q,ZQ,XA,YB), (R1C,R2Q,ZQ,XA,YB), (R1D,R2Q,ZQ,XA,YB), (R1E,R2Q,ZQ,XA,YB), (R1F, R2Q,ZQ,XA,YB), (R1G,R2Q,ZQ,XA,YB), (R1H,R2Q,ZQ, XA,YB), (R1I,R2Q,ZQ,XA,YB), (R1J,R2Q,ZQ,XA,YB), (R1K,R2Q,ZQ,XA,YB), (R1L,R2Q,ZQ,XA,YB), (R1M, R2Q,ZQ,XA,YB), (R1N,R2Q,ZQ,XA,YB), (R1O,R2Q,ZQ, XA,YB), (R1P,R2Q,ZQ,XA,YB), (R1Q,R2Q,ZQ,XA,YB), (R1A,R2A,ZR,XA,YB), (R1B,R2A,ZR,XA,YB), (R1C, R2A,ZR,XA,YB), (R1D,R2A,ZR,XA,YB), (R1E,R2A,ZR, XA,YB), (R1F,R2A,ZR,XA,YB), (R1G,R2A,ZR,XA,YB), (R1H,R2A,ZR,XA,YB), (R1I,R2A,ZR,XA,YB), (R1J,R2A, ZR,XA,YB), (R1K,R2A,ZR,XA,YB), (R1L,R2A,ZR,XA, YB), (R1M,R2A,ZR,XA,YB), (R1N,R2A,ZR,XA,YB), (R1O,R2A,ZR,XA,YB), (R1P,R2A,ZR,XA,YB), (R1Q, R2A,ZR,XA,YB), (R1A,R2B,ZR,XA,YB), (R1B,R2B,ZR, XA,YB), (R1C,R2B,ZR,XA,YB), (R1D,R2B,ZR,XA,YB), (R1E,R2B,ZR,XA,YB), (R1F,R2B,ZR,XA,YB), (R1G,R2B, ZR,XA,YB), (R1H,R2B,ZR,XA,YB), (R1I,R2B,ZR,XA, YB), (R1J,R2B,ZR,XA,YB), (R1K,R2B,ZR,XA,YB), (R1L, R2B,ZR,XA,YB), (R1M,R2B,ZR,XA,YB), (R1N,R2B,ZR, XA,YB), (R1O,R2B,ZR,XA,YB), (R1P,R2B,ZR,XA,YB), (R1Q,R2B,ZR,XA,YB), (R1A,R2C,ZR,XA,YB), (R1B, R2C,ZR,XA,YB), (R1C,R2C,ZR,XA,YB), (R1D,R2C, XA,YB), (R1E,R2C,ZR,XA,YB), (R1F,R2C,ZR,XA,YB), (R1G,R2C,ZR,XA,YB), (R1H,R2C,ZR,XA,YB), (R1I,R2C, ZR,XA,YB), (R1J,R2C,ZR,XA,YB), (R1K,R2C,ZR,XA, YB), (R1L,R2C,ZR,XA,YB), (R1M,R2C,ZR,XA,YB), (R1N,R2C,ZR,XA,YB), (R1O,R2C,ZR,XA,YB), (R1P,R2C,ZR,XA,YB), (R1Q,R2C,ZR,XA,YB), (R1A,R2D,ZR,XA,YB), (R1B,R2D,ZR,XA,YB), (R1C,R2D,ZR,XA,YB), (R1D,R2D,ZR,XA,YB), (R1E,R2D,ZR,XA,YB), (R1F,R2D,ZR,XA,YB), (R1G,R2D,ZR,XA,YB), (R1H,R2D,ZR,XA,YB), (R1I,R2D,ZR,XA,YB), (R1J,R2D,ZR,XA,YB), (R1K,R2D,ZR,XA,YB), (R1L,R2D,ZR,XA,YB), (R1M,R2D,ZR,XA,YB), (R1N,R2D,ZR,XA,YB), (R1O,R2D,ZR,XA,YB), (R1P,R2D,ZR,XA,YB), (R1Q,R2D,ZR,XA,YB), (R1A,R2E,ZR,XA,YB), (R1B,R2E,ZR,XA,YB), (R1C,R2E,ZR,XA,YB), (R1D,R2E,ZR,XA,YB), (R1E,R2E,ZR,XA,YB), (R1F,R2E,ZR,XA,YB), (R1G,R2E,ZR,XA,YB), (R1H,R2E,ZR,XA,YB), (R1I,R2E,ZR,XA,YB), (R1J,R2E,ZR,XA,YB), (R1K,R2E,ZR,XA,YB), (R1L,R2E,ZR,XA,YB), (R1M,R2E,ZR,XA,YB), (R1N,R2E,ZR,XA,YB), (R1O,R2E,ZR,XA,YB), (R1P,R2E,ZR,XA,YB), (R1Q,R2E,ZR,XA,YB), (R1A,R2F,ZR,XA,YB), (R1B,R2F,ZR,XA,YB), (R1C,R2F,ZR,XA,YB), (R1D,R2F,ZR,XA,YB), (R1E,R2F,ZR,XA,YB), (R1F,R2F,ZR,XA,YB), (R1G,R2F,ZR,XA,YB), (R1H,R2F,ZR,XA,YB), (R1I,R2F,ZR,XA,YB), (R1J,R2F,ZR,XA,YB), (R1K,R2F,ZR,XA,YB), (R1L,R2F,ZR,XA,YB), (R1M,R2F,ZR,XA,YB), (R1N,R2F,ZR,XA,YB), (R1O,R2F,ZR,XA,YB), (R1P,R2F,ZR,XA,YB), (R1Q,R2F,ZR,XA,YB), (R1A,R2G,ZR,XA,YB), (R1B,R2G,ZR,XA,YB), (R1C,R2G,ZR,XA,YB), (R1D,R2G,ZR,XA,YB), (R1E,R2G,ZR,XA,YB), (R1F,R2G,ZR,XA,YB), (R1G,R2G,ZR,XA,YB), (R1H,R2G,ZR,XA,YB), (R1I,R2G,ZR,XA,YB), (R1J,R2G,ZR,XA,YB), (R1K,R2G,ZR,XA,YB), (R1L,R2G,ZR,XA,YB), (R1M,R2G,ZR,XA,YB), (R1N,R2G,ZR,XA,YB), (R1O,R2G,ZR,XA,YB), (R1P,R2G,ZR,XA,YB), (R1Q,R2G,ZR,XA,YB), (R1A,R2H,ZR,XA,YB), (R1B,R2H,ZR,XA,YB), (R1C,R2H,ZR,XA,YB), (R1D,R2H,ZR,XA,YB), (R1E,R2H,ZR,XA,YB), (R1F,R2H,ZR,XA,YB), (R1G,R2H,ZR,XA,YB), (R1H,R2H,ZR,XA,YB), (R1I,R2H,ZR,XA,YB), (R1J,R2H,ZR,XA,YB), (R1K,R2H,ZR,XA,YB), (R1L,R2H,ZR,XA,YB), (R1M,R2H,ZR,XA,YB), (R1N,R2H,ZR,XA,YB), (R1O,R2H,ZR,XA,YB), (R1P,R2H,ZR,XA,YB), (R1Q,R2H,ZR,XA,YB), (R1A,R2I,ZR,XA,YB), (R1B,R2I,ZR,XA,YB), (R1C,R2I,ZR,XA,YB), (R1D,R2I,ZR,XA,YB), (R1E,R2I,ZR,XA,YB), (R1F,R2I,ZR,XA,YB), (R1G,R2I,ZR,XA,YB), (R1H,R2I,ZR,XA,YB), (R1I,R2I,ZR,XA,YB), (R1J,R2I,ZR,XA,YB), (R1K,R2I,ZR,XA,YB), (R1L,R2I,ZR,XA,YB), (R1M,R2I,ZR,XA,YB), (R1N,R2I,ZR,XA,YB), (R1O,R2I,ZR,XA,YB), (R1P,R2I,ZR,XA,YB), (R1Q,R2I,ZR,XA,YB), (R1A,R2J,ZR,XA,YB), (R1B,R2J,ZR,XA,YB), (R1C,R2J,ZR,XA,YB), (R1D,R2J,ZR,XA,YB), (R1E,R2J,ZR,XA,YB), (R1F,R2J,ZR,XA,YB), (R1G,R2J,ZR,XA,YB), (R1H,R2J,ZR,XA,YB), (R1I,R2J,ZR,XA,YB), (R1J,R2J,ZR,XA,YB), (R1K,R2J,ZR,XA,YB), (R1L,R2J,ZR,XA,YB), (R1M,R2J,ZR,XA,YB), (R1N,R2J,ZR,XA,YB), (R1O,R2J,ZR,XA,YB), (R1P,R2J,ZR,XA,YB), (R1Q,R2J,ZR,XA,YB), (R1A,R2K,ZR,XA,YB), (R1B,R2K,ZR,XA,YB), (R1C,R2K,ZR,XA,YB), (R1D,R2K,ZR,XA,YB), (R1E,R2K,ZR,XA,YB), (R1F,R2K,ZR,XA,YB), (R1G,R2K,ZR,XA,YB), (R1H,R2K,ZR,XA,YB), (R1I,R2K,ZR,XA,YB), (R1J,R2K,ZR,XA,YB), (R1K,R2K,ZR,XA,YB), (R1L,R2K,ZR,XA,YB), (R1M,R2K,ZR,XA,YB), (R1N,R2K,ZR,XA,YB), (R1O,R2K,ZR,XA,YB), (R1P,R2K,ZR,XA,YB), 1Q,R2K,ZR,XA,YB), (R1A,R2L,ZR,XA,YB), (R1B,R2L,ZR,XA,YB), (R1C,R2L,ZR,XA,YB), (R1D,R2L,ZR,XA,YB), (R1E,R2L,ZR,XA,YB), (R1F,R2L,ZR,XA,YB), (R1G,R2L,ZR,XA,YB), (R1H,R2L,ZR,XA,YB), (R1I,R2L,ZR,XA,YB), (R1J,R2L,ZR,XA,YB), (R1K,R2L,ZR,XA,YB), (R1L,R2L,ZR,XA,YB), (R1M,R2L,ZR,XA,YB), (R1N,R2L,ZR,XA,YB), (R1O,R2L,ZR,XA,YB), (R1P,R2L,ZR,XA,YB), (R1Q,R2L,ZR,XA,YB), (R1A,R2M,ZR,XA,YB), (R1B,R2M,ZR,XA,YB), (R1C,R2M,ZR,XA,YB), (R1D,R2M,ZR,XA,YB), (R1E,R2M,ZR,XA,YB), (R1F,R2M,ZR,XA,YB), (R1G,R2M,ZR,XA,YB), (R1H,R2M,ZR,XA,YB), (R1I,R2M,ZR,XA,YB), (R1J,R2M,ZR,XA,YB), (R1K,R2M,ZR,XA,YB), (R1L,R2M,ZR,XA,YB), (R1M,R2M,ZR,XA,YB), (R1N,R2M,ZR,XA,YB), (R1O,R2M,ZR,XA,YB), (R1P,R2M,ZR,XA,YB), (R1Q,R2M,ZR,XA,YB), (R1A,R2N,ZR,XA,YB), (R1B,R2N,ZR,XA,YB), (R1C,R2N,ZR,XA,YB), (R1D,R2N,ZR,XA,YB), (R1E,R2N,ZR,XA,YB), (R1F,R2N,ZR,XA,YB), (R1G,R2N,ZR,XA,YB), (R1H,R2N,ZR,XA,YB), (R1I,R2N,ZR,XA,YB), (R1J,R2N,ZR,XA,YB), (R1K,R2N,ZR,XA,YB), (R1L,R2N,ZR,XA,YB), (R1M,R2N,ZR,XA,YB), (R1N,R2N,ZR,XA,YB), (R1O,R2N,ZR,XA,YB), (R1P,R2N,ZR,XA,YB), (R1Q,R2N,ZR,XA,YB), (R1A,R2O,ZR,XA,YB), (R1B,R2O,ZR,XA,YB), (R1C,R2O,ZR,XA,YB), (R1D,R2O,ZR,XA,YB), (R1E,R2O,ZR,XA,YB), (R1F,R2O,ZR,XA,YB), (R1G,R2O,ZR,XA,YB), (R1H,R2O,ZR,XA,YB), (R1I,R2O,ZR,XA,YB), (R1J,R2O,ZR,XA,YB), (R1K,R2O,ZR,XA,YB), (R1L,R2O,ZR,XA,YB), (R1M,R2O,ZR,XA,YB), (R1N,R2O,ZR,XA,YB), (R1O,R2O,ZR,XA,YB), (R1P,R2O,ZR,XA,YB), (R1Q,R2O,ZR,XA,YB), (R1A,R2P,ZR,XA,YB), (R1B,R2P,ZR,XA,YB), (R1C,R2P,ZR,XA,YB), (R1D,R2P,ZR,XA,YB), (R1E,R2P,ZR,XA,YB), (R1F,R2P,ZR,XA,YB), (R1G,R2P,ZR,XA,YB), (R1H,R2P,ZR,XA,YB), (R1I,R2P,ZR,XA,YB), (R1J,R2P,ZR,XA,YB), (R1K,R2P,ZR,XA,YB), (R1L,R2P,ZR,XA,YB), (R1M,R2P,ZR,XA,YB), (R1N,R2P,ZR,XA,YB), (R1O,R2P,ZR,XA,YB), (R1P,R2P,ZR,XA,YB), (R1Q,R2P,ZR,XA,YB), (R1A,R2Q,ZR,XA,YB), (R1B,R2Q,ZR,XA,YB), (R1C,R2Q,ZR,XA,YB), (R1D,R2Q,ZR,XA,YB), (R1E,R2Q,ZR,XA,YB), (R1F,R2Q,ZR,XA,YB), (R1G,R2Q,ZR,XA,YB), (R1H,R2Q,ZR,XA,YB), (R1I,R2Q,ZR,XA,YB), (R1J,R2Q,ZR,XA,YB), (R1K,R2Q,ZR,XA,YB), (R1L,R2Q,ZR,XA,YB), (R1M,R2Q,ZR,XA,YB), (R1N,R2Q,ZR,XA,YB), (R1O,R2Q,ZR,XA,YB), (R1P,R2Q,ZR,XA,YB), (R1Q,R2Q,ZR,XA,YB), (R1A,R2A,ZS,XA,YB), (R1B,R2A,ZS,XA,YB), (R1C,R2A,ZS,XA,YB), (R1D,R2A,ZS,XA,YB), (R1E,R2A,ZS,XA,YB), (R1F,R2A,ZS,XA,YB), (R1G,R2A,ZS,XA,YB), (R1H,R2A,ZS,XA,YB), (R1I,R2A,ZS,XA,YB), (R1J,R2A,ZS,XA,YB), (R1K,R2A,ZS,XA,YB), (R1L,R2A,ZS,XA,YB), (R1M,R2A,ZS,XA,YB), (R1N,R2A,ZS,XA,YB), (R1O,R2A,ZS,XA,YB), (R1P,R2A,ZS,XA,YB), (R1Q,R2A,ZS,XA,YB), (R1A,R2B,ZS,XA,YB), (R1B,R2B,ZS,XA,YB), (R1C,R2B,ZS,XA,YB), (R1D,R2B,ZS,XA,YB), (R1E,R2B,ZS,XA,YB), (R1F,R2B,ZS,XA,YB), (R1G,R2B,ZS,XA,YB), (R1H,R2B,ZS,XA,YB), (R1L R2B,ZS,XA,YB), (R1J,R2B,ZS,XA,YB), (R1K,R2B,ZS,XA,YB), (R1L,R2B,ZS,XA,YB), (R1M,R2B,ZS,XA,YB), (R1N,R2B,ZS,XA,YB), (R1O,R2B,ZS,XA,YB), (R1P,R2B,ZS,XA,YB), (R1Q,R2B,ZS,XA,YB), (R1A,R2C,ZS,XA,YB), (R1B,R2C,ZS,XA,YB), (R1C,R2C,ZS,XA,YB), (R1D,R2C,ZS,XA,YB), (R1E,R2C,ZS,XA,YB), (R1F,R2C,ZS,XA,YB), (R1G,R2C,ZS,XA,YB), (R1H,R2C,ZS,XA,YB), (R1I,R2C,ZS,XA,YB), (R1J,R2C,ZS,XA,YB), (R1K,R2C,ZS,XA,YB), (R1L,R2C,ZS,XA,YB), (R1M,R2C,ZS,XA,YB), (R1N,R2C,ZS,XA,YB), (R1O,R2C,ZS,XA,YB), (R1P,R2C,ZS,XA,YB), (R1Q,R2C,ZS,XA,YB), (R1A,R2D,ZS,XA,YB), (R1B,R2D,ZS,XA,YB), (R1C,R2D,ZS,XA,YB), (R1D,R2D,ZS,XA,YB), (R1E,R2D,ZS,XA,YB), (R1F,R2D,ZS,XA,YB), (R1G,R2D,ZS,XA,YB), (R1H,R2D,ZS,XA,YB), (R1I,R2D,ZS,XA,YB), (R1J,R2D,ZS,XA,YB), (R1K,R2D,ZS,XA,YB), (R1L,R2D,ZS,XA,YB), (R1M,R2D,ZS,XA,YB), (R1N,R2D,ZS,XA,YB), (R1O,R2D,ZS,XA,YB), (R1P,R2D,ZS,XA,YB), (R1Q,R2D,ZS,XA,YB), (R1A,R2E,ZS,XA,YB), (R1B,R2E,ZS,XA,YB), (R1C,R2E,ZS,XA, YB), (R1D,R2E,ZS,XA,YB), (R1E,R2E,ZS,XA,YB), (R1F, R2E,ZS,XA,YB), (R1G,R2E,ZS,XA,YB), (R1H,R2E,ZS, XA,YB), (R1I,R2E,ZS,XA,YB), (R1J,R2E,ZS,XA,YB), (R1K,R2E,ZS,XA,YB), (R1L,R2E,ZS,XA,YB), (R1M, R2E,ZS,XA,YB), (R1N,R2E,ZS,XA,YB), (R1O,R2E,ZS, XA,YB), (R1P,R2E,ZS,XA,YB), (R1Q,R2E,ZS,XA,YB), (R1A,R2F,ZS,XA,YB), (R1B,R2F,ZS,XA,YB), (R1C,R2F, ZS,XA,YB), (R1D,R2F,ZS,XA,YB), (R1E,R2F,ZS,XA, YB), (R1F,R2F,ZS,XA,YB), (R1G,R2F,ZS,XA,YB), (R1H, R2F,ZS,XA,YB), (R1I,R2F,ZS,XA,YB), (R1J,R2F,ZS,XA, YB), (R1K,R2F,ZS,XA,YB), (R1L,R2F,ZS,XA,YB), (R1M, R2F,ZS,XA,YB), (R1N,R2F,ZS,XA,YB), (R1O,R2F,ZS, XA,YB), (R1P,R2F,ZS,XA,YB), (R1Q,R2F,ZS,XA,YB), (R1A,R2G,ZS,XA,YB), (R1B,R2G,ZS,XA,YB), (R1C, R2G,ZS,XA,YB), (R1D,R2G,ZS,XA,YB), (R1E,R2G,ZS, XA,YB), (R1F,R2G,ZS,XA,YB), (R1G,R2G,ZS,XA,YB), (R1H,R2G,ZS,XA,YB), (R1I,R2G,ZS,XA,YB), (R1J,R2G, ZS,XA,YB), (R1K,R2G,ZS,XA,YB), (R1L,R2G,ZS,XA, YB), (R1M,R2G,ZS,XA,YB), (R1N,R2G,ZS,XA,YB), (R1O,R2G,ZS,XA,YB), (R1P,R2G,ZS,XA,YB), (R1Q, R2G,ZS,XA,YB), (R1A,R2H,ZS,XA,YB), (R1B,R2H,ZS, XA,YB), (R1C,R2H,ZS,XA,YB), (R1D,R2H,ZS,XA,YB), (R1E,R2H,ZS,XA,YB), (R1F,R2H,ZS,XA,YB), (R1G,R2H, ZS,XA,YB), (R1H,R2H,ZS,XA,YB), (R1I,R2H,ZS,XA, YB), (R1J,R2H,ZS,XA,YB), (R1K,R2H,ZS,XA,YB), (R1L, R2H,ZS,XA,YB), (R1M,R2H,ZS,XA,YB), (R1N,R2H,ZS, XA,YB), (R1O,R2H,ZS,XA,YB), (R1P,R2H,ZS,XA,YB), (R1Q,R2H,ZS,XA,YB), (R1A,R2I,ZS,XA,YB), (R1B,R2I, ZS,XA,YB), (R1C,R2I,ZS,XA,YB), (R1D,R2I,ZS,XA,YB), (R1E,R2I,ZS,XA,YB), (R1F,R2I,ZS,XA,YB), (R1G,R2I, ZS,XA,YB), (R1H,R2I,ZS,XA,YB), (R1I,R2I,ZS,XA,YB), (R1J,R2I,ZS,XA,YB), (R1K,R2I,ZS,XA,YB), (R1L,R2I, ZS,XA,YB), (R1M,R2I,ZS,XA,YB), (R1N,R2I,ZS,XA, YB), (R1O,R2I,ZS,XA,YB), (R1P,R2I,ZS,XA,YB), (R1Q, R2I,ZS,XA,YB), (R1A,R2J,ZS,XA,YB), (R1B,R2J,ZS,XA, YB), (R1C,R2J,ZS,XA,YB), (R1D,R2J,ZS,XA,YB), (R1E, R2J,ZS,XA,YB), (R1F,R2J,ZS,XA,YB), (R1G,R2J,ZS,XA, YB), (R1H,R2J,ZS,XA,YB), (R1I,R2J,ZS,XA,YB), (R1J, R2J,ZS,XA,YB), (R1K,R2J,ZS,XA,YB), (R1L,R2J,ZS,XA, YB), (R1M,R2J,ZS,XA,YB), (R1N,R2J,ZS,XA,YB), (R1O, R2J,ZS,XA,YB), (R1P,R2J,ZS,XA,YB), (R1Q,R2J,ZS,XA, YB), (R1A,R2K,ZS,XA,YB), (R1B,R2K,ZS,XA,YB), (R1C,R2K,ZS,XA,YB), (R1D,R2K,ZS,XA,YB), (R1E, R2K,ZS,XA,YB), (R1F,R2K,ZS,XA,YB), (R1G,R2K,ZS, XA,YB), (R1H,R2K,ZS,XA,YB), (R1I,R2K,ZS,XA,YB), (R1J,R2K,ZS,XA,YB), (R1K,R2K,ZS,XA,YB), (R1L,R2K, ZS,XA,YB), (R1M,R2K,ZS,XA,YB), (R1N,R2K,ZS,XA, YB), (R1O,R2K,ZS,XA,YB), (R1P,R2K,ZS,XA,YB), (R1Q,R2K,ZS,XA,YB), (R1A,R2L,ZS,XA,YB), (R1B, R2L,ZS,XA,YB), (R1C,R2L,ZS,XA,YB), (R1D,R2L,ZS, XA,YB), (R1E,R2L,ZS,XA,YB), (R1F,R2L,ZS,XA,YB), (R1G,R2L,ZS,XA,YB), (R1H,R2L,ZS,XA,YB), (R1I,R2L, ZS,XA,YB), (R1J,R2L,ZS,XA,YB), (R1K,R2L,ZS,XA, YB), (R1L,R2L,ZS,XA,YB), (R1M,R2L,ZS,XA,YB), (R1N,R2L,ZS,XA,YB), (R1O,R2L,ZS,XA,YB), (R1P,R2L, ZS,XA,YB), (R1Q,R2L,ZS,XA,YB), (R1A,R2M,ZS,XA, YB), (R1B,R2M,ZS,XA,YB), (R1C,R2M,ZS,XA,YB), (R1D,R2M,ZS,XA,YB), (R1E,R2M,ZS,XA,YB), (R1F, R2M,ZS,XA,YB), (R1G,R2M,ZS,XA,YB), (R1H,R2M,ZS, XA,YB), (R1I,R2M,ZS,XA,YB), (R1J,R2M,ZS,XA,YB), (R1K,R2M,ZS,XA,YB), (R1L,R2M,ZS,XA,YB), (R1M, R2M,ZS,XA,YB), (R1N,R2M,ZS,XA,YB), (R1O,R2M,ZS, XA,YB), (R1P,R2M,ZS,XA,YB), (R1Q,R2M,ZS,XA,YB), (R1A,R2N,ZS,XA,YB), (R1B,R2N,ZS,XA,YB), (R1C, R2N,ZS,XA,YB), (R1D,R2N,ZS,XA,YB), (R1E,R2N,ZS, XA,YB), (R1F,R2N,ZS,XA,YB), (R1G,R2N,ZS,XA,YB), (R1H,R2N,ZS,XA,YB), (R1I,R2N,ZS,XA,YB), (R1J,R2N, ZS,XA,YB), (R1K,R2N,ZS,XA,YB), (R1L,R2N,ZS,XA, YB), (R1M,R2N,ZS,XA,YB), (R1N,R2N,ZS,XA,YB), (R1O,R2N,ZS,XA,YB), (R1P,R2N,ZS,XA,YB), (R1Q, R2N,ZS,XA,YB), (R1A,R2O,ZS,XA,YB), (R1B,R2O,ZS, XA,YB), (R1C,R2O,ZS,XA,YB), (R1D,R2O,ZS,XA,YB), (R1E,R2O,ZS,XA,YB), (R1F,R2O,ZS,XA,YB), (R1G,R2O, ZS,XA,YB), (R1H,R2O,ZS,XA,YB), (R1I,R2O,ZS,XA, YB), (R1J,R2O,ZS,XA,YB), (R1K,R2O,ZS,XA,YB), (R1L, R2O,ZS,XA,YB), (R1M,R2O,ZS,XA,YB), (R1N,R2O,ZS, XA,YB), (R1O,R2O,ZS,XA,YB), (R1P,R2O,ZS,XA,YB), (R1Q,R2O,ZS,XA,YB), (R1A,R2P,ZS,XA,YB), (R1B,R2P, ZS,XA,YB), (R1C,R2P,ZS,XA,YB), (R1D,R2P,ZS,XA, YB), (R1E,R2P,ZS,XA,YB), (R1F,R2P,ZS,XA,YB), (R1G, R2P,ZS,XA,YB), (R1H,R2P,ZS,XA,YB), (R1I,R2P,ZS,XA, YB), (R1J,R2P,ZS,XA,YB), (R1K,R2P,ZS,XA,YB), (R1L, R2P,ZS,XA,YB), (R1M,R2P,ZS,XA,YB), (R1N,R2P,ZS, XA,YB), (R1O,R2P,ZS,XA,YB), (R1P,R2P,ZS,XA,YB), (R1Q,R2P,ZS,XA,YB), (R1A,R2Q,ZS,XA,YB), (R1B,R2Q, ZS,XA,YB), (R1C,R2Q,ZS,XA,YB), (R1D,R2Q,ZS,XA, YB), (R1E,R2Q,ZS,XA,YB), (R1F,R2Q,ZS,XA,YB), (R1G, R2Q,ZS,XA,YB), (R1H,R2Q,ZS,XA,YB), (R1I,R2Q,ZS, XA,YB), (R1J,R2Q,ZS,XA,YB), (R1K,R2Q,ZS,XA,YB), (R1L,R2Q,ZS,XA,YB), (R1M,R2Q,ZS,XA,YB), (R1N, R2Q,ZS,XA,YB), (R1O,R2Q,ZS,XA,YB), (R1P,R2Q,ZS, XA,YB), (R1Q,R2Q,ZS,XA,YB), (R1A,R2A,ZT,XA,YB), (R1B,R2A,ZT,XA,YB), (R1C,R2A,ZT,XA,YB), (R1D, R2A,ZT,XA,YB), (R1E,R2A,ZT,XA,YB), (R1F,R2A,ZT, XA,YB), (R1G,R2A,ZT,XA,YB), (R1H,R2A,ZT,XA,YB), (R1I,R2A,ZT,XA,YB), (R1J,R2A,ZT,XA,YB), (R1K,R2A, ZT,XA,YB), (R1L,R2A,ZT,XA,YB), (R1M,R2A,ZT,XA, YB), (R1N,R2A,ZT,XA,YB), (R1O,R2A,ZT,XA,YB), (R1P, R2A,ZT,XA,YB), (R1Q,R2A,ZT,XA,YB), (R1A,R2B,ZT, XA,YB), (R1B,R2B,ZT,XA,YB), (R1C,R2B,ZT,XA,YB), (R1D,R2B,ZT,XA,YB), (R1E,R2B,ZT,XA,YB), (R1F,R2B, ZT,XA,YB), (R1G,R2B,ZT,XA,YB), (R1H,R2B,ZT,XA, YB), (R1I,R2B,ZT,XA,YB), (R1J,R2B,ZT,XA,YB), (R1K, R2B,ZT,XA,YB), (R1L,R2B,ZT,XA,YB), (R1M,R2B,ZT, XA,YB), (R1N,R2B,ZT,XA,YB), (R1O,R2B,ZT,XA,YB), (R1P,R2B,ZT,XA,YB), (R1Q,R2B,ZT,XA,YB), (R1A,R2C, ZT,XA,YB), (R1B,R2C,ZT,XA,YB), (R1C,R2C,ZT,XA, YB), (R1D,R2C,ZT,XA,YB), (R1E,R2C,ZT,XA,YB), (R1F, R2C,ZT,XA,YB), (R1G,R2C,ZT,XA,YB), (R1H,R22C,ZT, XA,YB), (R1I,R2C,ZT,XA,YB), (R1J,R2C,ZT,XA,YB), (R1K,R2C,ZT,XA,YB), (R1L,R22C,ZT,XA,YB), (R1M, R2C,ZT,XA,YB), (R1N,R2C,ZT,XA,YB), (R1O,R2C,ZT, XA,YB), (R1P,R22C,ZT,XA,YB), (R1Q,R2C,ZT,XA,YB), (R1A,R2D,ZT,XA,YB), (R1B,R2D,ZT,XA,YB), (R1C, R2D,ZT,XA,YB), (R1D,R2D,ZT,XA,YB), (R1E,R2D,ZT, XA,YB), (R1F,R2D,ZT,XA,YB), (R1G,R2D,ZT,XA,YB), (R1H,R2D,ZT,XA,YB), (R1I,R2D,ZT,XA,YB), (R1J,R2D, ZT,XA,YB), (R1K,R2D,ZT,XA,YB), (R1L,R2D,ZT,XA, YB), (R1M,R2D,ZT,XA,YB), (R1N,R2D,ZT,XA,YB), (R1O,R2D,ZT,XA,YB), (R1P,R2D,ZT,XA,YB), (R1Q,R2D, ZT,XA,YB), (R1A,R2E,ZT,XA,YB), (R1B,R2E,ZT,XA, YB), (R1C,R2E,ZT,XA,YB), (R1D,R2E,ZT,XA,YB), (R1E, R2E,ZT,XA,YB), (R1F,R2E,ZT,XA,YB), (R1G,R2E,ZT, XA,YB), (R1H,R2E,ZT,XA,YB), (R1I,R2E,ZT,XA,YB), (R1J,R2E,ZT,XA,YB), (R1K,R2E,ZT,XA,YB), (R1L,R2E, ZT,XA,YB), (R1M,R2E,ZT,XA,YB), (R1N,R2E,ZT,XA, YB), (R1O,R2E,ZT,XA,YB), (R1P,R2E,ZT,XA,YB), (R1Q, R2E,ZT,XA,YB), (R1A,R2F,ZT,XA,YB), (R1B,R2F,ZT, XA,YB), (R1C,R2F,ZT,XA,YB), (R1D,R2F,ZT,XA,YB), (R1E,R2F,ZT,XA,YB), (R1F,R2F,ZT,XA,YB), (R1G,R2F, ZT,XA,YB), (R1H,R2F,ZT,XA,YB), (R1I,R2F,ZT,XA,YB), (R1J,R2F,ZT,XA,YB), (R1K,R2F,ZT,XA,YB), (R1L,R2F, ZT,XA,YB), (R1M,R2F,ZT,XA,YB), (R1N,R2F,ZT,XA, YB), (R1O,R2F,ZT,XA,YB), (R1P,R2F,ZT,XA,YB), (R1Q, R2F,ZT,XA,YB), (R1A,R2G,ZT,XA,YB), (R1B,R2G,ZT,XA,YB), (R1C,R2G,ZT,XA,YB), (R1D,R2G,ZT,XA,YB), (R1E,R2G,ZT,XA,YB), (R1F,R2G,ZT,XA,YB), (R1G,R2G,ZT,XA,YB), (R1H,R2G,ZT,XA,YB), (R1I,R2G,ZT,XA,YB), (R1J,R2G,ZT,XA,YB), (R1K,R2G,ZT,XA,YB), (R1L,R2G,ZT,XA,YB), (R1M,R2G,ZT,XA,YB), (R1N,R2G,ZT,XA,YB), (R1O,R2G,ZT,XA,YB), (R1P,R2G,ZT,XA,YB), (R1Q,R2G,ZT,XA,YB), (R1A,R2H,ZT,XA,YB), (R1B,R2H,ZT,XA,YB), (R1C,R2H,ZT,XA,YB), (R1D,R2H,ZT,XA,YB), (R1E,R2H,ZT,XA,YB), (R1F,R2H,ZT,XA,YB), (R1G,R2H,ZT,XA,YB), (R1H,R2H,ZT,XA,YB), (R1I,R2H,ZT,XA,YB), (R1J,R2H,ZT,XA,YB), (R1K,R2H,ZT,XA,YB), (R1L,R2H,ZT,XA,YB), (R1M,R2H,ZT,XA,YB), (R1N,R2H,ZT,XA,YB), (R1O,R2H,ZT,XA,YB), (R1P,R2H,ZT,XA,YB), (R1Q,R2H,ZT,XA,YB), (R1A,R2I,ZT,XA,YB), (R1B,R2I,ZT,XA,YB), (R1C,R2I,ZT,XA,YB), (R1D,R2I,ZT,XA,YB), (R1E,R2I,ZT,XA,YB), (R1F,R2I,ZT,XA,YB), (R1G,R2I,ZT,XA,YB), (R1H,R2I,ZT,XA,YB), (R1I,R2I,ZT,XA,YB), (R1J,R2I,ZT,XA,YB), (R1K,R2I,ZT,XA,YB), (R1L,R2I,ZT,XA,YB), (R1M,R2I,ZT,XA,YB), (R1N,R2I,ZT,XA,YB), (R1O,R2I,ZT,XA,YB), (R1P,R2I,ZT,XA,YB), (R1Q,R2I,ZT,XA,YB), (R1A,R2J,ZT,XA,YB), (R1B,R2J,ZT,XA,YB), (R1C,R2J,ZT,XA,YB), (R1D,R2J,ZT,XA,YB), (R1E,R2J,ZT,XA,YB), (R1F,R2J,ZT,XA,YB), (R1G,R2J,ZT,XA,YB), (R1H,R2J,ZT,XA,YB), (R1I,R2J,ZT,XA,YB), (R1J,R2J,ZT,XA,YB), (R1K,R2J,ZT,XA,YB), (R1L,R2J,ZT,XA,YB), (R1M,R2J,ZT,XA,YB), (R1N,R2J,ZT,XA,YB), (R1O,R2J,ZT,XA,YB), (R1P,R2J,ZT,XA,YB), (R1Q,R2J,ZT,XA,YB), (R1A,R2K,ZT,XA,YB), (R1B,R2K,ZT,XA,YB), (R1C,R2K,ZT,XA,YB), (R1D,R2K,ZT,XA,YB), (R1E,R2K,ZT,XA,YB), (R1F,R2K,ZT,XA,YB), (R1G,R2K,ZT,XA,YB), (R1H,R2K,ZT,XA,YB), (R1I,R2K,ZT,XA,YB), (R1J,R2K,ZT,XA,YB), (R1K,R2K,ZT,XA,YB), (R1L,R2K,ZT,XA,YB), (R1M,R2K,ZT,XA,YB), (R1N,R2K,ZT,XA,YB), (R1O,R2K,ZT,XA,YB), (R1P,R2K,ZT,XA,YB), (R1Q,R2K,ZT,XA,YB), (R1A,R2L,ZT,XA,YB), (R1B,R2L,ZT,XA,YB), (R1C,R2L,ZT,XA,YB), (R1D,R2L,ZT,XA,YB), (R1E,R2L,ZT,XA,YB), (R1F,R2L,ZT,XA,YB), (R1G,R2L,ZT,XA,YB), (R1H,R2L,ZT,XA,YB), (R1I,R2L,ZT,XA,YB), (R1J,R2L,ZT,XA,YB), (R1K,R2L,ZT,XA,YB), (R1L,R2L,ZT,XA,YB), (R1M,R2L,ZT,XA,YB), (R1N,R2L,ZT,XA,YB), (R1O,R2L,ZT,XA,YB), (R1P,R2L,ZT,XA,YB), (R1Q,R2L,ZT,XA,YB), (R1A,R2M,ZT,XA,YB), (R1B,R2M,ZT,XA,YB), (R1C,R2M,ZT,XA,YB), (R1D,R2M,ZT,XA,YB), (R1E,R2M,ZT,XA,YB), (R1F,R2M,ZT,XA,YB), (R1G,R2M,ZT,XA,YB), (R1H,R2M,ZT,XA,YB), (R1I,R2M,ZT,XA,YB), (R1J,R2M,ZT,XA,YB), (R1K,R2M,ZT,XA,YB), (R1L,R2M,ZT,XA,YB), (R1M,R2M,ZT,XA,YB), (R1N,R2M,ZT,XA,YB), (R1O,R2M,ZT,XA,YB), (R1P,R2M,ZT,XA,YB), (R1Q,R2M,ZT,XA,YB), (R1A,R2N,ZT,XA,YB), (R1B,R2N,ZT,XA,YB), (R1C,R2N,ZT,XA,YB), (R1D,R2N,ZT,XA,YB), (R1E,R2N,ZT,XA,YB), (R1F,R2N,ZT,XA,YB), (R1G,R2N,ZT,XA,YB), (R1H,R2N,ZT,XA,YB), (R1I,R2N,ZT,XA,YB), (R1J,R2N,ZT,XA,YB), (R1K,R2N,ZT,XA,YB), (R1L,R2N,ZT,XA,YB), (R1M,R2N,ZT,XA,YB), (R1N,R2N,ZT,XA,YB), (R1O,R2N,ZT,XA,YB), (R1P,R2N,ZT,XA,YB), (R1Q,R2N,ZT,XA,YB), (R1A,R2O,ZT,XA,YB), (R1B,R2O,ZT,XA,YB), (R1C,R2O,ZT,XA,YB), (R1D,R2O,ZT,XA,YB), (R1E,R2O,ZT,XA,YB), (R1F,R2O,ZT,XA,YB), (R1G,R2O,ZT,XA,YB), (R1H,R2O,ZT,XA,YB), (R1I,R2O,ZT,XA,YB), (R1J,R2O,ZT,XA,YB), (R1K,R2O,ZT,XA,YB), (R1L,R2O,ZT,XA,YB), (R1M,R2O,ZT,XA,YB), (R1N,R2O,ZT,XA,YB), (R1O,R2O,ZT,XA,YB), (R1P,R2O,ZT,XA,YB), (R1Q,R2O,ZT,XA,YB), (R1A,R2P,ZT,XA,YB), (R1B,R2P,ZT,XA,YB), (R1C,R2P,ZT,XA,YB), (R1D,R2P,ZT,XA,YB), (R1E,R2P,ZT,XA,YB), (R1F,R2P,ZT,XA,YB), (R1G,R2P,ZT,XA,YB), (R1H,R2P,ZT,XA,YB), (R1I,R2P,ZT,XA,YB), (R1J,R2P,ZT,XA,YB), (R1K,R2P,ZT,XA,YB), (R1L,R2P,ZT,XA,YB), (R1M,R2P,ZT,XA,YB), (R1N,R2P,ZT,XA,YB), (R1O,R2P,ZT,XA,YB), (R1P,R2P,ZT,XA,YB), (R1Q,R2P,ZT,XA,YB), (R1A,R2Q,ZT,XA,YB), (R1B,R2Q,ZT,XA,YB), (R1C,R2Q,ZT,XA,YB), (R1D,R2Q,ZT,XA,YB), (R1E,R2Q,ZT,XA,YB), (R1F,R2Q,ZT,XA,YB), (R1G,R2Q,ZT,XA,YB), (R1H,R2Q,ZT,XA,YB), (R1I,R2Q,ZT,XA,YB), (R1J,R2Q,ZT,XA,YB), (R1K,R2Q,ZT,XA,YB), (R1L,R2Q,ZT,XA,YB), (R1M,R2Q,ZT,XA,YB), (R1N,R2Q,ZT,XA,YB), (R1O,R2Q,ZT,XA,YB), (R1P,R2Q,ZT,XA,YB), (R1Q,R2Q,ZT,XA,YB), (R1A,R2A,ZU,XA,YB), (R1B,R2A,ZU,XA,YB), (R1C,R2A,ZU,XA,YB), (R1D,R2A,ZU,XA,YB), (R1E,R2A,ZU,XA,YB), (R1F,R2A,ZU,XA,YB), (R1G,R2A,ZU,XA,YB), (R1H,R2A,ZU,XA,YB), (R1I,R2A,ZU,XA,YB), (R1J,R2A,ZU,XA,YB), (R1K,R2A,ZU,XA,YB), (R1L,R2A,ZU,XA,YB), (R1M,R2A,ZU,XA,YB), (R1N,R2A,ZU,XA,YB), (R1O,R2A,ZU,XA,YB), (R1P,R2A,ZU,XA,YB), (R1Q,R2A,ZU,XA,YB), (R1A,R2B,ZU,XA,YB), (R1B,R2B,ZU,XA,YB), (R1C,R2B,ZU,XA,YB), (R1D,R2B,ZU,XA,YB), (R1E,R2B,ZU,XA,YB), (R1F,R2B,ZU,XA,YB), (R1G,R2B,ZU,XA,YB), (R1H,R2B,ZU,XA,YB), (R1I,R2B,ZU,XA,YB), (R1J,R2B,ZU,XA,YB), (R1K,R2B,ZU,XA,YB), (R1L,R2B,ZU,XA,YB), (R1M,R2B,ZU,XA,YB), (R1N,R2B,ZU,XA,YB), (R1O,R2B,ZU,XA,YB), (R1P,R2B,ZU,XA,YB), (R1Q,R2B,ZU,XA,YB), (R1A,R2C,ZU,XA,YB), (R1B,R2C,ZU,XA,YB), (R1C,R2C,ZU,XA,YB), (R1D,R2C,ZU,XA,YB), (R1E,R2C,ZU,XA,YB), (R1F,R2C,ZU,XA,YB), (R1G,R2C,ZU,XA,YB), (R1H,R2C,ZU,XA,YB), (R1I,R2C,ZU,XA,YB), (R1J,R2C,ZU,XA,YB), (R1K,R2C,ZU,XA,YB), (R1L,R2C,ZU,XA,YB), (R1M,R2C,ZU,XA,YB), (R1N,R2C,ZU,XA,YB), (R1O,R2C,ZU,XA,YB), (R1P,R2C,ZU,XA,YB), (R1Q,R2C,ZU,XA,YB), (R1A,R2D,ZU,XA,YB), (R1B,R2D,ZU,XA,YB), (R1C,R2D,ZU,XA,YB), (R1D,R2D,ZU,XA,YB), (R1E,R2D,ZU,XA,YB), (R1F,R2D,ZU,XA,YB), (R1G,R2D,ZU,XA,YB), (R1H,R2D,ZU,XA,YB), (R1I,R2D,ZU,XA,YB), (R1J,R2D,ZU,XA,YB), (R1K,R2D,ZU,XA,YB), (R1L,R2D,ZU,XA,YB), (R1M,R2D,ZU,XA,YB), (R1N,R2D,ZU,XA,YB), (R1O,R2D,ZU,XA,YB), (R1P,R2D,ZU,XA,YB), (R1Q,R2D,ZU,XA,YB), (R1A,R2E,ZU,XA,YB), (R1B,R2E,ZU,XA,YB), (R1C,R2E,ZU,XA,YB), (R1D,R2E,ZU,XA,YB), (R1E,R2E,ZU,XA,YB), (R1F,R2E,ZU,XA,YB), (R1G,R2E,ZU,XA,YB), (R1H,R2E,ZU,XA,YB), (R1I,R2E,ZU,XA,YB), (R1J,R2E,ZU,XA,YB), (R1K,R2E,ZU,XA,YB), (R1L,R2E,ZU,XA,YB), (R1M,R2E,ZU,XA,YB), (R1N,R2E,ZU,XA,YB), (R1O,R2E,ZU,XA,YB), (R1P,R2E,ZU,XA,YB), (R1Q,R2E,ZU,XA,YB), (R1A,R2F,ZU,XA,YB), (R1B,R2F,ZU,XA,YB), (R1C,R2F,ZU,XA,YB), (R1D,R2F,ZU,XA,YB), (R1E,R2F,ZU,XA,YB), (R1F,R2F,ZU,XA,YB), (R1G,R2F,ZU,XA,YB), (R1H,R2F,ZU,XA,YB), (R1I,R2F,ZU,XA,YB), (R1J,R2F,ZU,XA,YB), (R1K,R2F,ZU,XA,YB), (R1L,R2F,ZU,XA,YB), (R1M,R2F,ZU,XA,YB), (R1N,R2F,ZU,XA,YB), (R1O,R2F,ZU,XA,YB), (R1P,R2F,ZU,XA,YB), (R1Q,R2F,ZU,XA,YB), (R1A,R2G,ZU,XA,YB), (R1B,R2G,ZU,XA,YB), (R1C,R2G,ZU,XA,YB), (R1D,R2G,ZU,XA,YB), (R1E,R2G,ZU,XA,YB), (R1F,R2G,ZU,XA,YB), (R1G,R2G,ZU,XA,YB), (R1H,R2G,ZU,XA,YB), (R1I,R2G,ZU,XA,YB), (R1J,R2G,ZU,XA,YB), (R1K,R2G,ZU,XA,YB), (R1L,R2G,ZU,XA,YB), (R1M,R2G,ZU,XA,YB), (R1N,R2G,ZU,XA,YB), (R1O,R2G,ZU,XA,YB), (R1P,R2G,ZU,XA,YB), (R1Q,R2G,ZU,XA,YB), (R1A,R2H,ZU,XA,YB), (R1B,R2H,ZU,XA,YB), (R1C,R2H,ZU,XA,YB), (R1D,R2H,ZU,XA,YB), (R1E,R2H,ZU,XA,YB), (R1F,R2H,ZU,XA,YB), (R1G,R2H,ZU,XA,YB), (R1H,R2H,ZU,XA,YB), (R1I,R2H,ZU,XA,YB), (R1J,R2H,ZU,XA,YB), (R1K,R2H,ZU,XA,YB), (R1L, R2H,ZU,XA,YB), (R1M,R2H,ZU,XA,YB), (R1N,R2H,ZU,XA,YB), (R1O,R2H,ZU,XA,YB), (R1P,R2H,ZU,XA,YB), (R1Q,R2H,ZU,XA,YB), (R1A,R2I,ZU,XA,YB), (R1B,R2I,ZU,XA,YB), (R1C,R2I,ZU,XA,YB), (R1D,R2I,ZU,XA,YB), (R1E,R2I,ZU,XA,YB), (R1F,R2I,ZU,XA,YB), (R1G,R2I,ZU,XA,YB), (R1H,R2I,ZU,XA,YB), (R1I,R2I,ZU,XA,YB), (R1J,R2I,ZU,XA,YB), (R1K,R2I,ZU,XA,YB), (R1L,R2I,ZU,XA,YB), (R1M,R2I,ZU,XA,YB), (R1N,R2I,ZU,XA,YB), (R1O,R2I,ZU,XA,YB), (R1P,R2I,ZU,XA,YB), (R1Q,R2I,ZU,XA,YB), (R1A,R2J,ZU,XA,YB), (R1B,R2J,ZU,XA,YB), (R1C,R2J,ZU,XA,YB), (R1D,R2J,ZU,XA,YB), (R1E,R2J,ZU,XA,YB), (R1F,R2J,ZU,XA,YB), (R1G,R2J,ZU,XA,YB), (R1H,R2J,ZU,XA,YB), (R1I,R2J,ZU,XA,YB), (R1J,R2J,ZU,XA,YB), (R1K,R2J,ZU,XA,YB), (R1L,R2J,ZU,XA,YB), (R1M,R2J,ZU,XA,YB), (R1N,R2J,ZU,XA,YB), (R1O,R2J,ZU,XA,YB), (R1P,R2J,ZU,XA,YB), (R1Q,R2J,ZU,XA,YB), (R1A,R2K,ZU,XA,YB), (R1B,R2K,ZU,XA,YB), (R1C,R2K,ZU,XA,YB), (R1D,R2K,ZU,XA,YB), (R1E,R2K,ZU,XA,YB), (R1F,R2K,ZU,XA,YB), (R1G,R2K,ZU,XA,YB), (R1H,R2K,ZU,XA,YB), (R1I,R2K,ZU,XA,YB), (R1J,R2K,ZU,XA,YB), (R1K,R2K,ZU,XA,YB), (R1L,R2K,ZU,XA,YB), (R1M,R2K,ZU,XA,YB), (R1N,R2K,ZU,XA,YB), (R1O,R2K,ZU,XA,YB), (R1P,R2K,ZU,XA,YB), (R1Q,R2K,ZU,XA,YB), (R1A,R2L,ZU,XA,YB), (R1B,R2L,ZU,XA,YB), (R1C,R2L,ZU,XA,YB), (R1D,R2L,ZU,XA,YB), (R1E,R2L,ZU,XA,YB), (R1F,R2L,ZU,XA,YB), (R1G,R2L,ZU,XA,YB), (R1H,R2L,ZU,XA,YB), (R1I,R2L,ZU,XA,YB), (R1J,R2L,ZU,XA,YB), (R1K,R2L,ZU,XA,YB), (R1L,R2L,ZU,XA,YB), (R1M,R2L,ZU,XA,YB), (R1N,R2L,ZU,XA,YB), (R1O,R2L,ZU,XA,YB), (R1P,R2L,ZU,XA,YB), (R1Q,R2L,ZU,XA,YB), (R1A,R2M,ZU,XA,YB), (R1B,R2M,ZU,XA,YB), (R1C,R2M,ZU,XA,YB), (R1D,R2M,ZU,XA,YB), (R1E,R2M,ZU,XA,YB), (R1F,R2M,ZU,XA,YB), (R1G,R2M,ZU,XA,YB), (R1H,R2M,ZU,XA,YB), (R1I,R2M,ZU,XA,YB), (R1J,R2M,ZU,XA,YB), (R1K,R2M,ZU,XA,YB), (R1L,R2M,ZU,XA,YB), (R1M,R2M,ZU,XA,YB), (R1N,R2M,ZU,XA,YB), (R1O,R2M,ZU,XA,YB), (R1P,R2M,ZU,XA,YB), (R1Q,R2M,ZU,XA,YB), (R1A,R2N,ZU,XA,YB), (R1B,R2N,ZU,XA,YB), (R1C,R2N,ZU,XA,YB), (R1D,R2N,ZU,XA,YB), (R1E,R2N,ZU,XA,YB), (R1F,R2N,ZU,XA,YB), (R1G,R2N,ZU,XA,YB), (R1H,R2N,ZU,XA,YB), (R1I,R2N,ZU,XA,YB), (R1J,R2N,ZU,XA,YB), (R1K,R2N,ZU,XA,YB), (R1L,R2N,ZU,XA,YB), (R1M,R2N,ZU,XA,YB), (R1N,R2N,ZU,XA,YB), (R1O,R2N,ZU,XA,YB), (R1P,R2N,ZU,XA,YB), (R1Q,R2N,ZU,XA,YB), (R1A,R2O,ZU,XA,YB), (R1B,R2O,ZU,XA,YB), (R1C,R2O,ZU,XA,YB), (R1D,R2O,ZU,XA,YB), (R1E,R2O,ZU,XA,YB), (R1F,R2O,ZU,XA,YB), (R1G,R2O,ZU,XA,YB), (R1H,R2O,ZU,XA,YB), (R1I,R2O,ZU,XA,YB), (R1J,R2O,ZU,XA,YB), (R1K,R2O,ZU,XA,YB), (R1L,R2O,ZU,XA,YB), (R1M,R2O,ZU,XA,YB), (R1N,R2O,ZU,XA,YB), (R1O,R2O,ZU,XA,YB), (R1P,R2O,ZU,XA,YB), (R1Q,R2O,ZU,XA,YB), (R1A,R2P,ZU,XA,YB), (R1B,R2P,ZU,XA,YB), (R1C,R2P,ZU,XA,YB), (R1D,R2P,ZU,XA,YB), (R1E,R2P,ZU,XA,YB), (R1F,R2P,ZU,XA,YB), (R1G,R2P,ZU,XA,YB), (R1H,R2P,ZU,XA,YB), (R1I,R2P,ZU,XA,YB), (R1J,R2P,ZU,XA,YB), (R1K,R2P,ZU,XA,YB), (R1L,R2P,ZU,XA,YB), (R1M,R2P,ZU,XA,YB), (R1N,R2P,ZU,XA,YB), (R1O,R2P,ZU,XA,YB), (R1P,R2P,ZU,XA,YB), (R1Q,R2P,ZU,XA,YB), (R1A,R2Q,ZU,XA,YB), (R1B,R2Q,ZU,XA,YB), (R1C,R2Q,ZU,XA,YB), (R1D,R2Q,ZU,XA,YB), (R1E,R2Q,ZU,XA,YB), (R1F,R2Q,ZU,XA,YB), (R1G,R2Q,ZU,XA,YB), (R1H,R2Q,ZU,XA,YB), (R1I,R2Q,ZU,XA,YB), (R1J,R2Q,ZU,XA,YB), (R1K,R2Q,ZU,XA,YB), (R1L,R2Q,ZU,XA,YB), (R1M,R2Q,ZU,XA,YB), (R1N,R2Q,ZU,XA,YB), (R1O,R2Q,ZU,XA,YB), (R1P,R2Q,ZU,XA,YB), (R1Q,R2Q,ZU,XA,YB), (R1A,R2A,ZA,XB,YB), (R1B,R2A,ZA,XB,YB), (R1C,R2A,ZA,XB,YB), (R1D,R2A,ZA,XB,YB), (R1E,R2A,ZA,XB,YB), (R1F,R2A,ZA,XB,YB), (R1G,R2A,ZA,XB,YB), (R1H,R2A,ZA,XB,YB), (R1I,R2A,ZA,XB,YB), (R1J,R2A,ZA,XB,YB), (R1K,R2A,ZA,XB,YB), (R1L,R2A,ZA,XB,YB), (R1M,R2A,ZA,XB,YB), (R1N,R2A,ZA,XB,YB), (R1O,R2A,ZA,XB,YB), (R1P,R2A,ZA,XB,YB), (R1Q,R2A,ZA,XB,YB), (R1A,R2B,ZA,XB,YB), (R1B,R2B,ZA,XB,YB), (R1C,R2B,ZA,XB,YB), (R1D,R2B,ZA,XB,YB), (R1E,R2B,ZA,XB,YB), (R1F,R2B,ZA,XB,YB), (R1G,R2B,ZA,XB,YB), (R1H,R2B,ZA,XB,YB), (R1I,R2B,ZA,XB,YB), (R1J,R2B,ZA,XB,YB), (R1K,R2B,ZA,XB,YB), (R1L,R2B,ZA,XB,YB), (R1M,R2B,ZA,XB,YB), (R1N,R2B,ZA,XB,YB), (R1O,R2B,ZA,XB,YB), (R1P,R2B,ZA,XB,YB), (R1Q,R2B,ZA,XB,YB), (R1A,R2C,ZA,XB,YB), (R1B,R2C,ZA,XB,YB), (R1C,R2C,ZA,XB,YB), (R1D,R22C,ZA,XB,YB), (R1E,R2C,ZA,XB,YB), (R1F,R2C,ZA,XB,YB), (R1G,R2C,ZA,XB,YB), (R1H,R2C,ZA,XB,YB), (R1I,R2C,ZA,XB,YB), (R1J,R2C,ZA,XB,YB), (R1K,R2C,ZA,XB,YB), (R1L,R2C,ZA,XB,YB), (R1M,R2C,ZA,XB,YB), (R1N,R2C,ZA,XB,YB), (R1O,R2C,ZA,XB,YB), (R1P,R2C,ZA,XB,YB), (R1Q,R2C,ZA,XB,YB), (R1A,R2D,ZA,XB,YB), (R1B,R2D,ZA,XB,YB), (R1C,R2D,ZA,XB,YB), (R1D,R2D,ZA,XB,YB), (R1E,R2D,ZA,XB,YB), (R1F,R2D,ZA,XB,YB), (R1G,R2D,ZA,XB,YB), (R1H,R2D,ZA,XB,YB), (R1I,R2D,ZA,XB,YB), (R1J,R2D,ZA,XB,YB), (R1K,R2D,ZA,XB,YB), (R1L,R2D,ZA,XB,YB), (R1M,R2D,ZA,XB,YB), (R1N,R2D,ZA,XB,YB), (R1O,R2D,ZA,XB,YB), (R1P,R2D,ZA,XB,YB), (R1Q,R2D,ZA,XB,YB), (R1A,R2E,ZA,XB,YB), (R1B,R2E,ZA,XB,YB), (R1C,R2E,ZA,XB,YB), (R1D,R2E,ZA,XB,YB), (R1E,R2E,ZA,XB,YB), (R1F,R2E,ZA,XB,YB), (R1G,R2E,ZA,XB,YB), (R1H,R2E,ZA,XB,YB), (R1I,R2E,ZA,XB,YB), (R1J,R2E,ZA,XB,YB), (R1K,R2E,ZA,XB,YB), (R1L,R2E,ZA,XB,YB), (R1M,R2E,ZA,XB,YB), (R1N,R2E,ZA,XB,YB), (R1O,R2E,ZA,XB,YB), (R1P,R2E,ZA,XB,YB), (R1Q,R2E,ZA,XB,YB), (R1A,R2F,ZA,XB,YB), (R1B,R2F,ZA,XB,YB), (R1C,R2F,ZA,XB,YB), (R1D,R2F,ZA,XB,YB), (R1E,R2F,ZA,XB,YB), (R1F,R2F,ZA,XB,YB), (R1G,R2F,ZA,XB,YB), (R1H,R2F,ZA,XB,YB), (R1I,R2F,ZA,XB,YB), (R1J,R2F,ZA,XB,YB), (R1K,R2F,ZA,XB,YB), (R1L,R2F,ZA,XB,YB), (R1M,R2F,ZA,XB,YB), (R1N,R2F,ZA,XB,YB), (R1O,R2F,ZA,XB,YB), (R1P,R2F,ZA,XB,YB), (R1Q,R2F,ZA,XB,YB), (R1A,R2G,ZA,XB,YB), (R1D,R2G,ZA,XB,YB), (R1C,R2G,ZA,XB,YB), (R1D,R2G,ZA,XB,YB), (R1E,R2G,ZA,XB,YB), (R1F,R2G,ZA,XB,YB), (R1G,R2G,ZA,XB,YB), (R1H,R2G,ZA,XB,YB), (R1I,R2G,ZA,XB,YB), (R1J,R2G,ZA,XB,YB), (R1K,R2G,ZA,XB,YB), (R1L,R2G,ZA,XB,YB), (R1M,R2G,ZA,XB,YB), (R1N,R2G,ZA,XB,YB), (R1O,R2G,ZA,XB,YB), (R1P,R2G,ZA,XB,YB), (R1Q,R2G,ZA,XB,YB), (R1A,R2H,ZA,XB,YB), (R1B,R2H,ZA,XB,YB), (R1C,R2H,ZA,XB,YB), (R1D,R2H,ZA,XB,YB), (R1E,R2H,ZA,XB,YB), (R1F,R2H,ZA,XB,YB), (R1G,R2H,ZA,XB,YB), (R1H,R2H,ZA,XB,YB), (R1I,R2H,ZA,XB,YB), (R1J,R2H,ZA,XB,YB), (R1K,R2H,ZA,XB,YB), (R1L,R2H,ZA,XB,YB), (R1M,R2H,ZA,XB,YB), (R1N,R2H,ZA,XB,YB), (R1O,R2H,ZA,XB,YB), (R1P,R2H,ZA,XB,YB), (R1Q,R2H,ZA,XB,YB), (R1A,R2I,ZA,XB,YB), (R1B,R2I,ZA,XB,YB), (R1C,R2I,ZA,XB,YB), (R1D,R2I,ZA,XB,YB), (R1E,R2I,ZA,XB,YB), (R1F,R2I,ZA,XB,YB), (R1G,R2I,ZA,XB,YB), (R1H,R2I,ZA,XB,YB), (R1I,R2I,ZA,XB,YB), (R1J,R2I,ZA,XB,YB), (R1K,R2I,ZA,XB,YB), (R1L,R2I,ZA,XB,YB), (R1M,R2I,ZA,XB,YB), (R1N,R2I,ZA,XB,YB), (R1O,R2I,ZA,XB,YB), (R1P,R2I,ZA,XB,YB), (R1Q,R2I,ZA,XB,YB), (R1A,R2J,ZA,XB,YB), (R1B,R2J,ZA,XB,YB), (R1C,R2J,ZA,XB,YB), (R1D,R2J,ZA,XB, YB), (R1E,R2J,ZA,XB,YB), (R1F,R2J,ZA,XB,YB), (R1G,R2J,ZA,XB,YB), (R1H,R2J,ZA,XB,YB), (R1I,R2J,ZA,XB,YB), (R1J,R2J,ZA,XB,YB), (R1K,R2J,ZA,XB,YB), (R1L,R2J,ZA,XB,YB), (R1M,R2J,ZA,XB,YB), (R1N,R2J,ZA,XB,YB), (R1O,R2J,ZA,XB,YB), (R1P,R2J,ZA,XB,YB), (R1Q,R2J,ZA,XB,YB), (R1A,R2K,ZA,XB,YB), (R1B,R2K,ZA,XB,YB), (R1C,R2K,ZA,XB,YB), (R1D,R2K,ZA,XB,YB), (R1E,R2K,ZA,XB,YB), (R1F,R2K,ZA,XB,YB), (R1G,R2K,ZA,XB,YB), (R1H,R2K,ZA,XB,YB), (R1I,R2K,ZA,XB,YB), (R1J,R2K,ZA,XB,YB), (R1K,R2K,ZA,XB,YB), (R1L,R2K,ZA,XB,YB), (R1M,R2K,ZA,XB,YB), (R1N,R2K,ZA,XB,YB), (R1O,R2K,ZA,XB,YB), (R1P,R2K,ZA,XB,YB), (R1Q,R2K,ZA,XB,YB), (R1A,R2L,ZA,XB,YB), (R1B,R2L,ZA,XB,YB), (R1C,R2L,ZA,XB,YB), (R1D,R2L,ZA,XB,YB), (R1E,R2L,ZA,XB,YB), (R1F,R2L,ZA,XB,YB), (R1G,R2L,ZA,XB,YB), (R1H,R2L,ZA,XB,YB), (R1I,R2L,ZA,XB,YB), (R1J,R2L,ZA,XB,YB), (R1K,R2L,ZA,XB,YB), (R1L,R2L,ZA,XB,YB), (R1M,R2L,ZA,XB,YB), (R1N,R2L,ZA,XB,YB), (R1O,R2L,ZA,XB,YB), (R1P,R2L,ZA,XB,YB), (R1Q,R2L,ZA,XB,YB), (R1A,R2M,ZA,XB,YB), (R1B,R2M,ZA,XB,YB), (R1C,R2M,ZA,XB,YB), (R1D,R2M,ZA,XB,YB), (R1E,R2M,ZA,XB,YB), (R1F,R2M,ZA,XB,YB), (R1G,R2M,ZA,XB,YB), (R1H,R2M,ZA,XB,YB), (R1J,R2M,ZA,XB,YB), (R1K,R2M,ZA,XB,YB), (R1L,R2M,ZA,XB,YB), (R1M,R2M,ZA,XB,YB), (R1N,R2M,ZA,XB,YB), (R1O,R2M,ZA,XB,YB), (R1P,R2M,ZA,XB,YB), (R1Q,R2M,ZA,XB,YB), (R1A,R2N,ZA,XB,YB), (R1B,R2N,ZA,XB,YB), (R1C,R2N,ZA,XB,YB), (R1D,R2N,ZA,XB,YB), (R1F,R2N,ZA,XB,YB), (R1F,R2N,ZA,XB,YB), (R1G,R2N,ZA,XB,YB), (R1H,R2N,ZA,XB,YB), (R1I,R2N,ZA,XB,YB), (R1J,R2N,ZA,XB,YB), (R1K,R2N,ZA,XB,YB), (R1L,R2N,ZA,XB,YB), (R1M,R2N,ZA,XB,YB), (R1N,R2N,ZA,XB,YB), (R1O,R2N,ZA,XB,YB), (R1P,R2N,ZA,XB,YB), (R1Q,R2N,ZA,XB,YB), (R1A,R2O,ZA,XB,YB), (R1B,R2O,ZA,XB,YB), (R1C,R2O,ZA,XB,YB), (R1D,R2O,ZA,XB,YB), (R1E,R2O,ZA,XB,YB), (R1F,R2O,ZA,XB,YB), (R1G,R2O,ZA,XB,YB), (R1H,R2O,ZA,XB,YB), (R1I,R2O,ZA,XB,YB), (R1J,R2O,ZA,XB,YB), (R1K,R2O,ZA,XB,YB), (R1L,R2O,ZA,XB,YB), (R1M,R2O,ZA,XB,YB), (R1N,R2O,ZA,XB,YB), (R1O,R2O,ZA,XB,YB), (R1P,R2O,ZA,XB,YB), (R1Q,R2O,ZA,XB,YB), (R1A,R2P,ZA,XB,YB), (R1B,R2P,ZA,XB,YB), (R1C,R2P,ZA,XB,YB), (R1D,R2P,ZA,XB,YB), (R1E,R2P,ZA,XB,YB), (R1F,R2P,ZA,XB,YB), (R1G,R2P,ZA,XB,YB), (R1H,R2P,ZA,XB,YB), (R1I,R2P,ZA,XB,YB), (R1J,R2P,ZA,XB,YB), (R1K,R2P,ZA,XB,YB), (R1L,R2P,ZA,XB,YB), (R1M,R2P,ZA,XB,YB), (R1N,R2P,ZA,XB,YB), (R1O,R2P,ZA,XB,YB), (R1P,R2P,ZA,XB,YB), (R1Q,R2P,ZA,XB,YB), (R1A,R2Q,ZA,XB,YB), (R1B,R2Q,ZA,XB,YB), (R1C,R2Q,ZA,XB,YB), (R1D,R2Q,ZA,XB,YB), (R1E,R2Q,ZA,XB,YB), (R1F,R2Q,ZA,XB,YB), (R1G,R2Q,ZA,XB,YB), (R1H,R2Q,ZA,XB,YB), (R1I,R2Q,ZA,XB,YB), (R1J,R2Q,ZA,XB,YB), (R1K,R2Q,ZA,XB,YB), (R1L,R2Q,ZA,XB,YB), (R1M,R2Q,ZA,XB,YB), (R1N,R2Q,ZA,XB,YB), (R1O,R2Q,ZA,XB,YB), (R1P,R2Q,ZA,XB,YB), (R1Q,R2Q,ZA,XB,YB), (R1A,R2A,ZB,XB,YB), (R1B,R2A,ZB,XB,YB), (R1C,R2A,ZB,XB,YB), (R1D,R2A,ZB,XB,YB), (R1E,R2A,ZB,XB,YB), (R1F,R2A,ZB,XB,YB), (R1G,R2A,ZB,XB,YB), (R1H,R2A,ZB,XB,YB), (R1I,R2A,ZB,XB,YB), (R1J,R2A,ZB,XB,YB), (R1K,R2A,ZB,XB,YB), (R1L,R2A,ZB,XB,YB), (R1M,R2A,ZB,XB,YB), (R1N,R2A,ZB,XB,YB), (R1O,R2A,ZB,XB,YB), (R1P,R2A,ZB,XB,YB), (R1Q,R2A,ZB,XB,YB), (R1A,R2B,ZB,XB,YB), (R1B,R2B,ZB,XB,YB), (R1C,R2B,ZB,XB,YB), (R1D,R2B,ZB,XB,YB), (R1E,R2B,ZB,XB,YB), (R1F,R2B,ZB,XB,YB), (R1G,R2B,ZB,XB,YB), (R1H,R2B,ZB,XB,YB), (R1I,R2B,ZB,XB,YB), (R1J,R2B,ZB,XB,YB), (R1K,R2B,ZB,XB,YB), (R1L,R2B,ZB,XB,YB), (R1M,R2B,ZB,XB,YB), (R1N,R2B,ZB,XB,YB), (R1O,R2B,ZB,XB,YB), (R1P,R2B,ZB,XB,YB), (R1Q,R2B,ZB,XB,YB), (R1A,R2C,ZB,XB,YB), (R1B,R2C,ZB,XB,YB), (R1C,R2C,ZB,XB,YB), (R1D,R2C,ZB,XB,YB), (R1E,R2C,ZB,XB,YB), (R1F,R2C,ZB,XB,YB), (R1G,R2C,ZB,XB,YB), (R1H,R2C,ZB,XB,YB), (R1I,R2C,ZB,XB,YB), (R1J,R2C,ZB,XB,YB), (R1K,R2C,ZB,XB,YB), (R1L,R2C,ZB,XB,YB), (R1M,R2C,ZB,XB,YB), (R1N,R2C,ZB,XB,YB), (R1O,R2C,ZB,XB,YB), (R1P,R2C,ZB,XB,YB), (R1Q,R2C,ZB,XB,YB), (R1A,R2D,ZB,XB,YB), (R1B,R2D,ZB,XB,YB), (R1C,R2D,ZB,XB,YB), (R1D,R2D,ZB,XB,YB), (R1E,R2D,ZB,XB,YB), (R1F,R2D,ZB,XB,YB), (R1G,R2D,ZB,XB,YB), (R1H,R2D,ZB,XB,YB), (R1I,R2D,ZB,XB,YB), (R1J,R2D,ZB,XB,YB), (R1K,R2D,ZB,XB,YB), (R1L,R2D,ZB,XB,YB), (R1M,R2D,ZB,XB,YB), (R1N,R2D,ZB,XB,YB), (R1O,R2D,ZB,XB,YB), (R1P,R2D,ZB,XB,YB), (R1Q,R2D,ZB,XB,YB), (R1A,R2E,ZB,XB,YB), (R1B,R2E,ZB,XB,YB), (R1C,R2E,ZB,XB,YB), (R1D,R2E,ZB,XB,YB), (R1E,R2E,ZB,XB,YB), (R1F,R2E,ZB,XB,YB), (R1G,R2E,ZB,XB,YB), (R1H,R2E,ZB,XB,YB), (R1I,R2E,ZB,XB,YB), (R1J,R2E,ZB,XB,YB), (R1K,R2E,ZB,XB,YB), (R1L,R2E,ZB,XB,YB), (R1M,R2E,ZB,XB,YB), (R1N,R2E,ZB,XB,YB), (R1O,R2E,ZB,XB,YB), (R1P,R2E,ZB,XB,YB), (R1Q,R2E,ZB,XB,YB), (R1A,R2F,ZB,XB,YB), (R1B,R2F,ZB,XB,YB), (R1C,R2F,ZB,XB,YB), (R1D,R2F,ZB,XB,YB), (R1E,R2F,ZB,XB,YB), (R1F,R2F,ZB,XB,YB), (R1G,R2F,ZB,XB,YB), (R1H,R2F,ZB,XB,YB), (R1I,R2F,ZB,XB,YB), (R1J,R2F,ZB,XB,YB), (R1K,R2F,ZB,XB,YB), (R1L,R2F,ZB,XB,YB), (R1M,R2F,ZB,XB,YB), (R1N,R2F,ZB,XB,YB), (R1O,R2F,ZB,XB,YB), (R1P,R2F,ZB,XB,YB), (R1Q,R2F,ZB,XB,YB), (R1A,R2G,ZB,XB,YB), (R1B,R2G,ZB,XB,YB), (R1C,R2G,ZB,XB,YB), (R1D,R2G,ZB,XB,YB), (R1E,R2G,ZB,XB,YB), (R1F,R2G,ZB,XB,YB), (R1G,R2G,ZB,XB,YB), (R1H,R2G,ZB,XB,YB), (R1I,R2G,ZB,XB,YB), (R1J,R2G,ZB,XB,YB), (R1K,R2G,ZB,XB,YB), (R1L,R2G,ZB,XB,YB), (R1M,R2G,ZB,XB,YB), (R1N,R2G,ZB,XB,YB), (R1O,R2G,ZB,XB,YB), (R1P,R2G,ZB,XB,YB), (R1Q,R2G,ZB,XB,YB), (R1A,R2H,ZB,XB,YB), (R1B,R2H,ZB,XB,YB), (R1C,R2H,ZB,XB,YB), (R1D,R2H,ZB,XB,YB), (R1E,R2H,ZB,XB,YB), (R1F,R2H,ZB,XB,YB), (R1G,R2H,ZB,XB,YB), (R1H,R2H,ZB,XB,YB), (R1I,R2H,ZB,XB,YB), (R1J,R2H,ZB,XB,YB), (R1K,R2H,ZB,XB,YB), (R1L,R2H,ZB,XB,YB), (R1M,R2H,ZB,XB,YB), (R1N,R2H,ZB,XB,YB), (R1O,R2H,ZB,XB,YB), (R1P,R2H,ZB,XB,YB), (R1Q,R2H,ZB,XB,YB), (R1A,R2I,ZB,XB,YB), (R1B,R2I,ZB,XB,YB), (R1C,R2I,ZB,XB,YB), (R1D,R2I,ZB,XB,YB), (R1E,R2I,ZB,XB,YB), (R1F,R2I,ZB,XB,YB), (R1G,R2I,ZB,XB,YB), (R1H,R2I,ZB,XB,YB), (R1I,R2I,ZB,XB,YB), (R1J,R2I,ZB,XB,YB), (R1K,R2I,ZB,XB,YB), (R1L,R2I,ZB,XB,YB), (R1M,R2I,ZB,XB,YB), (R1N,R2I,ZB,XB,YB), (R1O,R2I,ZB,XB,YB), (R1P,R2I,ZB,XB,YB), (R1Q,R2I,ZB,XB,YB), (R1A,R2J,ZB,XB,YB), (R1B,R2J,ZB,XB,YB), (R1C,R2J,ZB,XB,YB), (R1D,R2J,ZB,XB,YB), (R1E,R2J,ZB,XB,YB), (R1F,R2J,ZB,XB,YB), (R1G,R2J,ZB,XB,YB), (R1H,R2J,ZB,XB,YB), (R1I,R2J,ZB,XB,YB), (R1J,R2J,ZB,XB,YB), (R1K,R2J,ZB,XB,YB), (R1L,R2J,ZB,XB,YB), (R1M,R2J,ZB,XB,YB), (R1N,R2J,ZB,XB,YB), (R1O,R2J,ZB,XB,YB), (R1P,R2J,ZB,XB,YB), (R1Q,R2J,ZB,XB,YB), (R1A,R2K,ZB,XB,YB), (R1B,R2K,ZB,XB,YB), (R1C,R2K,ZB,XB,YB), (R1D,R2K,ZB,XB,YB), (R1E,R2K,ZB,XB,YB), (R1F,R2K,ZB,XB,YB), (R1G,R2K,ZB,XB,YB), (R1H,R2K,ZB,XB,YB), (R1I,R2K,ZB,XB,YB), (R1J,R2K,ZB,XB,YB), (R1K,R2K,ZB,XB,YB), (R1L,R2K,ZB,XB,YB), (R1M,R2K,ZB,XB,YB), (R1N,R2K,ZB,XB,YB), (R1O,R2K,ZB,XB,YB), (R1P,R2K,ZB,XB,YB), (R1Q,R2K,ZB,XB,YB), (R1A, R2L,ZB,XB,YB), (R1B,R2L,ZB,XB,YB), (R1C,R2L,ZB, XB,YB), (R1D,R2L,ZB,XB,YB), (R1E,R2L,ZB,XB,YB), (R1F,R2L,ZB,XB,YB), (R1G,R2L,ZB,XB,YB), (R1H,R2L, ZB,XB,YB), (R1I,R2L,ZB,XB,YB), (R1J,R2L,ZB,XB,YB), (R1K,R2L,ZB,XB,YB), (R1L,R2L,ZB,XB,YB), (R1M, R2L,ZB,XB,YB), (R1N,R2L,ZB,XB,YB), (R1O,R2L,ZB, XB,YB), (R1P,R2L,ZB,XB,YB), (R1Q,R2L,ZB,XB,YB), (R1A,R2M,ZB,XB,YB), (R1B,R2M,ZB,XB,YB), (R1C, R2M,ZB,XB,YB), (R1D,R2M,ZB,XB,YB), (R1E,R2M,ZB, XB,YB), (R1F,R2M,ZB,XB,YB), (R1G,R2M,ZB,XB,YB), (R1H,R2M,ZB,XB,YB), (R1I,R2M,ZB,XB,YB), (R1J, R2M,ZB,XB,YB), (R1K,R2M,ZB,XB,YB), (R1L,R2M,ZB, XB,YB), (R1M,R2M,ZB,XB,YB), (R1N,R2M,ZB,XB,YB), (R1O,R2M,ZB,XB,YB), (R1P,R2M,ZB,XB,YB), (R1Q, R2M,ZB,XB,YB), (R1A,R2N,ZB,XB,YB), (R1B,R2N,ZB, XB,YB), (R1C,R2N,ZB,XB,YB), (R1D,R2N,ZB,XB,YB), (R1E,R2N,ZB,XB,YB), (R1F,R2N,ZB,XB,YB), (R1G, R2N,ZB,XB,YB), (R1H,R2N,ZB,XB,YB), (R1I,R2N,ZB, XB,YB), (R1J,R2N,ZB,XB,YB), (R1K,R2N,ZB,XB,YB), (R1L,R2N,ZB,XB,YB), (R1M,R2N,ZB,XB,YB), (R1N, R2N,ZB,XB,YB), (R1O,R2N,ZB,XB,YB), (R1P,R2N,ZB, XB,YB), (R1Q,R2N,ZB,XB,YB), (R1A,R2O,ZB,XB,YB), (R1B,R2O,ZB,XB,YB), (R1C,R2O,ZB,XB,YB), (R1D, R2O,ZB,XB,YB), (R1E,R2O,ZB,XB,YB), (R1F,R2O,ZB, XB,YB), (R1G,R2O,ZB,XB,YB), (R1H,R2O,ZB,XB,YB), (R1I,R2O,ZB,XB,YB), (R1J,R2O,ZB,XB,YB), (R1K,R2O, ZB,XB,YB), (R1L,R2O,ZB,XB,YB), (R1M,R2O,ZB,XB, YB), (R1N,R2O,ZB,XB,YB), (R1O,R2O,ZB,XB,YB), (R1P,R2O,ZB,XB,YB), (R1Q,R2O,ZB,XB,YB), (R1A,R2P, ZB,XB,YB), (R1B,R2P,ZB,XB,YB), (R1C,R2P,ZB,XB, YB), (R1D,R2P,ZB,XB,YB), (R1E,R2P,ZB,XB,YB), (R1F, R2P,ZB,XB,YB), (R1G,R2P,ZB,XB,YB), (R1H,R2P,ZB, XB,YB), (R1I,R2P,ZB,XB,YB), (R1J,R2P,ZB,XB,YB), (R1K,R2P,ZB,XB,YB), (R1L,R2P,ZB,XB,YB), (R1M,R2P, ZB,XB,YB), (R1N,R2P,ZB,XB,YB), (R1O,R2P,ZB,XB, YB), (R1P,R2P,ZB,XB,YB), (R1Q,R2P,ZB,XB,YB), (R1A, R2Q,ZB,XB,YB), (R1B,R2Q,ZB,XB,YB), (R1C,R2Q,ZB, XB,YB), (R1D,R2Q,ZB,XB,YB), (R1E,R2Q,ZB,XB,YB), (R1F,R2Q,ZB,XB,YB), (R1G,R2Q,ZB,XB,YB), (R1H, R2Q,ZB,XB,YB), (R1I,R2Q,ZB,XB,YB), (R1J,R2Q,ZB, XB,YB), (R1K,R2Q,ZB,XB,YB), (R1L,R2Q,ZB,XB,YB), (R1M,R2Q,ZB,XB,YB), (R1N,R2Q,ZB,XB,YB), (R1O, R2Q,ZB,XB,YB), (R1P,R2Q,ZB,XB,YB), (R1Q,R2Q,ZB, XB,YB), (R1A,R2A,ZC,XB,YB), (R1B,R2A,ZC,XB,YB), (R1C,R2A,ZC,XB,YB), (R1D,R2A,ZC,XB,YB), (R1E, R2A,ZC,XB,YB), (R1F,R2A,ZC,XB,YB), (R1G,R2A,ZC, XB,YB), (R1H,R2A,ZC,XB,YB), (R1I,R2A,ZC,XB,YB), (R1J,R2A,ZC,XB,YB), (R1K,R2A,ZC,XB,YB), (R1L,R2A, ZC,XB,YB), (R1M,R2A,ZC,XB,YB), (R1N,R2A,ZC,XB, YB), (R1O,R2A,ZC,XB,YB), (R1P,R2A,ZC,XB,YB), (R1Q,R2A,ZC,XB,YB), (R1A,R2B,ZC,XB,YB), (R1B, R2B,ZC,XB,YB), (R1C,R2B,ZC,XB,YB), (R1D,R2B,ZC, XB,YB), (R1E,R2B,ZC,XB,YB), (R1F,R2B,ZC,XB,YB), (R1G,R2B,ZC,XB,YB), (R1H,R2B,ZC,XB,YB), (R1I,R2B, ZC,XB,YB), (R1J,R2B,ZC,XB,YB), (R1K,R2B,ZC,XB, YB), (R1L,R2B,ZC,XB,YB), (R1M,R2B,ZC,XB,YB), (R1N,R2B,ZC,XB,YB), (R1O,R2B,ZC,XB,YB), (R1P,R2B, ZC,XB,YB), (R1Q,R2B,ZC,XB,YB), (R1A,R2C,ZC,XB, YB), (R1B,R2C,ZC,XB,YB), (R1C,R2C,ZC,XB,YB), (R1D,R2C,ZC,XB,YB), (R1E,R2C,ZC,XB,YB), (R1F,R2C, ZC,XB,YB), (R1G,R2C,ZC,XB,YB), (R1H,R2C,ZC,XB, YB), (R1I,R22C,ZC,XB,YB), (R1J,R2C,ZC,XB,YB), (R1K,R2C,ZC,XB,YB), (R1L,R2C,ZC,XB,YB), (R1M, R22C,ZC,XB,YB), (R1N,R2C,ZC,XB,YB), (R1O,R2C,ZC, XB,YB), (R1P,R2C,ZC,XB,YB), (R1Q,R2C,ZC,XB,YB), (R1A,R2D,ZC,XB,YB), (R1B,R2D,ZC,XB,YB), (R1C, R2D,ZC,XB,YB), (R1D,R2D,ZC,XB,YB), (R1E,R2D,ZC, XB,YB), (R1F,R2D,ZC,XB,YB), (R1G,R2D,ZC,XB,YB), (R1H,R2D,ZC,XB,YB), (R1I,R2D,ZC,XB,YB), (R1J,R2D, ZC,XB,YB), (R1K,R2D,ZC,XB,YB), (R1L,R2D,ZC,XB, YB), (R1M,R2D,ZC,XB,YB), (R1N,R2D,ZC,XB,YB), (R1O,R2D,ZC,XB,YB), (R1P,R2D,ZC,XB,YB), (R1Q, R2D,ZC,XB,YB), (R1A,R2E,ZC,XB,YB), (R1B,R2E,ZC, XB,YB), (R1C,R2E,ZC,XB,YB), (R1D,R2E,ZC,XB,YB), (R1E,R2E,ZC,XB,YB), (R1F,R2E,ZC,XB,YB), (R1G,R2E, ZC,XB,YB), (R1H,R2E,ZC,XB,YB), (R1L R2E,ZC,XB, YB), (R1J,R2E,ZC,XB,YB), (R1K,R2E,ZC,XB,YB), (R1L, R2E,ZC,XB,YB), (R1M,R2E,ZC,XB,YB), (R1N,R2E,ZC, XB,YB), (R1O,R2E,ZC,XB,YB), (R1P,R2E,ZC,XB,YB), (R1Q,R2E,ZC,XB,YB), (R1A,R2F,ZC,XB,YB), (R1B,R2F, ZC,XB,YB), (R1C,R2F,ZC,XB,YB), (R1D,R2F,ZC,XB, YB), (R1E,R2F,ZC,XB,YB), (R1F,R2F,ZC,XB,YB), (R1G, R2F,ZC,XB,YB), (R1H,R2F,ZC,XB,YB), (R1I,R2F,ZC,XB, YB), (R1J,R2F,ZC,XB,YB), (R1K,R2F,ZC,XB,YB), (R1L, R2F,ZC,XB,YB), (R1M,R2F,ZC,XB,YB), (R1N,R2F,ZC, XB,YB), (R1O,R2F,ZC,XB,YB), (R1P,R2F,ZC,XB,YB), (R1Q,R2F,ZC,XB,YB), (R1A,R2G,ZC,XB,YB), (R1B, R2G,ZC,XB,YB), (R1C,R2G,ZC,XB,YB), (R1D,R2G,ZC, XB,YB), (R1E,R2G,ZC,XB,YB), (R1F,R2G,ZC,XB,YB), (R1G,R2G,ZC,XB,YB), (R1H,R2G,ZC,XB,YB), (R1I, R2G,ZC,XB,YB), (R1J,R2G,ZC,XB,YB), (R1K,R2G,ZC, XB,YB), (R1L,R2G,ZC,XB,YB), (R1M,R2G,ZC,XB,YB), (R1N,R2G,ZC,XB,YB), (R1O,R2G,ZC,XB,YB), (R1P, R2G,ZC,XB,YB), (R1Q,R2G,ZC,XB,YB), (R1A,R2H,ZC, XB,YB), (R1B,R2H,ZC,XB,YB), (R1C,R2H,ZC,XB,YB), (R1D,R2H,ZC,XB,YB), (R1E,R2H,ZC,XB,YB), (R1F, R2H,ZC,XB,YB), (R1G,R2H,ZC,XB,YB), (R1H,R2H,ZC, XB,YB), (R1I,R2H,ZC,XB,YB), (R1J,R2H,ZC,XB,YB), (R1K,R2H,ZC,XB,YB), (R1L,R2H,ZC,XB,YB), (R1M, R2H,ZC,XB,YB), (R1N,R2H,ZC,XB,YB), (R1O,R2H,ZC, XB,YB), (R1P,R2H,ZC,XB,YB), (R1Q,R2H,ZC,XB,YB), (R1A,R2I,ZC,XB,YB), (R1B,R2I,ZC,XB,YB), (R1C,R2I, ZC,XB,YB), (R1D,R2I,ZC,XB,YB), (R1E,R2I,ZC,XB, YB), (R1F,R2I,ZC,XB,YB), (R1G,R2I,ZC,XB,YB), (R1H, R2I,ZC,XB,YB), (R1I,R2I,ZC,XB,YB), (R1J,R2I,ZC,XB, YB), (R1K,R2I,ZC,XB,YB), (R1L,R2I,ZC,XB,YB), (R1M, R2I,ZC,XB,YB), (R1N,R2I,ZC,XB,YB), (R1O,R2I,ZC,XB, YB), (R1P,R2I,ZC,XB,YB), (R1Q,R2I,ZC,XB,YB), (R1A, R2J,ZC,XB,YB), (R1B,R2J,ZC,XB,YB), (R1C,R2J,ZC,XB, YB), (R1D,R2J,ZC,XB,YB), (R1E,R2J,ZC,XB,YB), (R1F, R2J,ZC,XB,YB), (R1G,R2J,ZC,XB,YB), (R1H,R2J,ZC, XB,YB), (R1I,R2J,ZC,XB,YB), (R1J,R2J,ZC,XB,YB), (R1K,R2J,ZC,XB,YB), (R1L,R2J,ZC,XB,YB), (R1M,R2J, ZC,XB,YB), (R1N,R2J,ZC,XB,YB), (R1O,R2J,ZC,XB, YB), (R1P,R2J,ZC,XB,YB), (R1Q,R2J,ZC,XB,YB), (R1A, R2K,ZC,XB,YB), (R1B,R2K,ZC,XB,YB), (R1C,R2K,ZC, XB,YB), (R1D,R2K,ZC,XB,YB), (R1E,R2K,ZC,XB,YB), (R1F,R2K,ZC,XB,YB), (R1G,R2K,ZC,XB,YB), (R1H, R2K,ZC,XB,YB), (R1I,R2K,ZC,XB,YB), (R1J,R2K,ZC, XB,YB), (R1K,R2K,ZC,XB,YB), (R1L,R2K,ZC,XB,YB), (R1M,R2K,ZC,XB,YB), (R1N,R2K,ZC,XB,YB), (R1O, R2K,ZC,XB,YB), (R1P,R2K,ZC,XB,YB), (R1Q,R2K,ZC, XB,YB), (R1A,R2L,ZC,XB,YB), (R1B,R2L,ZC,XB,YB), (R1C,R2L,ZC,XB,YB), (R1D,R2L,ZC,XB,YB), (R1E,R2L, ZC,XB,YB), (R1F,R2L,ZC,XB,YB), (R1G,R2L,ZC,XB, YB), (R1H,R2L,ZC,XB,YB), (R1I,R2L,ZC,XB,YB), (R1J, R2L,ZC,XB,YB), (R1K,R2L,ZC,XB,YB), (R1L,R2L,ZC, XB,YB), (R1M,R2L,ZC,XB,YB), (R1N,R2L,ZC,XB,YB), (R1O,R2L,ZC,XB,YB), (R1P,R2L,ZC,XB,YB), (R1Q,R2L, ZC,XB,YB), (R1A,R2M,ZC,XB,YB), (R1B,R2M,ZC,XB, YB), (R1C,R2M,ZC,XB,YB), (R1D,R2M,ZC,XB,YB), (R1E,R2M,ZC,XB,YB), (R1F,R2M,ZC,XB,YB), (R1G, R2M,ZC,XB,YB), (R1H,R2M,ZC,XB,YB), (R1I,R2M,ZC, XB,YB), (R1J,R2M,ZC,XB,YB), (R1K,R2M,ZC,XB,YB), (R1L,R2M,ZC,XB,YB), (R1M,R2M,ZC,XB,YB), (R1N,R2M,ZC,XB,YB), (R1O,R2M,ZC,XB,YB), (R1P,R2M,ZC,XB,YB), (R1Q,R2M,ZC,XB,YB), (R1A,R2N,ZC,XB,YB), (R1B,R2N,ZC,XB,YB), (R1C,R2N,ZC,XB,YB), (R1D,R2N,ZC,XB,YB), (R1E,R2N,ZC,XB,YB), (R1F,R2N,ZC,XB,YB), (R1G,R2N,ZC,XB,YB), (R1H,R2N,ZC,XB,YB), (R1I,R2N,ZC,XB,YB), (R1J,R2N,ZC,XB,YB), (R1K,R2N,ZC,XB,YB), (R1L,R2N,ZC,XB,YB), (R1M,R2N,ZC,XB,YB), (R1N,R2N,ZC,XB,YB), (R1O,R2N,ZC,XB,YB), (R1P,R2N,ZC,XB,YB), (R1Q,R2N,ZC,XB,YB), (R1A,R2O,ZC,XB,YB), (R1B,R2O,ZC,XB,YB), (R1C,R2O,ZC,XB,YB), (R1D,R2O,ZC,XB,YB), (R1E,R2O,ZC,XB,YB), (R1F,R2O,ZC,XB,YB), (R1G,R2O,ZC,XB,YB), (R1H,R2O,ZC,XB,YB), (R1I,R2O,ZC,XB,YB), (R1J,R2O,ZC,XB,YB), (R1K,R2O,ZC,XB,YB), (R1L,R2O,ZC,XB,YB), (R1M,R2O,ZC,XB,YB), (R1N,R2O,ZC,XB,YB), (R1O,R2O,ZC,XB,YB), (R1P,R2O,ZC,XB,YB), (R1Q,R2O,ZC,XB,YB), (R1A,R2P,ZC,XB,YB), (R1B,R2P,ZC,XB,YB), (R1C,R2P,ZC,XB,YB), (R1D,R2P,ZC,XB,YB), (R1E,R2P,ZC,XB,YB), (R1F,R2P,ZC,XB,YB), (R1G,R2P,ZC,XB,YB), (R1H,R2P,ZC,XB,YB), (R1I,R2P,ZC,XB,YB), (R1J,R2P,ZC,XB,YB), (R1K,R2P,ZC,XB,YB), (R1L,R2P,ZC,XB,YB), (R1M,R2P,ZC,XB,YB), (R1N,R2P,ZC,XB,YB), (R1O,R2P,ZC,XB,YB), (R1P,R2P,ZC,XB,YB), (R1Q,R2P,ZC,XB,YB), (R1A,R2Q,ZC,XB,YB), (R1B,R2Q,ZC,XB,YB), (R1C,R2Q,ZC,XB,YB), (R1D,R2Q,ZC,XB,YB), (R1E,R2Q,ZC,XB,YB), (R1F,R2Q,ZC,XB,YB), (R1G,R2Q,ZC,XB,YB), (R1H,R2Q,ZC,XB,YB), (R1I,R2Q,ZC,XB,YB), (R1J,R2Q,ZC,XB,YB), (R1K,R2Q,ZC,XB,YB), (R1L,R2Q,ZC,XB,YB), (R1M,R2Q,ZC,XB,YB), (R1N,R2Q,ZC,XB,YB), (R1O,R2Q,ZC,XB,YB), (R1P,R2Q,ZC,XB,YB), (R1Q,R2Q,ZC,XB,YB), (R1A,R2A,ZD,XB,YB), (R1B,R2A,ZD,XB,YB), (R1C,R2A,ZD,XB,YB), (R1D,R2A,ZD,XB,YB), (R1E,R2A,ZD,XB,YB), (R1F,R2A,ZD,XB,YB), (R1G,R2A,ZD,XB,YB), (R1H,R2A,ZD,XB,YB), (R1I,R2A,ZD,XB,YB), (R1J,R2A,ZD,XB,YB), (R1K,R2A,ZD,XB,YB), (R1L,R2A,ZD,XB,YB), (R1M,R2A,ZD,XB,YB), (R1N,R2A,ZD,XB,YB), (R1O,R2A,ZD,XB,YB), (R1P,R2A,ZD,XB,YB), (R1Q,R2A,ZD,XB,YB), (R1A,R2B,ZD,XB,YB), (R1B,R2B,ZD,XB,YB), (R1C,R2B,ZD,XB,YB), (R1D,R2B,ZD,XB,YB), (R1E,R2B,ZD,XB,YB), (R1F,R2B,ZD,XB,YB), (R1G,R2B,ZD,XB,YB), (R1H,R2B,ZD,XB,YB), (R1I,R2B,ZD,XB,YB), (R1J,R2B,ZD,XB,YB), (R1K,R2B,ZD,XB,YB), (R1L,R2B,ZD,XB,YB), (R1M,R2B,ZD,XB,YB), (R1N,R2B,ZD,XB,YB), (R1O,R2B,ZD,XB,YB), (R1P,R2B,ZD,XB,YB), (R1Q,R2B,ZD,XB,YB), (R1A,R2C,ZD,XB,YB), (R1B,R2C,ZD,XB,YB), (R1C,R2C,ZD,XB,YB), (R1D,R2C,ZD,XB,YB), (R1E,R2C,ZD,XB,YB), (R1F,R2C,ZD,XB,YB), (R1G,R2C,ZD,XB,YB), (R1H,R2C,ZD,XB,YB), (R1I,R2C,ZD,XB,YB), (R1J,R2C,ZD,XB,YB), (R1K,R2C,ZD,XB,YB), (R1L,R2C,ZD,XB,YB), (R1M,R22C,ZD,XB,YB), (R1N,R2C,ZD,XB,YB), (R1O,R2C,ZD,XB,YB), (R1P,R2C,ZD,XB,YB), (R1Q,R2C,ZD,XB,YB), (R1A,R2D,ZD,XB,YB), (R1B,R2D,ZD,XB,YB), (R1C,R2D,ZD,XB,YB), (R1D,R2D,ZD,XB,YB), (R1E,R2D,ZD,XB,YB), (R1F,R2D,ZD,XB,YB), (R1G,R2D,ZD,XB,YB), (R1H,R2D,ZD,XB,YB), (R1I,R2D,ZD,XB,YB), (R1J,R2D,ZD,XB,YB), (R1K,R2D,ZD,XB,YB), (R1L,R2D,ZD,XB,YB), (R1M,R2D,ZD,XB,YB), (R1N,R2D,ZD,XB,YB), (R1O,R2D,ZD,XB,YB), (R1P,R2D,ZD,XB,YB), (R1Q,R2D,ZD,XB,YB), (R1A,R2E,ZD,XB,YB), (R1B,R2E,ZD,XB,YB), (R1C,R2E,ZD,XB,YB), (R1D,R2E,ZD,XB,YB), (R1E,R2E,ZD,XB,YB), (R1F,R2E,ZD,XB,YB), (R1G,R2E,ZD,XB,YB), (R1H,R2E,ZD,XB,YB), (R1I,R2E,ZD,XB,YB), (R1J,R2E,ZD,XB,YB), (R1K,R2E,ZD,XB,YB), (R1L,R2E,ZD,XB,YB), (R1M,R2E,ZD,XB,YB), (R1N,R2E,ZD,XB,YB), (R1O,R2E,ZD,XB,YB), (R1P,R2E,ZD,XB,YB), (R1Q,R2E,ZD,XB,YB), (R1A,R2F,ZD,XB,YB), (R1B,R2F,ZD,XB,YB), (R1C,R2F,ZD,XB,YB), (R1D,R2F,ZD,XB,YB), (R1E,R2F,ZD,XB,YB), (R1F,R2F,ZD,XB,YB), (R1G,R2F,ZD,XB,YB), (R1H,R2F,ZD,XB,YB), (R1I,R2F,ZD,XB,YB), (R1J,R2F,ZD,XB,YB), (R1K,R2F,ZD,XB,YB), (R1L,R2F,ZD,XB,YB), (R1M,R2F,ZD,XB,YB), (R1N,R2F,ZD,XB,YB), (R1O,R2F,ZD,XB,YB), (R1P,R2F,ZD,XB,YB), (R1Q,R2F,ZD,XB,YB), (R1A,R2G,ZD,XB,YB), (R1B,R2G,ZD,XB,YB), (R1C,R2G,ZD,XB,YB), (R1D,R2G,ZD,XB,YB), (R1E,R2G,ZD,XB,YB), (R1F,R2G,ZD,XB,YB), (R1G,R2G,ZD,XB,YB), (R1H,R2G,ZD,XB,YB), (R1I,R2G,ZD,XB,YB), (R1J,R2G,ZD,XB,YB), (R1K,R2G,ZD,XB,YB), (R1L,R2G,ZD,XB,YB), (R1M,R2G,ZD,XB,YB), (R1N,R2G,ZD,XB,YB), (R1O,R2G,ZD,XB,YB), (R1P,R2G,ZD,XB,YB), (R1Q,R2G,ZD,XB,YB), (R1A,R2H,ZD,XB,YB), (R1B,R2H,ZD,XB,YB), (R1C,R2H,ZD,XB,YB), (R1D,R2H,ZD,XB,YB), (R1E,R2H,ZD,XB,YB), (R1F,R2H,ZD,XB,YB), (R1G,R2H,ZD,XB,YB), (R1H,R2H,ZD,XB,YB), (R1I,R2H,ZD,XB,YB), (R1J,R2H,ZD,XB,YB), (R1K,R2H,ZD,XB,YB), (R1L,R2H,ZD,XB,YB), (R1M,R2H,ZD,XB,YB), (R1N,R2H,ZD,XB,YB), (R1O,R2H,ZD,XB,YB), (R1P,R2H,ZD,XB,YB), (R1Q,R2H,ZD,XB,YB), (R1A,R2I,ZD,XB,YB), (R1B,R2I,ZD,XB,YB), (R1C,R2I,ZD,XB,YB), (R1D,R2I,ZD,XB,YB), (R1E,R2I,ZD,XB,YB), (R1F,R2I,ZD,XB,YB), (R1G,R2I,ZD,XB,YB), (R1H,R2I,ZD,XB,YB), (R1I,R2I,ZD,XB,YB), (R1J,R2I,ZD,XB,YB), (R1K,R2I,ZD,XB,YB), (R1L,R2I,ZD,XB,YB), (R1M,R2I,ZD,XB,YB), (R1N,R2I,ZD,XB,YB), (R1O,R2I,ZD,XB,YB), (R1P,R2I,ZD,XB,YB), (R1Q,R2I,ZD,XB,YB), (R1A,R2J,ZD,XB,YB), (R1B,R2J,ZD,XB,YB), (R1C,R2J,ZD,XB,YB), (R1D,R2J,ZD,XB,YB), (R1E,R2J,ZD,XB,YB), (R1F,R2J,ZD,XB,YB), (R1G,R2J,ZD,XB,YB), (R1H,R2J,ZD,XB,YB), (R1I,R2J,ZD,XB,YB), (R1J,R2J,ZD,XB,YB), (R1K,R2J,ZD,XB,YB), (R1L,R2J,ZD,XB,YB), (R1M,R2J,ZD,XB,YB), (R1N,R2J,ZD,XB,YB), (R1O,R2J,ZD,XB,YB), (R1P,R2J,ZD,XB,YB), (R1Q,R2J,ZD,XB,YB), (R1A,R2K,ZD,XB,YB), (R1B,R2K,ZD,XB,YB), (R1C,R2K,ZD,XB,YB), (R1D,R2K,ZD,XB,YB), (R1E,R2K,ZD,XB,YB), (R1F,R2K,ZD,XB,YB), (R1G,R2K,ZD,XB,YB), (R1H,R2K,ZD,XB,YB), (R1I,R2K,ZD,XB,YB), (R1J,R2K,ZD,XB,YB), (R1K,R2K,ZD,XB,YB), (R1L,R2K,ZD,XB,YB), (R1M,R2K,ZD,XB,YB), (R1N,R2K,ZD,XB,YB), (R1O,R2K,ZD,XB,YB), (R1P,R2K,ZD,XB,YB), (R1Q,R2K,ZD,XB,YB), (R1A,R2L,ZD,XB,YB), (R1B,R2L,ZD,XB,YB), (R1C,R2L,ZD,XB,YB), (R1D,R2L,ZD,XB,YB), (R1E,R2L,ZD,XB,YB), (R1F,R2L,ZD,XB,YB), (R1G,R2L,ZD,XB,YB), (R1H,R2L,ZD,XB,YB), (R1I,R2L,ZD,XB,YB), (R1J,R2L,ZD,XB,YB), (R1K,R2L,ZD,XB,YB), (R1L,R2L,ZD,XB,YB), (R1M,R2L,ZD,XB,YB), (R1N,R2L,ZD,XB,YB), (R1O,R2L,ZD,XB,YB), (R1P,R2L,ZD,XB,YB), (R1Q,R2L,ZD,XB,YB), (R1A,R2M,ZD,XB,YB), (R1B,R2M,ZD,XB,YB), (R1C,R2M,ZD,XB,YB), (R1D,R2M,ZD,XB,YB), (R1E,R2M,ZD,XB,YB), (R1F,R2M,ZD,XB,YB), (R1G,R2M,ZD,XB,YB), (R1H,R2M,ZD,XB,YB), (R1I,R2M,ZD,XB,YB), (R1J,R2M,ZD,XB,YB), (R1K,R2M,ZD,XB,YB), (R1L,R2M,ZD,XB,YB), (R1M,R2M,ZD,XB,YB), (R1N,R2M,ZD,XB,YB), (R1O,R2M,ZD,XB,YB), (R1P,R2M,ZD,XB,YB), (R1Q,R2M,ZD,XB,YB), (R1A,R2N,ZD,XB,YB), (R1B,R2N,ZD,XB,YB), (R1C,R2N,ZD,XB,YB), (R1D,R2N,ZD,XB,YB), (R1E,R2N,ZD,XB,YB), (R1F,R2N,ZD,XB,YB), (R1G,R2N,ZD,XB,YB), (R1H,R2N,ZD,XB,YB), (R1I,R2N,ZD,XB,YB), (R1J,R2N,ZD,XB,YB), (R1K,R2N,ZD,XB,YB), (R1L,R2N,ZD,XB,YB), (R1M,R2N,ZD,XB,YB), (R1N,R2N,ZD,XB,YB), (R1O,R2N,ZD,XB,YB), (R1P,R2N,ZD,XB,YB), (R1Q,R2N,ZD,XB,YB), (R1A,R2O,ZD, XB,YB), (R1B,R2O,ZD,XB,YB), (R1C,R2O,ZD,XB,YB), (R1D,R2O,ZD,XB,YB), (R1E,R2O,ZD,XB,YB), (R1F,R2O,ZD,XB,YB), (R1G,R2O,ZD,XB,YB), (R1H,R2O,ZD,XB,YB), (R1I,R2O,ZD,XB,YB), (R1J,R2O,ZD,XB,YB), (R1K,R2O,ZD,XB,YB), (R1L,R2O,ZD,XB,YB), (R1M,R2O,ZD,XB,YB), (R1N,R2O,ZD,XB,YB), (R1O,R2O,ZD,XB,YB), (R1P,R2O,ZD,XB,YB), (R1Q,R2O,ZD,XB,YB), (R1A,R2P,ZD,XB,YB), (R1B,R2P,ZD,XB,YB), (R1C,R2P,ZD,XB,YB), (R1D,R2P,ZD,XB,YB), (R1E,R2P,ZD,XB,YB), (R1F,R2P,ZD,XB,YB), (R1G,R2P,ZD,XB,YB), (R1H,R2P,ZD,XB,YB), (R1I,R2P,ZD,XB,YB), (R1J,R2P,ZD,XB,YB), (R1K,R2P,ZD,XB,YB), (R1L,R2P,ZD,XB,YB), (R1M,R2P,ZD,XB,YB), (R1N,R2P,ZD,XB,YB), (R1O,R2P,ZD,XB,YB), (R1P,R2P,ZD,XB,YB), (R1Q,R2P,ZD,XB,YB), (R1A,R2Q,ZD,XB,YB), (R1B,R2Q,ZD,XB,YB), (R1C,R2Q,ZD,XB,YB), (R1D,R2Q,ZD,XB,YB), (R1E,R2Q,ZD,XB,YB), (R1F,R2Q,ZD,XB,YB), (R1G,R2Q,ZD,XB,YB), (R1H,R2Q,ZD,XB,YB), (R1I,R2Q,ZD,XB,YB), (R1J,R2Q,ZD,XB,YB), (R1K,R2Q,ZD,XB,YB), (R1L,R2Q,ZD,XB,YB), (R1M,R2Q,ZD,XB,YB), (R1N,R2Q,ZD,XB,YB), (R1O,R2Q,ZD,XB,YB), (R1P,R2Q,ZD,XB,YB), (R1Q,R2Q,ZD,XB,YB), (R1A,R2A,ZE,XB,YB), (R1B,R2A,ZE,XB,YB), (R1C,R2A,ZE,XB,YB), (R1D,R2A,ZE,XB,YB), (R1E,R2A,ZE,XB,YB), (R1F,R2A,ZE,XB,YB), (R1G,R2A,ZE,XB,YB), (R1H,R2A,ZE,XB,YB), (R1I,R2A,ZE,XB,YB), (R1J,R2A,ZE,XB,YB), (R1K,R2A,ZE,XB,YB), (R1L,R2A,ZE,XB,YB), (R1M,R2A,ZE,XB,YB), (R1N,R2A,ZE,XB,YB), (R1O,R2A,ZE,XB,YB), (R1P,R2A,ZE,XB,YB), (R1Q,R2A,ZE,XB,YB), (R1A,R2B,ZE,XB,YB), (R1B,R2B,ZE,XB,YB), (R1C,R2B,ZE,XB,YB), (R1D,R2B,ZE,XB,YB), (R1E,R2B,ZE,XB,YB), (R1F,R2B,ZE,XB,YB), (R1G,R2B,ZE,XB,YB), (R1H,R2B,ZE,XB,YB), (R1I,R2B,ZE,XB,YB), (R1J,R2B,ZE,XB,YB), (R1K,R2B,ZE,XB,YB), (R1L,R2B,ZE,XB,YB), (R1M,R2B,ZE,XB,YB), (R1N,R2B,ZE,XB,YB), (R1O,R2B,ZE,XB,YB), (R1P,R2B,ZE,XB,YB), (R1Q,R2B,ZE,XB,YB), (R1A,R2C,ZE,XB,YB), (R1B,R2C,ZE,XB,YB), (R1C,R2C,ZE,XB,YB), (R1D,R2C,ZE,XB,YB), (R1E,R2C,ZE,XB,YB), (R1F,R2C,ZE,XB,YB), (R1G,R2C,ZE,XB,YB), (R1H,R2C,ZE,XB,YB), (R1I,R2C,ZE,XB,YB), (R1J,R2C,ZE,XB,YB), (R1K,R2C,ZE,XB,YB), (R1L,R2C,ZE,XB,YB), (R1M,R2C,ZE,XB,YB), (R1N,R2C,ZE,XB,YB), (R1O,R2C,ZE,XB,YB), (R1P,R2C,ZE,XB,YB), (R1Q,R2C,ZE,XB,YB), (R1A,R2D,ZE,XB,YB), (R1B,R2D,ZE,XB,YB), (R1C,R2D,ZE,XB,YB), (R1D,R2D,ZE,XB,YB), (R1E,R2D,ZE,XB,YB), (R1F,R2D,ZE,XB,YB), (R1G,R2D,ZE,XB,YB), (R1H,R2D,ZE,XB,YB), (R1I,R2D,ZE,XB,YB), (R1J,R2D,ZE,XB,YB), (R1K,R2D,ZE,XB,YB), (R1L,R2D,ZE,XB,YB), (R1M,R2D,ZE,XB,YB), (R1N,R2D,ZE,XB,YB), (R1O,R2D,ZE,XB,YB), (R1P,R2D,ZE,XB,YB), (R1Q,R2D,ZE,XB,YB), (R1A,R2E,ZE,XB,YB), (R1B,R2E,ZE,XB,YB), (R1C,R2E,ZE,XB,YB), (R1D,R2E,ZE,XB,YB), (R1E,R2E,ZE,XB,YB), (R1F,R2E,ZE,XB,YB), (R1G,R2E,ZE,XB,YB), (R1H,R2E,ZE,XB,YB), (R1I,R2E,ZE,XB,YB), (R1J,R2E,ZE,XB,YB), (R1K,R2E,ZE,XB,YB), (R1L,R2E,ZE,XB,YB), (R1M,R2E,ZE,XB,YB), (R1N,R2E,ZE,XB,YB), (R1O,R2E,ZE,XB,YB), (R1P,R2E,ZE,XB,YB), (R1Q,R2E,ZE,XB,YB), (R1A,R2F,ZE,XB,YB), (R1B,R2F,ZE,XB,YB), (R1C,R2F,ZE,XB,YB), (R1D,R2F,ZE,XB,YB), (R1E,R2F,ZE,XB,YB), (R1F,R2F,ZE,XB,YB), (R1G,R2F,ZE,XB,YB), (R1H,R2F,ZE,XB,YB), (R1I,R2F,ZE,XB,YB), (R1J,R2F,ZE,XB,YB), (R1K,R2F,ZE,XB,YB), (R1L,R2F,ZE,XB,YB), (R1M,R2F,ZE,XB,YB), (R1N,R2F,ZE,XB,YB), (R1O,R2F,ZE,XB,YB), (R1P,R2F,ZE,XB,YB), (R1Q,R2F,ZE,XB,YB), (R1A,R2G,ZE,XB,YB), (R1B,R2G,ZE,XB,YB), (R1C,R2G,ZE,XB,YB), (R1D,R2G,ZE,XB,YB), (R1E,R2G,ZE,XB,YB), (R1F,R2G,ZE,XB,YB), (R1G,R2G,ZE,XB,YB), (R1H,R2G,ZE,XB,YB), (R1I,R2G,ZE,XB,YB), (R1J,R2G,ZE,XB,YB), (R1K,R2G,ZE,XB,YB), (R1L,R2G,ZE,XB,YB), (R1M,R2G,ZE,XB,YB), (R1N,R2G,ZE,XB,YB), (R1O,R2G,ZE,XB,YB), (R1P,R2G,ZE,XB,YB), (R1Q,R2G,ZE,XB,YB), (R1A,R2H,ZE,XB,YB), (R1B,R2H,ZE,XB,YB), (R1C,R2H,ZE,XB,YB), (R1D,R2H,ZE,XB,YB), (R1E,R2H,ZE,XB,YB), (R1F,R2H,ZE,XB,YB), (R1G,R2H,ZE,XB,YB), (R1H,R2H,ZE,XB,YB), (R1I,R2H,ZE,XB,YB), (R1J,R2H,ZE,XB,YB), (R1K,R2H,ZE,XB,YB), (R1L,R2H,ZE,XB,YB), (R1M,R2H,ZE,XB,YB), (R1N,R2H,ZE,XB,YB), (R1O,R2H,ZE,XB,YB), (R1P,R2H,ZE,XB,YB), (R1Q,R2H,ZE,XB,YB), (R1A,R2I,ZE,XB,YB), (R1B,R2I,ZE,XB,YB), (R1C,R2I,ZE,XB,YB), (R1D,R2I,ZE,XB,YB), (R1E,R2I,ZE,XB,YB), (R1F,R2I,ZE,XB,YB), (R1G,R2I,ZE,XB,YB), (R1H,R2I,ZE,XB,YB), (R1I,R2I,ZE,XB,YB), (R1J,R2I,ZE,XB,YB), (R1K,R2I,ZE,XB,YB), (R1L,R2I,ZE,XB,YB), (R1M,R2I,ZE,XB,YB), (R1N,R2I,ZE,XB,YB), (R1O,R2I,ZE,XB,YB), (R1P,R2I,ZE,XB,YB), (R1Q,R2I,ZE,XB,YB), (R1A,R2J,ZE,XB,YB), (R1B,R2J,ZE,XB,YB), (R1C,R2J,ZE,XB,YB), (R1D,R2J,ZE,XB,YB), (R1E,R2J,ZE,XB,YB), (R1F,R2J,ZE,XB,YB), (R1G,R2J,ZE,XB,YB), (R1H,R2J,ZE,XB,YB), (R1I,R2J,ZE,XB,YB), (R1J,R2J,ZE,XB,YB), (R1K,R2J,ZE,XB,YB), (R1L,R2J,ZE,XB,YB), (R1M,R2J,ZE,XB,YB), (R1N,R2J,ZE,XB,YB), (R1O,R2J,ZE,XB,YB), (R1P,R2J,ZE,XB,YB), (R1Q,R2J,ZE,XB,YB), (R1A,R2K,ZE,XB,YB), (R1B,R2K,ZE,XB,YB), (R1C,R2K,ZE,XB,YB), (R1D,R2K,ZE,XB,YB), (R1E,R2K,ZE,XB,YB), (R1F,R2K,ZE,XB,YB), (R1G,R2K,ZE,XB,YB), (R1H,R2K,ZE,XB,YB), (R1I,R2K,ZE,XB,YB), (R1J,R2K,ZE,XB,YB), (R1K,R2K,ZE,XB,YB), (R1L,R2K,ZE,XB,YB), (R1M,R2K,ZE,XB,YB), (R1N,R2K,ZE,XB,YB), (R1O,R2K,ZE,XB,YB), (R1P,R2K,ZE,XB,YB), (R1Q,R2K,ZE,XB,YB), (R1A,R2L,ZE,XB,YB), (R1B,R2L,ZE,XB,YB), (R1C,R2L,ZE,XB,YB), (R1D,R2L,ZE,XB,YB), (R1E,R2L,ZE,XB,YB), (R1F,R2L,ZE,XB,YB), (R1G,R2L,ZE,XB,YB), (R1H,R2L,ZE,XB,YB), (R1I,R2L,ZE,XB,YB), (R1J,R2L,ZE,XB,YB), (R1K,R2L,ZE,XB,YB), (R1L,R2L,ZE,XB,YB), (R1M,R2L,ZE,XB,YB), (R1N,R2L,ZE,XB,YB), (R1O,R2L,ZE,XB,YB), (R1P,R2L,ZE,XB,YB), (R1Q,R2L,ZE,XB,YB), (R1A,R2M,ZE,XB,YB), (R1B,R2M,ZE,XB,YB), (R1C,R2M,ZE,XB,YB), (R1D,R2M,ZE,XB,YB), (R1E,R2M,ZE,XB,YB), (R1F,R2M,ZE,XB,YB), (R1G,R2M,ZE,XB,YB), (R1H,R2M,ZE,XB,YB), (R1I,R2M,ZE,XB,YB), (R1J,R2M,ZE,XB,YB), (R1K,R2M,ZE,XB,YB), (R1L,R2M,ZE,XB,YB), (R1M,R2M,ZE,XB,YB), (R1N,R2M,ZE,XB,YB), (R1O,R2M,ZE,XB,YB), (R1P,R2M,ZE,XB,YB), (R1Q,R2M,ZE,XB,YB), (R1A,R2N,ZE,XB,YB), (R1B,R2N,ZE,XB,YB), (R1C,R2N,ZE,XB,YB), (R1D,R2N,ZE,XB,YB), (R1E,R2N,ZE,XB,YB), (R1F,R2N,ZE,XB,YB), (R1G,R2N,ZE,XB,YB), (R1H,R2N,ZE,XB,YB), (R1I,R2N,ZE,XB,YB), (R1J,R2N,ZE,XB,YB), (R1K,R2N,ZE,XB,YB), (R1L,R2N,ZE,XB,YB), (R1M,R2N,ZE,XB,YB), (R1N,R2N,ZE,XB,YB), (R1O,R2N,ZE,XB,YB), (R1P,R2N,ZE,XB,YB), (R1Q,R2N,ZE,XB,YB), (R1A,R2O,ZE,XB,YB), (R1B,R2O,ZE,XB,YB), (R1C,R2O,ZE,XB,YB), (R1D,R2O,ZE,XB,YB), (R1E,R2O,ZE,XB,YB), (R1F,R2O,ZE,XB,YB), (R1G,R2O,ZE,XB,YB), (R1H,R2O,ZE,XB,YB), (R1I,R2O,ZE,XB,YB), (R1J,R2O,ZE,XB,YB), (R1K,R2O,ZE,XB,YB), (R1L,R2O,ZE,XB,YB), (R1M,R2O,ZE,XB,YB), (R1N,R2O,ZE,XB,YB), (R1O,R2O,ZE,XB,YB), (R1P,R2O,ZE,XB,YB), (R1Q,R2O,ZE,XB,YB), (R1A,R2P,ZE,XB,YB), (R1B,R2P,ZE,XB,YB), (R1C,R2P,ZE,XB,YB), (R1D,R2P,ZE,XB,YB), (R1E,R2P,ZE,XB,YB), (R1F,R2P,ZE,XB,YB), (R1G,R2P,ZE,XB,YB), (R1H,R2P,ZE,XB,YB), (R1I,R2P,ZE,XB,YB), (R1J,R2P,ZE,XB,YB), (R1K,R2P,ZE,XB,YB), (R1L,R2P,ZE,XB,YB), (R1M,R2P,ZE, XB,YB), (R1N,R2P,ZE,XB,YB), (R1O,R2P,ZE,XB,YB), (R1P,R2P,ZE,XB,YB), (R1Q,R2P,ZE,XB,YB), (R1A,R2Q, ZE,XB,YB), (R1B,R2Q,ZE,XB,YB), (R1C,R2Q,ZE,XB, YB), (R1D,R2Q,ZE,XB,YB), (R1E,R2Q,ZE,XB,YB), (R1F, R2Q,ZE,XB,YB), (R1G,R2Q,ZE,XB,YB), (R1H,R2Q,ZE, XB,YB), (R1I,R2Q,ZE,XB,YB), (R1J,R2Q,ZE,XB,YB), (R1K,R2Q,ZE,XB,YB), (R1L,R2Q,ZE,XB,YB), (R1M, R2Q,ZE,XB,YB), (R1N,R2Q,ZE,XB,YB), (R1O,R2Q,ZE, XB,YB), (R1P,R2Q,ZE,XB,YB), (R1Q,R2Q,ZE,XB,YB), (R1A,R2A,ZF,XB,YB), (R1B,R2A,ZF,XB,YB), (R1C,R2A, ZF,XB,YB), (R1 D,R2A,ZF,XB,YB), (R1E,R2A,ZF,XB, YB), (R1F,R2A,ZF,XB,YB), (R1G,R2A,ZF,XB,YB), (R1H, R2A,ZF,XB,YB), (R1I,R2A,ZF,XB,YB), (R1J,R2A,ZF, YB), (R1K,R2A,ZF,XB,YB), (R1L,R2A,ZF,XB,YB), (R1M,R2A,ZF,XB,YB), (R1N,R2A,ZF,XB,YB), (R1O, R2A,ZF,XB,YB), (R1P,R2A,ZF,XB,YB), (R1Q,R2A,ZF, XB,YB), (R1A,R2B,ZF,XB,YB), (R1B,R2B,ZF,XB,YB), (R1C,R2B,ZF,XB,YB), (R1D,R2B,ZF,XB,YB), (R1E,R2B, ZF,XB,YB), (R1F,R2B,ZF,XB,YB), (R1G,R2B,ZF,XB, YB), (R1H,R2B,ZF,XB,YB), (R1I,R2B,ZF,XB,YB), (R1J, R2B,ZF,XB,YB), (R1K,R2B,ZF,XB,YB), (R1L,R2B,ZF, XB,YB), (R1M,R2B,ZF,XB,YB), (R1N,R2B,ZF,XB,YB), (R1O,R2B,ZF,XB,YB), (R1P,R2B,ZF,XB,YB), (R1Q,R2B, ZF,XB,YB), (R1A,R2C,ZF,XB,YB), (R1B,R2C,ZF,XB, YB), (R1C,R2C,ZF,XB,YB), (R1D,R2C,ZF,XB,YB), (R1E, R2C,ZF,XB,YB), (R1F,R2C,ZF,XB,YB), (R1G,R2C,ZF, XB,YB), (R1H,R2C,ZF,XB,YB), (R1I,R2C,ZF,XB,YB), (R1J,R2C,ZF,XB,YB), (R1K,R2C,ZF,XB,YB), (R1L,R2C, ZF,XB,YB), (R1M,R2C,ZF,XB,YB), (R1N,R2C,ZF,XB, YB), (R1O,R2C,ZF,XB,YB), (R1P,R2D,ZF,XB,YB), (R1Q, R22C,ZF,XB,YB), (R1A,R2D,ZF,XB,YB), (R1B,R2D,ZF, XB,YB), (R1C,R2D,ZF,XB,YB), (R1D,R2D,ZF,XB,YB), (R1E,R2D,ZF,XB,YB), (R1F,R2D,ZF,XB,YB), (R1G,R2D, ZF,XB,YB), (R1R2D,ZF,XB,YB), (R1I,R2D,ZF,XB,YB), (R1J,R2D,ZF,XB,YB), (R1K,R2D,ZF,XB,YB), (R1L,R2D, ZF,XB,YB), (R1M,R2D,ZF,XB,YB), (R1N,R2D,ZF,XB, YB), (R1O,R2D,ZF,XB,YB), (R1P,R2D,ZF,XB,YB), (R1Q, R2D,ZF,XB,YB), (R1A,R2E,ZF,XB,YB), (R1B,R2E,ZF, XB,YB), (R1C,R2E,ZF,XB,YB), (R1D,R2E,ZF,XB,YB), (R1E,R2E,ZF,XB,YB), (R1F,R2E,ZF,XB,YB), (R1G,R2E, ZF,XB,YB), (R1H,R2E,ZF,XB,YB), (R1I,R2E,ZF,XB,YB), (R1J,R2E,ZF,XB,YB), (R1K,R2E,ZF,XB,YB), (R1L,R2E, ZF,XB,YB), (R1M,R2E,ZF,XB,YB), (R1N,R2E,ZF,XB, YB), (R1O,R2E,ZF,XB,YB), (R1P,R2E,ZF,XB,YB), (R1Q, R2E,ZF,XB,YB), (R1A,R2F,ZF,XB,YB), (R1B,R2F,ZF,XB, YB), (R1C,R2F,ZF,XB,YB), (R1D,R2F,ZF,XB,YB), (R1E, R2F,ZF,XB,YB), (R1F,R2F,ZF,XB,YB), (R1G,R2F,ZF,XB, YB), (R1H,R2F,ZF,XB,YB), (R1I,R2F,ZF,XB,YB), (R1J, R2F,ZF,XB,YB), (R1K,R2F,ZF,XB,YB), (R1L,R2F,ZF,XB, YB), (R1M,R2F,ZF,XB,YB), (R1N,R2F,ZF,XB,YB), (R1O, R2F,ZF,XB,YB), (R1P,R2F,ZF,XB,YB), (R1Q,R2F,ZF,XB, YB), (R1A,R2G,ZF,XB,YB), (R1B,R2G,ZF,XB,YB), (R1C, R2G,ZF,XB,YB), (R1D,R2G,ZF,XB,YB), (R1E,R2G,ZF, XB,YB), (R1F,R2G,ZF,XB,YB), (R1G,R2G,ZF,XB,YB), (R1H,R2G,ZF,XB,YB), (R1I,R2G,ZF,XB,YB), (R1J,R2G, ZF,XB,YB), (R1K,R2G,ZF,XB,YB), (R1L,R2G,ZF,XB, YB), (R1M,R2G,ZF,XB,YB), (R1N,R2G,ZF,XB,YB), (R1O,R2G,ZF,XB,YB), (R1P,R2G,ZF,XB,YB), (R1Q,R2G, ZF,XB,YB), (R1A,R2H,ZF,XB,YB), (R1B,R2H,ZF,XB, YB), (R1C,R2H,ZF,XB,YB), (R1D,R2H,ZF,XB,YB), (R1E, R2H,ZF,XB,YB), (R1F,R2H,ZF,XB,YB), (R1G,R2H,ZF, XB,YB), (R1H,R2H,ZF,XB,YB), (R1I,R2H,ZF,XB,YB), (R1J,R2H,ZF,XB,YB), (R1K,R2H,ZF,XB,YB), (R1L,R2H, ZF,XB,YB), (R1M,R2H,ZF,XB,YB), (R1N,R2H,ZF,XB, YB), (R1O,R2H,ZF,XB,YB), (R1P,R2H,ZF,XB,YB), (R1Q, R2H,ZF,XB,YB), (R1A,R2I,ZF,XB,YB), (R1B,R2I,ZF,XB, YB), (R1C,R2I,ZF,XB,YB), (R1D,R2I,ZF,XB,YB), (R1E, R2I,ZF,XB,YB), (R1F,R2I,ZF,XB,YB), (R1G,R2I,ZF,XB, YB), (R1H,R2I,ZF,XB,YB), (R1I,R2I,ZF,XB,YB), (R1J, R2I,ZF,XB,YB), (R1K,R2I,ZF,XB,YB), (R1L,R2I,ZF,XB, YB), (R1M,R2I,ZF,XB,YB), (R1N,R2I,ZF,XB,YB), (R1O, R2I,ZF,XB,YB), (R1P,R2I,ZF,XB,YB), (R1Q,R2I,ZF,XB, YB), (R1A,R2J,ZF,XB,YB), (R1B,R2J,ZF,XB,YB), (R1C, R2J,ZF,XB,YB), (R1D,R2J,ZF,XB,YB), (R1E,R2J,ZF, YB), (R1F,R2J,ZF,XB,YB), (R1G,R2J,ZF,XB,YB), (R1H, R2J,ZF,XB,YB), (R1I,R2J,ZF,XB,YB), (R1J,R2J,ZF,XB, YB), (R1K,R2J,ZF,XB,YB), (R1L,R2J,ZF,XB,YB), (R1M, R2J,ZF,XB,YB), (R1N,R2J,ZF,XB,YB), (R1O,R2J,ZF,XB, YB), (R1P,R2J,ZF,XB,YB), (R1Q,R2J,ZF,XB,YB), (R1A, R2K,ZF,XB,YB), (R1B,R2K,ZF,XB,YB), (R1C,R2K,ZF, XB,YB), (R1D,R2K,ZF,XB,YB), (R1E,R2K,ZF,XB,YB), (R1F,R2K,ZF,XB,YB), (R1G,R2K,ZF,XB,YB), (R1H,R2K, ZF,XB,YB), (R1I,R2K,ZF,XB,YB), (R1J,R2K,ZF,XB,YB), (R1K,R2K,ZF,XB,YB), (R1L,R2K,ZF,XB,YB), (R1M, R2K,ZF,XB,YB), (R1N,R2K,ZF,XB,YB), (R1O,R2K,ZF, XB,YB), (R1P,R2K,ZF,XB,YB), (R1Q,R2K,ZF,XB,YB), (R1A,R2L,ZF,XB,YB), (R1B,R2L,ZF,XB,YB), (R1C,R2L, ZF,XB,YB), (R1D,R2L,ZF,XB,YB), (R1E,R2L,ZF,XB, YB), (R1F,R2L,ZF,XB,YB), (R1G,R2L,ZF,XB,YB), (R1H, R2L,ZF,XB,YB), (R1I,R2L,ZF,XB,YB), (R1J,R2L,ZF,XB, YB), (R1K,R2L,ZF,XB,YB), (R1L,R2L,ZF,XB,YB), (R1M, R2L,ZF,XB,YB), (R1N,R2L,ZF,XB,YB), (R1O,R2L,ZF, XB,YB), (R1P,R2L,ZF,XB,YB), (R1Q,R2L,ZF,XB,YB), (R1A,R2M,ZF,XB,YB), (R1B,R2M,ZF,XB,YB), (R1C, R2M,ZF,XB,YB), (R1D,R2M,ZF,XB,YB), (R1E,R2M,ZF, XB,YB), (R1F,R2M,ZF,XB,YB), (R1G,R2M,ZF,XB,YB), (R1H,R2M,ZF,XB,YB), (R1I,R2M,ZF,XB,YB), (R1J,R2M, ZF,XB,YB), (R1K,R2M,ZF,XB,YB), (R1L,R2M,ZF,XB, YB), (R1M,R2M,ZF,XB,YB), (R1N,R2M,ZF,XB,YB), (R1O,R2M,ZF,XB,YB), (R1P,R2M,ZF,XB,YB), (R1Q, R2M,ZF,XB,YB), (R1A,R2N,ZF,XB,YB), (R1B,R2N,ZF, XB,YB), (R1C,R2N,ZF,XB,YB), (R1D,R2N,ZF,XB,YB), (R1E,R2N,ZF,XB,YB), (R1F,R2N,ZF,XB,YB), (R1G,R2N, ZF,XB,YB), (R1H,R2N,ZF,XB,YB), (R1I,R2N,ZF,XB,YB), (R1J,R2N,ZF,XB,YB), (R1K,R2N,ZF,XB,YB), (R1L,R2N, ZF,XB,YB), (R1M,R2N,ZF,XB,YB), (R1N,R2N,ZF,XB, YB), (R1O,R2N,ZF,XB,YB), (R1P,R2N,ZF,XB,YB), (R1Q, R2N,ZF,XB,YB), (R1A,R2O,ZF,XB,YB), (R1B,R2O,ZF, XB,YB), (R1C,R2O,ZF,XB,YB), (R1D,R2O,ZF,XB,YB), (R1E,R2O,ZF,XB,YB), (R1F,R2O,ZF,XB,YB), (R1G,R2O, ZF,XB,YB), (R1H,R2O,ZF,XB,YB), (R1I,R2O,ZF,XB,YB), (R1J,R2O,ZF,XB,YB), (R1K,R2O,ZF,XB,YB), (R1L,R2O, ZF,XB,YB), (R1M,R2O,ZF,XB,YB), (R1N,R2O,ZF,XB, YB), (R1O,R2O,ZF,XB,YB), (R1P,R2O,ZF,XB,YB), (R1Q, R2O,ZF,XB,YB), (R1A,R2P,ZF,XB,YB), (R1B,R2P,ZF,XB, YB), (R1C,R2P,ZF,XB,YB), (R1D,R2P,ZF,XB,YB), (R1E, R2P,ZF,XB,YB), (R1F,R2P,ZF,XB,YB), (R1G,R2P,ZF,XB, YB), (R1H,R2P,ZF,XB,YB), (R1I,R2P,ZF,XB,YB), (R1J, R2P,ZF,XB,YB), (R1K,R2P,ZF,XB,YB), (R1L,R2P,ZF,XB, YB), (R1M,R2P,ZF,XB,YB), (R1N,R2P,ZF,XB,YB), (R1O, R2P,ZF,XB,YB), (R1P,R2P,ZF,XB,YB), (R1Q,R2P,ZF,XB, YB), (R1A,R2Q,ZF,XB,YB), (R1B,R2Q,ZF,XB,YB), (R1C, R2Q,ZF,XB,YB), (R1D,R2Q,ZF,XB,YB), (R1E,R2Q,ZF, XB,YB), (R1F,R2Q,ZF,XB,YB), (R1G,R2Q,ZF,XB,YB), (R1H,R2Q,ZF,XB,YB), (R1I,R2Q,ZF,XB,YB), (R1J,R2Q, ZF,XB,YB), (R1K,R2Q,ZF,XB,YB), (R1L,R2Q,ZF,XB, YB), (R1M,R2Q,ZF,XB,YB), (R1N,R2Q,ZF,XB,YB), (R1O,R2Q,ZF,XB,YB), (R1P,R2Q,ZF,XB,YB), (R1Q,R2Q, ZF,XB,YB), (R1A,R2A,ZG,XB,YB), (R1B,R2A,ZG,XB, YB), (R1C,R2A,ZG,XB,YB), (R1D,R2A,ZG,XB,YB), (R1E,R2A,ZG,XB,YB), (R1F,R2A,ZG,XB,YB), (R1G, R2A,ZG,XB,YB), (R1H,R2A,ZG,XB,YB), (R1I,R2A,ZG, XB,YB), (R1J,R2A,ZG,XB,YB), (R1K,R2A,ZG,XB,YB), (R1L,R2A,ZG,XB,YB), (R1M,R2A,ZG,XB,YB), (R1N, R2A,ZG,XB,YB), (R1O,R2A,ZG,XB,YB), (R1P,R2A,ZG,XB,YB), (R1Q,R2A,ZG,XB,YB), (R1A,R2B,ZG,XB,YB), (R1B,R2B,ZG,XB,YB), (R1C,R2B,ZG,XB,YB), (R1D,R2B,ZG,XB,YB), (R1E,R2B,ZG,XB,YB), (R1F,R2B,ZG,XB,YB), (R1G,R2B,ZG,XB,YB), (R1H,R2B,ZG,XB,YB), (R1I,R2B,ZG,XB,YB), (R1J,R2B,ZG,XB,YB), (R1K,R2B,ZG,XB,YB), (R1L,R2B,ZG,XB,YB), (R1M,R2B,ZG,XB,YB), (R1N,R2B,ZG,XB,YB), (R1O,R2B,ZG,XB,YB), (R1P,R2B,ZG,XB,YB), (R1Q,R2B,ZG,XB,YB), (R1A,R2C,ZG,XB,YB), (R1B,R2C,ZG,XB,YB), (R1C,R22C,ZG,XB,YB), (R1D,R2C,ZG,XB,YB), (R1E,R2C,ZG,XB,YB), (R1F,R2C,ZG,XB,YB), (R1G,R2C,ZG,XB,YB), (R1H,R2C,ZG,XB,YB), (R1I,R2C,ZG,XB,YB), (R1J,R2C,ZG,XB,YB), (R1K,R2C,ZG,XB,YB), (R1L,R2C,ZG,XB,YB), (R1M,R2C,ZG,XB,YB), (R1N,R2C,ZG,XB,YB), (R1O,R2C,ZG,XB,YB), (R1P,R2C,ZG,XB,YB), (R1Q,R2C,ZG,XB,YB), (R1A,R2D,ZG,XB,YB), (R1B,R2D,ZG,XB,YB), (R1C,R2D,ZG,XB,YB), (R1D,R2D,ZG,XB,YB), (R1E,R2D,ZG,XB,YB), (R1F,R2D,ZG,XB,YB), (R1G,R2D,ZG,XB,YB), (R1H,R2D,ZG,XB,YB), (R1I,R2D,ZG,XB,YB), (R1J,R2D,ZG,XB,YB), (R1K,R2D,ZG,XB,YB), (R1L,R2D,ZG,XB,YB), (R1M,R2D,ZG,XB,YB), (R1N,R2D,ZG,XB,YB), (R1O,R2D,ZG,XB,YB), (R1P,R2D,ZG,XB,YB), (R1Q,R2D,ZG,XB,YB), (R1A,R2E,ZG,XB,YB), (R1B,R2E,ZG,XB,YB), (R1C,R2E,ZG,XB,YB), (R1D,R2E,ZG,XB,YB), (R1E,R2E,ZG,XB,YB), (R1F,R2E,ZG,XB,YB), (R1G,R2E,ZG,XB,YB), (R1H,R2E,ZG,XB,YB), (R1I,R2E,ZG,XB,YB), (R1J,R2E,ZG,XB,YB), (R1K,R2E,ZG,XB,YB), (R1L,R2E,ZG,XB,YB), (R1M,R2E,ZG,XB,YB), (R1N,R2E,ZG,XB,YB), (R1O,R2E,ZG,XB,YB), (R1P,R2E,ZG,XB,YB), (R1Q,R2E,ZG,XB,YB), (R1A,R2F,ZG,XB,YB), (R1B,R2F,ZG,XB,YB), (R1C,R2F,ZG,XB,YB), (R1D,R2F,ZG,XB,YB), (R1E,R2F,ZG,XB,YB), (R1F,R2F,ZG,XB,YB), (R1G,R2F,ZG,XB,YB), (R1H,R2F,ZG,XB,YB), (R1I,R2F,ZG,XB,YB), (R1J,R2F,ZG,XB,YB), (R1K,R2F,ZG,XB,YB), (R1L,R2F,ZG,XB,YB), (R1M,R2F,ZG,XB,YB), (R1N,R2F,ZG,XB,YB), (R1O,R2F,ZG,XB,YB), (R1P,R2F,ZG,XB,YB), (R1Q,R2F,ZG,XB,YB), (R1A,R2G,ZG,XB,YB), (R1B,R2G,ZG,XB,YB), (R1C,R2G,ZG,XB,YB), (R1D,R2G,ZG,XB,YB), (R1E,R2G,ZG,XB,YB), (R1F,R2G,ZG,XB,YB), (R1G,R2G,ZG,XB,YB), (R1H,R2G,ZG,XB,YB), (R1I,R2G,ZG,XB,YB), (R1J,R2G,ZG,XB,YB), (R1K,R2G,ZG,XB,YB), (R1L,R2G,ZG,XB,YB), (R1M,R2G,ZG,XB,YB), (R1N,R2G,ZG,XB,YB), (R1O,R2G,ZG,XB,YB), (R1P,R2G,ZG,XB,YB), (R1Q,R2G,ZG,XB,YB), (R1A,R2H,ZG,XB,YB), (R1B,R2H,ZG,XB,YB), (R1C,R2H,ZG,XB,YB), (R1D,R2H,ZG,XB,YB), (R1E,R2H,ZG,XB,YB), (R1F,R2H,ZG,XB,YB), (R1G,R2H,ZG,XB,YB), (R1H,R2H,ZG,XB,YB), (R1I,R2H,ZG,XB,YB), (R1J,R2H,ZG,XB,YB), (R1K,R2H,ZG,XB,YB), (R1L,R2H,ZG,XB,YB), (R1M,R2H,ZG,XB,YB), (R1N,R2H,ZG,XB,YB), (R1O,R2H,ZG,XB,YB), (R1P,R2H,ZG,XB,YB), (R1Q,R2H,ZG,XB,YB), (R1A,R2I,ZG,XB,YB), (R1B,R2I,ZG,XB,YB), (R1C,R2I,ZG,XB,YB), (R1D,R2I,ZG,XB,YB), (R1E,R2I,ZG,XB,YB), (R1F,R2I,ZG,XB,YB), (R1G,R2I,ZG,XB,YB), (R1H,R2I,ZG,XB,YB), (R1I,R2I,ZG,XB,YB), (R1J,R2I,ZG,XB,YB), (R1K,R2I,ZG,XB,YB), (R1L,R2I,ZG,XB,YB), (R1M,R2I,ZG,XB,YB), (R1N,R2I,ZG,XB,YB), (R1O,R2I,ZG,XB,YB), (R1P,R2I,ZG,XB,YB), (R1Q,R2I,ZG,XB,YB), (R1A,R2J,ZG,XB,YB), (R1B,R2J,ZG,XB,YB), (R1C,R2J,ZG,XB,YB), (R1D,R2J,ZG,XB,YB), (R1E,R2J,ZG,XB,YB), (R1F,R2J,ZG,XB,YB), (R1G,R2J,ZG,XB,YB), (R1H,R2J,ZG,XB,YB), (R1I,R2J,ZG,XB,YB), (R1J,R2J,ZG,XB,YB), (R1K,R2J,ZG,XB,YB), (R1L,R2J,ZG,XB,YB), (R1M,R2J,ZG,XB,YB), (R1N,R2J,ZG,XB,YB), (R1O,R2J,ZG,XB,YB), (R1P,R2J,ZG,XB,YB), (R1Q,R2J,ZG,XB,YB), (R1A,R2K,ZG,XB,YB), (R1B,R2K,ZG,XB,YB), (R1C,R2K,ZG,XB,YB), (R1D,R2K,ZG,XB,YB), (R1E,R2K,ZG,XB,YB), (R1F,R2K,ZG,XB,YB), (R1G,R2K,ZG,XB,YB), (R1H,R2K,ZG,XB,YB), (R1I,R2K,ZG,XB,YB), (R1J,R2K,ZG,XB,YB), (R1K,R2K,ZG,XB,YB), (R1L,R2K,ZG,XB,YB), (R1M,R2K,ZG,XB,YB), (R1N,R2K,ZG,XB,YB), (R1O,R2K,ZG,XB,YB), (R1P,R2K,ZG,XB,YB), (R1Q,R2K,ZG,XB,YB), (R1A,R2L,ZG,XB,YB), (R1B,R2L,ZG,XB,YB), (R1C,R2L,ZG,XB,YB), (R1D,R2L,ZG,XB,YB), (R1E,R2L,ZG,XB,YB), (R1F,R2L,ZG,XB,YB), (R1G,R2L,ZG,XB,YB), (R1H,R2L,ZG,XB,YB), (R1I,R2L,ZG,XB,YB), (R1J,R2L,ZG,XB,YB), (R1K,R2L,ZG,XB,YB), (R1L,R2L,ZG,XB,YB), (R1M,R2L,ZG,XB,YB), (R1N,R2L,ZG,XB,YB), (R1O,R2L,ZG,XB,YB), (R1P,R2L,ZG,XB,YB), (R1Q,R2L,ZG,XB,YB), (R1A,R2M,ZG,XB,YB), (R1B,R2M,ZG,XB,YB), (R1C,R2M,ZG,XB,YB), (R1D,R2M,ZG,XB,YB), (R1E,R2M,ZG,XB,YB), (R1F,R2M,ZG,XB,YB), (R1G,R2M,ZG,XB,YB), (R1H,R2M,ZG,XB,YB), (R1I,R2M,ZG,XB,YB), (R1J,R2M,ZG,XB,YB), (R1K,R2M,ZG,XB,YB), (R1L,R2M,ZG,XB,YB), (R1M,R2M,ZG,XB,YB), (R1N,R2M,ZG,XB,YB), (R1O,R2M,ZG,XB,YB), (R1P,R2M,ZG,XB,YB), (R1Q,R2M,ZG,XB,YB), (R1A,R2N,ZG,XB,YB), (R1B,R2N,ZG,XB,YB), (R1C,R2N,ZG,XB,YB), (R1D,R2N,ZG,XB,YB), (R1E,R2N,ZG,XB,YB), (R1F,R2N,ZG,XB,YB), (R1G,R2N,ZG,XB,YB), (R1H,R2N,ZG,XB,YB), (R1I,R2N,ZG,XB,YB), (R1J,R2N,ZG,XB,YB), (R1K,R2N,ZG,XB,YB), (R1L,R2N,ZG,XB,YB), (R1M,R2N,ZG,XB,YB), (R1N,R2N,ZG,XB,YB), (R1O,R2N,ZG,XB,YB), (R1P,R2N,ZG,XB,YB), (R1Q,R2N,ZG,XB,YB), (R1A,R2O,ZG,XB,YB), (R1B,R2O,ZG,XB,YB), (R1C,R2O,ZG,XB,YB), (R1D,R2O,ZG,XB,YB), (R1E,R2O,ZG,XB,YB), (R1F,R2O,ZG,XB,YB), (R1G,R2O,ZG,XB,YB), (R1H,R2O,ZG,XB,YB), (R1I,R2O,ZG,XB,YB), (R1J,R2O,ZG,XB,YB), (R1K,R2O,ZG,XB,YB), (R1L,R2O,ZG,XB,YB), (R1M,R2O,ZG,XB,YB), (R1N,R2O,ZG,XB,YB), (R1O,R2O,ZG,XB,YB), (R1P,R2O,ZG,XB,YB), (R1Q,R2O,ZG,XB,YB), (R1A,R2P,ZG,XB,YB), (R1B,R2P,ZG,XB,YB), (R1C,R2P,ZG,XB,YB), (R1D,R2P,ZG,XB,YB), (R1E,R2P,ZG,XB,YB), (R1F,R2P,ZG,XB,YB), (R1G,R2P,ZG,XB,YB), (R1H,R2P,ZG,XB,YB), (R1I,R2P,ZG,XB,YB), (R1J,R2P,ZG,XB,YB), (R1K,R2P,ZG,XB,YB), (R1L,R2P,ZG,XB,YB), (R1M,R2P,ZG,XB,YB), (R1N,R2P,ZG,XB,YB), (R1O,R2P,ZG,XB,YB), (R1P,R2P,ZG,XB,YB), (R1Q,R2P,ZG,XB,YB), (R1A,R2Q,ZG,XB,YB), (R1B,R2Q,ZG,XB,YB), (R1C,R2Q,ZG,XB,YB), (R1D,R2Q,ZG,XB,YB), (R1E,R2Q,ZG,XB,YB), (R1F,R2Q,ZG,XB,YB), (R1G,R2Q,ZG,XB,YB), (R1H,R2Q,ZG,XB,YB), (R1I,R2Q,ZG,XB,YB), (R1J,R2Q,ZG,XB,YB), (R1K,R2Q,ZG,XB,YB), (R1L,R2Q,ZG,XB,YB), (R1M,R2Q,ZG,XB,YB), (R1N,R2Q,ZG,XB,YB), (R1O,R2Q,ZG,XB,YB), (R1P,R2Q,ZG,XB,YB), (R1Q,R2Q,ZG,XB,YB), (R1A,R2A,ZH,XB,YB), (R1B,R2A,ZH,XB,YB), (R1C,R2A,ZH,XB,YB), (R1D,R2A,ZH,XB,YB), (R1E,R2A,ZH,XB,YB), (R1F,R2A,ZH,XB,YB), (R1G,R2A,ZH,XB,YB), (R1H,R2A,ZH,XB,YB), (R1I,R2A,ZH,XB,YB), (R1J,R2A,ZH,XB,YB), (R1K,R2A,ZH,XB,YB), (R1L,R2A,ZH,XB,YB), (R1M,R2A,ZH,XB,YB), (R1N,R2A,ZH,XB,YB), (R1O,R2A,ZH,XB,YB), (R1P,R2A,ZH,XB,YB), (R1Q,R2A,ZH,XB,YB), (R1A,R2B,ZH,XB,YB), (R1B,R2B,ZH,XB,YB), (R1C,R2B,ZH,XB,YB), (R1D,R2B,ZH,XB,YB), (R1E,R2B,ZH,XB,YB), (R1F,R2B,ZH,XB,YB), (R1G,R2B,ZH,XB,YB), (R1H,R2B,ZH,XB,YB), (R1I,R2B,ZH,XB,YB), (R1J,R2B,ZH,XB,YB), (R1K,R2B,ZH,XB,YB), (R1L,R2B,ZH,XB,YB), (R1M,R2B,ZH,XB,YB), (R1N,R2B,ZH,XB,YB), (R1O,R2B,ZH,XB,YB), (R1P,R2B,ZH,XB,YB), (R1Q,R2B,ZH,XB,YB), (R1A,R2C,ZH,XB,YB), (R1B,R2C,ZH,XB,YB), (R1C,R2C,ZH,XB,YB), (R1D,R2C,ZH,XB,YB), (R1E,R2C,ZH,XB,YB), (R1F,R2C,ZH,XB,YB), (R1G,R2C,ZH,XB,YB), (R1H,R2C,ZH,XB,YB), (R1I,R2C,ZH,XB,YB), (R1J,R2C,ZH,XB,YB), (R1K,R2C,ZH,XB,YB), (R1L,R2C,ZH,XB,YB), (R1M,R22C,ZH,XB,YB), (R1N,R2C,ZH,XB,YB), (R1O,R2C,ZH,XB,YB), (R1P,R2C,ZH,XB,YB), (R1Q,R2C,ZH,XB,YB), (R1A,R2D,ZH,XB,YB), (R1B,R2D,ZH,XB,YB), (R1C,R2D,ZH,XB,YB), (R1D,R2D,ZH,XB,YB), (R1E,R2D,ZH,XB,YB), (R1F,R2D,ZH,XB,YB), (R1G,R2D,ZH,XB,YB), (R1H,R2D,ZH,XB,YB), (R1I,R2D,ZH,XB,YB), (R1J,R2D,ZH,XB,YB), (R1K,R2D,ZH,XB,YB), (R1L,R2D,ZH,XB,YB), (R1M,R2D,ZH,XB,YB), (R1N,R2D,ZH,XB,YB), (R1O,R2D,ZH,XB,YB), (R1P,R2D,ZH,XB,YB), (R1Q,R2D,ZH,XB,YB), (R1A,R2E,ZH,XB,YB), (R1B,R2E,ZH,XB,YB), (R1C,R2E,ZH,XB,YB), (R1D,R2E,ZH,XB,YB), (R1E,R2E,ZH,XB,YB), (R1F,R2E,ZH,XB,YB), (R1G,R2E,ZH,XB,YB), (R1H,R2E,ZH,XB,YB), (R1I,R2E,ZH,XB,YB), (R1J, R2E,ZH,XB,YB), (R1K,R2E,ZH,XB,YB), (R1L,R2E,ZH,XB,YB), (R1M,R2E,ZH,XB,YB), (R1N,R2E,ZH,XB,YB), (R1O,R2E,ZH,XB,YB), (R1P,R2E,ZH,XB,YB), (R1Q,R2E,ZH,XB,YB), (R1A,R2F,ZH,XB,YB), (R1B,R2F,ZH,XB,YB), (R1C,R2F,ZH,XB,YB), (R1D,R2F,ZH,XB,YB), (R1E,R2F,ZH,XB,YB), (R1F,R2F,ZH,XB,YB), (R1G,R2F,ZH,XB,YB), (R1H,R2F,ZH,XB,YB), (R1I,R2F,ZH,XB,YB), (R1J,R2F,ZH,XB,YB), (R1K,R2F,ZH,XB,YB), (R1L,R2F,ZH,XB,YB), (R1M,R2F,ZH,XB,YB), (R1N,R2F,ZH,XB,YB), (R1O,R2F,ZH,XB,YB), (R1P,R2F,ZH,XB,YB), (R1Q,R2F,ZH,XB,YB), (R1A,R2G,ZH,XB,YB), (R1B,R2G,ZH,XB,YB), (R1C,R2G,ZH,XB,YB), (R1D,R2G,ZH,XB,YB), (R1E,R2G,ZH,XB,YB), (R1F,R2G,ZH,XB,YB), (R1G,R2G,ZH,XB,YB), (R1H,R2G,ZH,XB,YB), (R1I,R2G,ZH,XB,YB), (R1J,R2G,ZH,XB,YB), (R1K,R2G,ZH,XB,YB), (R1L,R2G,ZH,XB,YB), (R1M,R2G,ZH,XB,YB), (R1N,R2G,ZH,XB,YB), (R1O,R2G,ZH,XB,YB), (R1P,R2G,ZH,XB,YB), (R1Q,R2G,ZH,XB,YB), (R1A,R2H,ZH,XB,YB), (R1B,R2H,ZH,XB,YB), (R1C,R2H,ZH,XB,YB), (R1D,R2H,ZH,XB,YB), (R1E,R2H,ZH,XB,YB), (R1F,R2H,ZH,XB,YB), (R1G,R2H,ZH,XB,YB), (R1H,R2H,ZH,XB,YB), (R1I,R2H,ZH,XB,YB), (R1J,R2H,ZH,XB,YB), (R1K,R2H,ZH,XB,YB), (R1L,R2H,ZH,XB,YB), (R1M,R2H,ZH,XB,YB), (R1N,R2H,ZH,XB,YB), (R1O,R2H,ZH,XB,YB), (R1P,R2H,ZH,XB,YB), (R1Q,R2H,ZH,XB,YB), (R1A,R2I,ZH,XB,YB), (R1B,R2I,ZH,XB,YB), (R1C,R2I,ZH,XB,YB), (R1D,R2I,ZH,XB,YB), (R1E,R2I,ZH,XB,YB), (R1F,R2I,ZH,XB,YB), (R1G,R2I,ZH,XB,YB), (R1H,R2I,ZH,XB,YB), (R1I,R2I,ZH,XB,YB), (R1J,R2I,ZH,XB,YB), (R1K,R2I,ZH,XB,YB), (R1L,R2I,ZH,XB,YB), (R1M,R2I,ZH,XB,YB), (R1N,R2I,ZH,XB,YB), (R1O,R2I,ZH,XB,YB), (R1P,R2I,ZH,XB,YB), (R1Q,R2I,ZH,XB,YB), (R1A,R2J,ZH,XB,YB), (R1B,R2J,ZH,XB,YB), (R1C,R2J,ZH,XB,YB), (R1D,R2J,ZH,XB,YB), (R1E,R2J,ZH,XB,YB), (R1F,R2J,ZH,XB,YB), (R1G,R2J,ZH,XB,YB), (R1H,R2J,ZH,XB,YB), (R1I,R2J,ZH,XB,YB), (R1J,R2J,ZH,XB,YB), (R1K,R2J,ZH,XB,YB), (R1L,R2J,ZH,XB,YB), (R1M,R2J,ZH,XB,YB), (R1N,R2J,ZH,XB,YB), (R1O,R2J,ZH,XB,YB), (R1P,R2J,ZH,XB,YB), (R1Q,R2J,ZH,XB,YB), (R1A,R2K,ZH,XB,YB), (R1B,R2K,ZH,XB,YB), (R1C,R2K,ZH,XB,YB), (R1D,R2K,ZH,XB,YB), (R1E,R2K,ZH,XB,YB), (R1F,R2K,ZH,XB,YB), (R1G,R2K,ZH,XB,YB), (R1H,R2K,ZH,XB,YB), (R1I,R2K,ZH,XB,YB), (R1J,R2K,ZH,XB,YB), (R1K,R2K,ZH,XB,YB), (R1L,R2K,ZH,XB,YB), (R1M,R2K,ZH,XB,YB), (R1N,R2K,ZH,XB,YB), (R1O,R2K,ZH,XB,YB), (R1P,R2K,ZH,XB,YB), (R1Q,R2K,ZH,XB,YB), (R1A,R2L,ZH,XB,YB), (R1B,R2L,ZH,XB,YB), (R1C,R2L,ZH,XB,YB), (R1D,R2L,ZH,XB,YB), (R1E,R2L,ZH,XB,YB), (R1F,R2L,ZH,XB,YB), (R1G,R2L,ZH,XB,YB), (R1H,R2L,ZH,XB,YB), (R1I,R2L,ZH,XB,YB), (R1J,R2L,ZH,XB,YB), (R1K,R2L,ZH,XB,YB), (R1L,R2L,ZH,XB,YB), (R1M,R2L,ZH,XB,YB), (R1N,R2L,ZH,XB,YB), (R1O,R2L,ZH,XB,YB), (R1P,R2L,ZH,XB,YB), (R1Q,R2L,ZH,XB,YB), (R1A,R2M,ZH,XB,YB), (R1B,R2M,ZH,XB,YB), (R1C,R2M,ZH,XB,YB), (R1D,R2M,ZH,XB,YB), (R1E,R2M,ZH,XB,YB), (R1F,R2M,ZH,XB,YB), (R1G,R2M,ZH,XB,YB), (R1H,R2M,ZH,XB,YB), (R1I,R2M,ZH,XB,YB), (R1J,R2M,ZH,XB,YB), (R1K,R2M,ZH,XB,YB), (R1L,R2M,ZH,XB,YB), (R1M,R2M,ZH,XB,YB), (R1N,R2M,ZH,XB,YB), (R1O,R2M,ZH,XB,YB), (R1P,R2M,ZH,XB,YB), (R1Q,R2M,ZH,XB,YB), (R1A,R2N,ZH,XB,YB), (R1B,R2N,ZH,XB,YB), (R1C,R2N,ZH,XB,YB), (R1D,R2N,ZH,XB,YB), (R1E,R2N,ZH,XB,YB), (R1F,R2N,ZH,XB,YB), (R1G,R2N,ZH,XB,YB), (R1H,R2N,ZH,XB,YB), (R1I,R2N,ZH,XB,YB), (R1J,R2N,ZH,XB,YB), (R1K,R2N,ZH,XB,YB), (R1L,R2N,ZH,XB,YB), (R1M,R2N,ZH,XB,YB), (R1N,R2N,ZH,XB,YB), (R1O,R2N,ZH,XB,YB), (R1P,R2N,ZH,XB,YB), (R1Q,R2N,ZH,XB,YB), (R1A,R2O,ZH,XB,YB), (R1B,R2O,ZH,XB,YB), (R1C,R2O,ZH,XB,YB), (R1D,R2O,ZH,XB,YB), (R1E,R2O,ZH,XB,YB), (R1F,R2O,ZH,XB,YB), (R1G,R2O,ZH,XB,YB), (R1H,R2O,ZH,XB,YB), (R1I,R2O,ZH,XB,YB), (R1J,R2O,ZH,XB,YB), (R1K,R2O,ZH,XB,YB), (R1L,R2O,ZH,XB,YB), (R1M,R2O,ZH,XB,YB), (R1N,R2O,ZH,XB,YB), (R1O,R2O,ZH,XB,YB), (R1P,R2O,ZH,XB,YB), (R1Q,R2O,ZH,XB,YB), (R1A,R2P,ZH,XB,YB), (R1B,R2P,ZH,XB,YB), (R1C,R2P,ZH,XB,YB), (R1D,R2P,ZH,XB,YB), (R1E,R2P,ZH,XB,YB), (R1F,R2P,ZH,XB,YB), (R1G,R2P,ZH,XB,YB), (R1H,R2P,ZH,XB,YB), (R1I,R2P,ZH,XB,YB), (R1J,R2P,ZH,XB,YB), (R1K,R2P,ZH,XB,YB), (R1L,R2P,ZH,XB,YB), (R1M,R2P,ZH,XB,YB), (R1N,R2P,ZH,XB,YB), (R1O,R2P,ZH,XB,YB), (R1P,R2P,ZH,XB,YB), (R1Q,R2P,ZH,XB,YB), (R1A,R2Q,ZH,XB,YB), (R1B,R2Q,ZH,XB,YB), (R1C,R2Q,ZH,XB,YB), (R1D,R2Q,ZH,XB,YB), (R1E,R2Q,ZH,XB,YB), (R1F,R2Q,ZH,XB,YB), (R1G,R2Q,ZH,XB,YB), (R1H,R2Q,ZH,XB,YB), (R1I,R2Q,ZH,XB,YB), (R1J,R2Q,ZH,XB,YB), (R1K,R2Q,ZH,XB,YB), (R1L,R2Q,ZH,XB,YB), (R1M,R2Q,ZH,XB,YB), (R1N,R2Q,ZH,XB,YB), (R1O,R2Q,ZH,XB,YB), (R1P,R2Q,ZH,XB,YB), (R1Q,R2Q,ZH,XB,YB), (R1A,R2A,ZI,XB,YB), (R1B,R2A,ZI,XB,YB), (R1C,R2A,ZI,XB,YB), (R1D,R2A,ZI,XB,YB), (R1E,R2A,ZI,XB,YB), (R1F,R2A,ZI,XB,YB), (R1G,R2A,ZI,XB,YB), (R1H,R2A,ZI,XB,YB), (R1I,R2A,ZI,XB,YB), (R1J,R2A,ZI,XB,YB), (R1K,R2A,ZI,XB,YB), (R1L,R2A,ZI,XB,YB), (R1M,R2A,ZI,XB,YB), (R1N,R2A,ZI,XB,YB), (R1O,R2A,ZI,XB,YB), (R1P,R2A,ZI,XB,YB), (R1Q,R2A,ZI,XB,YB), (R1A,R2B,ZI,XB,YB), (R1B,R2B,ZI,XB,YB), (R1C,R2B,ZI,XB,YB), (R1D,R2B,ZI,XB,YB), (R1E,R2B,ZI,XB,YB), (R1F,R2B,ZI,XB,YB), (R1G,R2B,ZI,XB,YB), (R1H,R2B,ZI,XB,YB), (R1I,R2B,ZI,XB,YB), (R1J,R2B,ZI,XB,YB), (R1K,R2B,ZI,XB,YB), (R1L,R2B,ZI,XB,YB), (R1M,R2B,ZI,XB,YB), (R1N,R2B,ZI,XB,YB), (R1O,R2B,ZI,XB,YB), (R1P,R2B,ZI,XB,YB), (R1Q,R2B,ZI,XB,YB), (R1A,R2C,ZI,XB,YB), (R1B,R2C,ZI,XB,YB), (R1C,R2C,ZI,XB,YB), (R1D,R2C,ZI,XB,YB), (R1E,R2C,ZI,XB,YB), (R1F,R2C,ZI,XB,YB), (R1G,R2C,ZI,XB,YB), (R1H,R2C,ZI,XB,YB), (R1I,R2C,ZI,XB,YB), (R1J,R2C,ZI,XB,YB), (R1K,R2C,ZI,XB,YB), (R1L,R2C,ZI,XB,YB), (R1M,R2C,ZI,XB,YB), (R1N,R2C,ZI,XB,YB), (R1O,R2C,ZI,XB,YB), (R1P,R2C,ZI,XB,YB), (R1Q,R2C,ZI,XB,YB), (R1A,R2D,ZI,XB,YB), (R1B,R2D,ZI,XB,YB), (R1C,R2D,ZI,XB,YB), (R1D,R2D,ZI,XB,YB), (R1E,R2D,ZI,XB,YB), (R1F,R2D,ZI,XB,YB), (R1G,R2D,ZI,XB,YB), (R1H,R2D,ZI,XB,YB), (R1I,R2D,ZI,XB,YB), (R1J,R2D,ZI,XB,YB), (R1K,R2D,ZI,XB,YB), (R1L,R2D,ZI,XB,YB), (R1M,R2D,ZI,XB,YB), (R1N,R2D,ZI,XB,YB), (R1O,R2D,ZI,XB,YB), (R1P,R2D,ZI,XB,YB), (R1Q,R2D,ZI,XB,YB), (R1A,R2E, ZI,XB,YB), (R1B,R2E,ZI,XB,YB), (R1C,R2E,ZI,XB,YB), (R1D,R2E,ZI,XB,YB), (R1E,R2E,ZI,XB,YB), (R1F,R2E, ZI,XB,YB), (R1G,R2E,ZI,XB,YB), (R1H,R2E,ZI,XB,YB), (R1I,R2E,ZI,XB,YB), (R1J,R2E,ZI,XB,YB), (R1K,R2E,ZI, XB,YB), (R1L,R2E,ZI,XB,YB), (R1M,R2E,ZI,XB,YB), (R1N,R2E,ZI,XB,YB), (R1O,R2E,ZI,XB,YB), (R1P,R2E, ZI,XB,YB), (R1Q,R2E,ZI,XB,YB), (R1A,R2F,ZI,XB,YB), (R1B,R2F,ZI,XB,YB), (R1C,R2F,ZI,XB,YB), (R1D,R2F, ZI,XB,YB), (R1E,R2F,ZI,XB,YB), (R1F,R2F,ZI,XB,YB), (R1G,R2F,ZI,XB,YB), (R1H,R2F,ZI,XB,YB), (R1I,R2F,ZI, XB,YB), (R1J,R2F,ZI,XB,YB), (R1K,R2F,ZI,XB,YB), (R1L,R2F,ZI,XB,YB), (R1M,R2F,ZI,XB,YB), (R1N,R2F, ZI,XB,YB), (R1O,R2F,ZI,XB,YB), (R1P,R2F,ZI,XB,YB), (R1Q,R2F,ZI,XB,YB), (R1A,R2G,ZI,XB,YB), (R1B,R2G, ZI,XB,YB), (R1C,R2G,ZI,XB,YB), (R1D,R2G,ZI,XB,YB), (R1E,R2G,ZI,XB,YB), (R1F,R2G,ZI,XB,YB), (R1G,R2G, ZI,XB,YB), (R1H,R2G,ZI,XB,YB), (R1I,R2G,ZI,XB,YB), (R1J,R2G,ZI,XB,YB), (R1K,R2G,ZI,XB,YB), (R1L,R2G, ZI,XB,YB), (R1M,R2G,ZI,XB,YB), (R1N,R2G,ZI,XB, YB), (R1O,R2G,ZI,XB,YB), (R1P,R2G,ZI,XB,YB), (R1Q, R2G,ZI,XB,YB), (R1A,R2H,ZI,XB,YB), (R1B,R2H,ZI, XB,YB), (R1C,R2H,ZI,XB,YB), (R1D,R2H,ZI,XB,YB), (R1E,R2H,ZI,XB,YB), (R1F,R2H,ZI,XB,YB), (R1G,R2H, ZI,XB,YB), (R1H,R2H,ZI,XB,YB), (R1I,R2H,ZI,XB,YB), (R1J,R2H,ZI,XB,YB), (R1K,R2H,ZI,XB,YB), (R1L,R2H, ZI,XB,YB), (R1M,R2H,ZI,XB,YB), (R1N,R2H,ZI,XB, YB), (R1O,R2H,ZI,XB,YB), (R1P,R2H,ZI,XB,YB), (R1Q, R2H,ZI,XB,YB), (R1A,R2I,ZI,XB,YB), (R1B,R2I,ZI,XB, YB), (R1C,R2I,ZI,XB,YB), (R1D,R2I,ZI,XB,YB), (R1E, R2I,ZI,XB,YB), (R1F,R2I,ZI,XB,YB), (R1G,R2I,ZI,XB, YB), (R1H,R2I,ZI,XB,YB), (R1I,R2I,ZI,XB,YB), (R1J,R2I, ZI,XB,YB), (R1K,R2I,ZI,XB,YB), (R1L,R2I,ZI,XB,YB), (R1M,R2I,ZI,XB,YB), (R1N,R2I,ZI,XB,YB), (R1O,R2I,ZI, XB,YB), (R1P,R2I,ZI,XB,YB), (R1Q,R2I,ZI,XB,YB), (R1A,R2J,ZI,XB,YB), (R1B,R2J,ZI,XB,YB), (R1C,R2J,ZI, XB,YB), (R1D,R2J,ZI,XB,YB), (R1E,R2J,ZI,XB,YB), (R1F,R2J,ZI,XB,YB), (R1G,R2J,ZI,XB,YB), (R1H,R2J,ZI, XB,YB), (R1I,R2J,ZI,XB,YB), (R1J,R2J,ZI,XB,YB), (R1K, R2J,ZI,XB,YB), (R1L,R2J,ZI,XB,YB), (R1M,R2J,ZI,XB, YB), (R1N,R2J,ZI,XB,YB), (R1O,R2J,ZI,XB,YB), (R1P, R2J,ZI,XB,YB), (R1Q,R2J,ZI,XB,YB), (R1A,R2K,ZI,XB, YB), (R1B,R2K,ZI,XB,YB), (R1C,R2K,ZI,XB,YB), (R1D, R2K,ZI,XB,YB), (R1E,R2K,ZI,XB,YB), (R1F,R2K,ZI,XB, YB), (R1G,R2K,ZI,XB,YB), (R1H,R2K,ZI,XB,YB), (R1I, R2K,ZI,XB,YB), (R1J,R2K,ZI,XB,YB), (R1K,R2K,ZI,XB, YB), (R1L,R2K,ZI,XB,YB), (R1M,R2K,ZI,XB,YB), (R1N, R2K,ZI,XB,YB), (R1O,R2K,ZI,XB,YB), (R1P,R2K,ZI,XB, YB), (R1Q,R2K,ZI,XB,YB), (R1A,R2L,ZI,XB,YB), (R1B, R2L,ZI,XB,YB), (R1C,R2L,ZI,XB,YB), (R1D,R2L,ZI,XB, YB), (R1E,R2L,ZI,XB,YB), (R1F,R2L,ZI,XB,YB), (R1G, R2L,ZI,XB,YB), (R1H,R2L,ZI,XB,YB), (R1I,R2L,ZI,XB, YB), (R1J,R2L,ZI,XB,YB), (R1K,R2L,ZI,XB,YB), (R1L, R2L,ZI,XB,YB), (R1M,R2L,ZI,XB,YB), (R1N,R2L,ZI,XB, YB), (R1O,R2L,ZI,XB,YB), (R1P,R2L,ZI,XB,YB), (R1Q, R2L,ZI,XB,YB), (R1A,R2M,ZI,XB,YB), (R1B,R2M,ZI, XB,YB), (R1C,R2M,ZI,XB,YB), (R1D,R2M,ZI,XB,YB), (R1E,R2M,ZI,XB,YB), (R1F,R2M,ZI,XB,YB), (R1G,R2M, ZI,XB,YB), (R1H,R2M,ZI,XB,YB), (R1I,R2M,ZI,XB,YB), (R1J,R2M,ZI,XB,YB), (R1K,R2M,ZI,XB,YB), (R1L,R2M, ZI,XB,YB), (R1M,R2M,ZI,XB,YB), (R1N,R2M,ZI,XB, YB), (R1O,R2M,ZI,XB,YB), (R1P,R2M,ZI,XB,YB), (R1Q, R2M,ZI,XB,YB), (R1A,R2N,ZI,XB,YB), (R1B,R2N,ZI, XB,YB), (R1C,R2N,ZI,XB,YB), (R1D,R2N,ZI,XB,YB), (R1E,R2N,ZI,XB,YB), (R1F,R2N,ZI,XB,YB), (R1G,R2N, ZI,XB,YB), (R1H,R2N,ZI,XB,YB), (R1I,R2N,ZI,XB,YB), (R1J,R2N,ZI,XB,YB), (R1K,R2N,ZI,XB,YB), (R1L,R2N, ZI,XB,YB), (R1M,R2N,ZI,XB,YB), (R1N,R2N,ZI,XB, YB), (R1O,R2N,ZI,XB,YB), (R1P,R2N,ZI,XB,YB), (R1Q, R2N,ZI,XB,YB), (R1A,R2O,ZI,XB,YB), (R1B,R2O,ZI, XB,YB), (R1C,R2O,ZI,XB,YB), (R1D,R2O,ZI,XB,YB), (R1E,R2O,ZI,XB,YB), (R1F,R2O,ZI,XB,YB), (R1G,R2O, ZI,XB,YB), (R1H,R2O,ZI,XB,YB), (R1I,R2O,ZI,XB,YB), (R1J,R2O,ZI,XB,YB), (R1K,R2O,ZI,XB,YB), (R1L,R2O, ZI,XB,YB), (R1M,R2O,ZI,XB,YB), (R1N,R2O,ZI,XB, YB), (R1O,R2O,ZI,XB,YB), (R1P,R2O,ZI,XB,YB), (R1Q, R2O,ZI,XB,YB), (R1A,R2P,ZI,XB,YB), (R1B,R2P,ZI,XB, YB), (R1C,R2P,ZI,XB,YB), (R1D,R2P,ZI,XB,YB), (R1E, R2P,ZI,XB,YB), (R1F,R2P,ZI,XB,YB), (R1G,R2P,ZI,XB, YB), (R1H,R2P,ZI,XB,YB), (R1I,R2P,ZI,XB,YB), (R1J, R2P,ZI,XB,YB), (R1K,R2P,ZI,XB,YB), (R1L,R2P,ZI,XB, YB), (R1M,R2P,ZI,XB,YB), (R1N,R2P,ZI,XB,YB), (R1O, R2P,ZI,XB,YB), (R1P,R2P,ZI,XB,YB), (R1Q,R2P,ZI,XB, YB), (R1A,R2Q,ZI,XB,YB), (R1B,R2Q,ZI,XB,YB), (R1C, R2Q,ZI,XB,YB), (R1D,R2Q,ZI,XB,YB), (R1E,R2Q,ZI,XB, YB), (R1F,R2Q,ZI,XB,YB), (R1G,R2Q,ZI,XB,YB), (R1H, R2Q,ZI,XB,YB), (R1I,R2Q,ZI,XB,YB), (R1J,R2Q,ZI,XB, YB), (R1K,R2Q,ZI,XB,YB), (R1L,R2Q,ZI,XB,YB), (R1M, R2Q,ZI,XB,YB), (R1N,R2Q,ZI,XB,YB), (R1O,R2Q,ZI, XB,YB), (R1P,R2Q,ZI,XB,YB), (R1Q,R2Q,ZI,XB,YB), (R1A,R2A,ZJ,XB,YB), (R1B,R2A,ZJ,XB,YB), (R1C,R2A, ZJ,XB,YB), (R1D,R2A,ZJ,XB,YB), (R1E,R2A,ZJ,XB,YB), (R1F,R2A,ZJ,XB,YB), (R1G,R2A,ZJ,XB,YB), (R1H,R2A, ZJ,XB,YB), (R1I,R2A,ZJ,XB,YB), (R1J,R2A,ZJ,XB,YB), (R1K,R2A,ZJ,XB,YB), (R1L,R2A,ZJ,XB,YB), (R1M,R2A, ZJ,XB,YB), (R1N,R2A,ZJ,XB,YB), (R1O,R2A,ZJ,XB, YB), (R1P,R2A,ZJ,XB,YB), (R1Q,R2A,ZJ,XB,YB), (R1A, R2B,ZJ,XB,YB), (R1B,R2B,ZJ,XB,YB), (R1C,R2B,ZJ,XB, YB), (R1D,R2B,ZJ,XB,YB), (R1E,R2B,ZJ,XB,YB), (R1F, R2B,ZJ,XB,YB), (R1G,R2B,ZJ,XB,YB), (R1H,R2B,ZJ, XB,YB), (R1I,R2B,ZJ,XB,YB), (R1J,R2B,ZJ,XB,YB), (R1K,R2B,ZJ,XB,YB), (R1L,R2B,ZJ,XB,YB), (R1M,R2B, ZJ,XB,YB), (R1N,R2B,ZJ,XB,YB), (R1O,R2B,ZJ,XB,YB), (R1P,R2B,ZJ,XB,YB), (R1Q,R2B,ZJ,XB,YB), (R1A,R2C, ZJ,XB,YB), (R1B,R2C,ZJ,XB,YB), (R1C,R2C,ZJ,XB,YB), (R1D,R2C,ZJ,XB,YB), (R1E,R2C,ZJ,XB,YB), (R1F,R2C, ZJ,XB,YB), (R1G,R2C,ZJ,XB,YB), (R1H,R2C,ZJ,XB,YB), (R1I,R2C,ZJ,XB,YB), (R1J,R2C,ZJ,XB,YB), (R1K,R2C, ZJ,XB,YB), (R1L,R2C,ZJ,XB,YB), (R1M,R2C,ZJ,XB, YB), (R1N,R2C,ZJ,XB,YB), (R1O,R2C,ZJ,XB,YB), (R1P, R2C,ZJ,XB,YB), (R1Q,R2C,ZJ,XB,YB), (R1A,R2D,ZJ, XB,YB), (R1B,R2D,ZJ,XB,YB), (R1C,R2D,ZJ,XB,YB), (R1D,R2D,ZJ,XB,YB), (R1E,R2D,ZJ,XB,YB), (R1F,R2D, ZJ,XB,YB), (R1G,R2D,ZJ,XB,YB), (R1H,R2D,ZJ,XB, YB), (R1I,R2D,ZJ,XB,YB), (R1J,R2D,ZJ,XB,YB), (R1K, R2D,ZJ,XB,YB), (R1L,R2D,ZJ,XB,YB), (R1M,R2D,ZJ, XB,YB), (R1N,R2D,ZJ,XB,YB), (R1O,R2D,ZJ,XB,YB), (R1P,R2D,ZJ,XB,YB), (R1Q,R2D,ZJ,XB,YB), (R1A,R2E, ZJ,XB,YB), (R1B,R2E,ZJ,XB,YB), (R1C,R2E,ZJ,XB,YB), (R1D,R2E,ZJ,XB,YB), (R1E,R2E,ZJ,XB,YB), (R1F,R2E, ZJ,XB,YB), (R1G,R2E,ZJ,XB,YB), (R1H,R2E,ZJ,XB,YB), (R1L R2E,ZJ,XB,YB), (R1J,R2E,ZJ,XB,YB), (R1K,R2E, ZJ,XB,YB), (R1L,R2E,ZJ,XB,YB), (R1M,R2E,ZJ,XB,YB), (R1N,R2E,ZJ,XB,YB), (R1O,R2E,ZJ,XB,YB), (R1P,R2E, ZJ,XB,YB), (R1Q,R2E,ZJ,XB,YB), (R1A,R2F,ZJ,XB,YB), (R1B,R2F,ZJ,XB,YB), (R1C,R2F,ZJ,XB,YB), (R1D,R2F, ZJ,XB,YB), (R1E,R2F,ZJ,XB,YB), (R1F,R2F,ZJ,XB,YB), (R1G,R2F,ZJ,XB,YB), (R1H,R2F,ZJ,XB,YB), (R1I,R2F,ZJ, XB,YB), (R1J,R2F,ZJ,XB,YB), (R1K,R2F,ZJ,XB,YB), (R1L,R2F,ZJ,XB,YB), (R1M,R2F,ZJ,XB,YB), (R1N,R2F, ZJ,XB,YB), (R1O,R2F,ZJ,XB,YB), (R1P,R2F,ZJ,XB,YB), (R1Q,R2F,ZJ,XB,YB), (R1A,R2G,ZJ,XB,YB), (R1B,R2G, ZJ,XB,YB), (R1C,R2G,ZJ,XB,YB), (R1D,R2G,ZJ,XB, YB), (R1E,R2G,ZJ,XB,YB), (R1F,R2G,ZJ,XB,YB), (R1G, R2G,ZJ,XB,YB), (R1H,R2G,ZJ,XB,YB), (R1I,R2G,ZJ,XB, YB), (R1J,R2G,ZJ,XB,YB), (R1K,R2G,ZJ,XB,YB), (R1L, R2G,ZJ,XB,YB), (R1M,R2G,ZJ,XB,YB), (R1N,R2G,ZJ, XB,YB), (R1O,R2G,ZJ,XB,YB), (R1P,R2G,ZJ,XB,YB), (R1Q,R2G,ZJ,XB,YB), (R1A,R2H,ZJ,XB,YB), (R1B,R2H, ZJ,XB,YB), (R1C,R2H,ZJ,XB,YB), (R1D,R2H,ZJ,XB, YB), (R1E,R2H,ZJ,XB,YB), (R1F,R2H,ZJ,XB,YB), (R1G, R2H,ZJ,XB,YB), (R1H,R2H,ZJ,XB,YB), (R1I,R2H,ZJ,XB, YB), (R1J,R2H,ZJ,XB,YB), (R1K,R2H,ZJ,XB,YB), (R1L, R2H,ZJ,XB,YB), (R1M,R2H,ZJ,XB,YB), (R1N,R2H,ZJ, XB,YB), (R1O,R2H,ZJ,XB,YB), (R1P,R2H,ZJ,XB,YB), (R1Q,R2H,ZJ,XB,YB), (R1A,R2I,ZJ,XB,YB), (R1B,R2H, ZJ,XB,YB), (R1C,R2I,ZJ,XB,YB), (R1D,R2I,ZJ,XB,YB), (R1E,R2I,ZJ,XB,YB), (R1F,R2I,ZJ,XB,YB), (R1G,R2I,ZJ, XB,YB), (R1H,R2I,ZJ,XB,YB), (R1I,R2I,ZJ,XB,YB), (R1J, R2I,ZJ,XB,YB), (R1K,R2I,ZJ,XB,YB), (R1L,R2I,ZJ,XB, YB), (R1M,R2I,ZJ,XB,YB), (R1N,R2I,ZJ,XB,YB), (R1O, R2I,ZJ,XB,YB), (R1P,R2I,ZJ,XB,YB), (R1Q,R2I,ZJ,XB, YB), (R1A,R2J,ZJ,XB,YB), (R1B,R2J,ZJ,XB,YB), (R1C, R2J,ZJ,XB,YB), (R1D,R2J,ZJ,XB,YB), (R1E,R2J,ZJ,XB, YB), (R1F,R2J,ZJ,XB,YB), (R1G,R2J,ZJ,XB,YB), (R1H, R2J,ZJ,XB,YB), (R1I,R2J,ZJ,XB,YB), (R1J,R2J,ZJ,XB,YB), (R1K,R2J,ZJ,XB,YB), (R1L,R2J,ZJ,XB,YB), (R1M, R2J,ZJ,XB,YB), (R1N,R2J,ZJ,XB,YB), (R1O,R2J,ZJ,XB, YB), (R1P,R2J,ZJ,XB,YB), (R1Q,R2J,ZJ,XB,YB), (R1A, R2K,ZJ,XB,YB), (R1B,R2K,ZJ,XB,YB), (R1C,R2K,ZJ, XB,YB), (R1D,R2K,ZJ,XB,YB), (R1E,R2K,ZJ,XB,YB), (R1F,R2K,ZJ,XB,YB), (R1G,R2K,ZJ,XB,YB), (R1H,R2K, ZJ,XB,YB), (R1I,R2K,ZJ,XB,YB), (R1J,R2K,ZJ,XB,YB), (R1K,R2K,ZJ,XB,YB), (R1L,R2K,ZJ,XB,YB), (R1M,R2K, ZJ,XB,YB), (R1N,R2K,ZJ,XB,YB), (R1O,R2K,ZJ,XB, YB), (R1P,R2K,ZJ,XB,YB), (R1Q,R2K,ZJ,XB,YB), (R1A, R2L,ZJ,XB,YB), (R1B,R2L,ZJ,XB,YB), (R1C,R2L,ZJ,XB, YB), (R1D,R2L,ZJ,XB,YB), (R1E,R2L,ZJ,XB,YB), (R1F, R2L,ZJ,XB,YB), (R1G,R2L,ZJ,XB,YB), (R1H,R2L,ZJ,XB, YB), (R1I,R2L,ZJ,XB,YB), (R1J,R2L,ZJ,XB,YB), (R1K, R2L,ZJ,XB,YB), (R1L,R2L,ZJ,XB,YB), (R1M,R2L,ZJ,XB, YB), (R1N,R2L,ZJ,XB,YB), (R1O,R2L,ZJ,XB,YB), (R1P, R2L,ZJ,XB,YB), (R1Q,R2L,ZJ,XB,YB), (R1A,R2M,ZJ, XB,YB), (R1B,R2M,ZJ,XB,YB), (R1C,R2M,ZJ,XB,YB), (R1D,R2M,ZJ,XB,YB), (R1E,R2M,ZJ,XB,YB), (R1F,R2M, ZJ,XB,YB), (R1G,R2M,ZJ,XB,YB), (R1H,R2M,ZJ,XB, YB), (R1I,R2M,ZJ,XB,YB), (R1J,R2M,ZJ,XB,YB), (R1K, R2M,ZJ,XB,YB), (R1L,R2M,ZJ,XB,YB), (R1M,R2M,ZJ, XB,YB), (R1N,R2M,ZJ,XB,YB), (R1O,R2M,ZJ,XB,YB), (R1P,R2M,ZJ,XB,YB), (R1Q,R2M,ZJ,XB,YB), (R1A,R2N, ZJ,XB,YB), (R1B,R2N,ZJ,XB,YB), (R1C,R2N,ZJ,XB,YB), (R1D,R2N,ZJ,XB,YB), (R1E,R2N,ZJ,XB,YB), (R1F,R2N, ZJ,XB,YB), (R1G,R2N,ZJ,XB,YB), (R1H,R2N,ZJ,XB, YB), (R1I,R2N,ZJ,XB,YB), (R1J,R2N,ZJ,XB,YB), (R1K, R2N,ZJ,XB,YB), (R1L,R2N,ZJ,XB,YB), (R1M,R2N,ZJ, XB,YB), (R1N,R2N,ZJ,XB,YB), (R1O,R2N,ZJ,XB,YB), (R1P,R2N,ZJ,XB,YB), (R1Q,R2N,ZJ,XB,YB), (R1A,R2O, ZJ,XB,YB), (R1B,R2O,ZJ,XB,YB), (R1C,R2O,ZJ,XB,YB), (R1D,R2O,ZJ,XB,YB), (R1E,R2O,ZJ,XB,YB), (R1F,R2O, ZJ,XB,YB), (R1G,R2O,ZJ,XB,YB), (R1H,R2O,ZJ,XB, YB), (R1I,R2O,ZJ,XB,YB), (R1J,R2O,ZJ,XB,YB), (R1K, R2O,ZJ,XB,YB), (R1L,R2O,ZJ,XB,YB), (R1M,R2O,ZJ, XB,YB), (R1N,R2O,ZJ,XB,YB), (R1O,R2O,ZJ,XB,YB), (R1P,R2O,ZJ,XB,YB), (R1Q,R2O,ZJ,XB,YB), (R1A,R2P, ZJ,XB,YB), (R1B,R2P,ZJ,XB,YB), (R1C,R2P,ZJ,XB,YB), (R1D,R2P,ZJ,XB,YB), (R1E,R2P,ZJ,XB,YB), (R1F,R2P,ZJ, XB,YB), (R1G,R2P,ZJ,XB,YB), (R1H,R2P,ZJ,XB,YB), (R1I,R2P,ZJ,XB,YB), (R1J,R2P,ZJ,XB,YB), (R1K,R2P,ZJ, XB,YB), (R1L,R2P,ZJ,XB,YB), (R1M,R2P,ZJ,XB,YB), (R1N,R2P,ZJ,XB,YB), (R1O,R2P,ZJ,XB,YB), (R1P,R2P,ZJ, XB,YB), (R1Q,R2P,ZJ,XB,YB), (R1A,R2Q,ZJ,XB,YB), (R1B,R2Q,ZJ,XB,YB), (R1C,R2Q,ZJ,XB,YB), (R1D,R2Q, ZJ,XB,YB), (R1E,R2Q,ZJ,XB,YB), (R1F,R2Q,ZJ,XB,YB), (R1G,R2Q,ZJ,XB,YB), (R1H,R2Q,ZJ,XB,YB), (R1I,R2Q, ZJ,XB,YB), (R1J,R2Q,ZJ,XB,YB), (R1K,R2Q,ZJ,XB,YB), (R1L,R2Q,ZJ,XB,YB), (R1M,R2Q,ZJ,XB,YB), (R1N,R2Q, ZJ,XB,YB), (R1O,R2Q,ZJ,XB,YB), (R1P,R2Q,ZJ,XB,YB), (R1Q,R2Q,ZJ,XB,YB), (R1A,R2A,ZK,XB,YB), (R1B, R2A,ZK,XB,YB), (R1C,R2A,ZK,XB,YB), (R1D,R2A,ZK, XB,YB), (R1E,R2A,ZK,XB,YB), (R1F,R2A,ZK,XB,YB), (R1G,R2A,ZK,XB,YB), (R1H,R2A,ZK,XB,YB), (R1I, R2A,ZK,XB,YB), (R1J,R2A,ZK,XB,YB), (R1K,R2A,ZK, XB,YB), (R1L,R2A,ZK,XB,YB), (R1M,R2A,ZK,XB,YB), (R1N,R2A,ZK,XB,YB), (R1O,R2A,ZK,XB,YB), (R1P, R2A,ZK,XB,YB), (R1Q,R2A,ZK,XB,YB), (R1A,R2B,ZK, XB,YB), (R1B,R2B,ZK,XB,YB), (R1C,R2B,ZK,XB,YB), (R1D,R2B,ZK,XB,YB), (R1E,R2B,ZK,XB,YB), (R1F,R2B, ZK,XB,YB), (R1G,R2B,ZK,XB,YB), (R1H,R2B,ZK,XB, YB), (R1I,R2B,ZK,XB,YB), (R1J,R2B,ZK,XB,YB), (R1K, R2B,ZK,XB,YB), (R1L,R2B,ZK,XB,YB), (R1M,R2B,ZK, XB,YB), (R1N,R2B,ZK,XB,YB), (R1O,R2B,ZK,XB,YB), (R1P,R2B,ZK,XB,YB), (R1Q,R2B,ZK,XB,YB), (R1A, R2C,ZK,XB,YB), (R1B,R2C,ZK,XB,YB), (R1C,R2C,ZK, XB,YB), (R1D,R2C,ZK,XB,YB), (R1E,R2C,ZK,XB,YB), (R1F,R2C,ZK,XB,YB), (R1G,R2C,ZK,XB,YB), (R1H, R2C,ZK,XB,YB), (R1I,R2C,ZK,XB,YB), (R1J,R2C,ZK, XB,YB), (R1K,R2C,ZK,XB,YB), (R1L,R2C,ZK,XB,YB), (R1M,R22C,ZK,XB,YB), (R1N,R2C,ZK,XB,YB), (R1O, R2C,ZK,XB,YB), (R1P,R2C,ZK,XB,YB), (R1Q,R2C,ZK, XB,YB), (R1A,R2D,ZK,XB,YB), (R1B,R2D,ZK,XB,YB), (R1C,R2D,ZK,XB,YB), (R1D,R2D,ZK,XB,YB), (R1E, R2D,ZK,XB,YB), (R1F,R2D,ZK,XB,YB), (R1G,R2D,ZK, XB,YB), (R1H,R2D,ZK,XB,YB), (R1I,R2D,ZK,XB,YB), (R1J,R2D,ZK,XB,YB), (R1K,R2D,ZK,XB,YB), (R1L, R2D,ZK,XB,YB), (R1M,R2D,ZK,XB,YB), (R1N,R2D,ZK, XB,YB), (R1O,R2D,ZK,XB,YB), (R1P,R2D,ZK,XB,YB), (R1Q,R2D,ZK,XB,YB), (R1A,R2E,ZK,XB,YB), (R1B, R2E,ZK,XB,YB), (R1C,R2E,ZK,XB,YB), (R1D,R2E,ZK, XB,YB), (R1E,R2E,ZK,XB,YB), (R1F,R2E,ZK,XB,YB), (R1G,R2E,ZK,XB,YB), (R1H,R2E,ZK,XB,YB), (R1I,R2E, ZK,XB,YB), (R1J,R2E,ZK,XB,YB), (R1K,R2E,ZK,XB, YB), (R1L,R2E,ZK,XB,YB), (R1M,R2E,ZK,XB,YB), (R1N,R2E,ZK,XB,YB), (R1O,R2E,ZK,XB,YB), (R1P,R2E, ZK,XB,YB), (R1Q,R2E,ZK,XB,YB), (R1A,R2F,ZK,XB, YB), (R1B,R2F,ZK,XB,YB), (R1C,R2F,ZK,XB,YB), (R1D, R2F,ZK,XB,YB), (R1E,R2F,ZK,XB,YB), (R1F,R2F,ZK, XB,YB), (R1G,R2F,ZK,XB,YB), (R1H,R2F,ZK,XB,YB), (R1I,R2F,ZK,XB,YB), (R1J,R2F,ZK,XB,YB), (R1K,R2F, ZK,XB,YB), (R1L,R2F,ZK,XB,YB), (R1M,R2F,ZK,XB, YB), (R1N,R2F,ZK,XB,YB), (R1O,R2F,ZK,XB,YB), (R1P, R2F,ZK,XB,YB), (R1Q,R2F,ZK,XB,YB), (R1A,R2G,ZK, XB,YB), (R1B,R2G,ZK,XB,YB), (R1C,R2G,ZK,XB,YB), (R1D,R2G,ZK,XB,YB), (R1E,R2G,ZK,XB,YB), (R1F, R2G,ZK,XB,YB), (R1G,R2G,ZK,XB,YB), (R1H,R2G,ZK, XB,YB), (R1I,R2G,ZK,XB,YB), (R1J,R2G,ZK,XB,YB), (R1K,R2G,ZK,XB,YB), (R1L,R2G,ZK,XB,YB), (R1M, R2G,ZK,XB,YB), (R1N,R2G,ZK,XB,YB), (R1O,R2G,ZK, XB,YB), (R1P,R2G,ZK,XB,YB), (R1Q,R2G,ZK,XB,YB), (R1A,R2H,ZK,XB,YB), (R1B,R2H,ZK,XB,YB), (R1C, R2H,ZK,XB,YB), (R1D,R2H,ZK,XB,YB), (R1E,R2H,ZK, XB,YB), (R1F,R2H,ZK,XB,YB), (R1G,R2H,ZK,XB,YB), (R1H,R2H,ZK,XB,YB), (R1I,R2H,ZK,XB,YB), (R1J,R2H, ZK,XB,YB), (R1K,R2H,ZK,XB,YB), (R1L,R2H,ZK,XB, YB), (R1M,R2H,ZK,XB,YB), (R1N,R2H,ZK,XB,YB), (R1O,R2H,ZK,XB,YB), (R1P,R2H,ZK,XB,YB), (R1Q, R2H,ZK,XB,YB), (R1A,R2I,ZK,XB,YB), (R1B,R2I, XB,YB), (R1C,R2I,ZK,XB,YB), (R1D,R2I,ZK,XB,YB), (R1E,R2I,ZK,XB,YB), (R1F,R2I,ZK,XB,YB), (R1G,R2I, ZK,XB,YB), (R1H,R2I,ZK,XB,YB), (R1I,R2I,ZK,XB,YB), (R1J,R2I,ZK,XB,YB), (R1K,R2I,ZK,XB,YB), (R1L,R2I,ZK,XB,YB), (R1M,R2I,ZK,XB,YB), (R1N,R2I,ZK,XB,YB), (R1O,R2I,ZK,XB,YB), (R1P,R2I,ZK,XB,YB), (R1Q,R2I,ZK,XB,YB), (R1A,R2J,ZK,XB,YB), (R1B,R2J,ZK,XB,YB), (R1C,R2J,ZK,XB,YB), (R1D,R2J,ZK,XB,YB), (R1E,R2J,ZK,XB,YB), (R1F,R2J,ZK,XB,YB), (R1G,R2J,ZK,XB,YB), (R1H,R2J,ZK,XB,YB), (R1I,R2J,ZK,XB,YB), (R1J,R2J,ZK,XB,YB), (R1K,R2J,ZK,XB,YB), (R1L,R2J,ZK,XB,YB), (R1M,R2J,ZK,XB,YB), (R1N,R2J,ZK,XB,YB), (R1O,R2J,ZK,XB,YB), (R1P,R2J,ZK,XB,YB), (R1Q,R2J,ZK,XB,YB), (R1A,R2K,ZK,XB,YB), (R1B,R2K,ZK,XB,YB), (R1C,R2K,ZK,XB,YB), (R1D,R2K,ZK,XB,YB), (R1E,R2K,ZK,XB,YB), (R1F,R2K,ZK,XB,YB), (R1G,R2K,ZK,XB,YB), (R1H,R2K,ZK,XB,YB), (R1I,R2K,ZK,XB,YB), (R1J,R2K,ZK,XB,YB), (R1K,R2K,ZK,XB,YB), (R1L,R2K,ZK,XB,YB), (R1M,R2K,ZK,XB,YB), (R1N,R2K,ZK,XB,YB), (R1O,R2K,ZK,XB,YB), (R1P,R2K,ZK,XB,YB), (R1Q,R2K,ZK,XB,YB), (R1A,R2L,ZK,XB,YB), (R1B,R2L,ZK,XB,YB), (R1C,R2L,ZK,XB,YB), (R1D,R2L,ZK,XB,YB), (R1E,R2L,ZK,XB,YB), (R1F,R2L,ZK,XB,YB), (R1G,R2L,ZK,XB,YB), (R1H,R2L,ZK,XB,YB), (R1I,R2L,ZK,XB,YB), (R1J,R2L,ZK,XB,YB), (R1K,R2L,ZK,XB,YB), (R1L,R2L,ZK,XB,YB), (R1M,R2L,ZK,XB,YB), (R1N,R2L,ZK,XB,YB), (R1O,R2L,ZK,XB,YB), (R1P,R2L,ZK,XB,YB), (R1Q,R2L,ZK,XB,YB), (R1A,R2M,ZK,XB,YB), (R1B,R2M,ZK,XB,YB), (R1C,R2M,ZK,XB,YB), (R1D,R2M,ZK,XB,YB), (R1E,R2M,ZK,XB,YB), (R1F,R2M,ZK,XB,YB), (R1G,R2M,ZK,XB,YB), (R1H,R2M,ZK,XB,YB), (R1I,R2M,ZK,XB,YB), (R1J,R2M,ZK,XB,YB), (R1K,R2M,ZK,XB,YB), (R1L,R2M,ZK,XB,YB), (R1M,R2M,ZK,XB,YB), (R1N,R2M,ZK,XB,YB), (R1O,R2M,ZK,XB,YB), (R1P,R2M,ZK,XB,YB), (R1Q,R2M,ZK,XB,YB), (R1A,R2N,ZK,XB,YB), (R1B,R2N,ZK,XB,YB), (R1C,R2N,ZK,XB,YB), (R1D,R2N,ZK,XB,YB), (R1E,R2N,ZK,XB,YB), (R1F,R2N,ZK,XB,YB), (R1G,R2N,ZK,XB,YB), (R1H,R2N,ZK,XB,YB), (R1I,R2N,ZK,XB,YB), (R1J,R2N,ZK,XB,YB), (R1K,R2N,ZK,XB,YB), (R1L,R2N,ZK,XB,YB), (R1M,R2N,ZK,XB,YB), (R1N,R2N,ZK,XB,YB), (R1O,R2N,ZK,XB,YB), (R1P,R2N,ZK,XB,YB), (R1Q,R2N,ZK,XB,YB), (R1A,R2O,ZK,XB,YB), (R1B,R2O,ZK,XB,YB), (R1C,R2O,ZK,XB,YB), (R1D,R2O,ZK,XB,YB), (R1E,R2O,ZK,XB,YB), (R1F,R2O,ZK,XB,YB), (R1G,R2O,ZK,XB,YB), (R1H,R2O,ZK,XB,YB), (R1I,R2O,ZK,XB,YB), (R1J,R2O,ZK,XB,YB), (R1K,R2O,ZK,XB,YB), (R1L,R2O,ZK,XB,YB), (R1M,R2O,ZK,XB,YB), (R1N,R2O,ZK,XB,YB), (R1O,R2O,ZK,XB,YB), (R1P,R2O,ZK,XB,YB), (R1Q,R2O,ZK,XB,YB), (R1A,R2P,ZK,XB,YB), (R1B,R2P,ZK,XB,YB), (R1C,R2P,ZK,XB,YB), (R1D,R2P,ZK,XB,YB), (R1E,R2P,ZK,XB,YB), (R1F,R2P,ZK,XB,YB), (R1G,R2P,ZK,XB,YB), (R1H,R2P,ZK,XB,YB), (R1I,R2P,ZK,XB,YB), (R1J,R2P,ZK,XB,YB), (R1K,R2P,ZK,XB,YB), (R1L,R2P,ZK,XB,YB), (R1M,R2P,ZK,XB,YB), (R1N,R2P,ZK,XB,YB), (R1O,R2P,ZK,XB,YB), (R1P,R2P,ZK,XB,YB), (R1Q,R2P,ZK,XB,YB), (R1A,R2Q,ZK,XB,YB), (R1B,R2Q,ZK,XB,YB), (R1C,R2Q,ZK,XB,YB), (R1D,R2Q,ZK,XB,YB), (R1E,R2Q,ZK,XB,YB), (R1F,R2Q,ZK,XB,YB), (R1G,R2Q,ZK,XB,YB), (R1H,R2Q,ZK,XB,YB), (R1I,R2Q,ZK,XB,YB), (R1J,R2Q,ZK,XB,YB), (R1K,R2Q,ZK,XB,YB), (R1L,R2Q,ZK,XB,YB), (R1M,R2Q,ZK,XB,YB), (R1N,R2Q,ZK,XB,YB), (R1O,R2Q,ZK,XB,YB), (R1P,R2Q,ZK,XB,YB), (R1Q,R2Q,ZK,XB,YB), (R1A,R2A,ZL,XB,YB), (R1B,R2A,ZL,XB,YB), (R1C,R2A,ZL,XB,YB), (R1D,R2A,ZL,XB,YB), (R1E,R2A,ZL,XB,YB), (R1F,R2A,ZL,XB,YB), (R1G,R2A,ZL,XB,YB), (R1H,R2A,ZL,XB,YB), (R1I,R2A,ZL,XB,YB), (R1J,R2A,ZL,XB,YB), (R1K,R2A,ZL,XB,YB), (R1L,R2A,ZL,XB,YB), (R1M,R2A,ZL,XB,YB), (R1N,R2A,ZL,XB,YB), (R1O,R2A,ZL,XB,YB), (R1P,R2A,ZL,XB,YB), (R1Q,R2A,ZL,XB,YB), (R1A,R2B,ZL,XB,YB), (R1B,R2B,ZL,XB,YB), (R1C,R2B,ZL,XB,YB), (R1D,R2B,ZL,XB,YB), (R1E,R2B,ZL,XB,YB), (R1F,R2B,ZL,XB,YB), (R1G,R2B,ZL,XB,YB), (R1H,R2B,ZL,XB,YB), (R1I,R2B,ZL,XB,YB), (R1J,R2B,ZL,XB,YB), (R1K,R2B,ZL,XB,YB), (R1L,R2B,ZL,XB,YB), (R1M,R2B,ZL,XB,YB), (R1N,R2B,ZL,XB,YB), (R1O,R2B,ZL,XB,YB), (R1P,R2B,ZL,XB,YB), (R1Q,R2B,ZL,XB,YB), (R1A,R2C,ZL,XB,YB), (R1B,R2C,ZL,XB,YB), (R1C,R2C,ZL,XB,YB), (R1D,R2C,ZL,XB,YB), (R1E,R2C,ZL,XB,YB), (R1F,R2C,ZL,XB,YB), (R1G,R2C,ZL,XB,YB), (R1H,R2C,ZL,XB,YB), (R1I,R2C,ZL,XB,YB), (R1J,R2C,ZL,XB,YB), (R1K,R2C,ZL,XB,YB), (R1L,R2C,ZL,XB,YB), (R1M,R2C,ZL,XB,YB), (R1N,R2C,ZL,XB,YB), (R1O,R2C,ZL,XB,YB), (R1P,R2C,ZL,XB,YB), (R1Q,R2C,ZL,XB,YB), (R1A,R2D,ZL,XB,YB), (R1B,R2D,ZL,XB,YB), (R1C,R2D,ZL,XB,YB), (R1D,R2D,ZL,XB,YB), (R1E,R2D,ZL,XB,YB), (R1F,R2D,ZL,XB,YB), (R1G,R2D,ZL,XB,YB), (R1H,R2D,ZL,XB,YB), (R1I,R2D,ZL,XB,YB), (R1J,R2D,ZL,XB,YB), (R1K,R2D,ZL,XB,YB), (R1L,R2D,ZL,XB,YB), (R1M,R2D,ZL,XB,YB), (R1N,R2D,ZL,XB,YB), (R1O,R2D,ZL,XB,YB), (R1P,R2D,ZL,XB,YB), (R1Q,R2D,ZL,XB,YB), (R1A,R2E,ZL,XB,YB), (R1B,R2E,ZL,XB,YB), (R1C,R2E,ZL,XB,YB), (R1D,R2E,ZL,XB,YB), (R1E,R2E,ZL,XB,YB), (R1F,R2E,ZL,XB,YB), (R1G,R2E,ZL,XB,YB), (R1H,R2E,ZL,XB,YB), (R1I,R2E,ZL,XB,YB), (R1J,R2E,ZL,XB,YB), (R1K,R2E,ZL,XB,YB), (R1L,R2E,ZL,XB,YB), (R1M,R2E,ZL,XB,YB), (R1N, R2E,ZL,XB,YB), (R1O,R2E,ZL,XB,YB), (R1P,R2E,ZL,XB,YB), (R1Q,R2E,ZL,XB,YB), (R1A,R2F,ZL,XB,YB), (R1B,R2F,ZL,XB,YB), (R1C,R2F,ZL,XB,YB), (R1D,R2F,ZL,XB,YB), (R1E,R2F,ZL,XB,YB), (R1F,R2F,ZL,XB,YB), (R1G,R2F,ZL,XB,YB), (R1H,R2F,ZL,XB,YB), (R1I,R2F,ZL,XB,YB), (R1J,R2F,ZL,XB,YB), (R1K,R2F,ZL,XB,YB), (R1L,R2F,ZL,XB,YB), (R1M,R2F,ZL,XB,YB), (R1N,R2F,ZL,XB,YB), (R1O,R2F,ZL,XB,YB), (R1P,R2F,ZL,XB,YB), (R1Q,R2F,ZL,XB,YB),(R1A,R2G,ZL,XB,YB),(R1B,R2G,ZL,XB,YB), (R1C,R2G,ZL,XB,YB), (R1D,R2G,ZL,XB,YB),(R1E,R2G,ZL,XB,YB),(R1F,R2G,ZL,XB,YB),(R1G,R2G,ZL,XB,YB), (R1H,R2G,ZL,XB,YB), (R1I,R2G,ZL,XB,YB), (R1J,R2G,ZL,XB,YB), (R1K,R2G,ZL,XB,YB), (R1L,R2G,ZL,XB,YB), (R1M,R2G,ZL,XB,YB), (R1N,R2G,ZL,XB,YB), (R1O,R2G,ZL,XB,YB), (R1P,R2G,ZL,XB,YB), (R1Q,R2G,ZL,XB,YB), (R1A,R2H,ZL,XB,YB), (R1B,R2H,ZL,XB,YB), (R1C,R2H,ZL,XB,YB), (R1D,R2H,ZL,XB,YB), (R1E,R2H,ZL,XB,YB), (R1F,R2H,ZL,XB,YB), (R1G,R2H,ZL,XB,YB), (R1H,R2H,ZL,XB,YB), (R1I,R2H,ZL,XB,YB), (R1J,R2H,ZL,XB,YB), (R1K,R2H,ZL,XB,YB), (R1L,R2H,ZL,XB,YB), (R1M,R2H,ZL,XB,YB), (R1N,R2H,ZL,XB,YB), (R1O,R2H,ZL,XB,YB), (R1P,R2H,ZL,XB,YB), (R1Q,R2H,ZL,XB,YB), (R1A,R2I,ZL,XB,YB), (R1B,R2I,ZL,XB,YB), (R1C,R2I,ZL,XB,YB), (R1D,R2I,ZL,XB,YB), (R1E,R2I,ZL,XB,YB), (R1F,R2I,ZL,XB,YB), (R1G,R2I,ZL,XB,YB), (R1H,R2I,ZL,XB,YB), (R1I,R2I,ZL,XB,YB), (R1J,R2I,ZL,XB,YB), (R1K,R2I,ZL,XB,YB), (R1L,R2I,ZL,XB,YB), (R1M,R2I,ZL,XB,YB), (R1N,R2I,ZL,XB,YB), (R1O,R2I,ZL,XB,YB), (R1P,R2I,ZL,XB,YB), (R1Q,R2I,ZL,XB,YB), (R1A,R2J,ZL,XB,YB), (R1B,R2J,ZL,XB,YB), (R1C,R2J,ZL,XB,YB), (R1D,R2J,ZL,XB,YB), (R1E,R2J,ZL,XB,YB), (R1F,R2J,ZL,XB,YB), (R1G,R2J,ZL,XB,YB), (R1H,R2J,ZL,XB,YB), (R1I,R2J,ZL,XB,YB), (R1J,R2J,ZL,XB,YB), (R1K,R2J,ZL,XB,YB), (R1L,R2J,ZL,XB,YB), (R1M,R2J,ZL,XB,YB), (R1N,R2J,ZL,XB,YB), (R1O,R2J,ZL,XB,YB), (R1P,R2J,ZL,XB,YB), (R1Q,R2J,ZL,XB,YB), (R1A,R2K,ZL,XB,YB), (R1B,R2K,ZL,XB,YB), (R1C,R2K,ZL,XB,YB), (R1D,R2K,ZL, XB,YB), (R1E,R2K,ZL,XB,YB), (R1F,R2K,ZL,XB,YB), (R1G,R2K,ZL,XB,YB), (R1H,R2K,ZL,XB,YB), (R1I,R2K,ZL,XB,YB), (R1J,R2K,ZL,XB,YB), (R1K,R2K,ZL,XB,YB), (R1L,R2K,ZL,XB,YB), (R1M,R2K,ZL,XB,YB), (R1N,R2K,ZL,XB,YB), (R1O,R2K,ZL,XB,YB), (R1P,R2K,ZL,XB,YB), (R1Q,R2K,ZL,XB,YB), (R1A,R2L,ZL,XB,YB), (R1B,R2L,ZL,XB,YB), (R1C,R2L,ZL,XB,YB), (R1D,R2L,ZL,XB,YB), (R1E,R2L,ZL,XB,YB), (R1F,R2L,ZL,XB,YB), (R1G,R2L,ZL,XB,YB), (R1H,R2L,ZL,XB,YB), (R1I,R2L,ZL,XB,YB), (R1J,R2L,ZL,XB,YB), (R1K,R2L,ZL,XB,YB), (R1L,R2L,ZL,XB,YB), (R1M,R2L,ZL,XB,YB), (R1N,R2L,ZL,XB,YB), (R1O,R2L,ZL,XB,YB), (R1P,R2L,ZL,XB,YB),(R1Q,R2L,ZL,XB,YB), (R1A,R2M,ZL,XB,YB), (R1B,R2M,ZL,XB,YB), (R1C,R2M,ZL,XB,YB), (R1D,R2M,ZL,XB,YB), (R1E,R2M,ZL,XB,YB), (R1F,R2M,ZL,XB,YB), (R1G,R2M,ZL,XB,YB), (R1H,R2M,ZL,XB,YB), (R1I,R2M,ZL,XB,YB), (R1J,R2M,ZL,XB,YB), (R1K,R2M,ZL,XB,YB), (R1L,R2M,ZL,XB,YB), (R1M,R2M,ZL,XB,YB), (R1N,R2M,ZL,XB,YB), (R1O,R2M,ZL,XB,YB), (R1P,R2M,ZL,XB,YB), (R1Q,R2M,ZL,XB,YB), (R1A,R2N,ZL,XB,YB), (R1B,R2N,ZL,XB,YB), (R1C,R2N,ZL,XB,YB), (R1D,R2N,ZL,XB,YB), (R1E,R2N,ZL,XB,YB), (R1F,R2N,ZL,XB,YB), (R1G,R2N,ZL,XB,YB), (R1H,R2N,ZL,XB,YB), (R1I,R2N,ZL,XB,YB), (R1J,R2N,ZL,XB,YB), (R1K,R2N,ZL,XB,YB), (R1L,R2N,ZL,XB,YB), (R1M,R2N,ZL,XB,YB), (R1N,R2N,ZL,XB,YB), (R1O,R2N,ZL,XB,YB), (R1P,R2N,ZL,XB,YB), (R1Q,R2N,ZL,XB,YB), (R1A,R2O,ZL,XB,YB), (R1B,R2O,ZL,XB,YB), (R1C,R2O,ZL,XB,YB), (R1D,R2O,ZL,XB,YB), (R1E,R2O,ZL,XB,YB), (R1F,R2O,ZL,XB,YB), (R1G,R2O,ZL,XB,YB), (R1H,R2O,ZL,XB,YB), (R1I,R2O,ZL,XB,YB), (R1J,R2O,ZL,XB,YB), (R1K,R2O,ZL,XB,YB), (R1L,R2O,ZL,XB,YB), (R1M,R2O,ZL,XB,YB), (R1N,R2O,ZL,XB,YB), (R1O,R2O,ZL,XB,YB), (R1P,R2O,ZL,XB,YB), (R1Q,R2O,ZL,XB,YB), (R1A,R2P,ZL,XB,YB), (R1B,R2P,ZL,XB,YB), (R1C,R2P,ZL,XB,YB), (R1D,R2P,ZL,XB,YB), (R1E,R2P,ZL,XB,YB), (R1F,R2P,ZL,XB,YB), (R1G,R2P,ZL,XB,YB), (R1H,R2P,ZL,XB,YB), (R1I,R2P,ZL,XB,YB), (R1J,R2P,ZL,XB,YB), (R1K,R2P,ZL,XB,YB), (R1L,R2P,ZL,XB,YB), (R1M,R2P,ZL,XB,YB), (R1N,R2P,ZL,XB,YB), (R1O,R2P,ZL,XB,YB), (R1P,R2P,ZL,XB,YB), (R1Q,R2P,ZL,XB,YB), (R1A,R2Q,ZL,XB,YB), (R1B,R2Q,ZL,XB,YB), (R1C,R2Q,ZL,XB,YB), (R1D,R2Q,ZL,XB,YB), (R1E,R2Q,ZL,XB,YB), (R1F,R2Q,ZL,XB,YB), (R1G,R2Q,ZL,XB,YB), (R1H,R2Q,ZL,XB,YB), (R1I,R2Q,ZL,XB,YB), (R1J,R2Q,ZL,XB,YB), (R1K,R2Q,ZL,XB,YB), (R1L,R2Q,ZL,XB,YB), (R1M,R2Q,ZL,XB,YB), (R1N,R2Q,ZL,XB,YB), (R1O,R2Q,ZL,XB,YB), (R1P,R2Q,ZL,XB,YB), (R1Q,R2Q,ZL,XB,YB), (R1A,R2A,ZM,XB,YB), (R1B,R2A,ZM,XB,YB), (R1C,R2A,ZM,XB,YB), (R1D,R2A,ZM,XB,YB), (R1E,R2A,ZM,XB,YB), (R1F,R2A,ZM,XB,YB), (R1G,R2A,ZM,XB,YB), (R1H,R2A,ZM,XB,YB), (R1I,R2A,ZM,XB,YB), (R1J,R2A,ZM,XB,YB), (R1K,R2A,ZM,XB,YB), (R1L,R2A,ZM,XB,YB), (R1M,R2A,ZM,XB,YB), (R1N,R2A,ZM,XB,YB), (R1O,R2A,ZM,XB,YB), (R1P,R2A,ZM,XB,YB), (R1Q,R2A,ZM,XB,YB), (R1A,R2B,ZM,XB,YB), (R1B,R2B,ZM,XB,YB), (R1C,R2B,ZM,XB,YB), (R1D,R2B,ZM,XB,YB), (R1E,R2B,ZM,XB,YB), (R1F,R2B,ZM,XB,YB), (R1G,R2B,ZM,XB,YB), (R1H,R2B,ZM,XB,YB), (R1I,R2B,ZM,XB,YB), (R1J,R2B,ZM,XB,YB), (R1K,R2B,ZM,XB,YB), (R1L,R2B,ZM,XB,YB), (R1M,R2B,ZM,XB,YB), (R1N,R2B,ZM,XB,YB), (R1O,R2B,ZM,XB,YB), (R1P,R2B,ZM,XB,YB), (R1Q,R2B,ZM,XB,YB), (R1A,R2C,ZM,XB,YB), (R1B,R2C,ZM,XB,YB), (R1C,R2C,ZM,XB,YB), (R1D,R2C,ZM,XB,YB), (R1E,R2C,ZM,XB,YB), (R1F,R2C,ZM,XB,YB), (R1G,R2C,ZM,XB,YB), (R1H,R2C,ZM,XB,YB), (R1I,R2C,ZM,XB,YB), (R1J,R2C,ZM,XB,YB), (R1K,R2C,ZM,XB,YB), (R1L,R2C,ZM,XB,YB), (R1M,R2C,ZM,XB,YB), (R1N,R2C,ZM,XB,YB), (R1O,R2C,ZM,XB,YB), (R1P,R2C,ZM,XB,YB), (R1Q,R2C,ZM,XB,YB), (R1A,R2D,ZM,XB,YB), (R1B,R2D,ZM,XB,YB), (R1C,R2D,ZM,XB,YB), (R1D,R2D,ZM,XB,YB), (R1E,R2D,ZM,XB,YB), (R1F,R2D,ZM,XB,YB), (R1G,R2D,ZM,XB,YB), (R1H,R2D,ZM,XB,YB), (R1I,R2D,ZM,XB,YB), (R1J,R2D,ZM,XB,YB), (R1K,R2D,ZM,XB,YB), (R1L,R2D,ZM,XB,YB), (R1M,R2D,ZM,XB,YB), (R1N,R2D,ZM,XB,YB), (R1O,R2D,ZM,XB,YB), (R1P,R2D,ZM,XB,YB), (R1Q,R2D,ZM,XB,YB), (R1A,R2E,ZM,XB,YB), (R1B,R2E,ZM,XB,YB), (R1C,R2E,ZM,XB,YB), (R1D,R2E,ZM,XB,YB), (R1E,R2E,ZM,XB,YB), (R1F,R2E,ZM,XB,YB), (R1G,R2E,ZM,XB,YB), (R1H,R2E,ZM,XB,YB), (R1I,R2E,ZM,XB,YB), (R1J,R2E,ZM,XB,YB), (R1K,R2E,ZM,XB,YB), (R1L,R2E,ZM,XB,YB), (R1M,R2E,ZM,XB,YB), (R1N,R2E,ZM,XB,YB), (R1O,R2E,ZM,XB,YB), (R1P,R2E,ZM,XB,YB), (R1Q,R2E,ZM,XB,YB), (R1A,R2F,ZM,XB,YB), (R1B,R2F,ZM,XB,YB), (R1C,R2F,ZM,XB,YB), (R1D,R2F,ZM,XB,YB), (R1E,R2F,ZM,XB,YB), (R1F,R2F,ZM,XB,YB), (R1G,R2F,ZM,XB,YB), (R1H,R2F,ZM,XB,YB), (R1I,R2F,ZM,XB,YB), (R1J,R2F,ZM,XB,YB), (R1K,R2F,ZM,XB,YB), (R1L,R2F,ZM,XB,YB), (R1M,R2F,ZM,XB,YB), (R1N,R2F,ZM,XB,YB), (R1O,R2F,ZM,XB,YB), (R1P,R2F,ZM,XB,YB), (R1Q,R2F,ZM,XB,YB), (R1A,R2G,ZM,XB,YB), (R1B,R2G,ZM,XB,YB), (R1C,R2G,ZM,XB,YB), (R1D,R2G,ZM,XB,YB), (R1E,R2G,ZM,XB,YB), (R1F,R2G,ZM,XB,YB), (R1G,R2G,ZM,XB,YB), (R1H,R2G,ZM,XB,YB), (R1I,R2G,ZM,XB,YB), (R1J,R2G,ZM,XB,YB), (R1K,R2G,ZM,XB,YB), (R1L,R2G,ZM,XB,YB), (R1M,R2G,ZM,XB,YB), (R1N,R2G,ZM,XB,YB), (R1O,R2G,ZM,XB,YB), (R1P,R2G,ZM,XB,YB), (R1Q,R2G,ZM,XB,YB), (R1A,R2H,ZM,XB,YB), (R1B,R2H,ZM,XB,YB), (R1C,R2H,ZM,XB,YB), (R1D,R2H,ZM,XB,YB), (R1E,R2H,ZM,XB,YB), (R1F,R2H,ZM,XB,YB), (R1G,R2H,ZM,XB,YB), (R1H,R2H,ZM,XB,YB), (R1I,R2H,ZM,XB,YB), (R1J,R2H,ZM,XB,YB), (R1K,R2H,ZM,XB,YB), (R1L,R2H,ZM,XB,YB), (R1M,R2H,ZM,XB,YB), (R1N,R2H,ZM,XB,YB), (R1O,R2H,ZM,XB,YB), (R1P,R2H,ZM,XB,YB), (R1Q,R2H,ZM,XB,YB), (R1A,R2I,ZM,XB,YB), (R1B,R2I,ZM,XB,YB), (R1C,R2I,ZM,XB,YB), (R1D,R2I,ZM,XB,YB), (R1E,R2I,ZM,XB,YB), (R1F,R2I,ZM,XB,YB), (R1G,R2I,ZM,XB,YB), (R1H,R2I,ZM,XB,YB), (R1I,R2I,ZM,XB,YB), (R1J,R2I,ZM,XB,YB), (R1K,R2I,ZM,XB,YB), (R1L,R2I,ZM,XB,YB), (R1M,R2I,ZM,XB,YB), (R1N,R2I,ZM,XB,YB), (R1O,R2I,ZM,XB,YB), (R1P,R2I,ZM,XB,YB), (R1Q,R2I,ZM,XB,YB), (R1A,R2J,ZM,XB,YB), (R1B,R2J,ZM,XB,YB), (R1C,R2J,ZM,XB,YB), (R1D,R2J,ZM,XB,YB), (R1E,R2J,ZM,XB,YB), (R1F,R2J,ZM,XB,YB), (R1G,R2J,ZM,XB,YB), (R1H,R2J,ZM,XB,YB), (R1I,R2J,ZM,XB,YB), (R1J,R2J,ZM,XB,YB), (R1K,R2J,ZM,XB,YB), (R1L,R2J,ZM,XB,YB), (R1M,R2J,ZM,XB,YB), (R1N,R2J,ZM,XB,YB), (R1O,R2J,ZM,XB,YB), (R1P,R2J,ZM,XB,YB), (R1Q,R2J,ZM,XB,YB), (R1A,R2K,ZM,XB,YB), (R1B,R2K,ZM,XB,YB), (R1C,R2K,ZM,XB,YB), (R1D,R2K,ZM,XB,YB), (R1E,R2K,ZM,XB,YB), (R1F,R2K,ZM,XB,YB), (R1G,R2K,ZM,XB,YB), (R1H,R2K,ZM,XB,YB), (R1I,R2K,ZM,XB,YB), (R1J,R2K,ZM,XB,YB), (R1K,R2K,ZM,XB,YB), (R1L,R2K,ZM,XB,YB), (R1M,R2K,ZM,XB,YB), (R1N,R2K,ZM,XB,YB), (R1O,R2K,ZM,XB,YB), (R1P,R2K,ZM,XB,YB), (R1Q,R2K,ZM,XB,YB), (R1A,R2L,ZM,XB,YB), (R1B,R2L,ZM,XB,YB), (R1C,R2L,ZM,XB,YB), (R1D,R2L,ZM,XB,YB), (R1E,R2L,ZM,XB,YB), (R1F,R2L,ZM,XB,YB), (R1G,R2L,ZM,XB,YB), (R1H,R2L,ZM,XB,YB), (R1I,R2L,ZM,XB,YB), (R1J,R2L,ZM,XB,YB), (R1K,R2L, ZM,XB,YB), (R1L,R2L,ZM,XB,YB), (R1M,R2L,ZM,XB,YB), (R1N,R2L,ZM,XB,YB), (R1O,R2L,ZM,XB,YB), (R1P,R2L,ZM,XB,YB), (R1Q,R2L,ZM,XB,YB), (R1A,R2M,ZM,XB,YB), (R1B,R2M,ZM,XB,YB), (R1C,R2M,ZM,XB,YB), (R1D,R2M,ZM,XB,YB), (R1E,R2M,ZM,XB,YB), (R1F,R2M,ZM,XB,YB), (R1G,R2M,ZM,XB,YB), (R1H,R2M,ZM,XB,YB), (R1I,R2M,ZM,XB,YB), (R1J,R2M,ZM,XB,YB), (R1K,R2M,ZM,XB,YB), (R1L,R2M,ZM,XB,YB), (R1M,R2M,ZM,XB,YB), (R1N,R2M,ZM,XB,YB), (R1O,R2M,ZM,XB,YB), (R1P,R2M,ZM,XB,YB), (R1Q,R2M,ZM,XB,YB), (R1A,R2N,ZM,XB,YB), (R1B,R2N,ZM,XB,YB), (R1C,R2N,ZM,XB,YB), (R1D,R2N,ZM,XB,YB), (R1E,R2N,ZM,XB,YB), (R1F,R2N,ZM,XB,YB), (R1G,R2N,ZM,XB,YB), (R1H,R2N,ZM,XB,YB), (R1I,R2N,ZM,XB,YB), (R1J,R2N,ZM,XB,YB), (R1K,R2N,ZM,XB,YB), (R1L,R2N,ZM,XB,YB), (R1M,R2N,ZM,XB,YB), (R1N,R2N,ZM,XB,YB), (R1O,R2N,ZM,XB,YB), (R1P,R2N,ZM,XB,YB), (R1Q,R2N,ZM,XB,YB), (R1A,R2O,ZM,XB,YB), (R1B,R2O,ZM,XB,YB), (R1C,R2O,ZM,XB,YB), (R1D,R2O,ZM,XB,YB), (R1E,R2O,ZM,XB,YB), (R1F,R2O,ZM,XB,YB), (R1G,R2O,ZM,XB,YB), (R1H,R2O,ZM,XB,YB), (R1I,R2O,ZM,XB,YB), (R1J,R2O,ZM,XB,YB), (R1K,R2O,ZM,XB,YB), (R1L,R2O,ZM,XB,YB), (R1M,R2O,ZM,XB,YB), (R1N,R2O,ZM,XB,YB), (R1O,R2O,ZM,XB,YB), (R1P,R2O,ZM,XB,YB), (R1Q,R2O,ZM,XB,YB), (R1A,R2P,ZM,XB,YB), (R1B,R2P,ZM,XB,YB), (R1C,R2P,ZM,XB,YB), (R1D,R2P,ZM,XB,YB), (R1E,R2P,ZM,XB,YB), (R1F,R2P,ZM,XB,YB), (R1G,R2P,ZM,XB,YB), (R1H,R2P,ZM,XB,YB), (R1I,R2P,ZM,XB,YB), (R1J,R2P,ZM,XB,YB), (R1K,R2P,ZM,XB,YB), (R1L,R2P,ZM,XB,YB), (R1M,R2P,ZM,XB,YB), (R1N,R2P,ZM,XB,YB), (R1O,R2P,ZM,XB,YB), (R1P,R2P,ZM,XB,YB), (R1Q,R2P,ZM,XB,YB), (R1A,R2Q,ZM,XB,YB), (R1B,R2Q,ZM,XB,YB), (R1C,R2Q,ZM,XB,YB), (R1D,R2Q,ZM,XB,YB), (R1E,R2Q,ZM,XB,YB), (R1F,R2Q,ZM,XB,YB), (R1G,R2Q,ZM,XB,YB), (R1H,R2Q,ZM,XB,YB), (R1I,R2Q,ZM,XB,YB), (R1J,R2Q,ZM,XB,YB), (R1K,R2Q,ZM,XB,YB), (R1L,R2Q,ZM,XB,YB), (R1M,R2Q,ZM,XB,YB), (R1N,R2Q,ZM,XB,YB), (R1O,R2Q,ZM,XB,YB), (R1P,R2Q,ZM,XB,YB), (R1Q,R2Q,ZM,XB,YB), (R1A,R2A,ZN,XB,YB), (R1B,R2A,ZN,XB,YB), (R1C,R2A,ZN,XB,YB), (R1D,R2A,ZN,XB,YB), (R1E,R2A,ZN,XB,YB), (R1F,R2A,ZN,XB,YB), (R1G,R2A,ZN,XB,YB), (R1H,R2A,ZN,XB,YB), (R1I,R2A,ZN,XB,YB), (R1J,R2A,ZN,XB,YB), (R1K,R2A,ZN,XB,YB), (R1L,R2A,ZN,XB,YB), (R1M,R2A,ZN,XB,YB), (R1N,R2A,ZN,XB,YB), (R1O,R2A,ZN,XB,YB), (R1P,R2A,ZN,XB,YB), (R1Q,R2A,ZN,XB,YB), (R1A,R2B,ZN,XB,YB), (R1B,R2B,ZN,XB,YB), (R1C,R2B,ZN,XB,YB), (R1D,R2B,ZN,XB,YB), (R1E,R2B,ZN,XB,YB), (R1F,R2B,ZN,XB,YB), (R1G,R2B,ZN,XB,YB), (R1H,R2B,ZN,XB,YB), (R1I,R2B,ZN,XB,YB), (R1J,R2B,ZN,XB,YB), (R1K,R2B,ZN,XB,YB), (R1L,R2B,ZN,XB,YB), (R1M,R2B,ZN,XB,YB), (R1N,R2B,ZN,XB,YB), (R1O,R2B,ZN,XB,YB), (R1P,R2B,ZN,XB,YB), (R1Q,R2B,ZN,XB,YB), (R1A,R2C,ZN,XB,YB), (R1B,R2C,ZN,XB,YB), (R1C,R2C,ZN,XB,YB), (R1D,R2C,ZN,XB,YB), (R1E,R2C,ZN,XB,YB), (R1F,R2C,ZN,XB,YB), (R1G,R2C,ZN,XB,YB), (R1H,R2C,ZN,XB,YB), (R1I,R2C,ZN,XB,YB), (R1J,R2C,ZN,XB,YB), (R1K,R2C,ZN,XB,YB), (R1L,R2C,ZN,XB,YB), (R1M,R2C,ZN,XB,YB), (R1N,R2C,ZN,XB,YB), (R1O,R2C,ZN,XB,YB), (R1P,R2C,ZN,XB,YB), (R1Q,R2C,ZN,XB,YB), (R1A,R2D,ZN,XB,YB), (R1B,R2D,ZN,XB,YB), (R1C,R2D,ZN,XB,YB), (R1D,R2D,ZN,XB,YB), (R1E,R2D,ZN,XB,YB), (R1F,R2D,ZN,XB,YB), (R1G,R2D,ZN,XB,YB), (R1H,R2D,ZN,XB,YB), (R1I,R2D,ZN,XB,YB), (R1J,R2D,ZN,XB,YB), (R1K,R2D,ZN,XB,YB), (R1L,R2D,ZN,XB,YB), (R1M,R2D,ZN,XB,YB), (R1N,R2D,ZN,XB,YB), (R1O,R2D,ZN,XB,YB), (R1P,R2D,ZN,XB,YB), (R1Q,R2D,ZN,XB,YB), (R1A,R2E,ZN,XB,YB), (R1B,R2E,ZN,XB,YB), (R1C,R2E,ZN,XB,YB), (R1D,R2E,ZN,XB,YB), (R1E,R2E,ZN,XB,YB), (R1F,R2E,ZN,XB,YB), (R1G,R2E,ZN,XB,YB), (R1H,R2E,ZN,XB,YB), (R1I,R2E,ZN,XB,YB), (R1J,R2E,ZN,XB,YB), (R1K,R2E,ZN,XB,YB), (R1L,R2E,ZN,XB,YB), (R1M,R2E,ZN,XB,YB), (R1N,R2E,ZN,XB,YB), (R1O,R2E,ZN,XB,YB), (R1P,R2E,ZN,XB,YB), (R1Q,R2E,ZN,XB,YB), (R1A,R2F,ZN,XB,YB), (R1B,R2F,ZN,XB,YB), (R1C,R2F,ZN,XB,YB), (R1D,R2F,ZN,XB,YB), (R1E,R2F,ZN,XB,YB), (R1F,R2F,ZN,XB,YB), (R1G,R2F,ZN,XB,YB), (R1H,R2F,ZN,XB,YB), (R1I,R2F,ZN,XB,YB), (R1J,R2F,ZN,XB,YB), (R1K,R2F,ZN,XB,YB), (R1L,R2F,ZN,XB,YB), (R1M,R2F,ZN,XB,YB), (R1N,R2F,ZN,XB,YB), (R1O,R2F,ZN,XB,YB), (R1P,R2F,ZN,XB,YB), (R1Q,R2F,ZN,XB,YB), (R1A,R2G,ZN,XB,YB), (R1B,R2G,ZN,XB,YB), (R1C,R2G,ZN,XB,YB), (R1D,R2G,ZN,XB,YB), (R1E,R2G,ZN,XB,YB), (R1F,R2G,ZN,XB,YB), (R1G,R2G,ZN,XB,YB), (R1H,R2G,ZN,XB,YB), (R1I,R2G,ZN,XB,YB), (R1J,R2G,ZN,XB,YB), (R1K,R2G,ZN,XB,YB), (R1L,R2G,ZN,XB,YB), (R1M,R2G,ZN,XB,YB), (R1N,R2G,ZN,XB,YB), (R1O,R2G,ZN,XB,YB), (R1P,R2G,ZN,XB,YB), (R1Q,R2G,ZN,XB,YB), (R1A,R2H,ZN,XB,YB), (R1B,R2H,ZN,XB,YB), (R1C,R2H,ZN,XB,YB), (R1D,R2H,ZN,XB,YB), (R1E,R2H,ZN,XB,YB), (R1F,R2H,ZN,XB,YB), (R1G,R2H,ZN,XB,YB), (R1H,R2H,ZN,XB,YB), (R1I,R2H,ZN,XB,YB), (R1J,R2H,ZN,XB,YB), (R1K,R2H,ZN,XB,YB), (R1L,R2H,ZN,XB,YB), (R1M,R2H,ZN,XB,YB), (R1N,R2H,ZN,XB,YB), (R1O,R2H,ZN,XB,YB), (R1P,R2H,ZN,XB,YB), (R1Q,R2H,ZN,XB,YB), (R1A,R2I,ZN,XB,YB), (R1B,R2I,ZN,XB,YB), (R1C,R2I,ZN,XB,YB), (R1D,R2I,ZN,XB,YB), (R1E,R2I,ZN,XB,YB), (R1F,R2I,ZN,XB,YB), (R1G,R2I,ZN,XB,YB), (R1H,R2I,ZN,XB,YB), (R1I,R2I,ZN,XB,YB), (R1J,R2I,ZN,XB,YB), (R1K,R2I,ZN,XB,YB), (R1L,R2I,ZN,XB,YB), (R1M,R2I,ZN,XB,YB), (R1N,R2I,ZN,XB,YB), (R1O,R2I,ZN,XB,YB), (R1P,R2I,ZN,XB,YB), (R1Q,R2I,ZN,XB,YB), (R1A,R2J,ZN,XB,YB), (R1B,R2J,ZN,XB,YB), (R1C,R2J,ZN,XB,YB), (R1D,R2J,ZN,XB,YB), (R1E,R2J,ZN,XB,YB), (R1F,R2J,ZN,XB,YB), (R1G,R2J,ZN,XB,YB), (R1H,R2J,ZN,XB,YB), (R1I,R2J,ZN,XB,YB), (R1J,R2J,ZN,XB,YB), (R1K,R2J,ZN,XB,YB), (R1L,R2J,ZN,XB,YB), (R1M,R2J,ZN,XB,YB), (R1N,R2J,ZN,XB,YB), (R1O,R2J,ZN,XB,YB), (R1P,R2J,ZN,XB,YB), (R1Q,R2J,ZN,XB,YB), (R1A,R2K,ZN,XB,YB), (R1B,R2K,ZN,XB,YB), (R1C,R2K,ZN,XB,YB), (R1D,R2K,ZN,XB,YB), (R1E,R2K,ZN,XB,YB), (R1F,R2K,ZN,XB,YB), (R1G,R2K,ZN,XB,YB), (R1H,R2K,ZN,XB,YB), (R1I,R2K,ZN,XB,YB), (R1J,R2K,ZN,XB,YB), (R1K,R2K,ZN,XB,YB), (R1L,R2K,ZN,XB,YB), (R1M,R2K,ZN,XB,YB), (R1N,R2K,ZN,XB,YB), (R1O,R2K,ZN,XB,YB), (R1P,R2K,ZN,XB,YB), (R1Q,R2K,ZN,XB,YB), (R1A,R2L,ZN,XB,YB), (R1B,R2L,ZN,XB,YB), (R1C,R2L,ZN,XB,YB), (R1D,R2L,ZN,XB,YB), (R1E,R2L,ZN,XB,YB), (R1F,R2L,ZN,XB,YB), (R1G,R2L,ZN,XB,YB), (R1H,R2L,ZN,XB,YB), (R1I,R2L,ZN,XB,YB), (R1J,R2L,ZN,XB,YB), (R1K,R2L,ZN,XB,YB), (R1L,R2L,ZN,XB,YB), (R1M,R2L,ZN,XB,YB), (R1N,R2L,ZN,XB,YB), (R1O,R2L,ZN,XB,YB), (R1P,R2L,ZN,XB,YB), (R1Q,R2L,ZN,XB,YB), (R1A,R2M,ZN,XB,YB), (R1B,R2M,ZN,XB,YB), (R1C,R2M,ZN,XB,YB), (R1D,R2M,ZN,XB,YB), (R1E,R2M,ZN,XB,YB), (R1F,R2M,ZN,XB,YB), (R1G,R2M,ZN,XB,YB), (R1H,R2M,ZN,XB,YB), (R1I,R2M,ZN,XB,YB), (R1J,R2M,ZN,XB,YB), (R1K,R2M,ZN,XB,YB), (R1L,R2M,ZN,XB,YB), (R1M,R2M,ZN,XB,YB), (R1N,R2M,ZN,XB,YB), (R1O,R2M,ZN,XB,YB), (R1P,R2M,ZN,XB,YB), (R1Q,R2M,ZN,XB,YB), (R1A,R2N,ZN,XB,YB), (R1B, R2N,ZN,XB,YB), (R1C,R2N,ZN,XB,YB), (R1D,R2N,ZN, XB,YB), (R1E,R2N,ZN,XB,YB), (R1F,R2N,ZN,XB,YB), (R1G,R2N,ZN,XB,YB), (R1H,R2N,ZN,XB,YB), (R1I, R2N,ZN,XB,YB), (R1J,R2N,ZN,XB,YB), (R1K,R2N,ZN, XB,YB), (R1L,R2N,ZN,XB,YB), (R1M,R2N,ZN,XB,YB), (R1N,R2N,ZN,XB,YB), (R1O,R2N,ZN,XB,YB), (R1P, R2N,ZN,XB,YB), (R1Q,R2N,ZN,XB,YB), (R1A,R2O,ZN, XB,YB), (R1B,R2O,ZN,XB,YB), (R1C,R2O,ZN,XB,YB), (R1D,R2O,ZN,XB,YB), (R1E,R2O,ZN,XB,YB), (R1F, R2O,ZN,XB,YB), (R1G,R2O,ZN,XB,YB), (R1H,R2O,ZN, XB,YB), (R1I,R2O,ZN,XB,YB), (R1J,R2O,ZN,XB,YB), (R1K,R2O,ZN,XB,YB), (R1L,R2O,ZN,XB,YB), (R1M, R2O,ZN,XB,YB), (R1N,R2O,ZN,XB,YB), (R1O,R2O,ZN, XB,YB), (R1P,R2O,ZN,XB,YB), (R1Q,R2O,ZN,XB,YB), (R1A,R2P,ZN,XB,YB), (R1B,R2P,ZN,XB,YB), (R1C,R2P, ZN,XB,YB), (R1D,R2P,ZN,XB,YB), (R1E,R2P,ZN,XB, YB), (R1F,R2P,ZN,XB,YB), (R1G,R2P,ZN,XB,YB), (R1H, R2P,ZN,XB,YB), (R1I,R2P,ZN,XB,YB), (R1J,R2P,ZN,XB, YB), (R1K,R2P,ZN,XB,YB), (R1L,R2P,ZN,XB,YB), (R1M,R2P,ZN,XB,YB), (R1N,R2P,ZN,XB,YB), (R1O,R2P, ZN,XB,YB), (R1P,R2P,ZN,XB,YB), (R1Q,R2P,ZN,XB, YB), (R1A,R2Q,ZN,XB,YB), (R1B,R2Q,ZN,XB,YB), (R1C,R2Q,ZN,XB,YB), (R1D,R2Q,ZN,XB,YB), (R1E, R2Q,ZN,XB,YB), (R1F,R2Q,ZN,XB,YB), (R1G,R2Q,ZN, XB,YB), (R1H,R2Q,ZN,XB,YB), (R1I,R2Q,ZN,XB,YB), (R1J,R2Q,ZN,XB,YB), (R1K,R2Q,ZN,XB,YB), (R1L, R2Q,ZN,XB,YB), (R1M,R2Q,ZN,XB,YB), (R1N,R2Q,ZN, XB,YB), (R1O,R2Q,ZN,XB,YB), (R1P,R2Q,ZN,XB,YB), (R1Q,R2Q,ZN,XB,YB), (R1A,R2A,ZO,XB,YB), (R1B, R2A,ZO,XB,YB), (R1C,R2A,ZO,XB,YB), (R1D,R2A,ZO, XB,YB), (R1E,R2A,ZO,XB,YB), (R1F,R2A,ZO,XB,YB), (R1G,R2A,ZO,XB,YB), (R1H,R2A,ZO,XB,YB), (R1I, R2A,ZO,XB,YB), (R1J,R2A,ZO,XB,YB), (R1K,R2A,ZO, XB,YB), (R1L,R2A,ZO,XB,YB), (R1M,R2A,ZO,XB,YB), (R1N,R2A,ZO,XB,YB), (R1O,R2A,ZO,XB,YB), (R1P, R2A,ZO,XB,YB), (R1Q,R2A,ZO,XB,YB), (R1A,R2B,ZO, XB,YB), (R1B,R2B,ZO,XB,YB), (R1C,R2B,ZO,XB,YB), (R1D,R2B,ZO,XB,YB),(R1E,R2B,ZO,XB,YB),(R1F,R2B, ZO,XB,YB), (R1G,R2B,ZO,XB,YB), (R1H,R2B,ZO,XB, YB), (R1I,R2B,ZO,XB,YB), (R1J,R2B,ZO,XB,YB), (R1K, R2B,ZO,XB,YB), (R1L,R2B,ZO,XB,YB), (R1M,R2B,ZO, XB,YB), (R1N,R2B,ZO,XB,YB), (R1O,R2B,ZO,XB,YB), (R1P,R2B,ZO,XB,YB), (R1Q,R2B,ZO,XB,YB), (R1A, R2C,ZO,XB,YB), (R1B,R2C,ZO,XB,YB), (R1C,R2C,ZO, XB,YB), (R1D,R2C,ZO,XB,YB), (R1E,R2C,ZO,XB,YB), (R1F,R2C,ZO,XB,YB), (R1G,R2C,ZO,XB,YB), (R1H, R2C,ZO,XB,YB), (R1I,R2C,ZO,XB,YB), (R1J,R2C,ZO, XB,YB), (R1K,R2C,ZO,XB,YB), (R1L,R2C,ZO,XB,YB), (R1M,R2C,ZO,XB,YB), (R1N,R2C,ZO,XB,YB), (R1O, R2C,ZO,XB,YB), (R1P,R2C,ZO,XB,YB), (R1Q,R2C,ZO, XB,YB), (R1A,R2D,ZO,XB,YB), (R1B,R2D,ZO,XB,YB), (R1C,R2D,ZO,XB,YB), (R1D,R2D,ZO,XB,YB), (R1E, R2D,ZO,XB,YB), (R1F,R2D,ZO,XB,YB), (R1G,R2D,ZO, XB,YB), (R1H,R2D,ZO,XB,YB), (R1I,R2D,ZO,XB,YB), (R1J,R2D,ZO,XB,YB), (R1K,R2D,ZO,XB,YB), (R1L, R2D,ZO,XB,YB), (R1M,R2D,ZO,XB,YB), (R1N,R2D,ZO, XB,YB), (R1O,R2D,ZO,XB,YB), (R1P,R2D,ZO,XB,YB), (R1Q,R2D,ZO,XB,YB), (R1A,R2E,ZO,XB,YB), (R1B, R2E,ZO,XB,YB), (R1C,R2E,ZO,XB,YB), (R1D,R2E,ZO, XB,YB), (R1E,R2E,ZO,XB,YB), (R1F,R2E,ZO,XB,YB), (R1G,R2E,ZO,XB,YB), (R1H,R2E,ZO,XB,YB), (R1I,R2E, ZO,XB,YB), (R1J,R2E,ZO,XB,YB), (R1K,R2E,ZO,XB, YB), (R1L,R2E,ZO,XB,YB), (R1M,R2E,ZO,XB,YB), (R1N,R2E,ZO,XB,YB), (R1O,R2E,ZO,XB,YB),(R1P,R2E, ZO,XB,YB), (R1Q,R2E,ZO,XB,YB), (R1A,R2F,ZO,XB, YB), (R1B,R2F,ZO,XB,YB), (R1C,R2F,ZO,XB,YB), (R1D, R2F,ZO,XB,YB), (R1E,R2F,ZO,XB,YB), (R1F,R2F,ZO, XB,YB), (R1G,R2F,ZO,XB,YB), (R1H,R2F,ZO,XB,YB), (R1I,R2F,ZO,XB,YB), (R1J,R2F,ZO,XB,YB), (R1K,R2F, ZO,XB,YB), (R1L,R2F,ZO,XB,YB), (R1M,R2F,ZO,XB, YB), (R1N,R2F,ZO,XB,YB), (R1O,R2F,ZO,XB,YB), (R1P, R2F,ZO,XB,YB), (R1Q,R2F,ZO,XB,YB), (R1A,R2G,ZO, XB,YB), (R1B,R2G,ZO,XB,YB), (R1C,R2G,ZO,XB,YB), (R1D,R2G,ZO,XB,YB), (R1E,R2G,ZO,XB,YB), (R1F, R2G,ZO,XB,YB), (R1G,R2G,ZO,XB,YB), (R1H,R2G,ZO, XB,YB), (R1I,R2G,ZO,XB,YB), (R1J,R2G,ZO,XB,YB), (R1K,R2G,ZO,XB,YB), (R1L,R2G,ZO,XB,YB), (R1M, R2G,ZO,XB,YB), (R1N,R2G,ZO,XB,YB), (R1O,R2G,ZO, XB,YB), (R1P,R2G,ZO,XB,YB), (R1Q,R2G,ZO,XB,YB), (R1A,R2H,ZO,XB,YB), (R1B,R2H,ZO,XB,YB), (R1C, R2H,ZO,XB,YB), (R1D,R2H,ZO,XB,YB), (R1E,R2H,ZO, XB,YB), (R1F,R2H,ZO,XB,YB), (R1G,R2H,ZO,XB,YB), (R1H,R2H,ZO,XB,YB), (R1I,R2H,ZO,XB,YB), (R1J,R2H, ZO,XB,YB), (R1K,R2H,ZO,XB,YB), (R1L,R2H,ZO,XB, YB), (R1M,R2H,ZO,XB,YB), (R1N,R2H,ZO,XB,YB), (R1O,R2H,ZO,XB,YB), (R1P,R2H,ZO,XB,YB), (R1Q, R2H,ZO,XB,YB), (R1A,R2I,ZO,XB,YB), (R1B,R2I,ZO, XB,YB), (R1C,R2I,ZO,XB,YB), (R1D,R2I,ZO,XB,YB), (R1E,R2I,ZO,XB,YB), (R1F,R2I,ZO,XB,YB), (R1G,R2I, ZO,XB,YB), (R1H,R2I,ZO,XB,YB), (R1I,R2I,ZO,XB,YB), (R1J,R2I,ZO,XB,YB), (R1K,R2I,ZO,XB,YB), (R1L,R2I, ZO,XB,YB), (R1M,R2I,ZO,XB,YB), (R1N,R2I,ZO,XB, YB), (R1O,R2I,ZO,XB,YB), (R1P,R2I,ZO,XB,YB), (R1Q, R2I,ZO,XB,YB), (R1A,R2J,ZO,XB,YB), (R1B,R2J,ZO, XB,YB), (R1C,R2J,ZO,XB,YB), (R1D,R2J,ZO,XB,YB), (R1E,R2J,ZO,XB,YB), (R1F,R2J,ZO,XB,YB), (R1G,R2J, ZO,XB,YB), (R1H,R2J,ZO,XB,YB), (R1I,R2J,ZO,XB, YB), (R1J,R2J,ZO,XB,YB), (R1K,R2J,ZO,XB,YB), (R1L, R2J,ZO,XB,YB), (R1M,R2J,ZO,XB,YB), (R1N,R2J,ZO, XB,YB), (R1O,R2J,ZO,XB,YB), (R1P,R2J,ZO,XB,YB), (R1Q,R2J,ZO,XB,YB), (R1A,R2K,ZO,XB,YB), (R1B, R2K,ZO,XB,YB), (R1C,R2K,ZO,XB,YB), (R1D,R2K,ZO, XB,YB), (R1E,R2K,ZO,XB,YB), (R1F,R2K,ZO,XB,YB), (R1G,R2K,ZO,XB,YB), (R1H,R2K,ZO,XB,YB), (R1I, R2K,ZO,XB,YB), (R1J,R2K,ZO,XB,YB), (R1K,R2K,ZO, XB,YB), (R1L,R2K,ZO,XB,YB), (R1M,R2K,ZO,XB,YB), (R1N,R2K,ZO,XB,YB), (R1O,R2K,ZO,XB,YB), (R1P, R2K,ZO,XB,YB), (R1Q,R2K,ZO,XB,YB), (R1A,R2L,ZO, XB,YB), (R1B,R2L,ZO,XB,YB), (R1C,R2L,ZO,XB,YB), (R1D,R2L,ZO,XB,YB), (R1E,R2L,ZO,XB,YB), (R1F,R2L, ZO,XB,YB), (R1G,R2L,ZO,XB,YB), (R1H,R2L,ZO,XB, YB), (R1I,R2L,ZO,XB,YB), (R1J,R2L,ZO,XB,YB), (R1K, R2L,ZO,XB,YB), (R1L,R2L,ZO,XB,YB), (R1M,R2L,ZO, XB,YB), (R1N,R2L,ZO,XB,YB), (R1O,R2L,ZO,XB,YB), (R1P,R2L,ZO,XB,YB), (R1Q,R2L,ZO,XB,YB), (R1A, R2M,ZO,XB,YB), (R1B,R2M,ZO,XB,YB), (R1C,R2M, ZO,XB,YB), (R1D,R2M,ZO,XB,YB), (R1E,R2M,ZO,XB, YB), (R1F,R2M,ZO,XB,YB), (R1G,R2M,ZO,XB,YB), (R1H,R2M,ZO,XB,YB), (R1I,R2M,ZO,XB,YB), (R1J, R2M,ZO,XB,YB), (R1K,R2M,ZO,XB,YB), (R1L,R2M, ZO,XB,YB), (R1M,R2M,ZO,XB,YB), (R1N,R2M,ZO,XB, YB), (R1O,R2M,ZO,XB,YB), (R1P,R2M,ZO,XB,YB), (R1Q,R2M,ZO,XB,YB), (R1A,R2N,ZO,XB,YB), (R1B, R2N,ZO,XB,YB), (R1C,R2N,ZO,XB,YB), (R1D,R2N,ZO, XB,YB), (R1E,R2N,ZO,XB,YB), (R1F,R2N,ZO,XB,YB), (R1G,R2N,ZO,XB,YB), (R1H,R2N,ZO,XB,YB), (R1I, R2N,ZO,XB,YB), (R1J,R2N,ZO,XB,YB), (R1K,R2N,ZO, XB,YB), (R1L,R2N,ZO,XB,YB), (R1M,R2N,ZO,XB,YB), (R1N,R2N,ZO,XB,YB), (R1O,R2N,ZO,XB,YB), (R1P, R2N,ZO,XB,YB), (R1Q,R2N,ZO,XB,YB), (R1A,R2O,ZO, XB,YB), (R1B,R2O,ZO,XB,YB), (R1C,R2O,ZO,XB,YB), (R1D,R2O,ZO,XB,YB), (R1E,R2O,ZO,XB,YB), (R1F, R2O,ZO,XB,YB), (R1G,R2O,ZO,XB,YB), (R1H,R2O,ZO, XB,YB), (R1I,R2O,ZO,XB,YB), (R1J,R2O,ZO,XB,YB), (R1K,R2O,ZO,XB,YB), (R1L,R2O,ZO,XB,YB), (R1M,R2O,ZO,XB,YB), (R1N,R2O,ZO,XB,YB), (R1O,R2O,ZO,XB,YB), (R1P,R2O,ZO,XB,YB), (R1Q,R2O,ZO,XB,YB), (R1A,R2P,ZO,XB,YB), (R1B,R2P,ZO,XB,YB), (R1C,R2P,ZO,XB,YB), (R1D,R2P,ZO,XB,YB), (R1E,R2P,ZO,XB,YB), (R1F,R2P,ZO,XB,YB), (R1G,R2P,ZO,XB,YB), (R1H,R2P,ZO,XB,YB), (R1I,R2P,ZO,XB,YB), (R1J,R2P,ZO,XB,YB), (R1K,R2P,ZO,XB,YB), (R1L,R2P,ZO,XB,YB), (R1M,R2P,ZO,XB,YB), (R1N,R2P,ZO,XB,YB), (R1O,R2P,ZO,XB,YB), (R1P,R2P,ZO,XB,YB), (R1Q,R2P,ZO,XB,YB), (R1A,R2Q,ZO,XB,YB), (R1B,R2Q,ZO,XB,YB), (R1C,R2Q,ZO,XB,YB), (R1D,R2Q,ZO,XB,YB), (R1E,R2Q,ZO,XB,YB), (R1F,R2Q,ZO,XB,YB), (R1G,R2Q,ZO,XB,YB), (R1H,R2Q,ZO,XB,YB), (R1I,R2Q,ZO,XB,YB), (R1J,R2Q,ZO,XB,YB), (R1K,R2Q,ZO,XB,YB), (R1L,R2Q,ZO,XB,YB), (R1M,R2Q,ZO,XB,YB), (R1N,R2Q,ZO,XB,YB), (R1O,R2Q,ZO,XB,YB), (R1P,R2Q,ZO,XB,YB), (R1Q,R2Q,ZO,XB,YB), (R1A,R2A,ZP,XB,YB), (R1B,R2A,ZP,XB,YB), (R1C,R2A,ZP,XB,YB), (R1D,R2A,ZP,XB,YB), (R1E,R2A,ZP,XB,YB), (R1F,R2A,ZP,XB,YB), (R1G,R2A,ZP,XB,YB), (R1H,R2A,ZP,XB,YB), (R1I,R2A,ZP,XB,YB), (R1J,R2A,ZP,XB,YB), (R1K,R2A,ZP,XB,YB), (R1L,R2A,ZP,XB,YB), (R1M,R2A,ZP,XB,YB), (R1N,R2A,ZP,XB,YB), (R1O,R2A,ZP,XB,YB), (R1P,R2A,ZP,XB,YB), (R1Q,R2A,ZP,XB,YB), (R1A,R2B,ZP,XB,YB), (R1B,R2B,ZP,XB,YB), (R1C,R2B,ZP,XB,YB), (R1D,R2B,ZP,XB,YB), (R1E,R2B,ZP,XB,YB), (R1F,R2B,ZP,XB,YB), (R1G,R2B,ZP,XB,YB), (R1H,R2B,ZP,XB,YB), (R1I,R2B,ZP,XB,YB), (R1J,R2B,ZP,XB,YB), (R1K,R2B,ZP,XB,YB), (R1L,R2B,ZP,XB,YB), (R1M,R2B,ZP,XB,YB), (R1N,R2B,ZP,XB,YB), (R1O,R2B,ZP,XB,YB), (R1P,R2B,ZP,XB,YB), (R1Q,R2B,ZP,XB,YB), (R1A,R2C,ZP,XB,YB), (R1B,R22C,ZP,XB,YB), (R1C,R2C,ZP,XB,YB), (R1D,R2C,ZP,XB,YB), (R1E,R2C,ZP,XB,YB), (R1F,R22C,ZP,XB,YB), (R1G,R2C,ZP,XB,YB), (R1H,R2C,ZP,XB,YB), (R1I,R2C,ZP,XB,YB), (R1J,R22C,ZP,XB,YB), (R1K,R2C,ZP,XB,YB), (R1L,R2C,ZP,XB,YB), (R1M,R2C,ZP,XB,YB), (R1N,R2C,ZP,XB,YB), (R1O,R2C,ZP,XB,YB), (R1P,R2C,ZP,XB,YB), (R1Q,R2C,ZP,XB,YB), (R1A,R2D,ZP,XB,YB), (R1B,R2D,ZP,XB,YB), (R1C,R2D,ZP,XB,YB), (R1D,R2D,ZP,XB,YB), (R1E,R2D,ZP,XB,YB), (R1F,R2D,ZP,XB,YB), (R1G,R2D,ZP,XB,YB), (R1H,R2D,ZP,XB,YB), (R1I,R2D,ZP,XB,YB), (R1J,R2D,ZP,XB,YB), (R1K,R2D,ZP,XB,YB), (R1L,R2D,ZP,XB,YB), (R1M,R2D,ZP,XB,YB), (R1N,R2D,ZP,XB,YB), (R1O,R2D,ZP,XB,YB), (R1P,R2D,ZP,XB,YB), (R1Q,R2D,ZP,XB,YB), (R1A,R2E,ZP,XB,YB), (R1B,R2E,ZP,XB,YB), (R1C,R2E,ZP,XB,YB), (R1D,R2E,ZP,XB,YB), (R1E,R2E,ZP,XB,YB), (R1F,R2E,ZP,XB,YB), (R1G,R2E,ZP,XB,YB), (R1H,R2E,ZP,XB,YB), (R1I,R2E,ZP,XB,YB), (R1J,R2E,ZP,XB,YB), (R1K,R2E,ZP,XB,YB), (R1L,R2E,ZP,XB,YB), (R1M,R2E,ZP,XB,YB), (R1N,R2E,ZP,XB,YB), (R1O,R2E,ZP,XB,YB), (R1P,R2E,ZP,XB,YB), (R1Q,R2E,ZP,XB,YB), (R1A,R2F,ZP,XB,YB), (R1B,R2F,ZP,XB,YB), (R1C,R2F,ZP,XB,YB), (R1D,R2F,ZP,XB,YB), (R1E,R2F,ZP,XB,YB), (R1F,R2F,ZP,XB,YB), (R1G,R2F,ZP,XB,YB), (R1H,R2F,ZP,XB,YB), (R1I,R2F,ZP,XB,YB), (R1J,R2F,ZP,XB,YB), (R1K,R2F,ZP,XB,YB), (R1L,R2F,ZP,XB,YB), (R1M,R2F,ZP,XB,YB), (R1N,R2F,ZP,XB,YB), (R1O,R2F,ZP,XB,YB), (R1P,R2F,ZP,XB,YB), (R1Q,R2F,ZP,XB,YB), (R1A,R2G,ZP,XB,YB), (R1B,R2G,ZP,XB,YB), (R1C,R2G,ZP,XB,YB), (R1D,R2G,ZP,XB,YB), (R1E,R2G,ZP,XB,YB), (R1F,R2G,ZP,XB,YB), (R1G,R2G,ZP,XB,YB), (R1H,R2G,ZP,XB,YB), (R1I,R2G,ZP,XB,YB), (R1J,R2G,ZP,XB,YB), (R1K,R2G,ZP,XB,YB), (R1L,R2G,ZP,XB,YB), (R1M,R2G,ZP,XB,YB), (R1N,R2G,ZP,XB,YB), (R1O,R2G,ZP,XB,YB), (R1P,R2G,ZP,XB,YB), (R1Q,R2G,ZP,XB,YB), (R1A,R2H,ZP,XB,YB), (R1B,R2H,ZP,XB,YB), (R1C,R2H,ZP,XB,YB), (R1D,R2H,ZP,XB,YB), (R1E,R2H,ZP,XB,YB), (R1F,R2H,ZP,XB,YB), (R1G,R2H,ZP,XB,YB), (R1H,R2H,ZP,XB,YB), (R1I,R2H,ZP,XB,YB), (R1J,R2H,ZP,XB,YB), (R1K,R2H,ZP,XB,YB), (R1L,R2H,ZP,XB,YB), (R1M,R2H,ZP,XB,YB), (R1N,R2H,ZP,XB,YB), (R1O,R2H,ZP,XB,YB), (R1P,R2H,ZP,XB,YB), (R1Q,R2H,ZP,XB,YB), (R1A,R2I,ZP,XB,YB), (R1B,R2I,ZP,XB,YB), (R1C,R2I,ZP,XB,YB), (R1D,R2I,ZP,XB,YB), (R1E,R2I,ZP,XB,YB), (R1F,R2I,ZP,XB,YB), (R1G,R2I,ZP,XB,YB), (R1H,R2I,ZP,XB,YB), (R1I,R2I,ZP,XB,YB), (R1J,R2I,ZP,XB,YB), (R1K,R2I,ZP,XB,YB), (R1L,R2I,ZP,XB,YB), (R1M,R2I,ZP,XB,YB), (R1N,R2I,ZP,XB,YB), (R1O,R2I,ZP,XB,YB), (R1P,R2I,ZP,XB,YB), (R1Q,R2I,ZP,XB,YB), (R1A,R2J,ZP,XB,YB), (R1B,R2J,ZP,XB,YB), (R1C,R2J,ZP,XB,YB), (R1D,R2J,ZP,XB,YB), (R1E,R2J,ZP,XB,YB), (R1F,R2J,ZP,XB,YB), (R1G,R2J,ZP,XB,YB), (R1H,R2J,ZP,XB,YB), (R1I,R2J,ZP,XB,YB), (R1J,R2J,ZP,XB,YB), (R1K,R2J,ZP,XB,YB), (R1L,R2J,ZP,XB,YB), (R1M,R2J,ZP,XB,YB), (R1N,R2J,ZP,XB,YB), (R1O,R2J,ZP,XB,YB), (R1P,R2J,ZP,XB,YB), (R1Q,R2J,ZP,XB,YB), (R1A,R2K,ZP,XB,YB), (R1B,R2K,ZP,XB,YB), (R1C,R2K,ZP,XB,YB), (R1D,R2K,ZP,XB,YB), (R1E,R2K,ZP,XB,YB), (R1F,R2K,ZP,XB,YB), (R1G,R2K,ZP,XB,YB), (R1H,R2K,ZP,XB,YB), (R1I,R2K,ZP,XB,YB), (R1J,R2K,ZP,XB,YB), (R1K,R2K,ZP,XB,YB), (R1L,R2K,ZP,XB,YB), (R1M,R2K,ZP,XB,YB), (R1N,R2K,ZP,XB,YB), (R1O,R2K,ZP,XB,YB), (R1P,R2K,ZP,XB,YB), (R1Q,R2K,ZP,XB,YB), (R1A,R2L,ZP,XB,YB), (R1B,R2L,ZP,XB,YB), (R1C,R2L,ZP,XB,YB), (R1D,R2L,ZP,XB,YB), (R1E,R2L,ZP,XB,YB), (R1F,R2L,ZP,XB,YB), (R1G,R2L,ZP,XB,YB), (R1H,R2L,ZP,XB,YB), (R1I,R2L,ZP,XB,YB), (R1J,R2L,ZP,XB,YB), (R1K,R2L,ZP,XB,YB), (R1L,R2L,ZP,XB,YB), (R1M,R2L,ZP,XB,YB), (R1N,R2L,ZP,XB,YB), (R1O,R2L,ZP,XB,YB), (R1P,R2L,ZP,XB,YB), (R1Q,R2L,ZP,XB,YB), (R1A,R2M,ZP,XB,YB), (R1B,R2M,ZP,XB,YB), (R1C,R2M,ZP,XB,YB), (R1D,R2M,ZP,XB,YB), (R1E,R2M,ZP,XB,YB), (R1F,R2M,ZP,XB,YB), (R1G,R2M,ZP,XB,YB), (R1H,R2M,ZP,XB,YB), (R1I,R2M,ZP,XB,YB), (R1J,R2M,ZP,XB,YB), (R1K,R2M,ZP,XB,YB), (R1L,R2M,ZP,XB,YB), (R1M,R2M,ZP,XB,YB), (R1N,R2M,ZP,XB,YB), (R1O,R2M,ZP,XB,YB), (R1P,R2M,ZP,XB,YB), (R1Q,R2M,ZP,XB,YB), (R1A,R2N,ZP,XB,YB), (R1B,R2N,ZP,XB,YB), (R1C,R2N,ZP,XB,YB), (R1D,R2N,ZP,XB,YB), (R1E,R2N,ZP,XB,YB), (R1F,R2N,ZP,XB,YB), (R1G,R2N,ZP,XB,YB), (R1H,R2N,ZP,XB,YB), (R1I,R2N,ZP,XB,YB), (R1J,R2N,ZP,XB,YB), (R1K,R2N,ZP,XB,YB), (R1L,R2N,ZP,XB,YB), (R1M,R2N,ZP,XB,YB), (R1N,R2N,ZP,XB,YB), (R1O,R2N,ZP,XB,YB), (R1P,R2N,ZP,XB,YB), (R1Q,R2N,ZP,XB,YB), (R1A,R2O,ZP,XB,YB), (R1B,R2O,ZP,XB,YB), (R1C,R2O,ZP,XB,YB), (R1D,R2O,ZP,XB,YB), (R1E,R2O,ZP,XB,YB), (R1F,R2O,ZP,XB,YB), (R1G,R2O,ZP,XB,YB), (R1H,R2O,ZP,XB,YB), (R1I,R2O,ZP,XB,YB), (R1J,R2O,ZP,XB,YB), (R1K,R2O,ZP,XB,YB), (R1L,R2O,ZP,XB,YB), (R1M,R2O,ZP,XB,YB), (R1N,R2O,ZP,XB,YB), (R1O,R2O,ZP,XB,YB), (R1P,R2O,ZP,XB,YB), (R1Q,R2O,ZP,XB,YB), (R1A,R2P,ZP,XB,YB), (R1B,R2P,ZP,XB,YB), (R1C,R2P,ZP,XB,YB), (R1D,R2P,ZP,XB,YB), (R1E,R2P,ZP,XB,YB), (R1F,R2P,ZP,XB,YB), (R1G,R2P,ZP,XB,YB), (R1H,R2P,ZP,XB,YB), (R1I,R2P,ZP,XB,YB), (R1J,R2P,ZP,XB,YB), (R1K,R2P,ZP,XB,YB), (R1L,R2P,ZP,XB,YB), (R1M,R2P,ZP,XB,YB), (R1N,R2P,ZP,XB,YB), (R1O,R2P,ZP,XB,YB), (R1P,R2P,ZP,XB,YB), (R1Q,R2P,ZP,XB,YB), (R1A,R2Q,ZP,XB,YB), (R1B,R2Q,ZP,XB,YB), (R1C,R2Q,ZP,XB,YB), (R1D,R2Q,ZP,XB,YB), (R1E,R2Q,ZP,XB,YB), (R1F,R2Q,ZP,XB,YB), (R1G,R2Q,ZP,XB,YB), (R1H,R2Q,ZP,XB,YB), (R1I,R2Q,ZP,XB,YB), (R1J,R2Q, ZP,XB,YB), (R1K,R2Q,ZP,XB,YB), (R1L,R2Q,ZP,XB,YB), (R1M,R2Q,ZP,XB,YB), (R1N,R2Q,ZP,XB,YB), (R1O,R2Q,ZP,XB,YB), (R1P,R2Q,ZP,XB,YB), (R1Q,R2Q,ZP,XB,YB), (R1A,R2A,ZQ,XB,YB), (R1B,R2A,ZQ,XB,YB), (R1C,R2A,ZQ,XB,YB), (R1D,R2A,ZQ,XB,YB), (R1E,R2A,ZQ,XB,YB), (R1F,R2A,ZQ,XB,YB), (R1G,R2A,ZQ,XB,YB), (R1H,R2A,ZQ,XB,YB), (R1I,R2A,ZQ,XB,YB), (R1J,R2A,ZQ,XB,YB), (R1K,R2A,ZQ,XB,YB), (R1L,R2A,ZQ,XB,YB), (R1M,R2A,ZQ,XB,YB), (R1N,R2A,ZQ,XB,YB), (R1O,R2A,ZQ,XB,YB), (R1P,R2A,ZQ,XB,YB), (R1Q,R2A,ZQ,XB,YB), (R1A,R2B,ZQ,XB,YB), (R1B,R2B,ZQ,XB,YB), (R1C,R2B,ZQ,XB,YB), (R1D,R2B,ZQ,XB,YB), (R1E,R2B,ZQ,XB,YB), (R1F,R2B,ZQ,XB,YB), (R1G,R2B,ZQ,XB,YB), (R1H,R2B,ZQ,XB,YB), (R1I,R2B,ZQ,XB,YB), (R1J,R2B,ZQ,XB,YB), (R1K,R2B,ZQ,XB,YB), (R1R2B,ZQ,XB,YB), (R1M,R2B,ZQ,XB,YB), (R1N,R2B,ZQ,XB,YB), (R1O,R2B,ZQ,XB,YB), (R1P,R2B,ZQ,XB,YB), (R1Q,R2B,ZQ,XB,YB), (R1A,R2C,ZQ,XB,YB), (R1B,R2C,ZQ,XB,YB), (R1C,R2C,ZQ,XB,YB), (R1D,R2C,ZQ,XB,YB), (R1E,R2C,ZQ,XB,YB), (R1F,R2C,ZQ,XB,YB), (R1G,R2C,ZQ,XB,YB), (R1H,R2C,ZQ,XB,YB), (R1I,R2C,ZQ,XB,YB), (R1J,R2C,ZQ,XB,YB), (R1K,R2C,ZQ,XB,YB), (R1L,R2C,ZQ,XB,YB), (R1M,R2C,ZQ,XB,YB), (R1N,R2C,ZQ,XB,YB), (R1O,R2C,ZQ,XB,YB), (R1P,R2C,ZQ,XB,YB), (R1Q,R2C,ZQ,XB,YB), (R1A,R2D,ZQ,XB,YB), (R1B,R2D,ZQ,XB,YB), (R1C,R2D,ZQ,XB,YB), (R1D,R2D,ZQ,XB,YB), (R1E,R2D,ZQ,XB,YB), 1F,R2D,ZQ,XB,YB), (R1G,R2D,ZQ,XB,YB), (R1H,R2D,ZQ,XB,YB), (R1I,R2D,ZQ,XB,YB), (R1J,R2D,ZQ,XB,YB), (R1K,R2D,ZQ,XB,YB), (R1L,R2D,ZQ,XB,YB), (R1M,R2D,ZQ,XB,YB), (R1N,R2D,ZQ,XB,YB), (R1O,R2D,ZQ,XB,YB), 1P,R2D,ZQ,XB,YB), (R1Q,R2D,ZQ,XB,YB), (R1A,R2E,ZQ,XB,YB), (R1B,R2E,ZQ,XB,YB), (R1C,R2E,ZQ,XB,YB), (R1D,R2E,ZQ,XB,YB), (R1E,R2E,ZQ,XB,YB), (R1F,R2E,ZQ,XB,YB), (R1G,R2E,ZQ,XB,YB), (R1H,R2E,ZQ,XB,YB), (R1I,R2E,ZQ,XB,YB), (R1J,R2E,ZQ,XB,YB), (R1K,R2E,ZQ,XB,YB), (R1L,R2E,ZQ,XB,YB), (R1M,R2E,ZQ,XB,YB), (R1N,R2E,ZQ,XB,YB), (R1O,R2E,ZQ,XB,YB), (R1P,R2E,ZQ,XB,YB), (R1Q,R2E,ZQ,XB,YB), (R1A,R2F,ZQ,XB,YB), (R1B,R2F,ZQ,XB,YB), (R1C,R2F,ZQ,XB,YB), (R1D,R2F,ZQ,XB,YB), (R1E,R2F,ZQ,XB,YB), (R1F,R2F,ZQ,XB,YB), (R1G,R2F,ZQ,XB,YB), (R1H,R2F,ZQ,XB,YB), (R1I,R2F,ZQ,XB,YB), (R1J,R2F,ZQ,XB,YB), (R1K,R2F,ZQ,XB,YB), (R1L,R2F,ZQ,XB,YB), (R1M,R2F,ZQ,XB,YB), (R1N,R2F,ZQ,XB,YB), (R1O,R2F,ZQ,XB,YB), (R1P,R2F,ZQ,XB,YB), (R1Q,R2F,ZQ,XB,YB), (R1A,R2G,ZQ,XB,YB), (R1B,R2G,ZQ,XB,YB), (R1C,R2G,ZQ,XB,YB), (R1D,R2G,ZQ,XB,YB), (R1E,R2G,ZQ,XB,YB), (R1F,R2G,ZQ,XB,YB), (R1G,R2G,ZQ,XB,YB), (R1H,R2G,ZQ,XB,YB), (R1I,R2G,ZQ,XB,YB), (R1J,R2G,ZQ,XB,YB), (R1K,R2G,ZQ,XB,YB), (R1L,R2G,ZQ,XB,YB), (R1M,R2G,ZQ,XB,YB), (R1N,R2G,ZQ,XB,YB), (R1O,R2G,ZQ,XB,YB), (R1P,R2G,ZQ,XB,YB), (R1Q,R2G,ZQ,XB,YB), (R1A,R2H,ZQ,XB,YB), (R1B,R2H,ZQ,XB,YB), (R1C,R2H,ZQ,XB,YB), (R1D,R2H,ZQ,XB,YB), (R1E,R2H,ZQ,XB,YB), (R1F,R2H,ZQ,XB,YB), (R1G,R2H,ZQ,XB,YB), (R1H,R2H,ZQ,XB,YB), (R1I,R2H,ZQ,XB,YB), (R1J,R2H,ZQ,XB,YB), (R1K,R2H,ZQ,XB,YB), (R1L,R2H,ZQ,XB,YB), (R1M,R2H,ZQ,XB,YB), (R1N,R2H,ZQ,XB,YB), (R1O,R2H,ZQ,XB,YB), (R1P,R2H,ZQ,XB,YB), (R1Q,R2H,ZQ,XB,YB), (R1A,R2I,ZQ,XB,YB), (R1B,R2I,ZQ,XB,YB), (R1C,R2I,ZQ,XB,YB), (R1D,R2I,ZQ,XB,YB), (R1E,R2I,ZQ,XB,YB), (R1F,R2I,ZQ,XB,YB), (R1G,R2I,ZQ,XB,YB), (R1H,R2I,ZQ,XB,YB), (R1I,R2I,ZQ,XB,YB), (R1J,R2I,ZQ,XB,YB), (R1K,R2I,ZQ,XB,YB), (R1L,R2I,ZQ,XB,YB), (R1M,R2I,ZQ,XB,YB), (R1N,R2I,ZQ,XB,YB), (R1O,R2I,ZQ,XB,YB), (R1P,R2I,ZQ,XB,YB), (R1Q,R2I,ZQ,XB,YB), (R1A,R2J,ZQ,XB,YB), (R1B,R2J,ZQ,XB,YB), (R1C,R2J,ZQ,XB,YB), (R1D,R2J,ZQ,XB,YB), (R1E,R2J,ZQ,XB,YB), (R1F,R2J,ZQ,XB,YB), (R1G,R2J,ZQ,XB,YB), (R1H,R2J,ZQ,XB,YB), (R1I,R2J,ZQ,XB,YB), (R1J,R2J,ZQ,XB,YB), (R1K,R2J,ZQ,XB,YB), (R1L,R2J,ZQ,XB,YB), (R1M,R2J,ZQ,XB,YB), (R1N,R2J,ZQ,XB,YB), (R1O,R2J,ZQ,XB,YB), (R1P,R2J,ZQ,XB,YB), (R1Q,R2J,ZQ,XB,YB), (R1A,R2K,ZQ,XB,YB), (R1B,R2K,ZQ,XB,YB), (R1C,R2K,ZQ,XB,YB), (R1D,R2K,ZQ,XB,YB), (R1E,R2K,ZQ,XB,YB), (R1F,R2K,ZQ,XB,YB), (R1G,R2K,ZQ,XB,YB), (R1H,R2K,ZQ,XB,YB), (R1I,R2K,ZQ,XB,YB), (R1J,R2K,ZQ,XB,YB), (R1K,R2K,ZQ,XB,YB), (R1L,R2K,ZQ,XB,YB), (R1M,R2K,ZQ,XB,YB), (R1N,R2K,ZQ,XB,YB), (R1O,R2K,ZQ,XB,YB), (R1P,R2K,ZQ,XB,YB), (R1Q,R2K,ZQ,XB,YB), (R1A,R2L,ZQ,XB,YB), (R1B,R2L,ZQ,XB,YB), (R1C,R2L,ZQ,XB,YB), (R1D,R2L,ZQ,XB,YB), (R1E,R2L,ZQ,XB,YB), (R1F,R2L,ZQ,XB,YB), (R1G,R2L,ZQ,XB,YB), (R1H,R2L,ZQ,XB,YB), (R1I,R2L,ZQ,XB,YB), (R1J,R2L,ZQ,XB,YB), (R1K,R2L,ZQ,XB,YB), (R1L,R2L,ZQ,XB,YB), (R1M,R2L,ZQ,XB,YB), (R1N,R2L,ZQ,XB,YB), (R1O,R2L,ZQ,XB,YB), (R1P,R2L,ZQ,XB,YB), (R1Q,R2L,ZQ,XB,YB), (R1A,R2M,ZQ,XB,YB), (R1B,R2M,ZQ,XB,YB), (R1C,R2M,ZQ,XB,YB), (R1D,R2M,ZQ,XB,YB), (R1E,R2M,ZQ,XB,YB), (R1F,R2M,ZQ,XB,YB), (R1G,R2M,ZQ,XB,YB), (R1H,R2M,ZQ,XB,YB), (R1I,R2M,ZQ,XB,YB), (R1J,R2M,ZQ,XB,YB), (R1K,R2M,ZQ,XB,YB), (R1L,R2M,ZQ,XB,YB), (R1M,R2M,ZQ,XB,YB), (R1N,R2M,ZQ,XB,YB), (R1O,R2M,ZQ,XB,YB), (R1P,R2M,ZQ,XB,YB), (R1Q,R2M,ZQ,XB,YB), (R1A,R2N,ZQ,XB,YB), (R1B,R2N,ZQ,XB,YB), (R1C,R2N,ZQ,XB,YB), (R1D,R2N,ZQ,XB,YB), (R1E,R2N,ZQ,XB,YB), (R1F,R2N,ZQ,XB,YB), (R1G,R2N,ZQ,XB,YB), (R1H,R2N,ZQ,XB,YB), (R1I,R2N,ZQ,XB,YB), (R1J,R2N,ZQ,XB,YB), (R1K,R2N,ZQ,XB,YB), (R1L,R2N,ZQ,XB,YB), (R1M,R2N,ZQ,XB,YB), (R1N,R2N,ZQ,XB,YB), (R1O,R2N,ZQ,XB,YB), (R1P,R2N,ZQ,XB,YB), (R1Q,R2N,ZQ,XB,YB), (R1A,R2O,ZQ,XB,YB), (R1B,R2O,ZQ,XB,YB), (R1C,R2O,ZQ,XB,YB), (R1D,R2O,ZQ,XB,YB), (R1E,R2O,ZQ,XB,YB), (R1F,R2O,ZQ,XB,YB), (R1G,R2O,ZQ,XB,YB), (R1H,R2O,ZQ,XB,YB), (R1I,R2O,ZQ,XB,YB), (R1J,R2O,ZQ,XB,YB), (R1K,R2O,ZQ,XB,YB), (R1L,R2O,ZQ,XB,YB), (R1M,R2O,ZQ,XB,YB), (R1N,R2O,ZQ,XB,YB), (R1O,R2O,ZQ,XB,YB), (R1P,R2O,ZQ,XB,YB), (R1Q,R2O,ZQ,XB,YB), (R1A,R2P,ZQ,XB,YB), (R1B,R2P,ZQ,XB,YB), (R1C,R2P,ZQ,XB,YB), (R1D,R2P,ZQ,XB,YB), (R1E,R2P,ZQ,XB,YB), (R1F,R2P,ZQ,XB,YB), (R1G,R2P,ZQ,XB,YB), (R1H,R2P,ZQ,XB,YB), (R1I,R2P,ZQ,XB,YB), (R1J,R2P,ZQ,XB,YB), (R1K,R2P,ZQ,XB,YB), (R1L,R2P,ZQ,XB,YB), (R1M,R2P,ZQ,XB,YB), (R1N,R2P,ZQ,XB,YB), (R1O,R2P,ZQ,XB,YB), (R1P,R2P,ZQ,XB,YB), (R1Q,R2P,ZQ,XB,YB), (R1A,R2Q,ZQ,XB,YB), (R1B,R2Q,ZQ,XB,YB), (R1C,R2Q,ZQ,XB,YB), (R1D,R2Q,ZQ,XB,YB), (R1E,R2Q,ZQ,XB,YB), (R1F,R2Q,ZQ,XB,YB), (R1G,R2Q,ZQ,XB,YB), (R1H,R2Q,ZQ,XB,YB), (R1I,R2Q,ZQ,XB,YB), (R1J,R2Q,ZQ,XB,YB), (R1K,R2Q,ZQ,XB,YB), (R1L,R2Q,ZQ,XB,YB), (R1M,R2Q,ZQ,XB,YB), (R1N,R2Q,ZQ,XB,YB), (R1O,R2Q,ZQ,XB,YB), (R1P,R2Q,ZQ,XB,YB), (R1Q,R2Q,ZQ,XB,YB), (R1A,R2A,ZR,XB,YB), (R1B,R2A,ZR,XB,YB), (R1C,R2A,ZR,XB,YB), (R1D,R2A,ZR,XB,YB), (R1E,R2A,ZR,XB,YB), (R1F,R2A,ZR,XB,YB), (R1G,R2A,ZR,XB,YB), (R1H,R2A,ZR,XB,YB), (R1I,R2A,ZR,XB,YB), (R1J,R2A,ZR,XB,YB), (R1K,R2A,ZR,XB,YB), (R1L,R2A,ZR,XB,YB), (R1M,R2A,ZR,XB,YB), (R1N,R2A,ZR,XB,YB), (R1O,R2A,ZR,XB,YB), (R1P,R2A,ZR,XB,YB), (R1Q,R2A,ZR,XB,YB), (R1A,R2B,ZR, XB,YB), (R1B,R2B,ZR,XB,YB), (R1C,R2B,ZR,XB,YB), (R1D,R2B,ZR,XB,YB), (R1E,R2B,ZR,XB,YB), (R1F,R2B,ZR,XB,YB), (R1G,R2B,ZR,XB,YB), (R1H,R2B,ZR,XB,YB), (R1I,R2B,ZR,XB,YB), (R1J,R2B,ZR,XB,YB), (R1K,R2B,ZR,XB,YB), (R1L,R2B,ZR,XB,YB), (R1M,R2B,ZR,XB,YB), (R1N,R2B,ZR,XB,YB), (R1O,R2B,ZR,XB,YB), (R1P,R2B,ZR,XB,YB), (R1Q,R2B,ZR,XB,YB), (R1A,R2C,ZR,XB,YB), (R1B,R2C,ZR,XB,YB), (R1C,R2C,ZR,XB,YB), (R1D,R2C,ZR,XB,YB), (R1E,R2C,ZR,XB,YB), (R1F,R2C,ZR,XB,YB), (R1G,R2C,ZR,XB,YB), (R1H,R2C,ZR,XB,YB), (R1I,R2C,ZR,XB,YB), (R1J,R2C,ZR,XB,YB), (R1K,R2C,ZR,XB,YB), (R1L,R2C,ZR,XB,YB), (R1M,R2C,ZR,XB,YB), (R1N,R2C,ZR,XB,YB), (R1O,R2C,ZR,XB,YB), (R1P,R2C,ZR,XB,YB), (R1Q,R2C,ZR,XB,YB), (R1A,R2D,ZR,XB,YB), (R1B,R2D,ZR,XB,YB), (R1C,R2D,ZR,XB,YB), (R1D,R2D,ZR,XB,YB), (R1E,R2D,ZR,XB,YB), (R1F,R2D,ZR,XB,YB), (R1G,R2D,ZR,XB,YB), (R1H,R2D,ZR,XB,YB), (R1I,R2D,ZR,XB,YB), (R1J,R2D,ZR,XB,YB), (R1K,R2D,ZR,XB,YB), (R1L,R2D,ZR,XB,YB), (R1M,R2D,ZR,XB,YB), (R1N,R2D,ZR,XB,YB), (R1O,R2D,ZR,XB,YB), (R1P,R2D,ZR,XB,YB), (R1Q,R2D,ZR,XB,YB), (R1A,R2E,ZR,XB,YB), (R1B,R2E,ZR,XB,YB), (R1C,R2E,ZR,XB,YB), (R1D,R2E,ZR,XB,YB), (R1E,R2E,ZR,XB,YB), (R1F,R2E,ZR,XB,YB), (R1G,R2E,ZR,XB,YB), (R1H,R2E,ZR,XB,YB), (R1I,R2E,ZR,XB,YB), (R1J,R2E,ZR,XB,YB), (R1K,R2E,ZR,XB,YB), (R1L,R2E,ZR,XB,YB), (R1M,R2E,ZR,XB,YB), (R1N,R2E,ZR,XB,YB), (R1O,R2E,ZR,XB,YB), (R1P,R2E,ZR,XB,YB), (R1Q,R2E,ZR,XB,YB), (R1A,R2F,ZR,XB,YB), (R1B,R2F,ZR,XB,YB), (R1C,R2F,ZR,XB,YB), (R1D,R2F,ZR,XB,YB), (R1E,R2F,ZR,XB,YB), (R1F,R2F,ZR,XB,YB), (R1G,R2F,ZR,XB,YB), (R1H,R2F,ZR,XB,YB), (R1I,R2F,ZR,XB,YB), (R1J,R2F,ZR,XB,YB), (R1K,R2F,ZR,XB,YB), (R1L,R2F,ZR,XB,YB), (R1M,R2F,ZR,XB,YB), (R1N,R2F,ZR,XB,YB), (R1O,R2F,ZR,XB,YB), (R1P,R2F,ZR,XB,YB), (R1Q,R2F,ZR,XB,YB), (R1A,R2G,ZR,XB,YB), (R1B,R2G,ZR,XB,YB), (R1C,R2G,ZR,XB,YB), (R1D,R2G,ZR,XB,YB), (R1E,R2G,ZR,XB,YB), (R1F,R2G,ZR,XB,YB), (R1G,R2G,ZR,XB,YB), (R1H,R2G,ZR,XB,YB), (R1I,R2G,ZR,XB,YB), (R1J,R2G,ZR,XB,YB), (R1K,R2G,ZR,XB,YB), (R1L,R2G,ZR,XB,YB), (R1M,R2G,ZR,XB,YB), (R1N,R2G,ZR,XB,YB), (R1O,R2G,ZR,XB,YB), (R1P,R2G,ZR,XB,YB), (R1Q,R2G,ZR,XB,YB), (R1A,R2H,ZR,XB,YB), (R1B,R2H,ZR,XB,YB), (R1C,R2H,ZR,XB,YB), (R1D,R2H,ZR,XB,YB), (R1E,R2H,ZR,XB,YB), (R1F,R2H,ZR,XB,YB), (R1G,R2H,ZR,XB,YB), (R1H,R2H,ZR,XB,YB), (R1I,R2H,ZR,XB,YB), (R1J,R2H,ZR,XB,YB), (R1K,R2H,ZR,XB,YB), (R1L,R2H,ZR,XB,YB), (R1M,R2H,ZR,XB,YB), (R1N,R2H,ZR,XB,YB), (R1O,R2H,ZR,XB,YB), (R1P,R2H,ZR,XB,YB), (R1Q,R2H,ZR,XB,YB), (R1A,R2I,ZR,XB,YB), (R1B,R2I,ZR,XB,YB), (R1C,R2I,ZR,XB,YB), (R1D,R2I,ZR,XB,YB), (R1E,R2I,ZR,XB,YB), (R1F,R2I,ZR,XB,YB), (R1G,R2I,ZR,XB,YB), (R1H,R2I,ZR,XB,YB), (R1I,R2I,ZR,XB,YB), (R1J,R2I,ZR,XB,YB), (R1K,R2I,ZR,XB,YB), (R1L,R2I,ZR,XB,YB), (R1M,R2I,ZR,XB,YB), (R1N,R2I,ZR,XB,YB), (R1O,R2I,ZR,XB,YB), (R1P,R2I,ZR,XB,YB), (R1Q,R2I,ZR,XB,YB), (R1A,R2J,ZR,XB,YB), (R1B,R2J,ZR,XB,YB), (R1C,R2J,ZR,XB,YB), (R1D,R2J,ZR,XB,YB), (R1E,R2J,ZR,XB,YB), (R1F,R2J,ZR,XB,YB), (R1G,R2J,ZR,XB,YB), (R1H,R2J,ZR,XB,YB), (R1I,R2J,ZR,XB,YB), (R1J,R2J,ZR,XB,YB), (R1K,R2J,ZR,XB,YB), (R1L,R2J,ZR,XB,YB), (R1M,R2J,ZR,XB,YB), (R1N,R2J,ZR,XB,YB), (R1O,R2J,ZR,XB,YB), (R1P,R2J,ZR,XB,YB), (R1Q,R2J,ZR,XB,YB), (R1A,R2K,ZR,XB,YB), (R1B,R2K,ZR,XB,YB), (R1C,R2K,ZR,XB,YB), (R1D,R2K,ZR,XB,YB), (R1E,R2K,ZR,XB,YB), (R1F,R2K,ZR,XB,YB), (R1G,R2K,ZR,XB,YB), (R1H,R2K,ZR,XB,YB), (R1I,R2K,ZR,XB,YB), (R1J,R2K,ZR,XB,YB), (R1K,R2K,ZR,XB,YB), (R1L,R2K,ZR,XB,YB), (R1M,R2K,ZR,XB,YB), (R1N,R2K,ZR,XB,YB), (R1O,R2K,ZR,XB,YB), (R1P,R2K,ZR,XB,YB), (R1Q,R2K,ZR,XB,YB), (R1A,R2L,ZR,XB,YB), (R1B,R2L,ZR,XB,YB), (R1C,R2L,ZR,XB,YB), (R1D,R2L,ZR,XB,YB), (R1E,R2L,ZR,XB,YB), (R1F,R2L,ZR,XB,YB), (R1G,R2L,ZR,XB,YB), (R1H,R2L,ZR,XB,YB), (R1I,R2L,ZR,XB,YB), (R1J,R2L,ZR,XB,YB), (R1K,R2L,ZR,XB,YB), (R1L,R2L,ZR,XB,YB), (R1M,R2L,ZR,XB,YB), (R1N,R2L,ZR,XB,YB), (R1O,R2L,ZR,XB,YB), (R1P,R2L,ZR,XB,YB), (R1Q,R2L,ZR,XB,YB), (R1A,R2M,ZR,XB,YB), (R1B,R2M,ZR,XB,YB), (R1C,R2M,ZR,XB,YB), (R1D,R2M,ZR,XB,YB), (R1E,R2M,ZR,XB,YB), (R1F,R2M,ZR,XB,YB), (R1G,R2M,ZR,XB,YB), (R1H,R2M,ZR,XB,YB), (R1I,R2M,ZR,XB,YB), (R1J,R2M,ZR,XB,YB), (R1K,R2M,ZR,XB,YB), (R1L,R2M,ZR,XB,YB), (R1M,R2M,ZR,XB,YB), (R1N,R2M,ZR,XB,YB), (R1O,R2M,ZR,XB,YB), (R1P,R2M,ZR,XB,YB), (R1Q,R2M,ZR,XB,YB), (R1A,R2N,ZR,XB,YB), (R1B,R2N,ZR,XB,YB), (R1C,R2N,ZR,XB,YB), (R1D,R2N,ZR,XB,YB), (R1E,R2N,ZR,XB,YB), (R1F,R2N,ZR,XB,YB), (R1G,R2N,ZR,XB,YB), (R1H,R2N,ZR,XB,YB), (R1I,R2N,ZR,XB,YB), (R1J,R2N,ZR,XB,YB), (R1K,R2N,ZR,XB,YB), (R1L,R2N,ZR,XB,YB), (R1M,R2N,ZR,XB,YB), (R1N,R2N,ZR,XB,YB), (R1O,R2N,ZR,XB,YB), (R1P,R2N,ZR,XB,YB), (R1Q,R2N,ZR,XB,YB), (R1A,R2O,ZR,XB,YB), (R1B,R2O,ZR,XB,YB), (R1C,R2O,ZR,XB,YB), (R1D,R2O,ZR,XB,YB), (R1E,R2O,ZR,XB,YB), (R1F,R2O,ZR,XB,YB), (R1G,R2O,ZR,XB,YB), (R1H,R2O,ZR,XB,YB), (R1I,R2O,ZR,XB,YB), (R1J,R2O,ZR,XB,YB), (R1K,R2O,ZR,XB,YB), (R1L,R2O,ZR,XB,YB), (R1M,R2O,ZR,XB,YB), (R1N,R2O,ZR,XB,YB), (R1O,R2O,ZR,XB,YB), (R1P,R2O,ZR,XB,YB), (R1Q,R2O,ZR,XB,YB), (R1A,R2P,ZR,XB,YB), (R1B,R2P,ZR,XB,YB), (R1C,R2P,ZR,XB,YB), (R1D,R2P,ZR,XB,YB), (R1E,R2P,ZR,XB,YB), (R1F,R2P,ZR,XB,YB), (R1G,R2P,ZR,XB,YB), (R1H,R2P,ZR,XB,YB), (R1I,R2P,ZR,XB,YB), (R1J,R2P,ZR,XB,YB), (R1K,R2P,ZR,XB,YB), (R1L,R2P,ZR,XB,YB), (R1M,R2P,ZR,XB,YB), (R1N,R2P,ZR,XB,YB), (R1O,R2P,ZR,XB,YB), (R1P,R2P,ZR,XB,YB), (R1Q,R2P,ZR,XB,YB), (R1A,R2Q,ZR,XB,YB), (R1B,R2Q,ZR,XB,YB), (R1C,R2Q,ZR,XB,YB), (R1D,R2Q,ZR,XB,YB), (R1E,R2Q,ZR,XB,YB), (R1F,R2Q,ZR,XB,YB), (R1G,R2Q,ZR,XB,YB), (R1H,R2Q,ZR,XB,YB), (R1I,R2Q,ZR,XB,YB), (R1J,R2Q,ZR,XB,YB), (R1K,R2Q,ZR,XB,YB), (R1L,R2Q,ZR,XB,YB), (R1M,R2Q,ZR,XB,YB), (R1N,R2Q,ZR,XB,YB), (R1O,R2Q,ZR,XB,YB), (R1P,R2Q,ZR,XB,YB), (R1Q,R2Q,ZR,XB,YB), (R1A,R2A,ZS,XB,YB), (R1B,R2A,ZS,XB,YB), (R1C,R2A,ZS,XB,YB), (R1D,R2A,ZS,XB,YB), (R1E,R2A,ZS,XB,YB), (R1F,R2A,ZS,XB,YB), (R1G,R2A,ZS,XB,YB), (R1H,R2A,ZS,XB,YB), (R1I,R2A,ZS,XB,YB), (R1J,R2A,ZS,XB,YB), (R1K,R2A,ZS,XB,YB), (R1L,R2A,ZS,XB,YB), (R1M,R2A,ZS,XB,YB), (R1N,R2A,ZS,XB,YB), (R1O,R2A,ZS,XB,YB), (R1P,R2A,ZS,XB,YB), (R1Q,R2A,ZS,XB,YB), (R1A,R2B,ZS,XB,YB), (R1B,R2B,ZS,XB,YB), (R1C,R2B,ZS,XB,YB), (R1D,R2B,ZS,XB,YB), (R1E,R2B,ZS,XB,YB), (R1F,R2B,ZS,XB,YB), (R1G,R2B,ZS,XB,YB), (R1H,R2B,ZS,XB,YB), (R1I,R2B,ZS,XB,YB), (R1J,R2B,ZS,XB,YB), (R1K,R2B,ZS,XB,YB), (R1L,R2B,ZS,XB,YB), (R1M,R2B,ZS,XB,YB), (R1N,R2B,ZS,XB,YB), (R1O,R2B,ZS,XB,YB), (R1P,R2B,ZS,XB,YB), (R1Q,R2B,ZS,XB,YB), (R1A,R2C,ZS,XB,YB), (R1B,R2C,ZS,XB,YB), (R1C,R22C,ZS,XB,YB), (R1D,R2C,ZS,XB,YB), (R1E,R2C,ZS,XB,YB), (R1F,R2C,ZS,XB,YB), (R1G,R22C,ZS,XB,YB), (R1H,R2C,ZS,XB,YB), (R1I,R2C,ZS,XB,YB), (R1J,R2C,ZS,XB,YB), (R1K,R22C,ZS,XB,YB), (R1L,R2C,ZS,XB,YB), (R1M, R2C,ZS,XB,YB), (R1N,R2C,ZS,XB,YB), (R1O,R2C,ZS, XB,YB), (R1P,R2C,ZS,XB,YB), (R1Q,R2C,ZS,XB,YB), (R1A,R2D,ZS,XB,YB), (R1B,R2D,ZS,XB,YB), (R1C, R2D,ZS,XB,YB), (R1D,R2D,ZS,XB,YB), (R1E,R2D,ZS, XB,YB), (R1F,R2D,ZS,XB,YB), (R1G,R2D,ZS,XB,YB), (R1H,R2D,ZS,XB,YB), (R1I,R2D,ZS,XB,YB), (R1J,R2D, ZS,XB,YB), (R1K,R2D,ZS,XB,YB), (R1L,R2D,ZS,XB, YB), (R1M,R2D,ZS,XB,YB), (R1N,R2D,ZS,XB,YB), (R1O,R2D,ZS,XB,YB), (R1P,R2D,ZS,XB,YB), (R1Q,R2D, ZS,XB,YB), (R1A,R2E,ZS,XB,YB), (R1B,R2E,ZS,XB, YB), (R1C,R2E,ZS,XB,YB), (R1D,R2E,ZS,XB,YB), (R1E, R2E,ZS,XB,YB), (R1F,R2E,ZS,XB,YB), (R1G,R2E,ZS, XB,YB), (R1H,R2E,ZS,XB,YB), (R1I,R2E,ZS,XB,YB), (R1J,R2E,ZS,XB,YB), (R1K,R2E,ZS,XB,YB), (R1L,R2E, ZS,XB,YB), (R1M,R2E,ZS,XB,YB), (R1N,R2E,ZS,XB, YB), (R1O,R2E,ZS,XB,YB), (R1P,R2E,ZS,XB,YB), (R1Q, R2E,ZS,XB,YB), (R1A,R2F,ZS,XB,YB), (R1B,R2F,ZS, XB,YB), (R1C,R2F,ZS,XB,YB), (R1D,R2F,ZS,XB,YB), (R1E,R2F,ZS,XB,YB), (R1F,R2F,ZS,XB,YB), (R1G,R2F, ZS,XB,YB), (R1H,R2F,ZS,XB,YB), (R1I,R2F,ZS,XB,YB), (R1J,R2F,ZS,XB,YB), (R1K,R2F,ZS,XB,YB), (R1L,R2F, ZS,XB,YB), (R1M,R2F,ZS,XB,YB), (R1N,R2F,ZS,XB, YB), (R1O,R2F,ZS,XB,YB), (R1P,R2F,ZS,XB,YB), (R1Q, R2F,ZS,XB,YB), (R1A,R2G,ZS,XB,YB), (R1B,R2G,ZS, XB,YB), (R1C,R2G,ZS,XB,YB), (R1D,R2G,ZS,XB,YB), (R1E,R2G,ZS,XB,YB), (R1F,R2G,ZS,XB,YB), (R1G,R2G, ZS,XB,YB), (R1H,R2G,ZS,XB,YB), (R1I,R2G,ZS,XB, YB), (R1J,R2G,ZS,XB,YB), (R1K,R2G,ZS,XB,YB), (R1L, R2G,ZS,XB,YB), (R1M,R2G,ZS,XB,YB), (R1N,R2G,ZS, XB,YB), (R1O,R2G,ZS,XB,YB), (R1P,R2G,ZS,XB,YB), (R1Q,R2G,ZS,XB,YB), (R1A,R2H,ZS,XB,YB), (R1B, R2H,ZS,XB,YB), (R1C,R2H,ZS,XB,YB), (R1D,R2H,ZS, XB,YB), (R1E,R2H,ZS,XB,YB), (R1F,R2H,ZS,XB,YB), (R1G,R2H,ZS,XB,YB), (R1H,R2H,ZS,XB,YB), (R1I,R2H, ZS,XB,YB), (R1J,R2H,ZS,XB,YB), (R1K,R2H,ZS,XB, YB), (R1L,R2H,ZS,XB,YB), (R1M,R2H,ZS,XB,YB), (R1N,R2H,ZS,XB,YB), (R1O,R2H,ZS,XB,YB), (R1P,R2H, ZS,XB,YB), (R1Q,R2H,ZS,XB,YB), (R1A,R2I,ZS,XB, YB), (R1B,R2I,ZS,XB,YB), (R1C,R2I,ZS,XB,YB), (R1D, R2I,ZS,XB,YB), (R1E,R2I,ZS,XB,YB), (R1F,R2I,ZS,XB, YB), (R1G,R2I,ZS,XB,YB), (R1H,R2I,ZS,XB,YB), (R1I, R2I,ZS,XB,YB), (R1J,R2I,ZS,XB,YB), (R1K,R2I,ZS,XB, YB), (R1L,R2I,ZS,XB,YB), (R1M,R2I,ZS,XB,YB), (R1N, R2I,ZS,XB,YB), (R1O,R2I,ZS,XB,YB), (R1P,R2I,ZS,XB, YB), (R1Q,R2I,ZS,XB,YB), (R1A,R2J,ZS,XB,YB), (R1B, R2J,ZS,XB,YB), (R1C,R2J,ZS,XB,YB), (R1D,R2J,ZS,XB, YB), (R1E,R2J,ZS,XB,YB), (R1F,R2J,ZS,XB,YB), (R1G, R2J,ZS,XB,YB), (R1H,R2J,ZS,XB,YB), (R1I,R2J,ZS,XB, YB), (R1J,R2J,ZS,XB,YB), (R1K,R2J,ZS,XB,YB), (R1L, R2J,ZS,XB,YB), (R1M,R2J,ZS,XB,YB), (R1N,R2J,ZS,XB, YB), (R1O,R2J,ZS,XB,YB), (R1P,R2J,ZS,XB,YB), (R1Q, R2J,ZS,XB,YB), (R1A,R2K,ZS,XB,YB), (R1B,R2K,ZS, XB,YB), (R1C,R2K,ZS,XB,YB), (R1D,R2K,ZS,XB,YB), (R1E,R2K,ZS,XB,YB), (R1F,R2K,ZS,XB,YB), (R1G,R2K, ZS,XB,YB), (R1H,R2K,ZS,XB,YB), (R1I,R2K,ZS,XB,YB), (R1J,R2K,ZS,XB,YB), (R1K,R2K,ZS,XB,YB), (R1L, R2K,ZS,XB,YB), (R1M,R2K,ZS,XB,YB), (R1N,R2K,ZS, XB,YB), (R1O,R2K,ZS,XB,YB), (R1P,R2K,ZS,XB,YB), (R1Q,R2K,ZS,XB,YB), (R1A,R2L,ZS,XB,YB), (R1B,R2L, ZS,XB,YB), (R1C,R2L,ZS,XB,YB), (R1D,R2L,ZS,XB, YB), (R1E,R2L,ZS,XB,YB), (R1F,R2L,ZS,XB,YB), (R1G, R2L,ZS,XB,YB), (R1H,R2L,ZS,XB,YB), (R1I,R2L,ZS, XB,YB), (R1J,R2L,ZS,XB,YB), (R1K,R2L,ZS,XB,YB), (R1L,R2L,ZS,XB,YB), (R1M,R2L,ZS,XB,YB), (R1N,R2L, ZS,XB,YB), (R1O,R2L,ZS,XB,YB), (R1P,R2L,ZS,XB, YB), (R1Q,R2L,ZS,XB,YB), (R1A,R2M,ZS,XB,YB), (R1B,R2M,ZS,XB,YB), (R1C,R2M,ZS,XB,YB), (R1D, R2M,ZS,XB,YB), (R1E,R2M,ZS,XB,YB), (R1F,R2M,ZS, XB,YB), (R1G,R2M,ZS,XB,YB), (R1H,R2M,ZS,XB,YB), (R1I,R2M,ZS,XB,YB), (R1J,R2M,ZS,XB,YB), (R1K,R2M, ZS,XB,YB), (R1L,R2M,ZS,XB,YB), (R1M,R2M,ZS,XB, YB), (R1N,R2M,ZS,XB,YB), (R1O,R2M,ZS,XB,YB), (R1P,R2M,ZS,XB,YB), (R1Q,R2M,ZS,XB,YB), (R1A, R2N,ZS,XB,YB), (R1B,R2N,ZS,XB,YB), (R1C,R2N,ZS, XB,YB), (R1D,R2N,ZS,XB,YB), (R1E,R2N,ZS,XB,YB), (R1F,R2N,ZS,XB,YB), (R1G,R2N,ZS,XB,YB), (R1H,R2N, ZS,XB,YB), (R1I,R2N,ZS,XB,YB), (R1J,R2N,ZS,XB,YB), (R1K,R2N,ZS,XB,YB), (R1L,R2N,ZS,XB,YB), (R1M, R2N,ZS,XB,YB), (R1N,R2N,ZS,XB,YB), (R1O,R2N,ZS, XB,YB), (R1P,R2N,ZS,XB,YB), (R1Q,R2N,ZS,XB,YB), (R1A,R2O,ZS,XB,YB), (R1B,R2O,ZS,XB,YB), (R1C, R2O,ZS,XB,YB), (R1D,R2O,ZS,XB,YB), (R1E,R2O,ZS, XB,YB), (R1F,R2O,ZS,XB,YB), (R1G,R2O,ZS,XB,YB), (R1H,R2O,ZS,XB,YB), (R1I,R2O,ZS,XB,YB), (R1J,R2O, ZS,XB,YB), (R1K,R2O,ZS,XB,YB), (R1L,R2O,ZS,XB, YB), (R1M,R2O,ZS,XB,YB), (R1N,R2O,ZS,XB,YB), (R1O,R2O,ZS,XB,YB), (R1P,R2O,ZS,XB,YB), (R1Q,R2O, ZS,XB,YB), (R1A,R2P,ZS,XB,YB), (R1B,R2P,ZS,XB,YB), (R1C,R2P,ZS,XB,YB), (R1D,R2P,ZS,XB,YB), (R1E,R2P, ZS,XB,YB), (R1F,R2P,ZS,XB,YB), (R1G,R2P,ZS,XB,YB), (R1H,R2P,ZS,XB,YB), (R1I,R2P,ZS,XB,YB), (R1J,R2P, ZS,XB,YB), (R1K,R2P,ZS,XB,YB), (R1L,R2P,ZS,XB,YB), (R1M,R2P,ZS,XB,YB), (R1N,R2P,ZS,XB,YB), (R1O,R2P, ZS,XB,YB), (R1P,R2P,ZS,XB,YB), (R1Q,R2P,ZS,XB,YB), (R1A,R2Q,ZS,XB,YB), (R1B,R2Q,ZS,XB,YB), (R1C, R2Q,ZS,XB,YB), (R1D,R2Q,ZS,XB,YB), (R1E,R2Q,ZS, XB,YB), (R1F,R2Q,ZS,XB,YB), (R1G,R2Q,ZS,XB,YB), (R1H,R2Q,ZS,XB,YB), (R1I,R2Q,ZS,XB,YB), (R1J,R2Q, ZS,XB,YB), (R1K,R2Q,ZS,XB,YB), (R1L,R2Q,ZS,XB, YB), (R1M,R2Q,ZS,XB,YB), (R1N,R2Q,ZS,XB,YB), (R1O,R2Q,ZS,XB,YB), (R1P,R2Q,ZS,XB,YB), (R1Q,R2Q, ZS,XB,YB), (R1A,R2A,ZT,XB,YB), (R1B,R2A,ZT,XB, YB), (R1C,R2A,ZT,XB,YB), (R1D,R2A,ZT,XB,YB), (R1E, R2A,ZT,XB,YB), (R1F,R2A,ZT,XB,YB), (R1G,R2A,ZT, XB,YB), (R1H,R2A,ZT,XB,YB), (R1I,R2A,ZT,XB,YB), (R1J,R2A,ZT,XB,YB), (R1K,R2A,ZT,XB,YB), (R1L,R2A, ZT,XB,YB), (R1M,R2A,ZT,XB,YB), (R1N,R2A,ZT,XB, YB), (R1O,R2A,ZT,XB,YB), (R1P,R2A,ZT,XB,YB), (R1Q, R2A,ZT,XB,YB), (R1A,R2B,ZT,XB,YB), (R1B,R2B,ZT, XB,YB), (R1C,R2B,ZT,XB,YB), (R1D,R2B,ZT,XB,YB), (R1E,R2B,ZT,XB,YB), (R1F,R2B,ZT,XB,YB), (R1G,R2B, ZT,XB,YB), (R1H,R2B,ZT,XB,YB), (R1I,R2B,ZT,XB, YB), (R1J,R2B,ZT,XB,YB), (R1K,R2B,ZT,XB,YB), (R1L, R2B,ZT,XB,YB), (R1M,R2B,ZT,XB,YB), (R1N,R2B,ZT, XB,YB), (R1O,R2B,ZT,XB,YB), (R1P,R2B,ZT,XB,YB), (R1Q,R2B,ZT,XB,YB), (R1A,R2C,ZT,XB,YB), (R1B, R22C,ZT,XB,YB), (R1C,R2C,ZT,XB,YB), (R1D,R2C,ZT, XB,YB), (R1E,R2C,ZT,XB,YB), (R1F,R22C,ZT,XB,YB), (R1G,R2C,ZT,XB,YB), (R1H,R2C,ZT,XB,YB), (R1I,R2C, ZT,XB,YB), (R1J,R22C,ZT,XB,YB), (R1K,R2C,ZT,XB, YB), (R1L,R2C,ZT,XB,YB), (R1M,R2C,ZT,XB,YB), (R1N,R2C,ZT,XB,YB), (R1O,R2C,ZT,XB,YB), (R1P,R2C, ZT,XB,YB), (R1Q,R2C,ZT,XB,YB), (R1A,R2D,ZT,XB, YB), (R1B,R2D,ZT,XB,YB), (R1C,R2D,ZT,XB,YB), (R1D,R2D,ZT,XB,YB), (R1E,R2D,ZT,XB,YB), (R1F,R2D, ZT,XB,YB), (R1G,R2D,ZT,XB,YB), (R1H,R2D,ZT,XB, YB), (R1I,R2D,ZT,XB,YB), (R1J,R2D,ZT,XB,YB), (R1K, R2D,ZT,XB,YB), (R1L,R2D,ZT,XB,YB), (R1M,R2D,ZT, XB,YB), (R1N,R2D,ZT,XB,YB), (R1O,R2D,ZT,XB,YB), (R1P,R2D,ZT,XB,YB), (R1Q,R2D,ZT,XB,YB), (R1A,R2E, ZT,XB,YB), (R1B,R2E,ZT,XB,YB), (R1C,R2E,ZT,XB, YB), (R1D,R2E,ZT,XB,YB), (R1E,R2E,ZT,XB,YB), (R1F, R2E,ZT,XB,YB), (R1G,R2E,ZT,XB,YB), (R1H,R2E,ZT, XB,YB), (R1I,R2E,ZT,XB,YB), (R1J,R2E,ZT,XB,YB), (R1K,R2E,ZT,XB,YB), (R1L,R2E,ZT,XB,YB), (R1M,R2E,ZT,XB,YB), (R1N,R2E,ZT,XB,YB), (R1O,R2E,ZT,XB,YB), (R1P,R2E,ZT,XB,YB), (R1Q,R2E,ZT,XB,YB), (R1A,R2F,ZT,XB,YB), (R1B,R2F,ZT,XB,YB), (R1C,R2F,ZT,XB,YB), (R1D,R2F,ZT,XB,YB), (R1E,R2F,ZT,XB,YB), (R1F,R2F,ZT,XB,YB), (R1G,R2F,ZT,XB,YB), (R1H,R2F,ZT,XB,YB), (R1I,R2F,ZT,XB,YB), (R1J,R2F,ZT,XB,YB), (R1K,R2F,ZT,XB,YB), (R1L,R2F,ZT,XB,YB), (R1M,R2F,ZT,XB,YB), (R1N,R2F,ZT,XB,YB), (R1O,R2F,ZT,XB,YB), (R1P,R2F,ZT,XB,YB), (R1Q,R2F,ZT,XB,YB), (R1A,R2G,ZT,XB,YB), (R1B,R2G,ZT,XB,YB), (R1C,R2G,ZT,XB,YB), (R1D,R2G,ZT,XB,YB), (R1E,R2G,ZT,XB,YB), (R1F,R2G,ZT,XB,YB), (R1G,R2G,ZT,XB,YB), (R1H,R2G,ZT,XB,YB), (R1I,R2G,ZT,XB,YB), (R1J,R2G,ZT,XB,YB), (R1K,R2G,ZT,XB,YB), (R1L,R2G,ZT,XB,YB), (R1M,R2G,ZT,XB,YB), (R1N,R2G,ZT,XB,YB), (R1O,R2G,ZT,XB,YB), (R1P,R2G,ZT,XB,YB), (R1Q,R2G,ZT,XB,YB), (R1A,R2H,ZT,XB,YB), (R1B,R2H,ZT,XB,YB), (R1C,R2H,ZT,XB,YB), (R1D,R2H,ZT,XB,YB), (R1E,R2H,ZT,XB,YB), (R1F,R2H,ZT,XB,YB), (R1G,R2H,ZT,XB,YB), (R1H,R2H,ZT,XB,YB), (R1I,R2H,ZT,XB,YB), (R1J,R2H,ZT,XB,YB), (R1K,R2H,ZT,XB,YB), (R1L,R2H,ZT,XB,YB), (R1M,R2H,ZT,XB,YB), (R1N,R2H,ZT,XB,YB), (R1O,R2H,ZT,XB,YB), (R1P,R2H,ZT,XB,YB), (R1Q,R2H,ZT,XB,YB), (R1A,R2I,ZT,XB,YB), (R1B,R2I,ZT,XB,YB), (R1C,R2I,ZT,XB,YB), (R1D,R2I,ZT,XB,YB), (R1E,R2I,ZT,XB,YB), (R1F,R2I,ZT,XB,YB), (R1G,R2I,ZT,XB,YB), (R1H,R2I,ZT,XB,YB), (R1I,R2I,ZT,XB,YB), (R1J,R2I,ZT,XB,YB), (R1K,R2I,ZT,XB,YB), (R1L,R2I,ZT,XB,YB), (R1M,R2I,ZT,XB,YB), (R1N,R2I,ZT,XB,YB), (R1O,R2I,ZT,XB,YB), (R1P,R2I,ZT,XB,YB), (R1Q,R2I,ZT,XB,YB), (R1A,R2J,ZT,XB,YB), (R1B,R2J,ZT,XB,YB), (R1C,R2J,ZT,XB,YB), (R1D,R2J,ZT,XB,YB), (R1E,R2J,ZT,XB,YB), (R1F,R2J,ZT,XB,YB), (R1G,R2J,ZT,XB,YB), (R1H,R2J,ZT,XB,YB), (R1I,R2J,ZT,XB,YB), (R1J,R2J,ZT,XB,YB), (R1K,R2J,ZT,XB,YB), (R1L,R2J,ZT,XB,YB), (R1M,R2J,ZT,XB,YB), (R1N,R2J,ZT,XB,YB), (R1O,R2J,ZT,XB,YB), (R1P,R2J,ZT,XB,YB), (R1Q,R2J,ZT,XB,YB), (R1A,R2K,ZT,XB,YB), (R1B,R2K,ZT,XB,YB), (R1C,R2K,ZT,XB,YB), (R1D,R2K,ZT,XB,YB), (R1E,R2K,ZT,XB,YB), (R1F,R2K,ZT,XB,YB), (R1G,R2K,ZT,XB,YB), (R1H,R2K,ZT,XB,YB), (R1I,R2K,ZT,XB,YB), (R1J,R2K,ZT,XB,YB), (R1K,R2K,ZT,XB,YB), (R1L,R2K,ZT,XB,YB), (R1M,R2K,ZT,XB,YB), (R1N,R2K,ZT,XB,YB), (R1O,R2K,ZT,XB,YB), (R1P,R2K,ZT,XB,YB), (R1Q,R2K,ZT,XB,YB), (R1A,R2L,ZT,XB,YB), (R1B,R2L,ZT,XB,YB), (R1C,R2L,ZT,XB,YB), (R1D,R2L,ZT,XB,YB), (R1E,R2L,ZT,XB,YB), (R1F,R2L,ZT,XB,YB), (R1G,R2L,ZT,XB,YB), (R1H,R2L,ZT,XB,YB), (R1I,R2L,ZT,XB,YB), (R1J,R2L,ZT,XB,YB), (R1K,R2L,ZT,XB,YB), (R1L,R2L,ZT,XB,YB), (R1M,R2L,ZT,XB,YB), (R1N,R2L,ZT,XB,YB), (R1O,R2L,ZT,XB,YB), (R1P,R2L,ZT,XB,YB), (R1Q,R2L,ZT,XB,YB), (R1A,R2M,ZT,XB,YB), (R1B,R2M,ZT,XB,YB), (R1C,R2M,ZT,XB,YB), (R1D,R2M,ZT,XB,YB), (R1E,R2M,ZT,XB,YB), (R1F,R2M,ZT,XB,YB), (R1G,R2M,ZT,XB,YB), (R1H,R2M,ZT,XB,YB), (R1I,R2M,ZT,XB,YB), (R1J,R2M,ZT,XB,YB), (R1K,R2M,ZT,XB,YB), (R1L,R2M,ZT,XB,YB), (R1M,R2M,ZT,XB,YB), (R1N,R2M,ZT,XB,YB), (R1O,R2M,ZT,XB,YB), (R1P,R2M,ZT,XB,YB), (R1Q,R2M,ZT,XB,YB), (R1A,R2N,ZT,XB,YB), (R1B,R2N,ZT,XB,YB), (R1C,R2N,ZT,XB,YB), (R1D,R2N,ZT,XB,YB), (R1E,R2N,ZT,XB,YB), (R1F,R2N,ZT,XB,YB), (R1G,R2N,ZT,XB,YB), (R1H,R2N,ZT,XB,YB), (R1I,R2N,ZT,XB,YB), (R1J,R2N,ZT,XB,YB), (R1K,R2N,ZT,XB,YB), (R1L,R2N,ZT,XB,YB), (R1M,R2N,ZT,XB,YB), (R1N,R2N,ZT,XB,YB), (R1O,R2N,ZT,XB,YB), (R1P,R2N,ZT,XB,YB), (R1Q,R2N,ZT,XB,YB), (R1A,R2O,ZT,XB,YB), (R1B,R2O,ZT,XB,YB), (R1C,R2O,ZT,XB,YB), (R1D,R2O,ZT,XB,YB), (R1E,R2O,ZT,XB,YB), (R1F,R2O,ZT,XB,YB), (R1G,R2O,ZT,XB,YB), (R1H,R2O,ZT,XB,YB), (R1I,R2O,ZT,XB,YB), (R1J,R2O,ZT,XB,YB), (R1K,R2O,ZT,XB,YB), (R1L,R2O,ZT,XB,YB), (R1M,R2O,ZT,XB,YB), (R1N,R2O,ZT,XB,YB), (R1O,R2O,ZT,XB,YB), (R1P,R2O,ZT,XB,YB), (R1Q,R2O,ZT,XB,YB), (R1A,R2P,ZT,XB,YB), (R1B,R2P,ZT,XB,YB), (R1C,R2P,ZT,XB,YB), (R1D,R2P,ZT,XB,YB), (R1E,R2P,ZT,XB,YB), (R1F,R2P,ZT,XB,YB), (R1G,R2P,ZT,XB,YB), (R1H,R2P,ZT,XB,YB), (R1I,R2P,ZT,XB,YB), (R1J,R2P,ZT,XB,YB), (R1K,R2P,ZT,XB,YB), (R1L,R2P,ZT,XB,YB), (R1M,R2P,ZT,XB,YB), (R1N,R2P,ZT,XB,YB), (R1O,R2P,ZT,XB,YB), (R1P,R2P,ZT,XB,YB), (R1Q,R2P,ZT,XB,YB), (R1A,R2Q,ZT,XB,YB), (R1B,R2Q,ZT,XB,YB), (R1C,R2Q,ZT,XB,YB), (R1D,R2Q,ZT,XB,YB), (R1E,R2Q,ZT,XB,YB), (R1F,R2Q,ZT,XB,YB), (R1G,R2Q,ZT,XB,YB), (R1H,R2Q,ZT,XB,YB), (R1I,R2Q,ZT,XB,YB), (R1J,R2Q,ZT,XB,YB), (R1K,R2Q,ZT,XB,YB), (R1L,R2Q,ZT,XB,YB), (R1M,R2Q,ZT,XB,YB), (R1N,R2Q,ZT,XB,YB), (R1O,R2Q,ZT,XB,YB), (R1P,R2Q,ZT,XB,YB), (R1Q,R2Q,ZT,XB,YB), (R1A,R2A,ZU,XB,YB), (R1B,R2A,ZU,XB,YB), (R1C,R2A,ZU,XB,YB), (R1D,R2A,ZU,XB,YB), (R1E,R2A,ZU,XB,YB), (R1F,R2A,ZU,XB,YB), (R1G,R2A,ZU,XB,YB), (R1H,R2A,ZU,XB,YB), (R1I,R2A,ZU,XB,YB), (R1J,R2A,ZU,XB,YB), (R1K,R2A,ZU,XB,YB), (R1L,R2A,ZU,XB,YB), (R1M,R2A,ZU,XB,YB), (R1N,R2A,ZU,XB,YB), (R1O,R2A,ZU,XB,YB), (R1P,R2A,ZU,XB,YB), (R1Q,R2A,ZU,XB,YB), (R1A,R2B,ZU,XB,YB), (R1B,R2B,ZU,XB,YB), (R1C,R2B,ZU,XB,YB), (R1D,R2B,ZU,XB,YB), (R1E,R2B,ZU,XB,YB), (R1F,R2B,ZU,XB,YB), (R1G,R2B,ZU,XB,YB), (R1H,R2B,ZU,XB,YB), (R1I,R2B,ZU,XB,YB), (R1J,R2B,ZU,XB,YB), (R1K,R2B,ZU,XB,YB), (R1L,R2B,ZU,XB,YB), (R1M,R2B,ZU,XB,YB), (R1N,R2B,ZU,XB,YB), (R1O,R2B,ZU,XB,YB), (R1P,R2B,ZU,XB,YB), (R1Q,R2B,ZU,XB,YB), (R1A,R2C,ZU,XB,YB), (R1B,R2C,ZU,XB,YB), (R1C,R2C,ZU,XB,YB), (R1D,R2C,ZU,XB,YB), (R1E,R2C,ZU,XB,YB), (R1F,R2C,ZU,XB,YB), (R1G,R2C,ZU,XB,YB), (R1H,R2C,ZU,XB,YB), (R1I,R2C,ZU,XB,YB), (R1J,R2C,ZU,XB,YB), (R1K,R2C,ZU,XB,YB), (R1L,R2C,ZU,XB,YB), (R1M,R2C,ZU,XB,YB), (R1N,R2C,ZU,XB,YB), (R1O,R2C,ZU,XB,YB), (R1P,R2C,ZU,XB,YB), (R1Q,R2C,ZU,XB,YB), (R1A,R2D,ZU,XB,YB), (R1B,R2D,ZU,XB,YB), (R1C,R2D,ZU,XB,YB), (R1D,R2D,ZU,XB,YB), (R1E,R2D,ZU,XB,YB), (R1F,R2D,ZU,XB,YB), (R1G,R2D,ZU,XB,YB), (R1H,R2D,ZU,XB,YB), (R1I,R2D,ZU,XB,YB), (R1J,R2D,ZU,XB,YB), (R1K,R2D,ZU,XB,YB), (R1L,R2D,ZU,XB,YB), (R1M,R2D,ZU,XB,YB), (R1N,R2D,ZU,XB,YB), (R1O,R2D,ZU,XB,YB), (R1P,R2D,ZU,XB,YB), (R1Q,R2D,ZU,XB,YB), (R1A,R2E,ZU,XB,YB), (R1B,R2E,ZU,XB,YB), (R1C,R2E,ZU,XB,YB), (R1D,R2E,ZU,XB,YB), (R1E,R2E,ZU,XB,YB), (R1F,R2E,ZU,XB,YB), (R1G,R2E,ZU,XB,YB), (R1H,R2E,ZU,XB,YB), (R1I,R2E,ZU,XB,YB), (R1J,R2E,ZU,XB,YB), (R1K,R2E,ZU,XB,YB), (R1L,R2E,ZU,XB,YB), (R1M,R2E,ZU,XB,YB), (R1N,R2E,ZU,XB,YB), (R1O,R2E,ZU,XB,YB), (R1P,R2E,ZU,XB,YB), (R1Q,R2E,ZU,XB,YB), (R1A,R2F,ZU,XB,YB), (R1B,R2F,ZU,XB,YB), (R1C,R2F,ZU,XB,YB), (R1D,R2F,ZU,XB,YB), (R1E,R2F,ZU,XB,YB), (R1F,R2F,ZU,XB,YB), (R1G,R2F,ZU,XB,YB), (R1H,R2F,ZU,XB,YB), (R1I,R2F,ZU,XB,YB), (R1J,R2F,ZU,XB,YB), (R1K,R2F,ZU,XB,YB), (R1L,R2F,ZU,XB,YB), (R1M,R2F,ZU,XB,YB), (R1N,R2F,ZU,XB,YB), (R1O,R2F,ZU,XB,YB), (R1P,R2F,ZU,XB,YB), (R1Q,R2F,ZU,XB,YB), (R1A,R2G,ZU,XB,YB), (R1B,R2G,ZU,XB,YB), (R1C,R2G,ZU,XB,YB), (R1D,R2G,ZU,XB,YB), (R1E,R2G,ZU,XB,YB), (R1F,R2G,ZU,XB,YB), (R1G,R2G,ZU,XB,YB), (R1H, R2G,ZU,XB,YB), (R1I,R2G,ZU,XB,YB), (R1J,R2G,ZU,XB,YB), (R1K,R2G,ZU,XB,YB), (R1L,R2G,ZU,XB,YB), (R1M,R2G,ZU,XB,YB), (R1N,R2G,ZU,XB,YB), (R1O,R2G,ZU,XB,YB), (R1P,R2G,ZU,XB,YB), (R1Q,R2G,ZU,XB,YB), (R1A,R2H,ZU,XB,YB), (R1B,R2H,ZU,XB,YB), (R1C,R2H,ZU,XB,YB), (R1D,R2H,ZU,XB,YB), (R1E,R2H,ZU,XB,YB), (R1F,R2H,ZU,XB,YB), (R1G,R2H,ZU,XB,YB), (R1H,R2H,ZU,XB,YB), (R1I,R2H,ZU,XB,YB), (R1J,R2H,ZU,XB,YB), (R1K,R2H,ZU,XB,YB), (R1L,R2H,ZU,XB,YB), (R1M,R2H,ZU,XB,YB), (R1N,R2H,ZU,XB,YB), (R1O,R2H,ZU,XB,YB), (R1P,R2H,ZU,XB,YB), (R1Q,R2H,ZU,XB,YB), (R1A,R2I,ZU,XB,YB), (R1B,R2I,ZU,XB,YB), (R1C,R2I,ZU,XB,YB), (R1D,R2I,ZU,XB,YB), (R1E,R2I,ZU,XB,YB), (R1F,R2I,ZU,XB,YB), (R1G,R2I,ZU,XB,YB), (R1H,R2I,ZU,XB,YB), (R1I,R2I,ZU,XB,YB), (R1J,R2I,ZU,XB,YB), (R1K,R2I,ZU,XB,YB), (R1L,R2I,ZU,XB,YB), (R1M,R2I,ZU,XB,YB), (R1N,R2I,ZU,XB,YB), (R1O,R2I,ZU,XB,YB), (R1P,R2I,ZU,XB,YB), (R1Q,R2I,ZU,XB,YB), (R1A,R2J,ZU,XB,YB), (R1B,R2J,ZU,XB,YB), (R1C,R2J,ZU,XB,YB), (R1D,R2J,ZU,XB,YB), (R1E,R2J,ZU,XB,YB), (R1F,R2J,ZU,XB,YB), (R1G,R2J,ZU,XB,YB), (R1H,R2J,ZU,XB,YB), (R1I,R2J,ZU,XB,YB), (R1J,R2J,ZU,XB,YB), (R1K,R2J,ZU,XB,YB), (R1L,R2J,ZU,XB,YB), (R1M,R2J,ZU,XB,YB), (R1N,R2J,ZU,XB,YB), (R1O,R2J,ZU,XB,YB), (R1P,R2J,ZU,XB,YB), (R1Q,R2J,ZU,XB,YB), (R1A,R2K,ZU,XB,YB), (R1B,R2K,ZU,XB,YB), (R1C,R2K,ZU,XB,YB), (R1D,R2K,ZU,XB,YB), (R1E,R2K,ZU,XB,YB), (R1F,R2K,ZU,XB,YB), (R1G,R2K,ZU,XB,YB), (R1H,R2K,ZU,XB,YB), (R1I,R2K,ZU,XB,YB), (R1J,R2K,ZU,XB,YB), (R1K,R2K,ZU,XB,YB), (R1L,R2K,ZU,XB,YB), (R1M,R2K,ZU,XB,YB), (R1N,R2K,ZU,XB,YB), (R1O,R2K,ZU,XB,YB), (R1P,R2K,ZU,XB,YB), (R1Q,R2K,ZU,XB,YB), (R1A,R2L,ZU,XB,YB), (R1B,R2L,ZU,XB,YB), (R1C,R2L,ZU,XB,YB), (R1D,R2L,ZU,XB,YB), (R1E,R2L,ZU,XB,YB), (R1F,R2L,ZU,XB,YB), (R1G,R2L,ZU,XB,YB), (R1H,R2L,ZU,XB,YB), (R1I,R2L,ZU,XB,YB), (R1J,R2L,ZU,XB,YB), (R1K,R2L,ZU,XB,YB), (R1L,R2L,ZU,XB,YB), (R1M,R2L,ZU,XB,YB), (R1N,R2L,ZU,XB,YB), (R1O,R2L,ZU,XB,YB), (R1P,R2L,ZU,XB,YB), (R1Q,R2L,ZU,XB,YB), (R1A,R2M,ZU,XB,YB), (R1B,R2M,ZU,XB,YB), (R1C,R2M,ZU,XB,YB), (R1D,R2M,ZU,XB,YB), (R1E,R2M,ZU,XB,YB), (R1F,R2M,ZU,XB,YB), (R1G,R2M,ZU,XB,YB), (R1H,R2M,ZU,XB,YB), (R1I,R2M,ZU,XB,YB), (R1J,R2M,ZU,XB,YB), (R1K,R2M,ZU,XB,YB), (R1L,R2M,ZU,XB,YB), (R1M,R2M,ZU,XB,YB), (R1N,R2M,ZU,XB,YB), (R1O,R2M,ZU,XB,YB), (R1P,R2M,ZU,XB,YB), (R1Q,R2M,ZU,XB,YB), (R1A,R2N,ZU,XB,YB), (R1B,R2N,ZU,XB,YB), (R1C,R2N,ZU,XB,YB), (R1D,R2N,ZU,XB,YB), (R1E,R2N,ZU,XB,YB), (R1F,R2N,ZU,XB,YB), (R1G,R2N,ZU,XB,YB), (R1H,R2N,ZU,XB,YB), (R1I,R2N,ZU,XB,YB), (R1J,R2N,ZU,XB,YB), (R1K,R2N,ZU,XB,YB), (R1L,R2N,ZU,XB,YB), (R1M,R2N,ZU,XB,YB), (R1N,R2N,ZU,XB,YB), (R1O,R2N,ZU,XB,YB), (R1P,R2N,ZU,XB,YB), (R1Q,R2N,ZU,XB,YB), (R1A,R2O,ZU,XB,YB), (R1B,R2O,ZU,XB,YB), (R1C,R2O,ZU,XB,YB), (R1D,R2O,ZU,XB,YB), (R1E,R2O,ZU,XB,YB), (R1F,R2O,ZU,XB,YB), (R1G,R2O,ZU,XB,YB), (R1H,R2O,ZU,XB,YB), (R1I,R2O,ZU,XB,YB), (R1J,R2O,ZU,XB,YB), (R1K,R2O,ZU,XB,YB), (R1L,R2O,ZU,XB,YB), (R1M,R2O,ZU,XB,YB), (R1N,R2O,ZU,XB,YB), (R1O,R2O,ZU,XB,YB), (R1P,R2O,ZU,XB,YB), (R1Q,R2O,ZU,XB,YB), (R1A,R2P,ZU,XB,YB), (R1B,R2P,ZU,XB,YB), (R1C,R2P,ZU,XB,YB), (R1D,R2P,ZU,XB,YB), (R1E,R2P,ZU,XB,YB), (R1F,R2P,ZU,XB,YB), (R1G,R2P,ZU,XB,YB), (R1H,R2P,ZU,XB,YB), (R1I,R2P,ZU,XB,YB), (R1J,R2P,ZU,XB,YB), (R1K,R2P,ZU,XB,YB), (R1L,R2P,ZU,XB,YB), (R1M,R2P,ZU,XB,YB), (R1N,R2P,ZU,XB,YB), (R1O,R2P,ZU,XB,YB), (R1P,R2P,ZU,XB,YB), (R1Q,R2P,ZU,XB,YB), (R1A,R2Q,ZU,XB,YB), (R1B,R2Q,ZU,XB,YB), (R1C,R2Q,ZU,XB,YB), (R1D,R2Q,ZU,XB,YB), (R1E,R2Q,ZU,XB,YB), (R1F,R2Q,ZU,XB,YB), (R1G,R2Q,ZU,XB,YB), (R1H,R2Q,ZU,XB,YB), (R1I,R2Q,ZU,XB,YB), (R1J,R2Q,ZU,XB,YB), (R1K,R2Q,ZU,XB,YB), (R1L,R2Q,ZU,XB,YB), (R1M,R2Q,ZU,XB,YB), (R1N,R2Q,ZU,XB,YB), (R1O,R2Q,ZU,XB,YB), (R1P,R2Q,ZU,XB,YB) and (R1Q,R2Q,ZU,XB,YB).

Other preferred embodiments of the compound of the invention are the compound having the following groups in the formula (a') to (f'):

[Chemical Formula 66]

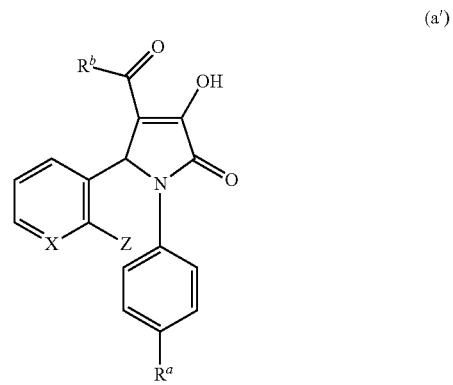

(a')

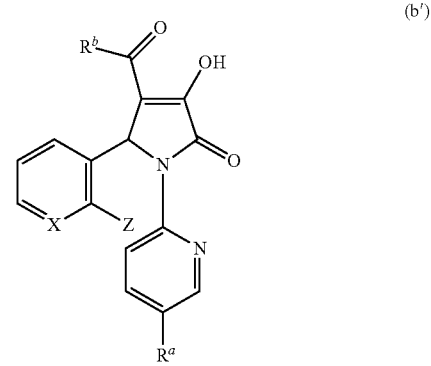

(b')

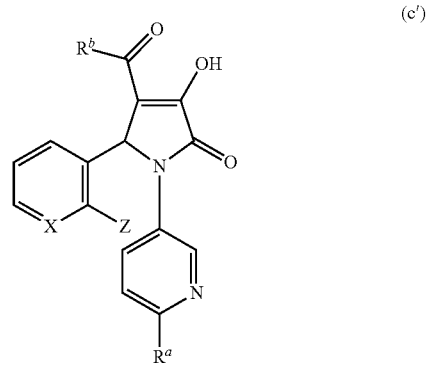

(c')

(d')

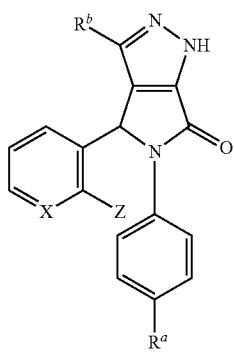

(e')

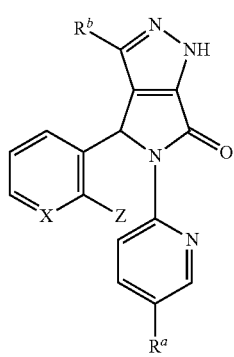

(f')

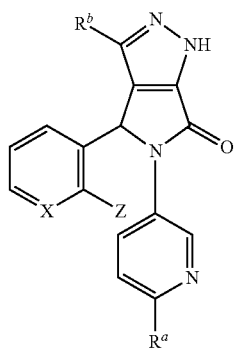

TABLE 6

| | $R^a$ |
|---|---|
| $R^a1$ | $R^a$ |
| $R^a2$ | COOEt |
| $R^a3$ | isoxazol-3-yl |
| $R^a4$ | 3-Me-isoxazol-5-yl |
| $R^a5$ | 5-Me-1,2,4-oxadiazol-3-yl |
| $R^a6$ | 3-Me-1,2,4-oxadiazol-5-yl |
| $R^a7$ | 2-thiazolynyl |
| $R^a8$ | 2-thiazolyl |
| $R^a9$ | 2- or 3-thienyl |
| $R^a10$ | 2- or 3-furyl |
| $R^a11$ | 5-Me-2- or 3-thienyl |
| $R^a12$ | 5-Me-2- or 3-furyl |
| $R^a13$ | SMe |
| $R^a14$ | 1-pyrrolidinyl |
| $R^a15$ | 1-cyclopentyl |
| $R^a16$ | 1-cyclopentenyl |

TABLE 7

| | $R^b$ |
|---|---|
| $R^b1$ | iPr |
| $R^b2$ | iBu |

TABLE 7-continued

| | $R^b$ |
|---|---|
| $R^b3$ | tBu |
| $R^b4$ | $HOCH_2C(Me)_2$ |
| $R^b5$ | $Me(CH_2OH)_2Me$ |
| $R^b6$ | $Me_2NCOC(Me)_2$ |
| $R^b7$ | $MeNHCOC(Me)_2$ |
| $R^b8$ | $H_2NCOC(Me)_2$ |

TABLE 8

| | Z |
|---|---|
| Z1 | $(HOCH_2)_2CHCH_2O$ |
| Z2 | c-PentylO |
| Z3 | Et(Me)NCO |
| Z4 | EtHNCO |
| Z5 | EtO |
| Z6 | $EtOCH_2O$ |
| Z7 | $H_2NCO(CH_2)_2$ |
| Z8 | $H_2NCOCH_2O$ |
| Z9 | $HO(CH_2)_2O$ |
| Z10 | $HO(CH_2)_3O$ |
| Z11 | i-BuO |
| Z12 | $i\text{-}PrHNCO(CH_2)_2$ |
| Z13 | i-PrO |
| Z14 | $i\text{-}PrOCH_2$ |
| Z15 | $Me_2N(CH_2)_2O$ |
| Z16 | $Me_2NCO$ |
| Z17 | $Me_2NCO(CH_2)_2$ |
| Z18 | $Me_2NCOCH_2$ |
| Z19 | $Me_2NCOCH_2O$ |
| Z20 | $MeHNCO(CH_2)_2$ |
| Z21 | $MeNHCOCH_2O$ |
| Z22 | MeO |
| Z23 | $MeO(CH_2)_2$ |
| Z24 | $MeO(CH_2)_2(Me)NCO$ |
| Z25 | $MeO(CH_2)_2O$ |
| Z26 | $MeO(CH_2)_2OCH_2$ |
| Z27 | $MeO(CH_2)_3O$ |
| Z28 | $MeOCH_2$ |
| Z29 | $MeOCH_2O$ |
| Z30 | MeS |
| Z31 | $MeSO(CH_2)_2O$ |
| Z32 | $MeSO_2$ |
| Z33 | Morpholino |
| Z34 | NC |
| Z35 | $NC(CH_2)_2O$ |
| Z36 | $NCCH_2$ |
| Z37 | 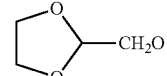 |
| Z38 | 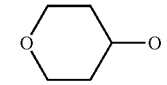 |
| Z39 | 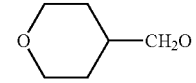 |

TABLE 9

| | X |
|---|---|
| X1 | CH |
| X2 | N |

The combination of Ra, Rb, X and Z (Ra,Rb,X,Z) is any one of the following combinations:

(Ra,Rb,X,Z)=(Ra1,Rb1,X1,Z1), (Ra1,Rb1,X1,Z2), (Ra1,Rb1,X1,Z3), (Ra1,Rb1,X1,Z4), (Ra1,Rb1,X1,Z5), (Ra1,Rb1,X1,Z6), (Ra1,Rb1,X1,Z7), (Ra1,Rb1,X1,Z8), (Ra1,Rb1,X1,Z9), (Ra1,Rb1,X1,Z10), (Ra1,Rb1,X1,Z11), (Ra1,Rb1,X1,Z12), (Ra1,Rb1,X1,Z13), (Ra1,Rb1,X1,Z14), (Ra1,Rb1,X1,Z15), (Ra1,Rb1,X1,Z16), (Ra1,Rb1,X1,Z17), (Ra1,Rb1,X1,Z18), (Ra1,Rb1,X1,Z19), (Ra1,Rb1,X1,Z20), (Ra1,Rb1,X1,Z21), (Ra1,Rb1,X1,Z22), (Ra1,Rb1,X1,Z23), (Ra1,Rb1,X1,Z24), (Ra1,Rb1,X1,Z25), (Ra1,Rb1,X1,Z26), (Ra1,Rb1,X1,Z27), (Ra1,Rb1,X1,Z28), (Ra1,Rb1,X1,Z29), (Ra1,Rb1,X1,Z30), (Ra1,Rb1,X1,Z31), (Ra1,Rb1,X1,Z32), (Ra1,Rb1,X1,Z33), (Ra1,Rb1,X1,Z34), (Ra1,Rb1,X1,Z35), (Ra1,Rb1,X1,Z36), (Ra1,Rb1,X1,Z37), (Ra1,Rb1,X1,Z38), (Ra1,Rb1,X1,Z39), (Ra1,Rb1,X2,Z1), (Ra1,Rb1,X2,Z2), (Ra1,Rb1,X2,Z3), (Ra1,Rb1,X2,Z4), (Ra1,Rb1,X2,Z5), (Ra1,Rb1,X2,Z6), (Ra1,Rb1,X2,Z7), (Ra1,Rb1,X2,Z8), (Ra1,Rb1,X2,Z9), (Ra1,Rb1,X2,Z10), (Ra1,Rb1,X2,Z11), (Ra1,Rb1,X2,Z12), (Ra1,Rb1,X2,Z13), (Ra1,Rb1,X2,Z14), (Ra1,Rb1,X2,Z15), (Ra1,Rb1,X2,Z16), (Ra1,Rb1,X2,Z17), (Ra1,Rb1,X2,Z18), (Ra1,Rb1,X2,Z19), (Ra1,Rb1,X2,Z20), (Ra1,Rb1,X2,Z21), (Ra1,Rb1,X2,Z22), (Ra1,Rb1,X2,Z23), (Ra1,Rb1,X2,Z24), (Ra1,Rb1,X2,Z25), (Ra1,Rb1,X2,Z26), (Ra1,Rb1,X2,Z27), (Ra1,Rb1,X2,Z28), (Ra1,Rb1,X2,Z29), (Ra1,Rb1,X2,Z30), (Ra1,Rb1,X2,Z31), (Ra1,Rb1,X2,Z32), (Ra1,Rb1,X2,Z33), (Ra1,Rb1,X2,Z34), (Ra1,Rb1,X2,Z35), (Ra1,Rb1,X2,Z36), (Ra1,Rb1,X2,Z37), (Ra1,Rb1,X2,Z38), (Ra1,Rb1,X2,Z39), (Ra1,Rb2,X1,Z1), (Ra1,Rb2,X1,Z2), (Ra1,Rb2,X1,Z3), (Ra1,Rb2,X1,Z4), (Ra1,Rb2,X1,Z5), (Ra1,Rb2,X1,Z6), (Ra1,Rb2,X1,Z7), (Ra1,Rb2,X1,Z8), (Ra1,Rb2,X1,Z9), (Ra1,Rb2,X1,Z10), (Ra1,Rb2,X1,Z11), (Ra1,Rb2,X1,Z12), (Ra1,Rb2,X1,Z13), (Ra1,Rb2,X1,Z14), (Ra1,Rb2,X1,Z15), (Ra1,Rb2,X1,Z16), (Ra1,Rb2,X1,Z17), (Ra1,Rb2,X1,Z18), (Ra1,Rb2,X1,Z19), (Ra1,Rb2,X1,Z20), (Ra1,Rb2,X1,Z21), (Ra1,Rb2,X1,Z22), (Ra1,Rb2,X1,Z23), (Ra1,Rb2,X1,Z24), (Ra1,Rb2,X1,Z25), (Ra1,Rb2,X1,Z26), (Ra1,Rb2,X1,Z27), (Ra1,Rb2,X1,Z28), (Ra1,Rb2,X1,Z29), (Ra1,Rb2,X1,Z30), (Ra1,Rb2,X1,Z31), (Ra1,Rb2,X1,Z32), (Ra1,Rb2,X1,Z33), (Ra1,Rb2,X1,Z34), (Ra1,Rb2,X1,Z35), (Ra1,Rb2,X1,Z36), (Ra1,Rb2,X1,Z37), (Ra1,Rb2,X1,Z38), (Ra1,Rb2,X1,Z39), (Ra1,Rb2,X2,Z1), (Ra1,Rb2,X2,Z2), (Ra1,Rb2,X2,Z3), (Ra1,Rb2,X2,Z4), (Ra1,Rb2,X2,Z5), (Ra1,Rb2,X2,Z6), (Ra1,Rb2,X2,Z7), (Ra1,Rb2,X2,Z8), (Ra1,Rb2,X2,Z9), (Ra1,Rb2,X2,Z10), (Ra1,Rb2,X2,Z11), (Ra1,Rb2,X2,Z12), (Ra1,Rb2,X2,Z13), (Ra1,Rb2,X2,Z14), (Ra1,Rb2,X2,Z15), (Ra1,Rb2,X2,Z16), (Ra1,Rb2,X2,Z17), (Ra1,Rb2,X2,Z18), (Ra1,Rb2,X2,Z19), (Ra1,Rb2,X2,Z20), (Ra1,Rb2,X2,Z21), (Ra1,Rb2,X2,Z22), (Ra1,Rb2,X2,Z23), (Ra1,Rb2,X2,Z24), (Ra1,Rb2,X2,Z25), (Ra1,Rb2,X2,Z26), (Ra1,Rb2,X2,Z27), (Ra1,Rb2,X2,Z28), (Ra1,Rb2,X2,Z29), (Ra1,Rb2,X2,Z30), (Ra1,Rb2,X2,Z31), (Ra1,Rb2,X2,Z32), (Ra1,Rb2,X2,Z33), (Ra1,Rb2,X2,Z34), (Ra1,Rb2,X2,Z35), (Ra1,Rb2,X2,Z36), (Ra1,Rb2,X2,Z37), (Ra1,Rb2,X2,Z38), (Ra1,Rb2,X2,Z39), (Ra1,Rb3,X1,Z1), (Ra1,Rb3,X1,Z2), (Ra1,Rb3,X1,Z3), (Ra1,Rb3,X1,Z4), (Ra1,Rb3,X1,Z5), (Ra1,Rb3,X1,Z6), (Ra1,Rb3,X1,Z7), (Ra1,Rb3,X1,Z8), (Ra1,Rb3,X1,Z9), (Ra1,Rb3,X1,Z10), (Ra1,Rb3,X1,Z11), (Ra1,Rb3,X1,Z12), (Ra1,Rb3,X1,Z13), (Ra1,Rb3,X1,Z14), (Ra1,Rb3,X1,Z15), (Ra1,Rb3,X1,Z16), (Ra1,Rb3,X1,Z17), (Ra1,Rb3,X1,Z18), (Ra1,Rb3,X1,Z19), (Ra1,Rb3,X1,Z20), (Ra1,Rb3,X1,Z21), (Ra1,Rb3,X1,Z22), (Ra1,Rb3,X1,Z23), (Ra1,Rb3,X1,Z24), (Ra1,Rb3,X1,Z25), (Ra1,Rb3,X1,Z26), (Ra1,Rb3,X1,Z27), (Ra1,Rb3,X1,Z28), (Ra1,Rb3,X1,Z29), (Ra1,Rb3,X1,Z30), (Ra1,Rb3,X1,Z31), (Ra1,Rb3,X1,Z32), (Ra1,Rb3,X1,Z33), (Ra1,Rb3,X1,Z34), (Ra1,Rb3,X1,Z35), (Ra1,Rb3,X1,Z36), (Ra1,Rb3,X1,Z37), (Ra1,Rb3,X1,Z38), (Ra1,Rb3,X1,Z39), (Ra1,Rb3,X2,Z1), (Ra1,Rb3,X2,Z2), (Ra1,Rb3,X2,Z3), (Ra1,Rb3,X2,Z4), (Ra1,Rb3,X2,Z5), (Ra1,Rb3,X2,Z6), (Ra1,Rb3,X2,Z7), (Ra1,Rb3,X2,Z8), (Ra1,Rb3,X2,Z9), (Ra1,Rb3,X2,Z10), (Ra1,Rb3,X2,Z11), (Ra1,Rb3,X2,Z12), (Ra1,Rb3,X2,Z13), (Ra1,Rb3,X2,Z14), (Ra1,Rb3,X2,Z15), (Ra1,Rb3,X2,Z16), (Ra1,Rb3,X2,Z17), (Ra1,Rb3,X2,Z18), (Ra1,Rb3,X2,Z19), (Ra1,Rb3,X2,Z20), (Ra1,Rb3,X2,Z21), (Ra1,Rb3,X2,Z22), (Ra1,Rb3,X2,Z23), (Ra1,Rb3,X2,Z24), (Ra1,Rb3,X2,Z25), (Ra1,Rb3,X2,Z26), (Ra1,Rb3,X2,Z27), (Ra1,Rb3,X2,Z28), (Ra1,Rb3,X2,Z29), (Ra1,Rb3,X2,Z30), (Ra1,Rb3,X2,Z31), (Ra1,Rb3,X2,Z32), (Ra1,Rb3,X2,Z33), (Ra1,Rb3,X2,Z34), (Ra1,Rb3,X2,Z35), (Ra1,Rb3,X2,Z36), (Ra1,Rb3,X2,Z37), (Ra1,Rb3,X2,Z38), (Ra1,Rb3,X2,Z39), (Ra1,Rb4,X1,Z1), (Ra1,Rb4,X1,Z2), (Ra1,Rb4,X1,Z3), (Ra1,Rb4,X1,Z4), (Ra1,Rb4,X1,Z5), (Ra1,Rb4,X1,Z6), (Ra1,Rb4,X1,Z7), (Ra1,Rb4,X1,Z8), (Ra1,Rb4,X1,Z9), (Ra1,Rb4,X1,Z10), (Ra1,Rb4,X1,Z11), (Ra1,Rb4,X1,Z12), (Ra1,Rb4,X1,Z13), (Ra1,Rb4,X1,Z14), (Ra1,Rb4,X1,Z15), (Ra1,Rb4,X1,Z16), (Ra1,Rb4,X1,Z17), (Ra1,Rb4,X1,Z18), (Ra1,Rb4,X1,Z19), (Ra1,Rb4,X1,Z20), (Ra1,Rb4,X1,Z21), (Ra1,Rb4,X1,Z22), (Ra1,Rb4,X1,Z23), (Ra1,Rb4,X1,Z24), (Ra1,Rb4,X1,Z25), (Ra1,Rb4,X1,Z26), (Ra1,Rb4,X1,Z27), (Ra1,Rb4,X1,Z28), (Ra1,Rb4,X1,Z29), (Ra1,Rb4,X1,Z30), (Ra1,Rb4,X1,Z31), (Ra1,Rb4,X1,Z32), (Ra1,Rb4,X1,Z33), (Ra1,Rb4,X1,Z34), (Ra1,Rb4,X1,Z35), (Ra1,Rb4,X1,Z36), (Ra1,Rb4,X1,Z37), (Ra1,Rb4,X1,Z38), (Ra1,Rb4,X1,Z39), (Ra1,Rb4,X2,Z1), (Ra1,Rb4,X2,Z2), (Ra1,Rb4,X2,Z3), (Ra1,Rb4,X2,Z4), (Ra1,Rb4,X2,Z5), (Ra1,Rb4,X2,Z6), (Ra1,Rb4,X2,Z7), (Ra1,Rb4,X2,Z8), (Ra1,Rb4,X2,Z9), (Ra1,Rb4,X2,Z10), (Ra1,Rb4,X2,Z11), (Ra1,Rb4,X2,Z12), (Ra1,Rb4,X2,Z13), (Ra1,Rb4,X2,Z14), (Ra1,Rb4,X2,Z15), (Ra1,Rb4,X2,Z16), (Ra1,Rb4,X2,Z17), (Ra1,Rb4,X2,Z18), (Ra1,Rb4,X2,Z19), (Ra1,Rb4,X2,Z20), (Ra1,Rb4,X2,Z21), (Ra1,Rb4,X2,Z22), (Ra1,Rb4,X2,Z23), (Ra1,Rb4,X2,Z24), (Ra1,Rb4,X2,Z25), (Ra1,Rb4,X2,Z26), (Ra1,Rb4,X2,Z27), (Ra1,Rb4,X2,Z28), (Ra1,Rb4,X2,Z29), (Ra1,Rb4,X2,Z30), (Ra1,Rb4,X2,Z31), (Ra1,Rb4,X2,Z32), (Ra1,Rb4,X2,Z33), (Ra1,Rb4,X2,Z34), (Ra1,Rb4,X2,Z35), (Ra1,Rb4,X2,Z36), (Ra1,Rb4,X2,Z37), (Ra1,Rb4,X2,Z38), (Ra1,Rb4,X2,Z39), (Ra1,Rb5,X1,Z1), (Ra1,Rb5,X1,Z2), (Ra1,Rb5,X1,Z3), (Ra1,Rb5,X1,Z4), (Ra1,Rb5,X1,Z5), (Ra1,Rb5,X1,Z6), (Ra1,Rb5,X1,Z7), (Ra1,Rb5,X1,Z8), (Ra1,Rb5,X1,Z9), (Ra1,Rb5,X1,Z10), (Ra1,Rb5,X1,Z11), (Ra1,Rb5,X1,Z12), (Ra1,Rb5,X1,Z13), (Ra1,Rb5,X1,Z14), (Ra1,Rb5,X1,Z15), (Ra1,Rb5,X1,Z16), (Ra1,Rb5,X1,Z17), (Ra1,Rb5,X1,Z18), (Ra1,Rb5,X1,Z19), (Ra1,Rb5,X1,Z20), (Ra1,Rb5,X1,Z21), (Ra1,Rb5,X1,Z22), (Ra1,Rb5,X1,Z23), (Ra1,Rb5,X1,Z24), (Ra1,Rb5,X1,Z25), (Ra1,Rb5,X1,Z26), (Ra1,Rb5,X1,Z27), (Ra1,Rb5,X1,Z28), (Ra1,Rb5,X1,Z29), (Ra1,Rb5,X1,Z30), (Ra1,Rb5,X1,Z31), (Ra1,Rb5,X1,Z32), (Ra1,Rb5,X1,Z33), (Ra1,Rb5,X1,Z34), (Ra1,Rb5,X1,Z35), (Ra1,Rb5,X1,Z36), (Ra1,Rb5,X1,Z37), (Ra1,Rb5,X1,Z38), (Ra1,Rb5,X1,Z39), (Ra1,Rb5,X2,Z1), (Ra1,Rb5,X2,Z2), (Ra1,Rb5,X2,Z3), (Ra1,Rb5,X2,Z4), (Ra1,Rb5,X2,Z5), (Ra1,Rb5,X2,Z6), (Ra1,Rb5,X2,Z7), (Ra1,Rb5,X2,Z8), (Ra1,Rb5,X2,Z9), (Ra1,Rb5,X2,Z10), (Ra1,Rb5,X2,Z11), (Ra1,Rb5,X2,Z12), (Ra1,Rb5,X2,Z13), (Ra1,Rb5,X2,Z14), (Ra1,Rb5,X2,Z15), (Ra1,Rb5,X2,Z16), (Ra1,Rb5,X2,Z17), (Ra1,Rb5,X2,Z18), (Ra1,Rb5,X2,Z19), (Ra1,Rb5,X2,Z20), (Ra1,Rb5,X2,Z21), (Ra1,Rb5,X2,Z22), (Ra1,Rb5,X2,Z23), (Ra1,Rb5,X2,Z24), (Ra1,Rb5,X2,Z25), (Ra1,Rb5,X2,Z26), (Ra1,Rb5,X2,Z27), (Ra1,Rb5,X2,Z28), (Ra1,Rb5,X2,Z29), (Ra1,Rb5,X2,Z30), (Ra1,Rb5,X2,Z31), (Ra1,Rb5,X2,Z32), (Ra1,Rb5,X2,Z33), (Ra1,Rb5,X2,Z34), (Ra1,Rb5,X2,Z35), (Ra1,Rb5,X2,Z36), (Ra1,Rb5,X2,Z37), (Ra1,Rb5,X2,Z38), (Ra1,Rb5,X2,Z39), (Ra1,Rb6,X1,Z1), (Ra1,Rb6,X1,Z2), (Ra1,Rb6,X1,Z3), (Ra1,Rb6,X1,Z4), (Ra1,Rb6,X1,Z5), (Ra1,Rb6,X1,Z6), (Ra1,Rb6,X1,Z7), (Ra1,Rb6,X1,Z8), (Ra1,Rb6,X1,Z9), (Ra1,Rb6,X1,Z10), (Ra1,Rb6,X1,Z11), (Ra1,

Rb6,X1,Z12), (Ra1,Rb6,X1,Z13), (Ra1,Rb6,X1,Z14), (Ra1, Rb6,X1,Z15), (Ra1,Rb6,X1,Z16), (Ra1,Rb6,X1,Z17), (Ra1, Rb6,X1,Z18), (Ra1,Rb6,X1,Z19), (Ra1,Rb6,X1,Z20), (Ra1, Rb6,X1,Z21), (Ra1,Rb6,X1,Z22), (Ra1,Rb6,X1,Z23), (Ra1, Rb6,X1,Z24), (Ra1,Rb6,X1,Z25), (Ra1,Rb6,X1,Z26), (Ra1, Rb6,X1,Z27), (Ra1,Rb6,X1,Z28), (Ra1,Rb6,X1,Z29), (Ra1, Rb6,X1,Z30), (Ra1,Rb6,X1,Z31), (Ra1,Rb6,X1,Z32), (Ra1, Rb6,X1,Z33), (Ra1,Rb6,X1,Z34), (Ra1,Rb6,X1,Z35), (Ra1, Rb6,X1,Z36), (Ra1,Rb6,X1,Z37), (Ra1,Rb6,X1,Z38), (Ra1, Rb6,X1,Z39), (Ra1,Rb6,X2,Z1), (Ra1,Rb6,X2,Z2), (Ra1, Rb6,X2,Z3), (Ra1,Rb6,X2,Z4), (Ra1,Rb6,X2,Z5), (Ra1, Rb6,X2,Z6), (Ra1,Rb6,X2,Z7), (Ra1,Rb6,X2,Z8), (Ra1, Rb6,X2,Z9), (Ra1,Rb6,X2,Z10), (Ra1,Rb6,X2,Z11), (Ra1, Rb6,X2,Z12), (Ra1,Rb6,X2,Z13), (Ra1,Rb6,X2,Z14), (Ra1, Rb6,X2,Z15), (Ra1,Rb6,X2,Z16), (Ra1,Rb6,X2,Z17), (Ra1, Rb6,X2,Z18), (Ra1,Rb6,X2,Z19), (Ra1,Rb6,X2,Z20), (Ra1, Rb6,X2,Z21), (Ra1,Rb6,X2,Z22), (Ra1,Rb6,X2,Z23), (Ra1, Rb6,X2,Z24), (Ra1,Rb6,X2,Z25), (Ra1,Rb6,X2,Z26), (Ra1, Rb6,X2,Z27), (Ra1,Rb6,X2,Z28), (Ra1,Rb6,X2,Z29), (Ra1, Rb6,X2,Z30), (Ra1,Rb6,X2,Z31), (Ra1,Rb6,X2,Z32), (Ra1, Rb6,X2,Z33), (Ra1,Rb6,X2,Z34), (Ra1,Rb6,X2,Z35), (Ra1, Rb6,X2,Z36), (Ra1,Rb6,X2,Z37), (Ra1,Rb6,X2,Z38), (Ra1, Rb6,X2,Z39), (Ra1,Rb7,X1,Z1), (Ra1,Rb7,X1,Z2), (Ra1, Rb7,X1,Z3), (Ra1,Rb7,X1,Z4), (Ra1,Rb7,X1,Z5), (Ra1, Rb7,X1,Z6), (Ra1,Rb7,X1,Z7), (Ra1,Rb7,X1,Z8), (Ra1, Rb7,X1,Z9), (Ra1,Rb7,X1,Z10), (Ra1,Rb7,X1,Z11), (Ra1, Rb7,X1,Z12), (Ra1,Rb7,X1,Z13), (Ra1,Rb7,X1,Z14), (Ra1, Rb7,X1,Z15), (Ra1,Rb7,X1,Z16), (Ra1,Rb7,X1,Z17), (Ra1, Rb7,X1,Z18), (Ra1,Rb7,X1,Z19), (Ra1,Rb7,X1,Z20), (Ra1, Rb7,X1,Z21), (Ra1,Rb7,X1,Z22), (Ra1,Rb7,X1,Z23), (Ra1, Rb7,X1,Z24), (Ra1,Rb7,X1,Z25), (Ra1,Rb7,X1,Z26), (Ra1, Rb7,X1,Z27), (Ra1,Rb7,X1,Z28), (Ra1,Rb7,X1,Z29), (Ra1, Rb7,X1,Z30), (Ra1,Rb7,X1,Z31), (Ra1,Rb7,X1,Z32), (Ra1, Rb7,X1,Z33), (Ra1,Rb7,X1,Z34), (Ra1,Rb7,X1,Z35), (Ra1, Rb7,X1,Z36), (Ra1,Rb7,X1,Z37), (Ra1,Rb7,X1,Z38), (Ra1, Rb7,X1,Z39), (Ra1,Rb7,X2,Z1), (Ra1,Rb7,X2,Z2), (Ra1, Rb7,X2,Z3), (Ra1,Rb7,X2,Z4), (Ra1,Rb7,X2,Z5), (Ra1, Rb7,X2,Z6), (Ra1,Rb7,X2,Z7), (Ra1,Rb7,X2,Z8), (Ra1, Rb7,X2,Z9), (Ra1,Rb7,X2,Z10), (Ra1,Rb7,X2,Z11), (Ra1, Rb7,X2,Z12), (Ra1,Rb7,X2,Z13), (Ra1,Rb7,X2,Z14), (Ra1, Rb7,X2,Z15), (Ra1,Rb7,X2,Z16), (Ra1,Rb7,X2,Z17), (Ra1, Rb7,X2,Z18), (Ra1,Rb7,X2,Z19), (Ra1,Rb7,X2,Z20), (Ra1, Rb7,X2,Z21), (Ra1,Rb7,X2,Z22), (Ra1,Rb7,X2,Z23), (Ra1, Rb7,X2,Z24), (Ra1,Rb7,X2,Z25), (Ra1,Rb7,X2,Z26), (Ra1, Rb7,X2,Z27), (Ra1,Rb7,X2,Z28), (Ra1,Rb7,X2,Z29), (Ra1, Rb7,X2,Z30), (Ra1,Rb7,X2,Z31), (Ra1,Rb7,X2,Z32), (Ra1, Rb7,X2,Z33), (Ra1,Rb7,X2,Z34), (Ra1,Rb7,X2,Z35), (Ra1, Rb7,X2,Z36), (Ra1,Rb7,X2,Z37), (Ra1,Rb7,X2,Z38), (Ra1, Rb7,X2,Z39), (Ra1,Rb8,X1,Z1), (Ra1,Rb8,X1,Z2), (Ra1, Rb8,X1,Z3), (Ra1,Rb8,X1,Z4), (Ra1,Rb8,X1,Z5), (Ra1, Rb8,X1,Z6), (Ra1,Rb8,X1,Z7), (Ra1,Rb8,X1,Z8), (Ra1, Rb8,X1,Z9), (Ra1,Rb8,X1,Z10), (Ra1,Rb8,X1,Z11), (Ra1, Rb8,X1,Z12), (Ra1,Rb8,X1,Z13), (Ra1,Rb8,X1,Z14), (Ra1, Rb8,X1,Z15), (Ra1,Rb8,X1,Z16), (Ra1,Rb8,X1,Z17), (Ra1, Rb8,X1,Z18), (Ra1,Rb8,X1,Z19), (Ra1,Rb8,X1,Z20), (Ra1, Rb8,X1,Z21), (Ra1,Rb8,X1,Z22), (Ra1,Rb8,X1,Z23), (Ra1, Rb8,X1,Z24), (Ra1,Rb8,X1,Z25), (Ra1,Rb8,X1,Z26), (Ra1, Rb8,X1,Z27), (Ra1,Rb8,X1,Z28), (Ra1,Rb8,X1,Z29), (Ra1, Rb8,X1,Z30), (Ra1,Rb8,X1,Z31), (Ra1,Rb8,X1,Z32), (Ra1, Rb8,X1,Z33), (Ra1,Rb8,X1,Z34), (Ra1,Rb8,X1,Z35), (Ra1, Rb8,X1,Z36), (Ra1,Rb8,X1,Z37), (Ra1,Rb8,X1,Z38), (Ra1, Rb8,X1,Z39), (Ra1,Rb8,X2,Z1), (Ra1,Rb8,X2,Z2), (Ra1, Rb8,X2,Z3), (Ra1,Rb8,X2,Z4), (Ra1,Rb8,X2,Z5), (Ra1, Rb8,X2,Z6), (Ra1,Rb8,X2,Z7), (Ra1,Rb8,X2,Z8), (Ra1, Rb8,X2,Z9), (Ra1,Rb8,X2,Z10), (Ra1,Rb8,X2,Z11), (Ra1, Rb8,X2,Z12), (Ra1,Rb8,X2,Z13), (Ra1,Rb8,X2,Z14), (Ra1, Rb8,X2,Z15), (Ra1,Rb8,X2,Z16), (Ra1,Rb8,X2,Z17), (Ra1, Rb8,X2,Z18), (Ra1,Rb8,X2,Z19), (Ra1,Rb8,X2,Z20), (Ra1, Rb8,X2,Z21), (Ra1,Rb8,X2,Z22), (Ra1,Rb8,X2,Z23), (Ra1, Rb8,X2,Z24), (Ra1,Rb8,X2,Z25), (Ra1,Rb8,X2,Z26), (Ra1, Rb8,X2,Z27), (Ra1,Rb8,X2,Z28), (Ra1,Rb8,X2,Z29), (Ra1, Rb8,X2,Z30), (Ra1,Rb8,X2,Z31), (Ra1,Rb8,X2,Z32), (Ra1, Rb8,X2,Z33), (Ra1,Rb8,X2,Z34), (Ra1,Rb8,X2,Z35), (Ra1, Rb8,X2,Z36), (Ra1,Rb8,X2,Z37), (Ra1,Rb8,X2,Z38), (Ra1, Rb8,X2,Z39), (Ra2,Rb1,X1,Z1), (Ra2,Rb1,X1,Z2), (Ra2, Rb1,X1,Z3), (Ra2,Rb1,X1,Z4), (Ra2,Rb1,X1,Z5), (Ra2, Rb1,X1,Z6), (Ra2,Rb1,X1,Z7), (Ra2,Rb1,X1,Z8), (Ra2, Rb1,X1,Z9), (Ra2,Rb1,X1,Z10), (Ra2,Rb1,X1,Z11), (Ra2, Rb1,X1,Z12), (Ra2,Rb1,X1,Z13), (Ra2,Rb1,X1,Z14), (Ra2, Rb1,X1,Z15), (Ra2,Rb1,X1,Z16), (Ra2,Rb1,X1,Z17), (Ra2, Rb1,X1,Z18), (Ra2,Rb1,X1,Z19), (Ra2,Rb1,X1,Z20), (Ra2, Rb1,X1,Z21), (Ra2,Rb1,X1,Z22), (Ra2,Rb1,X1,Z23), (Ra2, Rb1,X1,Z24), (Ra2,Rb1,X1,Z25), (Ra2,Rb1,X1,Z26), (Ra2, Rb1,X1,Z27), (Ra2,Rb1,X1,Z28), (Ra2,Rb1,X1,Z29), (Ra2, Rb1,X1,Z30), (Ra2,Rb1,X1,Z31), (Ra2,Rb1,X1,Z32), (Ra2, Rb1,X1,Z33), (Ra2,Rb1,X1,Z34), (Ra2,Rb1,X1,Z35), (Ra2, Rb1,X1,Z36), (Ra2,Rb1,X1,Z37), (Ra2,Rb1,X1,Z38), (Ra2, Rb1,X1,Z39), (Ra2,Rb1,X2,Z1), (Ra2,Rb1,X2,Z2), (Ra2, Rb1,X2,Z3), (Ra2,Rb1,X2,Z4), (Ra2,Rb1,X2,Z5), (Ra2, Rb1,X2,Z6), (Ra2,Rb1,X2,Z7), (Ra2,Rb1,X2,Z8), (Ra2, Rb1,X2,Z9), (Ra2,Rb1,X2,Z10), (Ra2,Rb1,X2,Z11), (Ra2, Rb1,X2,Z12), (Ra2,Rb1,X2,Z13), (Ra2,Rb1,X2,Z14), (Ra2, Rb1,X2,Z15), (Ra2,Rb1,X2,Z16), (Ra2,Rb1,X2,Z17), (Ra2, Rb1,X2,Z18), (Ra2,Rb1,X2,Z19), (Ra2,Rb1,X2,Z20), (Ra2, Rb1,X2,Z21), (Ra2,Rb1,X2,Z22), (Ra2,Rb1,X2,Z23), (Ra2, Rb1,X2,Z24), (Ra2,Rb1,X2,Z25), (Ra2,Rb1,X2,Z26), (Ra2, Rb1,X2,Z27), (Ra2,Rb1,X2,Z28), (Ra2,Rb1,X2,Z29), (Ra2, Rb1,X2,Z30), (Ra2,Rb1,X2,Z31), (Ra2,Rb1,X2,Z32), (Ra2, Rb1,X2,Z33), (Ra2,Rb1,X2,Z34), (Ra2,Rb1,X2,Z35), (Ra2, Rb1,X2,Z36), (Ra2,Rb1,X2,Z37), (Ra2,Rb1,X2,Z38), (Ra2, Rb1,X2,Z39), (Ra2,Rb2,X1,Z1), (Ra2,Rb2,X1,Z2), (Ra2, Rb2,X1,Z3), (Ra2,Rb2,X1,Z4), (Ra2,Rb2,X1,Z5), (Ra2, Rb2,X1,Z6), (Ra2,Rb2,X1,Z7), (Ra2,Rb2,X1,Z8), (Ra2, Rb2,X1,Z9), (Ra2,Rb2,X1,Z10), (Ra2,Rb2,X1,Z11), (Ra2, Rb2,X1,Z12), (Ra2,Rb2,X1,Z13), (Ra2,Rb2,X1,Z14), (Ra2, Rb2,X1,Z15), (Ra2,Rb2,X1,Z16), (Ra2,Rb2,X1,Z17), (Ra2, Rb2,X1,Z18), (Ra2,Rb2,X1,Z19), (Ra2,Rb2,X1,Z20), (Ra2, Rb2,X1,Z21), (Ra2,Rb2,X1,Z22), (Ra2,Rb2,X1,Z23), (Ra2, Rb2,X1,Z24), (Ra2,Rb2,X1,Z25), (Ra2,Rb2,X1,Z26), (Ra2, Rb2,X1,Z27), (Ra2,Rb2,X1,Z28), (Ra2,Rb2,X1,Z29), (Ra2, Rb2,X1,Z30), (Ra2,Rb2,X1,Z31), (Ra2,Rb2,X1,Z32), (Ra2, Rb2,X1,Z33), (Ra2,Rb2,X1,Z34), (Ra2,Rb2,X1,Z35), (Ra2, Rb2,X1,Z36), (Ra2,Rb2,X1,Z37), (Ra2,Rb2,X1,Z38), (Ra2, Rb2,X1,Z39), (Ra2,Rb2,X2,Z1), (Ra2,Rb2,X2,Z2), (Ra2, Rb2,X2,Z3), (Ra2,Rb2,X2,Z4), (Ra2,Rb2,X2,Z5), (Ra2, Rb2,X2,Z6), (Ra2,Rb2,X2,Z7), (Ra2,Rb2,X2,Z8), (Ra2, Rb2,X2,Z9), (Ra2,Rb2,X2,Z10), (Ra2,Rb2,X2,Z11), (Ra2, Rb2,X2,Z12), (Ra2,Rb2,X2,Z13), (Ra2,Rb2,X2,Z14), (Ra2, Rb2,X2,Z15), (Ra2,Rb2,X2,Z16), (Ra2,Rb2,X2,Z17), (Ra2, Rb2,X2,Z18), (Ra2,Rb2,X2,Z19), (Ra2,Rb2,X2,Z20), (Ra2, Rb2,X2,Z21), (Ra2,Rb2,X2,Z22), (Ra2,Rb2,X2,Z23), (Ra2, Rb2,X2,Z24), (Ra2,Rb2,X2,Z25), (Ra2,Rb2,X2,Z26), (Ra2, Rb2,X2,Z27), (Ra2,Rb2,X2,Z28), (Ra2,Rb2,X2,Z29), (Ra2, Rb2,X2,Z30), (Ra2,Rb2,X2,Z31), (Ra2,Rb2,X2,Z32), (Ra2, Rb2,X2,Z33), (Ra2,Rb2,X2,Z34), (Ra2,Rb2,X2,Z35), (Ra2, Rb2,X2,Z36), (Ra2,Rb2,X2,Z37), (Ra2,Rb2,X2,Z38), (Ra2, Rb2,X2,Z39), (Ra2,Rb3,X1,Z1), (Ra2,Rb3,X1,Z2), (Ra2, Rb3,X1,Z3), (Ra2,Rb3,X1,Z4), (Ra2,Rb3,X1,Z5), (Ra2, Rb3,X1,Z6), (Ra2,Rb3,X1,Z7), (Ra2,Rb3,X1,Z8), (Ra2, Rb3,X1,Z9), (Ra2,Rb3,X1,Z10), (Ra2,Rb3,X1,Z11), (Ra2, Rb3,X1,Z12), (Ra2,Rb3,X1,Z13), (Ra2,Rb3,X1,Z14), (Ra2, Rb3,X1,Z15), (Ra2,Rb3,X1,Z16), (Ra2,Rb3,X1,Z17), (Ra2, Rb3,X1,Z18), (Ra2,Rb3,X1,Z19), (Ra2,Rb3,X1,Z20), (Ra2, Rb3,X1,Z21), (Ra2,Rb3,X1,Z22), (Ra2,Rb3,X1,Z23), (Ra2,

Rb3,X1,Z24), (Ra2,Rb3,X1,Z25), (Ra2,Rb3,X1,Z26), (Ra2,Rb3,X1,Z27), (Ra2,Rb3,X1,Z28), (Ra2,Rb3,X1,Z29), (Ra2,Rb3,X1,Z30), (Ra2,Rb3,X1,Z31), (Ra2,Rb3,X1,Z32), (Ra2,Rb3,X1,Z33), (Ra2,Rb3,X1,Z34), (Ra2,Rb3,X1,Z35), (Ra2,Rb3,X1,Z36), (Ra2,Rb3,X1,Z37), (Ra2,Rb3,X1,Z38), (Ra2,Rb3,X1,Z39), (Ra2,Rb3,X2,Z1), (Ra2,Rb3,X2,Z2), (Ra2,Rb3,X2,Z3), (Ra2,Rb3,X2,Z4), (Ra2,Rb3,X2,Z5), (Ra2,Rb3,X2,Z6), (Ra2,Rb3,X2,Z7), (Ra2,Rb3,X2,Z8), (Ra2,Rb3,X2,Z9), (Ra2,Rb3,X2,Z10), (Ra2,Rb3,X2,Z11), (Ra2,Rb3,X2,Z12), (Ra2,Rb3,X2,Z13), (Ra2,Rb3,X2,Z14), (Ra2,Rb3,X2,Z15), (Ra2,Rb3,X2,Z16), (Ra2,Rb3,X2,Z17), (Ra2,Rb3,X2,Z18), (Ra2,Rb3,X2,Z19), (Ra2,Rb3,X2,Z20), (Ra2,Rb3,X2,Z21), (Ra2,Rb3,X2,Z22), (Ra2,Rb3,X2,Z23), (Ra2,Rb3,X2,Z24), (Ra2,Rb3,X2,Z25), (Ra2,Rb3,X2,Z26), (Ra2,Rb3,X2,Z27), (Ra2,Rb3,X2,Z28), (Ra2,Rb3,X2,Z29), (Ra2,Rb3,X2,Z30), (Ra2,Rb3,X2,Z31), (Ra2,Rb3,X2,Z32), (Ra2,Rb3,X2,Z33), (Ra2,Rb3,X2,Z34), (Ra2,Rb3,X2,Z35), (Ra2,Rb3,X2,Z36), (Ra2,Rb3,X2,Z37), (Ra2,Rb3,X2,Z38), (Ra2,Rb3,X2,Z39), (Ra2,Rb4,X1,Z1), (Ra2,Rb4,X1,Z2), (Ra2,Rb4,X1,Z3), (Ra2,Rb4,X1,Z4), (Ra2,Rb4,X1,Z5), (Ra2,Rb4,X1,Z6), (Ra2,Rb4,X1,Z7), (Ra2,Rb4,X1,Z8), (Ra2,Rb4,X1,Z9), (Ra2,Rb4,X1,Z10), (Ra2,Rb4,X1,Z11), (Ra2,Rb4,X1,Z12), (Ra2,Rb4,X1,Z13), (Ra2,Rb4,X1,Z14), (Ra2,Rb4,X1,Z15), (Ra2,Rb4,X1,Z16), (Ra2,Rb4,X1,Z17), (Ra2,Rb4,X1,Z18), (Ra2,Rb4,X1,Z19), (Ra2,Rb4,X1,Z20), (Ra2,Rb4,X1,Z21), (Ra2,Rb4,X1,Z22), (Ra2,Rb4,X1,Z23), (Ra2,Rb4,X1,Z24), (Ra2,Rb4,X1,Z25), (Ra2,Rb4,X1,Z26), (Ra2,Rb4,X1,Z27), (Ra2,Rb4,X1,Z28), (Ra2,Rb4,X1,Z29), (Ra2,Rb4,X1,Z30), (Ra2,Rb4,X1,Z31), (Ra2,Rb4,X1,Z32), (Ra2,Rb4,X1,Z33), (Ra2,Rb4,X1,Z34), (Ra2,Rb4,X1,Z35), (Ra2,Rb4,X1,Z36), (Ra2,Rb4,X1,Z37), (Ra2,Rb4,X1,Z38), (Ra2,Rb4,X1,Z39), (Ra2,Rb4,X2,Z1), (Ra2,Rb4,X2,Z2), (Ra2,Rb4,X2,Z3), (Ra2,Rb4,X2,Z4), (Ra2,Rb4,X2,Z5), (Ra2,Rb4,X2,Z6), (Ra2,Rb4,X2,Z7), (Ra2,Rb4,X2,Z8), (Ra2,Rb4,X2,Z9), (Ra2,Rb4,X2,Z10), (Ra2,Rb4,X2,Z11), (Ra2,Rb4,X2,Z12), (Ra2,Rb4,X2,Z13), (Ra2,Rb4,X2,Z14), (Ra2,Rb4,X2,Z15), (Ra2,Rb4,X2,Z16), (Ra2,Rb4,X2,Z17), (Ra2,Rb4,X2,Z18), (Ra2,Rb4,X2,Z19), (Ra2,Rb4,X2,Z20), (Ra2,Rb4,X2,Z21), (Ra2,Rb4,X2,Z22), (Ra2,Rb4,X2,Z23), (Ra2,Rb4,X2,Z24), (Ra2,Rb4,X2,Z25), (Ra2,Rb4,X2,Z26), (Ra2,Rb4,X2,Z27), (Ra2,Rb4,X2,Z28), (Ra2,Rb4,X2,Z29), (Ra2,Rb4,X2,Z30), (Ra2,Rb4,X2,Z31), (Ra2,Rb4,X2,Z32), (Ra2,Rb4,X2,Z33), (Ra2,Rb4,X2,Z34), (Ra2,Rb4,X2,Z35), (Ra2,Rb4,X2,Z36), (Ra2,Rb4,X2,Z37), (Ra2,Rb4,X2,Z38), (Ra2,Rb4,X2,Z39), (Ra2,Rb5,X1,Z1), (Ra2,Rb5,X1,Z2), (Ra2,Rb5,X1,Z3), (Ra2,Rb5,X1,Z4), (Ra2,Rb5,X1,Z5), (Ra2,Rb5,X1,Z6), (Ra2,Rb5,X1,Z7), (Ra2,Rb5,X1,Z8), (Ra2,Rb5,X1,Z9), (Ra2,Rb5,X1,Z10), (Ra2,Rb5,X1,Z11), (Ra2,Rb5,X1,Z12), (Ra2,Rb5,X1,Z13), (Ra2,Rb5,X1,Z14), (Ra2,Rb5,X1,Z15), (Ra2,Rb5,X1,Z16), (Ra2,Rb5,X1,Z17), (Ra2,Rb5,X1,Z18), (Ra2,Rb5,X1,Z19), (Ra2,Rb5,X1,Z20), (Ra2,Rb5,X1,Z21), (Ra2,Rb5,X1,Z22), (Ra2,Rb5,X1,Z23), (Ra2,Rb5,X1,Z24), (Ra2,Rb5,X1,Z25), (Ra2,Rb5,X1,Z26), (Ra2,Rb5,X1,Z27), (Ra2,Rb5,X1,Z28), (Ra2,Rb5,X1,Z29), (Ra2,Rb5,X1,Z30), (Ra2,Rb5,X1,Z31), (Ra2,Rb5,X1,Z32), (Ra2,Rb5,X1,Z33), (Ra2,Rb5,X1,Z34), (Ra2,Rb5,X1,Z35), (Ra2,Rb5,X1,Z36), (Ra2,Rb5,X1,Z37), (Ra2,Rb5,X1,Z38), (Ra2,Rb5,X1,Z39), (Ra2,Rb5,X2,Z1), (Ra2,Rb5,X2,Z2), (Ra2,Rb5,X2,Z3), (Ra2,Rb5,X2,Z4), (Ra2,Rb5,X2,Z5), (Ra2,Rb5,X2,Z6), (Ra2,Rb5,X2,Z7), (Ra2,Rb5,X2,Z8), (Ra2,Rb5,X2,Z9), (Ra2,Rb5,X2,Z10), (Ra2,Rb5,X2,Z11), (Ra2,Rb5,X2,Z12), (Ra2,Rb5,X2,Z13), (Ra2,Rb5,X2,Z14), (Ra2,Rb5,X2,Z15), (Ra2,Rb5,X2,Z16), (Ra2,Rb5,X2,Z17), (Ra2,Rb5,X2,Z18), (Ra2,Rb5,X2,Z19), (Ra2,Rb5,X2,Z20), (Ra2,Rb5,X2,Z21), (Ra2,Rb5,X2,Z22), (Ra2,Rb5,X2,Z23), (Ra2,Rb5,X2,Z24), (Ra2,Rb5,X2,Z25), (Ra2,Rb5,X2,Z26), (Ra2,Rb5,X2,Z27), (Ra2,Rb5,X2,Z28), (Ra2,Rb5,X2,Z29), (Ra2,Rb5,X2,Z30), (Ra2,Rb5,X2,Z31), (Ra2,Rb5,X2,Z32), (Ra2,Rb5,X2,Z33), (Ra2,Rb5,X2,Z34), (Ra2,Rb5,X2,Z35), (Ra2,Rb5,X2,Z36), (Ra2,Rb5,X2,Z37), (Ra2,Rb5,X2,Z38), (Ra2,Rb5,X2,Z39), (Ra2,Rb6,X1,Z1), (Ra2,Rb6,X1,Z2), (Ra2,Rb6,X1,Z3), (Ra2,Rb6,X1,Z4), (Ra2,Rb6,X1,Z5), (Ra2,Rb6,X1,Z6), (Ra2,Rb6,X1,Z7), (Ra2,Rb6,X1,Z8), (Ra2,Rb6,X1,Z9), (Ra2,Rb6,X1,Z10), (Ra2,Rb6,X1,Z11), (Ra2,Rb6,X1,Z12), (Ra2,Rb6,X1,Z13), (Ra2,Rb6,X1,Z14), (Ra2,Rb6,X1,Z15), (Ra2,Rb6,X1,Z16), (Ra2,Rb6,X1,Z17), (Ra2,Rb6,X1,Z18), (Ra2,Rb6,X1,Z19), (Ra2,Rb6,X1,Z20), (Ra2,Rb6,X1,Z21), (Ra2,Rb6,X1,Z22), (Ra2,Rb6,X1,Z23), (Ra2,Rb6,X1,Z24), (Ra2,Rb6,X1,Z25), (Ra2,Rb6,X1,Z26), (Ra2,Rb6,X1,Z27), (Ra2,Rb6,X1,Z28), (Ra2,Rb6,X1,Z29), (Ra2,Rb6,X1,Z30), (Ra2,Rb6,X1,Z31), (Ra2,Rb6,X1,Z32), (Ra2,Rb6,X1,Z33), (Ra2,Rb6,X1,Z34), (Ra2,Rb6,X1,Z35), (Ra2,Rb6,X1,Z36), (Ra2,Rb6,X1,Z37), (Ra2,Rb6,X1,Z38), (Ra2,Rb6,X1,Z39), (Ra2,Rb6,X2,Z1), (Ra2,Rb6,X2,Z2), (Ra2,Rb6,X2,Z3), (Ra2,Rb6,X2,Z4), (Ra2,Rb6,X2,Z5), (Ra2,Rb6,X2,Z6), (Ra2,Rb6,X2,Z7), (Ra2,Rb6,X2,Z8), (Ra2,Rb6,X2,Z9), (Ra2,Rb6,X2,Z10), (Ra2,Rb6,X2,Z11), (Ra2,Rb6,X2,Z12), (Ra2,Rb6,X2,Z13), (Ra2,Rb6,X2,Z14), (Ra2,Rb6,X2,Z15), (Ra2,Rb6,X2,Z16), (Ra2,Rb6,X2,Z17), (Ra2,Rb6,X2,Z18), (Ra2,Rb6,X2,Z19), (Ra2,Rb6,X2,Z20), (Ra2,Rb6,X2,Z21), (Ra2,Rb6,X2,Z22), (Ra2,Rb6,X2,Z23), (Ra2,Rb6,X2,Z24), (Ra2,Rb6,X2,Z25), (Ra2,Rb6,X2,Z26), (Ra2,Rb6,X2,Z27), (Ra2,Rb6,X2,Z28), (Ra2,Rb6,X2,Z29), (Ra2,Rb6,X2,Z30), (Ra2,Rb6,X2,Z31), (Ra2,Rb6,X2,Z32), (Ra2,Rb6,X2,Z33), (Ra2,Rb6,X2,Z34), (Ra2,Rb6,X2,Z35), (Ra2,Rb6,X2,Z36), (Ra2,Rb6,X2,Z37), (Ra2,Rb6,X2,Z38), (Ra2,Rb6,X2,Z39), (Ra2,Rb7,X1,Z1), (Ra2,Rb7,X1,Z2), (Ra2,Rb7,X1,Z3), (Ra2,Rb7,X1,Z4), (Ra2,Rb7,X1,Z5), (Ra2,Rb7,X1,Z6), (Ra2,Rb7,X1,Z7), (Ra2,Rb7,X1,Z8), (Ra2,Rb7,X1,Z9), (Ra2,Rb7,X1,Z10), (Ra2,Rb7,X1,Z11), (Ra2,Rb7,X1,Z12), (Ra2,Rb7,X1,Z13), (Ra2,Rb7,X1,Z14), (Ra2,Rb7,X1,Z15), (Ra2,Rb7,X1,Z16), (Ra2,Rb7,X1,Z17), (Ra2,Rb7,X1,Z18), (Ra2,Rb7,X1,Z19), (Ra2,Rb7,X1,Z20), (Ra2,Rb7,X1,Z21), (Ra2,Rb7,X1,Z22), (Ra2,Rb7,X1,Z23), (Ra2,Rb7,X1,Z24), (Ra2,Rb7,X1,Z25), (Ra2,Rb7,X1,Z26), (Ra2,Rb7,X1,Z27), (Ra2,Rb7,X1,Z28), (Ra2,Rb7,X1,Z29), (Ra2,Rb7,X1,Z30), (Ra2,Rb7,X1,Z31), (Ra2,Rb7,X1,Z32), (Ra2,Rb7,X1,Z33), (Ra2,Rb7,X1,Z34), (Ra2,Rb7,X1,Z35), (Ra2,Rb7,X1,Z36), (Ra2,Rb7,X1,Z37), (Ra2,Rb7,X1,Z38), (Ra2,Rb7,X1,Z39), (Ra2,Rb7,X2,Z1), (Ra2,Rb7,X2,Z2), (Ra2,Rb7,X2,Z3), (Ra2,Rb7,X2,Z4), (Ra2,Rb7,X2,Z5), (Ra2,Rb7,X2,Z6), (Ra2,Rb7,X2,Z7), (Ra2,Rb7,X2,Z8), (Ra2,Rb7,X2,Z9), (Ra2,Rb7,X2,Z10), (Ra2,Rb7,X2,Z11), (Ra2,Rb7,X2,Z12), (Ra2,Rb7,X2,Z13), (Ra2,Rb7,X2,Z14), (Ra2,Rb7,X2,Z15), (Ra2,Rb7,X2,Z16), (Ra2,Rb7,X2,Z17), (Ra2,Rb7,X2,Z18), (Ra2,Rb7,X2,Z19), (Ra2,Rb7,X2,Z20), (Ra2,Rb7,X2,Z21), (Ra2,Rb7,X2,Z22), (Ra2,Rb7,X2,Z23), (Ra2,Rb7,X2,Z24), (Ra2,Rb7,X2,Z25), (Ra2,Rb7,X2,Z26), (Ra2,Rb7,X2,Z27), (Ra2,Rb7,X2,Z28), (Ra2,Rb7,X2,Z29), (Ra2,Rb7,X2,Z30), (Ra2,Rb7,X2,Z31), (Ra2,Rb7,X2,Z32), (Ra2,Rb7,X2,Z33), (Ra2,Rb7,X2,Z34), (Ra2,Rb7,X2,Z35), (Ra2,Rb7,X2,Z36), (Ra2,Rb7,X2,Z37), (Ra2,Rb7,X2,Z38), (Ra2,Rb7,X2,Z39), (Ra2,Rb8,X1,Z1), (Ra2,Rb8,X1,Z2), (Ra2,Rb8,X1,Z3), (Ra2,Rb8,X1,Z4), (Ra2,Rb8,X1,Z5), (Ra2,Rb8,X1,Z6), (Ra2,Rb8,X1,Z7), (Ra2,Rb8,X1,Z8), (Ra2,Rb8,X1,Z9), (Ra2,Rb8,X1,Z10), (Ra2,Rb8,X1,Z11), (Ra2,Rb8,X1,Z12), (Ra2,Rb8,X1,Z13), (Ra2,Rb8,X1,Z14), (Ra2,Rb8,X1,Z15), (Ra2,Rb8,X1,Z16), (Ra2,Rb8,X1,Z17), (Ra2,Rb8,X1,Z18), (Ra2,Rb8,X1,Z19), (Ra2,Rb8,X1,Z20), (Ra2,Rb8,X1,Z21), (Ra2,Rb8,X1,Z22), (Ra2,Rb8,X1,Z23), (Ra2,Rb8,X1,Z24), (Ra2,Rb8,X1,Z25), (Ra2,Rb8,X1,Z26), (Ra2,Rb8,X1,Z27), (Ra2,Rb8,X1,Z28), (Ra2,Rb8,X1,Z29), (Ra2,Rb8,X1,Z30), (Ra2,Rb8,X1,Z31), (Ra2,Rb8,X1,Z32), (Ra2,Rb8,X1,Z33), (Ra2,Rb8,X1,Z34), (Ra2,Rb8,X1,Z35), (Ra2,

Rb8,X1,Z36), (Ra2,Rb8,X1,Z37), (Ra2,Rb8,X1,Z38), (Ra2, Rb8,X1,Z39), (Ra2,Rb8,X2,Z1), (Ra2,Rb8,X2,Z2), (Ra2, Rb8,X2,Z3), (Ra2,Rb8,X2,Z4), (Ra2,Rb8,X2,Z5), (Ra2, Rb8,X2,Z6), (Ra2,Rb8,X2,Z7), (Ra2,Rb8,X2,Z8), (Ra2, Rb8,X2,Z9), (Ra2,Rb8,X2,Z10), (Ra2,Rb8,X2,Z11), (Ra2, Rb8,X2,Z12), (Ra2,Rb8,X2,Z13), (Ra2,Rb8,X2,Z14), (Ra2, Rb8,X2,Z15), (Ra2,Rb8,X2,Z16), (Ra2,Rb8,X2,Z17), (Ra2, Rb8,X2,Z18), (Ra2,Rb8,X2,Z19), (Ra2,Rb8,X2,Z20), (Ra2, Rb8,X2,Z21), (Ra2,Rb8,X2,Z22), (Ra2,Rb8,X2,Z23), (Ra2, Rb8,X2,Z24), (Ra2,Rb8,X2,Z25), (Ra2,Rb8,X2,Z26), (Ra2, Rb8,X2,Z27), (Ra2,Rb8,X2,Z28), (Ra2,Rb8,X2,Z29), (Ra2, Rb8,X2,Z30), (Ra2,Rb8,X2,Z31), (Ra2,Rb8,X2,Z32), (Ra2, Rb8,X2,Z33), (Ra2,Rb8,X2,Z34), (Ra2,Rb8,X2,Z35), (Ra2, Rb8,X2,Z36), (Ra2,Rb8,X2,Z37), (Ra2,Rb8,X2,Z38), (Ra2, Rb8,X2,Z39), (Ra3,Rb1,X1,Z1), (Ra3,Rb1,X1,Z2), (Ra3, Rb1,X1,Z3), (Ra3,Rb1,X1,Z4), (Ra3,Rb1,X1,Z5), (Ra3, Rb1,X1,Z6), (Ra3,Rb1,X1,Z7), (Ra3,Rb1,X1,Z8), (Ra3, Rb1,X1,Z9), (Ra3,Rb1,X1,Z10), (Ra3,Rb1,X1,Z11), (Ra3, Rb1,X1,Z12), (Ra3,Rb1,X1,Z13), (Ra3,Rb1,X1,Z14), (Ra3, Rb1,X1,Z15), (Ra3,Rb1,X1,Z16), (Ra3,Rb1,X1,Z17), (Ra3, Rb1,X1,Z18), (Ra3,Rb1,X1,Z19), (Ra3,Rb1,X1,Z20), (Ra3, Rb1,X1,Z21), (Ra3,Rb1,X1,Z22), (Ra3,Rb1,X1,Z23), (Ra3, Rb1,X1,Z24), (Ra3,Rb1,X1,Z25), (Ra3,Rb1,X1,Z26), (Ra3, Rb1,X1,Z27), (Ra3,Rb1,X1,Z28), (Ra3,Rb1,X1,Z29), (Ra3, Rb1,X1,Z30), (Ra3,Rb1,X1,Z31), (Ra3,Rb1,X1,Z32), (Ra3, Rb1,X1,Z33), (Ra3,Rb1,X1,Z34), (Ra3,Rb1,X1,Z35), (Ra3, Rb1,X1,Z36), (Ra3,Rb1,X1,Z37), (Ra3,Rb1,X1,Z38), (Ra3, Rb1,X1,Z39), (Ra3,Rb1,X2,Z1), (Ra3,Rb1,X2,Z2), (Ra3, Rb1,X2,Z3), (Ra3,Rb1,X2,Z4), (Ra3,Rb1,X2,Z5), (Ra3, Rb1,X2,Z6), (Ra3,Rb1,X2,Z7), (Ra3,Rb1,X2,Z8), (Ra3, Rb1,X2,Z9), (Ra3,Rb1,X2,Z10), (Ra3,Rb1,X2,Z11), (Ra3, Rb1,X2,Z12), (Ra3,Rb1,X2,Z13), (Ra3,Rb1,X2,Z14), (Ra3, Rb1,X2,Z15), (Ra3,Rb1,X2,Z16), (Ra3,Rb1,X2,Z17), (Ra3, Rb1,X2,Z18), (Ra3,Rb1,X2,Z19), (Ra3,Rb1,X2,Z20), (Ra3, Rb1,X2,Z21), (Ra3,Rb1,X2,Z22), (Ra3,Rb1,X2,Z23), (Ra3, Rb1,X2,Z24), (Ra3,Rb1,X2,Z25), (Ra3,Rb1,X2,Z26), (Ra3, Rb1,X2,Z27), (Ra3,Rb1,X2,Z28), (Ra3,Rb1,X2,Z29), (Ra3, Rb1,X2,Z30), (Ra3,Rb1,X2,Z31), (Ra3,Rb1,X2,Z32), (Ra3, Rb1,X2,Z33), (Ra3,Rb1,X2,Z34), (Ra3,Rb1,X2,Z35), (Ra3, Rb1,X2,Z36), (Ra3,Rb1,X2,Z37), (Ra3,Rb1,X2,Z38), (Ra3, Rb1,X2,Z39), (Ra3,Rb2,X1,Z1), (Ra3,Rb2,X1,Z2), (Ra3, Rb2,X1,Z3), (Ra3,Rb2,X1,Z4), (Ra3,Rb2,X1,Z5), (Ra3, Rb2,X1,Z6), (Ra3,Rb2,X1,Z7), (Ra3,Rb2,X1,Z8), (Ra3, Rb2,X1,Z9), (Ra3,Rb2,X1,Z10), (Ra3,Rb2,X1,Z11), (Ra3, Rb2,X1,Z12), (Ra3,Rb2,X1,Z13), (Ra3,Rb2,X1,Z14), (Ra3, Rb2,X1,Z15), (Ra3,Rb2,X1,Z16), (Ra3,Rb2,X1,Z17), (Ra3, Rb2,X1,Z18), (Ra3,Rb2,X1,Z19), (Ra3,Rb2,X1,Z20), (Ra3, Rb2,X1,Z21), (Ra3,Rb2,X1,Z22), (Ra3,Rb2,X1,Z23), (Ra3, Rb2,X1,Z24), (Ra3,Rb2,X1,Z25), (Ra3,Rb2,X1,Z26), (Ra3, Rb2,X1,Z27), (Ra3,Rb2,X1,Z28), (Ra3,Rb2,X1,Z29), (Ra3, Rb2,X1,Z30), (Ra3,Rb2,X1,Z31), (Ra3,Rb2,X1,Z32), (Ra3, Rb2,X1,Z33), (Ra3,Rb2,X1,Z34), (Ra3,Rb2,X1,Z35), (Ra3, Rb2,X1,Z36), (Ra3,Rb2,X1,Z37), (Ra3,Rb2,X1,Z38), (Ra3, Rb2,X1,Z39), (Ra3,Rb2,X2,Z1), (Ra3,Rb2,X2,Z2), (Ra3, Rb2,X2,Z3), (Ra3,Rb2,X2,Z4), (Ra3,Rb2,X2,Z5), (Ra3, Rb2,X2,Z6), (Ra3,Rb2,X2,Z7), (Ra3,Rb2,X2,Z8), (Ra3, Rb2,X2,Z9), (Ra3,Rb2,X2,Z10), (Ra3,Rb2,X2,Z11), (Ra3, Rb2,X2,Z12), (Ra3,Rb2,X2,Z13), (Ra3,Rb2,X2,Z14), (Ra3, Rb2,X2,Z15), (Ra3,Rb2,X2,Z16), (Ra3,Rb2,X2,Z17), (Ra3, Rb2,X2,Z18), (Ra3,Rb2,X2,Z19), (Ra3,Rb2,X2,Z20), (Ra3, Rb2,X2,Z21), (Ra3,Rb2,X2,Z22), (Ra3,Rb2,X2,Z23), (Ra3, Rb2,X2,Z24), (Ra3,Rb2,X2,Z25), (Ra3,Rb2,X2,Z26), (Ra3, Rb2,X2,Z27), (Ra3,Rb2,X2,Z28), (Ra3,Rb2,X2,Z29), (Ra3, Rb2,X2,Z30), (Ra3,Rb2,X2,Z31), (Ra3,Rb2,X2,Z32), (Ra3, Rb2,X2,Z33), (Ra3,Rb2,X2,Z34), (Ra3,Rb2,X2,Z35), (Ra3, Rb2,X2,Z36), (Ra3,Rb2,X2,Z37), (Ra3,Rb2,X2,Z38), (Ra3, Rb2,X2,Z39), (Ra3,Rb3,X1,Z1), (Ra3,Rb3,X1,Z2), (Ra3, Rb3,X1,Z3), (Ra3,Rb3,X1,Z4), (Ra3,Rb3,X1,Z5), (Ra3, Rb3,X1,Z6), (Ra3,Rb3,X1,Z7), (Ra3,Rb3,X1,Z8), (Ra3, Rb3,X1,Z9), (Ra3,Rb3,X1,Z10), (Ra3,Rb3,X1,Z11), (Ra3, Rb3,X1,Z12), (Ra3,Rb3,X1,Z13), (Ra3,Rb3,X1,Z14), (Ra3, Rb3,X1,Z15), (Ra3,Rb3,X1,Z16), (Ra3,Rb3,X1,Z17), (Ra3, Rb3,X1,Z18), (Ra3,Rb3,X1,Z19), (Ra3,Rb3,X1,Z20), (Ra3, Rb3,X1,Z21), (Ra3,Rb3,X1,Z22), (Ra3,Rb3,X1,Z23), (Ra3, Rb3,X1,Z24), (Ra3,Rb3,X1,Z25), (Ra3,Rb3,X1,Z26), (Ra3, Rb3,X1,Z27), (Ra3,Rb3,X1,Z28), (Ra3,Rb3,X1,Z29), (Ra3, Rb3,X1,Z30), (Ra3,Rb3,X1,Z31), (Ra3,Rb3,X1,Z32), (Ra3, Rb3,X1,Z33), (Ra3,Rb3,X1,Z34), (Ra3,Rb3,X1,Z35), (Ra3, Rb3,X1,Z36), (Ra3,Rb3,X1,Z37), (Ra3,Rb3,X1,Z38), (Ra3, Rb3,X1,Z39), (Ra3,Rb3,X2,Z1), (Ra3,Rb3,X2,Z2), (Ra3, Rb3,X2,Z3), (Ra3,Rb3,X2,Z4), (Ra3,Rb3,X2,Z5), (Ra3, Rb3,X2,Z6), (Ra3,Rb3,X2,Z7), (Ra3,Rb3,X2,Z8), (Ra3, Rb3,X2,Z9), (Ra3,Rb3,X2,Z10), (Ra3,Rb3,X2,Z11), (Ra3, Rb3,X2,Z12), (Ra3,Rb3,X2,Z13), (Ra3,Rb3,X2,Z14), (Ra3, Rb3,X2,Z15), (Ra3,Rb3,X2,Z16), (Ra3,Rb3,X2,Z17), (Ra3, Rb3,X2,Z18), (Ra3,Rb3,X2,Z19), (Ra3,Rb3,X2,Z20), (Ra3, Rb3,X2,Z21), (Ra3,Rb3,X2,Z22), (Ra3,Rb3,X2,Z23), (Ra3, Rb3,X2,Z24), (Ra3,Rb3,X2,Z25), (Ra3,Rb3,X2,Z26), (Ra3, Rb3,X2,Z27), (Ra3,Rb3,X2,Z28), (Ra3,Rb3,X2,Z29), (Ra3, Rb3,X2,Z30), (Ra3,Rb3,X2,Z31), (Ra3,Rb3,X2,Z32), (Ra3, Rb3,X2,Z33), (Ra3,Rb3,X2,Z34), (Ra3,Rb3,X2,Z35), (Ra3, Rb3,X2,Z36), (Ra3,Rb3,X2,Z37), (Ra3,Rb3,X2,Z38), (Ra3, Rb3,X2,Z39), (Ra3,Rb4,X1,Z1), (Ra3,Rb4,X1,Z2), (Ra3, Rb4,X1,Z3), (Ra3,Rb4,X1,Z4), (Ra3,Rb4,X1,Z5), (Ra3, Rb4,X1,Z6), (Ra3,Rb4,X1,Z7), (Ra3,Rb4,X1,Z8), (Ra3, Rb4,X1,Z9), (Ra3,Rb4,X1,Z10), (Ra3,Rb4,X1,Z11), (Ra3, Rb4,X1,Z12), (Ra3,Rb4,X1,Z13), (Ra3,Rb4,X1,Z14), (Ra3, Rb4,X1,Z15), (Ra3,Rb4,X1,Z16), (Ra3,Rb4,X1,Z17), (Ra3, Rb4,X1,Z18), (Ra3,Rb4,X1,Z19), (Ra3,Rb4,X1,Z20), (Ra3, Rb4,X1,Z21), (Ra3,Rb4,X1,Z22), (Ra3,Rb4,X1,Z23), (Ra3, Rb4,X1,Z24), (Ra3,Rb4,X1,Z25), (Ra3,Rb4,X1,Z26), (Ra3, Rb4,X1,Z27), (Ra3,Rb4,X1,Z28), (Ra3,Rb4,X1,Z29), (Ra3, Rb4,X1,Z30), (Ra3,Rb4,X1,Z31), (Ra3,Rb4,X1,Z32), (Ra3, Rb4,X1,Z33), (Ra3,Rb4,X1,Z34), (Ra3,Rb4,X1,Z35), (Ra3, Rb4,X1,Z36), (Ra3,Rb4,X1,Z37), (Ra3,Rb4,X1,Z38), (Ra3, Rb4,X1,Z39), (Ra3,Rb4,X2,Z1), (Ra3,Rb4,X2,Z2), (Ra3, Rb4,X2,Z3), (Ra3,Rb4,X2,Z4), (Ra3,Rb4,X2,Z5), (Ra3, Rb4,X2,Z6), (Ra3,Rb4,X2,Z7), (Ra3,Rb4,X2,Z8), (Ra3, Rb4,X2,Z9), (Ra3,Rb4,X2,Z10), (Ra3,Rb4,X2,Z11), (Ra3, Rb4,X2,Z12), (Ra3,Rb4,X2,Z13), (Ra3,Rb4,X2,Z14), (Ra3, Rb4,X2,Z15), (Ra3,Rb4,X2,Z16), (Ra3,Rb4,X2,Z17), (Ra3, Rb4,X2,Z18), (Ra3,Rb4,X2,Z19), (Ra3,Rb4,X2,Z20), (Ra3, Rb4,X2,Z21), (Ra3,Rb4,X2,Z22), (Ra3,Rb4,X2,Z23), (Ra3, Rb4,X2,Z24), (Ra3,Rb4,X2,Z25), (Ra3,Rb4,X2,Z26), (Ra3, Rb4,X2,Z27), (Ra3,Rb4,X2,Z28), (Ra3,Rb4,X2,Z29), (Ra3, Rb4,X2,Z30), (Ra3,Rb4,X2,Z31), (Ra3,Rb4,X2,Z32), (Ra3, Rb4,X2,Z33), (Ra3,Rb4,X2,Z34), (Ra3,Rb4,X2,Z35), (Ra3, Rb4,X2,Z36), (Ra3,Rb4,X2,Z37), (Ra3,Rb4,X2,Z38), (Ra3, Rb4,X2,Z39), (Ra3,Rb5,X1,Z1), (Ra3,Rb5,X1,Z2), (Ra3, Rb5,X1,Z3), (Ra3,Rb5,X1,Z4), (Ra3,Rb5,X1,Z5), (Ra3, Rb5,X1,Z6), (Ra3,Rb5,X1,Z7), (Ra3,Rb5,X1,Z8), (Ra3, Rb5,X1,Z9), (Ra3,Rb5,X1,Z10), (Ra3,Rb5,X1,Z11), (Ra3, Rb5,X1,Z12), (Ra3,Rb5,X1,Z13), (Ra3,Rb5,X1,Z14), (Ra3, Rb5,X1,Z15), (Ra3,Rb5,X1,Z16), (Ra3,Rb5,X1,Z17), (Ra3, Rb5,X1,Z18), (Ra3,Rb5,X1,Z19), (Ra3,Rb5,X1,Z20), (Ra3, Rb5,X1,Z21), (Ra3,Rb5,X1,Z22), (Ra3,Rb5,X1,Z23), (Ra3, Rb5,X1,Z24), (Ra3,Rb5,X1,Z25), (Ra3,Rb5,X1,Z26), (Ra3, Rb5,X1,Z27), (Ra3,Rb5,X1,Z28), (Ra3,Rb5,X1,Z29), (Ra3, Rb5,X1,Z30), (Ra3,Rb5,X1,Z31), (Ra3,Rb5,X1,Z32), (Ra3, Rb5,X1,Z33), (Ra3,Rb5,X1,Z34), (Ra3,Rb5,X1,Z35), (Ra3, Rb5,X1,Z36), (Ra3,Rb5,X1,Z37), (Ra3,Rb5,X1,Z38), (Ra3, Rb5,X1,Z39), (Ra3,Rb5,X2,Z1), (Ra3,Rb5,X2,Z2), (Ra3, Rb5,X2,Z3), (Ra3,Rb5,X2,Z4), (Ra3,Rb5,X2,Z5), (Ra3, Rb5,X2,Z6), (Ra3,Rb5,X2,Z7), (Ra3,Rb5,X2,Z8), (Ra3,

Rb5,X2,Z9), (Ra3,Rb5,X2,Z10), (Ra3,Rb5,X2,Z11), (Ra3, Rb5,X2,Z12), (Ra3,Rb5,X2,Z13), (Ra3,Rb5,X2,Z14), (Ra3, Rb5,X2,Z15), (Ra3,Rb5,X2,Z16), (Ra3,Rb5,X2,Z17), (Ra3, Rb5,X2,Z18), (Ra3,Rb5,X2,Z19), (Ra3,Rb5,X2,Z20), (Ra3, Rb5,X2,Z21), (Ra3,Rb5,X2,Z22), (Ra3,Rb5,X2,Z23), (Ra3, Rb5,X2,Z24), (Ra3,Rb5,X2,Z25), (Ra3,Rb5,X2,Z26), (Ra3, Rb5,X2,Z27), (Ra3,Rb5,X2,Z28), (Ra3,Rb5,X2,Z29), (Ra3, Rb5,X2,Z30), (Ra3,Rb5,X2,Z31), (Ra3,Rb5,X2,Z32), (Ra3, Rb5,X2,Z33), (Ra3,Rb5,X2,Z34), (Ra3,Rb5,X2,Z35), (Ra3, Rb5,X2,Z36), (Ra3,Rb5,X2,Z37), (Ra3,Rb5,X2,Z38), (Ra3, Rb5,X2,Z39), (Ra3,Rb6,X1,Z1), (Ra3,Rb6,X1,Z2), (Ra3, Rb6,X1,Z3), (Ra3,Rb6,X1,Z4), (Ra3,Rb6,X1,Z5), (Ra3, Rb6,X1,Z6), (Ra3,Rb6,X1,Z7), (Ra3,Rb6,X1,Z8), (Ra3, Rb6,X1,Z9), (Ra3,Rb6,X1,Z10), (Ra3,Rb6,X1,Z11), (Ra3, Rb6,X1,Z12), (Ra3,Rb6,X1,Z13), (Ra3,Rb6,X1,Z14), (Ra3, Rb6,X1,Z15), (Ra3,Rb6,X1,Z16), (Ra3,Rb6,X1,Z17), (Ra3, Rb6,X1,Z18), (Ra3,Rb6,X1,Z19), (Ra3,Rb6,X1,Z20), (Ra3, Rb6,X1,Z21), (Ra3,Rb6,X1,Z22), (Ra3,Rb6,X1,Z23), (Ra3, Rb6,X1,Z24), (Ra3,Rb6,X1,Z25), (Ra3,Rb6,X1,Z26), (Ra3, Rb6,X1,Z27), (Ra3,Rb6,X1,Z28), (Ra3,Rb6,X1,Z29), (Ra3, Rb6,X1,Z30), (Ra3,Rb6,X1,Z31), (Ra3,Rb6,X1,Z32), (Ra3, Rb6,X1,Z33), (Ra3,Rb6,X1,Z34), (Ra3,Rb6,X1,Z35), (Ra3, Rb6,X1,Z36), (Ra3,Rb6,X1,Z37), (Ra3,Rb6,X1,Z38), (Ra3, Rb6,X1,Z39), (Ra3,Rb6,X2,Z1), (Ra3,Rb6,X2,Z2), (Ra3, Rb6,X2,Z3), (Ra3,Rb6,X2,Z4), (Ra3,Rb6,X2,Z5), (Ra3, Rb6,X2,Z6), (Ra3,Rb6,X2,Z7), (Ra3,Rb6,X2,Z8), (Ra3, Rb6,X2,Z9), (Ra3,Rb6,X2,Z10), (Ra3,Rb6,X2,Z11), (Ra3, Rb6,X2,Z12), (Ra3,Rb6,X2,Z13), (Ra3,Rb6,X2,Z14), (Ra3, Rb6,X2,Z15), (Ra3,Rb6,X2,Z16), (Ra3,Rb6,X2,Z17), (Ra3, Rb6,X2,Z18), (Ra3,Rb6,X2,Z19), (Ra3,Rb6,X2,Z20), (Ra3, Rb6,X2,Z21), (Ra3,Rb6,X2,Z22), (Ra3,Rb6,X2,Z23), (Ra3, Rb6,X2,Z24), (Ra3,Rb6,X2,Z25), (Ra3,Rb6,X2,Z26), (Ra3, Rb6,X2,Z27), (Ra3,Rb6,X2,Z28), (Ra3,Rb6,X2,Z29), (Ra3, Rb6,X2,Z30), (Ra3,Rb6,X2,Z31), (Ra3,Rb6,X2,Z32), (Ra3, Rb6,X2,Z33), (Ra3,Rb6,X2,Z34), (Ra3,Rb6,X2,Z35), (Ra3, Rb6,X2,Z36), (Ra3,Rb6,X2,Z37), (Ra3,Rb6,X2,Z38), (Ra3, Rb6,X2,Z39), (Ra3,Rb7,X1,Z1), (Ra3,Rb7,X1,Z2), (Ra3, Rb7,X1,Z3), (Ra3,Rb7,X1,Z4), (Ra3,Rb7,X1,Z5), (Ra3, Rb7,X1,Z6), (Ra3,Rb7,X1,Z7), (Ra3,Rb7,X1,Z8), (Ra3, Rb7,X1,Z9), (Ra3,Rb7,X1,Z10), (Ra3,Rb7,X1,Z11), (Ra3, Rb7,X1,Z12), (Ra3,Rb7,X1,Z13), (Ra3,Rb7,X1,Z14), (Ra3, Rb7,X1,Z15), (Ra3,Rb7,X1,Z16), (Ra3,Rb7,X1,Z17), (Ra3, Rb7,X1,Z18), (Ra3,Rb7,X1,Z19), (Ra3,Rb7,X1,Z20), (Ra3, Rb7,X1,Z21), (Ra3,Rb7,X1,Z22), (Ra3,Rb7,X1,Z23), (Ra3, Rb7,X1,Z24), (Ra3,Rb7,X1,Z25), (Ra3,Rb7,X1,Z26), (Ra3, Rb7,X1,Z27), (Ra3,Rb7,X1,Z28), (Ra3,Rb7,X1,Z29), (Ra3, Rb7,X1,Z30), (Ra3,Rb7,X1,Z31), (Ra3,Rb7,X1,Z32), (Ra3, Rb7,X1,Z33), (Ra3,Rb7,X1,Z34), (Ra3,Rb7,X1,Z35), (Ra3, Rb7,X1,Z36), (Ra3,Rb7,X1,Z37), (Ra3,Rb7,X1,Z38), (Ra3, Rb7,X1,Z39), (Ra3,Rb7,X2,Z1), (Ra3,Rb7,X2,Z2), (Ra3, Rb7,X2,Z3), (Ra3,Rb7,X2,Z4), (Ra3,Rb7,X2,Z5), (Ra3, Rb7,X2,Z6), (Ra3,Rb7,X2,Z7), (Ra3,Rb7,X2,Z8), (Ra3, Rb7,X2,Z9), (Ra3,Rb7,X2,Z10), (Ra3,Rb7,X2,Z11), (Ra3, Rb7,X2,Z12), (Ra3,Rb7,X2,Z13), (Ra3,Rb7,X2,Z14), (Ra3, Rb7,X2,Z15), (Ra3,Rb7,X2,Z16), (Ra3,Rb7,X2,Z17), (Ra3, Rb7,X2,Z18), (Ra3,Rb7,X2,Z19), (Ra3,Rb7,X2,Z20), (Ra3, Rb7,X2,Z21), (Ra3,Rb7,X2,Z22), (Ra3,Rb7,X2,Z23), (Ra3, Rb7,X2,Z24), (Ra3,Rb7,X2,Z25), (Ra3,Rb7,X2,Z26), (Ra3, Rb7,X2,Z27), (Ra3,Rb7,X2,Z28), (Ra3,Rb7,X2,Z29), (Ra3, Rb7,X2,Z30), (Ra3,Rb7,X2,Z31), (Ra3,Rb7,X2,Z32), (Ra3, Rb7,X2,Z33), (Ra3,Rb7,X2,Z34), (Ra3,Rb7,X2,Z35), (Ra3, Rb7,X2,Z36), (Ra3,Rb7,X2,Z37), (Ra3,Rb7,X2,Z38), (Ra3, Rb7,X2,Z39), (Ra3,Rb8,X1,Z1), (Ra3,Rb8,X1,Z2), (Ra3, Rb8,X1,Z3), (Ra3,Rb8,X1,Z4), (Ra3,Rb8,X1,Z5), (Ra3, Rb8,X1,Z6), (Ra3,Rb8,X1,Z7), (Ra3,Rb8,X1,Z8), (Ra3, Rb8,X1,Z9), (Ra3,Rb8,X1,Z10), (Ra3,Rb8,X1,Z11), (Ra3, Rb8,X1,Z12), (Ra3,Rb8,X1,Z13), (Ra3,Rb8,X1,Z14), (Ra3, Rb8,X1,Z15), (Ra3,Rb8,X1,Z16), (Ra3,Rb8,X1,Z17), (Ra3, Rb8,X1,Z18), (Ra3,Rb8,X1,Z19), (Ra3,Rb8,X1,Z20), (Ra3, Rb8,X1,Z21), (Ra3,Rb8,X1,Z22), (Ra3,Rb8,X1,Z23), (Ra3, Rb8,X1,Z24), (Ra3,Rb8,X1,Z25), (Ra3,Rb8,X1,Z26), (Ra3, Rb8,X1,Z27), (Ra3,Rb8,X1,Z28), (Ra3,Rb8,X1,Z29), (Ra3, Rb8,X1,Z30), (Ra3,Rb8,X1,Z31), (Ra3,Rb8,X1,Z32), (Ra3, Rb8,X1,Z33), (Ra3,Rb8,X1,Z34), (Ra3,Rb8,X1,Z35), (Ra3, Rb8,X1,Z36), (Ra3,Rb8,X1,Z37), (Ra3,Rb8,X1,Z38), (Ra3, Rb8,X1,Z39), (Ra3,Rb8,X2,Z1), (Ra3,Rb8,X2,Z2), (Ra3, Rb8,X2,Z3), (Ra3,Rb8,X2,Z4), (Ra3,Rb8,X2,Z5), (Ra3, Rb8,X2,Z6), (Ra3,Rb8,X2,Z7), (Ra3,Rb8,X2,Z8), (Ra3, Rb8,X2,Z9), (Ra3,Rb8,X2,Z10), (Ra3,Rb8,X2,Z11), (Ra3, Rb8,X2,Z12), (Ra3,Rb8,X2,Z13), (Ra3,Rb8,X2,Z14), (Ra3, Rb8,X2,Z15), (Ra3,Rb8,X2,Z16), (Ra3,Rb8,X2,Z17), (Ra3, Rb8,X2,Z18), (Ra3,Rb8,X2,Z19), (Ra3,Rb8,X2,Z20), (Ra3, Rb8,X2,Z21), (Ra3,Rb8,X2,Z22), (Ra3,Rb8,X2,Z23), (Ra3, Rb8,X2,Z24), (Ra3,Rb8,X2,Z25), (Ra3,Rb8,X2,Z26), (Ra3, Rb8,X2,Z27), (Ra3,Rb8,X2,Z28), (Ra3,Rb8,X2,Z29), (Ra3, Rb8,X2,Z30), (Ra3,Rb8,X2,Z31), (Ra3,Rb8,X2,Z32), (Ra3, Rb8,X2,Z33), (Ra3,Rb8,X2,Z34), (Ra3,Rb8,X2,Z35), (Ra3, Rb8,X2,Z36), (Ra3,Rb8,X2,Z37), (Ra3,Rb8,X2,Z38), (Ra3, Rb8,X2,Z39), (Ra4,Rb1,X1,Z1), (Ra4,Rb1,X1,Z2), (Ra4, Rb1,X1,Z3), (Ra4,Rb1,X1,Z4), (Ra4,Rb1,X1,Z5), (Ra4, Rb1,X1,Z6), (Ra4,Rb1,X1,Z7), (Ra4,Rb1,X1,Z8), (Ra4, Rb1,X1,Z9), (Ra4,Rb1,X1,Z10), (Ra4,Rb1,X1,Z11), (Ra4, Rb1,X1,Z12), (Ra4,Rb1,X1,Z13), (Ra4,Rb1,X1,Z14), (Ra4, Rb1,X1,Z15), (Ra4,Rb1,X1,Z16), (Ra4,Rb1,X1,Z17), (Ra4, Rb1,X1,Z18), (Ra4,Rb1,X1,Z19), (Ra4,Rb1,X1,Z20), (Ra4, Rb1,X1,Z21), (Ra4,Rb1,X1,Z22), (Ra4,Rb1,X1,Z23), (Ra4, Rb1,X1,Z24), (Ra4,Rb1,X1,Z25), (Ra4,Rb1,X1,Z26), (Ra4, Rb1,X1,Z27), (Ra4,Rb1,X1,Z28), (Ra4,Rb1,X1,Z29), (Ra4, Rb1,X1,Z30), (Ra4,Rb1,X1,Z31), (Ra4,Rb1,X1,Z32), (Ra4, Rb1,X1,Z33), (Ra4,Rb1,X1,Z34), (Ra4,Rb1,X1,Z35), (Ra4, Rb1,X1,Z36), (Ra4,Rb1,X1,Z37), (Ra4,Rb1,X1,Z38), (Ra4, Rb1,X1,Z39), (Ra4,Rb1,X2,Z1), (Ra4,Rb1,X2,Z2), (Ra4, Rb1,X2,Z3), (Ra4,Rb1,X2,Z4), (Ra4,Rb1,X2,Z5), (Ra4, Rb1,X2,Z6), (Ra4,Rb1,X2,Z7), (Ra4,Rb1,X2,Z8), (Ra4, Rb1,X2,Z9), (Ra4,Rb1,X2,Z10), (Ra4,Rb1,X2,Z11), (Ra4, Rb1,X2,Z12), (Ra4,Rb1,X2,Z13), (Ra4,Rb1,X2,Z14), (Ra4, Rb1,X2,Z15), (Ra4,Rb1,X2,Z16), (Ra4,Rb1,X2,Z17), (Ra4, Rb1,X2,Z18), (Ra4,Rb1,X2,Z19), (Ra4,Rb1,X2,Z20), (Ra4, Rb1,X2,Z21), (Ra4,Rb1,X2,Z22), (Ra4,Rb1,X2,Z23), (Ra4, Rb1,X2,Z24), (Ra4,Rb1,X2,Z25), (Ra4,Rb1,X2,Z26), (Ra4, Rb1,X2,Z27), (Ra4,Rb1,X2,Z28), (Ra4,Rb1,X2,Z29), (Ra4, Rb1,X2,Z30), (Ra4,Rb1,X2,Z31), (Ra4,Rb1,X2,Z32), (Ra4, Rb1,X2,Z33), (Ra4,Rb1,X2,Z34), (Ra4,Rb1,X2,Z35), (Ra4, Rb1,X2,Z36), (Ra4,Rb1,X2,Z37), (Ra4,Rb1,X2,Z38), (Ra4, Rb1,X2,Z39), (Ra4,Rb2,X1,Z1), (Ra4,Rb2,X1,Z2), (Ra4, Rb2,X1,Z3), (Ra4,Rb2,X1,Z4), (Ra4,Rb2,X1,Z5), (Ra4, Rb2,X1,Z6), (Ra4,Rb2,X1,Z7), (Ra4,Rb2,X1,Z8), (Ra4, Rb2,X1,Z9), (Ra4,Rb2,X1,Z10), (Ra4,Rb2,X1,Z11), (Ra4, Rb2,X1,Z12), (Ra4,Rb2,X1,Z13), (Ra4,Rb2,X1,Z14), (Ra4, Rb2,X1,Z15), (Ra4,Rb2,X1,Z16), (Ra4,Rb2,X1,Z17), (Ra4, Rb2,X1,Z18), (Ra4,Rb2,X1,Z19), (Ra4,Rb2,X1,Z20), (Ra4, Rb2,X1,Z21), (Ra4,Rb2,X1,Z22), (Ra4,Rb2,X1,Z23), (Ra4, Rb2,X1,Z24), (Ra4,Rb2,X1,Z25), (Ra4,Rb2,X1,Z26), (Ra4, Rb2,X1,Z27), (Ra4,Rb2,X1,Z28), (Ra4,Rb2,X1,Z29), (Ra4, Rb2,X1,Z30), (Ra4,Rb2,X1,Z31), (Ra4,Rb2,X1,Z32), (Ra4, Rb2,X1,Z33), (Ra4,Rb2,X1,Z34), (Ra4,Rb2,X1,Z35), (Ra4, Rb2,X1,Z36), (Ra4,Rb2,X1,Z37), (Ra4,Rb2,X1,Z38), (Ra4, Rb2,X1,Z39), (Ra4,Rb2,X2,Z1), (Ra4,Rb2,X2,Z2), (Ra4, Rb2,X2,Z3), (Ra4,Rb2,X2,Z4), (Ra4,Rb2,X2,Z5), (Ra4, Rb2,X2,Z6), (Ra4,Rb2,X2,Z7), (Ra4,Rb2,X2,Z8), (Ra4, Rb2,X2,Z9), (Ra4,Rb2,X2,Z10), (Ra4,Rb2,X2,Z11), (Ra4, Rb2,X2,Z12), (Ra4,Rb2,X2,Z13), (Ra4,Rb2,X2,Z14), (Ra4, Rb2,X2,Z15), (Ra4,Rb2,X2,Z16), (Ra4,Rb2,X2,Z17), (Ra4, Rb2,X2,Z18), (Ra4,Rb2,X2,Z19), (Ra4,Rb2,X2,Z20), (Ra4,

Rb2,X2,Z21), (Ra4,Rb2,X2,Z22), (Ra4,Rb2,X2,Z23), (Ra4, Rb2,X2,Z24), (Ra4,Rb2,X2,Z25), (Ra4,Rb2,X2,Z26), (Ra4, Rb2,X2,Z27), (Ra4,Rb2,X2,Z28), (Ra4,Rb2,X2,Z29), (Ra4, Rb2,X2,Z30), (Ra4,Rb2,X2,Z31), (Ra4,Rb2,X2,Z32), (Ra4, Rb2,X2,Z33), (Ra4,Rb2,X2,Z34), (Ra4,Rb2,X2,Z35), (Ra4, Rb2,X2,Z36), (Ra4,Rb2,X2,Z37), (Ra4,Rb2,X2,Z38), (Ra4, Rb2,X2,Z39), (Ra4,Rb3,X1,Z1), (Ra4,Rb3,X1,Z2), (Ra4, Rb3,X1,Z3), (Ra4,Rb3,X1,Z4), (Ra4,Rb3,X1,Z5), (Ra4, Rb3,X1,Z6), (Ra4,Rb3,X1,Z7), (Ra4,Rb3,X1,Z8), (Ra4, Rb3,X1,Z9), (Ra4,Rb3,X1,Z10), (Ra4,Rb3,X1,Z11), (Ra4, Rb3,X1,Z12), (Ra4,Rb3,X1,Z13), (Ra4,Rb3,X1,Z14), (Ra4, Rb3,X1,Z15), (Ra4,Rb3,X1,Z16), (Ra4,Rb3,X1,Z17), (Ra4, Rb3,X1,Z18), (Ra4,Rb3,X1,Z19), (Ra4,Rb3,X1,Z20), (Ra4, Rb3,X1,Z21), (Ra4,Rb3,X1,Z22), (Ra4,Rb3,X1,Z23), (Ra4, Rb3,X1,Z24), (Ra4,Rb3,X1,Z25), (Ra4,Rb3,X1,Z26), (Ra4, Rb3,X1,Z27), (Ra4,Rb3,X1,Z28), (Ra4,Rb3,X1,Z29), (Ra4, Rb3,X1,Z30), (Ra4,Rb3,X1,Z31), (Ra4,Rb3,X1,Z32), (Ra4, Rb3,X1,Z33), (Ra4,Rb3,X1,Z34), (Ra4,Rb3,X1,Z35), (Ra4, Rb3,X1,Z36), (Ra4,Rb3,X1,Z37), (Ra4,Rb3,X1,Z38), (Ra4, Rb3,X1,Z39), (Ra4,Rb3,X2,Z1), (Ra4,Rb3,X2,Z2), (Ra4, Rb3,X2,Z3), (Ra4,Rb3,X2,Z4), (Ra4,Rb3,X2,Z5), (Ra4, Rb3,X2,Z6), (Ra4,Rb3,X2,Z7), (Ra4,Rb3,X2,Z8), (Ra4, Rb3,X2,Z9), (Ra4,Rb3,X2,Z10), (Ra4,Rb3,X2,Z11), (Ra4, Rb3,X2,Z12), (Ra4,Rb3,X2,Z13), (Ra4,Rb3,X2,Z14), (Ra4, Rb3,X2,Z15), (Ra4,Rb3,X2,Z16), (Ra4,Rb3,X2,Z17), (Ra4, Rb3,X2,Z18), (Ra4,Rb3,X2,Z19), (Ra4,Rb3,X2,Z20), (Ra4, Rb3,X2,Z21), (Ra4,Rb3,X2,Z22), (Ra4,Rb3,X2,Z23), (Ra4, Rb3,X2,Z24), (Ra4,Rb3,X2,Z25), (Ra4,Rb3,X2,Z26), (Ra4, Rb3,X2,Z27), (Ra4,Rb3,X2,Z28), (Ra4,Rb3,X2,Z29), (Ra4, Rb3,X2,Z30), (Ra4,Rb3,X2,Z31), (Ra4,Rb3,X2,Z32), (Ra4, Rb3,X2,Z33), (Ra4,Rb3,X2,Z34), (Ra4,Rb3,X2,Z35), (Ra4, Rb3,X2,Z36), (Ra4,Rb3,X2,Z37), (Ra4,Rb3,X2,Z38), (Ra4, Rb3,X2,Z39), (Ra4,Rb4,X1,Z1), (Ra4,Rb4,X1,Z2), (Ra4, Rb4,X1,Z3), (Ra4,Rb4,X1,Z4), (Ra4,Rb4,X1,Z5), (Ra4, Rb4,X1,Z6), (Ra4,Rb4,X1,Z7), (Ra4,Rb4,X1,Z8), (Ra4, Rb4,X1,Z9), (Ra4,Rb4,X1,Z10), (Ra4,Rb4,X1,Z11), (Ra4, Rb4,X1,Z12), (Ra4,Rb4,X1,Z13), (Ra4,Rb4,X1,Z14), (Ra4, Rb4,X1,Z15), (Ra4,Rb4,X1,Z16), (Ra4,Rb4,X1,Z17), (Ra4, Rb4,X1,Z18), (Ra4,Rb4,X1,Z19), (Ra4,Rb4,X1,Z20), (Ra4, Rb4,X1,Z21), (Ra4,Rb4,X1,Z22), (Ra4,Rb4,X1,Z23), (Ra4, Rb4,X1,Z24), (Ra4,Rb4,X1,Z25), (Ra4,Rb4,X1,Z26), (Ra4, Rb4,X1,Z27), (Ra4,Rb4,X1,Z28), (Ra4,Rb4,X1,Z29), (Ra4, Rb4,X1,Z30), (Ra4,Rb4,X1,Z31), (Ra4,Rb4,X1,Z32), (Ra4, Rb4,X1,Z33), (Ra4,Rb4,X1,Z34), (Ra4,Rb4,X1,Z35), (Ra4, Rb4,X1,Z36), (Ra4,Rb4,X1,Z37), (Ra4,Rb4,X1,Z38), (Ra4, Rb4,X1,Z39), (Ra4,Rb4,X2,Z1), (Ra4,Rb4,X2,Z2), (Ra4, Rb4,X2,Z3), (Ra4,Rb4,X2,Z4), (Ra4,Rb4,X2,Z5), (Ra4, Rb4,X2,Z6), (Ra4,Rb4,X2,Z7), (Ra4,Rb4,X2,Z8), (Ra4, Rb4,X2,Z9), (Ra4,Rb4,X2,Z10), (Ra4,Rb4,X2,Z11), (Ra4, Rb4,X2,Z12), (Ra4,Rb4,X2,Z13), (Ra4,Rb4,X2,Z14), (Ra4, Rb4,X2,Z15), (Ra4,Rb4,X2,Z16), (Ra4,Rb4,X2,Z17), (Ra4, Rb4,X2,Z18), (Ra4,Rb4,X2,Z19), (Ra4,Rb4,X2,Z20), (Ra4, Rb4,X2,Z21), (Ra4,Rb4,X2,Z22), (Ra4,Rb4,X2,Z23), (Ra4, Rb4,X2,Z24), (Ra4,Rb4,X2,Z25), (Ra4,Rb4,X2,Z26), (Ra4, Rb4,X2,Z27), (Ra4,Rb4,X2,Z28), (Ra4,Rb4,X2,Z29), (Ra4, Rb4,X2,Z30), (Ra4,Rb4,X2,Z31), (Ra4,Rb4,X2,Z32), (Ra4, Rb4,X2,Z33), (Ra4,Rb4,X2,Z34), (Ra4,Rb4,X2,Z35), (Ra4, Rb4,X2,Z36), (Ra4,Rb4,X2,Z37), (Ra4,Rb4,X2,Z38), (Ra4, Rb4,X2,Z39), (Ra4,Rb5,X1,Z1), (Ra4,Rb5,X1,Z2), (Ra4, Rb5,X1,Z3), (Ra4,Rb5,X1,Z4), (Ra4,Rb5,X1,Z5), (Ra4, Rb5,X1,Z6), (Ra4,Rb5,X1,Z7), (Ra4,Rb5,X1,Z8), (Ra4, Rb5,X1,Z9), (Ra4,Rb5,X1, Z10), (Ra4,Rb5,X1,Z11), (Ra4, Rb5,X1,Z12), (Ra4,Rb5,X1,Z13), (Ra4,Rb5,X1,Z14), (Ra4, Rb5,X1,Z15), (Ra4,Rb5,X1,Z16), (Ra4,Rb5,X1,Z17), (Ra4, Rb5,X1,Z18), (Ra4,Rb5,X1,Z19), (Ra4,Rb5,X1,Z20), (Ra4, Rb5,X1,Z21), (Ra4,Rb5,X1,Z22), (Ra4,Rb5,X1,Z23), (Ra4, Rb5,X1,Z24), (Ra4,Rb5,X1,Z25), (Ra4,Rb5,X1,Z26), (Ra4, Rb5,X1,Z27), (Ra4,Rb5,X1,Z28), (Ra4,Rb5,X1,Z29), (Ra4, Rb5,X1,Z30), (Ra4,Rb5,X1,Z31), (Ra4,Rb5,X1,Z32), (Ra4, Rb5,X1,Z33), (Ra4,Rb5,X1,Z34), (Ra4,Rb5,X1,Z35), (Ra4, Rb5,X1,Z36), (Ra4,Rb5,X1,Z37), (Ra4,Rb5,X1,Z38), (Ra4, Rb5,X1,Z39), (Ra4,Rb5,X2,Z1), (Ra4,Rb5,X2,Z2), (Ra4, Rb5,X2,Z3), (Ra4,Rb5,X2,Z4), (Ra4,Rb5,X2,Z5), (Ra4, Rb5,X2,Z6), (Ra4,Rb5,X2,Z7), (Ra4,Rb5,X2,Z8), (Ra4, Rb5,X2,Z9), (Ra4,Rb5,X2,Z10), (Ra4,Rb5,X2,Z11), (Ra4, Rb5,X2,Z12), (Ra4,Rb5,X2,Z13), (Ra4,Rb5,X2,Z14), (Ra4, Rb5,X2,Z15), (Ra4,Rb5,X2,Z16), (Ra4,Rb5,X2,Z17), (Ra4, Rb5,X2,Z18), (Ra4,Rb5,X2,Z19), (Ra4,Rb5,X2,Z20), (Ra4, Rb5,X2,Z21), (Ra4,Rb5,X2,Z22), (Ra4,Rb5,X2,Z23), (Ra4, Rb5,X2,Z24), (Ra4,Rb5,X2,Z25), (Ra4,Rb5,X2,Z26), (Ra4, Rb5,X2,Z27), (Ra4,Rb5,X2,Z28), (Ra4,Rb5,X2,Z29), (Ra4, Rb5,X2,Z30), (Ra4,Rb5,X2,Z31), (Ra4,Rb5,X2,Z32), (Ra4, Rb5,X2,Z33), (Ra4,Rb5,X2,Z34), (Ra4,Rb5,X2,Z35), (Ra4, Rb5,X2,Z36), (Ra4,Rb5,X2,Z37), (Ra4,Rb5,X2,Z38), (Ra4, Rb5,X2,Z39), (Ra4,Rb6,X1,Z1), (Ra4,Rb6,X1,Z2), (Ra4, Rb6,X1,Z3), (Ra4,Rb6,X1,Z4), (Ra4,Rb6,X1,Z5), (Ra4, Rb6,X1,Z6), (Ra4,Rb6,X1,Z7), (Ra4,Rb6,X1,Z8), (Ra4, Rb6,X1,Z9), (Ra4,Rb6,X1,Z10), (Ra4,Rb6,X1,Z11), (Ra4, Rb6,X1,Z12), (Ra4,Rb6,X1,Z13), (Ra4,Rb6,X1,Z14), (Ra4, Rb6,X1,Z15), (Ra4,Rb6,X1,Z16), (Ra4,Rb6,X1,Z17), (Ra4, Rb6,X1,Z18), (Ra4,Rb6,X1,Z19), (Ra4,Rb6,X1,Z20), (Ra4, Rb6,X1,Z21), (Ra4,Rb6,X1,Z22), (Ra4,Rb6,X1,Z23), (Ra4, Rb6,X1,Z24), (Ra4,Rb6,X1,Z25), (Ra4,Rb6,X1,Z26), (Ra4, Rb6,X1,Z27), (Ra4,Rb6,X1,Z28), (Ra4,Rb6,X1,Z29), (Ra4, Rb6,X1,Z30), (Ra4,Rb6,X1,Z31), (Ra4,Rb6,X1,Z32), (Ra4, Rb6,X1,Z33), (Ra4,Rb6,X1,Z34), (Ra4,Rb6,X1,Z35), (Ra4, Rb6,X1,Z36), (Ra4,Rb6,X1,Z37), (Ra4,Rb6,X1,Z38), (Ra4, Rb6,X1,Z39), (Ra4,Rb6,X2,Z1), (Ra4,Rb6,X2,Z2), (Ra4, Rb6,X2,Z3), (Ra4,Rb6,X2,Z4), (Ra4,Rb6,X2,Z5), (Ra4, Rb6,X2,Z6), (Ra4,Rb6,X2,Z7), (Ra4,Rb6,X2,Z8), (Ra4, Rb6,X2,Z9), (Ra4,Rb6,X2,Z10), (Ra4,Rb6,X2,Z11), (Ra4, Rb6,X2,Z12), (Ra4,Rb6,X2,Z13), (Ra4,Rb6,X2,Z14), (Ra4, Rb6,X2,Z15), (Ra4,Rb6,X2,Z16), (Ra4,Rb6,X2,Z17), (Ra4, Rb6,X2,Z18), (Ra4,Rb6,X2,Z19), (Ra4,Rb6,X2,Z20), (Ra4, Rb6,X2,Z21), (Ra4,Rb6,X2,Z22), (Ra4,Rb6,X2,Z23), (Ra4, Rb6,X2,Z24), (Ra4,Rb6,X2,Z25), (Ra4,Rb6,X2,Z26), (Ra4, Rb6,X2,Z27), (Ra4,Rb6,X2,Z28), (Ra4,Rb6,X2,Z29), (Ra4, Rb6,X2,Z30), (Ra4,Rb6,X2,Z31), (Ra4,Rb6,X2,Z32), (Ra4, Rb6,X2,Z33), (Ra4,Rb6,X2,Z34), (Ra4,Rb6,X2,Z35), (Ra4, Rb6,X2,Z36), (Ra4,Rb6,X2,Z37), (Ra4,Rb6,X2,Z38), (Ra4, Rb6,X2,Z39), (Ra4,Rb7,X1,Z1), (Ra4,Rb7,X1,Z2), (Ra4, Rb7,X1,Z3), (Ra4,Rb7,X1,Z4), (Ra4,Rb7,X1,Z5), (Ra4, Rb7,X1,Z6), (Ra4,Rb7,X1,Z7), (Ra4,Rb7,X1,Z8), (Ra4, Rb7,X1,Z9), (Ra4,Rb7,X1,Z10), (Ra4,Rb7,X1,Z11), (Ra4, Rb7,X1,Z12), (Ra4,Rb7,X1,Z13), (Ra4,Rb7,X1,Z14), (Ra4, Rb7,X1,Z15), (Ra4,Rb7,X1,Z16), (Ra4,Rb7,X1,Z17), (Ra4, Rb7,X1,Z18), (Ra4,Rb7,X1,Z19), (Ra4,Rb7,X1,Z20), (Ra4, Rb7,X1,Z21), (Ra4,Rb7,X1,Z22), (Ra4,Rb7,X1,Z23), (Ra4, Rb7,X1,Z24), (Ra4,Rb7,X1,Z25), (Ra4,Rb7,X1,Z26), (Ra4, Rb7,X1,Z27), (Ra4,Rb7,X1,Z28), (Ra4,Rb7,X1,Z29), (Ra4, Rb7,X1,Z30), (Ra4,Rb7,X1,Z31), (Ra4,Rb7,X1,Z32), (Ra4, Rb7,X1,Z33), (Ra4,Rb7,X1,Z34), (Ra4,Rb7,X1,Z35), (Ra4, Rb7,X1,Z (Ra4,Rb7,X1,Z37), (Ra4,Rb7,X1,Z38), (Ra4, Rb7,X1,Z39), (Ra4,Rb7,X2,Z1), (Ra4,Rb7,X2,Z2), (Ra4, Rb7,X2,Z3), (Ra4,Rb7,X2,Z4), (Ra4,Rb7,X2,Z5), (Ra4, Rb7,X2,Z6), (Ra4,Rb7,X2,Z7), (Ra4,Rb7,X2,Z8), (Ra4, Rb7,X2,Z9), (Ra4,Rb7,X2,Z10), (Ra4,Rb7,X2,Z11), (Ra4, Rb7,X2,Z12), (Ra4,Rb7,X2,Z13), (Ra4,Rb7,X2,Z14), (Ra4, Rb7,X2,Z15), (Ra4,Rb7,X2,Z16), (Ra4,Rb7,X2,Z17), (Ra4, Rb7,X2,Z18), (Ra4,Rb7,X2,Z19), (Ra4,Rb7,X2,Z20), (Ra4, Rb7,X2,Z21), (Ra4,Rb7,X2,Z22), (Ra4,Rb7,X2,Z23), (Ra4, Rb7,X2,Z24), (Ra4,Rb7,X2,Z25), (Ra4,Rb7,X2,Z26), (Ra4, Rb7,X2,Z27), (Ra4,Rb7,X2,Z28), (Ra4,Rb7,X2,Z29), (Ra4, Rb7,X2,Z30), (Ra4,Rb7,X2,Z31), (Ra4,Rb7,X2,Z32), (Ra4,

Rb7,X2,Z33), (Ra4,Rb7,X2,Z34), (Ra4,Rb7,X2,Z35), (Ra4, Rb7,X2,Z36), (Ra4,Rb7,X2,Z37), (Ra4,Rb7,X2,Z38), (Ra4, Rb7,X2,Z39), (Ra4,Rb8,X1,Z1), (Ra4,Rb8,X1,Z2), (Ra4, Rb8,X1,Z3), (Ra4,Rb8,X1,Z4), (Ra4,Rb8,X1,Z5), (Ra4, Rb8,X1,Z6), (Ra4,Rb8,X1,Z7), (Ra4,Rb8,X1,Z8), (Ra4, Rb8,X1,Z9), (Ra4,Rb8,X1,Z10), (Ra4,Rb8,X1,Z11), (Ra4, Rb8,X1,Z12), (Ra4,Rb8,X1,Z13), (Ra4,Rb8,X1,Z14), (Ra4, Rb8,X1,Z15), (Ra4,Rb8,X1,Z16), (Ra4,Rb8,X1,Z17), (Ra4, Rb8,X1,Z18), (Ra4,Rb8,X1,Z19), (Ra4,Rb8,X1,Z20), (Ra4, Rb8,X1,Z21), (Ra4,Rb8,X1,Z22), (Ra4,Rb8,X1,Z23), (Ra4, Rb8,X1,Z24), (Ra4,Rb8,X1,Z25), (Ra4,Rb8,X1,Z26), (Ra4, Rb8,X1,Z27), (Ra4,Rb8,X1,Z28), (Ra4,Rb8,X1,Z29), (Ra4, Rb8,X1,Z30), (Ra4,Rb8,X1,Z31), (Ra4,Rb8,X1,Z32), (Ra4, Rb8,X1,Z33), (Ra4,Rb8,X1,Z34), (Ra4,Rb8,X1,Z35), (Ra4, Rb8,X1,Z36), (Ra4,Rb8,X1,Z37), (Ra4,Rb8,X1,Z38), (Ra4, Rb8,X1,Z39), (Ra4,Rb8,X2,Z1), (Ra4,Rb8,X2,Z2), (Ra4, Rb8,X2,Z3), (Ra4,Rb8,X2,Z4), (Ra4,Rb8,X2,Z5), (Ra4, Rb8,X2,Z6), (Ra4,Rb8,X2,Z7), (Ra4,Rb8,X2,Z8), (Ra4, Rb8,X2,Z9), (Ra4,Rb8,X2,Z10), (Ra4,Rb8,X2,Z11), (Ra4, Rb8,X2,Z12), (Ra4,Rb8,X2,Z13), (Ra4,Rb8,X2,Z14), (Ra4, Rb8,X2,Z15), (Ra4,Rb8,X2,Z16), (Ra4,Rb8,X2,Z17), (Ra4, Rb8,X2,Z18), (Ra4,Rb8,X2,Z19), (Ra4,Rb8,X2,Z20), (Ra4, Rb8,X2,Z21), (Ra4,Rb8,X2,Z22), (Ra4,Rb8,X2,Z23), (Ra4, Rb8,X2,Z24), (Ra4,Rb8,X2,Z25), (Ra4,Rb8,X2,Z26), (Ra4, Rb8,X2,Z27), (Ra4,Rb8,X2,Z28), (Ra4,Rb8,X2,Z29), (Ra4, Rb8,X2,Z30), (Ra4,Rb8,X2,Z31), (Ra4,Rb8,X2,Z32), (Ra4, Rb8,X2,Z33), (Ra4,Rb8,X2,Z34), (Ra4,Rb8,X2,Z35), (Ra4, Rb8,X2,Z36), (Ra4,Rb8,X2,Z37), (Ra4,Rb8,X2,Z38), (Ra4, Rb8,X2,Z39), (Ra5,Rb1,X1,Z1), (Ra5,Rb1,X1,Z2), (Ra5, Rb1,X1,Z3), (Ra5,Rb1,X1,Z4), (Ra5,Rb1,X1,Z5), (Ra5, Rb1,X1,Z6), (Ra5,Rb1,X1,Z7), (Ra5,Rb1,X1,Z8), (Ra5, Rb1,X1,Z9), (Ra5,Rb1,X1,Z10), (Ra5,Rb1,X1,Z11), (Ra5, Rb1,X1,Z12), (Ra5,Rb1,X1,Z13), (Ra5,Rb1,X1,Z14), (Ra5, Rb1,X1,Z15), (Ra5,Rb1,X1,Z16), (Ra5,Rb1,X1,Z17), (Ra5, Rb1,X1,Z18), (Ra5,Rb1,X1,Z19), (Ra5,Rb1,X1,Z20), (Ra5, Rb1,X1,Z21), (Ra5,Rb1,X1,Z22), (Ra5,Rb1,X1,Z23), (Ra5, Rb1,X1,Z24), (Ra5,Rb1,X1,Z25), (Ra5,Rb1,X1,Z26), (Ra5, Rb1,X1,Z27), (Ra5,Rb1,X1,Z28), (Ra5,Rb1,X1,Z29), (Ra5, Rb1,X1,Z30), (Ra5,Rb1,X1,Z31), (Ra5,Rb1,X1,Z32), (Ra5, Rb1,X1,Z33), (Ra5,Rb1,X1,Z34), (Ra5,Rb1,X1,Z35), (Ra5, Rb1,X1,Z36), (Ra5,Rb1,X1,Z37), (Ra5,Rb1,X1,Z38), (Ra5, Rb1,X1,Z39), (Ra5,Rb1,X2,Z1), (Ra5,Rb1,X2,Z2), (Ra5, Rb1,X2,Z3), (Ra5,Rb1,X2,Z4), (Ra5,Rb1,X2,Z5), (Ra5, Rb1,X2,Z6), (Ra5,Rb1,X2,Z7), (Ra5,Rb1,X2,Z8), (Ra5, Rb1,X2,Z9), (Ra5,Rb1,X2,Z10), (Ra5,Rb1,X2,Z11), (Ra5, Rb1,X2,Z12), (Ra5,Rb1,X2,Z13), (Ra5,Rb1,X2,Z14), (Ra5, Rb1,X2,Z15), (Ra5,Rb1,X2,Z16), (Ra5,Rb1,X2,Z17), (Ra5, Rb1,X2,Z18), (Ra5,Rb1,X2,Z19), (Ra5,Rb1,X2,Z20), (Ra5, Rb1,X2,Z21), (Ra5,Rb1,X2,Z22), (Ra5,Rb1,X2,Z23), (Ra5, Rb1,X2,Z24), (Ra5,Rb1,X2,Z25), (Ra5,Rb1,X2,Z26), (Ra5, Rb1,X2,Z27), (Ra5,Rb1,X2,Z28), (Ra5,Rb1,X2,Z29), (Ra5, Rb1,X2,Z30), (Ra5,Rb1,X2,Z31), (Ra5,Rb1,X2,Z32), (Ra5, Rb1,X2,Z33), (Ra5,Rb1,X2,Z34), (Ra5,Rb1,X2,Z35), (Ra5, Rb1,X2,Z36), (Ra5,Rb1,X2,Z37), (Ra5,Rb1,X2,Z38), (Ra5, Rb1,X2,Z39), (Ra5,Rb2,X1,Z1), (Ra5,Rb2,X1,Z2), (Ra5, Rb2,X1,Z3), (Ra5,Rb2,X1,Z4), (Ra5,Rb2,X1,Z5), (Ra5, Rb2,X1,Z6), (Ra5,Rb2,X1,Z7), (Ra5,Rb2,X1,Z8), (Ra5, Rb2,X1,Z9), (Ra5,Rb2,X1,Z10), (Ra5,Rb2,X1,Z11), (Ra5, Rb2,X1,Z12), (Ra5,Rb2,X1,Z13), (Ra5,Rb2,X1,Z14), (Ra5, Rb2,X1,Z15), (Ra5,Rb2,X1,Z16), (Ra5,Rb2,X1,Z17), (Ra5, Rb2,X1,Z18), (Ra5,Rb2,X1,Z19), (Ra5,Rb2,X1,Z20), (Ra5, Rb2,X1,Z21), (Ra5,Rb2,X1,Z22), (Ra5,Rb2,X1,Z23), (Ra5, Rb2,X1,Z24), (Ra5,Rb2,X1,Z25), (Ra5,Rb2,X1,Z26), (Ra5, Rb2,X1,Z27), (Ra5,Rb2,X1,Z28), (Ra5,Rb2,X1,Z29), (Ra5, Rb2,X1,Z30), (Ra5,Rb2,X1,Z31), (Ra5,Rb2,X1,Z32), (Ra5, Rb2,X1,Z33), (Ra5,Rb2,X1,Z34), (Ra5,Rb2,X1,Z35), (Ra5, Rb2,X1,Z36), (Ra5,Rb2,X1,Z37), (Ra5,Rb2,X1,Z38), (Ra5, Rb2,X1,Z39), (Ra5,Rb2,X2,Z1), (Ra5,Rb2,X2,Z2), (Ra5, Rb2,X2,Z3), (Ra5,Rb2,X2,Z4), (Ra5,Rb2,X2,Z5), (Ra5, Rb2,X2,Z6), (Ra5,Rb2,X2,Z7), (Ra5,Rb2,X2,Z8), (Ra5, Rb2,X2,Z9), (Ra5,Rb2,X2,Z10), (Ra5,Rb2,X2,Z11), (Ra5, Rb2,X2,Z12), (Ra5,Rb2,X2,Z13), (Ra5,Rb2,X2,Z14), (Ra5, Rb2,X2,Z15), (Ra5,Rb2,X2,Z16), (Ra5,Rb2,X2,Z17), (Ra5, Rb2,X2,Z18), (Ra5,Rb2,X2,Z19), (Ra5,Rb2,X2,Z20), (Ra5, Rb2,X2,Z21), (Ra5,Rb2,X2,Z22), (Ra5,Rb2,X2,Z23), (Ra5, Rb2,X2,Z24), (Ra5,Rb2,X2,Z25), (Ra5,Rb2,X2,Z26), (Ra5, Rb2,X2,Z27), (Ra5,Rb2,X2,Z28), (Ra5,Rb2,X2,Z29), (Ra5, Rb2,X2,Z30), (Ra5,Rb2,X2,Z31), (Ra5,Rb2,X2,Z32), (Ra5, Rb2,X2,Z33), (Ra5,Rb2,X2,Z34), (Ra5,Rb2,X2,Z35), (Ra5, Rb2,X2,Z36), (Ra5,Rb2,X2,Z37), (Ra5,Rb2,X2,Z38), (Ra5, Rb2,X2,Z39), (Ra5,Rb3,X1,Z1), (Ra5,Rb3,X1,Z2), (Ra5, Rb3,X1,Z3), (Ra5,Rb3,X1,Z4), (Ra5,Rb3,X1,Z5), (Ra5, Rb3,X1,Z6), (Ra5,Rb3,X1,Z7), (Ra5,Rb3,X1,Z8), (Ra5, Rb3,X1,Z9), (Ra5,Rb3,X1,Z10), (Ra5,Rb3,X1,Z11), (Ra5, Rb3,X1,Z12), (Ra5,Rb3,X1,Z13), (Ra5,Rb3,X1,Z14), (Ra5, Rb3,X1,Z15), (Ra5,Rb3,X1,Z16), (Ra5,Rb3,X1,Z17), (Ra5, Rb3,X1,Z18), (Ra5,Rb3,X1,Z19), (Ra5,Rb3,X1,Z20), (Ra5, Rb3,X1,Z21), (Ra5,Rb3,X1,Z22), (Ra5,Rb3,X1,Z23), (Ra5, Rb3,X1,Z24), (Ra5,Rb3,X1,Z25), (Ra5,Rb3,X1,Z26), (Ra5, Rb3,X1,Z27), (Ra5,Rb3,X1,Z28), (Ra5,Rb3,X1,Z29), (Ra5, Rb3,X1,Z30), (Ra5,Rb3,X1,Z31), (Ra5,Rb3,X1,Z32), (Ra5, Rb3,X1,Z33), (Ra5,Rb3,X1,Z34), (Ra5,Rb3,X1,Z35), (Ra5, Rb3,X1,Z36), (Ra5,Rb3,X1,Z37), (Ra5,Rb3,X1,Z38), (Ra5, Rb3,X1,Z39), (Ra5,Rb3,X2,Z1), (Ra5,Rb3,X2,Z2), (Ra5, Rb3,X2,Z3), (Ra5,Rb3,X2,Z4), (Ra5,Rb3,X2,Z5), (Ra5, Rb3,X2,Z6), (Ra5,Rb3,X2,Z7), (Ra5,Rb3,X2,Z8), (Ra5, Rb3,X2,Z9), (Ra5,Rb3,X2,Z10), (Ra5,Rb3,X2,Z11), (Ra5, Rb3,X2,Z12), (Ra5,Rb3,X2,Z13), (Ra5,Rb3,X2,Z14), (Ra5, Rb3,X2,Z15), (Ra5,Rb3,X2,Z16), (Ra5,Rb3,X2,Z17), (Ra5, Rb3,X2,Z18), (Ra5,Rb3,X2,Z19), (Ra5,Rb3,X2,Z20), (Ra5, Rb3,X2,Z21), (Ra5,Rb3,X2,Z22), (Ra5,Rb3,X2,Z23), (Ra5, Rb3,X2,Z24), (Ra5,Rb3,X2,Z25), (Ra5,Rb3,X2,Z26), (Ra5, Rb3,X2,Z27), (Ra5,Rb3,X2,Z28), (Ra5,Rb3,X2,Z29), (Ra5, Rb3,X2,Z30), (Ra5,Rb3,X2,Z31), (Ra5,Rb3,X2,Z32), (Ra5, Rb3,X2,Z33), (Ra5,Rb3,X2,Z34), (Ra5,Rb3,X2,Z35), (Ra5, Rb3,X2,Z36), (Ra5,Rb3,X2,Z37), (Ra5,Rb3,X2,Z38), (Ra5, Rb3,X2,Z39), (Ra5,Rb4,X1,Z1), (Ra5,Rb4,X1,Z2), (Ra5, Rb4,X1,Z3), (Ra5,Rb4,X1,Z4), (Ra5,Rb4,X1,Z5), (Ra5, Rb4,X1,Z6), (Ra5,Rb4,X1,Z7), (Ra5,Rb4,X1,Z8), (Ra5, Rb4,X1,Z9), (Ra5,Rb4,X1,Z10), (Ra5,Rb4,X1,Z11), (Ra5, Rb4,X1,Z12), (Ra5,Rb4,X1,Z13), (Ra5,Rb4,X1,Z14), (Ra5, Rb4,X1,Z15), (Ra5,Rb4,X1,Z16), (Ra5,Rb4,X1,Z17), (Ra5, Rb4,X1,Z18), (Ra5,Rb4,X1,Z19), (Ra5,Rb4,X1,Z20), (Ra5, Rb4,X1,Z21), (Ra5,Rb4,X1,Z22), (Ra5,Rb4,X1,Z23), (Ra5, Rb4,X1,Z24), (Ra5,Rb4,X1,Z25), (Ra5,Rb4,X1,Z26), (Ra5, Rb4,X1,Z27), (Ra5,Rb4,X1,Z28), (Ra5,Rb4,X1,Z29), (Ra5, Rb4,X1,Z30), (Ra5,Rb4,X1,Z31), (Ra5,Rb4,X1,Z32), (Ra5, Rb4,X1,Z33), (Ra5,Rb4,X1,Z34), (Ra5,Rb4,X1,Z35), (Ra5, Rb4,X1,Z36), (Ra5,Rb4,X1,Z37), (Ra5,Rb4,X1,Z38), (Ra5, Rb4,X1,Z39), (Ra5,Rb4,X2,Z1), (Ra5,Rb4,X2,Z2), (Ra5, Rb4,X2,Z3), (Ra5,Rb4,X2,Z4), (Ra5,Rb4,X2,Z5), (Ra5, Rb4,X2,Z6), (Ra5,Rb4,X2,Z7), (Ra5,Rb4,X2,Z8), (Ra5, Rb4,X2,Z9), (Ra5,Rb4,X2,Z10), (Ra5,Rb4,X2,Z11), (Ra5, Rb4,X2,Z12), (Ra5,Rb4,X2,Z13), (Ra5,Rb4,X2,Z14), (Ra5, Rb4,X2,Z15), (Ra5,Rb4,X2,Z16), (Ra5,Rb4,X2,Z17), (Ra5, Rb4,X2,Z18), (Ra5,Rb4,X2,Z19), (Ra5,Rb4,X2,Z20), (Ra5, Rb4,X2,Z21), (Ra5,Rb4,X2,Z22), (Ra5,Rb4,X2,Z23), (Ra5, Rb4,X2,Z24), (Ra5,Rb4,X2,Z25), (Ra5,Rb4,X2,Z26), (Ra5, Rb4,X2,Z27), (Ra5,Rb4,X2,Z28), (Ra5,Rb4,X2,Z29), (Ra5, Rb4,X2,Z30), (Ra5,Rb4,X2,Z31), (Ra5,Rb4,X2,Z32), (Ra5, Rb4,X2,Z33), (Ra5,Rb4,X2,Z34), (Ra5,Rb4,X2,Z35), (Ra5, Rb4,X2,Z36), (Ra5,Rb4,X2,Z37), (Ra5,Rb4,X2,Z38), (Ra5, Rb4,X2,Z39), (Ra5,Rb5,X1,Z1), (Ra5,Rb5,X1,Z2), (Ra5, Rb5,X1,Z3), (Ra5,Rb5,X1,Z4), (Ra5,Rb5,X1,Z5), (Ra5,

Rb5,X1,Z6), (Ra5,Rb5,X1,Z7), (Ra5,Rb5,X1,Z8), (Ra5,Rb5,X1,Z9), (Ra5,Rb5,X1,Z10), (Ra5,Rb5,X1,Z11), (Ra5,Rb5,X1,Z12), (Ra5,Rb5,X1,Z13), (Ra5,Rb5,X1,Z14), (Ra5,Rb5,X1,Z15), (Ra5,Rb5,X1,Z16), (Ra5,Rb5,X1,Z17), (Ra5,Rb5,X1,Z18), (Ra5,Rb5,X1,Z19), (Ra5,Rb5,X1,Z20), (Ra5,Rb5,X1,Z21), (Ra5,Rb5,X1,Z22), (Ra5,Rb5,X1,Z23), (Ra5,Rb5,X1,Z24), (Ra5,Rb5,X1,Z25), (Ra5,Rb5,X1,Z26), (Ra5,Rb5,X1,Z27), (Ra5,Rb5,X1,Z28), (Ra5,Rb5,X1,Z29), (Ra5,Rb5,X1,Z30), (Ra5,Rb5,X1,Z31), (Ra5,Rb5,X1,Z32), (Ra5,Rb5,X1,Z33), (Ra5,Rb5,X1,Z34), (Ra5,Rb5,X1,Z35), (Ra5,Rb5,X1,Z36), (Ra5,Rb5,X1,Z37), (Ra5,Rb5,X1,Z38), (Ra5,Rb5,X1,Z39), (Ra5,Rb5,X2,Z1), (Ra5,Rb5,X2,Z2), (Ra5,Rb5,X2,Z3), (Ra5,Rb5,X2,Z4), (Ra5,Rb5,X2,Z5), (Ra5,Rb5,X2,Z6), (Ra5,Rb5,X2,Z7), (Ra5,Rb5,X2,Z8), (Ra5,Rb5,X2,Z9), (Ra5,Rb5,X2,Z10), (Ra5,Rb5,X2,Z11), (Ra5,Rb5,X2,Z12), (Ra5,Rb5,X2,Z13), (Ra5,Rb5,X2,Z14), (Ra5,Rb5,X2,Z15), (Ra5,Rb5,X2,Z16), (Ra5,Rb5,X2,Z17), (Ra5,Rb5,X2,Z18), (Ra5,Rb5,X2,Z19), (Ra5,Rb5,X2,Z20), (Ra5,Rb5,X2,Z21), (Ra5,Rb5,X2,Z22), (Ra5,Rb5,X2,Z23), (Ra5,Rb5,X2,Z24), (Ra5,Rb5,X2,Z25), (Ra5,Rb5,X2,Z26), (Ra5,Rb5,X2,Z27), (Ra5,Rb5,X2,Z28), (Ra5,Rb5,X2,Z29), (Ra5,Rb5,X2,Z30), (Ra5,Rb5,X2,Z31), (Ra5,Rb5,X2,Z32), (Ra5,Rb5,X2,Z33), (Ra5,Rb5,X2,Z34), (Ra5,Rb5,X2,Z35), (Ra5,Rb5,X2,Z36), (Ra5,Rb5,X2,Z37), (Ra5,Rb5,X2,Z38), (Ra5,Rb5,X2,Z39), (Ra5,Rb6,X1,Z1), (Ra5,Rb6,X1,Z2), (Ra5,Rb6,X1,Z3), (Ra5,Rb6,X1,Z4), (Ra5,Rb6,X1,Z5), (Ra5,Rb6,X1,Z6), (Ra5,Rb6,X1,Z7), (Ra5,Rb6,X1,Z8), (Ra5,Rb6,X1,Z9), (Ra5,Rb6,X1,Z10), (Ra5,Rb6,X1,Z11), (Ra5,Rb6,X1,Z12), (Ra5,Rb6,X1,Z13), (Ra5,Rb6,X1,Z14), (Ra5,Rb6,X1,Z15), (Ra5,Rb6,X1,Z16), (Ra5,Rb6,X1,Z17), (Ra5,Rb6,X1,Z18), (Ra5,Rb6,X1,Z19), (Ra5,Rb6,X1,Z20), (Ra5,Rb6,X1,Z21), (Ra5,Rb6,X1,Z22), (Ra5,Rb6,X1,Z23), (Ra5,Rb6,X1,Z24), (Ra5,Rb6,X1,Z25), (Ra5,Rb6,X1,Z26), (Ra5,Rb6,X1,Z27), (Ra5,Rb6,X1,Z28), (Ra5,Rb6,X1,Z29), (Ra5,Rb6,X1,Z30), (Ra5,Rb6,X1,Z31), (Ra5,Rb6,X1,Z32), (Ra5,Rb6,X1,Z33), (Ra5,Rb6,X1,Z34), (Ra5,Rb6,X1,Z35), (Ra5,Rb6,X1,Z36), (Ra5,Rb6,X1,Z37), (Ra5,Rb6,X1,Z38), (Ra5,Rb6,X1,Z39), (Ra5,Rb6,X2,Z1), (Ra5,Rb6,X2,Z2), (Ra5,Rb6,X2,Z3), (Ra5,Rb6,X2,Z4), (Ra5,Rb6,X2,Z5), (Ra5,Rb6,X2,Z6), (Ra5,Rb6,X2,Z7), (Ra5,Rb6,X2,Z8), (Ra5,Rb6,X2,Z9), (Ra5,Rb6,X2,Z10), (Ra5,Rb6,X2,Z11), (Ra5,Rb6,X2,Z12), (Ra5,Rb6,X2,Z13), (Ra5,Rb6,X2,Z14), (Ra5,Rb6,X2,Z15), (Ra5,Rb6,X2,Z16), (Ra5,Rb6,X2,Z17), (Ra5,Rb6,X2,Z18), (Ra5,Rb6,X2,Z19), (Ra5,Rb6,X2,Z20), (Ra5,Rb6,X2,Z21), (Ra5,Rb6,X2,Z22), (Ra5,Rb6,X2,Z23), (Ra5,Rb6,X2,Z24), (Ra5,Rb6,X2,Z25), (Ra5,Rb6,X2,Z26), (Ra5,Rb6,X2,Z27), (Ra5,Rb6,X2,Z28), (Ra5,Rb6,X2,Z29), (Ra5,Rb6,X2,Z30), (Ra5,Rb6,X2,Z31), (Ra5,Rb6,X2,Z32), (Ra5,Rb6,X2,Z33), (Ra5,Rb6,X2,Z34), (Ra5,Rb6,X2,Z35), (Ra5,Rb6,X2,Z36), (Ra5,Rb6,X2,Z37), (Ra5,Rb6,X2,Z38), (Ra5,Rb6,X2,Z39), (Ra5,Rb7,X1,Z1), (Ra5,Rb7,X1,Z2), (Ra5,Rb7,X1,Z3), (Ra5,Rb7,X1,Z4), (Ra5,Rb7,X1,Z5), (Ra5,Rb7,X1,Z6), (Ra5,Rb7,X1,Z7), (Ra5,Rb7,X1,Z8), (Ra5,Rb7,X1,Z9), (Ra5,Rb7,X1,Z10), (Ra5,Rb7,X1,Z11), (Ra5,Rb7,X1,Z12), (Ra5,Rb7,X1,Z13), (Ra5,Rb7,X1,Z14), (Ra5,Rb7,X1,Z15), (Ra5,Rb7,X1,Z16), (Ra5,Rb7,X1,Z17), (Ra5,Rb7,X1,Z18), (Ra5,Rb7,X1,Z19), (Ra5,Rb7,X1,Z20), (Ra5,Rb7,X1,Z21), (Ra5,Rb7,X1,Z22), (Ra5,Rb7,X1,Z23), (Ra5,Rb7,X1,Z24), (Ra5,Rb7,X1,Z25), (Ra5,Rb7,X1,Z26), (Ra5,Rb7,X1,Z27), (Ra5,Rb7,X1,Z28), (Ra5,Rb7,X1,Z29), (Ra5,Rb7,X1,Z30), (Ra5,Rb7,X1,Z31), (Ra5,Rb7,X1,Z32), (Ra5,Rb7,X1,Z33), (Ra5,Rb7,X1,Z34), (Ra5,Rb7,X1,Z35), (Ra5,Rb7,X1,Z36), (Ra5,Rb7,X1,Z37), (Ra5,Rb7,X1,Z38), (Ra5,Rb7,X1,Z39), (Ra5,Rb7,X2,Z1), (Ra5,Rb7,X2,Z2), (Ra5,Rb7,X2,Z3), (Ra5,Rb7,X2,Z4), (Ra5,Rb7,X2,Z5), (Ra5,Rb7,X2,Z6), (Ra5,Rb7,X2,Z7), (Ra5,Rb7,X2,Z8), (Ra5,Rb7,X2,Z9), (Ra5,Rb7,X2,Z10), (Ra5,Rb7,X2,Z11), (Ra5,Rb7,X2,Z12), (Ra5,Rb7,X2,Z13), (Ra5,Rb7,X2,Z14), (Ra5,Rb7,X2,Z15), (Ra5,Rb7,X2,Z16), (Ra5,Rb7,X2,Z17), (Ra5,Rb7,X2,Z18), (Ra5,Rb7,X2,Z19), (Ra5,Rb7,X2,Z20), (Ra5,Rb7,X2,Z21), (Ra5,Rb7,X2,Z22), (Ra5,Rb7,X2,Z23), (Ra5,Rb7,X2,Z24), (Ra5,Rb7,X2,Z25), (Ra5,Rb7,X2,Z26), (Ra5,Rb7,X2,Z27), (Ra5,Rb7,X2,Z28), (Ra5,Rb7,X2,Z29), (Ra5,Rb7,X2,Z30), (Ra5,Rb7,X2,Z31), (Ra5,Rb7,X2,Z32), (Ra5,Rb7,X2,Z33), (Ra5,Rb7,X2,Z34), (Ra5,Rb7,X2,Z35), (Ra5,Rb7,X2,Z36), (Ra5,Rb7,X2,Z37), (Ra5,Rb7,X2,Z38), (Ra5,Rb7,X2,Z39), (Ra5,Rb8,X1,Z1), (Ra5,Rb8,X1,Z2), (Ra5,Rb8,X1,Z3), (Ra5,Rb8,X1,Z4), (Ra5,Rb8,X1,Z5), (Ra5,Rb8,X1,Z6), (Ra5,Rb8,X1,Z7), (Ra5,Rb8,X1,Z8), (Ra5,Rb8,X1,Z9), (Ra5,Rb8,X1,Z10), (Ra5,Rb8,X1,Z11), (Ra5,Rb8,X1,Z12), (Ra5,Rb8,X1,Z13), (Ra5,Rb8,X1,Z14), (Ra5,Rb8,X1,Z15), (Ra5,Rb8,X1,Z16), (Ra5,Rb8,X1,Z17), (Ra5,Rb8,X1,Z18), (Ra5,Rb8,X1,Z19), (Ra5,Rb8,X1,Z20), (Ra5,Rb8,X1,Z21), (Ra5,Rb8,X1,Z22), (Ra5,Rb8,X1,Z23), (Ra5,Rb8,X1,Z24), (Ra5,Rb8,X1,Z25), (Ra5,Rb8,X1,Z26), (Ra5,Rb8,X1,Z27), (Ra5,Rb8,X1,Z28), (Ra5,Rb8,X1,Z29), (Ra5,Rb8,X1,Z30), (Ra5,Rb8,X1,Z31), (Ra5,Rb8,X1,Z32), (Ra5,Rb8,X1,Z33), (Ra5,Rb8,X1,Z34), (Ra5,Rb8,X1,Z35), (Ra5,Rb8,X1,Z36), (Ra5,Rb8,X1,Z37), (Ra5,Rb8,X1,Z38), (Ra5,Rb8,X1,Z39), (Ra5,Rb8,X2,Z1), (Ra5,Rb8,X2,Z2), (Ra5,Rb8,X2,Z3), (Ra5,Rb8,X2,Z4), (Ra5,Rb8,X2,Z5), (Ra5,Rb8,X2,Z6), (Ra5,Rb8,X2,Z7), (Ra5,Rb8,X2,Z8), (Ra5,Rb8,X2,Z9), (Ra5,Rb8,X2,Z10), (Ra5,Rb8,X2,Z11), (Ra5,Rb8,X2,Z12), (Ra5,Rb8,X2,Z13), (Ra5,Rb8,X2,Z14), (Ra5,Rb8,X2,Z15), (Ra5,Rb8,X2,Z16), (Ra5,Rb8,X2,Z17), (Ra5,Rb8,X2,Z18), (Ra5,Rb8,X2,Z19), (Ra5,Rb8,X2,Z20), (Ra5,Rb8,X2,Z21), (Ra5,Rb8,X2,Z22), (Ra5,Rb8,X2,Z23), (Ra5,Rb8,X2,Z24), (Ra5,Rb8,X2,Z25), (Ra5,Rb8,X2,Z26), (Ra5,Rb8,X2,Z27), (Ra5,Rb8,X2,Z28), (Ra5,Rb8,X2,Z29), (Ra5,Rb8,X2,Z30), (Ra5,Rb8,X2,Z31), (Ra5,Rb8,X2,Z32), (Ra5,Rb8,X2,Z33), (Ra5,Rb8,X2,Z34), (Ra5,Rb8,X2,Z35), (Ra5,Rb8,X2,Z36), (Ra5,Rb8,X2,Z37), (Ra5,Rb8,X2,Z38), (Ra5,Rb8,X2,Z39), (Ra6,Rb1,X1,Z1), (Ra6,Rb1,X1,Z2), (Ra6,Rb1,X1,Z3), (Ra6,Rb1,X1,Z4), (Ra6,Rb1,X1,Z5), (Ra6,Rb1,X1,Z6), (Ra6,Rb1,X1,Z7), (Ra6,Rb1,X1,Z8), (Ra6,Rb1,X1,Z9), (Ra6,Rb1,X1,Z10), (Ra6,Rb1,X1,Z11), (Ra6,Rb1,X1,Z12), (Ra6,Rb1,X1,Z13), (Ra6,Rb1,X1,Z14), (Ra6,Rb1,X1,Z15), (Ra6,Rb1,X1,Z16), (Ra6,Rb1,X1,Z17), (Ra6,Rb1,X1,Z18), (Ra6,Rb1,X1,Z19), (Ra6,Rb1,X1,Z20), (Ra6,Rb1,X1,Z21), (Ra6,Rb1,X1,Z22), (Ra6,Rb1,X1,Z23), (Ra6,Rb1,X1,Z24), (Ra6,Rb1,X1,Z25), (Ra6,Rb1,X1,Z26), (Ra6,Rb1,X1,Z27), (Ra6,Rb1,X1,Z28), (Ra6,Rb1,X1,Z29), (Ra6,Rb1,X1,Z30), (Ra6,Rb1,X1,Z31), (Ra6,Rb1,X1,Z32), (Ra6,Rb1,X1,Z33), (Ra6,Rb1,X1,Z34), (Ra6,Rb1,X1,Z35), (Ra6,Rb1,X1,Z36), (Ra6,Rb1,X1,Z37), (Ra6,Rb1,X1,Z38), (Ra6,Rb1,X1,Z39), (Ra6,Rb1,X2,Z1), (Ra6,Rb1,X2,Z2), (Ra6,Rb1,X2,Z3), (Ra6,Rb1,X2,Z4), (Ra6,Rb1,X2,Z5), (Ra6,Rb1,X2,Z6), (Ra6,Rb1,X2,Z7), (Ra6,Rb1,X2,Z8), (Ra6,Rb1,X2,Z9), (Ra6,Rb1,X2,Z10), (Ra6,Rb1,X2,Z11), (Ra6,Rb1,X2,Z12), (Ra6,Rb1,X2,Z13), (Ra6,Rb1,X2,Z14), (Ra6,Rb1,X2,Z15), (Ra6,Rb1,X2,Z16), (Ra6,Rb1,X2,Z17), (Ra6,Rb1,X2,Z18), (Ra6,Rb1,X2,Z19), (Ra6,Rb1,X2,Z20), (Ra6,Rb1,X2,Z21), (Ra6,Rb1,X2,Z22), (Ra6,Rb1,X2,Z23), (Ra6,Rb1,X2,Z24), (Ra6,Rb1,X2,Z25), (Ra6,Rb1,X2,Z26), (Ra6,Rb1,X2,Z27), (Ra6,Rb1,X2,Z28), (Ra6,Rb1,X2,Z29), (Ra6,Rb1,X2,Z30), (Ra6,Rb1,X2,Z31), (Ra6,Rb1,X2,Z32), (Ra6,Rb1,X2,Z33), (Ra6,Rb1,X2,Z34), (Ra6,Rb1,X2,Z35), (Ra6,Rb1,X2,Z36), (Ra6,Rb1,X2,Z37), (Ra6,Rb1,X2,Z38), (Ra6,Rb1,X2,Z39), (Ra6,Rb2,X1,Z1), (Ra6,Rb2,X1,Z2), (Ra6,Rb2,X1,Z3), (Ra6,Rb2,X1,Z4), (Ra6,Rb2,X1,Z5), (Ra6,Rb2,X1,Z6), (Ra6,Rb2,X1,Z7), (Ra6,Rb2,X1,Z8), (Ra6,Rb2,X1,Z9), (Ra6,Rb2,X1,Z10), (Ra6,Rb2,X1,Z11), (Ra6,Rb2,X1,Z12), (Ra6,Rb2,X1,Z13), (Ra6,Rb2,X1,Z14), (Ra6,Rb2,X1,Z15), (Ra6,Rb2,X1,Z16), (Ra6,Rb2,X1,Z17), (Ra6,

Rb2,X1,Z18), (Ra6,Rb2,X1,Z19), (Ra6,Rb2,X1,Z20), (Ra6, Rb2,X1,Z21), (Ra6,Rb2,X1,Z22), (Ra6,Rb2,X1,Z23), (Ra6, Rb2,X1,Z24), (Ra6,Rb2,X1,Z25), (Ra6,Rb2,X1,Z26), (Ra6, Rb2,X1,Z27), (Ra6,Rb2,X1,Z28), (Ra6,Rb2,X1,Z29), (Ra6, Rb2,X1,Z30), (Ra6,Rb2,X1,Z31), (Ra6,Rb2,X1,Z32), (Ra6, Rb2,X1,Z33), (Ra6,Rb2,X1,Z34), (Ra6,Rb2,X1,Z35), (Ra6, Rb2,X1,Z36), (Ra6,Rb2,X1,Z37), (Ra6,Rb2,X1,Z38), (Ra6, Rb2,X1,Z39), (Ra6,Rb2,X2,Z1), (Ra6,Rb2,X2,Z2), (Ra6, Rb2,X2,Z3), (Ra6,Rb2,X2,Z4), (Ra6,Rb2,X2,Z5), (Ra6, Rb2,X2,Z6), (Ra6,Rb2,X2,Z7), (Ra6,Rb2,X2,Z8), (Ra6, Rb2,X2,Z9), (Ra6,Rb2,X2,Z10), (Ra6,Rb2,X2,Z11), (Ra6, Rb2,X2,Z12), (Ra6,Rb2,X2,Z13), (Ra6,Rb2,X2,Z14), (Ra6, Rb2,X2,Z15), (Ra6,Rb2,X2,Z16), (Ra6,Rb2,X2,Z17), (Ra6, Rb2,X2,Z18), (Ra6,Rb2,X2,Z19), (Ra6,Rb2,X2,Z20), (Ra6, Rb2,X2,Z21), (Ra6,Rb2,X2,Z22), (Ra6,Rb2,X2,Z23), (Ra6, Rb2,X2,Z24), (Ra6,Rb2,X2,Z25), (Ra6,Rb2,X2,Z26), (Ra6, Rb2,X2,Z27), (Ra6,Rb2,X2,Z28), (Ra6,Rb2,X2,Z29), (Ra6, Rb2,X2,Z30), (Ra6,Rb2,X2,Z31), (Ra6,Rb2,X2,Z32), (Ra6, Rb2,X2,Z33), (Ra6,Rb2,X2,Z34), (Ra6,Rb2,X2,Z35), (Ra6, Rb2,X2,Z36), (Ra6,Rb2,X2,Z37), (Ra6,Rb2,X2,Z38), (Ra6, Rb2,X2,Z39), (Ra6,Rb3,X1,Z1), (Ra6,Rb3,X1,Z2), (Ra6, Rb3,X1,Z3), (Ra6,Rb3,X1,Z4), (Ra6,Rb3,X1,Z5), (Ra6, Rb3,X1,Z6), (Ra6,Rb3,X1,Z7), (Ra6,Rb3,X1,Z8), (Ra6, Rb3,X1,Z9), (Ra6,Rb3,X1,Z10), (Ra6,Rb3,X1,Z11), (Ra6, Rb3,X1,Z12), (Ra6,Rb3,X1,Z13), (Ra6,Rb3,X1,Z14), (Ra6, Rb3,X1,Z15), (Ra6,Rb3,X1,Z16), (Ra6,Rb3,X1,Z17), (Ra6, Rb3,X1,Z18), (Ra6,Rb3,X1,Z19), (Ra6,Rb3,X1,Z20), (Ra6, Rb3,X1,Z21), (Ra6,Rb3,X1,Z22), (Ra6,Rb3,X1,Z23), (Ra6, Rb3,X1,Z24), (Ra6,Rb3,X1,Z25), (Ra6,Rb3,X1,Z26), (Ra6, Rb3,X1,Z27), (Ra6,Rb3,X1,Z28), (Ra6,Rb3,X1,Z29), (Ra6, Rb3,X1,Z30), (Ra6,Rb3,X1,Z31), (Ra6,Rb3,X1,Z32), (Ra6, Rb3,X1,Z33), (Ra6,Rb3,X1,Z34), (Ra6,Rb3,X1,Z35), (Ra6, Rb3,X1,Z36), (Ra6,Rb3,X1,Z37), (Ra6,Rb3,X1,Z38), (Ra6, Rb3,X1,Z39), (Ra6,Rb3,X2,Z1), (Ra6,Rb3,X2,Z2), (Ra6, Rb3,X2,Z3), (Ra6,Rb3,X2,Z4), (Ra6,Rb3,X2,Z5), (Ra6, Rb3,X2,Z6), (Ra6,Rb3,X2,Z7), (Ra6,Rb3,X2,Z8), (Ra6, Rb3,X2,Z9), (Ra6,Rb3,X2,Z10), (Ra6,Rb3,X2,Z11), (Ra6, Rb3,X2,Z12), (Ra6,Rb3,X2,Z13), (Ra6,Rb3,X2,Z14), (Ra6, Rb3,X2,Z15), (Ra6,Rb3,X2,Z16), (Ra6,Rb3,X2,Z17), (Ra6, Rb3,X2,Z18), (Ra6,Rb3,X2,Z19), (Ra6,Rb3,X2,Z20), (Ra6, Rb3,X2,Z21), (Ra6,Rb3,X2,Z22), (Ra6,Rb3,X2,Z23), (Ra6, Rb3,X2,Z24), (Ra6,Rb3,X2,Z25), (Ra6,Rb3,X2,Z26), (Ra6, Rb3,X2,Z27), (Ra6,Rb3,X2,Z28), (Ra6,Rb3,X2,Z29), (Ra6, Rb3,X2,Z30), (Ra6,Rb3,X2,Z31), (Ra6,Rb3,X2,Z32), (Ra6, Rb3,X2,Z33), (Ra6,Rb3,X2,Z34), (Ra6,Rb3,X2,Z35), (Ra6, Rb3,X2,Z36), (Ra6,Rb3,X2,Z37), (Ra6,Rb3,X2,Z38), (Ra6, Rb3,X2,Z39), (Ra6,Rb4,X1,Z1), (Ra6,Rb4,X1,Z2), (Ra6, Rb4,X1,Z3), (Ra6,Rb4,X1,Z4), (Ra6,Rb4,X1,Z5), (Ra6, Rb4,X1,Z6), (Ra6,Rb4,X1,Z7), (Ra6,Rb4,X1,Z8), (Ra6, Rb4,X1,Z9), (Ra6,Rb4,X1,Z10), (Ra6,Rb4,X1,Z11), (Ra6, Rb4,X1,Z12), (Ra6,Rb4,X1,Z13), (Ra6,Rb4,X1,Z14), (Ra6, Rb4,X1,Z15), (Ra6,Rb4,X1,Z16), (Ra6,Rb4,X1,Z17), (Ra6, Rb4,X1,Z18), (Ra6,Rb4,X1,Z19), (Ra6,Rb4,X1,Z20), (Ra6, Rb4,X1,Z21), (Ra6,Rb4,X1,Z22), (Ra6,Rb4,X1,Z23), (Ra6, Rb4,X1,Z24), (Ra6,Rb4,X1,Z25), (Ra6,Rb4,X1,Z26), (Ra6, Rb4,X1,Z27), (Ra6,Rb4,X1,Z28), (Ra6,Rb4,X1,Z29), (Ra6, Rb4,X1,Z30), (Ra6,Rb4,X1,Z31), (Ra6,Rb4,X1,Z32), (Ra6, Rb4,X1,Z33), (Ra6,Rb4,X1,Z34), (Ra6,Rb4,X1,Z35), (Ra6, Rb4,X1,Z36), (Ra6,Rb4,X1,Z37), (Ra6,Rb4,X1,Z38), (Ra6, Rb4,X1,Z39), (Ra6,Rb4,X2,Z1), (Ra6,Rb4,X2,Z2), (Ra6, Rb4,X2,Z3), (Ra6,Rb4,X2,Z4), (Ra6,Rb4,X2,Z5), (Ra6, Rb4,X2,Z6), (Ra6,Rb4,X2,Z7), (Ra6,Rb4,X2,Z8), (Ra6, Rb4,X2,Z9), (Ra6,Rb4,X2,Z10), (Ra6,Rb4,X2,Z11), (Ra6, Rb4,X2,Z12), (Ra6,Rb4,X2,Z13), (Ra6,Rb4,X2,Z14), (Ra6, Rb4,X2,Z15), (Ra6,Rb4,X2,Z16), (Ra6,Rb4,X2,Z17), (Ra6, Rb4,X2,Z18), (Ra6,Rb4,X2,Z19), (Ra6,Rb4,X2,Z20), (Ra6, Rb4,X2,Z21), (Ra6,Rb4,X2,Z22), (Ra6,Rb4,X2,Z23), (Ra6, Rb4,X2,Z24), (Ra6,Rb4,X2,Z25), (Ra6,Rb4,X2,Z26), (Ra6, Rb4,X2,Z27), (Ra6,Rb4,X2,Z28), (Ra6,Rb4,X2,Z29), (Ra6, Rb4,X2,Z30), (Ra6,Rb4,X2,Z31), (Ra6,Rb4,X2,Z32), (Ra6, Rb4,X2,Z33), (Ra6,Rb4,X2,Z34), (Ra6,Rb4,X2,Z35), (Ra6, Rb4,X2,Z36), (Ra6,Rb4,X2,Z37), (Ra6,Rb4,X2,Z38), (Ra6, Rb4,X2,Z39), (Ra6,Rb5,X1,Z1), (Ra6,Rb5,X1,Z2), (Ra6, Rb5,X1,Z3), (Ra6,Rb5,X1,Z4), (Ra6,Rb5,X1,Z5), (Ra6, Rb5,X1,Z6), (Ra6,Rb5,X1,Z7), (Ra6,Rb5,X1,Z8), (Ra6, Rb5,X1,Z9), (Ra6,Rb5,X1,Z10), (Ra6,Rb5,X1,Z11), (Ra6, Rb5,X1,Z12), (Ra6,Rb5,X1,Z13), (Ra6,Rb5,X1,Z14), (Ra6, Rb5,X1,Z15), (Ra6,Rb5,X1,Z16), (Ra6,Rb5,X1,Z17), (Ra6, Rb5,X1,Z18), (Ra6,Rb5,X1,Z19), (Ra6,Rb5,X1,Z20), (Ra6, Rb5,X1,Z21), (Ra6,Rb5,X1,Z22), (Ra6,Rb5,X1,Z23), (Ra6, Rb5,X1,Z24), (Ra6,Rb5,X1,Z25), (Ra6,Rb5,X1,Z26), (Ra6, Rb5,X1,Z27), (Ra6,Rb5,X1,Z28), (Ra6,Rb5,X1,Z29), (Ra6, Rb5,X1,Z30), (Ra6,Rb5,X1,Z31), (Ra6,Rb5,X1,Z32), (Ra6, Rb5,X1,Z33), (Ra6,Rb5,X1,Z34), (Ra6,Rb5,X1,Z35), (Ra6, Rb5,X1,Z36), (Ra6,Rb5,X1,Z37), (Ra6,Rb5,X1,Z38), (Ra6, Rb5,X1,Z39), (Ra6,Rb5,X2,Z1), (Ra6,Rb5,X2,Z2), (Ra6, Rb5,X2,Z3), (Ra6,Rb5,X2,Z4), (Ra6,Rb5,X2,Z5), (Ra6, Rb5,X2,Z6), (Ra6,Rb5,X2,Z7), (Ra6,Rb5,X2,Z8), (Ra6, Rb5,X2,Z9), (Ra6,Rb5,X2,Z10), (Ra6,Rb5,X2,Z11), (Ra6, Rb5,X2,Z12), (Ra6,Rb5,X2,Z13), (Ra6,Rb5,X2,Z14), (Ra6, Rb5,X2,Z15), (Ra6,Rb5,X2,Z16), (Ra6,Rb5,X2,Z17), (Ra6, Rb5,X2,Z18), (Ra6,Rb5,X2,Z19), (Ra6,Rb5,X2,Z20), (Ra6, Rb5,X2,Z21), (Ra6,Rb5,X2,Z22), (Ra6,Rb5,X2,Z23), (Ra6, Rb5,X2,Z24), (Ra6,Rb5,X2,Z25), (Ra6,Rb5,X2,Z26), (Ra6, Rb5, X2,Z27), (Ra6,Rb5,X2,Z28), (Ra6,Rb5,X2,Z29), (Ra6, Rb5,X2,Z30), (Ra6,Rb5,X2,Z31), (Ra6,Rb5,X2,Z32), (Ra6, Rb5,X2,Z33), (Ra6,Rb5,X2,Z34), (Ra6,Rb5,X2,Z35), (Ra6, Rb5,X2,Z36), (Ra6,Rb5,X2,Z37), (Ra6,Rb5,X2,Z38), (Ra6, Rb5,X2,Z39), (Ra6,Rb6,X1,Z1), (Ra6,Rb6,X1,Z2), (Ra6, Rb6,X1,Z3), (Ra6,Rb6,X1,Z4), (Ra6,Rb6,X1,Z5), (Ra6, Rb6,X1,Z6), (Ra6,Rb6,X1,Z7), (Ra6,Rb6,X1,Z8), (Ra6, Rb6,X1,Z9), (Ra6,Rb6,X1,Z10), (Ra6,Rb6,X1,Z11), (Ra6, Rb6,X1,Z12), (Ra6,Rb6,X1,Z13), (Ra6,Rb6,X1,Z14), (Ra6, Rb6,X1,Z15), (Ra6,Rb6,X1,Z16), (Ra6,Rb6,X1,Z17), (Ra6, Rb6,X1,Z18), (Ra6,Rb6,X1,Z19), (Ra6,Rb6,X1,Z20), (Ra6, Rb6,X1,Z21), (Ra6,Rb6,X1,Z22), (Ra6,Rb6,X1,Z23), (Ra6, Rb6,X1,Z24), (Ra6,Rb6,X1,Z25), (Ra6,Rb6,X1,Z26), (Ra6, Rb6,X1,Z27), (Ra6,Rb6,X1,Z28), (Ra6,Rb6,X1,Z29), (Ra6, Rb6,X1,Z30), (Ra6,Rb6,X1,Z31), (Ra6,Rb6,X1,Z32), (Ra6, Rb6,X1,Z33), (Ra6,Rb6,X1,Z34), (Ra6,Rb6,X1,Z35), (Ra6, Rb6,X1,Z36), (Ra6,Rb6,X1,Z37), (Ra6,Rb6,X1,Z38), (Ra6, Rb6,X1,Z39), (Ra6,Rb6,X2,Z1), (Ra6,Rb6,X2,Z2), (Ra6, Rb6,X2,Z3), (Ra6,Rb6,X2,Z4), (Ra6,Rb6,X2,Z5), (Ra6, Rb6,X2,Z6), (Ra6,Rb6,X2,Z7), (Ra6,Rb6,X2,Z8), (Ra6, Rb6,X2,Z9), (Ra6,Rb6,X2,Z10), (Ra6,Rb6,X2,Z11), (Ra6, Rb6,X2,Z12), (Ra6,Rb6,X2,Z13), (Ra6,Rb6,X2,Z14), (Ra6, Rb6,X2,Z15), (Ra6,Rb6,X2,Z16), (Ra6,Rb6,X2,Z17), (Ra6, Rb6,X2,Z18), (Ra6,Rb6,X2,Z19), (Ra6,Rb6,X2,Z20), (Ra6, Rb6,X2,Z21), (Ra6,Rb6,X2,Z22), (Ra6,Rb6,X2,Z23), (Ra6, Rb6,X2,Z24), (Ra6,Rb6,X2,Z25), (Ra6,Rb6,X2,Z26), (Ra6, Rb6,X2,Z27), (Ra6,Rb6,X2,Z28), (Ra6,Rb6,X2,Z29), (Ra6, Rb6,X2,Z30), (Ra6,Rb6,X2,Z31), (Ra6,Rb6,X2,Z32), (Ra6, Rb6,X2,Z33), (Ra6,Rb6,X2,Z34), (Ra6,Rb6,X2,Z35), (Ra6, Rb6,X2,Z36), (Ra6,Rb6,X2,Z37), (Ra6,Rb6,X2,Z38), (Ra6, Rb6,X2,Z39), (Ra6,Rb7,X1,Z1), (Ra6,Rb7,X1,Z2), (Ra6, Rb7,X1,Z3), (Ra6,Rb7,X1,Z4), (Ra6,Rb7,X1,Z5), (Ra6, Rb7,X1,Z6), (Ra6,Rb7,X1,Z7), (Ra6,Rb7,X1,Z8), (Ra6, Rb7,X1,Z9), (Ra6,Rb7,X1,Z10), (Ra6,Rb7,X1,Z11), (Ra6, Rb7,X1,Z12), (Ra6,Rb7,X1,Z13), (Ra6,Rb7,X1,Z14), (Ra6, Rb7,X1,Z15), (Ra6,Rb7,X1,Z16), (Ra6,Rb7,X1,Z17), (Ra6, Rb7,X1,Z18), (Ra6,Rb7,X1,Z19), (Ra6,Rb7,X1,Z20), (Ra6, Rb7,X1,Z21), (Ra6,Rb7,X1,Z22), (Ra6,Rb7,X1,Z23), (Ra6, Rb7,X1,Z24), (Ra6,Rb7,X1,Z25), (Ra6,Rb7,X1,Z26), (Ra6, Rb7,X1,Z27), (Ra6,Rb7,X1,Z28), (Ra6,Rb7,X1,Z29), (Ra6,

Rb7,X1,Z30), (Ra6,Rb7,X1,Z31), (Ra6,Rb7,X1,Z32), (Ra6,Rb7,X1,Z33), (Ra6,Rb7,X1,Z34), (Ra6,Rb7,X1,Z35), (Ra6,Rb7,X1,Z36), (Ra6,Rb7,X1,Z37), (Ra6,Rb7,X1,Z38), (Ra6,Rb7,X2,Z1), (Ra6,Rb7,X2,Z2), (Ra6,Rb7,X2,Z3), (Ra6,Rb7,X2,Z4), (Ra6,Rb7,X2,Z5), (Ra6,Rb7,X2,Z6), (Ra6,Rb7,X2,Z7), (Ra6,Rb7,X2,Z8), (Ra6,Rb7,X2,Z9), (Ra6,Rb7,X2,Z10), (Ra6,Rb7,X2,Z11), (Ra6,Rb7,X2,Z12), (Ra6,Rb7,X2,Z13), (Ra6,Rb7,X2,Z14), (Ra6,Rb7,X2,Z15), (Ra6,Rb7,X2,Z16), (Ra6,Rb7,X2,Z17), (Ra6,Rb7,X2,Z18), (Ra6,Rb7,X2,Z19), (Ra6,Rb7,X2,Z20), (Ra6,Rb7,X2,Z21), (Ra6,Rb7,X2,Z22), (Ra6,Rb7,X2,Z23), (Ra6,Rb7,X2,Z24), (Ra6,Rb7,X2,Z25), (Ra6,Rb7,X2,Z26), (Ra6,Rb7,X2,Z27), (Ra6,Rb7,X2,Z28), (Ra6,Rb7,X2,Z29), (Ra6,Rb7,X2,Z30), (Ra6,Rb7,X2,Z31), (Ra6,Rb7,X2,Z32), (Ra6,Rb7,X2,Z33), (Ra6,Rb7,X2,Z34), (Ra6,Rb7,X2,Z35), (Ra6,Rb7,X2,Z36), (Ra6,Rb7,X2,Z37), (Ra6,Rb7,X2,Z38), (Ra6,Rb7,X2,Z39), (Ra6,Rb8,X1,Z1), (Ra6,Rb8,X1,Z2), (Ra6,Rb8,X1,Z3), (Ra6,Rb8,X1,Z4), (Ra6,Rb8,X1,Z5), (Ra6,Rb8,X1,Z6), (Ra6,Rb8,X1,Z7), (Ra6,Rb8,X1,Z8), (Ra6,Rb8,X1,Z9), (Ra6,Rb8,X1,Z10), (Ra6,Rb8,X1,Z11), (Ra6,Rb8,X1,Z12), (Ra6,Rb8,X1,Z13), (Ra6,Rb8,X1,Z14), (Ra6,Rb8,X1,Z15), (Ra6,Rb8,X1,Z16), (Ra6,Rb8,X1,Z17), (Ra6,Rb8,X1,Z18), (Ra6,Rb8,X1,Z19), (Ra6,Rb8,X1,Z20), (Ra6,Rb8,X1,Z21), (Ra6,Rb8,X1,Z22), (Ra6,Rb8,X1,Z23), (Ra6,Rb8,X1,Z24), (Ra6,Rb8,X1,Z25), (Ra6,Rb8,X1,Z26), (Ra6,Rb8,X1,Z27), (Ra6,Rb8,X1,Z28), (Ra6,Rb8,X1,Z29), (Ra6,Rb8,X1,Z30), (Ra6,Rb8,X1,Z31), (Ra6,Rb8,X1,Z32), (Ra6,Rb8,X1,Z33), (Ra6,Rb8,X1,Z34), (Ra6,Rb8,X1,Z35), (Ra6,Rb8,X1,Z36), (Ra6,Rb8,X1,Z37), (Ra6,Rb8,X1,Z38), (Ra6,Rb8,X1,Z39), (Ra6,Rb8,X2,Z1), (Ra6,Rb8,X2,Z2), (Ra6,Rb8,X2,Z3), (Ra6,Rb8,X2,Z4), (Ra6,Rb8,X2,Z5), (Ra6,Rb8,X2,Z6), (Ra6,Rb8,X2,Z7), (Ra6,Rb8,X2,Z8), (Ra6,Rb8,X2,Z9), (Ra6,Rb8,X2,Z10), (Ra6,Rb8,X2,Z11), (Ra6,Rb8,X2,Z12), (Ra6,Rb8,X2,Z13), (Ra6,Rb8,X2,Z14), (Ra6,Rb8,X2,Z15), (Ra6,Rb8,X2,Z16), (Ra6,Rb8,X2,Z17), (Ra6,Rb8,X2,Z18), (Ra6,Rb8,X2,Z19), (Ra6,Rb8,X2,Z20), (Ra6,Rb8,X2,Z21), (Ra6,Rb8,X2,Z22), (Ra6,Rb8,X2,Z23), (Ra6,Rb8,X2,Z24), (Ra6,Rb8,X2,Z25), (Ra6,Rb8,X2,Z26), (Ra6,Rb8,X2,Z27), (Ra6,Rb8,X2,Z28), (Ra6,Rb8,X2,Z29), (Ra6,Rb8,X2,Z30), (Ra6,Rb8,X2,Z31), (Ra6,Rb8,X2,Z32), (Ra6,Rb8,X2,Z33), (Ra6,Rb8,X2,Z34), (Ra6,Rb8,X2,Z35), (Ra6,Rb8,X2,Z36), (Ra6,Rb8,X2,Z37), (Ra6,Rb8,X2,Z38), (Ra6,Rb8,X2,Z39), (Ra7,Rb1,X1,Z1), (Ra7,Rb1,X1,Z2), (Ra7,Rb1,X1,Z3), (Ra7,Rb1,X1,Z4), (Ra7,Rb1,X1,Z5), (Ra7,Rb1,X1,Z6), (Ra7,Rb1,X1,Z7), (Ra7,Rb1,X1,Z8), (Ra7,Rb1,X1,Z9), (Ra7,Rb1,X1,Z10), (Ra7,Rb1,X1,Z11), (Ra7,Rb1,X1,Z12), (Ra7,Rb1,X1,Z13), (Ra7,Rb1,X1,Z14), (Ra7,Rb1,X1,Z15), (Ra7,Rb1,X1,Z16), (Ra7,Rb1,X1,Z17), (Ra7,Rb1,X1,Z18), (Ra7,Rb1,X1,Z19), (Ra7,Rb1,X1,Z20), (Ra7,Rb1,X1,Z21), (Ra7,Rb1,X1,Z22), (Ra7,Rb1,X1,Z23), (Ra7,Rb1,X1,Z24), (Ra7,Rb1,X1,Z25), (Ra7,Rb1,X1,Z26), (Ra7,Rb1,X1,Z27), (Ra7,Rb1,X1,Z28), (Ra7,Rb1,X1,Z29), (Ra7,Rb1,X1,Z30), (Ra7,Rb1,X1,Z31), (Ra7,Rb1,X1,Z32), (Ra7,Rb1,X1,Z33), (Ra7,Rb1,X1,Z34), (Ra7,Rb1,X1,Z35), (Ra7,Rb1,X1,Z36), (Ra7,Rb1,X1,Z37), (Ra7,Rb1,X1,Z38), (Ra7,Rb1,X1,Z39), (Ra7,Rb1,X2,Z1), (Ra7,Rb1,X2,Z2), (Ra7,Rb1,X2,Z3), (Ra7,Rb1,X2,Z4), (Ra7,Rb1,X2,Z5), (Ra7,Rb1,X2,Z6), (Ra7,Rb1,X2,Z7), (Ra7,Rb1,X2,Z8), (Ra7,Rb1,X2,Z9), (Ra7,Rb1,X2,Z10), (Ra7,Rb1,X2,Z11), (Ra7,Rb1,X2,Z12), (Ra7,Rb1,X2,Z13), (Ra7,Rb1,X2,Z14), (Ra7,Rb1,X2,Z15), (Ra7,Rb1,X2,Z16), (Ra7,Rb1,X2,Z17), (Ra7,Rb1,X2,Z18), (Ra7,Rb1,X2,Z19), (Ra7,Rb1,X2,Z20), (Ra7,Rb1,X2,Z21), (Ra7,Rb1,X2,Z22), (Ra7,Rb1,X2,Z23), (Ra7,Rb1,X2,Z24), (Ra7,Rb1,X2,Z25), (Ra7,Rb1,X2,Z26), (Ra7,Rb1,X2,Z27), (Ra7,Rb1,X2,Z28), (Ra7,Rb1,X2,Z29), (Ra7,Rb1,X2,Z30), (Ra7,Rb1,X2,Z31), (Ra7,Rb1,X2,Z32), (Ra7,Rb1,X2,Z33), (Ra7,Rb1,X2,Z34), (Ra7,Rb1,X2,Z35), (Ra7,Rb1,X2,Z36), (Ra7,Rb1,X2,Z37), (Ra7,Rb1,X2,Z38), (Ra7,Rb1,X2,Z39), (Ra7,Rb2,X1,Z1), (Ra7,Rb2,X1,Z2), (Ra7,Rb2,X1,Z3), (Ra7,Rb2,X1,Z4), (Ra7,Rb2,X1,Z5), (Ra7,Rb2,X1,Z6), (Ra7,Rb2,X1,Z7), (Ra7,Rb2,X1,Z8), (Ra7,Rb2,X1,Z9), (Ra7,Rb2,X1,Z10), (Ra7,Rb2,X1,Z11), (Ra7,Rb2,X1,Z12), (Ra7,Rb2,X1,Z13), (Ra7,Rb2,X1,Z14), (Ra7,Rb2,X1,Z15), (Ra7,Rb2,X1,Z16), (Ra7,Rb2,X1,Z17), (Ra7,Rb2,X1,Z18), (Ra7,Rb2,X1,Z19), (Ra7,Rb2,X1,Z20), (Ra7,Rb2,X1,Z21), (Ra7,Rb2,X1,Z22), (Ra7,Rb2,X1,Z23), (Ra7,Rb2,X1,Z24), (Ra7,Rb2,X1,Z25), (Ra7,Rb2,X1,Z26), (Ra7,Rb2,X1,Z27), (Ra7,Rb2,X1,Z28), (Ra7,Rb2,X1,Z29), (Ra7,Rb2,X1,Z30), (Ra7,Rb2,X1,Z31), (Ra7,Rb2,X1,Z32), (Ra7,Rb2,X1,Z33), (Ra7,Rb2,X1,Z34), (Ra7,Rb2,X1,Z35), (Ra7,Rb2,X1,Z36), (Ra7,Rb2,X1,Z37), (Ra7,Rb2,X1,Z38), (Ra7,Rb2,X1,Z39), (Ra7,Rb2,X2,Z1), (Ra7,Rb2,X2,Z2), (Ra7,Rb2,X2,Z3), (Ra7,Rb2,X2,Z4), (Ra7,Rb2,X2,Z5), (Ra7,Rb2,X2,Z6), (Ra7,Rb2,X2,Z7), (Ra7,Rb2,X2,Z8), (Ra7,Rb2,X2,Z9), (Ra7,Rb2,X2,Z10), (Ra7,Rb2,X2,Z11), (Ra7,Rb2,X2,Z12), (Ra7,Rb2,X2,Z13), (Ra7,Rb2,X2,Z14), (Ra7,Rb2,X2,Z15), (Ra7,Rb2,X2,Z16), (Ra7,Rb2,X2,Z17), (Ra7,Rb2,X2,Z18), (Ra7,Rb2,X2,Z19), (Ra7,Rb2,X2,Z20), (Ra7,Rb2,X2,Z21), (Ra7,Rb2,X2,Z22), (Ra7,Rb2,X2,Z23), (Ra7,Rb2,X2,Z24), (Ra7,Rb2,X2,Z25), (Ra7,Rb2,X2,Z26), (Ra7,Rb2,X2,Z27), (Ra7,Rb2,X2,Z28), (Ra7,Rb2,X2,Z29), (Ra7,Rb2,X2,Z30), (Ra7,Rb2,X2,Z31), (Ra7,Rb2,X2,Z32), (Ra7,Rb2,X2,Z33), (Ra7,Rb2,X2,Z34), (Ra7,Rb2,X2,Z35), (Ra7,Rb2,X2,Z36), (Ra7,Rb2,X2,Z37), (Ra7,Rb2,X2,Z38), (Ra7,Rb2,X2,Z39), (Ra7,Rb3,X1,Z1), (Ra7,Rb3,X1,Z2), (Ra7,Rb3,X1,Z3), (Ra7,Rb3,X1,Z4), (Ra7,Rb3,X1,Z5), (Ra7,Rb3,X1,Z6), (Ra7,Rb3,X1,Z7), (Ra7,Rb3,X1,Z8), (Ra7,Rb3,X1,Z9), (Ra7,Rb3,X1,Z10), (Ra7,Rb3,X1,Z11), (Ra7,Rb3,X1,Z12), (Ra7,Rb3,X1,Z13), (Ra7,Rb3,X1,Z14), (Ra7,Rb3,X1,Z15), (Ra7,Rb3,X1,Z16), (Ra7,Rb3,X1,Z17), (Ra7,Rb3,X1,Z18), (Ra7,Rb3,X1,Z19), (Ra7,Rb3,X1,Z20), (Ra7,Rb3,X1,Z21), (Ra7,Rb3,X1,Z22), (Ra7,Rb3,X1,Z23), (Ra7,Rb3,X1,Z24), (Ra7,Rb3,X1,Z25), (Ra7,Rb3,X1,Z26), (Ra7,Rb3,X1,Z27), (Ra7,Rb3,X1,Z28), (Ra7,Rb3,X1,Z29), (Ra7,Rb3,X1,Z30), (Ra7,Rb3,X1,Z31), (Ra7,Rb3,X1,Z32), (Ra7,Rb3,X1,Z33), (Ra7,Rb3,X1,Z34), (Ra7,Rb3,X1,Z35), (Ra7,Rb3,X1,Z36), (Ra7,Rb3,X1,Z37), (Ra7,Rb3,X1,Z38), (Ra7,Rb3,X1,Z39), (Ra7,Rb3,X2,Z1), (Ra7,Rb3,X2,Z2), (Ra7,Rb3,X2,Z3), (Ra7,Rb3,X2,Z4), (Ra7,Rb3,X2,Z5), (Ra7,Rb3,X2,Z6), (Ra7,Rb3,X2,Z7), (Ra7,Rb3,X2,Z8), (Ra7,Rb3,X2,Z9), (Ra7,Rb3,X2,Z10), (Ra7,Rb3,X2,Z11), (Ra7,Rb3,X2,Z12), (Ra7,Rb3,X2,Z13), (Ra7,Rb3,X2,Z14), (Ra7,Rb3,X2,Z15), (Ra7,Rb3,X2,Z16), (Ra7,Rb3,X2,Z17), (Ra7,Rb3,X2,Z18), (Ra7,Rb3,X2,Z19), (Ra7,Rb3,X2,Z20), (Ra7,Rb3,X2,Z21), (Ra7,Rb3,X2,Z22), (Ra7,Rb3,X2,Z23), (Ra7,Rb3,X2,Z24), (Ra7,Rb3,X2,Z25), (Ra7,Rb3,X2,Z26), (Ra7,Rb3,X2,Z27), (Ra7,Rb3,X2,Z28), (Ra7,Rb3,X2,Z29), (Ra7,Rb3,X2,Z30), (Ra7,Rb3,X2,Z31), (Ra7,Rb3,X2,Z32), (Ra7,Rb3,X2,Z33), (Ra7,Rb3,X2,Z34), (Ra7,Rb3,X2,Z35), (Ra7,Rb3,X2,Z36), (Ra7,Rb3,X2,Z37), (Ra7,Rb3,X2,Z38), (Ra7,Rb3,X2,Z39), (Ra7,Rb4,X1,Z1), (Ra7,Rb4,X1,Z2), (Ra7,Rb4,X1,Z3), (Ra7,Rb4,X1,Z4), (Ra7,Rb4,X1,Z5), (Ra7,Rb4,X1,Z6), (Ra7,Rb4,X1,Z7), (Ra7,Rb4,X1,Z8), (Ra7,Rb4,X1,Z9), (Ra7,Rb4,X1,Z10), (Ra7,Rb4,X1,Z11), (Ra7,Rb4,X1,Z12), (Ra7,Rb4,X1,Z13), (Ra7,Rb4,X1,Z14), (Ra7,Rb4,X1,Z15), (Ra7,Rb4,X1,Z16), (Ra7,Rb4,X1,Z17), (Ra7,Rb4,X1,Z18), (Ra7,Rb4,X1,Z19), (Ra7,Rb4,X1,Z20), (Ra7,Rb4,X1,Z21), (Ra7,Rb4,X1,Z22), (Ra7,Rb4,X1,Z23), (Ra7,Rb4,X1,Z24), (Ra7,Rb4,X1,Z25), (Ra7,Rb4,X1,Z26), (Ra7,Rb4,X1,Z27), (Ra7,Rb4,X1,Z28), (Ra7,Rb4,X1,Z29), (Ra7,Rb4,X1,Z30), (Ra7,Rb4,X1,Z31), (Ra7,Rb4,X1,Z32), (Ra7,Rb4,X1,Z33), (Ra7,Rb4,X1,Z34), (Ra7,Rb4,X1,Z35), (Ra7,Rb4,X1,Z36), (Ra7,Rb4,X1,Z37), (Ra7,Rb4,X1,Z38), (Ra7,Rb4,X1,Z39), (Ra7,Rb4,X2,Z1), (Ra7,Rb4,X2,Z2), (Ra7,

Rb4,X2,Z3), (Ra7,Rb4,X2,Z4), (Ra7,Rb4,X2,Z5), (Ra7,Rb4,X2,Z6), (Ra7,Rb4,X2,Z7), (Ra7,Rb4,X2,Z8), (Ra7,Rb4,X2,Z9), (Ra7,Rb4,X2,Z10), (Ra7,Rb4,X2,Z11), (Ra7,Rb4,X2,Z12), (Ra7,Rb4,X2,Z13), (Ra7,Rb4,X2,Z14), (Ra7,Rb4,X2,Z15), (Ra7,Rb4,X2,Z16), (Ra7,Rb4,X2,Z17), (Ra7,Rb4,X2,Z18), (Ra7,Rb4,X2,Z19), (Ra7,Rb4,X2,Z20), (Ra7,Rb4,X2,Z21), (Ra7,Rb4,X2,Z22), (Ra7,Rb4,X2,Z23), (Ra7,Rb4,X2,Z24), (Ra7,Rb4,X2,Z25), (Ra7,Rb4,X2,Z26), (Ra7,Rb4,X2,Z27), (Ra7,Rb4,X2,Z28), (Ra7,Rb4,X2,Z29), (Ra7,Rb4,X2,Z30), (Ra7,Rb4,X2,Z31), (Ra7,Rb4,X2,Z32), (Ra7,Rb4,X2,Z33), (Ra7,Rb4,X2,Z34), (Ra7,Rb4,X2,Z35), (Ra7,Rb4,X2,Z36), (Ra7,Rb4,X2,Z37), (Ra7,Rb4,X2,Z38), (Ra7,Rb4,X2,Z39), (Ra7,Rb5,X1,Z1), (Ra7,Rb5,X1,Z2), (Ra7,Rb5,X1,Z3), (Ra7,Rb5,X1,Z4), (Ra7,Rb5,X1,Z5), (Ra7,Rb5,X1,Z6), (Ra7,Rb5,X1,Z7), (Ra7,Rb5,X1,Z8), (Ra7,Rb5,X1,Z9), (Ra7,Rb5,X1,Z10), (Ra7,Rb5,X1,Z11), (Ra7,Rb5,X1,Z12), (Ra7,Rb5,X1,Z13), (Ra7,Rb5,X1,Z14), (Ra7,Rb5,X1,Z15), (Ra7,Rb5,X1,Z16), (Ra7,Rb5,X1,Z17), (Ra7,Rb5,X1,Z18), (Ra7,Rb5,X1,Z19), (Ra7,Rb5,X1,Z20), (Ra7,Rb5,X1,Z21), (Ra7,Rb5,X1,Z22), (Ra7,Rb5,X1,Z23), (Ra7,Rb5,X1,Z24), (Ra7,Rb5,X1,Z25), (Ra7,Rb5,X1,Z26), (Ra7,Rb5,X1,Z27), (Ra7,Rb5,X1,Z28), (Ra7,Rb5,X1,Z29), (Ra7,Rb5,X1,Z30), (Ra7,Rb5,X1,Z31), (Ra7,Rb5,X1,Z32), (Ra7,Rb5,X1,Z33), (Ra7,Rb5,X1,Z34), (Ra7,Rb5,X1,Z35), (Ra7,Rb5,X1,Z36), (Ra7,Rb5,X1,Z37), (Ra7,Rb5,X1,Z38), (Ra7,Rb5,X1,Z39), (Ra7,Rb5,X2,Z1), (Ra7,Rb5,X2,Z2), (Ra7,Rb5,X2,Z3), (Ra7,Rb5,X2,Z4), (Ra7,Rb5,X2,Z5), (Ra7,Rb5,X2,Z6), (Ra7,Rb5,X2,Z7), (Ra7,Rb5,X2,Z8), (Ra7,Rb5,X2,Z9), (Ra7,Rb5,X2,Z10), (Ra7,Rb5,X2,Z11), (Ra7,Rb5,X2,Z12), (Ra7,Rb5,X2,Z13), (Ra7,Rb5,X2,Z14), (Ra7,Rb5,X2,Z15), (Ra7,Rb5,X2,Z16), (Ra7,Rb5,X2,Z17), (Ra7,Rb5,X2,Z18), (Ra7,Rb5,X2,Z19), (Ra7,Rb5,X2,Z20), (Ra7,Rb5,X2,Z21), (Ra7,Rb5,X2,Z22), (Ra7,Rb5,X2,Z23), (Ra7,Rb5,X2,Z24), (Ra7,Rb5,X2,Z25), (Ra7,Rb5,X2,Z26), (Ra7,Rb5,X2,Z27), (Ra7,Rb5,X2,Z28), (Ra7,Rb5,X2,Z29), (Ra7,Rb5,X2,Z30), (Ra7,Rb5,X2,Z31), (Ra7,Rb5,X2,Z32), (Ra7,Rb5,X2,Z33), (Ra7,Rb5,X2,Z34), (Ra7,Rb5,X2,Z35), (Ra7,Rb5,X2,Z36), (Ra7,Rb5,X2,Z37), (Ra7,Rb5,X2,Z38), (Ra7,Rb5,X2,Z39), (Ra7,Rb6,X1,Z1), (Ra7,Rb6,X1,Z2), (Ra7,Rb6,X1,Z3), (Ra7,Rb6,X1,Z4), (Ra7,Rb6,X1,Z5), (Ra7,Rb6,X1,Z6), (Ra7,Rb6,X1,Z7), (Ra7,Rb6,X1,Z8), (Ra7,Rb6,X1,Z9), (Ra7,Rb6,X1,Z10), (Ra7,Rb6,X1,Z11), (Ra7,Rb6,X1,Z12), (Ra7,Rb6,X1,Z13), (Ra7,Rb6,X1,Z14), (Ra7,Rb6,X1,Z15), (Ra7,Rb6,X1,Z16), (Ra7,Rb6,X1,Z17), (Ra7,Rb6,X1,Z18), (Ra7,Rb6,X1,Z19), (Ra7,Rb6,X1,Z20), (Ra7,Rb6,X1,Z21), (Ra7,Rb6,X1,Z22), (Ra7,Rb6,X1,Z23), (Ra7,Rb6,X1,Z24), (Ra7,Rb6,X1,Z25), (Ra7,Rb6,X1,Z26), (Ra7,Rb6,X1,Z27), (Ra7,Rb6,X1,Z28), (Ra7,Rb6,X1,Z29), (Ra7,Rb6,X1,Z30), (Ra7,Rb6,X1,Z31), (Ra7,Rb6,X1,Z32), (Ra7,Rb6,X1,Z33), (Ra7,Rb6,X1,Z34), (Ra7,Rb6,X1,Z35), (Ra7,Rb6,X1,Z36), (Ra7,Rb6,X1,Z37), (Ra7,Rb6,X1,Z38), (Ra7,Rb6,X1,Z39), (Ra7,Rb6,X2,Z1), (Ra7,Rb6,X2,Z2), (Ra7,Rb6,X2,Z3), (Ra7,Rb6,X2,Z4), (Ra7,Rb6,X2,Z5), (Ra7,Rb6,X2,Z6), (Ra7,Rb6,X2,Z7), (Ra7,Rb6,X2,Z8), (Ra7,Rb6,X2,Z9), (Ra7,Rb6,X2,Z10), (Ra7,Rb6,X2,Z11), (Ra7,Rb6,X2,Z12), (Ra7,Rb6,X2,Z13), (Ra7,Rb6,X2,Z14), (Ra7,Rb6,X2,Z15), (Ra7,Rb6,X2,Z16), (Ra7,Rb6,X2,Z17), (Ra7,Rb6,X2,Z18), (Ra7,Rb6,X2,Z19), (Ra7,Rb6,X2,Z20), (Ra7,Rb6,X2,Z21), (Ra7,Rb6,X2,Z22), (Ra7,Rb6,X2,Z23), (Ra7,Rb6,X2,Z24), (Ra7,Rb6,X2,Z25), (Ra7,Rb6,X2,Z26), (Ra7,Rb6,X2,Z27), (Ra7,Rb6,X2,Z28), (Ra7,Rb6,X2,Z29), (Ra7,Rb6,X2,Z30), (Ra7,Rb6,X2,Z31), (Ra7,Rb6,X2,Z32), (Ra7,Rb6,X2,Z33), (Ra7,Rb6,X2,Z34), (Ra7,Rb6,X2,Z35), (Ra7,Rb6,X2,Z36), (Ra7,Rb6,X2,Z37), (Ra7,Rb6,X2,Z38), (Ra7,Rb6,X2,Z39), (Ra7,Rb7,X1,Z1), (Ra7,Rb7,X1,Z2), (Ra7,Rb7,X1,Z3), (Ra7,Rb7,X1,Z4), (Ra7,Rb7,X1,Z5), (Ra7,Rb7,X1,Z6), (Ra7,Rb7,X1,Z7), (Ra7,Rb7,X1,Z8), (Ra7,Rb7,X1,Z9), (Ra7,Rb7,X1,Z10), (Ra7,Rb7,X1,Z11), (Ra7,Rb7,X1,Z12), (Ra7,Rb7,X1,Z13), (Ra7,Rb7,X1,Z14), (Ra7,Rb7,X1,Z15), (Ra7,Rb7,X1,Z16), (Ra7,Rb7,X1,Z17), (Ra7,Rb7,X1,Z18), (Ra7,Rb7,X1,Z19), (Ra7,Rb7,X1,Z20), (Ra7,Rb7,X1,Z21), (Ra7,Rb7,X1,Z22), (Ra7,Rb7,X1,Z23), (Ra7,Rb7,X1,Z24), (Ra7,Rb7,X1,Z25), (Ra7,Rb7,X1,Z26), (Ra7,Rb7,X1,Z27), (Ra7,Rb7,X1,Z28), (Ra7,Rb7,X1,Z29), (Ra7,Rb7,X1,Z30), (Ra7,Rb7,X1,Z31), (Ra7,Rb7,X1,Z32), (Ra7,Rb7,X1,Z33), (Ra7,Rb7,X1,Z34), (Ra7,Rb7,X1,Z35), (Ra7,Rb7,X1,Z36), (Ra7,Rb7,X1,Z37), (Ra7,Rb7,X1,Z38), (Ra7,Rb7,X1,Z39), (Ra7,Rb7,X2,Z1), (Ra7,Rb7,X2,Z2), (Ra7,Rb7,X2,Z3), (Ra7,Rb7,X2,Z4), (Ra7,Rb7,X2,Z5), (Ra7,Rb7,X2,Z6), (Ra7,Rb7,X2,Z7), (Ra7,Rb7,X2,Z8), (Ra7,Rb7,X2,Z9), (Ra7,Rb7,X2,Z10), (Ra7,Rb7,X2,Z11), (Ra7,Rb7,X2,Z12), (Ra7,Rb7,X2,Z13), (Ra7,Rb7,X2,Z14), (Ra7,Rb7,X2,Z15), (Ra7,Rb7,X2,Z16), (Ra7,Rb7,X2,Z17), (Ra7,Rb7,X2,Z18), (Ra7,Rb7,X2,Z19), (Ra7,Rb7,X2,Z20), (Ra7,Rb7,X2,Z21), (Ra7,Rb7,X2,Z22), (Ra7,Rb7,X2,Z23), (Ra7,Rb7,X2,Z24), (Ra7,Rb7,X2,Z25), (Ra7,Rb7,X2,Z26), (Ra7,Rb7,X2,Z27), (Ra7,Rb7,X2,Z28), (Ra7,Rb7,X2,Z29), (Ra7,Rb7,X2,Z30), (Ra7,Rb7,X2,Z31), (Ra7,Rb7,X2,Z32), (Ra7,Rb7,X2,Z33), (Ra7,Rb7,X2,Z34), (Ra7,Rb7,X2,Z35), (Ra7,Rb7,X2,Z36), (Ra7,Rb7,X2,Z37), (Ra7,Rb7,X2,Z38), (Ra7,Rb7,X2,Z39), (Ra7,Rb8,X1,Z1), (Ra7,Rb8,X1,Z2), (Ra7,Rb8,X1,Z3), (Ra7,Rb8,X1,Z4), (Ra7,Rb8,X1,Z5), (Ra7,Rb8,X1,Z6), (Ra7,Rb8,X1,Z7), (Ra7,Rb8,X1,Z8), (Ra7,Rb8,X1,Z9), (Ra7,Rb8,X1,Z10), (Ra7,Rb8,X1,Z11), (Ra7,Rb8,X1,Z12), (Ra7,Rb8,X1,Z13), (Ra7,Rb8,X1,Z14), (Ra7,Rb8,X1,Z15), (Ra7,Rb8,X1,Z16), (Ra7,Rb8,X1,Z17), (Ra7,Rb8,X1,Z18), (Ra7,Rb8,X1,Z19), (Ra7,Rb8,X1,Z20), (Ra7,Rb8,X1,Z21), (Ra7,Rb8,X1,Z22), (Ra7,Rb8,X1,Z23), (Ra7,Rb8,X1,Z24), (Ra7,Rb8,Z25), (Ra7,Rb8,X1,Z26), (Ra7,Rb8,X1,Z27), (Ra7,Rb8,X1,Z28), (Ra7,Rb8,X1,Z29), (Ra7,Rb8,X1,Z30), (Ra7,Rb8,X1,Z31), (Ra7,Rb8,X1,Z32), (Ra7,Rb8,X1,Z33), (Ra7,Rb8,X1,Z34), (Ra7,Rb8,X1,Z35), (Ra7,Rb8,X1,Z36), (Ra7,Rb8,X1,Z37), (Ra7,Rb8,X1,Z38), (Ra7,Rb8,X1,Z39), (Ra7,Rb8,X2,Z1), (Ra7,Rb8,X2,Z2), (Ra7,Rb8,X2,Z3), (Ra7,Rb8,X2,Z4), (Ra7,Rb8,X2,Z5), (Ra7,Rb8,X2,Z6), (Ra7,Rb8,X2,Z7), (Ra7,Rb8,X2,Z8), (Ra7,Rb8,X2,Z9), (Ra7,Rb8,X2,Z10), (Ra7,Rb8,X2,Z11), (Ra7,Rb8,X2,Z12), (Ra7,Rb8,X2,Z13), (Ra7,Rb8,X2,Z14), (Ra7,Rb8,X2,Z15), (Ra7,Rb8,X2,Z16), (Ra7,Rb8,X2,Z17), (Ra7,Rb8,X2,Z18), (Ra7,Rb8,X2,Z19), (Ra7,Rb8,X2,Z20), (Ra7,Rb8,X2,Z21), (Ra7,Rb8,X2,Z22), (Ra7,Rb8,X2,Z23), (Ra7,Rb8,X2,Z24), (Ra7,Rb8,X2,Z25), (Ra7,Rb8,X2,Z26), (Ra7,Rb8,X2,Z27), (Ra7,Rb8,X2,Z28), (Ra7,Rb8,X2,Z29), (Ra7,Rb8,X2,Z30), (Ra7,Rb8,X2,Z31), (Ra7,Rb8,X2,Z32), (Ra7,Rb8,X2,Z33), (Ra7,Rb8,X2,Z34), (Ra7,Rb8,X2,Z35), (Ra7,Rb8,X2,Z36), (Ra7,Rb8,X2,Z37), (Ra7,Rb8,X2,Z38), (Ra7,Rb8,X2,Z39), (Ra8,Rb1,X1,Z1), (Ra8,Rb1,X1,Z2), (Ra8,Rb1,X1,Z3), (Ra8,Rb1,X1,Z4), (Ra8,Rb1,X1,Z5), (Ra8,Rb1,X1,Z6), (Ra8,Rb1,X1,Z7), (Ra8,Rb1,X1,Z8), (Ra8,Rb1,X1,Z9), (Ra8,Rb1,X1,Z10), (Ra8,Rb1,X1,Z11), (Ra8,Rb1,X1,Z12), (Ra8,Rb1,X1,Z13), (Ra8,Rb1,X1,Z14), (Ra8,Rb1,X1,Z15), (Ra8,Rb1,X1,Z16), (Ra8,Rb1,X1,Z17), (Ra8,Rb1,X1,Z18), (Ra8,Rb1,X1,Z19), (Ra8,Rb1,X1,Z20), (Ra8,Rb1,X1,Z21), (Ra8,Rb1,X1,Z22), (Ra8,Rb1,X1,Z23), (Ra8,Rb1,X1,Z24), (Ra8,Rb1,X1,Z25), (Ra8,Rb1,X1,Z26), (Ra8,Rb1,X1,Z27), (Ra8,Rb1,X1,Z28), (Ra8,Rb1,X1,Z29), (Ra8,Rb1,X1,Z30), (Ra8,Rb1,X1,Z31), (Ra8,Rb1,X1,Z32), (Ra8,Rb1,X1,Z33), (Ra8,Rb1,X1,Z34), (Ra8,Rb1,X1,Z35), (Ra8,Rb1,X1,Z36), (Ra8,Rb1,X1,Z37), (Ra8,Rb1,X1,Z38), (Ra8,Rb1,X1,Z39), (Ra8,Rb1,X2,Z1), (Ra8,Rb1,X2,Z2), (Ra8,Rb1,X2,Z3), (Ra8,Rb1,X2,Z4), (Ra8,Rb1,X2,Z5), (Ra8,Rb1,X2,Z6), (Ra8,Rb1,X2,Z7), (Ra8,Rb1,X2,Z8), (Ra8,Rb1,X2,Z9), (Ra8,Rb1,X2,Z10), (Ra8,Rb1,X2,Z11), (Ra8,Rb1,X2,Z12), (Ra8,Rb1,X2,Z13), (Ra8,Rb1,X2,Z14), (Ra8,

Rb1,X2,Z15), (Ra8,Rb1,X2,Z16), (Ra8,Rb1,X2,Z17), (Ra8, Rb1,X2,Z18), (Ra8,Rb1,X2,Z19), (Ra8,Rb1,X2,Z20), (Ra8, Rb1,X2,Z21), (Ra8,Rb1,X2,Z22), (Ra8,Rb1,X2,Z23), (Ra8, Rb1,X2,Z24), (Ra8,Rb1,X2,Z25), (Ra8,Rb1,X2,Z26), (Ra8, Rb1,X2,Z27), (Ra8,Rb1,X2,Z28), (Ra8,Rb1,X2,Z29), (Ra8, Rb1,X2,Z30), (Ra8,Rb1,X2,Z31), (Ra8,Rb1,X2,Z32), (Ra8, Rb1,X2,Z33), (Ra8,Rb1,X2,Z34), (Ra8,Rb1,X2,Z35), (Ra8, Rb1,X2,Z36), (Ra8,Rb1,X2,Z37), (Ra8,Rb1,X2,Z38), (Ra8, Rb1,X2,Z39), (Ra8,Rb2,X1,Z1), (Ra8,Rb2,X1,Z2), (Ra8, Rb2,X1,Z3), (Ra8,Rb2,X1,Z4), (Ra8,Rb2,X1,Z5), (Ra8, Rb2,X1,Z6), (Ra8,Rb2,X1,Z7), (Ra8,Rb2,X1,Z8), (Ra8, Rb2,X1,Z9), (Ra8,Rb2,X1,Z10), (Ra8,Rb2,X1,Z11), (Ra8, Rb2,X1,Z12), (Ra8,Rb2,X1,Z13), (Ra8,Rb2,X1,Z14), (Ra8, Rb2,X1,Z15), (Ra8,Rb2,X1,Z16), (Ra8,Rb2,X1,Z17), (Ra8, Rb2,X1,Z18), (Ra8,Rb2,X1,Z19), (Ra8,Rb2,X1,Z20), (Ra8, Rb2,X1,Z21), (Ra8,Rb2,X1,Z22), (Ra8,Rb2,X1,Z23), (Ra8, Rb2,X1,Z24), (Ra8,Rb2,X1,Z25), (Ra8,Rb2,X1,Z26), (Ra8, Rb2,X1,Z27), (Ra8,Rb2,X1,Z28), (Ra8,Rb2,X1,Z29), (Ra8, Rb2,X1,Z30), (Ra8,Rb2,X1,Z31), (Ra8,Rb2,X1,Z32), (Ra8, Rb2,X1,Z33), (Ra8,Rb2,X1,Z34), (Ra8,Rb2,X1,Z35), (Ra8, Rb2,X1,Z36), (Ra8,Rb2,X1,Z37), (Ra8,Rb2,X1,Z38), (Ra8, Rb2,X1,Z39), (Ra8,Rb2,X2,Z1), (Ra8,Rb2,X2,Z2), (Ra8, Rb2,X2,Z3), (Ra8,Rb2,X2,Z4), (Ra8,Rb2,X2,Z5), (Ra8, Rb2,X2,Z6), (Ra8,Rb2,X2,Z7), (Ra8,Rb2,X2,Z8), (Ra8, Rb2,X2,Z9), (Ra8,Rb2,X2,Z10), (Ra8,Rb2,X2,Z11), (Ra8, Rb2,X2,Z12), (Ra8,Rb2,X2,Z13), (Ra8,Rb2,X2,Z14), (Ra8, Rb2,X2,Z15), (Ra8,Rb2,X2,Z16), (Ra8,Rb2,X2,Z17), (Ra8, Rb2,X2,Z18), (Ra8,Rb2,X2,Z19), (Ra8,Rb2,X2,Z20), (Ra8, Rb2,X2,Z21), (Ra8,Rb2,X2,Z22), (Ra8,Rb2,X2,Z23), (Ra8, Rb2,X2,Z24), (Ra8,Rb2,X2,Z25), (Ra8,Rb2,X2,Z26), (Ra8, Rb2,X2,Z27), (Ra8,Rb2,X2,Z28), (Ra8,Rb2,X2,Z29), (Ra8, Rb2,X2,Z30), (Ra8,Rb2,X2,Z31), (Ra8,Rb2,X2,Z32), (Ra8, Rb2,X2,Z33), (Ra8,Rb2,X2,Z34), (Ra8,Rb2,X2,Z35), (Ra8, Rb2,X2,Z36), (Ra8,Rb2,X2,Z37), (Ra8,Rb2,X2,Z38), (Ra8, Rb2,X2,Z39), (Ra8,Rb3,X1,Z1), (Ra8,Rb3,X1,Z2), (Ra8, Rb3,X1,Z3), (Ra8,Rb3,X1,Z4), (Ra8,Rb3,X1,Z5), (Ra8, Rb3,X1,Z6), (Ra8,Rb3,X1,Z7), (Ra8,Rb3,X1,Z8), (Ra8, Rb3,X1,Z9), (Ra8,Rb3,X1,Z10), (Ra8,Rb3,X1,Z11), (Ra8, Rb3,X1,Z12), (Ra8,Rb3,X1,Z13), (Ra8,Rb3,X1,Z14), (Ra8, Rb3,X1,Z15), (Ra8,Rb3,X1,Z16), (Ra8,Rb3,X1,Z17), (Ra8, Rb3,X1,Z18), (Ra8,Rb3,X1,Z19), (Ra8,Rb3,X1,Z20), (Ra8, Rb3,X1,Z21), (Ra8,Rb3,X1,Z22), (Ra8,Rb3,X1,Z23), (Ra8, Rb3,X1,Z24), (Ra8,Rb3,X1,Z25), (Ra8,Rb3,X1,Z26), (Ra8, Rb3,X1,Z27), (Ra8,Rb3,X1,Z28), (Ra8,Rb3,X1,Z29), (Ra8, Rb3,X1,Z30), (Ra8,Rb3,X1,Z31), (Ra8,Rb3,X1,Z32), (Ra8, Rb3,X1,Z33), (Ra8,Rb3,X1,Z34), (Ra8,Rb3,X1,Z35), (Ra8, Rb3,X1,Z36), (Ra8,Rb3,X1,Z37), (Ra8,Rb3,X1,Z38), (Ra8, Rb3,X1,Z39), (Ra8,Rb3,X2,Z1), (Ra8,Rb3,X2,Z2), (Ra8, Rb3,X2,Z3), (Ra8,Rb3,X2,Z4), (Ra8,Rb3,X2,Z5), (Ra8, Rb3,X2,Z6), (Ra8,Rb3,X2,Z7), (Ra8,Rb3,X2,Z8), (Ra8, Rb3,X2,Z9), (Ra8,Rb3,X2,Z10), (Ra8,Rb3,X2,Z11), (Ra8, Rb3,X2,Z12), (Ra8,Rb3,X2,Z13), (Ra8,Rb3,X2,Z14), (Ra8, Rb3,X2,Z15), (Ra8,Rb3,X2,Z16), (Ra8,Rb3,X2,Z17), (Ra8, Rb3,X2,Z18), (Ra8,Rb3,X2,Z19), (Ra8,Rb3,X2,Z20), (Ra8, Rb3,X2,Z21), (Ra8,Rb3,X2,Z22), (Ra8,Rb3,X2,Z23), (Ra8, Rb3,X2,Z24), (Ra8,Rb3,X2,Z25), (Ra8,Rb3,X2,Z26), (Ra8, Rb3,X2,Z27), (Ra8,Rb3,X2,Z28), (Ra8,Rb3,X2,Z29), (Ra8, Rb3,X2,Z30), (Ra8,Rb3,X2,Z31), (Ra8,Rb3,X2,Z32), (Ra8, Rb3,X2,Z33), (Ra8,Rb3,X2,Z34), (Ra8,Rb3,X2,Z35), (Ra8, Rb3,X2,Z36), (Ra8,Rb3,X2,Z37), (Ra8,Rb3,X2,Z38), (Ra8, Rb3,X2,Z39), (Ra8,Rb4,X1,Z1), (Ra8,Rb4,X1,Z2), (Ra8, Rb4,X1,Z3), (Ra8,Rb4,X1,Z4), (Ra8,Rb4,X1,Z5), (Ra8, Rb4,X1,Z6), (Ra8,Rb4,X1,Z7), (Ra8,Rb4,X1,Z8), (Ra8, Rb4,X1,Z9), (Ra8,Rb4,X1,Z10), (Ra8,Rb4,X1,Z11), (Ra8, Rb4,X1,Z12), (Ra8,Rb4,X1,Z13), (Ra8,Rb4,X1,Z14), (Ra8, Rb4,X1,Z15), (Ra8,Rb4,X1,Z16), (Ra8,Rb4,X1,Z17), (Ra8, Rb4,X1,Z18), (Ra8,Rb4,X1,Z19), (Ra8,Rb4,X1,Z20), (Ra8, Rb4,X1,Z21), (Ra8,Rb4,X1,Z22), (Ra8,Rb4,X1,Z23), (Ra8, Rb4,X1,Z24), (Ra8,Rb4,X1,Z25), (Ra8,Rb4,X1,Z26), (Ra8, Rb4,X1,Z27), (Ra8,Rb4,X1,Z28), (Ra8,Rb4,X1,Z29), (Ra8, Rb4,X1,Z30), (Ra8,Rb4,X1,Z31), (Ra8,Rb4,X1,Z32), (Ra8, Rb4,X1,Z33), (Ra8,Rb4,X1,Z34), (Ra8,Rb4,X1,Z35), (Ra8, Rb4,X1,Z36), (Ra8,Rb4,X1,Z37), (Ra8,Rb4,X1,Z38), (Ra8, Rb4,X1,Z39), (Ra8,Rb4,X2,Z1), (Ra8,Rb4,X2,Z2), (Ra8, Rb4,X2,Z3), (Ra8,Rb4,X2,Z4), (Ra8,Rb4,X2,Z5), (Ra8, Rb4,X2,Z6), (Ra8,Rb4,X2,Z7), (Ra8,Rb4,X2,Z8), (Ra8, Rb4,X2,Z9), (Ra8,Rb4,X2,Z10), (Ra8,Rb4,X2,Z11), (Ra8, Rb4,X2,Z12), (Ra8,Rb4,X2,Z13), (Ra8,Rb4,X2,Z14), (Ra8, Rb4,X2,Z15), (Ra8,Rb4,X2,Z16), (Ra8,Rb4,X2,Z17), (Ra8, Rb4,X2,Z18), (Ra8,Rb4,X2,Z19), (Ra8,Rb4,X2,Z20), (Ra8, Rb4,X2,Z21), (Ra8,Rb4,X2,Z22), (Ra8,Rb4,X2,Z23), (Ra8, Rb4,X2,Z24), (Ra8,Rb4,X2,Z25), (Ra8,Rb4,X2,Z26), (Ra8, Rb4,X2,Z27), (Ra8,Rb4,X2,Z28), (Ra8,Rb4,X2,Z29), (Ra8, Rb4,X2,Z30), (Ra8,Rb4,X2,Z31), (Ra8,Rb4,X2,Z32), (Ra8, Rb4,X2,Z33), (Ra8,Rb4,X2,Z34), (Ra8,Rb4,X2,Z35), (Ra8, Rb4,X2,Z36), (Ra8,Rb4,X2,Z37), (Ra8,Rb4,X2,Z38), (Ra8, Rb4,X2,Z39), (Ra8,Rb5,X1,Z1), (Ra8,Rb5,X1,Z2), (Ra8, Rb5,X1,Z3), (Ra8,Rb5,X1,Z4), (Ra8,Rb5,X1,Z5), (Ra8, Rb5,X1,Z6), (Ra8,Rb5,X1,Z7), (Ra8,Rb5,X1,Z8), (Ra8, Rb5,X1,Z9), (Ra8,Rb5,X1,Z10), (Ra8,Rb5,X1,Z11), (Ra8, Rb5,X1,Z12), (Ra8,Rb5,X1,Z13), (Ra8,Rb5,X1,Z14), (Ra8, Rb5,X1,Z15), (Ra8,Rb5,X1,Z16), (Ra8,Rb5,X1,Z17), (Ra8, Rb5,X1,Z18), (Ra8,Rb5,X1,Z19), (Ra8,Rb5,X1,Z20), (Ra8, Rb5,X1,Z21), (Ra8,Rb5,X1,Z22), (Ra8,Rb5,X1,Z23), (Ra8, Rb5,X1,Z24), (Ra8,Rb5,X1,Z25), (Ra8,Rb5,X1,Z26), (Ra8, Rb5,X1,Z27), (Ra8,Rb5,X1,Z28), (Ra8,Rb5,X1,Z29), (Ra8, Rb5,X1,Z30), (Ra8,Rb5,X1,Z31), (Ra8,Rb5,X1,Z32), (Ra8, Rb5,X1,Z33), (Ra8,Rb5,X1,Z34), (Ra8,Rb5,X1,Z35), (Ra8, Rb5,X1,Z36), (Ra8,Rb5,X1,Z37), (Ra8,Rb5,X1,Z38), (Ra8, Rb5,X1,Z39), (Ra8,Rb5,X2,Z1), (Ra8,Rb5,X2,Z2), (Ra8, Rb5,X2,Z3), (Ra8,Rb5,X2,Z4), (Ra8,Rb5,X2,Z5), (Ra8, Rb5,X2,Z6), (Ra8,Rb5,X2,Z7), (Ra8,Rb5,X2,Z8), (Ra8, Rb5,X2,Z9), (Ra8,Rb5,X2,Z10), (Ra8,Rb5,X2,Z11), (Ra8, Rb5,X2,Z12), (Ra8,Rb5,X2,Z13), (Ra8,Rb5,X2,Z14), (Ra8, Rb5,X2,Z15), (Ra8,Rb5,X2,Z16), (Ra8,Rb5,X2,Z17), (Ra8, Rb5,X2,Z18), (Ra8,Rb5,X2,Z19), (Ra8,Rb5,X2,Z20), (Ra8, Rb5,X2,Z21), (Ra8,Rb5,X2,Z22), (Ra8,Rb5,X2,Z23), (Ra8, Rb5,X2,Z24), (Ra8,Rb5,X2,Z25), (Ra8,Rb5,X2,Z26), (Ra8, Rb5,X2,Z27), (Ra8,Rb5,X2,Z28), (Ra8,Rb5,X2,Z29), (Ra8, Rb5,X2,Z30), (Ra8,Rb5,X2,Z31), (Ra8,Rb5,X2,Z32), (Ra8, Rb5,X2,Z33), (Ra8,Rb5,X2,Z34), (Ra8,Rb5,X2,Z35), (Ra8, Rb5,X2,Z36), (Ra8,Rb5,X2,Z37), (Ra8,Rb5,X2,Z38), (Ra8, Rb5,X2,Z39), (Ra8,Rb6,X1,Z1), (Ra8,Rb6,X1,Z2), (Ra8, Rb6,X1,Z3), (Ra8,Rb6,X1,Z4), (Ra8,Rb6,X1,Z5), (Ra8, Rb6,X1,Z6), (Ra8,Rb6,X1,Z7), (Ra8,Rb6,X1,Z8), (Ra8, Rb6,X1,Z9), (Ra8,Rb6,X1,Z10), (Ra8,Rb6,X1,Z11), (Ra8, Rb6,X1,Z12), (Ra8,Rb6,X1,Z13), (Ra8,Rb6,X1,Z14), (Ra8, Rb6,X1,Z15), (Ra8,Rb6,X1,Z16), (Ra8,Rb6,X1,Z17), (Ra8, Rb6,X1,Z18), (Ra8,Rb6,X1,Z19), (Ra8,Rb6,X1,Z20), (Ra8, Rb6,X1,Z21), (Ra8,Rb6,X1,Z22), (Ra8,Rb6,X1,Z23), (Ra8, Rb6,X1,Z24), (Ra8,Rb6,X1,Z25), (Ra8,Rb6,X1,Z26), (Ra8, Rb6,X1,Z27), (Ra8,Rb6,X1,Z28), (Ra8,Rb6,X1,Z29), (Ra8, Rb6,X1,Z30), (Ra8,Rb6,X1,Z31), (Ra8,Rb6,X1,Z32), (Ra8, Rb6,X1,Z33), (Ra8,Rb6,X1,Z34), (Ra8,Rb6,X1,Z35), (Ra8, Rb6,X1,Z36), (Ra8,Rb6,X1,Z37), (Ra8,Rb6,X1,Z38), (Ra8, Rb6,X1,Z39), (Ra8,Rb6,X2,Z1), (Ra8,Rb6,X2,Z2), (Ra8, Rb6,X2,Z3), (Ra8,Rb6,X2,Z4), (Ra8,Rb6,X2,Z5), (Ra8, Rb6,X2,Z6), (Ra8,Rb6,X2,Z7), (Ra8,Rb6,X2,Z8), (Ra8, Rb6,X2,Z9), (Ra8,Rb6,X2,Z10), (Ra8,Rb6,X2,Z11), (Ra8, Rb6,X2,Z12), (Ra8,Rb6,X2,Z13), (Ra8,Rb6,X2,Z14), (Ra8, Rb6,X2,Z15), (Ra8,Rb6,X2,Z16), (Ra8,Rb6,X2,Z17), (Ra8, Rb6,X2,Z18), (Ra8,Rb6,X2,Z19), (Ra8,Rb6,X2,Z20), (Ra8, Rb6,X2,Z21), (Ra8,Rb6,X2,Z22), (Ra8,Rb6,X2,Z23), (Ra8, Rb6,X2,Z24), (Ra8,Rb6,X2,Z25), (Ra8,Rb6,X2,Z26), (Ra8,

Rb6,X2,Z27), (Ra8,Rb6,X2,Z28), (Ra8,Rb6,X2,Z29), (Ra8, Rb6,X2,Z30), (Ra8,Rb6,X2,Z31), (Ra8,Rb6,X2,Z32), (Ra8, Rb6,X2,Z33), (Ra8,Rb6,X2,Z34), (Ra8,Rb6,X2,Z35), (Ra8, Rb6,X2,Z36), (Ra8,Rb6,X2,Z37), (Ra8,Rb6,X2,Z38), (Ra8, Rb6,X2,Z39), (Ra8,Rb7,X1,Z1), (Ra8,Rb7,X1,Z2), (Ra8, Rb7,X1,Z3), (Ra8,Rb7,X1,Z4), (Ra8,Rb7,X1,Z5), (Ra8, Rb7,X1,Z6), (Ra8,Rb7,X1,Z7), (Ra8,Rb7,X1,Z8), (Ra8, Rb7,X1,Z9), (Ra8,Rb7,X1,Z10), (Ra8,Rb7,X1,Z11), (Ra8, Rb7,X1,Z12), (Ra8,Rb7,X1,Z13), (Ra8,Rb7,X1,Z14), (Ra8, Rb7,X1,Z15), (Ra8,Rb7,X1,Z16), (Ra8,Rb7,X1,Z17), (Ra8, Rb7,X1,Z18), (Ra8,Rb7,X1,Z19), (Ra8,Rb7,X1,Z20), (Ra8, Rb7,X1,Z21), (Ra8,Rb7,X1,Z22), (Ra8,Rb7,X1,Z23), (Ra8, Rb7,X1,Z24), (Ra8,Rb7,X1,Z25), (Ra8,Rb7,X1,Z26), (Ra8, Rb7,X1,Z27), (Ra8,Rb7,X1,Z28), (Ra8,Rb7,X1,Z29), (Ra8, Rb7,X1,Z30), (Ra8,Rb7,X1,Z31), (Ra8,Rb7,X1,Z32), (Ra8, Rb7,X1,Z33), (Ra8,Rb7,X1,Z34), (Ra8,Rb7,X1,Z35), (Ra8, Rb7,X1,Z36), (Ra8,Rb7,X1,Z37), (Ra8,Rb7,X1,Z38), (Ra8, Rb7,X1,Z39), (Ra8,Rb7,X2,Z1), (Ra8,Rb7,X2,Z2), (Ra8, Rb7,X2,Z3), (Ra8,Rb7,X2,Z4), (Ra8,Rb7,X2,Z5), (Ra8, Rb7,X2,Z6), (Ra8,Rb7,X2,Z7), (Ra8,Rb7,X2,Z8), (Ra8, Rb7,X2,Z9), (Ra8,Rb7,X2,Z10), (Ra8,Rb7,X2,Z11), (Ra8, Rb7,X2,Z12), (Ra8,Rb7,X2,Z13), (Ra8,Rb7,X2,Z14), (Ra8, Rb7,X2,Z15), (Ra8,Rb7,X2,Z16), (Ra8,Rb7,X2,Z17), (Ra8, Rb7,X2,Z18), (Ra8,Rb7,X2,Z19), (Ra8,Rb7,X2,Z20), (Ra8, Rb7,X2,Z21), (Ra8,Rb7,X2,Z22), (Ra8,Rb7,X2,Z23), (Ra8, Rb7,X2,Z24), (Ra8,Rb7,X2,Z25), (Ra8,Rb7,X2,Z26), (Ra8, Rb7,X2,Z27), (Ra8,Rb7,X2,Z28), (Ra8,Rb7,X2,Z29), (Ra8, Rb7,X2,Z30), (Ra8,Rb7,X2,Z31), (Ra8,Rb7,X2,Z32), (Ra8, Rb7,X2,Z33), (Ra8,Rb7,X2,Z34), (Ra8,Rb7,X2,Z35), (Ra8, Rb7,X2,Z36), (Ra8,Rb7,X2,Z37), (Ra8,Rb7,X2,Z38), (Ra8, Rb7,X2,Z39), (Ra8,Rb8,X1,Z1), (Ra8,Rb8,X1,Z2), (Ra8, Rb8,X1,Z3), (Ra8,Rb8,X1,Z4), (Ra8,Rb8,X1,Z5), (Ra8, Rb8,X1,Z6), (Ra8,Rb8,X1,Z7), (Ra8,Rb8,X1,Z8), (Ra8, Rb8,X1,Z9), (Ra8,Rb8,X1,Z10), (Ra8,Rb8,X1,Z11), (Ra8, Rb8,X1,Z12), (Ra8,Rb8,X1,Z13), (Ra8,Rb8,X1,Z14), (Ra8, Rb8,X1,Z15), (Ra8,Rb8,X1,Z16), (Ra8,Rb8,X1,Z17), (Ra8, Rb8,X1,Z18), (Ra8,Rb8,X1,Z19), (Ra8,Rb8,X1,Z20), (Ra8, Rb8,X1,Z21), (Ra8,Rb8,X1,Z22), (Ra8,Rb8,X1,Z23), (Ra8, Rb8,X1,Z24), (Ra8,Rb8,X1,Z25), (Ra8,Rb8,X1,Z26), (Ra8, Rb8,X1,Z27), (Ra8,Rb8,X1,Z28), (Ra8,Rb8,X1,Z29), (Ra8, Rb8,X1,Z30), (Ra8,Rb8,X1,Z31), (Ra8,Rb8,X1,Z32), (Ra8, Rb8,X1,Z33), (Ra8,Rb8,X1,Z34), (Ra8,Rb8,X1,Z35), (Ra8, Rb8,X1,Z36), (Ra8,Rb8,X1,Z37), (Ra8,Rb8,X1,Z38), (Ra8, Rb8,X1,Z39), (Ra8,Rb8,X2,Z1), (Ra8,Rb8,X2,Z2), (Ra8, Rb8,X2,Z3), (Ra8,Rb8,X2,Z4), (Ra8,Rb8,X2,Z5), (Ra8, Rb8,X2,Z6), (Ra8,Rb8,X2,Z7), (Ra8,Rb8,X2,Z8), (Ra8, Rb8,X2,Z9), (Ra8,Rb8,X2,Z10), (Ra8,Rb8,X2,Z11), (Ra8, Rb8,X2,Z12), (Ra8,Rb8,X2,Z13), (Ra8,Rb8,X2,Z14), (Ra8, Rb8,X2,Z15), (Ra8,Rb8,X2,Z16), (Ra8,Rb8,X2,Z17), (Ra8, Rb8,X2,Z18), (Ra8,Rb8,X2,Z19), (Ra8,Rb8,X2,Z20), (Ra8, Rb8,X2,Z21), (Ra8,Rb8,X2,Z22), (Ra8,Rb8,X2,Z23), (Ra8, Rb8,X2,Z24), (Ra8,Rb8,X2,Z25), (Ra8,Rb8,X2,Z26), (Ra8, Rb8,X2,Z27), (Ra8,Rb8,X2,Z28), (Ra8,Rb8,X2,Z29), (Ra8, Rb8,X2,Z30), (Ra8,Rb8,X2,Z31), (Ra8,Rb8,X2,Z32), (Ra8, Rb8,X2,Z33), (Ra8,Rb8,X2,Z34), (Ra8,Rb8,X2,Z35), (Ra8, Rb8,X2,Z36), (Ra8,Rb8,X2,Z37), (Ra8,Rb8,X2,Z38), (Ra8, Rb8,X2,Z39), (Ra9,Rb1,X1,Z1), (Ra9,Rb1,X1,Z2), (Ra9, Rb1,X1,Z3), (Ra9,Rb1,X1,Z4), (Ra9,Rb1,X1,Z5), (Ra9, Rb1,X1,Z6), (Ra9,Rb1,X1,Z7), (Ra9,Rb1,X1,Z8), (Ra9, Rb1,X1,Z9), (Ra9,Rb1,X1,Z10), (Ra9,Rb1,X1,Z11), (Ra9, Rb1,X1,Z12), (Ra9,Rb1,X1,Z13), (Ra9,Rb1,X1,Z14), (Ra9, Rb1,X1,Z15), (Ra9,Rb1,X1,Z16), (Ra9,Rb1,X1,Z17), (Ra9, Rb1,X1,Z18), (Ra9,Rb1,X1,Z19), (Ra9,Rb1,X1,Z20), (Ra9, Rb1,X1,Z21), (Ra9,Rb1,X1,Z22), (Ra9,Rb1,X1,Z23), (Ra9, Rb1,X1,Z24), (Ra9,Rb1,X1,Z25), (Ra9,Rb1,X1,Z26), (Ra9, Rb1,X1,Z27), (Ra9,Rb1,X1,Z28), (Ra9,Rb1,X1,Z29), (Ra9, Rb1,X1,Z30), (Ra9,Rb1,X1,Z31), (Ra9,Rb1,X1,Z32), (Ra9, Rb1,X1,Z33), (Ra9,Rb1,X1,Z34), (Ra9,Rb1,X1,Z35), (Ra9, Rb1,X1,Z36), (Ra9,Rb1,X1,Z37), (Ra9,Rb1,X1,Z38), (Ra9, Rb1,X1,Z39), (Ra9,Rb1,X2,Z1), (Ra9,Rb1,X2,Z2), (Ra9, Rb1,X2,Z3), (Ra9,Rb1,X2,Z4), (Ra9,Rb1,X2,Z5), (Ra9, Rb1,X2,Z6), (Ra9,Rb1,X2,Z7), (Ra9,Rb1,X2,Z8), (Ra9, Rb1,X2,Z9), (Ra9,Rb1,X2,Z10), (Ra9,Rb1,X2,Z11), (Ra9, Rb1,X2,Z12), (Ra9,Rb1,X2,Z13), (Ra9,Rb1,X2,Z14), (Ra9, Rb1,X2,Z15), (Ra9,Rb1,X2,Z16), (Ra9,Rb1,X2,Z17), (Ra9, Rb1,X2,Z18), (Ra9,Rb1,X2,Z19), (Ra9,Rb1,X2,Z20), (Ra9, Rb1,X2,Z21), (Ra9,Rb1,X2,Z22), (Ra9,Rb1,X2,Z23), (Ra9, Rb1,X2,Z24), (Ra9,Rb1,X2,Z25), (Ra9,Rb1,X2,Z26), (Ra9, Rb1,X2,Z27), (Ra9,Rb1,X2,Z28), (Ra9,Rb1,X2,Z29), (Ra9, Rb1,X2,Z30), (Ra9,Rb1,X2,Z31), (Ra9,Rb1,X2,Z32), (Ra9, Rb1,X2,Z33), (Ra9,Rb1,X2,Z34), (Ra9,Rb1,X2,Z35), (Ra9, Rb1,X2,Z36), (Ra9,Rb1,X2,Z37), (Ra9,Rb1,X2,Z38), (Ra9, Rb1,X2,Z39), (Ra9,Rb2,X1,Z1), (Ra9,Rb2,X1,Z2), (Ra9, Rb2,X1,Z3), (Ra9,Rb2,X1,Z4), (Ra9,Rb2,X1,Z5), (Ra9, Rb2,X1,Z6), (Ra9,Rb2,X1,Z7), (Ra9,Rb2,X1,Z8), (Ra9, Rb2,X1,Z9), (Ra9,Rb2,X1,Z10), (Ra9,Rb2,X1,Z11), (Ra9, Rb2,X1,Z12), (Ra9,Rb2,X1,Z13), (Ra9,Rb2,X1,Z14), (Ra9, Rb2,X1,Z15), (Ra9,Rb2,X1,Z16), (Ra9,Rb2,X1,Z17), (Ra9, Rb2,X1,Z18), (Ra9,Rb2,X1,Z19), (Ra9,Rb2,X1,Z20), (Ra9, Rb2,X1,Z21), (Ra9,Rb2,X1,Z22), (Ra9,Rb2,X1,Z23), (Ra9, Rb2,X1,Z24), (Ra9,Rb2,X1,Z25), (Ra9,Rb2,X1,Z26), (Ra9, Rb2,X1,Z27), (Ra9,Rb2,X1,Z28), (Ra9,Rb2,X1,Z29), (Ra9, Rb2,X1,Z30), (Ra9,Rb2,X1,Z31), (Ra9,Rb2,X1,Z32), (Ra9, Rb2,X1,Z33), (Ra9,Rb2,X1,Z34), (Ra9,Rb2,X1,Z35), (Ra9, Rb2,X1,Z36), (Ra9,Rb2,X1,Z37), (Ra9,Rb2,X1,Z38), (Ra9, Rb2,X1,Z39), (Ra9,Rb2,X2,Z1), (Ra9,Rb2,X2,Z2), (Ra9, Rb2,X2,Z3), (Ra9,Rb2,X2,Z4), (Ra9,Rb2,X2,Z5), (Ra9, Rb2,X2,Z6), (Ra9,Rb2,X2,Z7), (Ra9,Rb2,X2,Z8), (Ra9, Rb2,X2,Z9), (Ra9,Rb2,X2,Z10), (Ra9,Rb2,X2,Z11), (Ra9, Rb2,X2,Z12), (Ra9,Rb2,X2,Z13), (Ra9,Rb2,X2,Z14), (Ra9, Rb2,X2,Z15), (Ra9,Rb2,X2,Z16), (Ra9,Rb2,X2,Z17), (Ra9, Rb2,X2,Z18), (Ra9,Rb2,X2,Z19), (Ra9,Rb2,X2,Z20), (Ra9, Rb2,X2,Z21), (Ra9,Rb2,X2,Z22), (Ra9,Rb2,X2,Z23), (Ra9, Rb2,X2,Z24), (Ra9,Rb2,X2,Z25), (Ra9,Rb2,X2,Z26), (Ra9, Rb2,X2,Z27), (Ra9,Rb2,X2,Z28), (Ra9,Rb2,X2,Z29), (Ra9, Rb2,X2,Z30), (Ra9,Rb2,X2,Z31), (Ra9,Rb2,X2,Z32), (Ra9, Rb2,X2,Z33), (Ra9,Rb2,X2,Z34), (Ra9,Rb2,X2,Z35), (Ra9, Rb2,X2,Z36), (Ra9,Rb2,X2,Z37), (Ra9,Rb2,X2,Z38), (Ra9, Rb2,X2,Z39), (Ra9,Rb3,X1,Z1), (Ra9,Rb3,X1,Z2), (Ra9, Rb3,X1,Z3), (Ra9,Rb3,X1,Z4), (Ra9,Rb3,X1,Z5), (Ra9, Rb3,X1,Z6), (Ra9,Rb3,X1,Z7), (Ra9,Rb3,X1,Z8), (Ra9, Rb3,X1,Z9), (Ra9,Rb3,X1,Z10), (Ra9,Rb3,X1,Z11), (Ra9, Rb3,X1,Z12), (Ra9,Rb3,X1,Z13), (Ra9,Rb3,X1,Z14), (Ra9, Rb3,X1,Z15), (Ra9,Rb3,X1,Z16), (Ra9,Rb3,X1,Z17), (Ra9, Rb3,X1,Z18), (Ra9,Rb3,X1,Z19), (Ra9,Rb3,X1,Z20), (Ra9, Rb3,X1,Z21), (Ra9,Rb3,X1,Z22), (Ra9,Rb3,X1,Z23), (Ra9, Rb3,X1,Z24), (Ra9,Rb3,X1,Z25), (Ra9,Rb3,X1,Z26), (Ra9, Rb3,X1,Z27), (Ra9,Rb3,X1,Z28), (Ra9,Rb3,X1,Z29), (Ra9, Rb3,X1,Z30), (Ra9,Rb3,X1,Z31), (Ra9,Rb3,X1,Z32), (Ra9, Rb3,X1,Z33), (Ra9,Rb3,X1,Z34), (Ra9,Rb3,X1,Z35), (Ra9, Rb3,X1,Z36), (Ra9,Rb3,X1,Z37), (Ra9,Rb3,X1,Z38), (Ra9, Rb3,X1,Z39), (Ra9,Rb3,X2,Z1), (Ra9,Rb3,X2,Z2), (Ra9, Rb3,X2,Z3), (Ra9,Rb3,X2,Z4), (Ra9,Rb3,X2,Z5), (Ra9, Rb3,X2,Z6), (Ra9,Rb3,X2,Z7), (Ra9,Rb3,X2,Z8), (Ra9, Rb3,X2,Z9), (Ra9,Rb3,X2,Z (Ra9,Rb3,X2,Z11), (Ra9,Rb3, X2,Z12), (Ra9,Rb3,X2,Z13), (Ra9,Rb3,X2,Z14), (Ra9,Rb3, X2,Z15), (Ra9,Rb3,X2,Z16), (Ra9,Rb3,X2,Z17), (Ra9,Rb3, X2,Z18), (Ra9,Rb3,X2,Z19), (Ra9,Rb3,X2,Z20), (Ra9,Rb3, X2,Z21), (Ra9,Rb3,X2,Z22), (Ra9,Rb3,X2,Z23), (Ra9,Rb3, X2,Z24), (Ra9,Rb3,X2,Z25), (Ra9,Rb3,X2,Z26), (Ra9,Rb3, X2,Z27), (Ra9,Rb3,X2,Z28), (Ra9,Rb3,X2,Z29), (Ra9,Rb3, X2,Z30), (Ra9,Rb3,X2,Z31), (Ra9,Rb3,X2,Z32), (Ra9,Rb3, X2,Z33), (Ra9,Rb3,X2,Z34), (Ra9,Rb3,X2,Z35), (Ra9,Rb3, X2,Z36), (Ra9,Rb3,X2,Z37), (Ra9,Rb3,X2,Z38), (Ra9,Rb3,

X2,Z39), (Ra9,Rb4,X1,Z1), (Ra9,Rb4,X1,Z2), (Ra9,Rb4,X1,Z3), (Ra9,Rb4,X1,Z4), (Ra9,Rb4,X1,Z5), (Ra9,Rb4,X1,Z6), (Ra9,Rb4,X1,Z7), (Ra9,Rb4,X1,Z8), (Ra9,Rb4,X1,Z9), (Ra9,Rb4,X1,Z10), (Ra9,Rb4,X1,Z11), (Ra9,Rb4,X1,Z12), (Ra9,Rb4,X1,Z13), (Ra9,Rb4,X1,Z14), (Ra9,Rb4,X1,Z15), (Ra9,Rb4,X1,Z16), (Ra9,Rb4,X1,Z17), (Ra9,Rb4,X1,Z18), (Ra9,Rb4,X1,Z19), (Ra9,Rb4,X1,Z20), (Ra9,Rb4,X1,Z21), (Ra9,Rb4,X1,Z22), (Ra9,Rb4,X1,Z23), (Ra9,Rb4,X1,Z24), (Ra9,Rb4,X1,Z25), (Ra9,Rb4,X1,Z26), (Ra9,Rb4,X1,Z27), (Ra9,Rb4,X1,Z28), (Ra9,Rb4,X1,Z29), (Ra9,Rb4,X1,Z30), (Ra9,Rb4,X1,Z31), (Ra9,Rb4,X1,Z32), (Ra9,Rb4,X1,Z33), (Ra9,Rb4,X1,Z34), (Ra9,Rb4,X1,Z35), (Ra9,Rb4,X1,Z36), (Ra9,Rb4,X1,Z37), (Ra9,Rb4,X1,Z38), (Ra9,Rb4,X1,Z39), (Ra9,Rb4,X2,Z1), (Ra9,Rb4,X2,Z2), (Ra9,Rb4,X2,Z3), (Ra9,Rb4,X2,Z4), (Ra9,Rb4,X2,Z5), (Ra9,Rb4,X2,Z6), (Ra9,Rb4,X2,Z7), (Ra9,Rb4,X2,Z8), (Ra9,Rb4,X2,Z9), (Ra9,Rb4,X2,Z10), (Ra9,Rb4,X2,Z11), (Ra9,Rb4,X2,Z12), (Ra9,Rb4,X2,Z13), (Ra9,Rb4,X2,Z14), (Ra9,Rb4,X2,Z15), (Ra9,Rb4,X2,Z16), (Ra9,Rb4,X2,Z17), (Ra9,Rb4,X2,Z18), (Ra9,Rb4,X2,Z19), (Ra9,Rb4,X2,Z20), (Ra9,Rb4,X2,Z21), (Ra9,Rb4,X2,Z22), (Ra9,Rb4,X2,Z23), (Ra9,Rb4,X2,Z24), (Ra9,Rb4,X2,Z25), (Ra9,Rb4,X2,Z26), (Ra9,Rb4,X2,Z27), (Ra9,Rb4,X2,Z28), (Ra9,Rb4,X2,Z29), (Ra9,Rb4,X2,Z30), (Ra9,Rb4,X2,Z31), (Ra9,Rb4,X2,Z32), (Ra9,Rb4,X2,Z33), (Ra9,Rb4,X2,Z34), (Ra9,Rb4,X2,Z35), (Ra9,Rb4,X2,Z36), (Ra9,Rb4,X2,Z37), (Ra9,Rb4,X2,Z38), (Ra9,Rb4,X2,Z39), (Ra9,Rb5,X1,Z1), (Ra9,Rb5,X1,Z2), (Ra9,Rb5,X1,Z3), (Ra9,Rb5,X1,Z4), (Ra9,Rb5,X1,Z5), (Ra9,Rb5,X1,Z6), (Ra9,Rb5,X1,Z7), (Ra9,Rb5,X1,Z8), (Ra9,Rb5,X1,Z9), (Ra9,Rb5,X1,Z10), (Ra9,Rb5,X1,Z11), (Ra9,Rb5,X1,Z12), (Ra9,Rb5,X1,Z13), (Ra9,Rb5,X1,Z14), (Ra9,Rb5,X1,Z15), (Ra9,Rb5,X1,Z16), (Ra9,Rb5,X1,Z17), (Ra9,Rb5,X1,Z18), (Ra9,Rb5,X1,Z19), (Ra9,Rb5,X1,Z20), (Ra9,Rb5,X1,Z21), (Ra9,Rb5,X1,Z22), (Ra9,Rb5,X1,Z23), (Ra9,Rb5,X1,Z24), (Ra9,Rb5,X1,Z25), (Ra9,Rb5,X1,Z26), (Ra9,Rb5,X1,Z27), (Ra9,Rb5,X1,Z28), (Ra9,Rb5,X1,Z29), (Ra9,Rb5,X1,Z30), (Ra9,Rb5,X1,Z31), (Ra9,Rb5,X1,Z32), (Ra9,Rb5,X1,Z33), (Ra9,Rb5,X1,Z34), (Ra9,Rb5,X1,Z35), (Ra9,Rb5,X1,Z36), (Ra9,Rb5,X1,Z37), (Ra9,Rb5,X1,Z38), (Ra9,Rb5,X1,Z39), (Ra9,Rb5,X2,Z1), (Ra9,Rb5,X2,Z2), (Ra9,Rb5,X2,Z3), (Ra9,Rb5,X2,Z4), (Ra9,Rb5,X2,Z5), (Ra9,Rb5,X2,Z6), (Ra9,Rb5,X2,Z7), (Ra9,Rb5,X2,Z8), (Ra9,Rb5,X2,Z9), (Ra9,Rb5,X2,Z10), (Ra9,Rb5,X2,Z11), (Ra9,Rb5,X2,Z12), (Ra9,Rb5,X2,Z13), (Ra9,Rb5,X2,Z14), (Ra9,Rb5,X2,Z15), (Ra9,Rb5,X2,Z16), (Ra9,Rb5,X2,Z17), (Ra9,Rb5,X2,Z18), (Ra9,Rb5,X2,Z19), (Ra9,Rb5,X2,Z20), (Ra9,Rb5,X2,Z21), (Ra9,Rb5,X2,Z22), (Ra9,Rb5,X2,Z23), (Ra9,Rb5,X2,Z24), (Ra9,Rb5,X2,Z25), (Ra9,Rb5,X2,Z26), (Ra9,Rb5,X2,Z27), (Ra9,Rb5,X2,Z28), (Ra9,Rb5,X2,Z29), (Ra9,Rb5,X2,Z30), (Ra9,Rb5,X2,Z31), (Ra9,Rb5,X2,Z32), (Ra9,Rb5,X2,Z33), (Ra9,Rb5,X2,Z34), (Ra9,Rb5,X2,Z35), (Ra9,Rb5,X2,Z36), (Ra9,Rb5,X2,Z37), (Ra9,Rb5,X2,Z38), (Ra9,Rb5,X2,Z39), (Ra9,Rb6,X1,Z1), (Ra9,Rb6,X1,Z2), (Ra9,Rb6,X1,Z3), (Ra9,Rb6,X1,Z4), (Ra9,Rb6,X1,Z5), (Ra9,Rb6,X1,Z6), (Ra9,Rb6,X1,Z7), (Ra9,Rb6,X1,Z8), (Ra9,Rb6,X1,Z9), (Ra9,Rb8,X1,Z10), (Ra9,Rb6,X1,Z11), (Ra9,Rb6,X1,Z12), (Ra9,Rb6,X1,Z13), (Ra9,Rb6,X1,Z14), (Ra9,Rb6,X1,Z15), (Ra9,Rb6,X1,Z16), (Ra9,Rb6,X1,Z17), (Ra9,Rb6,X1,Z18), (Ra9,Rb6,X1,Z19), (Ra9,Rb6,X1,Z20), (Ra9,Rb6,X1,Z21), (Ra9,Rb6,X1,Z22), (Ra9,Rb6,X1,Z23), (Ra9,Rb6,X1,Z24), (Ra9,Rb6,X1,Z25), (Ra9,Rb6,X1,Z26), (Ra9,Rb6,X1,Z27), (Ra9,Rb6,X1,Z28), (Ra9,Rb6,X1,Z29), (Ra9,Rb6,X1,Z30), (Ra9,Rb6,X1,Z31), (Ra9,Rb6,X1,Z32), (Ra9,Rb6,X1,Z33), (Ra9,Rb6,X1,Z34), (Ra9,Rb6,X1,Z35), (Ra9,Rb6,X1,Z36), (Ra9,Rb6,X1,Z37), (Ra9,Rb6,X1,Z38), (Ra9,Rb6,X1,Z39), (Ra9,Rb6,X2,Z1), (Ra9,Rb6,X2,Z2), (Ra9,Rb6,X2,Z3), (Ra9,Rb6,X2,Z4), (Ra9,Rb6,X2,Z5), (Ra9,Rb6,X2,Z6), (Ra9,Rb6,X2,Z7), (Ra9,Rb6,X2,Z8), (Ra9,Rb6,X2,Z9), (Ra9,Rb6,X2,Z10), (Ra9,Rb6,X2,Z11), (Ra9,Rb6,X2,Z12), (Ra9,Rb6,X2,Z13), (Ra9,Rb6,X2,Z14), (Ra9,Rb6,X2,Z15), (Ra9,Rb6,X2,Z16), (Ra9,Rb6,X2,Z17), (Ra9,Rb6,X2,Z18), (Ra9,Rb6,X2,Z19), (Ra9,Rb6,X2,Z20), (Ra9,Rb6,X2,Z21), (Ra9,Rb6,X2,Z22), (Ra9,Rb6,X2,Z23), (Ra9,Rb6,X2,Z24), (Ra9,Rb6,X2,Z25), (Ra9,Rb6,X2,Z26), (Ra9,Rb6,X2,Z27), (Ra9,Rb6,X2,Z28), (Ra9,Rb6,X2,Z29), (Ra9,Rb6,X2,Z30), (Ra9,Rb6,X2,Z31), (Ra9,Rb6,X2,Z32), (Ra9,Rb6,X2,Z33), (Ra9,Rb6,X2,Z34), (Ra9,Rb6,X2,Z35), (Ra9,Rb6,X2,Z36), (Ra9,Rb6,X2,Z37), (Ra9,Rb8,X2,Z38), (Ra9,Rb6,X2,Z39), (Ra9,Rb7,X1,Z1), (Ra9,Rb7,X1,Z2), (Ra9,Rb7,X1,Z3), (Ra9,Rb7,X1,Z4), (Ra9,Rb7,X1,Z5), (Ra9,Rb7,X1,Z6), (Ra9,Rb7,X1,Z7), (Ra9,Rb7,X1,Z8), (Ra9,Rb7,X1,Z9), (Ra9,Rb7,X1,Z10), (Ra9,Rb7,X1,Z11), (Ra9,Rb7,X1,Z12), (Ra9,Rb7,X1,Z13), (Ra9,Rb7,X1,Z14), (Ra9,Rb7,X1,Z15), (Ra9,Rb7,X1,Z16), (Ra9,Rb7,X1,Z17), (Ra9,Rb7,X1,Z18), (Ra9,Rb7,X1,Z19), (Ra9,Rb7,X1,Z20), (Ra9,Rb7,X1,Z21), (Ra9,Rb7,X1,Z22), (Ra9,Rb7,X1,Z23), (Ra9,Rb7,X1,Z24), (Ra9,Rb7,X1,Z25), (Ra9,Rb7,X1,Z26), (Ra9,Rb7,X1,Z27), (Ra9,Rb7,X1,Z28), (Ra9,Rb7,X1,Z29), (Ra9,Rb7,X1,Z30), (Ra9,Rb7,X1,Z31), (Ra9,Rb7,X1,Z32), (Ra9,Rb7,X1,Z33), (Ra9,Rb7,X1,Z34), (Ra9,Rb7,X1,Z35), (Ra9,Rb7,X1,Z36), (Ra9,Rb7,X1,Z37), (Ra9,Rb7,X1,Z38), (Ra9,Rb7,X1,Z39), (Ra9,Rb7,X2,Z1), (Ra9,Rb7,X2,Z2), (Ra9,Rb7,X2,Z3), (Ra9,Rb7,X2,Z4), (Ra9,Rb7,X2,Z5), (Ra9,Rb7,X2,Z8), (Ra9,Rb7,X2,Z7), (Ra9,Rb7,X2,Z8), (Ra9,Rb7,X2,Z9), (Ra9,Rb7,X2,Z10), (Ra9,Rb7,X2,Z11), (Ra9,Rb7,X2,Z12), (Ra9,Rb7,X2,Z13), (Ra9,Rb7,X2,Z14), (Ra9,Rb7,X2,Z15), (Ra9,Rb7,X2,Z16), (Ra9,Rb7,X2,Z17), (Ra9,Rb7,X2,Z18), (Ra9,Rb7,X2,Z19), (Ra9,Rb7,X2,Z20), (Ra9,Rb7,X2,Z21), (Ra9,Rb7,X2,Z22), (Ra9,Rb7,X2,Z23), (Ra9,Rb7,X2,Z24), (Ra9,Rb7,X2,Z25), (Ra9,Rb7,X2,Z26), (Ra9,Rb7,X2,Z27), (Ra9,Rb7,X2,Z28), (Ra9,Rb7,X2,Z29), (Ra9,Rb7,X2,Z30), (Ra9,Rb7,X2,Z31), (Ra9,Rb7,X2,Z32), (Ra9,Rb7,X2,Z33), (Ra9,Rb7,X2,Z34), (Ra9,Rb7,X2,Z35), (Ra9,Rb7,X2,Z36), (Ra9,Rb7,X2,Z37), (Ra9,Rb7,X2,Z38), (Ra9,Rb7,X2,Z39), (Ra9,Rb8,X1,Z1), (Ra9,Rb8,X1,Z2), (Ra9,Rb8,X1,Z3), (Ra9,Rb8,X1,Z4), (Ra9,Rb8,X1,Z5), (Ra9,Rb8,X1,Z6), (Ra9,Rb8,X1,Z7), (Ra9,Rb8,X1,Z8), (Ra9,Rb8,X1,Z9), (Ra9,Rb8,X1,Z10), (Ra9,Rb8,X1,Z11), (Ra9,Rb8,X1,Z12), (Ra9,Rb8,X1,Z13), (Ra9,Rb8,X1,Z14), (Ra9,Rb8,X1,Z15), (Ra9,Rb8,X1,Z16), (Ra9,Rb8,X1,Z17), (Ra9,Rb8,X1,Z18), (Ra9,Rb8,X1,Z19), (Ra9,Rb8,X1,Z20), (Ra9,Rb8,X1,Z21), (Ra9,Rb8,X1,Z22), (Ra9,Rb8,X1,Z23), (Ra9,Rb8,X1,Z24), (Ra9,Rb8,X1,Z25), (Ra9,Rb8,X1,Z26), (Ra9,Rb8,X1,Z27), (Ra9,Rb8,X1,Z28), (Ra9,Rb8,X1,Z29), (Ra9,Rb8,X1,Z30), (Ra9,Rb8,X1,Z31), (Ra9,Rb8,X1,Z32), (Ra9,Rb8,X1,Z33), (Ra9,Rb8,X1,Z34), (Ra9,Rb8,X1,Z35), (Ra9,Rb8,X1,Z36), (Ra9,Rb8,X1,Z37), (Ra9,Rb8,X1,Z38), (Ra9,Rb8,X1,Z39), (Ra9,Rb8,X2,Z1), (Ra9,Rb8,X2,Z2), (Ra9,Rb8,X2,Z3), (Ra9,Rb8,X2,Z4), (Ra9,Rb8,X2,Z5), (Ra9,Rb8,X2,Z6), (Ra9,Rb8,X2,Z7), (Ra9,Rb8,X2,Z8), (Ra9,Rb8,X2,Z9), (Ra9,Rb8,X2,Z10), (Ra9,Rb8,X2,Z11), (Ra9,Rb8,X2,Z12), (Ra9,Rb8,X2,Z13), (Ra9,Rb8,X2,Z14), (Ra9,Rb8,X2,Z15), (Ra9,Rb8,X2,Z16), (Ra9,Rb8,X2,Z17), (Ra9,Rb8,X2,Z18), (Ra9,Rb8,X2,Z19), (Ra9,Rb8,X2,Z20), (Ra9,Rb8,X2,Z21), (Ra9,Rb8,X2,Z22), (Ra9,Rb8,X2,Z23), (Ra9,Rb8,X2,Z24), (Ra9,Rb8,X2,Z25), (Ra9,Rb8,X2,Z26), (Ra9,Rb8,X2,Z27), (Ra9,Rb8,X2,Z28), (Ra9,Rb8,X2,Z29), (Ra9,Rb8,X2,Z30), (Ra9,Rb8,X2,Z31), (Ra9,Rb8,X2,Z32), (Ra9,Rb8,X2,Z33), (Ra9,Rb8,X2,Z34), (Ra9,Rb8,X2,Z35), (Ra9,Rb8,X2,Z36), (Ra9,Rb8,X2,Z37), (Ra9,Rb8,X2,Z38), (Ra9,Rb8,X2,Z39), (Ra10,Rb1,X1,Z1), (Ra10,Rb1,X1,Z2), (Ra10,Rb1,X1,Z3), (Ra10,Rb1,X1,Z4), (Ra10,Rb1,X1,Z5), (Ra10,Rb1,X1,Z6), (Ra10,Rb1,X1,Z7), (Ra10,Rb1,X1,Z8), (Ra10,Rb1,X1,Z9), (Ra10,Rb1,X1,Z10), (Ra10,Rb1,X1,Z11), (Ra10,Rb1,X1,

Z12), (Ra10,Rb1,X1,Z13), (Ra10,Rb1,X1,Z14), (Ra10,Rb1,X1,Z15), (Ra10,Rb1,X1,Z16), (Ra10,Rb1,X1,Z17), (Ra10,Rb1,X1,Z18), (Ra10,Rb1,X1,Z19), (Ra10,Rb1,X1,Z20), (Ra10,Rb1,X1,Z21), (Ra10,Rb1,X1,Z22), (Ra10,Rb1,X1,Z23), (Ra10,Rb1,X1,Z24), (Ra10,Rb1,X1,Z25), (Ra10,Rb1,X1,Z26), (Ra10,Rb1,X1,Z27), (Ra10,Rb1,X1,Z28), (Ra10,Rb1,X1,Z29), (Ra10,Rb1,X1,Z30), (Ra10,Rb1,X1,Z31), (Ra10,Rb1,X1,Z32), (Ra10,Rb1,X1,Z33), (Ra10,Rb1,X1,Z34), (Ra10,Rb1,X1,Z35), (Ra10,Rb1,X1,Z36), (Ra10,Rb1,X1,Z37), (Ra10,Rb1,X1,Z38), (Ra10,Rb1,X1,Z39), (Ra10,Rb1,X2,Z1), (Ra10,Rb1,X2,Z2), (Ra10,Rb1,X2,Z3), (Ra10,Rb1,X2,Z4), (Ra10,Rb1,X2,Z5), (Ra10,Rb1,X2,Z6), (Ra10,Rb1,X2,Z7), (Ra10,Rb1,X2,Z8), (Ra10,Rb1,X2,Z9), (Ra10,Rb1,X2,Z10), (Ra10,Rb1,X2,Z11), (Ra10,Rb1,X2,Z12), (Ra10,Rb1,X2,Z13), (Ra10,Rb1,X2,Z14), (Ra10,Rb1,X2,Z15), (Ra10,Rb1,X2,Z16), (Ra10,Rb1,X2,Z17), (Ra10,Rb1,X2,Z18), (Ra10,Rb1,X2,Z19), (Ra10,Rb1,X2,Z20), (Ra10,Rb1,X2,Z21), (Ra10,Rb1,X2,Z22), (Ra10,Rb1,X2,Z23), (Ra10,Rb1,X2,Z24), (Ra10,Rb1,X2,Z25), (Ra10,Rb1,X2,Z26), (Ra10,Rb1,X2,Z27), (Ra10,Rb1,X2,Z28), (Ra10,Rb1,X2,Z29), (Ra10,Rb1,X2,Z30), (Ra10,Rb1,X2,Z31), (Ra10,Rb1,X2,Z32), (Ra10,Rb1,X2,Z33), (Ra10,Rb1,X2,Z34), (Ra10,Rb1,X2,Z35), (Ra10,Rb1,X2,Z36), (Ra10,Rb1,X2,Z37), (Ra10,Rb1,X2,Z38), (Ra10,Rb1,X2,Z39), (Ra10,Rb2,X1,Z1), (Ra10,Rb2,X1,Z2), (Ra10,Rb2,X1,Z3), (Ra10,Rb2,X1,Z4), (Ra10,Rb2,X1,Z5), (Ra10,Rb2,X1,Z6), (Ra10,Rb2,X1,Z7), (Ra10,Rb2,X1,Z8), (Ra10,Rb2,X1,Z9), (Ra10,Rb2,X1,Z10), (Ra10,Rb2,X1,Z11), (Ra10,Rb2,X1,Z12), (Ra10,Rb2,X1,Z13), (Ra10,Rb2,X1,Z14), (Ra10,Rb2,X1,Z15), (Ra10,Rb2,X1,Z16), (Ra10,Rb2,X1,Z17), (Ra10,Rb2,X1,Z18), (Ra10,Rb2,X1,Z19), (Ra10,Rb2,X1,Z20), (Ra10,Rb2,X1,Z21), (Ra10,Rb2,X1,Z22), (Ra10,Rb2,X1,Z23), (Ra10,Rb2,X1,Z24), (Ra10,Rb2,X1,Z25), (Ra10,Rb2,X1,Z26), (Ra10,Rb2,X1,Z27), (Ra10,Rb2,X1,Z28), (Ra10,Rb2,X1,Z29), (Ra10,Rb2,X1,Z30), (Ra10,Rb2,X1,Z31), (Ra10,Rb2,X1,Z32), (Ra10,Rb2,X1,Z33), (Ra10,Rb2,X1,Z34), (Ra10,Rb2,X1,Z35), (Ra10,Rb2,X1,Z36), (Ra10,Rb2,X1,Z37), (Ra10,Rb2,X1,Z38), (Ra10,Rb2,X1,Z39), (Ra10,Rb2,X2,Z1), (Ra10,Rb2,X2,Z2), (Ra10,Rb2,X2,Z3), (Ra10,Rb2,X2,Z4), (Ra10,Rb2,X2,Z5), (Ra10,Rb2,X2,Z6), (Ra10,Rb2,X2,Z7), (Ra10,Rb2,X2,Z8), (Ra10,Rb2,X2,Z9), (Ra10,Rb2,X2,Z10), (Ra10,Rb2,X2,Z11), (Ra10,Rb2,X2,Z12), (Ra10,Rb2,X2,Z13), (Ra10,Rb2,X2,Z14), (Ra10,Rb2,X2,Z15), (Ra10,Rb2,X2,Z16), (Ra10,Rb2,X2,Z17), (Ra10,Rb2,X2,Z18), (Ra10,Rb2,X2,Z19), (Ra10,Rb2,X2,Z20), (Ra10,Rb2,X2,Z21), (Ra10,Rb2,X2,Z22), (Ra10,Rb2,X2,Z23), (Ra10,Rb2,X2,Z24), (Ra10,Rb2,X2,Z25), (Ra10,Rb2,X2,Z26), (Ra10,Rb2,X2,Z27), (Ra10,Rb2,X2,Z28), (Ra10,Rb2,X2,Z29), (Ra10,Rb2,X2,Z30), (Ra10,Rb2,X2,Z31), (Ra10,Rb2,X2,Z32), (Ra10,Rb2,X2,Z33), (Ra10,Rb2,X2,Z34), (Ra10,Rb2,X2,Z35), (Ra10,Rb2,X2,Z36), (Ra10,Rb2,X2,Z37), (Ra10,Rb2,X2,Z38), (Ra10,Rb2,X2,Z39), (Ra10,Rb3,X1,Z1), (Ra10,Rb3,X1,Z2), (Ra10,Rb3,X1,Z3), (Ra10,Rb3,X1,Z4), (Ra10,Rb3,X1,Z5), (Ra10,Rb3,X1,Z6), (Ra10,Rb3,X1,Z7), (Ra10,Rb3,X1,Z8), (Ra10,Rb3,X1,Z9), (Ra10,Rb3,X1,Z10), (Ra10,Rb3,X1,Z11), (Ra10,Rb3,X1,Z12), (Ra10,Rb3,X1,Z13), (Ra10,Rb3,X1,Z14), (Ra10,Rb3,X1,Z15), (Ra10,Rb3,X1,Z16), (Ra10,Rb3,X1,Z17), (Ra10,Rb3,X1,Z18), (Ra10,Rb3,X1,Z19), (Ra10,Rb3,X1,Z20), (Ra10,Rb3,X1,Z21), (Ra10,Rb3,X1,Z22), (Ra10,Rb3,X1,Z23), (Ra10,Rb3,X1,Z24), (Ra10,Rb3,X1,Z25), (Ra10,Rb3,X1,Z26), (Ra10,Rb3,X1,Z27), (Ra10,Rb3,X1,Z28), (Ra10,Rb3,X1,Z29), (Ra10,Rb3,X1,Z30), (Ra10,Rb3,X1,Z31), (Ra10,Rb3,X1,Z32), (Ra10,Rb3,X1,Z33), (Ra10,Rb3,X1,Z34), (Ra10,Rb3,X1,Z35), (Ra10,Rb3,X1,Z36), (Ra10,Rb3,X1,Z37), (Ra10,Rb3,X1,Z38), (Ra10,Rb3,X1,Z39), (Ra10,Rb3,X2,Z1), (Ra10,Rb3,X2,Z2), (Ra10,Rb3,X2,Z3), (Ra10,Rb3,X2,Z4), (Ra10,Rb3,X2,Z5), (Ra10,Rb3,X2,Z6), (Ra10,Rb3,X2,Z7), (Ra10,Rb3,X2,Z8), (Ra10,Rb3,X2,Z9), (Ra10,Rb3,X2,Z10), (Ra10,Rb3,X2,Z11), (Ra10,Rb3,X2,Z12), (Ra10,Rb3,X2,Z13), (Ra10,Rb3,X2,Z14), (Ra10,Rb3,X2,Z15), (Ra10,Rb3,X2,Z16), (Ra10,Rb3,X2,Z17), (Ra10,Rb3,X2,Z18), (Ra10,Rb3,X2,Z19), (Ra10,Rb3,X2,Z20), (Ra10,Rb3,X2,Z21), (Ra10,Rb3,X2,Z22), (Ra10,Rb3,X2,Z23), (Ra10,Rb3,X2,Z24), (Ra10,Rb3,X2,Z25), (Ra10,Rb3,X2,Z26), (Ra10,Rb3,X2,Z27), (Ra10,Rb3,X2,Z28), (Ra10,Rb3,X2,Z29), (Ra10,Rb3,X2,Z30), (Ra10,Rb3,X2,Z31), (Ra10,Rb3,X2,Z32), (Ra10,Rb3,X2,Z33), (Ra10,Rb3,X2,Z34), (Ra10,Rb3,X2,Z35), (Ra10,Rb3,X2,Z36), (Ra10,Rb3,X2,Z37), (Ra10,Rb3,X2,Z38), (Ra10,Rb3,X2,Z39), (Ra10,Rb4,X1,Z1), (Ra10,Rb4,X1,Z2), (Ra10,Rb4,X1,Z3), (Ra10,Rb4,X1,Z4), (Ra10,Rb4,X1,Z5), (Ra10,Rb4,X1,Z6), (Ra10,Rb4,X1,Z7), (Ra10,Rb4,X1,Z8), (Ra10,Rb4,X1,Z9), (Ra10,Rb4,X1,Z10), (Ra10,Rb4,X1,Z11), (Ra10,Rb4,X1,Z12), (Ra10,Rb4,X1,Z13), (Ra10,Rb4,X1,Z14), (Ra10,Rb4,X1,Z15), (Ra10,Rb4,X1,Z16), (Ra10,Rb4,X1,Z17), (Ra10,Rb4,X1,Z18), (Ra10,Rb4,X1,Z19), (Ra10,Rb4,X1,Z20), (Ra10,Rb4,X1,Z21), (Ra10,Rb4,X1,Z22), (Ra10,Rb4,X1,Z23), (Ra10,Rb4,X1,Z24), (Ra10,Rb4,X1,Z25), (Ra10,Rb4,X1,Z26), (Ra10,Rb4,X1,Z27), (Ra10,Rb4,X1,Z28), (Ra10,Rb4,X1,Z29), (Ra10,Rb4,X1,Z30), (Ra10,Rb4,X1,Z31), (Ra10,Rb4,X1,Z32), (Ra10,Rb4,X1,Z33), (Ra10,Rb4,X1,Z34), (Ra10,Rb4,X1,Z35), (Ra10,Rb4,X1,Z36), (Ra10,Rb4,X1,Z37), (Ra10,Rb4,X1,Z38), (Ra10,Rb4,X1,Z39), (Ra10,Rb4,X2,Z1), (Ra10,Rb4,X2,Z2), (Ra10,Rb4,X2,Z3), (Ra10,Rb4,X2,Z4), (Ra10,Rb4,X2,Z5), (Ra10,Rb4,X2,Z6), (Ra10,Rb4,X2,Z7), (Ra10,Rb4,X2,Z8), (Ra10,Rb4,X2,Z9), (Ra10,Rb4,X2,Z10), (Ra10,Rb4,X2,Z11), (Ra10,Rb4,X2,Z12), (Ra10,Rb4,X2,Z13), (Ra10,Rb4,X2,Z14), (Ra10,Rb4,X2,Z15), (Ra10,Rb4,X2,Z10, (Ra10,Rb4,X2,Z17), (Ra10,Rb4,X2,Z18), (Ra10,Rb4,X2,Z19), (Ra10,Rb4,X2,Z20), (Ra10,Rb4,X2,Z21), (Ra10,Rb4,X2,Z22), (Ra10,Rb4,X2,Z23), (Ra10,Rb4,X2,Z24), (Ra10,Rb4,X2,Z25), (Ra10,Rb4,X2,Z26), (Ra10,Rb4,X2,Z27), (Ra10,Rb4,X2,Z28), (Ra10,Rb4,X2,Z29), (Ra10,Rb4,X2,Z30), (Ra10,Rb4,X2,Z31), (Ra10,Rb4,X2,Z32), (Ra10,Rb4,X2,Z33), (Ra10,Rb4,X2,Z34), (Ra10,Rb4,X2,Z35), (Ra10,Rb4,X2,Z36), (Ra10,Rb4,X2,Z37), (Ra10,Rb4,X2,Z38), (Ra10,Rb4,X2,Z39), (Ra10,Rb5,X1,Z1), (Ra10,Rb5,X1,Z2), (Ra10,Rb5,X1,Z3), (Ra10,Rb5,X1,Z4), (Ra10,Rb5,X1,Z5), (Ra10,Rb5,X1,Z6), (Ra10,Rb5,X1,Z7), (Ra10,Rb5,X1,Z8), (Ra10,Rb5,X1,Z9), (Ra10,Rb5,X1,Z10), (Ra10,Rb5,X1,Z11), (Ra10,Rb5,X1,Z12), (Ra10,Rb5,X1,Z13), (Ra10,Rb5,X1,Z14), (Ra10,Rb5,X1,Z15), (Ra10,Rb5,X1,Z16), (Ra10,Rb5,X1,Z17), (Ra10,Rb5,X1,Z18), (Ra10,Rb5,X1,Z19), (Ra10,Rb5,X1,Z20), (Ra10,Rb5,X1,Z21), (Ra10,Rb5,X1,Z22), (Ra10,Rb5,X1,Z23), (Ra10,Rb5,X1,Z24), (Ra10,Rb5,X1,Z25), (Ra10,Rb5,X1,Z26), (Ra10,Rb5,X1,Z27), (Ra10,Rb5,X1,Z28), (Ra10,Rb5,X1,Z29), (Ra10,Rb5,X1,Z30), (Ra10,Rb5,X1,Z31), (Ra10,Rb5,X1,Z32), (Ra10,Rb5,X1,Z33), (Ra10,Rb5,X1,Z34), (Ra10,Rb5,X1,Z35), (Ra10,Rb5,X1,Z36), (Ra10,Rb5,X1,Z37), (Ra10,Rb5,X1,Z38), (Ra10,Rb5,X1,Z39), (Ra10,Rb5,X2,Z1), (Ra10,Rb5,X2,Z2), (Ra10,Rb5,X2,Z3), (Ra10,Rb5,X2,Z4), (Ra10,Rb5,X2,Z5), (Ra10,Rb5,X2,Z6), (Ra10,Rb5,X2,Z7), (Ra10,Rb5,X2,Z8), (Ra10,Rb5,X2,Z9), (Ra10,Rb5,X2,Z10), (Ra10,Rb5,X2,Z11), (Ra10,Rb5,X2,Z12), (Ra10,Rb5,X2,Z13), (Ra10,Rb5,X2,Z14), (Ra10,Rb5,X2,Z15), (Ra10,Rb5,X2,Z16), (Ra10,Rb5,X2,Z17), (Ra10,Rb5,X2,Z18), (Ra10,Rb5,X2,Z19), (Ra10,Rb5,X2,Z20), (Ra10,Rb5,X2,Z21), (Ra10,Rb5,X2,Z22), (Ra10,Rb5,X2,Z23), (Ra10,Rb5,X2,Z24), (Ra10,Rb5,X2,Z25), (Ra10,Rb5,X2,Z26), (Ra10,Rb5,X2,Z27), (Ra10,Rb5,X2,Z28), (Ra10,Rb5,X2,Z29), (Ra10,Rb5,X2,Z30), (Ra10,Rb5,X2,Z31), (Ra10,Rb5,X2,Z32), (Ra10,Rb5,X2,Z33), (Ra10,Rb5,X2,Z34), (Ra10,Rb5,

X2,Z35), (Ra10,Rb5,X2,Z36), (Ra10,Rb5,X2,Z37), (Ra10, Rb5,X2,Z38), (Ra10,Rb5,X2,Z39), (Ra10,Rb6,X1,Z1), (Ra10,Rb6,X1,Z2), (Ra10,Rb6,X1,Z3), (Ra10,Rb6,X1,Z4), (Ra10,Rb6,X1,Z5), (Ra10,Rb6,X1,Z6), (Ra10,Rb6,X1,Z7), (Ra10,Rb6,X1,Z8), (Ra10,Rb6,X1,Z9), (Ra10,Rb6,X1,Z10), (Ra10,Rb6,X1,Z11), (Ra10,Rb6,X1,Z12), (Ra10,Rb6,X1,Z13), (Ra10,Rb6,X1,Z14), (Ra10,Rb6,X1,Z15), (Ra10,Rb6,X1,Z16), (Ra10,Rb6,X1,Z17), (Ra10,Rb6,X1,Z18), (Ra10,Rb6,X1,Z19), (Ra10,Rb6,X1,Z20), (Ra10,Rb6,X1,Z21), (Ra10,Rb6,X1,Z22), (Ra10,Rb6,X1,Z23), (Ra10,Rb6,X1,Z24), (Ra10,Rb6,X1,Z25), (Ra10,Rb6,X1,Z26), (Ra10,Rb6,X1,Z27), (Ra10,Rb6,X1,Z28), (Ra10,Rb6,X1,Z29), (Ra10,Rb6,X1,Z30), (Ra10,Rb6,X1,Z31), (Ra10,Rb6,X1,Z32), (Ra10,Rb6,X1,Z33), (Ra10,Rb6,X1,Z34), (Ra10,Rb6,X1,Z35), (Ra10,Rb6,X1,Z36), (Ra10,Rb6,X1,Z37), (Ra10,Rb6,X1,Z38), (Ra10,Rb6,X1,Z39), (Ra10,Rb6,X2,Z1), (Ra10,Rb6,X2,Z2), (Ra10,Rb6,X2,Z3), (Ra10,Rb6,X2,Z4), (Ra10,Rb6,X2,Z5), (Ra10,Rb6,X2,Z6), (Ra10,Rb6,X2,Z7), (Ra10,Rb6,X2,Z8), (Ra10,Rb6,X2,Z9), (Ra10,Rb6,X2,Z10), (Ra10,Rb6,X2,Z11), (Ra10,Rb6,X2,Z12), (Ra10,Rb6,X2,Z13), (Ra10,Rb6,X2,Z14), (Ra10,Rb6,X2,Z15), (Ra10,Rb6,X2,Z16), (Ra10,Rb6,X2,Z17), (Ra10,Rb6,X2,Z18), (Ra10,Rb6,X2,Z19), (Ra10,Rb6,X2,Z20), (Ra10,Rb6,X2,Z21), (Ra10,Rb6,X2,Z22), (Ra10,Rb6,X2,Z23), (Ra10,Rb6,X2,Z24), (Ra10,Rb6,X2,Z25), (Ra10,Rb6,X2,Z26), (Ra10,Rb6,X2,Z27), (Ra10,Rb6,X2,Z28), (Ra10,Rb6,X2,Z29), (Ra10,Rb6,X2,Z30), (Ra10,Rb6,X2,Z31), (Ra10,Rb6,X2,Z32), (Ra10,Rb6,X2,Z33), (Ra10,Rb6,X2,Z34), (Ra10,Rb6,X2,Z35), (Ra10,Rb6,X2,Z36), (Ra10,Rb6,X2,Z37), (Ra10,Rb6,X2,Z38), (Ra10,Rb6,X2,Z39), (Ra10,Rb7,X1,Z1), (Ra10,Rb7,X1,Z2), (Ra10,Rb7,X1,Z3), (Ra10,Rb7,X1,Z4), (Ra10,Rb7,X1,Z5), (Ra10,Rb7,X1,Z6), (Ra10,Rb7,X1,Z7), (Ra10,Rb7,X1,Z8), (Ra10,Rb7,X1,Z9), (Ra10,Rb7,X1,Z10), (Ra10,Rb7,X1,Z11), (Ra10,Rb7,X1,Z12), (Ra10,Rb7,X1,Z13), (Ra10,Rb7,X1,Z14), (Ra10,Rb7,X1,Z15), (Ra10,Rb7,X1,Z16), (Ra10,Rb7,X1,Z17), (Ra10,Rb7,X1,Z18), (Ra10,Rb7,X1,Z19), (Ra10,Rb7,X1,Z20), (Ra10,Rb7,X1,Z21), (Ra10,Rb7,X1,Z22), (Ra10,Rb7,X1,Z23), (Ra10,Rb7,X1,Z24), (Ra10,Rb7,X1,Z25), (Ra10,Rb7,X1,Z26), (Ra10,Rb7,X1,Z27), (Ra10,Rb7,X1,Z28), (Ra10,Rb7,X1,Z29), (Ra10,Rb7,X1,Z30), (Ra10,Rb7,X1,Z31), (Ra10,Rb7,X1,Z32), (Ra10,Rb7,X1,Z33), (Ra10,Rb7,X1,Z34), (Ra10,Rb7,X1,Z35), (Ra10,Rb7,X1,Z36), (Ra10,Rb7,X1,Z37), (Ra10,Rb7,X1,Z38), (Ra10,Rb7,X1,Z39), (Ra10,Rb7,X2,Z1), (Ra10,Rb7,X2,Z2), (Ra10,Rb7,X2,Z3), (Ra10,Rb7,X2,Z4), (Ra10,Rb7,X2,Z5), (Ra10,Rb7,X2,Z6), (Ra10,Rb7,X2,Z7), (Ra10,Rb7,X2,Z8), (Ra10,Rb7,X2,Z9), (Ra10,Rb7,X2,Z10), (Ra10,Rb7,X2,Z11), (Ra10,Rb7,X2,Z12), (Ra10,Rb7,X2,Z13), (Ra10,Rb7,X2,Z14), (Ra10,Rb7,X2,Z15), (Ra10,Rb7,X2,Z16), (Ra10,Rb7,X2,Z17), (Ra10,Rb7,X2,Z18), (Ra10,Rb7,X2,Z19), (Ra10,Rb7,X2,Z20), (Ra10,Rb7,X2,Z21), (Ra10,Rb7,X2,Z22), (Ra10,Rb7,X2,Z23), (Ra10,Rb7,X2,Z24), (Ra10,Rb7,X2,Z25), (Ra10,Rb7,X2,Z26), (Ra10,Rb7,X2,Z27), (Ra10,Rb7,X2,Z28), (Ra10,Rb7,X2,Z29), (Ra10,Rb7,X2,Z30), (Ra10,Rb7,X2,Z31), (Ra10,Rb7,X2,Z32), (Ra10,Rb7,X2,Z33), (Ra10,Rb7,X2,Z34), (Ra10,Rb7,X2,Z35), (Ra10,Rb7,X2,Z36), (Ra10,Rb7,X2,Z37), (Ra10,Rb7,X2,Z38), (Ra10,Rb7,X2,Z39), (Ra10,Rb8,X1,Z1), (Ra10,Rb8,X1,Z2), (Ra10,Rb8,X1,Z3), (Ra10,Rb8,X1,Z4), (Ra10,Rb8,X1,Z5), (Ra10,Rb8,X1,Z6), (Ra10,Rb8,X1,Z7), (Ra10,Rb8,X1,Z8), (Ra10,Rb8,X1,Z9), (Ra10,Rb8,X1,Z10), (Ra10,Rb8,X1,Z11), (Ra10,Rb8,X1,Z12), (Ra10,Rb8,X1,Z13), (Ra10,Rb8,X1,Z14), (Ra10,Rb8,X1,Z15), (Ra10,Rb8,X1,Z16), (Ra10,Rb8,X1,Z17), (Ra10,Rb8,X1,Z18), (Ra10,Rb8,X1,Z19), (Ra10,Rb8,X1,Z20), (Ra10,Rb8,X1,Z21), (Ra10,Rb8,X1,Z22), (Ra10,Rb8,X1,Z23), (Ra10,Rb8,X1,Z24), (Ra10,Rb8,X1,Z25), (Ra10,Rb8,X1,Z26), (Ra10,Rb8,X1,Z27), (Ra10,Rb8,X1,Z28), (Ra10,Rb8,X1,Z29), (Ra10,Rb8,X1,Z30), (Ra10,Rb8,X1,Z31), (Ra10,Rb8,X1,Z32), (Ra10,Rb8,X1,Z33), (Ra10,Rb8,X1,Z34), (Ra10,Rb8,X1,Z35), (Ra10,Rb8,X1,Z36), (Ra10,Rb8,X1,Z37), (Ra10,Rb8,X1,Z38), (Ra10,Rb8,X1,Z39), (Ra10,Rb8,X2,Z1), (Ra10,Rb8,X2,Z2), (Ra10,Rb8,X2,Z3), (Ra10,Rb8,X2,Z4), (Ra10,Rb8,X2,Z5), (Ra10,Rb8,X2,Z6), (Ra10,Rb8,X2,Z7), (Ra10,Rb8,X2,Z8), (Ra10,Rb8,X2,Z9), (Ra10,Rb8,X2,Z10), (Ra10,Rb8,X2,Z11), (Ra10,Rb8,X2,Z12), (Ra10,Rb8,X2,Z13), (Ra10,Rb8,X2,Z14), (Ra10,Rb8,X2,Z15), (Ra10,Rb8,X2,Z16), (Ra10,Rb8,X2,Z17), (Ra10,Rb8,X2,Z18), (Ra10,Rb8,X2,Z19), (Ra10,Rb8,X2,Z20), (Ra10,Rb8,X2,Z21), (Ra10,Rb8,X2,Z22), (Ra10,Rb8,X2,Z23), (Ra10,Rb8,X2,Z24), (Ra10,Rb8,X2,Z25), (Ra10,Rb8,X2,Z26), (Ra10,Rb8,X2,Z27), (Ra10,Rb8,X2,Z28), (Ra10,Rb8,X2,Z29), (Ra10,Rb8,X2,Z30), (Ra10,Rb8,X2,Z31), (Ra10,Rb8,X2,Z32), (Ra10,Rb8,X2,Z33), (Ra10,Rb8,X2,Z34), (Ra10,Rb8,X2,Z35), (Ra10,Rb8,X2,Z36), (Ra10,Rb8,X2,Z37), (Ra10,Rb8,X2,Z38), (Ra10,Rb8,X2,Z39), (Ra11,Rb1,X1,Z1), (Ra11,Rb1,X1,Z2), (Ra11,Rb1,X1,Z3), (Ra11,Rb1,X1,Z4), (Ra11,Rb1,X1,Z5), (Ra11,Rb1,X1,Z6), (Ra11,Rb1,X1,Z7), (Ra11,Rb1,X1,Z8), (Ra11,Rb1,X1,Z9), (Ra11,Rb1,X1,Z10), (Ra11,Rb1,X1,Z11), (Ra11,Rb1,X1,Z12), (Ra11,Rb1,X1,Z13), (Ra11,Rb1,X1,Z14), (Ra11,Rb1,X1,Z15), (Ra11,Rb1,X1,Z16), (Ra11,Rb1,X1,Z17), (Ra11,Rb1,X1,Z18), (Ra11,Rb1,X1,Z19), (Ra11,Rb1,X1,Z20), (Ra11,Rb1,X1,Z21), (Ra11,Rb1,X1,Z22), (Ra11,Rb1,X1,Z23), (Ra11,Rb1,X1,Z24), (Ra11,Rb1,X1,Z25), (Ra11,Rb1,X1,Z26), (Ra11,Rb1,X1,Z27), (Ra11,Rb1,X1,Z28), (Ra11,Rb1,X1,Z29), (Ra11,Rb1,X1,Z30), (Ra11,Rb1,X1,Z31), (Ra11,Rb1,X1,Z32), (Ra11,Rb1,X1,Z33), (Ra11,Rb1,X1,Z34), (Ra11,Rb1,X1,Z35), (Ra11,Rb1,X1,Z36), (Ra11,Rb1,X1,Z37), (Ra11,Rb1,X1,Z38), (Ra11,Rb1,X1,Z39), (Ra11,Rb1,X2,Z1), (Ra11,Rb1,X2,Z2), (Ra11,Rb1,X2,Z3), (Ra11,Rb1,X2,Z4), (Ra11,Rb1,X2,Z5), (Ra11,Rb1,X2,Z6), (Ra11,Rb1,X2,Z7), (Ra11,Rb1,X2,Z8), (Ra11,Rb1,X2,Z9), (Ra11,Rb1,X2,Z10), (Ra11,Rb1,X2,Z11), (Ra11,Rb1,X2,Z12), (Ra11,Rb1,X2,Z13), (Ra11,Rb1,X2,Z14), (Ra11Rb1,X2,Z15), (Ra11,Rb1,X2,Z16), (Ra11,Rb1,X2,Z17), (Ra11,Rb1,X2,Z18), (Ra11,Rb1,X2,Z19), (Ra11,Rb1,X2,Z20), (Ra11,Rb1,X2,Z21), (Ra11,Rb1,X2,Z22), (Ra11,Rb1,X2,Z23), (Ra11,Rb1,X2,Z24), (Ra11,Rb1,X2,Z25), (Ra11,Rb1,X2,Z26), (Ra11,Rb1,X2,Z27), (Ra11,Rb1,X2,Z28), (Ra11,Rb1,X2,Z29), (Ra11,Rb1,X2,Z30), (Ra11,Rb1,X2,Z31), (Ra11,Rb1,X2,Z32), (Ra11,Rb1,X2,Z33), (Ra11,Rb1,X2,Z34), (Ra11,Rb1,X2,Z35), (Ra11,Rb1,X2,Z36), (Ra11,Rb1,X2,Z37), (Ra11,Rb1,X2,Z38), (Ra11,Rb1,X2,Z39), (Ra11,Rb2,X1,Z1), (Ra11,Rb2,X1,Z2), (Ra11,Rb2,X1,Z3), (Ra11,Rb2,X1,Z4), (Ra11,Rb2,X1,Z5), (Ra11,Rb2,X1,Z6), (Ra11,Rb2,X1,Z7), (Ra11,Rb2,X1,Z8), (Ra11,Rb2,X1,Z9), (Ra11,Rb2,X1,Z10), (Ra11,Rb2,X1,Z11), (Ra11,Rb2,X1,Z12), (Ra11,Rb2,X1,Z13), (Ra11,Rb2,X1,Z14), (Ra11,Rb2,X1,Z15), (Ra11,Rb2,X1,Z16), (Ra11,Rb2,X1,Z17), (Ra11,Rb2,X1,Z18), (Ra11,Rb2,X1,Z19), (Ra11,Rb2,X1,Z20), (Ra11,Rb2,X1,Z21), (Ra11,Rb2,X1,Z22), (Ra11,Rb2,X1,Z23), (Ra11,Rb2,X1,Z24), (Ra11,Rb2,X1,Z25), (Ra11,Rb2,X1,Z26), (Ra11,Rb2,X1,Z27), (Ra11,Rb2,X1,Z28), (Ra11,Rb2,X1,Z29), (Ra11,Rb2,X1,Z30), (Ra11,Rb2,X1,Z31), (Ra11,Rb2,X1,Z32), (Ra11,Rb2,X1,Z33), (Ra11,Rb2,X1,Z34), (Ra11,Rb2,X1,Z35), (Ra11,Rb2,X1,Z36), (Ra11,Rb2,X1,Z37), (Ra11,Rb2,X1,Z38), (Ra11,Rb2,X1,Z39), (Ra11,Rb2,X2,Z1), (Ra11,Rb2,X2,Z2), (Ra11,Rb2,X2,Z3), (Ra11,Rb2,X2,Z4), (Ra11,Rb2,X2,Z5), (Ra11,Rb2,X2,Z6), (Ra11,Rb2,X2,Z7), (Ra11,Rb2,X2,Z8), (Ra11,Rb2,X2,Z9), (Ra11,Rb2,X2,Z10), (Ra11,Rb2,X2,Z11), (Ra11,Rb2,X2,Z12), (Ra11,Rb2,X2,Z13), (Ra11,Rb2,X2,Z14), (Ra11,Rb2,X2,Z15), (Ra11,Rb2,X2,Z16), (Ra11,Rb2,X2,Z17), (Ra11,Rb2,X2,Z18), (Ra11,Rb2,X2,Z19), (Ra11,Rb2,X2,Z20), (Ra11,Rb2,X2,Z21), (Ra11,Rb2,X2,Z22), (Ra11,Rb2,X2,Z23), (Ra11,Rb2,X2,Z24), (Ra11,Rb2,X2,Z25), (Ra11,Rb2,X2,Z26), (Ra11,Rb2,X2,Z27), (Ra11,Rb2,X2,Z28), (Ra11,Rb2,X2,Z29), (Ra11,Rb2,X2,Z30), (Ra11,Rb2,X2,Z31), (Ra11,Rb2,X2,Z32), (Ra11,Rb2,X2,Z33), (Ra11,Rb2,X2,Z34), (Ra11,Rb2,X2,Z35), (Ra11,Rb2,X2,Z36), (Ra11,Rb2,X2,Z37), (Ra11,Rb2,X2,Z38), (Ra11,Rb2,X2,Z39), (Ra11,Rb3,X1,Z1), (Ra11,Rb3,X1,Z2), (Ra11,Rb3,X1,Z3), (Ra11,Rb3,X1,Z4), (Ra11,Rb3,X1,Z5), (Ra11,Rb3,X1,Z6), (Ra11,Rb3,X1,Z7), (Ra11,Rb3,X1,Z8), (Ra11,Rb3,X1,Z9), (Ra11,Rb3,X1,Z10), (Ra11,Rb3,X1,Z11), (Ra11,Rb3,X1,Z12), (Ra11,Rb3,X1,Z13), (Ra11,Rb3,X1,Z14), (Ra11,Rb3,X1,Z15), (Ra11,Rb3,X1,Z16), (Ra11,Rb3,X1,Z17), (Ra11,Rb3,X1,Z18), (Ra11,Rb3,X1,Z19), (Ra11,Rb3,X1,Z20), (Ra11,Rb3,X1,Z21), (Ra11,Rb3,X1,Z22), (Ra11,Rb3,X1,Z23), (Ra11,Rb3,X1,Z24), (Ra11,Rb3,X1,Z25), (Ra11,Rb3,X1,Z26), (Ra11,Rb3,X1,Z27), (Ra11,Rb3,X1,Z28), (Ra11,Rb3,X1,Z29), (Ra11,Rb3,X1,Z30), (Ra11,Rb3,X1,Z31), (Ra11,Rb3,X1,Z32), (Ra11,Rb3,X1,Z33), (Ra11,Rb3,X1,Z34), (Ra11,Rb3,X1,Z35), (Ra11,Rb3,X1,Z36), (Ra11,Rb3,X1,Z37), (Ra11,Rb3,X1,Z38), (Ra11,Rb3,X1,Z39), (Ra11,Rb3,X2,Z1), (Ra11,Rb3,X2,Z2), (Ra11,Rb3,X2,Z3), (Ra11,Rb3,X2,Z4), (Ra11,Rb3,X2,Z5), (Ra11,Rb3,X2,Z6), (Ra11,Rb3,X2,Z7), (Ra11,Rb3,X2,Z8), (Ra11,Rb3,X2,Z9), (Ra11,Rb3,X2,Z10), (Ra11,Rb3,X2,Z11), (Ra11,Rb3,X2,Z12), (Ra11,Rb3,X2,Z13), (Ra11,Rb3,X2,Z14), (Ra11,Rb3,X2,Z15), (Ra11,Rb3,X2,Z16), (Ra11,Rb3,X2,Z17), (Ra11,Rb3,X2,Z18), (Ra11,Rb3,X2,Z19), (Ra11,Rb3,X2,Z20), (Ra11,Rb3,X2,Z21), (Ra11,Rb3,X2,Z22), (Ra11,Rb3,X2,Z23), (Ra11,Rb3,X2,Z24), (Ra11,Rb3,X2,Z25), (Ra11,Rb3,X2,Z26), (Ra11,Rb3,X2,Z27), (Ra11,Rb3,X2,Z28), (Ra11,Rb3,X2,Z29), (Ra11,Rb3,X2,Z30), (Ra11,Rb3,X2,Z31), (Ra11,Rb3,X2,Z32), (Ra11,Rb3,X2,Z33), (Ra11,Rb3,X2,Z34), (Ra11,Rb3,X2,Z35), (Ra11,Rb3,X2,Z36), (Ra11,Rb3,X2,Z37), (Ra11,Rb3,X2,Z38), (Ra11,Rb3,X2,Z39), (Ra11,Rb4,X1,Z1), (Ra11,Rb4,X1,Z2), (Ra11,Rb4,X1,Z3), (Ra11,Rb4,X1,Z4), (Ra11,Rb4,X1,Z5), (Ra11,Rb4,X1,Z6), (Ra11,Rb4,X1,Z7), (Ra11,Rb4,X1,Z8), (Ra11,Rb4,X1,Z9), (Ra11,Rb4,X1,Z10), (Ra11,Rb4,X1,Z11), (Ra11,Rb4,X1,Z12), (Ra11,Rb4,X1,Z13), (Ra11,Rb4,X1,Z14), (Ra11,Rb4,X1,Z15), (Ra11,Rb4,X1,Z16), (Ra11,Rb4,X1,Z17), (Ra11,Rb4,X1,Z18), (Ra11,Rb4,X1,Z19), (Ra11,Rb4,X1,Z20), (Ra11,Rb4,X1,Z21), (Ra11,Rb4,X1,Z22), (Ra11,Rb4,X1,Z23), (Ra11,Rb4,X1,Z24), (Ra11,Rb4,X1,Z25), (Ra11,Rb4,X1,Z26), (Ra11,Rb4,X1,Z27), (Ra11,Rb4,X1,Z28), (Ra11,Rb4,X1,Z29), (Ra11,Rb4,X1,Z30), (Ra11,Rb4,X1,Z31), (Ra11,Rb4,X1,Z32), (Ra11,Rb4,X1,Z33), (Ra11,Rb4,X1,Z34), (Ra11,Rb4,X1,Z35), (Ra11,Rb4,X1,Z36), (Ra11,Rb4,X1,Z37), (Ra11,Rb4,X1,Z38), (Ra11,Rb4,X1,Z39), (Ra11,Rb4,X2,Z1), (Ra11,Rb4,X2,Z2), (Ra11,Rb4,X2,Z3), (Ra11,Rb4,X2,Z4), (Ra11,Rb4,X2,Z5), (Ra11,Rb4,X2,Z6), (Ra11,Rb4,X2,Z7), (Ra11,Rb4,X2,Z8), (Ra11,Rb4,X2,Z9), (Ra11,Rb4,X2,Z10), (Ra11,Rb4,X2,Z11), (Ra11,Rb4,X2,Z12), (Ra11,Rb4,X2,Z13), (Ra11,Rb4,X2,Z14), (Ra11,Rb4,X2,Z15), (Ra11,Rb4,X2,Z16), (Ra11,Rb4,X2,Z17), (Ra11,Rb4,X2,Z18), (Ra11,Rb4,X2,Z19), (Ra11,Rb4,X2,Z20), (Ra11,Rb4,X2,Z21), (Ra11,Rb4,X2,Z22), (Ra11,Rb4,X2,Z23), (Ra11,Rb4,X2,Z24), (Ra11,Rb4,X2,Z25), (Ra11,Rb4,X2,Z26), (Ra11,Rb4,X2,Z27), (Ra11,Rb4,X2,Z28), (Ra11,Rb4,X2,Z29), (Ra11,Rb4,X2,Z30), (Ra11,Rb4,X2,Z31), (Ra11,Rb4,X2,Z32), (Ra11,Rb4,X2,Z33), (Ra11,Rb4,X2,Z34), (Ra11,Rb4,X2,Z35), (Ra11,Rb4,X2,Z36), (Ra11,Rb4,X2,Z37), (Ra11,Rb4,X2,Z38), (Ra11,Rb4,X2,Z39), (Ra11,Rb5,X1,Z1), (Ra11,Rb5,X1,Z2), (Ra11,Rb5,X1,Z3), (Ra11,Rb5,X1,Z4), (Ra11,Rb5,X1,Z5), (Ra11,Rb5,X1,Z6), (Ra11,Rb5,X1,Z7), (Ra11,Rb5,X1,Z8), (Ra11,Rb5,X1,Z9), (Ra11,Rb5,X1,Z10), (Ra11,Rb5,X1,Z11), (Ra11,Rb5,X1,Z12), (Ra11,Rb5,X1,Z13), (Ra11,Rb5,X1,Z14), (Ra11,Rb5,X1,Z15), (Ra11,Rb5,X1,Z16), (Ra11,Rb5,X1,Z17), (Ra11,Rb5,X1,Z18), (Ra11,Rb5,X1,Z19), (Ra11,Rb5,X1,Z20), (Ra11,Rb5,X1,Z21), (Ra11,Rb5,X1,Z22), (Ra11,Rb5,X1,Z23), (Ra11,Rb5,X1,Z24), (Ra11,Rb5,X1,Z25), (Ra11,Rb5,X1,Z26), (Ra11,Rb5,X1,Z27), (Ra11,Rb5,X1,Z28), (Ra11,Rb5,X1,Z29), (Ra11,Rb5,X1,Z30), (Ra11,Rb5,X1,Z31), (Ra11,Rb5,X1,Z32), (Ra11,Rb5,X1,Z33), (Ra11,Rb5,X1,Z34), (Ra11,Rb5,X1,Z35), (Ra11,Rb5,X1,Z36), (Ra11,Rb5,X1,Z37), (Ra11,Rb5,X1,Z38), (Ra11,Rb5,X1,Z39), (Ra11,Rb5,X2,Z1), (Ra11,Rb5,X2,Z2), (Ra11,Rb5,X2,Z3), (Ra11,Rb5,X2,Z4), (Ra11,Rb5,X2,Z5), (Ra11,Rb5,X2,Z6), (Ra11,Rb5,X2,Z7), (Ra11,Rb5,X2,Z8), (Ra11,Rb5,X2,Z9), (Ra11,Rb5,X2,Z10), (Ra11,Rb5,X2,Z11), (Ra11,Rb5,X2,Z12), (Ra11,Rb5,X2,Z13), (Ra11,Rb5,X2,Z14), (Ra11,Rb5,X2,Z15), (Ra11,Rb5,X2,Z16), (Ra11,Rb5,X2,Z17), (Ra11,Rb5,X2,Z18), (Ra11,Rb5,X2,Z19), (Ra11,Rb5,X2,Z20), (Ra11,Rb5,X2,Z21), (Ra11,Rb5,X2,Z22), (Ra11,Rb5,X2,Z23), (Ra11,Rb5,X2,Z24), (Ra11,Rb5,X2,Z25), (Ra11,Rb5,X2,Z26), (Ra11,Rb5,X2,Z27), (Ra11,Rb5,X2,Z28), (Ra11,Rb5,X2,Z29), (Ra11,Rb5,X2,Z30), (Ra11,Rb5,X2,Z31), (Ra11,Rb5,X2,Z32), (Ra11,Rb5,X2,Z33), (Ra11,Rb5,X2,Z34), (Ra11,Rb5,X2,Z35), (Ra11,Rb5,X2,Z36), (Ra11,Rb5,X2,Z37), (Ra11,Rb5,X2,Z38), (Ra11,Rb5,X2,Z39), (Ra11,Rb6,X1,Z1), (Ra11,Rb6,X1,Z2), (Ra11,Rb6,X1,Z3), (Ra11,Rb6,X1,Z4), (Ra11,Rb6,X1,Z5), (Ra11,Rb6,X1,Z6), (Ra11,Rb6,X1,Z7), (Ra11,Rb6,X1,Z8), (Ra11,Rb6,X1,Z9), (Ra11,Rb6,X1,Z10), (Ra11,Rb6,X1,Z11), (Ra11,Rb6,X1,Z12), (Ra11,Rb6,X1,Z13), (Ra11,Rb6,X1,Z14), (Ra11,Rb6,X1,Z15), (Ra11,Rb6,X1,Z16), (Ra11,Rb6,X1,Z17), (Ra11,Rb6,X1,Z18), (Ra11,Rb6,X1,Z19), (Ra11,Rb6,X1,Z20), (Ra11,Rb6,X1,Z21), (Ra11,Rb6,X1,Z22), (Ra11,Rb6,X1,Z23), (Ra11,Rb6,X1,Z24), (Ra11,Rb8,X1,Z25), (Ra11,Rb8,X1,Z26), (Ra11,Rb6,X1,Z27), (Ra11,Rb6,X1,Z28), (Ra11,Rb6,X1,Z29), (Ra11,Rb6,X1,Z30), (Ra11,Rb6,X1,Z31), (Ra11,Rb6,X1,Z32), (Ra11,Rb6,X1,Z33), (Ra11,Rb6,X1,Z34), (Ra11,Rb6,X1,Z35), (Ra11,Rb6,X1,Z36), (Ra11,Rb6,X1,Z37), (Ra11,Rb6,X1,Z38), (Ra11,Rb6,X1,Z39), (Ra11,Rb6,X2,Z1), (Ra11,Rb6,X2,Z2), (Ra11,Rb6,X2,Z3), (Ra11,Rb6,X2,Z4), (Ra11,Rb6,X2,Z5), (Ra11,Rb6,X2,Z6), (Ra11,Rb6,X2,Z7), (Ra11,Rb6,X2,Z8), (Ra11,Rb6,X2,Z9), (Ra11,Rb6,X2,Z10), (Ra11,Rb6,X2,Z11), (Ra11,Rb6,X2,Z12), (Ra11,Rb6,X2,Z13), (Ra11,Rb6,X2,Z14), (Ra11,Rb6,X2,Z15), (Ra11,Rb6,X2,Z16), (Ra11,Rb6,X2,Z17), (Ra11,Rb6,X2,Z18), (Ra11,Rb6,X2,Z19), (Ra11,Rb6,X2,Z20), (Ra11,Rb6,X2,Z21), (Ra11,Rb6,X2,Z22), (Ra11,Rb6,X2,Z23), (Ra11,Rb6,X2,Z24), (Ra11,Rb6,X2,Z25), (Ra11,Rb6,X2,Z26), (Ra11,Rb6,X2,Z27), (Ra11,Rb6,X2,Z28), (Ra11,Rb6,X2,Z29), (Ra11,Rb6,X2,Z30), (Ra11,Rb6,X2,Z31), (Ra11,Rb6,X2,Z32), (Ra11,Rb6,X2,Z33), (Ra11,Rb6,X2,Z34), (Ra11,Rb6,X2,Z35), (Ra11,Rb6,X2,Z36), (Ra11,Rb6,X2,Z37), (Ra11,Rb6,X2,Z38), (Ra11,Rb6,X2,Z39), (Ra11,Rb7,X1,Z1), (Ra11,Rb7,X1,Z2), (Ra11,Rb7,X1,Z3), (Ra11,Rb7,X1,Z4), (Ra11,Rb7,X1,Z5), (Ra11,Rb7,X1,Z6), (Ra11,Rb7,X1,Z7), (Ra11,Rb7,X1,Z8), (Ra11,Rb7,X1,Z9), (Ra11,Rb7,X1,Z10), (Ra11,Rb7,X1,Z11), (Ra11,Rb7,X1,Z12), (Ra11,Rb7,X1,Z13), (Ra11,Rb7,X1,Z14), (Ra11,Rb7,X1,Z15), (Ra11,Rb7,X1,Z16), (Ra11,Rb7,X1,Z17), (Ra11,Rb7,X1,Z18), (Ra11,Rb7,X1,Z19), (Ra11,Rb7,X1,Z20), (Ra11,Rb7,X1,Z21), (Ra11,Rb7,X1,Z22), (Ra11,Rb7,X1,Z23), (Ra11,Rb7,X1,Z24), (Ra11,Rb7,X1,Z25), (Ra11,Rb7,X1,Z26), (Ra11,Rb7,X1,Z27), (Ra11,Rb7,X1,Z28), (Ra11,Rb7,X1,Z29), (Ra11,Rb7,X1,Z30), (Ra11,Rb7,X1,Z31), (Ra11,Rb7,X1,Z32), (Ra11,Rb7,X1,Z33), (Ra11,Rb7,X1,Z34), (Ra11,Rb7,X1,Z35), (Ra11,Rb7,X1,Z36), (Ra11,Rb7,X1,Z37), (Ra11,Rb7,X1,Z38), (Ra11,Rb7,X1,Z39), (Ra11,Rb7,X2,Z1), (Ra11,Rb7,X2,Z2), (Ra11,Rb7,X2,Z3), (Ra11,Rb7,X2,Z4), (Ra11,Rb7,X2,Z5), (Ra11,Rb7,X2,Z6), (Ra11,Rb7,X2,Z7), (Ra11,Rb7,X2,Z8), (Ra11,Rb7,X2,Z9), (Ra11,Rb7,X2,Z10), (Ra11,Rb7,X2,Z11), (Ra11,Rb7,X2,Z12), (Ra11,Rb7,X2,Z13), (Ra11,Rb7,X2,Z14), (Ra11,Rb7,X2,Z15), (Ra11,Rb7,X2,Z16), (Ra11,Rb7,X2,Z17), (Ra11,Rb7,X2,Z18), (Ra11,Rb7,X2,Z19), (Ra11,Rb7,X2,Z20), (Ra11,Rb7,X2,Z21), (Ra11,Rb7,X2,Z22), (Ra11,Rb7,X2,Z23), (Ra11,Rb7,X2,Z24), (Ra11,Rb7,X2,Z25), (Ra11,Rb7,X2,Z26), (Ra11,Rb7,X2,Z27), (Ra11,Rb7,X2,Z28), (Ra11,Rb7,X2,Z29), (Ra11,Rb7,X2,Z30), (Ra11,Rb7,X2,Z31), (Ra11,Rb7,X2,Z32), (Ra11,Rb7,X2,Z33), (Ra11,Rb7,X2,Z34), (Ra11,Rb7,X2,Z35), (Ra11,Rb7,X2,Z36), (Ra11,Rb7,X2,Z37), (Ra11,Rb7,X2,Z38), (Ra11,Rb7,X2,Z39), (Ra11,Rb8,X1,Z1), (Ra11,Rb8,X1,Z2), (Ra11,Rb8,X1,Z3), (Ra11,Rb8,X1,Z4), (Ra11,Rb8,X1,Z5), (Ra11,Rb8,X1,Z6), (Ra11,Rb8,X1,Z7), (Ra11,Rb8,X1,Z8), (Ra11,Rb8,X1,Z9), (Ra11,Rb8,X1,Z10), (Ra11,Rb8,X1,Z11), (Ra11,Rb8,X1,Z12), (Ra11,Rb8,X1,Z13), (Ra11,Rb8,X1,Z14), (Ra11,Rb8,X1,Z15), (Ra11,Rb8,X1,Z16), (Ra11,Rb8,X1,Z17), (Ra11,Rb8,X1,Z18), (Ra11,Rb8,X1,Z19), (Ra11,Rb8,X1,Z20), (Ra11,Rb8,X1,Z21), (Ra11,Rb8,X1,Z22), (Ra11,Rb8,X1,Z23), (Ra11,Rb8,X1,Z24), (Ra11,Rb8,X1,Z25), (Ra11,Rb8,X1,Z26), (Ra11,Rb8,X1,Z27), (Ra11,Rb8,X1,Z28), (Ra11,Rb8,X1,Z29), (Ra11,Rb8,X1,Z30), (Ra11,Rb8,X1,Z31), (Ra11,Rb8,X1,Z32), (Ra11,Rb8,X1,Z33), (Ra11,Rb8,X1,Z34), (Ra11,Rb8,X1,Z35), (Ra11,Rb8,X1,Z36), (Ra11,Rb8,X1,Z37), (Ra11,Rb8,X1,Z38), (Ra11,Rb8,X1,Z39), (Ra11,Rb8,X2,Z1), (Ra11,Rb8,X2,Z2), (Ra11,Rb8,X2,Z3), (Ra11,Rb8,X2,Z4), (Ra11,Rb8,X2,Z5), (Ra11,Rb8,X2,Z6), (Ra11,Rb8,X2,Z7), (Ra11,Rb8,X2,Z8), (Ra11,Rb8,X2,Z9), (Ra11,Rb8,X2,Z10), (Ra11,Rb8,X2,Z11), (Ra11,Rb8,X2,Z12), (Ra11,Rb8,X2,Z13), (Ra11,Rb8,X2,Z14), (Ra11,Rb8,X2,Z15), (Ra11,Rb8,X2,Z16), (Ra11,Rb8,X2,Z17), (Ra11,Rb8,X2,Z18), (Ra11,Rb8,X2,Z19), (Ra11,Rb8,X2,Z20), (Ra11,Rb8,X2,Z21), (Ra11,Rb8,X2,Z22), (Ra11,Rb8,X2,Z23), (Ra11,Rb8,X2,Z24), (Ra11,Rb8,X2,Z25), (Ra11,Rb8,X2,Z26), (Ra11,Rb8,X2,Z27), (Ra11,Rb8,X2,Z28), (Ra11,Rb8,X2,Z29), (Ra11,Rb8,X2,Z30), (Ra11,Rb8,X2,Z31), (Ra11,Rb8,X2,Z32), (Ra11,Rb8,X2,Z33), (Ra11,Rb8,X2,Z34), (Ra11,Rb8,X2,Z35), (Ra11,Rb8,X2,Z36), (Ra11,Rb8,X2,Z37), (Ra11,Rb8,X2,Z38), (Ra11,Rb8,X2,Z39), (Ra12,Rb1,X1,Z1), (Ra12,Rb1,X1,Z2), (Ra12,Rb1,X1,Z3), (Ra12,Rb1,X1,Z4), (Ra12,Rb1,X1,Z5), (Ra12,Rb1,X1,Z6), (Ra12,Rb1,X1,Z7), (Ra12,Rb1,X1,Z8), (Ra12,Rb1,X1,Z9), (Ra12,Rb1,X1,Z10), (Ra12,Rb1,X1,Z11), (Ra12,Rb1,X1,Z12), (Ra12,Rb1,X1,Z13), (Ra12,Rb1,X1,Z14), (Ra12,Rb1,X1,Z15), (Ra12,Rb1,X1,Z16), (Ra12,Rb1,X1,Z17), (Ra12,Rb1,X1,Z18), (Ra12,Rb1,X1,Z19), (Ra12,Rb1,X1,Z20), (Ra12,Rb1,X1,Z21), (Ra12,Rb1,X1,Z22), (Ra12,Rb1,X1,Z23), (Ra12,Rb1,X1,Z24), (Ra12,Rb1,X1,Z25), (Ra12,Rb1,X1,Z26), (Ra12,Rb1,X1,Z27), (Ra12,Rb1,X1,Z28), (Ra12,Rb1,X1,Z29), (Ra12,Rb1,X1,Z30), (Ra12,Rb1,X1,Z31), (Ra12,Rb1,X1,Z32), (Ra12,Rb1,X1,Z33), (Ra12,Rb1,X1,Z34), (Ra12,Rb1,X1,Z35), (Ra12,Rb1,X1,Z36), (Ra12,Rb1,X1,Z37), (Ra12,Rb1,X1,Z38), (Ra12,Rb1,X1,Z39), (Ra12,Rb1,X2,Z1), (Ra12,Rb1,X2,Z2), (Ra12,Rb1,X2,Z3), (Ra12,Rb1,X2,Z4), (Ra12,Rb1,X2,Z5), (Ra12,Rb1,X2,Z6), (Ra12,Rb1,X2,Z7), (Ra12,Rb1,X2,Z8), (Ra12,Rb1,X2,Z9), (Ra12,Rb1,X2,Z10), (Ra12,Rb1,X2,Z11), (Ra12,Rb1,X2,Z12), (Ra12,Rb1,X2,Z13), (Ra12,Rb1,X2,Z14), (Ra12,Rb1,X2,Z15), (Ra12,Rb1,X2,Z16), (Ra12,Rb1,X2,Z17), (Ra12,Rb1,X2,Z18), (Ra12,Rb1,X2,Z19), (Ra12,Rb1,X2,Z20), (Ra12,Rb1,X2,Z21), (Ra12,Rb1,X2,Z22), (Ra12,Rb1,X2,Z23), (Ra12,Rb1,X2,Z24), (Ra12,Rb1,X2,Z25), (Ra12,Rb1,X2,Z26), (Ra12,Rb1,X2,Z27), (Ra12,Rb1,X2,Z28), (Ra12,Rb1,X2,Z29), (Ra12,Rb1,X2,Z30), (Ra12,Rb1,X2,Z31), (Ra12,Rb1,X2,Z32), (Ra12,Rb1,X2,Z33), (Ra12,Rb1,X2,Z34), (Ra12,Rb1,X2,Z35), (Ra12,Rb1,X2,Z36), (Ra12,Rb1,X2,Z37), (Ra12,Rb1,X2,Z38), (Ra12,Rb1,X2,Z39), (Ra12,Rb2,X1,Z1), (Ra12,Rb2,X1,Z2), (Ra12,Rb2,X1,Z3), (Ra12,Rb2,X1,Z4), (Ra12,Rb2,X1,Z5), (Ra12,Rb2,X1,Z6), (Ra12,Rb2,X1,Z7), (Ra12,Rb2,X1,Z8), (Ra12,Rb2,X1,Z9), (Ra12,Rb2,X1,Z10), (Ra12,Rb2,X1,Z11), (Ra12,Rb2,X1,Z12), (Ra12,Rb2,X1,Z13), (Ra12,Rb2,X1,Z14), (Ra12,Rb2,X1,Z15), (Ra12,Rb2,X1,Z16), (Ra12,Rb2,X1,Z17), (Ra12,Rb2,X1,Z18), (Ra12,Rb2,X1,Z19), (Ra12,Rb2,X1,Z20), (Ra12,Rb2,X1,Z21), (Ra12,Rb2,X1,Z22), (Ra12,Rb2,X1,Z23), (Ra12,Rb2,X1,Z24), (Ra12,Rb2,X1,Z25), (Ra12,Rb2,X1,Z26), (Ra12,Rb2,X1,Z27), (Ra12,Rb2,X1,Z28), (Ra12,Rb2,X1,Z29), (Ra12,Rb2,X1,Z30), (Ra12,Rb2,X1,Z31), (Ra12,Rb2,X1,Z32), (Ra12,Rb2,X1,Z33), (Ra12,Rb2,X1,Z34), (Ra12,Rb2,X1,Z35), (Ra12,Rb2,X1,Z36), (Ra12,Rb2,X1,Z37), (Ra12,Rb2,X1,Z38), (Ra12,Rb2,X1,Z39), (Ra12,Rb2,X2,Z1), (Ra12,Rb2,X2,Z2), (Ra12,Rb2,X2,Z3), (Ra12,Rb2,X2,Z4), (Ra12,Rb2,X2,Z5), (Ra12,Rb2,X2,Z6), (Ra12,Rb2,X2,Z7), (Ra12,Rb2,X2,Z8), (Ra12,Rb2,X2,Z9), (Ra12,Rb2,X2,Z10), (Ra12,Rb2,X2,Z11), (Ra12,Rb2,X2,Z12), (Ra12,Rb2,X2,Z13), (Ra12,Rb2,X2,Z14), (Ra12,Rb2,X2,Z15), (Ra12,Rb2,X2,Z16), (Ra12,Rb2,X2,Z17), (Ra12,Rb2,X2,Z18), (Ra12,Rb2,X2,Z19), (Ra12,Rb2,X2,Z20), (Ra12,Rb2,X2,Z21), (Ra12,Rb2,X2,Z22), (Ra12,Rb2,X2,Z23), (Ra12,Rb2,X2,Z24), (Ra12,Rb2,X2,Z25), (Ra12,Rb2,X2,Z26), (Ra12,Rb2,X2,Z27), (Ra12,Rb2,X2,Z28), (Ra12,Rb2,X2,Z29), (Ra12,Rb2,X2,Z30), (Ra12,Rb2,X2,Z31), (Ra12,Rb2,X2,Z32), (Ra12,Rb2,X2,Z33), (Ra12,Rb2,X2,Z34), (Ra12,Rb2,X2,Z35), (Ra12,Rb2,X2,Z36), (Ra12,Rb2,X2,Z37), (Ra12,Rb2,X2,Z38), (Ra12,Rb2,X2,Z39), (Ra12,Rb3,X1,Z1), (Ra12,Rb3,X1,Z2), (Ra12,Rb3,X1,Z3), (Ra12,Rb3,X1,Z4), (Ra12,Rb3,X1,Z5), (Ra12,Rb3,X1,Z6), (Ra12,Rb3,X1,Z7), (Ra12,Rb3,X1,Z8), (Ra12,Rb3,X1,Z9), (Ra12,Rb3,X1,Z10), (Ra12,Rb3,X1,Z11), (Ra12,Rb3,X1,Z12), (Ra12,Rb3,X1,Z13), (Ra12,Rb3,X1,Z14), (Ra12,Rb3,X1,Z15), (Ra12,Rb3,X1,Z16), (Ra12,Rb3,X1,Z17), (Ra12,Rb3,X1,Z18), (Ra12,Rb3,X1,Z19), (Ra12,Rb3,X1,Z20), (Ra12,Rb3,X1,Z21), (Ra12,Rb3,X1,Z22), (Ra12,Rb3,X1,Z23), (Ra12,Rb3,X1,Z24), (Ra12,Rb3,X1,Z25), (Ra12,Rb3,X1,Z26), (Ra12,Rb3,X1,Z27), (Ra12,Rb3,X1,Z28), (Ra12,Rb3,X1,Z29), (Ra12,Rb3,X1,Z30), (Ra12,Rb3,X1,Z31), (Ra12,Rb3,X1,Z32), (Ra12,Rb3,X1,Z33), (Ra12,Rb3,X1,Z34), (Ra12,Rb3,X1,Z35), (Ra12,Rb3,X1,Z36), (Ra12,Rb3,X1,Z37), (Ra12,Rb3,X1,Z38), (Ra12,Rb3,X1,Z39), (Ra12,Rb3,X2,Z1), (Ra12,Rb3,X2,Z2), (Ra12,Rb3,X2,Z3), (Ra12,Rb3,X2,Z4), (Ra12,Rb3,X2,Z5), (Ra12,Rb3,X2,Z6), (Ra12,Rb3,X2,Z7), (Ra12,Rb3,X2,Z8), (Ra12,Rb3,X2,Z9), (Ra12,Rb3,X2,Z10), (Ra12,Rb3,X2,Z11), (Ra12,Rb3,X2,Z12), (Ra12,Rb3,X2,Z13), (Ra12,Rb3,X2,Z14), (Ra12,Rb3,X2,Z15), (Ra12,Rb3,X2,Z16), (Ra12,Rb3,X2,Z17), (Ra12,Rb3,X2,Z18), (Ra12,Rb3,X2,Z19), (Ra12,Rb3,X2,Z20), (Ra12, Rb3,X2,Z21), (Ra12,Rb3,X2,Z22), (Ra12,Rb3,X2,Z23), (Ra12,Rb3,X2,Z24), (Ra12,Rb3,X2,Z25), (Ra12,Rb3,X2,Z26), (Ra12,Rb3,X2,Z27), (Ra12,Rb3,X2,Z28), (Ra12,Rb3,X2,Z29), (Ra12,Rb3,X2,Z30), (Ra12,Rb3,X2,Z31), (Ra12,Rb3,X2,Z32), (Ra12,Rb3,X2,Z33), (Ra12,Rb3,X2,Z34), (Ra12,Rb3,X2,Z35), (Ra12,Rb3,X2,Z36), (Ra12,Rb3,X2,Z37), (Ra12,Rb3,X2,Z38), (Ra12,Rb3,X2,Z39), (Ra12,Rb4,X1,Z1), (Ra12,Rb4,X1,Z2), (Ra12,Rb4,X1,Z3), (Ra12,Rb4,X1,Z4), (Ra12,Rb4,X1,Z5), (Ra12,Rb4,X1,Z6), (Ra12,Rb4,X1,Z7), (Ra12,Rb4,X1,Z8), (Ra12,Rb4,X1,Z9), (Ra12,Rb4,X1,Z10), (Ra12,Rb4,X1,Z11), (Ra12,Rb4,X1,Z12), (Ra12,Rb4,X1,Z13), (Ra12,Rb4,X1,Z14), (Ra12,Rb4,X1,Z15), (Ra12,Rb4,X1,Z16), (Ra12,Rb4,X1,Z17), (Ra12,Rb4,X1,Z18), (Ra12,Rb4,X1,Z19), (Ra12,Rb4,X1,Z20), (Ra12,Rb4,X1,Z21), (Ra12,Rb4,X1,Z22), (Ra12,Rb4,X1,Z23), (Ra12,Rb4,

X1,Z24), (Ra12,Rb4,X1,Z25), (Ra12,Rb4,X1,Z26), (Ra12, Rb4,X1,Z27), (Ra12,Rb4,X1,Z28), (Ra12,Rb4,X1,Z29), (Ra12,Rb4,X1,Z30), (Ra12,Rb4,X1,Z31), (Ra12,Rb4,X1, Z32), (Ra12,Rb4,X1,Z33), (Ra12,Rb4,X1,Z34), (Ra12,Rb4, X1,Z35), (Ra12,Rb4,X1,Z36), (Ra12,Rb4,X1,Z37), (Ra12, Rb4,X1,Z38), (Ra12,Rb4,X1,Z39), (Ra12,Rb4,X2,Z1), (Ra12,Rb4,X2,Z2), (Ra12,Rb4,X2,Z3), (Ra12,Rb4,X2,Z4), (Ra12,Rb4,X2,Z5), (Ra12,Rb4,X2,Z6), (Ra12,Rb4,X2,Z7), (Ra12,Rb4,X2,Z8), (Ra12,Rb4,X2,Z9), (Ra12,Rb4,X2, Z10), (Ra12,Rb4,X2,Z11), (Ra12,Rb4,X2,Z12), (Ra12,Rb4, X2,Z13), (Ra12,Rb4,X2,Z14), (Ra12,Rb4,X2,Z15), (Ra12, Rb4,X2,Z16), (Ra12,Rb4,X2,Z17), (Ra12,Rb4,X2,Z18), (Ra12,Rb4,X2,Z19), (Ra12,Rb4,X2,Z20), (Ra12,Rb4,X2, Z21), (Ra12,Rb4,X2,Z22), (Ra12,Rb4,X2,Z23), (Ra12,Rb4, X2,Z24), (Ra12,Rb4,X2,Z25), (Ra12,Rb4,X2,Z26), (Ra12, Rb4,X2,Z27), (Ra12,Rb4,X2,Z28), (Ra12,Rb4,X2,Z29), (Ra12,Rb4,X2,Z30), (Ra12,Rb4,X2,Z31), (Ra12,Rb4,X2, Z32), (Ra12,Rb4,X2,Z33), (Ra12,Rb4,X2,Z34), (Ra12,Rb4, X2,Z35), (Ra12,Rb4,X2,Z36), (Ra12,Rb4,X2,Z37), (Ra12, Rb4,X2,Z38), (Ra12,Rb4,X2,Z39), (Ra12,Rb5,X1,Z1), (Ra12,Rb5,X1,Z2), (Ra12,Rb5,X1,Z3), (Ra12,Rb5,X1,Z4), (Ra12,Rb5,X1,Z5), (Ra12,Rb5,X1,Z6), (Ra12,Rb5,X1,Z7), (Ra12,Rb5,X1,Z8), (Ra12,Rb5,X1,Z9), (Ra12,Rb5,X1, Z10), (Ra12,Rb5,X1,Z11), (Ra12,Rb5,X1,Z12), (Ra12,Rb5, X1,Z13), (Ra12,Rb5,X1,Z14), (Ra12,Rb5,X1,Z15), (Ra12, Rb5,X1,Z16), (Ra12,Rb5,X1,Z17), (Ra12,Rb5,X1,Z18), (Ra12,Rb5,X1,Z19), (Ra12,Rb5,X1,Z20), (Ra12,Rb5,X1, Z21), (Ra12,Rb5,X1,Z22), (Ra12,Rb5,X1,Z23), (Ra12,Rb5, X1,Z24), (Ra12,Rb5,X1,Z25), (Ra12,Rb5,X1,Z26), (Ra12, Rb5,X1,Z27), (Ra12,Rb5,X1,Z28), (Ra12,Rb5,X1,Z29), (Ra12,Rb5,X1,Z30), (Ra12,Rb5,X1,Z31), (Ra12,Rb5,X1, Z32), (Ra12,Rb5,X1,Z33), (Ra12,Rb5,X1,Z34), (Ra12,Rb5, X1,Z35), (Ra12,Rb5,X1,Z36), (Ra12,Rb5,X1,Z37), (Ra12, Rb5,X1,Z38), (Ra12,Rb5,X1,Z39), (Ra12,Rb5,X2,Z1), (Ra12,Rb5,X2,Z2), (Ra12,Rb5,X2,Z3), (Ra12,Rb5,X2,Z4), (Ra12,Rb5,X2,Z5), (Ra12,Rb5,X2,Z6), (Ra12,Rb5,X2,Z7), (Ra12,Rb5,X2,Z8), (Ra12,Rb5,X2,Z9), (Ra12,Rb5,X2, Z10), (Ra12,Rb5,X2,Z11), (Ra12,Rb5,X2,Z12), (Ra12,Rb5, X2,Z13), (Ra12,Rb5,X2,Z14), (Ra12,Rb5,X2,Z15), (Ra12, Rb5,X2,Z16), (Ra12,Rb5,X2,Z17), (Ra12,Rb5,X2,Z18), (Ra12,Rb5,X2,Z19), (Ra12,Rb5,X2,Z20), (Ra12,Rb5,X2, Z21), (Ra12,Rb5,X2,Z22), (Ra12,Rb5,X2,Z23), (Ra12,Rb5, X2,Z24), (Ra12,Rb5,X2,Z25), (Ra12,Rb5,X2,Z26), (Ra12, Rb5,X2,Z27), (Ra12,Rb5,X2,Z28), (Ra12,Rb5,X2,Z29), (Ra12,Rb5,X2,Z30), (Ra12,Rb5,X2,Z31), (Ra12,Rb5,X2, Z32), (Ra12,Rb5,X2,Z33), (Ra12,Rb5,X2,Z34), (Ra12,Rb5, X2,Z35), (Ra12,Rb5,X2,Z36), (Ra12,Rb5,X2,Z37), (Ra12, Rb5,X2,Z38), (Ra12,Rb5,X2,Z39), (Ra12,Rb6,X1,Z1), (Ra12,Rb6,X1,Z2), (Ra12,Rb6,X1,Z3), (Ra12,Rb6,X1,Z4), (Ra12,Rb6,X1,Z5), (Ra12,Rb6,X1,Z6), (Ra12,Rb6,X1,Z7), (Ra12,Rb6,X1,Z8), (Ra12,Rb6,X1,Z9), (Ra12,Rb6,X1, Z10), (Ra12,Rb6,X1,Z11), (Ra12,Rb6,X1,Z12), (Ra12,Rb6, X1,Z13), (Ra12,Rb6,X1,Z14), (Ra12,Rb6,X1,Z15), (Ra12, Rb6,X1,Z16), (Ra12,Rb6,X1,Z17), (Ra12,Rb6,X1,Z18), (Ra12,Rb6,X1,Z19), (Ra12,Rb6,X1,Z20), (Ra12,Rb6,X1, Z21), (Ra12,Rb6,X1,Z22), (Ra12,Rb6,X1,Z23), (Ra12,Rb6, X1,Z24), (Ra12,Rb6,X1,Z25), (Ra12,Rb6,X1,Z26), (Ra12, Rb6,X1,Z27), (Ra12,Rb6,X1,Z28), (Ra12,Rb6,X1,Z29), (Ra12,Rb6,X1,Z30), (Ra12,Rb6,X1,Z31), (Ra12,Rb6,X1, Z32), (Ra12,Rb6,X1,Z33), (Ra12,Rb6,X1,Z34), (Ra12,Rb6, X1,Z35), (Ra12,Rb6,X1,Z36), (Ra12,Rb6,X1,Z37), (Ra12, Rb6,X1,Z38), (Ra12,Rb6,X1,Z39), (Ra12,Rb6,X2,Z1), (Ra12,Rb6,X2,Z2), (Ra12,Rb6,X2,Z3), (Ra12,Rb6,X2,Z4), (Ra12,Rb6,X2,Z5), (Ra12,Rb6,X2,Z6), (Ra12,Rb6,X2,Z7), (Ra12,Rb6,X2,Z8), (Ra12,Rb6,X2,Z9), (Ra12,Rb6,X2, Z10), (Ra12,Rb6,X2,Z11), (Ra12,Rb6,X2,Z12), (Ra12,Rb6, X2,Z13), (Ra12,Rb6,X2,Z14), (Ra12,Rb6,X2,Z15), (Ra12, Rb6,X2,Z16), (Ra12,Rb6,X2,Z17), (Ra12,Rb6,X2,Z18), (Ra12,Rb6,X2,Z19), (Ra12,Rb6,X2,Z20), (Ra12,Rb6,X2, Z21), (Ra12,Rb6,X2,Z22), (Ra12,Rb6,X2,Z23), (Ra12,Rb6, X2,Z24), (Ra12,Rb6,X2,Z25), (Ra12,Rb6,X2,Z26), (Ra12, Rb6,X2,Z27), (Ra12,Rb6,X2,Z28), (Ra12,Rb6,X2,Z29), (Ra12,Rb6,X2,Z30), (Ra12,Rb6,X2,Z31), (Ra12,Rb6,X2, Z32), (Ra12,Rb6,X2,Z33), (Ra12,Rb6,X2,Z34), (Ra12,Rb6, X2,Z35), (Ra12,Rb6,X2,Z36), (Ra12,Rb6,X2,Z37), (Ra12, Rb6,X2,Z38), (Ra12,Rb6,X2,Z39), (Ra12,Rb7,X1,Z1), (Ra12,Rb7,X1,Z2), (Ra12,Rb7,X1,Z3), (Ra12,Rb7,X1,Z4), (Ra12,Rb7,X1,Z5), (Ra12,Rb7,X1,Z6), (Ra12,Rb7,X1,Z7), (Ra12,Rb7,X1,Z8), (Ra12,Rb7,X1,Z9), (Ra12,Rb7,X1, Z10), (Ra12,Rb7,X1,Z11), (Ra12,Rb7,X1,Z12), (Ra12,Rb7, X1,Z13), (Ra12,Rb7,X1,Z14), (Ra12,Rb7,X1,Z15), (Ra12, Rb7,X1,Z16), (Ra12,Rb7,X1,Z17), (Ra12,Rb7,X1,Z18), (Ra12,Rb7,X1,Z19), (Ra12,Rb7,X1,Z20), (Ra12,Rb7,X1, Z21), (Ra12,Rb7,X1,Z22), (Ra12,Rb7,X1,Z23), (Ra12,Rb7, X1,Z24), (Ra12,Rb7,X1,Z25), (Ra12,Rb7,X1,Z26), (Ra12, Rb7,X1,Z27), (Ra12,Rb7,X1,Z28), (Ra12,Rb7,X1,Z29), (Ra12,Rb7,X1,Z30), (Ra12,Rb7,X1,Z31), (Ra12,Rb7,X1, Z32), (Ra12,Rb7,X1,Z33), (Ra12,Rb7,X1,Z34), (Ra12,Rb7, X1,Z35), (Ra12,Rb7,X1,Z36), (Ra12,Rb7,X1,Z37), (Ra12, Rb7,X1,Z38), (Ra12,Rb7,X1,Z39), (Ra12,Rb7,X2,Z1), (Ra12,Rb7,X2,Z2), (Ra12,Rb7,X2,Z3), (Ra12,Rb7,X2,Z4), (Ra12,Rb7,X2,Z5), (Ra12,Rb7,X2,Z6), (Ra12,Rb7,X2,Z7), (Ra12,Rb7,X2,Z8), (Ra12,Rb7,X2,Z9), (Ra12,Rb7,X2, Z10), (Ra12,Rb7,X2,Z11), (Ra12,Rb7,X2,Z12), (Ra12,Rb7, X2,Z13), (Ra12,Rb7,X2,Z14), (Ra12,Rb7,X2,Z15), (Ra12, Rb7,X2,Z16), (Ra12,Rb7,X2,Z17), (Ra12,Rb7,X2,Z18), (Ra12,Rb7,X2,Z19), (Ra12,Rb7,X2,Z20), (Ra12,Rb7,X2, Z21), (Ra12,Rb7,X2,Z22), (Ra12,Rb7,X2,Z23), (Ra12,Rb7, X2,Z24), (Ra12,Rb7,X2,Z25), (Ra12,Rb7,X2,Z26), (Ra12, Rb7,X2,Z27), (Ra12,Rb7,X2,Z28), (Ra12,Rb7,X2,Z29), (Ra12,Rb7,X2,Z30), (Ra12,Rb7,X2,Z31), (Ra12,Rb7,X2, Z32), (Ra12,Rb7,X2,Z33), (Ra12,Rb7,X2,Z34), (Ra12,Rb7, X2,Z35), (Ra12,Rb7,X2,Z36), (Ra12,Rb7,X2,Z37), (Ra12, Rb7,X2,Z38), (Ra12,Rb7,X2,Z39), (Ra12,Rb8,X1,Z1), (Ra12,Rb8,X1,Z2), (Ra12,Rb8,X1,Z3), (Ra12,Rb8,X1,Z4), (Ra12,Rb8,X1,Z5), (Ra12,Rb8,X1,Z6), (Ra12,Rb8,X1,Z7), (Ra12,Rb8,X1,Z8), (Ra12,Rb8,X1,Z9), (Ra12,Rb8,X1, Z10), (Ra12,Rb8,X1,Z11), (Ra12,Rb8,X1,Z12), (Ra12,Rb8, X1,Z13), (Ra12,Rb8,X1,Z14), (Ra12,Rb8,X1,Z15), (Ra12, Rb8,X1,Z16), (Ra12,Rb8,X1,Z17), (Ra12,Rb8,X1,Z18), (Ra12,Rb8,X1,Z19), (Ra12,Rb8,X1,Z20), (Ra12,Rb8,X1, Z21), (Ra12,Rb8,X1,Z22), (Ra12,Rb8,X1,Z23), (Ra12,Rb8, X1,Z24), (Ra12,Rb8,X1,Z25), (Ra12,Rb8,X1,Z26), (Ra12, Rb8,X1,Z27), (Ra12,Rb8,X1,Z28), (Ra12,Rb8,X1,Z29), (Ra12,Rb8,X1,Z30), (Ra12,Rb8,X1,Z31), (Ra12,Rb8,X1, Z32), (Ra12,Rb8,X1,Z33), (Ra12,Rb8,X1,Z34), (Ra12,Rb8, X1,Z35), (Ra12,Rb8,X1,Z36), (Ra12,Rb8,X1,Z37), (Ra12, Rb8,X1,Z38), (Ra12,Rb8,X1,Z39), (Ra12,Rb8,X2,Z1), (Ra12,Rb8,X2,Z2), (Ra12,Rb8,X2,Z3), (Ra12,Rb8,X2,Z4), (Ra12,Rb8,X2,Z5), (Ra12,Rb8,X2,Z6), (Ra12,Rb8,X2,Z7), (Ra12,Rb8,X2,Z8), (Ra12,Rb8,X2,Z9), (Ra12,Rb8,X2, Z10), (Ra12,Rb8,X2,Z11), (Ra12,Rb8,X2,Z12), (Ra12,Rb8, X2,Z13), (Ra12,Rb8,X2,Z14), (Ra12,Rb8,X2,Z15), (Ra12, Rb8,X2,Z16), (Ra12,Rb8,X2,Z17), (Ra12,Rb8,X2,Z18), (Ra12,Rb8,X2,Z19), (Ra12,Rb8,X2,Z20), (Ra12,Rb8,X2, Z21), (Ra12,Rb8,X2,Z22), (Ra12,Rb8,X2,Z23), (Ra12,Rb8, X2,Z24), (Ra12,Rb8,X2,Z25), (Ra12,Rb8,X2,Z26), (Ra12, Rb8,X2,Z27), (Ra12,Rb8,X2,Z28), (Ra12,Rb8,X2,Z29), (Ra12,Rb8,X2,Z30), (Ra12,Rb8,X2,Z31), (Ra12,Rb8,X2, Z32), (Ra12,Rb8,X2,Z33), (Ra12,Rb8,X2,Z34), (Ra12,Rb8, X2,Z35), (Ra12,Rb8,X2,Z36), (Ra12,Rb8,X2,Z37), (Ra12, Rb8,X2,Z38), (Ra12,Rb8,X2,Z39), (Ra13,Rb1,X1,Z1), (Ra13,Rb1,X1,Z2), (Ra13,Rb1,X1,Z3), (Ra13,Rb1,X1,Z4), (Ra13,Rb1,X1,Z5), (Ra13,Rb1,X1,Z6), (Ra13,Rb1,X1,Z7), (Ra13,Rb1,X1,Z8), (Ra13,Rb1,X1,Z9), (Ra13,Rb1,X1,Z10), (Ra13,Rb1,X1,Z11), (Ra13,Rb1,X1,Z12), (Ra13,Rb1,X1,Z13), (Ra13,Rb1,X1,Z14), (Ra13,Rb1,X1,Z15), (Ra13,Rb1,X1,Z16), (Ra13,Rb1,X1,Z17), (Ra13,Rb1,X1,Z18), (Ra13,Rb1,X1,Z19), (Ra13,Rb1,X1,Z20), (Ra13,Rb1,X1,Z21), (Ra13,Rb1,X1,Z22), (Ra13,Rb1,X1,Z23), (Ra13,Rb1,X1,Z24), (Ra13,Rb1,X1,Z25), (Ra13,Rb1,X1,Z26), (Ra13,Rb1,X1,Z27), (Ra13,Rb1,X1,Z28), (Ra13,Rb1,X1,Z29), (Ra13,Rb1,X1,Z30), (Ra13,Rb1,X1,Z31), (Ra13,Rb1,X1,Z32), (Ra13,Rb1,X1,Z33), (Ra13,Rb1,X1,Z34), (Ra13,Rb1,X1,Z35), (Ra13,Rb1,X1,Z36), (Ra13,Rb1,X1,Z37), (Ra13,Rb1,X1,Z38), (Ra13,Rb1,X1,Z39), (Ra13,Rb1,X2,Z1), (Ra13,Rb1,X2,Z2), (Ra13,Rb1,X2,Z3), (Ra13,Rb1,X2,Z4), (Ra13,Rb1,X2,Z5), (Ra13,Rb1,X2,Z6), (Ra13,Rb1,X2,Z7), (Ra13,Rb1,X2,Z8), (Ra13,Rb1,X2,Z9), (Ra13,Rb1,X2,Z10), (Ra13,Rb1,X2,Z11), (Ra13,Rb1,X2,Z12), (Ra13,Rb1,X2,Z13), (Ra13,Rb1,X2,Z14), (Ra13,Rb1,X2,Z15), (Ra13,Rb1,X2,Z16), (Ra13,Rb1,X2,Z17), (Ra13,Rb1,X2,Z18), (Ra13,Rb1,X2,Z19), (Ra13,Rb1,X2,Z20), (Ra13,Rb1,X2,Z21), (Ra13,Rb1,X2,Z22), (Ra13,Rb1,X2,Z23), (Ra13,Rb1,X2,Z24), (Ra13,Rb1,X2,Z25), (Ra13,Rb1,X2,Z26), (Ra13,Rb1,X2,Z27), (Ra13,Rb1,X2,Z28), (Ra13,Rb1,X2,Z29), (Ra13,Rb1,X2,Z30), (Ra13,Rb1,X2,Z31), (Ra13,Rb1,X2,Z32), (Ra13,Rb1,X2,Z33), (Ra13,Rb1,X2,Z34), (Ra13,Rb1,X2,Z35), (Ra13,Rb1,X2,Z36), (Ra13,Rb1,X2,Z37), (Ra13,Rb1,X2,Z38), (Ra13,Rb1,X2,Z39), (Ra13,Rb2,X1,Z1), (Ra13,Rb2,X1,Z2), (Ra13,Rb2,X1,Z3), (Ra13,Rb2,X1,Z4), (Ra13,Rb2,X1,Z5), (Ra13,Rb2,X1,Z6), (Ra13,Rb2,X1,Z7), (Ra13,Rb2,X1,Z8), (Ra13,Rb2,X1,Z9), (Ra13,Rb2,X1,Z10), (Ra13,Rb2,X1,Z11), (Ra13,Rb2,X1,Z12), (Ra13,Rb2,X1,Z13), (Ra13,Rb2,X1,Z14), (Ra13,Rb2,X1,Z15), (Ra13,Rb2,X1,Z16), (Ra13,Rb2,X1,Z17), (Ra13,Rb2,X1,Z18), (Ra13,Rb2,X1,Z19), (Ra13,Rb2,X1,Z20), (Ra13,Rb2,X1,Z21), (Ra13,Rb2,X1,Z22), (Ra13,Rb2,X1,Z23), (Ra13,Rb2,X1,Z24), (Ra13,Rb2,X1,Z25), (Ra13,Rb2,X1,Z26), (Ra13,Rb2,X1,Z27), (Ra13,Rb2,X1,Z28), (Ra13,Rb2,X1,Z29), (Ra13,Rb2,X1,Z30), (Ra13,Rb2,X1,Z31), (Ra13,Rb2,X1,Z32), (Ra13,Rb2,X1,Z33), (Ra13,Rb2,X1,Z34), (Ra13,Rb2,X1,Z35), (Ra13,Rb2,X1,Z36), (Ra13,Rb2,X1,Z37), (Ra13,Rb2,X1,Z38), (Ra13,Rb2,X1,Z39), (Ra13,Rb2,X2,Z1), (Ra13,Rb2,X2,Z2), (Ra13,Rb2,X2,Z3), (Ra13,Rb2,X2,Z4), (Ra13,Rb2,X2,Z5), (Ra13,Rb2,X2,Z6), (Ra13,Rb2,X2,Z7), (Ra13,Rb2,X2,Z8), (Ra13,Rb2,X2,Z9), (Ra13,Rb2,X2,Z10), (Ra13,Rb2,X2,Z11), (Ra13,Rb2,X2,Z12), (Ra13,Rb2,X2,Z13), (Ra13,Rb2,X2,Z14), (Ra13,Rb2,X2,Z15), (Ra13,Rb2,X2,Z16), (Ra13,Rb2,X2,Z17), (Ra13,Rb2,X2,Z18), (Ra13,Rb2,X2,Z19), (Ra13,Rb2,X2,Z20), (Ra13,Rb2,X2,Z21), (Ra13,Rb2,X2,Z22), (Ra13,Rb2,X2,Z23), (Ra13,Rb2,X2,Z24), (Ra13,Rb2,X2,Z25), (Ra13,Rb2,X2,Z26), (Ra13,Rb2,X2,Z27), (Ra13,Rb2,X2,Z28), (Ra13,Rb2,X2,Z29), (Ra13,Rb2,X2,Z30), (Ra13,Rb2,X2,Z31), (Ra13,Rb2,X2,Z32), (Ra13,Rb2,X2,Z33), (Ra13,Rb2,X2,Z34), (Ra13,Rb2,X2,Z35), (Ra13,Rb2,X2,Z36), (Ra13,Rb2,X2,Z37), (Ra13,Rb2,X2,Z38), (Ra13,Rb2,X2,Z39), (Ra13,Rb3,X1,Z1), (Ra13,Rb3,X1,Z2), (Ra13,Rb3,X1,Z3), (Ra13,Rb3,X1,Z4), (Ra13,Rb3,X1,Z5), (Ra13,Rb3,X1,Z6), (Ra13,Rb3,X1,Z7), (Ra13,Rb3,X1,Z8), (Ra13,Rb3,X1,Z9), (Ra13,Rb3,X1,Z10), (Ra13,Rb3,X1,Z11), (Ra13,Rb3,X1,Z12), (Ra13,Rb3,X1,Z13), (Ra13,Rb3,X1,Z14), (Ra13,Rb3,X1,Z15), (Ra13,Rb3,X1,Z16), (Ra13,Rb3,X1,Z17), (Ra13,Rb3,X1,Z18), (Ra13,Rb3,X1,Z19), (Ra13,Rb3,X1,Z20), (Ra13,Rb3,X1,Z21), (Ra13,Rb3,X1,Z22), (Ra13,Rb3,X1,Z23), (Ra13,Rb3,X1,Z24), (Ra13,Rb3,X1,Z25), (Ra13,Rb3,X1,Z26), (Ra13,Rb3,X1,Z27), (Ra13,Rb3,X1,Z28), (Ra13,Rb3,X1,Z29), (Ra13,Rb3,X1,Z30), (Ra13,Rb3,X1,Z31), (Ra13,Rb3,X1,Z32), (Ra13,Rb3,X1,Z33), (Ra13,Rb3,X1,Z34), (Ra13,Rb3,X1,Z35), (Ra13,Rb3,X1,Z36), (Ra13,Rb3,X1,Z37), (Ra13,Rb3,X1,Z38), (Ra13,Rb3,X1,Z39), (Ra13,Rb3,X2,Z1), (Ra13,Rb3,X2,Z2), (Ra13,Rb3,X2,Z3), (Ra13,Rb3,X2,Z4), (Ra13,Rb3,X2,Z5), (Ra13,Rb3,X2,Z6), (Ra13,Rb3,X2,Z7), (Ra13,Rb3,X2,Z8), (Ra13,Rb3,X2,Z9), (Ra13,Rb3,X2,Z10), (Ra13,Rb3,X2,Z11), (Ra13,Rb3,X2,Z12), (Ra13,Rb3,X2,Z13), (Ra13,Rb3,X2,Z14), (Ra13,Rb3,X2,Z15), (Ra13,Rb3,X2,Z16), (Ra13,Rb3,X2,Z17), (Ra13,Rb3,X2,Z18), (Ra13,Rb3,X2,Z19), (Ra13,Rb3,X2,Z20), (Ra13,Rb3,X2,Z21), (Ra13,Rb3,X2,Z22), (Ra13,Rb3,X2,Z23), (Ra13,Rb3,X2,Z24), (Ra13,Rb3,X2,Z25), (Ra13,Rb3,X2,Z26), (Ra13,Rb3,X2,Z27), (Ra13,Rb3,X2,Z28), (Ra13,Rb3,X2,Z29), (Ra13,Rb3,X2,Z30), (Ra13,Rb3,X2,Z31), (Ra13,Rb3,X2,Z32), (Ra13,Rb3,X2,Z33), (Ra13,Rb3,X2,Z34), (Ra13,Rb3,X2,Z35), (Ra13,Rb3,X2,Z36), (Ra13,Rb3,X2,Z37), (Ra13,Rb3,X2,Z38), (Ra13,Rb3,X2,Z39), (Ra13,Rb4,X1,Z1), (Ra13,Rb4,X1,Z2), (Ra13,Rb4,X1,Z3), (Ra13,Rb4,X1,Z4), (Ra13,Rb4,X1,Z5), (Ra13,Rb4,X1,Z6), (Ra13,Rb4,X1,Z7), (Ra13,Rb4,X1,Z8), (Ra13,Rb4,X1,Z9), (Ra13,Rb4,X1,Z10), (Ra13,Rb4,X1,Z11), (Ra13,Rb4,X1,Z12), (Ra13,Rb4,X1,Z13), (Ra13,Rb4,X1,Z14), (Ra13,Rb4,X1,Z15), (Ra13,Rb4,X1,Z16), (Ra13,Rb4,X1,Z17), (Ra13,Rb4,X1,Z18), (Ra13,Rb4,X1,Z19), (Ra13,Rb4,X1,Z20), (Ra13,Rb4,X1,Z21), (Ra13,Rb4,X1,Z22), (Ra13,Rb4,X1,Z23), (Ra13,Rb4,X1,Z24), (Ra13,Rb4,X1,Z25), (Ra13,Rb4,X1,Z26), (Ra13,Rb4,X1,Z27), (Ra13,Rb4,X1,Z28), (Ra13,Rb4,X1,Z29), (Ra13,Rb4,X1,Z30), (Ra13,Rb4,X1,Z31), (Ra13,Rb4,X1,Z32), (Ra13,Rb4,X1,Z33), (Ra13,Rb4,X1,Z34), (Ra13,Rb4,X1,Z35), (Ra13,Rb4,X1,Z36), (Ra13,Rb4,X1,Z37), (Ra13,Rb4,X1,Z38), (Ra13,Rb4,X1,Z39), (Ra13,Rb4,X2,Z1), (Ra13,Rb4,X2,Z2), (Ra13,Rb4,X2,Z3), (Ra13,Rb4,X2,Z4), (Ra13,Rb4,X2,Z5), (Ra13,Rb4,X2,Z6), (Ra13,Rb4,X2,Z7), (Ra13,Rb4,X2,Z8), (Ra13,Rb4,X2,Z9), (Ra13,Rb4,X2,Z10), (Ra13,Rb4,X2,Z11), (Ra13,Rb4,X2,Z12), (Ra13,Rb4,X2,Z13), (Ra13,Rb4,X2,Z14), (Ra13,Rb4,X2,Z15), (Ra13,Rb4,X2,Z16), (Ra13,Rb4,X2,Z17), (Ra13,Rb4,X2,Z18), (Ra13,Rb4,X2,Z19), (Ra13,Rb4,X2,Z20), (Ra13,Rb4,X2,Z21), (Ra13,Rb4,X2,Z22), (Ra13,Rb4,X2,Z23), (Ra13,Rb4,X2,Z24), (Ra13,Rb4,X2,Z25), (Ra13,Rb4,X2,Z26), (Ra13,Rb4,X2,Z27), (Ra13,Rb4,X2,Z28), (Ra13,Rb4,X2,Z29), (Ra13,Rb4,X2,Z30), (Ra13,Rb4,X2,Z31), (Ra13,Rb4,X2,Z32), (Ra13,Rb4,X2,Z33), (Ra13,Rb4,X2,Z34), (Ra13,Rb4,X2,Z35), (Ra13,Rb4,X2,Z36), (Ra13,Rb4,X2,Z37), (Ra13,Rb4,X2,Z38), (Ra13,Rb4,X2,Z39), (Ra13,Rb5,X1,Z1), (Ra13,Rb5,X1,Z2), (Ra13,Rb5,X1,Z3), (Ra13,Rb5,X1,Z4), (Ra13,Rb5,X1,Z5), (Ra13,Rb5,X1,Z6), (Ra13,Rb5,X1,Z7), (Ra13,Rb5,X1,Z8), (Ra13,Rb5,X1,Z9), (Ra13,Rb5,X1,Z10), (Ra13,Rb5,X1,Z11), (Ra13,Rb5,X1,Z12), (Ra13,Rb5,X1,Z13), (Ra13,Rb5,X1,Z14), (Ra13,Rb5,X1,Z15), (Ra13,Rb5,X1,Z16), (Ra13,Rb5,X1,Z17), (Ra13,Rb5,X1,Z18), (Ra13,Rb5,X1,Z19), (Ra13,Rb5,X1,Z20), (Ra13,Rb5,X1,Z21), (Ra13,Rb5,X1,Z22), (Ra13,Rb5,X1,Z23), (Ra13,Rb5,X1,Z24), (Ra13,Rb5,X1,Z25), (Ra13,Rb5,X1,Z26), (Ra13,Rb5,X1,Z27), (Ra13,Rb5,X1,Z28), (Ra13,Rb5,X1,Z29), (Ra13,Rb5,X1,Z30), (Ra13,Rb5,X1,Z31), (Ra13,Rb5,X1,Z32), (Ra13,Rb5,X1,Z33), (Ra13,Rb5,X1,Z34), (Ra13,Rb5,X1,Z35), (Ra13,Rb5,X1,Z36), (Ra13,Rb5,X1,Z37), (Ra13,Rb5,X1,Z38), (Ra13,Rb5,X1,Z39), (Ra13,Rb5,X2,Z1), (Ra13,Rb5,X2,Z2), (Ra13,Rb5,X2,Z3), (Ra13,Rb5,X2,Z4), (Ra13,Rb5,X2,Z5), (Ra13,Rb5,X2,Z6), (Ra13,Rb5,X2,Z7), (Ra13,Rb5,X2,Z8), (Ra13,Rb5,X2,Z9), (Ra13,Rb5,X2,Z10), (Ra13,Rb5,X2,Z11), (Ra13,Rb5,X2,Z12), (Ra13,Rb5,X2,Z13), (Ra13,Rb5,X2,Z14), (Ra13,Rb5,X2,Z15), (Ra13,Rb5,X2,Z16), (Ra13,Rb5,X2,Z17), (Ra13,Rb5,X2,Z18), (Ra13,Rb5,X2,Z19), (Ra13,Rb5,X2,Z20), (Ra13,Rb5,X2,Z21), (Ra13,Rb5,X2,Z22), (Ra13,Rb5,X2,Z23), (Ra13,Rb5,X2,Z24), (Ra13,Rb5,X2,Z25), (Ra13,Rb5,X2,Z26), (Ra13,Rb5,X2,Z27), (Ra13,Rb5,X2,Z28), (Ra13,Rb5,X2,Z29), (Ra13,Rb5,X2,Z30), (Ra13,Rb5,X2,Z31), (Ra13,Rb5,X2,Z32), (Ra13,Rb5,X2,Z33), (Ra13,Rb5,X2,Z34), (Ra13,Rb5,X2,Z35), (Ra13,Rb5,X2,Z36), (Ra13,Rb5,X2,Z37), (Ra13,Rb5,X2,Z38), (Ra13,Rb5,X2,Z39), (Ra13,Rb6,X1,Z1), (Ra13,Rb6,X1,Z2), (Ra13,Rb6,X1,Z3), (Ra13,Rb6,X1,Z4), (Ra13,Rb6,X1,Z5), (Ra13,Rb6,X1,Z6), (Ra13,Rb6,X1,Z7), (Ra13,Rb6,X1,Z8), (Ra13,Rb6,X1,Z9), (Ra13,Rb6,X1,Z10), (Ra13,Rb6,X1,Z11), (Ra13,Rb6,X1,Z12), (Ra13,Rb6,X1,Z13), (Ra13,Rb6,X1,Z14), (Ra13,Rb6,X1,Z15), (Ra13,Rb6,X1,Z16), (Ra13,Rb6,X1,Z17), (Ra13,Rb6,X1,Z18), (Ra13,Rb6,X1,Z19), (Ra13,Rb6,X1,Z20), (Ra13,Rb6,X1,Z21), (Ra13,Rb6,X1,Z22), (Ra13,Rb6,X1,Z23), (Ra13,Rb6,X1,Z24), (Ra13,Rb6,X1,Z25), (Ra13,Rb6,X1,Z26), (Ra13,Rb6,X1,Z27), (Ra13,Rb6,X1,Z28), (Ra13,Rb6,X1,Z29), (Ra13,Rb6,X1,Z30), (Ra13,Rb6,X1,Z31), (Ra13,Rb6,X1,Z32), (Ra13,Rb6,X1,Z33), (Ra13,Rb6,X1,Z34), (Ra13,Rb6,X1,Z35), (Ra13,Rb6,X1,Z36), (Ra13,Rb6,X1,Z37), (Ra13,Rb6,X1,Z38), (Ra13,Rb6,X1,Z39), (Ra13,Rb6,X2,Z1), (Ra13,Rb6,X2,Z2), (Ra13,Rb6,X2,Z3), (Ra13,Rb6,X2,Z4), (Ra13,Rb6,X2,Z5), (Ra13,Rb6,X2,Z6), (Ra13,Rb6,X2,Z7), (Ra13,Rb6,X2,Z8), (Ra13,Rb6,X2,Z9), (Ra13,Rb6,X2,Z10), (Ra13,Rb6,X2,Z11), (Ra13,Rb6,X2,Z12), (Ra13,Rb6,X2,Z13), (Ra13,Rb6,X2,Z14), (Ra13,Rb6,X2,Z15), (Ra13,Rb6,X2,Z16), (Ra13,Rb6,X2,Z17), (Ra13,Rb6,X2,Z18), (Ra13,Rb6,X2,Z19), (Ra13,Rb6,X2,Z20), (Ra13,Rb6,X2,Z21), (Ra13,Rb6,X2,Z22), (Ra13,Rb6,X2,Z23), (Ra13,Rb6,X2,Z24), (Ra13,Rb6,X2,Z25), (Ra13,Rb6,X2,Z26), (Ra13,Rb6,X2,Z27), (Ra13,Rb6,X2,Z28), (Ra13,Rb6,X2,Z29), (Ra13,Rb6,X2,Z30), (Ra13,Rb6,X2,Z31), (Ra13,Rb6,X2,Z32), (Ra13,Rb6,X2,Z33), (Ra13,Rb6,X2,Z34), (Ra13,Rb6,X2,Z35), (Ra13,Rb6,X2,Z36), (Ra13,Rb6,X2,Z37), (Ra13,Rb6,X2,Z38), (Ra13,Rb6,X2,Z39), (Ra13,Rb7,X1,Z1), (Ra13,Rb7,X1,Z2), (Ra13,Rb7,X1,Z3), (Ra13,Rb7,X1,Z4), (Ra13,Rb7,X1,Z5), (Ra13,Rb7,X1,Z6), (Ra13,Rb7,X1,Z7), (Ra13,Rb7,X1,Z8), (Ra13,Rb7,X1,Z9), (Ra13,Rb7,X1,Z10), (Ra13,Rb7,X1,Z11), (Ra13,Rb7,X1,Z12), (Ra13,Rb7,X1,Z13), (Ra13,Rb7,X1,Z14), (Ra13,Rb7,X1,Z15), (Ra13,Rb7,X1,Z16), (Ra13,Rb7,X1,Z17), (Ra13,Rb7,X1,Z18), (Ra13,Rb7,X1,Z19), (Ra13,Rb7,X1,Z20), (Ra13,Rb7,X1,Z21), (Ra13,Rb7,X1,Z22), (Ra13,Rb7,X1,Z23), (Ra13,Rb7,X1,Z24), (Ra13,Rb7,X1,Z25), (Ra13,Rb7,X1,Z26), (Ra13,Rb7,X1,Z27), (Ra13,Rb7,X1,Z28), (Ra13,Rb7,X1,Z29), (Ra13,Rb7,X1,Z30), (Ra13,Rb7,X1,Z31), (Ra13,Rb7,X1,Z32), (Ra13,Rb7,X1,Z33), (Ra13,Rb7,X1,Z34), (Ra13,Rb7,X1,Z35), (Ra13,Rb7,X1,Z36), (Ra13,Rb7,X1,Z37), (Ra13,Rb7,X1,Z38), (Ra13,Rb7,X1,Z39), (Ra13,Rb7,X2,Z1), (Ra13,Rb7,X2,Z2), (Ra13,Rb7,X2,Z3), (Ra13,Rb7,X2,Z4), (Ra13,Rb7,X2,Z5), (Ra13,Rb7,X2,Z6), (Ra13,Rb7,X2,Z7), (Ra13,Rb7,X2,Z8), (Ra13,Rb7,X2,Z9), (Ra13,Rb7,X2,Z10), (Ra13,Rb7,X2,Z11), (Ra13,Rb7,X2,Z12), (Ra13,Rb7,X2,Z13), (Ra13,Rb7,X2,Z14), (Ra13,Rb7,X2,Z15), (Ra13,Rb7,X2,Z16), (Ra13,Rb7,X2,Z17), (Ra13,Rb7,X2,Z18), (Ra13,Rb7,X2,Z19), (Ra13,Rb7,X2,Z20), (Ra13,Rb7,X2,Z21), (Ra13,Rb7,X2,Z22), (Ra13,Rb7,X2,Z23), (Ra13,Rb7,X2,Z24), (Ra13,Rb7,X2,Z25), (Ra13,Rb7,X2,Z26), (Ra13,Rb7,X2,Z27), (Ra13,Rb7,X2,Z28), (Ra13,Rb7,X2,Z29), (Ra13,Rb7,X2,Z30), (Ra13,Rb7,X2,Z31), (Ra13,Rb7,X2,Z32), (Ra13,Rb7,X2,Z33), (Ra13,Rb7,X2,Z34), (Ra13,Rb7,X2,Z35), (Ra13,Rb7,X2,Z36), (Ra13,Rb7,X2,Z37), (Ra13,Rb7,X2,Z38), (Ra13,Rb7,X2,Z39), (Ra13,Rb8,X1,Z1), (Ra13,Rb8,X1,Z2), (Ra13,Rb8,X1,Z3), (Ra13,Rb8,X1,Z4), (Ra13,Rb8,X1,Z5), (Ra13,Rb8,X1,Z6), (Ra13,Rb8,X1,Z7), (Ra13,Rb8,X1,Z8), (Ra13,Rb8,X1,Z9), (Ra13,Rb8,X1,Z10), (Ra13,Rb8,X1,Z11), (Ra13,Rb8,X1,Z12), (Ra13,Rb8,X1,Z13), (Ra13,Rb8,X1,Z14), (Ra13,Rb8,X1,Z15), (Ra13,Rb8,X1,Z (Ra13,Rb8,X1,Z17), (Ra13,Rb8,X1,Z18), (Ra13,Rb8,X1,Z19), (Ra13,Rb8,X1,Z20), (Ra13,Rb8,X1,Z21), (Ra13,Rb8,X1,Z22), (Ra13,Rb8,X1,Z23), (Ra13,Rb8,X1,Z24), (Ra13,Rb8,X1,Z25), (Ra13,Rb8,X1,Z26), (Ra13,Rb8,X1,Z27), (Ra13,Rb8,X1,Z28), (Ra13,Rb8,X1,Z29), (Ra13,Rb8,X1,Z30), (Ra13,Rb8,X1,Z31), (Ra13,Rb8,X1,Z32), (Ra13,Rb8,X1,Z33), (Ra13,Rb8,X1,Z34), (Ra13,Rb8,X1,Z35), (Ra13,Rb8,X1,Z36), (Ra13,Rb8,X1,Z37), (Ra13,Rb8,X1,Z38), (Ra13,Rb8,X1,Z39), (Ra13,Rb8,X2,Z1), (Ra13,Rb8,X2,Z2), (Ra13,Rb8,X2,Z3), (Ra13,Rb8,X2,Z4), (Ra13,Rb8,X2,Z5), (Ra13,Rb8,X2,Z6), (Ra13,Rb8,X2,Z7), (Ra13,Rb8,X2,Z8), (Ra13,Rb8,X2,Z9), (Ra13,Rb8,X2,Z10), (Ra13,Rb8,X2,Z11), (Ra13,Rb8,X2,Z12), (Ra13,Rb8,X2,Z13), (Ra13,Rb8,X2,Z14), (Ra13,Rb8,X2,Z15), (Ra13,Rb8,X2,Z16), (Ra13,Rb8,X2,Z17), (Ra13,Rb8,X2,Z18), (Ra13,Rb8,X2,Z19), (Ra13,Rb8,X2,Z20), (Ra13,Rb8,X2,Z21), (Ra13,Rb8,X2,Z22), (Ra13,Rb8,X2,Z23), (Ra13,Rb8,X2,Z24), (Ra13,Rb8,X2,Z25), (Ra13,Rb8,X2,Z26), (Ra13,Rb8,X2,Z27), (Ra13,Rb8,X2,Z28), (Ra13,Rb8,X2,Z29), (Ra13,Rb8,X2,Z30), (Ra13,Rb8,X2,Z31), (Ra13,Rb8,X2,Z32), (Ra13,Rb8,X2,Z33), (Ra13,Rb8,X2,Z34), (Ra13,Rb8,X2,Z35), (Ra13,Rb8,X2,Z36), (Ra13,Rb8,X2,Z37), (Ra13,Rb8,X2,Z38), (Ra13,Rb8,X2,Z39), (Ra14,Rb1,X1,Z1), (Ra14,Rb1,X1,Z2), (Ra14,Rb1,X1,Z3), (Ra14,Rb1,X1,Z4), (Ra14,Rb1,X1,Z5), (Ra14,Rb1,X1,Z6), (Ra14,Rb1,X1,Z7), (Ra14,Rb1,X1,Z8), (Ra14,Rb1,X1,Z9), (Ra14,Rb1,X1,Z10), (Ra14,Rb1,X1,Z11), (Ra14,Rb1,X1,Z12), (Ra14,Rb1,X1,Z13), (Ra14,Rb1,X1,Z14), (Ra14,Rb1,X1,Z15), (Ra14,Rb1,X1,Z16), (Ra14,Rb1,X1,Z17), (Ra14,Rb1,X1,Z18), (Ra14,Rb1,X1,Z19), (Ra14,Rb1,X1,Z20), (Ra14,Rb1,X1,Z21), (Ra14,Rb1,X1,Z22), (Ra14,Rb1,X1,Z23), (Ra14,Rb1,X1,Z24), (Ra14,Rb1,X1,Z25), (Ra14,Rb1,X1,Z26), (Ra14,Rb1,X1,Z27), (Ra14,Rb1,X1,Z28), (Ra14,Rb1,X1,Z29), (Ra14,Rb1,X1,Z30), (Ra14,Rb1,X1,Z31), (Ra14,Rb1,X1,Z32), (Ra14,Rb1,X1,Z33), (Ra14,Rb1,X1,Z34), (Ra14,Rb1,X1,Z35), (Ra14,Rb1,X1,Z36), (Ra14,Rb1,X1,Z37), (Ra14,Rb1,X1,Z38), (Ra14,Rb1,X1,Z39), (Ra14,Rb1,X2,Z1), (Ra14,Rb1,X2,Z2), (Ra14,Rb1,X2,Z3), (Ra14,Rb1,X2,Z4), (Ra14,Rb1,X2,Z5), (Ra14,Rb1,X2,Z6), (Ra14,Rb1,X2,Z7), (Ra14,Rb1,X2,Z8), (Ra14,Rb1,X2,Z9), (Ra14,Rb1,X2,Z10), (Ra14,Rb1,X2,Z11), (Ra14,Rb1,X2,Z12), (Ra14,Rb1,X2,Z13), (Ra14,Rb1,X2,Z14), (Ra14,Rb1,X2,Z15), (Ra14,Rb1,X2,Z16), (Ra14,Rb1,X2,Z17), (Ra14,Rb1,X2,Z18), (Ra14,Rb1,X2,Z19), (Ra14,Rb1,X2,Z20), (Ra14,Rb1,X2,Z21), (Ra14,Rb1,X2,Z22), (Ra14,Rb1,X2,Z23), (Ra14,Rb1,X2,Z24), (Ra14,Rb1,X2,Z25), (Ra14,Rb1,X2,Z26), (Ra14,Rb1,X2,Z27), (Ra14,Rb1,X2,Z28), (Ra14,Rb1,X2,Z29), (Ra14,Rb1,X2,Z30), (Ra14,Rb1,X2,Z31), (Ra14,Rb1,X2,Z32), (Ra14,Rb1,X2,Z33), (Ra14,Rb1,X2,Z34), (Ra14,Rb1,X2,Z35), (Ra14,Rb1,X2,Z36), (Ra14,Rb1,X2,Z37), (Ra14,Rb1,X2,Z38), (Ra14,Rb1,X2,Z39), (Ra14,Rb2,X1,Z1), (Ra14,Rb2,X1,Z2), (Ra14,Rb2,X1,Z3), (Ra14,Rb2,X1,Z4), (Ra14,Rb2,X1,Z5), (Ra14,Rb2,X1,Z6), (Ra14,Rb2,X1,Z7), (Ra14,Rb2,X1,Z8), (Ra14,Rb2,X1,Z9), (Ra14,Rb2,X1,Z10), (Ra14,Rb2,X1,Z11), (Ra14,Rb2,X1,Z12), (Ra14,Rb2,X1,Z13), (Ra14,Rb2,X1,Z14), (Ra14,Rb2,X1,Z15), (Ra14,Rb2,X1,Z16), (Ra14,Rb2,X1,Z17), (Ra14,Rb2,X1,Z18), (Ra14,Rb2,X1,Z19), (Ra14,Rb2,X1,Z20), (Ra14,Rb2,X1,Z21), (Ra14,Rb2,X1,Z22), (Ra14,Rb2,X1,Z23), (Ra14,Rb2,X1,Z24), (Ra14,Rb2,X1,Z25), (Ra14,Rb2,X1,Z26), (Ra14,Rb2,X1,Z27), (Ra14,Rb2,X1,Z28), (Ra14,Rb2,X1,Z29), (Ra14,Rb2,X1,Z30), (Ra14,Rb2,X1,Z31), (Ra14,Rb2,X1,Z32), (Ra14,Rb2,X1,Z33), (Ra14,Rb2,X1,Z34), (Ra14,Rb2,X1,Z35), (Ra14,Rb2,X1,Z36), (Ra14,Rb2,X1,Z37), (Ra14,Rb2,X1,Z38), (Ra14,Rb2,X1,Z39), (Ra14,Rb2,X2,Z1), (Ra14,Rb2,X2,Z2), (Ra14,Rb2,X2,Z3), (Ra14,Rb2,X2,Z4), (Ra14,Rb2,X2,Z5), (Ra14,Rb2,X2,Z6), (Ra14,Rb2,X2,Z7), (Ra14,Rb2,X2,Z8), (Ra14,Rb2,X2,Z9), (Ra14,Rb2,X2,Z10), (Ra14,Rb2,X2,Z11), (Ra14,Rb2,X2,Z12), (Ra14,Rb2,X2,

Z13), (Ra14,Rb2,X2,Z14), (Ra14,Rb2,X2,Z15), (Ra14,Rb2, X2,Z16), (Ra14,Rb2,X2,Z17), (Ra14,Rb2,X2,Z18), (Ra14, Rb2,X2,Z19), (Ra14,Rb2,X2,Z20), (Ra14,Rb2,X2,Z21), (Ra14,Rb2,X2,Z22), (Ra14,Rb2,X2,Z23), (Ra14,Rb2,X2, Z24), (Ra14,Rb2,X2,Z25), (Ra14,Rb2,X2,Z26), (Ra14,Rb2, X2,Z27), (Ra14,Rb2,X2,Z28), (Ra14,Rb2,X2,Z29), (Ra14, Rb2,X2,Z30), (Ra14,Rb2,X2,Z31), (Ra14,Rb2,X2,Z32), (Ra14,Rb2,X2,Z33), (Ra14,Rb2,X2,Z34), (Ra14,Rb2,X2, Z35), (Ra14,Rb2,X2,Z36), (Ra14,Rb2,X2,Z37), (Ra14,Rb2, X2,Z38), (Ra14,Rb2,X2,Z39), (Ra14,Rb3,X1,Z1), (Ra14, Rb3,X1,Z2), (Ra14,Rb3,X1,Z3), (Ra14,Rb3,X1,Z4), (Ra14, Rb3,X1,Z5), (Ra14,Rb3,X1,Z6), (Ra14,Rb3,X1,Z7), (Ra14, Rb3,X1,Z8), (Ra14,Rb3,X1,Z9), (Ra14,Rb3,X1,Z10), (Ra14,Rb3,X1,Z11), (Ra14,Rb3,X1,Z12), (Ra14,Rb3,X1, Z13), (Ra14,Rb3,X1,Z14), (Ra14,Rb3,X1,Z15), (Ra14,Rb3, X1, Z16), (Ra14,Rb3,X1,Z17), (Ra14,Rb3,X1,Z18), (Ra14, Rb3,X1,Z19), (Ra14,Rb3,X1,Z20), (Ra14,Rb3,X1,Z21), (Ra14,Rb3,X1,Z22), (Ra14,Rb3,X1,Z23), (Ra14,Rb3,X1, Z24), (Ra14,Rb3,X1,Z25), (Ra14,Rb3,X1,Z26), (Ra14,Rb3, X1,Z27), (Ra14,Rb3,X1,Z28), (Ra14,Rb3,X1,Z29), (Ra14, Rb3,X1,Z30), (Ra14,Rb3,X1,Z31), (Ra14,Rb3,X1,Z32), (Ra14,Rb3,X1,Z33), (Ra14,Rb3,X1,Z34), (Ra14,Rb3,X1, Z35), (Ra14,Rb3,X1,Z36), (Ra14,Rb3,X1,Z37), (Ra14,Rb3, X1,Z38), (Ra14,Rb3,X1,Z39), (Ra14,Rb3,X2,Z1), (Ra14, Rb3,X2,Z2), (Ra14,Rb3,X2,Z3), (Ra14,Rb3,X2,Z4), (Ra14, Rb3,X2,Z5), (Ra14,Rb3,X2,Z6), (Ra14,Rb3,X2,Z7), (Ra14, Rb3,X2,Z8), (Ra14,Rb3,X2,Z9), (Ra14,Rb3,X2,Z10), (Ra14,Rb3,X2,Z11), (Ra14,Rb3,X2,Z12), (Ra14,Rb3,X2, Z13), (Ra14,Rb3,X2,Z14), (Ra14,Rb3,X2,Z15), (Ra14,Rb3, X2,Z16), (Ra14,Rb3,X2,Z17), (Ra14,Rb3,X2,Z18), (Ra14, Rb3,X2,Z19), (Ra14,Rb3,X2,Z20), (Ra14,Rb3,X2,Z21), (Ra14,Rb3,X2,Z22), (Ra14,Rb3,X2,Z23), (Ra14,Rb3,X2, Z24), (Ra14,Rb3,X2,Z25), (Ra14,Rb3,X2,Z26), (Ra14,Rb3, X2,Z27), (Ra14,Rb3,X2,Z28), (Ra14,Rb3,X2,Z29), (Ra14, Rb3,X2,Z30), (Ra14,Rb3,X2,Z31), (Ra14,Rb3,X2,Z32), (Ra14,Rb3,X2,Z33), (Ra14,Rb3,X2,Z34), (Ra14,Rb3,X2, Z35), (Ra14,Rb3,X2,Z36), (Ra14,Rb3,X2,Z37), (Ra14,Rb3, X2,Z38), (Ra14,Rb3,X2,Z39), (Ra14,Rb4,X1,Z1), (Ra14, Rb4,X1,Z2), (Ra14,Rb4,X1,Z3), (Ra14,Rb4,X1,Z4), (Ra14, Rb4,X1,Z5), (Ra14,Rb4,X1,Z6), (Ra14,Rb4,X1,Z7), (Ra14, Rb4,X1,Z8), (Ra14,Rb4,X1,Z9), (Ra14,Rb4,X1,Z10), (Ra14,Rb4,X1,Z11), (Ra14,Rb4,X1,Z12), (Ra14,Rb4,X1, Z13), (Ra14,Rb4,X1,Z14), (Ra14,Rb4,X1,Z15), (Ra14,Rb4, X1,Z16), (Ra14,Rb4,X1,Z17), (Ra14,Rb4,X1,Z18), (Ra14, Rb4,X1,Z19), (Ra14,Rb4,X1,Z20), (Ra14,Rb4,X1,Z21), (Ra14,Rb4,X1,Z22), (Ra14,Rb4,X1,Z23), (Ra14,Rb4,X1, Z24), (Ra14,Rb4,X1,Z25), (Ra14,Rb4,X1,Z26), (Ra14,Rb4, X1,Z27), (Ra14,Rb4,X1,Z28), (Ra14,Rb4,X1,Z29), (Ra14, Rb4,X1,Z30), (Ra14,Rb4,X1,Z31), (Ra14,Rb4,X1,Z32), (Ra14,Rb4,X1,Z33), (Ra14,Rb4,X1,Z34), (Ra14,Rb4,X1, Z35), (Ra14,Rb4,X1,Z36), (Ra14,Rb4,X1,Z37), (Ra14,Rb4, X1,Z38), (Ra14,Rb4,X1,Z39), (Ra14,Rb4,X2,Z1), (Ra14, Rb4,X2,Z2), (Ra14,Rb4,X2,Z3), (Ra14,Rb4,X2,Z4), (Ra14, Rb4,X2,Z5), (Ra14,Rb4,X2,Z6), (Ra14,Rb4,X2,Z7), (Ra14, Rb4,X2,Z8), (Ra14,Rb4,X2,Z9), (Ra14,Rb4,X2,Z10), (Ra14,Rb4,X2,Z11), (Ra14,Rb4,X2,Z12), (Ra14,Rb4,X2, Z13), (Ra14,Rb4,X2,Z14), (Ra14,Rb4,X2,Z15), (Ra14,Rb4, X2,Z16), (Ra14,Rb4,X2,Z17), (Ra14,Rb4,X2,Z18), (Ra14, Rb4,X2,Z19), (Ra14,Rb4,X2,Z20), (Ra14,Rb4,X2,Z21), (Ra14,Rb4,X2,Z22), (Ra14,Rb4,X2,Z23), (Ra14,Rb4,X2, Z24), (Ra14,Rb4,X2,Z25), (Ra14,Rb4,X2,Z26), (Ra14,Rb4, X2,Z27), (Ra14,Rb4,X2,Z28), (Ra14,Rb4,X2,Z29), (Ra14, Rb4,X2,Z30), (Ra14,Rb4,X2,Z31), (Ra14,Rb4,X2,Z32), (Ra14,Rb4,X2,Z33), (Ra14,Rb4,X2,Z34), (Ra14,Rb4,X2, Z35), (Ra14,Rb4,X2,Z36), (Ra14,Rb4,X2,Z37), (Ra14,Rb4, X2,Z38), (Ra14,Rb4,X2,Z39), (Ra14,Rb5,X1,Z1), (Ra14, Rb5,X1,Z2), (Ra14,Rb5,X1,Z3), (Ra14,Rb5,X1,Z4), (Ra14, Rb5,X1,Z5), (Ra14,Rb5,X1,Z6), (Ra14,Rb5,X1,Z7), (Ra14, Rb5,X1,Z8), (Ra14,Rb5,X1,Z9), (Ra14,Rb5,X1,Z10), (Ra14,Rb5,X1,Z11), (Ra14,Rb5,X1,Z12), (Ra14,Rb5,X1, Z13), (Ra14,Rb5,X1,Z14), (Ra14,Rb5,X1,Z15), (Ra14,Rb5, X1,Z16), (Ra14,Rb5,X1,Z17), (Ra14,Rb5,X1,Z18), (Ra14, Rb5,X1,Z19), (Ra14,Rb5,X1,Z20), (Ra14,Rb5,X1,Z21), (Ra14,Rb5,X1,Z22), (Ra14,Rb5,X1,Z23), (Ra14,Rb5,X1, Z24), (Ra14,Rb5,X1,Z25), (Ra14,Rb5,X1,Z26), (Ra14,Rb5, X1,Z27), (Ra14,Rb5,X1,Z28), (Ra14,Rb5,X1,Z29), (Ra14, Rb5,X1,Z30), (Ra14,Rb5,X1,Z31), (Ra14,Rb5,X1,Z32), (Ra14,Rb5,X1,Z33), (Ra14,Rb5,X1,Z34), (Ra14,Rb5,X1, Z35), (Ra14,Rb5,X1,Z36), (Ra14,Rb5,X1,Z37), (Ra14,Rb5, X1,Z38), (Ra14,Rb5,X1,Z39), (Ra14,Rb5,X2,Z1), (Ra14, Rb5,X2,Z2), (Ra14,Rb5,X2,Z3), (Ra14,Rb5,X2,Z4), (Ra14, Rb5,X2,Z5), (Ra14,Rb5,X2,Z6), (Ra14,Rb5,X2,Z7), (Ra14, Rb5,X2,Z8), (Ra14,Rb5,X2,Z9), (Ra14,Rb5,X2,Z10), (Ra14,Rb5,X2,Z11), (Ra14,Rb5,X2,Z12), (Ra14,Rb5,X2, Z13), (Ra14,Rb5,X2,Z14), (Ra14,Rb5,X2,Z15), (Ra14,Rb5, X2,Z16), (Ra14,Rb5,X2,Z17), (Ra14,Rb5,X2,Z18), (Ra14, Rb5,X2,Z19), (Ra14,Rb5,X2,Z20), (Ra14,Rb5,X2,Z21), (Ra14,Rb5,X2,Z22), (Ra14,Rb5,X2,Z23), (Ra14,Rb5,X2, Z24), (Ra14,Rb5,X2,Z25), (Ra14,Rb5,X2,Z26), (Ra14,Rb5, X2,Z27), (Ra14,Rb5,X2,Z28), (Ra14,Rb5,X2,Z29), (Ra14, Rb5,X2,Z30), (Ra14,Rb5,X2,Z31), (Ra14,Rb5,X2,Z32), (Ra14,Rb5,X2,Z33), (Ra14,Rb5,X2,Z34), (Ra14,Rb5,X2, Z35), (Ra14,Rb5,X2,Z36), (Ra14,Rb5,X2,Z37), (Ra14,Rb5, X2,Z38), (Ra14,Rb5,X2,Z39), (Ra14,Rb6,X1,Z1), (Ra14, Rb6,X1,Z2), (Ra14,Rb6,X1,Z3), (Ra14,Rb6,X1,Z4), (Ra14, Rb6,X1,Z5), (Ra14,Rb6,X1,Z6), (Ra14,Rb6,X1,Z7), (Ra14, Rb6,X1,Z8), (Ra14,Rb6,X1,Z9), (Ra14,Rb6,X1,Z10), (Ra14,Rb6,X1,Z11), (Ra14,Rb6,X1,Z12), (Ra14,Rb6,X1, Z13), (Ra14,Rb6,X1,Z14), (Ra14,Rb6,X1,Z15), (Ra14,Rb6, X1,Z16), (Ra14,Rb6,X1,Z17), (Ra14,Rb6,X1,Z18), (Ra14, Rb6,X1,Z19), (Ra14,Rb6,X1,Z20), (Ra14,Rb6,X1,Z21), (Ra14,Rb6,X1,Z22), (Ra14,Rb6,X1,Z23), (Ra14,Rb6,X1, Z24), (Ra14,Rb6,X1,Z25), (Ra14,Rb6,X1,Z26), (Ra14,Rb6, X1,Z27), (Ra14,Rb6,X1,Z28), (Ra14,Rb6,X1,Z29), (Ra14, Rb6,X1,Z30), (Ra14,Rb6,X1,Z31), (Ra14,Rb6,X1,Z32), (Ra14,Rb6,X1,Z33), (Ra14,Rb6,X1,Z34), (Ra14,Rb6,X1, Z35), (Ra14,Rb6,X1,Z36), (Ra14,Rb6,X1,Z37), (Ra14,Rb6, X1,Z38), (Ra14,Rb6,X1,Z39), (Ra14,Rb6,X2,Z1), (Ra14, Rb6,X2,Z2), (Ra14,Rb6,X2,Z3), (Ra14,Rb6,X2,Z4), (Ra14, Rb6,X2,Z5), (Ra14,Rb6,X2,Z6), (Ra14,Rb6,X2,Z7), (Ra14, Rb6,X2,Z8), (Ra14,Rb6,X2,Z9), (Ra14,Rb6,X2,Z10), (Ra14,Rb6,X2,Z11), (Ra14,Rb6,X2,Z12), (Ra14,Rb6,X2, Z13), (Ra14,Rb6,X2,Z14), (Ra14,Rb6,X2,Z15), (Ra14,Rb6, X2,Z16), (Ra14,Rb6,X2,Z17), (Ra14,Rb6,X2,Z18), (Ra14, Rb6,X2,Z19), (Ra14,Rb6,X2,Z20), (Ra14,Rb6,X2,Z21), (Ra14,Rb6,X2,Z22), (Ra14,Rb6,X2,Z23), (Ra14,Rb6,X2, Z24), (Ra14,Rb6,X2,Z25), (Ra14,Rb6,X2,Z26), (Ra14,Rb6, X2,Z27), (Ra14,Rb6,X2,Z28), (Ra14,Rb6,X2,Z29), (Ra14, Rb6,X2,Z30), (Ra14,Rb6,X2,Z31), (Ra14,Rb6,X2,Z32), (Ra14,Rb6,X2,Z33), (Ra14,Rb6,X2,Z34), (Ra14,Rb6,X2, Z35), (Ra14,Rb6,X2,Z36), (Ra14,Rb6,X2,Z37), (Ra14,Rb6, X2,Z38), (Ra14,Rb6,X2,Z39), (Ra14,Rb7,X1,Z1), (Ra14, Rb7,X1,Z2), (Ra14,Rb7,X1,Z3), (Ra14,Rb7,X1,Z4), (Ra14, Rb7,X1,Z5), (Ra14,Rb7,X1,Z6), (Ra14,Rb7,X1,Z7), (Ra14, Rb7,X1,Z8), (Ra14,Rb7,X1,Z9), (Ra14,Rb7,X1,Z10), (Ra14,Rb7,X1,Z11), (Ra14,Rb7,X1,Z12), (Ra14,Rb7,X1, Z13), (Ra14,Rb7,X1,Z14), (Ra14,Rb7,X1,Z15), (Ra14,Rb7, X1,Z16), (Ra14,Rb7,X1,Z17), (Ra14,Rb7,X1,Z18), (Ra14, Rb7,X1,Z19), (Ra14,Rb7,X1,Z20), (Ra14,Rb7,X1,Z21), (Ra14,Rb7,X1,Z22), (Ra14,Rb7,X1,Z23), (Ra14,Rb7,X1, Z24), (Ra14,Rb7,X1,Z25), (Ra14,Rb7,X1,Z26), (Ra14,Rb7, X1,Z27), (Ra14,Rb7,X1,Z28), (Ra14,Rb7,X1,Z29), (Ra14, Rb7,X1,Z30), (Ra14,Rb7,X1,Z31), (Ra14,Rb7,X1,Z32), (Ra14,Rb7,X1,Z33), (Ra14,Rb7,X1,Z34), (Ra14,Rb7,X1,

Z35), (Ra14,Rb7,X1,Z36), (Ra14,Rb7,X1,Z37), (Ra14,Rb7, X1,Z38), (Ra14,Rb7,X1,Z39), (Ra14,Rb7,X2,Z1), (Ra14, Rb7,X2,Z2), (Ra14,Rb7,X2,Z3), (Ra14,Rb7,X2,Z4), (Ra14, Rb7,X2,Z5), (Ra14,Rb7,X2,Z6), (Ra14,Rb7,X2,Z7), (Ra14, Rb7,X2,Z8), (Ra14,Rb7,X2,Z9), (Ra14,Rb7,X2,Z10), (Ra14,Rb7,X2,Z11), (Ra14,Rb7,X2,Z12), (Ra14,Rb7,X2, Z13), (Ra14,Rb7,X2,Z14), (Ra14,Rb7,X2,Z15), (Ra14,Rb7, X2,Z16), (Ra14,Rb7,X2,Z17), (Ra14,Rb7,X2,Z18), (Ra14, Rb7,X2,Z19), (Ra14,Rb7,X2,Z20), (Ra14,Rb7,X2,Z21), (Ra14,Rb7,X2,Z22), (Ra14,Rb7,X2,Z23), (Ra14,Rb7,X2, Z24), (Ra14,Rb7,X2,Z25), (Ra14,Rb7,X2,Z26), (Ra14,Rb7, X2,Z27), (Ra14,Rb7,X2,Z28), (Ra14,Rb7,X2,Z29), (Ra14, Rb7,X2,Z30), (Ra14,Rb7,X2,Z31), (Ra14,Rb7,X2,Z32), (Ra14,Rb7,X2,Z33), (Ra14,Rb7,X2,Z34), (Ra14,Rb7,X2, Z35), (Ra14,Rb7,X2,Z36), (Ra14,Rb7,X2,Z37), (Ra14,Rb7, X2,Z38), (Ra14,Rb7,X2,Z39), (Ra14,Rb8,X1,Z1), (Ra14, Rb8,X1,Z2), (Ra14,Rb8,X1,Z3), (Ra14,Rb8,X1,Z4), (Ra14, Rb8,X1,Z5), (Ra14,Rb8,X1,Z6), (Ra14,Rb8,X1,Z7), (Ra14, Rb8,X1,Z8), (Ra14,Rb8,X1,Z9), (Ra14,Rb8,X1,Z10), (Ra14,Rb8,X1,Z11), (Ra14,Rb8,X1,Z12), (Ra14,Rb8,X1, Z13), (Ra14,Rb8,X1,Z14), (Ra14,Rb8,X1,Z15), (Ra14,Rb8, X1,Z16), (Ra14,Rb8,X1,Z17), (Ra14,Rb8,X1,Z18), (Ra14, Rb8,X1,Z19), (Ra14,Rb8,X1,Z20), (Ra14,Rb8,X1,Z21), (Ra14,Rb8,X1,Z22), (Ra14,Rb8,X1,Z23), (Ra14,Rb8,X1, Z24), (Ra14,Rb8,X1,Z25), (Ra14,Rb8,X1,Z26), (Ra14,Rb8, X1,Z27), (Ra14,Rb8,X1,Z28), (Ra14,Rb8,X1,Z29), (Ra14, Rb8,X1,Z30), (Ra14,Rb8,X1,Z31), (Ra14,Rb8,X1,Z32), (Ra14,Rb8,X1,Z33), (Ra14,Rb8,X1,Z34), (Ra14,Rb8,X1, Z35), (Ra14,Rb8,X1,Z36), (Ra14,Rb8,X1,Z37), (Ra14,Rb8, X1,Z38), (Ra14,Rb8,X1,Z39), (Ra14,Rb8,X2,Z1), (Ra14, Rb8,X2,Z2), (Ra14,Rb8,X2,Z3), (Ra14,Rb8,X2,Z4), (Ra14, Rb8, X2,Z5), (Ra14,Rb8,X2,Z6), (Ra14,Rb8,X2,Z7), (Ra14, Rb8,X2,Z8), (Ra14,Rb8,X2,Z9), (Ra14,Rb8,X2,Z10), (Ra14,Rb8,X2,Z11), (Ra14,Rb8,X2,Z12), (Ra14,Rb8,X2, Z13), (Ra14,Rb8,X2,Z14), (Ra14,Rb8,X2,Z15), (Ra14,Rb8, X2,Z16), (Ra14,Rb8,X2,Z17), (Ra14,Rb8,X2,Z18), (Ra14, Rb8,X2,Z19), (Ra14,Rb8,X2,Z20), (Ra14,Rb8,X2,Z21), (Ra14,Rb8,X2,Z22), (Ra14,Rb8,X2,Z23), (Ra14,Rb8,X2, Z24), (Ra14,Rb8,X2,Z25), (Ra14,Rb8,X2,Z26), (Ra14,Rb8, X2,Z27), (Ra14,Rb8,X2,Z28), (Ra14,Rb8,X2,Z29), (Ra14, Rb8,X2,Z30), (Ra14,Rb8,X2,Z31), (Ra14,Rb8,X2,Z32), (Ra14,Rb8,X2,Z33), (Ra14,Rb8,X2,Z34), (Ra14,Rb8,X2, Z35), (Ra14,Rb8,X2,Z36), (Ra14,Rb8,X2,Z37), (Ra14,Rb8, X2,Z38), (Ra14,Rb8,X2,Z39), (Ra15,Rb1,X1,Z1), (Ra15, Rb1,X1,Z2), (Ra15,Rb1,X1,Z3), (Ra15,Rb1,X1,Z4), (Ra15, Rb1,X1,Z5), (Ra15,Rb1,X1,Z6), (Ra15,Rb1,X1,Z7), (Ra15, Rb1,X1,Z8), (Ra15,Rb1,X1,Z9), (Ra15,Rb1,X1,Z10), (Ra15,Rb1,X1,Z11), (Ra15,Rb1,X1,Z12), (Ra15,Rb1,X1, Z13), (Ra15,Rb1,X1,Z14), (Ra15,Rb1,X1,Z15), (Ra15,Rb1, X1,Z16), (Ra15,Rb1,X1,Z17), (Ra15,Rb1,X1,Z18), (Ra15, Rb1,X1,Z19), (Ra15,Rb1,X1,Z20), (Ra15,Rb1,X1,Z21), (Ra15,Rb1,X1,Z22), (Ra15,Rb1,X1,Z23), (Ra15,Rb1,X1, Z24), (Ra15,Rb1,X1,Z25), (Ra15,Rb1,X1,Z26), (Ra15,Rb1, X1,Z27), (Ra15,Rb1,X1,Z28), (Ra15,Rb1,X1,Z29), (Ra15, Rb1,X1,Z30), (Ra15,Rb1,X1,Z31), (Ra15,Rb1,X1,Z32), (Ra15,Rb1,X1,Z33), (Ra15,Rb1,X1,Z34), (Ra15,Rb1,X1, Z35), (Ra15,Rb1,X1,Z36), (Ra15,Rb1,X1,Z37), (Ra15,Rb1, X1,Z38), (Ra15,Rb1,X1,Z39), (Ra15,Rb1,X2,Z1), (Ra15, Rb1,X2,Z2), (Ra15,Rb1,X2,Z3), (Ra15,Rb1,X2,Z4), (Ra15, Rb1,X2,Z5), (Ra15,Rb1,X2,Z6), (Ra15,Rb1,X2,Z7), (Ra15, Rb1,X2,Z8), (Ra15,Rb1,X2,Z9), (Ra15,Rb1,X2,Z10), (Ra15,Rb1,X2,Z11), (Ra15,Rb1,X2,Z12), (Ra15,Rb1,X2, Z13), (Ra15,Rb1,X2,Z14), (Ra15,Rb1,X2,Z15), (Ra15,Rb1, X2,Z16), (Ra15,Rb1,X2,Z17), (Ra15,Rb1,X2,Z18), (Ra15, Rb1,X2,Z19), (Ra15,Rb1,X2,Z20), (Ra15,Rb1,X2,Z21), (Ra15,Rb1,X2,Z22), (Ra15,Rb1,X2,Z23), (Ra15,Rb1,X2, Z24), (Ra15,Rb1,X2,Z25), (Ra15,Rb1,X2,Z26), (Ra15,Rb1, X2,Z27), (Ra15,Rb1,X2,Z28), (Ra15,Rb1,X2,Z29), (Ra15, Rb1,X2,Z30), (Ra15,Rb1,X2,Z31), (Ra15,Rb1,X2,Z32), (Ra15,Rb1,X2,Z33), (Ra15,Rb1,X2,Z34), (Ra15,Rb1,X2, Z35), (Ra15,Rb1,X2,Z36), (Ra15,Rb1,X2,Z37), (Ra15,Rb1, X2,Z38), (Ra15,Rb1,X2,Z39), (Ra15,Rb2,X1,Z1), (Ra15, Rb2,X1,Z2), (Ra15,Rb2,X1,Z3), (Ra15,Rb2,X1,Z4), (Ra15, Rb2,X1,Z5), (Ra15,Rb2,X1,Z6), (Ra15,Rb2,X1,Z7), (Ra15, Rb2,X1,Z8), (Ra15,Rb2,X1,Z9), (Ra15,Rb2,X1,Z10), (Ra15,Rb2,X1,Z11), (Ra15,Rb2,X1,Z12), (Ra15,Rb2,X1, Z13), (Ra15,Rb2,X1,Z14), (Ra15,Rb2,X1,Z15), (Ra15,Rb2, X1,Z16), (Ra15,Rb2,X1,Z17), (Ra15,Rb2,X1,Z18), (Ra15, Rb2,X1,Z19), (Ra15,Rb2,X1,Z20), (Ra15,Rb2,X1,Z21), (Ra15,Rb2,X1,Z22), (Ra15,Rb2,X1,Z23), (Ra15,Rb2,X1, Z24), (Ra15,Rb2,X1,Z25), (Ra15,Rb2,X1,Z26), (Ra15,Rb2, X1,Z27), (Ra15,Rb2,X1,Z28), (Ra15,Rb2,X1,Z29), (Ra15, Rb2,X1,Z30), (Ra15,Rb2,X1,Z31), (Ra15,Rb2,X1,Z32), (Ra15,Rb2,X1,Z33), (Ra15,Rb2,X1,Z34), (Ra15,Rb2,X1, Z35), (Ra15,Rb2,X1,Z36), (Ra15,Rb2,X1,Z37), (Ra15,Rb2, X1,Z38), (Ra15,Rb2,X1,Z39), (Ra15,Rb2,X2,Z1), (Ra15, Rb2,X2,Z2), (Ra15,Rb2,X2,Z3), (Ra15,Rb2,X2,Z4), (Ra15, Rb2,X2,Z5), (Ra15,Rb2,X2,Z6), (Ra15,Rb2,X2,Z7), (Ra15, Rb2,X2,Z8), (Ra15,Rb2,X2,Z9), (Ra15,Rb2,X2,Z10), (Ra15,Rb2,X2,Z11), (Ra15,Rb2,X2,Z12), (Ra15,Rb2,X2, Z13), (Ra15,Rb2,X2,Z14), (Ra15,Rb2,X2,Z15), (Ra15,Rb2, X2,Z16), (Ra15,Rb2,X2,Z17), (Ra15,Rb2,X2,Z18), (Ra15, Rb2,X2,Z19), (Ra15,Rb2,X2,Z20), (Ra15,Rb2,X2,Z21), (Ra15,Rb2,X2,Z22), (Ra15,Rb2,X2,Z23), (Ra15,Rb2,X2, Z24), (Ra15,Rb2,X2,Z25), (Ra15,Rb2,X2,Z26), (Ra15,Rb2, X2,Z27), (Ra15,Rb2,X2,Z28), (Ra15,Rb2,X2,Z29), (Ra15, Rb2,X2,Z30), (Ra15,Rb2,X2,Z31), (Ra15,Rb2,X2,Z32), (Ra15,Rb2,X2,Z33), (Ra15,Rb2,X2,Z34), (Ra15,Rb2,X2, Z35), (Ra15,Rb2,X2,Z36), (Ra15,Rb2,X2,Z37), (Ra15,Rb2, X2,Z38), (Ra15,Rb2,X2,Z39), (Ra15,Rb3,X1,Z1), (Ra15, Rb3,X1,Z2), (Ra15,Rb3,X1,Z3), (Ra15,Rb3,X1,Z4), (Ra15, Rb3,X1,Z5), (Ra15,Rb3,X1,Z6), (Ra15,Rb3,X1,Z7), (Ra15, Rb3,X1,Z8), (Ra15,Rb3,X1,Z9), (Ra15,Rb3,X1,Z10), (Ra15,Rb3,X1,Z11), (Ra15,Rb3,X1,Z12), (Ra15,Rb3,X1, Z13), (Ra15,Rb3,X1,Z14), (Ra15,Rb3,X1,Z15), (Ra15,Rb3, X1,Z16), (Ra15,Rb3,X1,Z17), (Ra15,Rb3,X1,Z18), (Ra15, Rb3,X1,Z19), (Ra15,Rb3,X1,Z20), (Ra15,Rb3,X1,Z21), (Ra15,Rb3,X1,Z22), (Ra15,Rb3,X1,Z23), (Ra15,Rb3,X1, Z24), (Ra15,Rb3,X1,Z25), (Ra15,Rb3,X1,Z26), (Ra15,Rb3, X1,Z27), (Ra15,Rb3,X1,Z28), (Ra15,Rb3,X1,Z29), (Ra15, Rb3,X1,Z30), (Ra15,Rb3,X1,Z31), (Ra15,Rb3,X1,Z32), (Ra15,Rb3,X1,Z33), (Ra15,Rb3,X1,Z34), (Ra15,Rb3,X1, Z35), (Ra15,Rb3,X1,Z36), (Ra15,Rb3,X1,Z37), (Ra15,Rb3, X1,Z38), (Ra15,Rb3,X1,Z39), (Ra15,Rb3,X2,Z1), (Ra15, Rb3,X2,Z2), (Ra15,Rb3,X2,Z3), (Ra15,Rb3,X2,Z4), (Ra15, Rb3,X2,Z5), (Ra15,Rb3,X2,Z6), (Ra15,Rb3,X2,Z7), (Ra15, Rb3,X2,Z8), (Ra15,Rb3,X2,Z9), (Ra15,Rb3,X2,Z10), (Ra15,Rb3,X2,Z11), (Ra15,Rb3,X2,Z12), (Ra15,Rb3,X2, Z13), (Ra15,Rb3,X2,Z14), (Ra15,Rb3,X2,Z15), (Ra15,Rb3, X2,Z16), (Ra15,Rb3,X2,Z17), (Ra15,Rb3,X2, Z18), (Ra15, Rb3,X2,Z19), (Ra15,Rb3,X2,Z20), (Ra15,Rb3,X2,Z21), (Ra15,Rb3,X2,Z22), (Ra15,Rb3,X2,Z23), (Ra15,Rb3,X2, Z24), (Ra15,Rb3,X2,Z25), (Ra15,Rb3,X2,Z26), (Ra15,Rb3, X2,Z27), (Ra15,Rb3,X2,Z28), (Ra15,Rb3,X2,Z29), (Ra15, Rb3,X2,Z30), (Ra15,Rb3,X2,Z31), (Ra15,Rb3,X2,Z32), (Ra15,Rb3,X2,Z33), (Ra15,Rb3,X2,Z34), (Ra15,Rb3,X2, Z35), (Ra15,Rb3,X2,Z36), (Ra15,Rb3,X2,Z37), (Ra15,Rb3, X2,Z38), (Ra15,Rb3,X2,Z39), (Ra15,Rb4,X1,Z1), (Ra15, Rb4,X1,Z2), (Ra15,Rb4,X1,Z3), (Ra15,Rb4,X1,Z4), (Ra15, Rb4,X1,Z5), (Ra15,Rb4,X1,Z6), (Ra15,Rb4,X1,Z7), (Ra15, Rb4,X1,Z8), (Ra15,Rb4,X1,Z9), (Ra15,Rb4,X1,Z10), (Ra15,Rb4,X1,Z11), (Ra15,Rb4,X1,Z12), (Ra15,Rb4,X1, Z13), (Ra15,Rb4,X1,Z14), (Ra15,Rb4,X1,Z15), (Ra15,Rb4, X1,Z16), (Ra15,Rb4,X1,Z17), (Ra15,Rb4,X1,Z18), (Ra15,

Rb4,X1,Z19), (Ra15,Rb4,X1,Z20), (Ra15,Rb4,X1,Z21), (Ra15,Rb4,X1,Z22), (Ra15,Rb4,X1,Z23), (Ra15,Rb4,X1,Z24), (Ra15,Rb4,X1,Z25), (Ra15,Rb4,X1,Z26), (Ra15,Rb4,X1,Z27), (Ra15,Rb4,X1,Z28), (Ra15,Rb4,X1,Z29), (Ra15,Rb4,X1,Z30), (Ra15,Rb4,X1,Z31), (Ra15,Rb4,X1,Z32), (Ra15,Rb4,X1,Z33), (Ra15,Rb4,X1,Z34), (Ra15,Rb4,X1,Z35), (Ra15,Rb4,X1,Z36), (Ra15,Rb4,X1,Z37), (Ra15,Rb4,X1,Z38), (Ra15,Rb4,X1,Z39), (Ra15,Rb4,X2,Z1), (Ra15,Rb4,X2,Z2), (Ra15,Rb4,X2,Z3), (Ra15,Rb4,X2,Z4), (Ra15,Rb4,X2,Z5), (Ra15,Rb4,X2,Z6), (Ra15,Rb4,X2,Z7), (Ra15,Rb4,X2,Z8), (Ra15,Rb4,X2,Z9), (Ra15,Rb4,X2,Z10), (Ra15,Rb4,X2,Z11), (Ra15,Rb4,X2,Z12), (Ra15,Rb4,X2,Z13), (Ra15,Rb4,X2,Z14), (Ra15,Rb4,X2,Z15), (Ra15,Rb4,X2,Z16), (Ra15,Rb4,X2,Z17), (Ra15,Rb4,X2,Z18), (Ra15,Rb4,X2,Z19), (Ra15,Rb4,X2,Z20), (Ra15,Rb4,X2,Z21), (Ra15,Rb4,X2,Z22), (Ra15,Rb4,X2,Z23), (Ra15,Rb4,X2,Z24), (Ra15,Rb4,X2,Z25), (Ra15,Rb4,X2,Z26), (Ra15,Rb4,X2,Z27), (Ra15,Rb4,X2,Z28), (Ra15,Rb4,X2,Z29), (Ra15,Rb4,X2,Z30), (Ra15,Rb4,X2,Z31), (Ra15,Rb4,X2,Z32), (Ra15,Rb4,X2,Z33), (Ra15,Rb4,X2,Z34), (Ra15,Rb4,X2,Z35), (Ra15,Rb4,X2,Z36), (Ra15,Rb4,X2,Z37), (Ra15,Rb4,X2,Z38), (Ra15,Rb4,X2,Z39), (Ra15,Rb5,X1,Z1), (Ra15,Rb5,X1,Z2), (Ra15,Rb5,X1,Z3), (Ra15,Rb5,X1,Z4), (Ra15,Rb5,X1,Z5), (Ra15,Rb5,X1,Z6), (Ra15,Rb5,X1,Z7), (Ra15,Rb5,X1,Z8), (Ra15,Rb5,X1,Z9), (Ra15,Rb5,X1,Z10), (Ra15,Rb5,X1,Z11), (Ra15,Rb5,X1,Z12), (Ra15,Rb5,X1,Z13), (Ra15,Rb5,X1,Z14), (Ra15,Rb5,X1,Z15), (Ra15,Rb5,X1,Z16), (Ra15,Rb5,X1,Z17), (Ra15,Rb5,X1,Z18), (Ra15,Rb5,X1,Z19), (Ra15,Rb5,X1,Z20), (Ra15,Rb5,X1,Z21), (Ra15,Rb5,X1,Z22), (Ra15,Rb5,X1,Z23), (Ra15,Rb5,X1,Z24), (Ra15,Rb5,X1,Z25), (Ra15,Rb5,X1,Z26), (Ra15,Rb5,X1,Z27), (Ra15,Rb5,X1,Z28), (Ra15,Rb5,X1,Z29), (Ra15,Rb5,X1,Z30), (Ra15,Rb5,X1,Z31), (Ra15,Rb5,X1,Z32), (Ra15,Rb5,X1,Z33), (Ra15,Rb5,X1,Z34), (Ra15,Rb5,X1,Z35), (Ra15,Rb5,X1,Z36), (Ra15,Rb5,X1,Z37), (Ra15,Rb5,X1,Z38), (Ra15,Rb5,X1,Z39), (Ra15,Rb5,X2,Z1), (Ra15,Rb5,X2,Z2), (Ra15,Rb5,X2,Z3), (Ra15,Rb5,X2,Z4), (Ra15,Rb5,X2,Z5), (Ra15,Rb5,X2,Z6), (Ra15,Rb5,X2,Z7), (Ra15,Rb5,X2,Z8), (Ra15,Rb5,X2,Z9), (Ra15,Rb5,X2,Z10), (Ra15,Rb5,X2,Z11), (Ra15,Rb5,X2,Z12), (Ra15,Rb5,X2,Z13), (Ra15,Rb5,X2,Z14), (Ra15,Rb5,X2,Z15), (Ra15,Rb5,X2,Z16), (Ra15,Rb5,X2,Z17), (Ra15,Rb5,X2,Z18), (Ra15,Rb5,X2,Z19), (Ra15,Rb5,X2,Z20), (Ra15,Rb5,X2,Z21), (Ra15,Rb5,X2,Z22), (Ra15,Rb5,X2,Z23), (Ra15,Rb5,X2,Z24), (Ra15,Rb5,X2,Z25), (Ra15,Rb5,X2,Z26), (Ra15,Rb5,X2,Z27), (Ra15,Rb5,X2,Z28), (Ra15,Rb5,X2,Z29), (Ra15,Rb5,X2,Z30), (Ra15,Rb5,X2,Z31), (Ra15,Rb5,X2,Z32), (Ra15,Rb5,X2,Z33), (Ra15,Rb5,X2,Z34), (Ra15,Rb5,X2,Z35), (Ra15,Rb5,X2,Z36), (Ra15,Rb5,X2,Z37), (Ra15,Rb5,X2,Z38), (Ra15,Rb5,X2,Z39), (Ra15,Rb6,X1,Z1), (Ra15,Rb6,X1,Z2), (Ra15,Rb6,X1,Z3), (Ra15,Rb6,X1,Z4), (Ra15,Rb6,X1,Z5), (Ra15,Rb6,X1,Z6), (Ra15,Rb6,X1,Z7), (Ra15,Rb6,X1,Z8), (Ra15,Rb6,X1,Z9), (Ra15,Rb6,X1,Z10), (Ra15,Rb6,X1,Z11), (Ra15,Rb6,X1,Z12), (Ra15,Rb6,X1,Z13), (Ra15,Rb6,X1,Z14), (Ra15,Rb6,X1,Z15), (Ra15,Rb6,X1,Z16), (Ra15,Rb6,X1,Z17), (Ra15,Rb6,X1,Z18), (Ra15,Rb6,X1,Z19), (Ra15,Rb6,X1,Z20), (Ra15,Rb6,X1,Z21), (Ra15,Rb6,X1,Z22), (Ra15,Rb6,X1,Z23), (Ra15,Rb6,X1,Z24), (Ra15,Rb6,X1,Z25), (Ra15,Rb6,X1,Z26), (Ra15,Rb6,X1,Z27), (Ra15,Rb6,X1,Z28), (Ra15,Rb6,X1,Z29), (Ra15,Rb6,X1,Z30), (Ra15,Rb6,X1,Z31), (Ra15,Rb6,X1,Z32), (Ra15,Rb6,X1,Z33), (Ra15,Rb6,X1,Z34), (Ra15,Rb6,X1,Z35), (Ra15,Rb6,X1,Z36), (Ra15,Rb6,X1,Z37), (Ra15,Rb6,X1,Z38), (Ra15,Rb6,X1,Z39), (Ra15,Rb6,X2,Z1), (Ra15,Rb6,X2,Z2), (Ra15,Rb6,X2,Z3), (Ra15,Rb6,X2,Z4), (Ra15,Rb6,X2,Z5), (Ra15,Rb6,X2,Z6), (Ra15,Rb6,X2,Z7), (Ra15,Rb6,X2,Z8), (Ra15,Rb6,X2,Z9), (Ra15,Rb6,X2,Z10), (Ra15,Rb6,X2,Z11), (Ra15,Rb6,X2,Z12), (Ra15,Rb6,X2,Z13), (Ra15,Rb6,X2,Z14), (Ra15,Rb6,X2,Z15), (Ra15,Rb6,X2,Z16), (Ra15,Rb6,X2,Z17), (Ra15,Rb6,X2,Z18), (Ra15,Rb6,X2,Z19), (Ra15,Rb6,X2,Z20), (Ra15,Rb6,X2,Z21), (Ra15,Rb6,X2,Z22), (Ra15,Rb6,X2,Z23), (Ra15,Rb6,X2,Z24), (Ra15,Rb6,X2,Z25), (Ra15,Rb6,X2,Z26), (Ra15,Rb6,X2,Z27), (Ra15,Rb6,X2,Z28), (Ra15,Rb6,X2,Z29), (Ra15,Rb6,X2,Z30), (Ra15,Rb6,X2,Z31), (Ra15,Rb6,X2,Z32), (Ra15,Rb6,X2,Z33), (Ra15,Rb6,X2,Z34), (Ra15,Rb6,X2,Z35), (Ra15,Rb6,X2,Z36), (Ra15,Rb6,X2,Z37), (Ra15,Rb6,X2,Z38), (Ra15,Rb6,X2,Z39), (Ra15,Rb7,X1,Z1), (Ra15,Rb7,X1,Z2), (Ra15,Rb7,X1,Z3), (Ra15,Rb7,X1,Z4), (Ra15,Rb7,X1,Z5), (Ra15,Rb7,X1,Z6), (Ra15,Rb7,X1,Z7), (Ra15,Rb7,X1,Z8), (Ra15,Rb7,X1,Z9), (Ra15,Rb7,X1,Z10), (Ra15,Rb7,X1,Z11), (Ra15,Rb7,X1,Z12), (Ra15,Rb7,X1,Z13), (Ra15,Rb7,X1,Z14), (Ra15,Rb7,X1,Z15), (Ra15,Rb7,X1,Z16), (Ra15,Rb7,X1,Z17), (Ra15,Rb7,X1,Z18), (Ra15,Rb7,X1, Z19), (Ra15,Rb7,X1,Z20), (Ra15,Rb7,X1,Z21), (Ra15,Rb7,X1,Z22), (Ra15,Rb7,X1,Z23), (Ra15,Rb7,X1,Z24), (Ra15,Rb7,X1,Z25), (Ra15,Rb7,X1,Z26), (Ra15,Rb7,X1,Z27), (Ra15,Rb7,X1,Z28), (Ra15,Rb7,X1,Z29), (Ra15,Rb7,X1,Z30), (Ra15,Rb7,X1,Z31), (Ra15,Rb7,X1,Z32), (Ra15,Rb7,X1,Z33), (Ra15,Rb7,X1,Z34), (Ra15,Rb7,X1,Z35), (Ra15,Rb7,X1,Z36), (Ra15,Rb7,X1,Z37), (Ra15,Rb7,X1,Z38), (Ra15,Rb7,X1,Z39), (Ra15,Rb7,X2,Z1), (Ra15,Rb7,X2,Z2), (Ra15,Rb7,X2,Z3), (Ra15,Rb7,X2,Z4), (Ra15,Rb7,X2,Z5), (Ra15,Rb7,X2,Z6), (Ra15,Rb7,X2,Z7), (Ra15,Rb7,X2,Z8), (Ra15,Rb7,X2,Z9), (Ra15,Rb7,X2,Z10), (Ra15,Rb7,X2,Z11), (Ra15,Rb7,X2,Z12), (Ra15,Rb7,X2,Z13), (Ra15,Rb7,X2,Z14), (Ra15,Rb7,X2,Z15), (Ra15,Rb7,X2,Z16), (Ra15,Rb7,X2,Z17), (Ra15,Rb7,X2,Z18), (Ra15,Rb7,X2,Z19), (Ra15,Rb7,X2,Z20), (Ra15,Rb7,X2,Z21), (Ra15,Rb7,X2,Z22), (Ra15,Rb7,X2,Z23), (Ra15,Rb7,X2,Z24), (Ra15,Rb7,X2,Z25), (Ra15,Rb7,X2,Z26), (Ra15,Rb7,X2,Z27), (Ra15,Rb7,X2,Z28), (Ra15,Rb7,X2,Z29), (Ra15,Rb7,X2,Z30), (Ra15,Rb7,X2,Z31), (Ra15,Rb7,X2,Z32), (Ra15,Rb7,X2,Z33), (Ra15,Rb7,X2,Z34), (Ra15,Rb7,X2,Z35), (Ra15,Rb7,X2,Z36), (Ra15,Rb7,X2,Z37), (Ra15,Rb7,X2,Z38), (Ra15,Rb7,X2,Z39), (Ra15,Rb8,X1,Z1), (Ra15,Rb8,X1,Z2), (Ra15,Rb8,X1,Z3), (Ra15,Rb8,X1,Z4), (Ra15,Rb8,X1,Z5), (Ra15,Rb8,X1,Z6), (Ra15,Rb8,X1,Z7), (Ra15,Rb8,X1,Z8), (Ra15,Rb8,X1,Z9), (Ra15,Rb8,X1,Z10), (Ra15,Rb8,X1,Z11), (Ra15,Rb8,X1,Z12), (Ra15,Rb8,X1,Z13), (Ra15,Rb8,X1,Z14), (Ra15,Rb8,X1,Z15), (Ra15,Rb8,X1,Z16), (Ra15,Rb8,X1,Z17), (Ra15,Rb8,X1,Z18), (Ra15,Rb8,X1,Z19), (Ra15,Rb8,X1,Z20), (Ra15,Rb8,X1,Z21), (Ra15,Rb8,X1,Z22), (Ra15,Rb8,X1,Z23), (Ra15,Rb8,X1,Z24), (Ra15,Rb8,X1,Z25), (Ra15,Rb8,X1,Z26), (Ra15,Rb8,X1,Z27), (Ra15,Rb8,X1,Z28), (Ra15,Rb8,X1,Z29), (Ra15,Rb8,X1,Z30), (Ra15,Rb8,X1,Z31), (Ra15,Rb8,X1,Z32), (Ra15,Rb8,X1,Z33), (Ra15,Rb8,X1,Z34), (Ra15,Rb8,X1,Z35), (Ra15,Rb8,X1,Z36), (Ra15,Rb8,X1,Z37), (Ra15,Rb8,X1,Z38), (Ra15,Rb8,X1,Z39), (Ra15,Rb8,X2,Z1), (Ra15,Rb8,X2,Z2), (Ra15,Rb8,X2,Z3), (Ra15,Rb8,X2,Z4), (Ra15,Rb8,X2,Z5), (Ra15,Rb8,X2,Z6), (Ra15,Rb8,X2,Z7), (Ra15,Rb8,X2,Z8), (Ra15,Rb8,X2,Z9), (Ra15,Rb8,X2,Z10), (Ra15,Rb8,X2,Z11), (Ra15,Rb8,X2,Z12), (Ra15,Rb8,X2,Z13), (Ra15,Rb8,X2,Z14), (Ra15,Rb8,X2,Z15), (Ra15,Rb8,X2,Z16), (Ra15,Rb8,X2,Z17), (Ra15,Rb8,X2,Z18), (Ra15,Rb8,X2,Z19), (Ra15,Rb8,X2,Z20), (Ra15,Rb8,X2,Z21), (Ra15,Rb8,X2,Z22), (Ra15,Rb8,X2,Z23), (Ra15,Rb8,X2,Z24), (Ra15,Rb8,X2,Z25), (Ra15,Rb8,X2,Z26), (Ra15,Rb8,X2,Z27), (Ra15, Rb8,X2,Z28), (Ra15,Rb8,X2,Z29), (Ra15,Rb8,X2,Z30), (Ra15,Rb8,X2,Z31), (Ra15,Rb8,X2,Z32), (Ra15,Rb8,X2,Z33), (Ra15,Rb8,X2,Z34), (Ra15,Rb8,X2,Z35), (Ra15,Rb8,X2,Z36), (Ra15,Rb8,X2,Z37), (Ra15,Rb8,X2,Z38), and (Ra15,Rb8,X2,Z39)

EXAMPLES

Following examples illustrate the present invention in more detail, but the present invention is not limited by these examples. The meaning of each abbreviation is following.
Me: methyl
Et: ethyl
Bu: butyl
Ac: acetyl
TMS: tetramethylsilane
TMS-Cl: trimethylsilyl chloride
DMSO: dimethyl sulfoxide
DMF: dimethylformamide
THF: tetrahydrofuran
rt: room temperature

Example 1

Preparation of 4-(2,2-dimethylpropionyl)-3-hydroxy-5-(2-methoxycarbonylmethyloxyphenyl-1-(4-thiophene-3-ylphenyl)-1,5-dihydropyrrole-2-one

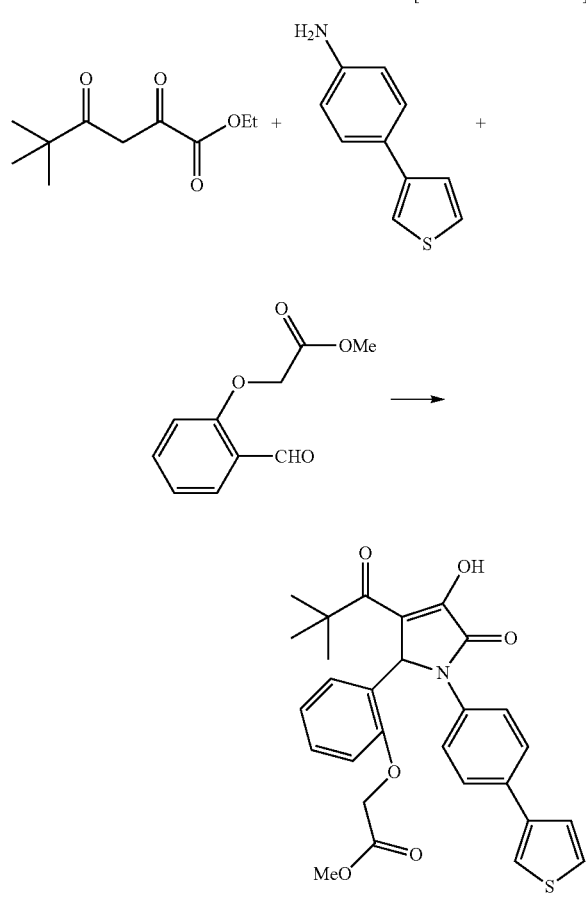

[Chemical Formula 68]

A mixture of ethyl trimethylacetopyruvate (0.40 g, 2 mmol), 4-thiophene-3-ylaniline (0.35 g, 2 mmol), 2-(methoxycarbonylmethyloxy)benzaldehyde (0.39, 2 mmol), acetic acid (0.057 mL, 1 mmol) and dioxane (4 mL) was heated at reflux overnight. After the reaction was completed, saturated sodium bicarbonate solution and brine were poured into the reaction mixture, and the resulting mixture was extracted with ethyl acetate. The extract was dried over anhydrous sodium sulphate, and then concentrated in vacuo. The resulting residue was purified on a silica gel column chromatography (methanol/chloroform), and the aimed compound was triturated with ethyl acetate and diisopropyl ether to give 4-(2,2-dimethylpropionyl)-3-hydroxy-5-(2-methoxycarbonylmethyloxyphenyl)-1-(4-thiophene-3-ylphenyl)-1,5-dihydropyrrole-2-one (0.42 g, yield: 41%) as pale brown solid.

1H-NMR (δ ppm TMS/DMSO-d6): 1.10 (9H, s), 3.78 (3H, s), 4.50-4.90 (2H, m), 6.00-6.45 (1H, m), 6.60-7.11 (11H, m).

Example 2

Preparation of 5-(2-hydroxycarbonylmethyloxyphenyl)-4-(2,2-dimethylpropionyl)-3-hydroxy-1-(4-thiophene-3-ylphenyl)-1,5-dihydropyrrole-2-one

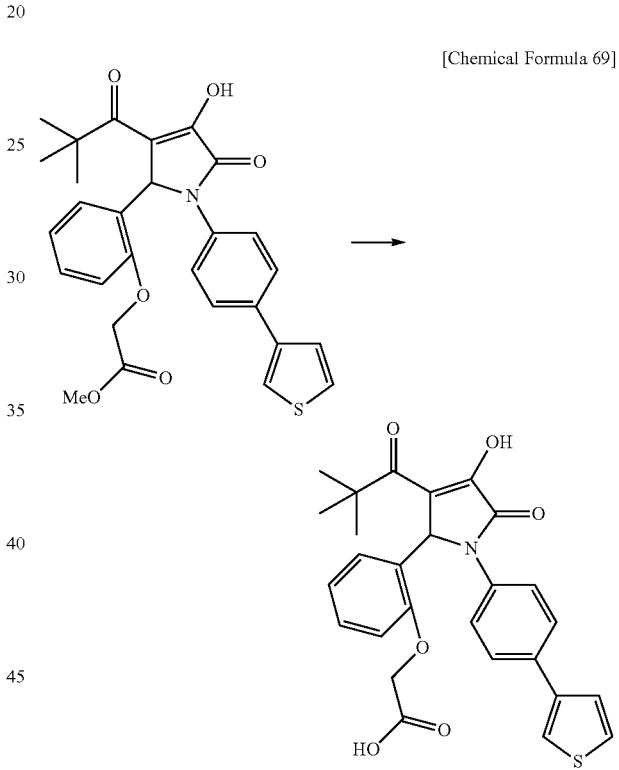

[Chemical Formula 69]

To a mixture of 4-(2,2-dimethylpropionyl)-3-hydroxy-5-(2-methoxycarbonylmethyloxyphenyl)-1-(4-thiophene-3-ylphenyl)-1,5-dihydropyrrole-2-one (0.172 g, 0.34 mmol), THF (1.72 mL), and methanol (1.72 mL) was added 1 mol/L aqueous lithium hydroxide solution (1.02 mL), and the resulting mixture was stirred at room temperature for 1 hour. After the reaction was completed, 2 mol/L hydrochloric acid (0.52 mL) and water (14 mL) were added to the reaction mixture, and the precipitated aimed compound was collected by filtration. The resulting aimed compound was dissolved in ethyl acetate, and the mixture was dried over anhydrous sodium sulphate and then concentrated in vacuo. The resulting residue was triturated with ethyl ether and diisopropyl ether to give 5-(2-hydroxycarbonylmethyloxyphenyl)-4-(2,2-dimethylpropionyl)-3-hydroxy-1-(4-thiophene-3-ylphenyl)-1,5-dihydropyrrole-2-one (0.137 g, yield: 82%) as pale yellow solid.

1H-NMR (δ ppm TMS/DMSO-d6): 1.10 (9H, s), 4.85 (2H, s), 6.46 (1H, brs), 6.76-7.75 (11H, m).

Example 3

Preparation of 3-t-butyl-5-(4-thiophene-3-ylphenyl)-4-(2-methoxycarbonylmethyloxyphenyl)-4,5-dihydro-1H-pyrrolo[3,4-c]pyrazole-6-one

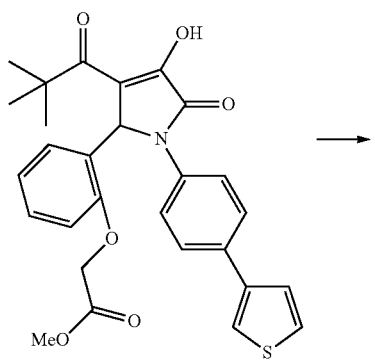

[Chemical Formula 70]

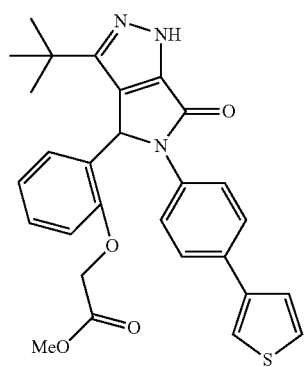

A mixture of 4-(2,2-dimethylpropionyl)-3-hydroxy-5-(2-methoxycarbonylmethyloxyphenyl)-1-(4-thiophene-3-ylphenyl)-1,5-dihydropyrrole-2-one (0.207 g, 0.41 mmol), hydrazine hydrate (0.022 mL, 0.45 mmol) and acetic acid (3.1 mL) was stirred at 95° C. for 1 hour. After the reaction was completed, saturated sodium bicarbonate solution was poured into the reaction mixture, and the mixture was extracted with chloroform. The extract was washed with brine, dried over anhydrous sodium sulphate, and then concentrated in vacuo. The resulting residue was triturated with ethyl ether and diisopropyl ether to give 3-t-butyl-5-(4-thiophene-3-ylphenyl)-4-(2-methoxycarbonylmethyloxyphenyl)-4,5-dihydro-1H-pyrrolo[3,4-c]pyrazole-6-one (0.191 g, yield: 93%) as pale brown solid.

1H-NMR (δ ppm TMS/DMSO-d6): 1.05 (9H, s), 3.78 (3H, s), 4.94 (2H, s), 6.70-7.77 (12H, m), 13.4 (1H, brs).

Example 4

Preparation of 3-t-butyl-5-(4-thiophene-3-ylphenyl)-4-(2-hydroxycarbonylmethyloxyphenyl)-4,5-dihydro-1H-pyrrolo[3,4-c]pyrazole-6-one

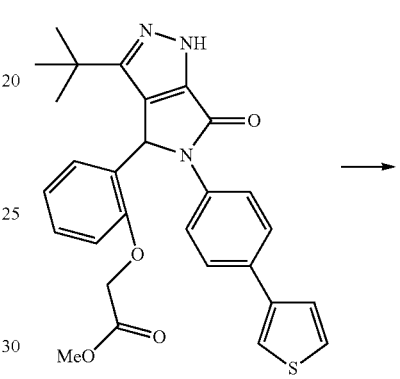

[Chemical Formula 71]

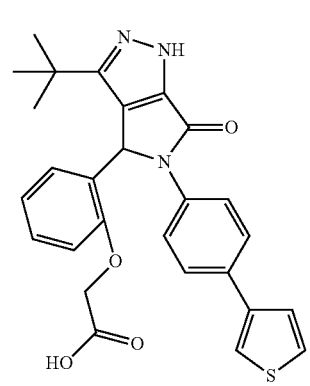

To a mixture of 3-t-butyl-5-(4-thiophene-3-ylphenyl)-4-(2-methoxycarbonylmethyloxyphenyl)-4,5-dihydro-1H-pyrrolo[3,4-c]pyrazole-6-one (0.124 g, 0.25 mmol), THF (1.24 mL) and methanol (1.24 mL) was added 1 mol/L aqueous lithium hydroxide solution (0.74 mL), and the resulting mixture was stirred at room temperature for 1.5 hours. After the reaction was completed, 2 mol/L hydrochloric acid (0.38 mL) and water (10 mL) were poured into the reaction mixture, and the precipitated aimed compound was collected by filtration. The resulting aimed compound was dissolved in ethyl acetate, and the solution was dried over anhydrous sodium sulphate and then concentrated in vacuo. The resulting residue was triturated with ethyl ether and diisopropyl ether to give 5-(2-hydroxycarbonylmethyloxyphenyl)-4-(2, 2-dimethylpropionyl)-3-hydroxy-1-(4-thiophene-3-ylphenyl)-1,5-dihydropyrrole-2-one (0.104 g, yield: 87%) as pale brown solid.

1H-NMR (δ ppm TMS/DMSO-d6): 1.05 (9H, s), 4.78 (2H, s), 6.70-7.80 (12H, m), 13.33 (1H, brs).

Example 5

Preparation of 1-(6-furan-3-yl-3-pyridyl)-4-(2,2-dimethylpropionyl)-3-hydroxy-5-(2-methoxy-3-pyridyl)-1,5-dihydropyrrole-2-one

[Chemical Formula 72]

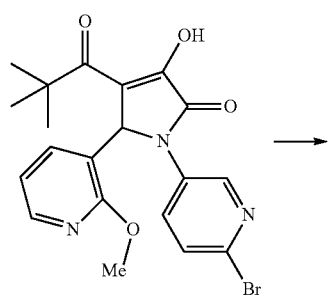

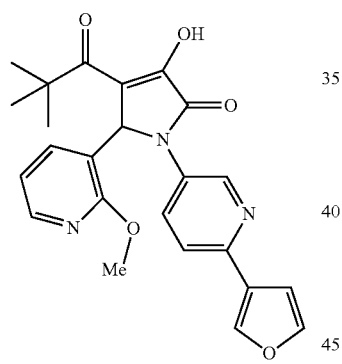

A mixture of 1-(6-bromo-3-pyridyl)-4-(2,2-dimethylpropionyl)-3-hydroxy-5-(2-methoxy-3-pyridyl)-1,5-dihydropyrrole-2-one (0.10 g, 0.22 mmol), furan-3-yl boronic acid (0.038 g, 0.34 mmol), tripotassium phosphate (0.14 mg, 0.67 mmol), 1,2-Dimethoxyethane (3 mL) and water (0.6 mL) was placed in a flask under nitrogen. To the mixture was added 1,1'-Bis(diphenylphosphino)ferrocene-palladium(II)dichloride dichloromethane complex (0.018 g, 0.022 mmol), and the resulting mixture was heated at reflux for 4 hours. After the reaction was completed, saturated ammonium chloride aqueous solution was poured into the mixture and the resulting mixture was extracted with ethyl acetate. The extract was washed with brine, dried over anhydrous sodium sulphate, and concentrated in vacuo. The resulting residue was purified on a silica gel column chromatography (ethyl acetate/n-hexane) and the aimed compound was triturated with ethyl acetate and n-hexane to give 1-(6-furan-3-yl-3-pyridyl)-4-(2, 2-dimethylpropionyl)-3-hydroxy-1-5-(2-methoxy-3-pyridyl)-1,5-dihydropyrrole-2-one (0.045 g, yield: 46%) as colorless solid.

1H-NMR (δ ppm TMS/DMSO-d6): 1.11 (9H, s), 3.79 (3H, brs), 6.24 (1H, brs), 6.86 (1H, m), 6.96 (1H, m), 7.64-7.95 (4H, m), 8.23 (1H, s), 8.71 (1H, s), 12.31 (1H, brs).

Example 6

Preparation of 3-t-butyl-5-(6-thiophene-2-yl-3-pyridyl)-4-(2-methoxy-3-pyridyl)-4,5-dihydro-1H-pyrrolo[3,4-c]pyrazole-6-one

[Chemical Formula 7]

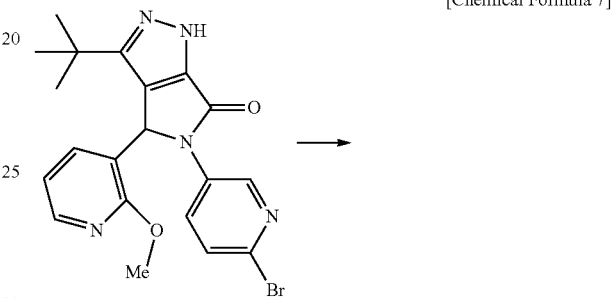

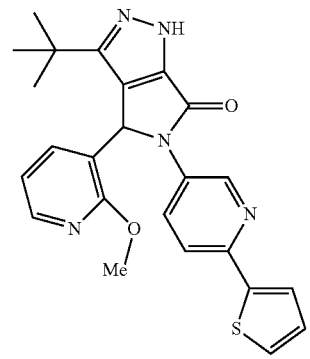

A mixture of 5-(6-bromo-3-pyridyl)-3-t-butyl-4-(2-methoxy-3-pyridyl)-4,5-dihydro-1H-pyrrolo[3,4-c]pyrazole-6-one (0.10 g, 0.23 mmol), thiophene-2-yl boronic acid (0.043 g, 0.34 mmol), tripotassium phosphate (0.14 mg, 0.67 mmol), 1,2-Dimethoxyethane (3 mL) and water (0.6 mL) was placed in a flask under nitrogen. To the mixture was added 1,1'-Bis(diphenylphosphino)ferrocene-palladium(II) dichloride dichloromethane complex (0.018 g, 0.022 mmol) and the resulting mixture was heated at reflux for 3 hours. After the reaction was completed, water was added to the mixture, and the resulting mixture was extracted with ethyl acetate. The extract was dried over anhydrous sodium sulphate and concentrated in vacuo. The resulting residue was purified on a silica gel column chromatography (ethyl acetate/n-hexane). The aimed compound was triturated with ethyl acetate and n-hexane to give 1-(6-furan-3-yl-3-pyridyl)-4-(2,2-dimethylpropionyl)-3-hydroxy-1-5-(2-methoxy-3-pyridyl)-1,5-dihydropyrrole-2-one (0.089 g, yield: 88%) as colorless solid.

1H-NMR (δ ppm TMS/DMSO-d6): 1.07 (9H, s), 3.97 (3.55) (3H, s), 6.56-7.28 (4H, m), 7.58 (1H, d, J=5.0), 7.69 (1H, d, J=3.7), 7.87-8.10 (3H, m), 8.64 (1H, s), 13.36 (1H, m).

Example 7

Preparation of 3-(1-hydroxymethyl-1-methylethyl)-4-(2-methoxyphenyl)-5-(4-thiophene-3-ylphenyl)-4,5-dihydro-1H-pyrrolo[3,4-c]pyrazole-6-one

[Chemical Formula 74]

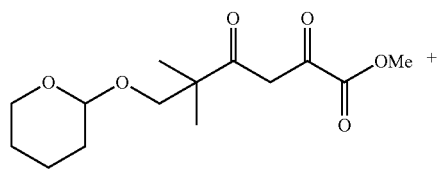

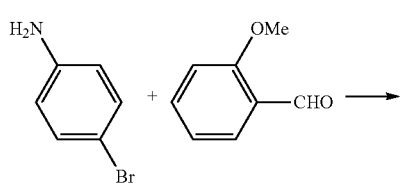

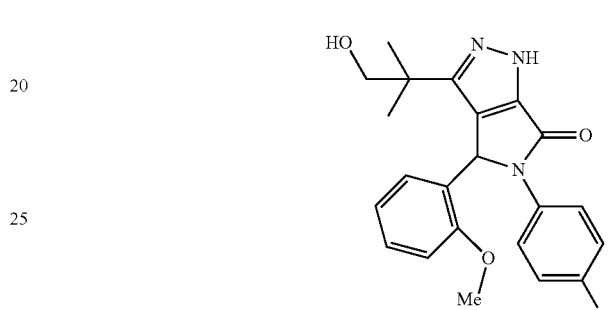

A mixture of methyl 5,5-dimethyl-2,4-dioxo-6-(tetrahydro-2H-pyrane-2-yloxy)hexanoate (4.29 g, 15 mmol), 4-bromoaniline (2.58 g, 15 mmol), 2-methoxybenzaldehyde (1.812 mL, 15 mmol), acetic acid (0.343 mL, 6 mmol) and dioxane (15 ml) was heated at reflux overnight. After the reaction was completed, the mixture was concentrated in vacuo and the resulting residue was purified on a silica gel column chromatography (ethyl acetate/n-hexane). The resulting aimed compound was triturated with ethyl acetate and n-hexane to give 1-(4-bromophenyl)-4-(2,2-dimethyl-3-tetrahydro-2H-pyrane-2-yloxypropionyl)-3-hydroxy-5-(2-methoxyphenyl)-1,5-dihydropyrrole-2-one (2.69 g, yield: 33%) as colorless solid.

1H-NMR (δ ppm TMS/DMSO-d6): 1.08 (3H, s), 1.13 (3H, s), 1.20-1.40 (6H, m), 3.50-3.90 (7H, m), 4.37 (1H, m), 6.31 (1H, brs), 6.70-7.44 (8H, m), 12.23 (1H, brs).

[Chemical Formula 75]

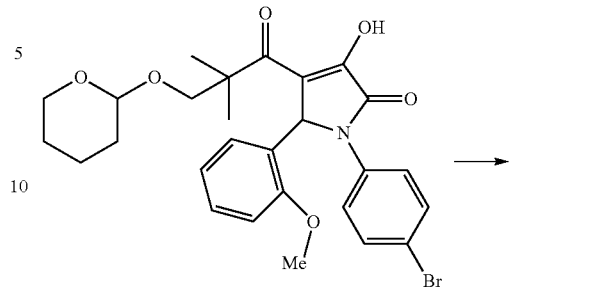

A mixture of 1-(4-bromophenyl)-4-(2,2-dimethyl-3-tetrahydro-2H-pyrane-2-yloxypropionyl)-3-hydroxy-5-(2-methoxyphenyl)-1,5-dihydropyrrole-2-one (1.51 g, 2.77 mmol), hydrazine hydrate (0.204 mL, 4.16 mmol) and acetic acid (3 mL) was stirred at 95° C. for 2 hours. After the reaction was completed, saturated sodium bicarbonate solution (150 mL) was poured into the reaction mixture, and the resulting mixture was extracted with ethyl acetate. The extract was washed with saturated sodium bicarbonate solution, dried over anhydrous sodium sulphate, and concentrated in vacuo. The resulting residue was triturated with ethyl acetate to give 5-(4-bromophenyl)-3-(1-hydroxymethyl-1-methylethyl)-4-(2-methoxyphenyl)-4,5-dihydro-1H-pyrrolo[3,4-c]pyrazole-6-one (1.02 g, yield: 81%) as colorless solid.

1H-NMR (δ ppm TMS/DMSO-d6): 0.88 (3H, s), 1.00 (3H, s), 3.11 (2H, m), 3.87 (3H, s), 4.73 (1H, brs), 6.30-7.50 (9H, m), 13.21 (1H, m).

[Chemical Formula 76]

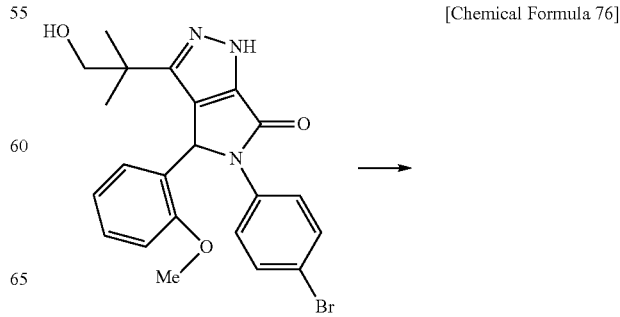

-continued

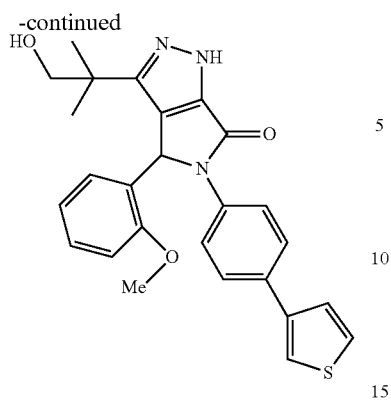

A mixture of 5-(4-bromophenyl)-3-(1-hydroxymethyl-1-methylethyl)-4-(2-methoxyphenyl)-4,5-dihydro-1H-pyrrolo[3,4-c]pyrazole-6-one (0.15 g, 0.33 mmol), thiophene-3-yl boronic acid (0.063. g, 0.49 mmol), tripotassium phosphate (0.21 mg, 0.99 mmol), 1,2-Dimethoxyethane (3 mL) and water (0.6 mL) was placed in a flask under nitrogen. To the mixture was added 1,1'-Bis(diphenylphosphino)ferrocene-palladium(II) dichloride dichloromethane complex (0.027 mg, 0.033 mmol) and the resulting mixture was heated at reflux for 5 hours. After the reaction was completed, the reaction mixture was purified on a silica gel column chromatography (ethyl acetate/n-hexane). The resulting aimed compound was triturated with ethyl acetate and n-hexane to give 3-(1-hydroxymethyl-1-methylethyl)-4-(2-methoxyphenyl)-5-(4-thiophene-3-ylphenyl)-4,5-dihydro-1H-pyrrolo[3,4-c]pyrazole-6-one (0.038 g, yield: 25%) as colorless solid.

1H-NMR (5 ppm TMS/DMSO-d6): 0.91 (3H, s), 1.04 (3H, s), 3.25 (2H, m), 3.91 (3H, s), 4.74 (1H, s), 6.33-7.78 (9H, m), 13.21 (1H, m)

Example 8

Preparation of 3-(1-hydroxymethyl-1-methylethyl)-4-(2-methoxy-3-pyridyl)-5-(4-thiophene-3-ylphenyl)-4,5-dihydro-1H-pyrrolo[3,4-c]pyrazole-6-one

[Chemical Formula 77]

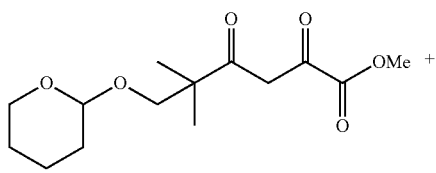

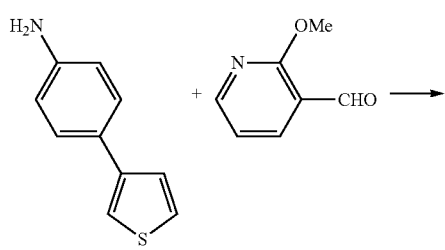

-continued

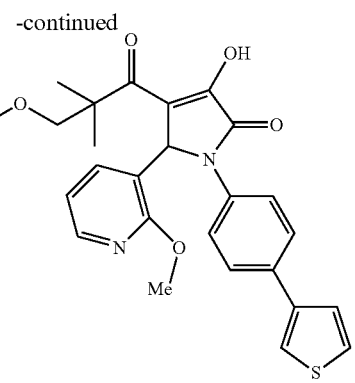

A mixture of methyl 5,5-dimethyl-2,4-dioxo-6-(tetrahydro-2H-pyrane-2-yloxy)hexanoate (0.29 mg, 1.0 mmol), 4-(3-thienyl)aniline (0.18 g, 1.0 mmol), 2-methoxynicotinaldehyde (0.14 g, 1.0 mmol), acetic acid (0.043 mL, 0.75 mmol) and dioxane (2 ml) was heated at reflux overnight. After the reaction was completed, the reaction mixture was concentrated in vacuo. The resulting residue was purified on a silica gel column chromatography (methanol/chloroform) to give 4-(2,2-dimethyl-3-tetrahydro-2H-pyrane-2-yloxypropionyl)-3-hydroxy-5-(2-methoxy-3-pyridyl)-1-(4-thiophene-3-ylphenyl)-1,5-dihydropyrrole-2-one (0.30 g, yield: 55%) as pale yellow solid.

[Chemical Formula 78]

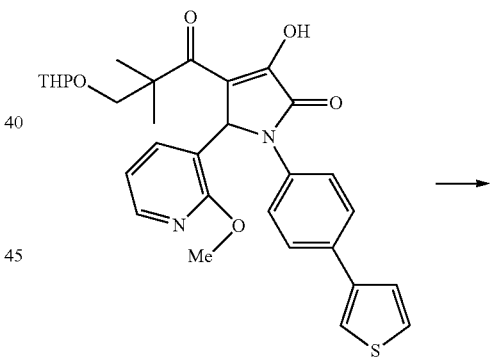

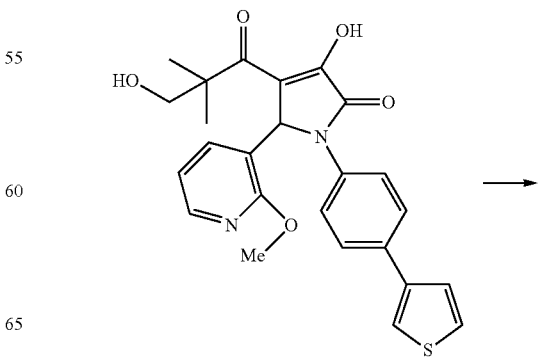

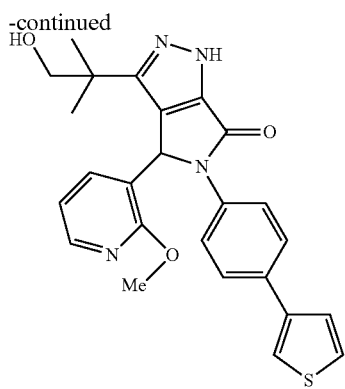

To a mixture of 4-(2,2-dimethyl-3-tetrahydro-2H-pyrane-2-yloxypropionyl)-3-hydroxy-5-(2-methoxy-3-pyridyl)-1-(4-thiophene-3-ylphenyl)-1,5-dihydropyrrole-2-one (0.30 g, 0.55 mmol), methanol (3 mL) and chloroform (3 mL) was added p-toluenesulfonic acid hydrate (0.158 g, 0.8 mmol), and the resulting mixture was stirred at room temperature for 3 hours. After the reaction was completed, saturated sodium bicarbonate solution and brine were poured into the mixture. The resulting mixture was extracted with chloroform. The extract was dried over anhydrous sodium sulphate and concentrated in vacuo. To the obtained crude 4-(2,2-dimethyl-3-hydroxypropionyl)-3-hydroxy-5-(2-methoxy-3-pyridyl)-1-(4-thiophene-3-ylphenyl)-1,5-dihydropyrrole-2-one (0.233 g), acetic acid (2 mL) and hydrazine hydrate (0.074 mL, 1.5 mmol) were added, and the resulting mixture was stirred at 50° C. for 1 hour. After the reaction was completed, saturated sodium bicarbonate solution was poured into the mixture, and the resulting mixture was extracted with chloroform. The extract was dried over anhydrous sodium sulphate and concentrated in vacuo. The resulting residue was triturated with ethyl acetate to give 3-(1-hydroxymethyl-1-methylethyl)-4-(2-methoxy-3-pyridyl)-5-(4-thiophene-3-ylphenyl)-4,5-dihydro-1H-pyrrolo[3,4-c]pyrazole-6-one (0.061 g, yield: 26%) as colorless solid.

1H-NMR (δ ppm TMS/DMSO-d6): 0.95 (3H, s), 1.06 (3H, s), 3.23 (2H, m), 4.06 (2H, s), 4.78 (1H, brs), 6.43-8.10 (10H, m), 13.40 (1H, m).

Example 9

Preparation of 3-(1,1-dihydroxymethylethyl)-4-(2-methoxyphenyl)-5-(4-thiophene-3-ylphenyl)-4,5-dihydro-1H-pyrrolo[3,4-c]pyrazole-6-one

[Chemical Formula 79]

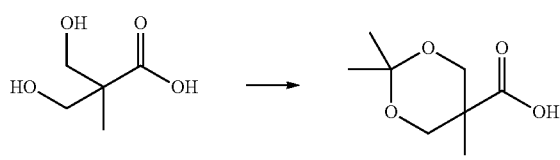

To a mixture of 3-hydroxy-2-hydroxymethyl-2-methylpropionic acid (6.71 g, 50 mmol), dimethoxypropane (7.99 mL, 65 mmol) and acetone (50 mL), p-toluenesulfonic acid hydrate (0.048 g, 0.25 mmol) was added and the resulting mixture was stirred at room temperature for 2.5 hours. After the reaction was completed, sodium bicarbonate (0.1 g) was added to the reaction mixture, and the resulting mixture was stirred at room temperature for 5 minutes and concentrated in vacuo. To the resulting residue was added water and the resulting mixture was extracted with ethyl ether. The extract was dried over anhydrous sodium sulphate and concentrated in vacuo to give 2,2,5-trimethyl-1,3-dioxane5-carboxylic acid (7.87 g, yield: 90%) as colorless oil.

1H-NMR (δ ppm TMS/CDCl3): 1.20 (3H, s), 1.43 (3H, s), 1.46 (3H, s), 3.70 (2H, d, J=11.7), 4.16 (2H, d, J=11.7).

[Chemical Formula 80]

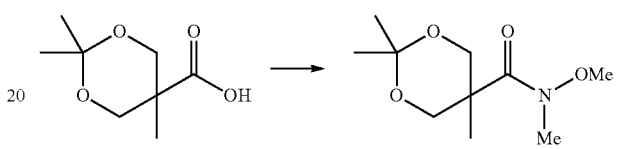

To a mixture of 2,2,5-trimethyl-1,3-dioxane5-carboxylic acid (1.0 g, 5.74 mmol) and DMF (10 mL) were added N,O-dimethylhydroxylamine hydrochloride (0.84 g, 8.6 mmol), 1-hydroxybenzotriazole hydrate (1.32 g, 8.6 mmol), 1-ethyl-3-(3-dimethylaminopropyl)carbodiimide hydrochloric acid (1.651 g, 8.61 mmol) and triethylamine (2.39 mL, 17.2 mmol) under nitrogen atmosphere, and the resulting mixture was stirred at room temperature for 3 hours. After the reaction was completed, water was added to the reaction mixture and the resulting mixture was extracted with ethyl acetate. The extract was washed with brine, dried over anhydrous sodium sulphate, and concentrated in vacuo to give N-methoxy-N,2,2,5-tetramethyl-1,3-dioxane5-carboxylic acid amid (1.08 g, yield: 86%) as colorless oil.

1H-NMR (δ ppm TMS/CDCl3): 1.38 (3H, s), 1.41 (3H, s), 1.42 (3H, s), 3.18 (3H, s), 3.69 (3H, s), 3.76 (2H, d, J=11.7), 4.19 (2H, d, J=11.7).

[Chemical Formula 81]

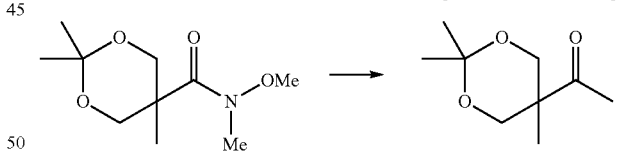

To a mixture of N-methoxy-N,2,2,5-tetramethyl-1,3-dioxane5-carboxylic acid amid (1.07 g, 4.92 mmol) and THF (10 mL) was gradually added 3 mol/L methylmagnesium bromide in THF (2.46 mL, 7.4 mmol) at 0° C. under nitrogen atmosphere, and the resulting mixture was stirred at 0° C. for 4 hours. After the reaction was completed, saturated ammonium chloride aqueous solution was added to the reaction mixture and the resulting mixture was extracted with ethyl acetate. The extract was washed with brine, dried over anhydrous sodium sulphate, and concentrated in vacuo to give 1-(2,2,5-trimethyl-1,3-dioxane5-yl)ethanone (0.76 g, yield: 90%) as colorless oil.

1H-NMR (δ ppm TMS/CDCl3): 1.03 (3H, s), 1.37 (3H, d, J=0.5), 1.45 (3H, d, J=0.5), 2.28 (3H, s), 3.68 (2H, d, J=12.2), 4.16 (2H, d, J=12.2).

[Chemical Formula 82]

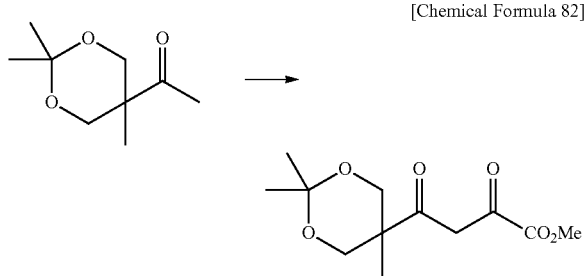

To a mixture of 1-(2,2,5-trimethyl-1,3-dioxane5-yl)ethanone (0.76 g, 4.4 mmol) and THF (7.6 mL) was added sodium hydride (0.16 g, 6.6 mmol) under nitrogen atmosphere, and the resulting mixture was stirred at room temperature for 0.5 hour. To the resulting reaction mixture was added dimethyl oxalate (0.78 g, 6.6 mmol) and the mixture was heated at reflux for 2 hours. After the reaction was completed, saturated ammonium chloride aqueous solution was added to mixture and the resulting mixture was extracted with ethyl acetate. The extract was washed with brine, dried over anhydrous sodium sulphate, and concentrated in vacuo. The resulting residue was purified on a silica gel column chromatography (ethyl acetate/n-hexane) to give methyl 2,4-dioxo-4-(2,2,5-trimethyl-1,3-dioxane5-yl)butanoate (1.0 g, yield: 88%) as colorless oil.

[Chemical Formula 83]

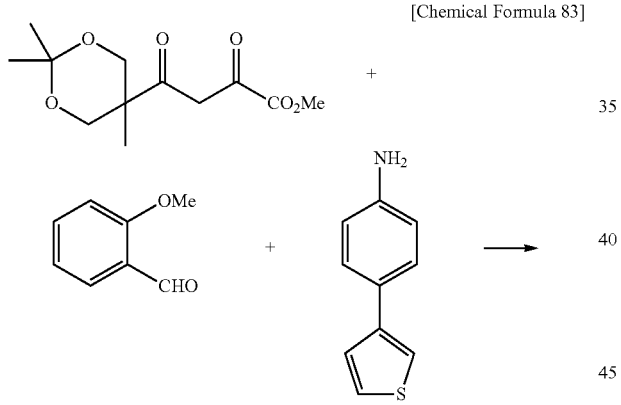

A mixture of methyl 2,4-dioxo-4-(2,2,5-trimethyl-1,3-dioxane5-yl)butanoate (0.26 mg, 1.0 mmol), 4-(3-thienyl)aniline (0.18 g, 1.0 mmol), 2-methooxybenzaldehyde (0.12 mL, 1.0 mmol), acetic acid (0.023 mL, 0.40 mmol) and dioxane (2 ml) was heated at reflux overnight. After the reaction was completed, the mixture was concentrated in vacuo. To the residue was added diisopropyl ether, and the resulting mixture was stirred under ice-cooling. The precipitated aimed compound was collected by filtration to give 3-hydroxy-4-(2,2,5-trimethyl-1,3-dioxane5-yl)carbonyl-5-(2-methoxyphenyl)-1-(4-thiophene-3-ylphenyl)-1,5-dihydropyrrole-2-one (0.29 g, yield: 56%) as pale yellow solid.

1H-NMR (δ ppm TMS/CDCl3): 0.99 (3H, s), 1.12 (3H, s), 1.40 (3H, s), 3.63-3.76 (2H, m), 3.89 (3H, brs), 4.20-4.37 (2H, m), 6.50-7.58 (12H, m), 9.00 (1H, brs).

[Chemical Formula 84]

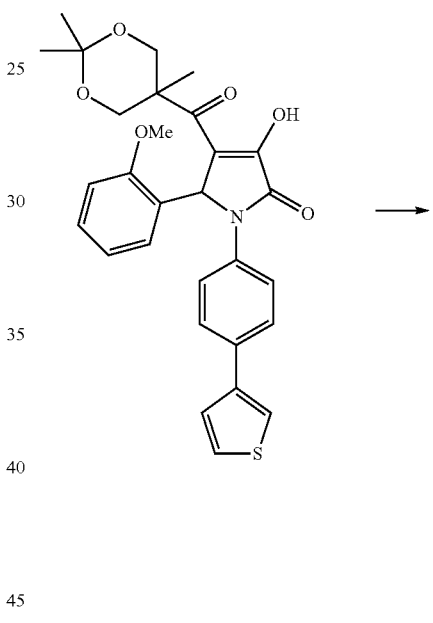

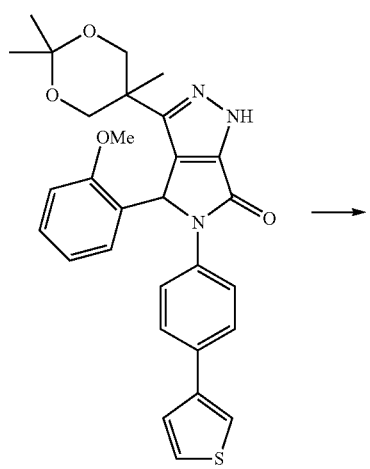

-continued

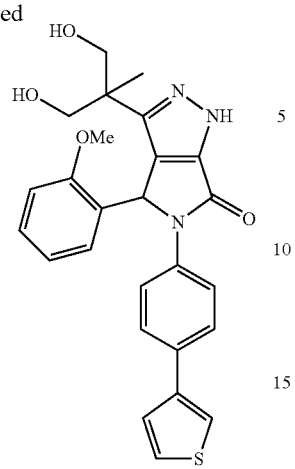

A mixture of 3-hydroxy-4-(2,2,5-trimethyl-1,3-dioxane5-yl)carbonyl-5-(2-methoxyphenyl)-1-(4-thiophene-3-ylphenyl)-1,5-dihydropyrrole-2-one (0.15 g, 0.3 mmol), hydrazine hydrate (0.07 mL, 1.4 mmol) and acetic acid (1 mL) was heated at reflux overnight. After the reaction mixture was concentrated in vacuo, to the resulting residue was added 2 mol/L hydrochloric acid/methanol solution (2.89 mL, 5.8 mmol) and the resulting mixture was heated at reflux for 6 hours. After the reaction mixture was concentrated in vacuo, saturated sodium bicarbonate solution was added to the residue and the mixture was extracted with chloroform. The extract was dried over anhydrous magnesium sulfate and concentrated in vacuo. The resulting residue was purified on a silica gel column chromatography (methanol/chloroform). The resulting compound was triturated with ethyl acetate and n-hexane to give 3-(1,1-dihydroxymethylethyl) 4-(2-methoxyphenyl)-5-(4-thiophene-3-ylphenyl)-4,5-dihydro-1H-pyrrolo[3,4-c]pyrazole-6-one (0.105 g, yield: 77%) as colorless solid.

1H-NMR (δ ppm TMS/DMSO-d6): 0.95 (3H, s), 3.91 (2H, m), 4.57 (2H, m), 6.29-7.78 (12H, m), 12.97 (1H, m).

Example 10

Preparation of 3-(1-hydroxy carbonyl-1-methylethyl)-5-(4-isoxazolyl-3-ylphenyl)-4-(2-methoxyphenyl)-4,5-dihydro-1H-pyrrolo[3,4-c]pyrazole-6-one

[Chemical Formula 85]

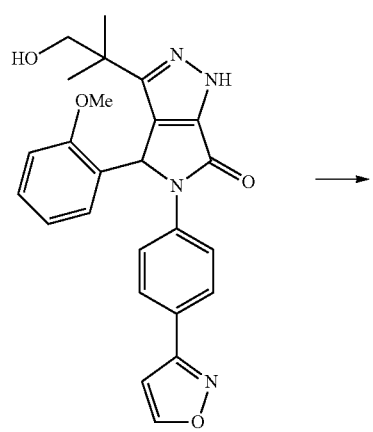 →

To a solution of periodic acid (0.32 mg, 1.4 mmol) in acetonitrile (15 mL), a solution of 3-(1-hydroxymethyl-1-methylethyl)-5-(4-isoxazolyl-3-ylphenyl)-4-(2-methoxyphenyl)-4,5-dihydro-1H-pyrrolo[3,4-c]pyrazole-6-one (0.206 g, 0.463 mmol) in dichloromethane (15 mL) and pyridiniumchlorochromate (0.01 g, 0.046 mmol) were added, and the resulting mixture was stirred at room temperature for 4 hours. After the reaction was completed, water was added to the reaction mixture, and the resulting mixture was extracted with ethyl acetate. The extract was washed with brine, and dried over anhydrous sodium sulphate, and then concentrated in vacuo. To the resulting residue was added dichloromethane, and the precipitated compound was collected by filtration to give 3-(1-hydroxy carbonyl-1-methylethyl)-5-(4-isoxazolyl-3-ylphenyl)-4-(2-methoxyphenyl)-4,5-dihydro-1H-pyrrolo[3,4-c]pyrazole-6-one (0.11 g, yield: 49%) as pale yellow solid.

1H-NMR (δ ppm TMS/DMSO-d6): 1.19 (3H, s), 1.30 (3H, s), 3.91 (3H, brs), 6.40-7.19 (6H, m), 7.66-7.80 (4H, m), 8.94 (1H, d, J=1.7), 12.50 (1H, brs), 13.55 (1H, brs).

Example 11

Preparation of 5-(4-isoxazolyl-3-ylphenyl)-4-(2-methoxyphenyl)-3-[1-(N-methylcarbamoyl)-1-methylethyl]-4,5-dihydro-1H-pyrrolo[3,4-c]pyrazole-6-one

[Chemical Formula 86]

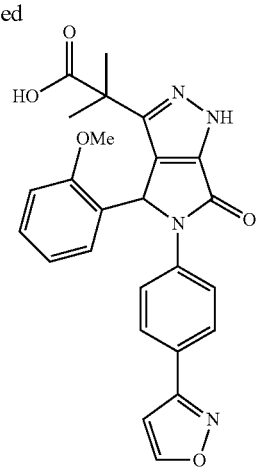

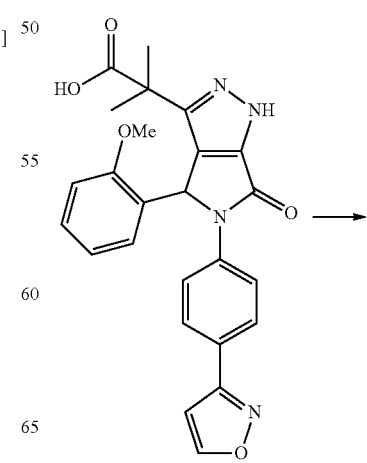 →

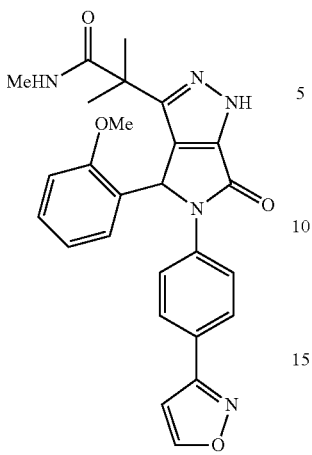

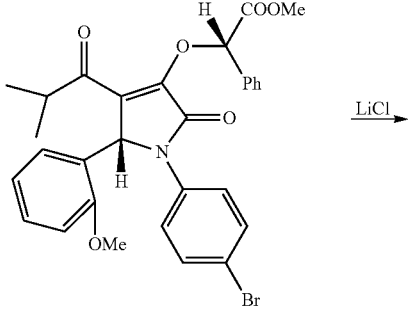

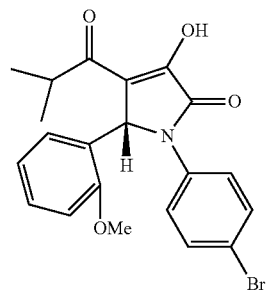

(-)-isomer

To a mixture of 3-(1-hydroxy carbonyl-1-methylethyl)-5-(4-isoxazolyl-3-ylphenyl)-4-(2-methoxyphenyl)-4,5-dihydro-1H-pyrrolo[3,4-c]pyrazole-6-one (0.05 g, 0.11 mmol) and DMF (2 mL) were added methylamine hydrochloride (0.013 g, 0.19 mmol), 1-hydroxybenzotriazole (0.039 g, 0.29 mmol), 4-dimethylaminopyridine (0.005 g, 0.04 mmol), 1-ethyl-3-(3-dimethylaminopropyl)carbodiimide hydrochloric acid (0.058 g, 0.3 mmol) and triethylamine (0.040 mL, 0.29 mmol), and the resulting mixture was stirred at room temperature for 2 hours. After the reaction was completed, water (2 mL) was added to the reaction mixture, and the resulting mixture was stirred under ice-cooling for a while. The precipitated compound was filtered off, and the residue was purified on a silica gel column chromatography (ethyl acetate/n-hexane) to give 5-(4-isoxazolyl-3-ylphenyl)-4-(2-methoxyphenyl)-3-[1-(N-methylcarbamoyl)-1-methylethyl]-4,5-dihydro-1H-pyrrolo[3,4-c]pyrazole-6-one (0.036 g, yield: 40%) as pale brown solid.

1H-NMR (δ ppm TMS/DMSO-d6) 1.12 (3H, s), 1.29 (3H, s), 2.43 (3H, brs), 3.91 (3H, brs), 6.63-7.20 (7H, m), 7.67-7.82 (4H, m), 8.95 (1H, d, J=1.7), 13.43 (1H, brs).

Example 12

Preparation of (−)-4-(2-methylpropionyl)-3-hydroxy-1-(4-bromophenyl)-5-(2-methoxyphenyl)-1,5-dihydropyrrole-2-one

[Chemical Formula 87]

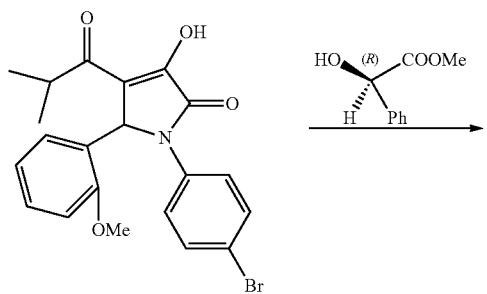

To a mixture of 4-(2-methylpropionyl)-3-hydroxy-1-(4-bromophenyl)-5-(2-methoxyphenyl)-1,5-dihydropyrrole-2-one (2.15 g, 5 mmol), (R)-methyl 2-hydroxy-2-phenylacetate (1.00 g, 6.0 mmol), triphenylphosphine (1.44 g, 5.5 mmol) and dioxane (15 mL) was added dimethoxyethyl azodicarboxylate (1.29 g, 5.5 mmol) at room temperature over 1 minute, and the resulting mixture was stirred at room temperature for 6 hours. To the reaction mixture was added water (200 mL) and the resulting mixture was extracted with ethyl acetate (200 mL). The extract was washed with brine (200 mL), dried over anhydrous magnesium sulfate, and concentrated in vacuo. The resulting residue was purified on a silica gel column chromatography (ethyl acetate/n-hexane). The resulting mixture of diastereomers was recrystallized (ethyl acetate/n-hexane) to give the diastereomer (0.80 g, yield: 28%) as pale yellow crystalline.

A mixture of the resulting diastereomer (0.59 g, 1 mmol), lithium chloride (0.127 g, 3 mmol) and 1,3-dimethyl-2-imidazolidinone (3 mL) was stirred at 80° C. for 6 hours. To the reaction mixture were added water (200 mL) and 1 mol/L hydrochloric acid (3 mL), and the resulting mixture was extracted with toluene (200 mL). The extract was washed with brine (200 mL), dried over anhydrous magnesium sulfate, and concentrated in vacuo. The resulting residue was purified on a silica gel column chromatography (ethyl acetate/n-hexane). The resulting compound was recrystallized (ethyl acetate/n-hexane) to give (−)-4-(2-methylpropionyl)-3-hydroxy-1-(4-bromophenyl)-5-(2-methoxyphenyl)-1,5-dihydropyrrole-2-one (0.40 g, yield: 93%) as pale yellow crystalline.

$[\alpha]_D$: −142.2±3.6° (in CHCl3),

1H-NMR (δ ppm TMS/DMSO-d6) 0.88 (3H, d, J=6.9), 0.91 (3H, d, J=6.9), 3.33 (1H, sept, J=6.9), 3.81 (3H, brs), 6.23 (1H, brs), 6.75-7.15 (4H, m), 7.45-7.53 (4H, m), 12.00 (1H, brs).

Example 13

Preparation of (−)-4-(2-methylpropionyl)-3-hydroxy-1-(4-thiophene-3-ylphenyl)-5-(2-methoxyphenyl)-1,5-dihydropyrrole-2-one

[Chemical Formula 88]

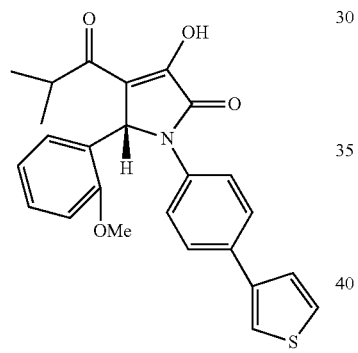

After a mixture of (−)-4-(2-methylpropionyl)-3-hydroxy-1-(4-bromophenyl)-5-(2-methoxyphenyl)-1,5-dihydropyrrole-2-one (0.10 g, 0.23 mmol), 3-thiophene-boronic acid (0.045 g, 0.35 mmol), tripotassium phosphate (0.148 g, 0.7 mmol), 1,2-dimethoxyethane (3 mL) and water (3 mL) was placed in a flask under nitrogen, 1,1′-Bis(diphenylphosphino) ferrocene-palladium(II)dichloride dichloromethane complex (0.019 g, 0.023 mmol) was added to the mixture, and the resulting mixture was stirred at reflux for 3 hours. To the reaction mixture was added water (50 mL), and the resulting mixture was extracted with dichloromethane (50 mL). The extract was washed with brine (50 mL), dried over anhydrous magnesium sulfate, and concentrated in vacuo. The resulting residue was purified on a silica gel column chromatography (methanol/chloroform). The resulting compound was triturated with ethyl acetate/n-hexane to give (−)-4-(2-methylpropionyl)-3-hydroxy-1-(4-thiophene-3-ylphenyl)-5-(2-methoxyphenyl)-1,5-dihydropyrrole-2-one (0.029 g, yield: 29%) as pale brown powder.

$[\alpha]_D$: −57.4±1.9° (in CHCl3),

1H-NMR (δ ppm TMS/DMSO-d6) 0.89 (3H, d, J=6.9), 0.92 (3H, d, J=6.9), 3.34 (1H, sept, J=6.9), 3.87 (3H, brs), 6.32 (1H, brs), 6.75-7.15 (5H, m), 7.51 (1H, d, J=1.1), 7.58-7.63 (4H, m), 7.81 (1H, m), 12.00 (1H, brs).

Example 14

Preparation of 3-i-propyl-5-(4-thiophene-3-ylphenyl)-4-(2-methoxyphenyl)-1,4,5,6-tetrahydro-1H-pyrrolo[3,4-c]pyrazole

[Chemical Formula 89]

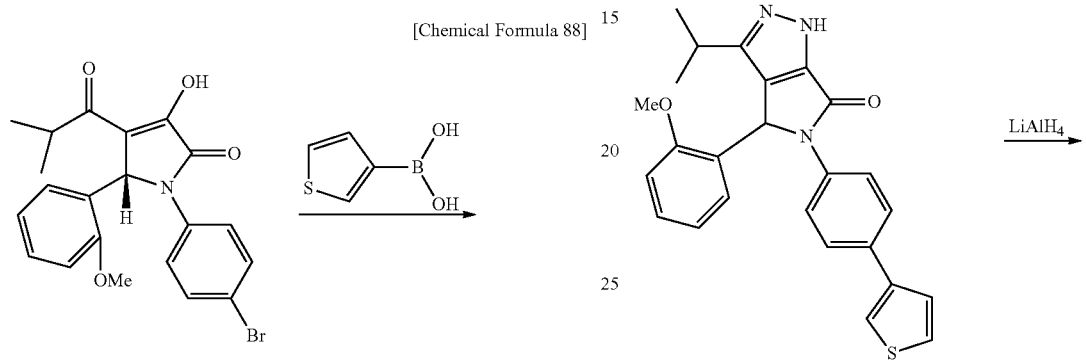

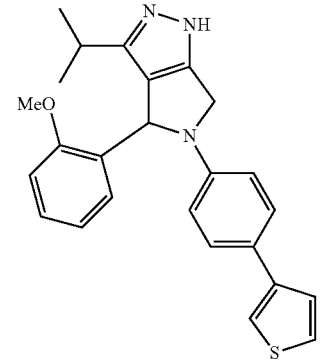

To a mixture of 3-i-propyl-5-(4-thiophene-3-ylphenyl)-4-(2-methoxyphenyl)-4,5-dihydro-1H-pyrrolo[3,4-c]pyrazole-6-one (0.72 g, 1.65 mmol) and dioxane (40 mL), lithium aluminum hydride (0.19 g, 5 mmol) was added and the resulting mixture was heated at reflux for 2 hours. The reaction mixture was added to a mixture of ice-water (100 mL) and 2 mol/L hydrochloric acid (10 mL), and the resulting mixture was extracted with chloroform (100 mL). The extract was washed with brine (100 mL), and dried over anhydrous sodium sulphate, and concentrated in vacuo. The resulting residue was purified on a silica gel column chromatography (methanol/chloroform). The resulting compound was triturated with ether to give 3-i-propyl-5-(4-thiophene-3-ylphenyl)-4-(2-methoxyphenyl)-1,4,5,6-tetrahydro-1H-pyrrolo[3,4-c]pyrazole (0.029 g, yield: 29%) as pale brown powder.

1H-NMR (δ ppm TMS/DMSO-d6) 0.86 (3H, d, J=7.0), 0.97 (3H, d, J=7.0), 2.78 (1H, sept, J=7.0), 3.94 (3H, s), 4.42

(1H, d, J=12.6), 4.77 (1H, d, J=12.6), 6.11 (1H, d, J=2.0), 6.55-7.53 (11H, m), 12.32 (1H, s).

Example 15

Preparation of (−)-4-(2-methylpropionyl)-3-hydroxy-1-(4-thiophene-3-ylphenyl)-5-(2-methoxyethoxyphenyl)-1,5-dihydropyrrole-2-one

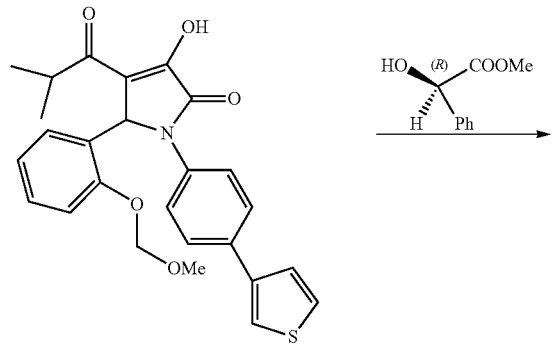

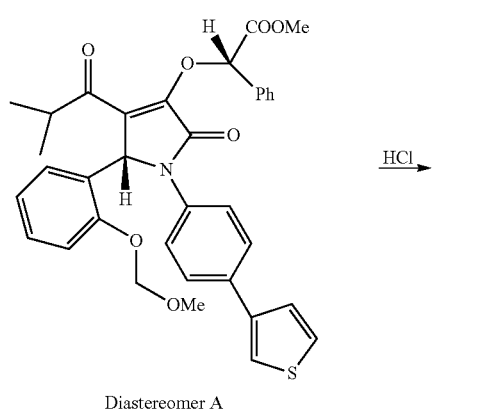

Diastereomer A

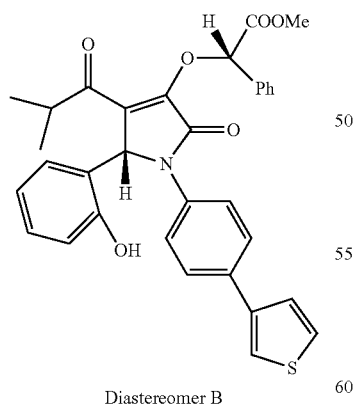

Diastereomer B

To a mixture of 4-(2-methylpropionyl)-3-hydroxy-1-(4-bromophenyl)-5-(2-methoxymethylphenyl)-1,5-dihydropyrrole-2-one (11.0 g, 23.7 mmol), (R)-methyl 2-hydroxy-2-phenylacetate (4.73 g, 28.5 mmol), triphenylphosphine (7.47 g, 28.5 mmol) and THF (150 mL) was added dimethoxyethyl azodicarboxylate (6.67 g, 28.5 mmol) at room temperature over 2 minutes, and the resulting mixture was stirred at room temperature overnight. To the reaction mixture was added water (200 mL), and the resulting mixture was extracted with toluene (200 mL). The extract was washed with brine (200 mL), dried over anhydrous magnesium sulfate, and concentrated in vacuo. The resulting residue was purified on a silica gel column chromatography (ethyl acetate/n-hexane). The resulting mixture of diastereomers was recrystallized by ethyl acetate/n-hexane to give diastereomer A (4.98 g, yield: 34%) as pale yellow crystalline.

1H-NMR (δ ppm TMS/CDCl3) 0.85 (3H, d, J=7.0), 1.15 (3H, d, J=7.0), 3.49 sept, J=7.0), 3.57 (3H, brs), 3.73 (3H, s), 5.25 (2H, brs), 6.40-6.80 (2H, m), 7.05-7.63 (16H, m).

To a solution of Diastereomer A (4.0 g, 6.5 mmol) in ethyl acetate (33 mL) was added 2 mol/l hydrochloric acid/methanol solution (32.7 mL), and the resulting mixture was stirred at 60° C. for 1 hour. To the reaction mixture was added water (200 mL), the resulting mixture was extracted with ethyl acetate (200 mL). The extract was washed with brine (200 mL), dried over anhydrous magnesium sulfate, and concentrated in vacuo. The resulting residue was purified on a silica gel column chromatography (ethyl acetate/n-hexane). The resulting mixture of diastereomers was triturated with ethyl acetate/n-hexane to give diastereomer B (2.93 g, yield: 79%) as yellow powder.

1H-NMR (δ ppm TMS/CDCl3) 0.90 (3H, d, J=6.9), 1.24 (3H, d, J=6.9), 3.52 (1H, sept, J=6.9), 3.75 (3H, s), 6.22 (1H, s), 6.68-6.75 (2H, m), 6.97-7.56 (15H, m), 7.95 (1H, s).

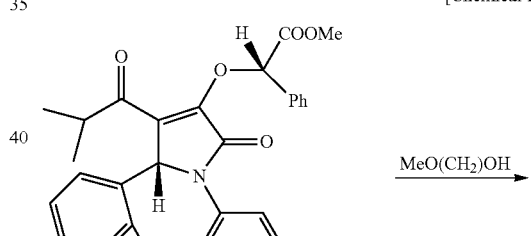

Diastereomer B

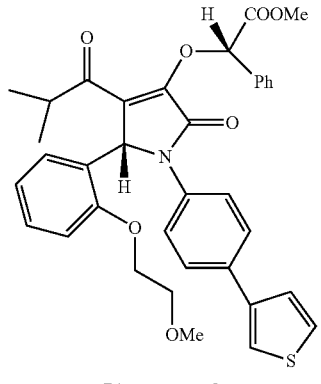

Diastereomer C

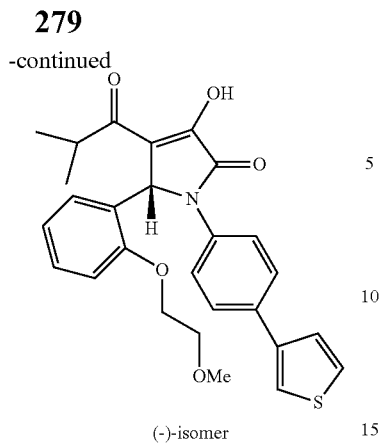

(-)-isomer

To a mixture of Diastereomer B (2.65 g, 4.7 mmol), 2-methoxyethanol (0.71 g, 9.3 mmol), triphenylphosphine (1.84 g, 7.0 mmol) and THF (50 mL) was added dimethoxyethyl azodicarboxylate (1.64 g, 7.0 mmol) at room temperature over 2 minutes, and the resulting mixture was stirred at room temperature overnight. To the reaction mixture was added water (200 mL), and the resulting mixture was extracted with toluene (200 mL). The extract was washed with brine (200 mL), dried over anhydrous magnesium sulfate, and concentrated in vacuo. The resulting residue was purified on a silica gel column chromatography (ethyl acetate/n-hexane) to give diastereomer C (2.44 g, yield: 84%) as yellow amorphous.

A mixture of the obtained diastereomer C (2.25 g, 3.6 mmol), lithium chloride (0.46 g, 10.8 mmol) and 1,3-dimethyl-2-imidazolidinone (45 mL) was stirred at 100° C. for 16 hours. To the reaction mixture were added water (200 mL) and 2 mol/L hydrochloric acid (15 mL), and the resulting mixture was extracted with toluene (200 mL). The extract was washed with brine (200 mL), dried over anhydrous magnesium sulfate, and concentrated in vacuo. The resulting residue was purified on a silica gel column chromatography (methanol/chloroform). The resulting compound was triturated with ethyl acetate/n-hexane to give (-)-4-(2-methylpropionyl)-3-hydroxy-1-(4-thiophene-3-ylphenyl)-5-(2-methoxyethoxyphenyl)-1,5-dihydropyrrole-2-one (1.01 g, yield: 59%) as pale yellow powder.

$[\alpha]_D$: -39.3±1.6° (in CHCl3),

1H-NMR (δ ppm TMS/DMSO-d6) 0.89 (3H, d, J=7.0), 0.93 (3H, d, J=7.0), 3.44 (3H, s), 3.57 (2H, brs), 3.83 (3H, s), 4.15 (1H, m), 4.29 (1H, m), 6.01 (1H, s), 6.38 (1H, s), 6.63-7.13 (4H, m), 7.40-7.76 (7H, m), 7.78 (1H, m), 12.5 (1H, brs)

Example 16

Preparation of 4-(i-propylsulfonyl)-3-hydroxy-1-(4-thiophene-3-ylphenyl)-5-(2-methoxyphenyl)-1,5-dihydropyrrole-2-one

[Chemical Formula 92]

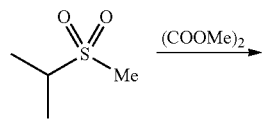

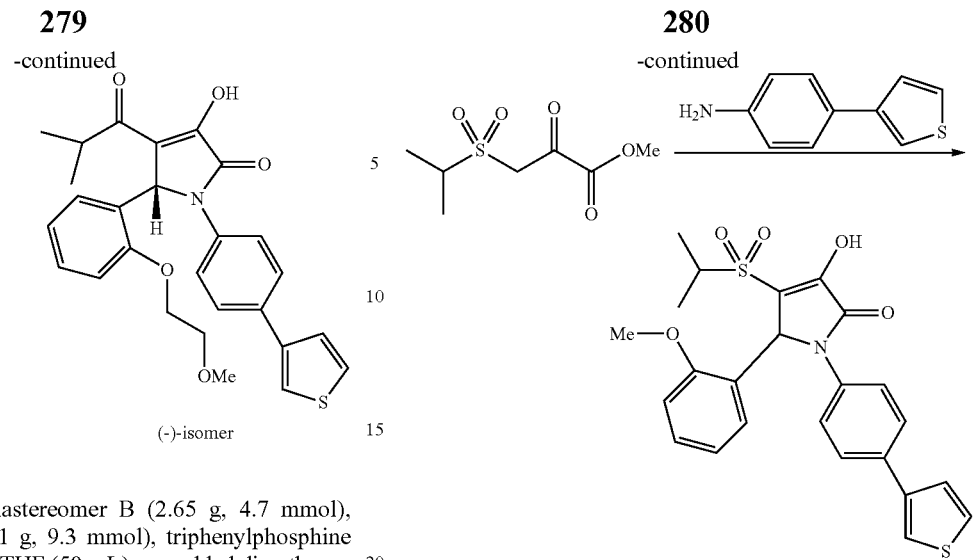

To a mixture of i-propylmethylsulfone (5.17 g, 42.3 mmol) and THF (20 mL) was added 28% sodium methoxide methanol solution (8.58 g, 44.5 mmol) at room temperature, and then methyl oxalate (5.0 g, 42.3 mmol) was gradually added to the mixture at room temperature. The resulting mixture was stirred at room temperature overnight. To the reaction mixture was added ice-water (200 mL), and the pH of the resulting mixture was adjusted pH3 or less than pH3 with 2 mol/L hydrochloric acid. The mixture was extracted with ethyl acetate (200 mL). The extract was washed with brine (200 mL), dried over anhydrous sodium sulphate, and concentrated in vacuo. The resulting residue was purified on a silica gel column chromatography (ethyl acetate/n-hexane) to give methyl 3-(i-propylsulfonyl)-2-oxopropanoate (2.7 g, yield: 28%) as colorless oil.

1H-NMR (δ ppm TMS/DMSO-d6) 1.26 (6H, d, J=6.7), 3.46 (1H, sept, J=6.7), 3.81 (3H, s), 4.74 (2H, s).

A mixture of methyl 3-(i-propylsulfonyl)-2-oxopropanoate (0.23 g, 1 mmol), 4-thiophene-3-ylaniline (0.18 g, 1 mmol), 2-methoxybenzaldehyde (0.14, 1 mmol), acetic acid (0.023 mL, 0.4 mmol) and toluene (3 mL) was heated at reflux overnight. After the reaction was completed, the reaction mixture was allowed to cool to room temperature. To the mixture was added ether and precipitated compound was collected by filtration. The resulting aimed compound was washed with ether/n-hexane solution to give 4-(i-propylsulfonyl)-3-hydroxy-1-(4-thiophene-3-ylphenyl)-5-(2-methoxyphenyl)-1,5-dihydropyrrole-2-one (0.37 g, yield: 79%) as pale brown solid.

1H-NMR (δ ppm TMS/DMSO-d6): 0.97-1.15 (6H, m), 3.62 (3.87) (3H, s), 6.13 (6.50) (1H, s), 6.82-7.27 (3H, m), 7.48-7.81 (8H, m), 12.20 (1H, brs).

The following compounds were synthesized in a manner similar to those described in the above synthetic scheme, general, general procedures for the synthesis of the compound of the invention, and Examples. The chemical structure of the compounds and the physical properties of them are described below.

(Method of Identification for the Compound)

LC/MS data of compound of the present invention were measured under any one of the following 2 conditions (Method 1 to 3), and a retention time and [M+H]+ are shown.
(Method 1)
Column: Xbridge C18(5 μm, i.d. 4.6×50 mm) (Waters)
Flow rate: 3 mL/min
UV detection wavelength: 254 nm Mobile phase: [A] is 0.1% formic acid-containing aqueous solution, and [B] is 0.1% formic acid-containing acetonitrile solution Gradient: Linear gradient of 10% to 100% solvent[B] for 3 minutes was performed, and 100% solvent [B] was maintained for 1 minute.

(Method 2)

Column: Shim-pack XR-ODS (2.2 μm, i.d. 50×3.0 mm) (Shimadzu)

Flow rate: 1.6 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent[B] for 3 minutes was performed, and 100% solvent [B] was maintained for 1 minute.

(Method 3)

Column: Gemini-NX (5 μm, i.d. 4.6×50 mm) (Phenomenex)

Flow rate: 3 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent[B] for 3.5 minutes was performed, and 100% solvent [B] was maintained for 0.5 minute.

TABLE 10

| Chemical Structure | Compound No. | MS [M + H]$^+$ | LC method | LC/MS retention time (min) |
|---|---|---|---|---|
| 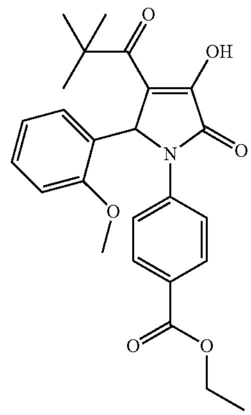 [SMILES: CCOC(=O)c1ccc(N2C(=O)C(O)=C(C(=O)C(C)(C)C)C2c2ccccc2OC)cc1] | I-001 | 438 | 2 | 2.49 |
| 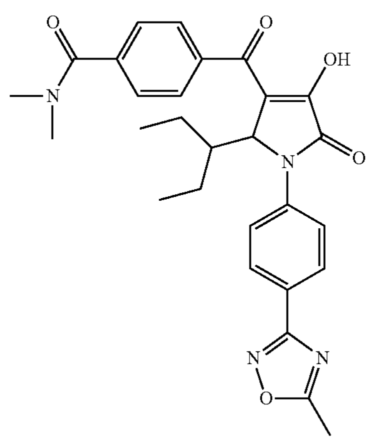 [SMILES: CCC(CC)C1C(C(=O)c2ccc(C(=O)N(C)C)cc2)=C(O)C(=O)N1c1ccc(-c2noc(C)n2)cc1] | I-002 | 503 | 2 | 2.30 |

TABLE 10-continued

| Chemical Structure | Compound No. | MS [M + H]+ | LC method | LC/MS retention time (min) |
|---|---|---|---|---|
| 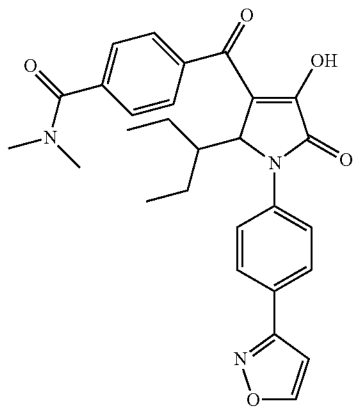 [SMILES: CCC(CC)C1C(C(=O)c2ccc(C(=O)N(C)C)cc2)=C(O)C(=O)N1c1ccc(-c2ccon2)cc1] | I-003 | 488 | 2 | 2.17 |
| 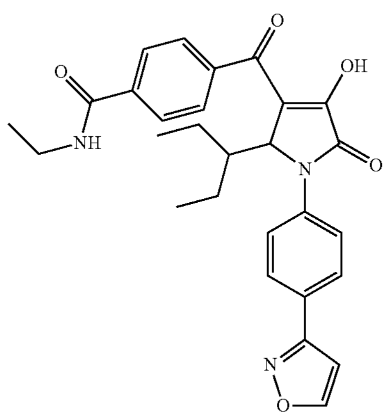 [SMILES: CCNC(=O)c1ccc(C(=O)C2=C(O)C(=O)N(c3ccc(-c4ccon4)cc3)C2C(CC)CC)cc1] | I-004 | 488 | 2 | 2.20 |
| 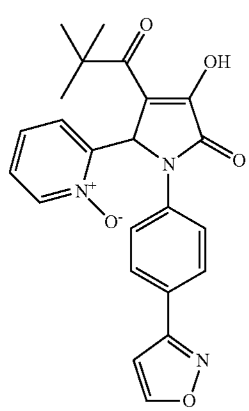 [SMILES: CC(C)(C)C(=O)C1=C(O)C(=O)N(c2ccc(-c3ccon3)cc2)C1c1cccc[n+]1[O-]] | I-005 | 420 | 2 | 1.60 |

TABLE 11

| Chemical Structure | Compound No. | MS [M + H]+ | LC method | LC/MS retention time (min) |
|---|---|---|---|---|
| 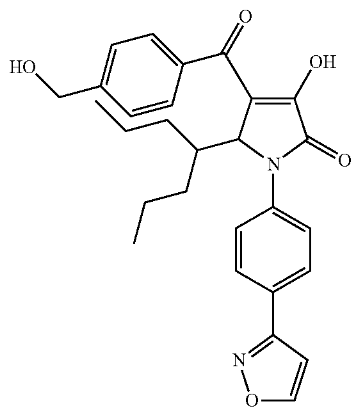 [SMILES: CCCC(CCC)C1C(C(=O)c2ccc(CO)cc2)=C(O)C(=O)N1c1ccc(-c2ccon2)cc1] | I-006 | 475 | 2 | 2.36 |
| 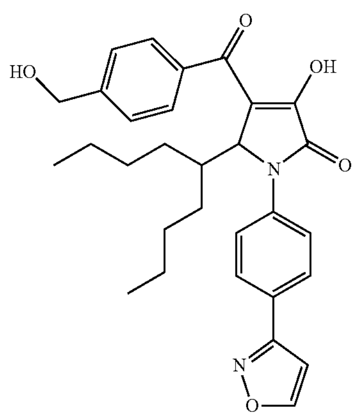 [SMILES: CCCCC(CCCC)C1C(C(=O)c2ccc(CO)cc2)=C(O)C(=O)N1c1ccc(-c2ccon2)cc1] | I-007 | 503 | 2 | 2.61 |
| 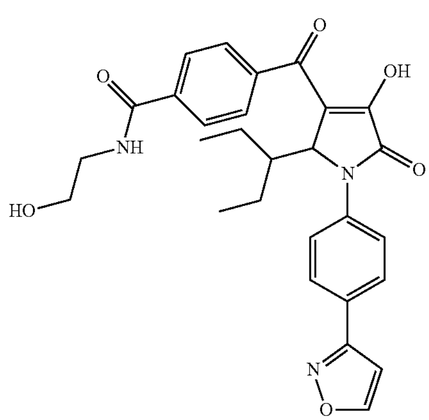 [SMILES: CCC(CC)C1C(C(=O)c2ccc(C(=O)NCCO)cc2)=C(O)C(=O)N1c1ccc(-c2ccon2)cc1] | I-008 | 504 | 2 | 1.90 |

TABLE 11-continued
| Chemical Structure | Compound No. | MS [M + H]+ | LC method | LC/MS retention time (min) |
|---|---|---|---|---|
| 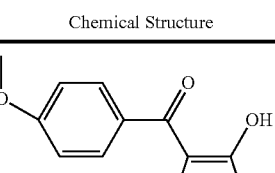 | I-009 | 479 | 2 | 2.80 |
| 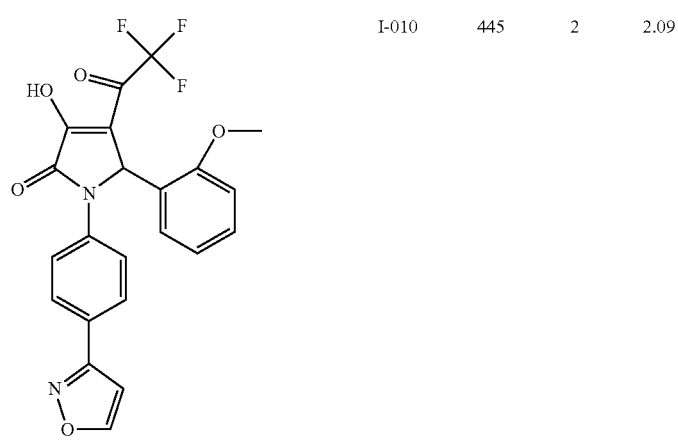 | I-010 | 445 | 2 | 2.09 |
TABLE 12
| Chemical Structure | Compound No. | MS [M + H]+ | LC method | LC/MS retention time (min) |
|---|---|---|---|---|
| 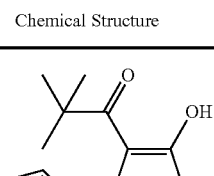 | I-011 | 451 | 2 | 2.34 |

TABLE 12-continued
| Chemical Structure | Compound No. | MS [M + H]+ | LC method | LC/MS retention time (min) |
|---|---|---|---|---|
| 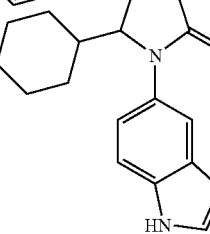 | I-012 | 431 | 2 | 2.26 |
| 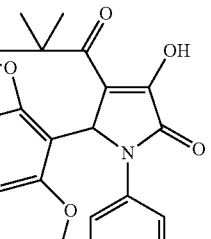 | I-013 | 463 | 2 | 2.26 |
| 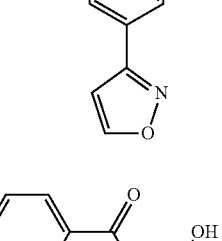 | I-014 | 471 | 2 | 2.70 |
| 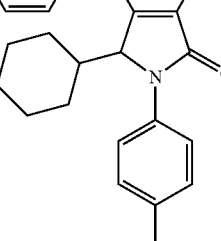 | I-015 | 458 | 2 | 2.80 |

TABLE 13
| Chemical Structure | Compound No. | MS [M + H]⁺ | LC method | LC/MS retention time (min) |
| --- | --- | --- | --- | --- |
| 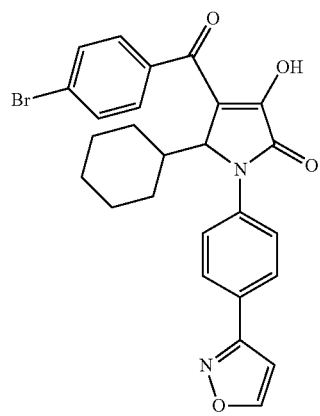 [SMILES: O=C(C1=C(O)C(=O)N(c2ccc(-c3ccon3)cc2)C1C1CCCCC1)c1ccc(Br)cc1] | I-016 | 507 | 2 | 2.77 |
| 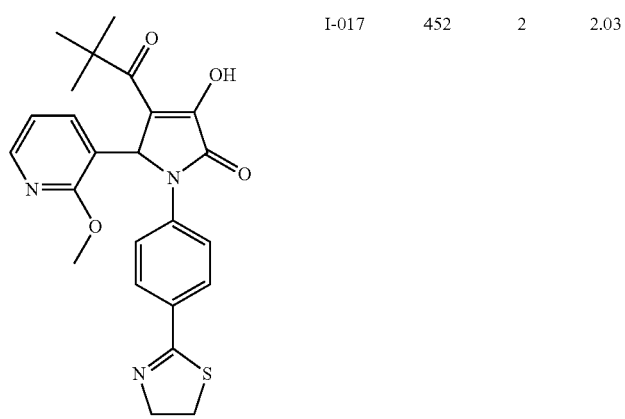 | I-017 | 452 | 2 | 2.03 |
| 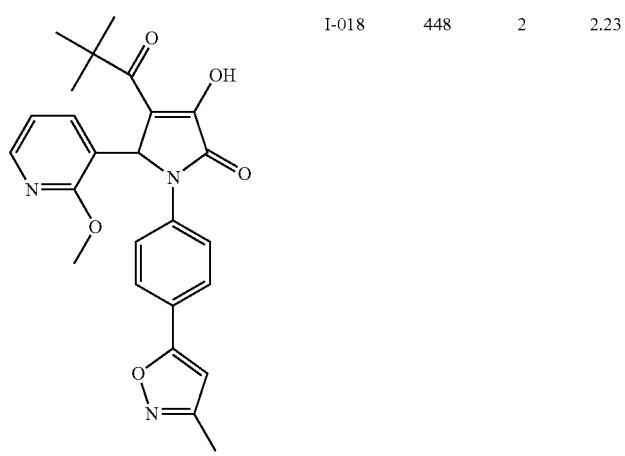 | I-018 | 448 | 2 | 2.23 |

TABLE 13-continued

| Chemical Structure | Compound No. | MS [M + H]⁺ | LC method | LC/MS retention time (min) |
|---|---|---|---|---|
| 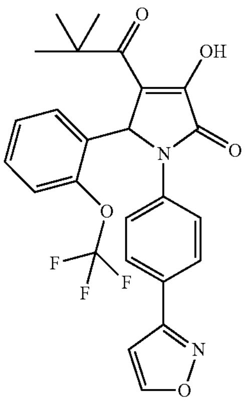 [SMILES: CC(C)(C)C(=O)C1=C(O)C(=O)N(c2ccc(-c3ccon3)cc2)C1c1ccccc1OC(F)(F)F] | I-019 | 487 | 2 | 2.47 |
| 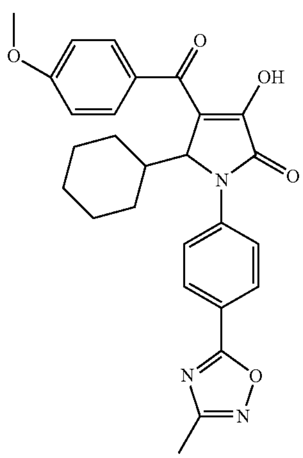 [SMILES: COc1ccc(C(=O)C2=C(O)C(=O)N(c3ccc(-c4nc(C)no4)cc3)C2C2CCCCC2)cc1] | I-020 | 474 | 2 | 2.55 |

TABLE 14

| Chemical Structure | Compound No. | MS [M + H]⁺ | LC method | LC/MS retention time (min) |
|---|---|---|---|---|
| 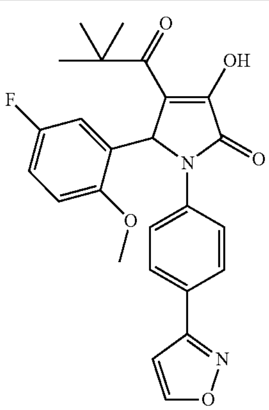 [SMILES: COc1ccc(F)cc1C1C(C(=O)C(C)(C)C)=C(O)C(=O)N1c1ccc(-c2ccon2)cc1] | I-021 | 451 | 2 | 2.31 |

TABLE 14-continued
| Chemical Structure | Compound No. | MS [M + H]+ | LC method | LC/MS retention time (min) |
|---|---|---|---|---|
| 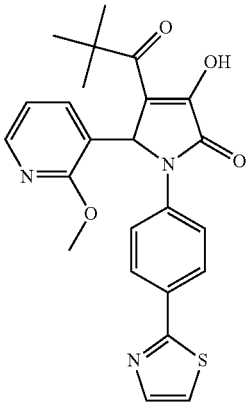 [SMILES: COc1ncccc1C1C(C(=O)C(C)(C)C)=C(O)C(=O)N1c1ccc(-c2nccs2)cc1] | I-022 | 450 | 2 | 2.22 |
| 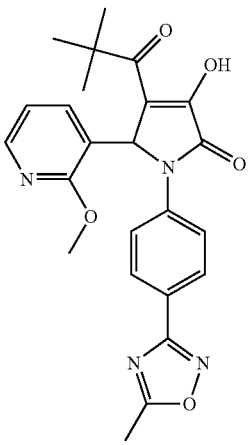 [SMILES: COc1ncccc1C1C(C(=O)C(C)(C)C)=C(O)C(=O)N1c1ccc(-c2noc(C)n2)cc1] | I-023 | 449 | 2 | 2.19 |
| 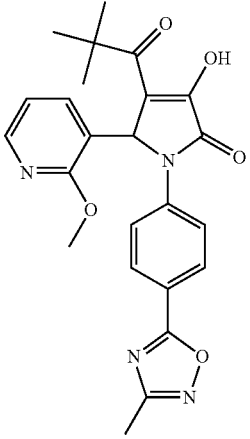 [SMILES: COc1ncccc1C1C(C(=O)C(C)(C)C)=C(O)C(=O)N1c1ccc(-c2nc(C)no2)cc1] | I-024 | 449 | 2 | 2.23 |

TABLE 14-continued

| Chemical Structure | Compound No. | MS [M + H]+ | LC method | LC/MS retention time (min) |
|---|---|---|---|---|
| 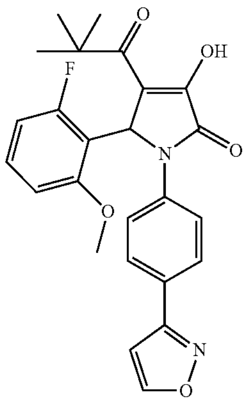 [SMILES: COc1cccc(F)c1C1C(C(=O)C(C)(C)C)=C(O)C(=O)N1c1ccc(-c2ccon2)cc1] | I-025 | 451 | 2 | 2.25 |

TABLE 15

| Chemical Structure | Compound No. | MS [M + H]+ | LC method | LC/MS retention time (min) |
|---|---|---|---|---|
| 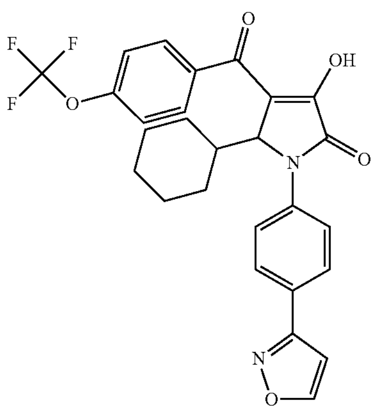 [SMILES: O=C(C1=C(O)C(=O)N(c2ccc(-c3ccon3)cc2)C1C1CCCCC1)c1ccc(OC(F)(F)F)cc1] | I-026 | 513 | 2 | 2.73 |
| 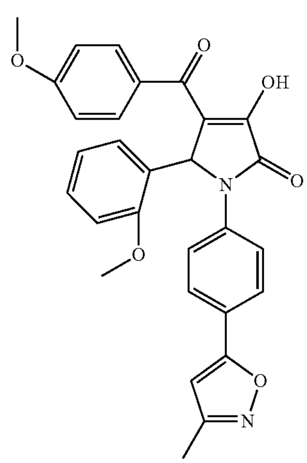 | I-027 | 497 | 2 | 2.10 |

TABLE 15-continued
| Chemical Structure | Compound No. | MS [M + H]+ | LC method | LC/MS retention time (min) |
|---|---|---|---|---|
| 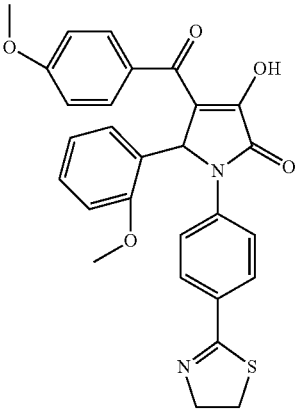 [SMILES: COc1ccc(C(=O)C2=C(O)C(=O)N(c3ccc(C4=NCCS4)cc3)C2c2ccccc2OC)cc1] | I-028 | 501 | 2 | 2.00 |
| 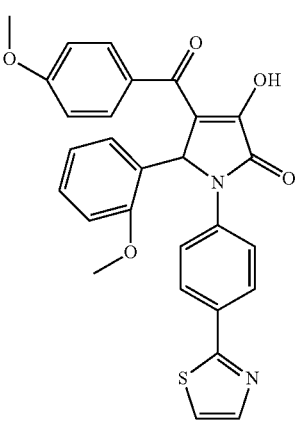 [SMILES: COc1ccc(C(=O)C2=C(O)C(=O)N(c3ccc(-c4nccs4)cc3)C2c2ccccc2OC)cc1] | I-029 | 499 | 2 | 2.20 |
| 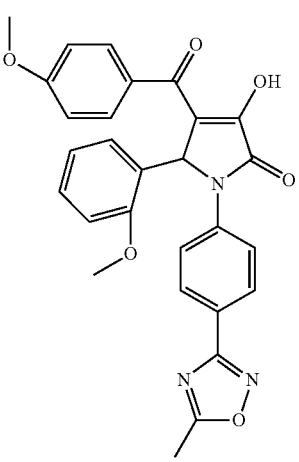 [SMILES: COc1ccc(C(=O)C2=C(O)C(=O)N(c3ccc(-c4noc(C)n4)cc3)C2c2ccccc2OC)cc1] | I-030 | 498 | 2 | 2.10 |

TABLE 16
| Chemical Structure | Compound No. | MS [M + H]+ | LC method | LC/MS retention time (min) |
|---|---|---|---|---|
| 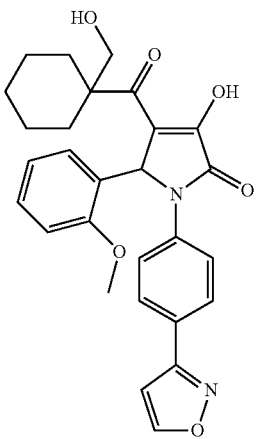 [SMILES: COc1ccccc1C1C(C(=O)C2(CO)CCCCC2)=C(O)C(=O)N1c1ccc(-c2ccon2)cc1] | I-031 | 489 | 2 | 2.08 |
| 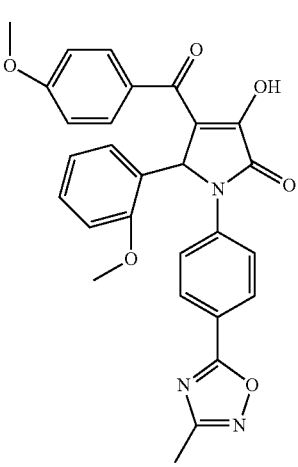 [SMILES: COc1ccc(C(=O)C2=C(O)C(=O)N(c3ccc(-c4nc(C)no4)cc3)C2c2ccccc2OC)cc1] | I-032 | 498 | 2 | 2.10 |
| 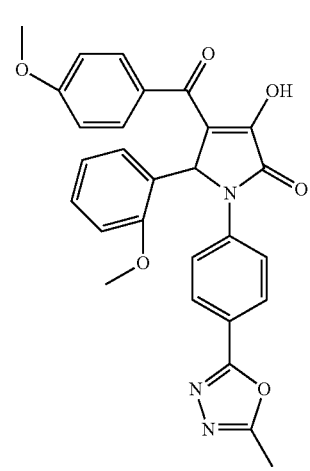 [SMILES: COc1ccc(C(=O)C2=C(O)C(=O)N(c3ccc(-c4nnc(C)o4)cc3)C2c2ccccc2OC)cc1] | I-033 | 498 | 2 | 1.90 |

TABLE 16-continued

| Chemical Structure | Compound No. | MS [M + H]⁺ | LC method | LC/MS retention time (min) |
|---|---|---|---|---|
| 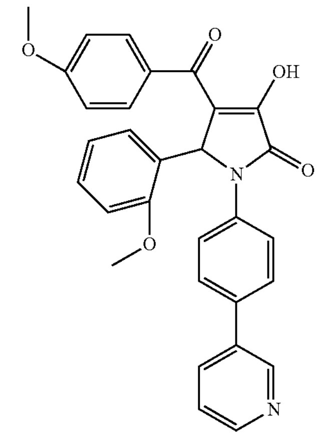 [SMILES: COc1ccc(C(=O)C2=C(O)C(=O)N(c3ccc(-c4cccnc4)cc3)C2c2ccccc2OC)cc1] | I-034 | 493 | 2 | 1.60 |
| 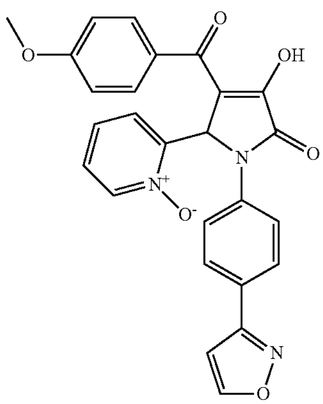 [SMILES: COc1ccc(C(=O)C2=C(O)C(=O)N(c3ccc(-c4ccon4)cc3)C2c2cccc[n+]2[O-])cc1] | I-035 | 470 | 2 | 1.52 |

TABLE 17

| Chemical Structure | Compound No. | MS [M + H]⁺ | LC method | LC/MS retention time (min) |
|---|---|---|---|---|
| 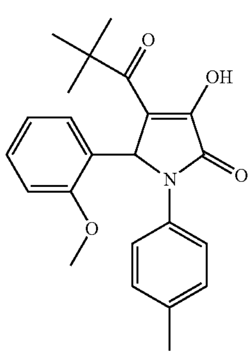 [SMILES: COc1ccccc1C1C(C(=O)C(C)(C)C)=C(O)C(=O)N1c1ccc(C)cc1] | I-036 | 380 | 2 | 2.46 |

TABLE 17-continued

| Chemical Structure | Compound No. | MS [M + H]+ | LC method | LC/MS retention time (min) |
|---|---|---|---|---|
| 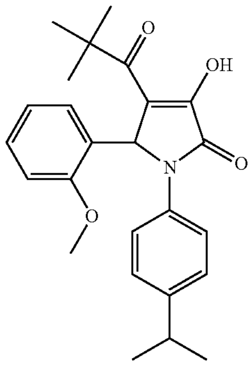 [SMILES: COc1ccccc1C1C(C(=O)C(C)(C)C)=C(O)C(=O)N1c1ccc(C(C)C)cc1] | I-037 | 408 | 2 | 2.69 |
| 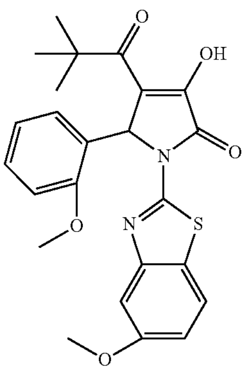 [SMILES: COc1ccc2sc(N3C(=O)C(O)=C(C(=O)C(C)(C)C)C3c3ccccc3OC)nc2c1] | I-038 | 453 | 2 | 2.50 |
| 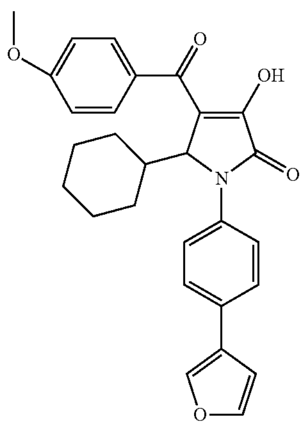 [SMILES: COc1ccc(C(=O)C2=C(O)C(=O)N(c3ccc(-c4ccoc4)cc3)C2C2CCCCC2)cc1] | I-039 | 458 | 2 | 2.60 |
| 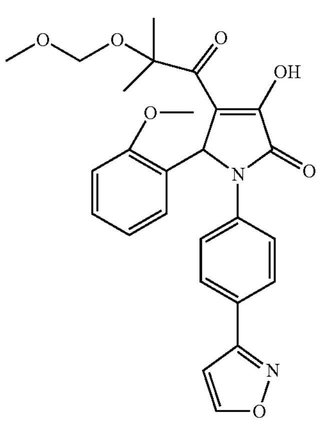 [SMILES: COCOC(C)(C)C(=O)C1=C(O)C(=O)N(c2ccc(-c3ccon3)cc2)C1c1ccccc1OC] | I-040 | 478 | 2 | 2.11 |

TABLE 18
| Chemical Structure | Compound No. | MS {M + H}+ | LC method | LC/MS retention time (min) |
|---|---|---|---|---|
| 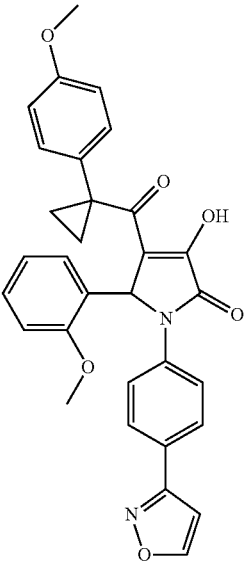 [SMILES: COc1ccc(C2(C(=O)C3=C(O)C(=O)N(c4ccc(-c5ccon5)cc4)C3c3ccccc3OC)CC2)cc1] | I-041 | 523 | 2 | 2.41 |
| 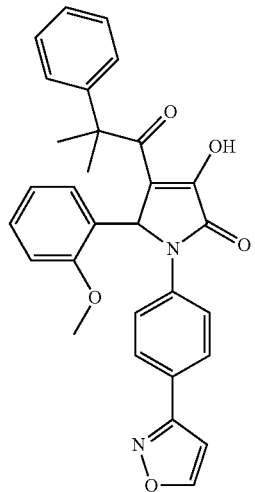 [SMILES: COc1ccccc1C1C(C(=O)C(C)(C)c2ccccc2)=C(O)C(=O)N1c1ccc(-c2ccon2)cc1] | I-042 | 495 | 2 | 2.52 |
| 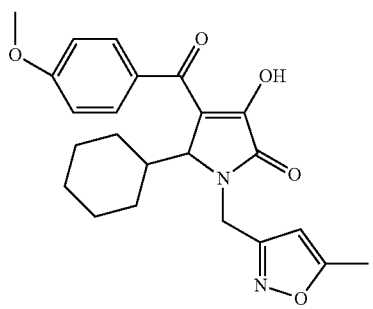 [SMILES: COc1ccc(C(=O)C2=C(O)C(=O)N(Cc3cc(C)on3)C2C2CCCCC2)cc1] | I-043 | 411 | 2 | 2.28 |

TABLE 18-continued

| Chemical Structure | Compound No. | MS {M + H}+ | LC method | LC/MS retention time (min) |
|---|---|---|---|---|
| 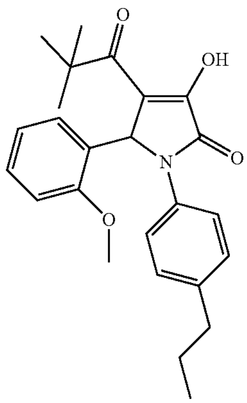 [SMILES: CCCc1ccc(N2C(=O)C(O)=C(C(=O)C(C)(C)C)C2c2ccccc2OC)cc1] | I-044 | 408 | 1 | 2.50 |
| 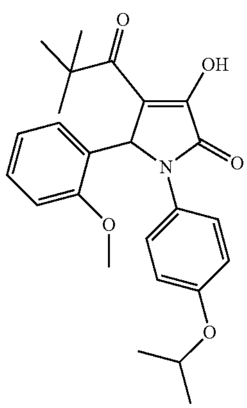 [SMILES: COc1ccccc1C1C(C(=O)C(C)(C)C)=C(O)C(=O)N1c1ccc(OC(C)C)cc1] | I-045 | 424 | 1 | 2.30 |

TABLE 19

| Chemical Structure | Compound No. | MS [M + H]+ | LC method | LC/MS retention time (min) |
|---|---|---|---|---|
| 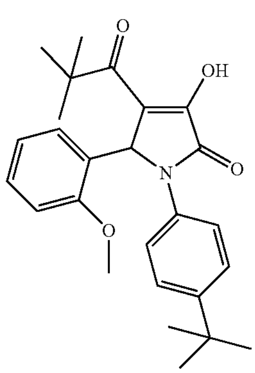 [SMILES: COc1ccccc1C1C(C(=O)C(C)(C)C)=C(O)C(=O)N1c1ccc(C(C)(C)C)cc1] | I-046 | 422 | 1 | 2.50 |

TABLE 19-continued
| Chemical Structure | Compound No. | MS [M + H]+ | LC method | LC/MS retention time (min) |
|---|---|---|---|---|
| 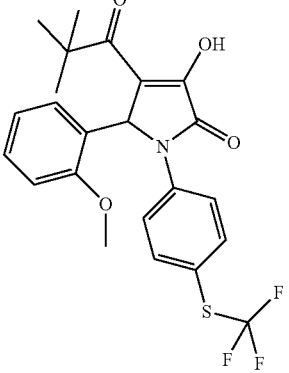 | I-047 | 466 | 1 | 2.50 |
| 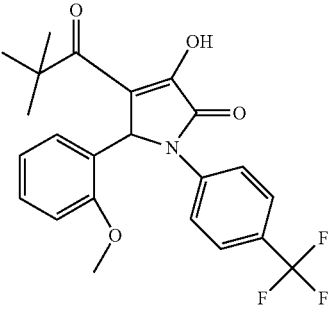 [SMILES: COc1ccccc1C1C(C(=O)C(C)(C)C)=C(O)C(=O)N1c1ccc(C(F)(F)F)cc1] | I-048 | 433 | 1 | 2.40 |
| 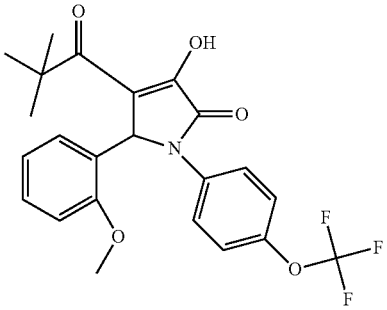 [SMILES: COc1ccccc1C1C(C(=O)C(C)(C)C)=C(O)C(=O)N1c1ccc(OC(F)(F)F)cc1] | I-049 | 449 | 1 | 2.40 |
| 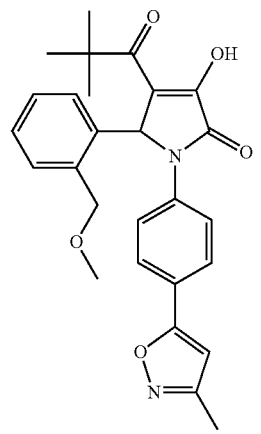 [SMILES: COCc1ccccc1C1C(C(=O)C(C)(C)C)=C(O)C(=O)N1c1ccc(-c2cc(C)no2)cc1] | I-050 | 461 | 2 | 2.53 |

TABLE 20

| Chemical Structure | Compound No. | MS [M + H]+ | LC method | LC/MS retention time (min) |
| --- | --- | --- | --- | --- |
| 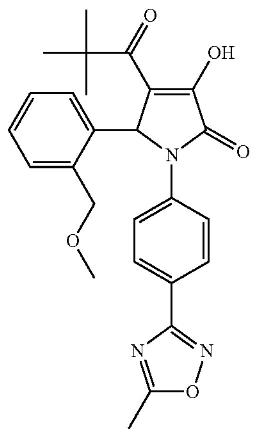 [SMILES: COCc1ccccc1C1C(C(=O)C(C)(C)C)=C(O)C(=O)N1c1ccc(-c2noc(C)n2)cc1] | I-051 | 462 | 2 | 2.49 |
| 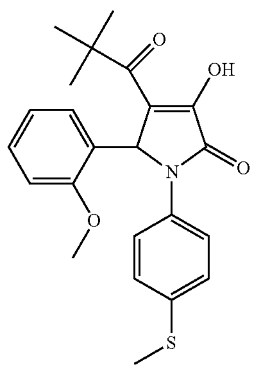 [SMILES: COc1ccccc1C1C(C(=O)C(C)(C)C)=C(O)C(=O)N1c1ccc(SC)cc1] | I-052 | 412 | 1 | 2.26 |
| 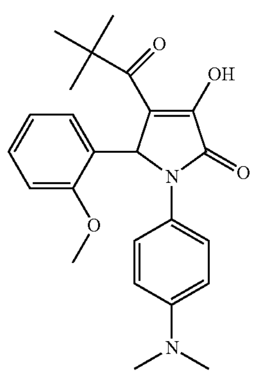 [SMILES: COc1ccccc1C1C(C(=O)C(C)(C)C)=C(O)C(=O)N1c1ccc(N(C)C)cc1] | I-053 | 409 | 2 | 2.23 |
| 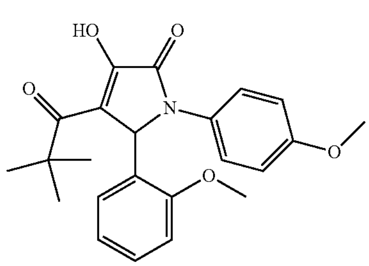 [SMILES: COc1ccc(N2C(=O)C(O)=C(C(=O)C(C)(C)C)C2c2ccccc2OC)cc1] | I-054 | 396 | 1 | 2.10 |

TABLE 20-continued

| Chemical Structure | Compound No. | MS [M + H]⁺ | LC method | LC/MS retention time (min) |
|---|---|---|---|---|
| 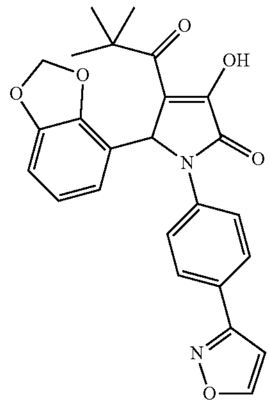 [SMILES: CC(C)(C)C(=O)C1=C(O)C(=O)N(c2ccc(-c3ccon3)cc2)C1c1cccc2c1OCO2] | I-055 | 447 | 1 | 2.00 |

TABLE 21

| Chemical Structure | Compound No. | MS [M + H]⁺ | LC method | LC/MS retention time (min) |
|---|---|---|---|---|
| 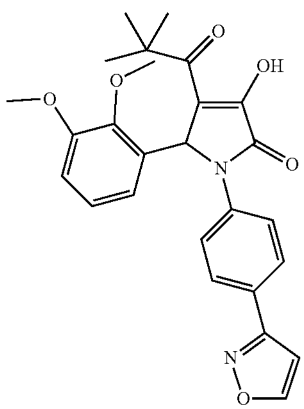 [SMILES: COc1cccc(C2C(C(=O)C(C)(C)C)=C(O)C(=O)N2c2ccc(-c3ccon3)cc2)c1OC] | I-056 | 463 | 1 | 2.10 |
| 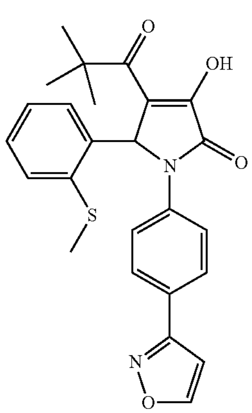 [SMILES: CSc1ccccc1C1C(C(=O)C(C)(C)C)=C(O)C(=O)N1c1ccc(-c2ccon2)cc1] | I-057 | 449 | 1 | 2.20 |

TABLE 21-continued
| Chemical Structure | Compound No. | MS [M + H]+ | LC method | LC/MS retention time (min) |
|---|---|---|---|---|
| 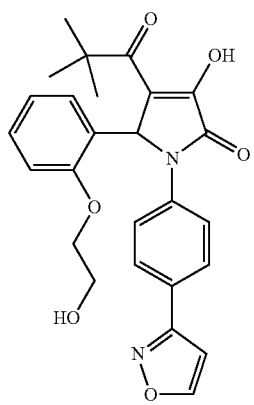 [SMILES: CC(C)(C)C(=O)C1=C(O)C(=O)N(c2ccc(-c3ccon3)cc2)C1c1ccccc1OCCO] | I-058 | 463 | 1 | 1.80 |
| 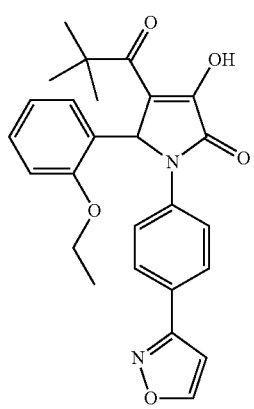 [SMILES: CCOc1ccccc1C1C(C(=O)C(C)(C)C)=C(O)C(=O)N1c1ccc(-c2ccon2)cc1] | I-059 | 447 | 1 | 2.20 |
| 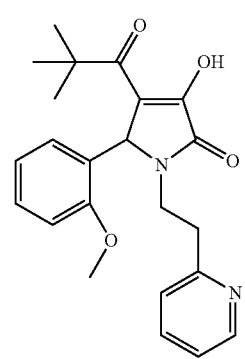 [SMILES: COc1ccccc1C1C(C(=O)C(C)(C)C)=C(O)C(=O)N1CCc1ccccn1] | I-060 | 395 | 2 | 1.51 |

TABLE 22

| Chemical Structure | Compound No. | MS [M + H]+ | LC method | LC/MS retention time (min) |
|---|---|---|---|---|
| 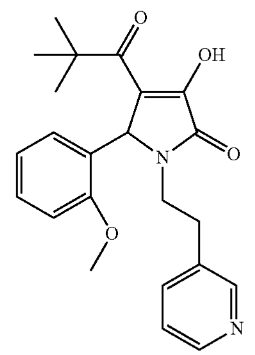 [SMILES: COc1ccccc1C1C(C(=O)C(C)(C)C)=C(O)C(=O)N1CCc1cccnc1] | I-061 | 395 | 2 | 1.43 |
| 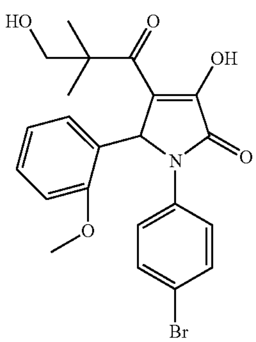 [SMILES: COc1ccccc1C1C(C(=O)C(C)(C)CO)=C(O)C(=O)N1c1ccc(Br)cc1] | I-062 | 461 | 1 | 1.90 |
| 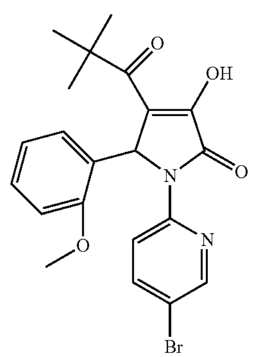 [SMILES: COc1ccccc1C1C(C(=O)C(C)(C)C)=C(O)C(=O)N1c1ccc(Br)cn1] | I-063 | 445 | 2 | 2.52 |
| 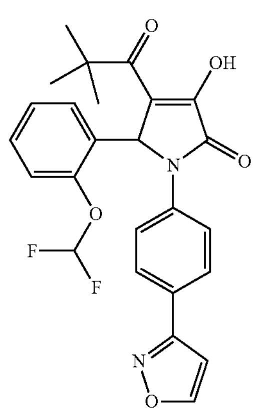 [SMILES: CC(C)(C)C(=O)C1=C(O)C(=O)N(c2ccc(-c3ccon3)cc2)C1c1ccccc1OC(F)F] | I-064 | 469 | 1 | 2.20 |

TABLE 22-continued

| Chemical Structure | Compound No. | MS [M + H]+ | LC method | LC/MS retention time (min) |
|---|---|---|---|---|
| | I-065 | 384 | 2 | 2.40 |

TABLE 23

| Chemical Structure | Compound No. | MS [M + H]+ | LC method | LC/MS retention time (min) |
|---|---|---|---|---|
| 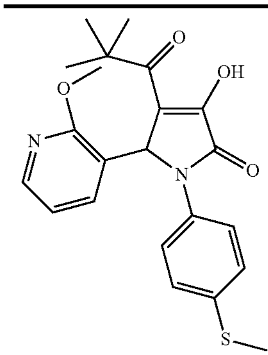 | I-066 | 413 | 1 | 2.10 |
| 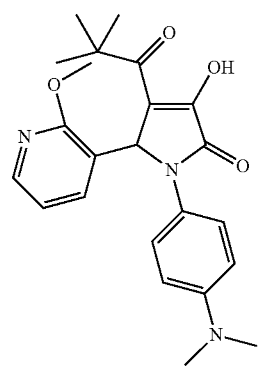 [SMILES: COc1ncccc1C1C(C(=O)C(C)(C)C)=C(O)C(=O)N1c1ccc(N(C)C)cc1] | I-067 | 410 | 1 | 1.80 |
| 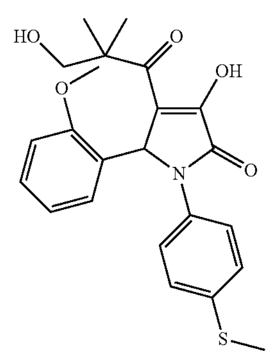 [SMILES: COc1ccccc1C1C(C(=O)C(C)(C)CO)=C(O)C(=O)N1c1ccc(SC)cc1] | I-068 | 428 | 1 | 1.80 |

TABLE 23-continued
| Chemical Structure | Compound No. | MS [M + H]+ | LC method | LC/MS retention time (min) |
|---|---|---|---|---|
| 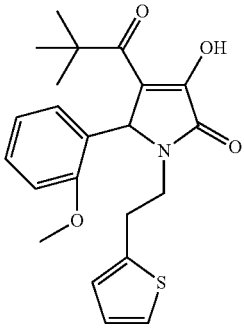 [SMILES: COc1ccccc1C1C(C(=O)C(C)(C)C)=C(O)C(=O)N1CCc1cccs1] | I-069 | 400 | 2 | 2.50 |
| 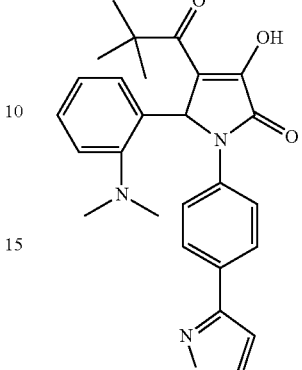 | I-070 | 446 | 1 | 2.00 |
TABLE 24
| Chemical Structure | Compound No. | MS [M + H]+ | LC method | LC/MS retention time (min) |
|---|---|---|---|---|
| 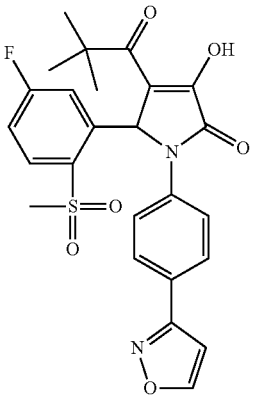 | I-071 | 499 | 1 | 1.90 |
| 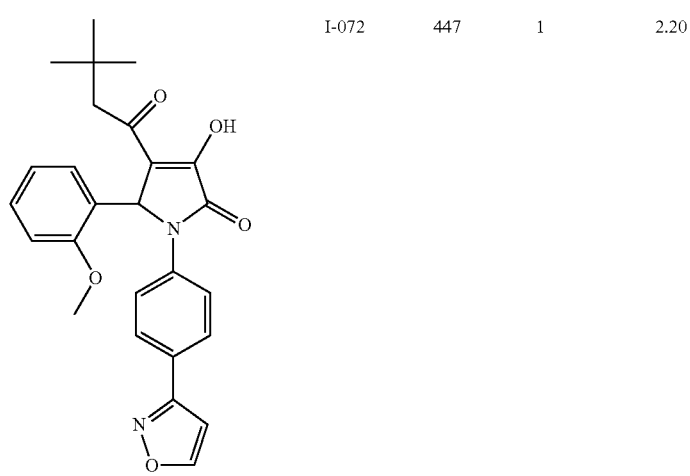 | I-072 | 447 | 1 | 2.20 |

TABLE 24-continued

| Chemical Structure | Compound No. | MS [M + H]⁺ | LC method | LC/MS retention time (min) |
|---|---|---|---|---|
| 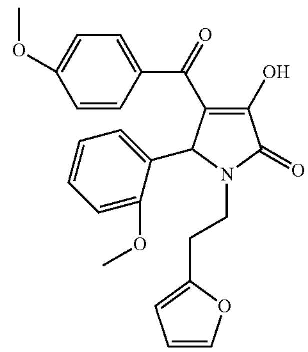 [SMILES: COc1ccc(C(=O)C2=C(O)C(=O)N(CCc3ccco3)C2c2ccccc2OC)cc1] | I-073 | 434 | 2 | 2.20 |
| 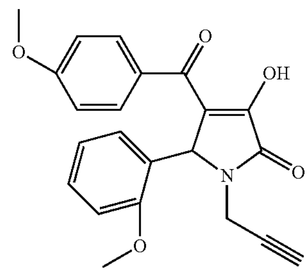 [SMILES: C#CCN1C(=O)C(O)=C(C(=O)c2ccc(OC)cc2)C1c1ccccc1OC] | I-074 | 378 | 2 | 2.00 |
| 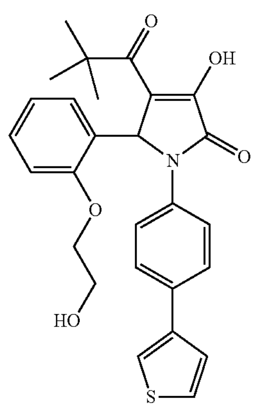 [SMILES: CC(C)(C)C(=O)C1=C(O)C(=O)N(c2ccc(-c3ccsc3)cc2)C1c1ccccc1OCCO] | I-075 | 478 | 1 | 2.10 |

TABLE 25

| Chemical Structure | Compound No. | MS [M + H]⁺ | LC method | LC/MS retention time (min) |
|---|---|---|---|---|
| 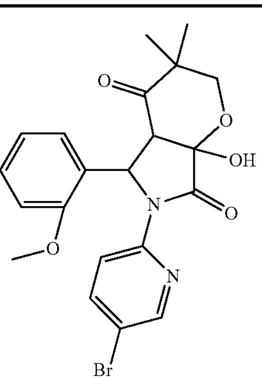 | I-076 | 461 | 2 | 2.27 |

TABLE 25-continued
| Chemical Structure | Compound No. | MS [M + H]+ | LC method | LC/MS retention time (min) |
|---|---|---|---|---|
| 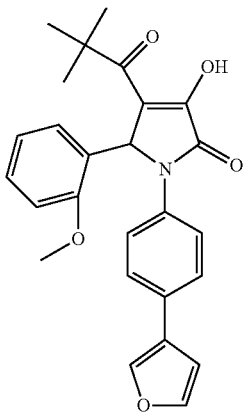 [SMILES: COc1ccccc1C1C(C(=O)C(C)(C)C)=C(O)C(=O)N1c1ccc(-c2ccoc2)cc1] | I-077 | 432 | 2 | 2.54 |
| 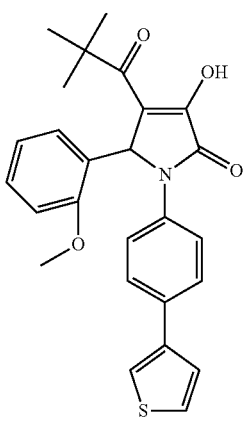 [SMILES: COc1ccccc1C1C(C(=O)C(C)(C)C)=C(O)C(=O)N1c1ccc(-c2ccsc2)cc1] | I-078 | 448 | 2 | 2.65 |
| 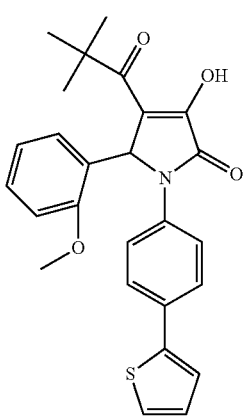 [SMILES: COc1ccccc1C1C(C(=O)C(C)(C)C)=C(O)C(=O)N1c1ccc(-c2cccs2)cc1] | I-079 | 448 | 2 | 2.69 |

TABLE 25-continued

| Chemical Structure | Compound No. | MS [M + H]+ | LC method | LC/MS retention time (min) |
|---|---|---|---|---|
| 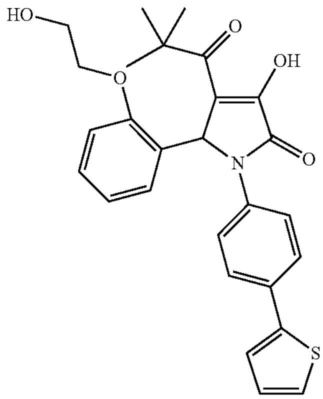 [SMILES: CC(C)(C)C(=O)C1=C(O)C(=O)N(c2ccc(-c3cccs3)cc2)C1c1ccccc1OCCO] | I-080 | 478 | 1 | 2.10 |

TABLE 26

| Chemical Structure | Compound No. | MS [M + H]+ | LC method | LC/MS retention time (min) |
|---|---|---|---|---|
| 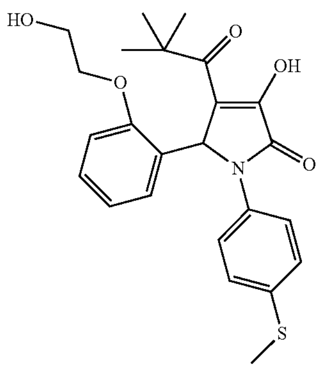 [SMILES: CSc1ccc(N2C(=O)C(O)=C(C(=O)C(C)(C)C)C2c2ccccc2OCCO)cc1] | I-081 | 442 | 1 | 2.00 |
| 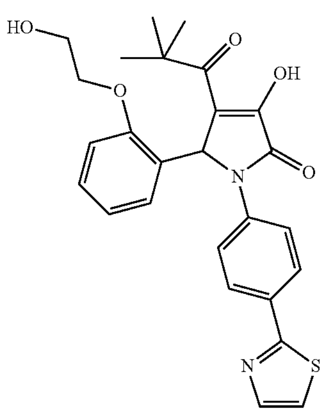 [SMILES: CC(C)(C)C(=O)C1=C(O)C(=O)N(c2ccc(-c3nccs3)cc2)C1c1ccccc1OCCO] | I-082 | 479 | 1 | 1.90 |

TABLE 26-continued

| Chemical Structure | Compound No. | MS [M + H]+ | LC method | LC/MS retention time (min) |
|---|---|---|---|---|
| 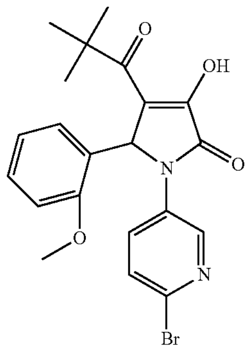 [SMILES: COc1ccccc1C1C(C(=O)C(C)(C)C)=C(O)C(=O)N1c1ccc(Br)nc1] | I-083 | 445 | 2 | 2.36 |
| 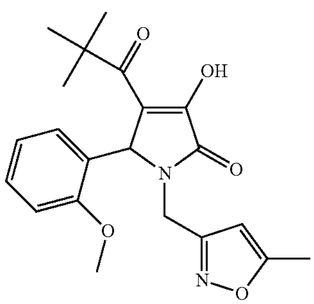 [SMILES: COc1ccccc1C1C(C(=O)C(C)(C)C)=C(O)C(=O)N1Cc1cc(C)on1] | I-084 | 385 | 1 | 1.91 |
| 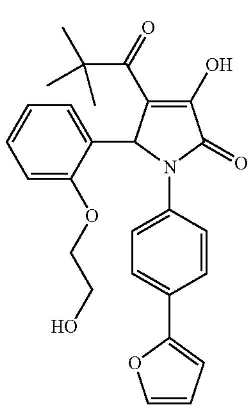 [SMILES: CC(C)(C)C(=O)C1=C(O)C(=O)N(c2ccc(-c3ccco3)cc2)C1c1ccccc1OCCO] | I-085 | 462 | 1 | 2.10 |

TABLE 27

| Chemical Structure | Compound No. | MS [M + H]+ | LC method | LC/MS retention time (min) |
|---|---|---|---|---|
| 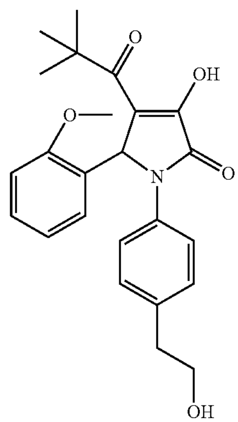 [SMILES: COc1ccccc1C1C(C(=O)C(C)(C)C)=C(O)C(=O)N1c1ccc(CCO)cc1] | I-086 | | 2 | 2.05 |
| 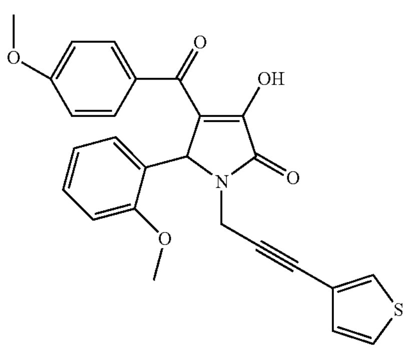 [SMILES: COc1ccc(C(=O)C2=C(O)C(=O)N(CC#Cc3ccsc3)C2c2ccccc2OC)cc1] | I-087 | 460 | 2 | 2.40 |
| 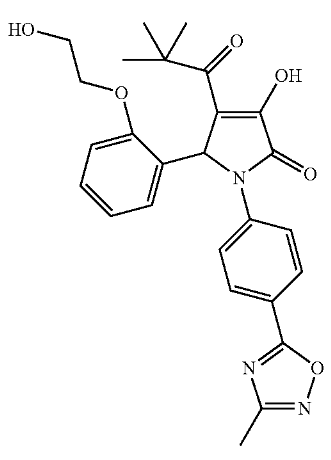 [SMILES: Cc1noc(-c2ccc(N3C(=O)C(O)=C(C(=O)C(C)(C)C)C3c3ccccc3OCCO)cc2)n1] | I-088 | 478 | 1 | 1.90 |

TABLE 27-continued

| Chemical Structure | Compound No. | MS [M + H]+ | LC method | LC/MS retention time (min) |
|---|---|---|---|---|
| (structure) | I-089 | 478 | 1 | 1.80 |
| (structure) | I-090 | 477 | 1 | 1.90 |

TABLE 28

| Chemical Structure | Compound No. | MS [M + H]+ | LC method | LC/MS retention time (min) | Chemical Structure | Compound No. | MS [M + H]+ | LC method | LC/MS retention time (min) |
|---|---|---|---|---|---|---|---|---|---|
| (structure) | I-091 | 431 | 1 | 2.30 | (structure) | I-092 | 432 | 2 | 2.61 |

TABLE 28-continued
| Chemical Structure | Compound No. | MS [M + H]+ | LC method | LC/MS retention time (min) |
|---|---|---|---|---|
| 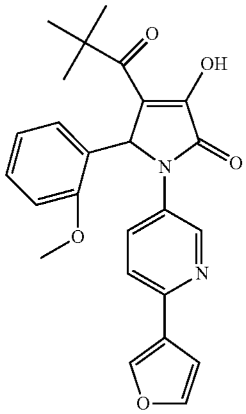 [SMILES: COc1ccccc1C1C(C(=O)C(C)(C)C)=C(O)C(=O)N1c1ccc(-c2ccoc2)nc1] | I-093 | 433 | 2 | 1.19 |
| 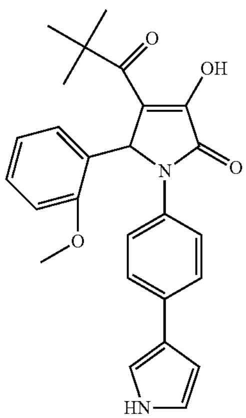 [SMILES: COc1ccccc1C1C(C(=O)C(C)(C)C)=C(O)C(=O)N1c1ccc(-c2cc[nH]c2)cc1] | I-094 | 431 | 2 | 1.17 |
| 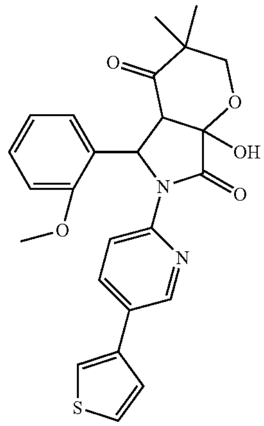 [SMILES: COc1ccccc1C1C2C(=O)C(C)(C)COC2(O)C(=O)N1c1ccc(-c2ccsc2)cn1] | I-095 | 465 | 2 | 2.14 |
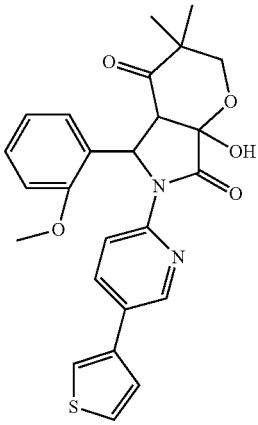
TABLE 29
| Chemical Structure | Compound No. | MS [M + H]+ | LC method | LC/MS retention time (min) |
|---|---|---|---|---|
| 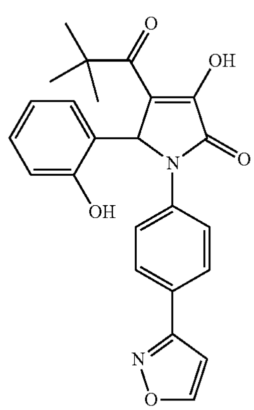 [SMILES: CC(C)(C)C(=O)C1=C(O)C(=O)N(c2ccc(-c3ccon3)cc2)C1c1ccccc1O] | I-096 | 419 | 1 | 1.90 |
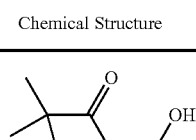

TABLE 29-continued

| Chemical Structure | Compound No. | MS [M + H]+ | LC method | LC/MS retention time (min) |
|---|---|---|---|---|
| 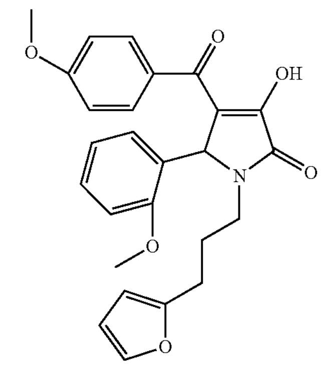 [SMILES: COc1ccc(C(=O)C2=C(O)C(=O)N(CCCc3ccco3)C2c2ccccc2OC)cc1] | I-097 | 448 | 2 | 2.20 |
| 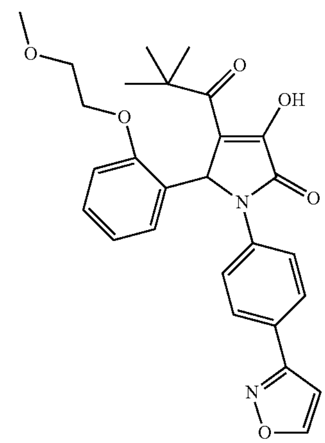 [SMILES: COCCOc1ccccc1C1C(C(=O)C(C)(C)C)=C(O)C(=O)N1c1ccc(-c2ccon2)cc1] | I-098 | 477 | 1 | 2.10 |
| 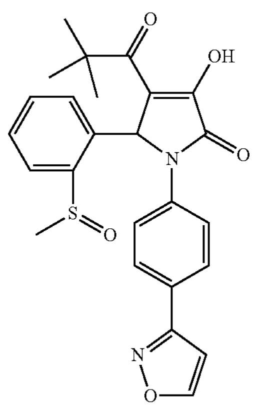 [SMILES: CS(=O)c1ccccc1C1C(C(=O)C(C)(C)C)=C(O)C(=O)N1c1ccc(-c2ccon2)cc1] | I-099 | 465 | 2 | 1.80 |

TABLE 29-continued
| Chemical Structure | Compound No. | MS [M + H]+ | LC method | LC/MS retention time (min) |
|---|---|---|---|---|
| 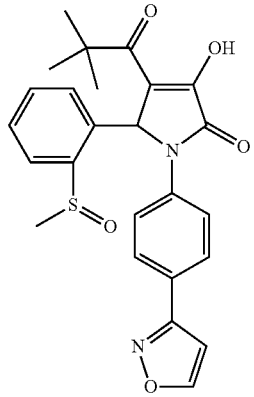 [SMILES: CS(=O)c1ccccc1C1C(C(=O)C(C)(C)C)=C(O)C(=O)N1c1ccc(-c2ccon2)cc1] | I-100 | 465 | 2 | 1.90 |
TABLE 30
| Chemical Structure | Compound No. | MS [M + H]+ | LC method | LC/MS retention time (min) |
|---|---|---|---|---|
| 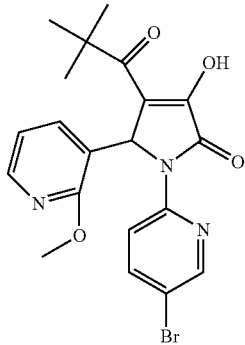 [SMILES: COc1ncccc1C1C(C(=O)C(C)(C)C)=C(O)C(=O)N1c1ccc(Br)cn1] | I-101 | 446 | 2 | 2.42 |
| 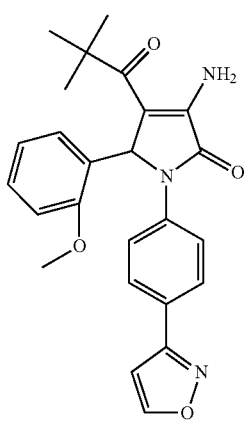 [SMILES: COc1ccccc1C1C(C(=O)C(C)(C)C)=C(N)C(=O)N1c1ccc(-c2ccon2)cc1] | I-102 | 432 | 2 | 1.98 |
| 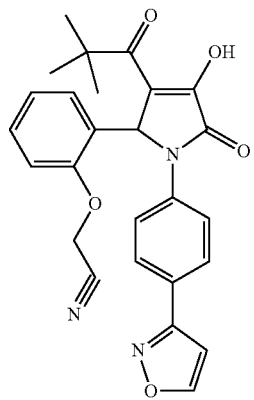 [SMILES: CC(C)(C)C(=O)C1=C(O)C(=O)N(c2ccc(-c3ccon3)cc2)C1c1ccccc1OCC#N] | I-103 | 458 | 1 | 1.90 |
| 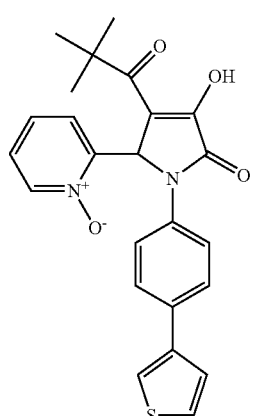 | I-104 | 435 | 2 | 1.96 |

TABLE 30-continued
| Chemical Structure | Compound No. | MS [M + H]+ | LC method | LC/MS retention time (min) |
|---|---|---|---|---|
| 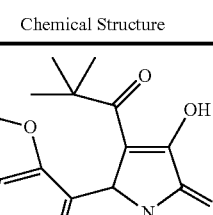 | I-105 | 461 | 1 | 2.30 |
TABLE 31
| Chemical Structure | Compound No. | MS [M + H]+ | LC method | LC/MS retention time (min) |
|---|---|---|---|---|
| 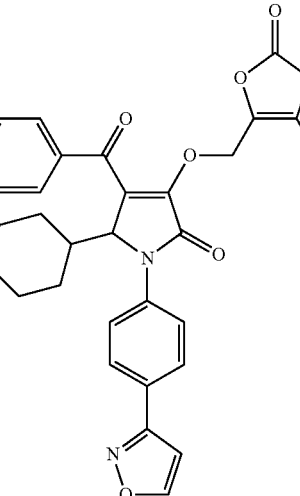 | I-106 | 459 | 2 | 2.70 |
| 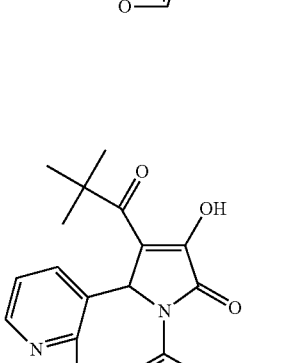 | I-107 | 446 | 2 | 2.21 |

TABLE 31-continued

| Chemical Structure | Compound No. | MS [M + H]+ | LC method | LC/MS retention time (min) |
|---|---|---|---|---|
| 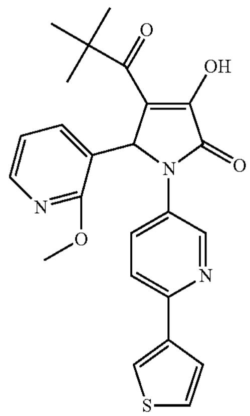 | I-108 | 450 | 2 | 2.30 |
| 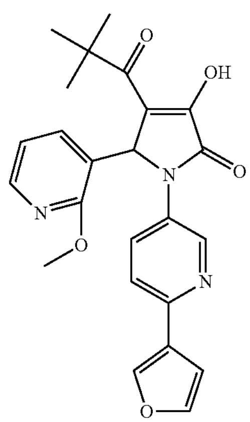 [SMILES: COc1ncccc1C1C(C(=O)C(C)(C)C)=C(O)C(=O)N1c1ccc(-c2ccoc2)nc1] | I-109 | 434 | 2 | 2.16 |
| 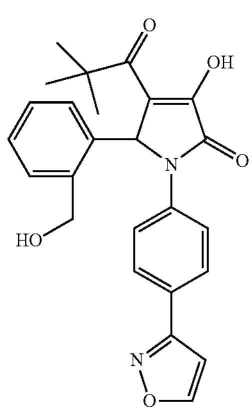 [SMILES: CC(C)(C)C(=O)C1=C(O)C(=O)N(c2ccc(-c3ccon3)cc2)C1c1ccccc1CO] | I-110 | 433 | 1 | 1.80 |

TABLE 32
| Chemical Structure | Compound No. | MS [M + H]+ | LC method | LC/MS retention time (min) |
|---|---|---|---|---|
| 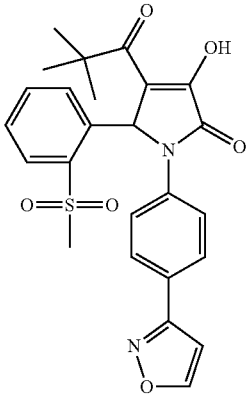 [SMILES: CC(C)(C)C(=O)C1=C(O)C(=O)N(c2ccc(-c3ccon3)cc2)C1c1ccccc1S(C)(=O)=O] | I-111 | 481 | 1 | 1.90 |
| 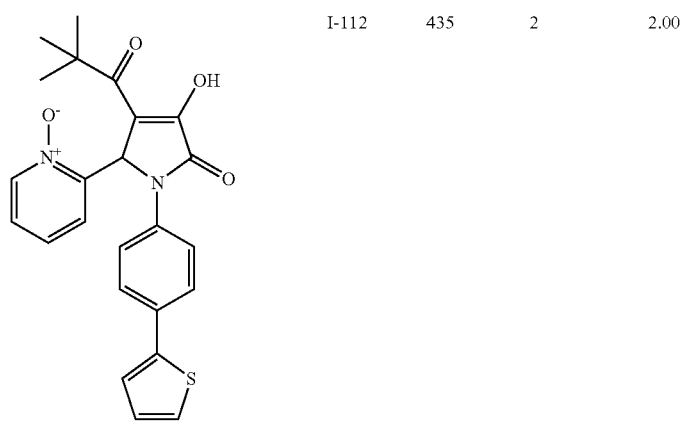 | I-112 | 435 | 2 | 2.00 |
| 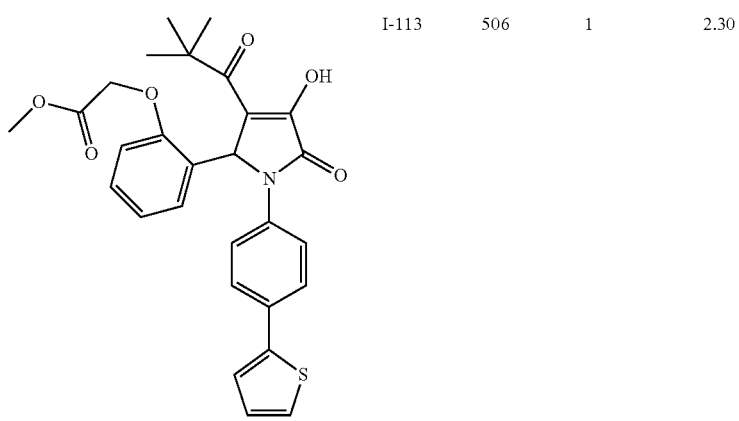 | I-113 | 506 | 1 | 2.30 |

TABLE 32-continued
| Chemical Structure | Compound No. | MS [M + H]+ | LC method | LC/MS retention time (min) |
|---|---|---|---|---|
| 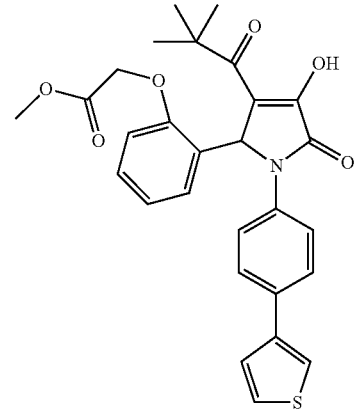 [SMILES: COC(=O)COc1ccccc1C1C(C(=O)C(C)(C)C)=C(O)C(=O)N1c1ccc(-c2ccsc2)cc1] | I-114 | 506 | 1 | 2.30 |
| 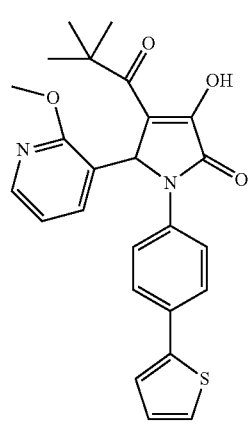 [SMILES: COc1ncccc1C1C(C(=O)C(C)(C)C)=C(O)C(=O)N1c1ccc(-c2cccs2)cc1] | I-115 | 449 | 1 | 2.30 |
TABLE 33
| Chemical Structure | Compound No. | MS [M + H]+ | LC method | LC/MS retention time (min) |
|---|---|---|---|---|
| 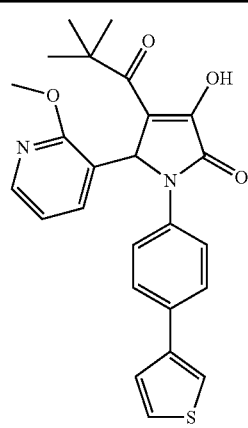 | I-116 | 449 | 1 | 2.20 |

TABLE 33-continued
| Chemical Structure | Compound No. | MS [M + H]+ | LC method | LC/MS retention time (min) |
|---|---|---|---|---|
| 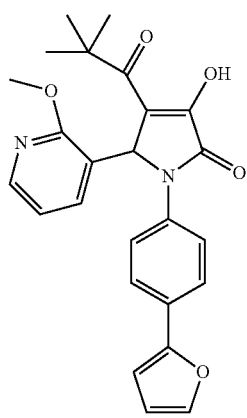 [SMILES: COc1ncccc1C1C(C(=O)C(C)(C)C)=C(O)C(=O)N1c1ccc(-c2ccco2)cc1] | I-117 | 433 | 1 | 2.20 |
| 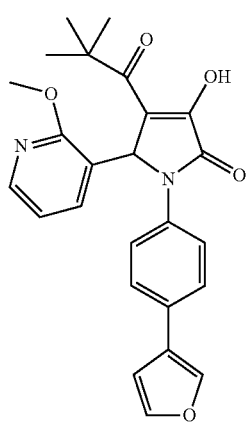 [SMILES: COc1ncccc1C1C(C(=O)C(C)(C)C)=C(O)C(=O)N1c1ccc(-c2ccoc2)cc1] | I-118 | 433 | 1 | 2.10 |
| 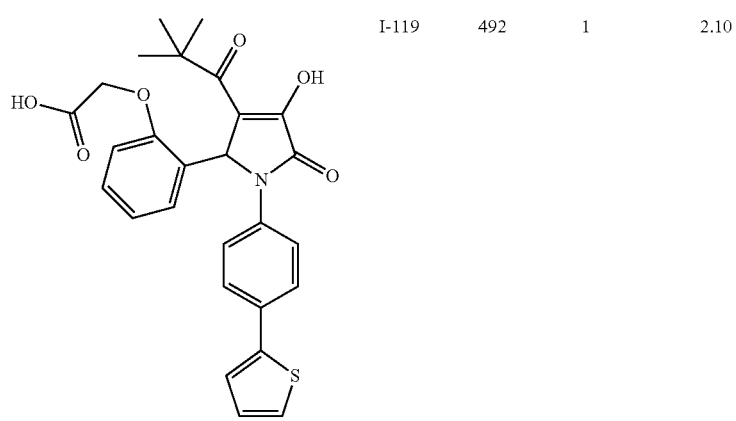 | I-119 | 492 | 1 | 2.10 |

TABLE 33-continued

| Chemical Structure | Compound No. | MS [M + H]+ | LC method | LC/MS retention time (min) |
|---|---|---|---|---|
| 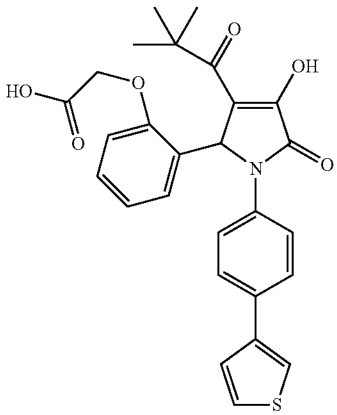 [SMILES: CC(C)(C)C(=O)C1=C(O)C(=O)N(c2ccc(-c3ccsc3)cc2)C1c1ccccc1OCC(=O)O] | I-120 | 492 | 1 | 2.00 |

TABLE 34

| Chemical Structure | Compound No. | MS [M + H]+ | LC method | LC/MS retention time (min) |
|---|---|---|---|---|
| 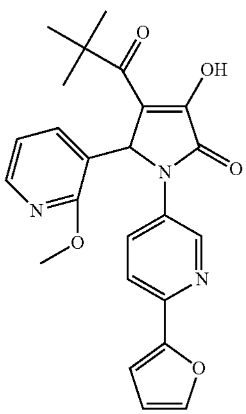 [SMILES: COc1ncccc1C1C(C(=O)C(C)(C)C)=C(O)C(=O)N1c1ccc(-c2ccco2)nc1] | I-121 | 434 | 2 | 2.19 |
| 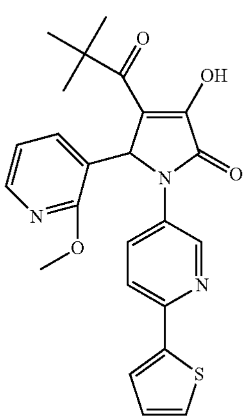 [SMILES: COc1ncccc1C1C(C(=O)C(C)(C)C)=C(O)C(=O)N1c1ccc(-c2cccs2)nc1] | I-122 | 450 | 2 | 2.36 |

TABLE 34-continued

| Chemical Structure | Compound No. | MS [M + H]+ | LC method | LC/MS retention time (min) |
|---|---|---|---|---|
| 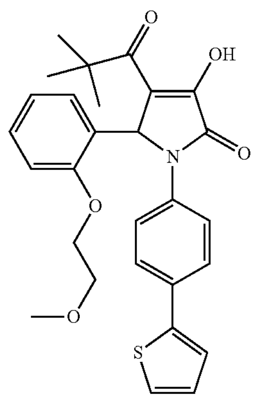 [SMILES: COCCOc1ccccc1C1C(C(=O)C(C)(C)C)=C(O)C(=O)N1c1ccc(-c2cccs2)cc1] | I-123 | 492 | 1 | 2.40 |
| 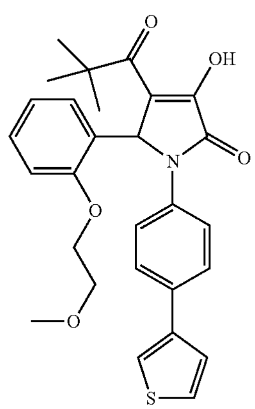 [SMILES: COCCOc1ccccc1C1C(C(=O)C(C)(C)C)=C(O)C(=O)N1c1ccc(-c2ccsc2)cc1] | I-124 | 492 | 1 | 2.30 |
| 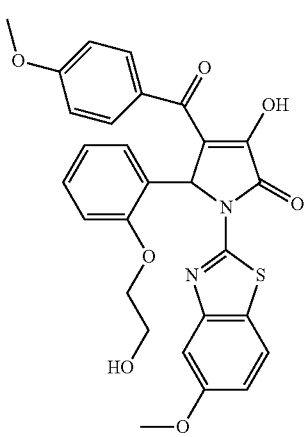 [SMILES: COc1ccc(C(=O)C2=C(O)C(=O)N(c3nc4cc(OC)ccc4s3)C2c2ccccc2OCCO)cc1] | I-125 | 533 | 1 | 1.90 |

TABLE 35
| Chemical Structure | Compound No. | MS [M + H]+ | LC method | LC/MS retention time (min) |
|---|---|---|---|---|
| 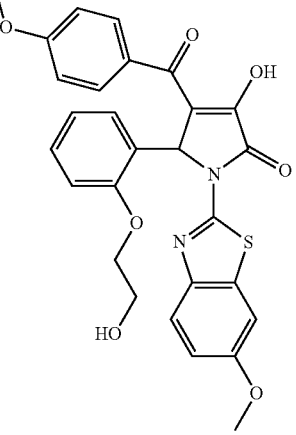 | I-126 | 533 | 1 | 1.90 |
| 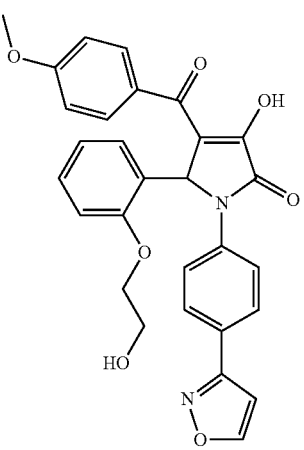 [SMILES: COc1ccc(C(=O)C2=C(O)C(=O)N(c3ccc(-c4ccon4)cc3)C2c2ccccc2OCCO)cc1] | I-127 | 513 | 1 | 1.70 |
| 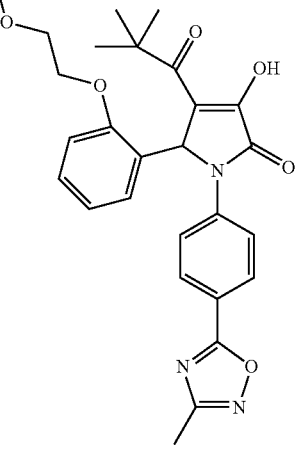 | I-128 | 492 | 1 | 2.10 |

TABLE 35-continued
| Chemical Structure | Compound No. | MS [M + H]⁺ | LC method | LC/MS retention time (min) |
|---|---|---|---|---|
| 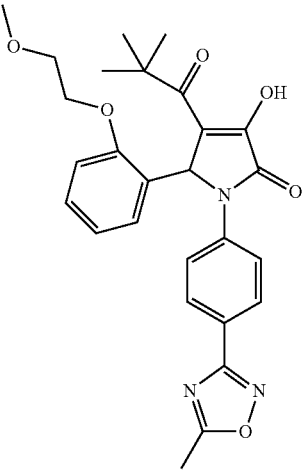 [SMILES: COCCOc1ccccc1C1C(C(=O)C(C)(C)C)=C(O)C(=O)N1c1ccc(-c2noc(C)n2)cc1] | I-129 | 492 | 1 | 2.10 |
| 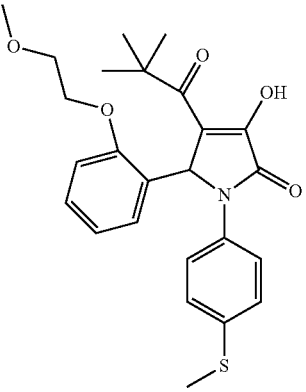 [SMILES: COCCOc1ccccc1C1C(C(=O)C(C)(C)C)=C(O)C(=O)N1c1ccc(SC)cc1] | I-130 | 456 | 1 | 2.20 |
TABLE 36
| Chemical Structure | Compound No. | MS [M + H]⁺ | LC method | LC/MS retention time (min) |
|---|---|---|---|---|
| 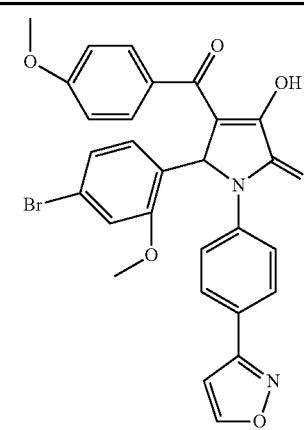 | I-131 | 561 | 2 | 2.40 |

TABLE 36-continued
| Chemical Structure | Compound No. | MS [M + H]+ | LC method | LC/MS retention time (min) |
|---|---|---|---|---|
| 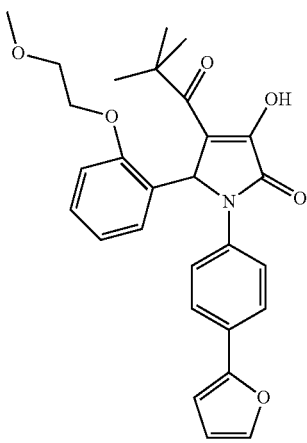 [SMILES: COCCOc1ccccc1C1C(C(=O)C(C)(C)C)=C(O)C(=O)N1c1ccc(-c2ccco2)cc1] | I-132 | 476 | 1 | 2.30 |
| 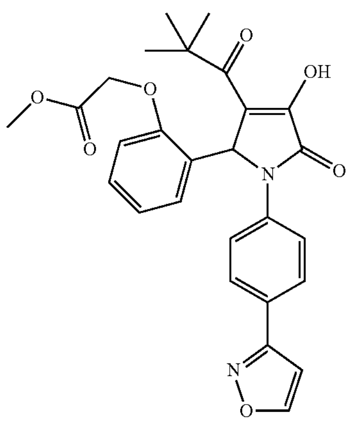 [SMILES: COC(=O)COc1ccccc1C1C(C(=O)C(C)(C)C)=C(O)C(=O)N1c1ccc(-c2ccon2)cc1] | I-133 | 491 | 1 | 2.00 |
| 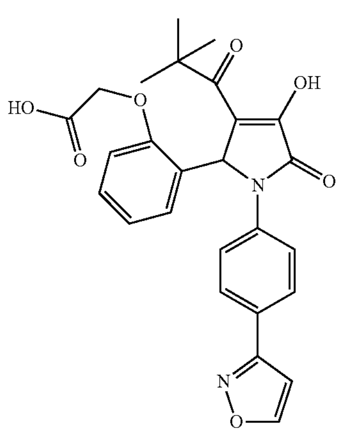 [SMILES: CC(C)(C)C(=O)C1=C(O)C(=O)N(c2ccc(-c3ccon3)cc2)C1c1ccccc1OCC(=O)O] | I-134 | 477 | 1 | 1.80 |

TABLE 36-continued
| Chemical Structure | Compound No. | MS [M + H]+ | LC method | LC/MS retention time (min) |
|---|---|---|---|---|
| 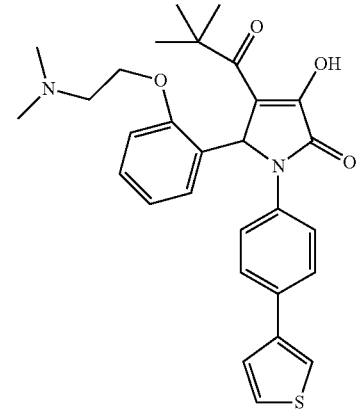 [SMILES: CN(C)CCOc1ccccc1C1C(C(=O)C(C)(C)C)=C(O)C(=O)N1c1ccc(-c2ccsc2)cc1] | I-135 | 505 | 1 | 1.50 |
TABLE 37
| Chemical Structure | Compound No. | MS [M + H]+ | LC method | LC/MS retention time (min) |
|---|---|---|---|---|
| 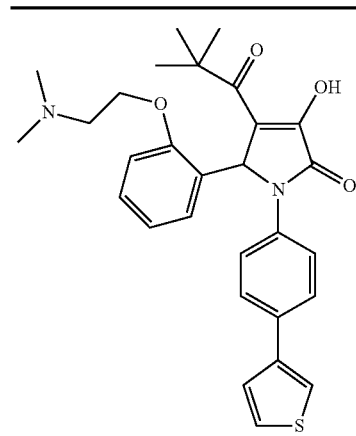 | I-136 | 505 | 1 | 1.90 |
| 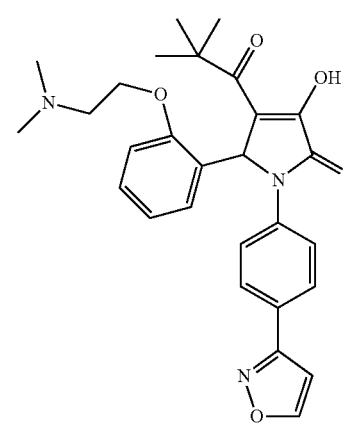 | I-137 | 490 | 1 | 1.30 |

TABLE 37-continued

| Chemical Structure | Compound No. | MS [M + H]+ | LC method | LC/MS retention time (min) |
|---|---|---|---|---|
| 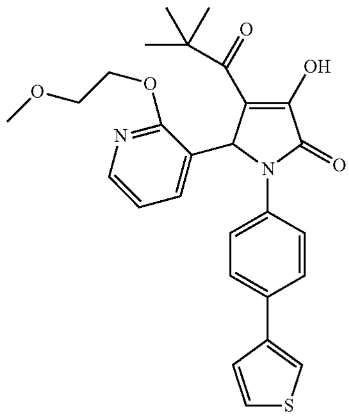 [SMILES: COCCOc1ncccc1C1C(C(=O)C(C)(C)C)=C(O)C(=O)N1c1ccc(-c2ccsc2)cc1] | I-138 | 493 | 1 | 2.20 |
| 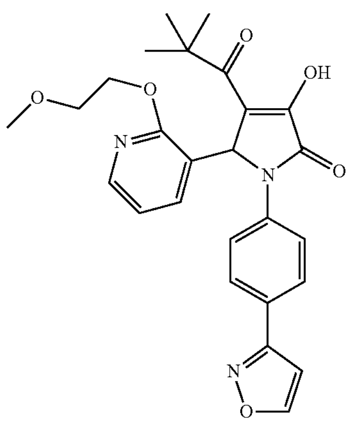 [SMILES: COCCOc1ncccc1C1C(C(=O)C(C)(C)C)=C(O)C(=O)N1c1ccc(-c2ccon2)cc1] | I-139 | 478 | 1 | 1.90 |
| 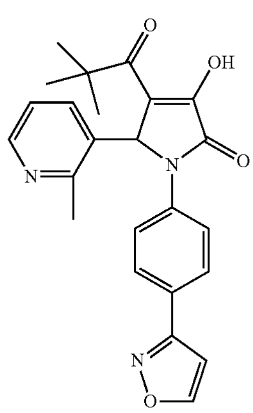 [SMILES: Cc1ncccc1C1C(C(=O)C(C)(C)C)=C(O)C(=O)N1c1ccc(-c2ccon2)cc1] | I-140 | 418 | 1 | 1.20 |

TABLE 38
| Chemical Structure | Compound No. | MS [M + H]+ | LC method | LC/MS retention time (min) |
|---|---|---|---|---|
| 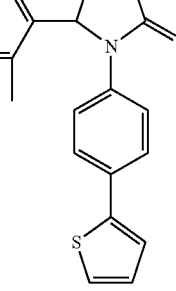 | I-141 | 433 | 1 | 1.50 |
| 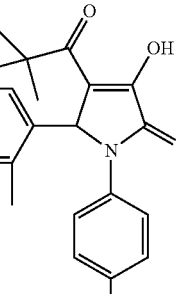 | I-142 | 417 | 1 | 1.40 |
| 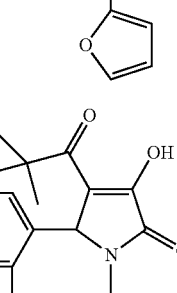 | I-143 | 433 | 1 | 1.40 |
| 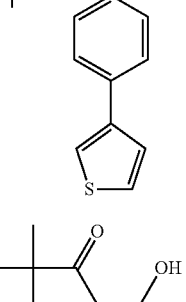 | I-144 | 476 | 1 | 1.67 |

TABLE 38-continued
| Chemical Structure | Compound No. | MS [M + H]+ | LC method | LC/MS retention time (min) |
|---|---|---|---|---|
| 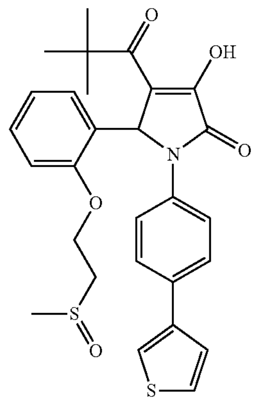 [SMILES: CS(=O)CCOc1ccccc1C1C(C(=O)C(C)(C)C)=C(O)C(=O)N1c1ccc(-c2ccsc2)cc1] | I-145 | 524 | 1 | 1.91 |
TABLE 39
| Chemical Structure | Compound No. | MS [M + H]+ | LC method | LC/MS retention time (min) |
|---|---|---|---|---|
| 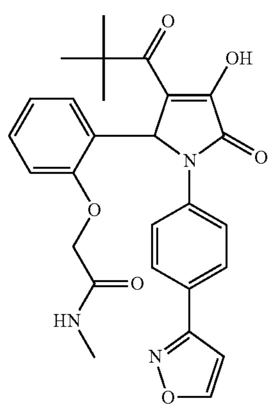 [SMILES: CNC(=O)COc1ccccc1C1C(C(=O)C(C)(C)C)=C(O)C(=O)N1c1ccc(-c2ccon2)cc1] | I-146 | 490 | 1 | 1.81 |
| 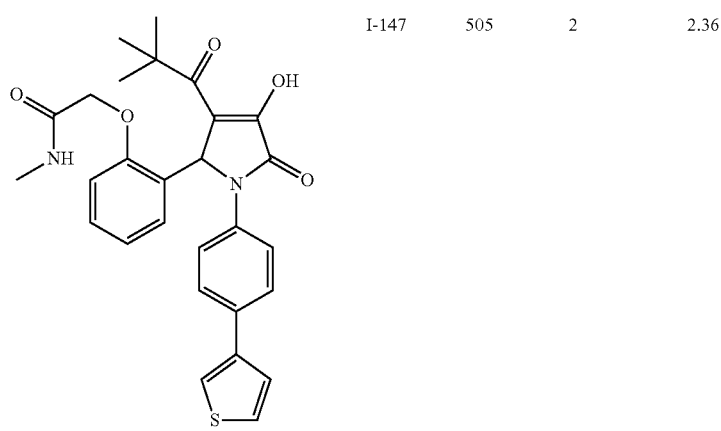 | I-147 | 505 | 2 | 2.36 |

TABLE 39-continued
| Chemical Structure | Compound No. | MS [M + H]+ | LC method | LC/MS retention time (min) |
|---|---|---|---|---|
| 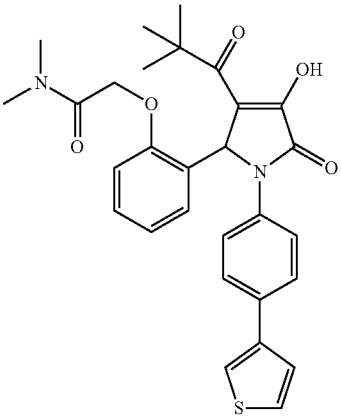 [SMILES: CN(C)C(=O)COc1ccccc1C1C(C(=O)C(C)(C)C)=C(O)C(=O)N1c1ccc(-c2ccsc2)cc1] | I-148 | 519 | 2 | 2.39 |
| 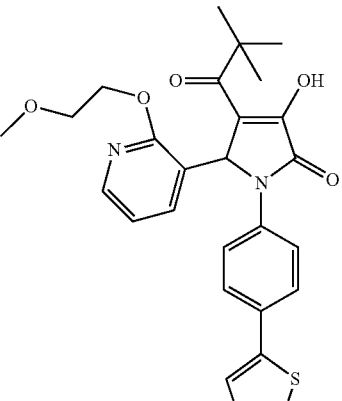 | I-149 | 493 | 1 | 2.30 |
| 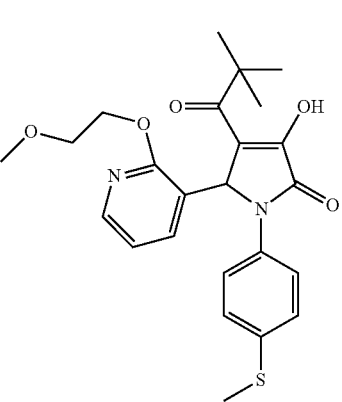 [SMILES: COCCOc1ncccc1C1C(C(=O)C(C)(C)C)=C(O)C(=O)N1c1ccc(SC)cc1] | I-150 | 457 | 1 | 2.10 |

TABLE 40
| Chemical Structure | Compound No. | MS [M + H]+ | LC method | LC/MS retention time (min) |
|---|---|---|---|---|
| 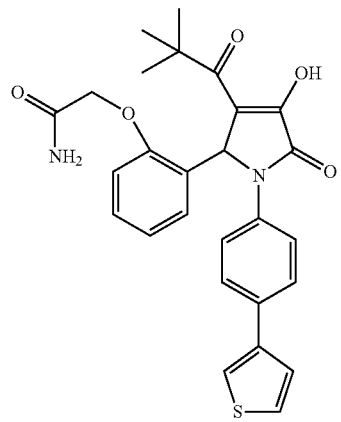 [SMILES: CC(C)(C)C(=O)C1=C(O)C(=O)N(c2ccc(-c3ccsc3)cc2)C1c1ccccc1OCC(N)=O] | I-151 | 491 | 2 | 2.22 |
| 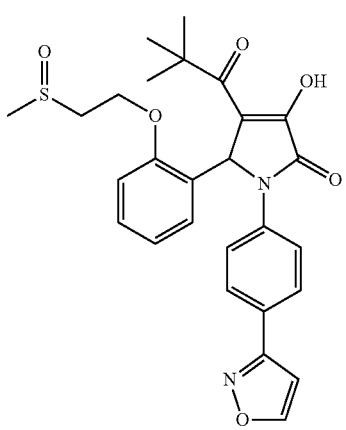 [SMILES: CS(=O)CCOc1ccccc1C1C(C(=O)C(C)(C)C)=C(O)C(=O)N1c1ccc(-c2ccon2)cc1] | I-152 | 509 | 2 | 1.94 |
| 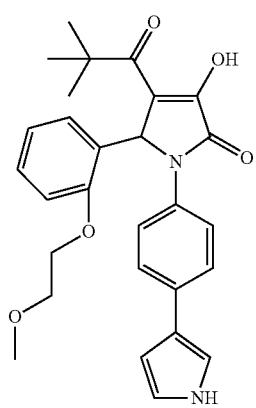 [SMILES: COCCOc1ccccc1C1C(C(=O)C(C)(C)C)=C(O)C(=O)N1c1ccc(-c2cc[nH]c2)cc1] | I-153 | 475 | 2 | 1.76 |

TABLE 40-continued
| Chemical Structure | Compound No. | MS [M + H]+ | LC method | LC/MS retention time (min) |
|---|---|---|---|---|
| 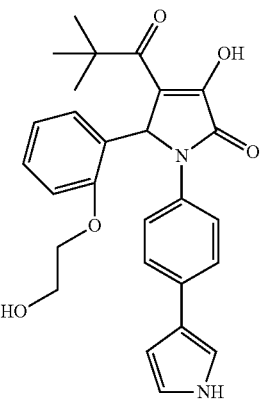 [SMILES: CC(C)(C)C(=O)C1=C(O)C(=O)N(c2ccc(-c3cc[nH]c3)cc2)C1c1ccccc1OCCO] | I-154 | 461 | 2 | 2.10 |
| 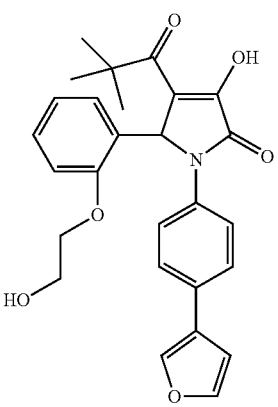 [SMILES: CC(C)(C)C(=O)C1=C(O)C(=O)N(c2ccc(-c3ccoc3)cc2)C1c1ccccc1OCCO] | I-155 | 462 | 1 | 1.90 |
TABLE 41
| Chemical Structure | Compound No. | MS [M + H]+ | LC method | LC/MS retention time (min) |
|---|---|---|---|---|
| 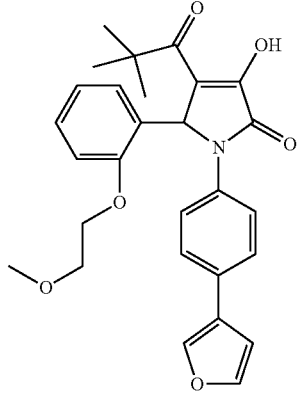 [SMILES: COCCOc1ccccc1C1C(C(=O)C(C)(C)C)=C(O)C(=O)N1c1ccc(-c2ccoc2)cc1] | I-156 | 476 | 1 | 2.20 |

TABLE 41-continued

| Chemical Structure | Compound No. | MS [M + H]+ | LC method | LC/MS retention time (min) |
|---|---|---|---|---|
| 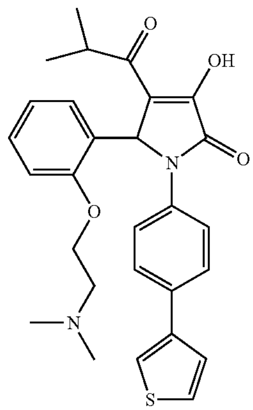 [SMILES: CC(C)C(=O)C1=C(O)C(=O)N(c2ccc(-c3ccsc3)cc2)C1c1ccccc1OCCN(C)C] | I-157 | 491 | 1 | 1.50 |
| 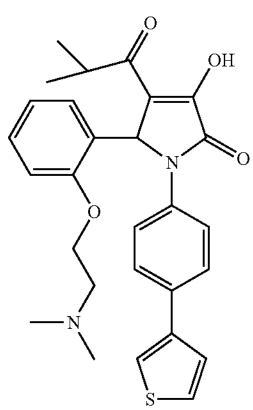 [SMILES: CC(C)C(=O)C1=C(O)C(=O)N(c2ccc(-c3ccsc3)cc2)C1c1ccccc1OCCN(C)C] | I-158 | 491 | 1 | 1.55 |
| 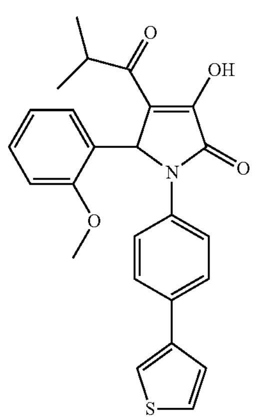 [SMILES: COc1ccccc1C1C(C(=O)C(C)C)=C(O)C(=O)N1c1ccc(-c2ccsc2)cc1] | I-159 | 434 | 1 | 2.20 |

TABLE 41-continued

| Chemical Structure | Compound No. | MS [M + H]+ | LC method | LC/MS retention time (min) |
|---|---|---|---|---|
| (structure) | I-160 | 464 | 2 | 2.27 |

TABLE 42

| Chemical Structure | Compound No. | MS [M + H]+ | LC method | LC/MS retention time (min) |
|---|---|---|---|---|
| (structure) | I-161 | 478 | 2 | 2.56 |
| (structure) | I-162 | 463 | 1 | 1.70 |

TABLE 42-continued

| Chemical Structure | Compound No. | MS [M + H]+ | LC method | LC/MS retention time (min) |
|---|---|---|---|---|
| 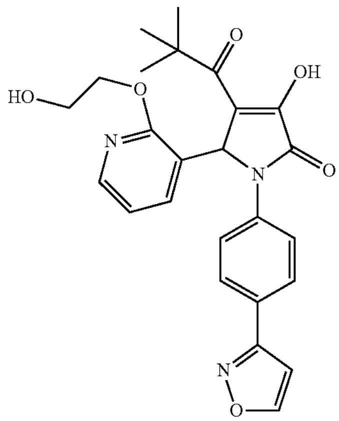 [SMILES: CC(C)(C)C(=O)C1=C(O)C(=O)N(c2ccc(-c3ccon3)cc2)C1c1cccnc1OCCO] | I-163 | 464 | 1 | 1.60 |
| 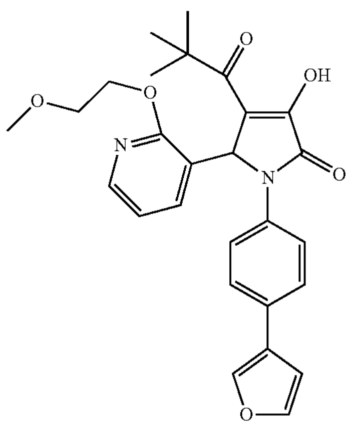 [SMILES: COCCOc1ncccc1C1C(C(=O)C(C)(C)C)=C(O)C(=O)N1c1ccc(-c2ccoc2)cc1] | I-164 | 477 | 1 | 2.10 |
| 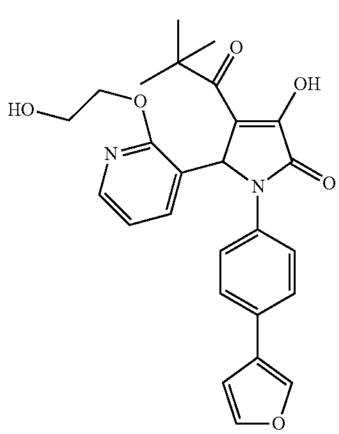 [SMILES: CC(C)(C)C(=O)C1=C(O)C(=O)N(c2ccc(-c3ccoc3)cc2)C1c1cccnc1OCCO] | I-165 | 463 | 1 | 1.80 |

TABLE 43

| Chemical Structure | Compound No. | MS [M + H]+ | LC method | LC/MS retention time (min) |
|---|---|---|---|---|
| 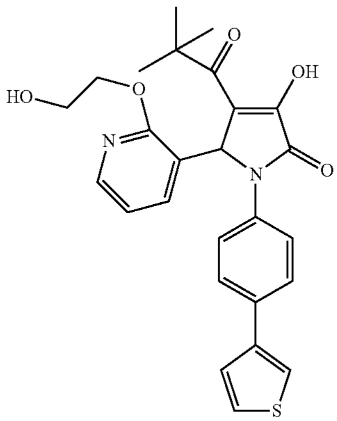 [SMILES: CC(C)(C)C(=O)C1=C(O)C(=O)N(c2ccc(-c3ccsc3)cc2)C1c1cccnc1OCCO] | I-166 | 479 | 1 | 2.00 |
| 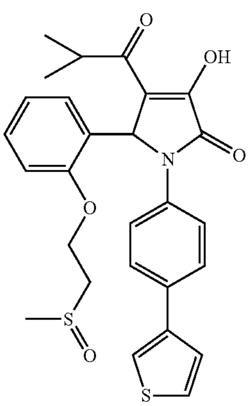 [SMILES: CC(C)C(=O)C1=C(O)C(=O)N(c2ccc(-c3ccsc3)cc2)C1c1ccccc1OCCS(C)=O] | I-167 | 510 | 1 | 1.79 |
| 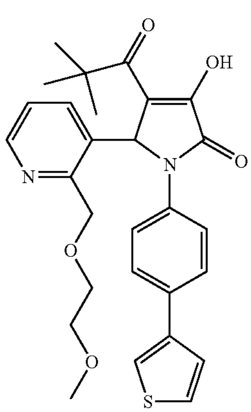 [SMILES: COCCOCc1ncccc1C1C(C(=O)C(C)(C)C)=C(O)C(=O)N1c1ccc(-c2ccsc2)cc1] | I-168 | 507 | 1 | 1.65 |

TABLE 43-continued

| Chemical Structure | Compound No. | MS [M + H]⁺ | LC method | LC/MS retention time (min) |
|---|---|---|---|---|
| 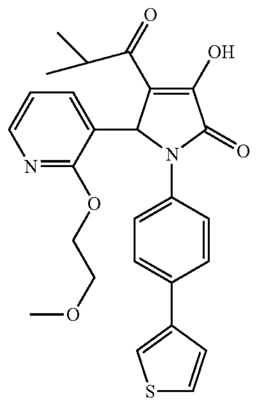 [SMILES: COCCOc1ncccc1C1C(C(=O)C(C)C)=C(O)C(=O)N1c1ccc(-c2ccsc2)cc1] | I-169 | 479 | 2 | 2.45 |
| 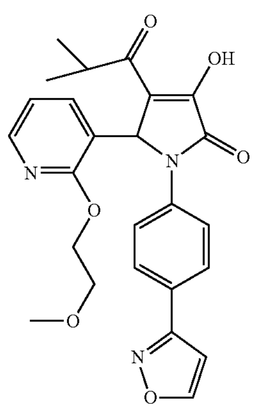 [SMILES: COCCOc1ncccc1C1C(C(=O)C(C)C)=C(O)C(=O)N1c1ccc(-c2ccon2)cc1] | I-170 | 464 | 2 | 2.11 |

TABLE 44

| Chemical Structure | Compound No. | MS [M + H]⁺ | LC method | LC/MS retention time (min) |
|---|---|---|---|---|
| 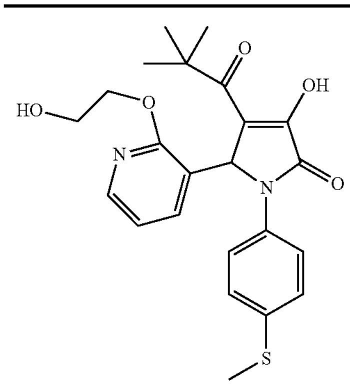 | I-171 | 443 | 1 | 1.80 |

TABLE 44-continued

| Chemical Structure | Compound No. | MS [M + H]+ | LC method | LC/MS retention time (min) |
|---|---|---|---|---|
| 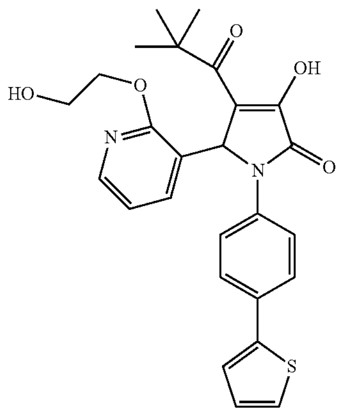 [SMILES: CC(C)(C)C(=O)C1=C(O)C(=O)N(c2ccc(-c3cccs3)cc2)C1c1cccnc1OCCO] | I-172 | 479 | 1 | 2.00 |
| 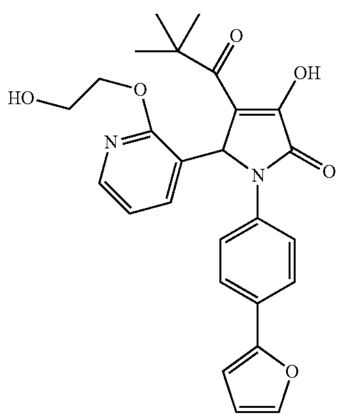 [SMILES: CC(C)(C)C(=O)C1=C(O)C(=O)N(c2ccc(-c3ccco3)cc2)C1c1cccnc1OCCO] | I-173 | 463 | 1 | 1.90 |
| 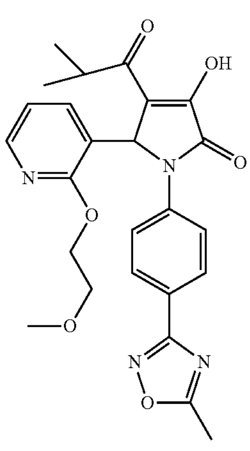 [SMILES: COCCOc1ncccc1C1C(C(=O)C(C)C)=C(O)C(=O)N1c1ccc(-c2noc(C)n2)cc1] | I-174 | 479 | 2 | 2.15 |

TABLE 44-continued
| Chemical Structure | Compound No. | MS [M + H]+ | LC method | LC/MS retention time (min) |
|---|---|---|---|---|
| 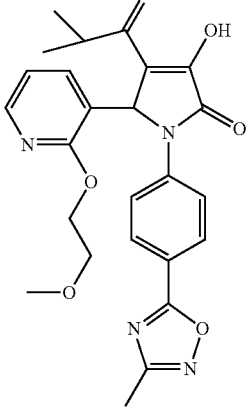 | I-175 | 479 | 2 | 2.18 |
TABLE 45
| Chemical Structure | Compound No. | MS [M + H]+ | LC method | LC/MS retention time (min) |
|---|---|---|---|---|
| 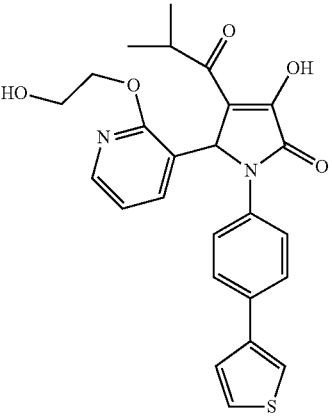 [SMILES: CC(C)C(=O)C1=C(O)C(=O)N(c2ccc(-c3ccsc3)cc2)C1c1cccnc1OCCO] | I-176 | 465 | 1 | 1.80 |
| 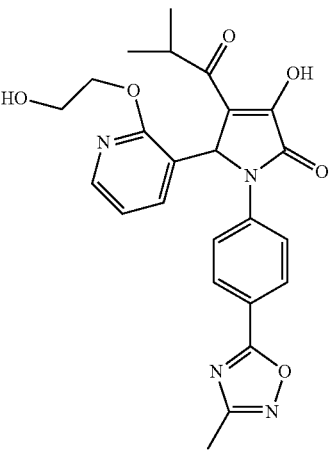 [SMILES: Cc1noc(-c2ccc(N3C(=O)C(O)=C(C(=O)C(C)C)C3c3cccnc3OCCO)cc2)n1] | I-177 | 465 | 1 | 1.60 |

TABLE 45-continued
| Chemical Structure | Compound No. | MS [M + H]+ | LC method | LC/MS retention time (min) |
|---|---|---|---|---|
| 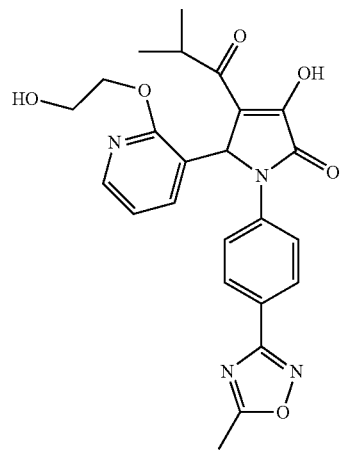 [SMILES: Cc1nc(-c2ccc(N3C(=O)C(O)=C(C(=O)C(C)C)C3c3cccnc3OCCO)cc2)no1] | I-178 | 465 | 1 | 1.50 |
| 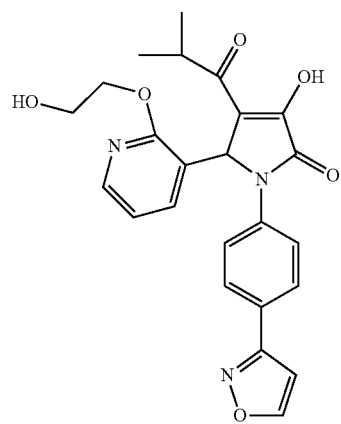 [SMILES: CC(C)C(=O)C1=C(O)C(=O)N(c2ccc(-c3ccon3)cc2)C1c1cccnc1OCCO] | I-179 | 450 | 1 | 1.50 |
| 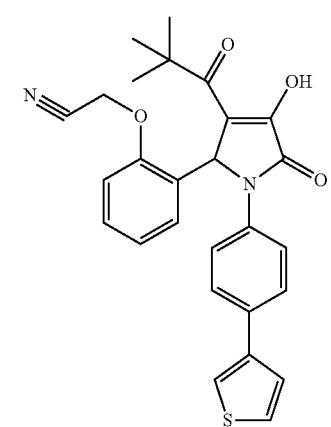 [SMILES: CC(C)(C)C(=O)C1=C(O)C(=O)N(c2ccc(-c3ccsc3)cc2)C1c1ccccc1OCC#N] | I-180 | 473 | 2 | 2.52 |

TABLE 46
| Chemical Structure | Compound No. | MS [M + H]⁺ | LC method | LC/MS retention time (min) |
|---|---|---|---|---|
| 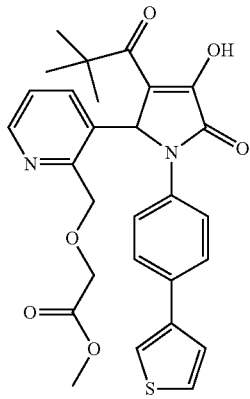 [SMILES: COC(=O)COCc1ncccc1C1C(C(=O)C(C)(C)C)=C(O)C(=O)N1c1ccc(-c2ccsc2)cc1] | I-181 | 521 | 1 | 1.79 |
| 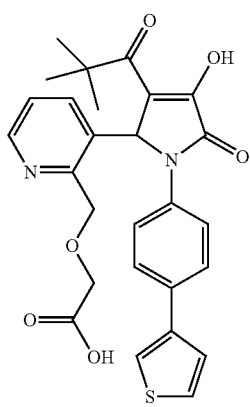 [SMILES: CC(C)(C)C(=O)C1=C(O)C(=O)N(c2ccc(-c3ccsc3)cc2)C1c1cccnc1COCC(=O)O] | I-182 | 507 | 1 | 1.51 |
| 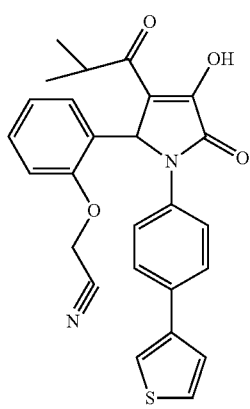 [SMILES: CC(C)C(=O)C1=C(O)C(=O)N(c2ccc(-c3ccsc3)cc2)C1c1ccccc1OCC#N] | I-183 | 459 | 1 | 2.11 |

TABLE 46-continued

| Chemical Structure | Compound No. | MS [M + H]+ | LC method | LC/MS retention time (min) |
|---|---|---|---|---|
| 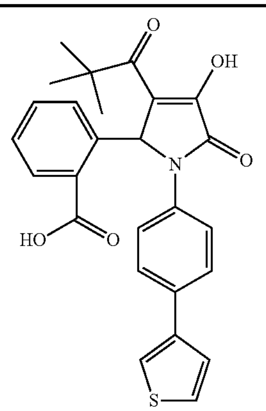 | I-184 | 462 | 1 | 2.05 |
| 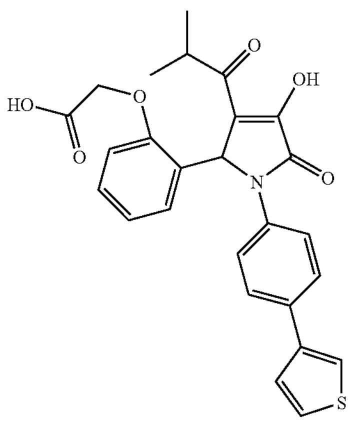 [SMILES: CC(C)C(=O)C1=C(O)C(=O)N(c2ccc(-c3ccsc3)cc2)C1c1ccccc1OCC(=O)O] | I-185 | 478 | 1 | 1.90 |

TABLE 47

| Chemical Structure | Compound No. | MS [M + H]+ | LC method | LC/MS retention time (min) |
|---|---|---|---|---|
| 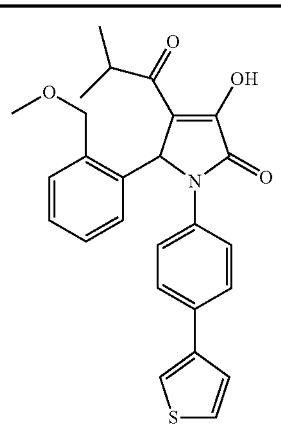 | I-186 | 448 | 2 | 2.56 |

TABLE 47-continued

| Chemical Structure | Compound No. | MS [M + H]⁺ | LC method | LC/MS retention time (min) |
|---|---|---|---|---|
| 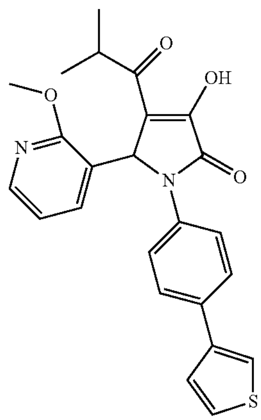 [SMILES: COc1ncccc1C1C(C(=O)C(C)C)=C(O)C(=O)N1c1ccc(-c2ccsc2)cc1] | I-187 | 435 | 1 | 2.10 |
| 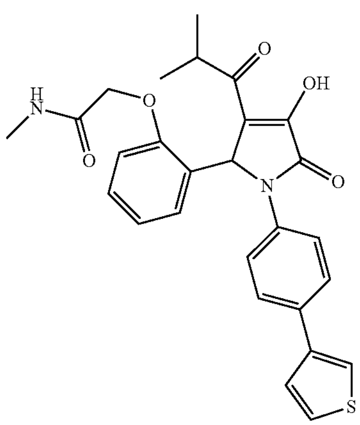 [SMILES: CNC(=O)COc1ccccc1C1C(C(=O)C(C)C)=C(O)C(=O)N1c1ccc(-c2ccsc2)cc1] | I-188 | 491 | 1 | 2.00 |
| 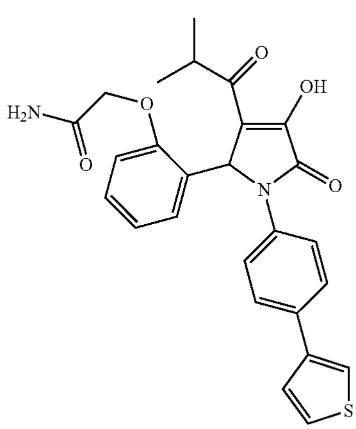 [SMILES: CC(C)C(=O)C1=C(O)C(=O)N(c2ccc(-c3ccsc3)cc2)C1c1ccccc1OCC(N)=O] | I-189 | 477 | 1 | 1.80 |

TABLE 47-continued
| Chemical Structure | Compound No. | MS [M + H]+ | LC method | LC/MS retention time (min) |
|---|---|---|---|---|
| 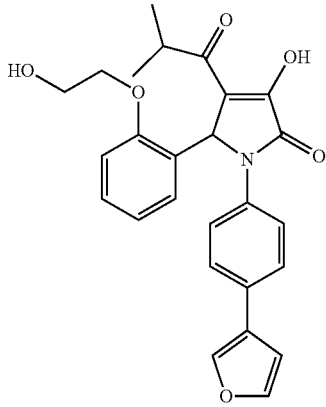 [SMILES: CC(C)C(=O)C1=C(O)C(=O)N(c2ccc(-c3ccoc3)cc2)C1c1ccccc1OCCO] | I-190 | 448 | 2 | 2.15 |
TABLE 48
| Chemical Structure | Compound No. | MS [M + H]+ | LC method | LC/MS retention time (min) |
|---|---|---|---|---|
| 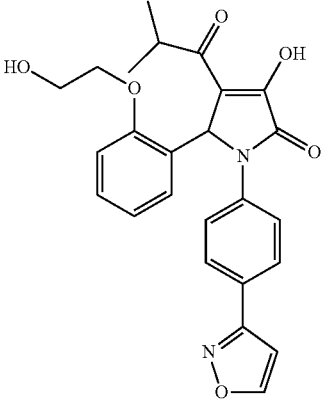 [SMILES: CC(C)C(=O)C1=C(O)C(=O)N(c2ccc(-c3ccon3)cc2)C1c1ccccc1OCCO] | I-191 | 449 | 2 | 1.87 |
| 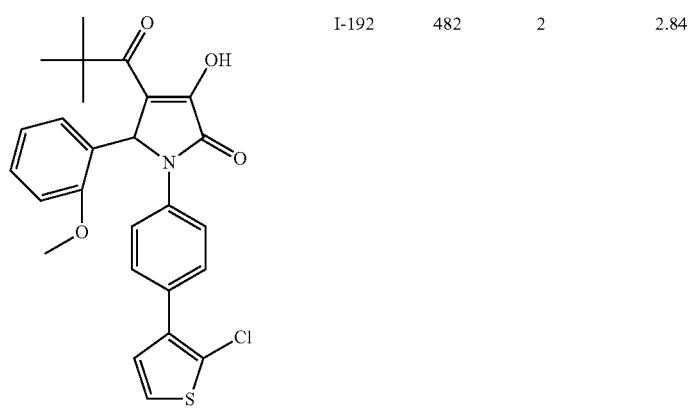 | I-192 | 482 | 2 | 2.84 |

TABLE 48-continued

| Chemical Structure | Compound No. | MS [M + H]+ | LC method | LC/MS retention time (min) |
|---|---|---|---|---|
| 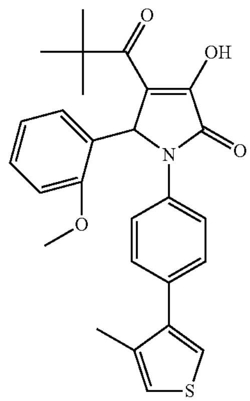 [SMILES: COc1ccccc1C1C(C(=O)C(C)(C)C)=C(O)C(=O)N1c1ccc(-c2cscc2C)cc1] | I-193 | 462 | 2 | 2.80 |
| 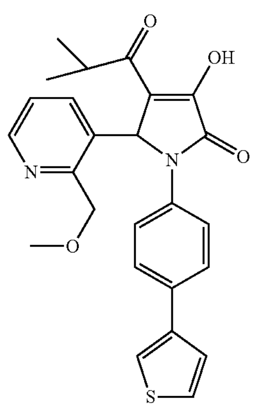 [SMILES: COCc1ncccc1C1C(C(=O)C(C)C)=C(O)C(=O)N1c1ccc(-c2ccsc2)cc1] | I-194 | 449 | 1 | 1.53 |
| 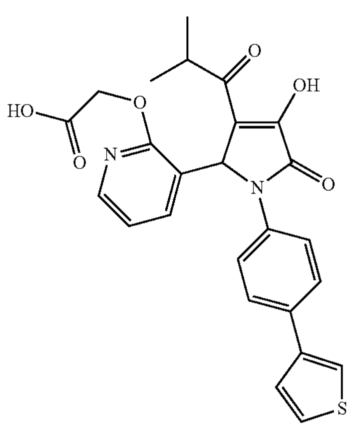 [SMILES: CC(C)C(=O)C1=C(O)C(=O)N(c2ccc(-c3ccsc3)cc2)C1c1cccnc1OCC(=O)O] | I-195 | 479 | 1 | 1.80 |

TABLE 49
| Chemical Structure | Compound No. | MS [M + H]+ | LC method | LC/MS retention time (min) |
|---|---|---|---|---|
| 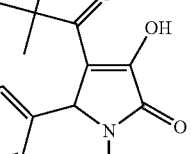 | I-196 | 476 | 2 | 2.52 |
| 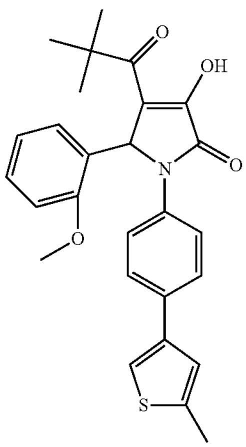 [SMILES: COc1ccccc1C1C(C(=O)C(C)(C)C)=C(O)C(=O)N1c1ccc(-c2csc(C)c2)cc1] | I-197 | 462 | 2 | 2.83 |
| 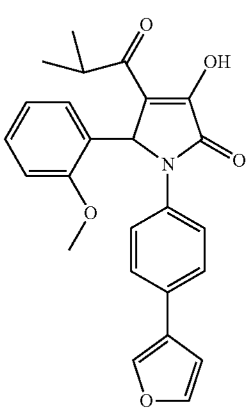 [SMILES: COc1ccccc1C1C(C(=O)C(C)C)=C(O)C(=O)N1c1ccc(-c2ccoc2)cc1] | I-198 | 418 | 1 | 2.16 |

TABLE 49-continued

| Chemical Structure | Compound No. | MS [M + H]+ | LC method | LC/MS retention time (min) |
|---|---|---|---|---|
| 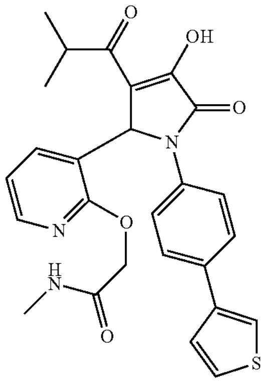 [SMILES: CNC(=O)COc1ncccc1C1C(C(=O)C(C)C)=C(O)C(=O)N1c1ccc(-c2ccsc2)cc1] | I-199 | 492 | 1 | 1.90 |
| 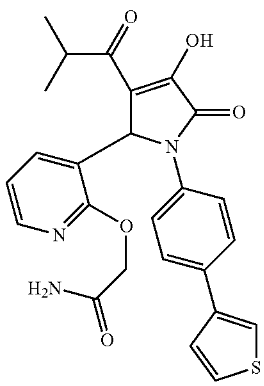 [SMILES: CC(C)C(=O)C1=C(O)C(=O)N(c2ccc(-c3ccsc3)cc2)C1c1cccnc1OCC(N)=O] | I-200 | 478 | 1 | 1.80 |

TABLE 50

| Chemical Structure | Compound No. | MS [M + H]+ | LC method | LC/MS retention time (min) |
|---|---|---|---|---|
| 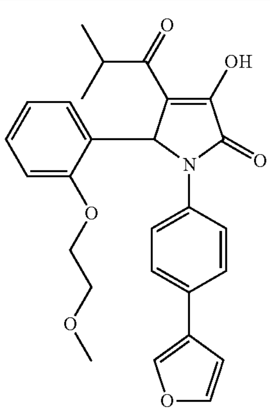 [SMILES: COCCOc1ccccc1C1C(C(=O)C(C)C)=C(O)C(=O)N1c1ccc(-c2ccoc2)cc1] | I-201 | 462 | 1 | 2.14 |

TABLE 50-continued

| Chemical Structure | Compound No. | MS [M + H]+ | LC method | LC/MS retention time (min) |
|---|---|---|---|---|
| 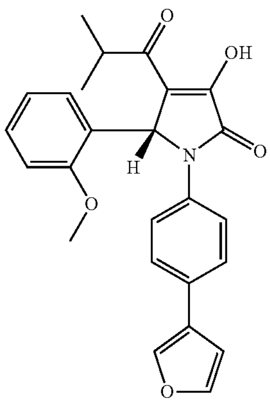 [SMILES: COc1ccccc1[C@@H]1C(C(=O)C(C)C)=C(O)C(=O)N1c1ccc(-c2ccoc2)cc1] | I-202 | 418 | 1 | 2.17 |
| 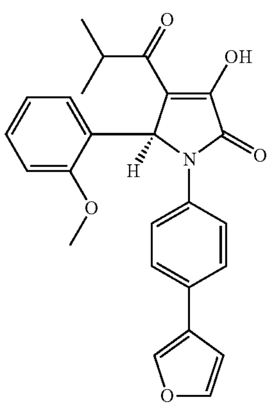 [SMILES: COc1ccccc1[C@H]1C(C(=O)C(C)C)=C(O)C(=O)N1c1ccc(-c2ccoc2)cc1] | I-203 | 418 | 1 | 2.17 |
| 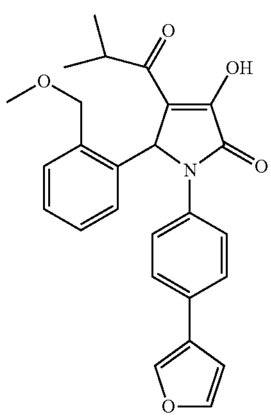 [SMILES: COCc1ccccc1C1C(C(=O)C(C)C)=C(O)C(=O)N1c1ccc(-c2ccoc2)cc1] | I-204 | 432 | 2 | 2.45 |
| 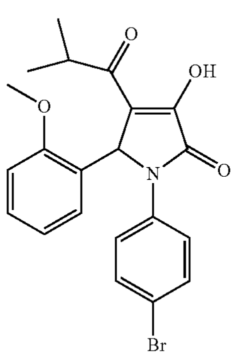 [SMILES: COc1ccccc1C1C(C(=O)C(C)C)=C(O)C(=O)N1c1ccc(Br)cc1] | I-205 | 431 | 2 | 2.48 |

TABLE 51
| Chemical Structure | Compound No. | MS [M + H]+ | LC method | LC/MS retention time (min) |
|---|---|---|---|---|
| 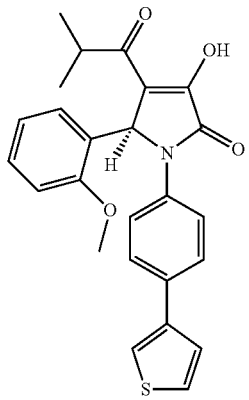 [SMILES: COc1ccccc1[C@H]1C(C(=O)C(C)C)=C(O)C(=O)N1c1ccc(-c2ccsc2)cc1] | I-206 | 434 | 2 | 2.58 |
| 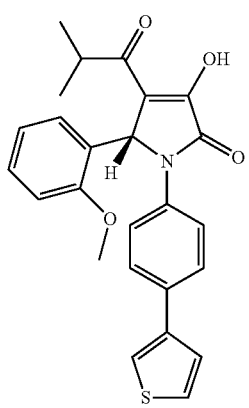 [SMILES: COc1ccccc1[C@@H]1C(C(=O)C(C)C)=C(O)C(=O)N1c1ccc(-c2ccsc2)cc1] | I-207 | 434 | 2 | 2.58 |
| 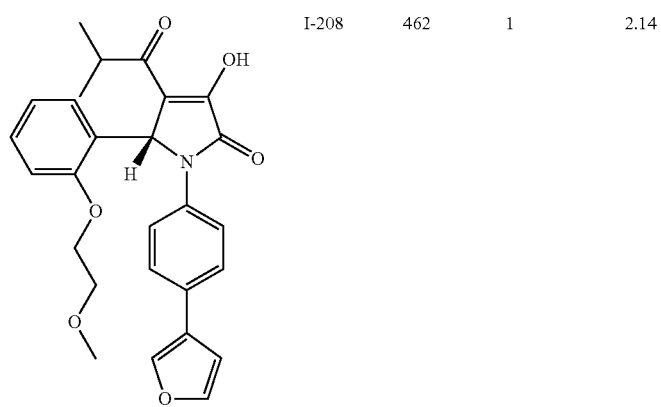 | I-208 | 462 | 1 | 2.14 |

TABLE 51-continued

| Chemical Structure | Compound No. | MS [M + H]+ | LC method | LC/MS retention time (min) |
|---|---|---|---|---|
| 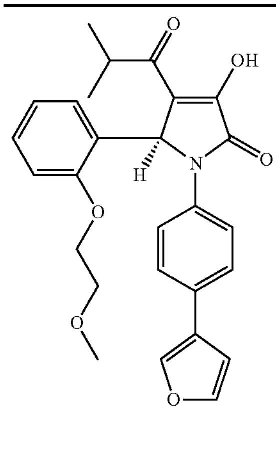 | I-209 | 462 | 1 | 2.14 |
| 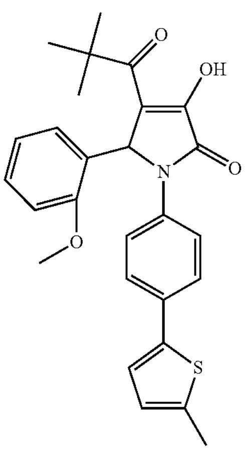 [SMILES: COc1ccccc1C1C(C(=O)C(C)(C)C)=C(O)C(=O)N1c1ccc(-c2ccc(C)s2)cc1] | I-210 | 462 | 2 | 2.87 |

TABLE 52

| Chemical Structure | Compound No. | MS [M + H]+ | LC method | LC/MS retention time (min) |
|---|---|---|---|---|
| 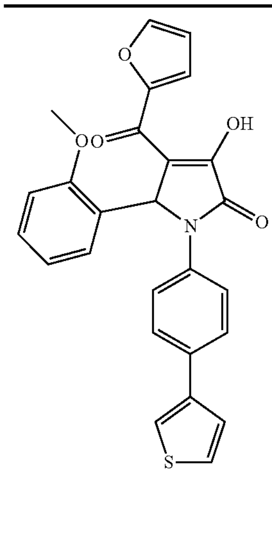 | I-211 | 458 | 2 | 2.38 |

TABLE 52-continued
| Chemical Structure | Compound No. | MS [M + H]+ | LC method | LC/MS retention time (min) |
| --- | --- | --- | --- | --- |
| 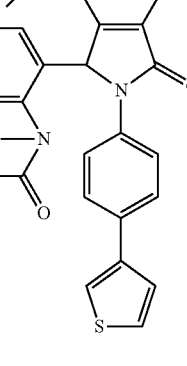 | I-212 | 475 | 1 | 1.90 |
| 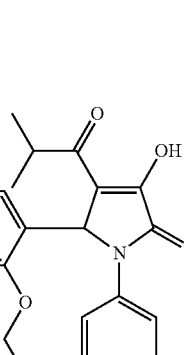 | I-213 | 464 | 1 | 2.29 |
| 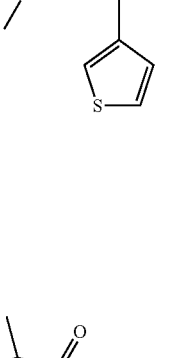 | I-214 | 434 | 2 | 2.57 |

TABLE 52-continued
| Chemical Structure | Compound No. | MS [M + H]+ | LC method | LC/MS retention time (min) |
|---|---|---|---|---|
| 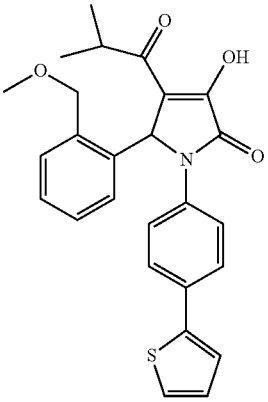 [SMILES: COCc1ccccc1C1C(C(=O)C(C)C)=C(O)C(=O)N1c1ccc(-c2cccs2)cc1] | I-215 | 448 | 2 | 2.59 |
TABLE 53
| Chemical Structure | Compound No. | MS [M + H]+ | LC method | LC/MS retention time (min) |
|---|---|---|---|---|
| 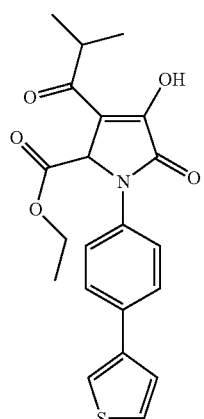 | I-216 | 400 | 2 | 2.47 |
| 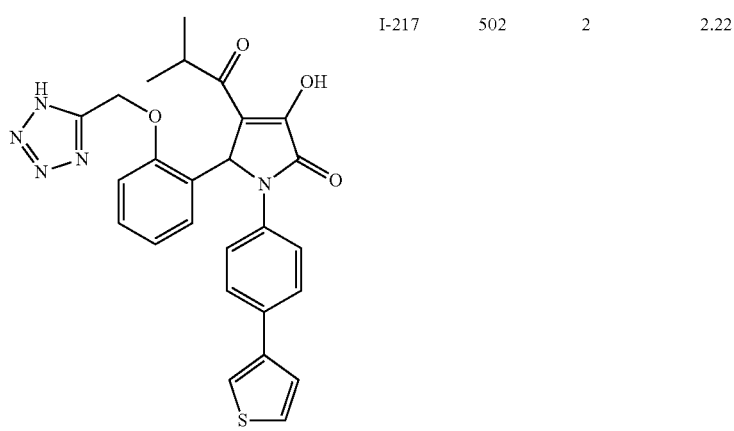 | I-217 | 502 | 2 | 2.22 |

TABLE 53-continued
| Chemical Structure | Compound No. | MS [M + H]+ | LC method | LC/MS retention time (min) |
|---|---|---|---|---|
| 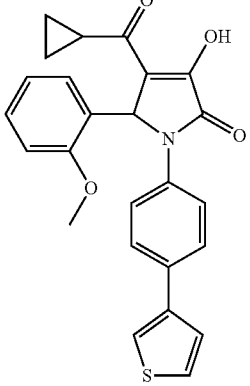 | I-218 | 432 | 1 | 2.20 |
| 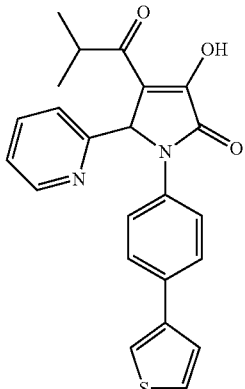 | I-219 | 405 | 2 | 2.28 |
| 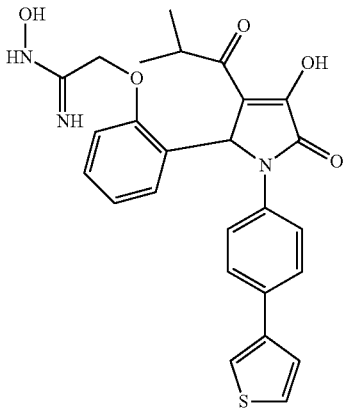 | I-220 | 492 | 2 | 1.84 |

TABLE 54

| Chemical Structure | Compound No. | MS [M + H]+ | LC method | LC/MS retention time (min) |
|---|---|---|---|---|
| 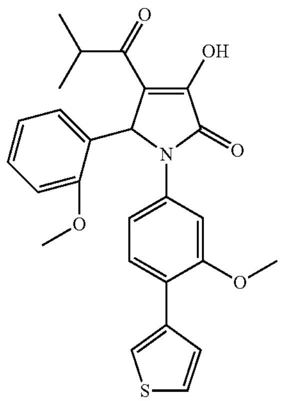 [SMILES: COc1cc(N2C(=O)C(O)=C(C(=O)C(C)C)C2c2ccccc2OC)ccc1-c1ccsc1] | I-221 | 464 | 2 | 2.61 |
| 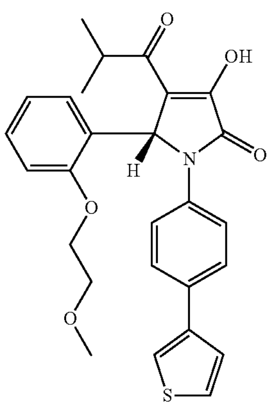 [SMILES: COCCOc1ccccc1[C@@H]1C(C(=O)C(C)C)=C(O)C(=O)N1c1ccc(-c2ccsc2)cc1] | I-222 | 478 | 1 | 2.26 |
| 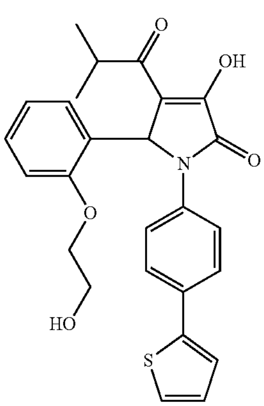 [SMILES: CC(C)C(=O)C1=C(O)C(=O)N(c2ccc(-c3cccs3)cc2)C1c1ccccc1OCCO] | I-223 | 464 | 1 | 2.04 |

TABLE 54-continued

| Chemical Structure | Compound No. | MS [M + H]⁺ | LC method | LC/MS retention time (min) |
|---|---|---|---|---|
| (structure) | I-224 | 418 | 2 | 2.51 |
| (structure) | I-225 | 448 | 2 | 2.21 |

TABLE 55

| Chemical Structure | Compound No. | MS [M + H]⁺ | LC method | LC/MS retention time (min) |
|---|---|---|---|---|
| (structure) | I-226 | 478 | 1 | 2.29 |

TABLE 55-continued

| Chemical Structure | Compound No. | MS [M + H]+ | LC method | LC/MS retention time (min) |
|---|---|---|---|---|
| 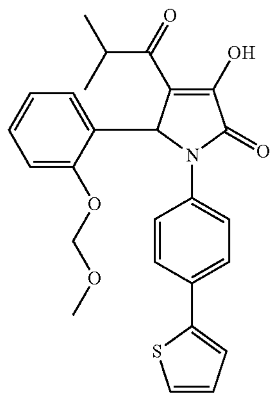 [SMILES: COCOc1ccccc1C1C(C(=O)C(C)C)=C(O)C(=O)N1c1ccc(-c2cccs2)cc1] | I-227 | 464 | 1 | 2.32 |
| 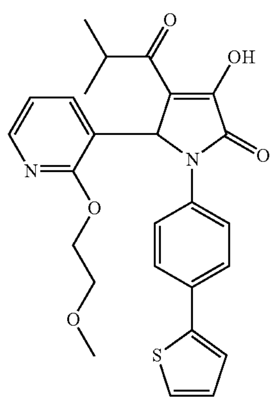 [SMILES: COCCOc1ncccc1C1C(C(=O)C(C)C)=C(O)C(=O)N1c1ccc(-c2cccs2)cc1] | I-228 | 479 | 1 | 2.15 |
| 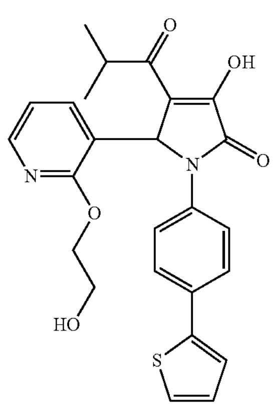 [SMILES: CC(C)C(=O)C1=C(O)C(=O)N(c2ccc(-c3cccs3)cc2)C1c1cccnc1OCCO] | I-229 | 465 | 1 | 1.87 |

TABLE 55-continued
| Chemical Structure | Compound No. | MS [M + H]+ | LC method | LC/MS retention time (min) |
|---|---|---|---|---|
| 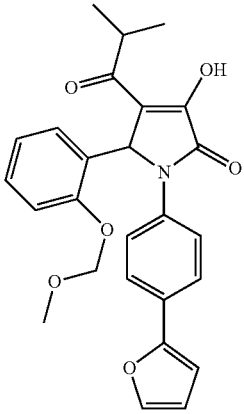 [SMILES: COCOc1ccccc1C1C(C(=O)C(C)C)=C(O)C(=O)N1c1ccc(-c2ccco2)cc1] | I-230 | 448 | 2 | 2.51 |
TABLE 56
| Chemical Structure | Compound No. | MS [M + H]+ | LC method | LC/MS retention time (min) |
|---|---|---|---|---|
| 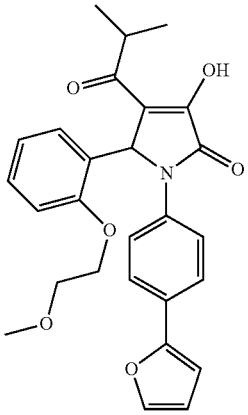 [SMILES: COCCOc1ccccc1C1C(C(=O)C(C)C)=C(O)C(=O)N1c1ccc(-c2ccco2)cc1] | I-231 | 462 | 2 | 2.47 |
| 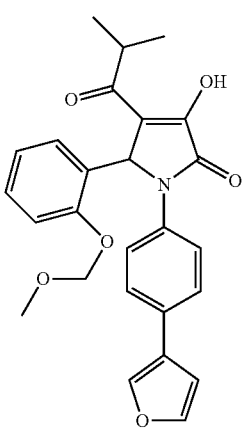 [SMILES: COCOc1ccccc1C1C(C(=O)C(C)C)=C(O)C(=O)N1c1ccc(-c2ccoc2)cc1] | I-232 | 448 | 1 | 2.18 |

TABLE 56-continued

| Chemical Structure | Compound No. | MS [M + H]+ | LC method | LC/MS retention time (min) |
|---|---|---|---|---|
| 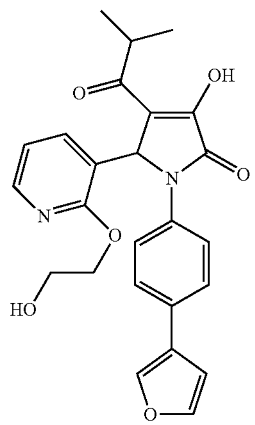 [SMILES: CC(C)C(=O)C1=C(O)C(=O)N(c2ccc(-c3ccoc3)cc2)C1c1cccnc1OCCO] | I-233 | 449 | 2 | 2.00 |
| 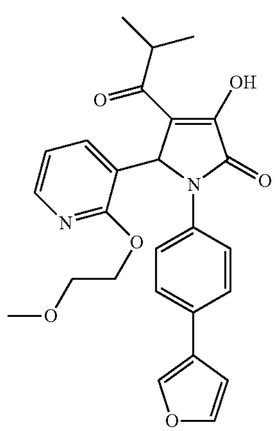 [SMILES: COCCOc1ncccc1C1C(C(=O)C(C)C)=C(O)C(=O)N1c1ccc(-c2ccoc2)cc1] | I-234 | 462 | 1 | 1.99 |
| 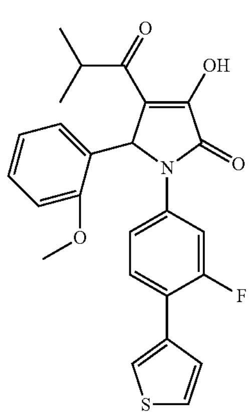 [SMILES: COc1ccccc1C1C(C(=O)C(C)C)=C(O)C(=O)N1c1ccc(-c2ccsc2)c(F)c1] | I-235 | 452 | 2 | 2.67 |

TABLE 57
| Chemical Structure | Compound No. | MS [M + H]+ | LC method | LC/MS retention time (min) |
|---|---|---|---|---|
| 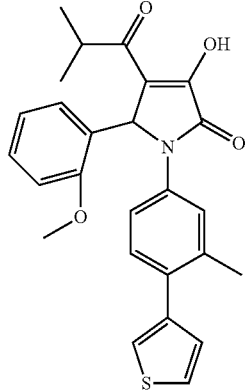 [SMILES: COc1ccccc1C1C(C(=O)C(C)C)=C(O)C(=O)N1c1ccc(-c2ccsc2)c(C)c1] | I-236 | 448 | 2 | 2.66 |
| 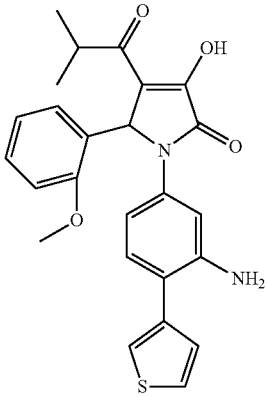 [SMILES: COc1ccccc1C1C(C(=O)C(C)C)=C(O)C(=O)N1c1ccc(-c2ccsc2)c(N)c1] | I-237 | 449 | 2 | 2.38 |
| 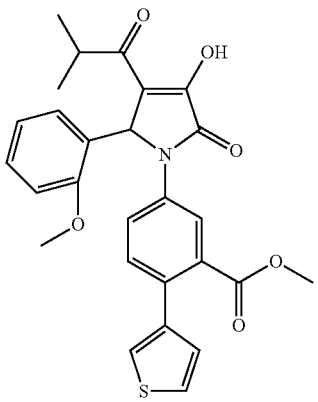 [SMILES: COC(=O)c1cc(N2C(=O)C(O)=C(C(=O)C(C)C)C2c2ccccc2OC)ccc1-c1ccsc1] | I-238 | 492 | 2 | 2.51 |

TABLE 57-continued
| Chemical Structure | Compound No. | MS [M + H]+ | LC method | LC/MS retention time (min) |
|---|---|---|---|---|
| 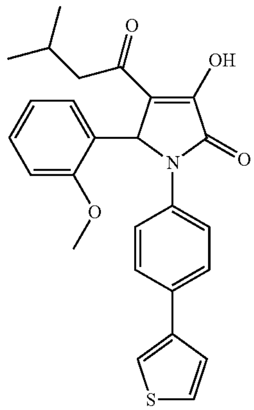 [SMILES: COc1ccccc1C1C(C(=O)CC(C)C)=C(O)C(=O)N1c1ccc(-c2ccsc2)cc1] | I-239 | 448 | 1 | 2.37 |
| 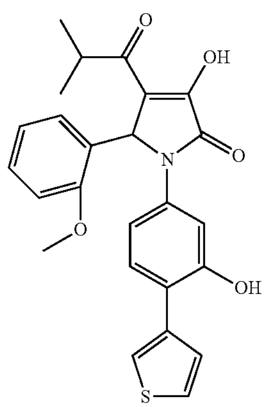 [SMILES: COc1ccccc1C1C(C(=O)C(C)C)=C(O)C(=O)N1c1ccc(-c2ccsc2)c(O)c1] | I-240 | 450 | 1 | 2.09 |
TABLE 58
| Chemical Structure | Compound No. | MS [M + H]+ | LC method | LC/MS retention time (min) |
|---|---|---|---|---|
| 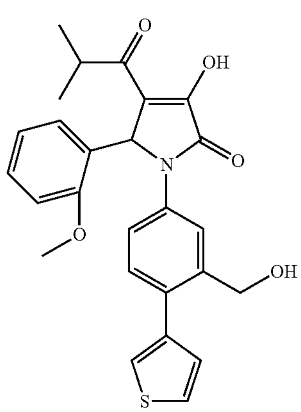 [SMILES: COc1ccccc1C1C(C(=O)C(C)C)=C(O)C(=O)N1c1ccc(-c2ccsc2)c(CO)c1] | I-241 | 464 | 1 | 2.03 |
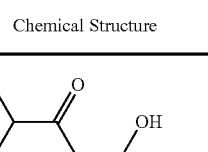

TABLE 58-continued
| Chemical Structure | Compound No. | MS [M + H]+ | LC method | LC/MS retention time (min) |
|---|---|---|---|---|
| 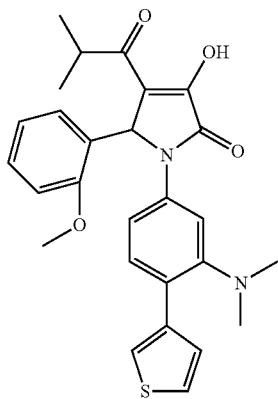 [SMILES: COc1ccccc1C1C(C(=O)C(C)C)=C(O)C(=O)N1c1ccc(-c2ccsc2)c(N(C)C)c1] | I-242 | 477 | 1 | 2.39 |
| 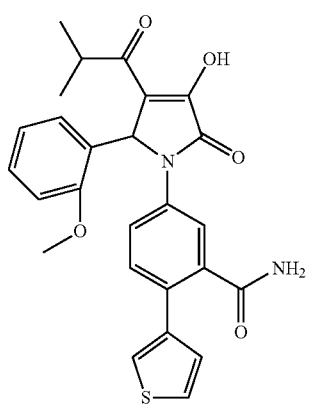 [SMILES: COc1ccccc1C1C(C(=O)C(C)C)=C(O)C(=O)N1c1ccc(-c2ccsc2)c(C(N)=O)c1] | I-243 | 477 | 2 | 2.05 |
| 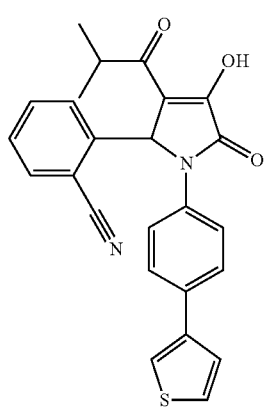 [SMILES: CC(C)C(=O)C1=C(O)C(=O)N(c2ccc(-c3ccsc3)cc2)C1c1ccccc1C#N] | I-244 | 428 | 1 | 2.12 |

TABLE 58-continued

| Chemical Structure | Compound No. | MS [M + H]+ | LC method | LC/MS retention time (min) |
|---|---|---|---|---|
| 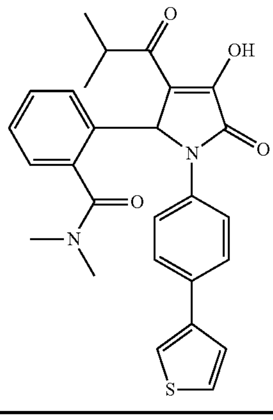 | I-245 | 475 | 1 | 2.10 |

TABLE 59

| Chemical Structure | Compound No. | MS [M + H]+ | LC method | LC/MS retention time (min) |
|---|---|---|---|---|
| 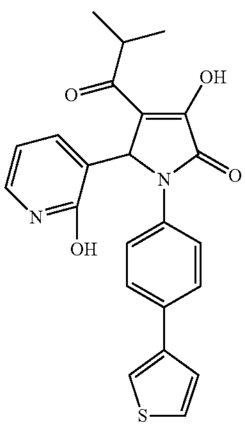 [SMILES: CC(C)C(=O)C1=C(O)C(=O)N(c2ccc(-c3ccsc3)cc2)C1c1cccnc1O] | I-246 | 421 | 2 | 1.87 |
| 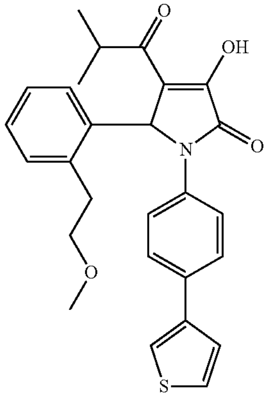 [SMILES: COCCc1ccccc1C1C(C(=O)C(C)C)=C(O)C(=O)N1c1ccc(-c2ccsc2)cc1] | I-247 | 462 | 1 | 2.28 |

TABLE 59-continued

| Chemical Structure | Compound No. | MS [M + H]⁺ | LC method | LC/MS retention time (min) |
|---|---|---|---|---|
| 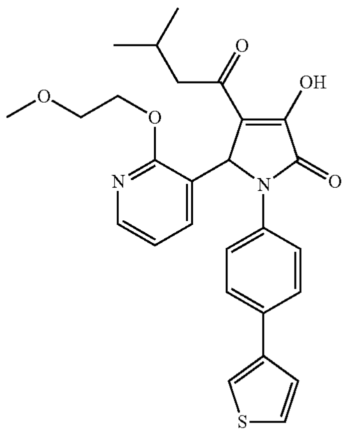 [SMILES: COCCOc1ncccc1C1C(C(=O)CC(C)C)=C(O)C(=O)N1c1ccc(-c2ccsc2)cc1] | I-248 | 493 | 1 | 2.19 |
| 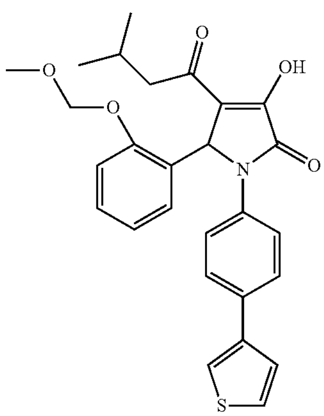 [SMILES: COCOc1ccccc1C1C(C(=O)CC(C)C)=C(O)C(=O)N1c1ccc(-c2ccsc2)cc1] | I-249 | 478 | 1 | 2.38 |
| 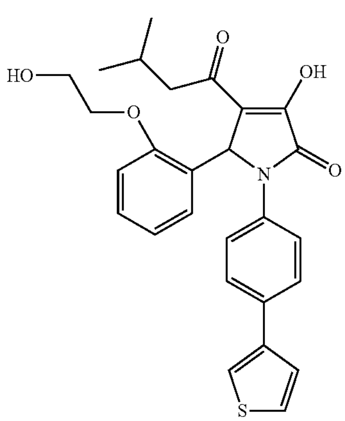 [SMILES: CC(C)CC(=O)C1=C(O)C(=O)N(c2ccc(-c3ccsc3)cc2)C1c1ccccc1OCCO] | I-250 | 478 | 1 | 2.09 |

TABLE 60

| Chemical Structure | Compound No. | MS [M + H]+ | LC method | LC/MS retention time (min) |
|---|---|---|---|---|
| 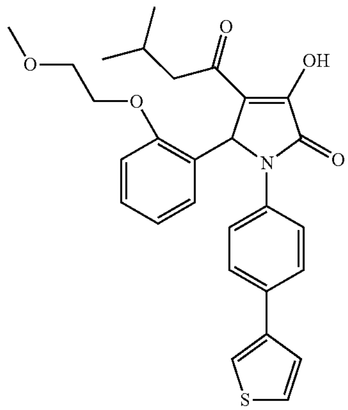 [SMILES: COCCOc1ccccc1C1C(C(=O)CC(C)C)=C(O)C(=O)N1c1ccc(-c2ccsc2)cc1] | I-251 | 492 | 1 | 2.37 |
| 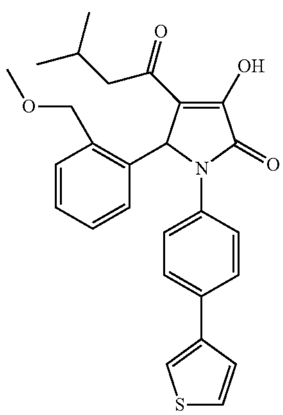 [SMILES: COCc1ccccc1C1C(C(=O)CC(C)C)=C(O)C(=O)N1c1ccc(-c2ccsc2)cc1] | I-252 | 462 | 1 | 2.39 |
| 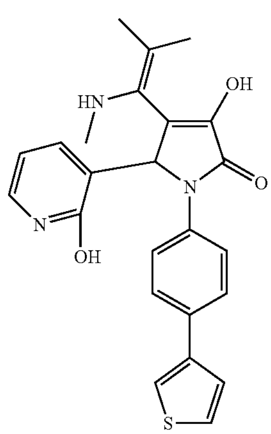 [SMILES: CNC(=C(C)C)C1=C(O)C(=O)N(c2ccc(-c3ccsc3)cc2)C1c1cccnc1O] | I-253 | 434 | 1 | 1.41 |

TABLE 60-continued
| Chemical Structure | Compound No. | MS [M + H]⁺ | LC method | LC/MS retention time (min) |
|---|---|---|---|---|
| 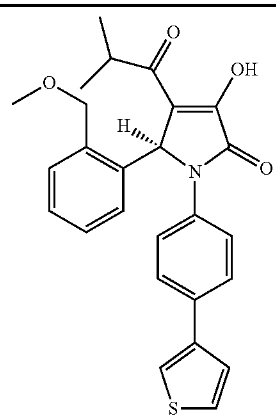 | I-254 | 448 | 2 | 2.59 |
| 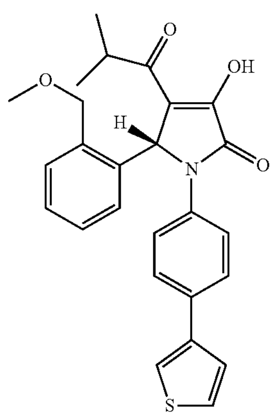 [SMILES: COCc1ccccc1[C@@H]1C(C(=O)C(C)C)=C(O)C(=O)N1c1ccc(-c2ccsc2)cc1] | I-255 | 448 | 2 | 2.59 |
TABLE 61
| Chemical Structure | Compound No. | MS [M + H]⁺ | LC method | LC/MS retention time (min) |
|---|---|---|---|---|
| 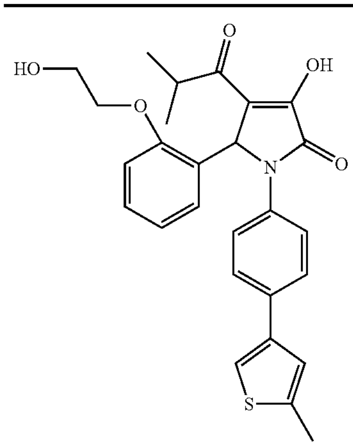 | I-256 | 478 | 1 | 2.14 |
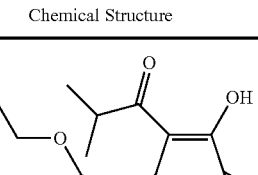

TABLE 61-continued
| Chemical Structure | Compound No. | MS [M + H]+ | LC method | LC/MS retention time (min) |
| --- | --- | --- | --- | --- |
| 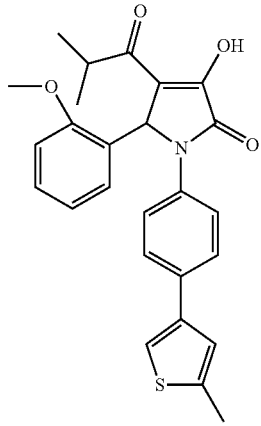 [SMILES: COc1ccccc1C1C(C(=O)C(C)C)=C(O)C(=O)N1c1ccc(-c2csc(C)c2)cc1] | I-257 | 448 | 1 | 2.39 |
| 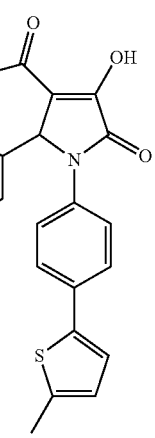 | I-258 | 478 | 1 | 2.16 |
| 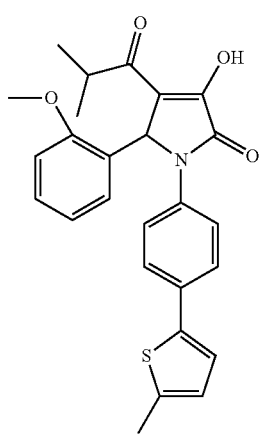 [SMILES: COc1ccccc1C1C(C(=O)C(C)C)=C(O)C(=O)N1c1ccc(-c2ccc(C)s2)cc1] | I-259 | 448 | 1 | 2.42 |

TABLE 61-continued
| Chemical Structure | Compound No. | MS [M + H]+ | LC method | LC/MS retention time (min) |
|---|---|---|---|---|
| 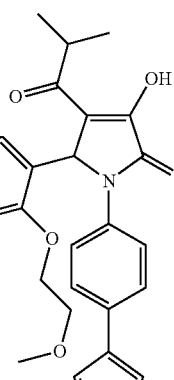 | I-260 | 438 | 2 | 2.33 |
TABLE 62
| Chemical Structure | Compound No. | MS [M + H]+ | LC method | LC/MS retention time (min) |
|---|---|---|---|---|
| 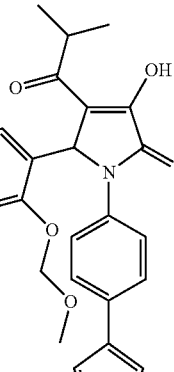 | I-261 | 492 | 2 | 2.70 |
| 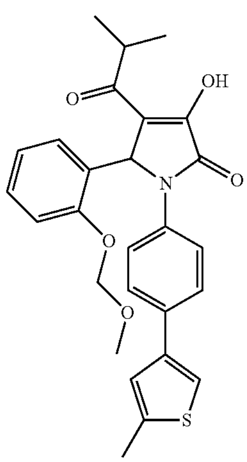 [SMILES: COCOc1ccccc1C1C(C(=O)C(C)C)=C(O)C(=O)N1c1ccc(-c2csc(C)c2)cc1] | I-262 | 478 | 2 | 2.71 |

TABLE 62-continued
| Chemical Structure | Compound No. | MS [M + H]+ | LC method | LC/MS retention time (min) |
|---|---|---|---|---|
| 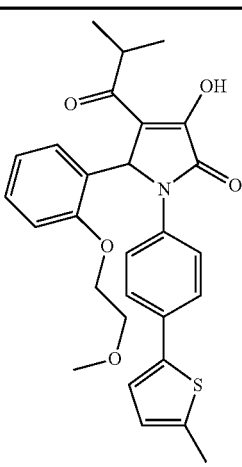 | I-263 | 492 | 2 | 2.73 |
| 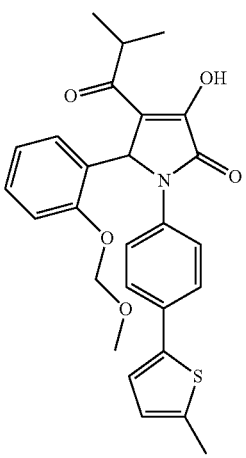 [SMILES: COCOc1ccccc1C1C(C(=O)C(C)C)=C(O)C(=O)N1c1ccc(-c2ccc(C)s2)cc1] | I-264 | 478 | 2 | 2.75 |
| 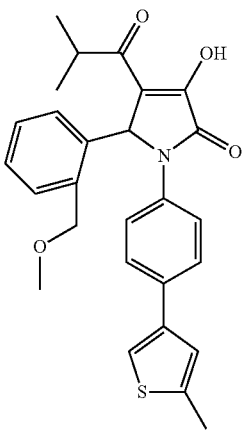 [SMILES: COCc1ccccc1C1C(C(=O)C(C)C)=C(O)C(=O)N1c1ccc(-c2csc(C)c2)cc1] | I-265 | 462 | 2 | 2.73 |

TABLE 63

| Chemical Structure | Compound No. | MS [M + H]+ | LC method | LC/MS retention time (min) |
|---|---|---|---|---|
| 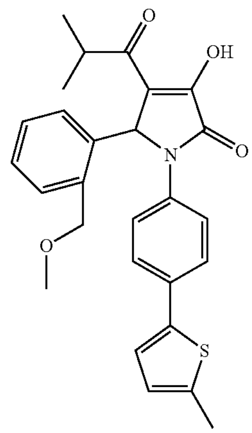 [SMILES: COCc1ccccc1C1C(C(=O)C(C)C)=C(O)C(=O)N1c1ccc(-c2ccc(C)s2)cc1] | I-266 | 462 | 2 | 2.76 |
| 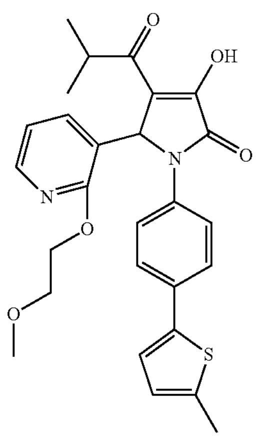 [SMILES: COCCOc1ncccc1C1C(C(=O)C(C)C)=C(O)C(=O)N1c1ccc(-c2ccc(C)s2)cc1] | I-267 | 493 | 2 | 2.60 |
| 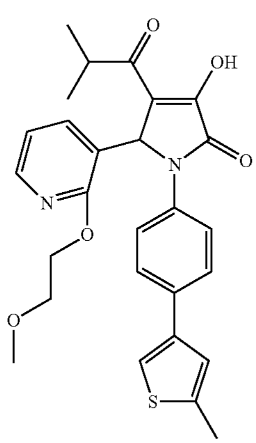 [SMILES: COCCOc1ncccc1C1C(C(=O)C(C)C)=C(O)C(=O)N1c1ccc(-c2csc(C)c2)cc1] | I-268 | 493 | 2 | 2.56 |

TABLE 63-continued
| Chemical Structure | Compound No. | MS [M + H]⁺ | LC method | LC/MS retention time (min) |
|---|---|---|---|---|
| 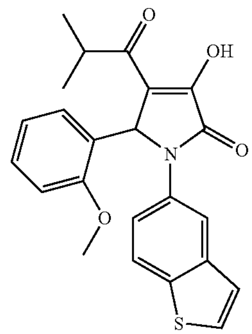 [SMILES: COc1ccccc1C1C(C(=O)C(C)C)=C(O)C(=O)N1c1ccc2sccc2c1] | I-269 | 408 | 2 | 2.42 |
| 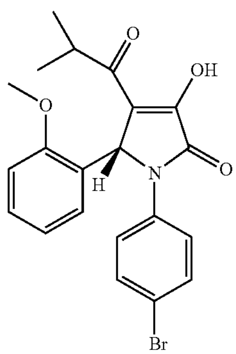 [SMILES: COc1ccccc1[C@@H]1C(C(=O)C(C)C)=C(O)C(=O)N1c1ccc(Br)cc1] | I-270 | 431 | 2 | 2.49 |
TABLE 64
| Chemical Structure | Compound No. | MS [M + H]⁺ | LC method | LC/MS retention time (min) |
|---|---|---|---|---|
| 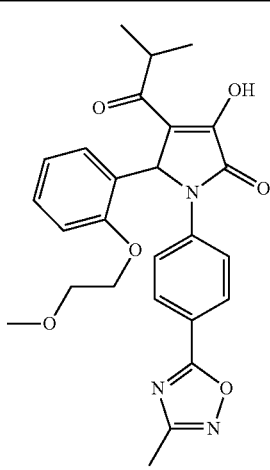 | I-271 | 478 | 1 | 2.02 |

TABLE 64-continued
| Chemical Structure | Compound No. | MS [M + H]+ | LC method | LC/MS retention time (min) |
|---|---|---|---|---|
| 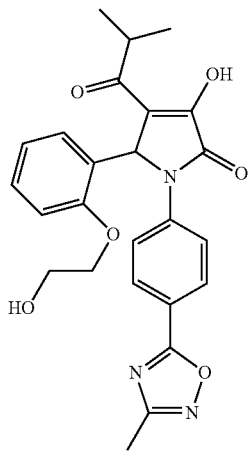 [SMILES: Cc1noc(-c2ccc(N3C(=O)C(O)=C(C(=O)C(C)C)C3c3ccccc3OCCO)cc2)n1] | I-272 | 464 | 1 | 1.73 |
| 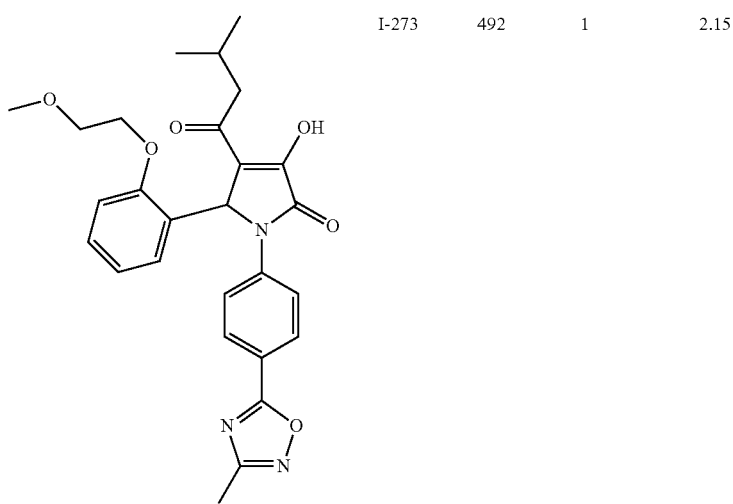 | I-273 | 492 | 1 | 2.15 |
| 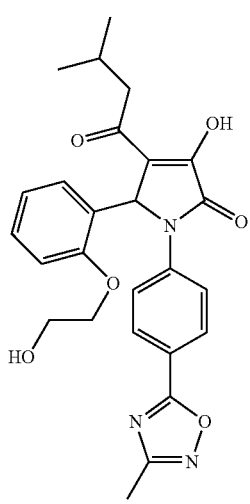 [SMILES: Cc1noc(-c2ccc(N3C(=O)C(O)=C(C(=O)CC(C)C)C3c3ccccc3OCCO)cc2)n1] | I-274 | 478 | 1 | 1.85 |

TABLE 64-continued
| Chemical Structure | Compound No. | MS [M + H]⁺ | LC method | LC/MS retention time (min) |
|---|---|---|---|---|
| 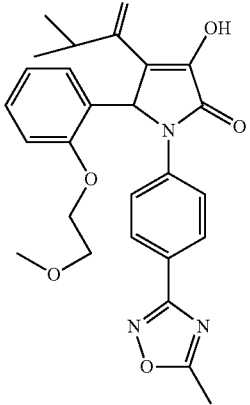 | I-275 | 478 | 1 | 1.97 |
TABLE 65
| Chemical Structure | Compound No. | MS [M + H]⁺ | LC method | LC/MS retention time (min) |
|---|---|---|---|---|
| 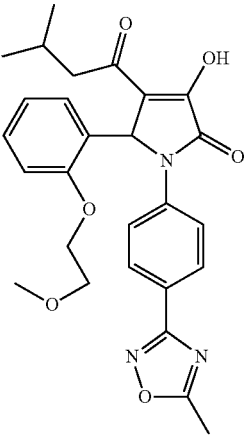 [SMILES: COCCOc1ccccc1C1C(C(=O)CC(C)C)=C(O)C(=O)N1c1ccc(-c2noc(C)n2)cc1] | I-276 | 492 | 1 | 2.12 |
| 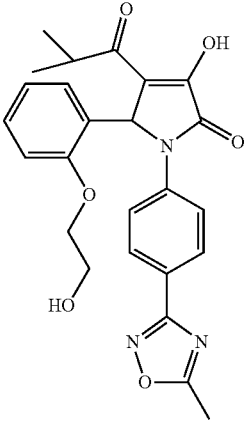 [SMILES: Cc1nc(-c2ccc(N3C(=O)C(O)=C(C(=O)C(C)C)C3c3ccccc3OCCO)cc2)no1] | I-277 | 464 | 1 | 1.72 |

TABLE 65-continued

| Chemical Structure | Compound No. | MS [M + H]+ | LC method | LC/MS retention time (min) |
|---|---|---|---|---|
| 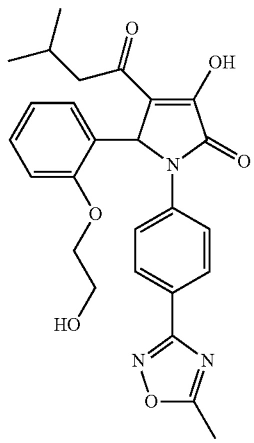 [SMILES: Cc1nc(-c2ccc(N3C(=O)C(O)=C(C(=O)CC(C)C)C3c3ccccc3OCCO)cc2)no1] | I-278 | 478 | 1 | 1.86 |
| 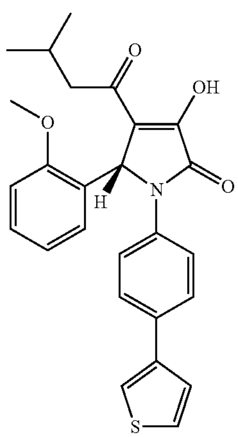 [SMILES: COc1ccccc1[C@@H]1C(C(=O)CC(C)C)=C(O)C(=O)N1c1ccc(-c2ccsc2)cc1] | I-279 | 448 | 2 | 2.68 |
| 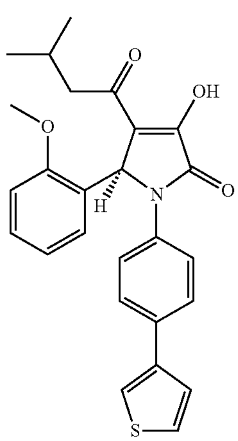 [SMILES: COc1ccccc1[C@H]1C(C(=O)CC(C)C)=C(O)C(=O)N1c1ccc(-c2ccsc2)cc1] | I-280 | 448 | 2 | 2.67 |

TABLE 66

| Chemical Structure | Compound No. | MS [M + H]+ | LC method | LC/MS retention time (min) |
|---|---|---|---|---|
| 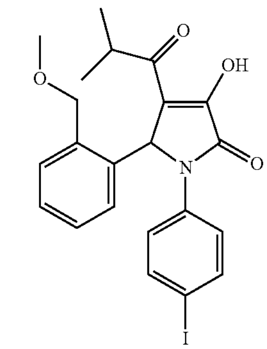 [SMILES: COCc1ccccc1C1C(C(=O)C(C)C)=C(O)C(=O)N1c1ccc(I)cc1] | I-281 | 492 | 1 | 2.30 |
| 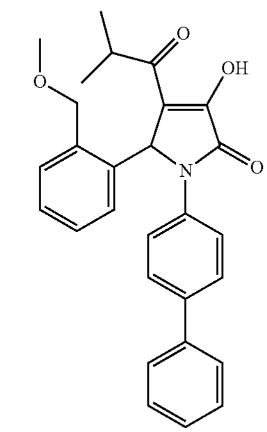 [SMILES: COCc1ccccc1C1C(C(=O)C(C)C)=C(O)C(=O)N1c1ccc(-c2ccccc2)cc1] | I-282 | 442 | 1 | 2.37 |
| 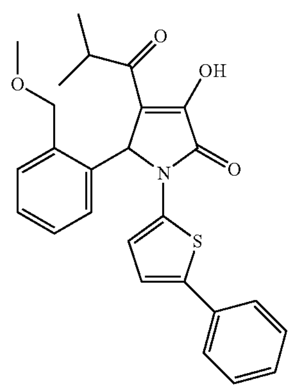 [SMILES: COCc1ccccc1C1C(C(=O)C(C)C)=C(O)C(=O)N1c1ccc(-c2ccccc2)s1] | I-283 | 448 | 1 | 2.40 |
| 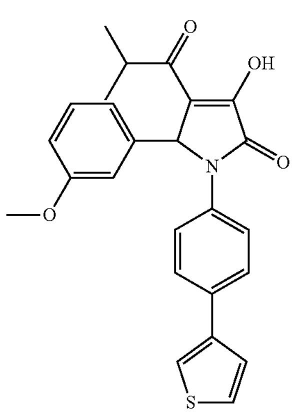 [SMILES: COc1cccc(C2C(C(=O)C(C)C)=C(O)C(=O)N2c2ccc(-c3ccsc3)cc2)c1] | I-284 | 434 | 2 | 2.50 |

TABLE 66-continued

| Chemical Structure | Compound No. | MS [M + H]+ | LC method | LC/MS retention time (min) |
|---|---|---|---|---|
| (structure) | I-285 | 434 | 2 | 2.50 |

TABLE 67

| Chemical Structure | Compound No. | MS [M + H]+ | LC method | LC/MS retention time (min) |
|---|---|---|---|---|
| (structure) | I-286 | 478 | 2 | 2.45 |
| (structure) | I-287 | 442 | 1 | 2.10 |

TABLE 67-continued

| Chemical Structure | Compound No. | MS [M + H]+ | LC method | LC/MS retention time (min) |
|---|---|---|---|---|
| 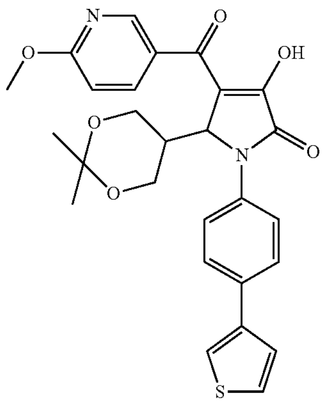 [SMILES: COc1ccc(C(=O)C2=C(O)C(=O)N(c3ccc(-c4ccsc4)cc3)C2C2COC(C)(C)OC2)cn1] | I-288 | 507 | 1 | 2.04 |
| 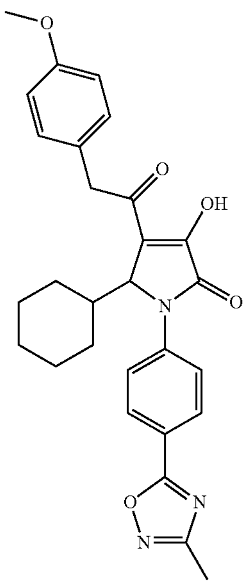 [SMILES: COc1ccc(CC(=O)C2=C(O)C(=O)N(c3ccc(-c4nc(C)no4)cc3)C2C2CCCCC2)cc1] | I-289 | 488 | 2 | 2.63 |
| 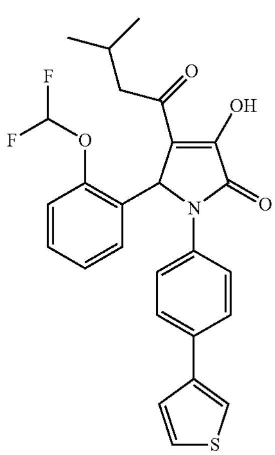 [SMILES: CC(C)CC(=O)C1=C(O)C(=O)N(c2ccc(-c3ccsc3)cc2)C1c1ccccc1OC(F)F] | I-290 | 484 | 1 | 2.44 |

TABLE 68

| Chemical Structure | Compound No. | MS [M + H]+ | LC method | LC/MS retention time (min) |
|---|---|---|---|---|
| 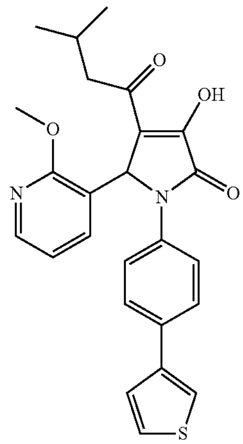 [SMILES: COc1ncccc1C1C(C(=O)CC(C)C)=C(O)C(=O)N1c1ccc(-c2ccsc2)cc1] | I-291 | 449 | 2 | 2.51 |
| 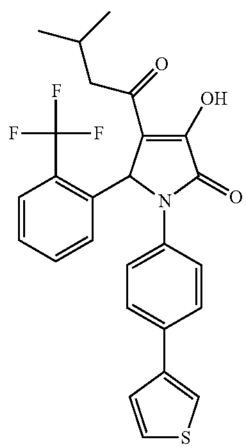 [SMILES: CC(C)CC(=O)C1=C(O)C(=O)N(c2ccc(-c3ccsc3)cc2)C1c1ccccc1C(F)(F)F] | I-292 | 486 | 2 | 2.72 |
| 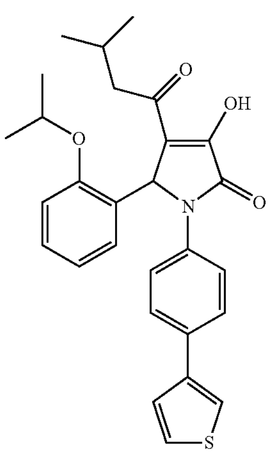 [SMILES: CC(C)CC(=O)C1=C(O)C(=O)N(c2ccc(-c3ccsc3)cc2)C1c1ccccc1OC(C)C] | I-293 | 476 | 2 | 2.87 |

TABLE 68-continued

| Chemical Structure | Compound No. | MS [M + H]+ | LC method | LC/MS retention time (min) |
|---|---|---|---|---|
| 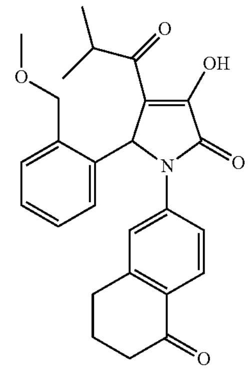 [SMILES: COCc1ccccc1C1C(C(=O)C(C)C)=C(O)C(=O)N1c1ccc2c(c1)CCCC2=O] | I-294 | 434 | 1 | 1.99 |
| 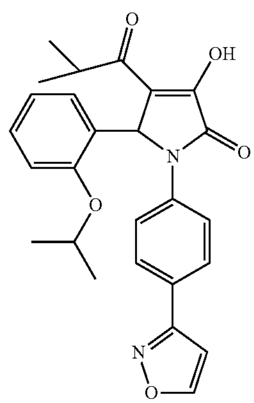 [SMILES: CC(C)Oc1ccccc1C1C(C(=O)C(C)C)=C(O)C(=O)N1c1ccc(-c2ccon2)cc1] | I-295 | 477 | 1 | 2.18 |

TABLE 69

| Chemical Structure | Compound No. | MS [M + H]+ | LC method | LC/MS retention time (min) |
|---|---|---|---|---|
| 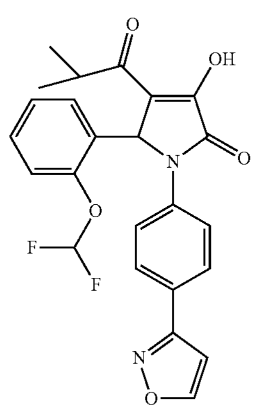 [SMILES: CC(C)C(=O)C1=C(O)C(=O)N(c2ccc(-c3ccon3)cc2)C1c1ccccc1OC(F)F] | I-296 | 430 | 1 | 2.07 |

TABLE 69-continued

| Chemical Structure | Compound No. | MS [M + H]+ | LC method | LC/MS retention time (min) |
|---|---|---|---|---|
| 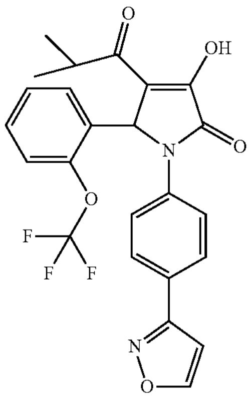 [SMILES: CC(C)C(=O)C1=C(O)C(=O)N(c2ccc(-c3ccon3)cc2)C1c1ccccc1OC(F)(F)F] | I-297 | 473 | 1 | 2.11 |
| 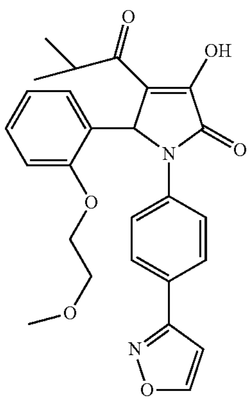 [SMILES: COCCOc1ccccc1C1C(C(=O)C(C)C)=C(O)C(=O)N1c1ccc(-c2ccon2)cc1] | I-298 | 463 | 1 | 1.96 |
| 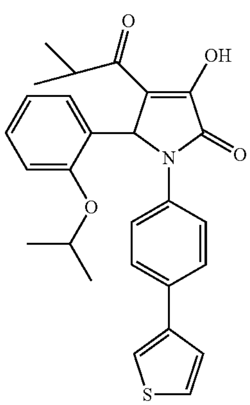 [SMILES: CC(C)Oc1ccccc1C1C(C(=O)C(C)C)=C(O)C(=O)N1c1ccc(-c2ccsc2)cc1] | I-299 | 462 | 1 | 2.48 |
| 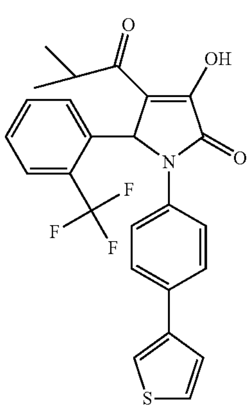 [SMILES: CC(C)C(=O)C1=C(O)C(=O)N(c2ccc(-c3ccsc3)cc2)C1c1ccccc1C(F)(F)F] | I-300 | 472 | 1 | 2.33 |

TABLE 70
| Chemical Structure | Compound No. | MS [M + H]⁺ | LC method | LC/MS retention time (min) |
|---|---|---|---|---|
| 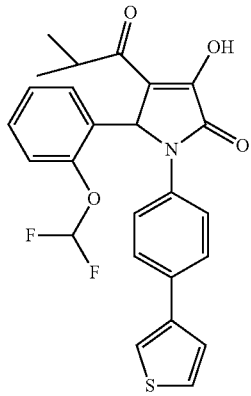 [SMILES: CC(C)C(=O)C1=C(O)C(=O)N(c2ccc(-c3ccsc3)cc2)C1c1ccccc1OC(F)F] | I-301 | 470 | 1 | 2.35 |
| 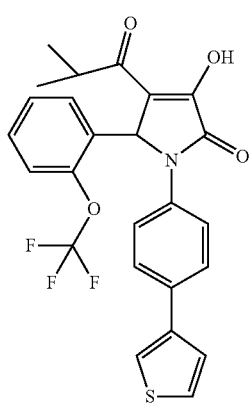 [SMILES: CC(C)C(=O)C1=C(O)C(=O)N(c2ccc(-c3ccsc3)cc2)C1c1ccccc1OC(F)(F)F] | I-302 | 488 | 1 | 2.39 |
| 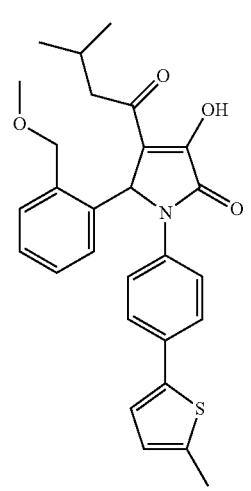 [SMILES: COCc1ccccc1C1C(C(=O)CC(C)C)=C(O)C(=O)N1c1ccc(-c2ccc(C)s2)cc1] | I-303 | 476 | 1 | 2.54 |

TABLE 70-continued

| Chemical Structure | Compound No. | MS [M + H]⁺ | LC method | LC/MS retention time (min) |
|---|---|---|---|---|
| 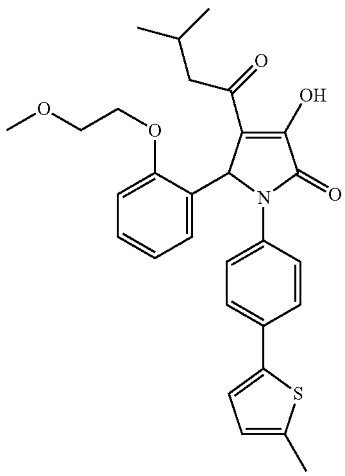 [SMILES: COCCOc1ccccc1C1C(C(=O)CC(C)C)=C(O)C(=O)N1c1ccc(-c2ccc(C)s2)cc1] | I-304 | 506 | 1 | 2.53 |
| 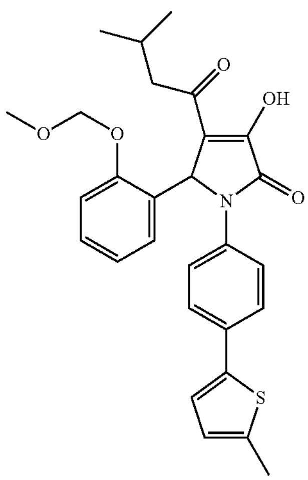 [SMILES: COCOc1ccccc1C1C(C(=O)CC(C)C)=C(O)C(=O)N1c1ccc(-c2ccc(C)s2)cc1] | I-305 | 492 | 1 | 2.51 |

TABLE 71

| Chemical Structure | Compound No. | MS [M + H]⁺ | LC method | LC/MS retention time (min) |
|---|---|---|---|---|
| 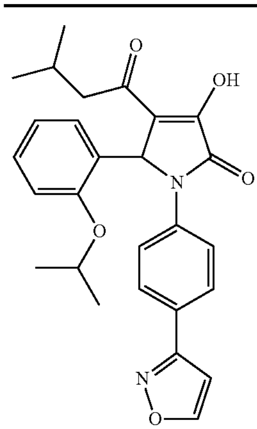 | I-306 | 461 | 1 | 2.27 |

TABLE 71-continued

| Chemical Structure | Compound No. | MS [M + H]+ | LC method | LC/MS retention time (min) |
| --- | --- | --- | --- | --- |
| 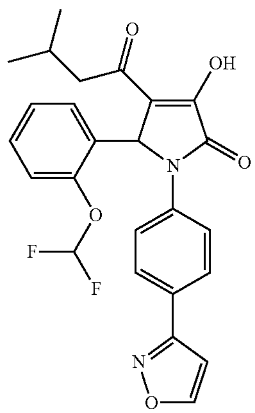 [SMILES: CC(C)CC(=O)C1=C(O)C(=O)N(c2ccc(-c3ccon3)cc2)C1c1ccccc1OC(C)C] | I-307 | 469 | 1 | 2.17 |
| 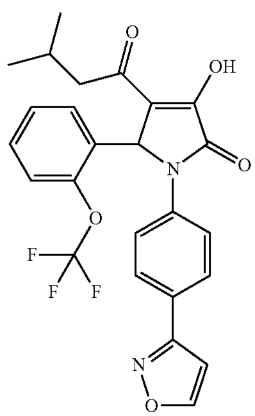 [SMILES: CC(C)CC(=O)C1=C(O)C(=O)N(c2ccc(-c3ccon3)cc2)C1c1ccccc1OC(F)(F)F] | I-308 | 487 | 1 | 2.21 |
| 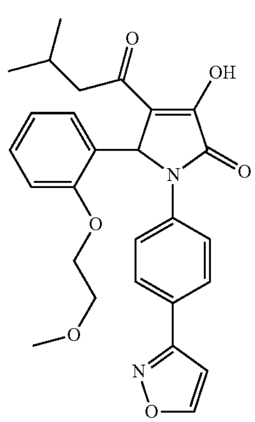 [SMILES: COCCOc1ccccc1C1C(C(=O)CC(C)C)=C(O)C(=O)N1c1ccc(-c2ccon2)cc1] | I-309 | 477 | 1 | 2.09 |

TABLE 71-continued
| Chemical Structure | Compound No. | MS [M + H]⁺ | LC method | LC/MS retention time (min) |
|---|---|---|---|---|
| 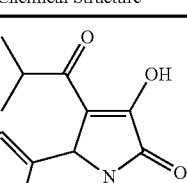 | I-310 | 448 | 2 | 2.29 |
TABLE 72
| Chemical Structure | Compound No. | MS [M + H]⁺ | LC method | LC/MS retention time (min) |
|---|---|---|---|---|
| 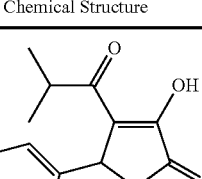 | I-311 | 464 | 2 | 2.28 |
| 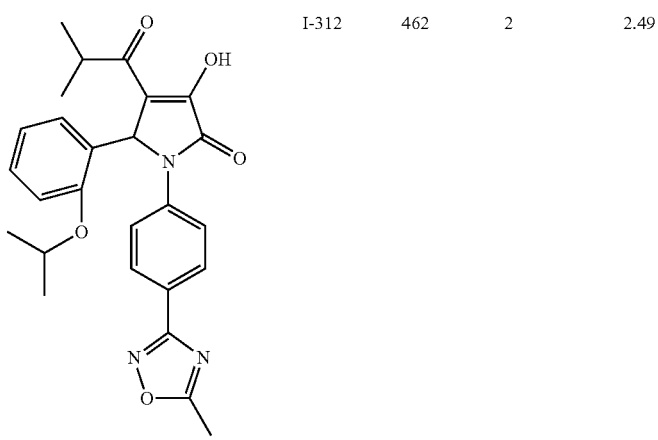 | I-312 | 462 | 2 | 2.49 |

TABLE 72-continued

| Chemical Structure | Compound No. | MS [M + H]+ | LC method | LC/MS retention time (min) |
|---|---|---|---|---|
| 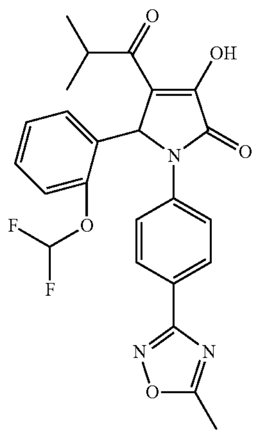 [SMILES: Cc1nc(-c2ccc(N3C(=O)C(O)=C(C(=O)C(C)C)C3c3ccccc3OC(F)F)cc2)no1] | I-313 | 470 | 2 | 2.34 |
| 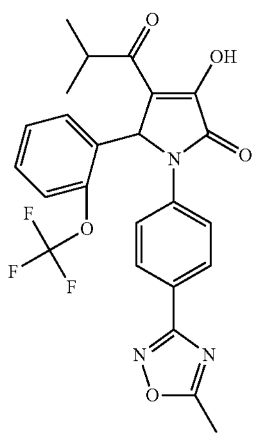 [SMILES: Cc1nc(-c2ccc(N3C(=O)C(O)=C(C(=O)C(C)C)C3c3ccccc3OC(F)(F)F)cc2)no1] | I-314 | 488 | 2 | 2.43 |
| 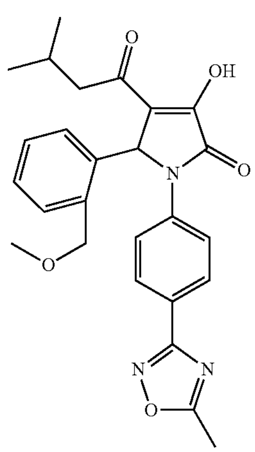 [SMILES: COCc1ccccc1C1C(C(=O)CC(C)C)=C(O)C(=O)N1c1ccc(-c2noc(C)n2)cc1] | I-315 | 462 | 2 | 2.42 |

TABLE 73
| Chemical Structure | Compound No. | MS [M + H]+ | LC method | LC/MS retention time (min) |
|---|---|---|---|---|
| 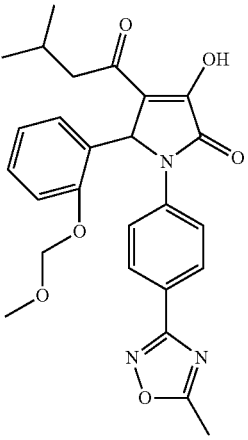 [SMILES: COCOc1ccccc1C1C(C(=O)CC(C)C)=C(O)C(=O)N1c1ccc(-c2noc(C)n2)cc1] | I-316 | 478 | 2 | 2.40 |
| 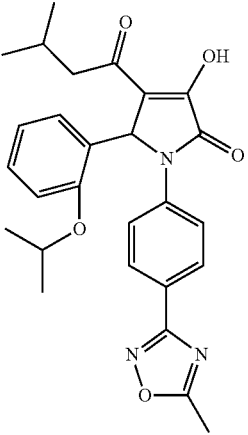 | I-317 | 476 | 2 | 2.61 |
| 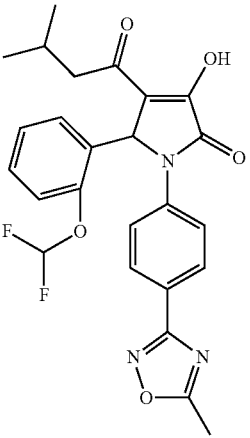 [SMILES: Cc1nc(-c2ccc(N3C(=O)C(O)=C(C(=O)CC(C)C)C3c3ccccc3OC(C)C)cc2)no1] | I-318 | 484 | 2 | 2.45 |

TABLE 73-continued

| Chemical Structure | Compound No. | MS [M + H]⁺ | LC method | LC/MS retention time (min) |
| --- | --- | --- | --- | --- |
| 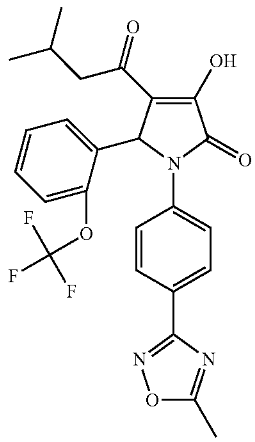 | I-319 | 502 | 2 | 2.54 |
| 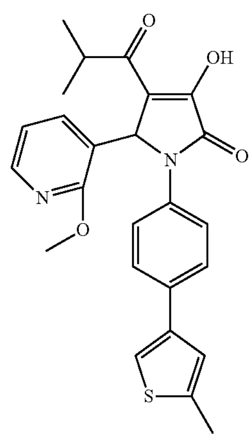 [SMILES: COc1ncccc1C1C(C(=O)C(C)C)=C(O)C(=O)N1c1ccc(-c2csc(C)c2)cc1] | I-320 | 449 | 2 | 2.53 |

TABLE 74

| Chemical Structure | Compound No. | MS [M + H]⁺ | LC method | LC/MS retention time (min) |
| --- | --- | --- | --- | --- |
| 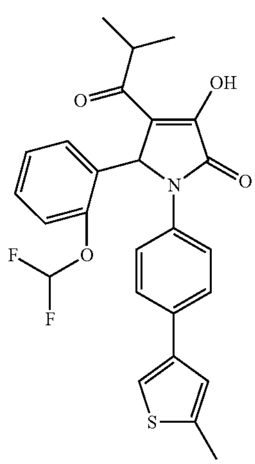 [SMILES: Cc1cc(-c2ccc(N3C(=O)C(O)=C(C(=O)C(C)C)C3c3ccccc3OC(F)F)cc2)cs1] | I-321 | 484 | 2 | 2.73 |

TABLE 74-continued
| Chemical Structure | Compound No. | MS [M + H]+ | LC method | LC/MS retention time (min) |
|---|---|---|---|---|
| 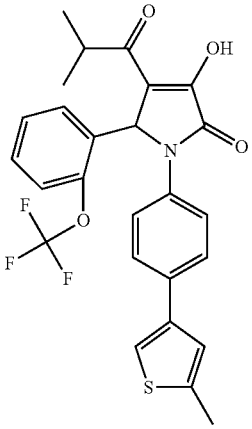 [SMILES: Cc1cc(-c2ccc(N3C(=O)C(O)=C(C(=O)C(C)C)C3c3ccccc3OC(F)(F)F)cc2)cs1] | I-322 | 502 | 2 | 2.80 |
| 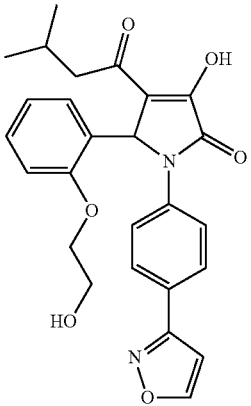 [SMILES: CC(C)CC(=O)C1=C(O)C(=O)N(c2ccc(-c3ccon3)cc2)C1c1ccccc1OCCO] | I-323 | 463 | 1 | 1.83 |
| 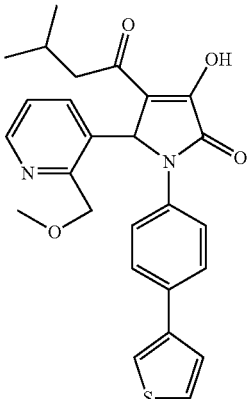 | I-324 | 463 | 1 | 1.69 |

TABLE 74-continued

| Chemical Structure | Compound No. | MS [M + H]+ | LC method | LC/MS retention time (min) |
|---|---|---|---|---|
| 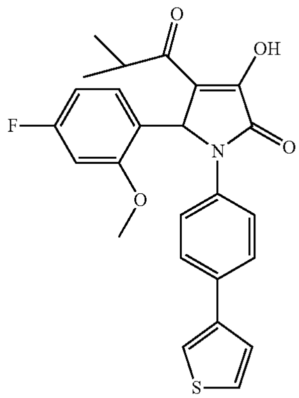 [SMILES: COc1cc(F)ccc1C1C(C(=O)C(C)C)=C(O)C(=O)N1c1ccc(-c2ccsc2)cc1] | I-325 | 452 | 1 | 2.27 |

TABLE 75

| Chemical Structure | Compound No. | MS [M + H]+ | LC method | LC/MS retention time (min) |
|---|---|---|---|---|
| 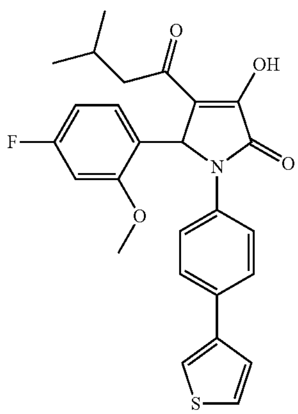 [SMILES: COc1cc(F)ccc1C1C(C(=O)CC(C)C)=C(O)C(=O)N1c1ccc(-c2ccsc2)cc1] | I-326 | 466 | 1 | 2.40 |
| 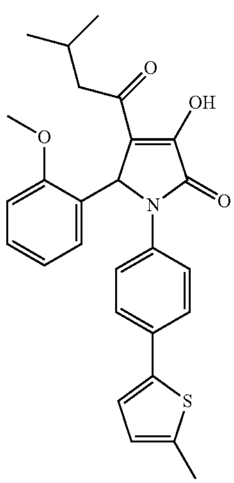 | I-327 | 462 | 1 | 2.52 |

TABLE 75-continued

| Chemical Structure | Compound No. | MS [M + H]+ | LC method | LC/MS retention time (min) |
|---|---|---|---|---|
| 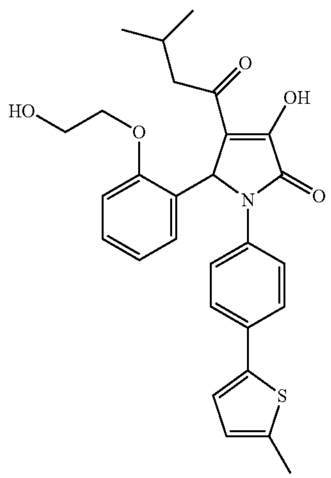 | I-328 | 492 | 1 | 2.27 |
| 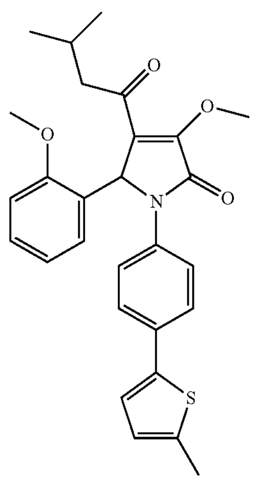 [SMILES: COC1=C(C(=O)CC(C)C)C(c2ccccc2OC)N(c2ccc(-c3ccc(C)s3)cc2)C1=O] | I-329 | 476 | 1 | 2.74 |
| 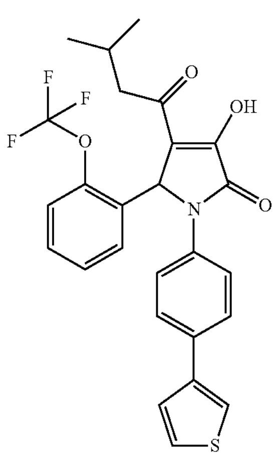 [SMILES: CC(C)CC(=O)C1=C(O)C(=O)N(c2ccc(-c3ccsc3)cc2)C1c1ccccc1OC(F)(F)F] | I-330 | 502 | 1 | 2.51 |

TABLE 76

| Chemical Structure | Compound No. | MS [M + H]⁺ | LC method | LC/MS retention time (min) |
|---|---|---|---|---|
| 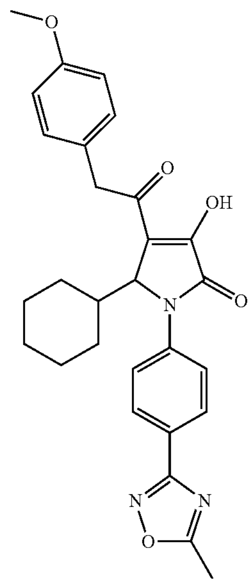 [SMILES: COc1ccc(CC(=O)C2=C(O)C(=O)N(c3ccc(-c4noc(C)n4)cc3)C2C2CCCCC2)cc1] | I-331 | 488 | 2 | 2.61 |
| 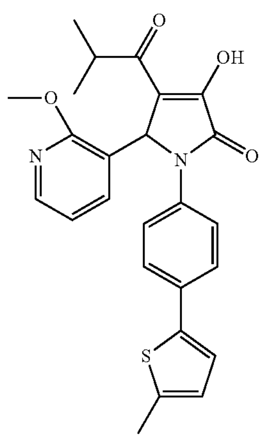 [SMILES: COc1ncccc1C1C(C(=O)C(C)C)=C(O)C(=O)N1c1ccc(-c2ccc(C)s2)cc1] | I-332 | 449 | 1 | 2.26 |
| 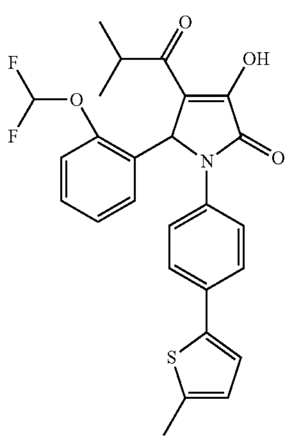 [SMILES: Cc1ccc(-c2ccc(N3C(=O)C(O)=C(C(=O)C(C)C)C3c3ccccc3OC(F)F)cc2)s1] | I-333 | 484 | 1 | 2.50 |

TABLE 76-continued

| Chemical Structure | Compound No. | MS [M + H]+ | LC method | LC/MS retention time (min) |
|---|---|---|---|---|
| 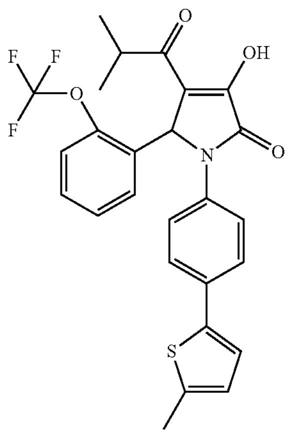 [SMILES: Cc1ccc(-c2ccc(N3C(=O)C(O)=C(C(=O)C(C)C)C3c3ccccc3OC(F)(F)F)cc2)s1] | I-334 | 502 | 1 | 2.55 |
| 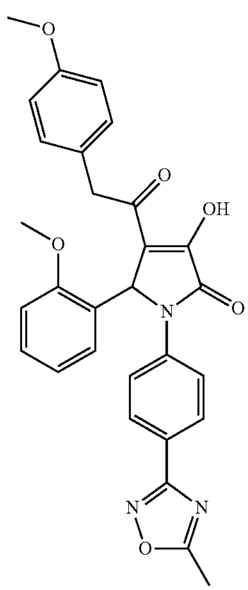 [SMILES: COc1ccc(CC(=O)C2=C(O)C(=O)N(c3ccc(-c4noc(C)n4)cc3)C2c2ccccc2OC)cc1] | I-335 | 512 | 2 | 2.36 |

TABLE 77
| Chemical Structure | Compound No. | MS [M + H]+ | LC method | LC/MS retention time (min) |
|---|---|---|---|---|
| 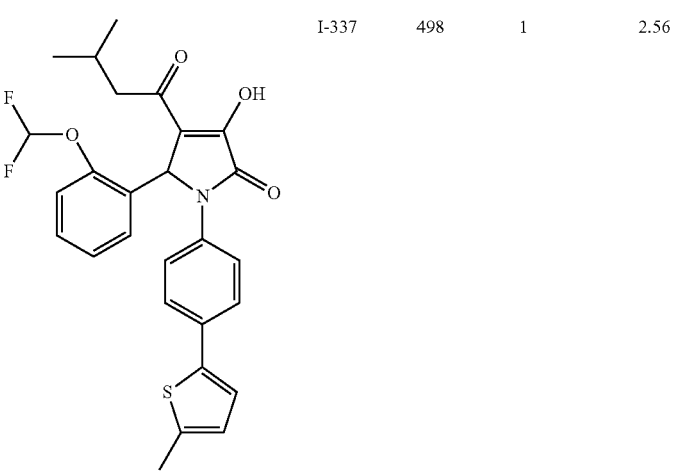 | I-336 | 463 | 1 | 2.40 |
| 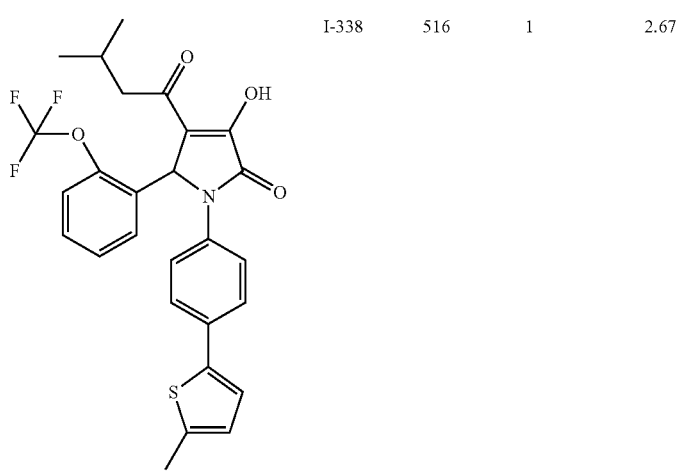 | I-337 | 498 | 1 | 2.56 |
| 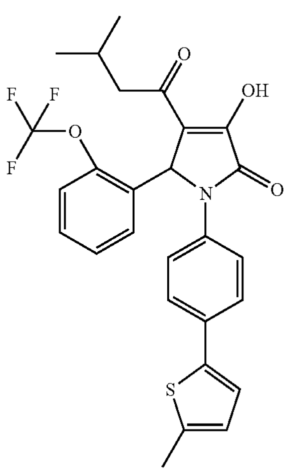 [SMILES: Cc1ccc(-c2ccc(N3C(=O)C(O)=C(C(=O)CC(C)C)C3c3ccccc3OC(F)(F)F)cc2)s1] | I-338 | 516 | 1 | 2.67 |

TABLE 77-continued

| Chemical Structure | Compound No. | MS [M + H]+ | LC method | LC/MS retention time (min) |
|---|---|---|---|---|
| 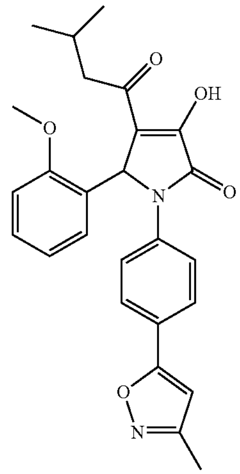 [SMILES: COc1ccccc1C1C(C(=O)CC(C)C)=C(O)C(=O)N1c1ccc(-c2cc(C)no2)cc1] | I-339 | 447 | 2 | 2.47 |
| 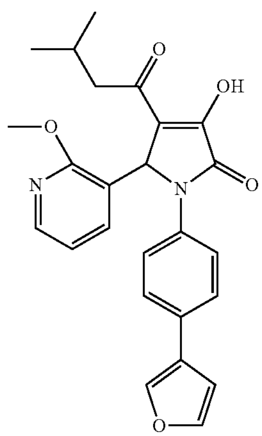 [SMILES: COc1ncccc1C1C(C(=O)CC(C)C)=C(O)C(=O)N1c1ccc(-c2ccoc2)cc1] | I-340 | 433 | 1 | 2.10 |

TABLE 78

| Chemical Structure | Compound No. | MS [M + H]+ | LC method | LC/MS retention time (min) |
|---|---|---|---|---|
| 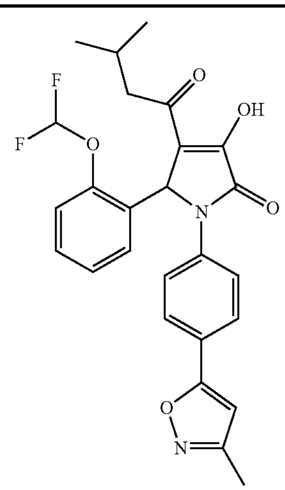 | I-341 | 483 | 2 | 2.53 |

TABLE 78-continued

| Chemical Structure | Compound No. | MS [M + H]⁺ | LC method | LC/MS retention time (min) |
|---|---|---|---|---|
| 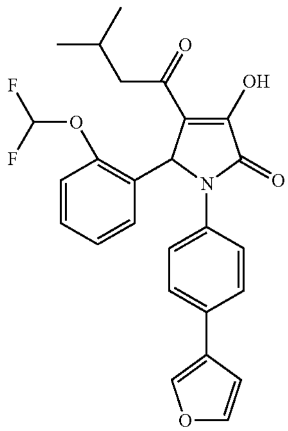 [SMILES: CC(C)CC(=O)C1=C(O)C(=O)N(c2ccc(-c3ccoc3)cc2)C1c1ccccc1OC(F)F] | I-342 | 468 | 1 | 2.30 |
| 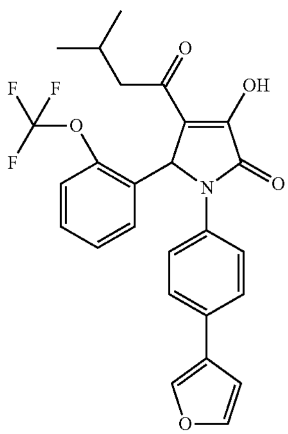 [SMILES: CC(C)CC(=O)C1=C(O)C(=O)N(c2ccc(-c3ccoc3)cc2)C1c1ccccc1OC(F)(F)F] | I-343 | 486 | 1 | 2.40 |
| 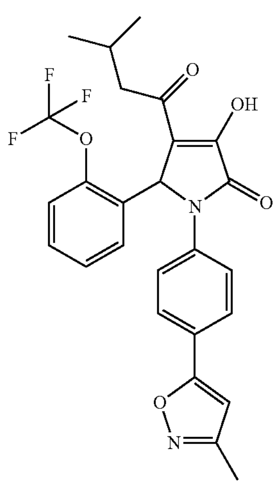 [SMILES: Cc1cc(-c2ccc(N3C(=O)C(O)=C(C(=O)CC(C)C)C3c3ccccc3OC(F)(F)F)cc2)on1] | I-344 | 501 | 2 | 2.59 |

TABLE 78-continued

| Chemical Structure | Compound No. | MS [M + H]+ | LC method | LC/MS retention time (min) |
|---|---|---|---|---|
| 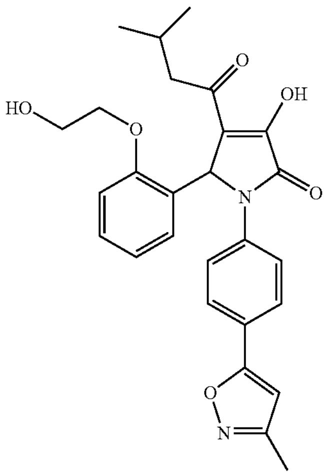 [SMILES: Cc1cc(-c2ccc(N3C(=O)C(O)=C(C(=O)CC(C)C)C3c3ccccc3OCCO)cc2)on1] | I-345 | 477 | 2 | 2.19 |

TABLE 79

| Chemical Structure | Compound No. | MS [M + H]+ | LC method | LC/MS retention time (min) |
|---|---|---|---|---|
| 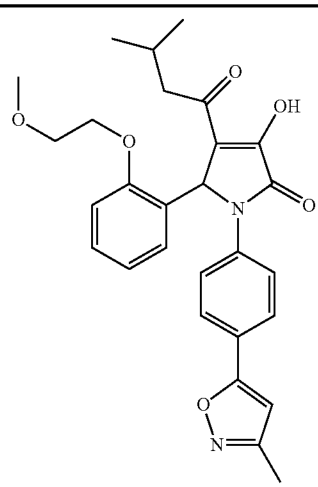 | I-346 | 491 | 2 | 2.46 |
| 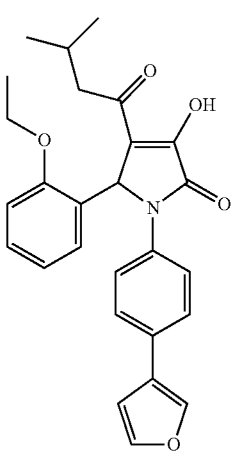 [SMILES: CCOc1ccccc1C1C(C(=O)CC(C)C)=C(O)C(=O)N1c1ccc(-c2ccoc2)cc1] | I-347 | 446 | 1 | 2.25 |

TABLE 79-continued

| Chemical Structure | Compound No. | MS [M + H]⁺ | LC method | LC/MS retention time (min) |
|---|---|---|---|---|
| 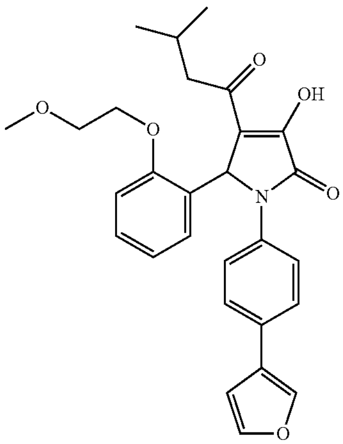 [SMILES: COCCOc1ccccc1C1C(C(=O)CC(C)C)=C(O)C(=O)N1c1ccc(-c2ccoc2)cc1] | I-348 | 476 | 1 | 2.21 |
| 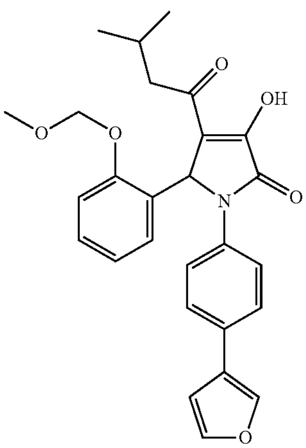 [SMILES: COCOc1ccccc1C1C(C(=O)CC(C)C)=C(O)C(=O)N1c1ccc(-c2ccoc2)cc1] | I-349 | 462 | 1 | 2.26 |
| 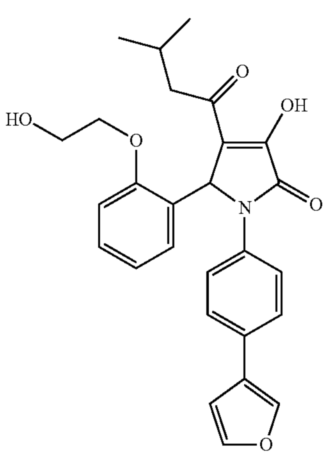 [SMILES: CC(C)CC(=O)C1=C(O)C(=O)N(c2ccc(-c3ccoc3)cc2)C1c1ccccc1OCCO] | I-350 | 462 | 1 | 1.98 |

TABLE 80
| Chemical Structure | Compound No. | MS [M + H]+ | LC method | LC/MS retention time (min) |
| --- | --- | --- | --- | --- |
| 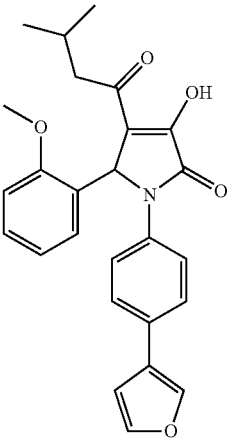 [SMILES: COc1ccccc1C1C(C(=O)CC(C)C)=C(O)C(=O)N1c1ccc(-c2ccoc2)cc1] | I-351 | 432 | 1 | 2.27 |
| 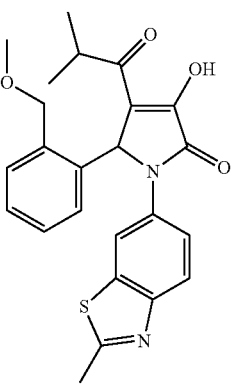 [SMILES: COCc1ccccc1C1C(C(=O)C(C)C)=C(O)C(=O)N1c1ccc2nc(C)sc2c1] | I-352 | 437 | 1 | 1.92 |
| 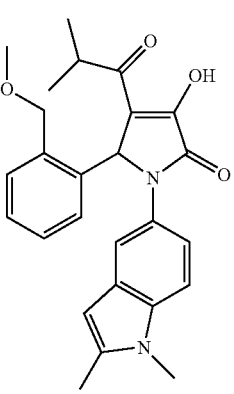 [SMILES: COCc1ccccc1C1C(C(=O)C(C)C)=C(O)C(=O)N1c1ccc2c(c1)cc(C)n2C] | I-353 | 433 | 1 | 2.09 |

TABLE 80-continued

| Chemical Structure | Compound No. | MS [M + H]+ | LC method | LC/MS retention time (min) |
|---|---|---|---|---|
| 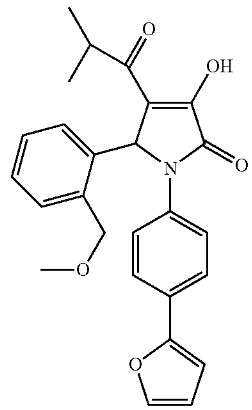 [SMILES: COCc1ccccc1C1C(C(=O)C(C)C)=C(O)C(=O)N1c1ccc(-c2ccco2)cc1] | I-354 | 432 | 2 | 2.53 |
| 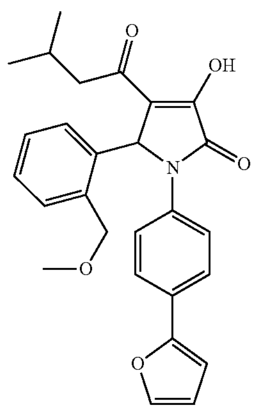 [SMILES: COCc1ccccc1C1C(C(=O)CC(C)C)=C(O)C(=O)N1c1ccc(-c2ccco2)cc1] | I-355 | 446 | 2 | 2.64 |

TABLE 81

| Chemical Structure | Compound No. | MS [M + H]+ | LC method | LC/MS retention time (min) |
|---|---|---|---|---|
| 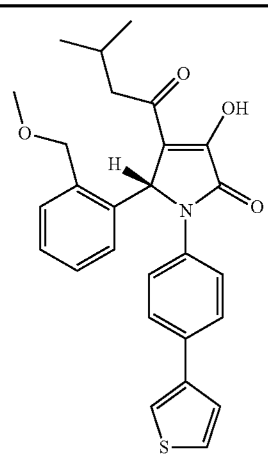 | I-356 | 462 | 2 | 2.67 |

TABLE 81-continued
| Chemical Structure | Compound No. | MS [M + H]+ | LC method | LC/MS retention time (min) |
|---|---|---|---|---|
| 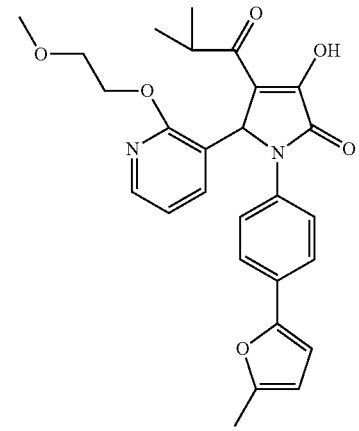 [SMILES: COCCOc1ncccc1C1C(C(=O)C(C)C)=C(O)C(=O)N1c1ccc(-c2ccc(C)o2)cc1] | I-357 | 477 | 1 | 2.16 |
| 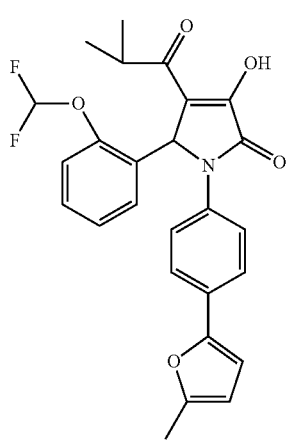 [SMILES: Cc1ccc(-c2ccc(N3C(=O)C(O)=C(C(=O)C(C)C)C3c3ccccc3OC(F)F)cc2)o1] | I-358 | 468 | 1 | 2.41 |
| 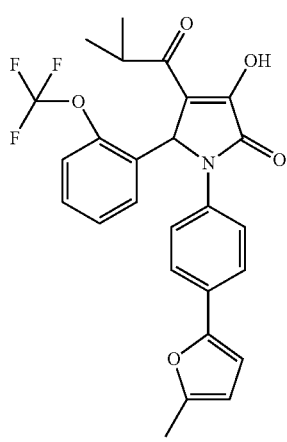 [SMILES: Cc1ccc(-c2ccc(N3C(=O)C(O)=C(C(=O)C(C)C)C3c3ccccc3OC(F)(F)F)cc2)o1] | I-359 | 486 | 1 | 2.46 |

TABLE 81-continued

| Chemical Structure | Compound No. | MS [M + H]+ | LC method | LC/MS retention time (min) |
|---|---|---|---|---|
| 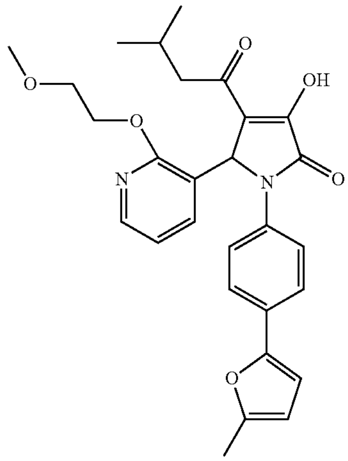 [SMILES: COCCOc1ncccc1C1C(C(=O)CC(C)C)=C(O)C(=O)N1c1ccc(-c2ccc(C)o2)cc1] | I-360 | 491 | 1 | 2.29 |

TABLE 82

| Chemical Structure | Compound No. | MS [M + H]+ | LC method | LC/MS retention time (min) |
|---|---|---|---|---|
| 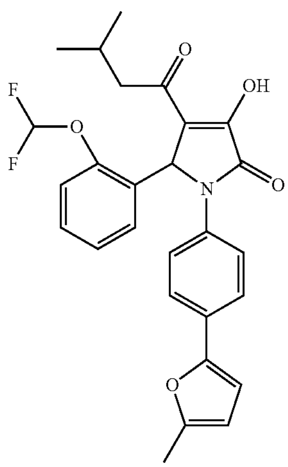 | I-361 | 482 | 1 | 2.47 |
| 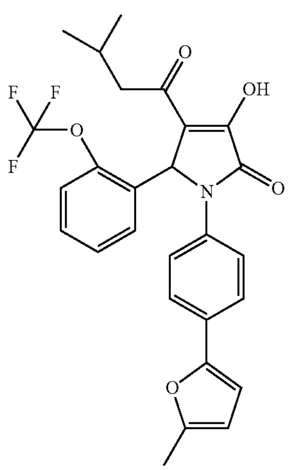 [SMILES: Cc1ccc(-c2ccc(N3C(=O)C(O)=C(C(=O)CC(C)C)C3c3ccccc3OC(F)(F)F)cc2)o1] | I-362 | 500 | 1 | 2.56 |

TABLE 82-continued

| Chemical Structure | Compound No. | MS [M + H]+ | LC method | LC/MS retention time (min) |
|---|---|---|---|---|
| 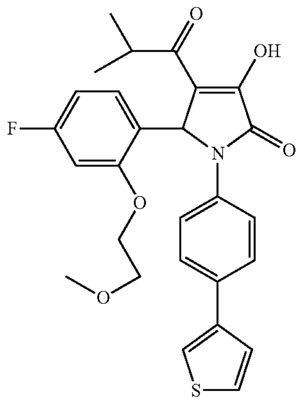 | I-363 | 496 | 1 | 2.26 |
| 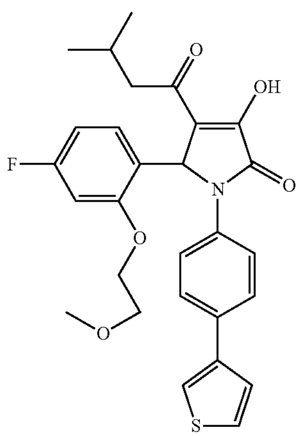 [SMILES: COCCOc1cc(F)ccc1C1C(C(=O)CC(C)C)=C(O)C(=O)N1c1ccc(-c2ccsc2)cc1] | I-364 | 510 | 1 | 2.39 |
| 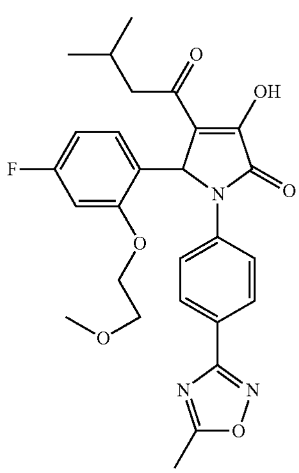 [SMILES: COCCOc1cc(F)ccc1C1C(C(=O)CC(C)C)=C(O)C(=O)N1c1ccc(-c2noc(C)n2)cc1] | I-365 | 510 | 1 | 2.11 |

TABLE 83
| Chemical Structure | Compound No. | MS [M + H]+ | LC method | LC/MS retention time (min) |
|---|---|---|---|---|
| 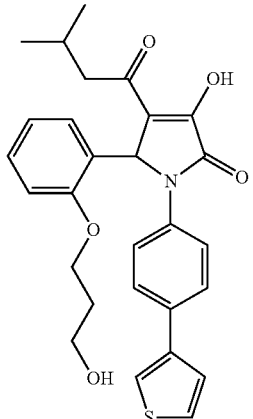 | I-366 | 492 | 1 | 2.12 |
| 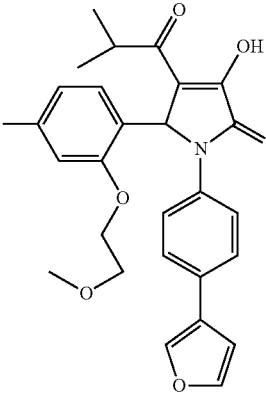 | I-367 | 480 | 1 | 2.15 |
| 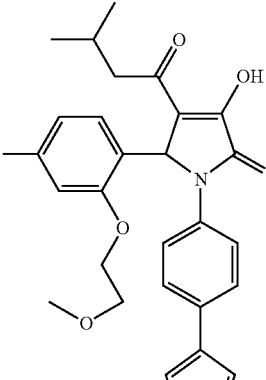 | I-368 | 494 | 1 | 2.27 |

TABLE 83-continued

| Chemical Structure | Compound No. | MS [M + H]⁺ | LC method | LC/MS retention time (min) |
|---|---|---|---|---|
| 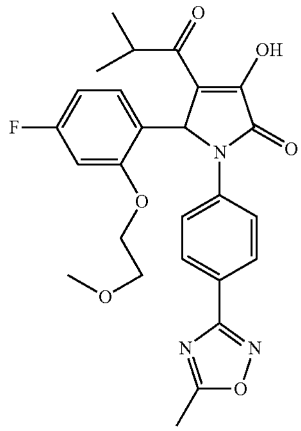 [SMILES: COCCOc1cc(F)ccc1C1C(C(=O)C(C)C)=C(O)C(=O)N1c1ccc(-c2noc(C)n2)cc1] | I-369 | 496 | 1 | 2.00 |
| 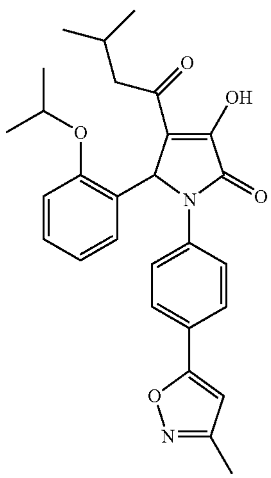 [SMILES: Cc1cc(-c2ccc(N3C(=O)C(O)=C(C(=O)CC(C)C)C3c3ccccc3OC(C)C)cc2)on1] | I-370 | 475 | 1 | 2.38 |

TABLE 84

| Chemical Structure | Compound No. | MS [M + H]⁺ | LC method | LC/MS retention time (min) |
|---|---|---|---|---|
| 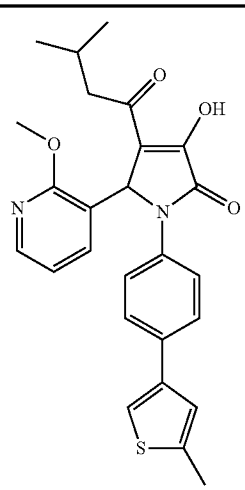 | I-371 | 463 | 2 | 2.67 |

TABLE 84-continued
| Chemical Structure | Compound No. | MS [M + H]+ | LC method | LC/MS retention time (min) |
|---|---|---|---|---|
| 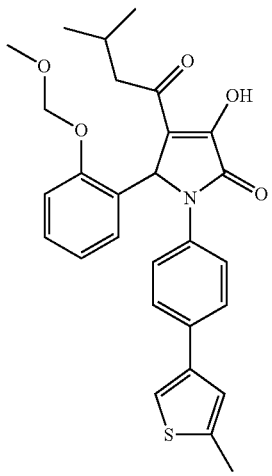 [SMILES: COCOc1ccccc1C1C(C(=O)CC(C)C)=C(O)C(=O)N1c1ccc(-c2csc(C)c2)cc1] | I-372 | 492 | 2 | 2.81 |
| 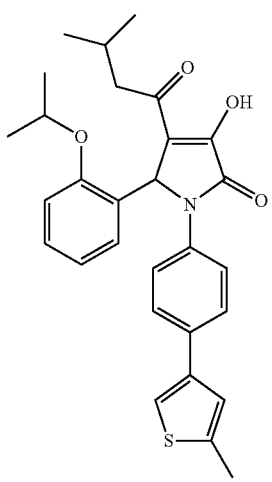 [SMILES: Cc1cc(-c2ccc(N3C(=O)C(O)=C(C(=O)CC(C)C)C3c3ccccc3OC(C)C)cc2)cs1] | I-373 | 490 | 2 | 2.97 |
| 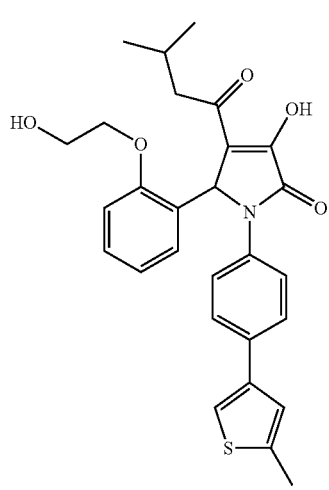 [SMILES: Cc1cc(-c2ccc(N3C(=O)C(O)=C(C(=O)CC(C)C)C3c3ccccc3OCCO)cc2)cs1] | I-374 | 492 | 2 | 2.51 |

TABLE 84-continued

| Chemical Structure | Compound No. | MS [M + H]⁺ | LC method | LC/MS retention time (min) |
|---|---|---|---|---|
| (structure) | I-375 | 506 | 2 | 2.79 |

TABLE 85

| Chemical Structure | Compound No. | MS [M + H]⁺ | LC method | LC/MS retention time (min) |
|---|---|---|---|---|
| (structure) | I-376 | 476 | 2 | 2.83 |
| (structure) | I-377 | 498 | 1 | 2.52 |

TABLE 85-continued

| Chemical Structure | Compound No. | MS [M + H]+ | LC method | LC/MS retention time (min) |
|---|---|---|---|---|
| 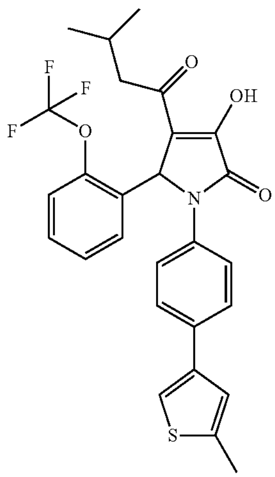 [SMILES: Cc1cc(-c2ccc(N3C(=O)C(O)=C(C(=O)CC(C)C)C3c3ccccc3OC(F)(F)F)cc2)cs1] | I-378 | 516 | 1 | 2.61 |
| 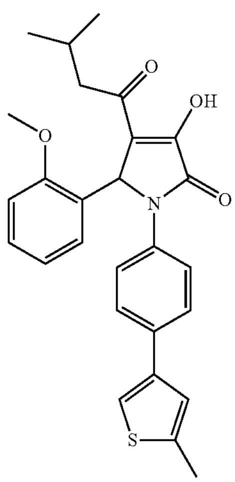 [SMILES: COc1ccccc1C1C(C(=O)CC(C)C)=C(O)C(=O)N1c1ccc(-c2csc(C)c2)cc1] | I-379 | 462 | 1 | 2.52 |
| 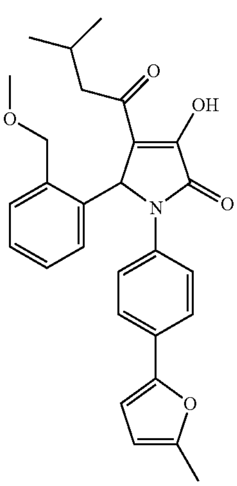 | I-380 | 460 | 1 | 2.48 |

TABLE 86
| Chemical Structure | Compound No. | MS [M + H]+ | LC method | LC/MS retention time (min) |
|---|---|---|---|---|
| 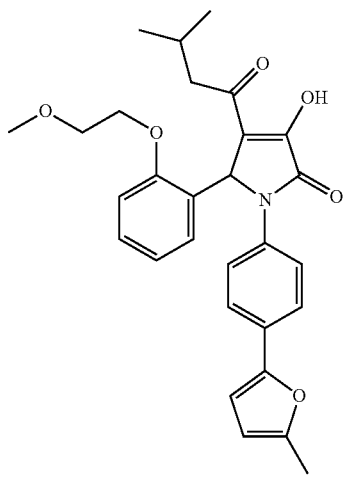 | I-381 | 490 | 1 | 2.40 |
| 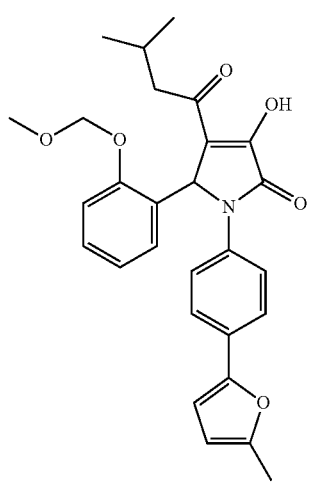 | I-382 | 476 | 1 | 2.45 |
| 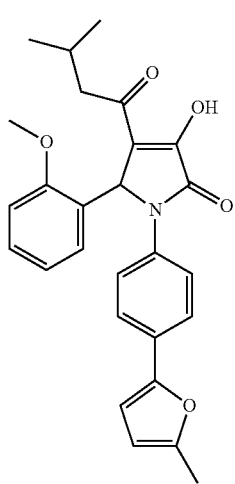 [SMILES: COc1ccccc1C1C(C(=O)CC(C)C)=C(O)C(=O)N1c1ccc(-c2ccc(C)o2)cc1] | I-383 | 446 | 1 | 2.43 |

TABLE 86-continued

| Chemical Structure | Compound No. | MS [M + H]+ | LC method | LC/MS retention time (min) |
| --- | --- | --- | --- | --- |
| 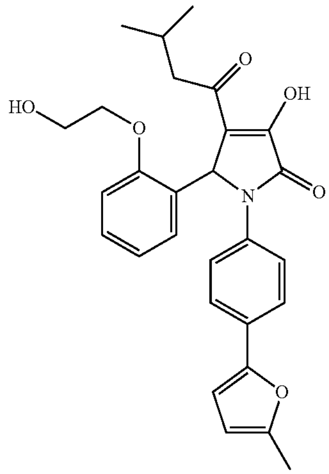 [SMILES: Cc1ccc(-c2ccc(N3C(=O)C(O)=C(C(=O)CC(C)C)C3c3ccccc3OCCO)cc2)o1] | I-384 | 476 | 1 | 2.18 |
| 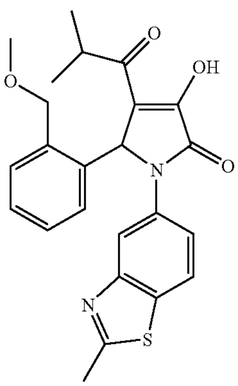 [SMILES: COCc1ccccc1C1C(C(=O)C(C)C)=C(O)C(=O)N1c1ccc2sc(C)nc2c1] | I-385 | 437 | 1 | 1.91 |

TABLE 87

| Chemical Structure | Compound No. | MS [M + H]+ | LC method | LC/MS retention time (min) |
| --- | --- | --- | --- | --- |
| 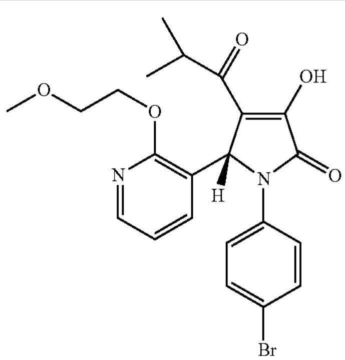 [SMILES: COCCOc1ncccc1[C@@H]1C(C(=O)C(C)C)=C(O)C(=O)N1c1ccc(Br)cc1] | I-386 | 476 | 2 | 2.32 |

TABLE 87-continued
| Chemical Structure | Compound No. | MS [M + H]+ | LC method | LC/MS retention time (min) |
|---|---|---|---|---|
| 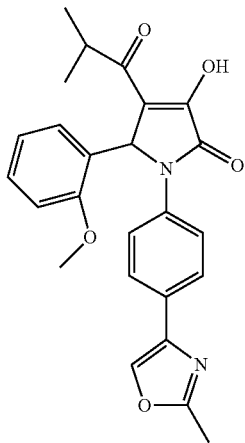 [SMILES: COc1ccccc1C1C(C(=O)C(C)C)=C(O)C(=O)N1c1ccc(-c2coc(C)n2)cc1] | I-387 | 433 | 2 | 2.18 |
| 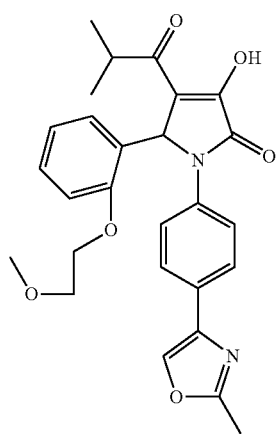 [SMILES: COCCOc1ccccc1C1C(C(=O)C(C)C)=C(O)C(=O)N1c1ccc(-c2coc(C)n2)cc1] | I-388 | 477 | 2 | 2.17 |
| 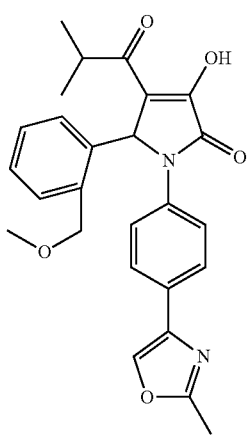 [SMILES: COCc1ccccc1C1C(C(=O)C(C)C)=C(O)C(=O)N1c1ccc(-c2coc(C)n2)cc1] | I-389 | 447 | 2 | 2.19 |

TABLE 87-continued

| Chemical Structure | Compound No. | MS [M + H]+ | LC method | LC/MS retention time (min) |
|---|---|---|---|---|
| 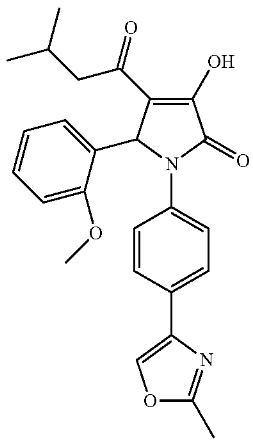 [SMILES: COc1ccccc1C1C(C(=O)CC(C)C)=C(O)C(=O)N1c1ccc(-c2coc(C)n2)cc1] | I-390 | 447 | 2 | 2.30 |

TABLE 88

| Chemical Structure | Compound No. | MS [M + H]+ | LC method | LC/MS retention time (min) |
|---|---|---|---|---|
| 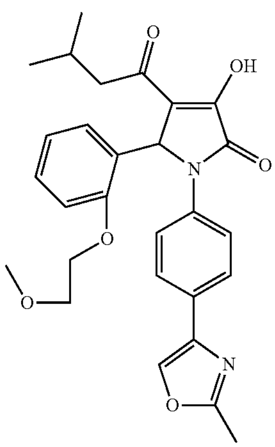 [SMILES: COCCOc1ccccc1C1C(C(=O)CC(C)C)=C(O)C(=O)N1c1ccc(-c2coc(C)n2)cc1] | I-391 | 491 | 2 | 2.32 |
| 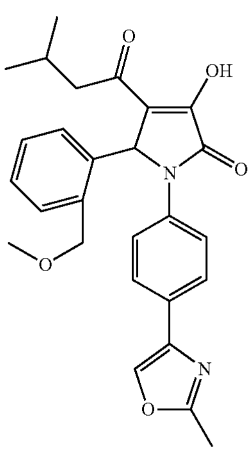 [SMILES: COCc1ccccc1C1C(C(=O)CC(C)C)=C(O)C(=O)N1c1ccc(-c2coc(C)n2)cc1] | I-392 | 461 | 2 | 2.35 |

TABLE 88-continued
| Chemical Structure | Compound No. | MS [M + H]+ | LC method | LC/MS retention time (min) |
|---|---|---|---|---|
| 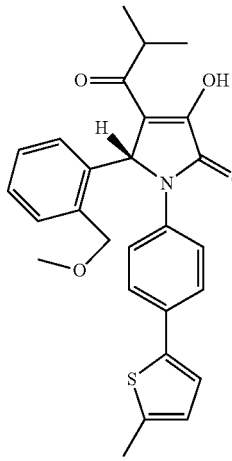 | I-393 | 462 | 1 | 2.47 |
| 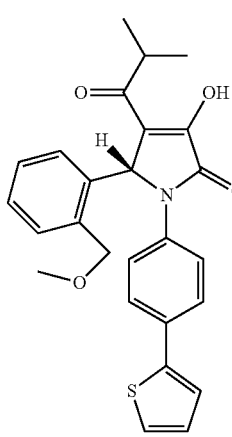 | I-394 | 448 | 1 | 2.29 |
| 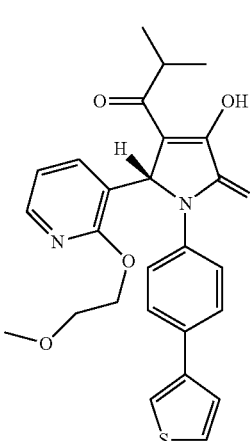 | I-395 | 479 | 1 | 2.11 |

TABLE 89

| Chemical Structure | Compound No. | MS [M + H]⁺ | LC method | LC/MS retention time (min) |
|---|---|---|---|---|
| 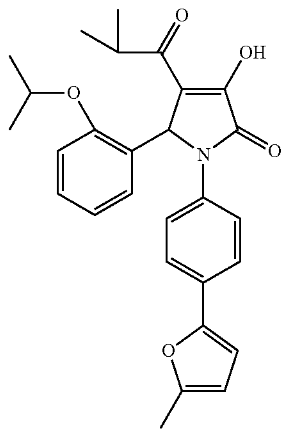 [SMILES: Cc1ccc(-c2ccc(N3C(=O)C(O)=C(C(=O)C(C)C)C3c3ccccc3OC(C)C)cc2)o1] | I-396 | 460 | 1 | 2.52 |
| 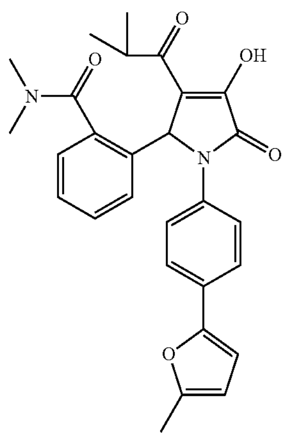 [SMILES: Cc1ccc(-c2ccc(N3C(=O)C(O)=C(C(=O)C(C)C)C3c3ccccc3C(=O)N(C)C)cc2)o1] | I-397 | 473 | 1 | 2.17 |
| 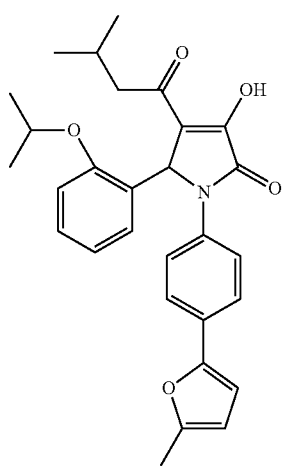 [SMILES: Cc1ccc(-c2ccc(N3C(=O)C(O)=C(C(=O)CC(C)C)C3c3ccccc3OC(C)C)cc2)o1] | I-398 | 474 | 1 | 2.65 |

TABLE 89-continued

| Chemical Structure | Compound No. | MS [M + H]+ | LC method | LC/MS retention time (min) |
|---|---|---|---|---|
| 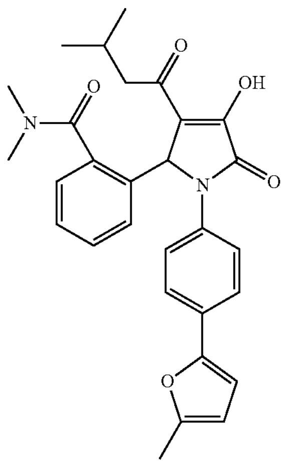 [SMILES: Cc1ccc(-c2ccc(N3C(=O)C(O)=C(C(=O)CC(C)C)C3c3ccccc3C(=O)N(C)C)cc2)o1] | I-399 | 487 | 1 | 2.25 |
| 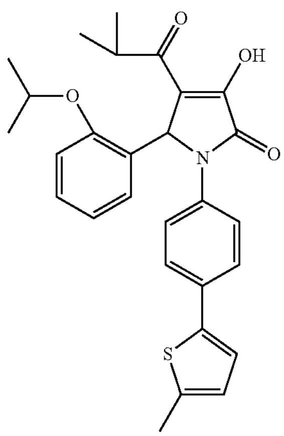 [SMILES: Cc1ccc(-c2ccc(N3C(=O)C(O)=C(C(=O)C(C)C)C3c3ccccc3OC(C)C)cc2)s1] | I-400 | 476 | 1 | 2.61 |

TABLE 90

| Chemical Structure | Compound No. | MS [M + H]+ | LC method | LC/MS retention time (min) |
|---|---|---|---|---|
| 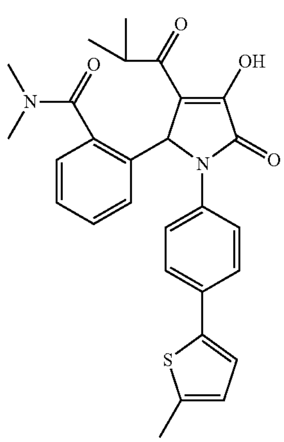 [SMILES: Cc1ccc(-c2ccc(N3C(=O)C(O)=C(C(=O)C(C)C)C3c3ccccc3C(=O)N(C)C)cc2)s1] | I-401 | 489 | 1 | 2.27 |

TABLE 90-continued

| Chemical Structure | Compound No. | MS [M + H]+ | LC method | LC/MS retention time (min) |
|---|---|---|---|---|
| 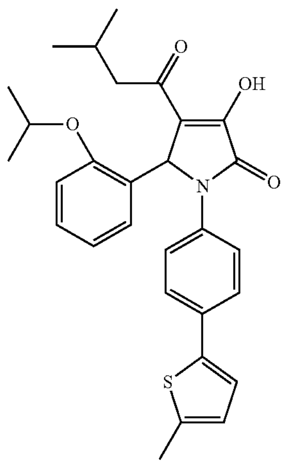 [SMILES: Cc1ccc(-c2ccc(N3C(=O)C(O)=C(C(=O)CC(C)C)C3c3ccccc3OC(C)C)cc2)s1] | I-402 | 490 | 1 | 2.70 |
| 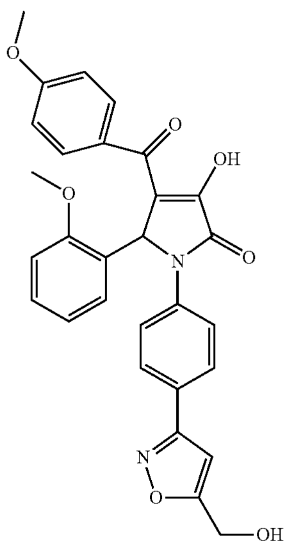 [SMILES: COc1ccc(C(=O)C2=C(O)C(=O)N(c3ccc(-c4cc(CO)on4)cc3)C2c2ccccc2OC)cc1] | I-403 | 513 | 2 | 2.00 |
| 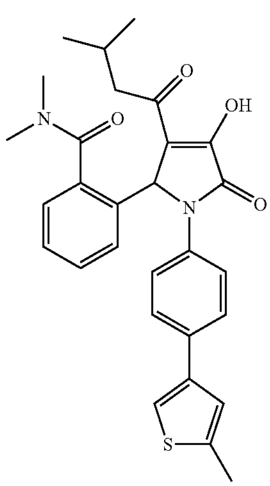 [SMILES: Cc1cc(-c2ccc(N3C(=O)C(O)=C(C(=O)CC(C)C)C3c3ccccc3C(=O)N(C)C)cc2)cs1] | I-404 | 503 | 2 | 2.64 |

TABLE 90-continued

| Chemical Structure | Compound No. | MS [M + H]⁺ | LC method | LC/MS retention time (min) |
|---|---|---|---|---|
| 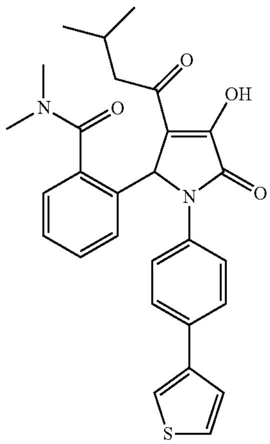 [SMILES: CC(C)CC(=O)C1=C(O)C(=O)N(c2ccc(-c3ccsc3)cc2)C1c1ccccc1C(=O)N(C)C] | I-405 | 489 | 2 | 2.51 |

TABLE 91

| Chemical Structure | Compound No. | MS [M + H]⁺ | LC method | LC/MS retention time (min) |
|---|---|---|---|---|
| 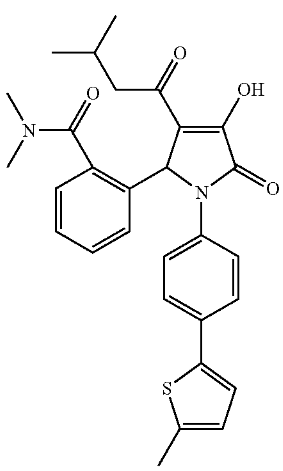 [SMILES: Cc1ccc(-c2ccc(N3C(=O)C(O)=C(C(=O)CC(C)C)C3c3ccccc3C(=O)N(C)C)cc2)s1] | I-406 | 503 | 1 | 2.38 |

TABLE 91-continued

| Chemical Structure | Compound No. | MS [M + H]⁺ | LC method | LC/MS retention time (min) |
|---|---|---|---|---|
| 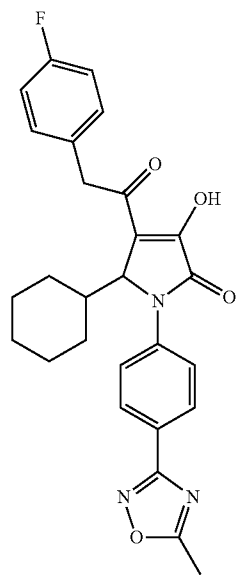 [SMILES: Cc1nc(-c2ccc(N3C(=O)C(O)=C(C(=O)Cc4ccc(F)cc4)C3C3CCCCC3)cc2)no1] | I-407 | 476 | 2 | 2.67 |
| 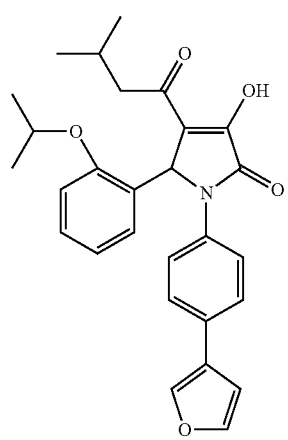 [SMILES: CC(C)CC(=O)C1=C(O)C(=O)N(c2ccc(-c3ccoc3)cc2)C1c1ccccc1OC(C)C] | I-408 | 460 | 1 | 2.44 |
| 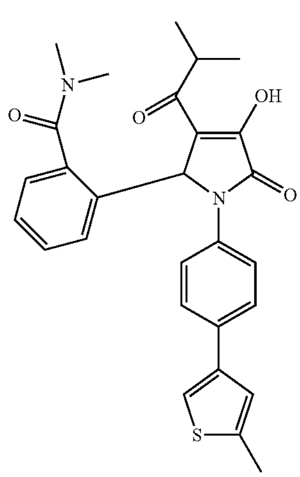 [SMILES: Cc1cc(-c2ccc(N3C(=O)C(O)=C(C(=O)C(C)C)C3c3ccccc3C(=O)N(C)C)cc2)cs1] | I-409 | 489 | 2 | 2.53 |

TABLE 91-continued

| Chemical Structure | Compound No. | MS [M + H]+ | LC method | LC/MS retention time (min) |
|---|---|---|---|---|
| (structure) | I-410 | 495 | 1 | 1.97 |

TABLE 92

| Chemical Structure | Compound No. | MS [M + H]+ | LC method | LC/MS retention time (min) |
|---|---|---|---|---|
| (structure) | I-411 | 476 | 1 | 2.09 |
| (structure) | I-412 | 451 | 1 | 2.00 |

TABLE 92-continued

| Chemical Structure | Compound No. | MS [M + H]+ | LC method | LC/MS retention time (min) |
|---|---|---|---|---|
| (structure) | I-413 | 479 | 1 | 2.21 |
| (structure) | I-414 | 465 | 1 | 2.02 |

TABLE 92-continued

| Chemical Structure | Compound No. | MS [M + H]+ | LC method | LC/MS retention time (min) |
|---|---|---|---|---|
| 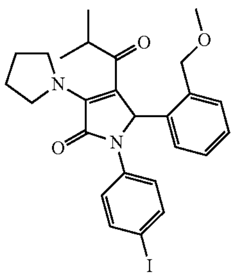 [SMILES: COCc1ccccc1C1C(C(=O)C(C)C)=C(N2CCCC2)C(=O)N1c1ccc(I)cc1] | I-415 | 545 | 1 | 2.58 |

TABLE 93

| Chemical Structure | Compound No. | MS [M + H]+ | LC method | LC/MS retention time (min) |
|---|---|---|---|---|
| 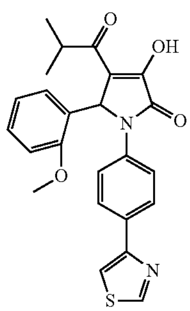 [SMILES: COc1ccccc1C1C(C(=O)C(C)C)=C(O)C(=O)N1c1ccc(-c2cscn2)cc1] | I-416 | 435 | 2 | 2.27 |
| 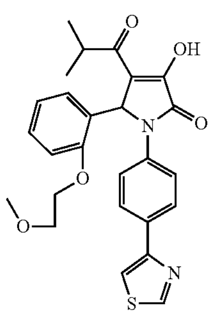 [SMILES: COCCOc1ccccc1C1C(C(=O)C(C)C)=C(O)C(=O)N1c1ccc(-c2cscn2)cc1] | I-417 | 479 | 2 | 2.27 |
| 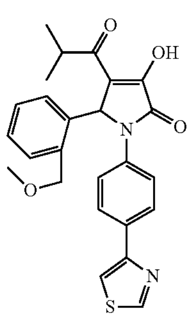 [SMILES: COCc1ccccc1C1C(C(=O)C(C)C)=C(O)C(=O)N1c1ccc(-c2cscn2)cc1] | I-418 | 449 | 2 | 2.28 |

TABLE 93-continued

| Chemical Structure | Compound No. | MS [M + H]+ | LC method | LC/MS retention time (min) |
|---|---|---|---|---|
| 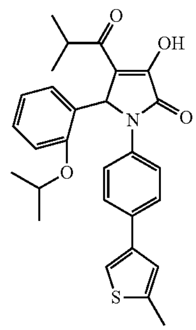 [SMILES: Cc1cc(-c2ccc(N3C(=O)C(O)=C(C(=O)C(C)C)C3c3ccccc3OC(C)C)cc2)cs1] | I-419 | 476 | 2 | 2.89 |
| 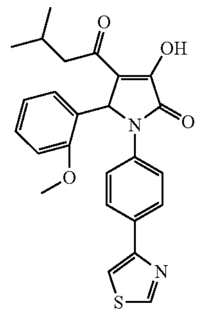 [SMILES: COc1ccccc1C1C(C(=O)CC(C)C)=C(O)C(=O)N1c1ccc(-c2cscn2)cc1] | I-420 | 449 | 2 | 2.39 |

TABLE 94

| Chemical Structure | Compound No. | MS [M + H]+ | LC method | LC/MS retention time (min) |
|---|---|---|---|---|
| 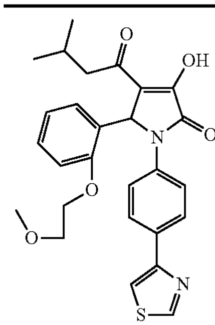 | I-421 | 493 | 2 | 2.40 |
| 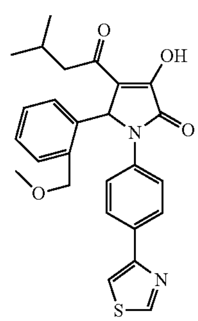 [SMILES: COCc1ccccc1C1C(C(=O)CC(C)C)=C(O)C(=O)N1c1ccc(-c2cscn2)cc1] | I-422 | 463 | 2 | 2.41 |

TABLE 94-continued

| Chemical Structure | Compound No. | MS [M + H]+ | LC method | LC/MS retention time (min) |
|---|---|---|---|---|
| 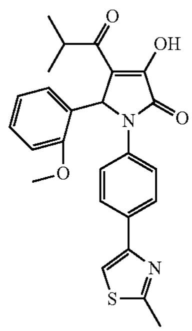 [SMILES: COc1ccccc1C1C(C(=O)C(C)C)=C(O)C(=O)N1c1ccc(-c2csc(C)n2)cc1] | I-423 | 449 | 2 | 2.41 |
| 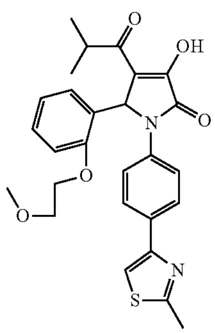 [SMILES: COCCOc1ccccc1C1C(C(=O)C(C)C)=C(O)C(=O)N1c1ccc(-c2csc(C)n2)cc1] | I-424 | 493 | 2 | 2.39 |
| 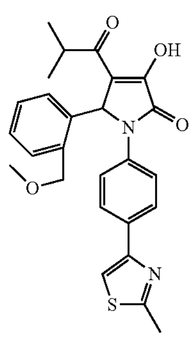 [SMILES: COCc1ccccc1C1C(C(=O)C(C)C)=C(O)C(=O)N1c1ccc(-c2csc(C)n2)cc1] | I-425 | 463 | 2 | 2.42 |

TABLE 95

| Chemical Structure | Compound No. | MS [M + H]+ | LC method | LC/MS retention time (min) |
|---|---|---|---|---|
| 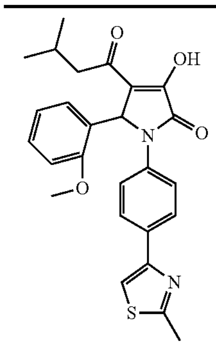 | I-426 | 463 | 2 | 2.53 |

TABLE 95-continued

| Chemical Structure | Compound No. | MS [M + H]+ | LC method | LC/MS retention time (min) |
|---|---|---|---|---|
| 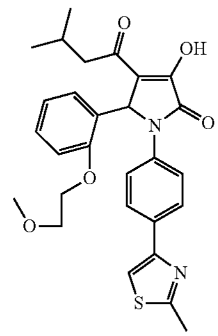 [SMILES: COCCOc1ccccc1C1C(C(=O)CC(C)C)=C(O)C(=O)N1c1ccc(-c2csc(C)n2)cc1] | I-427 | 507 | 2 | 2.52 |
| 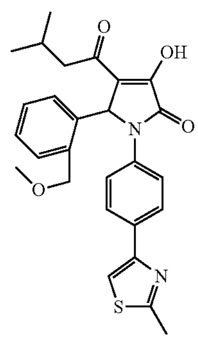 [SMILES: COCc1ccccc1C1C(C(=O)CC(C)C)=C(O)C(=O)N1c1ccc(-c2csc(C)n2)cc1] | I-428 | 477 | 2 | 2.55 |
| 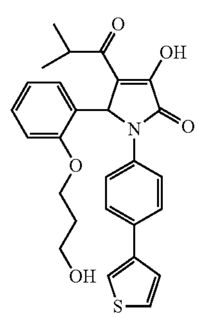 [SMILES: CC(C)C(=O)C1=C(O)C(=O)N(c2ccc(-c3ccsc3)cc2)C1c1ccccc1OCCCO] | I-429 | 478 | 1 | 2.00 |
| 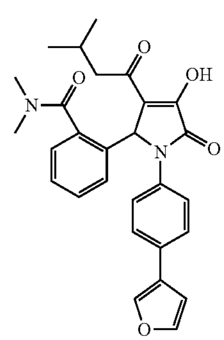 [SMILES: CC(C)CC(=O)C1=C(O)C(=O)N(c2ccc(-c3ccoc3)cc2)C1c1ccccc1C(=O)N(C)C] | I-430 | 473 | 1 | 2.08 |

TABLE 96

| Chemical Structure | Compound No. | MS [M + H]+ | LC method | LC/MS retention time (min) |
|---|---|---|---|---|
| 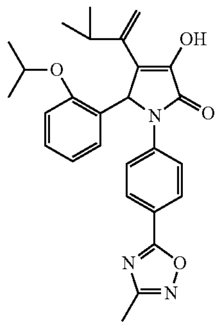 [SMILES: C=C(C1=C(O)C(=O)N(c2ccc(-c3nc(C)no3)cc2)C1c1ccccc1OC(C)C)C(C)C] | I-431 | 462 | 1 | 2.26 |
| 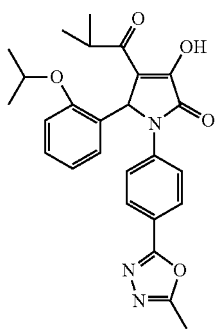 [SMILES: Cc1nnc(-c2ccc(N3C(=O)C(O)=C(C(=O)C(C)C)C3c3ccccc3OC(C)C)cc2)o1] | I-432 | 462 | 1 | 1.97 |
| 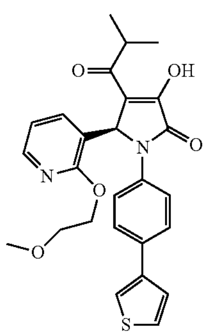 [SMILES: COCCOc1ncccc1[C@H]1C(C(=O)C(C)C)=C(O)C(=O)N1c1ccc(-c2ccsc2)cc1] | I-433 | 479 | 1 | 2.08 |
| 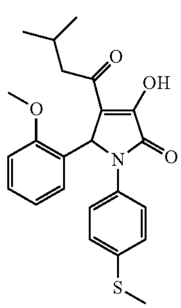 [SMILES: COc1ccccc1C1C(C(=O)CC(C)C)=C(O)C(=O)N1c1ccc(SC)cc1] | I-434 | 413 | 2 | 2.52 |

TABLE 96-continued

| Chemical Structure | Compound No. | MS [M + H]+ | LC method | LC/MS retention time (min) |
|---|---|---|---|---|
| 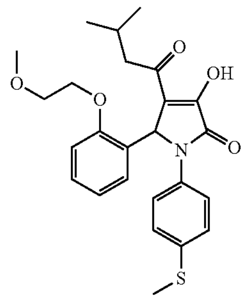 [SMILES: COCCOc1ccccc1C1C(C(=O)CC(C)C)=C(O)C(=O)N1c1ccc(SC)cc1] | I-435 | 456 | 2 | 2.48 |

TABLE 97

| Chemical Structure | Compound No. | MS [M + H]+ | LC method | LC/MS retention time (min) |
|---|---|---|---|---|
| 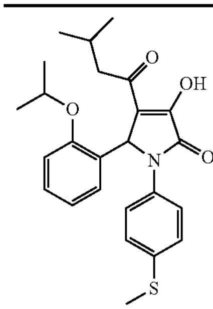 | I-436 | 440 | 2 | 2.71 |
| 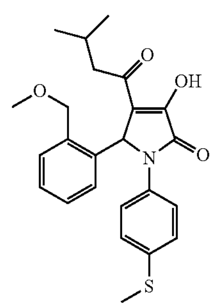 [SMILES: COCc1ccccc1C1C(C(=O)CC(C)C)=C(O)C(=O)N1c1ccc(SC)cc1] | I-437 | 426 | 2 | 2.55 |
| 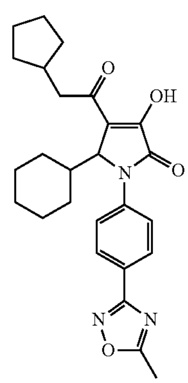 [SMILES: Cc1nc(-c2ccc(N3C(=O)C(O)=C(C(=O)CC4CCCC4)C3C3CCCCC3)cc2)no1] | I-438 | 450 | 2 | 2.91 |

TABLE 97-continued

| Chemical Structure | Compound No. | MS [M + H]⁺ | LC method | LC/MS retention time (min) |
|---|---|---|---|---|
| (cyclopentyl-CH2-C(O)- pyrrolinone with o-(methoxymethyl)phenyl and 4-(thiophen-3-yl)phenyl) | I-439 | 488 | 2 | 2.85 |
| (isobutyl ketone pyrrolinone with 2-ethoxypyridin-3-yl and 4-(thiophen-3-yl)phenyl) | I-440 | 463 | 1 | 2.32 |

TABLE 98

| Chemical Structure | Compound No. | MS [M + H]⁺ | LC method | LC/MS retention time (min) |
|---|---|---|---|---|
| (isobutyryl pyrrolinone with 2-ethoxypyridin-3-yl and 4-(thiophen-3-yl)phenyl) | I-441 | 449 | 1 | 2.18 |
| (isovaleryl pyrrolinone with 2-morpholinophenyl and 4-(thiophen-3-yl)phenyl) | I-442 | 503 | 1 | 2.37 |

TABLE 98-continued

| Chemical Structure | Compound No. | MS [M + H]⁺ | LC method | LC/MS retention time (min) |
|---|---|---|---|---|
| (isobutyryl pyrrolinone with 2-morpholinophenyl and 4-(thiophen-3-yl)phenyl) | I-443 | 489 | 1 | 2.26 |
| (isobutyryl pyrrolinone with 2-(3-hydroxypropoxy)phenyl and 4-(5-methyl-1,2,4-oxadiazol-3-yl)phenyl) | I-444 | 478 | 1 | 1.75 |
| (isovaleryl pyrrolinone with 2-(3-hydroxypropoxy)phenyl and 4-(5-methyl-1,2,4-oxadiazol-3-yl)phenyl) | I-445 | 492 | 1 | 1.84 |

TABLE 99

| Chemical Structure | Compound No. | MS [M + H]⁺ | LC method | LC/MS retention time (min) |
|---|---|---|---|---|
| (isovaleryl pyrrolinone with 2-(2-methoxyethoxy)phenyl and 4-(trifluoromethylthio)phenyl) | I-446 | 510 | 1 | 2.50 |

TABLE 99-continued

| Chemical Structure | Compound No. | MS [M + H]+ | LC method | LC/MS retention time (min) |
|---|---|---|---|---|
| 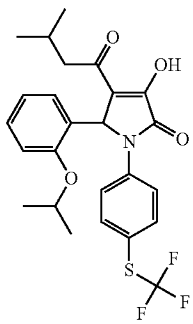 [SMILES: CC(C)CC(=O)C1=C(O)C(=O)N(c2ccc(SC(F)(F)F)cc2)C1c1ccccc1OC(C)C] | I-447 | 494 | 1 | 2.69 |
| 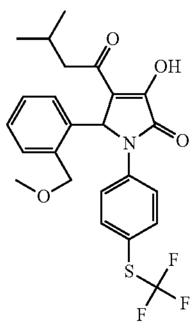 [SMILES: COCc1ccccc1C1C(C(=O)CC(C)C)=C(O)C(=O)N1c1ccc(SC(F)(F)F)cc1] | I-448 | 480 | 1 | 2.51 |
| 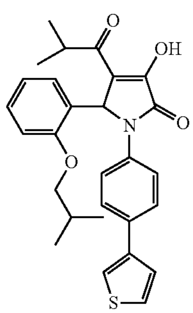 [SMILES: CC(C)COc1ccccc1C1C(C(=O)C(C)C)=C(O)C(=O)N1c1ccc(-c2ccsc2)cc1] | I-449 | 476 | 1 | 2.62 |
| 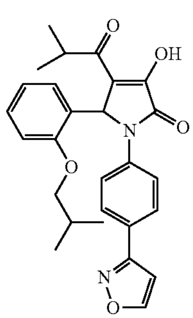 [SMILES: CC(C)COc1ccccc1C1C(C(=O)C(C)C)=C(O)C(=O)N1c1ccc(-c2ccon2)cc1] | I-450 | 461 | 1 | 2.31 |

TABLE 100

| Chemical Structure | Compound No. | MS [M + H]+ | LC method | LC/MS retention time (min) |
|---|---|---|---|---|
| 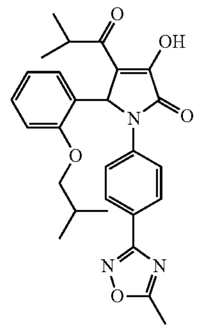 [SMILES: Cc1nc(-c2ccc(N3C(=O)C(O)=C(C(=O)C(C)C)C3c3ccccc3OCC(C)C)cc2)no1] | I-451 | 476 | 1 | 2.38 |
| 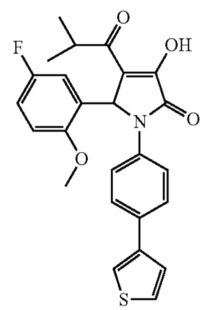 [SMILES: COc1ccc(F)cc1C1C(C(=O)C(C)C)=C(O)C(=O)N1c1ccc(-c2ccsc2)cc1] | I-452 | 452 | 1 | 2.23 |
| 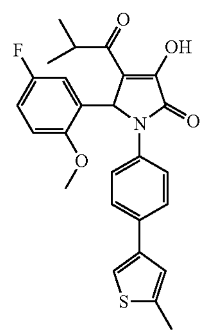 [SMILES: COc1ccc(F)cc1C1C(C(=O)C(C)C)=C(O)C(=O)N1c1ccc(-c2csc(C)c2)cc1] | I-453 | 466 | 1 | 2.41 |
| 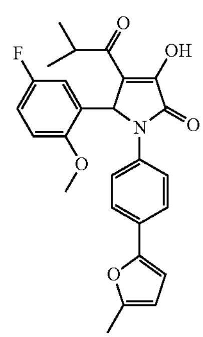 [SMILES: COc1ccc(F)cc1C1C(C(=O)C(C)C)=C(O)C(=O)N1c1ccc(-c2ccc(C)o2)cc1] | I-454 | 450 | 1 | 2.30 |

TABLE 100-continued
| Chemical Structure | Compound No. | MS [M + H]+ | LC method | LC/MS retention time (min) |
|---|---|---|---|---|
| (structure) | I-455 | 462 | 2 | 2.72 |
TABLE 101
| Chemical Structure | Compound No. | MS [M + H]+ | LC method | LC/MS retention time (min) |
|---|---|---|---|---|
| (structure) | I-456 | 508 | 2 | 2.12 |
| 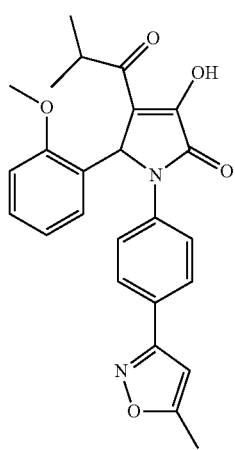 [SMILES: COc1ccccc1C1C(C(=O)C(C)C)=C(O)C(=O)N1c1ccc(-c2cc(C)on2)cc1] | I-457 | 433 | 2 | 2.36 |

TABLE 101-continued

| Chemical Structure | Compound No. | MS [M + H]+ | LC method | LC/MS retention time (min) |
|---|---|---|---|---|
| 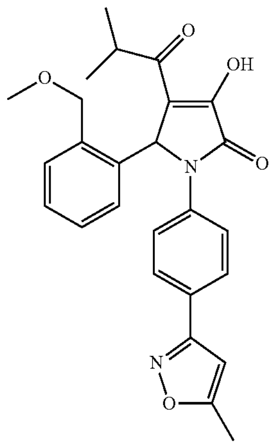 [SMILES: COCc1ccccc1C1C(C(=O)C(C)C)=C(O)C(=O)N1c1ccc(-c2cc(C)on2)cc1] | I-458 | 447 | 2 | 2.39 |
| 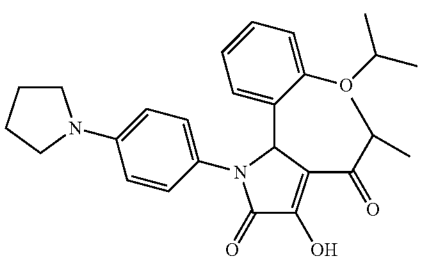 [SMILES: CC(C)Oc1ccccc1C1C(C(=O)C(C)C)=C(O)C(=O)N1c1ccc(N2CCCC2)cc1] | I-459 | 449 | 1 | 2.44 |
| 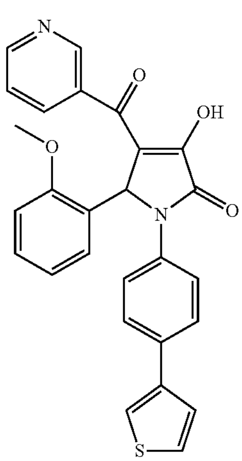 [SMILES: COc1ccccc1C1C(C(=O)c2cccnc2)=C(O)C(=O)N1c1ccc(-c2ccsc2)cc1] | I-460 | 469 | 2 | 2.04 |

TABLE 102

| Chemical Structure | Compound No. | MS [M + H]+ | LC method | LC/MS retention time (min) |
|---|---|---|---|---|
| 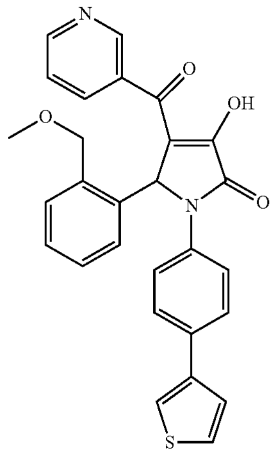 [SMILES: COCc1ccccc1C1C(C(=O)c2cccnc2)=C(O)C(=O)N1c1ccc(-c2ccsc2)cc1] | I-461 | 483 | 2 | 2.04 |
| 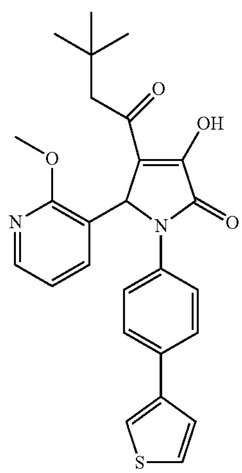 [SMILES: COc1ncccc1C1C(C(=O)CC(C)(C)C)=C(O)C(=O)N1c1ccc(-c2ccsc2)cc1] | I-462 | 463 | 2 | 2.61 |
| 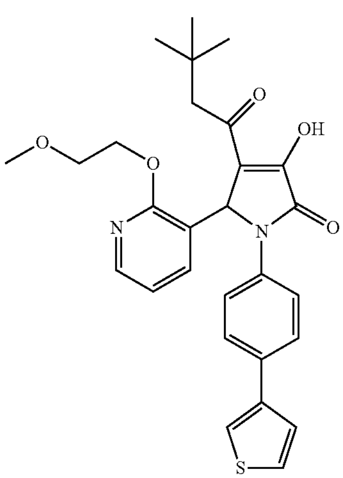 [SMILES: COCCOc1ncccc1C1C(C(=O)CC(C)(C)C)=C(O)C(=O)N1c1ccc(-c2ccsc2)cc1] | I-463 | 507 | 2 | 2.64 |

TABLE 102-continued

| Chemical Structure | Compound No. | MS [M + H]+ | LC method | LC/MS retention time (min) |
|---|---|---|---|---|
| 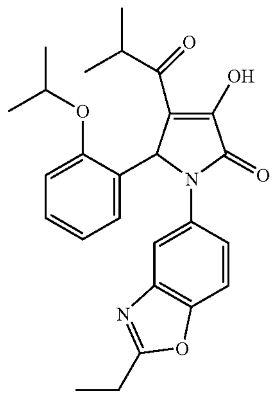 [SMILES: CCc1nc2cc(N3C(=O)C(O)=C(C(=O)C(C)C)C3c3ccccc3OC(C)C)ccc2o1] | I-464 | 449 | 1 | 2.19 |
| 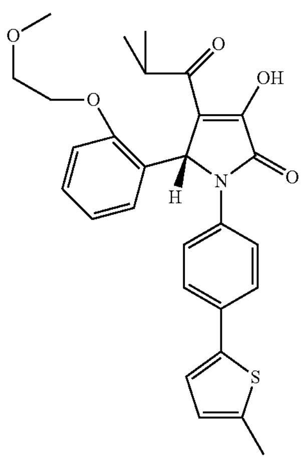 [SMILES: COCCOc1ccccc1[C@@H]1C(C(=O)C(C)C)=C(O)C(=O)N1c1ccc(-c2ccc(C)s2)cc1] | I-465 | 492 | 2 | 2.73 |

TABLE 103

| Chemical Structure | Compound No. | MS [M + H]+ | LC method | LC/MS retention time (min) |
|---|---|---|---|---|
| 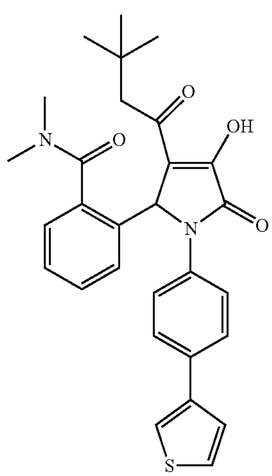 [SMILES: CN(C)C(=O)c1ccccc1C1C(C(=O)CC(C)(C)C)=C(O)C(=O)N1c1ccc(-c2ccsc2)cc1] | I-466 | 503 | 2 | 2.61 |

TABLE 103-continued

| Chemical Structure | Compound No. | MS [M + H]⁺ | LC method | LC/MS retention time (min) |
|---|---|---|---|---|
| 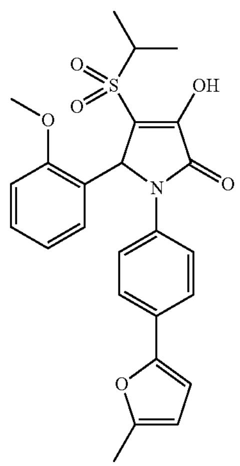 [SMILES: COc1ccccc1C1C(S(=O)(=O)C(C)C)=C(O)C(=O)N1c1ccc(-c2ccc(C)o2)cc1] | I-467 | 468 | 2 | 2.38 |
| 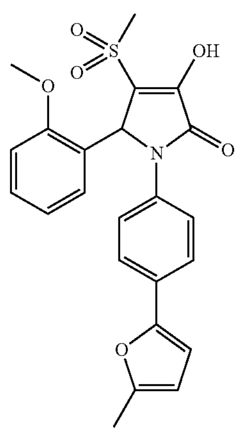 [SMILES: COc1ccccc1C1C(S(C)(=O)=O)=C(O)C(=O)N1c1ccc(-c2ccc(C)o2)cc1] | I-468 | 440 | 2 | 2.23 |
| 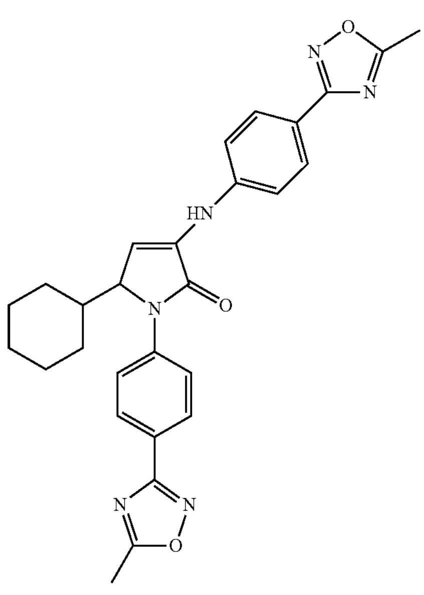 [SMILES: Cc1nc(-c2ccc(NC3=CC(C4CCCCC4)N(c4ccc(-c5noc(C)n5)cc4)C3=O)cc2)no1] | I-469 | 497 | 2 | 2.88 |

TABLE 103-continued

| Chemical Structure | Compound No. | MS [M + H]+ | LC method | LC/MS retention time (min) |
|---|---|---|---|---|
| 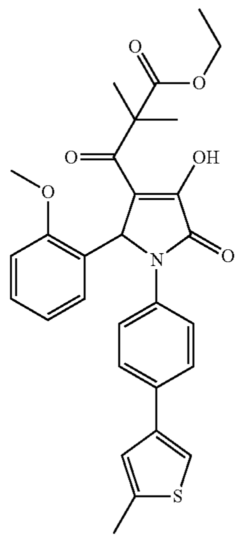 [SMILES: CCOC(=O)C(C)(C)C(=O)C1=C(O)C(=O)N(c2ccc(-c3csc(C)c3)cc2)C1c1ccccc1OC] | I-470 | 520 | 2 | 2.70 |

TABLE 104

| Chemical Structure | Compound No. | MS [M + H]+ | LC method | LC/MS retention time (min) |
|---|---|---|---|---|
| 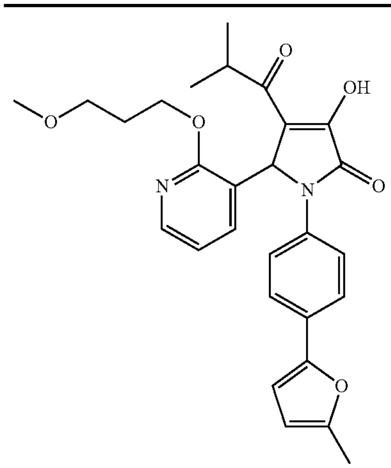 | I-471 | 491 | 1 | 2.24 |

TABLE 104-continued
| Chemical Structure | Compound No. | MS [M + H]+ | LC method | LC/MS retention time (min) |
|---|---|---|---|---|
| 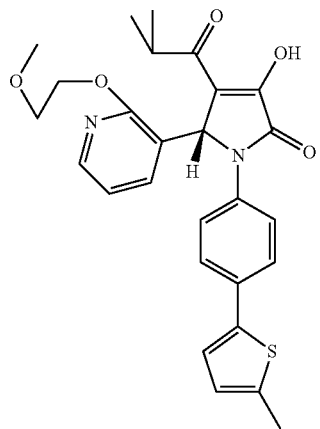 [SMILES: COCCOc1ncccc1[C@@H]1C(C(=O)C(C)C)=C(O)C(=O)N1c1ccc(-c2ccc(C)s2)cc1] | I-472 | 493 | 2 | 2.60 |
| 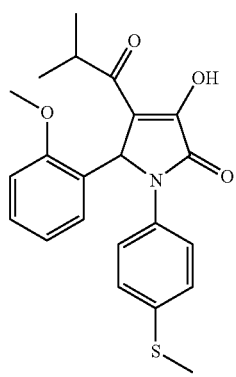 [SMILES: COc1ccccc1C1C(C(=O)C(C)C)=C(O)C(=O)N1c1ccc(SC)cc1] | I-473 | 398 | 2 | 2.38 |
| 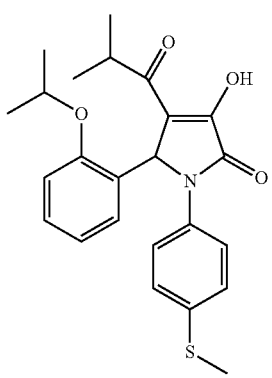 [SMILES: CSc1ccc(N2C(=O)C(O)=C(C(=O)C(C)C)C2c2ccccc2OC(C)C)cc1] | I-474 | 426 | 2 | 2.61 |

TABLE 104-continued
| Chemical Structure | Compound No. | MS [M + H]+ | LC method | LC/MS retention time (min) |
|---|---|---|---|---|
| 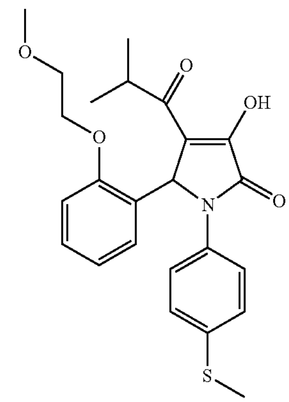 [SMILES: COCCOc1ccccc1C1C(C(=O)C(C)C)=C(O)C(=O)N1c1ccc(SC)cc1] | I-475 | 442 | 2 | 2.36 |
TABLE 105
| Chemical Structure | Compound No. | MS [M + H]+ | LC method | LC/MS retention time (min) |
|---|---|---|---|---|
| 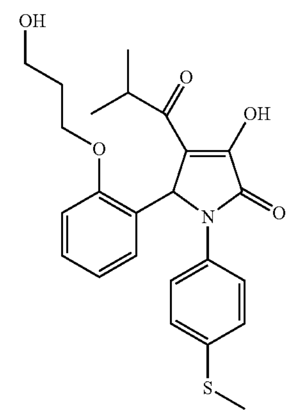 [SMILES: CSc1ccc(N2C(=O)C(O)=C(C(=O)C(C)C)C2c2ccccc2OCCCO)cc1] | I-476 | 442 | 2 | 2.12 |
| 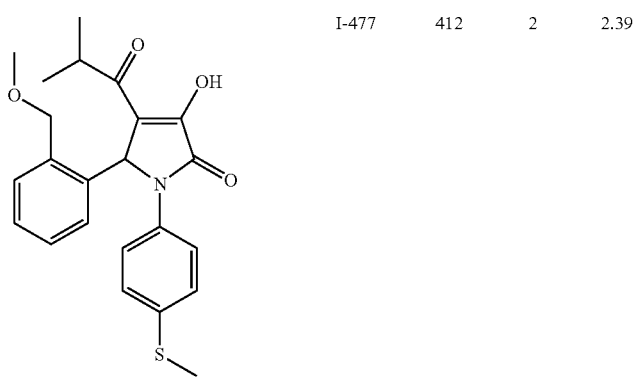 | I-477 | 412 | 2 | 2.39 |

TABLE 105-continued

| Chemical Structure | Compound No. | MS [M + H]+ | LC method | LC/MS retention time (min) |
|---|---|---|---|---|
| 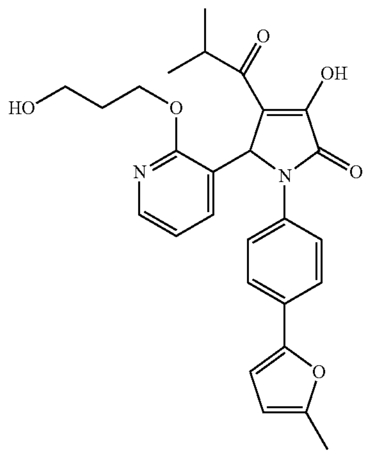 [SMILES: Cc1ccc(-c2ccc(N3C(=O)C(O)=C(C(=O)C(C)C)C3c3cccnc3OCCCO)cc2)o1] | I-478 | 477 | 1 | 1.89 |
| 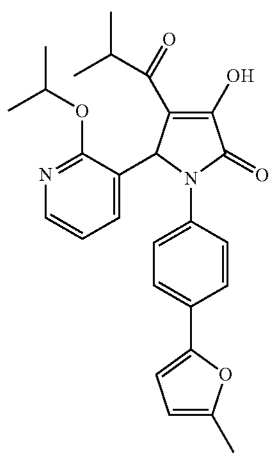 [SMILES: Cc1ccc(-c2ccc(N3C(=O)C(O)=C(C(=O)C(C)C)C3c3cccnc3OC(C)C)cc2)o1] | I-479 | 461 | 1 | 2.39 |
| 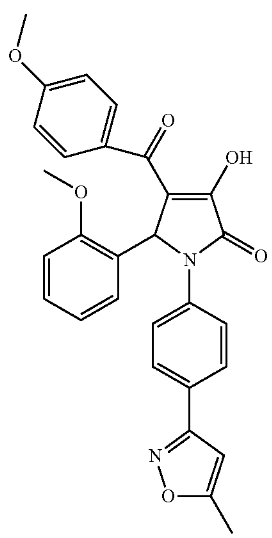 [SMILES: COc1ccc(C(=O)C2=C(O)C(=O)N(c3ccc(-c4cc(C)on4)cc3)C2c2ccccc2OC)cc1] | I-480 | 497 | 2 | 2.32 |

TABLE 106

| Chemical Structure | Compound No. | MS [M + H]⁺ | LC method | LC/MS retention time (min) |
| --- | --- | --- | --- | --- |
| 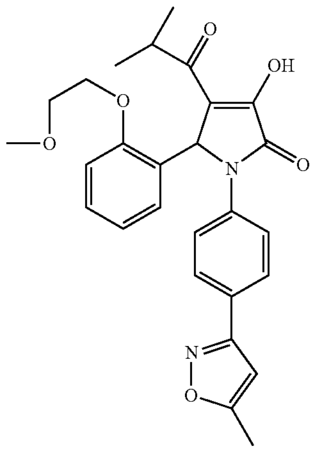 [SMILES: COCCOc1ccccc1C1C(C(=O)C(C)C)=C(O)C(=O)N1c1ccc(-c2cc(C)on2)cc1] | I-481 | 477 | 2 | 2.35 |
| 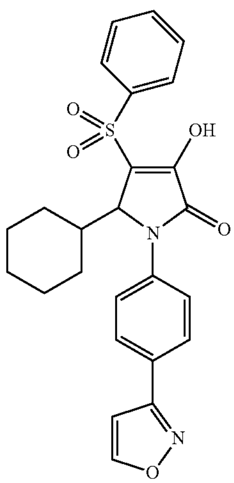 [SMILES: O=C1C(O)=C(S(=O)(=O)c2ccccc2)C(C2CCCCC2)N1c1ccc(-c2ccon2)cc1] | I-482 | 465 | 2 | 2.41 |
| 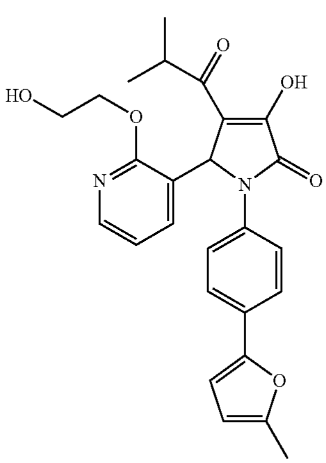 [SMILES: Cc1ccc(-c2ccc(N3C(=O)C(O)=C(C(=O)C(C)C)C3c3cccnc3OCCO)cc2)o1] | I-483 | 463 | 1 | 1.89 |

TABLE 106-continued

| Chemical Structure | Compound No. | MS [M + H]+ | LC method | LC/MS retention time (min) |
|---|---|---|---|---|
| 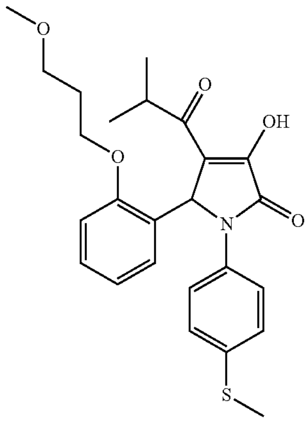 [SMILES: COCCCOc1ccccc1C1C(C(=O)C(C)C)=C(O)C(=O)N1c1ccc(SC)cc1] | I-484 | 456 | 2 | 2.47 |
| 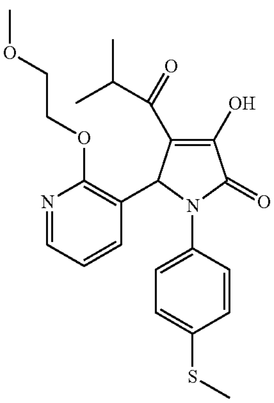 | I-485 | 443 | 2 | 2.24 |

TABLE 107

| Chemical Structure | Compound No. | MS [M + H]+ | LC method | LC/MS retention time (min) |
|---|---|---|---|---|
| 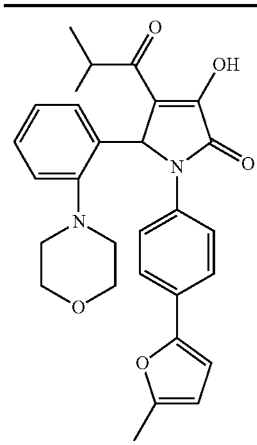 | I-486 | 487 | 1 | 2.28 |

TABLE 107-continued
| Chemical Structure | Compound No. | MS [M + H]+ | LC method | LC/MS retention time (min) |
|---|---|---|---|---|
| 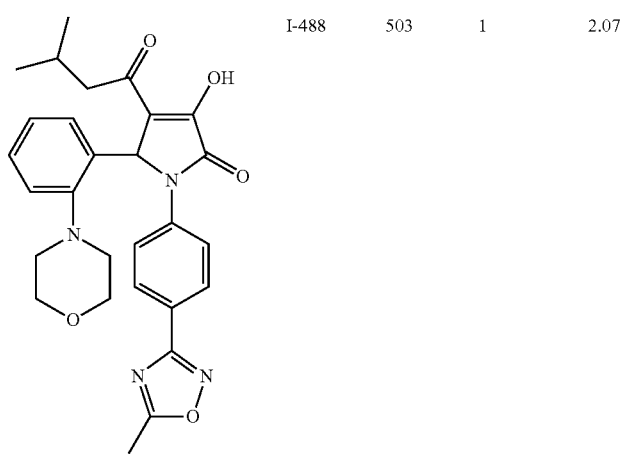 | I-487 | 489 | 1 | 1.97 |
| 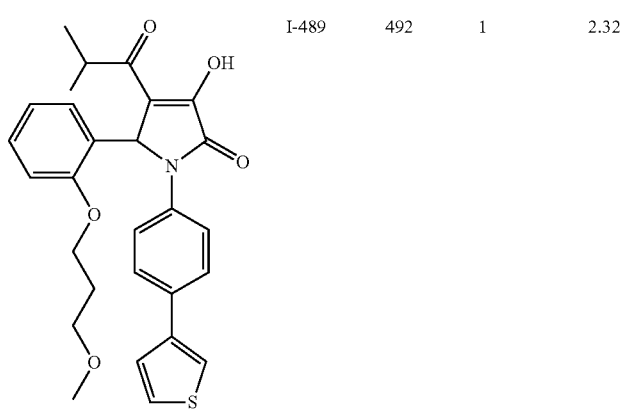 | I-488 | 503 | 1 | 2.07 |
| 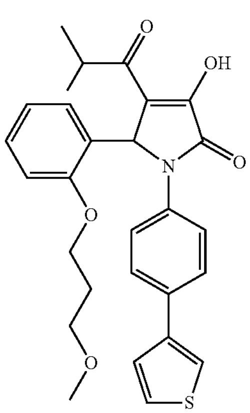 [SMILES: COCCCOc1ccccc1C1C(C(=O)C(C)C)=C(O)C(=O)N1c1ccc(-c2ccsc2)cc1] | I-489 | 492 | 1 | 2.32 |

TABLE 107-continued
| Chemical Structure | Compound No. | MS [M + H]⁺ | LC method | LC/MS retention time (min) |
|---|---|---|---|---|
| 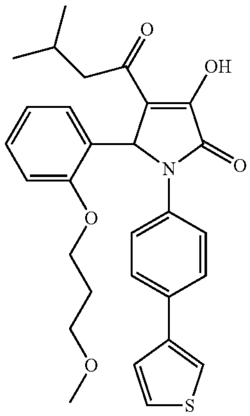 [SMILES: COCCCOc1ccccc1C1C(C(=O)CC(C)C)=C(O)C(=O)N1c1ccc(-c2ccsc2)cc1] | I-490 | 506 | 1 | 2.39 |
TABLE 108
| Chemical Structure | Compound No. | MS [M + H]⁺ | LC method | LC/MS retention time (min) |
|---|---|---|---|---|
| 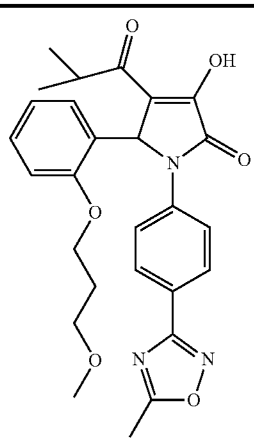 | I-491 | 492 | 1 | 2.06 |
| 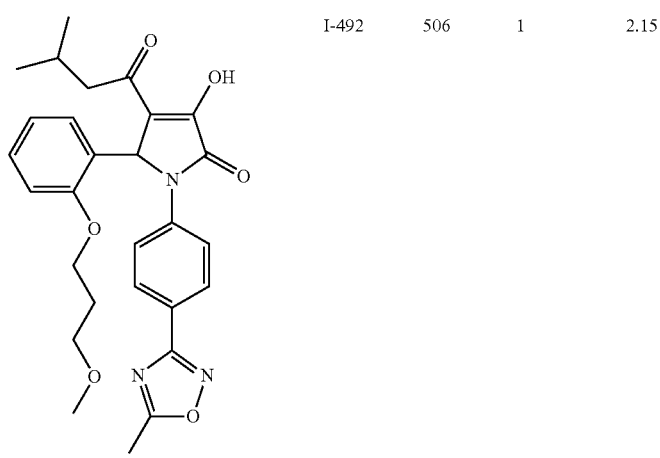 | I-492 | 506 | 1 | 2.15 |

TABLE 108-continued
| Chemical Structure | Compound No. | MS [M + H]⁺ | LC method | LC/MS retention time (min) |
|---|---|---|---|---|
| 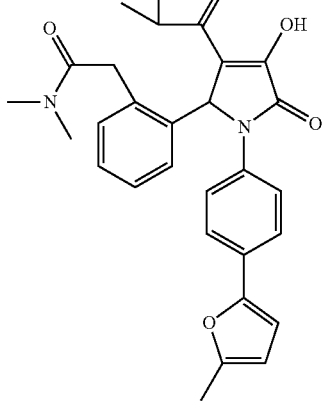 | I-493 | 487 | 1 | 1.98 |
| 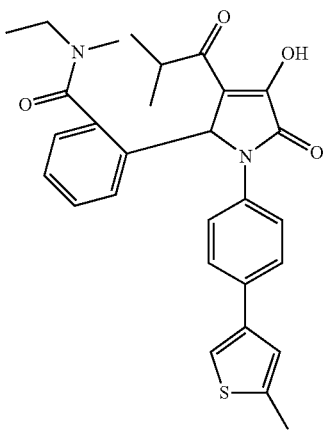 [SMILES: CCN(C)C(=O)c1ccccc1C1C(C(=O)C(C)C)=C(O)C(=O)N1c1ccc(-c2csc(C)c2)cc1] | I-494 | 503 | 2 | 2.65 |
| 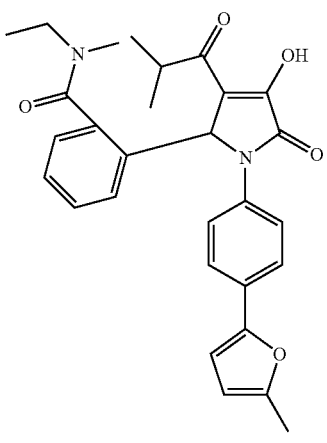 [SMILES: CCN(C)C(=O)c1ccccc1C1C(C(=O)C(C)C)=C(O)C(=O)N1c1ccc(-c2ccc(C)o2)cc1] | I-495 | 487 | 2 | 2.59 |

TABLE 109

| Chemical Structure | Compound No. | MS [M + H]+ | LC method | LC/MS retention time (min) |
| --- | --- | --- | --- | --- |
| 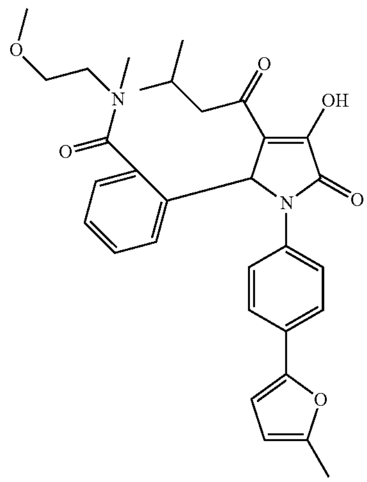 [SMILES: COCCN(C)C(=O)c1ccccc1C1C(C(=O)CC(C)C)=C(O)C(=O)N1c1ccc(-c2ccc(C)o2)cc1] | I-496 | 531 | 2 | 2.63 |
| 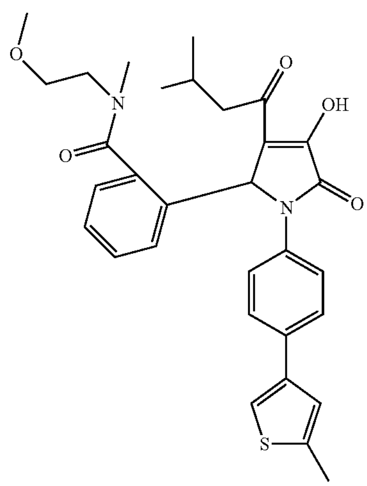 [SMILES: COCCN(C)C(=O)c1ccccc1C1C(C(=O)CC(C)C)=C(O)C(=O)N1c1ccc(-c2csc(C)c2)cc1] | I-497 | 547 | 2 | 2.70 |
| 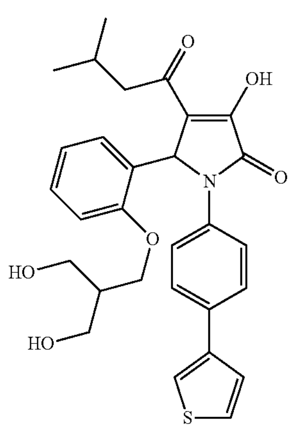 [SMILES: CC(C)CC(=O)C1=C(O)C(=O)N(c2ccc(-c3ccsc3)cc2)C1c1ccccc1OCC(CO)CO] | I-498 | 522 | 2 | 2.23 |

TABLE 109-continued

| Chemical Structure | Compound No. | MS [M + H]+ | LC method | LC/MS retention time (min) |
|---|---|---|---|---|
| 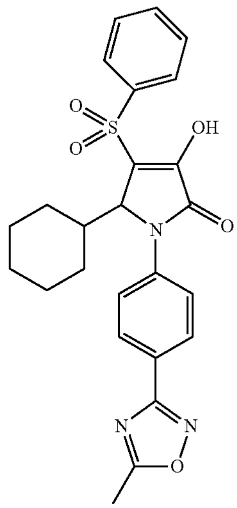 [SMILES: Cc1nc(-c2ccc(N3C(=O)C(O)=C(S(=O)(=O)c4ccccc4)C3C3CCCCC3)cc2)no1] | I-499 | 480 | 2 | 2.44 |
| 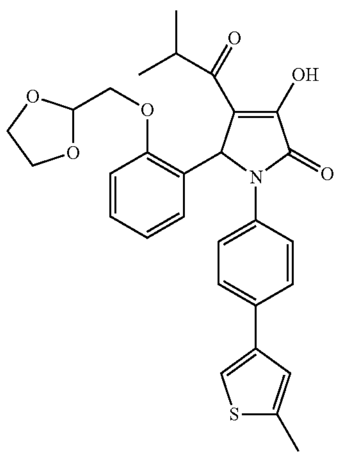 [SMILES: Cc1cc(-c2ccc(N3C(=O)C(O)=C(C(=O)C(C)C)C3c3ccccc3OCC3OCCO3)cc2)cs1] | I-500 | 520 | 2 | 2.63 |

TABLE 110

| Chemical Structure | Compound No. | MS [M + H]+ | LC method | LC/MS retention time (min) |
|---|---|---|---|---|
| 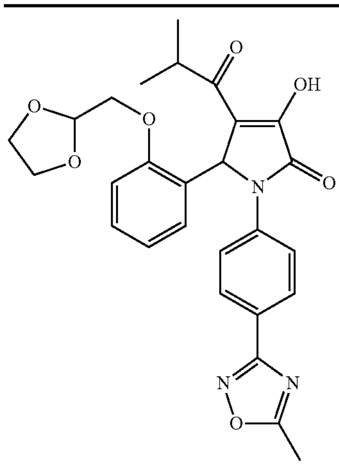 | I-501 | 506 | 2 | 2.24 |

TABLE 110-continued
| Chemical Structure | Compound No. | MS [M + H]⁺ | LC method | LC/MS retention time (min) |
|---|---|---|---|---|
| 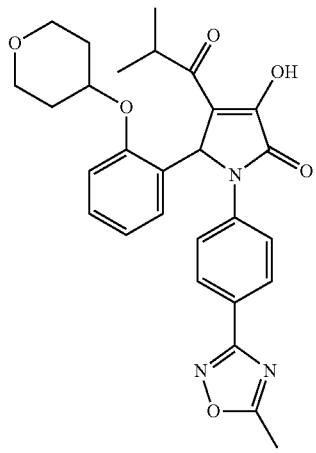 [SMILES: Cc1nc(-c2ccc(N3C(=O)C(O)=C(C(=O)C(C)C)C3c3ccccc3OC3CCOCC3)cc2)no1] | I-502 | 504 | 1 | 1.96 |
| 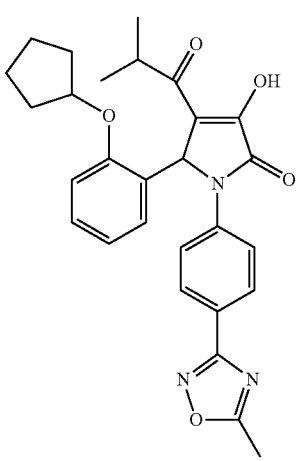 [SMILES: Cc1nc(-c2ccc(N3C(=O)C(O)=C(C(=O)C(C)C)C3c3ccccc3OC3CCCC3)cc2)no1] | I-503 | 487 | 1 | 2.34 |
| 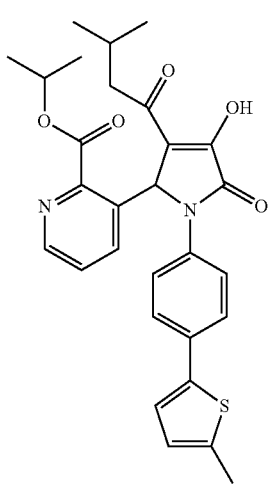 [SMILES: Cc1ccc(-c2ccc(N3C(=O)C(O)=C(C(=O)CC(C)C)C3c3cccnc3C(=O)OC(C)C)cc2)s1] | I-504 | 519 | 1 | 2.39 |

TABLE 110-continued

| Chemical Structure | Compound No. | MS [M + H]⁺ | LC method | LC/MS retention time (min) |
|---|---|---|---|---|
| 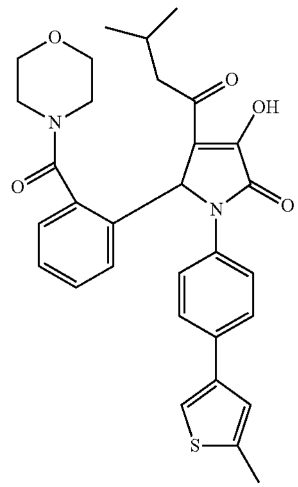 [SMILES: Cc1cc(-c2ccc(N3C(=O)C(O)=C(C(=O)CC(C)C)C3c3ccccc3C(=O)N3CCOCC3)cc2)cs1] | I-505 | 545 | 2 | 2.61 |

TABLE 111

| Chemical Structure | Compound No. | MS [M + H]⁺ | LC method | LC/MS retention time (min) |
|---|---|---|---|---|
| 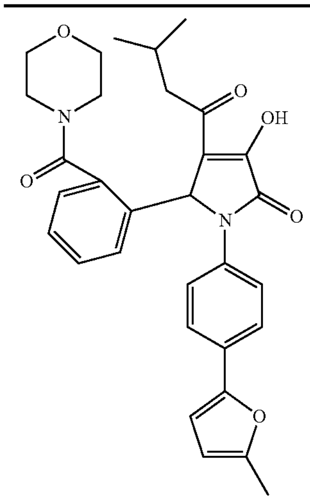 | I-506 | 529 | 2 | 2.55 |
| 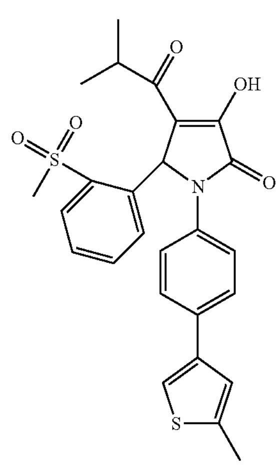 [SMILES: Cc1cc(-c2ccc(N3C(=O)C(O)=C(C(=O)C(C)C)C3c3ccccc3S(C)(=O)=O)cc2)cs1] | I-507 | 496 | 2 | 2.45 |

TABLE 111-continued
| Chemical Structure | Compound No. | MS [M + H]+ | LC method | LC/MS retention time (min) |
|---|---|---|---|---|
| 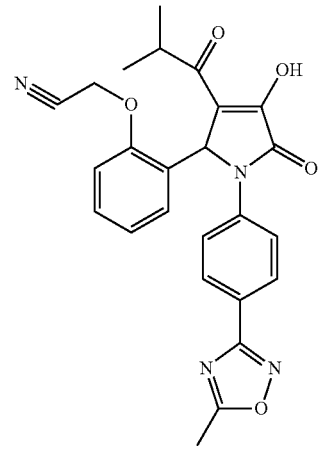 [SMILES: Cc1nc(-c2ccc(N3C(=O)C(O)=C(C(=O)C(C)C)C3c3ccccc3OCC#N)cc2)no1] | I-508 | 459 | 2 | 2.11 |
| 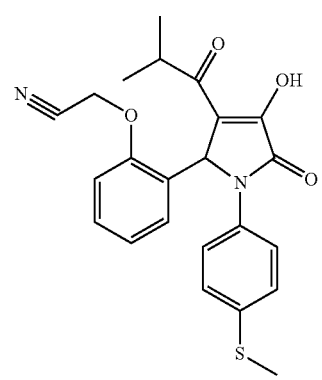 [SMILES: CSc1ccc(N2C(=O)C(O)=C(C(=O)C(C)C)C2c2ccccc2OCC#N)cc1] | I-509 | 423 | 2 | 2.20 |
| 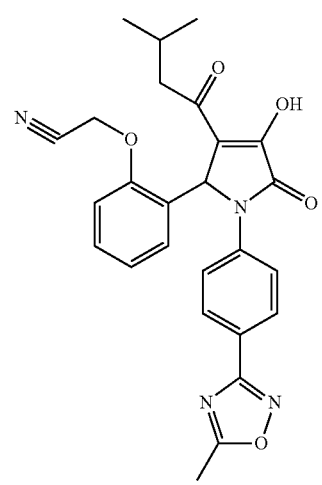 [SMILES: Cc1nc(-c2ccc(N3C(=O)C(O)=C(C(=O)CC(C)C)C3c3ccccc3OCC#N)cc2)no1] | I-510 | 474 | 2 | 2.21 |

TABLE 112
| Chemical Structure | Compound No. | MS [M + H]+ | LC method | LC/MS retention time (min) |
|---|---|---|---|---|
| 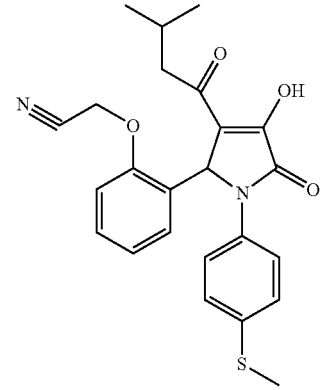 [SMILES: CSc1ccc(N2C(=O)C(O)=C(C(=O)CC(C)C)C2c2ccccc2OCC#N)cc1] | I-511 | 437 | 2 | 2.29 |
| 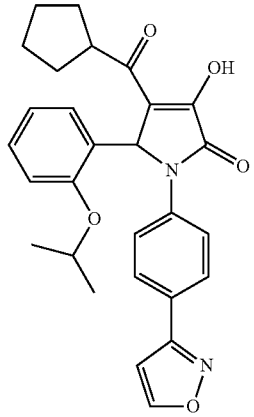 [SMILES: CC(C)Oc1ccccc1C1C(C(=O)C2CCCC2)=C(O)C(=O)N1c1ccc(-c2ccon2)cc1] | I-512 | 473 | 1 | 2.36 |
| 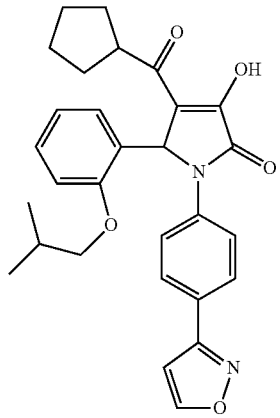 [SMILES: CC(C)COc1ccccc1C1C(C(=O)C2CCCC2)=C(O)C(=O)N1c1ccc(-c2ccon2)cc1] | I-513 | 487 | 1 | 2.49 |

TABLE 112-continued

| Chemical Structure | Compound No. | MS [M + H]+ | LC method | LC/MS retention time (min) |
|---|---|---|---|---|
| 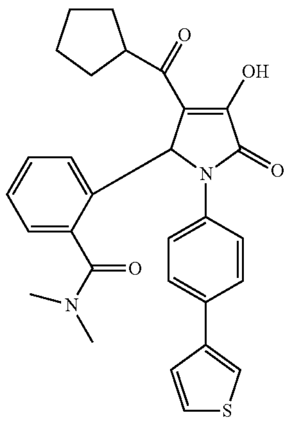 [SMILES: CN(C)C(=O)c1ccccc1C1C(C(=O)C2CCCC2)=C(O)C(=O)N1c1ccc(-c2ccsc2)cc1] | I-514 | 501 | 1 | 2.24 |
| 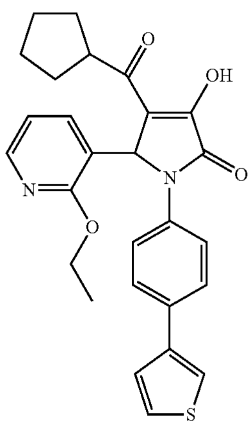 [SMILES: CCOc1ncccc1C1C(C(=O)C2CCCC2)=C(O)C(=O)N1c1ccc(-c2ccsc2)cc1] | I-515 | 475 | 1 | 2.38 |

TABLE 113

| Chemical Structure | Compound No. | MS [M + H]+ | LC method | LC/MS retention time (min) |
|---|---|---|---|---|
| 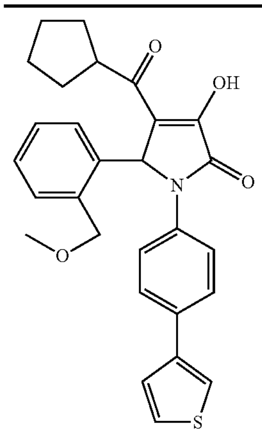 | I-516 | 474 | 1 | 2.43 |

TABLE 113-continued

| Chemical Structure | Compound No. | MS [M + H]+ | LC method | LC/MS retention time (min) |
| --- | --- | --- | --- | --- |
| 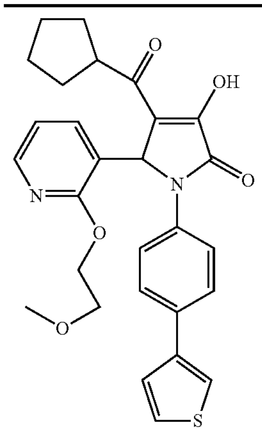 | I-517 | 505 | 1 | 2.26 |
| 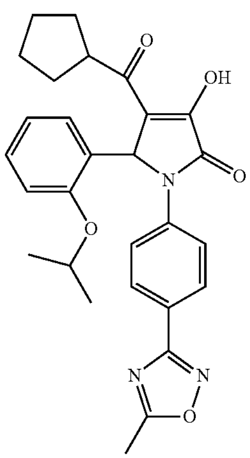 [SMILES: Cc1nc(-c2ccc(N3C(=O)C(O)=C(C(=O)C4CCCC4)C3c3ccccc3OC(C)C)cc2)no1] | I-518 | 488 | 1 | 2.39 |
| 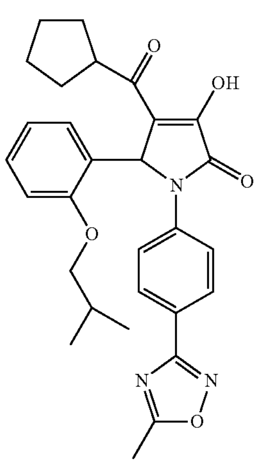 [SMILES: Cc1nc(-c2ccc(N3C(=O)C(O)=C(C(=O)C4CCCC4)C3c3ccccc3OCC(C)C)cc2)no1] | I-519 | 502 | 1 | 2.55 |

TABLE 113-continued

| Chemical Structure | Compound No. | MS [M + H]+ | LC method | LC/MS retention time (min) |
|---|---|---|---|---|
| (structure) | I-520 | 476 | 1 | 1.70 |

TABLE 114

| Chemical Structure | Compound No. | MS [M + H]+ | LC method | LC/MS retention time (min) |
|---|---|---|---|---|
| (structure) | I-521 | 490 | 1 | 1.96 |
| (structure) | I-522 | 491 | 1 | 1.71 |

TABLE 114-continued
| Chemical Structure | Compound No. | MS [M + H]+ | LC method | LC/MS retention time (min) |
|---|---|---|---|---|
| 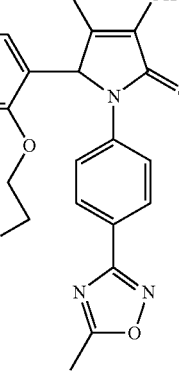 | I-523 | 505 | 1 | 1.98 |
| 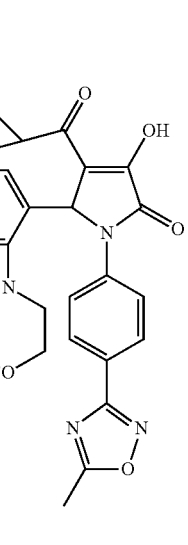 | I-524 | 490 | 1 | 1.65 |
| 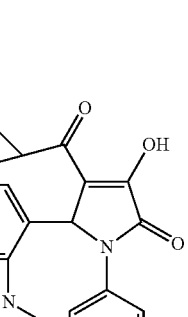 | I-525 | 490 | 1 | 1.91 |

TABLE 115
| Chemical Structure | Compound No. | MS [M + H]⁺ | LC method | LC/MS retention time (min) |
| --- | --- | --- | --- | --- |
| 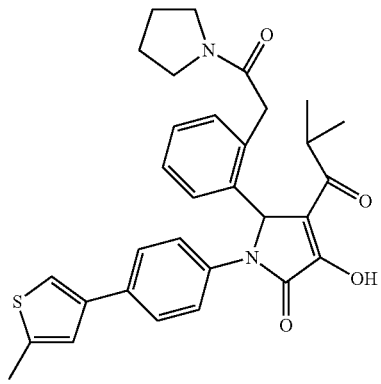 [SMILES: Cc1cc(-c2ccc(N3C(=O)C(O)=C(C(=O)C(C)C)C3c3ccccc3CC(=O)N3CCCC3)cc2)cs1] | I-526 | 529 | 2 | 2.43 |
| 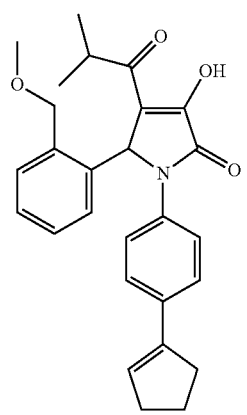 [SMILES: COCc1ccccc1C1C(C(=O)C(C)C)=C(O)C(=O)N1c1ccc(C2=CCCC2)cc1] | I-527 | 432 | 1 | 2.46 |
| 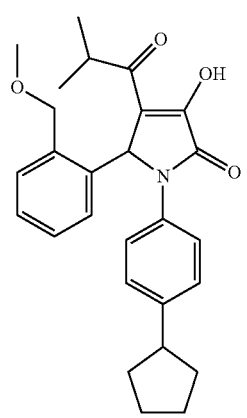 [SMILES: COCc1ccccc1C1C(C(=O)C(C)C)=C(O)C(=O)N1c1ccc(C2CCCC2)cc1] | I-528 | 434 | 1 | 2.50 |

TABLE 115-continued

| Chemical Structure | Compound No. | MS [M + H]+ | LC method | LC/MS retention time (min) |
|---|---|---|---|---|
| (structure) | I-529 | 477 | 1 | 1.76 |
| (structure) | I-530 | 504 | 1 | 2.30 |

TABLE 116

| Chemical Structure | Compound No. | MS [M + H]+ | LC method | LC/MS retention time (min) |
|---|---|---|---|---|
| (structure) | I-531 | 436 | 2 | 2.28 |

TABLE 116-continued

| Chemical Structure | Compound No. | MS [M + H]+ | LC method | LC/MS retention time (min) |
|---|---|---|---|---|
| 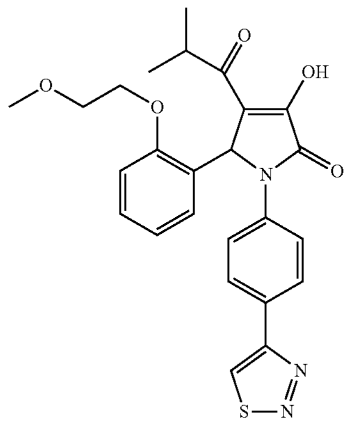 [SMILES: COCCOc1ccccc1C1C(C(=O)C(C)C)=C(O)C(=O)N1c1ccc(-c2csnn2)cc1] | I-532 | 480 | 2 | 2.25 |
| 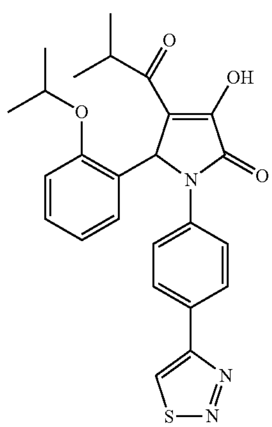 [SMILES: CC(C)Oc1ccccc1C1C(C(=O)C(C)C)=C(O)C(=O)N1c1ccc(-c2csnn2)cc1] | I-533 | 464 | 2 | 2.51 |
| 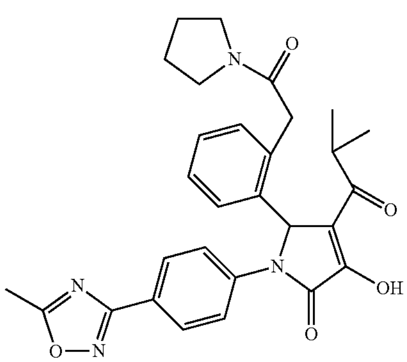 [SMILES: Cc1nc(-c2ccc(N3C(=O)C(O)=C(C(=O)C(C)C)C3c3ccccc3CC(=O)N3CCCC3)cc2)no1] | I-534 | 515 | 1 | 1.75 |

TABLE 116-continued

| Chemical Structure | Compound No. | MS [M + H]+ | LC method | LC/MS retention time (min) |
|---|---|---|---|---|
| 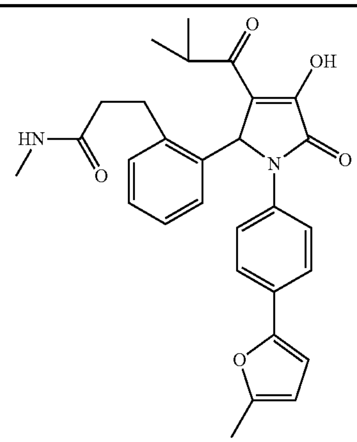 | I-535 | 487 | 1 | 1.89 |

TABLE 117

| Chemical Structure | Compound No. | MS [M + H]+ | LC method | LC/MS retention time (min) |
|---|---|---|---|---|
| 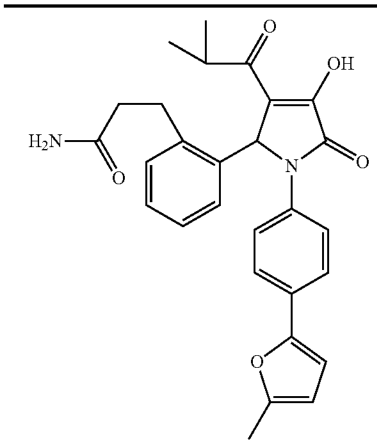 | I-536 | 473 | 1 | 1.80 |
| 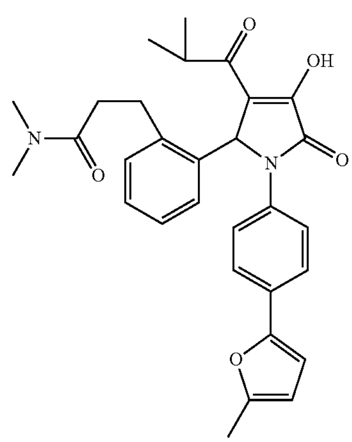 [SMILES: Cc1ccc(-c2ccc(N3C(=O)C(O)=C(C(=O)C(C)C)C3c3ccccc3CCC(=O)N(C)C)cc2)o1] | I-537 | 501 | 2 | 2.25 |

TABLE 117-continued
| Chemical Structure | Compound No. | MS [M + H]+ | LC method | LC/MS retention time (min) |
|---|---|---|---|---|
| 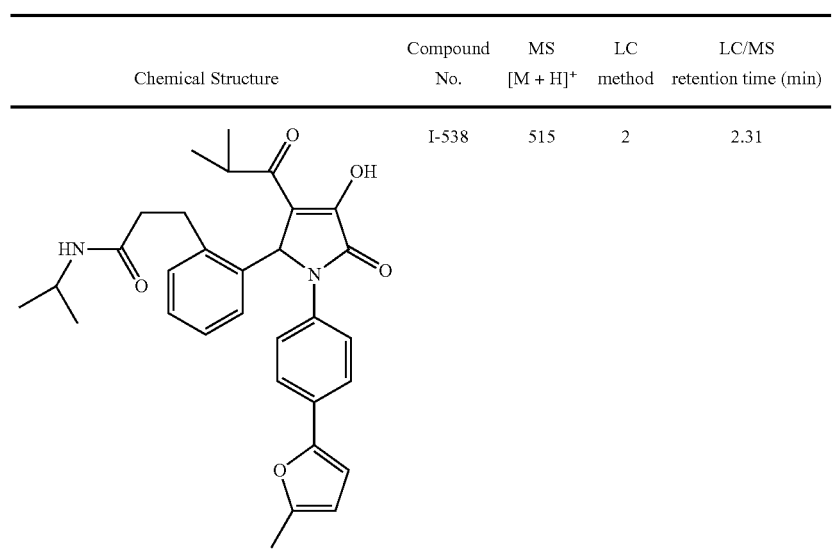 | I-538 | 515 | 2 | 2.31 |
| 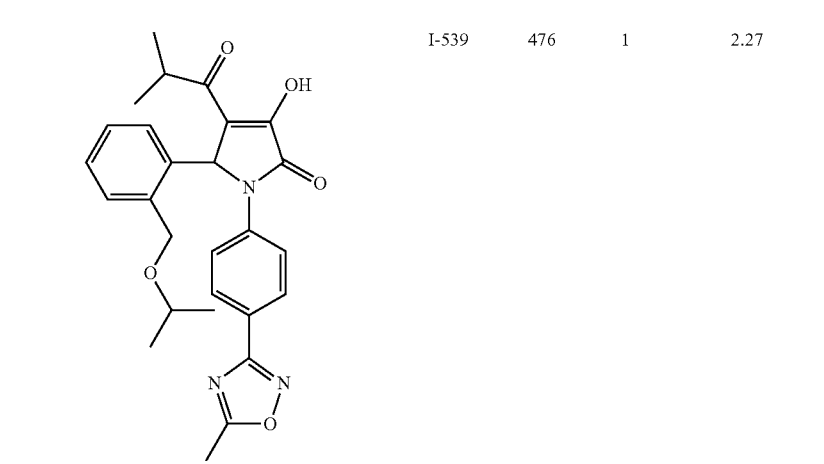 | I-539 | 476 | 1 | 2.27 |
| 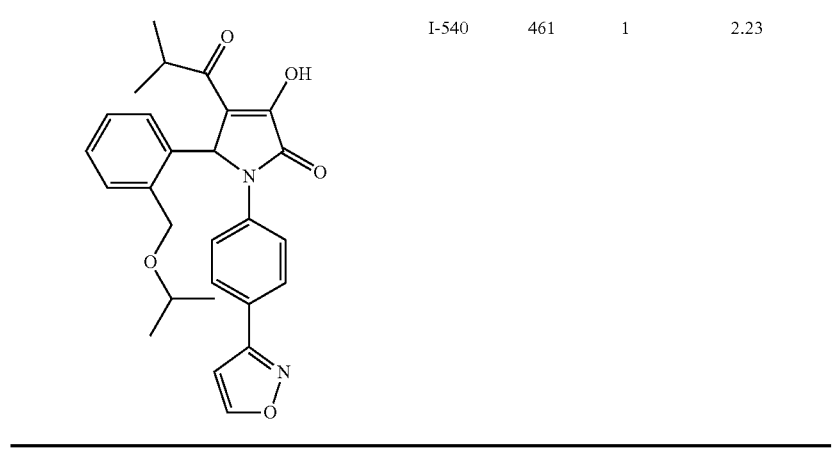 | I-540 | 461 | 1 | 2.23 |

TABLE 118
| Chemical Structure | Compound No. | MS [M + H]⁺ | LC method | LC/MS retention time (min) |
|---|---|---|---|---|
| 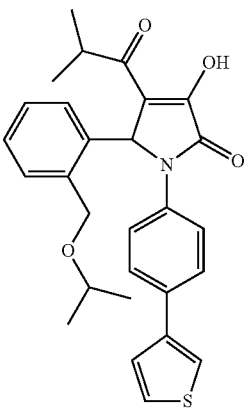 [SMILES: CC(C)OCc1ccccc1C1C(C(=O)C(C)C)=C(O)C(=O)N1c1ccc(-c2ccsc2)cc1] | I-541 | 476 | 1 | 2.51 |
| 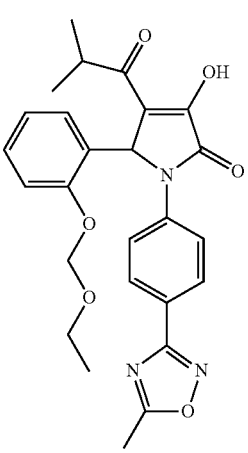 [SMILES: CCOCOc1ccccc1C1C(C(=O)C(C)C)=C(O)C(=O)N1c1ccc(-c2noc(C)n2)cc1] | I-542 | 478 | 1 | 2.12 |
| 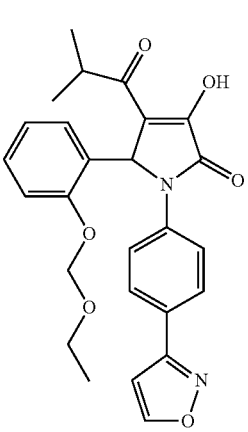 [SMILES: CCOCOc1ccccc1C1C(C(=O)C(C)C)=C(O)C(=O)N1c1ccc(-c2ccon2)cc1] | I-543 | 463 | 1 | 2.09 |

TABLE 118-continued
| Chemical Structure | Compound No. | MS [M + H]⁺ | LC method | LC/MS retention time (min) |
|---|---|---|---|---|
| 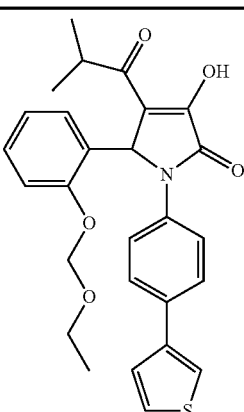 | I-544 | 478 | 1 | 2.37 |
| 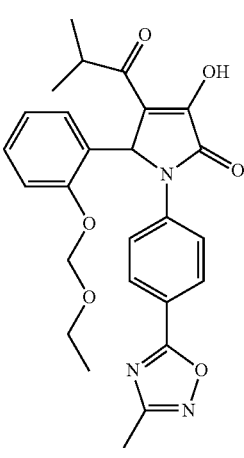 [SMILES: CCOCOc1ccccc1C1C(C(=O)C(C)C)=C(O)C(=O)N1c1ccc(-c2nc(C)no2)cc1] | I-545 | 478 | 1 | 2.14 |
TABLE 119
| Chemical Structure | Compound No. | MS [M + H]⁺ | LC method | LC/MS retention time (min) |
|---|---|---|---|---|
| 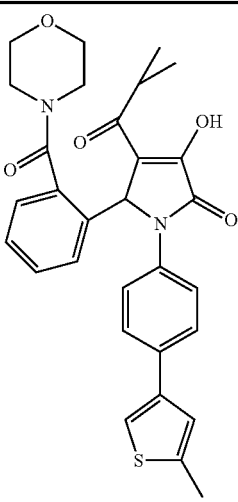 | I-546 | 531 | 2 | 2.52 |

TABLE 119-continued
| Chemical Structure | Compound No. | MS [M + H]+ | LC method | LC/MS retention time (min) |
|---|---|---|---|---|
| 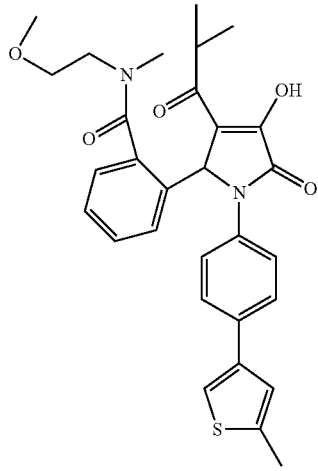 [SMILES: COCCN(C)C(=O)c1ccccc1C1C(C(=O)C(C)C)=C(O)C(=O)N1c1ccc(-c2csc(C)c2)cc1] | I-547 | 533 | 2 | 2.53 |
| 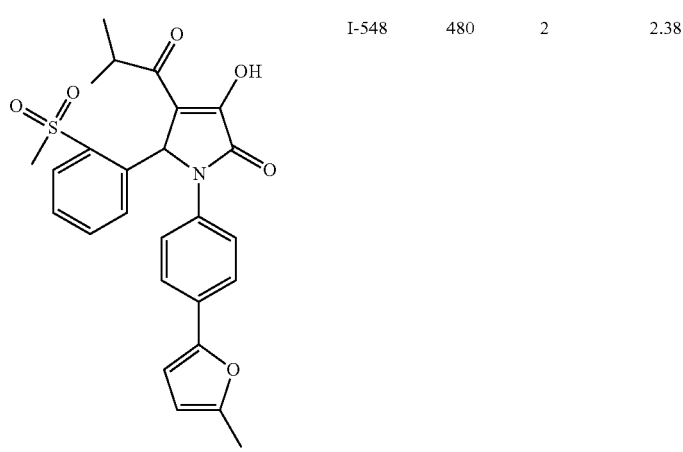 | I-548 | 480 | 2 | 2.38 |
| 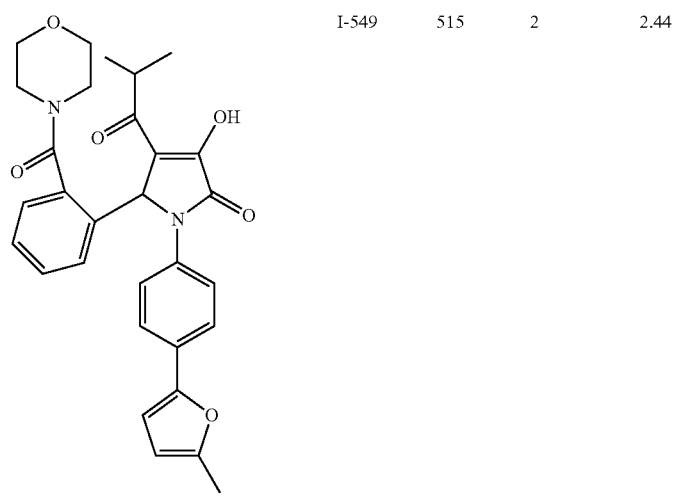 | I-549 | 515 | 2 | 2.44 |

TABLE 119-continued
| Chemical Structure | Compound No. | MS [M + H]⁺ | LC method | LC/MS retention time (min) |
|---|---|---|---|---|
| 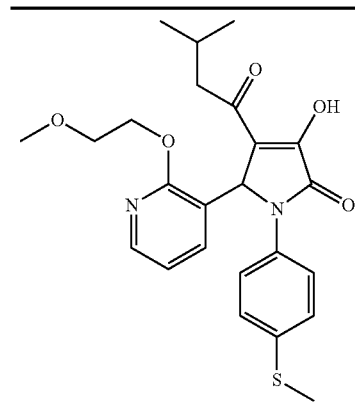 | I-550 | 457 | 2 | 2.22 |
TABLE 120
| Chemical Structure | Compound No. | MS [M + H]⁺ | LC method | LC/MS retention time (min) |
|---|---|---|---|---|
| 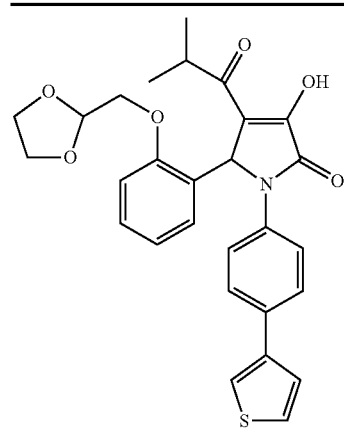 | I-551 | 506 | 2 | 2.39 |
| 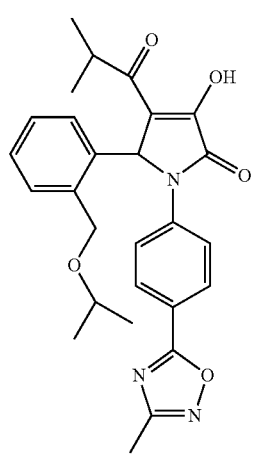 [SMILES: Cc1noc(-c2ccc(N3C(=O)C(O)=C(C(=O)C(C)C)C3c3ccccc3COC(C)C)cc2)n1] | I-552 | 476 | 1 | 2.32 |

TABLE 120-continued

| Chemical Structure | Compound No. | MS [M + H]⁺ | LC method | LC/MS retention time (min) |
|---|---|---|---|---|
| 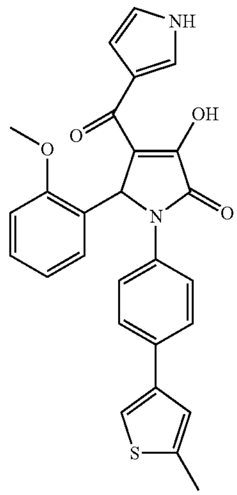 [SMILES: COc1ccccc1C1C(C(=O)c2cc[nH]c2)=C(O)C(=O)N1c1ccc(-c2csc(C)c2)cc1] | I-553 | 471 | 2 | 2.37 |
| 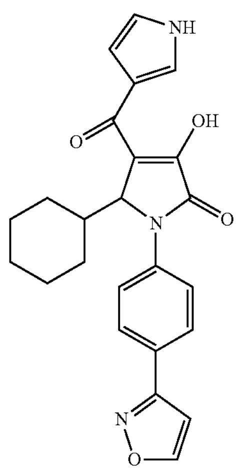 [SMILES: O=C(C1=C(O)C(=O)N(c2ccc(-c3ccon3)cc2)C1C1CCCCC1)c1cc[nH]c1] | I-554 | 418 | 2 | 2.08 |
| 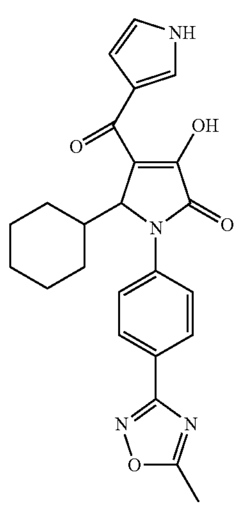 [SMILES: Cc1nc(-c2ccc(N3C(=O)C(O)=C(C(=O)c4cc[nH]c4)C3C3CCCCC3)cc2)no1] | I-555 | 433 | 2 | 2.11 |

TABLE 121

| Chemical Structure | Compound No. | MS [M + H]+ | LC method | LC/MS retention time (min) |
| --- | --- | --- | --- | --- |
| 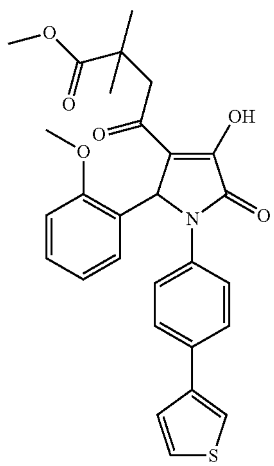 [SMILES: COC(=O)C(C)(C)CC(=O)C1=C(O)C(=O)N(c2ccc(-c3ccsc3)cc2)C1c1ccccc1OC] | I-556 | 506 | 2 | 2.43 |
| 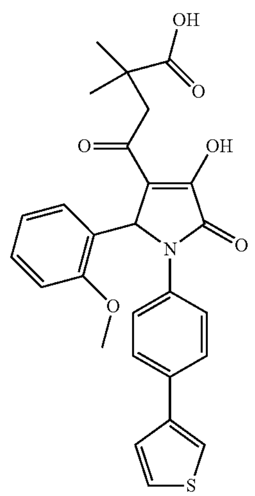 [SMILES: COc1ccccc1C1C(C(=O)CC(C)(C)C(=O)O)=C(O)C(=O)N1c1ccc(-c2ccsc2)cc1] | I-557 | 492 | 2 | 2.19 |
| 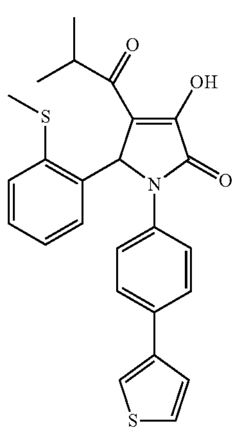 [SMILES: CSc1ccccc1C1C(C(=O)C(C)C)=C(O)C(=O)N1c1ccc(-c2ccsc2)cc1] | I-558 | 450 | 2 | 2.53 |

TABLE 121-continued

| Chemical Structure | Compound No. | MS [M + H]+ | LC method | LC/MS retention time (min) |
|---|---|---|---|---|
| 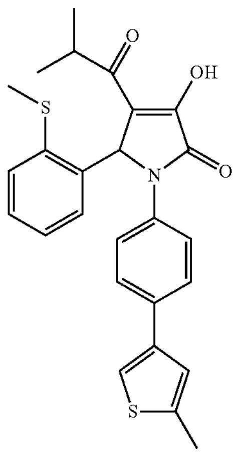 [SMILES: CSc1ccccc1C1C(C(=O)C(C)C)=C(O)C(=O)N1c1ccc(-c2csc(C)c2)cc1] | I-559 | 464 | 2 | 2.65 |
| 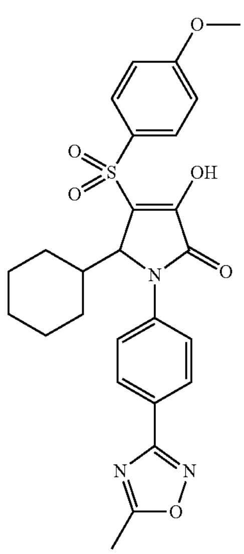 [SMILES: COc1ccc(S(=O)(=O)C2=C(O)C(=O)N(c3ccc(-c4noc(C)n4)cc3)C2C2CCCCC2)cc1] | I-560 | 510 | 2 | 2.35 |

TABLE 122
| Chemical Structure | Compound No. | MS [M + H]+ | LC method | LC/MS retention time (min) |
|---|---|---|---|---|
| 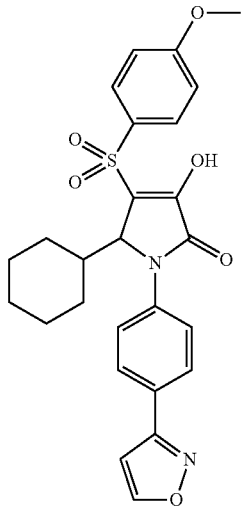 [SMILES: COc1ccc(S(=O)(=O)C2=C(O)C(=O)N(c3ccc(-c4ccon4)cc3)C2C2CCCCC2)cc1] | I-561 | 495 | 2 | 2.31 |
| 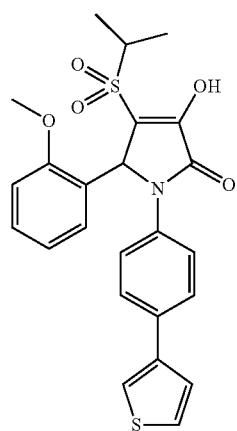 [SMILES: COc1ccccc1C1C(S(=O)(=O)C(C)C)=C(O)C(=O)N1c1ccc(-c2ccsc2)cc1] | I-562 | 479 | 2 | 2.19 |
| 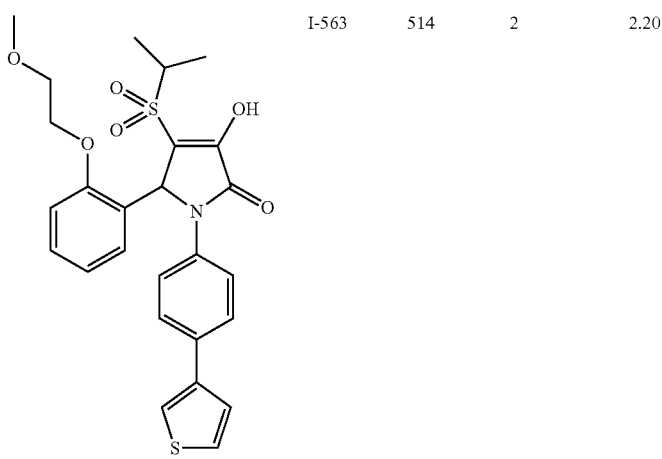 | I-563 | 514 | 2 | 2.20 |

TABLE 122-continued

| Chemical Structure | Compound No. | MS [M + H]+ | LC method | LC/MS retention time (min) |
|---|---|---|---|---|
| (structure) | I-564 | 479 | 1 | 1.83 |
| (structure) | I-565 | 493 | 1 | 2.14 |

TABLE 123

| Chemical Structure | Compound No. | MS [M + H]+ | LC method | LC/MS retention time (min) |
|---|---|---|---|---|
| (structure) | I-566 | 463 | 1 | 1.72 |

TABLE 123-continued
| Chemical Structure | Compound No. | MS [M + H]⁺ | LC method | LC/MS retention time (min) |
|---|---|---|---|---|
| 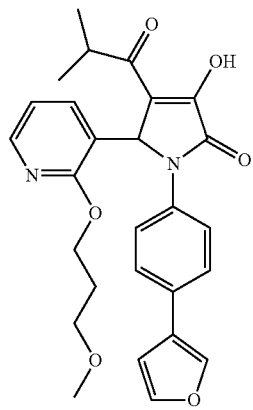 [SMILES: COCCCOc1ncccc1C1C(C(=O)C(C)C)=C(O)C(=O)N1c1ccc(-c2ccoc2)cc1] | I-567 | 477 | 1 | 2.02 |
| 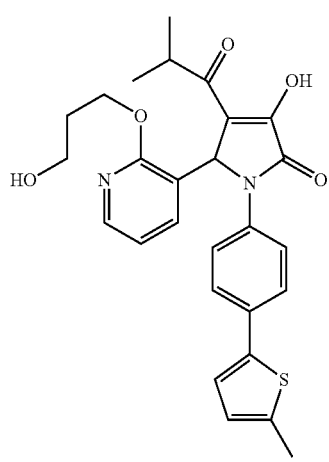 [SMILES: Cc1ccc(-c2ccc(N3C(=O)C(O)=C(C(=O)C(C)C)C3c3cccnc3OCCCO)cc2)s1] | I-568 | 493 | 2 | 2.21 |
| 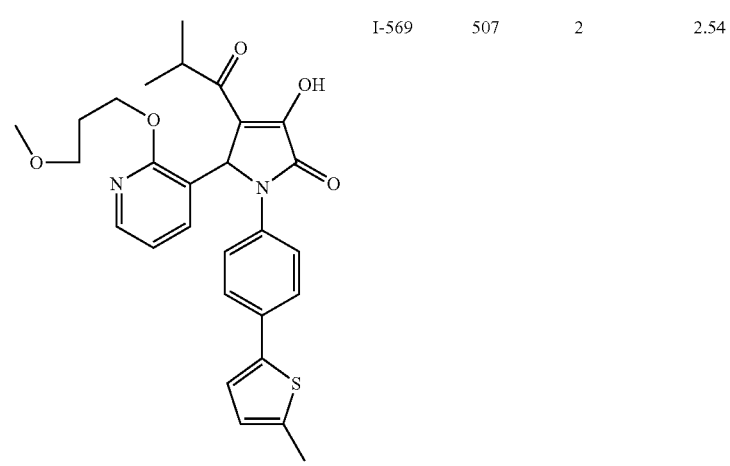 | I-569 | 507 | 2 | 2.54 |

TABLE 123-continued
| Chemical Structure | Compound No. | MS [M + H]+ | LC method | LC/MS retention time (min) |
|---|---|---|---|---|
| 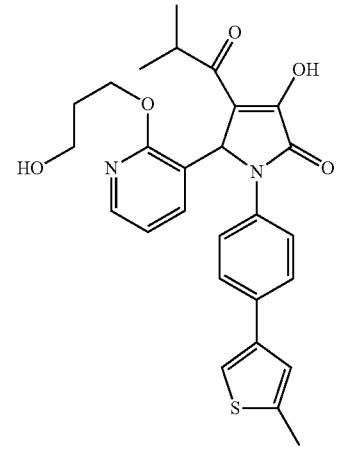 [SMILES: Cc1cc(-c2ccc(N3C(=O)C(O)=C(C(=O)C(C)C)C3c3cccnc3OCCCO)cc2)cs1] | I-570 | 493 | 2 | 2.19 |
TABLE 124
| Chemical Structure | Compound No. | MS [M + H]+ | LC method | LC/MS retention time (min) |
|---|---|---|---|---|
| 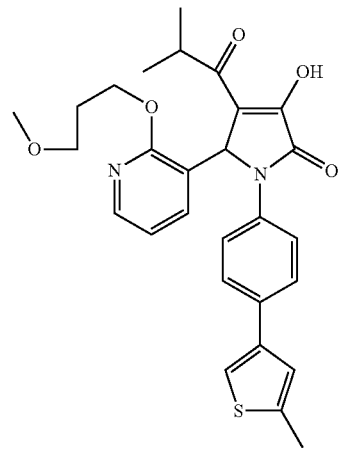 [SMILES: COCCCOc1ncccc1C1C(C(=O)C(C)C)=C(O)C(=O)N1c1ccc(-c2csc(C)c2)cc1] | I-571 | 507 | 2 | 2.51 |
| 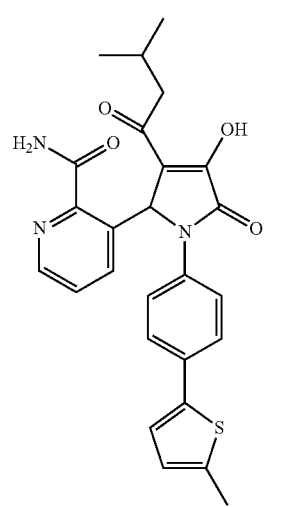 [SMILES: Cc1ccc(-c2ccc(N3C(=O)C(O)=C(C(=O)CC(C)C)C3c3cccnc3C(N)=O)cc2)s1] | I-572 | 476 | 3 | 3.28 |

TABLE 124-continued

| Chemical Structure | Compound No. | MS [M + H]+ | LC method | LC/MS retention time (min) |
|---|---|---|---|---|
| 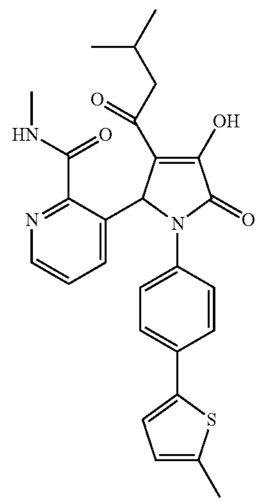 [SMILES: CNC(=O)c1ncccc1C1C(C(=O)CC(C)C)=C(O)C(=O)N1c1ccc(-c2ccc(C)s2)cc1] | I-573 | 490 | 3 | 3.35 |
| 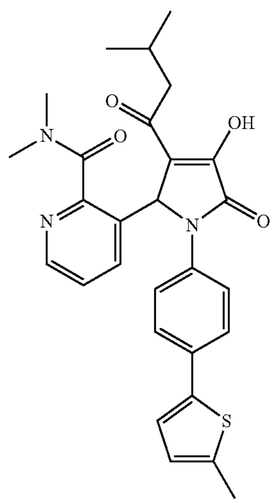 [SMILES: Cc1ccc(-c2ccc(N3C(=O)C(O)=C(C(=O)CC(C)C)C3c3cccnc3C(=O)N(C)C)cc2)s1] | I-574 | 504 | 3 | 3.32 |
| 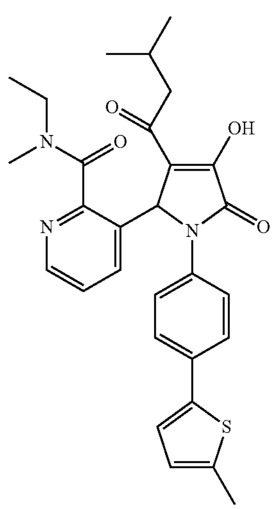 [SMILES: CCN(C)C(=O)c1ncccc1C1C(C(=O)CC(C)C)=C(O)C(=O)N1c1ccc(-c2ccc(C)s2)cc1] | I-575 | 518 | 3 | 3.41 |

TABLE 125

| Chemical Structure | Compound No. | MS [M + H]⁺ | LC method | LC/MS retention time (min) |
|---|---|---|---|---|
| 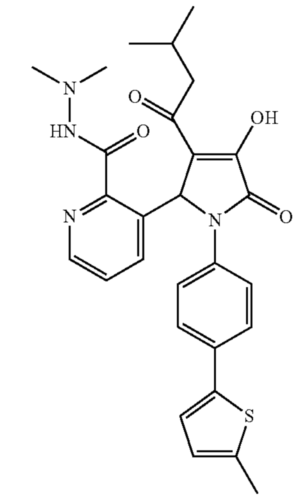 | I-576 | 519 | 3 | 3.40 |
| 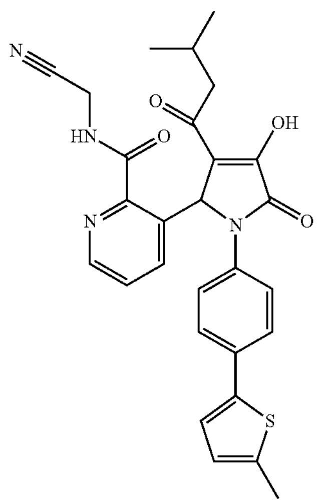 [SMILES: Cc1ccc(-c2ccc(N3C(=O)C(O)=C(C(=O)CC(C)C)C3c3cccnc3C(=O)NCC#N)cc2)s1] | I-577 | 515 | 3 | 3.24 |
| 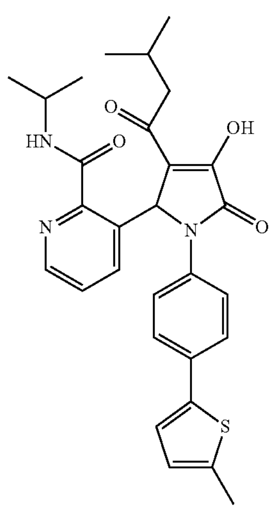 [SMILES: Cc1ccc(-c2ccc(N3C(=O)C(O)=C(C(=O)CC(C)C)C3c3cccnc3C(=O)NC(C)C)cc2)s1] | I-578 | 518 | 3 | 3.68 |

TABLE 125-continued

| Chemical Structure | Compound No. | MS [M + H]⁺ | LC method | LC/MS retention time (min) |
|---|---|---|---|---|
| 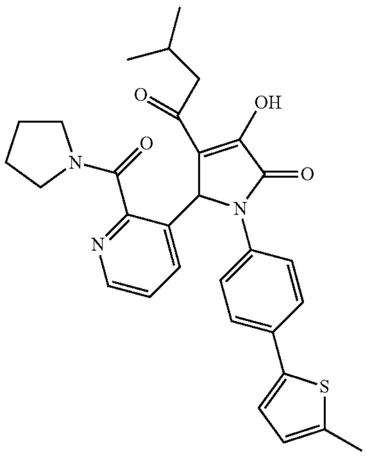 [SMILES: Cc1ccc(-c2ccc(N3C(=O)C(O)=C(C(=O)CC(C)C)C3c3cccnc3C(=O)N3CCCC3)cc2)s1] | I-579 | 530 | 3 | 3.45 |
| 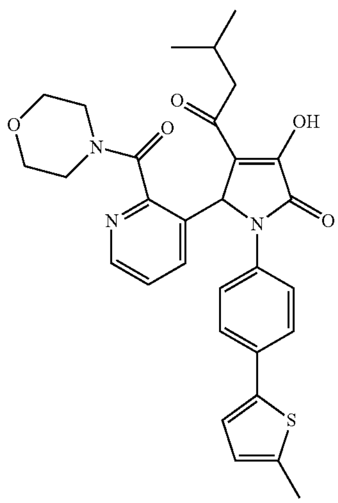 [SMILES: Cc1ccc(-c2ccc(N3C(=O)C(O)=C(C(=O)CC(C)C)C3c3cccnc3C(=O)N3CCOCC3)cc2)s1] | I-580 | 546 | 3 | 3.40 |

TABLE 126

| Chemical Structure | Compound No. | MS [M + H]⁺ | LC method | LC/MS retention time (min) |
|---|---|---|---|---|
| 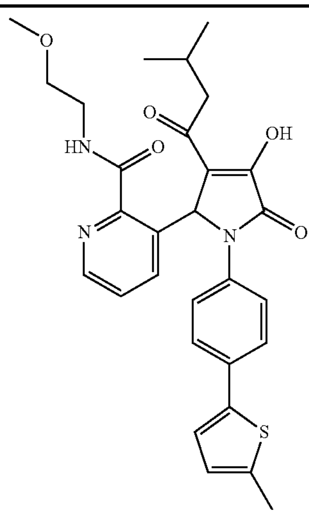 | I-581 | 534 | 3 | 3.50 |

TABLE 126-continued

| Chemical Structure | Compound No. | MS [M + H]+ | LC method | LC/MS retention time (min) |
|---|---|---|---|---|
| 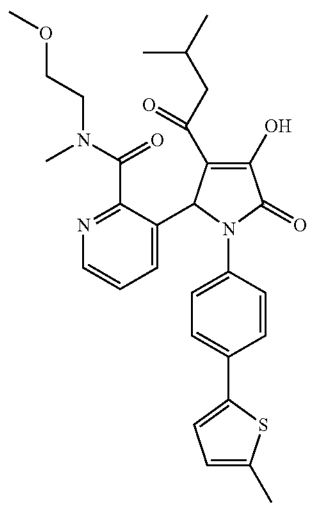 [SMILES: COCCN(C)C(=O)c1ncccc1C1C(C(=O)CC(C)C)=C(O)C(=O)N1c1ccc(-c2ccc(C)s2)cc1] | I-582 | 548 | 3 | 3.37 |
| 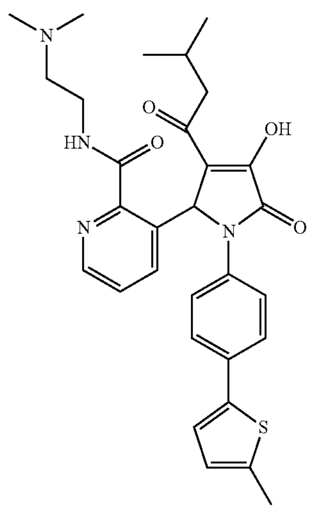 [SMILES: Cc1ccc(-c2ccc(N3C(=O)C(O)=C(C(=O)CC(C)C)C3c3cccnc3C(=O)NCCN(C)C)cc2)s1] | I-583 | 547 | 3 | 2.43 |
| 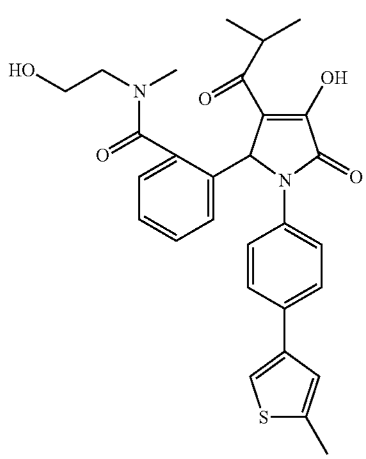 [SMILES: Cc1cc(-c2ccc(N3C(=O)C(O)=C(C(=O)C(C)C)C3c3ccccc3C(=O)N(C)CCO)cc2)cs1] | I-584 | 519 | 2 | 2.17 |

TABLE 126-continued

| Chemical Structure | Compound No. | MS [M + H]⁺ | LC method | LC/MS retention time (min) |
|---|---|---|---|---|
| 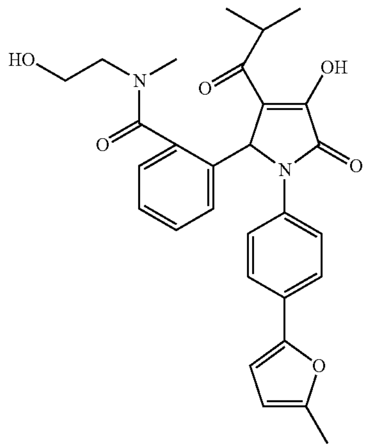 [SMILES: Cc1ccc(-c2ccc(N3C(=O)C(O)=C(C(=O)C(C)C)C3c3ccccc3C(=O)N(C)CCO)cc2)o1] | I-585 | 503 | 2 | 2.10 |

TABLE 127

| Chemical Structure | Compound No. | MS [M + H]⁺ | LC method | LC/MS retention time (min) |
|---|---|---|---|---|
| 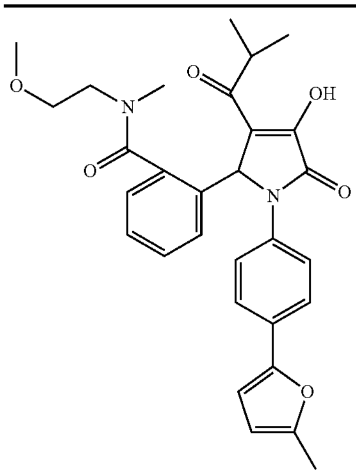 | I-586 | 517 | 2 | 2.39 |
| 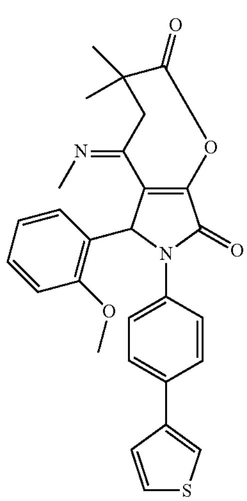 [SMILES: C/N=C1/CC(C)(C)C(=O)OC2=C1C(c1ccccc1OC)N(c1ccc(-c3ccsc3)cc1)C2=O] | I-587 | 487 | 2 | 2.24 |

TABLE 127-continued

| Chemical Structure | Compound No. | MS [M + H]+ | LC method | LC/MS retention time (min) |
|---|---|---|---|---|
| 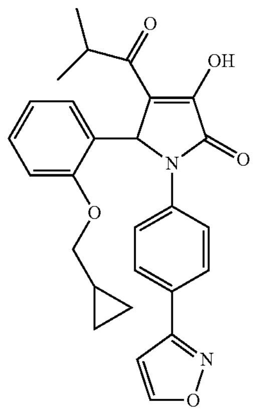 [SMILES: CC(C)C(=O)C1=C(O)C(=O)N(c2ccc(-c3ccon3)cc2)C1c1ccccc1OCC1CC1] | I-588 | 459 | 1 | 2.20 |
| 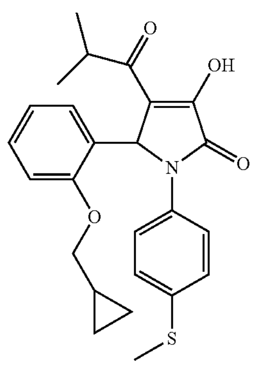 [SMILES: CSc1ccc(N2C(=O)C(O)=C(C(=O)C(C)C)C2c2ccccc2OCC2CC2)cc1] | I-589 | 438 | 1 | 2.34 |
| 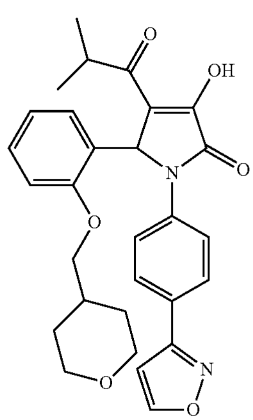 [SMILES: CC(C)C(=O)C1=C(O)C(=O)N(c2ccc(-c3ccon3)cc2)C1c1ccccc1OCC1CCOCC1] | I-590 | 503 | 1 | 2.01 |

TABLE 128

| Chemical Structure | Compound No. | MS [M + H]+ | LC method | LC/MS retention time (min) |
|---|---|---|---|---|
| 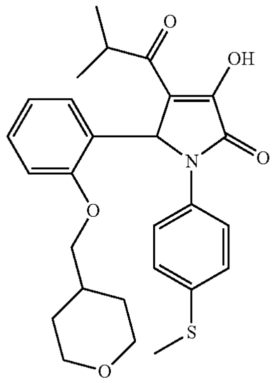 [SMILES: CSc1ccc(N2C(=O)C(O)=C(C(=O)C(C)C)C2c2ccccc2OCC2CCOCC2)cc1] | I-591 | 482 | 1 | 2.15 |
| 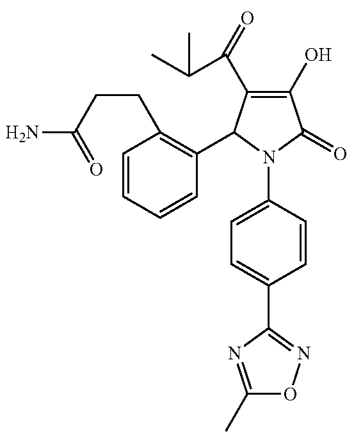 [SMILES: Cc1nc(-c2ccc(N3C(=O)C(O)=C(C(=O)C(C)C)C3c3ccccc3CCC(N)=O)cc2)no1] | I-592 | 475 | 1 | 1.52 |
| 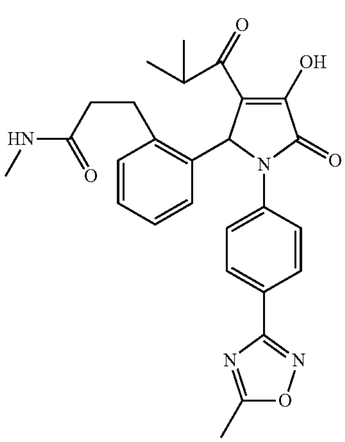 [SMILES: CNC(=O)CCc1ccccc1C1C(C(=O)C(C)C)=C(O)C(=O)N1c1ccc(-c2noc(C)n2)cc1] | I-593 | 489 | 1 | 1.60 |

TABLE 128-continued
| Chemical Structure | Compound No. | MS [M + H]+ | LC method | LC/MS retention time (min) |
|---|---|---|---|---|
| 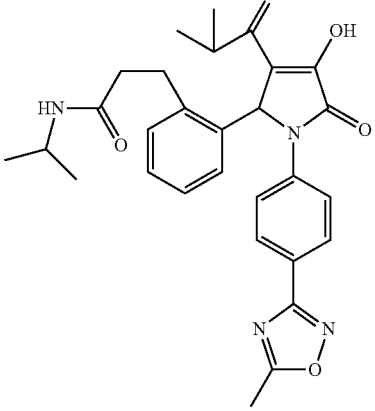 | I-594 | 517 | 1 | 1.83 |
| 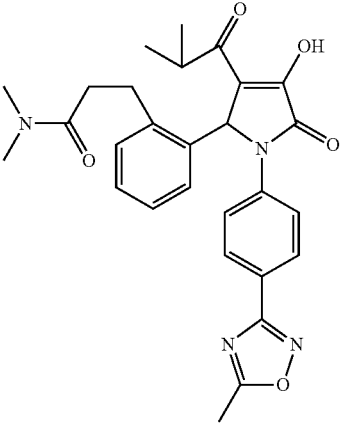 [SMILES: Cc1nc(-c2ccc(N3C(=O)C(O)=C(C(=O)C(C)C)C3c3ccccc3CCC(=O)N(C)C)cc2)no1] | I-595 | 503 | 1 | 1.75 |
TABLE 129
| Chemical Structure | Compound No. | MS [M + H]+ | LC method | LC/MS retention time (min) |
|---|---|---|---|---|
| 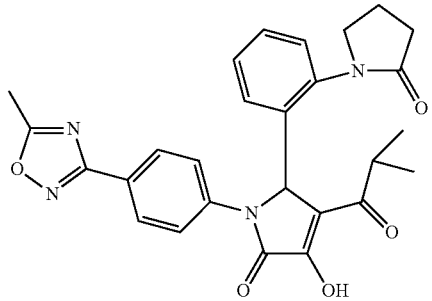 [SMILES: Cc1nc(-c2ccc(N3C(=O)C(O)=C(C(=O)C(C)C)C3c3ccccc3N3CCCC3=O)cc2)no1] | I-596 | 487 | 2 | 1.82 |

TABLE 129-continued

| Chemical Structure | Compound No. | MS [M + H]⁺ | LC method | LC/MS retention time (min) |
|---|---|---|---|---|
| | I-598 | 501 | 2 | 2.27 |
| | I-598 | 501 | 2 | 2.27 |

TABLE 130

| Chemical Structure | Compound No. | MS [M + H]⁺ | LC method | LC/MS retention time (min) |
|---|---|---|---|---|
| 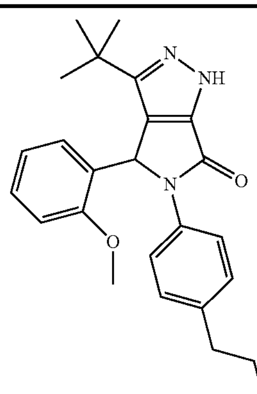 | II-001 | 404 | 1 | 2.30 |
| 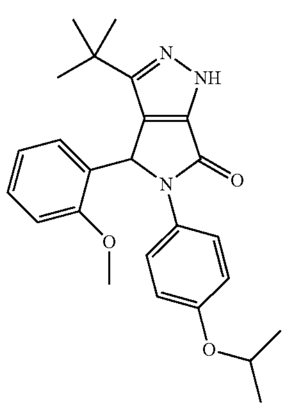 [SMILES: COc1ccccc1C1c2c(C(C)(C)C)n[nH]c2C(=O)N1c1ccc(OC(C)C)cc1] | II-002 | 420 | 1 | 2.10 |

TABLE 130-continued

| Chemical Structure | Compound No. | MS [M + H]+ | LC method | LC/MS retention time (min) |
|---|---|---|---|---|
| 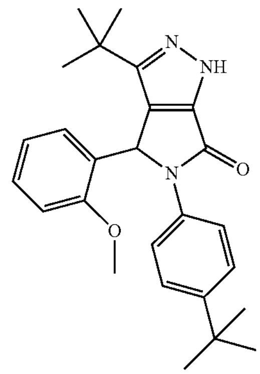 [SMILES: COc1ccccc1C1c2c(C(C)(C)C)n[nH]c2C(=O)N1c1ccc(C(C)(C)C)cc1] | II-003 | 418 | 1 | 2.40 |
| 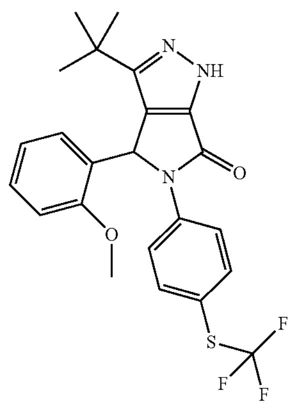 [SMILES: COc1ccccc1C1c2c(C(C)(C)C)n[nH]c2C(=O)N1c1ccc(SC(F)(F)F)cc1] | II-004 | 462 | 1 | 2.40 |
| 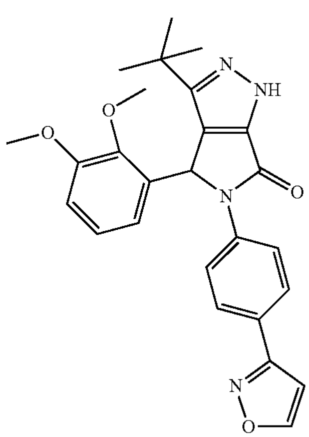 [SMILES: COc1cccc(C2c3c(C(C)(C)C)n[nH]c3C(=O)N2c2ccc(-c3ccon3)cc2)c1OC] | II-005 | 459 | 1 | 1.90 |

TABLE 131

| Chemical Structure | Compound No. | MS [M + H]+ | LC method | LC/MS retention time (min) |
|---|---|---|---|---|
| 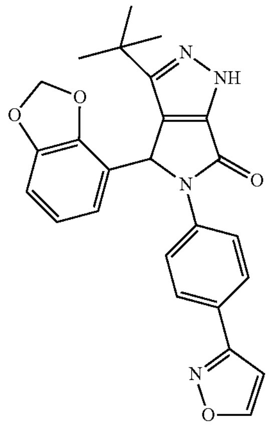 [SMILES: CC(C)(C)c1n[nH]c2c1C(c1cccc3c1OCO3)N(c1ccc(-c3ccon3)cc1)C2=O] | II-006 | 443 | 1 | 1.80 |
| 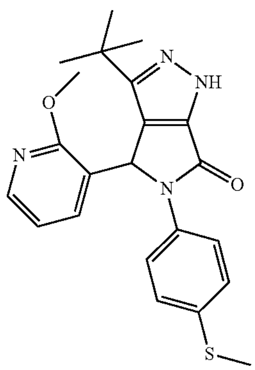 [SMILES: COc1ncccc1C1c2c(C(C)(C)C)n[nH]c2C(=O)N1c1ccc(SC)cc1] | II-007 | 409 | 1 | 1.90 |
| 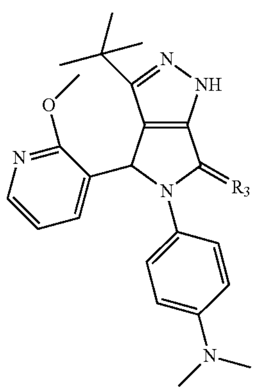 | II-008 | 406 | 1 | 1.50 |
| 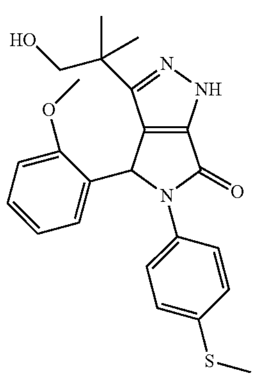 [SMILES: COc1ccccc1C1c2c(C(C)(C)CO)n[nH]c2C(=O)N1c1ccc(SC)cc1] | II-009 | 424 | 1 | 1.70 |

TABLE 131-continued

| Chemical Structure | Compound No. | MS [M + H]⁺ | LC method | LC/MS retention time (min) |
|---|---|---|---|---|
| 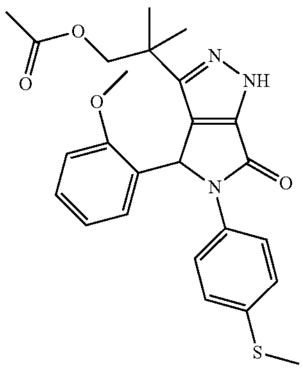 [SMILES: COc1ccccc1C1c2c(C(C)(C)COC(C)=O)n[nH]c2C(=O)N1c1ccc(SC)cc1] | II-010 | 466 | 1 | 1.90 |

TABLE 132

| Chemical Structure | Compound No. | MS [M + H]⁺ | LC method | LC/MS retention time (min) |
|---|---|---|---|---|
| 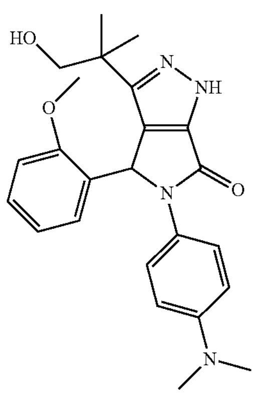 [SMILES: COc1ccccc1C1c2c(C(C)(C)CO)n[nH]c2C(=O)N1c1ccc(N(C)C)cc1] | II-011 | 421 | 1 | 1.30 |
| 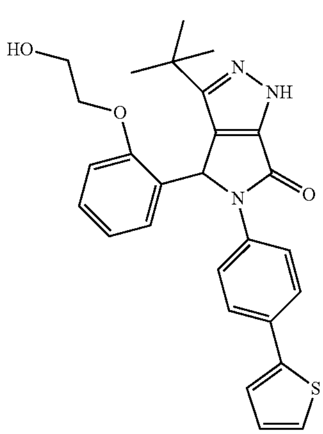 [SMILES: CC(C)(C)c1n[nH]c2c1C(c1ccccc1OCCO)N(c1ccc(-c3cccs3)cc1)C2=O] | II-012 | 474 | 1 | 2.00 |

TABLE 132-continued

| Chemical Structure | Compound No. | MS [M + H]+ | LC method | LC/MS retention time (min) |
|---|---|---|---|---|
| 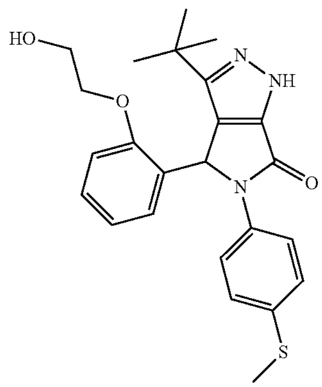 [SMILES: CSc1ccc(N2C(=O)c3[nH]nc(C(C)(C)C)c3C2c2ccccc2OCCO)cc1] | II-013 | 438 | 1 | 1.80 |
| 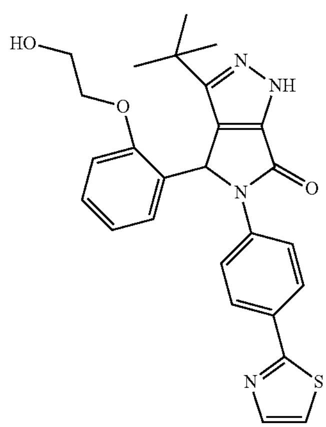 [SMILES: CC(C)(C)c1n[nH]c2c1C(c1ccccc1OCCO)N(c1ccc(-c3nccs3)cc1)C2=O] | II-014 | 475 | 1 | 1.70 |
| 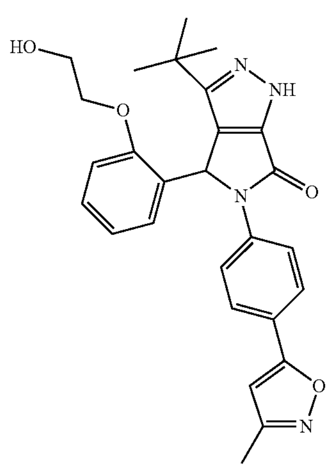 [SMILES: Cc1cc(-c2ccc(N3C(=O)c4[nH]nc(C(C)(C)C)c4C3c3ccccc3OCCO)cc2)on1] | II-015 | 473 | 1 | 1.70 |

TABLE 133

| Chemical Structure | Compound No. | MS [M + H]+ | LC method | LC/MS retention time (min) |
| --- | --- | --- | --- | --- |
| 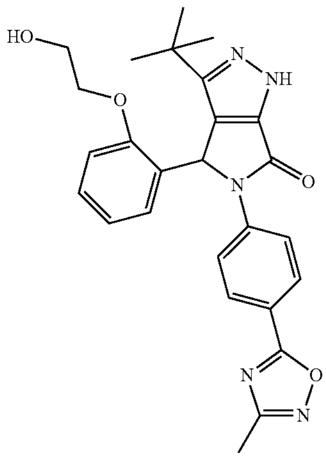 [SMILES: Cc1noc(-c2ccc(N3C(=O)c4[nH]nc(C(C)(C)C)c4C3c3ccccc3OCCO)cc2)n1] | II-016 | 474 | 1 | 1.70 |
| 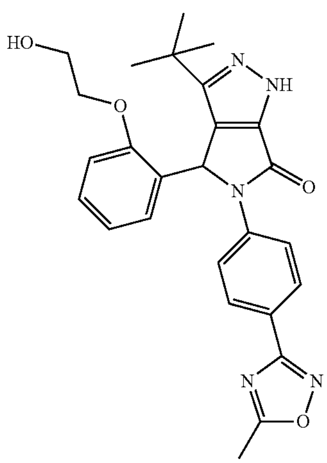 [SMILES: Cc1nc(-c2ccc(N3C(=O)c4[nH]nc(C(C)(C)C)c4C3c3ccccc3OCCO)cc2)no1] | II-017 | 474 | 1 | 1.70 |
| 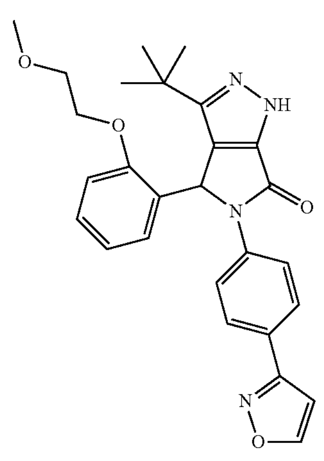 [SMILES: COCCOc1ccccc1C1c2c(C(C)(C)C)n[nH]c2C(=O)N1c1ccc(-c2ccon2)cc1] | II-018 | 473 | 1 | 1.90 |

TABLE 133-continued
| Chemical Structure | Compound No. | MS [M + H]+ | LC method | LC/MS retention time (min) |
|---|---|---|---|---|
| 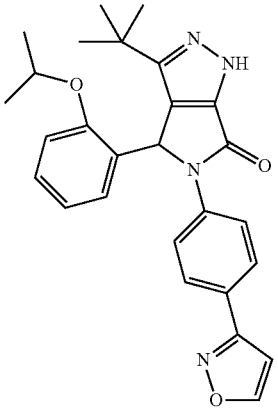 [SMILES: CC(C)Oc1ccccc1C1c2c(C(C)(C)C)n[nH]c2C(=O)N1c1ccc(-c2ccon2)cc1] | II-019 | 457 | 1 | 2.10 |
| 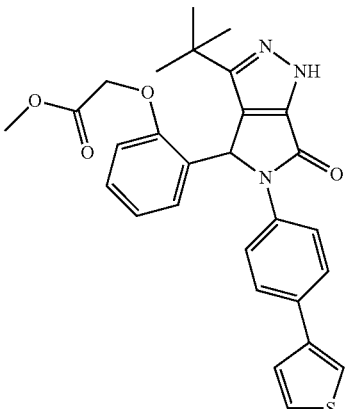 | II-020 | 502 | 1 | 2.10 |
TABLE 134
| Chemical Structure | Compound No. | MS [M + H]+ | LC method | LC/MS retention time (min) |
|---|---|---|---|---|
| 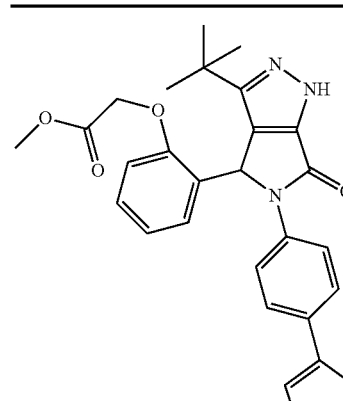 | II-021 | 502 | 1 | 2.10 |

TABLE 134-continued
| Chemical Structure | Compound No. | MS [M + H]+ | LC method | LC/MS retention time (min) |
|---|---|---|---|---|
| 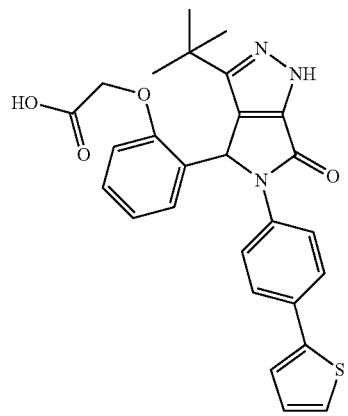 [SMILES: CC(C)(C)c1n[nH]c2c1C(c1ccccc1OCC(=O)O)N(c1ccc(-c3cccs3)cc1)C2=O] | II-022 | 488 | 1 | 1.80 |
| 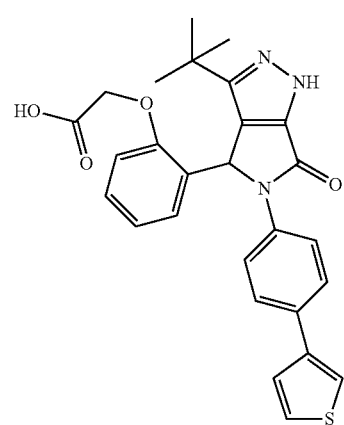 [SMILES: CC(C)(C)c1n[nH]c2c1C(c1ccccc1OCC(=O)O)N(c1ccc(-c3ccsc3)cc1)C2=O] | II-023 | 488 | 1 | 1.80 |
| 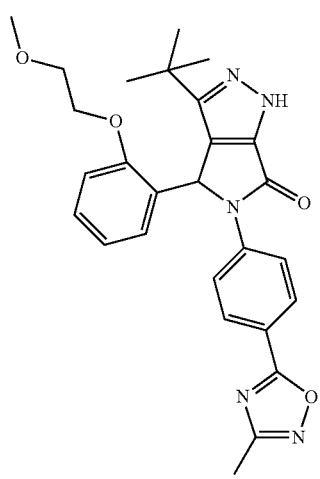 [SMILES: COCCOc1ccccc1C1c2c(C(C)(C)C)n[nH]c2C(=O)N1c1ccc(-c2nc(C)no2)cc1] | II-024 | 488 | 1 | 1.90 |

TABLE 134-continued
| Chemical Structure | Compound No. | MS [M + H]+ | LC method | LC/MS retention time (min) |
|---|---|---|---|---|
| 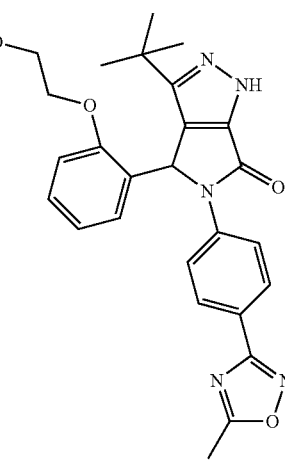 | II-025 | 488 | 1 | 1.90 |
TABLE 135
| Chemical Structure | Compound No. | MS [M + H]+ | LC method | LC/MS retention time (min) |
|---|---|---|---|---|
| 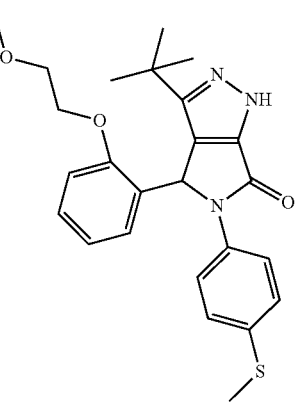 | II-026 | 452 | 1 | 2.00 |
| 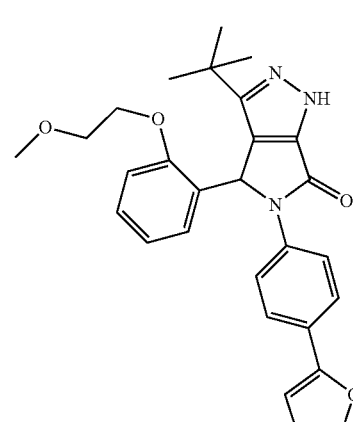 | II-027 | 472 | 1 | 2.10 |

TABLE 135-continued

| Chemical Structure | Compound No. | MS [M + H]+ | LC method | LC/MS retention time (min) |
|---|---|---|---|---|
| 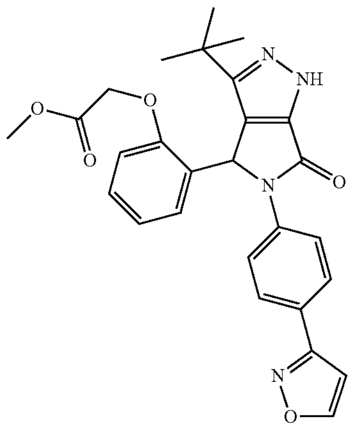 [SMILES: COC(=O)COc1ccccc1C1c2c(C(C)(C)C)n[nH]c2C(=O)N1c1ccc(-c2ccon2)cc1] | II-028 | 487 | 1 | 1.80 |
| 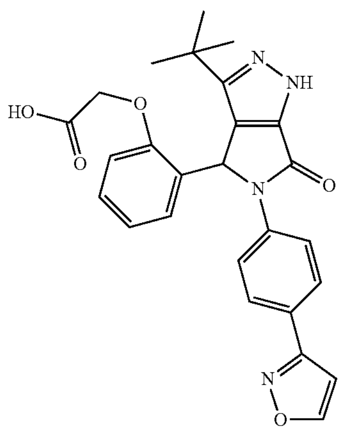 [SMILES: CC(C)(C)c1n[nH]c2c1C(c1ccccc1OCC(=O)O)N(c1ccc(-c3ccon3)cc1)C2=O] | II-029 | 473 | 1 | 1.60 |
| 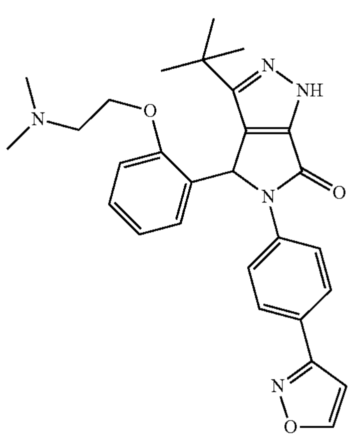 [SMILES: CN(C)CCOc1ccccc1C1c2c(C(C)(C)C)n[nH]c2C(=O)N1c1ccc(-c2ccon2)cc1] | II-030 | 486 | 1 | 1.20 |

TABLE 136

| Chemical Structure | Compound No. | MS [M + H]+ | LC method | LC/MS retention time (min) |
|---|---|---|---|---|
| 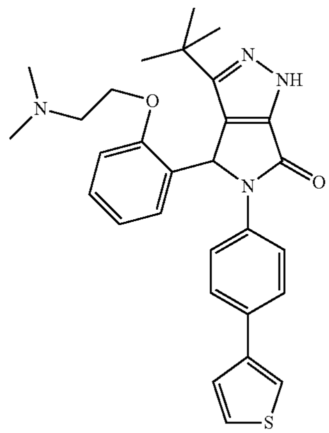 [SMILES: CN(C)CCOc1ccccc1C1c2c(C(C)(C)C)n[nH]c2C(=O)N1c1ccc(-c2ccsc2)cc1] | II-031 | 501 | 1 | 1.50 |
| 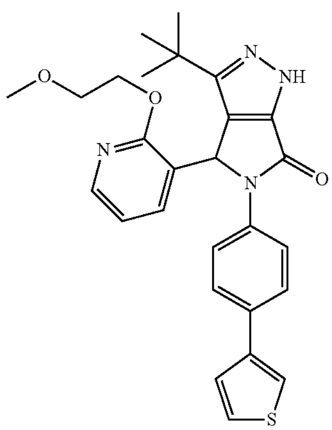 [SMILES: COCCOc1ncccc1C1c2c(C(C)(C)C)n[nH]c2C(=O)N1c1ccc(-c2ccsc2)cc1] | II-032 | 489 | 1 | 2.00 |
| 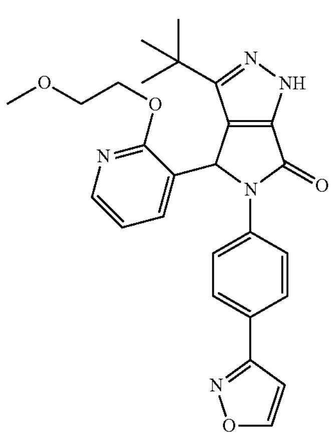 [SMILES: COCCOc1ncccc1C1c2c(C(C)(C)C)n[nH]c2C(=O)N1c1ccc(-c2ccon2)cc1] | II-033 | 474 | 1 | 1.70 |

TABLE 136-continued

| Chemical Structure | Compound No. | MS [M + H]+ | LC method | LC/MS retention time (min) |
|---|---|---|---|---|
| 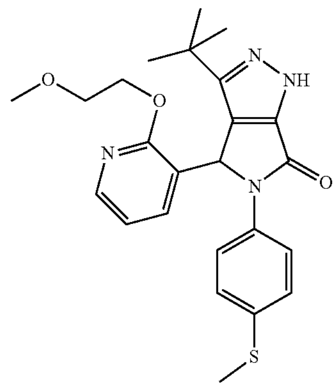 [SMILES: COCCOc1ncccc1C1c2c(C(C)(C)C)n[nH]c2C(=O)N1c1ccc(SC)cc1] | II-034 | 453 | 1 | 1.80 |
| 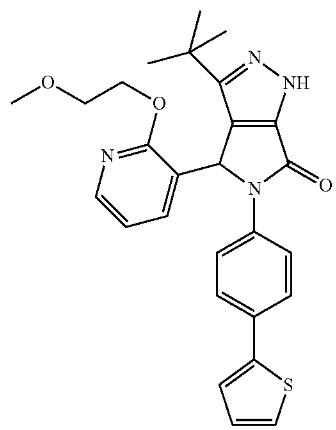 [SMILES: COCCOc1ncccc1C1c2c(C(C)(C)C)n[nH]c2C(=O)N1c1ccc(-c2cccs2)cc1] | II-035 | 489 | 1 | 2.10 |

TABLE 137

| Chemical Structure | Compound No. | MS [M + H]+ | LC method | LC/MS retention time (min) |
|---|---|---|---|---|
| 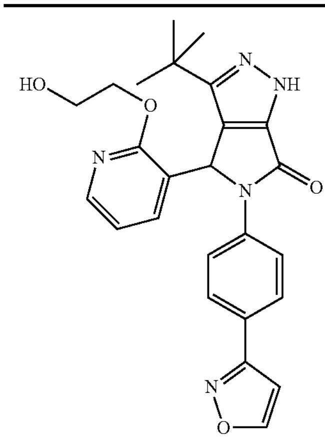 | II-036 | 460 | 1 | 1.50 |

TABLE 137-continued

| Chemical Structure | Compound No. | MS [M + H]+ | LC method | LC/MS retention time (min) |
|---|---|---|---|---|
| (structure) | II-037 | 473 | 1 | 2.00 |
| (structure) | II-038 | 473 | 1 | 1.90 |
| (structure) | II-039 | 475 | 1 | 1.80 |
| (structure) | II-040 | 439 | 1 | 1.60 |

Table 138

| Chemical Structure | Compound No. | MS [M + H]+ | LC method | LC/MS retention time (min) |
|---|---|---|---|---|
| (structure) | II-041 | 459 | 1 | 1.70 |
| (structure) | II-042 | 475 | 1 | 1.80 |

Table 138-continued
| Chemical Structure | Compound No. | MS [M+H]+ | LC method | LC/MS retention time (min) |
|---|---|---|---|---|
| 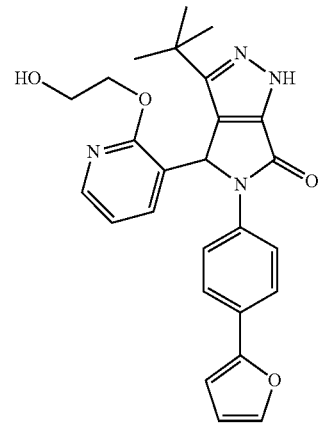 [SMILES: CC(C)(C)c1n[nH]c2c1C(c1cccnc1OCCO)N(c1ccc(-c3ccco3)cc1)C2=O] | II-043 | 459 | 1 | 1.70 |
| 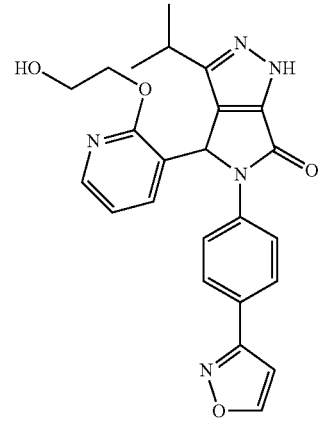 [SMILES: CC(C)c1n[nH]c2c1C(c1cccnc1OCCO)N(c1ccc(-c3ccon3)cc1)C2=O] | II-044 | 446 | 1 | 1.40 |
| 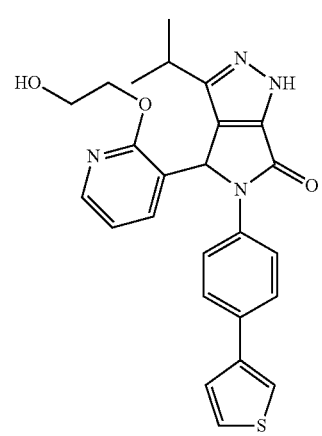 [SMILES: CC(C)c1n[nH]c2c1C(c1cccnc1OCCO)N(c1ccc(-c3ccsc3)cc1)C2=O] | II-045 | 461 | 1 | 1.70 |
TABLE 139
| Chemical Structure | Compound No. | MS [M+H]+ | LC method | LC/MS retention time (min) |
|---|---|---|---|---|
| 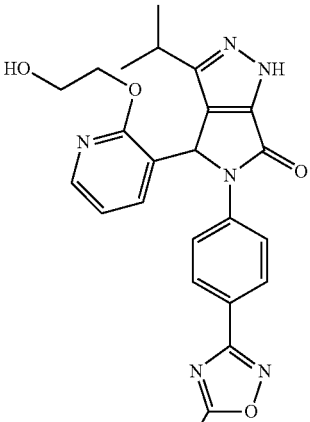 | II-046 | 461 | 1 | 1.40 |
| 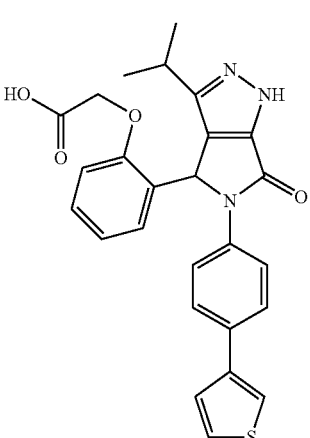 | II-047 | 474 | 1 | 1.80 |
| 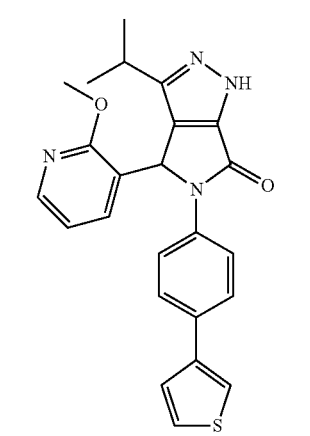 [SMILES: COc1ncccc1C1c2c(C(C)C)n[nH]c2C(=O)N1c1ccc(-c2ccsc2)cc1] | II-048 | 431 | 1 | 2.00 |

TABLE 139-continued
| Chemical Structure | Compound No. | MS [M + H]+ | LC method | LC/MS retention time (min) |
|---|---|---|---|---|
| 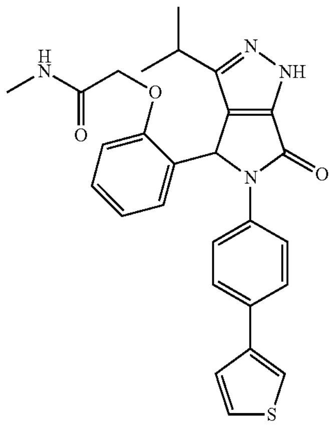 [SMILES: CNC(=O)COc1ccccc1C1c2c(C(C)C)n[nH]c2C(=O)N1c1ccc(-c2ccsc2)cc1] | II-049 | 487 | 1 | 1.80 |
| 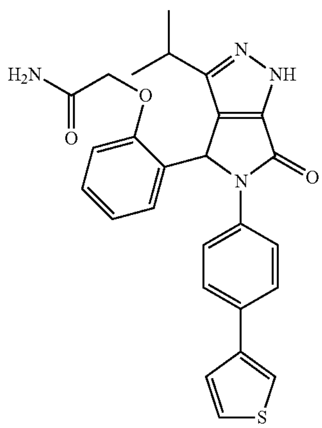 [SMILES: CC(C)c1n[nH]c2c1C(c1ccccc1OCC(N)=O)N(c1ccc(-c3ccsc3)cc1)C2=O] | II-050 | 473 | 1 | 1.70 |
TABLE 140
| Chemical Structure | Compound No. | MS [M + H]+ | LC method | LC/MS retention time (min) |
|---|---|---|---|---|
| | II-051 | 488 | 1 | 1.60 |
| 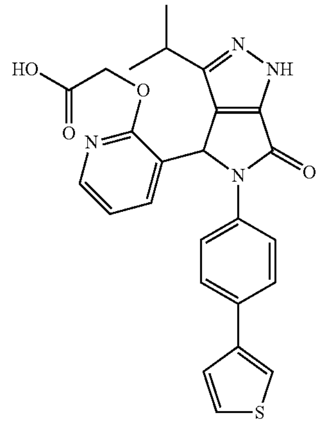 [SMILES: CC(C)c1n[nH]c2c1C(c1cccnc1OCC(=O)O)N(c1ccc(-c3ccsc3)cc1)C2=O] | II-052 | 475 | 1 | 1.70 |
| 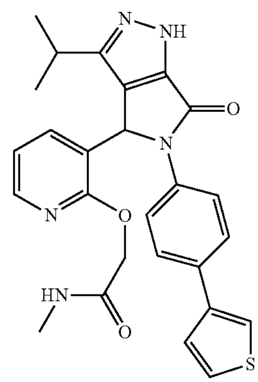 [SMILES: CNC(=O)COc1ncccc1C1c2c(C(C)C)n[nH]c2C(=O)N1c1ccc(-c2ccsc2)cc1] | II-053 | 488 | 1 | 1.70 |
| 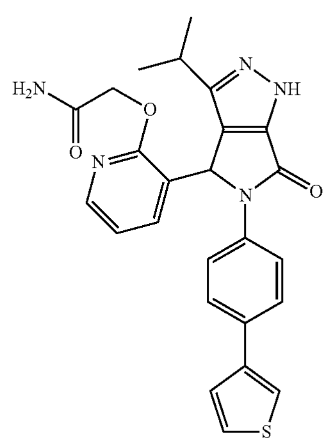 [SMILES: CC(C)c1n[nH]c2c1C(c1cccnc1OCC(N)=O)N(c1ccc(-c3ccsc3)cc1)C2=O] | II-054 | 474 | 1 | 1.60 |
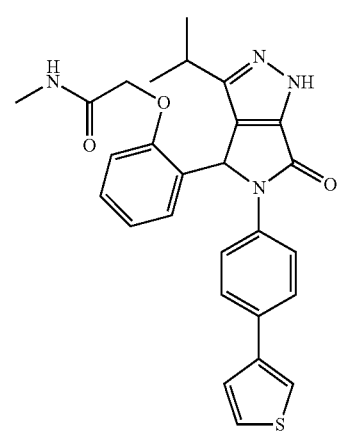

TABLE 140-continued

| Chemical Structure | Compound No. | MS [M + H]+ | LC method | LC/MS retention time (min) |
|---|---|---|---|---|
| (structure) | II-055 | 427 | 2 | 2.13 |

TABLE 141

| Chemical Structure | Compound No. | MS [M + H]+ | LC method | LC/MS retention time (min) |
|---|---|---|---|---|
| (structure) | II-056 | 509 | 1 | 2.43 |
| (structure) | II-057 | 434 | 1 | 2.09 |

TABLE 141-continued

| Chemical Structure | Compound No. | MS [M + H]+ | LC method | LC/MS retention time (min) |
|---|---|---|---|---|
| (structure) | II-058 | 416 | 1 | 1.23 |
| (structure) | II-059 | 447 | 1 | 1.93 |
| (structure) | II-060 | 459 | 2 | 2.07 |

TABLE 142
| Chemical Structure | Compound No. | MS [M + H]+ | LC method | LC/MS retention time (min) |
|---|---|---|---|---|
| 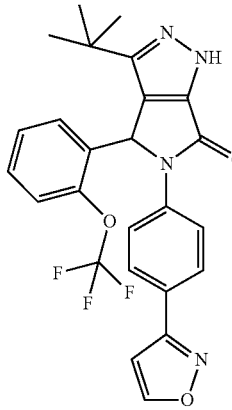 | II-061 | 483 | 2 | 2.23 |
| 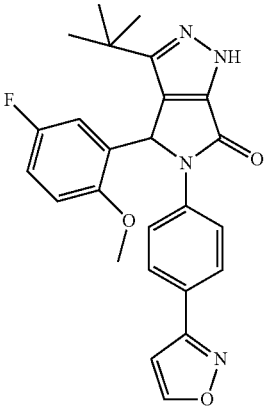 [SMILES: COc1ccc(F)cc1C1c2c(C(C)(C)C)n[nH]c2C(=O)N1c1ccc(-c2ccon2)cc1] | II-062 | 447 | 2 | 2.08 |
| 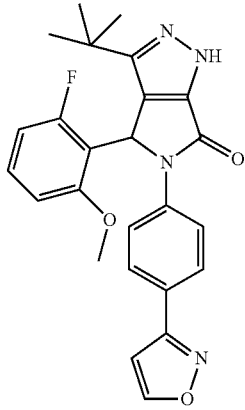 [SMILES: COc1cccc(F)c1C1c2c(C(C)(C)C)n[nH]c2C(=O)N1c1ccc(-c2ccon2)cc1] | II-063 | 447 | 1 | 1.9 |
TABLE 142-continued
| Chemical Structure | Compound No. | MS [M + H]+ | LC method | LC/MS retention time (min) |
|---|---|---|---|---|
| 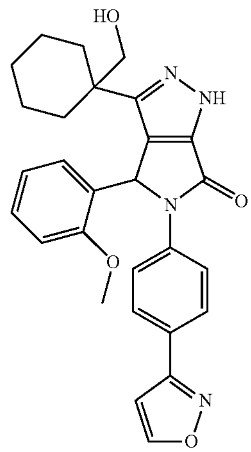 [SMILES: COc1ccccc1C1c2c(C3(CO)CCCCC3)n[nH]c2C(=O)N1c1ccc(-c2ccon2)cc1] | II-064 | 485 | 1 | 1.76 |
| 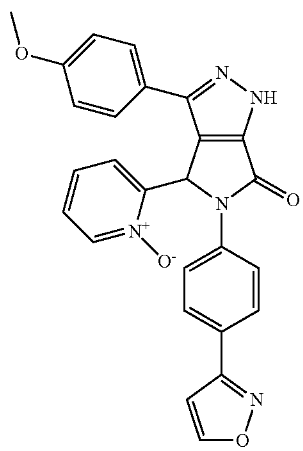 [SMILES: COc1ccc(-c2n[nH]c3c2C(c2cccc[n+]2[O-])N(c2ccc(-c4ccon4)cc2)C3=O)cc1] | II-065 | 466 | 1 | 1.36 |
TABLE 143
| Chemical Structure | Compound No. | MS [M + H]+ | LC method | LC/MS retention time (min) |
|---|---|---|---|---|
| 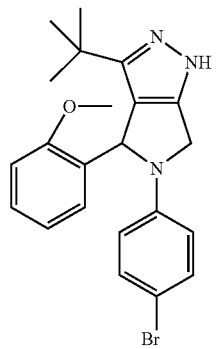 [SMILES: COc1ccccc1C1c2c(C(C)(C)C)n[nH]c2CN1c1ccc(Br)cc1] | II-066 | 426 | 1 | 2.47 |

TABLE 143-continued

| Chemical Structure | Compound No. | MS [M + H]+ | LC method | LC/MS retention time (min) |
|---|---|---|---|---|
| 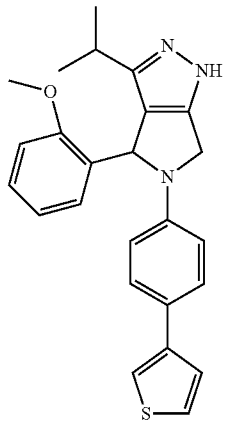 [SMILES: COc1ccccc1C1c2c(C(C)C)n[nH]c2CN1c1ccc(-c2ccsc2)cc1] | II-067 | 416 | 1 | 2.43 |
| 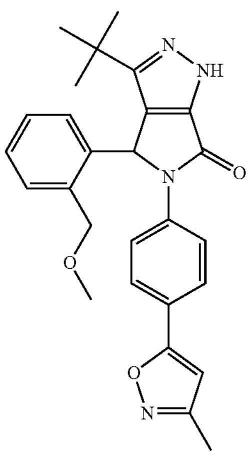 [SMILES: COCc1ccccc1C1c2c(C(C)(C)C)n[nH]c2C(=O)N1c1ccc(-c2cc(C)no2)cc1] | II-068 | 457 | 1 | 1.93 |
| 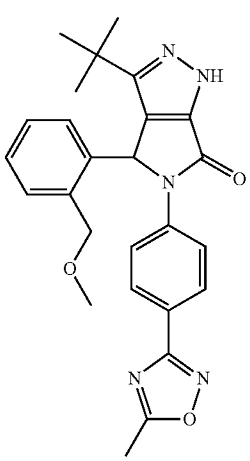 [SMILES: COCc1ccccc1C1c2c(C(C)(C)C)n[nH]c2C(=O)N1c1ccc(-c2noc(C)n2)cc1] | II-069 | 458 | 1 | 1.88 |

TABLE 143-continued

| Chemical Structure | Compound No. | MS [M + H]+ | LC method | LC/MS retention time (min) |
|---|---|---|---|---|
| | II-070 | 440 | 1 | 1.68 |

TABLE 144

| Chemical Structure | Compound No. | MS [M + H]+ | LC method | LC/MS retention time (min) |
|---|---|---|---|---|
| 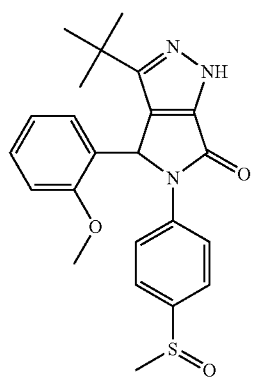 [SMILES: COc1ccccc1C1c2c(C(C)(C)C)n[nH]c2C(=O)N1c1ccc(S(C)=O)cc1] | II-071 | 424 | 1 | 1.49 |
| 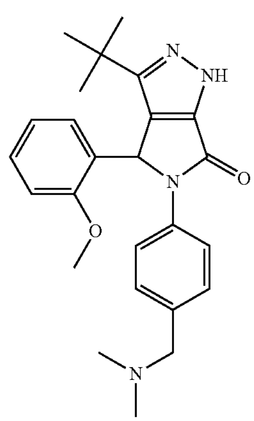 [SMILES: COc1ccccc1C1c2c(C(C)(C)C)n[nH]c2C(=O)N1c1ccc(CN(C)C)cc1] | II-072 | 419 | 1 | 1.25 |

TABLE 144-continued

| Chemical Structure | Compound No. | MS [M + H]+ | LC method | LC/MS retention time (min) |
|---|---|---|---|---|
| (structure) | II-073 | 443 | 1 | 2.03 |
| (structure) | II-074 | 431 | 1 | 1.55 |
| (structure) | II-075 | 472 | 1 | 1.48 |

TABLE 145

| Chemical Structure | Compound No. | MS [M + H]+ | LC method | LC/MS retention time (min) |
|---|---|---|---|---|
| (structure) | II-076 | 520 | 1 | 1.76 |
| (structure) | II-077 | 486 | 1 | 1.55 |
| (structure) | II-078 | 487 | 1 | 1.39 |

TABLE 145-continued

| Chemical Structure | Compound No. | MS [M + H]+ | LC method | LC/MS retention time (min) |
|---|---|---|---|---|
| 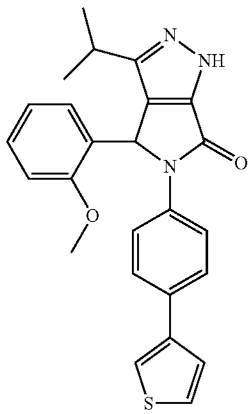 [SMILES: COc1ccccc1C1c2c(C(C)C)n[nH]c2C(=O)N1c1ccc(-c2ccsc2)cc1] | II-079 | 430 | 1 | 1.91 |
| 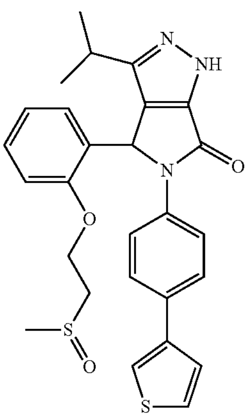 [SMILES: CC(C)c1n[nH]c2c1C(c1ccccc1OCCS(C)=O)N(c1ccc(-c3ccsc3)cc1)C2=O] | II-080 | 506 | 1 | 1.69 |

TABLE 146

| Chemical Structure | Compound No. | MS [M + H]+ | LC method | LC/MS retention time (min) |
|---|---|---|---|---|
| 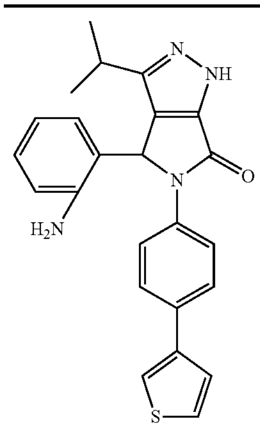 | II-081 | 415 | 1 | 1.96 |

TABLE 146-continued

| Chemical Structure | Compound No. | MS [M + H]+ | LC method | LC/MS retention time (min) |
|---|---|---|---|---|
| 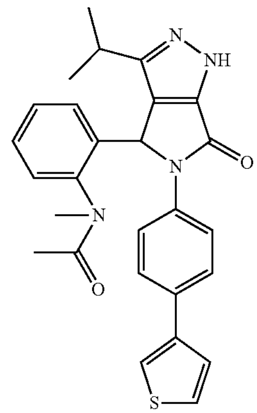 [SMILES: CC(=O)N(C)c1ccccc1C1c2c(C(C)C)n[nH]c2C(=O)N1c1ccc(-c2ccsc2)cc1] | II-082 | 471 | 1 | 1.78 |
| 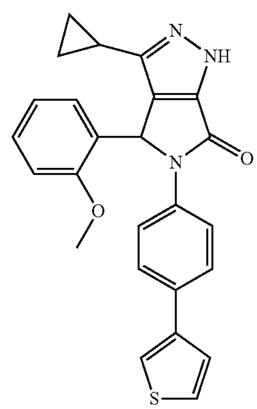 [SMILES: COc1ccccc1C1c2c(C3CC3)n[nH]c2C(=O)N1c1ccc(-c2ccsc2)cc1] | II-083 | 428 | 1 | 2.09 |
| 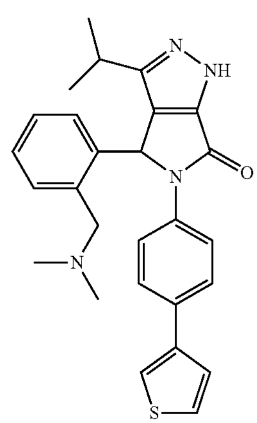 [SMILES: CC(C)c1n[nH]c2c1C(c1ccccc1CN(C)C)N(c1ccc(-c3ccsc3)cc1)C2=O] | II-084 | 457 | 1 | 1.23 |

TABLE 146-continued

| Chemical Structure | Compound No. | MS [M + H]+ | LC method | LC/MS retention time (min) |
|---|---|---|---|---|
| 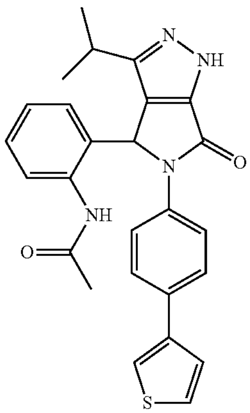 [SMILES: CC(=O)Nc1ccccc1C1c2c(C(C)C)n[nH]c2C(=O)N1c1ccc(-c2ccsc2)cc1] | II-085 | 457 | 1 | 1.72 |

TABLE 147

| Chemical Structure | Compound No. | MS [M + H]+ | LC method | LC/MS retention time (min) |
|---|---|---|---|---|
| 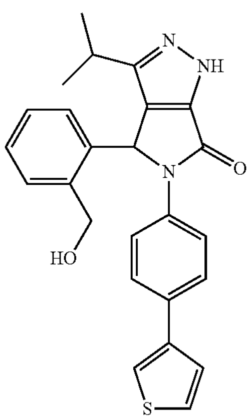 [SMILES: CC(C)c1n[nH]c2c1C(c1ccccc1CO)N(c1ccc(-c3ccsc3)cc1)C2=O] | II-086 | 430 | 1 | 1.79 |
| 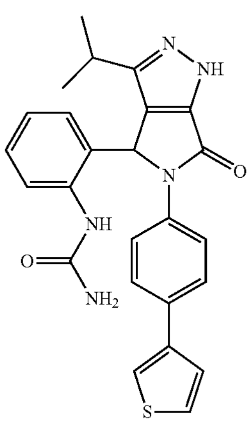 [SMILES: CC(C)c1n[nH]c2c1C(c1ccccc1NC(N)=O)N(c1ccc(-c3ccsc3)cc1)C2=O] | II-087 | 458 | 1 | 1.58 |

TABLE 147-continued

| Chemical Structure | Compound No. | MS [M + H]+ | LC method | LC/MS retention time (min) |
|---|---|---|---|---|
| 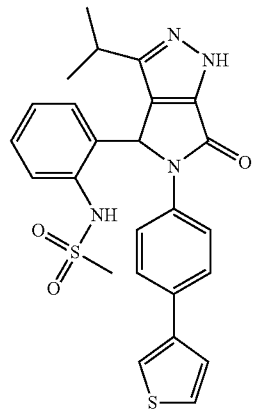 [SMILES: CC(C)c1n[nH]c2c1C(c1ccccc1NS(C)(=O)=O)N(c1ccc(-c3ccsc3)cc1)C2=O] | II-088 | 493 | 1 | 1.76 |
| 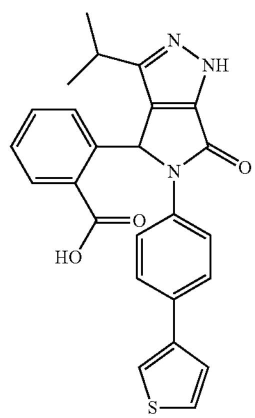 [SMILES: CC(C)c1n[nH]c2c1C(c1ccccc1C(=O)O)N(c1ccc(-c3ccsc3)cc1)C2=O] | II-089 | 444 | 1 | 1.77 |
| 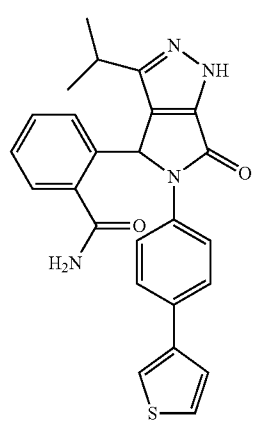 [SMILES: CC(C)c1n[nH]c2c1C(c1ccccc1C(N)=O)N(c1ccc(-c3ccsc3)cc1)C2=O] | II-090 | 443 | 1 | 1.62 |

TABLE 148
| Chemical Structure | Compound No. | MS [M + H]+ | LC method | LC/MS retention time (min) |
|---|---|---|---|---|
| 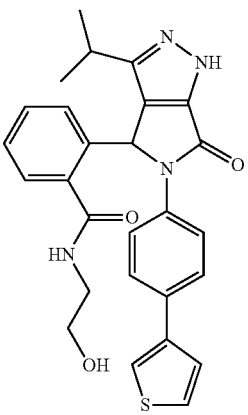 [SMILES: CC(C)c1n[nH]c2c1C(c1ccccc1C(=O)NCCO)N(c1ccc(-c3ccsc3)cc1)C2=O] | II-091 | 487 | 1 | 1.55 |
| 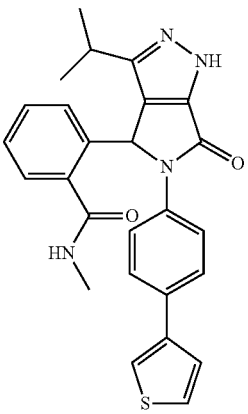 [SMILES: CNC(=O)c1ccccc1C1c2c(C(C)C)n[nH]c2C(=O)N1c1ccc(-c2ccsc2)cc1] | II-092 | 457 | 1 | 1.74 |
| 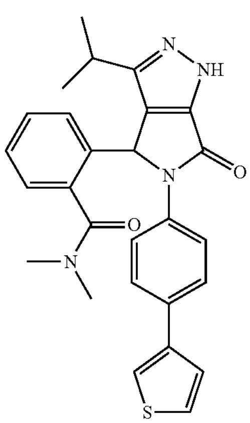 [SMILES: CC(C)c1n[nH]c2c1C(c1ccccc1C(=O)N(C)C)N(c1ccc(-c3ccsc3)cc1)C2=O] | II-093 | 471 | 1 | 1.86 |
TABLE 148-continued
| Chemical Structure | Compound No. | MS [M + H]+ | LC method | LC/MS retention time (min) |
|---|---|---|---|---|
| 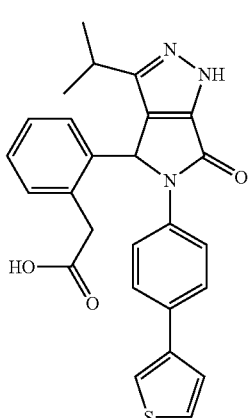 | II-094 | 458 | 1 | 1.75 |
| 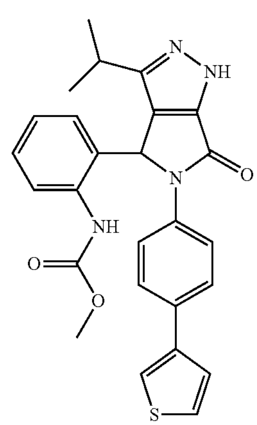 [SMILES: COC(=O)Nc1ccccc1C1c2c(C(C)C)n[nH]c2C(=O)N1c1ccc(-c2ccsc2)cc1] | II-095 | 473 | 1 | 1.87 |

TABLE 149
| Chemical Structure | Compound No. | MS [M + H]⁺ | LC method | LC/MS retention time (min) |
|---|---|---|---|---|
| 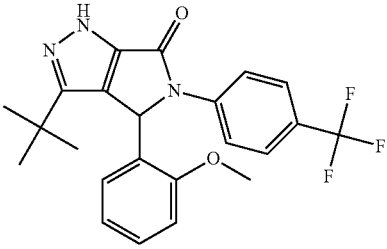 [SMILES: COc1ccccc1C1c2c(C(C)(C)C)n[nH]c2C(=O)N1c1ccc(C(F)(F)F)cc1] | II-096 | 425 | 1 | 2.30 |
| 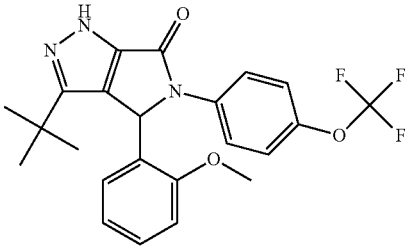 [SMILES: COc1ccccc1C1c2c(C(C)(C)C)n[nH]c2C(=O)N1c1ccc(OC(F)(F)F)cc1] | II-097 | 446 | 1 | 2.20 |
| 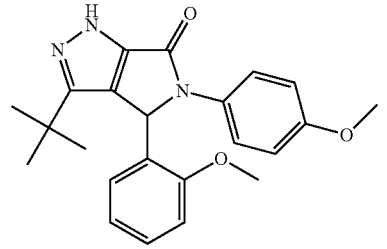 [SMILES: COc1ccc(N2C(=O)c3[nH]nc(C(C)(C)C)c3C2c2ccccc2OC)cc1] | II-098 | 392 | 1 | 1.90 |
| 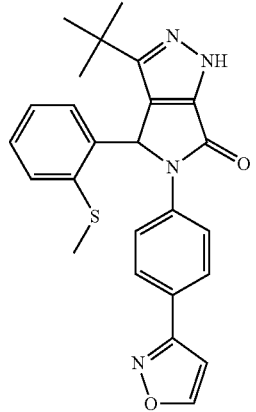 [SMILES: CSc1ccccc1C1c2c(C(C)(C)C)n[nH]c2C(=O)N1c1ccc(-c2ccon2)cc1] | II-099 | 445 | 1 | 2.00 |

TABLE 149-continued
| Chemical Structure | Compound No. | MS [M + H]+ | LC method | LC/MS retention time (min) |
|---|---|---|---|---|
| 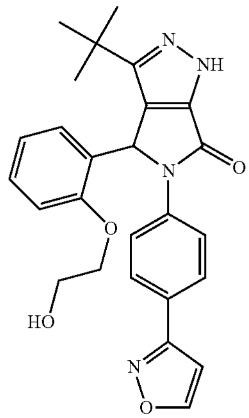 [SMILES: CC(C)(C)c1n[nH]c2c1C(c1ccccc1OCCO)N(c1ccc(-c3ccon3)cc1)C2=O] | II-100 | 459 | 1 | 1.60 |
TABLE 150
| Chemical Structure | Compound No. | MS [M + H]+ | LC method | LC/MS retention time (min) |
|---|---|---|---|---|
| 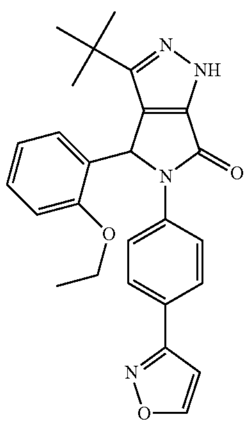 [SMILES: CCOc1ccccc1C1c2c(C(C)(C)C)n[nH]c2C(=O)N1c1ccc(-c2ccon2)cc1] | II-101 | 443 | 1 | 2.00 |
| 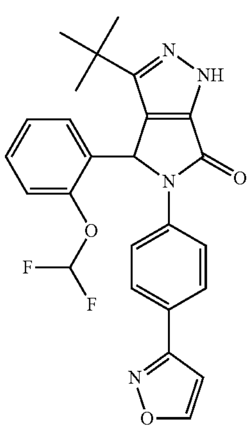 [SMILES: CC(C)(C)c1n[nH]c2c1C(c1ccccc1OC(F)F)N(c1ccc(-c3ccon3)cc1)C2=O] | II-102 | 465 | 1 | 1.90 |
TABLE 150-continued
| Chemical Structure | Compound No. | MS [M + H]+ | LC method | LC/MS retention time (min) |
|---|---|---|---|---|
| 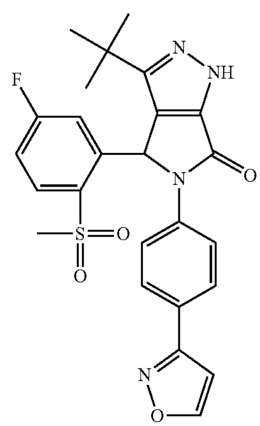 [SMILES: CC(C)(C)c1n[nH]c2c1C(c1cc(F)ccc1S(C)(=O)=O)N(c1ccc(-c3ccon3)cc1)C2=O] | II-103 | 495 | 1 | 1.60 |
| 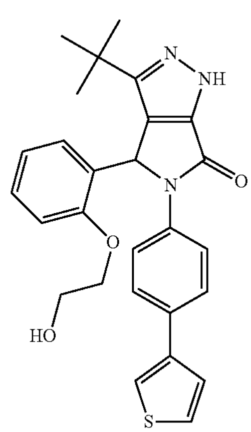 [SMILES: CC(C)(C)c1n[nH]c2c1C(c1ccccc1OCCO)N(c1ccc(-c3ccsc3)cc1)C2=O] | II-104 | 474 | 1 | 1.90 |
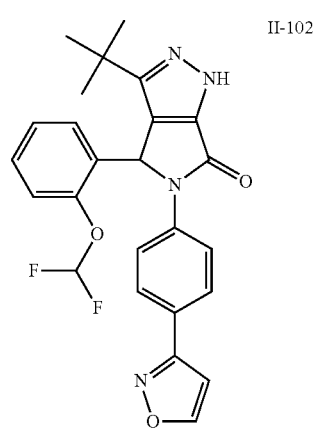
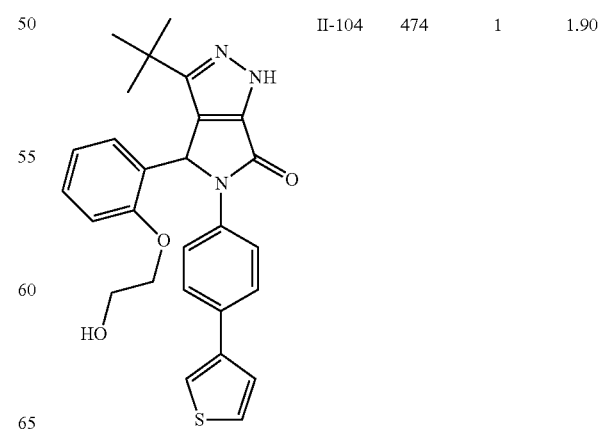

TABLE 150-continued

| Chemical Structure | Compound No. | MS [M + H]+ | LC method | LC/MS retention time (min) |
|---|---|---|---|---|
| 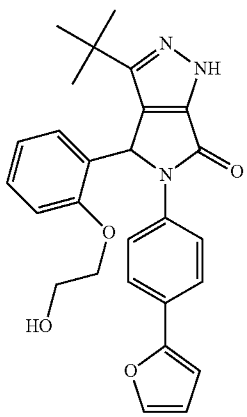 [SMILES: CC(C)(C)c1n[nH]c2c1C(c1ccccc1OCCO)N(c1ccc(-c3ccco3)cc1)C2=O] | II-105 | 458 | 1 | 1.90 |

TABLE 151

| Chemical Structure | Compound No. | MS [M + H]+ | LC method | LC/MS retention time (min) |
|---|---|---|---|---|
| 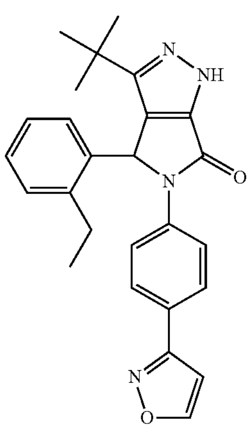 | II-106 | 427 | 1 | 2.40 |
| 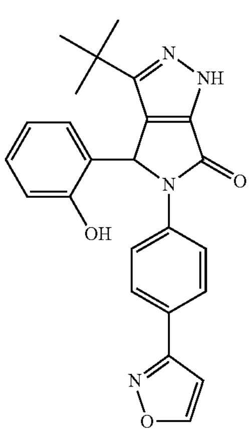 [SMILES: CC(C)(C)c1n[nH]c2c1C(c1ccccc1O)N(c1ccc(-c3ccon3)cc1)C2=O] | II-107 | 415 | 1 | 1.60 |

TABLE 151-continued

| Chemical Structure | Compound No. | MS [M + H]+ | LC method | LC/MS retention time (min) |
|---|---|---|---|---|
| 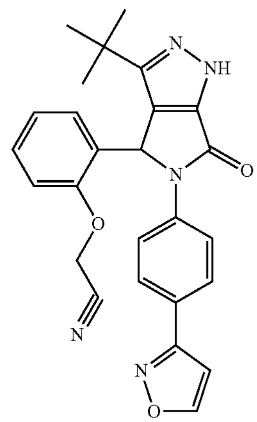 [SMILES: CC(C)(C)c1n[nH]c2c1C(c1ccccc1OCC#N)N(c1ccc(-c3ccon3)cc1)C2=O] | II-108 | 454 | 1 | 1.70 |
| 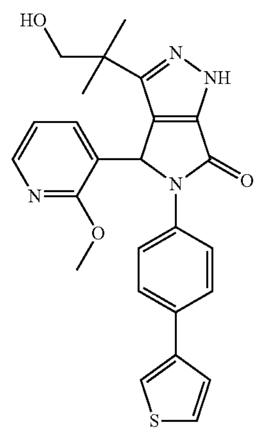 [SMILES: COc1ncccc1C1c2c(C(C)(C)CO)n[nH]c2C(=O)N1c1ccc(-c2ccsc2)cc1] | II-109 | 461 | 1 | 1.70 |
| 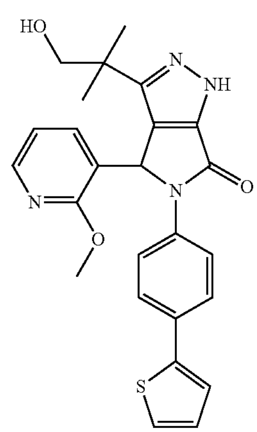 [SMILES: COc1ncccc1C1c2c(C(C)(C)CO)n[nH]c2C(=O)N1c1ccc(-c2cccs2)cc1] | II-110 | 461 | 1 | 1.80 |

TABLE 152

| Chemical Structure | Compound No. | MS [M + H]+ | LC method | LC/MS retention time (min) |
|---|---|---|---|---|
| (structure) | II-111 | 445 | 1 | 1.70 |
| (structure) | II-112 | 477 | 1 | 1.60 |
| (structure) | II-113 | 429 | 1 | 1.60 |
| (structure) | II-114 | 488 | 1 | 2.20 |
| (structure) | II-115 | 488 | 1 | 2.20 |

TABLE 153

| Chemical Structure | Compound No. | MS [M + H]⁺ | LC method | LC/MS retention time (min) |
|---|---|---|---|---|
| 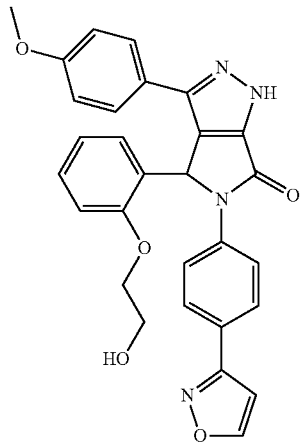 [SMILES: COc1ccc(-c2n[nH]c3c2C(c2ccccc2OCCO)N(c2ccc(-c4ccon4)cc2)C3=O)cc1] | II-116 | 509 | 1 | 1.70 |
| 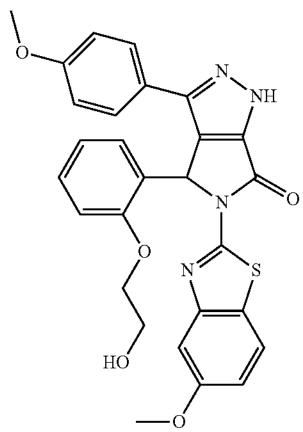 [SMILES: COc1ccc(-c2n[nH]c3c2C(c2ccccc2OCCO)N(c2nc4cc(OC)ccc4s2)C3=O)cc1] | II-117 | 529 | 1 | 1.90 |
| 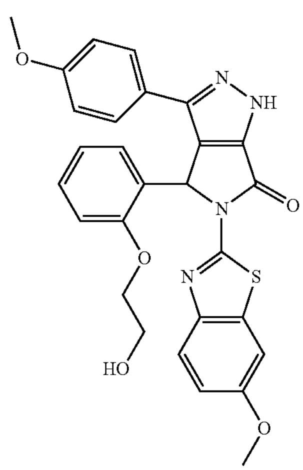 [SMILES: COc1ccc(-c2n[nH]c3c2C(c2ccccc2OCCO)N(c2nc4ccc(OC)cc4s2)C3=O)cc1] | II-118 | 529 | 1 | 2.00 |

TABLE 153-continued
| Chemical Structure | Compound No. | MS [M + H]+ | LC method | LC/MS retention time (min) |
|---|---|---|---|---|
| 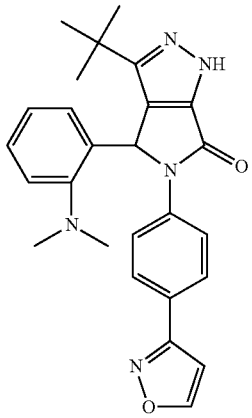 [SMILES: CN(C)c1ccccc1C1c2c(C(C)(C)C)n[nH]c2C(=O)N1c1ccc(-c2ccon2)cc1] | II-119 | 442 | 1 | 2.00 |
| 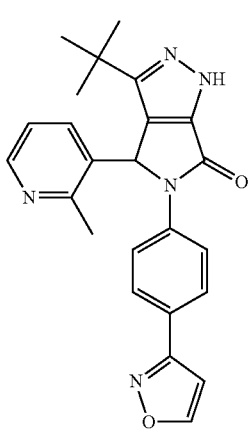 [SMILES: Cc1ncccc1C1c2c(C(C)(C)C)n[nH]c2C(=O)N1c1ccc(-c2ccon2)cc1] | II-120 | 414 | 1 | 1.10 |
TABLE 154
| Chemical Structure | Compound No. | MS [M + H]+ | LC method | LC/MS retention time (min) |
|---|---|---|---|---|
| 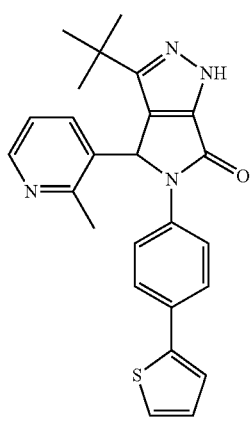 [SMILES: Cc1ncccc1C1c2c(C(C)(C)C)n[nH]c2C(=O)N1c1ccc(-c2cccs2)cc1] | II-121 | 429 | 1 | 1.50 |

TABLE 154-continued
| Chemical Structure | Compound No. | MS [M + H]+ | LC method | LC/MS retention time (min) |
| --- | --- | --- | --- | --- |
| 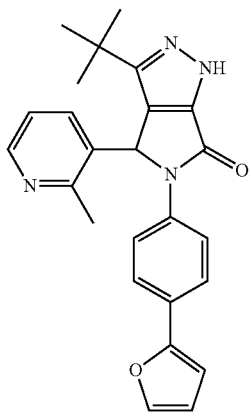 [SMILES: Cc1ncccc1C1c2c(C(C)(C)C)n[nH]c2C(=O)N1c1ccc(-c2ccco2)cc1] | II-122 | 413 | 1 | 1.40 |
| 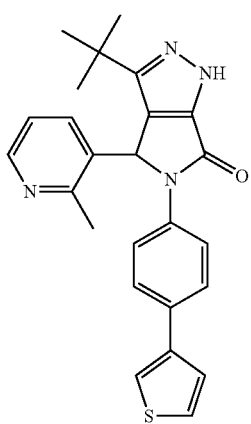 [SMILES: Cc1ncccc1C1c2c(C(C)(C)C)n[nH]c2C(=O)N1c1ccc(-c2ccsc2)cc1] | II-123 | 429 | 1 | 1.50 |
| 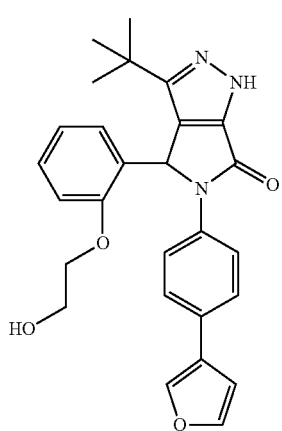 [SMILES: CC(C)(C)c1n[nH]c2c1C(c1ccccc1OCCO)N(c1ccc(-c3ccoc3)cc1)C2=O] | II-124 | 458 | 1 | 1.60 |

TABLE 154-continued
| Chemical Structure | Compound No. | MS [M + H]+ | LC method | LC/MS retention time (min) |
|---|---|---|---|---|
| 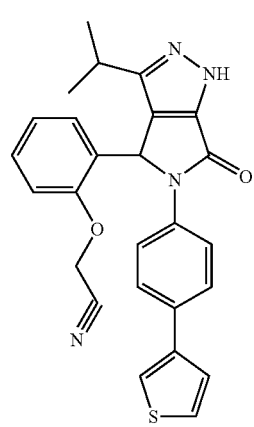 [SMILES: CC(C)c1n[nH]c2c1C(c1ccccc1OCC#N)N(c1ccc(-c3ccsc3)cc1)C2=O] | II-125 | 472 | 1 | 1.80 |
TABLE 155
| Chemical Structure | Compound No. | MS [M + H]+ | LC method | LC/MS retention time (min) |
|---|---|---|---|---|
| (II-126 structure) | II-126 | 459 | 1 | 1.70 |
| (II-127 structure) | II-127 | 455 | 1 | 1.95 |
TABLE 155-continued
| Chemical Structure | Compound No. | MS [M + H]+ | LC method | LC/MS retention time (min) |
|---|---|---|---|---|
| (II-128 structure) | II-128 | 517 | 1 | 1.72 |
| (II-129 structure) | II-129 | 503 | 1 | 1.48 |
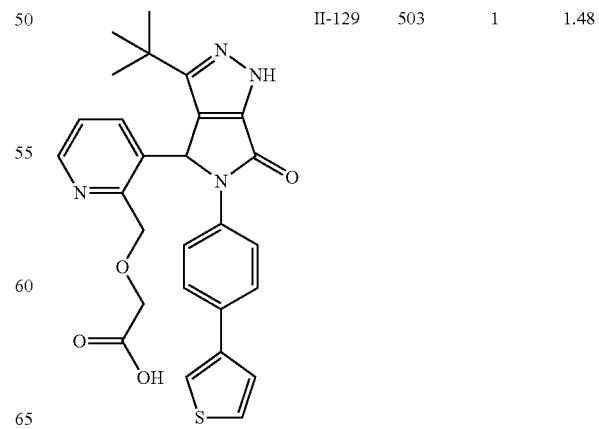

TABLE 155-continued
| Chemical Structure | Compound No. | MS [M + H]+ | LC method | LC/MS retention time (min) |
|---|---|---|---|---|
| 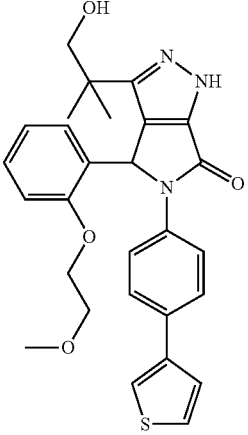 [SMILES: COCCOc1ccccc1C1c2c(C(C)(C)CO)n[nH]c2C(=O)N1c1ccc(-c2ccsc2)cc1] | II-130 | 504 | 1 | 1.88 |
TABLE 156
| Chemical Structure | Compound No. | MS [M + H]+ | LC method | LC/MS retention time (min) |
|---|---|---|---|---|
| 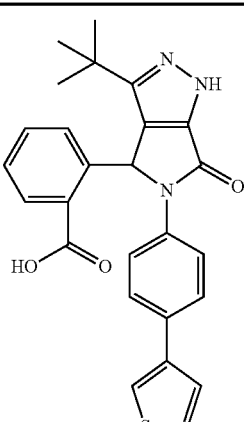 | II-131 | 458 | 1 | 1.81 |
| 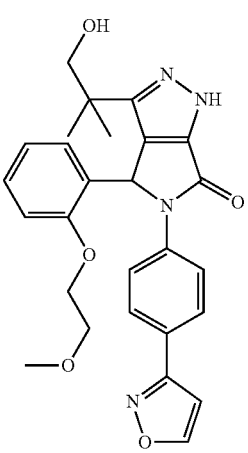 [SMILES: COCCOc1ccccc1C1c2c(C(C)(C)CO)n[nH]c2C(=O)N1c1ccc(-c2ccon2)cc1] | II-132 | 489 | 1 | 1.56 |
TABLE 156-continued
| Chemical Structure | Compound No. | MS [M + H]+ | LC method | LC/MS retention time (min) |
|---|---|---|---|---|
| 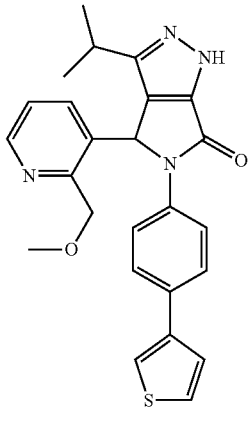 [SMILES: COCc1ncccc1C1c2c(C(C)C)n[nH]c2C(=O)N1c1ccc(-c2ccsc2)cc1] | II-133 | 445 | 1 | 1.67 |
| 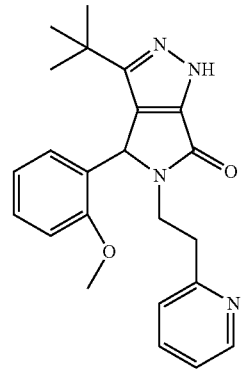 [SMILES: COc1ccccc1C1c2c(C(C)(C)C)n[nH]c2C(=O)N1CCc1ccccn1] | II-134 | 391 | 2 | 1.37 |
| 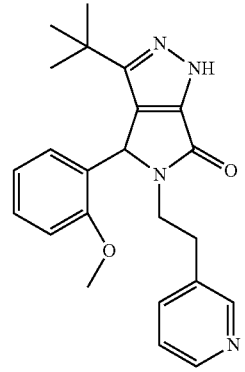 [SMILES: COc1ccccc1C1c2c(C(C)(C)C)n[nH]c2C(=O)N1CCc1cccnc1] | II-135 | 391 | 2 | 1.31 |

TABLE 157
| Chemical Structure | Compound No. | MS [M + H]+ | LC method | LC/MS retention time (min) |
|---|---|---|---|---|
| 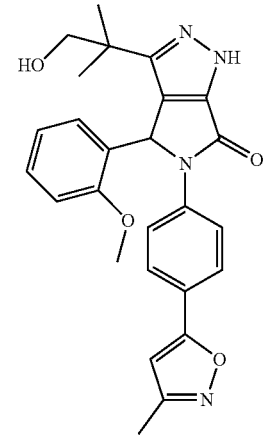 | II-136 | 459 | 2 | 1.90 |
| 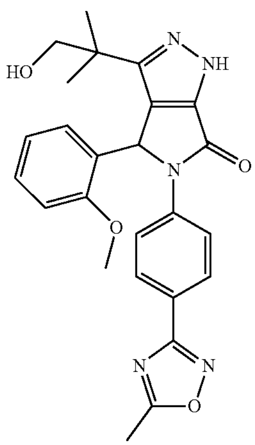 [SMILES: COc1ccccc1C1c2c(C(C)(C)CO)n[nH]c2C(=O)N1c1ccc(-c2noc(C)n2)cc1] | II-137 | 460 | 2 | 1.90 |
| 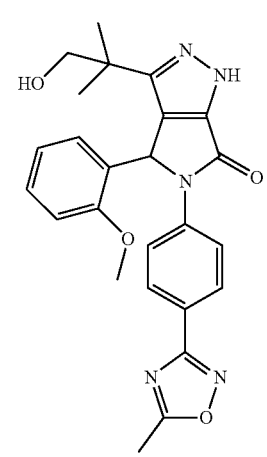 | | | | |
| 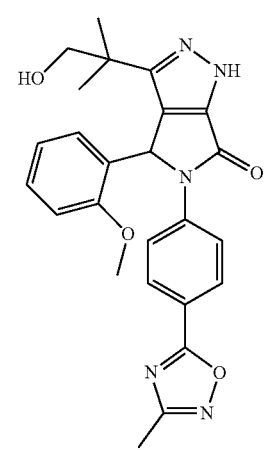 [SMILES: COc1ccccc1C1c2c(C(C)(C)CO)n[nH]c2C(=O)N1c1ccc(-c2nc(C)no2)cc1] | II-138 | 460 | 2 | 1.90 |
TABLE 157-continued
| Chemical Structure | Compound No. | MS [M + H]+ | LC method | LC/MS retention time (min) |
|---|---|---|---|---|
| 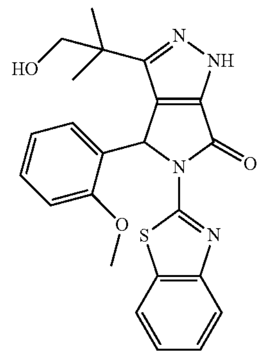 [SMILES: COc1ccccc1C1c2c(C(C)(C)CO)n[nH]c2C(=O)N1c1nc2ccccc2s1] | II-139 | 435 | 2 | 2.20 |
| 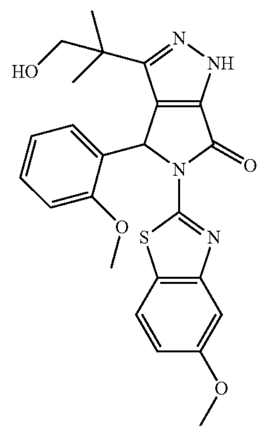 [SMILES: COc1ccc2sc(N3C(=O)c4[nH]nc(C(C)(C)CO)c4C3c3ccccc3OC)nc2c1] | II-140 | 465 | 2 | 2.10 |
TABLE 158
| Chemical Structure | Compound No. | MS [M + H]+ | LC method | LC/MS retention time (min) |
|---|---|---|---|---|
| 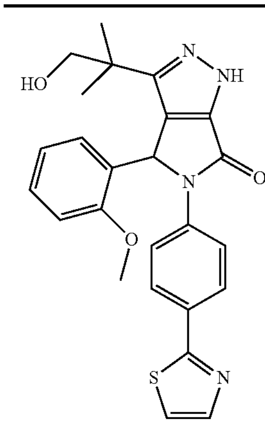 | II-141 | 461 | 2 | 1.90 |

TABLE 158-continued

| Chemical Structure | Compound No. | MS [M + H]+ | LC method | LC/MS retention time (min) |
|---|---|---|---|---|
| (structure) | II-142 | 465 | 2 | 2.20 |
| (structure) | II-143 | 419 | 2 | 2.10 |
| (structure) | II-144 | 432 | 2 | 1.90 |
| (structure) | II-145 | 473 | 2 | 1.70 |

TABLE 159

| Chemical Structure | Compound No. | MS [M + H]+ | LC method | LC/MS retention time (min) |
|---|---|---|---|---|
| (structure) | II-146 | 458 | 2 | 1.98 |
| (structure) | II-147 | 486 | 2 | 1.96 |
| (structure) | II-148 | 441 | 2 | 2.07 |

TABLE 159-continued

| Chemical Structure | Compound No. | MS [M + H]+ | LC method | LC/MS retention time (min) |
|---|---|---|---|---|
| 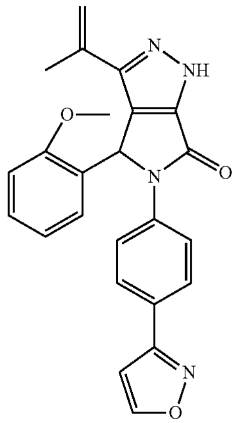 [SMILES: C=C(C)c1n[nH]c2c1C(c1ccccc1OC)N(c1ccc(-c3ccon3)cc1)C2=O] | II-149 | 413 | 2 | 1.85 |
| 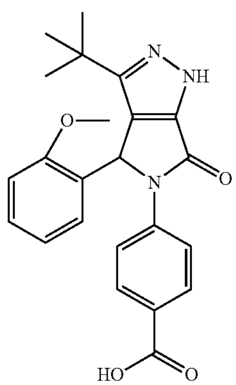 [SMILES: COc1ccccc1C1c2c(C(C)(C)C)n[nH]c2C(=O)N1c1ccc(C(=O)O)cc1] | II-150 | 406 | 2 | 1.88 |

TABLE 160

| Chemical Structure | Compound No. | MS [M + H]+ | LC method | LC/MS retention time (min) |
|---|---|---|---|---|
| 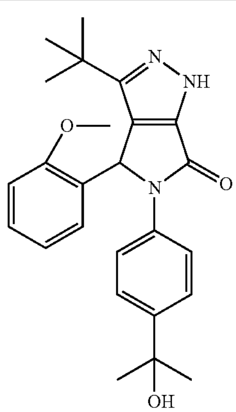 [SMILES: COc1ccccc1C1c2c(C(C)(C)C)n[nH]c2C(=O)N1c1ccc(C(C)(C)O)cc1] | II-151 | 420 | 2 | 2.03 |

TABLE 160-continued

| Chemical Structure | Compound No. | MS [M + H]+ | LC method | LC/MS retention time (min) |
|---|---|---|---|---|
| 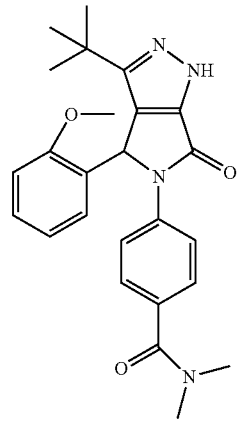 [SMILES: COc1ccccc1C1c2c(C(C)(C)C)n[nH]c2C(=O)N1c1ccc(C(=O)N(C)C)cc1] | II-152 | 433 | 2 | 1.97 |
| 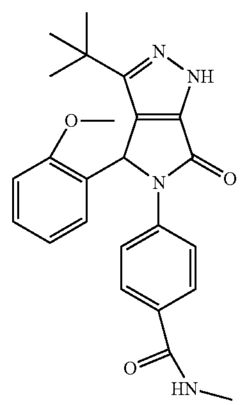 [SMILES: CNC(=O)c1ccc(N2C(=O)c3[nH]nc(C(C)(C)C)c3C2c2ccccc2OC)cc1] | II-153 | 419 | 2 | 1.79 |
| 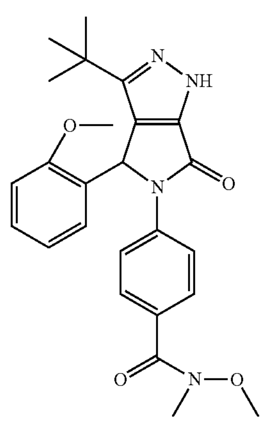 [SMILES: COc1ccccc1C1c2c(C(C)(C)C)n[nH]c2C(=O)N1c1ccc(C(=O)N(C)OC)cc1] | II-154 | 449 | 2 | 1.97 |

TABLE 160-continued

| Chemical Structure | Compound No. | MS [M + H]+ | LC method | LC/MS retention time (min) |
|---|---|---|---|---|
| (structure) | II-155 | 404 | 2 | 2.07 |

TABLE 161

| Chemical Structure | Compound No. | MS [M + H]+ | LC method | LC/MS retention time (min) |
|---|---|---|---|---|
| (structure) | II-156 | 433 | 2 | 2.40 |
| (structure) | II-157 | 458 | 2 | 1.77 |

TABLE 161-continued

| Chemical Structure | Compound No. | MS [M + H]+ | LC method | LC/MS retention time (min) |
|---|---|---|---|---|
| (structure) | II-158 | 486 | 2 | 1.21 |
| (structure) | II-159 | 472 | 2 | 1.20 |
| (structure) | II-160 | 420 | 2 | 2.41 |

TABLE 162

| Chemical Structure | Compound No. | MS [M + H]+ | LC method | LC/MS retention time (min) |
|---|---|---|---|---|
| 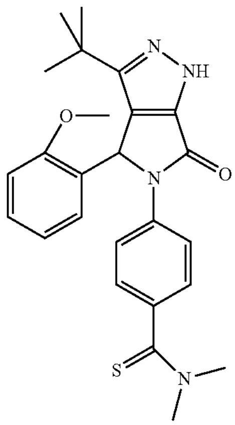 [SMILES: COc1ccccc1C1c2c(C(C)(C)C)n[nH]c2C(=O)N1c1ccc(C(=S)N(C)C)cc1] | II-161 | 449 | 2 | 1.88 |
| 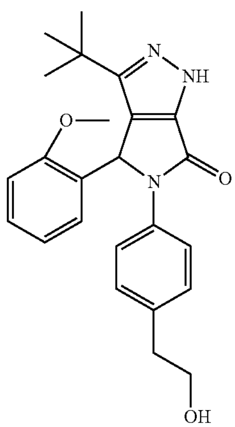 [SMILES: COc1ccccc1C1c2c(C(C)(C)C)n[nH]c2C(=O)N1c1ccc(CCO)cc1] | II-162 | 406 | 2 | 1.57 |
| 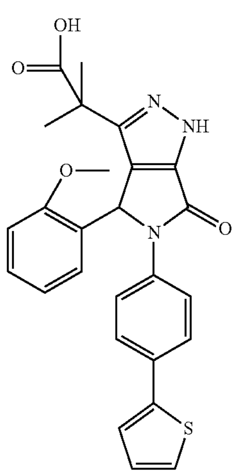 [SMILES: COc1ccccc1C1c2c(C(C)(C)C(=O)O)n[nH]c2C(=O)N1c1ccc(-c2cccs2)cc1] | II-163 | 474 | 2 | 2.16 |

TABLE 162-continued
| Chemical Structure | Compound No. | MS [M + H]+ | LC method | LC/MS retention time (min) |
|---|---|---|---|---|
| 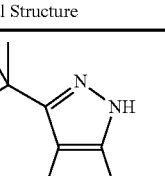 | II-164 | 431 | 2 | 1.86 |
| 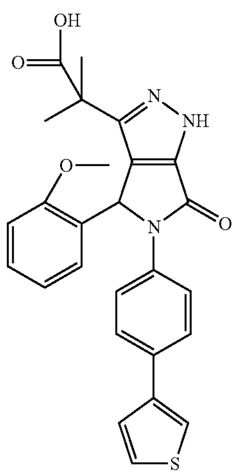 [SMILES: COc1ccccc1C1c2c(C(C)(C)C(=O)O)n[nH]c2C(=O)N1c1ccc(-c2ccsc2)cc1] | II-165 | 474 | 2 | 2.13 |
TABLE 163
| Chemical Structure | Compound No. | MS [M + H]+ | LC method | LC/MS retention time (min) |
|---|---|---|---|---|
| 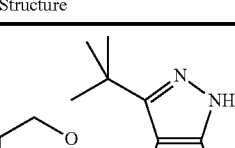 | II-166 | 515 | 2 | 2.19 |

TABLE 163-continued
| Chemical Structure | Compound No. | MS [M + H]⁺ | LC method | LC/MS retention time (min) |
|---|---|---|---|---|
| 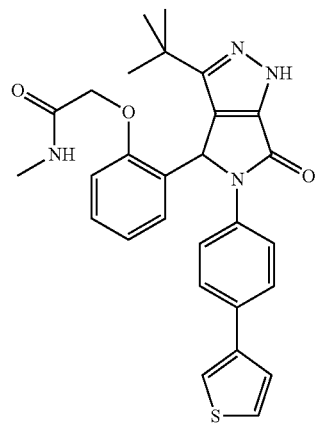 [SMILES: CNC(=O)COc1ccccc1C1c2c(C(C)(C)C)n[nH]c2C(=O)N1c1ccc(-c2ccsc2)cc1] | II-167 | 501 | 2 | 2.12 |
| 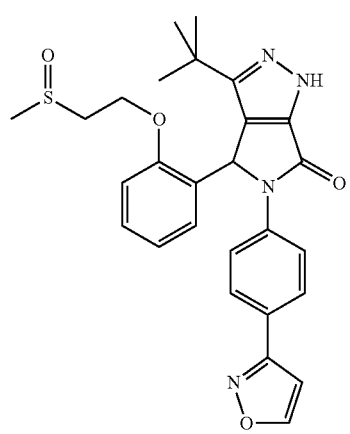 [SMILES: CS(=O)CCOc1ccccc1C1c2c(C(C)(C)C)n[nH]c2C(=O)N1c1ccc(-c2ccon2)cc1] | II-168 | 505 | 2 | 1.76 |
| 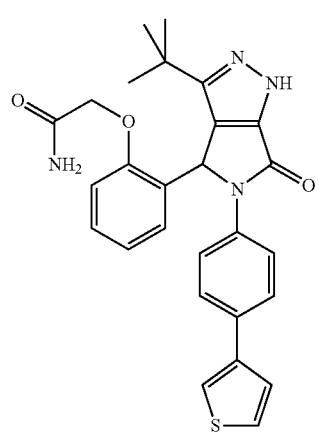 [SMILES: CC(C)(C)c1n[nH]c2c1C(c1ccccc1OCC(N)=O)N(c1ccc(-c3ccsc3)cc1)C2=O] | II-169 | 487 | 2 | 2.03 |

TABLE 163-continued
| Chemical Structure | Compound No. | MS [M + H]+ | LC method | LC/MS retention time (min) |
|---|---|---|---|---|
| 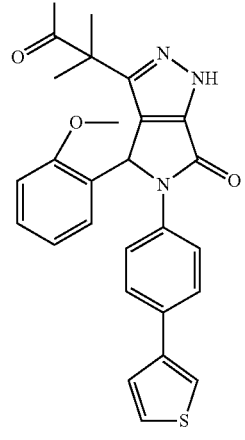 | II-170 | 487 | 2 | 2.06 |
TABLE 164
| Chemical Structure | Compound No. | MS [M + H]+ | LC method | LC/MS retention time (min) |
|---|---|---|---|---|
| 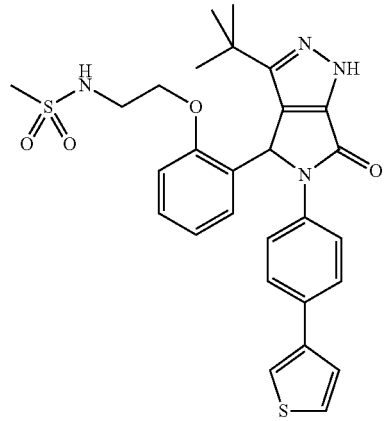 [SMILES: CC(C)(C)c1n[nH]c2c1C(c1ccccc1OCCNS(C)(=O)=O)N(c1ccc(-c3ccsc3)cc1)C2=O] | II-171 | 551 | 2 | 2.23 |
| 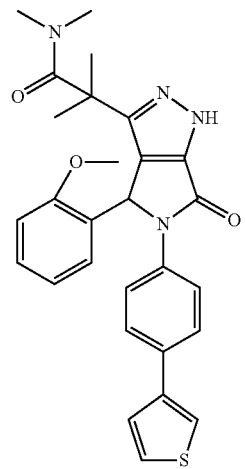 [SMILES: COc1ccccc1C1c2c(C(C)(C)C(=O)N(C)C)n[nH]c2C(=O)N1c1ccc(-c2ccsc2)cc1] | II-172 | 501 | 2 | 2.19 |

TABLE 164-continued

| Chemical Structure | Compound No. | MS [M + H]+ | LC method | LC/MS retention time (min) |
|---|---|---|---|---|
| 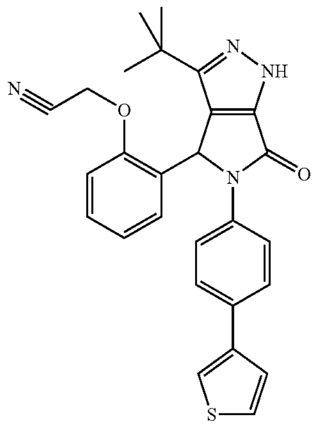 [SMILES: CC(C)(C)c1n[nH]c2c1C(c1ccccc1OCC#N)N(c1ccc(-c3ccsc3)cc1)C2=O] | II-173 | 469 | 2 | 2.39 |
| 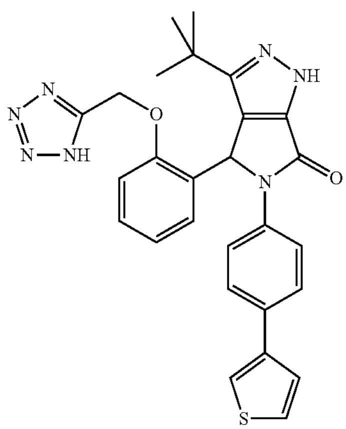 [SMILES: CC(C)(C)c1n[nH]c2c1C(c1ccccc1OCc1nnn[nH]1)N(c1ccc(-c3ccsc3)cc1)C2=O] | II-174 | 512 | 2 | 2.40 |
| 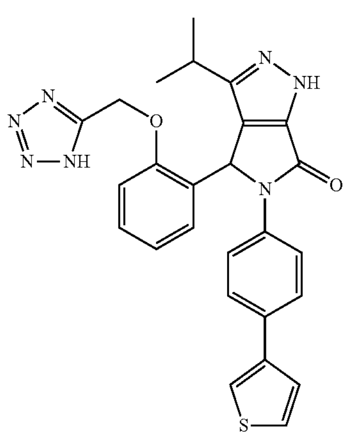 [SMILES: CC(C)c1n[nH]c2c1C(c1ccccc1OCc1nnn[nH]1)N(c1ccc(-c3ccsc3)cc1)C2=O] | II-175 | 498 | 2 | 2.05 |

TABLE 165

| Chemical Structure | Compound No. | MS [M + H]+ | LC method | LC/MS retention time (min) |
|---|---|---|---|---|
| 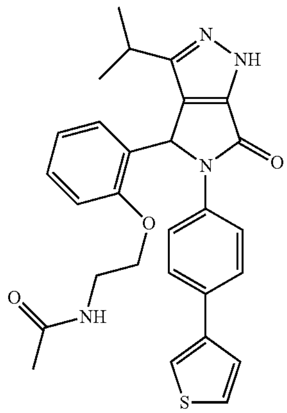 [SMILES: CC(=O)NCCOc1ccccc1C1c2c(C(C)C)n[nH]c2C(=O)N1c1ccc(-c2ccsc2)cc1] | II-176 | 501 | 2 | 2.10 |
| 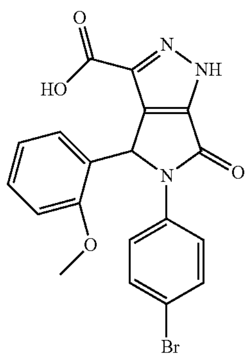 [SMILES: COc1ccccc1C1c2c(C(=O)O)n[nH]c2C(=O)N1c1ccc(Br)cc1] | II-177 | 428 | 2 | 1.97 |
| 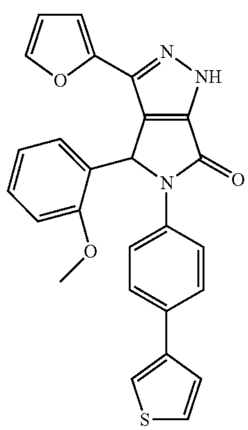 [SMILES: COc1ccccc1C1c2c(-c3ccco3)n[nH]c2C(=O)N1c1ccc(-c2ccsc2)cc1] | II-178 | 454 | 2 | 2.42 |
| 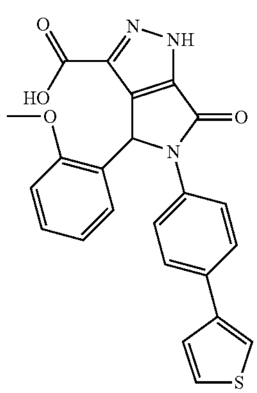 [SMILES: COc1ccccc1C1c2c(C(=O)O)n[nH]c2C(=O)N1c1ccc(-c2ccsc2)cc1] | II-179 | 432 | 2 | 2.10 |

TABLE 165-continued

| Chemical Structure | Compound No. | MS [M + H]+ | LC method | LC/MS retention time (min) |
|---|---|---|---|---|
| (structure) | II-180 | 459 | 2 | 2.15 |

TABLE 166

| Chemical Structure | Compound No. | MS [M + H]+ | LC method | LC/MS retention time (min) |
|---|---|---|---|---|
| (structure) | II-181 | 445 | 2 | 2.14 |
| (structure) | II-182 | 418 | 2 | 2.13 |

TABLE 166-continued

| Chemical Structure | Compound No. | MS [M + H]+ | LC method | LC/MS retention time (min) |
|---|---|---|---|---|
| 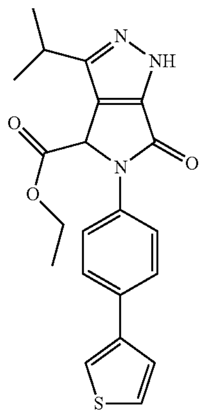 [SMILES: CCOC(=O)C1c2c(C(C)C)n[nH]c2C(=O)N1c1ccc(-c2ccsc2)cc1] | II-183 | 396 | 2 | 2.30 |
| 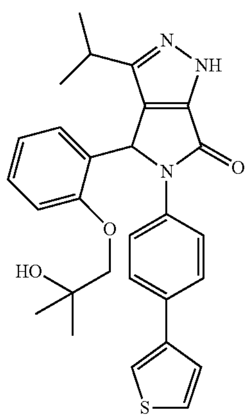 [SMILES: CC(C)c1n[nH]c2c1C(c1ccccc1OCC(C)(C)O)N(c1ccc(-c3ccsc3)cc1)C2=O] | II-184 | 488 | 2 | 2.27 |
| 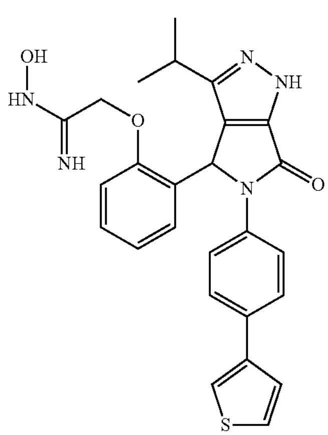 [SMILES: CC(C)c1n[nH]c2c1C(c1ccccc1OCC(=N)NO)N(c1ccc(-c3ccsc3)cc1)C2=O] | II-185 | 488 | 2 | 1.79 |

TABLE 167
| Chemical Structure | Compound No. | MS [M + H]+ | LC method | LC/MS retention time (min) |
|---|---|---|---|---|
| 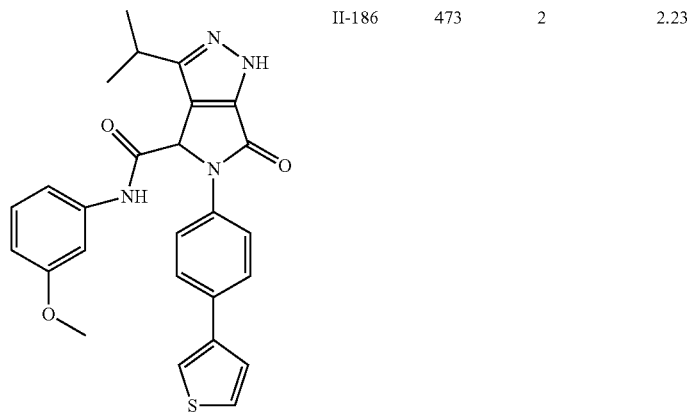 | II-186 | 473 | 2 | 2.23 |
| 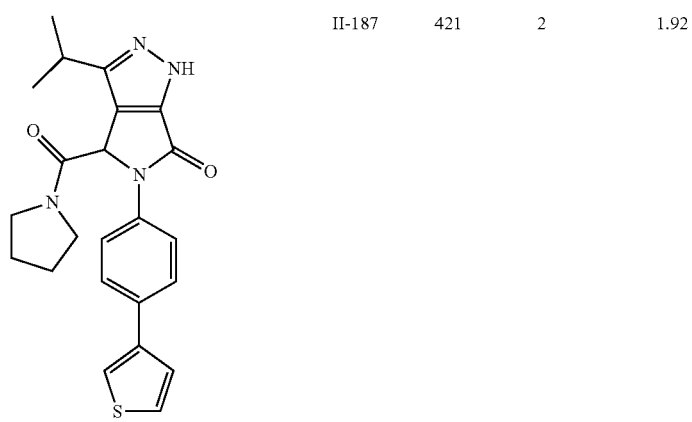 | II-187 | 421 | 2 | 1.92 |
| 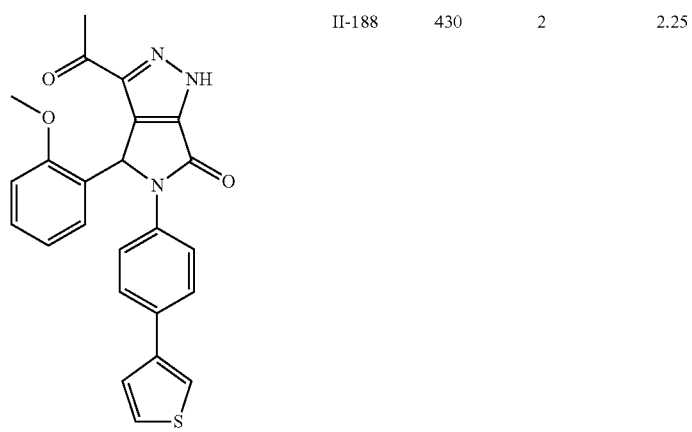 | II-188 | 430 | 2 | 2.25 |

TABLE 167-continued

| Chemical Structure | Compound No. | MS [M + H]+ | LC method | LC/MS retention time (min) |
|---|---|---|---|---|
| 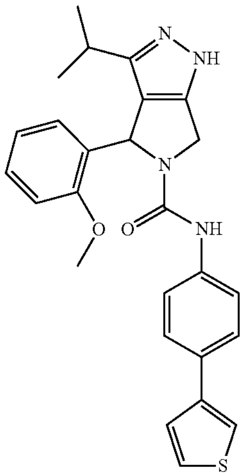 [SMILES: COc1ccccc1C1c2c(C(C)C)n[nH]c2CN1C(=O)Nc1ccc(-c2ccsc2)cc1] | II-189 | 459 | 2 | 2.40 |
| 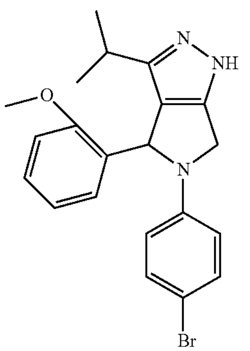 [SMILES: COc1ccccc1C1c2c(C(C)C)n[nH]c2CN1c1ccc(Br)cc1] | II-190 | 413 | 2 | 2.70 |

TABLE 168

| Chemical Structure | Compound No. | MS [M + H]+ | LC method | LC/MS retention time (min) |
|---|---|---|---|---|
| 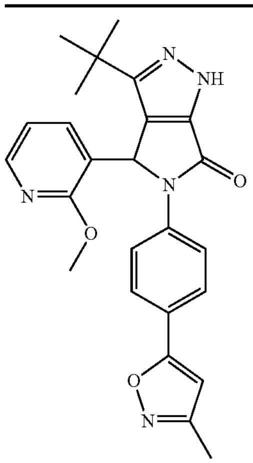 | II-191 | 444 | 2 | 2.06 |

TABLE 168-continued
| Chemical Structure | Compound No. | MS [M + H]+ | LC method | LC/MS retention time (min) |
|---|---|---|---|---|
| 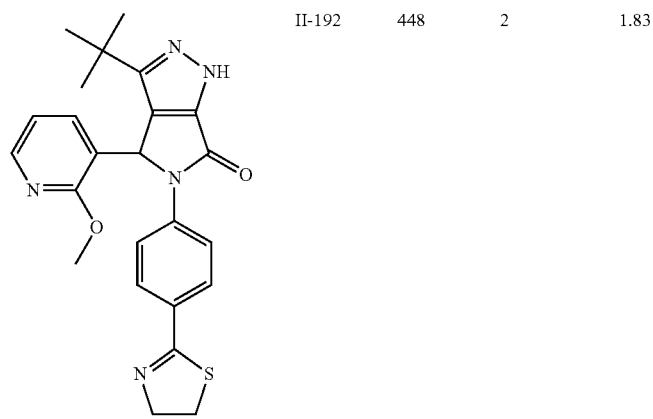 | II-192 | 448 | 2 | 1.83 |
| 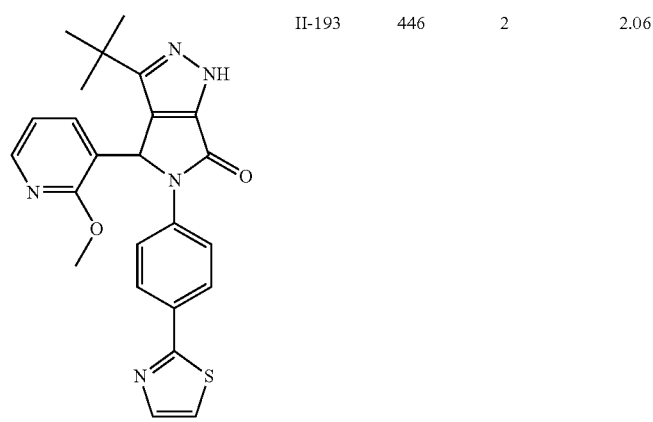 | II-193 | 446 | 2 | 2.06 |
| 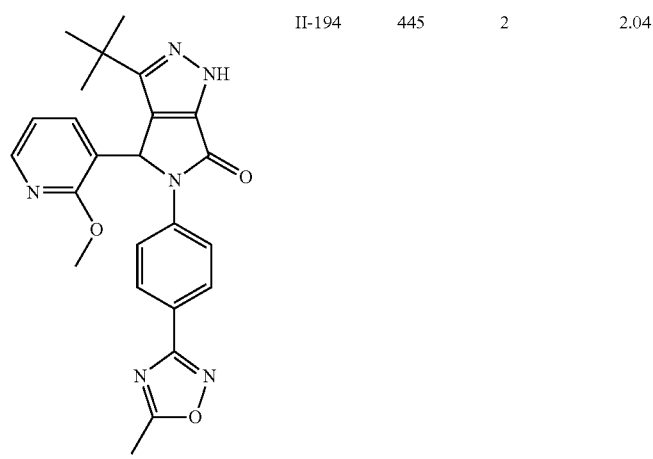 | II-194 | 445 | 2 | 2.04 |

TABLE 168-continued
| Chemical Structure | Compound No. | MS [M + H]+ | LC method | LC/MS retention time (min) |
|---|---|---|---|---|
| 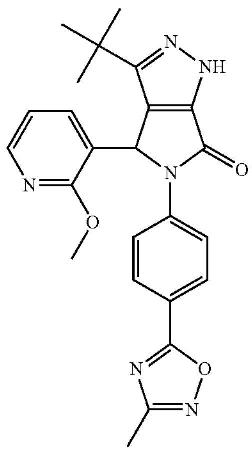 [SMILES: COc1ncccc1C1c2c(C(C)(C)C)n[nH]c2C(=O)N1c1ccc(-c2nc(C)no2)cc1] | II-195 | 445 | 2 | 2.08 |
TABLE 169
| Chemical Structure | Compound No. | MS [M + H]+ | LC method | LC/MS retention time (min) |
|---|---|---|---|---|
| 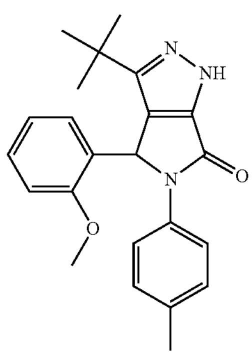 [SMILES: COc1ccccc1C1c2c(C(C)(C)C)n[nH]c2C(=O)N1c1ccc(C)cc1] | II-196 | 376 | 2 | 2.17 |
| 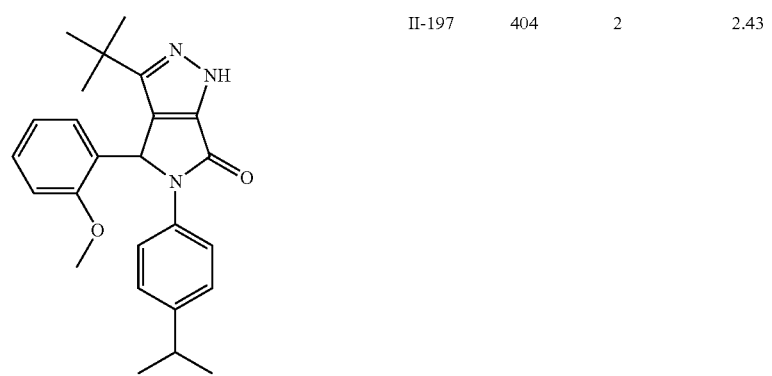 | II-197 | 404 | 2 | 2.43 |

TABLE 169-continued

| Chemical Structure | Compound No. | MS [M + H]+ | LC method | LC/MS retention time (min) |
|---|---|---|---|---|
| 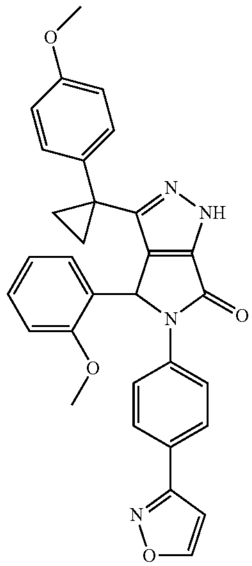 [SMILES: COc1ccc(C2(c3n[nH]c4c3C(c3ccccc3OC)N(c3ccc(-c5ccon5)cc3)C4=O)CC2)cc1] | II-198 | 519 | 2 | 2.34 |
| 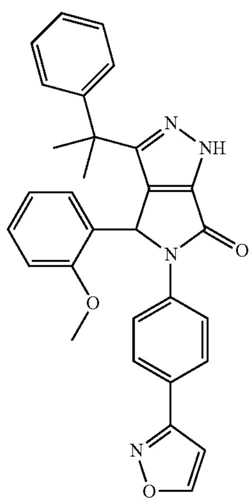 [SMILES: COc1ccccc1C1c2c(C(C)(C)c3ccccc3)n[nH]c2C(=O)N1c1ccc(-c2ccon2)cc1] | II-199 | 491 | 2 | 2.37 |
| 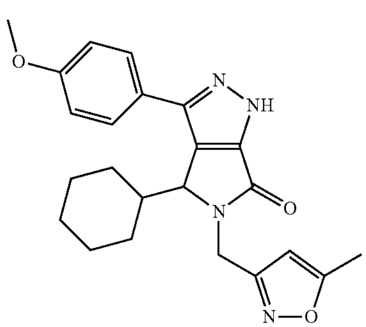 | II-200 | 407 | 2 | 2.22 |

TABLE 170

| Chemical Structure | Compound No. | MS [M + H]+ | LC method | LC/MS retention time (min) |
|---|---|---|---|---|
| 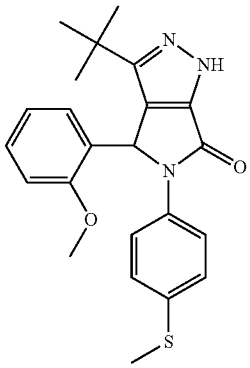 [SMILES: COc1ccccc1C1c2c(C(C)(C)C)n[nH]c2C(=O)N1c1ccc(SC)cc1] | II-201 | 408 | 2 | 2.35 |
| 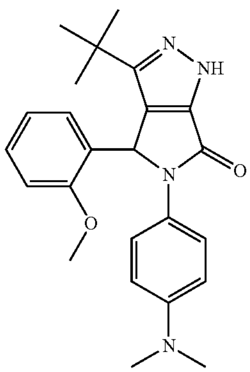 [SMILES: COc1ccccc1C1c2c(C(C)(C)C)n[nH]c2C(=O)N1c1ccc(N(C)C)cc1] | II-202 | 405 | 2 | 1.94 |
| 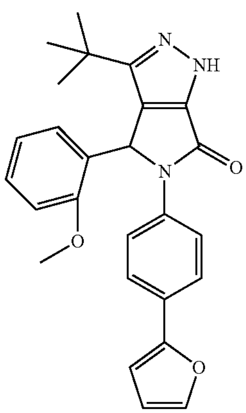 [SMILES: COc1ccccc1C1c2c(C(C)(C)C)n[nH]c2C(=O)N1c1ccc(-c2ccco2)cc1] | II-203 | 428 | 2 | 2.40 |
| 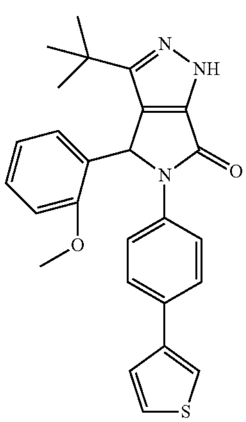 [SMILES: COc1ccccc1C1c2c(C(C)(C)C)n[nH]c2C(=O)N1c1ccc(-c2ccsc2)cc1] | II-204 | 444 | 2 | 2.50 |

TABLE 170-continued

| Chemical Structure | Compound No. | MS [M + H]+ | LC method | LC/MS retention time (min) |
|---|---|---|---|---|
| 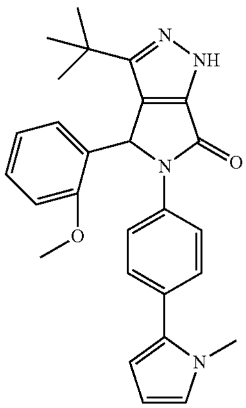 [SMILES: COc1ccccc1C1c2c(C(C)(C)C)n[nH]c2C(=O)N1c1ccc(-c2cccn2C)cc1] | II-205 | 441 | 2 | 2.40 |

TABLE 171

| Chemical Structure | Compound No. | MS [M + H]+ | LC method | LC/MS retention time (min) |
|---|---|---|---|---|
| 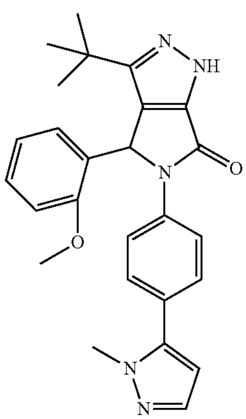 [SMILES: COc1ccccc1C1c2c(C(C)(C)C)n[nH]c2C(=O)N1c1ccc(-c2ccnn2C)cc1] | II-206 | 442 | 2 | 2.00 |
| 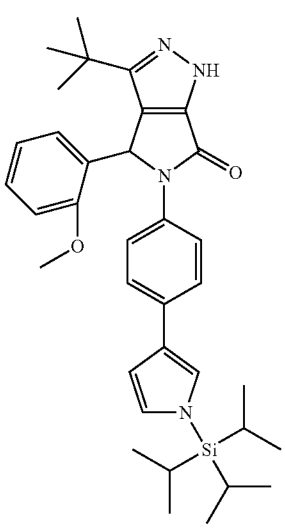 [SMILES: COc1ccccc1C1c2c(C(C)(C)C)n[nH]c2C(=O)N1c1ccc(-c2ccn([Si](C(C)C)(C(C)C)C(C)C)c2)cc1] | II-207 | 583 | 2 | 3.30 |

TABLE 171-continued

| Chemical Structure | Compound No. | MS [M + H]⁺ | LC method | LC/MS retention time (min) |
|---|---|---|---|---|
| 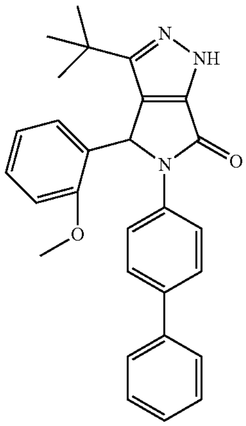 [SMILES: COc1ccccc1C1c2c(C(C)(C)C)n[nH]c2C(=O)N1c1ccc(-c2ccccc2)cc1] | II-208 | 438 | 2 | 2.50 |
| 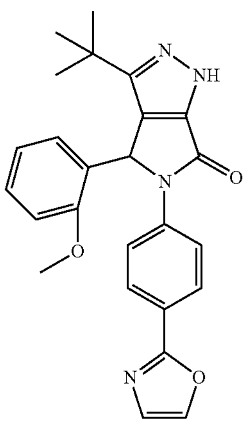 [SMILES: COc1ccccc1C1c2c(C(C)(C)C)n[nH]c2C(=O)N1c1ccc(-c2ncco2)cc1] | II-209 | 429 | 2 | 2.10 |
| 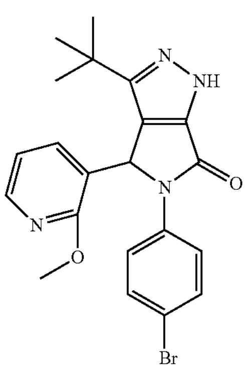 [SMILES: COc1ncccc1C1c2c(C(C)(C)C)n[nH]c2C(=O)N1c1ccc(Br)cc1] | II-210 | 442 | 2 | 2.30 |

TABLE 172

| Chemical Structure | Compound No. | MS [M + H]+ | LC method | LC/MS retention time (min) |
| --- | --- | --- | --- | --- |
| 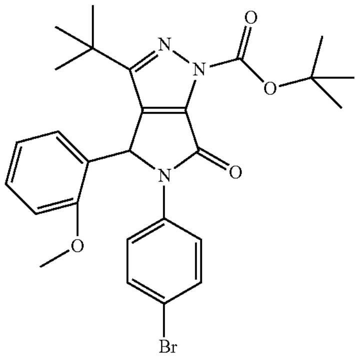 [SMILES: COc1ccccc1C1c2c(C(C)(C)C)nn(C(=O)OC(C)(C)C)c2C(=O)N1c1ccc(Br)cc1] | II-211 | 540 | 2 | 3.10 |
| 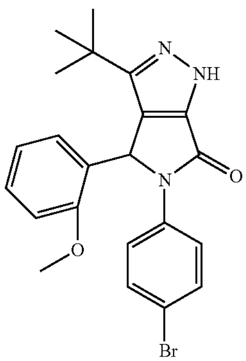 [SMILES: COc1ccccc1C1c2c(C(C)(C)C)n[nH]c2C(=O)N1c1ccc(Br)cc1] | II-212 | 441 | 2 | 2.40 |
| 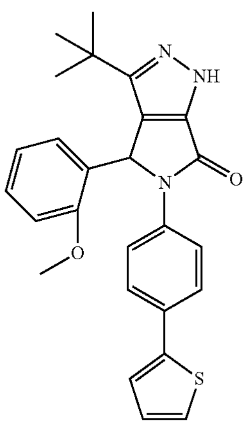 [SMILES: COc1ccccc1C1c2c(C(C)(C)C)n[nH]c2C(=O)N1c1ccc(-c2cccs2)cc1] | II-213 | 444 | 2 | 2.60 |
| 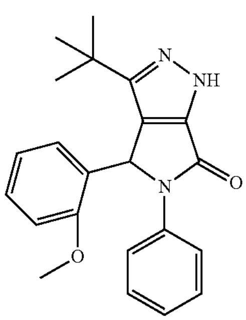 [SMILES: COc1ccccc1C1c2c(C(C)(C)C)n[nH]c2C(=O)N1c1ccccc1] | II-214 | 362 | 2 | 2.20 |

TABLE 172-continued

| Chemical Structure | Compound No. | MS [M + H]+ | LC method | LC/MS retention time (min) |
|---|---|---|---|---|
| (structure) | II-215 | 444 | 2 | 2.10 |

TABLE 173

| Chemical Structure | Compound No. | MS [M + H]+ | LC method | LC/MS retention time (min) |
|---|---|---|---|---|
| (structure) | II-216 | 457 | 2 | 2.10 |
| (structure) | II-217 | 460 | 2 | 2.20 |

TABLE 173-continued

| Chemical Structure | Compound No. | MS [M + H]+ | LC method | LC/MS retention time (min) |
|---|---|---|---|---|
| 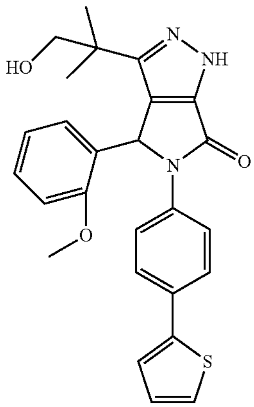 [SMILES: COc1ccccc1C1c2c(C(C)(C)CO)n[nH]c2C(=O)N1c1ccc(-c2cccs2)cc1] | II-218 | 460 | 2 | 2.20 |
| 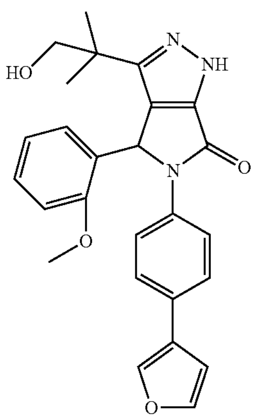 [SMILES: COc1ccccc1C1c2c(C(C)(C)CO)n[nH]c2C(=O)N1c1ccc(-c2ccoc2)cc1] | II-219 | 444 | 2 | 2.00 |
| 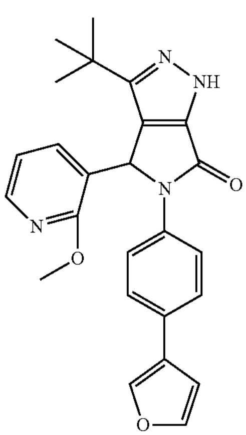 [SMILES: COc1ncccc1C1c2c(C(C)(C)C)n[nH]c2C(=O)N1c1ccc(-c2ccoc2)cc1] | II-220 | 429 | 2 | 2.20 |

TABLE 174

| Chemical Structure | Compound No. | MS [M + H]+ | LC method | LC/MS retention time (min) |
|---|---|---|---|---|
| 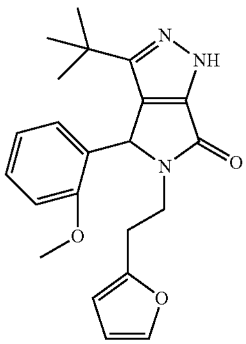 [SMILES: COc1ccccc1C1c2c(C(C)(C)C)n[nH]c2C(=O)N1CCc1ccco1] | II-221 | 380 | 2 | 2.20 |
| 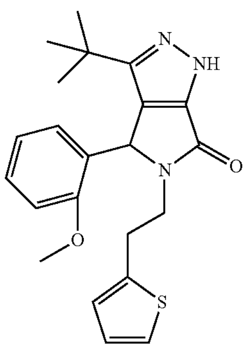 [SMILES: COc1ccccc1C1c2c(C(C)(C)C)n[nH]c2C(=O)N1CCc1cccs1] | II-222 | 396 | 2 | 2.30 |
| 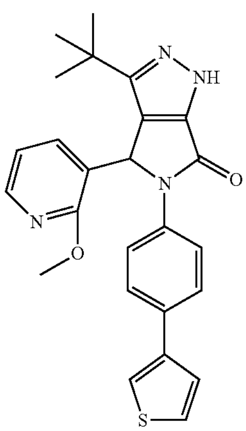 [SMILES: COc1ncccc1C1c2c(C(C)(C)C)n[nH]c2C(=O)N1c1ccc(-c2ccsc2)cc1] | II-223 | 445 | 2 | 2.40 |
| 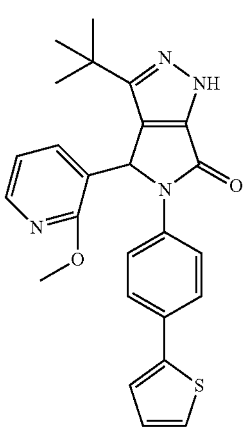 [SMILES: COc1ncccc1C1c2c(C(C)(C)C)n[nH]c2C(=O)N1c1ccc(-c2cccs2)cc1] | II-224 | 445 | 2 | 2.40 |

TABLE 174-continued

| Chemical Structure | Compound No. | MS [M + H]⁺ | LC method | LC/MS retention time (min) |
|---|---|---|---|---|
| (structure) | II-225 | 430 | 2 | 2.20 |

TABLE 175

| Chemical Structure | Compound No. | MS [M + H]⁺ | LC method | LC/MS retention time (min) |
|---|---|---|---|---|
| (structure) | II-226 | 445 | 2 | 1.80 |
| (structure) | II-227 | 445 | 2 | 1.80 |

TABLE 175-continued
| Chemical Structure | Compound No. | MS [M + H]⁺ | LC method | LC/MS retention time (min) |
|---|---|---|---|---|
| 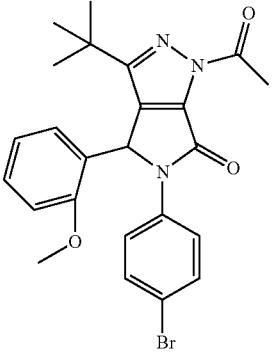 [SMILES: COc1ccccc1C1c2c(C(C)(C)C)nn(C(C)=O)c2C(=O)N1c1ccc(Br)cc1] | II-228 | 483 | 2 | 2.40 |
| 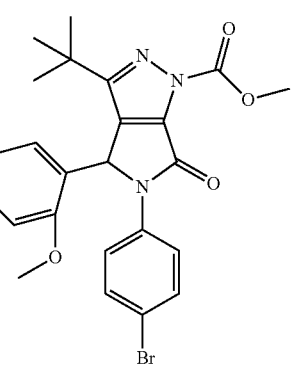 | II-229 | 498 | 2 | 2.20 |
| 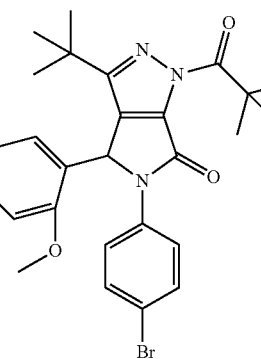 | II-230 | 524 | 2 | 1.40 |
TABLE 176
| Chemical Structure | Compound No. | MS [M + H]⁺ | LC method | LC/MS retention time (min) |
|---|---|---|---|---|
| 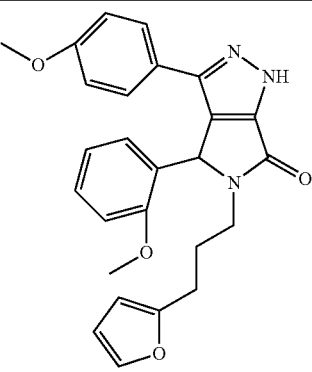 | II-231 | 444 | 2 | 2.00 |

TABLE 176-continued
| Chemical Structure | Compound No. | MS [M + H]+ | LC method | LC/MS retention time (min) |
|---|---|---|---|---|
| 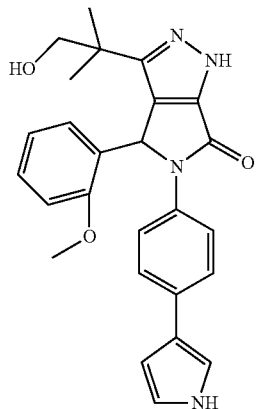 [SMILES: COc1ccccc1C1c2c(C(C)(C)CO)n[nH]c2C(=O)N1c1ccc(-c2cc[nH]c2)cc1] | II-232 | 443 | 2 | 1.70 |
| 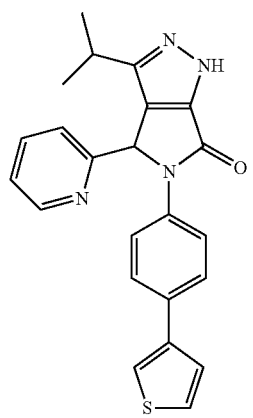 [SMILES: CC(C)c1n[nH]c2c1C(c1ccccn1)N(c1ccc(-c3ccsc3)cc1)C2=O] | II-233 | 401 | 2 | 2.12 |
| 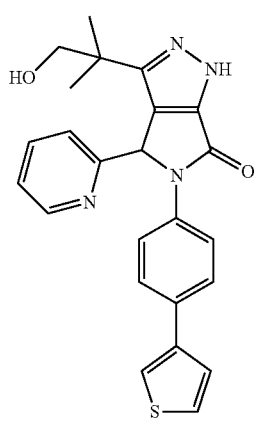 [SMILES: CC(C)(CO)c1n[nH]c2c1C(c1ccccn1)N(c1ccc(-c3ccsc3)cc1)C2=O] | II-234 | 431 | 2 | 1.85 |

TABLE 176-continued

| Chemical Structure | Compound No. | MS [M + H]+ | LC method | LC/MS retention time (min) |
|---|---|---|---|---|
| 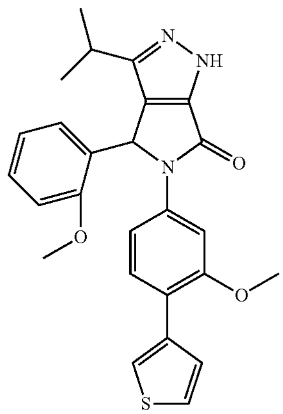 [SMILES: COc1cc(N2C(=O)c3[nH]nc(C(C)C)c3C2c2ccccc2OC)ccc1-c1ccsc1] | II-235 | 460 | 2 | 2.50 |

TABLE 177

| Chemical Structure | Compound No. | MS [M + H]+ | LC method | LC/MS retention time (min) |
|---|---|---|---|---|
| 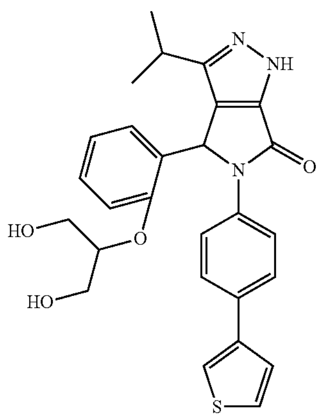 [SMILES: CC(C)c1n[nH]c2c1C(c1ccccc1OC(CO)CO)N(c1ccc(-c3ccsc3)cc1)C2=O] | II-236 | 490 | 2 | 1.88 |
| 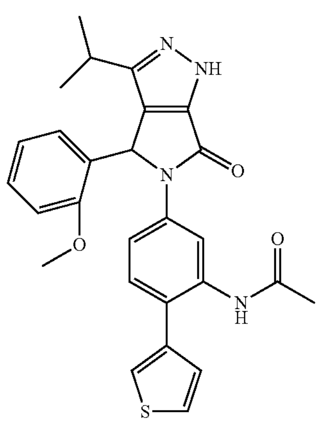 [SMILES: COc1ccccc1C1c2c(C(C)C)n[nH]c2C(=O)N1c1ccc(-c2ccsc2)c(NC(C)=O)c1] | II-237 | 487 | 2 | 2.07 |

TABLE 177-continued

| Chemical Structure | Compound No. | MS [M + H]+ | LC method | LC/MS retention time (min) |
|---|---|---|---|---|
| 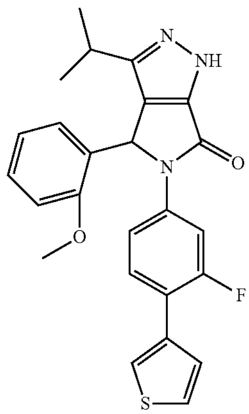 [SMILES: COc1ccccc1C1c2c(C(C)C)n[nH]c2C(=O)N1c1ccc(-c2ccsc2)c(F)c1] | II-238 | 448 | 2 | 2.56 |
| 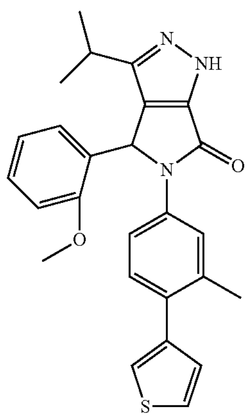 [SMILES: COc1ccccc1C1c2c(C(C)C)n[nH]c2C(=O)N1c1ccc(-c2ccsc2)c(C)c1] | II-239 | 444 | 2 | 2.55 |
| 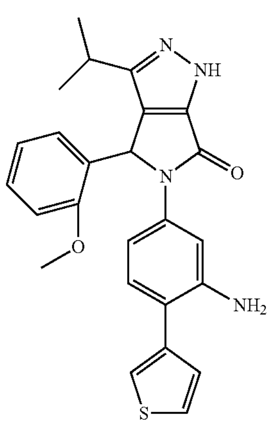 [SMILES: COc1ccccc1C1c2c(C(C)C)n[nH]c2C(=O)N1c1ccc(-c2ccsc2)c(N)c1] | II-240 | 445 | 2 | 2.24 |

TABLE 178

| Chemical Structure | Compound No. | MS [M + H]⁺ | LC method | LC/MS retention time (min) |
|---|---|---|---|---|
| 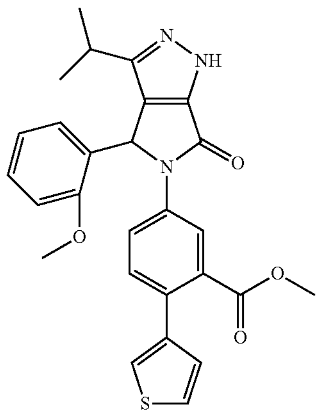 [SMILES: COC(=O)c1cc(N2C(=O)c3[nH]nc(C(C)C)c3C2c2ccccc2OC)ccc1-c1ccsc1] | II-241 | 488 | 2 | 2.39 |
| 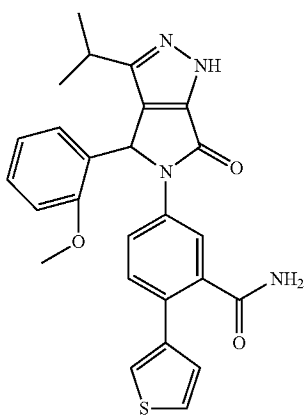 [SMILES: COc1ccccc1C1c2c(C(C)C)n[nH]c2C(=O)N1c1ccc(-c2ccsc2)c(C(N)=O)c1] | II-242 | 473 | 2 | 1.93 |
| 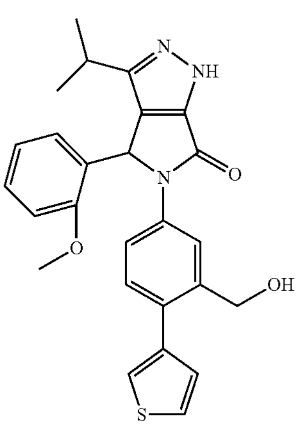 [SMILES: COc1ccccc1C1c2c(C(C)C)n[nH]c2C(=O)N1c1ccc(-c2ccsc2)c(CO)c1] | II-243 | 460 | 2 | 2.18 |

TABLE 178-continued

| Chemical Structure | Compound No. | MS [M + H]+ | LC method | LC/MS retention time (min) |
|---|---|---|---|---|
| 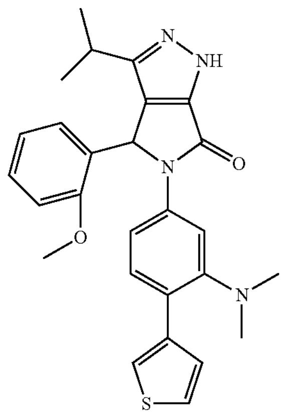 [SMILES: COc1ccccc1C1c2c(C(C)C)n[nH]c2C(=O)N1c1ccc(-c2ccsc2)c(N(C)C)c1] | II-244 | 473 | 2 | 2.51 |
| 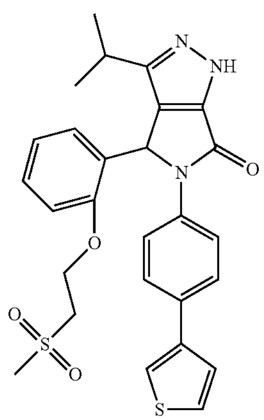 [SMILES: CC(C)c1n[nH]c2c1C(c1ccccc1OCCS(C)(=O)=O)N(c1ccc(-c3ccsc3)cc1)C2=O] | II-245 | 522 | 2 | 2.12 |

TABLE 179

| Chemical Structure | Compound No. | MS [M + H]+ | LC method | LC/MS retention time (min) |
|---|---|---|---|---|
| 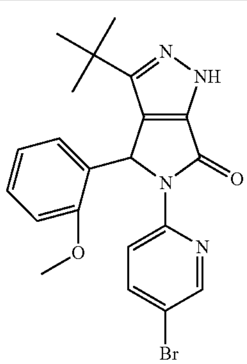 [SMILES: COc1ccccc1C1c2c(C(C)(C)C)n[nH]c2C(=O)N1c1ccc(Br)cn1] | II-246 | 441 | 2 | 2.46 |

TABLE 179-continued
| Chemical Structure | Compound No. | MS [M + H]+ | LC method | LC/MS retention time (min) |
| --- | --- | --- | --- | --- |
| 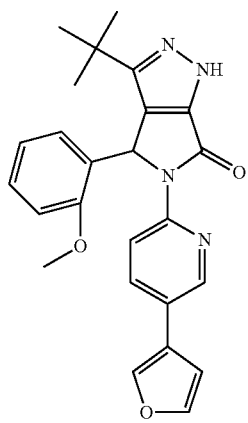 [SMILES: COc1ccccc1C1c2c(C(C)(C)C)n[nH]c2C(=O)N1c1ccc(-c2ccoc2)cn1] | II-247 | 429 | 2 | 2.37 |
| 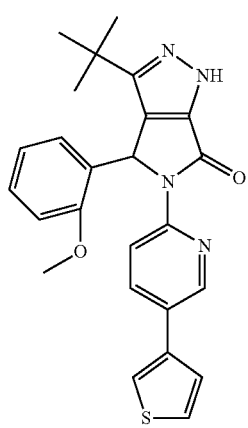 [SMILES: COc1ccccc1C1c2c(C(C)(C)C)n[nH]c2C(=O)N1c1ccc(-c2ccsc2)cn1] | II-248 | 445 | 2 | 2.52 |
| 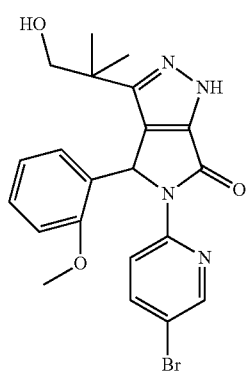 [SMILES: COc1ccccc1C1c2c(C(C)(C)CO)n[nH]c2C(=O)N1c1ccc(Br)cn1] | II-249 | 457 | 2 | 2.09 |

TABLE 179-continued

| Chemical Structure | Compound No. | MS [M + H]+ | LC method | LC/MS retention time (min) |
|---|---|---|---|---|
| 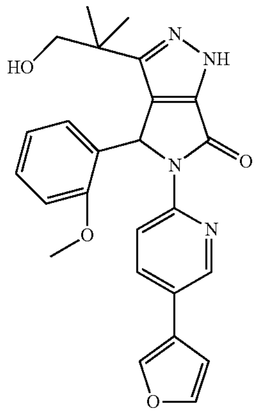 [SMILES: COc1ccccc1C1c2c(C(C)(C)CO)n[nH]c2C(=O)N1c1ccc(-c2ccoc2)cn1] | II-250 | 445 | 2 | 1.98 |

TABLE 180

| Chemical Structure | Compound No. | MS [M + H]+ | LC method | LC/MS retention time (min) |
|---|---|---|---|---|
| 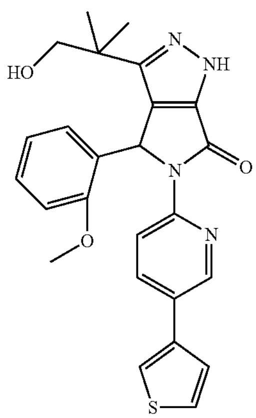 [SMILES: COc1ccccc1C1c2c(C(C)(C)CO)n[nH]c2C(=O)N1c1ccc(-c2ccsc2)cn1] | II-251 | 461 | 2 | 1.18 |
| 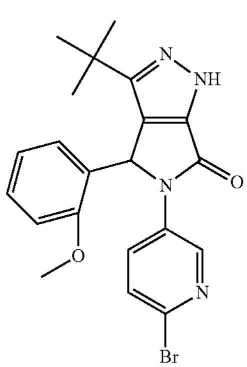 [SMILES: COc1ccccc1C1c2c(C(C)(C)C)n[nH]c2C(=O)N1c1ccc(Br)nc1] | II-252 | 441 | 2 | 2.20 |

TABLE 180-continued

| Chemical Structure | Compound No. | MS [M + H]+ | LC method | LC/MS retention time (min) |
|---|---|---|---|---|
| 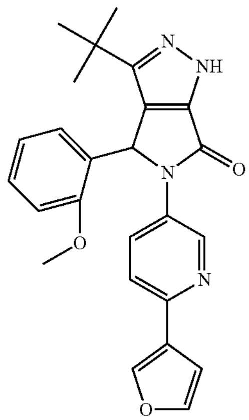 [SMILES: COc1ccccc1C1c2c(C(C)(C)C)n[nH]c2C(=O)N1c1ccc(-c2ccoc2)nc1] | II-253 | 429 | 2 | 1.90 |
| 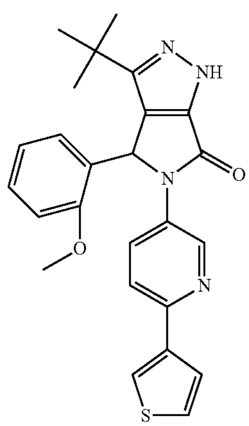 | II-254 | 445 | 2 | 2.06 |
| 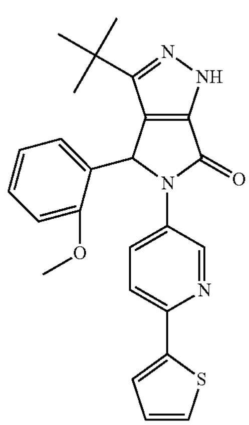 [SMILES: COc1ccccc1C1c2c(C(C)(C)C)n[nH]c2C(=O)N1c1ccc(-c2cccs2)nc1] | II-255 | 445 | 2 | 2.13 |

TABLE 181

| Chemical Structure | Compound No. | MS [M + H]+ | LC method | LC/MS retention time (min) |
|---|---|---|---|---|
| 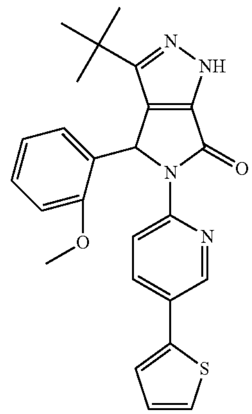 [SMILES: COc1ccccc1C1c2c(C(C)(C)C)n[nH]c2C(=O)N1c1ccc(-c2cccs2)cn1] | II-256 | 445 | 2 | 2.55 |
| 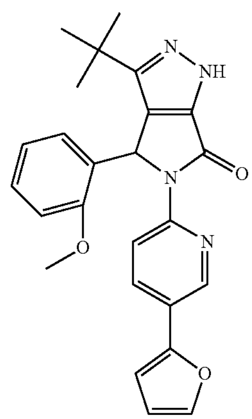 [SMILES: COc1ccccc1C1c2c(C(C)(C)C)n[nH]c2C(=O)N1c1ccc(-c2ccco2)cn1] | II-257 | 429 | 2 | 2.44 |
| 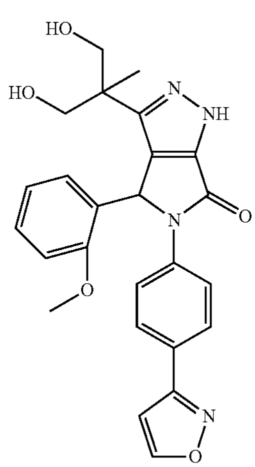 [SMILES: COc1ccccc1C1c2c(C(C)(CO)CO)n[nH]c2C(=O)N1c1ccc(-c2ccon2)cc1] | II-258 | 461 | 2 | 1.56 |

TABLE 181-continued

| Chemical Structure | Compound No. | MS [M + H]⁺ | LC method | LC/MS retention time (min) |
|---|---|---|---|---|
| 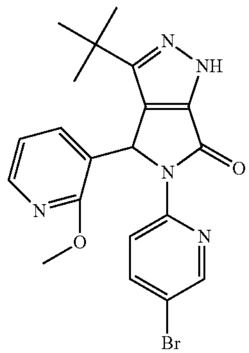 [SMILES: COc1ncccc1C1c2c(C(C)(C)C)n[nH]c2C(=O)N1c1ccc(Br)cn1] | II-259 | 442 | 2 | 2.39 |
| 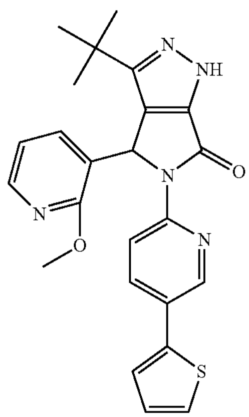 [SMILES: COc1ncccc1C1c2c(C(C)(C)C)n[nH]c2C(=O)N1c1ccc(-c2cccs2)cn1] | II-260 | 446 | 2 | 2.47 |

TABLE 182

| Chemical Structure | Compound No. | MS [M + H]⁺ | LC method | LC/MS retention time (min) |
|---|---|---|---|---|
| 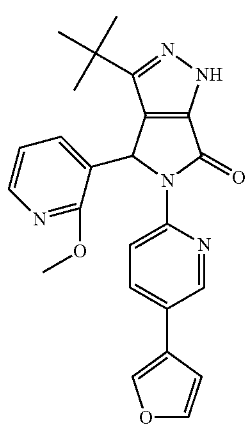 [SMILES: COc1ncccc1C1c2c(C(C)(C)C)n[nH]c2C(=O)N1c1ccc(-c2ccoc2)cn1] | II-261 | 430 | 2 | 2.25 |

TABLE 182-continued
| Chemical Structure | Compound No. | MS [M + H]+ | LC method | LC/MS retention time (min) |
|---|---|---|---|---|
| 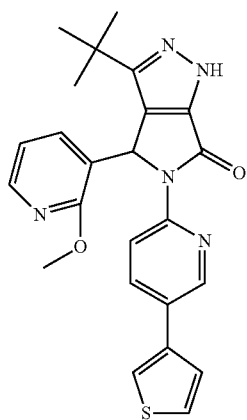 [SMILES: COc1ncccc1C1c2c(C(C)(C)C)n[nH]c2C(=O)N1c1ccc(-c2ccsc2)cn1] | II-262 | 446 | 2 | 2.41 |
| 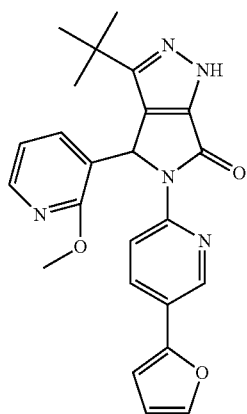 [SMILES: COc1ncccc1C1c2c(C(C)(C)C)n[nH]c2C(=O)N1c1ccc(-c2ccco2)cn1] | II-263 | 430 | 2 | 2.36 |
| 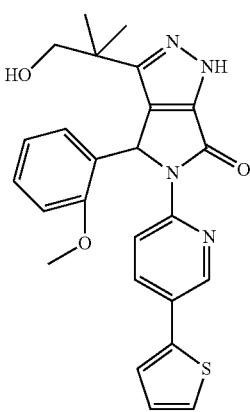 [SMILES: COc1ccccc1C1c2c(C(C)(C)CO)n[nH]c2C(=O)N1c1ccc(-c2cccs2)cn1] | II-264 | 461 | 2 | 2.20 |

TABLE 182-continued
| Chemical Structure | Compound No. | MS [M + H]+ | LC method | LC/MS retention time (min) |
|---|---|---|---|---|
| 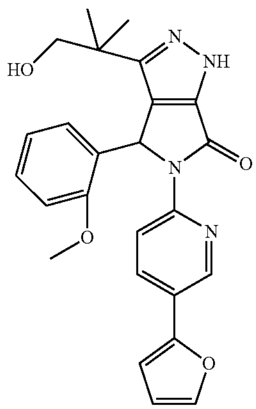 [SMILES: COc1ccccc1C1c2c(C(C)(C)CO)n[nH]c2C(=O)N1c1ccc(-c2ccco2)cn1] | II-265 | 445 | 2 | 2.09 |
TABLE 183
| Chemical Structure | Compound No. | MS [M + H]+ | LC method | LC/MS retention time (min) |
|---|---|---|---|---|
| 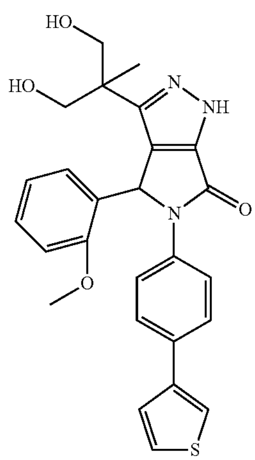 [SMILES: COc1ccccc1C1c2c(C(C)(CO)CO)n[nH]c2C(=O)N1c1ccc(-c2ccsc2)cc1] | II-266 | 476 | 2 | 1.93 |
| 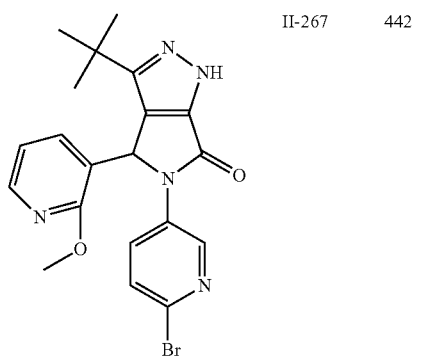 | II-267 | 442 | 2 | 2.05 |

TABLE 183-continued

| Chemical Structure | Compound No. | MS [M + H]+ | LC method | LC/MS retention time (min) |
| --- | --- | --- | --- | --- |
| 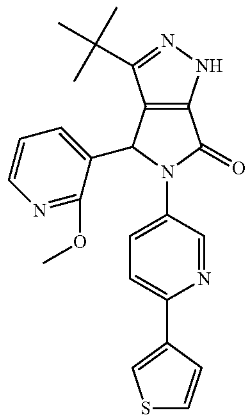 [SMILES: COc1ncccc1C1c2c(C(C)(C)C)n[nH]c2C(=O)N1c1ccc(-c2ccsc2)nc1] | II-268 | 446 | 2 | 2.09 |
| 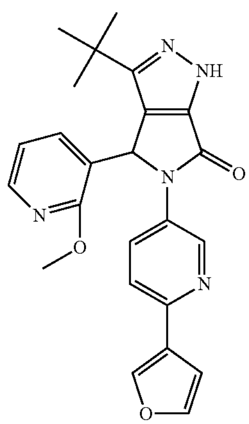 [SMILES: COc1ncccc1C1c2c(C(C)(C)C)n[nH]c2C(=O)N1c1ccc(-c2ccoc2)nc1] | II-269 | 430 | 2 | 1.94 |
| 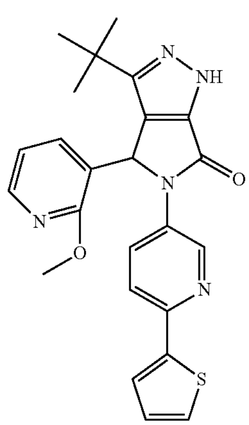 [SMILES: COc1ncccc1C1c2c(C(C)(C)C)n[nH]c2C(=O)N1c1ccc(-c2cccs2)nc1] | II-270 | 446 | 2 | 2.20 |

TABLE 184
| Chemical Structure | Compound No. | MS [M + H]+ | LC method | LC/MS retention time (min) |
|---|---|---|---|---|
| 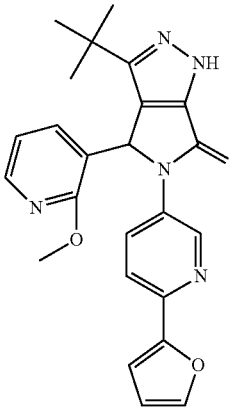 | II-271 | 430 | 2 | 2.03 |
| 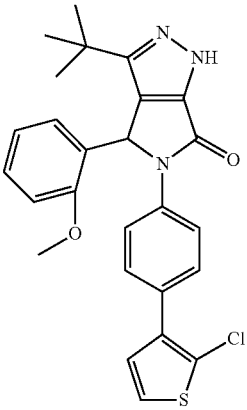 [SMILES: COc1ccccc1C1c2c(C(C)(C)C)n[nH]c2C(=O)N1c1ccc(-c2ccsc2Cl)cc1] | II-272 | 478 | 2 | 2.70 |
| 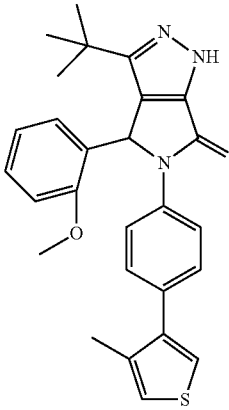 | II-273 | 458 | 2 | 2.65 |

TABLE 184-continued

| Chemical Structure | Compound No. | MS [M + H]+ | LC method | LC/MS retention time (min) |
|---|---|---|---|---|
| 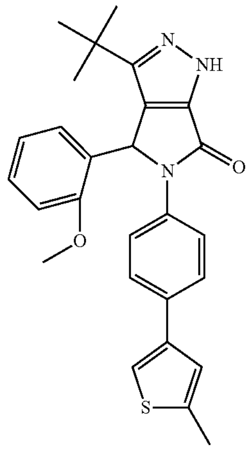 [SMILES: COc1ccccc1C1c2c(C(C)(C)C)n[nH]c2C(=O)N1c1ccc(-c2csc(C)c2)cc1] | II-274 | 458 | 2 | 2.68 |
| 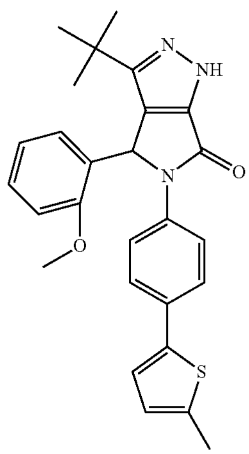 [SMILES: COc1ccccc1C1c2c(C(C)(C)C)n[nH]c2C(=O)N1c1ccc(-c2ccc(C)s2)cc1] | II-275 | 458 | 2 | 2.74 |

TABLE 185

| Chemical Structure | Compound No. | MS [M + H]+ | LC method | LC/MS retention time (min) |
|---|---|---|---|---|
| 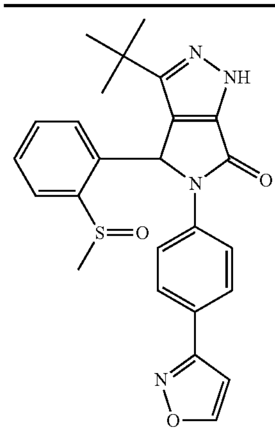 | II-276 | 461 | 2 | 1.60 |

TABLE 185-continued
| Chemical Structure | Compound No. | MS [M + H]+ | LC method | LC/MS retention time (min) |
|---|---|---|---|---|
| 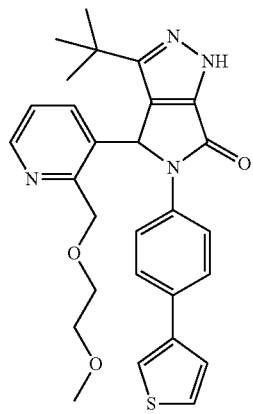 [SMILES: COCCOCc1ncccc1C1c2c(C(C)(C)C)n[nH]c2C(=O)N1c1ccc(-c2ccsc2)cc1] | II-277 | 503 | 2 | 1.98 |
| 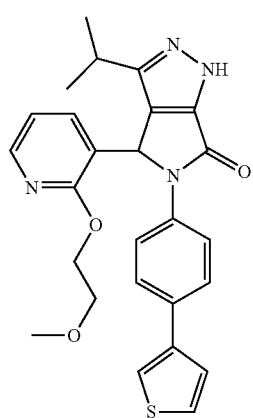 [SMILES: COCCOc1ncccc1C1c2c(C(C)C)n[nH]c2C(=O)N1c1ccc(-c2ccsc2)cc1] | II-278 | 475 | 2 | 2.29 |
| 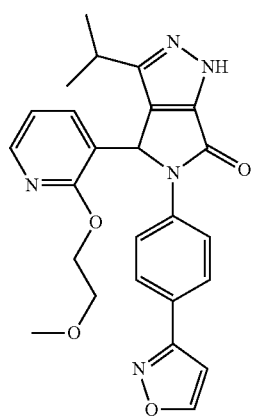 [SMILES: COCCOc1ncccc1C1c2c(C(C)C)n[nH]c2C(=O)N1c1ccc(-c2ccon2)cc1] | II-279 | 460 | 2 | 1.94 |

TABLE 185-continued

| Chemical Structure | Compound No. | MS [M + H]+ | LC method | LC/MS retention time (min) |
|---|---|---|---|---|
| (structure) | II-280 | 475 | 2 | 1.98 |

TABLE 186

| Chemical Structure | Compound No. | MS [M + H]+ | LC method | LC/MS retention time (min) |
|---|---|---|---|---|
| (structure) | II-281 | 475 | 2 | 2.03 |

Test Examples

Stably expressing cell line (C6BU-1 cell transfected with human P2X$_3$ receptor gene (GenBank accession number Y07683)) was used. The cells were seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. The medium was replaced with 4 μM Fluo-3-AM solution (pH7.5) containing 20 mM HEPES, 137 mM NaCl, 2.7 mM KCl, 0.9 mM MgCl$_2$, 5.0 mM CaCl$_2$, 5.6 mM D-glucose, 2.5 mM probenecid, 10% BSA, and 0.08% Pluronic F-127, and incubated at 37° C. under 5% dioxide carbon atmosphere for one hour. The plate was washed with washing buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, pH7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing different concentrations of the test compound as prepared by dilution with dilution buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, 0.1% Pluronic F-127, pH7.5) were dispensed to each well through the built-in automatic dispenser. Five minutes after, 40 nM ATP solution (50 μL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft™ Excel™ (Microsoft Corporation) and XLfit™ (ID Business Solutions Ltd.).

The results of the compounds of the invention are shown in the following tables.

TABLE 187

| Compound No. | P2X3 IC50 (μM) |
|---|---|
| I-001 | 0.032 |
| I-002 | 0.024 |
| I-003 | 0.040 |
| I-004 | 0.012 |
| I-005 | 0.247 |
| I-006 | 0.027 |
| I-007 | 0.100 |
| I-008 | 0.014 |
| I-009 | 0.014 |
| I-010 | 0.595 |
| I-011 | 0.270 |
| I-012 | 0.340 |
| I-014 | 0.134 |
| I-015 | 0.012 |
| I-016 | 0.079 |
| I-019 | 0.132 |
| I-020 | 0.021 |
| I-021 | 0.382 |
| I-026 | 0.339 |
| I-027 | 0.040 |
| I-028 | 0.075 |
| I-029 | 0.160 |
| I-030 | 0.053 |
| I-031 | 0.700 |
| I-032 | 0.160 |
| I-033 | 0.053 |
| I-034 | 0.700 |
| I-037 | 0.954 |
| I-038 | 0.926 |
| I-039 | 0.012 |
| I-044 | 0.468 |
| I-046 | 0.580 |
| I-047 | 0.221 |
| I-048 | 0.752 |
| I-050 | 0.642 |
| I-051 | 0.277 |
| I-052 | 0.187 |
| I-055 | 0.596 |
| I-057 | 0.159 |
| I-058 | 0.082 |
| I-059 | 0.260 |
| I-064 | 0.137 |
| I-066 | 0.434 |
| I-068 | 0.305 |
| I-070 | 0.519 |
| I-072 | 0.352 |
| I-075 | 0.013 |
| I-077 | 0.048 |
| I-078 | 0.016 |
| I-225 | 0.065 |
| I-226 | 0.012 |
| I-227 | 0.008 |
| I-228 | 0.015 |
| I-229 | 0.029 |
| I-230 | 0.018 |
| I-231 | 0.023 |
| I-232 | 0.024 |
| I-233 | 0.124 |
| I-234 | 0.056 |
| I-235 | 0.035 |
| I-236 | 0.431 |
| I-237 | 0.705 |
| I-239 | 0.035 |
| I-240 | 0.185 |

TABLE 187-continued

| Compound No. | P2X3 IC50 (μM) |
|---|---|
| I-241 | 0.822 |
| I-242 | 0.357 |
| I-244 | 0.027 |
| I-245 | 0.047 |
| I-247 | 0.015 |
| I-248 | 0.030 |
| I-249 | 0.010 |
| I-250 | 0.029 |
| I-251 | 0.017 |
| I-252 | 0.010 |
| I-253 | 0.193 |
| I-254 | 0.511 |
| I-255 | 0.008 |
| I-256 | 0.023 |
| I-257 | 0.037 |
| I-258 | 0.024 |
| I-259 | 0.030 |
| I-260 | 0.331 |
| I-261 | 0.019 |
| I-262 | 0.016 |
| I-263 | 0.008 |
| I-264 | 0.014 |
| I-265 | 0.028 |
| I-266 | 0.025 |
| I-267 | 0.014 |
| I-268 | 0.032 |
| I-269 | 0.347 |
| I-271 | 0.542 |
| I-273 | 0.491 |
| I-275 | 0.172 |
| I-276 | 0.117 |
| I-277 | 0.342 |
| I-278 | 0.366 |
| I-279 | 0.016 |
| I-416 | 0.322 |
| I-417 | 0.181 |
| I-418 | 0.593 |
| I-419 | 0.032 |
| I-420 | 0.257 |
| I-421 | 0.191 |
| I-422 | 0.361 |
| I-424 | 0.519 |
| I-425 | 0.697 |
| I-427 | 0.331 |
| I-428 | 0.399 |
| I-429 | 0.007 |
| I-430 | 0.153 |
| I-431 | 0.232 |
| I-433 | 0.425 |
| I-434 | 0.125 |
| I-435 | 0.082 |
| I-436 | 0.042 |
| I-437 | 0.111 |
| I-438 | 0.490 |
| I-439 | 0.116 |
| I-440 | 0.035 |
| I-441 | 0.013 |
| I-442 | 0.005 |
| I-443 | 0.006 |
| I-444 | 0.172 |
| I-445 | 0.152 |
| I-446 | 0.338 |
| I-447 | 0.128 |
| I-448 | 0.246 |
| I-449 | 0.013 |
| I-450 | 0.036 |
| I-451 | 0.019 |
| I-452 | 0.026 |
| I-453 | 0.041 |
| I-454 | 0.036 |
| I-455 | 0.014 |
| I-456 | 0.006 |
| I-457 | 0.488 |
| I-458 | 0.699 |
| I-459 | 0.026 |
| I-460 | 0.103 |
| I-461 | 0.036 |

TABLE 187-continued

| Compound No. | P2X3 IC50 (μM) |
|---|---|
| I-462 | 0.427 |
| I-463 | 0.127 |
| I-464 | 0.453 |
| I-465 | 0.007 |
| I-466 | 0.260 |
| I-467 | 0.286 |

TABLE 188

| Compound No. | P2X3 IC50 (μM) |
|---|---|
| I-079 | 0.023 |
| I-080 | 0.016 |
| I-081 | 0.151 |
| I-082 | 0.650 |
| I-085 | 0.048 |
| I-089 | 0.700 |
| I-090 | 0.555 |
| I-091 | 0.341 |
| I-092 | 0.092 |
| I-093 | 0.756 |
| I-094 | 0.301 |
| I-095 | 0.195 |
| I-098 | 0.370 |
| I-102 | 0.134 |
| I-103 | 0.355 |
| I-104 | 0.424 |
| I-105 | 0.097 |
| I-108 | 0.192 |
| I-111 | 0.624 |
| I-112 | 0.388 |
| I-113 | 0.012 |
| I-114 | 0.012 |
| I-115 | 0.108 |
| I-116 | 0.077 |
| I-117 | 0.383 |
| I-118 | 0.282 |
| I-119 | 0.098 |
| I-120 | 0.074 |
| I-122 | 0.342 |
| I-123 | 0.013 |
| I-124 | 0.011 |
| I-125 | 0.110 |
| I-126 | 0.015 |
| I-127 | 0.049 |
| I-128 | 0.155 |
| I-129 | 0.091 |
| I-130 | 0.476 |
| I-131 | 0.251 |
| I-132 | 0.043 |
| I-133 | 0.367 |
| I-134 | 0.776 |
| I-135 | 0.015 |
| I-136 | 0.015 |
| I-137 | 0.615 |
| I-138 | 0.016 |
| I-139 | 0.930 |
| I-141 | 0.346 |
| I-142 | 0.315 |
| I-143 | 0.331 |
| I-280 | 0.477 |
| I-281 | 0.637 |
| I-282 | 0.472 |
| I-283 | 0.144 |
| I-284 | 0.300 |
| I-285 | 0.648 |
| I-286 | 0.669 |
| I-288 | 0.036 |
| I-290 | 0.051 |
| I-291 | 0.130 |
| I-292 | 0.127 |
| I-293 | 0.012 |
| I-295 | 0.054 |

TABLE 188-continued

| Compound No. | P2X3 IC50 (μM) |
|---|---|
| I-296 | 0.244 |
| I-297 | 0.220 |
| I-298 | 0.269 |
| I-299 | 0.008 |
| I-300 | 0.114 |
| I-301 | 0.018 |
| I-302 | 0.034 |
| I-303 | 0.031 |
| I-304 | 0.021 |
| I-305 | 0.020 |
| I-306 | 0.054 |
| I-307 | 0.158 |
| I-308 | 0.193 |
| I-309 | 0.182 |
| I-310 | 0.337 |
| I-311 | 0.121 |
| I-312 | 0.054 |
| I-313 | 0.320 |
| I-314 | 0.329 |
| I-315 | 0.252 |
| I-316 | 0.130 |
| I-317 | 0.073 |
| I-318 | 0.328 |
| I-319 | 0.222 |
| I-320 | 0.274 |
| I-321 | 0.070 |
| I-322 | 0.102 |
| I-323 | 0.310 |
| I-324 | 0.109 |
| I-325 | 0.018 |
| I-326 | 0.027 |
| I-327 | 0.093 |
| I-328 | 0.065 |
| I-329 | 0.578 |
| I-330 | 0.070 |
| I-331 | 0.722 |
| I-468 | 0.467 |
| I-469 | 0.646 |
| I-470 | 0.972 |
| I-471 | 0.019 |
| I-472 | 0.007 |
| I-473 | 0.182 |
| I-474 | 0.071 |
| I-475 | 0.181 |
| I-476 | 0.051 |
| I-477 | 0.477 |
| I-478 | 0.034 |
| I-479 | 0.010 |
| I-480 | 0.042 |
| I-481 | 0.378 |
| I-482 | 0.333 |
| I-483 | 0.089 |
| I-484 | 0.091 |
| I-485 | 0.218 |
| I-486 | 0.004 |
| I-487 | 0.167 |
| I-488 | 0.067 |
| I-489 | 0.006 |
| I-490 | 0.017 |
| I-491 | 0.155 |
| I-492 | 0.104 |
| I-493 | 0.105 |
| I-494 | 0.053 |
| I-495 | 0.059 |
| I-496 | 0.055 |
| I-497 | 0.036 |
| I-498 | 0.008 |
| I-499 | 0.398 |
| I-500 | 0.012 |
| I-501 | 0.052 |
| I-502 | 0.067 |
| I-503 | 0.017 |
| I-504 | 0.238 |
| I-505 | 0.168 |
| I-506 | 0.112 |
| I-507 | 0.101 |
| I-508 | 0.133 |

TABLE 188-continued

| Compound No. | P2X3 IC50 (μM) |
| --- | --- |
| I-509 | 0.247 |
| I-510 | 0.174 |
| I-511 | 0.117 |
| I-512 | 0.062 |
| I-513 | 0.065 |
| I-514 | 0.138 |
| I-515 | 0.037 |
| I-516 | 0.033 |

TABLE 189

| Compound No. | P2X3 IC50 (μM) |
| --- | --- |
| I-144 | 0.365 |
| I-145 | 0.016 |
| I-146 | 0.727 |
| I-147 | 0.017 |
| I-148 | 0.073 |
| I-149 | 0.015 |
| I-150 | 0.415 |
| I-151 | 0.008 |
| I-152 | 0.219 |
| I-153 | 0.216 |
| I-154 | 0.192 |
| I-155 | 0.035 |
| I-156 | 0.032 |
| I-157 | 0.025 |
| I-158 | 0.023 |
| I-159 | 0.016 |
| I-160 | 0.013 |
| I-161 | 0.007 |
| I-162 | 0.041 |
| I-164 | 0.074 |
| I-165 | 0.095 |
| I-166 | 0.019 |
| I-167 | 0.013 |
| I-168 | 0.120 |
| I-169 | 0.019 |
| I-171 | 0.610 |
| I-172 | 0.024 |
| I-173 | 0.137 |
| I-174 | 0.572 |
| I-176 | 0.046 |
| I-178 | 0.374 |
| I-179 | 0.659 |
| I-180 | 0.005 |
| I-181 | 0.114 |
| I-183 | 0.004 |
| I-184 | 0.163 |
| I-185 | 0.111 |
| I-186 | 0.013 |
| I-187 | 0.086 |
| I-188 | 0.022 |
| I-189 | 0.014 |
| I-190 | 0.040 |
| I-191 | 0.279 |
| I-192 | 0.612 |
| I-193 | 0.994 |
| I-194 | 0.063 |
| I-195 | 0.235 |
| I-197 | 0.036 |
| I-198 | 0.064 |
| I-332 | 0.281 |
| I-333 | 0.058 |
| I-334 | 0.078 |
| I-336 | 0.351 |
| I-337 | 0.103 |
| I-338 | 0.147 |
| I-339 | 0.892 |
| I-340 | 0.336 |
| I-341 | 0.508 |
| I-342 | 0.067 |
| I-343 | 0.078 |

TABLE 189-continued

| Compound No. | P2X3 IC50 (μM) |
| --- | --- |
| I-344 | 0.594 |
| I-345 | 0.999 |
| I-346 | 0.677 |
| I-347 | 0.047 |
| I-348 | 0.055 |
| I-349 | 0.037 |
| I-350 | 0.066 |
| I-351 | 0.101 |
| I-353 | 0.210 |
| I-354 | 0.057 |
| I-355 | 0.044 |
| I-356 | 0.007 |
| I-357 | 0.020 |
| I-358 | 0.025 |
| I-359 | 0.024 |
| I-360 | 0.021 |
| I-361 | 0.048 |
| I-362 | 0.040 |
| I-363 | 0.007 |
| I-364 | 0.009 |
| I-365 | 0.082 |
| I-366 | 0.013 |
| I-367 | 0.019 |
| I-368 | 0.016 |
| I-369 | 0.091 |
| I-370 | 0.194 |
| I-371 | 0.447 |
| I-372 | 0.035 |
| I-373 | 0.051 |
| I-374 | 0.040 |
| I-375 | 0.030 |
| I-376 | 0.025 |
| I-377 | 0.148 |
| I-378 | 0.192 |
| I-379 | 0.118 |
| I-380 | 0.007 |
| I-381 | 0.007 |
| I-382 | 0.006 |
| I-517 | 0.026 |
| I-518 | 0.087 |
| I-519 | 0.033 |
| I-521 | 0.554 |
| I-523 | 0.351 |
| I-524 | 0.696 |
| I-525 | 0.018 |
| I-526 | 0.219 |
| I-527 | 0.039 |
| I-528 | 0.070 |
| I-530 | 0.237 |
| I-531 | 0.286 |
| I-532 | 0.204 |
| I-533 | 0.033 |
| I-535 | 0.049 |
| I-536 | 0.032 |
| I-537 | 0.083 |
| I-538 | 0.119 |
| I-539 | 0.062 |
| I-540 | 0.496 |
| I-541 | 0.010 |
| I-542 | 0.058 |
| I-543 | 0.240 |
| I-544 | 0.008 |
| I-545 | 0.142 |
| I-546 | 0.395 |
| I-547 | 0.217 |
| I-548 | 0.077 |
| I-549 | 0.213 |
| I-550 | 0.254 |
| I-551 | 0.005 |
| I-552 | 0.186 |
| I-553 | 0.337 |
| I-555 | 0.579 |
| I-556 | 0.032 |
| I-557 | 0.444 |
| I-558 | 0.008 |
| I-559 | 0.040 |
| I-560 | 0.275 |

TABLE 189-continued

| Compound No. | P2X3 IC50 (μM) |
|---|---|
| I-562 | 0.101 |
| I-563 | 0.042 |
| I-564 | 0.018 |
| I-565 | 0.013 |
| I-566 | 0.061 |
| I-567 | 0.057 |
| I-568 | 0.066 |
| I-569 | 0.035 |
| I-570 | 0.070 |
| I-571 | 0.060 |

TABLE 190

| Compound No. | P2X3 IC50 (μM) |
|---|---|
| I-199 | 0.019 |
| I-200 | 0.014 |
| I-201 | 0.039 |
| I-202 | 0.040 |
| I-204 | 0.043 |
| I-206 | 0.630 |
| I-207 | 0.008 |
| I-208 | 0.014 |
| I-209 | 0.234 |
| I-210 | 0.047 |
| I-211 | 0.157 |
| I-212 | 0.092 |
| I-213 | 0.006 |
| I-214 | 0.022 |
| I-215 | 0.013 |
| I-216 | 0.679 |
| I-217 | 0.012 |
| I-218 | 0.073 |
| I-219 | 0.324 |
| I-220 | 0.005 |
| I-221 | 0.081 |
| I-222 | 0.006 |
| I-223 | 0.012 |
| I-224 | 0.073 |
| I-383 | 0.036 |
| I-384 | 0.019 |
| I-385 | 0.227 |
| I-391 | 0.684 |
| I-392 | 0.946 |
| I-393 | 0.015 |
| I-394 | 0.011 |
| I-395 | 0.006 |
| I-396 | 0.007 |
| I-397 | 0.122 |
| I-398 | 0.014 |
| I-399 | 0.044 |
| I-400 | 0.022 |
| I-401 | 0.079 |
| I-402 | 0.080 |
| I-404 | 0.071 |
| I-405 | 0.031 |
| I-406 | 0.029 |
| I-408 | 0.018 |
| I-409 | 0.177 |
| I-410 | 0.151 |
| I-412 | 0.310 |
| I-413 | 0.042 |
| I-414 | 0.268 |
| I-572 | 0.171 |
| I-573 | 0.123 |
| I-574 | 0.280 |
| I-575 | 0.252 |
| I-576 | 0.237 |
| I-577 | 0.047 |
| I-578 | 0.386 |
| I-579 | 0.429 |
| I-581 | 0.466 |
| I-582 | 0.359 |

TABLE 190-continued

| Compound No. | P2X3 IC50 (μM) |
|---|---|
| I-583 | 0.010 |
| I-584 | 0.167 |
| I-585 | 0.157 |
| I-586 | 0.254 |
| I-587 | 0.374 |
| I-588 | 0.029 |
| I-589 | 0.032 |
| I-590 | 0.028 |
| I-591 | 0.031 |
| I-592 | 0.827 |
| I-593 | 0.811 |
| I-594 | 0.715 |
| I-597 | 0.668 |
| I-598 | 0.785 |

TABLE 191

| Compound No. | P2X3 IC50 (μM) |
|---|---|
| II-001 | 0.104 |
| II-002 | 0.217 |
| II-003 | 0.140 |
| II-004 | 0.378 |
| II-006 | 0.245 |
| II-007 | 0.062 |
| II-008 | 0.505 |
| II-009 | 0.054 |
| II-010 | 0.134 |
| II-011 | 0.319 |
| II-012 | 0.004 |
| II-013 | 0.019 |
| II-014 | 0.017 |
| II-015 | 0.087 |
| II-016 | 0.158 |
| II-017 | 0.054 |
| II-018 | 0.022 |
| II-019 | 0.021 |
| II-020 | 0.008 |
| II-021 | 0.009 |
| II-022 | 0.004 |
| II-023 | 0.004 |
| II-024 | 0.062 |
| II-025 | 0.015 |
| II-026 | 0.023 |
| II-027 | 0.008 |
| II-028 | 0.014 |
| II-029 | 0.090 |
| II-030 | 0.128 |
| II-031 | 0.018 |
| II-032 | 0.006 |
| II-033 | 0.117 |
| II-034 | 0.046 |
| II-035 | 0.006 |
| II-036 | 0.231 |
| II-037 | 0.008 |
| II-038 | 0.014 |
| II-039 | 0.005 |
| II-040 | 0.070 |
| II-041 | 0.027 |
| II-042 | 0.010 |
| II-043 | 0.017 |
| II-044 | 0.582 |
| II-045 | 0.016 |
| II-046 | 0.861 |
| II-047 | 0.011 |
| II-048 | 0.057 |
| II-049 | 0.011 |
| II-050 | 0.007 |
| II-088 | 0.004 |
| II-089 | 0.107 |
| II-090 | 0.002 |
| II-091 | 0.002 |
| II-092 | 0.002 |

TABLE 191-continued

| Compound No. | P2X3 IC50 (μM) |
|---|---|
| II-093 | 0.002 |
| II-094 | 0.065 |
| II-095 | 0.012 |
| II-096 | 0.223 |
| II-097 | 0.358 |
| II-098 | 0.761 |
| II-099 | 0.046 |
| II-100 | 0.031 |
| II-101 | 0.027 |
| II-102 | 0.076 |
| II-104 | 0.003 |
| II-105 | 0.013 |
| II-106 | 0.226 |
| II-107 | 0.114 |
| II-108 | 0.015 |
| II-109 | 0.021 |
| II-110 | 0.024 |
| II-111 | 0.091 |
| II-112 | 0.389 |
| II-113 | 0.838 |
| II-114 | 0.012 |
| II-115 | 0.011 |
| II-117 | 0.348 |
| II-118 | 0.429 |
| II-119 | 0.137 |
| II-121 | 0.464 |
| II-123 | 0.431 |
| II-124 | 0.008 |
| II-125 | 0.010 |
| II-126 | 0.221 |
| II-127 | 0.004 |
| II-128 | 0.216 |
| II-130 | 0.004 |
| II-131 | 0.088 |
| II-132 | 0.141 |
| II-133 | 0.116 |
| II-136 | 0.055 |
| II-137 | 0.148 |
| II-138 | 0.044 |
| II-139 | 0.332 |
| II-141 | 0.022 |
| II-142 | 0.104 |
| II-145 | 0.033 |
| II-146 | 0.416 |
| II-189 | 0.897 |
| II-191 | 0.322 |
| II-192 | 0.222 |
| II-193 | 0.195 |
| II-194 | 0.392 |
| II-195 | 0.944 |
| II-196 | 0.783 |
| II-197 | 0.106 |
| II-198 | 0.123 |
| II-199 | 0.113 |
| II-200 | 0.448 |
| II-201 | 0.033 |
| II-202 | 0.076 |
| II-203 | 0.028 |
| II-204 | 0.017 |
| II-205 | 0.811 |
| II-208 | 0.112 |
| II-209 | 0.087 |
| II-210 | 0.811 |
| II-211 | 0.135 |
| II-212 | 0.238 |
| II-213 | 0.011 |
| II-215 | 0.015 |
| II-216 | 0.473 |
| II-217 | 0.003 |
| II-218 | 0.005 |
| II-219 | 0.014 |
| II-220 | 0.069 |
| II-223 | 0.023 |
| II-224 | 0.031 |
| II-225 | 0.979 |
| II-227 | 0.034 |
| II-229 | 0.082 |
| II-231 | 0.344 |
| II-232 | 0.016 |
| II-233 | 0.092 |
| II-234 | 0.130 |
| II-235 | 0.017 |
| II-236 | 0.005 |
| II-237 | 0.853 |
| II-238 | 0.019 |
| II-239 | 0.205 |
| II-240 | 0.116 |
| II-241 | 0.213 |
| II-242 | 0.152 |
| II-243 | 0.138 |
| II-244 | 0.144 |
| II-245 | 0.006 |
| II-246 | 0.871 |

TABLE 192

| Compound No. | P2X3 IC50 (μM) |
|---|---|
| II-051 | 0.005 |
| II-052 | 0.033 |
| II-053 | 0.035 |
| II-054 | 0.026 |
| II-055 | 0.548 |
| II-057 | 0.017 |
| II-058 | 0.494 |
| II-059 | 0.046 |
| II-060 | 0.538 |
| II-061 | 0.166 |
| II-062 | 0.112 |
| II-064 | 0.075 |
| II-067 | 0.153 |
| II-068 | 0.508 |
| II-069 | 0.414 |
| II-072 | 0.739 |
| II-073 | 0.105 |
| II-074 | 0.032 |
| II-075 | 0.153 |
| II-076 | 0.012 |
| II-077 | 0.237 |
| II-078 | 0.016 |
| II-079 | 0.011 |
| II-080 | 0.011 |
| II-081 | 0.189 |
| II-082 | 0.044 |
| II-083 | 0.024 |
| II-084 | 0.018 |
| II-085 | 0.023 |
| II-086 | 0.032 |
| II-087 | 0.009 |
| II-147 | 0.977 |
| II-148 | 0.311 |
| II-149 | 0.377 |
| II-151 | 0.650 |
| II-155 | 0.322 |
| II-156 | 0.412 |
| II-157 | 0.524 |
| II-158 | 0.650 |
| II-159 | 0.360 |
| II-163 | 0.034 |
| II-164 | 0.036 |
| II-165 | 0.041 |
| II-166 | 0.007 |
| II-167 | 0.005 |
| II-168 | 0.101 |
| II-169 | 0.004 |
| II-170 | 0.034 |
| II-171 | 0.007 |
| II-172 | 0.011 |
| II-173 | 0.004 |
| II-174 | 0.003 |

TABLE 192-continued

| Compound No. | P2X3 IC50 (µM) |
|---|---|
| II-175 | 0.003 |
| II-176 | 0.010 |
| II-178 | 0.149 |
| II-180 | 0.262 |
| II-181 | 0.301 |
| II-182 | 0.060 |
| II-183 | 0.460 |
| II-184 | 0.012 |
| II-185 | 0.011 |
| II-188 | 0.156 |
| II-247 | 0.033 |
| II-248 | 0.013 |
| II-250 | 0.043 |
| II-251 | 0.008 |
| II-253 | 0.020 |
| II-254 | 0.002 |
| II-255 | 0.003 |
| II-256 | 0.018 |
| II-257 | 0.033 |
| II-258 | 0.304 |
| II-259 | 0.410 |
| II-260 | 0.036 |
| II-261 | 0.140 |
| II-262 | 0.039 |
| II-263 | 0.108 |
| II-264 | 0.011 |
| II-265 | 0.031 |
| II-266 | 0.007 |
| II-268 | 0.024 |
| II-269 | 0.363 |
| II-270 | 0.025 |
| II-271 | 0.153 |
| II-272 | 0.392 |
| II-274 | 0.019 |
| II-275 | 0.027 |
| II-277 | 0.274 |
| II-278 | 0.013 |
| II-279 | 0.378 |
| II-280 | 0.244 |
| II-281 | 0.664 |

As shown, the compounds of the invention showed inhibiting activity on P2X$_3$ receptor. Furthermore, as the compounds of the invention are effective to P2X$_3$ subtype, the compounds also have inhibiting activity on P2X$_{2/3}$ receptor, which comprises P2X$_3$ subtype.

(CYP3A4 Fluorescent MBI Test)

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 µmol/mL, at reaction 6.25 pmol/mL (at 10-fold dilution); test drug concentration, 0.625, 1.25, 2.5, 5, 10, 20 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)= 4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and IC$_{50}$ was calculated by reverse-presumption by a logistic model using a concentration and an inhibition rate. When a difference between IC$_{50}$ values is 5 µM or more, this was defined as (+) and, when the difference is 3 µM or less, this was defined as (−).

(CYP Inhibition Test)

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and IC$_{50}$ was calculated by reverse presumption by a logistic model using a concentration and an inhibition rate.

(FAT Test)

20 µl of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution, the bacteria was suspended in 9 mL of a Micro F buffer (K$_2$HPO$_4$: 3.5 g/L, KH$_2$PO$_4$: 1 g/L, (NH$_4$)$_2$SO$_4$: 1 g/L, trisodium citrate dehydrate: 0.25 g/L, MgSO$_4$.7H$_2$O: 0.1 g/L), the suspension was added to 110 mL of an Exposure medium (Micro F buffer containing Biotin: 8 μg/mL, histidine: 0.2 μg/mL, glucose: 8 mg/mL), and the TA100 strain was added to 120 mL of the Exposure medium relative to 3.16 mL of the bacterial solution to prepare a test bacterial solution. Each 12 μL of a test substance DMSO solution (8 stage dilution from maximum dose 50 mg/mL at 2-fold ratio), DMSO as a negative control, 50 μg/mL of 4-nitroquinoline-1-oxide DMSO solution for the TA98 strain, 0.25 μg/mL of 2-(furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to the test substance was mixed with 2300 μL of an Indicator medium (Micro F buffer containing biotin: 8 μg/mL, histidine 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

(Solubility Test)

The solubility of a compound is determined under a condition in which 1% DMSO is added. 10 mM compound solution is prepared using DMSO, and then 6 μL of the compound solution is added to 594 μL of artificial intestinal juice in pH 6.8 (to 250 mL of 0.2 mol/L potassium dihydrogen phosphate reagent solution is added 118 mL of 0.2 mol/L NaOH reagent solution and water to provide a final volume of 1000 mL). After standing at 25 degrees Celsius for 16 hours, the mixed solution is filtrated with suction. The filtrate is diluted twice with methanol/water (1/1), and then a concentration in the filtration is measured with HPLC or LC/MS/MS by the absolute calibration method.

(Metabolism Stability Test)

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

(hERG Test)

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

(Bioavailability (BA) Test)

Materials and Methods for experiment of BA (1) Animals:

Male Crl: CD(SD) rats of 6 weeks of age are purchased from Charles River Laboratories Japan, Inc., and housed during one week quarantine. Jugular vein c annulation surgery is performed more than 3 days before administration for the rats. The rats are used at 8 weeks of age in the experiments.

(2) Animal Husbandry:

Animal room is maintained under a 12-hr light (8:00-20:00)/dark (20:00-8:00) cycle and kept temperature (20-26° C.) and relative humidity (30-70%). Rats have free access to solid food (CRF-1, Japan Charles River Inc.,) and sterilized bottled tap water.

(3) Identification of Rats and Cage:

Each rat is identified by a tail or a back marked with an oil marker pen and individually housed in a cage labeled with name of the study director, date of receipt, strain, gender and supplier in the experiment. Five rats are housed in one cage before the experiments. One rat is housed in one cage in the experiments.

(4) Setting of Dose and Group Compositions:

Group compositions as shown below, are set by Dose of Oral and Intravenous administration, respectively.

Oral: 1 mg/5 mL/kg (n=2)

Intravenous: 0.5 mg/1 mL/kg (n=2)

(5) Preparation for Dosing Formulation:

In oral administration study, a test suspension is prepared by using 0.5% methylcellulose (MC, 400 cP) as test substance. In intravenous administration study, a test solution is prepared by using N,N-dimethylacetoamide (DMA)/propylenglycol (PG)=(1/1) as test substance.

(6) Dosing Procedure:

In oral administration study, the test suspension is dosed to the stomach of rats by using a gavage tube at 5 mL/kg In intravenous administration study, the test solution is dosed to rats via tail vein using a syringe with a needle.

(7) Evaluation Items:

Blood was collected at each time point and separated plasma. Plasma concentration of the test substance is determined by a LC/MS/MS system.

(8) Data Analysis:

Area under the plasma concentration-time curve (AUC) is calculated by means of WinNonline® program, respectively. Bioavailability (BA) is calculated by using AUC values in oral administration study and in intravenous administration study.

Preparation Example 1

A granule containing the following ingredient is prepared.

| Ingredient | Compound represented by the formula (I) | 10 mg |
| --- | --- | --- |
| | Lactose | 700 mg |
| | Corn starch | 274 mg |
| | HPC-L | 16 mg |

The compound represented by the formula (I) and lactose are passed through a 60 mesh sieve. Corn starch is passed through a 120 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

Preparation Example 2

A powder for filling into a capsule containing the following ingredients is prepared.

| Ingredient | Compound represented by the formula (I) | 10 mg |
| --- | --- | --- |
| | Lactose | 79 mg |
| | Corn starch | 10 mg |
| | Magnesium stearate | 1 mg |

The compound represented by the formula (I), and lactose are passed through a 60 mesh sieve. Corn starch is passed through a 120 mesh sieve. These and magnesium stearate are mixed with a V-type mixing machine. 10 trituration 100 mg is filled into a No. 5 hard gelatin capsule.

Preparation Example 3

A tablet containing the following ingredients is prepared.

| Ingredient | Compound represented by the formula (I) | 10 mg |
| --- | --- | --- |
| | Lactose | 90 mg |
| | Microcrystaline cellulose | 30 mg |
| | CMC-Na | 15 mg |
| | Magnesium stearate | 5 mg |

The compound represented by the formula (I), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Formulation Example 4

The following ingredients are warmed, mixed, and sterilized to obtain an injectable.

| Ingredient | Compound represented by the formula (I) | 3 mg |
| --- | --- | --- |
| | Nonionic surfactant | 15 mg |
| | Purified water for injection | 1 ml |

Formulation Example 5

A cataplasm containing the following ingredients is prepared.

| Ingredient | Compound represented by the formula (I) | 50 mg |
| --- | --- | --- |
| | aqueous-based (5% ethanol/5% butylene glycol/90% purified water) | 950 mg |
| | glycerin | |
| | kaoline | |
| | aqueous polyvinyl alcohol | |

The compound represented by the formula (I) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound represented by the formula (I). The obtained solution is mixed and to give a paste form and the resulting paste is applied to an onwoven fabric. The resulting composition is covered by polyester film to give a cataplasm.

INDUSTRIAL APPLICABILITY

The compound of the invention has antagonizing effect on $P2X_3$ and/or $P2X_{2/3}$ receptor and is useful in the treatment of diseases or conditions associated with a $P2X_3$ and/or $P2X_{2/3}$ receptor, such as chronic pain, overactive bladder, etc.

The invention claimed is:
1. A compound represented by the formula (I'):

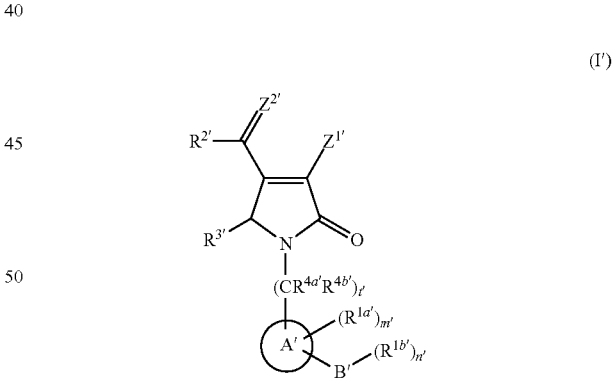

wherein
$Z^{1'}$ is optionally protected hydroxy or optionally protected mercapto;
$Z^{2'}$ is O;
t' is an integer of 0;
$R^{4a'}$ and $R^{4b'}$ are each independently hydrogen or lower alkyl;
m' and n' are each independently an integer of 0 to 2;
Ring A' is cycloalkane, cycloalkene, an aromatic carbocyclic ring or a heterocyclic ring;
B' is cycloalkane-diyl, cycloalkene-diyl, aromatic carbocyclic ring-diyl or heterocyclic ring-diyl, or; when n' is 0, B' may be methylthio, is methylthio, trifluoromethylthio, or —C(R$^{7a'}$)=N—O—R$^{7b'}$;

R$^{7a'}$ and R$^{7b'}$ are each independently hydrogen or substituted or unsubstituted lower alkyl;

R$^{1a'}$ and R$^{1b'}$ are each independently halogen, hydroxy, substituted or unsubstituted lower alkyl, substituted or unsubstituted lower alkenyl, substituted or unsubstituted lower alkynyl, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted sulfamoyl, cyano, or nitro;

R$^{2'}$ is substituted or unsubstituted tert-butyl, or substituted or unsubstituted i-propyl;

R$^{3'}$ is a group represented by the formula:

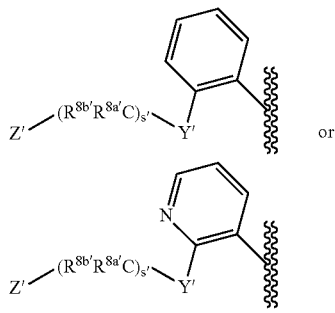 or wherein Y' is —O—, —S—, or —NR$^{9'}$—;

R$^{9'}$ is hydrogen or lower alkyl;

Z' is hydroxy, substituted or unsubstituted lower alkoxy, substituted or unsubstituted lower alkylthio, substituted or unsubstituted acyl, carboxy, substituted or unsubstituted lower alkoxycarbonyl, substituted or unsubstituted carbamoyl, substituted or unsubstituted amino, substituted or unsubstituted lower alkylsulfinyl, substituted or unsubstituted alkylsulfamoyl or cyano;

R$^{8a'}$ and R$^{8b'}$ are each independently hydrogen or substituted or unsubstituted lower alkyl;

s' is an integer of 1 to 4, or its pharmaceutically acceptable salt thereof.

2. A pharmaceutical composition comprising the compound according to claim 1, or its pharmaceutically acceptable salt thereof, together with a pharmaceutically acceptable carrier.

3. A pharmaceutical composition having an antagonistic activity for a P2X$_3$ and/or P2X$_{2/3}$ receptor, comprising the compound according to claim 1 or its pharmaceutically acceptable salt thereof, together with a pharmaceutically acceptable carrier.

* * * * *